(12) United States Patent
Abdel-Meguid et al.

(10) Patent No.: US 6,274,336 B1
(45) Date of Patent: *Aug. 14, 2001

(54) METHOD OF INHIBITING CATHEPSIN K

(75) Inventors: Sherin Salaheldin Abdel-Meguid, Exton; Renee Louise Desjarlais, St. Davids; Cheryl Ann Janson; Ward Whitlock Smith, Jr., both of Bryn Mawr; Baoguang Zhao, King of Prussia, all of PA (US)

(73) Assignee: SmithKline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,255

(22) PCT Filed: Oct. 30, 1996

(86) PCT No.: PCT/US96/17512

§ 371 Date: Jun. 26, 1997

§ 102(e) Date: Jun. 26, 1997

(87) PCT Pub. No.: WO97/16177

PCT Pub. Date: May 9, 1997

Related U.S. Application Data

(60) Provisional application No. 60/008,108, filed on Oct. 30, 1995, provisional application No. 60/007,473, filed on Nov. 22, 1995, provisional application No. 60/008,992, filed on Dec. 21, 1995, provisional application No. 60/013,748, filed on Mar. 20, 1996, provisional application No. 60/013,764, filed on Mar. 20, 1996, provisional application No. 60/013,747, filed on Mar. 20, 1996, provisional application No. 60/017,892, filed on May 17, 1996, provisional application No. 60/017,455, filed on May 17, 1996, provisional application No. 60/020,478, filed on Jun. 13, 1996, provisional application No. 60/022,047, filed on Jul. 22, 1996, provisional application No. 60/023,494, filed on Aug. 7, 1996, and provisional application No. 60/023,742, filed on Aug. 8, 1996.

(51) Int. Cl.[7] .............................. C12N 9/48; C12N 9/64; C12Q 1/37; G06F 19/00
(52) U.S. Cl. ................... 435/23; 435/226; 702/27
(58) Field of Search ........................... 435/23, 24, 212, 435/226; 514/2, 19, 365, 370, 400, 615, 617; 702/19, 22, 27, 30

(56) References Cited

U.S. PATENT DOCUMENTS 3,650,901 * 3/1972 Katchalski et al. ................. 435/180

(List continued on next page.)

FOREIGN PATENT DOCUMENTS

| 504938 | 9/1992 | (EP) . |
|---|---|---|
| WO 94/23033 | 10/1994 | (WO) . |
| WO 96/13523 | 5/1996 | (WO) . |
| WO 96/40737 | 12/1996 | (WO) . |

OTHER PUBLICATIONS

Baldwin et al, Crystal structures of native and inhibited forms . . . PNAS USA. vol. 90, pp. 6796–6800, Jul. 1993.*
Oxender, et al. Protein Engineering. New York: Alan R. Liss, Inc. 1987, p. 8, see entire document.

(List continued on next page.)

Primary Examiner—Jeffrey E. Russel
(74) Attorney, Agent, or Firm—Mary E. McCarthy; Stephen Venetianer; Charles M. Kinzig

(57) ABSTRACT

A novel cathepsin K crystalline stucture is identified. Also disclosed are methods of identifying inhibitors of this protease and methods of inhibiting cathepsin K using inhibitors with certain structural, physical and spatial characteristics.

1 Claim, 24 Drawing Sheets

U.S. PATENT DOCUMENTS

| | | | |
|---|---|---|---|
| 5,214,056 | * 5/1993 | Haruta et al. | 514/326 |
| 5,223,486 | 6/1993 | Gordon et al. | 514/18 |
| 5,331,573 | 7/1994 | Balaji et al. | 364/500 |
| 5,395,824 | 3/1995 | Higuchi et al. | 514/19 |
| 5,422,359 | 6/1995 | Ando et al. | 514/365 |
| 5,424,325 | 6/1995 | Ando et al. | 514/357 |
| 5,500,807 | 3/1996 | Lavin et al. | 364/496 |
| 5,501,969 | 3/1996 | Hastings et al. | 435/240.2 |
| 5,668,128 | * 9/1997 | Tsubotani et al. | 514/183 |
| 5,679,708 | * 10/1997 | Tsubotani et al. | 514/475 |
| 5,830,850 | * 11/1998 | Gelb et al. | 514/2 |

OTHER PUBLICATIONS

Bossard, et al., J. of Bio. Chem; May 1996, vol. 271, No. 21, pp. 12517–12524.

DesJarlais, et al., J. of Med. Chem; 1988, vol. 31, No. 4, pp. 722–729, especially abstract.

Bromme, et al., Biochemical Journal; 1996, vol. 315, pp. 85–89, especially abstract, Figure 1.

Velasco, et al., J. of Bio. Chem; Oct. 1994, vol. 269, No. 43, pp. 27136–27142, especially the abstract.

MaGrath, et al., J. of Med. Chem; 1992, vol. 35, No. 23, pp. 4279–4283, especially p. 4281, column 1, structures 1–4 and 7.

Graybill, et al., Bioorganic & Medicinal Chemistry Letters; 1992, vol. 2, No. 11, pp. 1375–1380, especially p. 1377, Scheme I.

Palmer, et al., J. of Med. Chem; Aug. 1995, vol. 38, No. 17, pp. 3193–3196.

Danheiser, Genetic Engineering News; Oct. 1995, vol. 15, No. 17, pp. 1–1 and 35–36.

Rasnick, Perspectives in Drug Discovery & Design; 1996, vol. 6, pp. 48–63.

Drake, et al., J. of Bio. Chem; May 1996, vol. 271, No. 21, pp. 12511–12516.

Bromme, et al., J. of Bio. Chem; Jan. 1996, vol. 271, No. 4, pp. 2126–2132.

Zhao, et al., Nature Structural Biology; Feb. 1997, vol. 4, No. 2, pp. 109–111.

McGrath, et al., Nature Structural Biology; Feb. 1997, vol. 4, No. 2, pp. 105–108.

Palmer, et al., ACS Presentation, Aug. 1995, Vinyl sulfones inhibit Cathepsin K.

* cited by examiner

FIGURE 1

```
                          1                                                       50
CatK                ..........  .MWGLKVLLL PVVSF....A  .LYPEEILDT HWELWKKTHR KQ.YNNKVDE ISRRLIWEKN LKYISIHNLE ASLGVHTYEL
CatS                ..........  .......... MKRLVCVLLV CSSAV....A  QLHKDPTLDH HWHLWKKTYG KQ.YKEKNEE AVRRLIWEKN LKFVMLHNLE HSMGMHSYDL
CatL                ..........  .......... ...MNPTLIL AAFCLGIASA TLTFDHSLEA QWTKWKAMHN RL.Y.GMNEE GWRRAVWEKN MKMIELHNQE YREGKHSFTM
Papain              ..........  .......... .......... .......... .......... .......... .......... .......... .......... ..........
Actinidin           MGLPKSFVSM  SLLFFSTLLI LSLAFNAKNL TQRTNDEVKA MYESWLIKYG KS.YNSLGEW ERRFEIFKET LRFIDEHNAD ...TNRSYKV
CatH                ......MWA   TLPLLCAGAW LLGVPVCGAA ELSVNSLEKF HFKSWMSKHR KT.Y.STEEY HHRLQTFASN WRKINAHN.. ..NGNHTFKM
CatB                ..........  .......... .......... .......... MWQLWASLCC LLVLANARSR PSFHPVSDEL VNYVNKRNTT WQAGHNFYNV 150
CatK        AMNHLGDMTS  EEVVQKMTGL KVPLSHSRSN DTLYIPEWEG RAPDSVDYRK KG.YVTPVKN QGQCGSCWAF SSVGALEGQL KKKTGKLLN.
CatS        GMNHLGDMTS  EEVMSLTSSL RVP.SQWQRN IT.YKSNPNR ILPDSVDWRE KG.CVTEVKY QGSCGACWAF SAVGALEAQL KLKTGKLVT.
CatL        AMNAFGDMTS  EEFRQVMNGF Q...NRKPRK GKVFQEPLFY EAPRSVDWRE KG.YVTPVKN QGQCGSCWAF SATGALEGQM FRKTGRLIS.
Papain      ..........  .......... .......... .......... .IPEYVDWRQ KG.AVTPVKN QGSCGSCWAF SAVVTIEGII KIRTGNLNQ.
Actinidin   GLNQFADLTD  EEFRSTYLGF .TSGSNKTKV SNRYEPRFGQ VLPSYVDWRS AG.AVVDIKS QGECGGCWAF SAIATVEGIN KIVTGVLIS.
CatH        ALNQFSDMSF  AEIKHK...Y LWSEPQNCSA TKSNYLRGTG PYPPSVDWRK KGNFVSPVKN QGACGSCWTF STTGALESAI AIATGKMLS.
CatB        DMSYLKRLCG  TFLGGPKPPQ RVMFTEDLKL PASFDAR... .......EQWP QCPTIKEIRD QGSCGSCWAF GAVEAISDRI CIHTNAHVSV 250
CatK        .LSPQNLVDC  VSE...NDGC GGGYMTNAFQ YVVQKNRGIDS EDAY...... .......... .......... .PYV GQEESCM... ......YNPTG
CatS        .LSAQNLVDC  STEKYGNKGC NGGFMTTAFQ YIIDNKGIDS DASY...... .......... .......... .PYK AMDQKCQ... ......YDSKY
CatL        .LSEQNLVDC  SGPQ.GNEGC NGGLMDYAFQ YVQDNGGLDS EESY...... .......... .......... .PYE ATEESCK... ......YNPKY
Papain      .YSEQELLDC  DR..RSY.GC NGGYPWSALQ LVAQY.GIHY RNTY...... .......... .......... .PYE GVQRYCR... ......SREKG
Actinidin   .LSEQELIDC  GRTQNTR.GC NGGYITDGFQ FIINNGGINT EENY...... .......... .......... .PYT AQDGECN... ......LDLQN
CatH        .LAEQQLVDC  A.QDFNNYGC QGGLPSQAFE YILYNKGIMG EDTY...... .......... .......... .PYQ GKDGYCK... ......FQP.G
CatB        EVSAEDLLTC  CGSMCG.DGC NGGYPAEAWN F.WTRKGLVS GGLYESHVGC RPYSIPPCEH HVNGSRPPCT GEGDTPKCSK ICEPGYSPTY
```

FIGURE 1A

```
                                                                                                    300                                                                                                 350
CatK        K.AAKCRGYR  EIPEGNEKAL  KRAVARVGPV  SVAIDASLTS  FQFYSKGVYY  DESC..NSDN  LNHAVLAVGY  G....IQKGN  KHWIIKNSWG
CatS        R.AATCSKYT  ELPYGREDVL  KEAVANKGPV  SVGVDARHPS  FFLYRSGVYY  EPSC...TQN  VNHGVLVVGY  G....DLNGK  EYWLVKNSWG
CatL        S.VANDTGFV  DIP.KQEKAL  MKAVATVGPI  SVAIDAGHES  FLFYKEGIYF  EPDC..SSED  MDHGVLVVGY  GFESTESDNN  KYWLVKNSWG
Papain      PYAAKTDGVR  QVQPYNQGAL  LYSIAN.QPV  SVVLQAAGKD  FQLYRGGIFV  GPC.....GNK  VDHAVAAVGY  G....P....  NYILIKNSWG
Actinidin   EKYVTIDTYE  NVPYNNEWAL  QTAVTY.QPV  SVALDAAGDA  FKHYSSGIFT  GPC.....GTA  IDHAVTIVGY  G....TEGGI  DYWIVKNSWD
CatH        KAIGFVKDVA  NITIYDEEAM  VEAVALYNPV  SFAFEVTQD.  FMMYRTGIYS  STSCHKTPDK  VNHAVLAVGY  G....EKNGI  PYWIVKNSWG
CatB        KQDKHYGYNS  YSVSNSEKDI  MAEIYKNGPV  EGAFSV.YSD  FLLYKSGVYQ  HVTGEMMG..  .GHAIRILGW  G....VENGT  PYWLVANSWN 400                                                     430
CatK        ENWGNKGYIL  MARNKNNA..  .CGIANLASF  PKM.......  ..........
CatS        HNFGEEGYIR  MARNKGNH..  .CGIASFPSY  PEI.......  ..........
CatL        EEWGMGGYVK  MAKDRRNH..  .CGIASAASY  PTV.......  ..........
Papain      TGWGENGYIR  IKRGTGNSYG  VCGLYTSSFY  PVKN......  ..........
Actinidin   TTWGEEGYMR  ILRNVGGA.G  TCGIATMPSY  PVKYNNQNHP  KPYSSLINPP  AFSMSKDGPV  GVDDGQRYSA
CatH        PQWGMNGYFL  IERGKN....  MCGLAACASY  PIPLV.....  ..........
CatB        TDWGDNGFFK  ILRGQDHCGI  ESEVVAGIPR  TDQYWEKI..  ..........
```

METHOD OF INHIBITING CATHEPSIN K

This application is a 371 of International Application PCT/US96/17512, filed Oct. 30, 1996, which claims benefit from the following U.S. Provisional Applications: 60/008,108, filed Oct. 30, 1995; 60/007,473, filed Nov. 22, 1995; 60/008,992, filed Dec. 21, 1995; 60/013,748, filed Mar. 20, 1996; 60/013,764, filed Mar. 20, 1996; 60/013,747, filed Mar. 20, 1996; 60/017,455, filed May 17, 1996; 60/017,892, filed May 17, 1996; 60/020,478, filed Jun. 13, 1996; 60/022,047, filed Jul. 22,1996; 60/023,494, filed Aug. 7, 1996; and 60,023,742, filed Aug. 8, 1996.

FIELD OF THE INVENTION

This invention relates to a method of inhibiting cathepsin K by administering compounds with certain structural, physical and spatial characteristics that allow for the interaction of said compounds with specific residues of the active site of the enzyme. This interaction between the compounds of this invention and the active site inhibits the activity of cathepsin K and these compounds are useful for treating diseases in which said inhibition is indicated, such as osteoporosis and periodontal disease. This invention also relates to a novel crystalline structure of cathepsin K, the identification of a novel protease catalytic active site for this enzyme and methods enabling the design and selection of inhibitors of said active site.

BACKGROUND OF THE INVENTION

Cathepsin K is a member of the family of enzymes which are part of the papain superfamily of cysteine proteases. Cathepsins B, H, L, N and S have been described in the literature. Recently, cathepsin K polypeptide and the cDNA encoding such polypeptide were disclosed in U.S. Pat. No. 5,501,969 (called cathepsin O therein). Cathepsin K has been recently expressed, purified, and characterized. Bossard, M. J., et al., (1996) *J. BioL Chem.* 271, 12517–12524; Drake, F. H., et al., (1996) *J. BioL Chem.* 271, 12511–12516; Bromme, D., et al., (1996) *J. BioL Chem.* 271, 2126–2132.

Cathepsin K has been variously denoted as cathepsin O, cathepsin X or cathepsin O2 in the literature. The designation cathepsin K is considered to be the more appropriate one (name assigned by Nomenclature Committee of the International Union of Biochemistry and Molecular Biology).

Cathepsins of the papain superfamily of cysteine proteases function in the normal physiological process of protein degradation in animals, including humans, e.g., in the degradation of connective tissue. However, elevated levels of these enzymes in the body can result in pathological conditions leading to disease. Thus, cathepsins have been implicated in various disease states, including but not limited to, infections by pneumocystis carinii, trypsanoma cruzi, trypsanoma brucei brucei, and Crithidia fusiculata; as well as in schistosomiasis malaria, tumor metastasis, metachromatic leukodystrophy, muscular dystrophy, amytrophy, and the like. See International Publication Number WO 94/04172, published on Mar. 3, 1994, and references cited therein. See also European Patent Application EP 0 603 873 A1, and references cited therein. Two bacterial cysteine proteases from P. gingivallis, called gingipains, have been implicated in the pathogenesis of gingivitis. Potempa, J., et al. (1994) *Perspectives in Drug Discovery and Design,* 2, 445–458.

Cathepsin K is believed to play a causative role in diseases of excessive bone or cartilage loss. Bone is composed of a protein matrix in which spindle- or plate-shaped crystals of hydroxyapatite are incorporated. Type I Collagen represents the major structural protein of bone comprising approximately 90% of the structural protein. The remaining 10% of matrix is composed of a number of non-collagenous proteins, including osteocalcin, proteoglycans, osteopontin, osteonectin, thrombospondin, fibronectin, and bone sialoprotein. Skeletal bone undergoes remodeling at discrete foci throughout life. These foci, or remodeling units, undergo a cycle consisting of a bone resorption phase followed by a phase of bone replacement.

Bone resorption is carried out by osteoclasts, which are multinuclear cells of hematopoietic lineage. The osteoclasts adhere to the bone surface and form a tight sealing zone, followed by extensive membrane ruffling on their apical (i.e., resorbing) surface. This creates an enclosed extracellular compartment on the bone surface that is acidified by proton pumps in the ruffled membrane, and into which the osteoclast secretes proteolytic enzymes. The low pH of the compartment dissolves hydroxyapatite crystals at the bone surface, while the proteolytic enzymes digest the protein matrix. In this way, a resorption lacuna, or pit, is formed. At the end of this phase of the cycle, osteoblasts lay down a new protein matrix that is subsequently mineralized. In several disease states, such as osteoporosis and Paget's disease, the normal balance between bone resorption and formation is disrupted, and there is a net loss of bone at each cycle. Ultimately, this leads to weakening of the bone and may result in increased fracture risk with minimal trauma.

The abundant selective expression of cathepsin K in osteoclasts strongly suggests that this enzyme is essential for bone resorption. Thus, selective inhibition of cathepsin K may provide an effective treatment for diseases of excessive bone loss, including, but not limited to, osteoporosis, gingival diseases such as gingivitis and periodontitis, Paget's disease, hypercalcemia of malignancy, and metabolic bone disease. Cathepsin K levels have also been demonstrated to be elevated in chondroclasts of osteoarthritic synovium. Thus, selective inhibition of cathepsin K may also be useful for treating diseases of excessive cartilage or matrix degradation, including, but not limited to, osteoarthritis and rheumatoid arthritis. Metastatic neoplastic cells also typically express high levels of proteolytic enzymes that degrade the surrounding matrix. Thus, selective inhibition of cathepsin K may also be useful for treating certain neoplastic diseases.

Surprisingly, it has been found that a broad, structurally diverse series of compounds have common structural, physical and spatial characteristics that allow for the interaction of said compounds with specific residues of the active site of cathepsin K and are useful for treating diseases in which inhibition of bone resorption is indicated, such as osteoporosis and periodontal disease. Thus, this invention relates to the method of inhibiting cathepsin K using compounds having the characteristics hereinbelow defined.

SUMMARY OF THE INVENTION

In one aspect, the present invention provides a method for inhibiting cathepsin K by administering compounds with certain structural, physical and spatial characteristics that allow for the interaction of said compounds with specific residues of the active site of the enzyme. This interaction inhibits the activity of cathepsin K and, thus, treats diseases in which bone resorption is a factor.

In another aspect, the present invention provides a novel cysteine protease in crystalline form.

In yet another aspect, the invention provides a novel protease composition characterized by a three dimensional catalytic site formed by the atoms of the amino acid residues listed in Table XXIX.

In still another aspect, the invention provides a method for identifying inhibitors of the compositions described above which methods involve the steps of: providing the coordinates of the protease structure of the invention to a computerized modeling system; identifying compounds which will bind to the structure; and screening the compounds or analogs derived therefrom identified for cathepsin K inhibitory bioaotivity.

Other aspects and advantages of the present invention are described further in the following detailed description of the preferred embodiments thereof

BRIEF DESCRIPTION OF THE DRAWINGS

FIG. 1 is the amino acid sequence of cathepsin K SEQ ID NO1 aligned with the amino acid sequences of other cysteine proteases SEQ ID NO: 2, SEQ ID NO: 3, SEQ ID NO: 4, SEQ ID NO: 5, SEQ ID NO: 6, SEQ ID NO: 7.

(FIG. 6: Inhibitor=3(S)-3-[(N-benzyloxycarbonyl)-L-leucinyl]amino-5-methyl-1-(1-propoxy)-2-hexane; FIG. 8: Inhibitor =bis-(cbz-leucinyl)-1,3-diamino-propan-2-one; FIG. 10: Inhibitor =2,2'-N,N'-bis-benzyloxycarbonyl-L-leucinylcarbohydrazide; FIG. 12: Inhibitor =(1 S)-N-[2-[(1-benzyloxycarbonylamino)-3-methylbutyl]thiazol4-ylcarbonyl]-N'-(N-benzyloxycarbonyl-L-leucinyl)hydrazide; FIG. 14: Inhibitor=2-[N-(3-benzyloxybenzoyl)]-2'-[N'-(N-benzyloxycarbonyl-L-leucinyl)]carbohydrazide; FIG. 16: Inhibitor=4-[N-[(phenylmethoxy)carbonyl]-L-leucyl]-1-[N-[(phenylmethoxy)carbonyl]-L-leucyl]-3-pyrrolidinone; FIG. 18: Inhibitor=4-[N-[(4-pyridylmethoxy)carbonyl]-L-leucyl]-1-[N-[(phenylmethoxy) carbonyl]-L-leucyl]-3-pyrrolidinone; FIG. 20: Inhibitor=4-[N-[(phenylmethoxy) carbonyl]-L-leucyl]-1-N[N-(methyl)-L-leucyl)]-3-pyrrolidinone; FIG. 22: Inhibitor=l-N-(N-imidazole acetyl-leucinyl)-amino-3-N-(4-phenoxy-phenyl-sulfonyl)-amino-propan-2-one.

(FIG. 7: Inhibitor=3(S)-3-[(N-benzyloxycarbonyl)-L-leucinyl]amino-5-methyl-1-(1-propoxy)-2-hexane; FIG. 9: Inhibitor=bis-(cbz-leucinyl)-1,3-diamino-propan-2-one; FIG. 11: Inhibitor=2,2'-N,N'-bis-benzyloxycarbonyl-L-leucinylcarbohydrazide; FIG. 13: Inhibitor=(1S)-N-[2-[(1-benzyloxycarbonylamino)-3-methylbutyl]thiazol-4-ylcarbonyl]-N'-(N-benzyloxycarbonyl-L-leucinyl)hydrazide; FIG. 15: Inhibitor=2-[N-(3-benzyloxybenzoyl)]-2'-[N'-(N-benzyloxycarbonyl-L-leucinyl)]carbohydrazide; FIG. 17: Inhibitor=4-[N-[(phenylmethoxy)carbonyl]-L-leucyl]-1-[N-[(phenylmethoxy)carbonyl]-L-leucyl]-3-pyrrolidinone; FIG. 19: Inhibitor=4-[N-[(4-pyridylmethoxy)carbonyl]-L-leucyl]-1-[N-[(phenylmethoxy) carbonyl]-L-leucyl]-3-pyrrolidinone; FIG. 21: Inhibitor=4-[N-[(4-pyridylmethoxy) carbonyl]-L-leucyl]-1-[N-[(phenylmethoxy) carbonyl]-L-leucyl]-3-pyrrolidinone; FIG. 23: Inhibitor=1-N-(N-imidazole acetyl-leucinyl)-amino-3-N-(4-phenoxy-phenyl-sulfonyl)-amino-propan-2-one.

Figure 2:
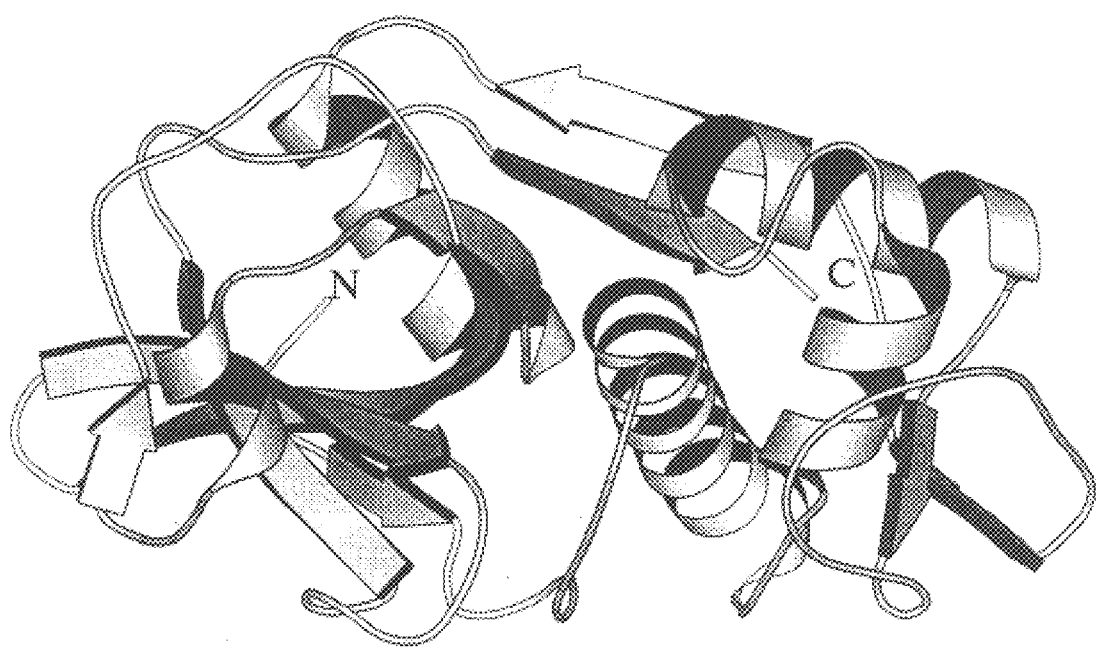
FIG. 2 is a ribbon diagram of cathepsin K. The amino and carboxyl-termini are indicated by N and C. The drawing was produced using the program MOLSCRIPT [Kraulis, P., *J. Appl. Crystallogr.*, 24, 946–950 (1991)].

These views depict the interaction of each inhibitor with all atoms of residues of the active site of cathepsin K within 5A of the inhibitors. For clarity, no hydrogen atoms or water molecules are shown.

DETAILED DESCRIPTION OF THE INVENTION

The present invention provides a novel cysteine protease crystalline structure, a novel cysteine protease active site, and methods of use of the crystalline form and active site to identify protease inhibitor compounds.

In particular, the present invention provides a method for inhibiting cathepsin K by administering compounds with certain structural, physical and spatial characteristics that allow for the interaction of said compounds with specific residues of the active site of the enzyme. This interaction inhibits the activity of cathepsin K and, thus, treats diseases in which bone resorption is a factor.

Specifically, the inhibitors of cathepsin K used in the present invention interact with any two or more of the following:

1. Tyrosine 67 sidechain;
2. Hydrophobic pocket lined with atoms from methinoine 68, leucine 209, alanine 163, alanine 134 and portions of tyrosine 67;
3. Hydrogen bonds donated by glycine 66 amide nitrogen;
4. Cysteine 25 the active site nucleophile;
5. Mainchain interactions from residues glutamine 21, cysteine 22, and glycine 23;
6. Tryptophan 184 sidechain; and
7. Hydrophobic contacts with the sidechain atoms of glutamine 143 and asparagine 161 and the mainchain of alanine 137 and serine 138.

Preferably, the inhibitors of cathepsin K used in the present invention interact with any three or more of the above-identified regions of the active site.

The compounds used in the methods of the present invention possess an electrophilic carbon and either a hydrophobic group whose centroid is 5.44–6.94 Å from the carbon or an aromatic group whose centroid is 9.24–11.24 Å from the carbon, or both the hydrophobic and the aromatic groups in which case the centroids of these two groups should be 15.67–16.67 Å apart. These features must be able to make the appropriate interactions with the cathepsin K active site. The electrophilic carbon atom should be 1.7–4.0 Å from the side chain sulfur atom (SG) on the amino acid cysteine 25. The hydrophobic group should be near the following amino acids with appropriate distance ranges between the centroid of the side chain atoms and the centroid of the hydrophobic group given in parentheses: tyrosine 67 (4.91–5.91 Å), methionine 68 (5.74–6.74 Å), alanine 134 (4.15–5.15), leucine 160 (6.18–7.18 Å), and leucine 209 (5.71–6.71 Å). The aromatic group should be near the either tryptophan 184 (4.10–7.10 Å) or tryptophan 188 (4.10–7.10 Å) or both.

The key structural features of the inhibitors of the present invention include an electrophilic carbon, preferably the carbon of a carbonyl group, a hydrophobic group, preferably an isobutyl group, and an aromatic group, preferably a phenyl group. The electrophilic carbon of the inhibitor may be in the same compound with two hydrophobic groups, such as two isobutyl groups, or two aromatic groups, such as two phenyl groups, or one hydrophobic group and one aromatic group.

Suitably, the method of inhibiting cathepsin K of the present invention comprises administering to a mammal, preferably a human, in need thereof a compound that fits spatially into the active site of cathepsin K, said compound comprising any two or more of the following:

(i) an electrophilic carbon atom that binds to the side chain sulfur atom of cysteine 25 wherein said electrophilic carbon atom is 1.7–4.0 Å from said sulfur atom;

(ii) a hydrophobic group that interacts with tryptophan 184 wherein the distance between the centroid of said hydrophobic group and the centroid of the side chain atoms of tryptophan 184 is 4.10–7.10 Å;

(iii) a hydrophobic group that interacts with tyrosine 67, methionine 68, alanine 134, leucine 160, and leucine 209, creating a hydrophobic pocket, and has distance ranges between the centroid of said hydrophobic group and the centroids of the side chain atoms of the amino acid residues of said hydrophobic pocket which are tyrosine 67: 4.91–5.91 Å, methionine 68: 5.74–6.74 Å, alanine 134: 4.15–5.15 Å, leucine 160: 6.18–7.18 Å, and leucine 209: 5.71–6.71 Å;

(iv) a hydrophobic group that interacts with tyrosine 67 wherein the distance between the centroid of said hydrophobic group and the centroid of the side chain atoms of tyrosine 67 is 4.10–7.10 Å;

(v) an amino group with a pKa of less than 7 or an oxygen atom, each of which interacts with a hydrogen atom donated by the amide nitrogen of glycine 66 wherein the distance between these two atoms is 2.7–3.5 Å;

(vi) a hydrophobic group that interacts with the main chain atoms of glutamine 21, cysteine 22 and glycine 23 wherein the distance between the centroid of said hydrophobic group and the centroids of glutamine 21, cysteine 22 and glycine 23 are 3.7–5.4, 4.9–5.7 and 5.4–6.7 Å, respectively; or (vii) a hydrophobic group that interacts with the side chain atoms of glutamine 143 and asparagine 161 and the main chain of alanine 137 and serine 138 wherein the distance between the centroid of the hydrophobic group and the centroids of glutamine 143, asparagine 161, alanine 137, and serine 138 are 7.9–9.6 Å, 4.7–5.4 Å, 4.2–5.5 Å, and 4.6–6.4 Å, respectively. Preferably, the inhibitors of cathepsin K used in the present invention comprise three or more of the above.

Suitably, the method of inhibiting cathepsin K of the present invention comprises administering to a mammal, preferably a human, in need thereof a compound that fits spatially into the active site of cathepsin K, said compound comprising:

(i) an electrophilic carbon atom that binds to the side chain sulfur atom of cysteine 25 wherein said electrophilic carbon atom is 1.7–4.0 Å from said sulfur atom; and (ii) a hydrophobic group that interacts with tryptophan 184 wherein the distance between the centroid of said hydrophobic group and the centroid of the side chain atoms of tryptophan 184 is 4.10–7.10 Å. Preferably, the hydrophobic group that interacts with tryptophan 184 is an aromatic group and the centroid of this aromatic group is 9.24–11.24 Å from the centroid of the electrophilic carbon that binds to the side chain sulfur atom of cysteine 25.

Preferably, the electrophilic carbon that binds to the side chain sulfur atom of cysteine 25 is a carbonyl carbon.

Suitably, the method of the present invention further comprises a compound with a hydrophobic group that:

has a centroid which is 5.44–6.94 Å from said electrophilic carbon;

interacts with tyrosine 67, methionine 68, alanine 134, leucine 160, and leucine 209, creating a hydrophobic pocket; and has distance ranges between the centroid of said hydrophobic group and the centroids of the side chain atoms of the amino acid residues of said hydrophobic pocket which are tyrosine 67: 4.91–5.91 Å, methionine 68: 5.74–6.74 Å, alanine 134: 4.15–5.15 Å, leucine 160: 6.18–7.18 Å, and leucine 209: 5.71–6.71 Å. Preferably, this hydrophobic group is an isobutyl group.

Alternately, the method of the present invention further comprises a compound with a hydrophobic group that interacts with tyrosine 67 wherein the distance between the centroid of said hydrophobic group and the centroid of the side chain atoms of tyrosine 67 is 4.10–7.10 Å. Preferably, this hydrophobic group is an aromatic group.

Alternately, the method of the present invention further comprises a compound with an amino group with a pKa of less than 7 or an oxygen atom, each of which interacts with a hydrogen atom donated by the amide nitrogen of glycine 66 wherein the distance between these two atoms is 2.7–3.5 Å. Preferably, the compound comprises an oxygen atom, such as an oxygen atom of a carbonyl group or an oxygen atom of a hydroxyl group.

Alternately, the method of the present invention further comprises a compound with a hydrophobic group that interacts with the main chain atoms of glutamine 21, cysteine 22 and glycine 23 wherein the distance between the centroid of the hydrophobic group and the centroids of glutamine 21, cysteine 22 and glycine 23 are 3.7–5.4, 4.9–5.7 and 5.4–6.7 Å, respectively. Preferably, this hydrophobic group is an isobutyl group.

Alternately, the method of the present invention further comprises a compound with a hydrophobic group that interacts with the side chain atoms of glutamine 143 and asparagine 161 and the mainchain of alanine 137 and serine 138 wherein the distance between the centroid of the hydrophobic group and the centroids of glutamine 143; asparagine 161, alanine 137, and serine 138 are 7.9–9.6 Å, 4.7–5.4 Å, 4.2–5.5 Å, and 4.6–6.4 Å, respectively.

Compounds used in the method of the present invention include, but are not limited to, the following:

3(S)-3-[(N-benzyloxycarbonyl)-L-leucinyl]amino-5-methyl-1-(1-propoxy)-2-hexanone;

4-[N-[(4-pyridylmethoxy)carbonyl]-L-leucyl]-1-[N-[(phenylmethoxy)carbonyl]-L-leucyl]-3-pyrrolidinone;

4-[N-[(phenylmethoxy)carbonyl]-L-leucyl]-1-N-[N-(methyl)-L-leucyl)]-3-pyrrolidinone;

4-[N-[(phenylmethoxy)carbonyl]-L-leucyl]-1-[N-[(phenylmethoxy)carbonyl]-L-leucyl]-3-pyrrolidinone;

bis-(Cbz-leucinyl)-1,3-diamino-propan-2-one;

2-[N-(3-benzyloxybenzoyl)]-2'-[N'-(N-benzyloxycarbonyl-L-leucinyl)]carbohydrazide;

(1S)-N-[2-[(1-benzyloxycarbonylamino)-3-methylbutyl] thiazol-4-ylcarbonyl]-N'-(N-benzyloxycarbonyl-L-leucinyl)hydrazide;

1-N-(N-imidazole acetyl-leucinyl)-amino-3-N-(4-phenoxy-phenyl-sulfonyl)-amino-propan-2-one; and 2,2'-N,N'-bis-benzyloxycarbonyl-L-leucinylcarbohydrazide; or a pharmaceutically acceptable salt thereof.

Table I provides the three dimensional protein coordinates of the cathepsin K crystalline structure of the invention.

Tables II–X provide the three dimensional coordinates for the cathepsin K complex with specific inhibitors of the present invention.

Tables XI–XIX provide listings of the three atom angles between atoms of the inhibitors and the protein for all inhibitor atoms within 5 Angstroms of the protein.

Tables XX–XXVIII provide listings of the distances between atoms of the inhibitors and the protein for all inhibitor atoms within 5 Angstroms of the protein.

Table XXIX provides the atoms of the amino acid residues of the catalytic site.

As stated herein, the interaction of the inhibitor at the side chain sulfur atom of cysteine 25 has as one of its requirements that the inhibitor contain an "electrophilic carbon" atom. By this term is meant an electron deficient carbon. This term includes, but is not limited to, a carbonyl carbon atom. This term also includes an epoxide, a thiocarbonyl, an imine, and a nitrile. Suitably, this term may also be represented by the formula —C=N—X, wherein X may be optionally tied back to C in a ring or wherein X is $CH_2$, H, O, S or $NR^a$ in which $R^a$ is H of $C_{1-4}$alkyl.

The hydrophobic groups that interact with tryptophan 184 or tyrosine 67 include, but are not limited to, aromatic groups. These hydrophobic groups include phenyl, $C_{1-6}$alkyl and heteroaryl, which is defined hereinbelow. The hydrophobic groups that interact with the hydrophobic pocket lined with atoms from tyrosine 67, methionine 68, alanine 134, leucine 160, and leucine 209 not only includes isobutyl, but also includes $C_{1-6}$alkyl, $C_{3-6}$cycloalkyl and adamantyl. The hydrophobic groups that interact with the main chain atoms of glutamine 21, cysteine 22 and glycine 23 or the side chain atoms of glutamine 143 and asparagine 161 and the mainchain of alanine 137 and serine 138 include $C_{1-10}$alkyl, $C_bF_{2b+1}$, in which b is 1–3, and aryl and heteroaryl, each of which are defined hereinbelow.

As used herein, the term "centroid" means the position for the stated atoms calculated by averaging the x coordinates of the atoms to obtain the x coordinate of the centroid, averaging the y coordinates of the atoms to obtain the y coordinate of the centroid, and averaging the z coordinates of the atoms to obtain the z coordinate of the centroid.

The compounds used in the method of the present invention include, but are not limited to, the compounds of formula (I):

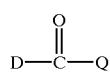

wherein:

D =

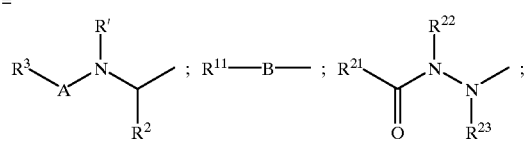

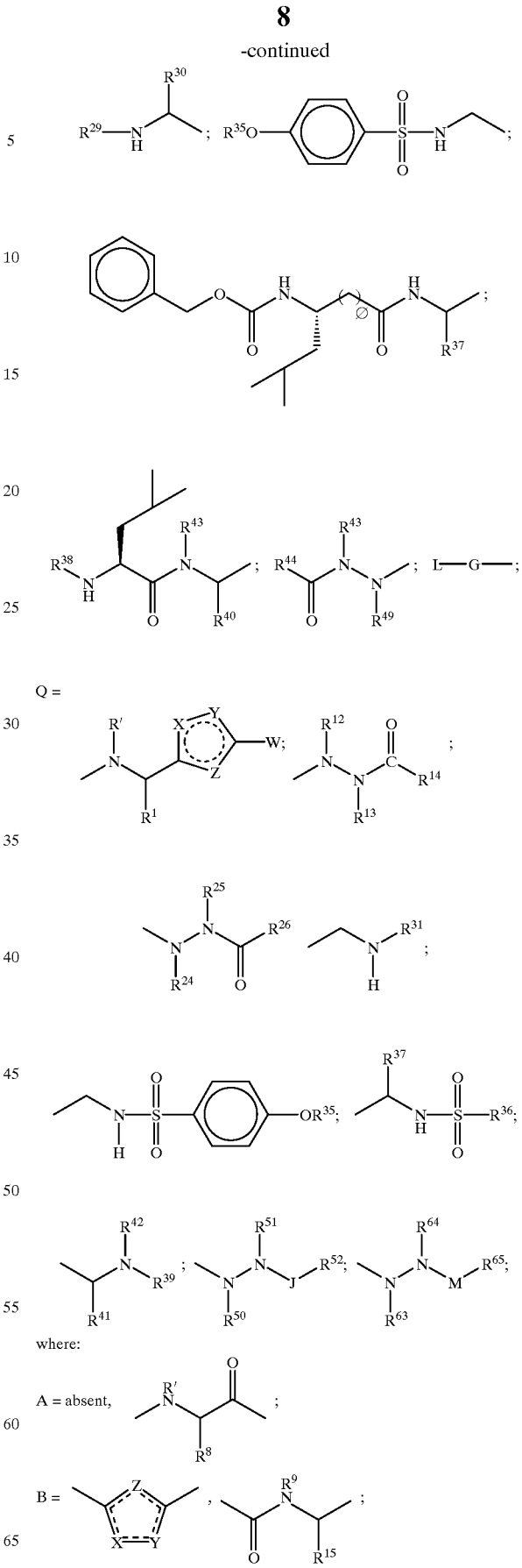

L=$C_{2-6}$alkyl, Ar-$C_{0-6}$alkyl, Het-$C_{0-6}$alkyl, CH($R^{66}$)N$R^{60}R^{68}$, CH($R^{66}$)Ar, CH($R^{66}$)OAr', N$R^{66}R^{67}$;

M=C(O), $SO_2$;

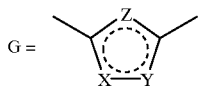

J=C(O), $SO_2$;

T=Ar, Het;

V=$C_{3-7}$cycloalkyl;

W=H, —CN, —$CF_3$, —$NO_2$, —$COR^7$, —$CO_2R^6$, —CON$HR^6$, —$SO_2NHR^6$, —$NHSO_2R^6$, —NHCO$R^7$, —O—CO$R^6$, —$SR^6$, N$R'R^6$, NR'(C=NH)NH$R^5$, Cl, Br, I, F;

X=Y=Z=N, O, S or $CR^4$,
  provided that at least two of X, Y and Z are heteroatoms and at least one of X, Y and Z is N, or one of X, Y and Z is C=N, C=C or N=N and the other two are $CR^4$ or N, provided that X, Y and Z together comprise at least two N;

=== indicates a single or double bond in the five-membered heterocycle;

m=0, 1, 2;

n=1 to 6;

f=0, 1, 2;

Ar=phenyl, naphthyl, optionally substituted by one or more of Ph-$C_{0-6}$alkyl, Het-$C_{0-6}$alkyl, $C_{1-6}$alkoxy, Ph-$C_{0-6}$alkoxy, Het-$C_{0-6}$alkoxy, OH, $(CH_2)_{1-6}$N$R^{58}R^{59}$, O$(CH_2)_{1-6}$N$R^{58}R^{59}$;

Ar'=phenyl or naphthyl, optionally substituted by one or more of Ph-$C_{0-6}$alkyl, Het-$C_{0-6}$alkyl, $C_{1-6}$alkoxy, Ph-$C_{0-6}$alkoxy, Het-$C_{0-6}$alkoxy, OH, $(CH_2)_{1-6}$N$R^{58}R^{59}$, O$(CH_2)_{1-6}$N$R^{58}R^{59}$, or halogen;

R'=H, $C_{1-6}$alkyl, Ar-$C_{0-6}$alkyl, Het-$C_{0-6}$alkyl;

$R^1$=H, $C_{1-6}$alkyl;

$R^2$=$C_{4-6}$alkyl, $C_{4-6}$alkenyl, benzyl;

$R^3$=$C_{1-6}$alkyl, Ar-$C_{0-6}$alkyl, Het-$C_{0-6}$alkyl, $R^5$CO—, $R^5SO_2$—, $R^5$OC(O)—, $R^5$NHCO—;

$R^4$=H, $C_{1-6}$alkyl, Ar-$C_{0-6}$alkyl, Het-$C_{0-6}$alkyl;

$R^5$=Ar-$_{0-6}$alkyl, Het-$C_{0-6}$alkyl;

$R^6$=H, $C_{1-6}$alkyl, $CH_2CF_3$, Ar-$C_{0-6}$alkyl, Het-$C_{0-6}$alkyl;

$R^7$=$C_{1-6}$alkyl, Ar-$C_{0-6}$alkyl, Het-$C_{0-6}$alkyl;

$R^8$=H; $C_{2-6}$alkenyl; $C_{2-6}$alkynyl; Het; Ar; $C_{1-6}$alkyl, optionally substituted by OR', SR', N$R'_2$, $CO_2R'$, $CO_2NR'_2$, N(C=NH)N$H_2$, Het or Ar;

$R^9$=H, $C_{1-6}$alkyl, Ar-$C_{0-6}$alkyl, Het-$C_{0-6}$alkyl;

$R^{10}$=$C_{1-6}$alkyl, Ar-$C_{0-6}$alkyl, Het-$C_{0-6}$alkyl;

$R^{11}$=H, $C_{1-6}$alkyl, Ar-$C_{1-6}$alkyl, Het-$C_{0-6}$alkyl, or

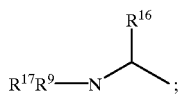

$R^{12}$=H, $C_{1-6}$alkyl, Ar-$C_{0-6}$alkyl, Het-$C_{0-6}$alkyl;

$R^{13}$=H, $C_{1-6}$alkyl, Ar-$C_{0-6}$alkyl, Het-$C_{0-6}$alkyl;

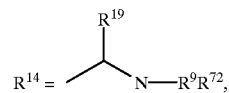

Ac;

$R^{15}$=H, $C_{1-6}$alkyl, $C_{2-6}$alkenyl, $C_{2-6}$alkynyl, Ar, Het, or $C_{1-6}$alkyl optionally substituted by $OR^9$, $NR^9_2$, $CONR^9_2$, N(C=NH)NH—, Het or Ar;

$R^{16}$=$C_{2-6}$alkyl, $C_{2-6}$alkenyl, $C_{2-6}$alkynyl, Ar, Het, or $C_{2-6}$alkyl optionally substituted by $OR^9$, $SR^9$, $NR^9_2$, $CO_2R^9$, $CONR^9_2$, N(C=NH)NH—, Het or Ar;

$R^{19}$=H, $C_{1-6}$alkyl, $C_{2-6}$alkenyl, $C_{2-6}$alkynyl, Ar, Het, or $C_{1-6}$alkyl optionally substituted by $OR^9$, $SR^9$, $NR^9_2$, $CO_2R^9$, $CONR^9_2$, N(C=NH)NH—, Het or Ar;

$R^{17}$=$R^{72}$=H, $C_{1-6}$alkyl, $R^{10}$, $R^{10}$ C(O)—, $R^{10}$C(S)—, $R^{10}$OC(O)—;

$R^{21}$=$R^{26}$=$C_{5-6}$alkyl; $C_{2-6}$alkenyl; $C_{3-11}$cycloalkyl; T-$C_{3-6}$alkyl; V-$C_{1-6}$alkyl; T-$C_{2-6}$alkenyl;
  T-$(CH_2)_n$CH(T)$(CH_2)_n$; optionally substituted by one or two halogens, $SR^{20}$, $OR^{20}$, $NR^{20}R^{27}$ or $C_{1-4}$alkyl;

$R^{27}$=$R^{28}$CO, $R^{28}$OCO;

$R^{28}$=$C_{1-6}$alkyl; $C_{3-11}$cycloalkyl; Ar; Het; T-$C_{1-6}$alkyl;
  T-$(CH_2)_n$CH(T)$(CH_2)_n$; optionally substituted by one or two halogens, $SR^{20}$, $OR^{20}$, $NR^{20}R^{73}$, $C_{1-4}$alkyl;

$R^{20}$=$R^{22}$=$R^{23}$=$R^{24}$=$R^{25}$=$R^{73}$=H, $C_{1-4}$alkyl, Ar-$C_{0-6}$alkyl, Het-$C_{0-6}$alkyl;

$R^{29}$ =

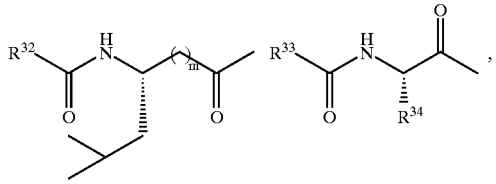

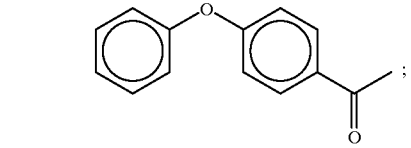

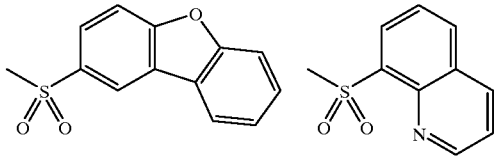

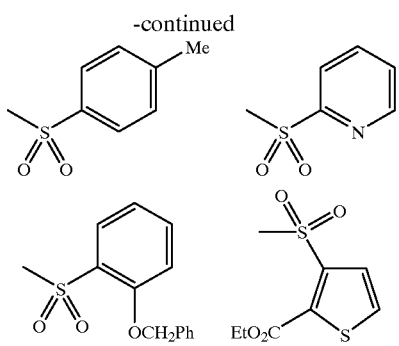
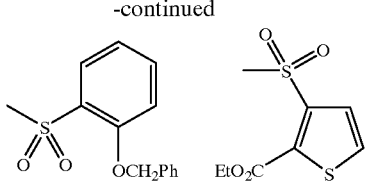

Cbz-leucinyl-; 2-, 3-, or 4-pyridyl methyloxycarbonyl-leucinyl-; 4-imidazole acetyl-leucinyl-, phenyl acetyl-leucinyl, N,N-dimethyl-glycinyl leucinyl, 4-pyridyl acetyl-leucinyl, 2-pyridyl sulfonyl-leucinyl, 4-pyridyl carbonyl-leucinyl, acetyl-leucinyl, benzoyl-leucinyl, 4-phenoxy-benzoyl-, 2- or 3-5 benzyloxybenzoyl-, biphenyl acetyl,alpha-isobutyl-biphenyl acentl, Cbz-phenylalaninyl, Cbz-norleucinyl-, Cbz-norvalinyl-, Cbz-glutamyl-, Cbz-epsilon-(t-butyl ester)-glutamyl; acetyl-leucinyl-, 6- or 8-quinoline carbonyl, biphenyl acetyl, alpha-isobutyl-biphenyl acetyl, acetyl, benzoyl, 2- or 3-benzyloxy benzoyl, 4-phenoxy benzoyl-, Cbz-amino acid-; 2-,3-, or 4-pyridylmethyloxycarbonyl-aminoacid-; aryl $C_0$–$C_6$alkyloxy carbonyl-amlno acid-, heteroaryl $C_0$–$C_6$alkyloxy carbonyl-arnino acid-,aryl $C_0$-$C_6$alkyloxy carbonyl-amino acid-, heteroaryl $C_0$-$C_6$alkyloxy carbonyl-amino acid-, $C_1$–$C_6$alkyloxy carbonyl-amino acid-; $C_1$–$C_6$alkyl carbonyl, aryl $C_0$–$C_6$alkyl carbonyl, heteroaryl $C_0$–$C_6$alkyl carbonyl, aryl $C_0$–$C_6$alkyl carbonyl, heteroaryl $C_0$–$C_6$alkyl carbonyl, $C_1$–$C_6$alkyl sulfonyl, aryl $C_0$–$C_6$alkyl sulfonyl, heteroaryl$C_0$–$C_6$alkyl sulfonyl, aryl CO-$C_6$alkyl sulfonyl, heteroaryl $C_0$–$C_6$alkyl sulfonyl;

$R^{30}$=—H, $C_{1-6}$alkyl;

$R^{31}$ =

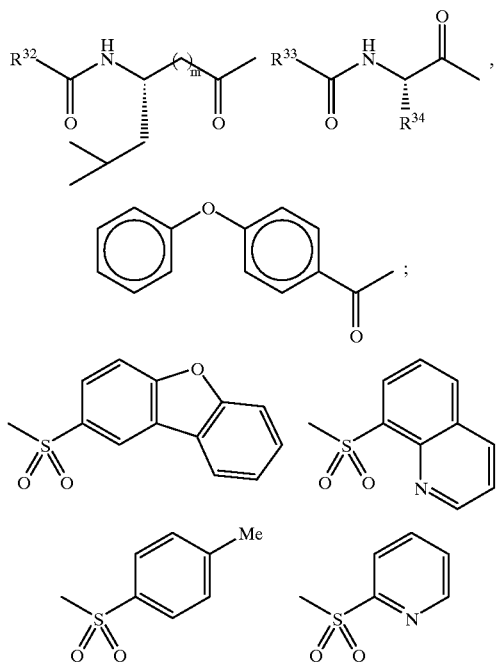

Cbz-leucinyl-; 2-, 3-, or 4-pyridyl methyloxycarbonyl-leucinyl-; 4-imidazole acetyl-leucinyl-, phenyl acetyl-leucinyl, N,N-dimethyl-glycinyl leucinyl, 4-pyridyl acetyl-leucinyl, 2-pyridyl sulfonyl-leucinyl, 4-pyridyl carbonyl-leucinyl, acetyl-leucinyl, benzoyl-leucinyl, 4-phenoxy-benzoyl-, 2- or 3-benzyloxybenzoyl-, biphenyl acetyl, alpha-isobutyl-biphenyl acetyl, Cbz-phenylalaninyl, Cbz-norleucinyl-, Cbz-norvalinyl-, Cbz-glutamyl-, Cbz-epsilon-(t-butyl ester)-glutamyl; acetyl-leucinyl-, 6- or 8-quinoline carbonyl, biphenyl acetyl, alpha-isobutyl-biphenyl acetyl, acetyl, benzoyl, 2- or 3-benzyloxy benzoyl, 4-phenoxy benzoyl-, Cbz-amino acid-; 2-,3-, or 4-pyridylmethyloxycarbonyl-aminoacid-; aryl CO-$C_6$alkyloxy carbonyl-amino acid-, heteroaryl $C_0$–$C_6$alkyloxy carbonyl-amino acid-,aryl $C_0$–$C_6$alkyloxy carbonyl-amino acid-, heteroaryl $C_0$–$C_6$alkyloxy carbonyl-amino acid-, $C_1$–$C_6$alkyloxy carbonyl-amino acid-; $C_1$–$C_6$alkyl carbonyl, aryl $C_0$–$C_6$alkyl carbonyl, heteroaryl $C_0$–$C_6$alkyl carbonyl, aryl $C_0$–$C_6$alkyl carbonyl, heteroaryl $C_0$–$C_6$alkyl carbonyl, $C_1$–$C_6$alkyl sulfonyl, aryl $C_0$–$C_6$alkyl sulfonyl, heteroaryl $C_0$–$C_6$alkyl sulfonyl, aryl $C_0$–$C_6$alkyl sulfonyl, heteroaryl $C_0$–$C_6$alkyl sulfonyl;

$R^{32}$=OCH$_2$Ar, OCH2$C_{1-6}$alkyl, aryl substituted $C_{0-6}$alkyl, heteroaryl substituted $C_{0-6}$alkyl,4-imidazole methylene; 2-, 3-, or 4-pyridylmethylneneoxy; 4-pyridyl methylene, 2-pyridyl sulfonyl, 4-pyridyl, aryl substituted $C_{0-6}$alkyloxy, heteroaryl substituted $C_{0-6}$alkyloxy;

$R^{33}$=$C_{1-6}$alkyl, —CH$_2$Ph, —CH$_2$CH$_2$CO$_2$R$^{34}$;

$R^{34}$=-H, $C_{1-6}$alkyl;

$R^{35}$=Ar, HetAr;

$R^{36}$=Aryl, heteroaryl, pyridyl, isoquinolinyl;

$R^{37}$=$C_{1-6}$alkyl, —CH$_2$Ph, —CH$_2$CH$_2$CO$_2$R$^{34}$;

$R^{38}$=Cbz; $C_{1-6}$alkyl or aryl substituted Cbz; $C_{1-6}$alkyl —CO; benzoyl; $C_{1-6}$alkyl or aryl substituted benzoyl;

$R^{39}$ =

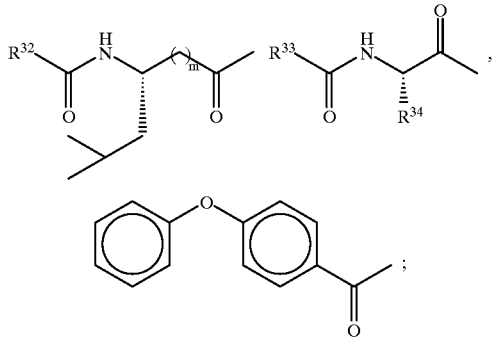

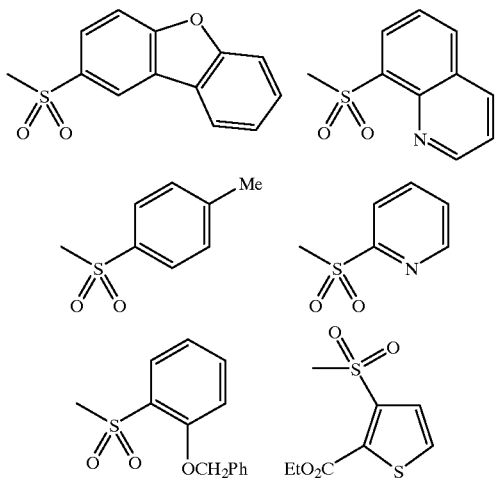

Cbz-leucinyl-; 2-, 3-, or 4-pyridyl methyloxycarbonyl-leucinyl-; 4-imidazole acetyl-leucinyl-, phenyl acetyl-leucinyl, N,N-dimethyl-glycinyl leucinyl, 4-pyridyl acetyl-leucinyl, 2-pyridyl sulfonyl-leucinyl, 4-pyridyl carbonyl-leucinyl, acetyl-leucinyl, benzoyl-leucinyl, 4-phenoxy-benzoyl-, 2- or 3-benzyloxybenzoyl-, biphenyl acetyl, alpha-isobutyl-biphenyl acetyl, Cbz-phenylalaninyl, Cbz-norleucinyl-, Cbz-norvalinyl-, Cbz-glutamyl-, Cbz-epsilon-(t-butyl ester)-glutamyl; acetyl-leucinyl-, 6- or 8-quinoline carbonyl, biphenyl acetyl, alpha-isobutyl-biphenyl acetyl, acetyl, benzoyl, 2-or 3-benzyloxy benzoyl, 4-phenoxy benzoyl-, Cbz-amino acid-; 2-,3-, or 4-pyridylmethyloxycarbonyl-aminoacid-; aryl $C_0$–$C_6$alkyloxy carbonyl-amino acid-, heteroaryl $C_0$–$C_6$alkyloxy carbonyl-amino acid-,aryl $C_0$–$C_6$alkyloxy carbonyl-amino acid-,heteroaryl $C_0$–$C_6$alkyloxy carbonyl-amino acid-, $C_1$–$C_6$alkyloxy carbonyl-amino acid-; $C_1$–$C_6$alyl carbonyl, aryl $C_0$–$C_6$alkyl carbonyl, heteroaryl $C_0$–$C_6$alkyl carbonyl, aryl $C_0$–$C_6$alkyl carbonyl, heteroaryl $C_0$–$C_6$alkyl carbonyl, $C_1$–$C_6$alkyl sulfonyl, aryl $C_0$–$C_6$alkyl sulfonyl, heteroaryl $C_0$–$C_6$alkyl sulfonyl, aryl $C_0$–$C_6$alkyl sulfonyl, heteroaryl $C_0$–$C_6$alkyl sulfonyl;

$R^{40}$=H and $C_{1-6}$alkyl;

$R^{41}$=H and $C_{1-6}$alkyl;

$R^{42}$=$C_{1-6}$alkyl, aryl substituted $C_{1-6}$alkyl and hetero aryl substituted $C_{1-6}$alkyl,; H when $R^{43}$ is $C_{1-6}$alkyl, aryl substituted $C_{1-6}$alkyl; and heteroaryl substituted $C_{1-6}$alkyl;

$R^{43}$=$C_{1-6}$alkyl, aryl substituted $C_{1-6}$alkyl and hetero aryl substituted $C_{1-6}$alkyl,; H when $R^{42}$ is $C_{1-6}$alkyl, aryl substituted $C_{1-6}$alkyl; and heteroaryl substituted $C_{1-6}$alkyl;

$R^{44}$=CH($R^{53}$)N$R^{45}$$R^{54}$, CH($R^{55}$)Ar, $C_{5-6}$alkyl;

$R^{45}$=$R^{46}$=$R^{47}$=$R^{48}$=$R^{49}$=$R^{50}$=$R^{51}$=H, $C_{1-6}$alkyl, Ar-$C_{0-6}$alkyl, Het-$C_{0-6}$alkyl;

$R^{52}$=Ar, Het, CH($R^{56}$)Ar, CH($R^{56}$)OAr, N($R^{56}$)Ar, $C_{1-6}$alkyl, CH($R^{56}$)N$R^{46}$$R^{57}$;

$R^{53}$=$C_{2-6}$alkyl, Ar-$C_{0-6}$alkyl, Het-$C_{0-6}$alkyl, $R^{53}$ and $R^{45}$ may be connected to form a pyrrolidine or piperidine ring;

$R^{54}$=$R^{57}$=$R^{47}$, $R^{47}$C(O), $R^{47}$C(S), $R^{47}$OC(O);

$R^{55}$=$R^{56}$=$R^{58}$=$R^{59}$=H, $C_{1-6}$alkyl, Ar-$C_{0-6}$alkyl, Het-$C_{0-6}$alkyl;

$R^{60}$=$R^{61}$=$R^{62}$=$R^{63}$=R64=H, $C_{1-6}$alkyl, Ar-$C_{0-6}$alkyl, or Het-$C_{0-6}$alkyl;

$R^{65}$=$C_{1-6}$alkyl, Ar, Het, CH($R^{69}$)Ar, CH($R^{69}$)OAr, N($R^{69}$)Ar, CH($R^{69}$)N$R^{61}$ $R^{70}$;

$R^{66}$=$R^{69}$=$R^{71}$=H, $C_{1-6}$alkyl, $(CH_2)_{0-6}$-$C_{3-6}$cycloalkyl, Ar-$C_{0-6}$alkyl, Het-$C_{0-6}$alkyl;

$R^{67}$=$C_{1-6}$alkyl, $(CH_2)_{0-6}$-$C_{3-6}$cycloalkyl, Ar-$C_{0-6}$alkyl, Het-$C_{0-6}$alkyl; $R^{66}$ and $R^{67}$ may be combined to form a 3–7 membered monocyclic or 7–10-membered bicyclic carbocyclic or heterocyclic ring, optionally substituted with 1–4 of $C_{1-6}$alkyl, Ph-$C_{0-6}$alkyl, Het-$C_{0-6}$alkyl, $C_{1-6}$alkoxy, Ph-$C_{0-6}$alkoxy, Het-$C_{0-6}$alkoxy, OH, $(CH_2)_{1-6}$N$R^{58}$$R^{59}$, O$(CH_2)_{1-6}$N$R^{58}$$R^{59}$;

$R^{68}$=$R^{70}$=$R^{62}$, $R^{62}$C(O), $R^{62}$C(S), $R^{62}$OC(O), $R^{62}$OC(O)N$R^{59}$CH($R^{71}$)(CO);

and pharmaceutically acceptable salts thereof.

The compounds of Formula I are hydrazidyl, bis-hydrazidyl and bis-aminomethyl carbonyl compounds having in common key structural features required of protease substrates, most particularly cathepsin K substrates. These structural features endow the present compounds with the appropriate molecular shape necessary to fit into the enzymatic active site, to bind to such active site, thereby blocking the site and inhibiting enzymatic biological activity. Referring to Formula I, such structural features include the central electrophilic carbonyl, a peptidyl or peptidomimetic molecular backbone on either side of the central carbonyl, a terminal carbobenzyloxy moiety (e.g., Cbz-leucinyl), or a mimic thereof, on the backbone on one or both sides of the carbonyl, and optionally, an isobutyl side chain extending from the backbone on one or both sides of the carbonyl.

Abbreviations and symbols commonly used in the peptide and chemical arts are used herein to describe the compounds of the present invention. In general, the amino acid abbreviations follow the IUPAC-IUB Joint Commission on Biochemical Nomenclature as described in *Eur. J. Biochem.*, 158, 9 (1984). The term "amino acid" as used herein refers to the D-or L-isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

"$C_{1-6}$alkyl" as applied herein is meant to include substituted and unsubstituted methyl, ethyl, n-propyl, isopropyl, n-butyl, isobutyl and t-butyl, pentyl, n-pentyl, isopentyl, neopentyl and hexyl and the simple aliphatic isomers thereof. Any $C_{1-6}$alkyl group may be optionally substituted independently by one or two halogens, SR', OR', N(R')$_2$, C(O)N(R')$_2$, carbamyl or $C_{1-4}$alkyl, where R' is $C_{1-6}$alkyl. Coalkyl means that no alkyl group is present in the moiety. Thus, Ar-$C_0$alkyl is equivalent to Ar.

"$C_{3-11}$cycloalkyl" as applied herein is meant to include substituted and unsubstituted cyclopropane, cyclobutane, cyclopentane, cyclohexane, cycloheptane, cyclooctane, cyclononane, cyclodecane, cycloundecane.

"$C_{2-6}$ alkenyl" as applied herein means an alkyl group of 2 to 6 carbons wherein a carbon-carbon single bond is replaced by a carbon-carbon double bond. $C_{2-6}$alkenyl includes ethylene, 1-propene, 2-propene, 1-butene, 2-butene, isobutene and the several isomeric pentenes and hexenes. Both cis and trans isomers are included.

"$C_{2-6}$alkynyl" means an alkyl group of 2 to 6 carbons wherein one carbon-carbon single bond is replaced by a carbon-carbon triple bond. $C_{2-6}$alkynyl includes acetylene, 1-propyne, 2-propyne, 1-butyne, 2-butyne, 3-butyne and the simple isomers of pentyne and hexyne.

"Halogen" means F, Cl, Br, and I.

"Ar" or "aryl" means phenyl or naphthyl, optionally substituted by one or more of Ph-$C_{0-6}$alkyl, Het-$C_{0-6}$alkyl, $C_{1-6}$alkoxy, Ph-$C_{0-6}$alkoxy, Het-$C_{0-6}$alkoxy, OH, $(CH_2)_{1-6}NR^{58}R^{59}$, $O(CH_2)_{1-6}NR^{58}R^{59}$; where $R^{58}$, $R^{59}$ is H, $C_{1-6}$alkyl, Ar-$C_{0-6}$alkyl; Het-$C_{0-6}$alkyl, from $C_{1-4}$alkyl, OR', $N(R')_2$, SR', $CF_3$, $NO_2$, CN, $CO_2R'$, CON(R'), F, Cl, Br and I.

As used herein "Het" or "heterocyclic" represents a stable 5- to 7-membered monocyclic or a stable 7- to 10-membered bicyclic heterocyclic ring, which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure, and may optionally be substituted with one or two moieties selected from $C_{1-4}$alkyl, OR', $N(R')_2$, SR', $CF_3$, $NO_2$, CN, $CO_2R'$, CON(R'), F, Cl, Br and I, where R' is $C_{1-6}$alkyl. Examples of such heterocycles include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, pyridyl, pyrazinyl, oxazolidinyl, oxazolinyl, oxazolyl, isoxazolyl, morpholinyl, thiazolidinyl, thiazolinyl, thiazolyl, quinuclidinyl, indolyl, quinolinyl, isoquinolinyl, benzimidazolyl, benzopyranyl, benzoxazolyl, furyl, pyranyl, tetrahydrofuryl, tetrahydropyranyl, thienyl, benzoxazolyl, thiamorpholinyl sulfoxide, thiamorpholinyl sulfone, and oxadiazolyl. "HetAr" or "heteroaryl" means any heterocyclic moiety encompassed by the above definition of Het which is aromatic in character, e.g., pyridine.

It will be appreciated that the heterocyclic ring,

includes thiazoles, oxazoles, triazoles, thiadiazoles, oxadiazoles, isoxazoles, isothiazols, imidazoles, pyrazines, pyridazines, pyrimidines, triazines and tetrazines which are available by routine chemical synthesis and are stable. The single and double bonds (i.e., ===) in such heterocycles are arranged based upon the heteroatoms present so that the heterocycle is aromatic (e.g., it is a heteroaryl group). The term heteroatom as applied herein refers to oxygen, nitrogen and sulfur. When the heteroaryl group comprises a five membered ring, W is preferably an electron withdrawing group, such as halogen, —CN, —$CF_3$, —$NO_2$, —$COR^7$, —$CO_2R^6$, —$CONHR^6$, —$SO_2NHR^6$, —$NHSO_2R^6$, —$NHCOR^7$, —O—$COR^6$, —$SR^6$ or $NR'R^6$, or a similar electron withdrawing substituent as known in the art.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical.

Certain reagents are abbreviated herein. DCC refers to dicyclohexylcarbodiimide, DMAP is 2,6-dimethylaminopyridine, EDC refers to N-ethyl-N'(dimethylaminopropyl)-carbodiimide. HOBT refers to 1-hydroxybenzotriazole, DMF refers to dimethyl formanide, BOP refers to benzotriazol-1-yloxy-tris(dimethylamino) phosphonium hexafluorophosphate, DMAP is dimethylaminopyridine, Lawesson's reagent is 2,4-bis(4-methoxyphenyl)-1,3-dithia-2,4-diphosphetane-2,4-disulfide, NMM is N-methylmorpho line, TFA refers to trifluoroacetic acid, TFAA refers to trifluoroacetic anhydride and THF refers to tetrahydrofuran. Jones reagent is a solution of chromium trioxide, water, and sulfuric acid well-known in the art.

Compounds of formula (I) are prepared according to the methods detailed in Schemes 1–25.

Scheme 1

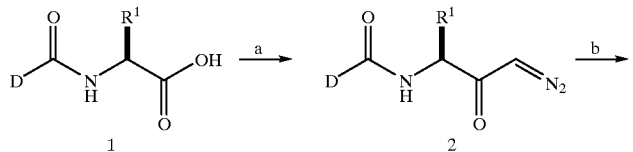

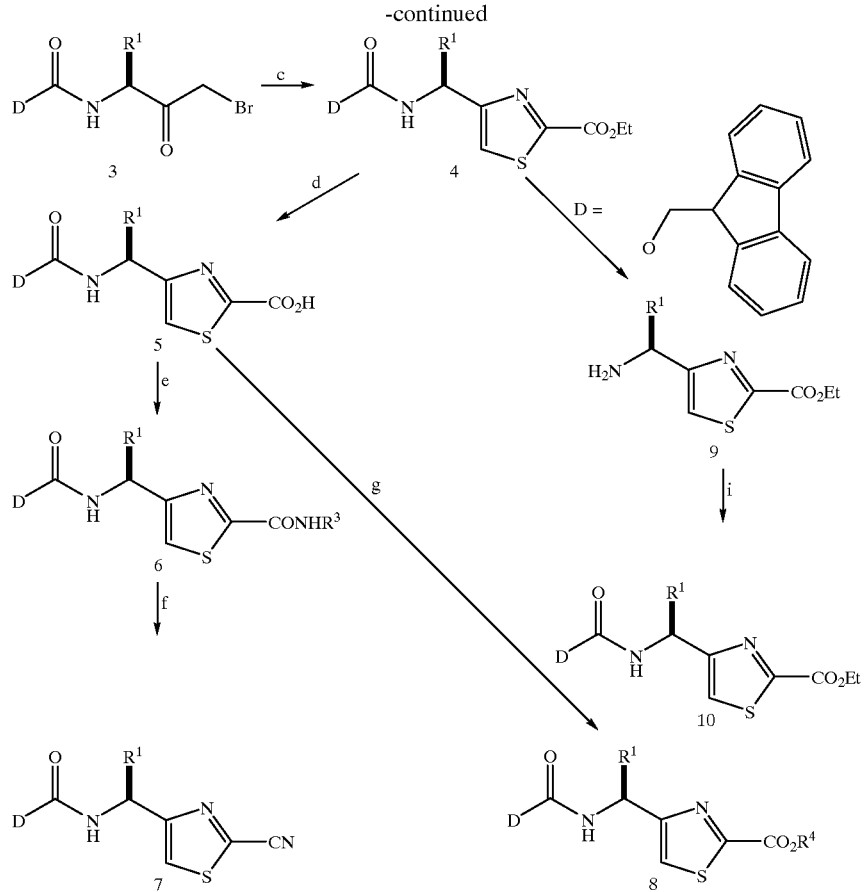
a) i-BuOCOCl, NMM, CH$_2$N$_2$, EtOAc, Et$_2$O; b) HBr, AcOH, EtOAc, Et$_2$O; c) H$_2$NCSCO$_2$Et, EtOH; d) NaOH, H$_2$O, THF; e) i-BuOCOCl, NMM, NH$_3$, THF or BOP, Et$_3$N, RNH$_2$, CH$_2$Cl$_2$; f) TFAA, pyridine, CH$_2$Cl$_2$; g) R$^4$OH, Boc$_2$O, Pyridine or R$^4$OH, EDCl, CH$_2$Cl$_2$; h) piperidine, DMF; i) BOP, Et$_3$N, D-CO$_2$H, CH$_2$Cl$_2$
Scheme 1A
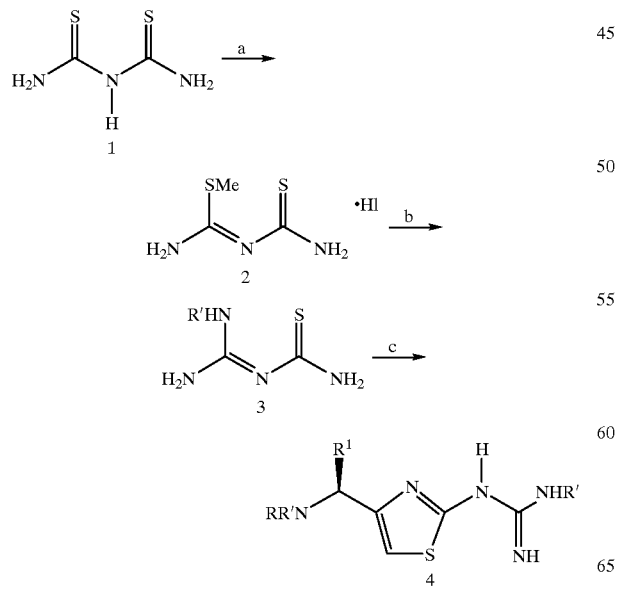
a) MeI, THF; b) R'NH$_2$, i-PrOH; c) Bromomethyl ketone, EtOH
Scheme 2
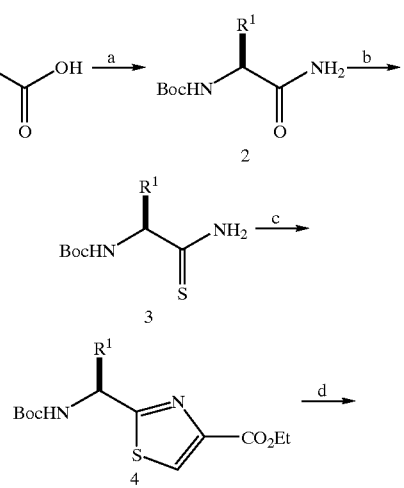

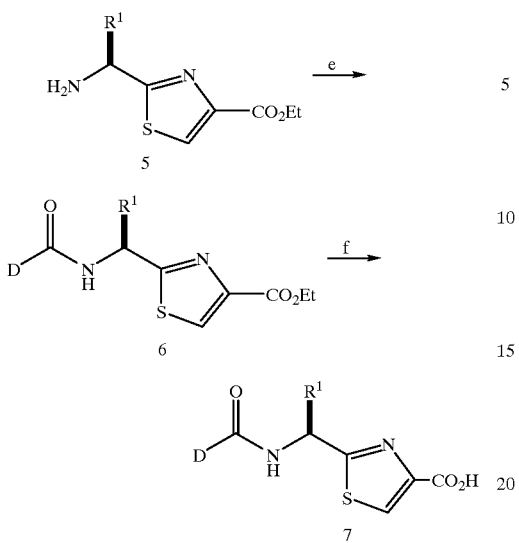

21
-continued

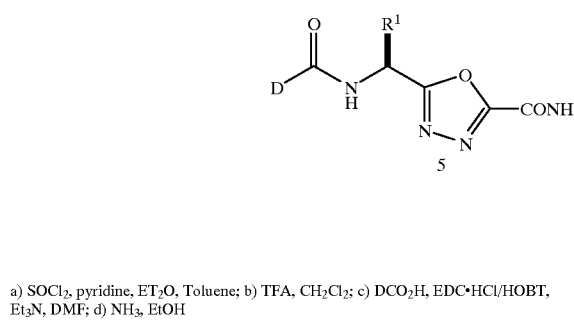

a) SOCl$_2$, pyridine, ET$_2$O, Toluene; b) TFA, CH$_2$Cl$_2$; c) DCO$_2$H, EDC·HCl/HOBT, Et$_3$N, DMF; d) NH$_3$, EtOH

Scheme 5

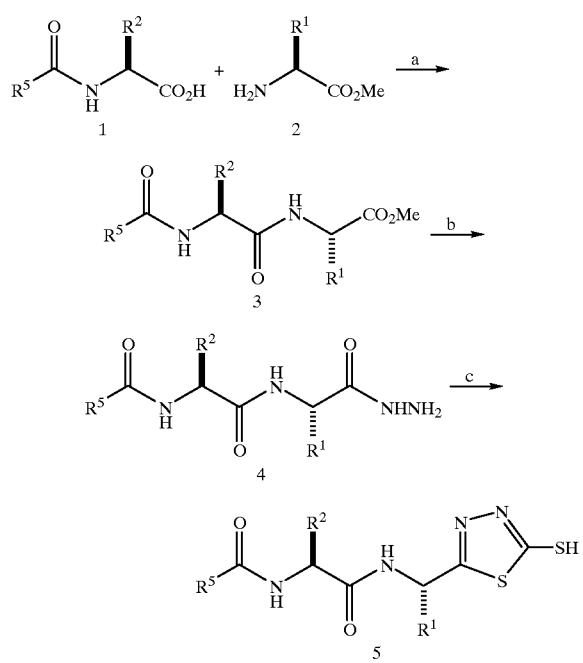

a) EDC·HCl/HOBT, ET$_3$N, DMF; b) H$_2$NNH$_2$·H$_2$O, MeOH; c) CSCl$_2$, ET$_3$N, CHCl$_3$

Scheme 6

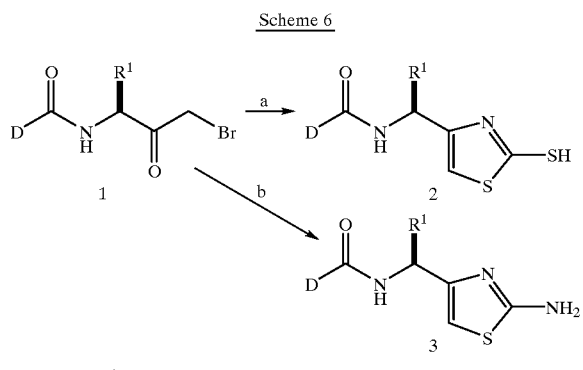

a) H$_2$NCS$_2$NH$_4^+$, EtOH; b) H$_2$NCSNH$_2$, EtOH

22

Scheme 7

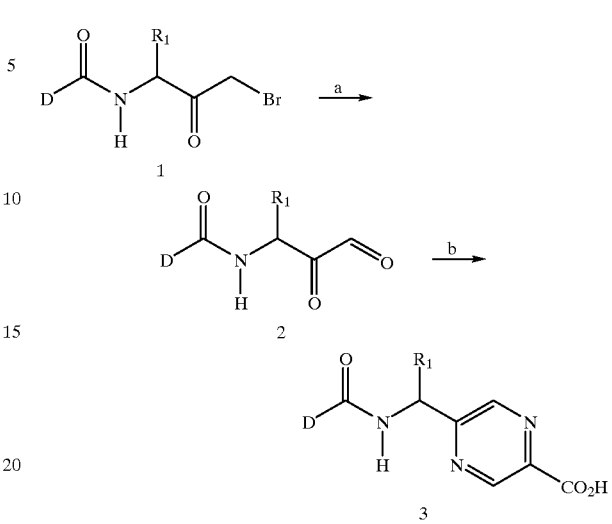

a) Et$_2$NO; b) H$_2$NCH$_2$CH(NH$_2$)CO$_2$H

Scheme 8

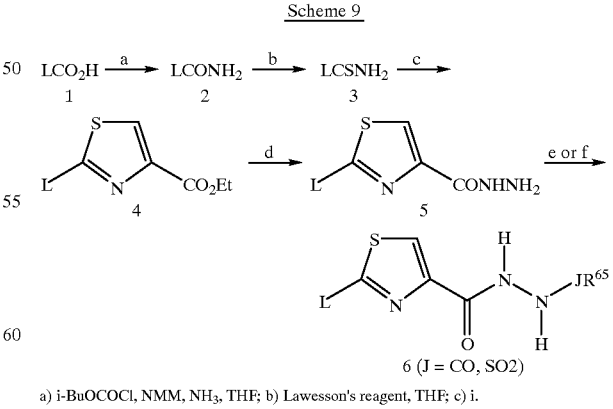

a) i. i-BuOCOCl, NMM, THF; ii. CH$_2$N$_2$, Et$_2$O; b) HBr, AcOH, Et$_2$O; c) H$_2$NCSCO$_2$Et, EtOH; d) R$^{63}$NHNH$_2$, EtOH; e) R$^{65}$CO$_2$H, EDC·HCl, 1-HOBT, DMF.

Scheme 9

LCO$_2$H →$^a$ LCONH$_2$ →$^b$ LCSNH$_2$ →$^c$

[thiazole structure 4: L-thiazole-CO$_2$Et] →$^d$ [thiazole structure 5: L-thiazole-CONHNH$_2$] →$^{e \text{ or } f}$

[structure 6 (J = CO, SO2)]

a) i-BuOCOCl, NMM, NH$_3$, THF; b) Lawesson's reagent, THF; c) i. EtO$_2$CCOCH$_2$Br; ii. TFAA, Py, CH$_2$Cl$_2$; d) H$_2$NNH$_2$·H$_2$O, EtOH; e) R$^{65}$SO$_2$Cl, Py, CH$_2$Cl$_2$; f) R$^{65}$CO$_2$H, EDC·HCl, 1-HOBT, DMF.

Scheme 10
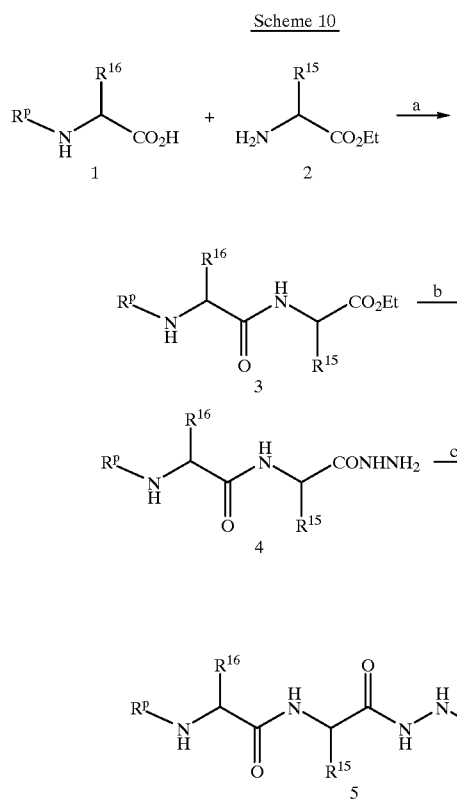
a) EDC·HCl, HOBT, DMF; b) H$_2$NNH$_2$·H$_2$O, EtOH; c) R$^{14}$—B—CO$_2$H, EDC·HCL, HOBT, DMF
Scheme 11
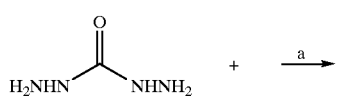
Scheme 12A
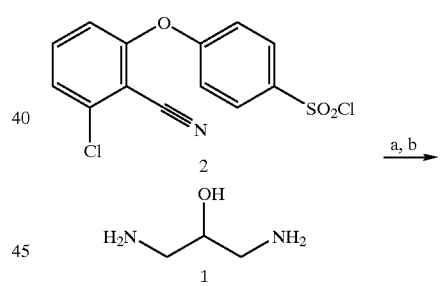
a) i. PhCHO, EtOH; ii. BH$_3$·THF; b) Cl$_2$CO, PhMe; c) H$_2$NNH$_2$·H$_2$O, MeOH; d) R$^{52}$CO$_2$H, EDC·HCl, 1-HOBT, DMF; e) R$^{52}$SO$_2$Cl or R$^{52}$COCl, pyridine, DMF; f) R$^{52}$CO$_2$COR$^{52}$
Scheme 13
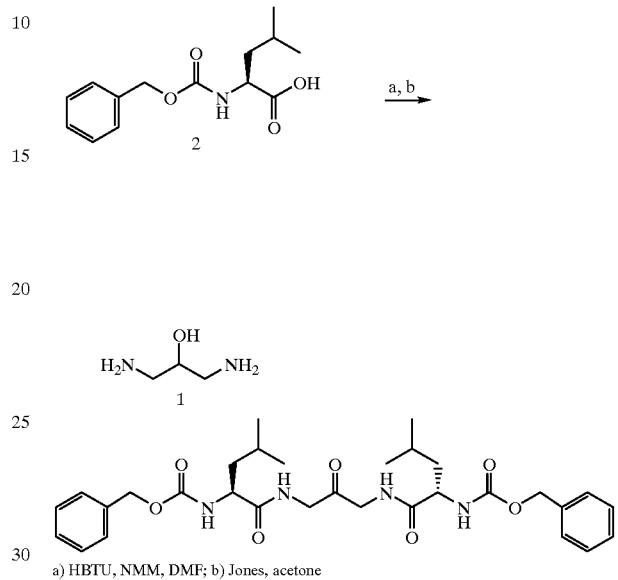
a) HBTU, NMM, DMF; b) Jones, acetone
Scheme 14
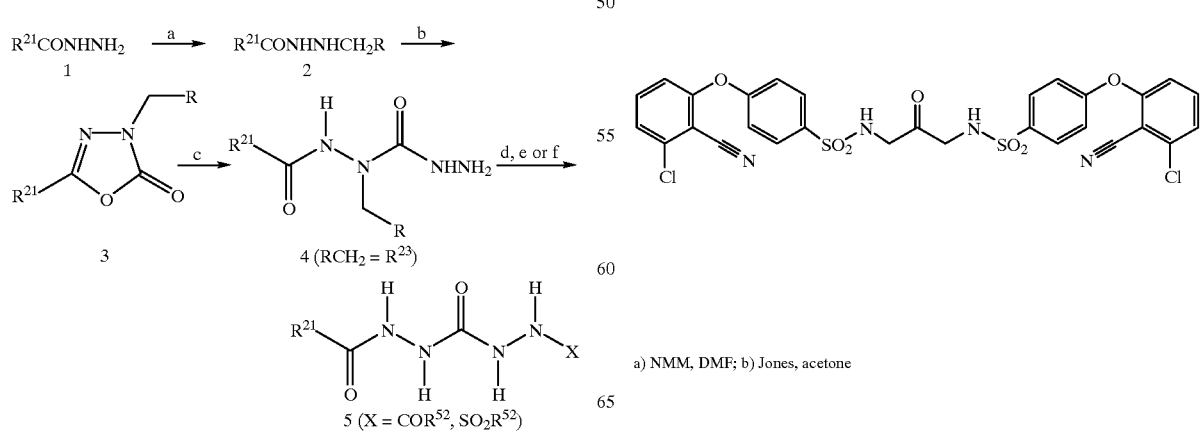
a) NMM, DMF; b) Jones, acetone Scheme 15
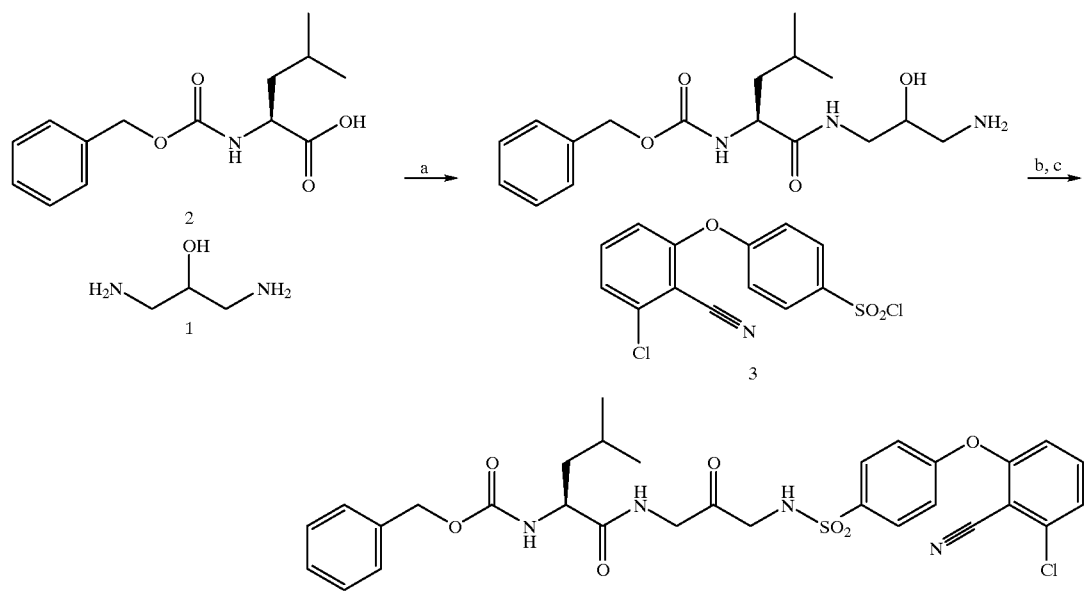
a) EDCI, HOBT, DMF; b) NMM, DMF, 3) Jones, acetone
Scheme 16
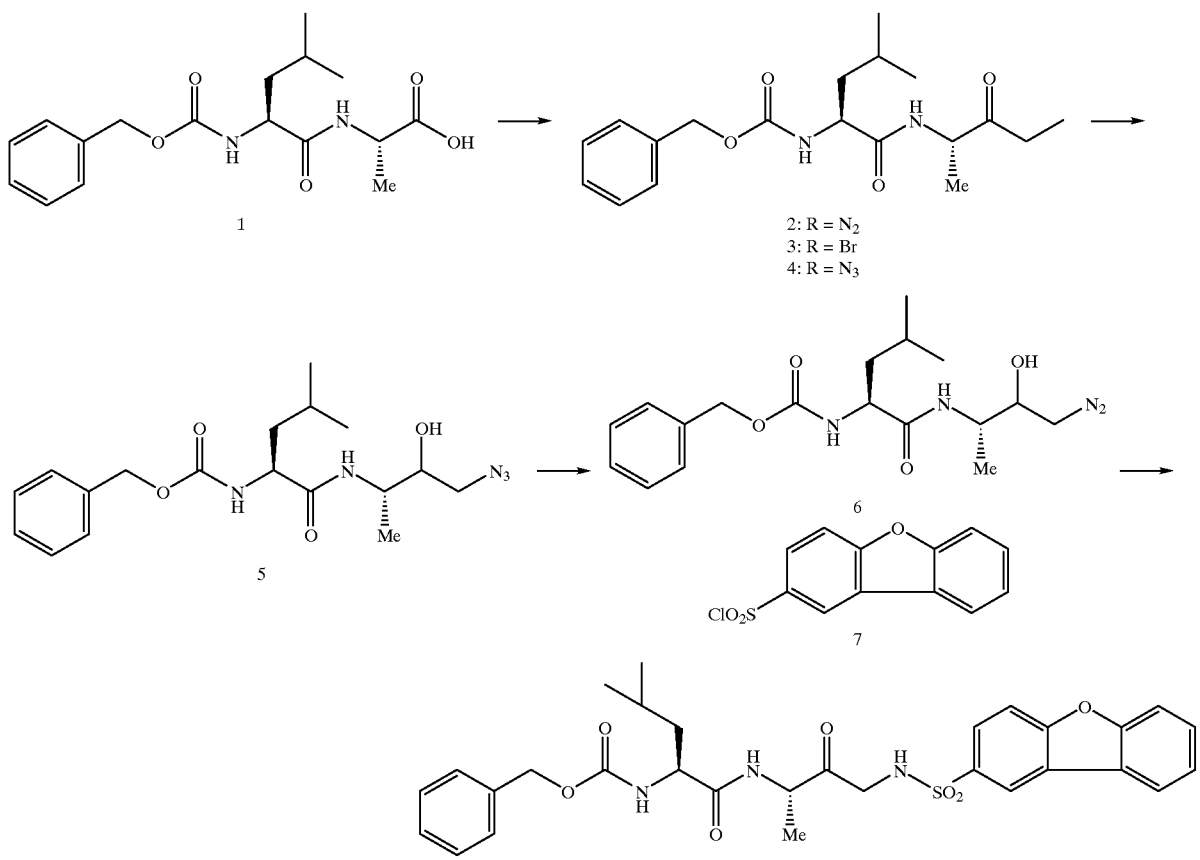

Scheme 17

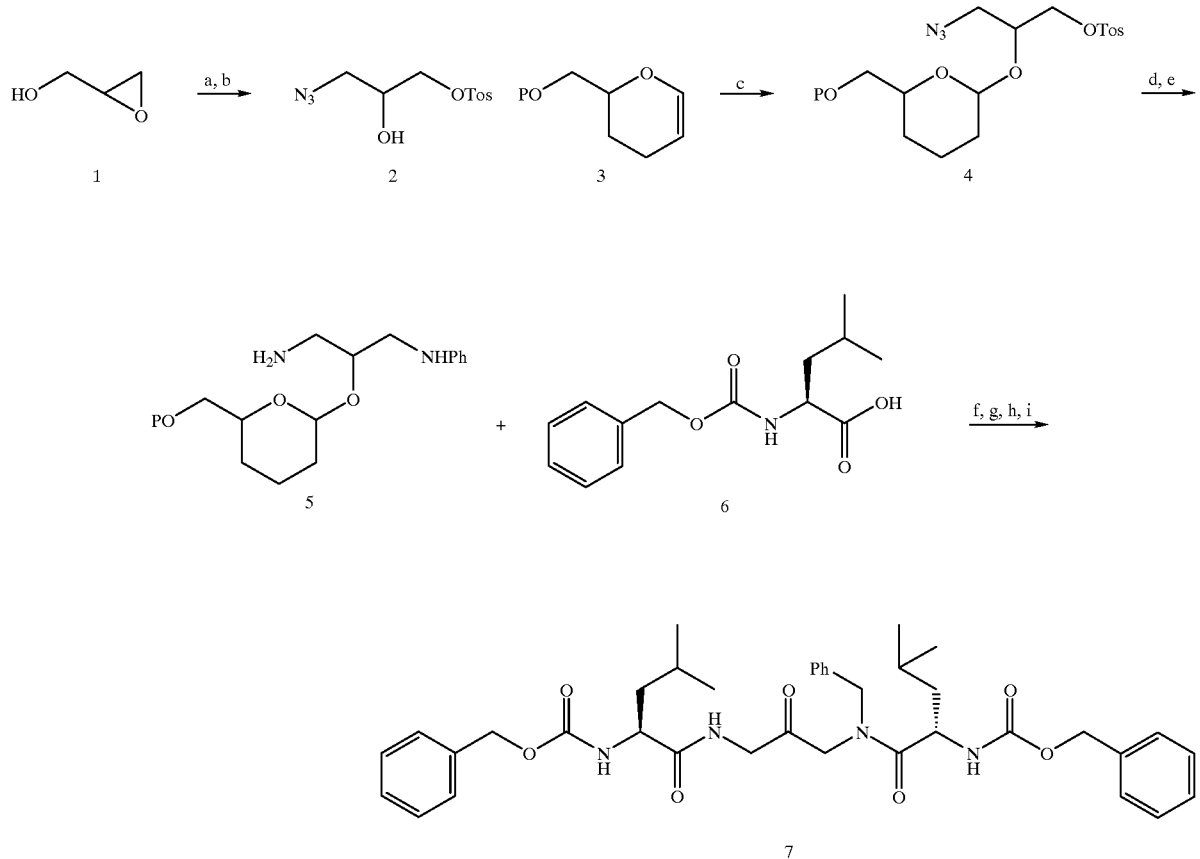

a) NaN₃, MeOH, H₂O; b) Tosyl chloride, triethylamine, CH₂Cl₂; c) Ellman dihydropyran resin (3), PPTS, Cl(CH₂)₂Cl; d) PhCH₂NH₂, toluene, 80 degrees C; e) HATU, N-methyl morpholine, NMP; f) HS(CH₂)₃SH, MeOH, Et₃N; g) Cbz-leucine (6), HBTU, N-methyl morpholine, NMP; h) TFA, CH₂Cl₂, Me₂S; i) Jones reagent, acetone

Scheme 18

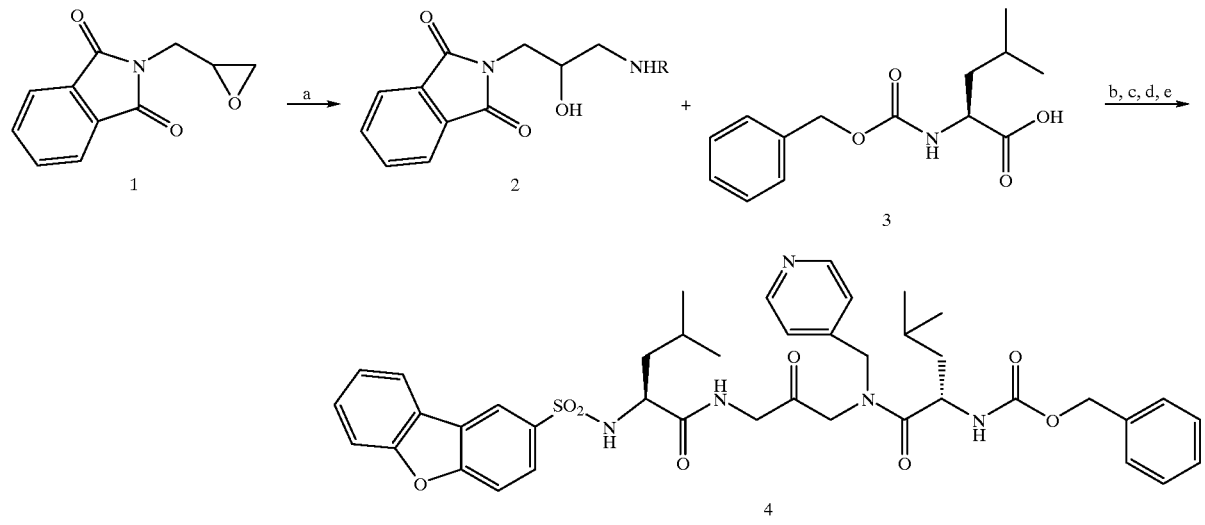

a) 4-pyridyl methyl amine, isopropanol, reflux; b) Cbz-leucine, HBTU, N-methyl morpholine, DMF; c) hydrazine, MeOH, reflux; d) 2-dibenzofuransulfonyl chloride, N-methyl morpholine, DMF; e) Jones reagent, acetone

Scheme 19

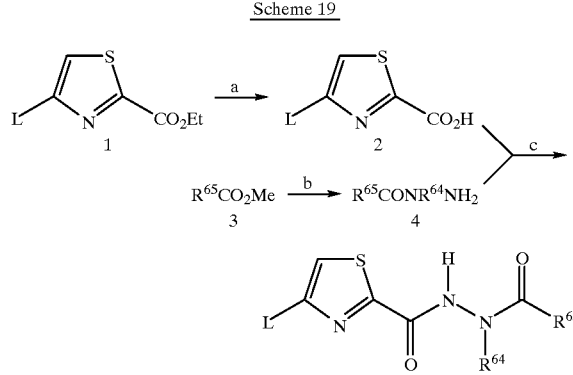

a) KOH, MeOH/H2O; b) R66NHNH2, EtOH; c) EDC·HCl, 1-HOBT, DMF

Scheme 20

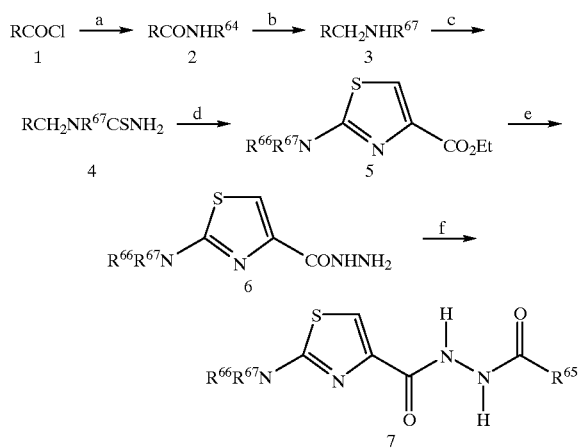

a) Thiourea, EtOH; b) i. NaNO2, 16% aqueous HBr; ii. CuBr, 16% aqueous HBr; iii. HBr (cat.), EtOH; c) ArB(OH)2, Pd(PPh3)4, CsF, DME; d) ArSnMe3, Pd(PPh3)4, PhMe; e) H2NNH2·H2O, EtOH; e) R65CO2H, EDC·HCl, 1-HOBT, DMF.

Scheme 21 a) R67NH2, Py, CH2Cl2; b) LiAlH4, THF; c) Cl2CS, Py, CH2Cl2; ii. NH3, MeOH or I. PhCONCS, CHCl3; ii. K2CO3, MeOH, H2O; d) EtO2CCOCH2Br, EtOH; e) H2NNH2·H2O, EtOH; e) R65CO2H, EDC·HCl, 1-HOBT, DMF.

Scheme 22

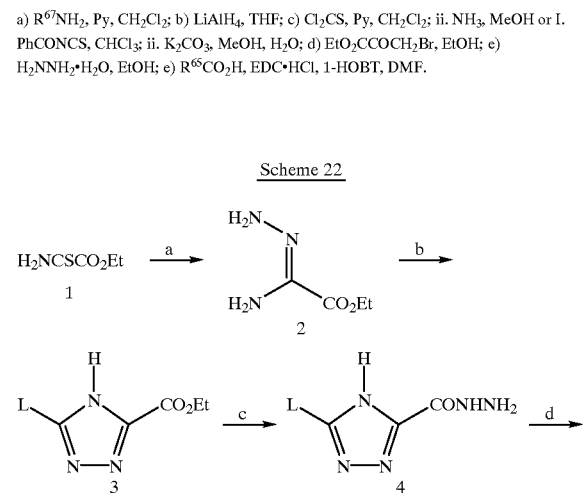

a) H2NNH2·H2O, EtOH; b) LCO2CO2i-Bu, 200° C.; c) H2NNH2·H2O, EtOH; d) R65CO2H, EDC·HCl, 1-HOBT, DMF

Scheme 23

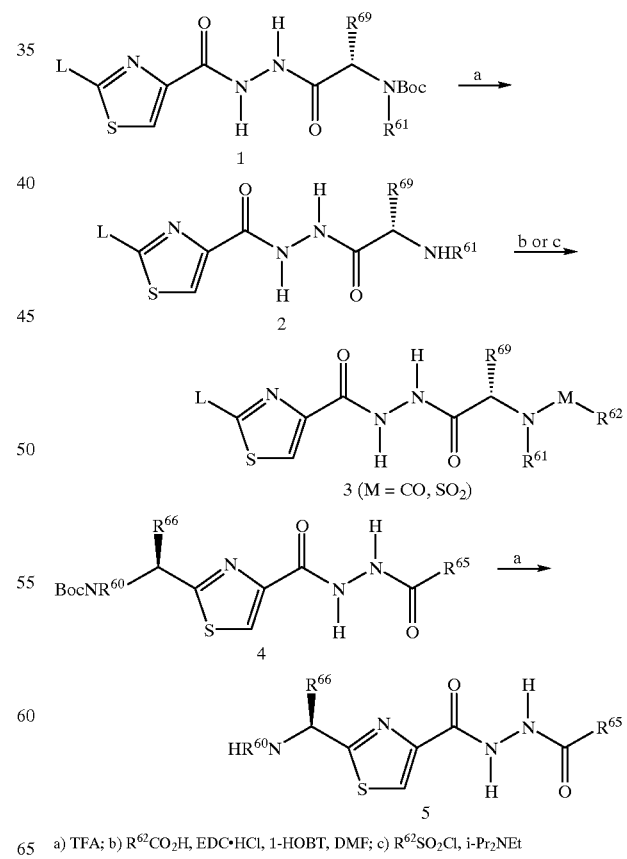

a) TFA; b) R62CO2H, EDC·HCl, 1-HOBT, DMF; c) R62SO2Cl, i-Pr2NEt

Scheme 24

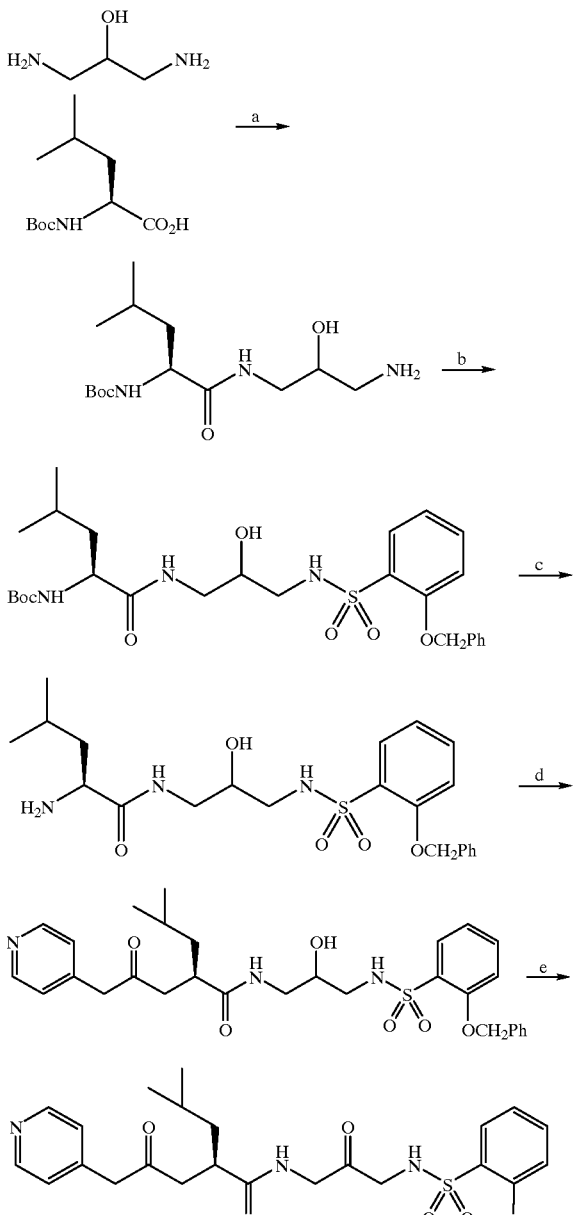

a) EDCI, DMF; b) 2-PhCH$_2$OPhSO$_2$Cl, NMM, DMF; c) TFA, DCM; d) 4-pyridyl acetic acid, HBTU, NMM, DMF; e) Jones

Scheme 25

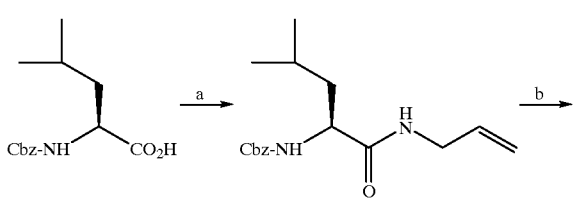

a) HBTU, NMM, DMF, allyl amine; b) mCPBA, DCM; c) MeNH$_2$, isopropanol, 70 C; d) Cbz-leucine, EDCI, DMF; e) Jones, acetone In another aspect, the present invention provides a novel cysteine protease in crystalline form, as defined by the positions in Table I herein.

In still another aspect, the present invention provides a novel protease composition characterized by a three dimensional catalytic site formed by the atoms of the amino acid residues listed in Table XXIX herein.

The three dimensional (3D) structure of the instant protease reveals that human cathepsin K is highly homologous to other known cysteine proteinases of the papain family. Cathepsin-K folds into two subdomains separated by the active site cleft, a characteristic of the papain family of cysteine proteases. The overall fold of cathepsin K is very similar to that of papain and actinidin. There is an insertion of one additional residue in cathepsin K at residue alanine 79 compared to papain. This insertion is easily accommodated in the turn at the carboxy terminal end of the helix formed by residues methionine 68-lysine 77 of cathepsin K. There is a different conformation for the backbone atoms of residues asparagine 99 to lysine 103 at the surface of cathepsin K compared to that in papain. Other differences in the backbone conformations between cathepsin K and papain are: a two residue insertion in loop residues 126–127, a two residue insertion at residue aspartate 152, the insertion of 4 residues at glutamine 172 and a difference in the conformation of the loop around residue lysine 200. There are many more differences in the structure of human cathepsin K and human cathepsin B, however, the secondary structure is preserved well between these two enzymes.

Listed in FIG. 1 are the known amino acid sequences for the papain superfamily of cysteine proteases cathepsin K, cathepsin S, cathepsin L, papain, actinidin, cathepsin H and cathepsin B, aligned to illustrate the homologies there between.

According to the present invention the crystal structure of human cathepsin K has been determined in the absence of inhibitor and in complex with nine separate inhibitors at resolutions from 3.0 to 2.2 Angstroms. The structures were determined using the method of molecular replacement and refined to $R_c$ values ranging from 0.190–0.267 with the exception of the enzyme in the absence of inhibitor which was not refined.

Further refinement of the atomic coordinates will change the numbers in Table I. Refinement of the crystal structure from another crystal form will result in a new set of coordinates, determination of the crystal structure of another cysteine rotease will also result in different set of numbers for coordinates in Table I which as an experimental error of approximately 0.4 Angstroms. Also for example, the amino acid sequence of the cysteine proteases can be varied by mutation derivatization or by use of a different source of the protein.

Human cathepsin K contains 215 amino acids and the model of the enzyme provided herein is represented by all 215 residues.

The cathepsin K crystal structure reveals an active site that is heretofor unknown and comprises a distinct three dimensional arrangement of atoms.

Table I discloses the protein coordinates of cathepsin K. These data are reported for the crystal structures described herein. The data are reported in Angstroms with reference to an orthogonal coordinate system in standard format, illustrating the atom, i.e., nitrogen, oxygen, carbon, sulfur (at $\alpha$, $\beta$, $\gamma$, $\delta$, or $\epsilon$, positions in the amino acid residues); the amino acid residue in which the atom is located with amino acid number, and the coordinates X, Y and Z in Angstroms (Å) from the crystal structure. Note that each atom in the active site and the entire structure has an unique position in the crystal. The data also report the B or Temperature Factor values, which indicate the degree of thermal motion of the atom in root mean square displacement measurements ($Å^2$).

FIG. 2 illustrates the cathepsin K structure of the invention, including the active site.

Figure 3:
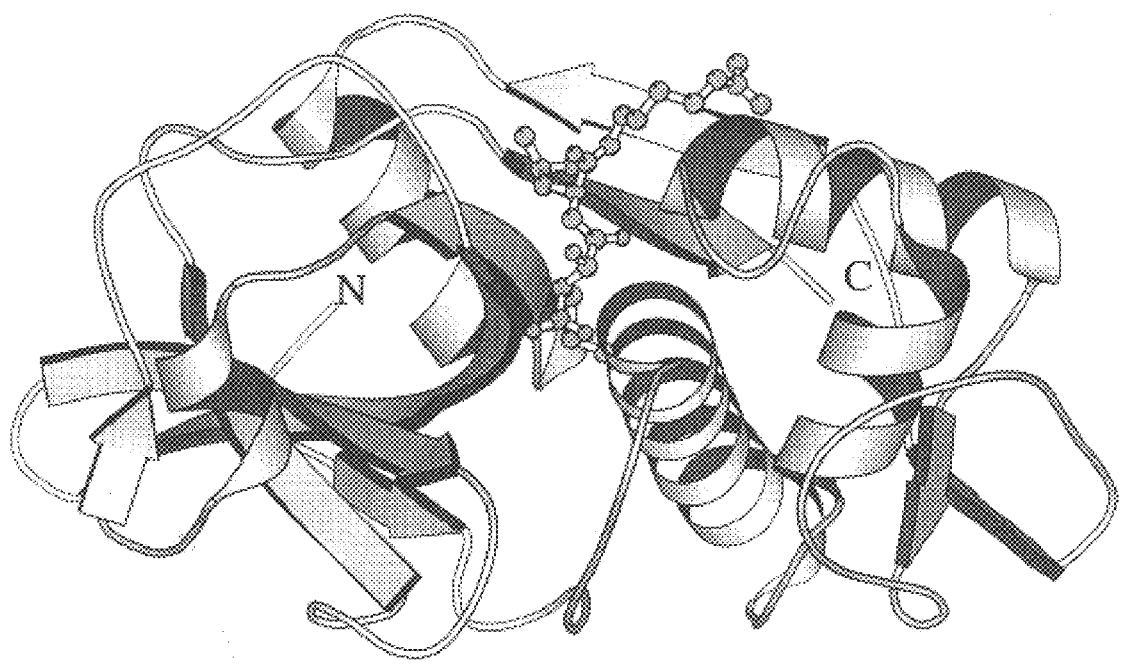
FIG. 3 is a ribbon diagram of cathepsin K in complex with E-64, a known inhibitor of cysteine proteases. The drawing was produced using the program MOLSCRIPT.
Figure 4:
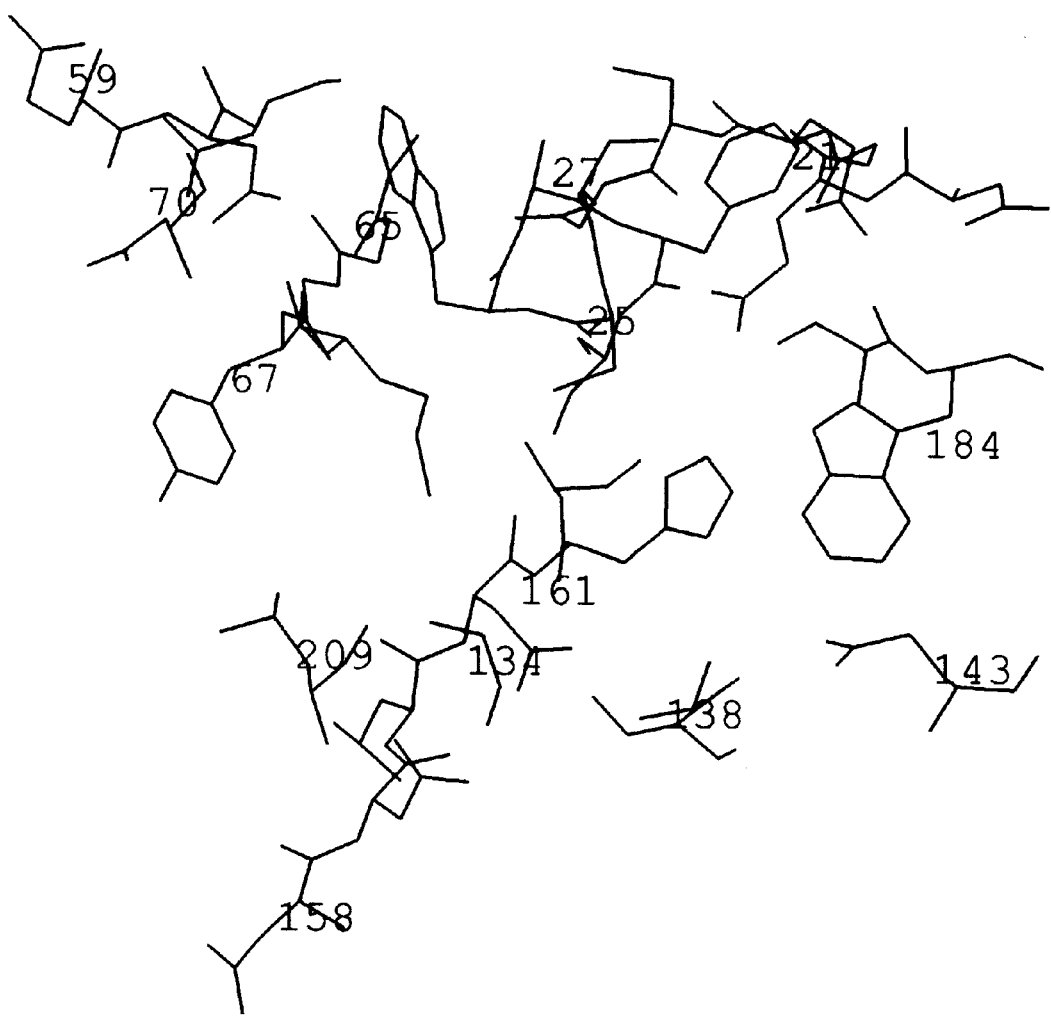
FIG. 4 is an illustration of the active site of cathepsin K.
Figure 5:
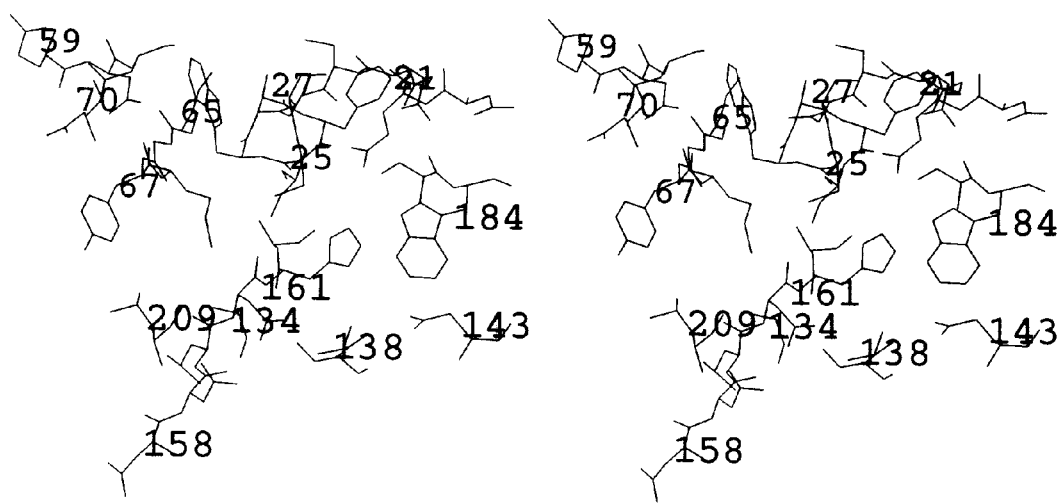
FIG. 5 is a stereoview of the active site of cathepsin K. For clarity, no hydrogen atoms or water molecules are shown.
Figure 6:
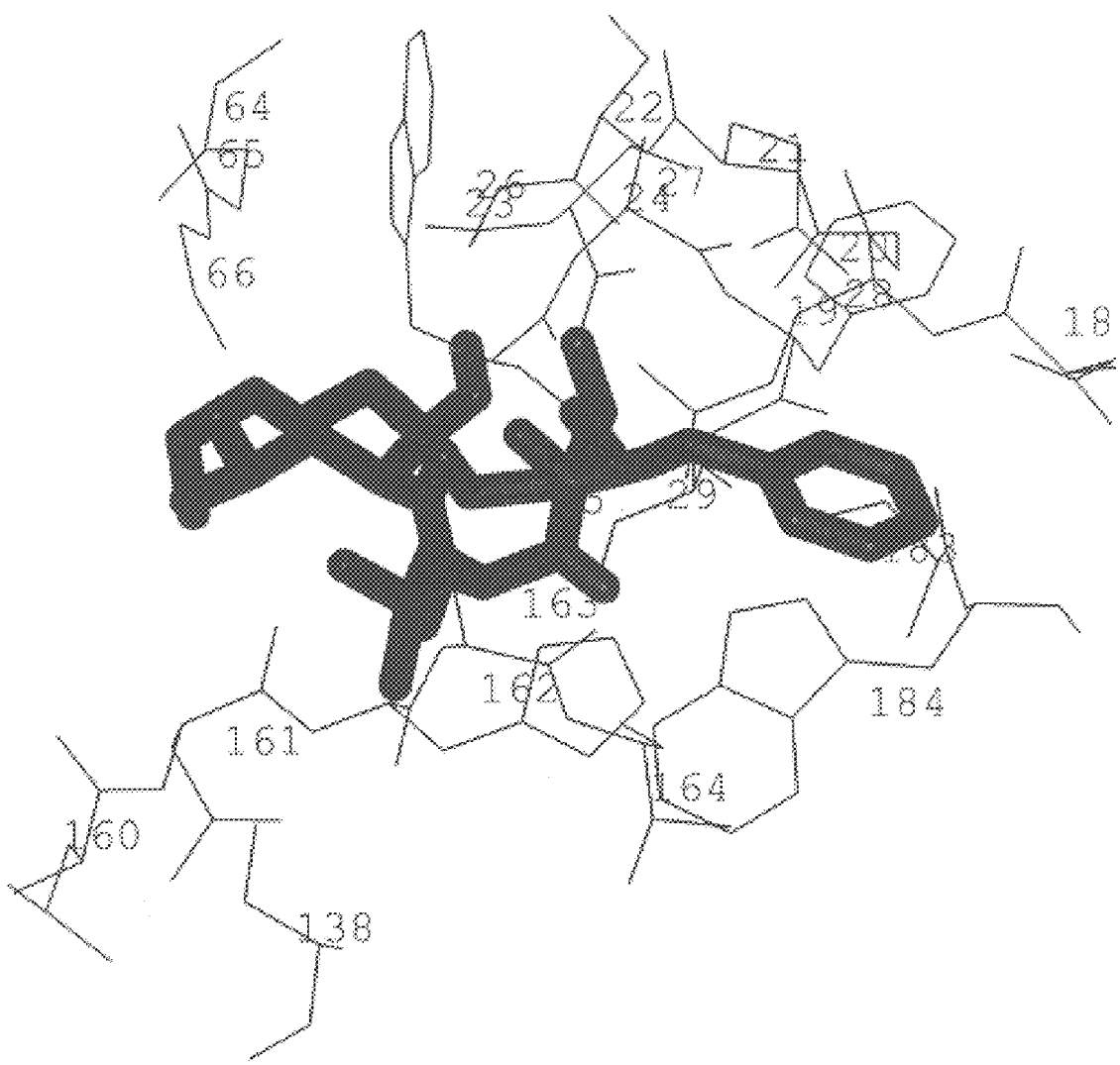
FIGS. 6, 8, 10, 12, 14, 16, 18, 20, and 22 are illustrations of the active site of cathepsin K in complex with novel inhibitors of cathepsin K.
Figure 7:
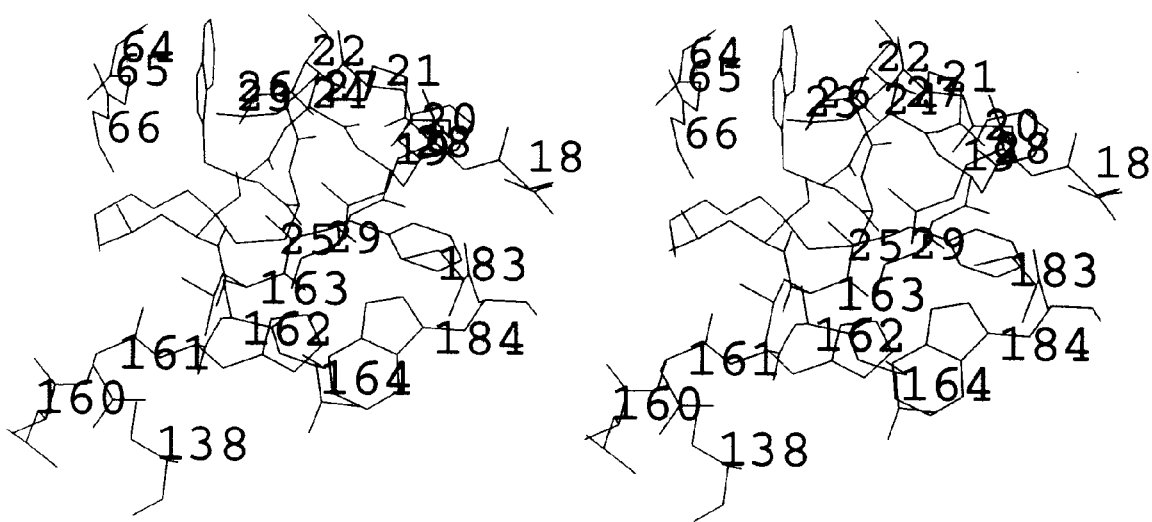
FIGS. 7, 9, 11, 13, 15, 17, 19, 21 and 23 are stereoviews of the active site of cathepsin K in complex with novel inhibitors of cathepsin K.
Figure 8:
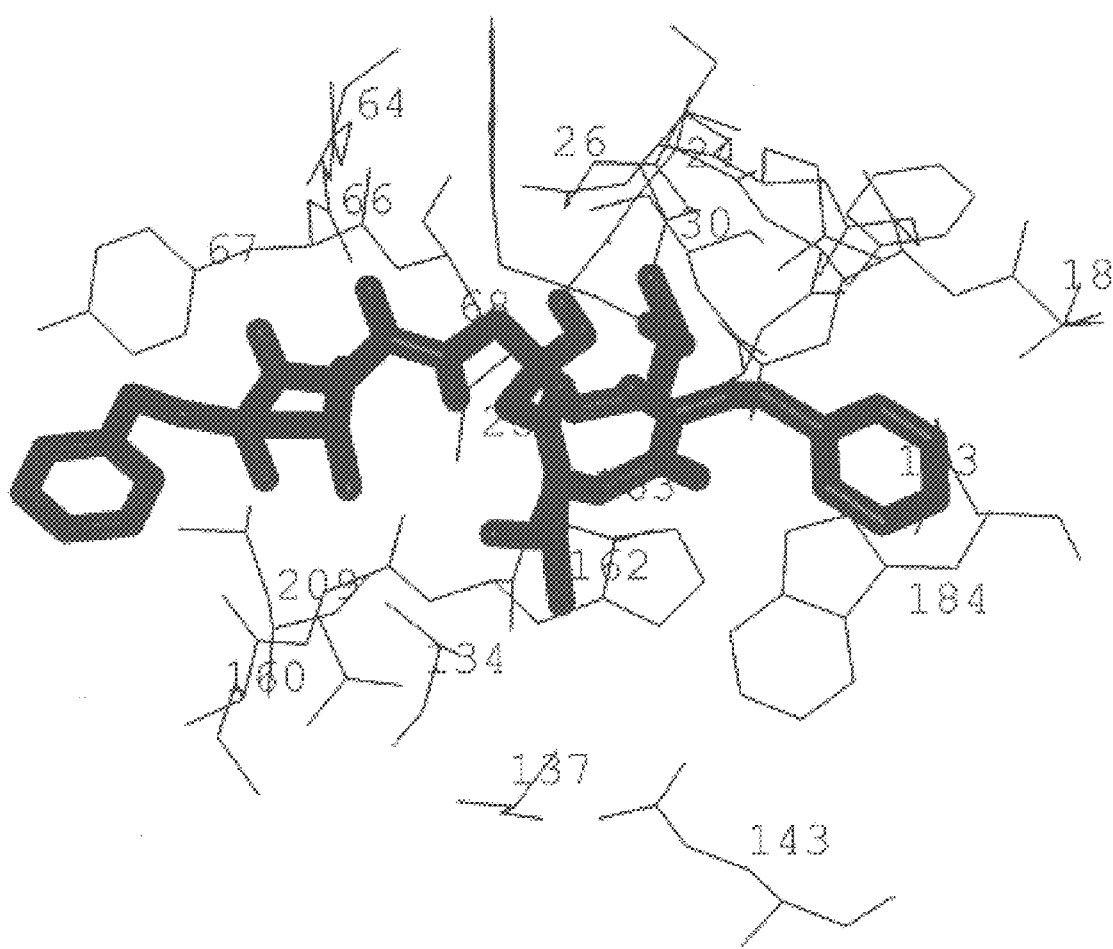
Figure 9:
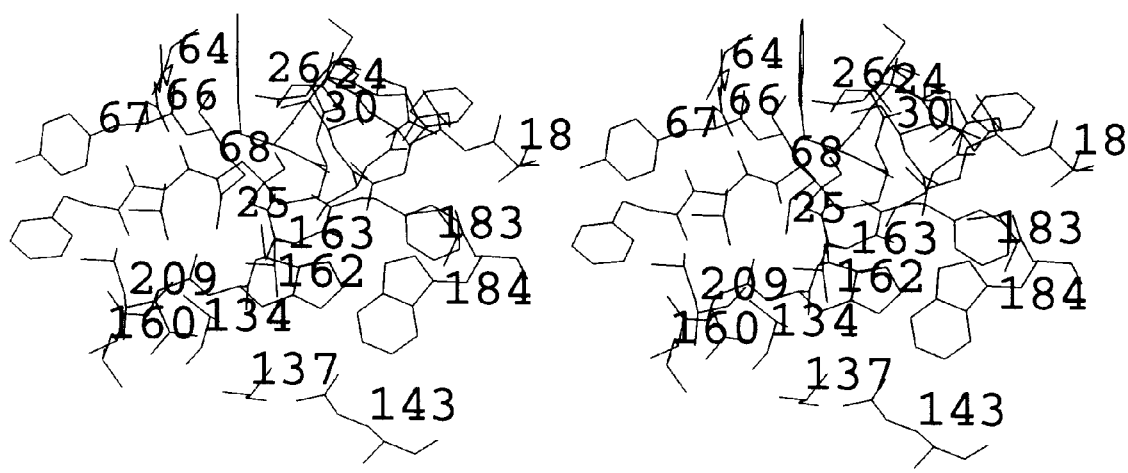
Figure 10:
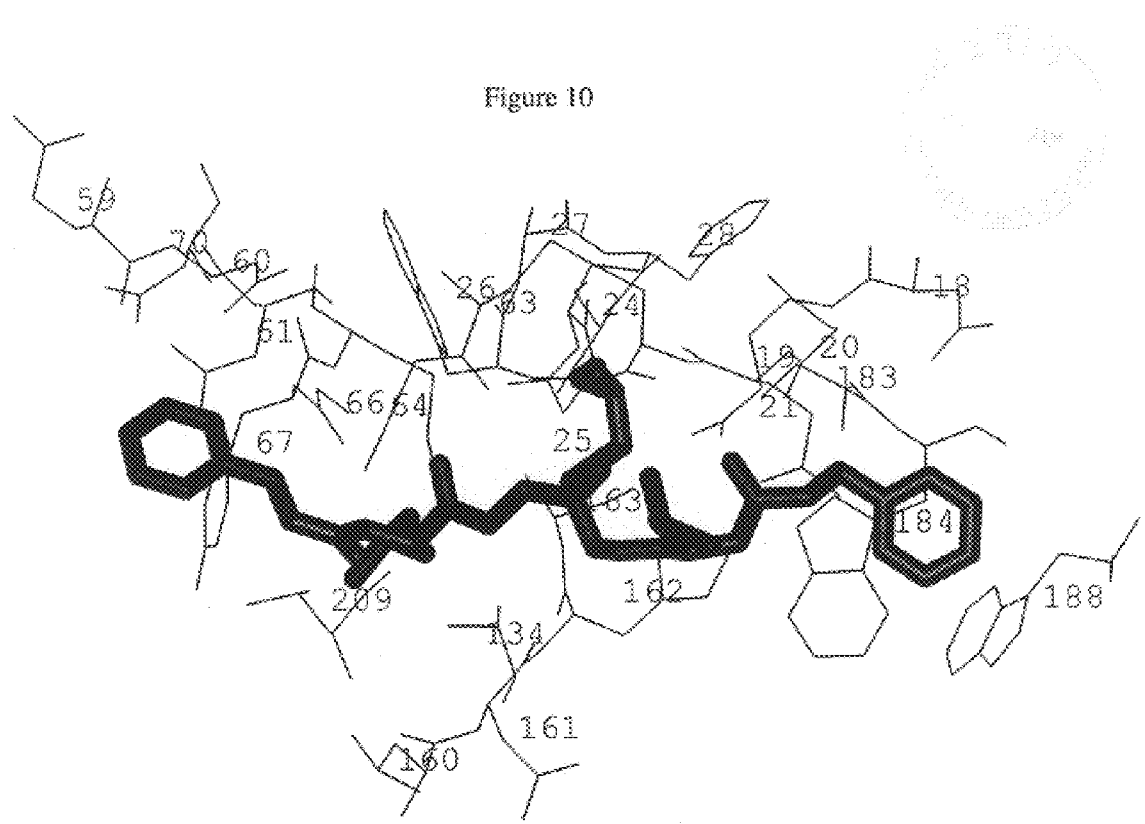
Figure 11:
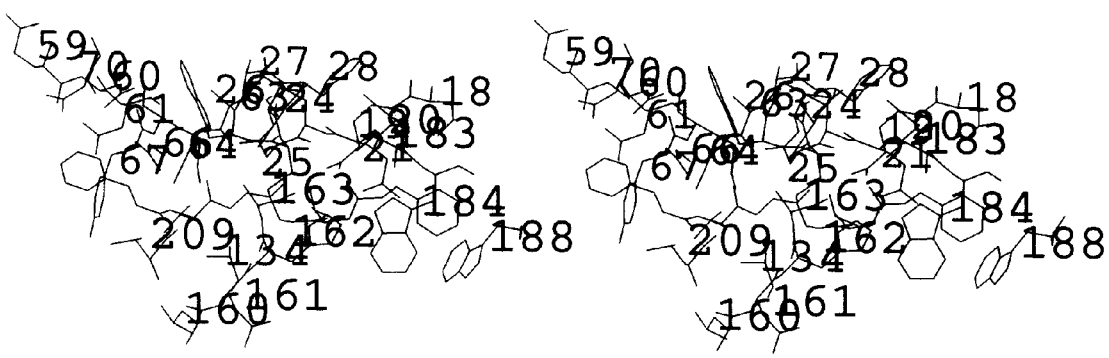
Figure 12:
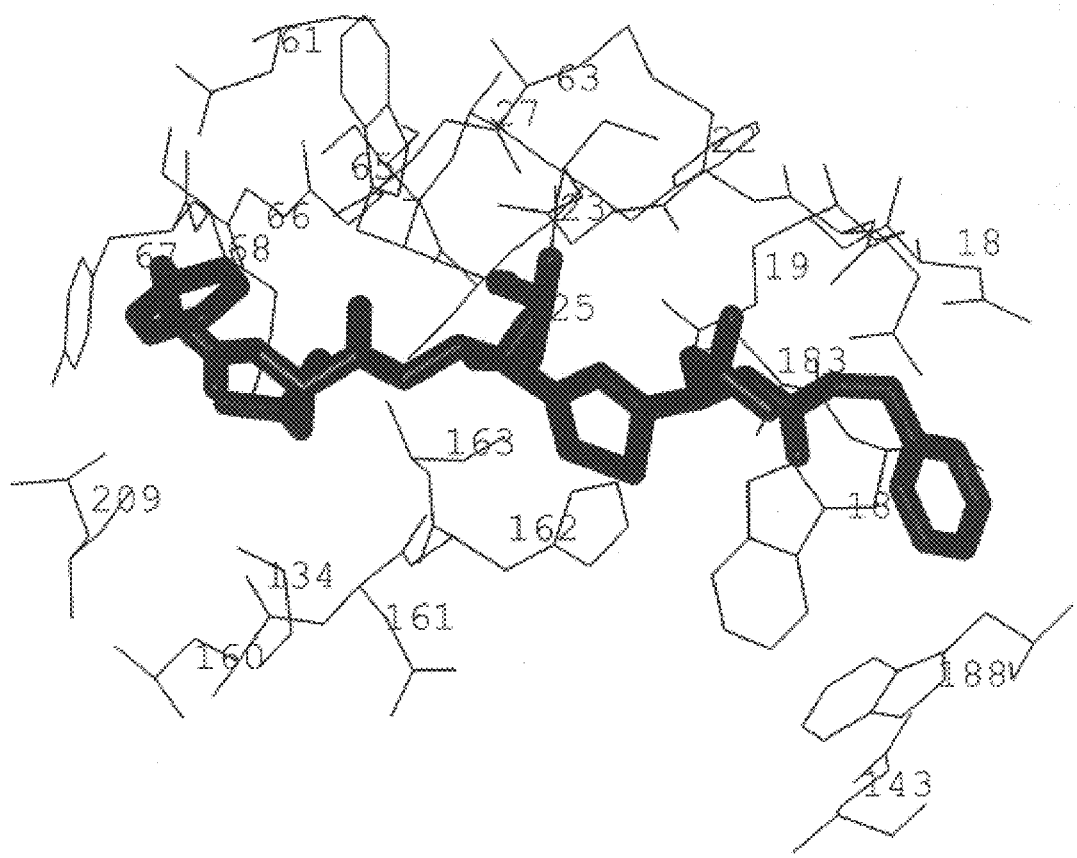
Figure 13:
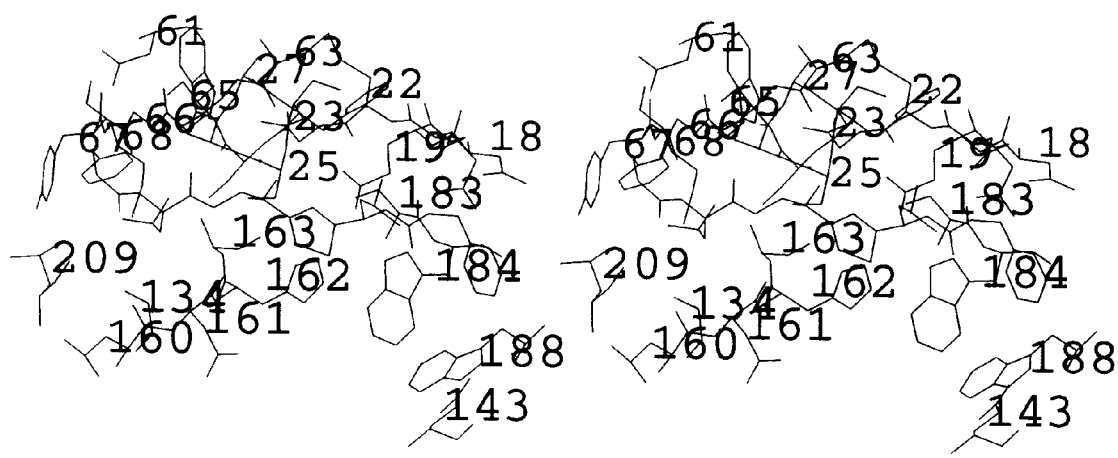
Figure 14:
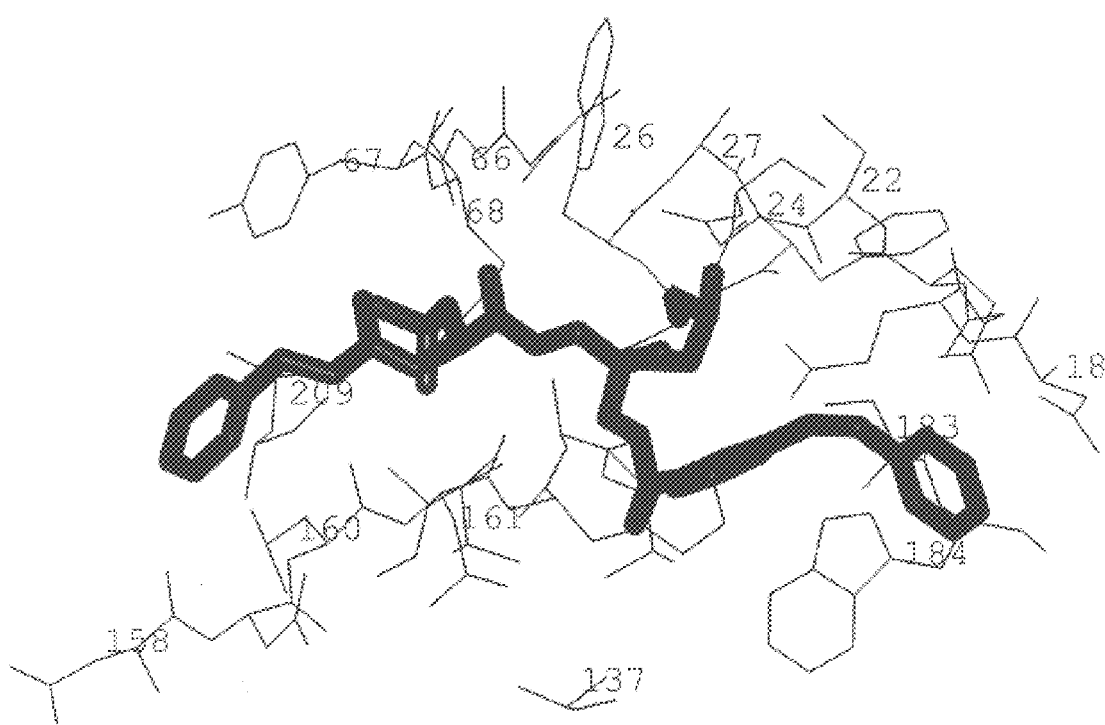
Figure 15:
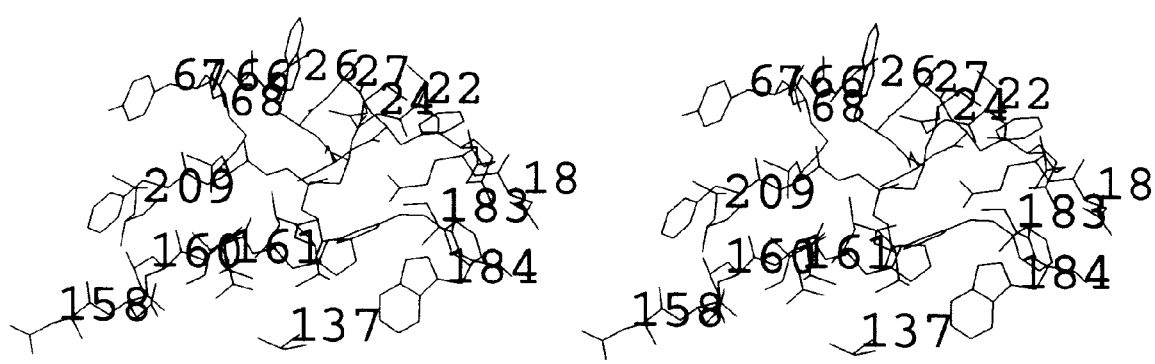
Figure 16:
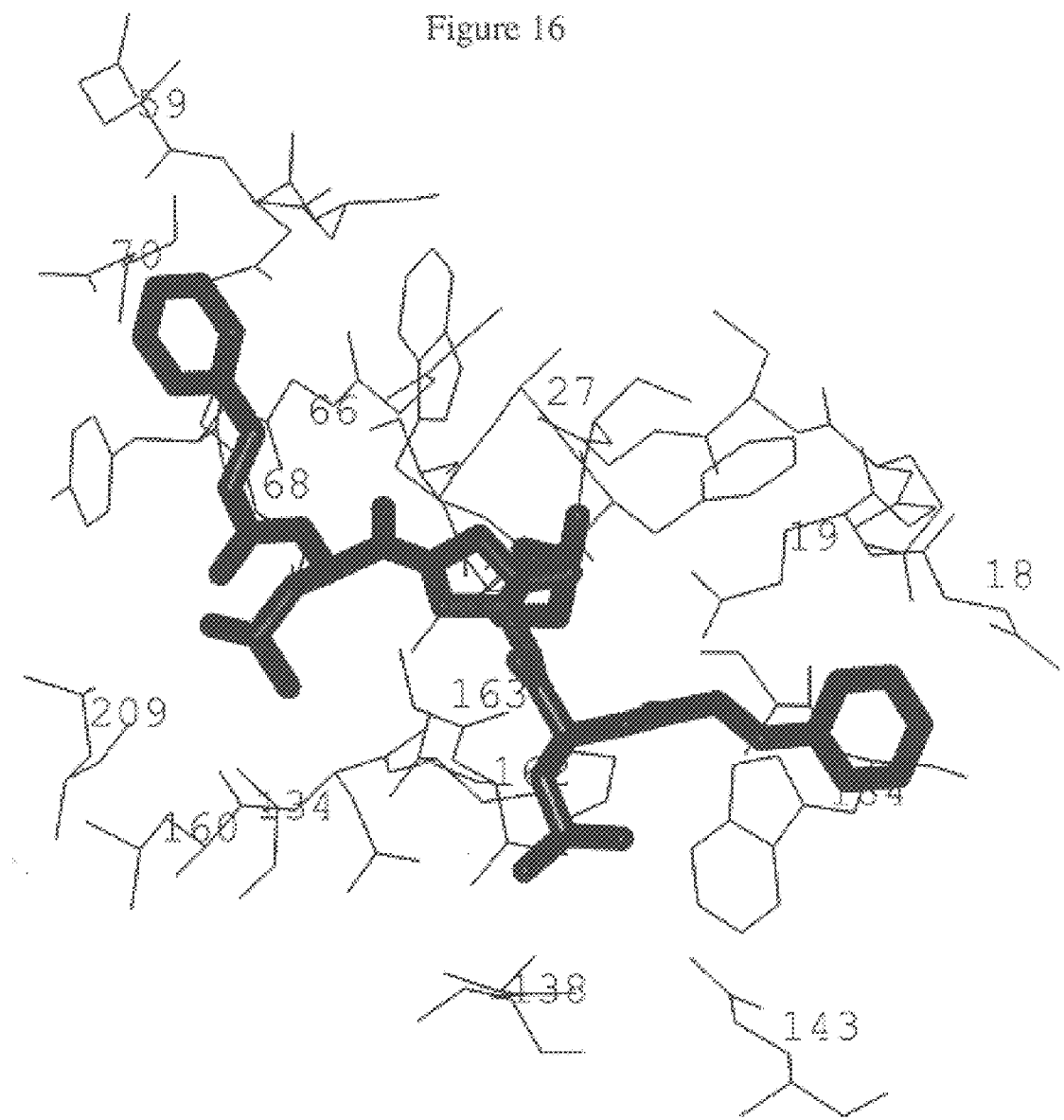
Figure 17:
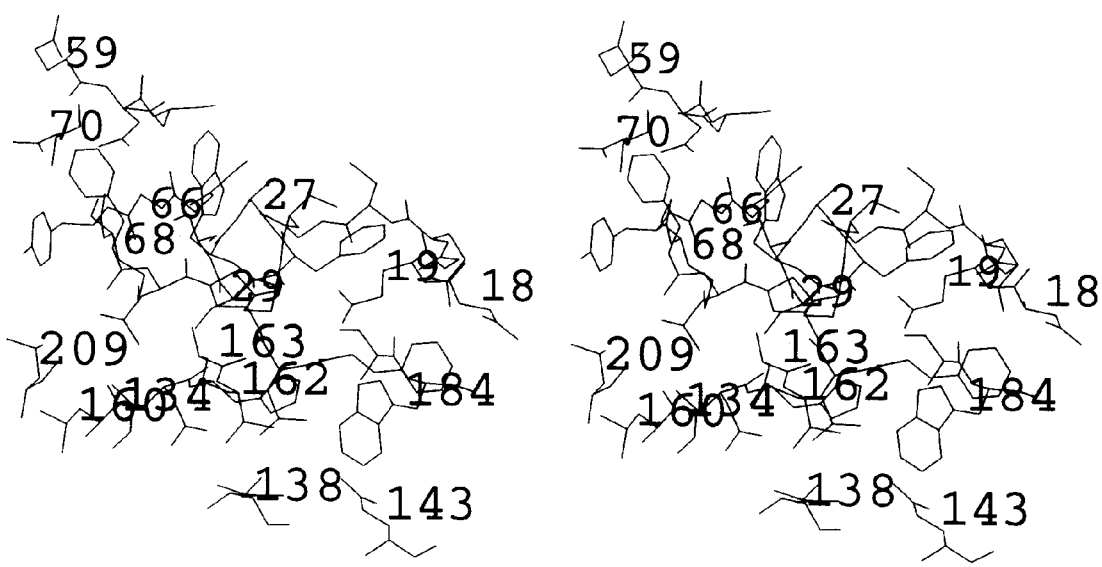
Figure 18:
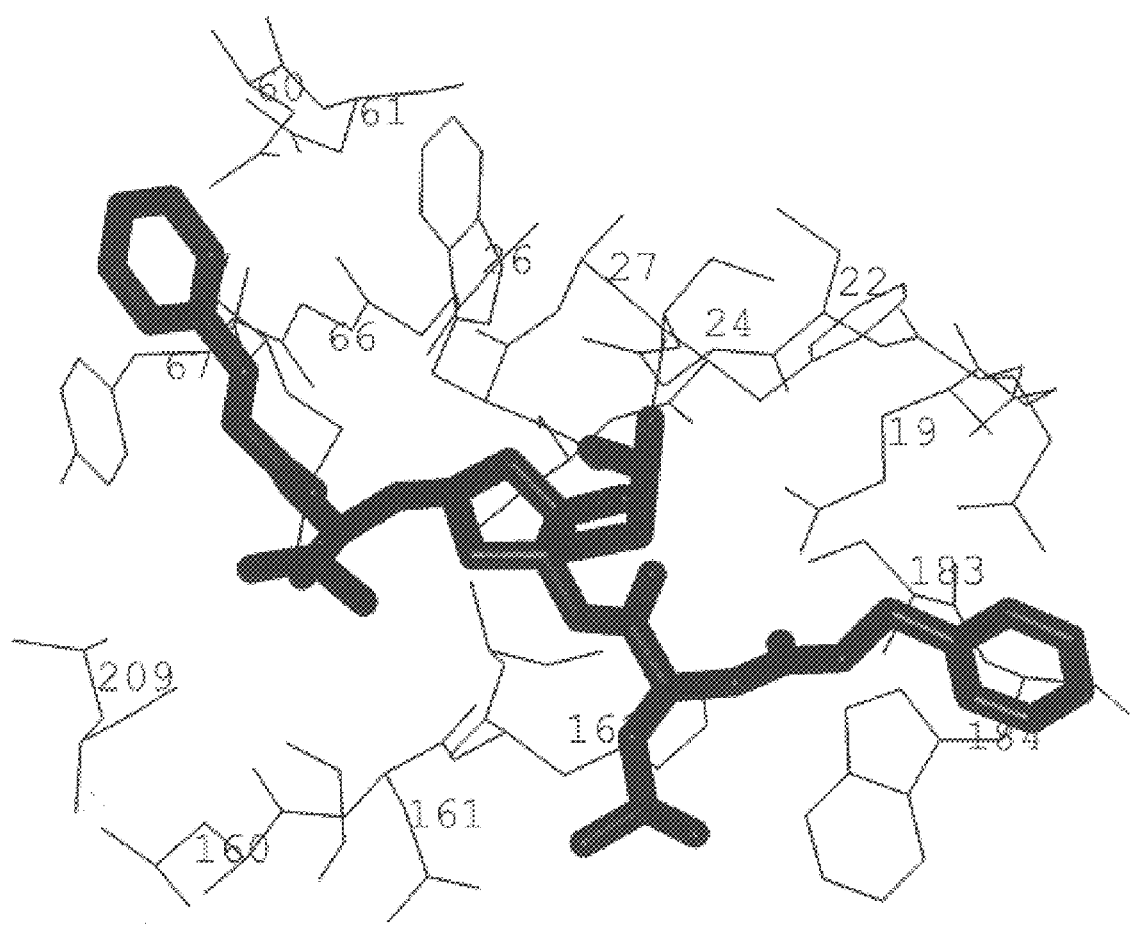
Figure 19:
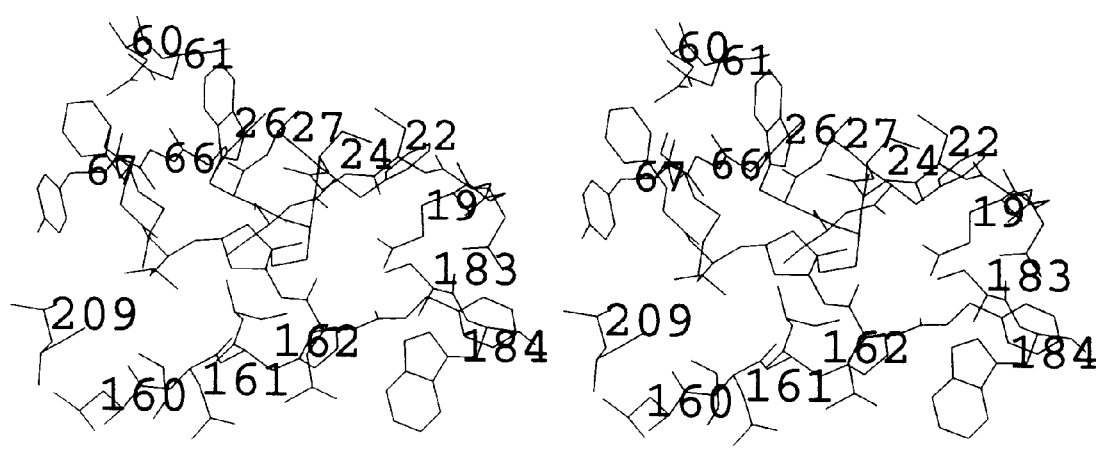
Figure 20:
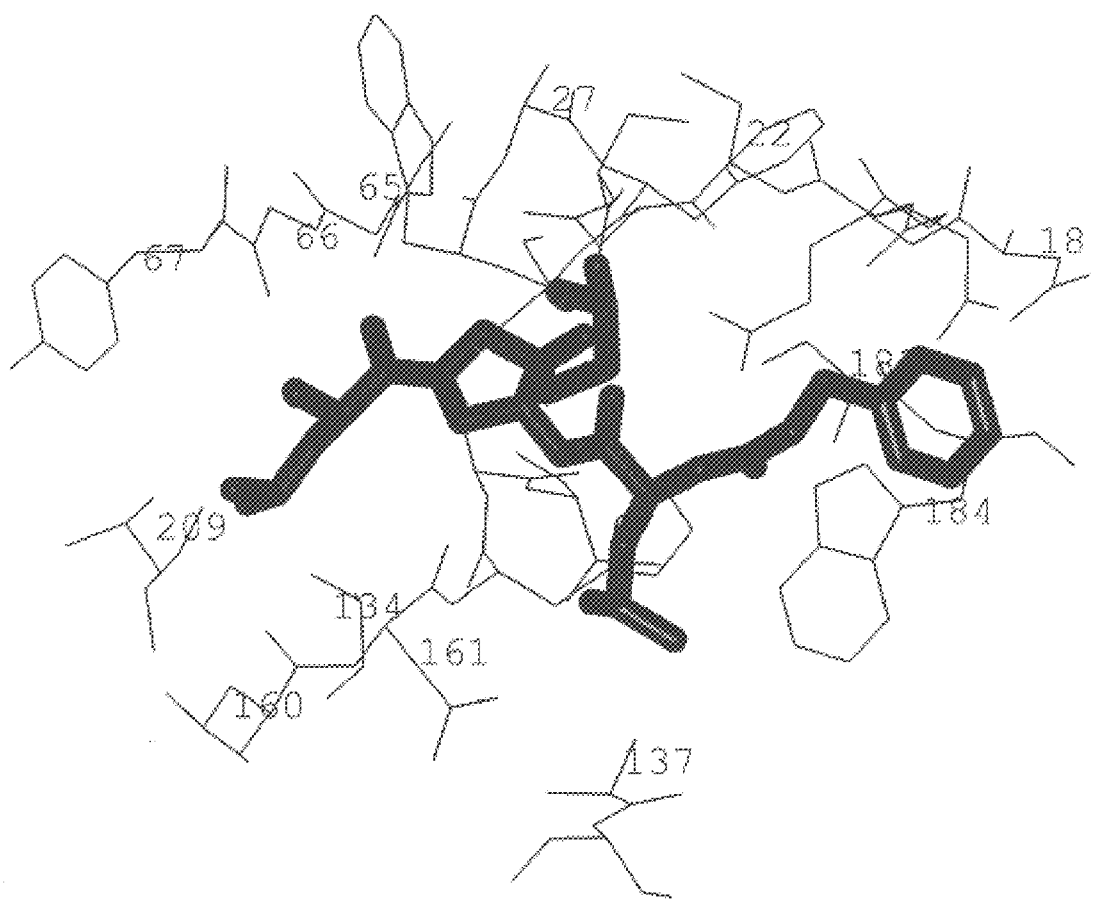
Figure 21:
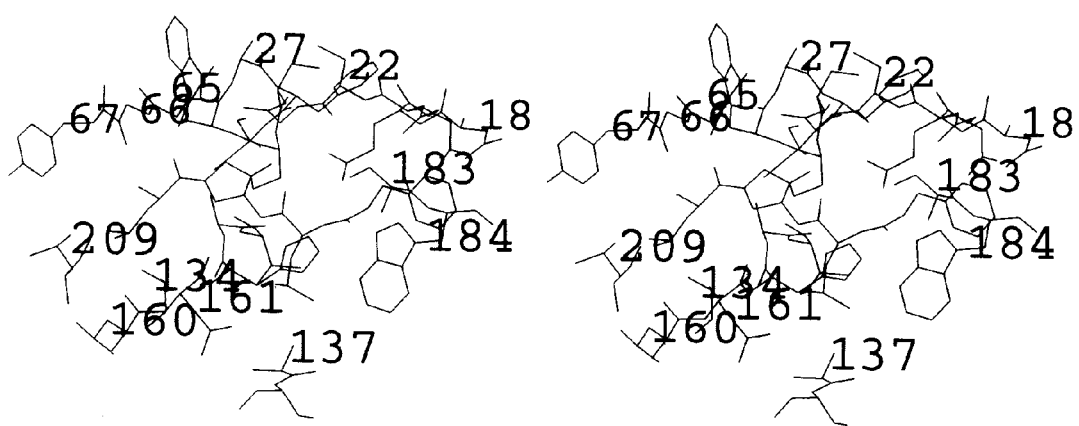
Figure 22:
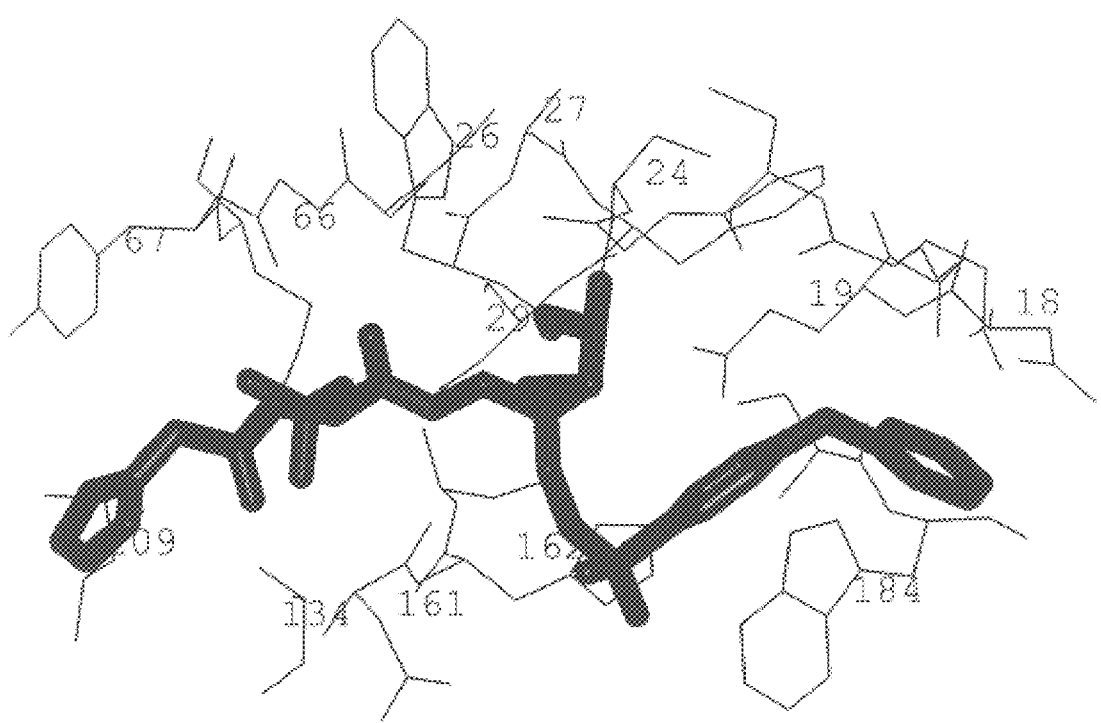
Figure 23:
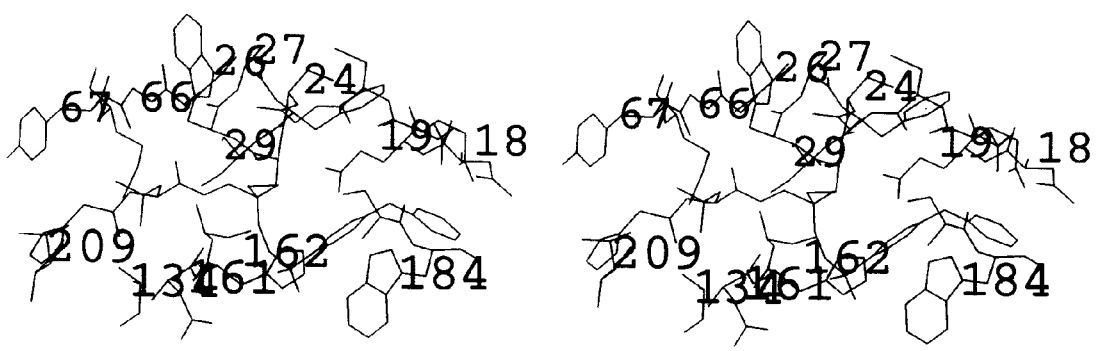

The active site of cathepsin K bound to E-64 is shown in FIG. 3. The conformation of E-64 bound to cathepsin K resembles that seen in the published structures of the papain-E-64 complex (Varughese, K. I., *Biochemistry* 28, 1330–1332 (1989)) and actinidin-E-64 Varughese, K. I., *Biochemistry* 31, 5172–5176 (1992)). The covalent bond between the sulfur of cysteine 25 and the carbon C2 of the inhibitor is very clear in the electron density. Differences in the sidechain atoms lining the active site pockets on the enzyme of the various members of the papain family of cysteine proteases give rise to different interactions between the atoms of E-64 and the protein in these structures. In cathepsin K, the isobutyl atoms of the leucine lie well buried in the hydrophobic pocket formed by the side chain atoms of the cathepsin K residues leucine 160, alanine 134 and methionine 68 shielding these atoms of E-64 from solvent. In papain the leucyl side chain atoms of E-64 do not penetrate as deeply into this hydrophobic pocket. Another pocket of cathepsin K is occupied by the guanidinium atoms of E-64. A hydrogen bond forms between N4 of E-64 and the backbone carbonyl oxygen of glutamate 59 and the OD2 oxygen of aspartate 61. The carboxylate oxygen of aspartate 61 also makes a hydrogen bond with the N3 atom of E-64. The sidechain atoms of aspartate 61 lie at the entrance to this pocket in cathepsin K. These interactions are not possible in papain because the corresponding residue in papain is tyrosine 61 which blocks access. The carboxylate oxygens of E-64 make hydrogen bonding interactions with the ND 1 atom of histidine 162 and the NE2 atom of glutamine 19. These interactions are also seen in papain and actinidin. The atoms of E-64 do not penetrate the complete region of the enzyme active site. As in papain, the backbone nitrogen atoms of residue glycine 66 in cathepsin K makes a hydrogen bond with the carbonyl oxygen atom O4 of the E-64. Also, the carbonyl oxygen of glycine 66 of cathepsin K forms a hydrogen bond with N2 of E-64. A portion of the regions of the active site are very similar in conformation in cathepsin K, papain and actinindin. A comparison of the active site of cathepsin K and cathepsin B reveals many more differences than observed in comparing papain or actinidin to cathepsin K. A portion of the active site of cathepsin B differs significantly from the corresponding portion of the active site in cathepsin K. The presence of the loop glutamate 107-proline 116 in human cathepsin B is presumed responsible for the dipeptidyl carboxypeptidase activity of this enzyme and has no equivalent in cathepsin K, papain or actinidin. This loop makes this region of the active site of cathepsin B much smaller than in the other members of this papain family of cysteine proteases including cathepsin K. Despite the differences between the active sites of human cathepsin B and cathepsin K, the active site cysteine residues are almost exactly superimposed by an alignment of structurally homologous alpha carbon atoms in cathepsin B and cathepsin K. Differences in the hydrophobic pocket near leucine 160 in cathepsin K are also evident in cathepsin B. The residues forming this pocket are replaced by proline 78 in place of methionine 68 in cathepsin K and glutamate 243 in cathepsin B is structurally equivalent to leucine 160 in cathepsin K. Interestingly, the residues whose sidechain atoms form hydrogen bonds to the E-64 inhibitor in cathepsin K, namely histidine 162, glutamine 19 and aspartate 61, have structurally homologous residues in cathepsin B, namely histidine 197, glutamine 23 and aspartate 67 respectively.

Specific interactions of certain inhibitors of the present invention at the active site of cathepsin K are detailed hereinbelow.

3(S)-3-[(N-benzyloxycarbonyl)-L-leucinyl]amino-5-methyl-1-(1-propoxy)-2-hexanone makes hydrophobic contacts with the enzyme residues indole ring of tryptophan 184 and the sidechain atom CG of glutamine 19. Oxygen O26 forms a bifurcated hydrogen bond with the amide nitrogen of cysteine 25 and the NE2 atom of glutamine 19. The active site nucleophilic sulfur of residue cysteine 25 is covalently linked to carbon C25 of the inhibitor, which adopts a tetrahedral conformation.

Bis-(Cbz-leucinyl)-1,3-diamino-propan-2-one exhibits the same interaction as 3(S)-3-[(N-benzyloxycarbonyl)-L-leucinyl]amino-5-methyl-1-(1-propoxy)-2-hexanone; carbon C21 of this inhibitor is covalently linked to SG of cysteine 25. The isopropyl atoms CC34,C35,C36 and C37 of the inhibitor form hydrophobic interactions with the sidechain atoms of residues on the enzyme surface, which form a hydrophobic pocket. This pocket is formed by atoms from methionine 68, leucine 209, alanine 163 and alanine 134 and portions of tyrosine 67.

2,2'-N,N'-bis-benzyloxycarbonyl-L-leucinylcarbohydrazide has interactions similar to bis-(Cbz-leucinyl)-1,3-diamino-propan-2-one and, in ajdition, the atoms C23–29 of the inhibitor CBZ group make an edge-face stacking interaction with the phenol ring of tyrosine 67. Inhibitor atom C21 is covalently bound the enzyme.

The sulfur atom of (1S)-N-[2-[(1-benzyloxycarbonylamino)-3-methylbutyl]thiazol4-ylcarbonyl]-N'-(N-benzyloxycarbonyl-L-leucinyl)hydrazide contacts the ND1 atom of histidine 163 and the indole ring of tryptophan 184. Carbon C22 is covalently attached to SG of cysteine 25.

The CBZ atoms C20–26 of 2-[N-(3-benzyloxybenzoyl)]-2'-[N'-(N-benzyloxycarbonyl-L-leucinyl)]carbohydrazide interact with the sidechain atoms of leucine 160. Carbon C 19 is covalently attached to SG of cysteine 25.

Cathepsin K binds selectively one stereoisomer of 4-[N-[(phenylmethoxy)carbonyl]-L-leucyl]-1-[N-[(phenylmethoxy)carbonyl]-L-Ieucyl]-3-pyrrolidinone. Carbon C22 is covalently attached to SG of cysteine 25. Atoms C14 and C15 of the inhibitor 4-[N-[(phenylmethoxy) carbonyl]-L-leucyl]-1-[N-[(phenylmethoxy)carbonyl]-L-leucyl]-3-pyrrolidinone form hydrophobic contacts with the sidechain atoms of glutamine 143 and asparagine 161 and the mainchain of alanine 137 and serine 138.

4-[N-[(4-pyridylmethoxy)carbonyl]-L-leucyl]-I-[N-[(phenylmethoxy)carbonyl]-L-leucyl]-3-pyrrolidinone interacts in a similar manner to 4-[N-[(phenylmethoxy) carbonyl]-L-leucyl]-1-[N-[(phenylmethoxy)carbonyl]-L-leucyl]-3-pyrrolidinone. Again one stereoisomer is bound. Carbon C17 is covalently attached to SG of cysteine 25. The interaction of 4-[N-[(phenylmethoxy)carbonyl]-L-leucyl]-1-N[N-(methyl)-L-leucyl)]-3-pyrrolidinone is the same as for 4-[N-[(4-pyridylmethoxy)carbonyl]-L-leucyl]-1-[N-[(phenylmethoxy)carbonyl]-L-leucyl]-3-pyrrolidinone, except carbon C22 is covalently attached to SG of cysteine 25.

Atom 024 of 1-N-(N-imidazole acetyl-leucinyl)-amino-3-N-(4-phenoxy-phenyl-sulfonyl)-amino-propan-2-one forms a hydrogen bond interaction with the amide NH of glycine 66. Carbon C19 is covalently attached to SG of cysteine 25.

In summary, all inhibitors exhibit an aromatic interaction with atoms of the indole of Tryptophan 184. Isopropyl atoms C12–15 of 2,2'-N,N'-bis-benzyloxycarbonyl-L-leucinylcarbohydrazide and (1S)-N-[2-[(1-benzyloxycarbonylamino)-3-methylbutyl]thiazol-4-ylcarbonyl-N'-(N-benzyloxycarbonyl-L-leucinyl)hydrazide make hydrophobic contacts with main chain atoms of residues glutamine 21, cysteine 22 and glycine 23. The NE2 atom of glutarnine 19 is able to donate a hydrogen bond to oxygen atom 2,2'-N,N'-bis-benzyloxycarbonyl-L-leucinylcarbohydrazide:O22, 1-N-(N-imidazole acetyl-leucinyl)-amino-3-N-(4-phenoxy-phenyl-sulfonyl)-amino-propan-2-one:O20, 2-[N-(3-benzyloxybenzoyl)]-2'-[N'-(N-benzyloxycarbonyl-L-leucinyl)]carbohydrazide:020, 4-[N-[(phenylmethoxy)carbonyl]-L-leucyl]-1-[N-[(phenylmethoxy)carbonyl]-L-leucyl]-3-pyrrolidinone:O23, bis-(Cbz-leucinyl)-1,3-diamino-propan-2-one:O22, 3(S)-3-[(N-benzyloxycarbonyl)-L-leucinyl]amnino-5-methyl-1-(1-propoxy)-2-hexanone:O26, 4-[N-[(4-pyridylmethoxy) carbonyl]-L-leucyl]-1-[N-[(phenylmethoxy)carbonyl]-L-leucyl]-3-pyrrolidinone:042, (1S, 2'R)-N-2-[[(1-benzyloxycarbonyl)amino]-3-methylbutyl]thiazol4-ylcarbonyl-N'-2'-(benzyloxycarbonyl)amino4'-methylpenanoylhydrazide:O23, 4-[N-[(phenylmethoxy) carbonyl]-L-leucyl]-1-N[N-(methyl)-L-leucyl)]-3-pyrrolidinone:O23. The backbone amide nitrogen of glycine 66 donates a hydrogen bond to 2,2'-N,N'-bis-benzyloxycarbonyl-L-leucinylcarbohydrazide:O39, 1-N-(N-imidazole acetyl-leucinyl)-amino-3-N-(4-phenoxy-phenyl-sulfonyl)-amino-propan-2-one:O24, 2-[N-(3-benzyloxybenzoyl)]-2'-[N'-(N-benzyloxycarbonyl-L-leucinyl)]carbohydrazide:O37, 4-[N-[(phenylmethoxy) carbonyl]-L-leucyl]-1-[N-[(phenylmethoxy)carbonyl]-L-leucyl]-3-pyrrolidinone:O40, bis-(Cbz-leucinyl)-1,3-diamino-propan-2-one:O39, (1S, 2'R)-N-2-[[(1-benzyloxycarbonyl)amino]-3-methylbutyl]thiazol4-ylcarbonyl-N'-2'-(benzyloxycarbonyl)amino4'-methylpenanoylhydrazide:O40, 4-[N-[(phenylmethoxy) carbonyl]-L-leucyl]-1-N[N-(methyl)-L-leucyl)]-3-pyrrolidinone:O31. The hydrophobic pocket lined with atoms from residues methionine 68, leucine 209, alanine 163 and alanine 134 and portions of tyrosine 67 interact with the isopropyl atoms; bis-(Cbz-leucinyl)-1,3-diamino-propan-2-one:C34–37, 2,2'-N,N'-bis-benzyloxycarbonyl-L-leucinylcarbohydrazide: C34–37, (1 S)-N-[2-[(1-benzyloxycarbonylamino)-3-methylbutyl]thiazol4-ylcarbonyl]-N'-(N-benzyloxycarbonyl-L-leucinyl) hydrazide; :C35–38, $^2$-[N-($^3$-benzyloxybenzoyl)]-2'-[N'-(N-benzyloxycarbonyl-L-leucinyl)]carbohydrazide:C32–35, 4-[N-[(phenylmethoxy)carbonyl]-L-leucyl]-1-[N-[(phenylmethoxy)carbonyl]-L-leucyl]-3-pyrrolidinone:C35–38, 4-[N-[(4-pyridylmethoxy)carbonyl]-L-leucyl]-1-[N-[(phenylmethoxy)carbonyl]-L-leucyl]-3-pyrrolidinone:C19–22, 1-N-(N-imidazole acetyl-leucinyl)-amino-3-N-(4-phenoxy-phenyl-sulfonyl)-amino-propan-2-one:C26–29. All inhibitors except 3(S)-3-[(N-benzyloxycarbonyl)-L-leucinyl]amino-5-methyl-1-(1-propoxy)-2-hexanone and 4-[N-[(phenylmethoxy) carbonyl]-L-leucyl]-1-N[N-(methyl)-L-leucyl)]-3-pyrrolidinone have aromatic groups that interact with tyrosine 67 on the protein. All inhibitors are covalently linked to the cysteine 25 SG atom through an inhibitor carbon atom.

The crystal structure of the protease of the present invention reveals the three dimensional structure of novel active site formed by the atoms of the amino acid residues listed in Table XXIX.

This structure is clearly useful in the structure-based design of protease inhibitors, which may be used as therapeutic agents against diseases in which inhibition of bone resorption is indicated. The discovery of the novel cathepsin K catalytic site permits the design of potent, highly selective protease inhibitors.

Another aspect of this invention involves a method for identifying inhibitors of cathepsin K characterized by the crystal structure and novel active site described herein, and the inhibitors themselves. The novel protease crystal structure of the invention permits the identification of inhibitors of protease activity. Such inhibitors may bind to all or a portion of the active site of cathepsin K; or even be competitive or non-competitive inhibitors. Once identified and screened for biological activity, these inhibitors may be used therapeutically or prophylactically to block protease activity.

One design approach is to probe the cathepsin K of the invention with molecules composed of a variety of different chemical entities to determine optimal sites for interaction between candidate cathepsin K inhibitors and the enzyme. For example, high resolution X-ray diffraction data collected from crystals saturated with solvent allows the determination of where each type of solvent molecule sticks. Small molecules that bind tightly to those sites can then be designed and synthesized and tested for their cathepsin K inhibitor activity.

This invention also enables the development of compounds that can isomerize to short-lived reaction intermediates in the chemical reaction of a substrate or other compound that binds to or with cathepsin K. Thus, the time-dependent analysis of structural changes in cathepsin K during its interaction with other molecules is permitted. The reaction intermediates of cathepsin K can also be deduced from the reaction product in co-complex with cathepsin K.

Such information is useful to design improved analogues of known cysteine protease inhibitors or to design novel classes of inhibitors based on the reaction intermediates of the cathepsin K enzyme and cathepsin K inhibitor co-complex. This provides a novel route for designing cathepsin K inhibitors with both high specificity and stability.

Another approach made possible by this invention, is to screen computationally small molecule data bases for chemical entities or compounds that can bind in whole, or in part, to the cathepsin K enzyme. In this screening, the quality of fit of such entities or compounds to the binding site may be judged either by shape complementarity [R. L. DesJarlais et al., *J. Med. Chem.* 31:722–729 (1988)] or by estimated interaction energy [E. C. Meng et al, *J. Comp. Chem.*, 13:505–524 (1992)].

Because cathepsin K may crystallize in more than one crystal form, the structure coordinates of cathepsin K, or portions thereof, as provided by this invention are particularly useful to solve the structure of those other crystal forms of cathepsin K. They may also be used to solve the structure of cathepsin K mutants, cathepsin K co-complexes, or of the crystalline form of any other protein with significant amino acid sequence homology to any functional domain of cathepsin K.

One method that may be employed for this purpose is molecular replacement. In this method, the unknown crystal structure, whether it is another crystal form of cathepsin K, a cathepsin K mutant, or a cathepsin K co-complex, or the crystal of some other protein with significant amino acid sequence homology to any functional domain of cathepsin K, may be determined using the cathepsin K structure coordinates of this invention as provided in Table I. This method will provide an accurate structural form for the unknown crystal more quickly and efficiently than attempting to determine such information ab initio.

Thus, the cathepsin K structure provided herein permits the screening of known molecules and/or the designing of new molecules which bind to the protease structure, particularly at the active site, via the use of computerized evaluation systems. For example, computer modeling systems are available in which the sequence of the protease, and the protease structure (i.e., atomic coordinates of cathepsin K and/or the atomic coordinate of the active site cavity, bond angles, dihedral angles, distances between atoms in the active site region, etc. as provided by Table I may be input. Thus, a machine readable medium may be encoded with data representing the coordinates of Table I in this process. The computer then generates structural details of the site into which a test compound should bind, thereby enabling the determination of the complementary structural details of said test compound.

More particularly, the design of compounds that bind to or inhibit cathepsin K according to this invention generally involves consideration of two factors. First, the compound must be capable of physically and structurally associating with cathepsin K. Non-covalent molecular interactions important in the association of cathepsin K with its substrate include hydrogen bonding, van der Waals and hydrophobic interactions.

Second, the compound must be able to assume a conformation that allows it to associate with cathepsin K. Although certain portions of the compound will not directly participate in this association with cathepsin K, those portions may still influence the overall conformation of the molecule. This, in turn, may have a significant impact on potency. Such conformational requirements include the overall three-dimensional structure and orientation of the chemical entity or compound in relation to all or a portion of the binding site, e.g., active site or accessory binding site of cathepsin K, or the spacing between functional groups of a compound comprising several chemical entities that directly interact with cathepsin K.

The potential inhibitory or binding effect of a chemical compound with cathepsin K may be estimated prior to its actual synthesis and testing by the use of computer modeling techniques. If the theoretical structure of the given compound suggests insufficient interaction and association between it and cathepsin K, synthesis and testing of the compound is obviated. However, if computer modeling indicates a strong interaction, the molecule may then be synthesized and tested for its ability to bind to cathepsin K in a suitable assay. In this manner, synthesis of inoperative compounds may be avoided.

An inhibitory or other binding compound of cathepsin K may be computationally evaluated and designed by means of a series of steps in which chemical entities or fragments are screened and selected for their ability to associate with the individual binding pockets or other areas of cathepsin K.

One skilled in the art may use one of several methods to screen chemical entities or fragments for their ability to associate with cathepsin K and more particularly with the individual binding pockets of the cathepsin K active site or accessory binding site. This process may begin by visual inspection of, for example, the active site on the computer screen based on the cathepsin K coordinates in Table I. Selected fragments or chemical entities may then be position cathepsin K. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities. These include:

GRID [P. J. Goodford, "A Computational Procedure for Determining Energetically Favorable Binding Sites on Biologically Important Macromolecules", *J. Med. Chem.*, 28:849–857 (1985)]. GRID is available from Oxford University, Oxford, UK.

MCSS [A. Miranker and M. Karplus, "Functionality Maps of Binding Sites: A Multiple Copy Simultaneous Search Method", *Proteins: Structure. Function and Genetics*, 11:29–34 (1991)]. MCSS is available from Molecular Simulations, Burlington, Mass.

AUTODOCK [D. S. Goodsell and A. J. Olsen, "Automated Docking of Substrates to Proteins by Simulated Annealing", *Proteins: Structure. Function. and Genetics*, 8:195–202 (1990)]. AUTODOCK is available from Scripps Research Institute, La Jolla, Calif.

DOCK [I. D. Kuntz et al, "A Geometric Approach to Macromolecule-Ligand Interactions", *J. Mol. Biol.*, 161:269–288 (1982)]. DOCK is available from University of California, San Francisco, Calif.

Additional commercially available computer databases for small molecular compounds includes Cambridge Structural Database and Fine Chemical Database, for a review see Rusinko, A., Chem. Des. Auto. News 8, 44–47 (1993).

Once suitable chemical entities or fragments have been selected, they can be assembled into a single compound or inhibitor. Assembly may be proceeded by visual inspection of the relationship of the fragments to each other on the three-dimensional image displayed on a computer screen in relation to the structure coordinates of cathepsin K. This would be followed by manual model building using software such as Quanta or Sybyl.

Useful programs to aid one of skill in the art in connecting the individual chemical entities or fragments include:

CAVEAT [P. A. Bartlett et al, "CAVEAT: A Program to Facilitate the Structure-Derived Design of Biologically Active Molecules", in *Molecular Recognition in Chemical and Biological Problems*", Special Pub., Royal Chem. Soc. 78, pp. 182–196 (1989)]. CAVEAT is available from the University of California, Berkeley, Calif.

3D Database systems such as MACCS-3D (MDL Information Systems, San Leandro, Calif). This area is reviewed in Y. C. Martin, "3D Database Searching in Drug Design", *J. Med. Chem.*, 35:2145–2154 (1992).

HOOK (available from Molecular Simulations, Burlington, Mass.).

Instead of proceeding to build a cathepsin K inhibitor in a step-wise fashion one fragment or chemical entity at a time as described above, inhibitory or other type of binding compounds may be designed as a whole or "de novo" using either an empty active site or optionally including some portion(s) of a known inhibitor(s). These methods include:

LUDI [H.-J. Bohm, "The Computer Program LUDI: A New Method for the De Novo Design of Enzyme Inhibitors", *J. Comp. Aid. Molec. Design* 6:61–78 (1992)]. LUDI is available from Biosym Technologies, San Diego, Calif.

LEGEND [Y. Nishibata and A. Itai, *Tetrahedron*, 47:8985 (1991)]. LEGEND is available from Molecular Simulations, Burlington, Mass.

LeapFrog (available from Tripos Associates, St. Louis, Mo.).

Other molecular modeling techniques may also be employed in accordance with this invention. See, e.g., N. C. Cohen et al, "Molecular Modeling Software and Methods for Medicinal Chemistry", *J. Med. Chem.*, 33:883–894 (1990). See also, M. A. Navia and M. A. Murcko, "The Use of Structural Information in Drug Design", *Current Opinions in Structural Biology*, 2:202–210 (1992). For example, where the structures of test compounds are known, a model of the test compound may be superimposed over the model of the structure of the invention. Numerous methods and techniques are known in the art for performing this step, any of which may be used. See, e.g., P. S. Farmer, Drug Design, Ariens, E. J., ed., Vol. 10, pp 119–143 (Academic Press, New York, 1980); U.S. Pat. No. 5,331,573; U.S. Pat. No. 5,500,807; C. Verlinde, Structure, 2:577–587 (1994); and I. D. Kuntz, *Science*, 257:1078–1082 (1992). The model building techniques and computer evaluation systems described herein are not a limitation on the present invention.

Thus, using these computer evaluation systems, a large number of compounds may be quickly and easily examined and expensive and lengthy biochemical testing avoided. Moreover, the need for actual synthesis of many compounds is effectively eliminated.

Once identified by the modeling techniques, the protease inhibitor may be tested for bioactivity using standard techniques. For example, structure of the invention may be used in binding assays using conventional formats to screen inhibitors. Suitable assays for use herein include, but are not limited to, the enzyme-linked immunosorbent assay (ELISA), or a fluoresence quench assay. See, for example, the cathepsin K activity assay of Example 2 below. Other assay formats may be used; these assay formats are not a limitation on the present invention.

In another aspect, the protease structure of the invention permit the design and identification of synthetic compounds and/or other molecules which have a shape complimentary to the conformation of the protease active site of the invention. Using known computer systems, the coordinates of the protease structure of the invention may be provided in machine readable form, the test compounds designed and/or screened and their conformations superimposed on the structure of the protease of the invention. Subsequently, suitable candidates identified as above may be screened for the desired protease inhibitory bioactivity, stability, and the like.

Once identified and screened for biological activity, these inhibitors may be used therapeutically or prophylactically to block cathepsin K activity.

The following examples illustrate various aspects of this invention. These examples do not limit the scope of this invention which is defined by the appended claims.

EXAMPLE 1

Analysis of the Structure of Cathepsin K

A. Expression, Purification and Crystalization

Cathepsin K (see FIG. 1) was expressed and purified as described in Bossard, M. J., et al., *J. BioL Chem.* 271, 12517–12524 (1996).

Crystals of cathepsin K were grown by vapor diffusion in hanging drops from a solution of 30% PEG 8000, 0.1 M Na+/K+phosphate at pH 4.5 containing 0.2M $Li_2SO_4$. Crystals of the complex are tetragonal, space group $P4_32_12$, with cell constants of a=57.7 Angstroms and c=131.1 Angstroms. The crystals contain one molecule in the asymmetric unit and contain 36% solvent with a $V_m$ value of 2.3 $Å^3$/Dalton. The structure was determined by molecular replacement using X-PLOR [Brunger, A.T., et al., *Science*, 235,458–460 (1987)]. The starting model consisted of the protein atoms from the cathepsin K E-64 complex structure described herein.

B. Model Building and Refinement

Using the three-dimensional electron density map obtained from above, the polypeptide chain of the cathepsin K can be traced without ambiguity. All 215 residues with side chains were built using the 3-D computer graphics program FRODO [Jones, T. A., *J. Appl. Crystallogr.*, 11, 268–272 (1978)]. Each of these 215 amino acids residues was manually positioned in its electron density, allowing for a unique position for each atom in cathepsin K in which each position is defined by a unique set of atomic coordinates (X,Y,Z) as shown in Table I. Starting with these atomic coordinates, a diffraction pattern was calculated and compared to the experimental data. The difference between the calculated and experimentally determined diffraction patterns was monitored by the value of $R_c$. The refinement (using X-PLOR) of the structural model necessitates adjustments of atomic positions to minimize the R-factor, where a value of below 20% is typical for a good quality protein structure and a value of higher than 25% usually indicates the need of further refinement.

EXAMPLE 2

Assays

Determination of cathepsin K proteolytic catalytic activity

All assays for cathepsin K were carried out with human recombinant enzyme. Standard assay conditions for the determination of kinetic constants used a fluorogenic peptide substrate, typically Cbz-Phe-Arg-AMC, and were determined in 100 mM Na acetate at pH 5.5 containing 20 mM cysteine and 5 mM EDTA. Stock substrate solutions were prepared at concentrations of 10 or 20 mM in DMSO with 20 uM final substrate concentration in the assays. All assays contained 10% DMSO. Independent experiments found that this level of DMSO had no effect on enzyme activity or kinetic constants. All assays were conducted at ambient temperature. Product fluorescence (excitation at 360 nM; emission at 460 nM) was monitored with a Perceptive Biosystems Cytofluor II fluorescent plate reader. Product progress curves were generated over 20 to 30 minutes following formation of AMC product.

Inhibition studies

Potential inhibitors were evaluated using the progress curve method. Assays were carried out in the presence of variable concentrations of test compound. Reactions were initiated by addition of enzyme to buffered solutions of inhibitor and substrate. Data analysis was conducted according to one of two procedures depending on the appearance of the progress curves in the presence of inhibitors. For those compounds whose progress curves were linear, apparent inhibition constants ($K_{i,app}$) were calculated according to equation 1 (Brandt et al., *Biochemistry*, 1989, 28, 140):

$$v = V_m A / [K_a(1 + I/K_{i,app}) + A] \quad (1)$$

where v is the velocity of the reaction with maximal velocity $V_m$, A is the concentration of substrate with Michaelis constant of $K_a$, and I is the concentration of inhibitor.

For those compounds whose progress curves showed downward curvature characteristic of time-dependent inhibition, the data from individual sets was analyzed to give kobs according to equation 2:

$$[AMC] = v_{ss}t + (v_0 - v_{ss})[1 - \exp(-k_{obs}t)]/k_{obs} \quad (2)$$

where [AMC] is the concentration of product formed over time t, $v_0$ is the initial reaction velocity and vss is the final steady state rate. Values for kobs were then analyzed as a linear function of inhibitor concentration to generate an apparent second order rate constant ($k_{obs}$/inhibitor concentration or $k_{obs}/[I]$) describing the time-dependent inhibition. A complete discussion of this kinetic treatment has been fully described (Morrison et al., *Adv. Enzymol. Relat. Areas Mol Biol*, 1988, 61, 201).

This assay measures the affinity of inhibitors to cathepsin K. One skilled in the art would consider any compound exhibiting a $K_i$ value of less than 50 micromolar to be a potential lead compound for further research. Preferably, the compounds used in the method of the present invention have a $K_i$ value of less than 1 micromolar. Most preferably, said compounds have a $K_i$ value of less than 100 nanomolar.

Human Osteoclast Resorption Assay

Aliquots of osteoclastoma-derived cell suspensions were removed from liquid nitrogen storage, warmed rapidly at 37° C. and washed ×1 in RPMI-1640 medium by centrifugation (1000 rpm, 5 min at 4° C.). The medium was aspirated and replaced with murine anti-HLA-DR antibody, diluted 1:3 in RPMI-1640 medium, and incubated for 30 min on ice The cell suspension was mixed frequently.

The cells were washed ×2 with cold RPMI-1640 by centrifugation (1000 rpm, 5 min at 4° C.) and then transferred to a sterile 15 mL centrifuge tube. The number of mononuclear cells were enumerated in an improved Neubauer counting chamber.

Sufficient magnetic beads (5/mononuclear cell), coated with goat anti-mouse IgG, were removed from their stock bottle and placed into 5 mL of fresh medium (this washes away the toxic azide preservative). The medium was removed by immobilizing the beads on a magnet and is replaced with fresh medium.

The beads were mixed with the cells and the suspension was incubated for 30 min on ice. The suspension was mixed frequently. The bead-coated cells were immobilized on a magnet and the remaining cells (osteoclast-rich fraction) were decanted into a sterile 50 mL centrifuge tube. Fresh medium was added to the bead-coated cells to dislodge any trapped osteoclasts. This wash process was repeated ×10. The bead-coated cells were discarded.

The osteoclasts were enumerated in a counting chamber, using a large-bore disposable plastic Pasteur pipette to charge the chamber with the sample. The cells were pelleted by centrifugation and the density of osteoclasts adjusted to $1.5 \times 10^4$/mL in EMEM medium, supplemented with 10% fetal calf serum and 1.7g/liter of sodium bicarbonate. 3 mL aliquots of the cell suspension (per treatment) were decanted into 15 mL centrifuge tubes. These cells were pelleted by centrifugation. To each tube 3 mL of the appropriate treatment was added (diluted to 50 uM in the EMEM medium). Also included were appropriate vehicle controls, a positive control (87MEM1 diluted to 100 ug/niL) and an isotype control (IgG2a diluted to 100 ug/mL). The tubes were incubate at 37° C. for 30 min. 0.5 mL aliquots of the cells were seeded onto sterile dentine slices in a 48- well plate and incubated at 37° C. for 2 h. Each treatment was screened in quadruplicate. The slices were washed in six changes of warm PBS (10 mL/well in a 6-well plate) and then placed into fresh treatment or control and incubated at 37° C. for 48 h. The slices were then washed in phosphate buffered saline and fixed in 2% glutaraldehyde (in 0.2M sodium cacodylate) for 5 min., following which they were washed in water and incubated in buffer for 5 min at 37° C. The slices were then washed in cold water and incubated in cold acetate buffer/fast red garnet for 5 min at 4° C. Excess buffer was aspirated, and the slices were air dried following a wash in water.

The TRAP positive osteoclasts were enumerated by bright-field microscopy and were then removed from the surface of the dentine by sonication. Pit volumes were determined using the Nikon/Lasertec ILM21W confocal microscope.

EXAMPLE 3

Method of Detecting Inhibitors

The three dimensional atomic structure can be readily used as a template for selecting potent inhibitors. Various computer programs and databases are available for the purpose. A good inhibitor should at least have excellent steric and electrostatic complementarity to the target, a fair amount of hydrophobic surface buried and sufficient conformational rigidity to minimize entropy loss upon binding. The approach usually comprises several steps:

1) Define a region to target. the active site cavity of cathepsin K can be selected, but any place that is essential to the protease activity could become a potential target. Since the crystal structure has been determined, the spatial and chemical properties of the target region is known.

2) Docking a small molecule onto the target. Many methods can be used to archive this. Computer databases of three-dimensional structures are available for screening millions of small molecular compounds. A negative image of these compounds can be calculated and used to match the shape of the target cavity. The profiles of hydrogen bond donor-acceptor and lipophilic points of these compounds can also be used to complement those of the target. Anyone skilled in the art would be able to identify many small molecules or fragments as hits.

3) Linking and extending recognition fragments. Using the hits identified by above procedure, one can incorporate different functional groups or small molecules into a single, larger molecule. The resulting molecule is likely to be more potent and have higher specificity. It is also possible to try to improve the "seed" inhibitor by adding more atoms or fragments that will interact with the target protein. The originally defined target region can be readily expanded to allow further necessary extension.

A limited number of promising compounds can be selected through the process. They can then be synthesized and assayed for their inhibitory properties.

The success rate can sometimes be as high as 20%, and it may still be higher with the rapid progresses in computing methods.

EXAMPLE 4

Crystallization of Enzyme with Inhibitors
A. Preparation of Inhibitors
Compound 1. Preparation of 4-[N-[(phenylmethoxy) carbonyl]-L-leucyl]-1-[N-[(phenvlmethoxy)carbonyl]-L-leucyl]-3-pyrrolidinone a) 3-hydroxy-4-[N-[(phenylmethoxy)carbonyl]-L-leucyl]-1-pyrrolidinecarboxylic acid 1,1dimethylethyl ester To a solution of 3-hydroxy-4-amino-1-pyrrolidinecarboxylic acid, 1,1-dimethylethyl ester (202 mg, 1.14 mmol) in $CH_2Cl_2$ (5 mL) was added CBZ-leucine (302.9 mg, 1.14 mmol), HOBT (154 mg, 1.14 mmol) and EDC (262.2 mg, 1.37 mmol). The reaction was allowed to stir until complete by TLC analysis whereupon it was diluted with EtOAc and washed sequentially with pH 4 buffer, sat. $K_2CO_3$, water and brine. The organic layer was dried (MgSO4), filtered and concentrated. Column chromatography of the residue (3:1 EtOAc:hexanes) gave 325 mg of the title compound: MS (ES+) 450.3 (MH+), 472.2 (M+Na).

b) 3-hydroxy-4-[N-[(phenylmethoxy)carbonyl]-L-leucyl]-1-pyrrolidine hydrochloride To a solution of the carbamate (310 mg, 0.69 mmol) in dry EtOAc (5.0 mL) was bubbled HCl gas for approximately 5 minutes. The reaction was stirred until TLC analysis indicated the complete consumption of the starting material. The reaction was then concentrated in vacuo to give 249 mg of the title compound: MS (ES+) 350.3 (MH+)

c) 4-[N-[(phenylmethoxy)carbonyl]-L-leucyl]-1-[N-[(phenylmethoxy)carbonyl]-L-leucyl]-3-pyrrolidinol To a solution of the amine hydrochloride from the previous step (249 mg, 0.64 mmol) in $CH_2Cl_2$ (10 mL) was added CBZ-leucine (170.4 mg, 0.64 mmol), HOBT (86.5 mg, 0.64 mmol), NMM (300 uL) and EDC (147.2 mg, 0.77 mmol). The reaction was allowed to stir at room temperature for 2 hours whereupon it was diluted with ethyl acetate and worked up as described previously. Column chromatography of the residue (3:1EtOAc:hexanes) gave 104 mg of the title compound: MS (ES+) 597.1 (MH+), 619.1 (M+Na).

d) 4-[N-[(phenylmethoxy)carbonyl]-L-leucyl]-1-[N-[(phenylmethoxy)carbonyl]-L-leucyl]-3-pyrrolidinone To a 0° C. solution of the alcohol (100 mg, 0.17 mmol) in acetone (5.0 mL) was added Jone's reagent dropwise until the brown color persisted. The reaction was allowed to warm to room temperature and stirred approximately 48 hours whereupon it was quenched with isopropanol, diluted with EtOAc and washed sequentially with sat. $K_2CO_3$, water and brine. The organic layer was dried (MgSO$_4$), filtered and concentrated. Column chromatography of the residue (3:1 EtOAc:hexanes) gave 31 mg of the title compound: MS (ES+) 595.1 (MH+), 617.0 (M+Na).

Compound 2. Preparation of 4-[N-[(phenylmethoxy) carbonyl]-L-leucyl]-1-N[N-(methyl)-L-leucyl)]3-pyrrolidinone a) 4-[N-[(phenylmethoxy)carbonyl]-L-leucyl]-1-[N-[(tert-butoxy)carbonyl]-N-(methyl)-L-leucyl]-3-pyrrolidinol To a solution of 3-hydroxy-4-[N-[(phenylmethoxy) carbonyl]-L-leucyl]-1-pyrrolidine (350 mg) was added N-BOC-N-methyl-leucine (222 mg, 0.0.91 mmol), HOBT (122.5 mg, 0.91 mmol), EDC (208.6 mg, 1.08 mmol) and N-methyl morpholine (0.3 mL, 2.72 mmol). The reaction was stirred at room temperature until complete by TLC analysis. Workup and column chromatography (1: 1 Hex:EtOAc ) gave 480 mg of the title compound which was used in the following reaction: MS (ES+) 477.4, 577.4 (MH+), 599.4 (M+Na).

b) 4-[N-[(phenylmethoxy)carbonyl]-L-leucyl]-1-[N-[(tert-butoxy)carbonyl]-N-(methyl)-L-leucyl]-3-pyrrolidinone To a -78° C. solution of oxalyl chloride (0.11 mL, 1.23 mmol) in $CH_2C_2$ was added DMSO (0.17 mL, 2.46 mmol) dropwise. The reaction was allowed to stir at -78° C. for 20 minutes whereupon a solution of the alcohol (474 mg, 0.82 mmol) in $CH_2Cl_2$ was added dropwise. The reaction was stirred at -78° C. for 30 minutes whereupon triethylamine (0.57 mL) was added in a single portion and allowed to warm to room temperature. Workup and column chromatography (2:1 hexanes:ethyl acetate) gave 247 mg of the title compound: MS (ES+) 475, 575 (M+H), 597 (M+Na).

c) 4-[N-[(phenylmethoxy)carbonyl]-L-leucyl]-1-N[N-(methyl)-L-leucyl)]-3-pyrrolidinone hydrochloride To a room temperature solution EtOAc/HCl was added the carbamate. The reaction was stirred until complete by TLC analysis. Concentration gave the title compound: MS (ES+) 475 (M+H, 100%).

Compound 3. Preparation of 4-[N-[(4-pyridylmethoxy) carbonyl]-L-leucyl]-1-[N-[(phenylmethox)carbonyl]-L-leucyl]-3-pyrrolidinone a) 3-hydroxy-4-[N-[(4-pyridylmethoxy)carbonyl]-L-leucyl]-1-pyrrolidinecarboxylic acid 1,1dimethylethyl ester 3-hydroxy4-amino-1-pyrrolidinecarboxylic acid, 1,1-dimethylethyl ester was coupled with iso-nicotinoyloxycarbonyl leucine in a similar manner as that described above to give 8.5 grams of the title compound: MS (ES+) 451 (MH+, 100%).

b) 3-hydroxy-4-[N-[(4-pyridylmethoxy)carbonyl]-L-leucyl]-1-pyrrolidine hydrochloride The carbamate from the previous step was deprotected with EtOAc/HCI to give 8.4 grams of the title compound after concentration: MS (ES+)351 (MH+, 100%).

c) 4-[N-[(4-pyridylmethoxy)carbonyl]-L-leucyl]-1-[N-[(phenylmethoxy)carbonyl]-L-leucyl]-3-pyrrolidinol To a solution of CBZ leucinal (155 mg) in $CH_2Cl_2$ was added triethylamine (0.09 mL) and the amine hydrochloride (200 mg, 0.52 mmol) from the previous step. The reaction was stirred at room temperature for 2 hours whereupon the majority of the solvent was removed in vacuo. The mixture was redissolved in $CH_2Cl_2$ and sodium triacetoxyborohydride was added. The reaction was stirred at room temperature for 4 hours. Workup and column chromatography (5% methanol/chloroform) gave 200.5 mg of the title compound: MS(ES+) 583 (MH+, 100%).

d) 4-[N-[(4-pyridylmethoxy)carbonyl]-L-leucyl]-1-[N-[(phenylmethoxy)carbonyl]-L-leucyl]-3-pyrrolidinone To a DMSO (2 mL) solution of the alcohol (50 mg, 0.09 mmol) from the previous step was added triethylamine (0.07 mL, 0.52 mmol) and pyridine/sulfur trioxide complex (41 mg, 0.26 mmol). The reaction was maintained at room temperature until complete by TLC analysis. Workup and chromatography (5% methanol/chloroform) gave 37 mg of the title compound: MS (ES+) 582 (MH+, 100%).

Compound 4. Preparation of (3S)-3-[(N-benzyloxycarbonyl)-L-leucinyl]-amino-1-(1-propoxy)-5-methyl-2-hexanone (3S)-3-[(N-benzyloxycarbonyl)-L-leucinyl]amino-1-diazo-5-methyl-2-hexanone (150 mg, 0.37 mmol) was dissolved in 1-propanol (2.5 ml), then rhodium acetate (2 mg) was added and the reaction was stirred at RT for 2h. The reaction mixture was chromatographed (silica gel, 20% EtOAc/hexanes) to yield the title compound as a white solid (59 mg, 37%). MS(ES) M+H$^+$=435, M+NH$_4$$^+$=452, 2M+H$^+$=869.6.

Compound 5. Preparation of bis-(Cbz-leucinyl)-1,3-diamino-propan-2-one Cbz-leucine (500 mg, 1.88 mmol), EDCI (558 mg, 1.88 mmol) was dissolved in DMF (4.0 ml) with 1,3-diamino-propan-2-ol (85 mg, 0.94 mmol) and Hunig's base (0.3 ml, 1.88 mmol) and was stirred at RT overnight. The reaction was diluted with EtOAc (20 ml) and was extracted with water (2×20 ml). The combined organics were dried with magnesium sulfate, filtered, concentrated in vacuo. The intermediate was then dissolved in acetone (4.0 ml) and Jones reagent (2.0 ml, 1.5 M) was added dropwise and the reaction was stirred at RT overnight. The excess Jones reagent was then quenched with isopropanol (1.0 ml), then the reaction was diluted with EtOAc (20 ml) and was extracted with water (2×20 ml) to remove the inorganic salts. The combined organics were dried with magnesium sulfate, filtered, concentrated, and chromatographed (silica gel, 2–5% MeOH/methylene chloride) to give the title compound as a white solid (410 mg, 75%). MS(ES) M+H$^+$= 583, M+Na$^+$=605.

Compound 6. Preparation of 2-[N-(3-benzyloxybenzoyl)-2'-[N'-(N-benzyloxycarbonyl]-L-leucinyl)]carbohydrazide a) methyl 3-benzyloxybenzoate To a suspension of NaH (0.395 g, 9.87 mmol, 60% in mineral oil) in DMF (20 mL) was added methyl 3-hydroxybenzoate (1.0 g, 6.58 mmol). After stirring for 15 min at room temperature, benzyl bromide (1.1 g, 6.58 mmol) was added. After stirring at room temperature for 3h, the solution was partitioned between ethyl acetate and water. The organic layer was washed with water (2×75 mL), saturated aqueous sodium bicarbonate, and brine, then dried (MgSO$_4$), filtered and concentrated to yield an off-white solid (1.013 g, 4.2 mmol). $^1$H NMR (400 MHz, CDCl$_3$) d 7.67 (m, 2H), 7.48–7.34 (m. 6H), 7.19 (m, 1H), 5.12 (s, 2H), 3.95 (s, 3H).

b) 3-benzyloxybenzoic acid

To a solution of the compound of Example 6(a) (0.400 g, 1.65 mmol) in THF (2 mL) and water (2 mL) was added lithium hydroxide monohydrate (0.076 g, 1.82 mmol). After stirring at reflux for 5 h, the solution was partitioned between ethyl acetate and 3N HCl. The organic layer was washed with brine, dried (MgSO$_4$), filtered and concentrated to yield a white solid (0.355 g, 1.56 mmol). $^1$H NMR (400 MHz, CD$_3$OD) d 7.58 (m, 2H), 7.36–7.24 (m. 6H), 7.10 (m, lH), 5.04 (s, 2H).

c) 2-[N-(3-benzyloxybenzoyl)]-2'-[N'-(N-benzyloxycarbonyl-L-leucinyl)]carbohydrazide Following the procedure of Example A, below, except substituting 3-benzyloxybenzoic acid for N-acetyl-L-leucine and 2-[N-(N-benzyloxycarbonyl-L-leucinyl)] carbohydrazide for 2-[N-(N-benzyloxycarbonyl-L-alanyl)] carbohydrazide, the title compound was prepared as a white solid (0.062 g, 25%). MS(ESI): 548.1 (M+H)$^+$.

EXAMPLE A

Preparation of 2-[N-(N-acetyl-L-leucinyl)-]2'-[N'-(N-benzyloxycarbonyl-L-alanyl)]carbohydrazide To a stirring solution of 2-[N-(N-benzyloxycarbonyl-L-alanyl)]carbohydrazide (0.15 g, 0.508 mmol) in DMF (2 mL) was added N-acetyl-L-leucine (0.092 g, 0.534 mmol), 1-hydroxybenzotriazole (0.014 g, 0.102 mmol), and 1-(3-dimethylaminopropyl)-3-ethylcarbodiimide hydrochloride (0.102 g, 0.534 mmol).

After stirring at room temperature for 16 h, the solution was diluted with ethyl acetate, washed successively with water, saturated aqueous sodium bicarbonate, and brine. The organic layer was dried (MgSO4), filtered and concentrated. The residue was purified by column chromatography (silica gel, methanol/dichloromethane) to yield the title compound as a white solid (0.028 g, 12%). MS(ESI): 451.1 (M+H)+.

Compound 7. Preparation of (1S)-N-[2-[(1-benzyloxycarbonylamino)-3-methylbutyl]thiazol4-ylcarbonyl]-N'-(N-benzyloxycarbonyl-L-leucinyl)hydrazide a) N-tert-butoxycarbonyl-(L)-leucinamide To a solution of N-tert-butoxycarbonyl-(L)-leucine (7.0g, 28. i mmol ) in dry THF (100 mL) at −40° C. was added isobutylchloroformate (3.8g, 28.1 mmol) and N-methylmorphiline (6.0, 59mmol). After 15 minutes of stirring, ammonia was bubbled through the mixture for an additional 15 minutes, then warmed to room temperature and allowed to stir for 2 hours. Mixture filtered and filtrate concentrated in vacuo to yield title compound as a white solid (6.5, 28.1 mmol). $^1$HNMR (400MHz, CDCl$_3$) d 6.38 (br s, 1H), 5.79 (br s, 1H), 5.04 (br d, 1H), 4.13 (m, 1H), 1.71–1.49 (m, 3H), 1.39 (s, 9H), 0.92 (dd, 6H).

b) N-tert-butoxycarbonyl-(L)-leucinethioamide

To a stirring solution of the compound of Example 7(a) (6.5, 28.0 mmol) in dry THF was added Lawesson's reagent (6.8g, 16.9 mmol) and the mixture was stirred at room temperature under argon overnight. The solvent was evaporated and the residue chromatographed (silica gel, 12% ethyl acetate/hexane) to give the title compound as a white solid (5.4g, 77%). 'HNMR (400MHz, CDCl$_3$) d 8.54 (br s, 1H), 7.97 (br s, 1H), 5.28 (br d, 1H), 4.52 (m, IH), 1.72–1.58 (m, 3H), 1.40 (s, 9H), 92 (m, 6H).

c) (1S)-1-(tert-butoxycarbonyl)amino-1-(4-carboethoxythiazol-2-yl)-3-methylbutane The compound of Example 7(b) (5.4g, 21.7 mmol) was stirred in dry acetone (100 mL) under argon at −10° C. Ethylbromopyruvate (4.7g, 23.9mmol) was added and stirred for 1 h at −10° C. The solution was poured into a well stirred mixture of chloroform and water and then into saturated sodium bicarbonate solution. The organic phase was separated and the aqueous layer extracted with chloroform. The combined organic extracts were dried over MgSO$_4$, filtered and concentrated to an oil. The oily residue was treated with TFAA (5.0 g, 23.9mmol) and pyridine (3.8g, 47.8mmol) in dichloromethane for 1 h at −20° C. Excess solvent was removed in vacuo and the residue was dissolved in dichloromethane. The solution was washed with saturated aqueous sodium bicarbonate and 1.0N KHSO$_4$ until pH 7. The solution was dried over magnesium sulfate, filtered and concentrated to an oil which was chromatographed (silica gel, 7.5% ethyl acetate/hexane) to give the title compound as a tan solid (4.5g, 61%). $^1$HNMR (400 MHz, CDCl$_3$) d 7.98 (s, 1H), 5.04 (br d, 1H), 4.95 (m, 1H), 4.31 (q, 2H), 1.88 (m, 1H), 1.63 (m, 2H), 1.40 (s, 9H),1.32 (t, 3H), 0.85 (dd, 6H).

d) (1 S)-1-(Benzyloxycarbonyl)amino-1-(4-carboethoxythiazol-2-yl)-3-methylbutane The compound of Example 7(c) (0.250 g, 0.731 mmol) was dissolved in TFA (2 mL) and stirred at room temperature for 15 minutes when diluted with methanol and concentrated in vacuo. The residue was dissolved in methylene chloride and treated with triethylamine (0.739 g, 7.3 mmol) followed by benzyl chloroformate (1 .2g, 7.31 mmol). The solution stirred at room temperature for 2 h when partition between ethyl acetate/water. The organic layer was washed with brine, collected, dried (MgSO$_4$) and concentrated to a residue that was chromatographed (silica gel, 15% ethyl acetate/hexane) to give the title compound as an oil (0.198 g, 72%). $^1$HNMR (400MHz, CDCl$_3$) d 8.01 (s, 1H), 7.32 (m, 5H), 5.51 (br d, 1H), 5.14 (m, 1H), 5.10 (s, 2H), 4.37 (q, 2H), 1.93 (m, 1H), 1.81–1.67 (m, 2H), 1.39 (t, 3H (m, 6H).

e) (1 S)-N-[2-[(1-benzyloxycarbonylamino)-3-methylbutyl]thiazol-4-ylcarbonyl]-N'-(N-benzyloxycarbonyl-L-leucinyl)hydrazide Following the procedure of Example B(a)–(d), below, except substituting (1S)-1-(Benzyloxycarbonyl)arnino-1-(4-carboethoxythiazol-2-yl)-3-methylbutane for (1S)-1-benzyloxycarbonylamino-1-(2-carboethoxythiazol4-yl)-3-methylbutane in step (c), the title compound was prepared. MS (MH$^+$): 610.0

EXAMPLE B

Preparation of (1S,2'R)-N-4-[[(1-benzyloxycarbonyl)amino]-3-methylbutyl]thiazol-2-ylcarbonyl-N'-2'-(benzyloxycarbonyl)amino4'-methylpentanoylhydrazide a) N-benzyloxycarbonyl-L-leucinyl bromomethyl ketone 1-methyl-3-nitro-1-nitrosoguanidine (6.65 g, 45.2 mmol) in ether (225 mL) is cooled to 0° C. 40% sodium hydroxide is added slowly and the diazomethane is allowed to collect in the ether solution for 30 minutes at 0° C. The ether solution is then decanted and left at 0° C.

N-Cbz-L-leucine (2.10 g, 7.6 mmol) was dissolved in THF (10 mL), cooled to –40° C., and 4-methylmorpholine (0.77 g, 7.6 mmol, 0.83 mL) was added, followed by dropwise addition of isobutyl chloroformate (1.04 g, 7.6 mmol, 0.98 mL). After 15 min, the solution was filtered into the previously prepared 0° C. solution of ethereal diazomethane. The resulting solution was allowed to stand at 0° C. for 23 h. HBr (30% in acetic acid) (45.2 mmol, 9 mL) was added and the resulting solution was stirred at 0° C. for 5 min, then washed sequentially with 0.1 N HCl, saturated aqueous NaHCO3 and saturated brine, then dried (MgSO4), filtered and concentrated to give the title compound as a colorless oil (2.43 g, 94%).

b) (1S)-1-benzyloxycarbonylamino-1-(2-carboethoxythiazol-4-yl)-3-methylbutane A solution of the compound of Example B(a) (1.57 g, 4.58 mmol) and ethyl thiooxamate (0.61 g, 4.58 mmol) in ethanol (10 mL) was heated at reflux for 4 h. The solution was then cooled, concentrated and the residue was purified by flash chromatography on 230–400 mesh silica gel, eluting with 1:4 ethyl acetate/hexanes, to give the title compound as a yellow oil (1.0 g, 58%). 1H NMR (400 MHz, CDC13) d 7.41 (s, 1H), 7.34–7.31 (m, 5H), 5.40 (d, 1H), 5.10 (d, 1H), 5.05 (d, 1H), 4.98 (q, 1H), 4.48 (q, 2H), 1.80–1.76 (m, 2H), 1.57–1.53 (m, 1H), 1.44 (t, 3H), 0.95 (d, 3H), 0.93 (d, 3H).

c) (1S)-1-benzyloxycarbonylamino-1-(2-hydrazinocarbonylthiazol-4-yl)-3-methylbutane A solution of the compound of Example B(b) (0.30 g, 0.8 mmol) and hydrazine hydrate (0.40 g, 8.0 mmol, 0.39 mL) in ethanol (8 mL) was allowed to stir at room temperature for 2 h. The solution was then concentrated to yield the title compound as a white foam (0.28 g, 98%). 1H NMR (400 MHz, CDC13) d 8.29 (s, 1H), 7.37–7.35 (m, 5H), 5.18 (d, 1H), 5.09 (dd, 2H), 4.95 (q, 1H), 4.07 (d, 2H), 1.71 (t, 2H), 1.55 (m, 1H), 0.96 (d, 3H), 0.94 (d, 3H).

d) (1S,2'R)-N-4-[[(1-benzyloxycarbonyl)amino]-3-methylbutyl]thiazol-2-ylcarbonyl-N'-2'-(benzyloxycarbonyl)amino-4'-methylpentanoylhydrazide A solution of the compound of Example B(c) (100 mg, 0.28 mmol), N-Cbz-L-leucine (80.5 mg, 0.30 mmol), 1-(3-dimethylaminopropyl)-3-ethylcarbodiimide hydrochloride (58.2 mg, 0.30 mmol) and 1-hydroxybenzotriazole (7.5 mg, 0.06 mmol) in DMF (0.6 mmol) was allowed to stir at room temperature for 18 h. The solution was diluted with ethyl acetate and washed successively with water, 0.1 N HCl, saturated aqueous NaHCO3 and saturated brine, then dried (MgSO4), filtered and concentrated. The residue was purified by flash chromatography on 230–400 mesh silica gel, eluting with 1:1 ethyl acetate/hexanes, to provide the title compound as a white solid (111.4 mg, 66%). mp 110–112° C.

Compound 8. Preparation of 2.2'-N.N'-bis-benzyloxycarbonyl-L-leucinylcarbohydrazide To a stirring solution of N-Cbz-L-leucine (Chemical Dynamics Corp.) (2.94 g, 11.1 mmol) in 22 mL of DMF was added carbohydrazide (0.5 g, 5.6 mmol), 1-(3-dimethylaminopropyl)-3-ethylcarbodiimide hydrochloride (2.13 g, 11.1 mmol) and 1-hydroxybenzotriazole (0.3 g, 2.2 mmol). After stirring at room temperature for 22 h, the solution was poured into 500 mL of water. The precipitate was collected by vacuum filtration and washed with water (4×150 mL) and dichloromethane (4×150 mL), then dried under vacuum to provide the title compound as a white solid (1.49 g, 46%). MS(ESI): 607.1 (M+Na)$^+$.

Compound 9. Preparation of 1-N-(N-imidazole acetyl-leucinyl)-amino-3-N-(4-phenoxy-phenyl-sulfonyl)-amino-propan-2-one a) 1-N-(N-imidazole acetyl-leucinyl)-amino-3-N-(4-phenoxy phenyl sulfonyl)-amino-propan-2-one Following the procedure of Example C(a)–(d), below, substituting "imidazole acetic acid" for "4-pyridyl acetic acid", the title compound was prepared: MS(ES) M+H$^+$542.

EXAMPLE C

Preparation of 1-N-(N-Cbz-leucinyl)-amino-3-N-(2-pyridyl-sulfonyl)-amino-propan-2-one a) 1-N-(N-Cbz-leucinyl)-amino-3-N-(4-phenoxy-phenyl-sulfonyl)-amino-1 0 propan-2-ol 1,3-Diamino propan-2-ol (6.75 g, 75 mmol) was dissolved in DMF (100 ml) and Cbz-leucine (20g, 75.5 mmol), HOBT-hydrate (1 Ig, 81.5 mmol), and EDCI (15.5 g, 81.2 mmol) were added. The reaction was stirred overnight at RT. A portion of the reaction mixture (30 ml) was concentrated in vacuo, then ether (50 15 ml) and MeOH (30 ml) were added. A 1N solution of hydrochloric acid in ether was added (1 M, 30 ml) and a white gum formed, which was washed several times with ether. MeOH-acetone were added and heated until the gum became a white solid. The white solid was dissolved in DMF (25 ml) and DIEA (5 ml), then 4-phenoxy phenyl sulfonyl chloride was added. The reaction was stirred for 2h, concentrated in vacuo, then chromatographed (silica gel, 1:1 EtOAc: hexanes) to provide the desired product as a white solid.

b) Leucinyl-amino-3-N-(4-phenoxy phenyl sulfonyl)-amino-propan-2-ol 1-N-(Cbz-leucinyl)-amino-3-N-(4-phenoxy-phenyl-sulfonyl)-amino-propan-2-ol (1.0g, 1.8 mmol) was dissolved in EtOH (30 ml), then 10% Pd/C (0.22g) was added followed by 6N hydrochloric acid (2.5 ml), and the reaction was stirred under a balloon of hydrogen gas for 4h at RT. The reaction mixture was filtered, concentrated, and azeotroped with toluene to provide a white glass which was used in the next reaction without further purification.

c) 1-N-(N-4-pyridyl acetyl-leucinyl)-amino-3-N-(4-phenoxy-phenyl-sulfonyl)-amino-propan-2-ol Leucinyl-amino-3-N-(4-phenoxy phenyl sulfonyl)-amino-propan-2-ol (0.36 g, 0.76 mmol) was dissolved in DMF (5 ml), then NMM (0.45 ml, 4 mmol) was added followed by 4-pyridyl acetic acid (0. 13g, 0.75 mmol) and HBTU (0.29g, 0.76 mmol) and the reaction was stirred at RT overnight. The reaction mixture was concentrated in vacuo, then chromatographed (silica gel, 5%MeOH: methylene chloride) to provide the desired product as a white solid (90 mg, MS(ES): M+H⁺=555.

d) 1-N-(N-4-pyridyl acetyl-leucinyl)-amino-3-N-(4-phenoxy-phenyl-sulfonyl)-amino-propan-2-one 1-N-(N4-pyridyl-acetyl-leucinyl)-amino-3-N-(4-phenoxy-phenyl-sulfonyl)-amino-propan-2-ol (45 mg, 0.08 mmol) was dissolved in acetone (5ml), then 1N hydrochloric acid (2 ml) was added. The reaction was concentrated in vacuo, then redissolved in acetone. Jones reagent (1.5 M, several drops) was added and the reaction mixture was stirred for 6h at RT. Isopropanol (0.5 ml) was added and the reaction mixture was concentrated in vacuo. The reaction was diluted with pH 7 buffer and then was extracted with EtOAc, dried with magnesium sulfate, filtered, concentrated in vacuo, then chromatographed (silica gel, 5% MeOH-methylene chloride) to give the desired product as a white solid (27 mg, 50%): MS(ES): M+H⁺=553.

B. Crystallization of the protein and protein-inhibitor complexes Human cathepsin K was expressed in baculovirus cells for the first eight of the nine inhibitors described below. Conditioned media containing expressed pro-cathepsin K was loaded directly onto an S-Sepharose column pre-equilibrated with 25 mM phosphate buffer at pH 8. The column was eluted with a NaCl gradient. Fractions containing pro-cathepsin K were pooled, concentrated to 2.5 mg/ml and activated to mature cathepsin K in 50 mM sodium acetate buffer pH 4.0 containing 20 mM L-cysteine and 1% mature cathepsin K as seed. The activation was monitored using CBZ-Phe-Arg-AMC,as fluorogenic substrate and by SDS-PAGE. When the increasing specific activity reached a plateau (ca. 15 μmol/min/mg), the reaction was stopped by the addition of inhibitor. The inhibited mature cathepsin K was concentrated and dialyzed against 20 mM MES, 50 mM NaCl, 2 mM L-cysteine, pH 6.

Protein preparation for cathepsin K complex with 4-[N-[(phenylmethoxy)carbonyl]-L-leucyl]-1-N[N-(methyl)-L-leucyl)]-3-pyrrolidinone (only) Human cathepsin K was expressed in $E.$ $coli$. The cell pellet from 1 L of bacterial culture weighing 2.35 gm. was washed with 50 mL of 50 mM Tris/HCl, 5 mM EDTA, 150 mM NaCl, pH 8.0. After centrifugation at 13,000×g for 15 mins, the washed pellet was resuspended into 25 mL of the same buffer prepared at 4° C. and lysed by passage twice through a cell disruptor (Avestin) at 10,000 psi. The lysate was centrifuged as above, the supernatant decanted and the pellet suspended in 25 mL 50 mM Tris/HCl, 10 mM DTT, 5 mM EDTA, 150 mM NaCl, pH 8.0 containing either 8 M urea or 6 M guanidine HCl. After stirring at 4° C. for 30 mins, insoluble cellular debris was removed by centrifugation at 23,000×g for 30 mins and the supernatant clarified by filtration (0.45 um, Millipore).

Varying amounts of the proenzyme form of cathepsin K were refolded by quick dilution into stirring, $N_2$ (g) sparged 50 mM Tris/HCl, 5 mM EDTA, 10 mM reduced and 1 mM oxidized glutathione, 0.7 M L-arginine pH 8.0 and stirred overnight at 4° C. After concentration to ca. 1 mg/mL using a stirred cell fitted with a YM-10 membrane (Amicon), the sample was clarified by centrifugation and filtration then dialyzed against 25 mM $Na_2PO_4$, 1.0 M NaCl, pH 7.0. The dialysate was applied at a LFR=23 cm/hr to a 2.6×90 cm column of Superdex 75 (Pharmacia) pre-equilibrated in 25 mM $Na_2PO_4$, 1.0 M NaCl, pH 7.0. The cathepsin K proenzyme was pooled based upon purity as observed on a reduced, SDS-PAGE gel.

Crystals of mature activated cathepsin K complexed with inhibitor grew to a size of approximately 0.2 mm³ in about six days at 20° C. The concentration of inhibited cathepsin K used in the crystallization was approximately 8 mg./ml. The method of vapor diffusion in hanging drops was used to grow crystals from the solution of cathepsin K-inhibitor complex. The initial crystal structure to be determined was that of cathepsin K in complex with the cysteine protease inhibitor E64. Crystals of mature activated cathepsin K complexed with E-64 grew to a size of approximately 0.2 mm³ in six days at 20° C. The concentration of E-64-inhibited cathepsin K used in the crystallization was 8 mg/ml. Vapor diffusion was used in hanging drops from a solution of 10% PEG 8000, 0.1 M $Na^+/K^+$phosphate at pH 6.2 containing 0.2M NaCl. Crystals of the complex are orthorhombic, space group $P2_12_12_1$, with cell constants of a=38.4, =50.7, and c=104.9 Angstroms. This crystal form will be referred to as Form II. The crystals contain one molecule in the asymmetric unit and contain approximately 40% solvent with a Vm value of 2.1 Å³/Dalton. X-ray diffraction data were measured from a single crystal using a Siemens two-dimensional position-sensitive detector on a Siemens rotating anode generate operating a 5 KW. The structure was determined by molecular replacement using X-PLOR. The starting model consisted of all atoms of the main chain of papain and those side chain atoms predicted to be homologous between the two proteins as determined from sequence alignment. The cross rotation function was calculated using x-ray diffraction data from 10 to 4 Å and a radius of integration of 32 Å. The highest peak was 6.0 σ. A translation search was carried out using data from 8 to 3.5 Angstroms resulting in the highest peak of 12.5. The resulting model gave an $R_c$ factor of 0.488. This model was refined by rigid-body refinement, and the resulting phases were used to calculate Fourier maps with coefficients $|F_o-F_c|$ and $|2F_o-F_c|$, into which the atomic model of cathepsin K was built using the molecular graphics program FRODO. Conventional positional refinement was used to refine the structure during model building. The structure was refined using X-PLOR. The electron density for E-64 was clear in the maps. The inhibitor was built into density and several additional cycles of map fitting and refinement were carried out to a final $R_c$ of 0.191.

Crystallization of the complex of cathepsin K with 3(S)-3-[(N-benzyloxycarbonyl)-L-leucinyl]amino-5-methyl-1-(1-propoxy)-2-hexanone Crystals of mature activated cathepsin K complexed with the inhibitor grew from a solution of 10% isopropanol, 0.1 M $NaPO_4$/citrate at pH 4.2. Crystals of the complex are tetragonal, space group $P4_32_12$, with cell constants of a=57.6 Å, and c=131.2 Å. This crystal form will be referred to as Form III. Diffraction data were collected as described above. The crystals contain one molecule in the asymmetric unit and contain 36% solvent with a $V_m$ value of 2.3 Å³/Dalton. The structure was determined by molecular replacement using X-PLOR at 2.5 Angstroms resolution. The starting model consisted of all protein atoms of the orthorhombic form of cathepsin K-E64 structure. Molecular replacement was carried out as described above for the cathepsin K-E64 structure determination. The model was refined by rigid-body refinement using X-PLOR, and the resulting phases were used to calculate Fourier maps with coefficients $|F_o-F_c|$ and $|2F_o-F_c|$, into which the atomic model of the inhibitor was built using the molecular graphics program FRODO. Conventional positional refinement was used to refine the structure during model building. The structure was refined using X-PLOR. Several cycles of map fitting and refinement were carried out to a final $R_c$ of 0.245.

Crystallization of the complex of cathepsin K with 2-[N-(3-benzyloxybenzoyl)]-2'-[N'-(N-benzyloxycarbonyl-L-leucinyl)]carbohydrazide Crystals of mature activated cathepsin K complexed with the inhibitor grew from a solution of 22.5% PEG 8000, 0.075 M sodium acetate at pH 4.5 containing 0.15 M $Li_2SO_4$. Crystals of the complex grew as Form III. Diffraction data were collected as described above. The structure was determined by rigid body refinement with X-PLOR utilizing the previous Form III protein model at 2.4 Angstroms resolution. Fourier maps with coefficients $|F_o-F_c|$ and $|2F_o-F_c|$ were used to fit the atomic model of the inhibitor using the molecular graphics program FRODO. Conventional positional refinement (X-PLOR) was used to refine the structure during model building. Several cycles of map fitting and refinement were carried out to a final $R_c$ of 0.237.

Crystallization of the complex of cathepsin K with bis-(Cbz-leucinyl)-1.3-diamino-propan-2-one Crystals of mature activated cathepsin K complexed with the inhibitor grew from a solution of 10% isopropanol, 0.1 M $NaPO_4$/citrate at pH 4.2. Crystals of the complex grow as Form III. Diffraction data were collected as described above. The structure was determined by rigid body refinement of the previous Form III protein model at 2.6 Angstroms resolution. Fourier maps with coefficients $|F_o-F_c|$ and $|2F_o-F_c|$ were used to fit the atomic model of the inhibitor using the molecular graphics program FRODO. Conventional positional refinement was used to refine the structure during model building. Several cycles of map fitting and refinement were carried out using X-PLOR to a final $R_c$ of 0.210.

Crystallization of the complex of cathepsin K with 4-[N-[(phenylmethoxy)carbonyl]-L-leucyl]-1-N[N-(methyl)-L-leucyl)]-3-pyrrolidinone Crystals of mature activated cathepsin K complexed with the inhibitor grew from a solution of 18% PEG 8000, 0.6 M sodium acetate at pH 4.5 containing 0.12 M $Li_2SO_4$. Crystals of the complex grow in Form III. Diffraction data were collected as described above. The structure was determined by rigid body refinement of the previous Form III protein model with X-PLOR at 2.4 Angstroms resolution. Fourier maps with coefficients $|F_o-F_c|$ and $|2F_o-F_c|$, were used to the atomic model of the inhibitor using the molecular graphics program FRODO. Conventional positional refinement was used to refine the structure during model building using X-PLOR. Several cycles of map fitting and refinement were carried out to a final $R_c$ of 0.218.

Crystallization of the complex of cathepsin K with (1S)-N-[2-[(1-benzyloxycarbonylamino)-3-methylbutyl]thiazol-4-ylcarbonyl]-N'-(N-benzyloxycarbonyl-L-leucinyl)hydrazide Crystals of mature activated cathepsin K complexed with the inhibitor grew from a solution of 30% MPD, 0.1 M MES at pH 7.0 and 0.1 M tris buffer at pH 7.0. Crystals of the complex are Form II. Diffraction data were collected as described above. The structure was determined by rigid body refinement of the previous Form II protein model with X-PLOR at 2.3 Angstroms resolution. Fourier maps with coefficients $|F_o-F_c|$ and $|2F_o-F_c|$, were used to the atomic model of the inhibitor using the molecular graphics program FRODO. Conventional positional refinement was used to refine the structure during model building using X-PLOR. Several cycles of map fitting and refinement were carried out to a final $R_c$ of 0.21 1.

Crystallization of the complex of cathepsin K with 2.2'-N.N'-bis-benzyloxycarbonyl-L-leucinylcarbohydrazide Crystals of mature activated cathepsin K complexed with the inhibitor grew from a solution of 33% MPD, 0.1 M MES at pH 7. Crystals of the complex grow as Form II. Diffraction data were collected as described above. The structure was determined by rigid body refinement of the previous Form II protein model with X-PLOR at 2.2 Angstroms resolution. Fourier maps with coefficients $|F_o-F_c|$ and $|2F_o-F_c|$, were used to the atomic model of the inhibitor using the molecular graphics program FRODO. Conventional positional refinement was used to refine the structure during model building using X-PLOR. Several cycles of map fitting and refinement were carried out to a final $R_c$ of 0.208.

Crystallization of the complex of cathepsin K with 4-[N-[(phenylmethoxy)carbonyl]-L-leucyl]-1-[N-[(phenylmethoxy)carbonyl]-L-leucyl]-3-pyrrolidinone Crystals of mature activated cathepsin K complexed with the inhibitor grew from a solution of 28% MPD, 0.1 M MES at pH 7.0 and 0.1 M tris buffer at pH 7.0. Crystals of the complex Form II. Diffraction data were collected as described above. The structure was determined by rigid body refinement of the previous Form II protein model with X-PLOR at 2.3 Angstroms resolution. Fourier maps with coefficients $|F_o-F_c|$ and $|2F_o-F_c|$, were used to the atomic model of the inhibitor using the molecular graphics program FRODO. Conventional positional refinement was used to refine the structure during model building using X-PLOR. Several cycles of map fitting and refinement were carried out to a final $R_c$ of 0.193.

Crystallization of the complex of cathepsin K with 4-[N-[(4-pyridylmethoxy)carbonyl]-L-leucyl]-1-[N-[(phenylmethoxy)carbonyl]-L-leucyl]-3-pyrrolidinone Crystals of mature activated cathepsin K complexed with the inhibitor grew from a solution of 30% MPD, 0.1 M MES at pH 7.0 and 0.1 M tris buffer at pH 7.0. Crystals of the complex Form II. Diffraction data were collected as described above. The structure was determined by rigid body refinement of the previous Form II protein model with X-PLOR at 2.2 Angstroms resolution. Fourier maps with coefficients $|F_o-F_c|$ and $|2F_o-F_c|$, were used to the atomic model of the inhibitor using the molecular graphics program FRODO. Conventional positional refinement was used to refine the structure during model building using X-PLOR. Several cycles of map fitting and refinement were carried out to a final $R_c$ of 0.267.

Crystallization of the complex of cathepsin K with 1-N-(N-imidazole acetyl-leucinyl)-amino-3-N-(4-phenoxy-phenyl-sulfonyl)-amino-propan-2-one Crystals of mature activated cathepsin K complexed with the inhibitor grew from a solution of 18% PEG 8000, 0.6 M sodium acetate at pH 4.5 containing 0.12 M $Li_2SO_4$. Crystals of the complex are Form III. Diffraction data were collected as described above. The structure was determined by rigid body refinement of the previous Form II protein model at 2.5 Angstroms resolution. Fourier maps with coefficients $|F_o-F_c|$ and $|2F_o-F_c|$ were used to fit the atomic model of the inhibitor using the molecular graphics program FRODO. Conventional positional refinement was used to refine the structure during model building. Several cycles of map fitting and refinement were carried out using X-PLOR to a final $R_c$ of 0.246.

Abbreviations

E-64, [1-[N-[(L-3-trans-carboxyoxirane-2carbonyl)-L-leucyl]amino]-4-guanidinobutane]

CBZ, benzyloxycarbonyl

AMC, aminomethylcoumarin

MPD, 2 methyl-2,4-pentanediol

PIPES, piperazone-N,N-bis(2-ethanesulfonic acid)

MES, 2-(N-morpholino)-ethanesulfonic acid tris, tris(hydroxymethyl)-aminomethane
PEG, polyethyleneglycol
M, Molar
$R_c = \Sigma |(F_o - F_c)|/F_o$
$F_o$=observed structure amplitude
$F_c$=calculated structure amplitude
EDTA, ethylenediaminetetraacetic acid
DTT, 1,4-dithiothreitol
SDS-PAGE, sodium dodecylsulfate polyacrylamide gel electrophoresis This invention is not to be limited in scope by the specific embodiments described herein. Indeed, various modifications of the invention in addition to those described herein will become apparent to those skilled in the art from the foregoing description. Such modifications are intended to fall within the scope of the appended claims.

The disclosures of the patents, patent applications and publications cited herein are incorporated by reference in their entireties.

TABLE I

Table of the orthogonal three dimensional coordinates in Ångstroms and B factors (Å²) for cathepsin K.

| Residue | Atom | X | Y | Z | B |
|---|---|---|---|---|---|
| 1 ALA | N | -3.94 | 11.01 | 90.45 | 15.00 |
| 1 ALA | CA | -4.70 | 12.30 | 90.45 | 15.00 |
| 1 ALA | C | -4.40 | 13.14 | 89.20 | 15.00 |
| 1 ALA | O | -3.34 | 12.99 | 88.57 | 15.00 |
| 1 ALA | CB | -4.36 | 13.12 | 91.73 | 15.00 |
| 2 PRO | N | -5.36 | 14.01 | 88.80 | 15.00 |
| 2 PRO | CA | -5.19 | 14.86 | 87.61 | 15.00 |
| 2 PRO | C | -4.35 | 16.05 | 88.06 | 15.00 |
| 2 PRO | O | -4.89 | 17.00 | 88.65 | 15.00 |
| 2 PRO | CB | -6.62 | 15.33 | 87.31 | 15.00 |
| 2 PRO | CG | -7.53 | 14.58 | 88.32 | 15.00 |
| 2 PRO | CD | -6.63 | 14.31 | 89.47 | 15.00 |
| 3 ASP | N | -3.04 | 16.00 | 87.87 | 15.00 |
| 3 ASP | CA | -2.25 | 17.14 | 88.30 | 15.00 |
| 3 ASP | C | -2.27 | 18.18 | 87.20 | 15.00 |
| 3 ASP | O | -1.57 | 18.02 | 86.20 | 15.00 |
| 3 ASP | CB | -0.82 | 16.75 | 88.67 | 15.00 |
| 3 ASP | CG | -0.09 | 17.85 | 89.45 | 15.00 |
| 3 ASP | OD1 | -0.74 | 18.83 | 89.89 | 15.00 |
| 3 ASP | OD2 | 1.14 | 17.73 | 89.63 | 15.00 |
| 4 SER | N | -3.10 | 19.21 | 87.36 | 15.00 |
| 4 SER | CA | -3.19 | 20.26 | 86.35 | 15.00 |
| 4 SER | C | -3.97 | 21.51 | 86.77 | 15.00 |
| 4 SER | O | -4.97 | 21.44 | 87.48 | 15.00 |
| 4 SER | CB | -3.77 | 19.72 | 85.03 | 15.00 |
| 4 SER | OG | -5.17 | 19.55 | 85.08 | 15.00 |
| 5 VAL | N | -3.50 | 22.65 | 86.28 | 15.00 |
| 5 VAL | CA | -4.10 | 23.94 | 86.54 | 15.00 |
| 5 VAL | C | -4.27 | 24.65 | 85.17 | 15.00 |
| 5 VAL | O | -3.43 | 24.48 | 84.28 | 15.00 |
| 5 VAL | CB | -3.22 | 24.79 | 87.51 | 15.00 |
| 5 VAL | CG1 | -1.80 | 24.88 | 87.00 | 15.00 |
| 5 VAL | CG2 | -3.79 | 26.17 | 87.69 | 15.00 |
| 6 ASP | N | -5.39 | 25.34 | 84.99 | 15.00 |
| 6 ASP | CA | -5.67 | 26.08 | 83.76 | 15.00 |
| 6 ASP | C | -6.40 | 27.34 | 84.22 | 15.00 |
| 6 ASP | O | -7.63 | 27.33 | 84.43 | 15.00 |
| 6 ASP | CB | -6.55 | 25.25 | 82.82 | 15.00 |
| 6 ASP | CG | -6.81 | 25.95 | 81.48 | 15.00 |
| 6 ASP | OD1 | -6.11 | 26.94 | 81.14 | 15.00 |
| 6 ASP | OD2 | -7.72 | 25.49 | 80.75 | 15.00 |
| 7 TYR | N | -5.64 | 28.42 | 84.37 | 15.00 |
| 7 TYR | CA | -6.15 | 29.70 | 84.84 | 15.00 |
| 7 TYR | C | -7.18 | 30.35 | 83.96 | 15.00 |
| 7 TYR | O | -7.76 | 31.36 | 84.33 | 15.00 |
| 7 TYR | CB | -5.00 | 30.67 | 85.09 | 15.00 |
| 7 TYR | CG | -4.06 | 30.20 | 86.18 | 15.00 |
| 7 TYR | OD1 | -4.41 | 30.29 | 87.52 | 15.00 |
| 7 TYR | OD2 | -2.82 | 29.64 | 85.86 | 15.00 |
| 7 TYR | CE1 | -3.55 | 29.86 | 88.52 | 15.00 |

TABLE I-continued

Table of the orthogonal three dimensional coordinates in Ångstroms and B factors (Å²) for cathepsin K.

| Residue | Atom | X | Y | Z | B |
|---|---|---|---|---|---|
| 7 TYR | CE2 | -1.96 | 29.21 | 86.84 | 15.00 |
| 7 TYR | CZ | -2.33 | 29.31 | 88.17 | 15.00 |
| 7 TYR | OH | -1.48 | 28.86 | 89.14 | 15.00 |
| 8 ARG | N | -7.41 | 29.78 | 82.79 | 15.00 |
| 8 ARG | CA | -8.41 | 30.30 | 81.87 | 15.00 |
| 8 ARG | C | -9.77 | 30.07 | 82.53 | 15.00 |
| 8 ARG | O | -10.65 | 30.93 | 82.49 | 15.00 |
| 8 ARG | CB | -8.33 | 29.58 | 80.53 | 15.00 |
| 8 ARG | CG | -7.00 | 29.76 | 79.85 | 15.00 |
| 8 ARG | CD | -7.00 | 29.12 | 78.48 | 15.00 |
| 8 ARG | NE | -7.27 | 27.69 | 78.52 | 15.00 |
| 8 ARG | CZ | -6.85 | 26.83 | 77.58 | 15.00 |
| 8 ARG | NH1 | -6.15 | 27.27 | 76.54 | 15.00 |
| 8 ARG | NH2 | -7.15 | 25.54 | 77.69 | 15.00 |
| 9 LYS | N | -9.90 | 28.94 | 83.20 | 15.00 |
| 9 LYS | CA | -11.12 | 28.60 | 83.91 | 15.00 |
| 9 LYS | C | -11.16 | 29.33 | 85.28 | 15.00 |
| 9 LYS | O | -11.96 | 28.99 | 86.15 | 15.00 |
| 9 LYS | CB | -11.18 | 27.08 | 84.13 | 15.00 |
| 9 LYS | CG | -11.04 | 26.25 | 82.86 | 15.00 |
| 9 LYS | CD | -11.09 | 24.72 | 83.11 | 15.00 |
| 9 LYS | CE | -9.80 | 24.15 | 83.76 | 15.00 |
| 9 LYS | NZ | -9.78 | 22.65 | 83.99 | 15.00 |
| 10 LYS | N | -10.33 | 30.35 | 85.47 | 15.00 |
| 10 LYS | CA | -10.28 | 31.03 | 86.76 | 15.00 |
| 10 LYS | C | -10.23 | 32.55 | 86.69 | 15.00 |
| 10 LYS | O | -10.11 | 33.20 | 87.73 | 15.00 |
| 10 LYS | CB | -9.10 | 30.51 | 87.58 | 15.00 |
| 10 LYS | CG | -9.05 | 28.98 | 87.72 | 15.00 |
| 10 LYS | CD | -7.68 | 28.45 | 88.13 | 15.00 |
| 10 LYS | CE | -7.54 | 28.31 | 89.63 | 15.00 |
| 10 LYS | NZ | -7.61 | 29.62 | 90.36 | 15.00 |
| 11 GLY | N | -10.29 | 33.11 | 85.48 | 15.00 |
| 11 GLY | CA | -10.27 | 34.56 | 85.31 | 15.00 |
| 11 GLY | C | -8.96 | 35.28 | 85.53 | 15.00 |
| 11 GLY | O | -8.93 | 36.49 | 85.77 | 15.00 |
| 12 TYR | N | -7.86 | 34.54 | 85.44 | 15.00 |
| 12 TYR | CA | -6.54 | 35.11 | 85.64 | 15.00 |
| 12 TYR | C | -5.97 | 35.67 | 84.36 | 15.00 |
| 12 TYR | O | -5.13 | 36.58 | 84.39 | 15.00 |
| 12 TYR | CB | -5.57 | 34.04 | 86.13 | 15.00 |
| 12 TYR | CG | -5.76 | 33.63 | 87.56 | 15.00 |
| 12 TYR | CD1 | -6.85 | 32.86 | 87.95 | 15.00 |
| 12 TYR | CD2 | -4.82 | 33.98 | 88.52 | 15.00 |
| 12 TYR | CE1 | -7.00 | 32.46 | 89.25 | 15.00 |
| 12 TYR | CE2 | -4.96 | 33.58 | 89.83 | 15.00 |
| 12 TYR | CZ | -6.04 | 32.81 | 90.19 | 15.00 |
| 12 TYR | OH | -6.16 | 32.38 | 91.49 | 15.00 |
| 13 VAL | N | -6.40 | 35.09 | 83.24 | 15.00 |
| 13 VAL | CA | -5.92 | 35.47 | 81.92 | 15.00 |
| 13 VAL | C | -6.95 | 36.24 | 81.09 | 15.00 |
| 13 VAL | O | -8.15 | 36.03 | 81.21 | 15.00 |
| 13 VAL | CB | -5.41 | 34.21 | 81.15 | 15.00 |
| 13 VAL | CG1 | -6.54 | 33.26 | 80.89 | 15.00 |
| 13 VAL | CG2 | -4.73 | 34.61 | 79.86 | 15.00 |
| 14 THR | N | -6.45 | 37.19 | 80.31 | 15.00 |
| 14 THR | CA | -7.27 | 38.02 | 79.44 | 15.00 |
| 14 THR | C | -7.39 | 37.38 | 78.05 | 15.00 |
| 14 THR | O | -6.69 | 36.41 | 77.74 | 15.00 |
| 14 THR | CB | -6.63 | 39.42 | 79.32 | 15.00 |
| 14 THR | OG1 | -5.21 | 39.28 | 79.27 | 15.00 |
| 14 THR | CG2 | -7.00 | 40.28 | 80.52 | 15.00 |
| 15 PRO | N | -8.31 | 37.88 | 77.20 | 15.00 |
| 15 PRO | CA | -8.50 | 37.34 | 75.86 | 15.00 |
| 15 PRO | C | -7.23 | 37.45 | 75.01 | 15.00 |
| 15 PRO | O | -6.38 | 38.30 | 75.30 | 15.00 |
| 15 PRO | CB | -9.61 | 38.22 | 75.30 | 15.00 |
| 15 PRO | CG | -10.38 | 38.60 | 76.51 | 15.00 |
| 15 PRO | CD | -9.28 | 38.96 | 77.45 | 15.00 |
| 16 VAL | N | -7.14 | 36.65 | 73.95 | 15.00 |
| 16 VAL | CA | -5.97 | 36.64 | 73.08 | 15.00 |
| 16 VAL | C | -5.86 | 37.87 | 72.18 | 15.00 |
| 16 VAL | O | -6.80 | 38.23 | 71.47 | 15.00 |
| 16 VAL | CB | -5.94 | 35.38 | 72.22 | 15.00 |

TABLE I-continued

Table of the orthogonal three dimensional coordinates in Ångstroms and B factors (Å²) for cathepsin K.

| Residue | Atom | X | Y | Z | B |
|---|---|---|---|---|---|
| 16 VAL | CG1 | −4.70 | 35.38 | 71.34 | 15.00 |
| 16 VAL | CG2 | −5.97 | 34.18 | 73.10 | 15.00 |
| 17 LYS | N | −4.70 | 38.52 | 72.22 | 15.00 |
| 17 LYS | CA | −4.47 | 39.71 | 71.43 | 15.00 |
| 17 LYS | C | −3.49 | 39.39 | 70.31 | 15.00 |
| 17 LYS | O | −2.82 | 38.36 | 70.34 | 15.00 |
| 17 LYS | CB | −3.93 | 40.85 | 72.30 | 15.00 |
| 17 LYS | CG | −4.99 | 41.75 | 72.95 | 15.00 |
| 17 LYS | CD | −5.84 | 41.01 | 73.99 | 15.00 |
| 17 LYS | CE | −5.88 | 41.72 | 75.34 | 15.00 |
| 17 LYS | NZ | −4.53 | 41.86 | 75.97 | 15.00 |
| 18 ASN | N | −3.43 | 40.30 | 69.35 | 15.00 |
| 18 ASN | CA | −2.58 | 40.20 | 68.17 | 15.00 |
| 18 ASN | C | −1.54 | 41.29 | 68.24 | 15.00 |
| 18 ASN | O | −1.89 | 42.46 | 68.35 | 15.00 |
| 18 ASN | CB | −3.42 | 40.41 | 66.91 | 15.00 |
| 18 ASN | CG | −2.71 | 39.96 | 65.64 | 15.00 |
| 18 ASN | OD1 | −1.74 | 40.58 | 65.19 | 15.00 |
| 18 ASN | ND2 | −3.19 | 38.87 | 65.06 | 15.00 |
| 19 GLN | N | −0.27 | 40.92 | 68.15 | 15.00 |
| 19 GLN | CA | 0.79 | 41.91 | 68.23 | 15.00 |
| 19 GLN | C | 0.97 | 42.67 | 66.95 | 15.00 |
| 19 GLN | O | 1.54 | 43.76 | 66.94 | 15.00 |
| 19 GLN | CB | 2.10 | 41.26 | 68.59 | 15.00 |
| 19 GLN | CG | 2.54 | 40.22 | 67.63 | 15.00 |
| 19 GLN | CD | 3.88 | 39.71 | 67.99 | 15.00 |
| 19 GLN | OE1 | 4.04 | 38.93 | 68.92 | 15.00 |
| 19 GLN | NE2 | 4.89 | 40.20 | 67.31 | 15.00 |
| 20 GLY | N | 0.51 | 42.07 | 65.86 | 15.00 |
| 20 GLY | CA | 0.62 | 42.69 | 64.56 | 15.00 |
| 20 GLY | C | 1.98 | 42.49 | 63.90 | 15.00 |
| 20 GLY | O | 2.53 | 41.39 | 63.86 | 15.00 |
| 21 GLN | N | 2.50 | 43.60 | 63.38 | 15.00 |
| 21 GLN | CA | 3.77 | 43.62 | 62.67 | 15.00 |
| 21 GLN | C | 4.94 | 43.82 | 63.62 | 15.00 |
| 21 GLN | O | 6.05 | 43.35 | 63.36 | 15.00 |
| 21 GLN | CB | 3.73 | 44.74 | 61.64 | 15.00 |
| 21 GLN | CG | 2.68 | 44.55 | 60.56 | 15.00 |
| 21 GLN | CD | 2.88 | 43.25 | 59.82 | 15.00 |
| 21 GLN | OE1 | 4.01 | 42.87 | 59.52 | 15.00 |
| 21 GLN | NE2 | 1.79 | 42.55 | 59.56 | 15.00 |
| 22 CYS | N | 4.68 | 44.56 | 64.69 | 15.00 |
| 22 CYS | CA | 5.65 | 44.87 | 65.73 | 15.00 |
| 22 CYS | C | 6.15 | 43.60 | 66.46 | 15.00 |
| 22 CYS | O | 5.37 | 42.68 | 66.72 | 15.00 |
| 22 CYS | CB | 4.97 | 45.82 | 66.71 | 15.00 |
| 22 CYS | SG | 5.96 | 46.40 | 68.11 | 15.00 |
| 23 GLY | N | 7.45 | 43.53 | 66.73 | 15.00 |
| 23 GLY | CA | 8.00 | 42.37 | 67.42 | 15.00 |
| 23 GLY | C | 7.84 | 42.62 | 68.90 | 15.00 |
| 23 GLY | O | 8.80 | 42.94 | 69.61 | 15.00 |
| 24 SER | N | 6.60 | 42.54 | 69.37 | 15.00 |
| 24 SER | CA | 6.33 | 42.80 | 70.77 | 15.00 |
| 24 SER | C | 5.75 | 41.63 | 71.54 | 15.00 |
| 24 SER | O | 4.72 | 41.77 | 72.20 | 15.00 |
| 24 SER | CB | 5.44 | 44.05 | 70.90 | 15.00 |
| 24 SER | OG | 4.14 | 43.81 | 70.40 | 15.00 |
| 25 CYC | N | 6.39 | 40.47 | 71.48 | 15.00 |
| 25 CYC | CA | 5.88 | 39.34 | 72.25 | 15.00 |
| 25 CYC | CB | 6.32 | 38.03 | 71.63 | 15.00 |
| 25 CYC | SG | 8.04 | 38.06 | 71.17 | 15.00 |
| 25 CYC | C | 6.33 | 39.44 | 73.72 | 15.00 |
| 25 CYC | O | 5.67 | 38.91 | 74.62 | 15.00 |
| 25 CYC | O1 | 7.96 | 38.09 | 69.44 | 15.00 |
| 26 TRP | N | 7.45 | 40.14 | 73.95 | 15.00 |
| 26 TRP | CA | 7.97 | 40.33 | 75.30 | 15.00 |
| 26 TRP | C | 7.04 | 41.24 | 76.05 | 15.00 |
| 26 TRP | O | 6.67 | 40.96 | 77.18 | 15.00 |
| 26 TRP | CB | 9.37 | 40.92 | 75.27 | 15.00 |
| 26 TRP | CG | 9.47 | 42.24 | 74.61 | 15.00 |
| 26 TRP | CD1 | 9.74 | 42.49 | 73.30 | 15.00 |
| 26 TRP | CD2 | 9.32 | 43.52 | 75.24 | 15.00 |
| 26 TRP | NE1 | 9.78 | 43.84 | 73.06 | 15.00 |
| 26 TRP | CE2 | 9.52 | 44.50 | 74.24 | 15.00 |
| 26 TRP | CE3 | 9.04 | 43.94 | 76.55 | 15.00 |
| 26 TRP | CZ2 | 9.45 | 45.88 | 74.51 | 15.00 |
| 26 TRP | CZ3 | 8.98 | 45.32 | 76.82 | 15.00 |
| 26 TRP | CH2 | 9.18 | 46.27 | 75.80 | 15.00 |
| 27 ALA | N | 6.63 | 42.32 | 75.39 | 15.00 |
| 27 ALA | CA | 5.70 | 43.30 | 75.95 | 15.00 |
| 27 ALA | C | 4.40 | 42.61 | 76.34 | 15.00 |
| 27 ALA | O | 3.92 | 42.75 | 77.47 | 15.00 |
| 27 ALA | CB | 5.43 | 44.39 | 74.93 | 15.00 |
| 28 PHE | N | 3.83 | 41.86 | 75.40 | 15.00 |
| 28 PHE | CA | 2.60 | 41.13 | 75.63 | 15.00 |
| 28 PHE | C | 2.79 | 40.08 | 76.73 | 15.00 |
| 28 PHE | O | 2.00 | 40.02 | 77.66 | 15.00 |
| 28 PHE | CB | 2.10 | 40.48 | 74.33 | 15.00 |
| 28 PHE | CG | 1.41 | 41.44 | 73.39 | 15.00 |
| 28 PHE | CD1 | 2.14 | 42.29 | 72.57 | 15.00 |
| 28 PHE | CD2 | 0.02 | 41.51 | 73.33 | 15.00 |
| 28 PHE | CE1 | 1.51 | 43.18 | 71.73 | 15.00 |
| 28 PHE | CE2 | −0.62 | 42.40 | 72.49 | 15.00 |
| 28 PHE | CZ | 0.12 | 43.24 | 71.69 | 15.00 |
| 29 SER | N | 3.85 | 39.28 | 76.64 | 15.00 |
| 29 SER | CA | 4.15 | 38.25 | 77.64 | 15.00 |
| 29 SER | C | 4.33 | 38.84 | 79.03 | 15.00 |
| 29 SER | O | 3.95 | 38.23 | 80.03 | 15.00 |
| 29 SER | CB | 5.43 | 37.50 | 77.25 | 15.00 |
| 29 SER | OG | 5.78 | 36.51 | 78.20 | 15.00 |
| 30 SER | N | 4.96 | 40.01 | 79.08 | 15.00 |
| 30 SER | CA | 5.18 | 40.71 | 80.33 | 15.00 |
| 30 SER | C | 3.84 | 41.16 | 80.89 | 15.00 |
| 30 SER | O | 3.48 | 40.84 | 82.03 | 15.00 |
| 30 SER | CB | 6.10 | 41.91 | 80.10 | 15.00 |
| 30 SER | OG | 7.39 | 41.48 | 79.72 | 15.00 |
| 31 VAL | N | 3.08 | 41.87 | 80.07 | 15.00 |
| 31 VAL | CA | 1.75 | 42.34 | 80.48 | 15.00 |
| 31 VAL | C | 0.85 | 41.18 | 80.88 | 15.00 |
| 31 VAL | O | 0.03 | 41.31 | 81.77 | 15.00 |
| 31 VAL | CB | 1.09 | 43.16 | 79.36 | 15.00 |
| 31 VAL | CG1 | −0.41 | 43.10 | 79.47 | 15.00 |
| 31 VAL | CG2 | 1.57 | 44.60 | 79.43 | 15.00 |
| 32 GLY | N | 1.05 | 40.04 | 80.24 | 15.00 |
| 32 GLY | CA | 0.26 | 38.85 | 80.51 | 15.00 |
| 32 GLY | C | 0.56 | 38.20 | 81.83 | 15.00 |
| 32 GLY | O | −0.24 | 37.41 | 82.32 | 15.00 |
| 33 ALA | N | 1.74 | 38.46 | 82.39 | 15.00 |
| 33 ALA | CA | 2.10 | 37.90 | 83.69 | 15.00 |
| 33 ALA | C | 1.61 | 38.88 | 84.75 | 15.00 |
| 33 ALA | O | 1.01 | 38.49 | 85.75 | 15.00 |
| 33 ALA | CB | 3.59 | 37.68 | 83.80 | 15.00 |
| 34 LEU | N | 1.79 | 40.17 | 84.49 | 15.00 |
| 34 LEU | CA | 1.35 | 41.21 | 85.40 | 15.00 |
| 34 LEU | C | −0.15 | 41.08 | 85.64 | 15.00 |
| 34 LEU | O | −0.65 | 41.47 | 86.69 | 15.00 |
| 34 LEU | CB | 1.64 | 42.59 | 84.83 | 15.00 |
| 34 LEU | CG | 3.09 | 42.99 | 84.57 | 15.00 |
| 34 LEU | CD1 | 3.08 | 44.29 | 83.81 | 15.00 |
| 34 LEU | CD2 | 3.84 | 43.15 | 85.87 | 15.00 |
| 35 GLU | N | −0.88 | 40.56 | 84.64 | 15.00 |
| 35 GLU | CA | −2.32 | 40.39 | 84.82 | 15.00 |
| 35 GLU | C | −2.66 | 39.14 | 85.64 | 15.00 |
| 35 GLU | O | −3.66 | 39.11 | 86.37 | 15.00 |
| 35 GLU | CB | −2.98 | 40.28 | 83.45 | 15.00 |
| 35 GLU | CG | −2.84 | 41.50 | 82.57 | 15.00 |
| 35 GLU | CD | −3.34 | 41.23 | 81.17 | 15.00 |
| 35 GLU | OE1 | −3.19 | 40.08 | 80.70 | 15.00 |
| 35 GLU | OE2 | −3.87 | 42.16 | 80.54 | 15.00 |
| 36 GLY | N | −1.84 | 38.10 | 85.50 | 15.00 |
| 36 GLY | CA | −2.08 | 36.89 | 86.26 | 15.00 |
| 36 GLY | C | −1.99 | 37.16 | 87.76 | 15.00 |
| 36 GLY | O | −2.78 | 36.62 | 88.55 | 15.00 |
| 37 GLN | N | −1.03 | 37.99 | 88.17 | 15.00 |
| 37 GLN | CA | −0.86 | 38.31 | 89.57 | 15.00 |
| 37 GLN | C | −1.88 | 39.32 | 90.06 | 15.00 |
| 37 GLN | O | −2.40 | 39.18 | 91.17 | 15.00 |
| 37 GLN | CB | 0.55 | 38.83 | 89.86 | 15.00 |

TABLE I-continued

Table of the orthogonal three dimensional coordinates in Ångstroms and B factors (Å²) for cathepsin K.

| Residue | Atom | X | Y | Z | B |
|---|---|---|---|---|---|
| 37 GLN | CG | 1.61 | 37.74 | 90.00 | 15.00 |
| 37 GLN | CD | 1.14 | 36.57 | 90.83 | 15.00 |
| 37 GLN | OE1 | 0.97 | 36.67 | 92.05 | 15.00 |
| 37 GLN | NE2 | 0.93 | 35.43 | 90.17 | 15.00 |
| 38 LEU | N | -2.17 | 40.32 | 89.23 | 15.00 |
| 38 LEU | CA | -3.14 | 41.34 | 89.61 | 15.00 |
| 38 LEU | C | -4.49 | 40.73 | 90.02 | 15.00 |
| 38 LEU | O | -5.12 | 41.20 | 90.95 | 15.00 |
| 38 LEU | CB | -3.34 | 42.35 | 88.48 | 15.00 |
| 38 LEU | CG | -4.22 | 43.54 | 88.86 | 15.00 |
| 38 LEU | CD1 | -3.64 | 44.20 | 90.08 | 15.00 |
| 38 LEU | CD2 | -4.33 | 44.53 | 87.71 | 15.00 |
| 39 LYS | N | -4.92 | 39.70 | 89.30 | 15.00 |
| 39 LYS | CA | -6.18 | 39.02 | 89.60 | 15.00 |
| 39 LYS | C | -6.00 | 38.22 | 90.90 | 15.00 |
| 39 LYS | O | -6.92 | 38.19 | 91.73 | 15.00 |
| 39 LYS | CB | -6.58 | 38.09 | 88.45 | 15.00 |
| 39 LYS | CG | -7.57 | 36.99 | 88.79 | 15.00 |
| 39 LYS | CD | -8.95 | 37.51 | 89.13 | 15.00 |
| 39 LYS | CE | -9.89 | 36.35 | 89.41 | 15.00 |
| 39 LYS | NZ | -11.25 | 36.77 | 89.82 | 15.00 |
| 40 LYS | N | -4.83 | 37.60 | 91.07 | 15.00 |
| 40 LYS | CA | -4.57 | 36.82 | 92.28 | 15.00 |
| 40 LYS | C | -4.64 | 37.74 | 93.49 | 15.00 |
| 40 LYS | O | -5.25 | 37.40 | 94.51 | 15.00 |
| 40 LYS | CB | -3.20 | 36.16 | 92.21 | 15.00 |
| 40 LYS | CG | -3.09 | 34.85 | 92.98 | 15.00 |
| 40 LYS | CD | -1.63 | 34.41 | 93.04 | 15.00 |
| 40 LYS | CE | -1.44 | 33.15 | 93.86 | 15.00 |
| 40 LYS | NZ | 0.00 | 32.80 | 94.08 | 15.00 |
| 41 LYS | N | -4.06 | 38.93 | 93.36 | 15.00 |
| 41 LYS | CA | -4.06 | 39.93 | 94.43 | 15.00 |
| 41 LYS | C | -5.40 | 40.66 | 94.59 | 15.00 |
| 41 LYS | O | -6.17 | 40.38 | 95.49 | 15.00 |
| 41 LYS | CB | -2.93 | 40.95 | 94.23 | 15.00 |
| 41 LYS | CG | -1.55 | 40.33 | 94.11 | 15.00 |
| 41 LYS | CD | -1.34 | 39.26 | 95.18 | 15.00 |
| 41 LYS | CE | -0.06 | 38.46 | 94.95 | 15.00 |
| 41 LYS | NZ | -0.04 | 37.19 | 95.74 | 15.00 |
| 42 THR | N | -5.69 | 41.58 | 93.67 | 15.00 |
| 42 THR | CA | -6.91 | 42.36 | 93.75 | 15.00 |
| 42 THR | C | -8.23 | 41.65 | 93.40 | 15.00 |
| 42 THR | O | -9.28 | 42.28 | 93.37 | 15.00 |
| 42 THR | CB | -6.77 | 43.64 | 92.91 | 15.00 |
| 42 THR | OG1 | -6.89 | 43.34 | 91.51 | 15.00 |
| 42 THR | CG2 | -5.40 | 44.26 | 93.16 | 15.00 |
| 43 GLY | N | -8.17 | 40.35 | 93.10 | 15.00 |
| 43 GLY | CA | -9.38 | 39.62 | 92.78 | 15.00 |
| 43 GLY | C | -10.09 | 39.89 | 91.44 | 15.00 |
| 43 GLY | O | -10.94 | 39.09 | 91.03 | 15.00 |
| 44 LYS | N | -9.82 | 41.02 | 90.79 | 15.00 |
| 44 LYS | CA | -10.45 | 41.31 | 89.50 | 15.00 |
| 44 LYS | C | -9.41 | 41.72 | 88.45 | 15.00 |
| 44 LYS | O | -8.48 | 42.49 | 88.73 | 15.00 |
| 44 LYS | CB | -11.57 | 42.34 | 89.64 | 15.00 |
| 44 LYS | CG | -11.20 | 43.55 | 90.45 | 15.00 |
| 44 LYS | CD | -12.43 | 44.28 | 90.95 | 15.00 |
| 44 LYS | CE | -12.02 | 45.39 | 91.93 | 15.00 |
| 44 LYS | NZ | -11.26 | 44.88 | 93.11 | 15.00 |
| 45 LEU | N | -9.60 | 41.19 | 87.25 | 15.00 |
| 45 LEU | CA | -8.69 | 41.41 | 86.13 | 15.00 |
| 45 LEU | C | -8.92 | 42.66 | 85.26 | 15.00 |
| 45 LEU | O | -10.04 | 43.15 | 85.12 | 15.00 |
| 45 LEU | CB | -8.71 | 40.16 | 85.25 | 15.00 |
| 45 LEU | CG | -7.54 | 39.90 | 84.33 | 15.00 |
| 45 LEU | CD1 | -6.25 | 39.87 | 85.12 | 15.00 |
| 45 LEU | CD2 | -7.75 | 38.59 | 83.63 | 15.00 |
| 46 LEU | N | -7.83 | 43.15 | 84.69 | 15.00 |
| 46 LEU | CA | -7.84 | 44.31 | 83.80 | 15.00 |
| 46 LEU | C | -6.81 | 44.09 | 82.69 | 15.00 |
| 46 LEU | O | -5.76 | 43.51 | 82.93 | 15.00 |
| 46 LEU | CB | -7.44 | 45.58 | 84.55 | 15.00 |
| 46 LEU | CG | -8.49 | 46.47 | 85.20 | 15.00 |
| 46 LEU | CD1 | -7.96 | 47.90 | 85.21 | 15.00 |
| 46 LEU | CD2 | -9.77 | 46.43 | 84.42 | 15.00 |
| 47 ASN | N | -7.11 | 44.56 | 81.49 | 15.00 |
| 47 ASN | CA | -6.17 | 44.43 | 80.38 | 15.00 |
| 47 ASN | C | -5.12 | 45.50 | 80.56 | 15.00 |
| 47 ASN | O | -5.45 | 46.67 | 80.62 | 15.00 |
| 47 ASN | CB | -6.88 | 44.66 | 79.03 | 15.00 |
| 47 ASN | CG | -7.67 | 43.45 | 78.57 | 15.00 |
| 47 ASN | OD1 | -7.13 | 42.37 | 78.38 | 15.00 |
| 47 ASN | ND2 | -8.97 | 43.65 | 78.34 | 15.00 |
| 48 LEU | N | -3.86 | 45.10 | 80.70 | 15.00 |
| 48 LEU | CA | -2.77 | 46.07 | 80.88 | 15.00 |
| 48 LEU | C | -2.15 | 46.34 | 79.52 | 15.00 |
| 48 LEU | O | -2.28 | 45.53 | 78.61 | 15.00 |
| 48 LEU | CB | -1.74 | 45.56 | 81.90 | 15.00 |
| 48 LEU | CG | -2.26 | 45.06 | 83.27 | 15.00 |
| 48 LEU | CD1 | -1.09 | 44.75 | 84.18 | 15.00 |
| 48 LEU | CD2 | -3.18 | 46.08 | 83.91 | 15.00 |
| 49 SER | N | -1.46 | 47.47 | 79.36 | 15.00 |
| 49 SER | CA | -0.91 | 47.82 | 78.06 | 15.00 |
| 49 SER | C | 0.51 | 47.42 | 77.67 | 15.00 |
| 49 SER | O | 1.48 | 47.79 | 78.33 | 15.00 |
| 49 SER | CB | -1.10 | 49.32 | 77.77 | 15.00 |
| 49 SER | OG | -0.19 | 50.13 | 78.51 | 15.00 |
| 50 PRO | N | 0.64 | 46.66 | 76.56 | 15.00 |
| 50 PRO | CA | 1.94 | 46.22 | 76.04 | 15.00 |
| 50 PRO | C | 2.59 | 47.44 | 75.41 | 15.00 |
| 50 PRO | O | 3.80 | 47.52 | 75.25 | 15.00 |
| 50 PRO | CB | 1.54 | 45.21 | 74.97 | 15.00 |
| 50 PRO | CG | 0.21 | 44.71 | 75.44 | 15.00 |
| 50 PRO | CD | -0.45 | 45.98 | 75.85 | 15.00 |
| 51 GLN | N | 1.74 | 48.40 | 75.03 | 15.00 |
| 51 GLN | CA | 2.18 | 49.65 | 74.43 | 15.00 |
| 51 GLN | C | 3.01 | 50.45 | 75.42 | 15.00 |
| 51 GLN | O | 4.12 | 50.87 | 75.11 | 15.00 |
| 51 GLN | CB | 0.97 | 50.49 | 74.00 | 15.00 |
| 51 GLN | CG | 1.33 | 51.66 | 73.08 | 15.00 |
| 51 GLN | CD | 1.77 | 51.20 | 71.71 | 15.00 |
| 51 GLN | OE1 | 0.96 | 50.74 | 70.92 | 15.00 |
| 51 GLN | NE2 | 3.06 | 51.26 | 71.44 | 15.00 |
| 52 ASN | N | 2.47 | 50.66 | 76.62 | 15.00 |
| 52 ASN | CA | 3.18 | 51.42 | 77.65 | 15.00 |
| 52 ASN | C | 4.59 | 50.85 | 77.83 | 15.00 |
| 52 ASN | O | 5.56 | 51.59 | 77.97 | 15.00 |
| 52 ASN | CB | 2.42 | 51.35 | 78.97 | 15.00 |
| 52 ASN | CG | 3.09 | 52.12 | 80.09 | 15.00 |
| 52 ASN | OD1 | 2.74 | 51.95 | 81.25 | 15.00 |
| 52 ASN | ND2 | 4.04 | 52.99 | 79.74 | 15.00 |
| 53 LEU | N | 4.68 | 49.53 | 77.81 | 15.00 |
| 53 LEU | CA | 5.95 | 48.86 | 77.94 | 15.00 |
| 53 LEU | C | 6.82 | 49.21 | 76.72 | 15.00 |
| 53 LEU | O | 7.87 | 49.84 | 76.88 | 15.00 |
| 53 LEU | CB | 5.75 | 47.35 | 78.08 | 15.00 |
| 53 LEU | CG | 5.11 | 46.95 | 79.41 | 15.00 |
| 53 LEU | CD1 | 4.91 | 45.45 | 79.49 | 15.00 |
| 53 LEU | CD2 | 6.00 | 47.41 | 80.54 | 15.00 |
| 54 VAL | N | 6.33 | 48.87 | 75.52 | 15.00 |
| 54 VAL | CA | 7.03 | 49.15 | 74.25 | 15.00 |
| 54 VAL | C | 7.63 | 50.55 | 74.20 | 15.00 |
| 54 VAL | O | 8.85 | 50.72 | 74.04 | 15.00 |
| 54 VAL | CB | 6.06 | 49.01 | 73.03 | 15.00 |
| 54 VAL | CG1 | 6.70 | 49.55 | 71.75 | 15.00 |
| 54 VAL | CG2 | 5.67 | 47.56 | 72.83 | 15.00 |
| 55 ASP | N | 6.76 | 51.55 | 74.37 | 15.00 |
| 55 ASP | CA | 7.12 | 52.96 | 74.31 | 15.00 |
| 55 ASP | C | 8.05 | 53.45 | 75.40 | 15.00 |
| 55 ASP | O | 8.84 | 54.37 | 75.19 | 15.00 |
| 55 ASP | CB | 5.85 | 53.84 | 74.36 | 15.00 |
| 55 ASP | CG | 4.87 | 53.56 | 73.22 | 15.00 |
| 55 ASP | OD1 | 5.23 | 52.86 | 72.24 | 15.00 |
| 55 ASP | OD2 | 3.72 | 54.05 | 73.29 | 15.00 |
| 56 CYS | N | 7.97 | 52.82 | 76.56 | 15.00 |
| 56 CYS | CA | 8.76 | 53.27 | 77.70 | 15.00 |
| 56 CYS | C | 9.97 | 52.47 | 78.16 | 15.00 |
| 56 CYS | O | 10.98 | 53.06 | 78.54 | 15.00 |

TABLE I-continued

Table of the orthogonal three dimensional coordinates in Ångstroms and B factors (Å²) for cathepsin K.

| Residue | Atom | X | Y | Z | B |
|---|---|---|---|---|---|
| 56 CYS | CB | 7.81 | 53.52 | 78.84 | 15.00 |
| 56 CYS | SG | 6.36 | 54.45 | 78.28 | 15.00 |
| 57 VAL | N | 9.87 | 51.15 | 78.17 | 15.00 |
| 57 VAL | CA | 10.98 | 50.31 | 78.60 | 15.00 |
| 57 VAL | C | 12.16 | 50.44 | 77.62 | 15.00 |
| 57 VAL | O | 12.50 | 49.50 | 76.90 | 15.00 |
| 57 VAL | CB | 10.54 | 48.83 | 78.71 | 15.00 |
| 57 VAL | CG1 | 11.66 | 47.98 | 79.32 | 15.00 |
| 57 VAL | CG2 | 9.26 | 48.72 | 79.52 | 15.00 |
| 58 SER | N | 12.85 | 51.57 | 77.67 | 15.00 |
| 58 SER | CA | 13.98 | 51.87 | 76.80 | 15.00 |
| 58 SER | C | 15.15 | 50.91 | 76.84 | 15.00 |
| 58 SER | O | 16.13 | 51.10 | 76.13 | 15.00 |
| 58 SER | CB | 14.48 | 53.27 | 77.09 | 15.00 |
| 58 SER | OG | 14.95 | 53.34 | 78.42 | 15.00 |
| 59 GLU | N | 15.09 | 49.92 | 77.71 | 15.00 |
| 59 GLU | CA | 16.15 | 48.93 | 77.82 | 15.00 |
| 59 GLU | C | 15.93 | 47.86 | 76.73 | 15.00 |
| 59 GLU | O | 16.77 | 46.99 | 76.50 | 15.00 |
| 59 GLU | CB | 16.14 | 48.30 | 79.22 | 15.00 |
| 59 GLU | CG | 16.39 | 49.27 | 80.39 | 15.00 |
| 59 GLU | CD | 15.13 | 49.97 | 80.88 | 15.00 |
| 59 GLU | OE1 | 14.38 | 49.38 | 81.70 | 15.00 |
| 59 GLU | OE2 | 14.90 | 51.13 | 80.46 | 15.00 |
| 60 ASN | N | 14.77 | 47.91 | 76.10 | 15.00 |
| 60 ASN | CA | 14.43 | 46.98 | 75.04 | 15.00 |
| 60 ASN | C | 14.26 | 47.73 | 73.71 | 15.00 |
| 60 ASN | O | 13.99 | 48.94 | 73.69 | 15.00 |
| 60 ASN | CB | 13.13 | 46.26 | 75.38 | 15.00 |
| 60 ASN | CG | 13.27 | 45.35 | 76.57 | 15.00 |
| 60 ASN | OD1 | 12.35 | 45.22 | 77.38 | 15.00 |
| 60 ASN | ND2 | 14.41 | 44.68 | 76.68 | 15.00 |
| 61 ASP | N | 14.39 | 47.02 | 72.61 | 15.00 |
| 61 ASP | CA | 14.25 | 47.65 | 71.31 | 15.00 |
| 61 ASP | C | 12.82 | 48.03 | 70.94 | 15.00 |
| 61 ASP | O | 12.60 | 48.65 | 69.91 | 15.00 |
| 61 ASP | CB | 14.84 | 46.75 | 70.23 | 15.00 |
| 61 ASP | CG | 15.93 | 47.43 | 69.44 | 15.00 |
| 61 ASP | OD1 | 15.87 | 48.66 | 69.28 | 15.00 |
| 61 ASP | OD2 | 16.85 | 46.72 | 68.98 | 15.00 |
| 62 GLY | N | 11.84 | 47.67 | 71.77 | 15.00 |
| 62 GLY | CA | 10.46 | 47.99 | 71.45 | 15.00 |
| 62 GLY | C | 9.91 | 47.03 | 70.41 | 15.00 |
| 62 GLY | O | 9.71 | 45.85 | 70.70 | 15.00 |
| 63 CYS | N | 9.68 | 47.50 | 69.20 | 15.00 |
| 63 CYS | CA | 9.19 | 46.60 | 68.16 | 15.00 |
| 63 CYS | C | 10.33 | 45.71 | 67.70 | 15.00 |
| 63 CYS | O | 10.09 | 44.70 | 67.04 | 15.00 |
| 63 CYS | CB | 8.59 | 47.36 | 66.99 | 15.00 |
| 63 CYS | SG | 6.94 | 48.02 | 67.38 | 15.00 |
| 64 GLY | N | 11.56 | 46.10 | 68.03 | 15.00 |
| 64 GLY | CA | 12.72 | 45.32 | 67.68 | 15.00 |
| 64 GLY | C | 12.90 | 44.16 | 68.64 | 15.00 |
| 64 GLY | O | 13.65 | 43.21 | 68.37 | 15.00 |
| 65 GLY | N | 12.20 | 44.23 | 69.78 | 15.00 |
| 65 GLY | CA | 12.28 | 43.17 | 70.77 | 15.00 |
| 65 GLY | C | 12.86 | 43.58 | 72.11 | 15.00 |
| 65 GLY | O | 13.34 | 44.70 | 72.31 | 15.00 |
| 66 GLY | N | 12.81 | 42.65 | 73.05 | 15.00 |
| 66 GLY | CA | 13.34 | 42.92 | 74.37 | 15.00 |
| 66 GLY | C | 13.08 | 41.77 | 75.32 | 15.00 |
| 66 GLY | O | 12.42 | 40.80 | 74.94 | 15.00 |
| 67 TYR | N | 13.57 | 41.90 | 76.55 | 15.00 |
| 67 TYR | CA | 13.40 | 40.87 | 77.56 | 15.00 |
| 67 TYR | C | 12.23 | 41.18 | 78.48 | 15.00 |
| 67 TYR | O | 11.93 | 42.34 | 78.75 | 15.00 |
| 67 TYR | CB | 14.68 | 40.76 | 78.39 | 15.00 |
| 67 TYR | CG | 15.91 | 40.56 | 77.55 | 15.00 |
| 67 TYR | CD1 | 16.20 | 39.32 | 76.98 | 15.00 |
| 67 TYR | CD2 | 16.77 | 41.61 | 77.29 | 15.00 |
| 67 TYR | CE1 | 17.33 | 39.13 | 76.18 | 15.00 |
| 67 TYR | CE2 | 17.90 | 41.44 | 76.49 | 15.00 |
| 67 TYR | CZ | 18.18 | 40.20 | 75.94 | 15.00 |
| 67 TYR | OH | 19.27 | 40.05 | 75.12 | 15.00 |
| 68 MET | N | 11.57 | 40.13 | 78.99 | 15.00 |
| 68 MET | CA | 10.45 | 40.33 | 79.90 | 15.00 |
| 68 MET | C | 10.90 | 40.92 | 81.23 | 15.00 |
| 68 MET | O | 10.21 | 41.72 | 81.83 | 15.00 |
| 68 MET | CB | 9.72 | 39.00 | 80.18 | 15.00 |
| 68 MET | CG | 8.97 | 38.38 | 79.00 | 15.00 |
| 68 MET | SD | 9.97 | 37.36 | 77.92 | 15.00 |
| 68 MET | CE | 11.01 | 36.45 | 79.11 | 15.00 |
| 69 THR | N | 12.09 | 40.53 | 81.68 | 15.00 |
| 69 THR | CA | 12.62 | 41.03 | 82.94 | 15.00 |
| 69 THR | C | 12.76 | 42.55 | 82.93 | 15.00 |
| 69 THR | O | 12.33 | 43.21 | 83.87 | 15.00 |
| 69 THR | CB | 13.98 | 40.37 | 83.29 | 15.00 |
| 69 THR | OG1 | 14.96 | 40.72 | 82.30 | 15.00 |
| 69 THR | CG2 | 13.84 | 38.85 | 83.35 | 15.00 |
| 70 ASN | N | 13.33 | 43.09 | 81.85 | 15.00 |
| 70 ASN | CA | 13.53 | 44.54 | 81.73 | 15.00 |
| 70 ASN | C | 12.24 | 45.34 | 81.80 | 15.00 |
| 70 ASN | O | 12.25 | 46.51 | 82.16 | 15.00 |
| 70 ASN | CB | 14.28 | 44.87 | 80.45 | 15.00 |
| 70 ASN | CG | 15.72 | 44.45 | 80.52 | 15.00 |
| 70 ASN | OD1 | 16.11 | 43.68 | 81.39 | 15.00 |
| 70 ASN | ND2 | 16.54 | 44.97 | 79.61 | 15.00 |
| 71 ALA | N | 11.14 | 44.68 | 81.45 | 15.00 |
| 71 ALA | CA | 9.81 | 45.28 | 81.50 | 15.00 |
| 71 ALA | C | 9.27 | 45.18 | 82.93 | 15.00 |
| 71 ALA | O | 8.72 | 46.14 | 83.46 | 15.00 |
| 71 ALA | CB | 8.88 | 44.57 | 80.51 | 15.00 |
| 72 PHE | N | 9.46 | 44.02 | 83.55 | 15.00 |
| 72 PHE | CA | 9.02 | 43.79 | 84.93 | 15.00 |
| 72 PHE | C | 9.63 | 44.86 | 85.81 | 15.00 |
| 72 PHE | O | 8.94 | 45.51 | 86.59 | 15.00 |
| 72 PHE | CB | 9.49 | 42.43 | 85.44 | 15.00 |
| 72 PHE | CG | 8.73 | 41.28 | 84.88 | 15.00 |
| 72 PHE | CD1 | 7.40 | 41.42 | 84.52 | 15.00 |
| 72 PHE | CD2 | 9.34 | 40.04 | 84.73 | 15.00 |
| 72 PHE | CE1 | 6.67 | 40.35 | 84.03 | 15.00 |
| 72 PHE | CE2 | 8.62 | 38.96 | 84.24 | 15.00 |
| 72 PHE | CZ | 7.29 | 39.12 | 83.89 | 15.00 |
| 73 GLN | N | 10.93 | 45.05 | 85.64 | 15.00 |
| 73 GLN | CA | 11.67 | 46.04 | 86.41 | 15.00 |
| 73 GLN | C | 11.17 | 47.48 | 86.11 | 15.00 |
| 73 GLN | O | 11.29 | 48.37 | 86.94 | 15.00 |
| 73 GLN | CB | 13.16 | 45.86 | 86.13 | 15.00 |
| 73 GLN | CG | 14.11 | 46.75 | 86.94 | 15.00 |
| 73 GLN | CD | 14.52 | 46.20 | 88.32 | 15.00 |
| 73 GLN | OE1 | 15.45 | 46.73 | 88.93 | 15.00 |
| 73 GLN | NE2 | 13.85 | 45.16 | 88.80 | 15.00 |
| 74 TYR | N | 10.54 | 47.68 | 84.96 | 15.00 |
| 74 TYR | CA | 10.04 | 49.00 | 84.58 | 15.00 |
| 74 TYR | C | 8.81 | 49.41 | 85.38 | 15.00 |
| 74 TYR | O | 8.69 | 50.56 | 85.81 | 15.00 |
| 74 TYR | CB | 9.72 | 49.05 | 83.08 | 15.00 |
| 74 TYR | CG | 8.90 | 50.26 | 82.67 | 15.00 |
| 74 TYR | CD1 | 9.48 | 51.52 | 82.60 | 15.00 |
| 74 TYR | CD2 | 7.54 | 50.14 | 82.44 | 15.00 |
| 74 TYR | CE1 | 8.71 | 52.63 | 82.31 | 15.00 |
| 74 TYR | CE2 | 6.77 | 51.25 | 82.15 | 15.00 |
| 74 TYR | CZ | 7.36 | 52.49 | 82.09 | 15.00 |
| 74 TYR | OH | 6.58 | 53.59 | 81.84 | 15.00 |
| 75 VAL | N | 7.87 | 48.48 | 85.54 | 15.00 |
| 75 VAL | CA | 6.65 | 48.74 | 86.31 | 15.00 |
| 75 VAL | C | 7.07 | 49.05 | 87.76 | 15.00 |
| 75 VAL | O | 6.41 | 49.80 | 88.47 | 15.00 |
| 75 VAL | CB | 5.73 | 47.48 | 86.38 | 15.00 |
| 75 VAL | CG1 | 4.32 | 47.87 | 86.73 | 15.00 |
| 75 VAL | CG2 | 5.77 | 46.72 | 85.07 | 15.00 |
| 76 GLN | N | 8.18 | 48.44 | 88.18 | 15.00 |
| 76 GLN | CA | 8.71 | 48.62 | 89.52 | 15.00 |
| 76 GLN | C | 9.26 | 50.02 | 89.71 | 15.00 |
| 76 GLN | O | 8.62 | 50.86 | 90.31 | 15.00 |
| 76 GLN | CB | 9.78 | 47.57 | 89.79 | 15.00 |
| 76 GLN | CG | 10.35 | 47.60 | 91.20 | 15.00 |
| 76 GLN | CD | 11.53 | 46.64 | 91.36 | 15.00 |

TABLE I-continued

Table of the orthogonal three dimensional coordinates in Ångstroms and B factors (Å²) for cathepsin K.

| Residue | Atom | X | Y | Z | B |
|---|---|---|---|---|---|
| 76 GLN | OE1 | 12.17 | 46.25 | 90.38 | 15.00 |
| 76 GLN | NE2 | 11.80 | 46.25 | 92.59 | 15.00 |
| 77 LYS | N | 10.43 | 50.30 | 89.15 | 15.00 |
| 77 LYS | CA | 11.04 | 51.62 | 89.32 | 15.00 |
| 77 LYS | C | 10.24 | 52.83 | 88.85 | 15.00 |
| 77 LYS | O | 10.34 | 53.90 | 89.44 | 15.00 |
| 77 LYS | CB | 12.44 | 51.64 | 88.71 | 15.00 |
| 77 LYS | CG | 12.52 | 51.06 | 87.30 | 15.00 |
| 77 LYS | CD | 13.96 | 50.69 | 86.97 | 15.00 |
| 77 LYS | CE | 14.06 | 49.75 | 85.79 | 15.00 |
| 77 LYS | NZ | 15.39 | 49.07 | 85.82 | 15.00 |
| 78 ASN | N | 9.48 | 52.69 | 87.77 | 15.00 |
| 78 ASN | CA | 8.67 | 53.81 | 87.31 | 15.00 |
| 78 ASN | C | 7.51 | 53.96 | 88.28 | 15.00 |
| 78 ASN | O | 6.94 | 55.03 | 88.41 | 15.00 |
| 78 ASN | CB | 8.12 | 53.56 | 85.90 | 15.00 |
| 78 ASN | CG | 7.17 | 54.66 | 85.44 | 15.00 |
| 78 ASN | OD1 | 7.61 | 55.76 | 85.09 | 15.00 |
| 78 ASN | ND2 | 5.88 | 54.37 | 85.44 | 15.00 |
| 79 ARG | N | 7.19 | 52.86 | 88.95 | 15.00 |
| 79 ARG | CA | 6.11 | 52.78 | 89.94 | 15.00 |
| 79 ARG | C | 4.71 | 52.88 | 89.33 | 15.00 |
| 79 ARG | O | 4.05 | 53.92 | 89.37 | 15.00 |
| 79 ARG | CB | 6.31 | 53.81 | 91.08 | 15.00 |
| 79 ARG | CG | 7.67 | 53.69 | 91.80 | 15.00 |
| 79 ARG | CD | 7.80 | 54.56 | 93.06 | 15.00 |
| 79 ARG | NE | 6.84 | 54.23 | 94.12 | 15.00 |
| 79 ARG | CZ | 6.60 | 53.00 | 94.59 | 15.00 |
| 79 ARG | NH1 | 7.24 | 51.94 | 94.09 | 15.00 |
| 79 ARG | NH2 | 5.73 | 52.83 | 95.58 | 15.00 |
| 80 GLY | N | 4.27 | 51.76 | 88.76 | 15.00 |
| 80 GLY | CA | 2.95 | 51.68 | 88.15 | 15.00 |
| 80 GLY | C | 2.98 | 51.54 | 86.64 | 15.00 |
| 80 GLY | O | 3.87 | 52.07 | 85.97 | 15.00 |
| 81 ILE | N | 1.98 | 50.85 | 86.10 | 15.00 |
| 81 ILE | CA | 1.88 | 50.64 | 84.66 | 15.00 |
| 81 ILE | C | 0.45 | 50.97 | 84.23 | 15.00 |
| 81 ILE | O | −0.49 | 50.68 | 84.96 | 15.00 |
| 81 ILE | CB | 2.19 | 49.17 | 84.30 | 15.00 |
| 81 ILE | CG1 | 2.27 | 48.99 | 82.78 | 15.00 |
| 81 ILE | CG2 | 1.14 | 48.24 | 84.90 | 15.00 |
| 81 ILE | CD1 | 2.64 | 47.59 | 82.36 | 15.00 |
| 82 ASP | N | 0.29 | 51.58 | 83.05 | 15.00 |
| 82 ASP | CA | −1.04 | 51.93 | 82.56 | 15.00 |
| 82 ASP | C | −1.89 | 50.76 | 82.07 | 15.00 |
| 82 ASP | O | −1.38 | 49.69 | 81.71 | 15.00 |
| 82 ASP | CB | −0.93 | 52.93 | 81.42 | 15.00 |
| 82 ASP | CG | −0.47 | 54.29 | 81.87 | 15.00 |
| 82 ASP | OD1 | −0.66 | 54.63 | 83.06 | 15.00 |
| 82 ASP | OD2 | 0.08 | 55.02 | 81.02 | 15.00 |
| 83 SER | N | −3.20 | 50.96 | 82.05 | 15.00 |
| 83 SER | CA | −4.12 | 49.95 | 81.56 | 15.00 |
| 83 SER | C | −4.32 | 50.20 | 80.07 | 15.00 |
| 83 SER | O | −4.22 | 51.34 | 79.61 | 15.00 |
| 83 SER | CB | −5.46 | 50.02 | 82.32 | 15.00 |
| 83 SER | CG | −6.06 | 51.30 | 82.22 | 15.00 |
| 84 GLU | N | −4.61 | 49.14 | 79.32 | 15.00 |
| 84 GLU | CA | −4.81 | 49.22 | 77.86 | 15.00 |
| 84 GLU | C | −5.66 | 50.40 | 77.38 | 15.00 |
| 84 GLU | O | −5.20 | 51.19 | 76.57 | 15.00 |
| 84 GLU | CB | −5.39 | 47.91 | 77.33 | 15.00 |
| 84 GLU | CG | −5.73 | 47.89 | 75.85 | 15.00 |
| 84 GLU | CD | −4.51 | 47.97 | 74.94 | 15.00 |
| 84 GLU | OE1 | −3.51 | 47.25 | 75.17 | 15.00 |
| 84 GLU | OE2 | −4.57 | 48.74 | 73.96 | 15.00 |
| 85 ASP | N | −6.87 | 50.53 | 77.90 | 15.00 |
| 85 ASP | CA | −7.72 | 51.61 | 77.45 | 15.00 |
| 85 ASP | C | −7.12 | 52.99 | 77.70 | 15.00 |
| 85 ASP | O | −7.49 | 53.97 | 77.03 | 15.00 |
| 85 ASP | CB | −9.10 | 51.52 | 78.07 | 15.00 |
| 85 ASP | CG | −10.07 | 52.52 | 77.46 | 15.00 |
| 85 ASP | OD1 | −9.97 | 52.79 | 76.24 | 15.00 |
| 85 ASP | OD2 | −10.93 | 53.06 | 78.21 | 15.00 |
| 86 ALA | N | −6.18 | 53.08 | 78.64 | 15.00 |
| 86 ALA | CA | −5.54 | 54.36 | 78.93 | 15.00 |
| 86 ALA | C | −4.30 | 54.57 | 78.04 | 15.00 |
| 86 ALA | O | −3.90 | 55.70 | 77.78 | 15.00 |
| 86 ALA | CB | −5.16 | 54.45 | 80.40 | 15.00 |
| 87 TYR | N | −3.74 | 53.48 | 77.53 | 15.00 |
| 87 TYR | CA | −2.56 | 53.54 | 76.67 | 15.00 |
| 87 TYR | C | −2.69 | 52.41 | 75.64 | 15.00 |
| 87 TYR | O | −1.98 | 51.39 | 75.73 | 15.00 |
| 87 TYR | CB | −1.32 | 53.33 | 77.55 | 15.00 |
| 87 TYR | CG | −0.03 | 53.89 | 77.01 | 15.00 |
| 87 TYR | CD1 | 0.20 | 53.93 | 75.64 | 15.00 |
| 87 TYR | CD2 | 0.99 | 54.29 | 77.89 | 15.00 |
| 87 TYR | CE1 | 1.41 | 54.47 | 75.16 | 15.00 |
| 87 TYR | CE2 | 2.20 | 54.77 | 77.41 | 15.00 |
| 87 TYR | CZ | 2.41 | 54.86 | 76.05 | 15.00 |
| 87 TYR | OH | 3.61 | 55.32 | 75.57 | 15.00 |
| 88 PRO | N | −3.60 | 52.58 | 74.65 | 15.00 |
| 88 PRO | CA | −3.93 | 51.66 | 73.55 | 15.00 |
| 88 PRO | C | −2.80 | 51.22 | 72.61 | 15.00 |
| 88 PRO | O | −2.08 | 52.05 | 72.06 | 15.00 |
| 88 PRO | CB | −5.01 | 52.43 | 72.79 | 15.00 |
| 88 PRO | CG | −5.64 | 53.28 | 73.84 | 15.00 |
| 88 PRO | CD | −4.42 | 53.80 | 74.54 | 15.00 |
| 89 TYR | N | −2.74 | 49.92 | 72.34 | 15.00 |
| 89 TYR | CA | −1.71 | 49.35 | 71.48 | 15.00 |
| 89 TYR | C | −1.83 | 49.79 | 70.01 | 15.00 |
| 89 TYR | O | −2.46 | 49.11 | 69.21 | 15.00 |
| 89 TYR | CB | −1.74 | 47.82 | 71.56 | 15.00 |
| 89 TYR | CG | −0.54 | 47.18 | 70.92 | 15.00 |
| 89 TYR | CD1 | 0.75 | 47.59 | 71.30 | 15.00 |
| 89 TYR | CD2 | −0.66 | 46.24 | 69.91 | 15.00 |
| 89 TYR | CE1 | 1.88 | 47.07 | 70.69 | 15.00 |
| 89 TYR | CE2 | 0.47 | 45.70 | 69.28 | 15.00 |
| 89 TYR | CZ | 1.74 | 46.13 | 69.68 | 15.00 |
| 89 TYR | OH | 2.87 | 45.65 | 69.09 | 15.00 |
| 90 VAL | N | −1.19 | 50.88 | 69.65 | 15.00 |
| 90 VAL | CA | −1.22 | 51.40 | 68.29 | 15.00 |
| 90 VAL | C | −0.55 | 50.51 | 67.23 | 15.00 |
| 90 VAL | O | −0.83 | 50.63 | 66.03 | 15.00 |
| 90 VAL | CB | −0.63 | 52.83 | 68.21 | 15.00 |
| 90 VAL | CG1 | −1.26 | 53.71 | 69.28 | 15.00 |
| 90 VAL | CG2 | 0.88 | 52.80 | 68.33 | 15.00 |
| 91 GLY | N | 0.37 | 49.65 | 67.64 | 15.00 |
| 91 GLY | CA | 1.01 | 48.77 | 66.67 | 15.00 |
| 91 GLY | C | 2.38 | 49.17 | 66.15 | 15.00 |
| 91 GLY | O | 2.89 | 48.57 | 65.20 | 15.00 |
| 92 GLN | N | 3.00 | 50.17 | 66.77 | 15.00 |
| 92 GLN | CA | 4.32 | 50.61 | 66.35 | 15.00 |
| 92 GLN | C | 4.96 | 51.34 | 67.52 | 15.00 |
| 92 GLN | O | 4.33 | 51.51 | 68.57 | 15.00 |
| 92 GLN | CB | 4.21 | 51.53 | 65.13 | 15.00 |
| 92 GLN | CG | 3.46 | 52.85 | 65.38 | 15.00 |
| 92 GLN | CD | 3.28 | 53.70 | 64.12 | 15.00 |
| 92 GLN | OE1 | 3.93 | 54.73 | 63.94 | 15.00 |
| 92 GLN | NE2 | 2.39 | 53.25 | 63.25 | 15.00 |
| 93 GLU | N | 6.19 | 51.79 | 67.34 | 15.00 |
| 93 GLU | CA | 6.90 | 52.49 | 68.39 | 15.00 |
| 93 GLU | C | 6.60 | 53.99 | 68.38 | 15.00 |
| 93 GLU | O | 6.84 | 54.67 | 67.38 | 15.00 |
| 93 GLU | CB | 8.41 | 52.27 | 68.23 | 15.00 |
| 93 GLU | CG | 8.80 | 50.81 | 68.17 | 15.00 |
| 93 GLU | CD | 10.30 | 50.60 | 68.23 | 15.00 |
| 93 GLU | OE1 | 10.85 | 50.53 | 69.35 | 15.00 |
| 93 GLU | OE2 | 10.93 | 50.50 | 67.15 | 15.00 |
| 94 GLU | N | 6.08 | 54.49 | 69.49 | 15.00 |
| 94 GLU | CA | 5.76 | 55.90 | 69.63 | 15.00 |
| 94 GLU | C | 6.54 | 56.47 | 70.80 | 15.00 |
| 94 GLU | O | 7.40 | 55.80 | 71.37 | 15.00 |
| 94 GLU | CB | 4.27 | 56.10 | 69.86 | 15.00 |
| 94 GLU | CG | 3.45 | 56.13 | 68.58 | 15.00 |
| 94 GLU | CD | 1.96 | 56.28 | 68.85 | 15.00 |
| 94 GLU | OE1 | 1.48 | 55.64 | 69.81 | 15.00 |
| 94 GLU | OE2 | 1.27 | 57.03 | 68.11 | 15.00 |
| 95 SER | N | 6.22 | 57.71 | 71.14 | 15.00 |

TABLE I-continued

Table of the orthogonal three dimensional coordinates in Ångstroms and B factors (Å²) for cathepsin K.

| Residue | Atom | X | Y | Z | B |
|---|---|---|---|---|---|
| 95 SER | CA | 6.84 | 58.41 | 72.26 | 15.00 |
| 95 SER | C | 6.16 | 57.91 | 73.52 | 15.00 |
| 95 SER | O | 4.92 | 57.82 | 73.58 | 15.00 |
| 95 SER | CB | 6.63 | 59.93 | 72.12 | 15.00 |
| 95 SER | OG | 5.25 | 60.23 | 71.89 | 15.00 |
| 96 CYS | N | 6.96 | 57.55 | 74.51 | 15.00 |
| 96 CYS | CA | 6.44 | 57.04 | 75.77 | 15.00 |
| 96 CYS | C | 5.44 | 58.02 | 76.39 | 15.00 |
| 96 CYS | O | 5.84 | 59.03 | 76.95 | 15.00 |
| 96 CYS | CB | 7.59 | 56.77 | 76.74 | 15.00 |
| 96 CYS | SG | 7.00 | 56.38 | 78.40 | 15.00 |
| 97 MET | N | 4.15 | 57.73 | 76.21 | 15.00 |
| 97 MET | CA | 3.06 | 58.55 | 76.74 | 15.00 |
| 97 MET | C | 2.40 | 58.00 | 78.01 | 15.00 |
| 97 MET | O | 1.16 | 57.90 | 78.06 | 15.00 |
| 97 MET | CB | 1.97 | 58.73 | 75.69 | 15.00 |
| 97 MET | CG | 2.36 | 59.52 | 74.45 | 15.00 |
| 97 MET | SD | 1.29 | 58.98 | 73.09 | 15.00 |
| 97 MET | CE | -0.36 | 59.43 | 73.71 | 15.00 |
| 98 TYR | N | 3.20 | 57.65 | 79.01 | 15.00 |
| 98 TYR | CA | 2.67 | 57.13 | 80.26 | 15.00 |
| 98 TYR | C | 1.93 | 58.21 | 81.06 | 15.00 |
| 98 TYR | O | 2.48 | 59.26 | 81.38 | 15.00 |
| 98 TYR | CB | 3.78 | 56.51 | 81.11 | 15.00 |
| 98 TYR | CG | 3.32 | 56.04 | 82.48 | 15.00 |
| 98 TYR | CD1 | 3.24 | 56.92 | 83.56 | 15.00 |
| 98 TYR | CD2 | 2.95 | 54.72 | 82.69 | 15.00 |
| 98 TYR | CE1 | 2.81 | 56.49 | 84.80 | 15.00 |
| 98 TYR | CE2 | 2.52 | 54.29 | 83.95 | 15.00 |
| 98 TYR | CZ | 2.45 | 55.18 | 84.99 | 15.00 |
| 98 TYR | OH | 2.02 | 54.77 | 86.22 | 15.00 |
| 99 ASN | N | 0.69 | 57.92 | 81.43 | 15.00 |
| 99 ASN | CA | -0.14 | 58.84 | 82.20 | 15.00 |
| 99 ASN | C | -0.54 | 58.20 | 83.54 | 15.00 |
| 99 ASN | O | -1.31 | 57.23 | 83.58 | 15.00 |
| 99 ASN | CB | -1.37 | 59.22 | 81.36 | 15.00 |
| 99 ASN | CG | -2.38 | 60.08 | 82.13 | 15.00 |
| 99 ASN | OD1 | -2.01 | 60.89 | 82.99 | 15.00 |
| 99 ASN | ND2 | -3.66 | 59.90 | 81.80 | 15.00 |
| 100 PRO | N | -0.02 | 58.74 | 84.65 | 15.00 |
| 100 PRO | CA | -0.30 | 58.24 | 86.00 | 15.00 |
| 100 PRO | C | -1.77 | 58.23 | 86.33 | 15.00 |
| 100 PRO | O | -2.22 | 57.46 | 87.19 | 15.00 |
| 100 PRO | CB | 0.45 | 59.22 | 86.90 | 15.00 |
| 100 PRO | CG | 1.58 | 59.70 | 86.02 | 15.00 |
| 100 PRO | CD | 0.86 | 59.92 | 84.71 | 15.00 |
| 101 THR | N | -2.53 | 59.08 | 85.65 | 15.00 |
| 101 THR | CA | -3.96 | 59.13 | 85.89 | 15.00 |
| 101 THR | C | -4.56 | 57.81 | 85.43 | 15.00 |
| 101 THR | O | -5.64 | 57.43 | 85.89 | 15.00 |
| 101 THR | CB | -4.63 | 60.25 | 85.10 | 15.00 |
| 101 THR | OG1 | -3.86 | 61.45 | 85.21 | 15.00 |
| 101 THR | CG2 | -6.03 | 60.52 | 85.66 | 15.00 |
| 102 GLY | N | -3.86 | 57.13 | 84.52 | 15.00 |
| 102 GLY | CA | -4.33 | 55.86 | 84.01 | 15.00 |
| 102 GLY | C | -3.55 | 54.62 | 84.42 | 15.00 |
| 102 GLY | O | -3.52 | 53.65 | 83.67 | 15.00 |
| 103 LYS | N | -2.90 | 54.62 | 85.59 | 15.00 |
| 103 LYS | CA | -2.15 | 53.44 | 86.02 | 15.00 |
| 103 LYS | C | -3.12 | 52.35 | 86.50 | 15.00 |
| 103 LYS | O | -4.26 | 52.65 | 86.86 | 15.00 |
| 103 LYS | CB | -1.13 | 53.83 | 87.11 | 15.00 |
| 103 LYS | CG | -1.51 | 53.50 | 88.56 | 15.00 |
| 103 LYS | CD | -0.97 | 52.13 | 88.98 | 15.00 |
| 103 LYS | CE | -1.39 | 51.77 | 90.40 | 15.00 |
| 103 LYS | NZ | -1.11 | 50.35 | 90.75 | 15.00 |
| 104 ALA | N | -2.68 | 51.10 | 86.52 | 15.00 |
| 104 ALA | CA | -3.55 | 50.01 | 86.96 | 15.00 |
| 104 ALA | C | -2.86 | 48.86 | 87.68 | 15.00 |
| 104 ALA | O | -3.52 | 47.92 | 88.12 | 15.00 |
| 104 ALA | CB | -4.37 | 49.49 | 85.79 | 15.00 |
| 105 ALA | N | -1.55 | 48.92 | 87.82 | 15.00 |
| 105 ALA | CA | -0.83 | 47.87 | 88.50 | 15.00 |
| 105 ALA | C | 0.53 | 48.36 | 88.97 | 15.00 |
| 105 ALA | O | 1.06 | 49.35 | 88.44 | 15.00 |
| 105 ALA | CB | -0.67 | 46.68 | 87.59 | 15.00 |
| 106 LYS | N | 1.07 | 47.69 | 90.00 | 15.00 |
| 106 LYS | CA | 2.39 | 48.03 | 90.56 | 15.00 |
| 106 LYS | C | 3.24 | 46.76 | 90.62 | 15.00 |
| 106 LYS | O | 2.73 | 45.65 | 90.44 | 15.00 |
| 106 LYS | CB | 2.24 | 48.66 | 91.95 | 15.00 |
| 106 LYS | CG | 1.78 | 50.12 | 91.94 | 15.00 |
| 106 LYS | CD | 1.32 | 50.56 | 93.31 | 15.00 |
| 106 LYS | CE | 2.44 | 50.52 | 94.34 | 15.00 |
| 106 LYS | NZ | 3.48 | 51.56 | 94.06 | 15.00 |
| 107 CYS | N | 4.54 | 46.92 | 90.90 | 15.00 |
| 107 CYS | CA | 5.42 | 45.76 | 90.90 | 15.00 |
| 107 CYS | C | 6.51 | 45.83 | 91.97 | 15.00 |
| 107 CYS | O | 7.16 | 46.86 | 92.14 | 15.00 |
| 107 CYS | CB | 6.07 | 45.65 | 89.52 | 15.00 |
| 107 CYS | SG | 6.62 | 44.03 | 89.03 | 15.00 |
| 108 ARG | N | 6.70 | 44.73 | 92.69 | 15.00 |
| 108 ARG | A | 7.71 | 44.62 | 93.74 | 15.00 |
| 108 ARG | C | 8.93 | 43.86 | 93.19 | 15.00 |
| 108 ARG | O | 9.61 | 43.14 | 93.93 | 15.00 |
| 108 ARG | CB | 7.16 | 43.87 | 94.96 | 15.00 |
| 108 ARG | CG | 6.08 | 44.58 | 95.79 | 15.00 |
| 108 ARG | CD | 5.41 | 43.58 | 96.74 | 15.00 |
| 108 ARG | NE | 6.38 | 42.60 | 97.25 | 15.00 |
| 108 ARG | CZ | 6.16 | 41.29 | 97.39 | 15.00 |
| 108 ARG | NH1 | 4.99 | 40.74 | 97.08 | 15.00 |
| 108 ARG | NH2 | 7.16 | 40.52 | 97.80 | 15.00 |
| 109 GLY | N | 9.21 | 44.02 | 91.90 | 15.00 |
| 109 GLY | CA | 10.34 | 43.34 | 91.30 | 15.00 |
| 109 GLY | C | 9.92 | 42.13 | 90.50 | 15.00 |
| 109 GLY | O | 8.77 | 42.01 | 90.10 | 15.00 |
| 110 TYR | N | 10.86 | 41.22 | 90.29 | 15.00 |
| 110 TYR | CA | 10.59 | 39.99 | 89.54 | 15.00 |
| 110 TYR | C | 11.44 | 38.82 | 90.02 | 15.00 |
| 110 TYR | O | 12.41 | 38.99 | 90.75 | 15.00 |
| 110 TYR | CB | 10.85 | 40.21 | 88.05 | 15.00 |
| 110 TYR | CG | 12.30 | 40.42 | 87.70 | 15.00 |
| 110 TYR | CD1 | 13.13 | 39.33 | 87.46 | 15.00 |
| 110 TYR | CD2 | 12.82 | 41.70 | 87.58 | 15.00 |
| 110 TYR | CE1 | 14.46 | 39.52 | 87.10 | 15.00 |
| 110 TYR | CE2 | 14.14 | 41.89 | 87.22 | 15.00 |
| 110 TYR | CZ | 14.95 | 40.80 | 86.98 | 15.00 |
| 110 TYR | OH | 16.25 | 40.99 | 86.61 | 15.00 |
| 111 ARG | N | 11.13 | 37.63 | 89.52 | 15.00 |
| 111 ARG | CA | 11.87 | 36.45 | 89.91 | 15.00 |
| 111 ARG | C | 11.88 | 35.46 | 88.75 | 15.00 |
| 111 ARG | O | 10.90 | 35.34 | 88.03 | 15.00 |
| 111 ARG | CB | 11.23 | 35.85 | 91.16 | 15.00 |
| 111 ARG | CG | 12.14 | 34.90 | 91.88 | 15.00 |
| 111 ARG | CD | 11.70 | 34.66 | 93.31 | 15.00 |
| 111 ARG | NE | 12.85 | 34.20 | 94.09 | 15.00 |
| 111 ARG | CZ | 13.87 | 34.98 | 94.44 | 15.00 |
| 111 ARG | NH1 | 13.87 | 36.28 | 94.12 | 15.00 |
| 111 ARG | NH2 | 14.89 | 34.48 | 95.13 | 15.00 |
| 112 GLU | N | 13.00 | 34.76 | 88.58 | 15.00 |
| 112 GLU | CA | 13.15 | 33.79 | 87.50 | 15.00 |
| 112 GLU | C | 13.25 | 32.35 | 87.94 | 15.00 |
| 112 GLU | O | 13.55 | 32.06 | 89.11 | 15.00 |
| 112 GLU | CB | 14.38 | 34.11 | 86.66 | 15.00 |
| 112 GLU | CG | 14.35 | 35.49 | 86.11 | 15.00 |
| 112 GLU | CD | 15.46 | 35.72 | 85.14 | 15.00 |
| 112 GLU | OE1 | 15.30 | 35.30 | 83.97 | 15.00 |
| 112 GLU | OE2 | 16.49 | 36.31 | 85.56 | 15.00 |
| 113 ILE | N | 12.98 | 31.46 | 86.99 | 15.00 |
| 113 ILE | CA | 13.02 | 30.03 | 87.20 | 15.00 |
| 113 ILE | C | 14.46 | 29.65 | 86.91 | 15.00 |
| 113 ILE | O | 15.13 | 30.34 | 86.15 | 15.00 |
| 113 ILE | CB | 12.04 | 29.30 | 86.23 | 15.00 |
| 113 ILE | CG1 | 10.60 | 29.50 | 86.70 | 15.00 |
| 113 ILE | CG2 | 12.36 | 27.81 | 86.13 | 15.00 |
| 113 ILE | CD1 | 10.10 | 30.93 | 86.65 | 15.00 |
| 114 PRO | N | 15.01 | 28.64 | 87.60 | 15.00 |
| 114 PRO | CA | 16.40 | 28.30 | 87.29 | 15.00 |

TABLE I-continued

Table of the orthogonal three dimensional coordinates in Ångstroms and B factors (Å²) for cathepsin K.

| Residue | Atom | X | Y | Z | B |
|---|---|---|---|---|---|
| 114 PRO | C | 16.50 | 27.74 | 85.87 | 15.00 |
| 114 PRO | O | 15.74 | 26.85 | 85.48 | 15.00 |
| 114 PRO | CB | 16.77 | 27.29 | 88.39 | 15.00 |
| 114 PRO | CG | 15.46 | 26.66 | 88.76 | 15.00 |
| 114 PRO | CD | 14.52 | 27.85 | 88.75 | 15.00 |
| 115 GLU | N | 17.41 | 28.32 | 85.09 | 15.00 |
| 115 GLU | CA | 17.61 | 27.97 | 83.68 | 15.00 |
| 115 GLU | C | 17.55 | 26.49 | 83.35 | 15.00 |
| 115 GLU | O | 18.36 | 25.70 | 83.84 | 15.00 |
| 115 GLU | CB | 18.93 | 28.56 | 83.15 | 15.00 |
| 115 GLU | CG | 18.92 | 30.09 | 82.86 | 15.00 |
| 115 GLU | CD | 20.11 | 30.56 | 81.97 | 15.00 |
| 115 GLU | OE1 | 20.75 | 29.70 | 81.31 | 15.00 |
| 115 GLU | OE2 | 20.39 | 31.79 | 81.92 | 15.00 |
| 116 GLY | N | 16.55 | 26.11 | 82.56 | 15.00 |
| 116 GLY | CA | 16.41 | 24.74 | 82.12 | 15.00 |
| 116 GLY | C | 15.76 | 23.78 | 83.08 | 15.00 |
| 116 GLY | O | 15.81 | 22.56 | 82.88 | 15.00 |
| 117 ASN | N | 15.13 | 24.31 | 84.11 | 15.00 |
| 117 ASN | CA | 14.47 | 23.47 | 85.10 | 15.00 |
| 117 ASN | C | 12.97 | 23.47 | 84.87 | 15.00 |
| 117 ASN | O | 12.28 | 24.43 | 85.22 | 15.00 |
| 117 ASN | CB | 14.77 | 23.97 | 86.51 | 15.00 |
| 117 ASN | CG | 14.21 | 23.05 | 87.58 | 15.00 |
| 117 ASN | OD1 | 13.32 | 22.23 | 87.32 | 15.00 |
| 117 ASN | ND2 | 14.72 | 23.19 | 88.80 | 15.00 |
| 118 GLU | N | 12.47 | 22.38 | 84.29 | 15.00 |
| 118 GLU | CA | 11.05 | 22.27 | 84.03 | 15.00 |
| 118 GLU | C | 10.22 | 22.01 | 85.27 | 15.00 |
| 118 GLU | O | 9.16 | 22.60 | 85.42 | 15.00 |
| 118 GLU | CB | 10.75 | 21.20 | 82.99 | 15.00 |
| 118 GLU | CG | 10.96 | 21.66 | 81.56 | 15.00 |
| 118 GLU | CD | 10.34 | 20.72 | 80.56 | 15.00 |
| 118 GLU | OE1 | 9.11 | 20.82 | 80.33 | 15.00 |
| 118 GLU | OE2 | 11.08 | 19.88 | 80.01 | 15.00 |
| 119 LYS | N | 10.73 | 21.18 | 86.18 | 15.00 |
| 119 LYS | CA | 10.00 | 20.87 | 87.41 | 15.00 |
| 119 LYS | C | 9.79 | 22.11 | 88.28 | 15.00 |
| 119 LYS | O | 8.78 | 22.21 | 88.98 | 15.00 |
| 119 LYS | CB | 10.68 | 19.76 | 88.21 | 15.00 |
| 119 LYS | CG | 9.94 | 18.40 | 88.14 | 15.00 |
| 119 LYS | CD | 10.13 | 17.64 | 86.81 | 15.00 |
| 119 LYS | CE | 9.28 | 16.35 | 86.76 | 15.00 |
| 119 LYS | NZ | 9.62 | 15.29 | 87.79 | 15.00 |
| 120 ALA | N | 10.73 | 23.04 | 88.21 | 15.00 |
| 120 ALA | CA | 10.61 | 24.30 | 88.94 | 15.00 |
| 120 ALA | C | 9.57 | 25.15 | 88.23 | 15.00 |
| 120 ALA | O | 8.72 | 25.75 | 88.88 | 15.00 |
| 120 ALA | CB | 11.93 | 25.04 | 88.99 | 15.00 |
| 121 LEU | N | 9.62 | 25.19 | 86.89 | 15.00 |
| 121 LEU | CA | 8.66 | 25.96 | 86.09 | 15.00 |
| 121 LEU | C | 7.23 | 25.51 | 86.39 | 15.00 |
| 121 LEU | O | 6.34 | 26.34 | 86.52 | 15.00 |
| 121 LEU | CB | 8.94 | 25.82 | 84.58 | 15.00 |
| 121 LEU | CG | 7.91 | 26.43 | 83.60 | 15.00 |
| 121 LEU | CD1 | 8.09 | 27.93 | 83.52 | 15.00 |
| 121 LEU | CD2 | 8.08 | 25.84 | 82.22 | 15.00 |
| 122 LYS | N | 7.02 | 24.21 | 86.51 | 15.00 |
| 122 LYS | CA | 5.69 | 23.70 | 86.81 | 15.00 |
| 122 LYS | C | 5.24 | 24.18 | 88.19 | 15.00 |
| 122 LYS | O | 4.07 | 24.52 | 88.38 | 15.00 |
| 122 LYS | CB | 5.66 | 22.17 | 86.76 | 15.00 |
| 122 LYS | CG | 4.31 | 21.58 | 87.17 | 15.00 |
| 122 LYS | CD | 4.36 | 20.07 | 87.30 | 15.00 |
| 122 LYS | CE | 5.50 | 19.63 | 88.22 | 15.00 |
| 122 LYS | NZ | 5.63 | 18.14 | 88.27 | 15.00 |
| 123 ARG | N | 6.16 | 24.19 | 89.15 | 15.00 |
| 123 ARG | CA | 5.84 | 24.63 | 90.51 | 15.00 |
| 123 ARG | C | 5.51 | 26.11 | 90.47 | 15.00 |
| 123 ARG | O | 4.53 | 26.54 | 91.07 | 15.00 |
| 123 ARG | CB | 6.99 | 24.36 | 91.49 | 15.00 |
| 123 ARG | CG | 7.32 | 22.88 | 91.65 | 15.00 |
| 123 ARG | CD | 8.14 | 22.58 | 92.89 | 15.00 |
| 123 ARG | NE | 9.59 | 22.54 | 92.68 | 15.00 |
| 123 ARG | CZ | 10.40 | 23.60 | 92.76 | 15.00 |
| 123 ARG | NH1 | 9.92 | 24.80 | 93.04 | 15.00 |
| 123 ARG | NH2 | 11.71 | 23.43 | 92.63 | 15.00 |
| 124 ALA | N | 6.30 | 26.87 | 89.73 | 15.00 |
| 124 ALA | CA | 6.09 | 28.30 | 89.58 | 15.00 |
| 124 ALA | C | 4.72 | 28.57 | 88.98 | 15.00 |
| 124 ALA | O | 3.98 | 29.41 | 89.47 | 15.00 |
| 124 ALA | CB | 7.19 | 28.91 | 88.71 | 15.00 |
| 125 VAL | N | 4.37 | 27.84 | 87.92 | 15.00 |
| 125 VAL | CA | 3.07 | 28.02 | 87.28 | 15.00 |
| 125 VAL | C | 1.95 | 27.63 | 88.24 | 15.00 |
| 125 VAL | O | 0.88 | 28.23 | 88.22 | 15.00 |
| 125 VAL | CB | 2.96 | 27.17 | 85.98 | 15.00 |
| 125 VAL | CG1 | 1.52 | 27.07 | 85.51 | 15.00 |
| 125 VAL | CG2 | 3.78 | 27.79 | 84.88 | 15.00 |
| 126 ALA | N | 2.21 | 26.64 | 89.08 | 15.00 |
| 126 ALA | CA | 1.22 | 26.16 | 90.04 | 15.00 |
| 126 ALA | C | 1.10 | 26.92 | 91.36 | 15.00 |
| 126 ALA | O | 0.03 | 26.95 | 91.97 | 15.00 |
| 126 ALA | CB | 1.43 | 24.68 | 90.31 | 15.00 |
| 127 ARG | N | 2.20 | 27.51 | 91.82 | 15.00 |
| 127 ARG | CA | 2.21 | 28.25 | 93.07 | 15.00 |
| 127 ARG | C | 1.97 | 29.74 | 92.86 | 15.00 |
| 127 ARG | O | 1.45 | 30.43 | 93.75 | 15.00 |
| 127 ARG | CB | 3.55 | 28.07 | 93.81 | 15.00 |
| 127 ARG | CG | 3.44 | 27.25 | 95.07 | 15.00 |
| 127 ARG | CD | 3.83 | 25.82 | 94.84 | 15.00 |
| 127 ARG | NE | 5.24 | 25.57 | 95.18 | 15.00 |
| 127 ARG | CZ | 5.76 | 24.37 | 95.39 | 15.00 |
| 127 ARG | NH1 | 5.03 | 23.27 | 95.29 | 15.00 |
| 127 ARG | NH2 | 7.04 | 24.27 | 95.69 | 15.00 |
| 128 VAL | N | 2.38 | 30.23 | 91.69 | 15.00 |
| 128 VAL | CA | 2.22 | 31.64 | 91.36 | 15.00 |
| 128 VAL | C | 1.08 | 31.86 | 90.37 | 15.00 |
| 128 VAL | O | 0.06 | 32.47 | 90.67 | 15.00 |
| 128 VAL | CB | 3.53 | 32.20 | 90.78 | 15.00 |
| 128 VAL | CG1 | 3.48 | 33.72 | 90.75 | 15.00 |
| 128 VAL | CG2 | 4.72 | 31.71 | 91.58 | 15.00 |
| 129 GLY | N | 1.27 | 31.35 | 89.16 | 15.00 |
| 129 GLY | CA | 0.26 | 31.49 | 88.14 | 15.00 |
| 129 GLY | C | 0.98 | 31.73 | 86.84 | 15.00 |
| 129 GLY | O | 2.11 | 31.28 | 86.67 | 15.00 |
| 130 PRO | N | 0.36 | 32.47 | 85.91 | 15.00 |
| 130 PRO | CA | 0.96 | 32.76 | 84.62 | 15.00 |
| 130 PRO | C | 2.37 | 33.32 | 84.72 | 15.00 |
| 130 PRO | O | 2.60 | 34.37 | 85.32 | 15.00 |
| 130 PRO | CB | −0.03 | 33.76 | 84.02 | 15.00 |
| 130 PRO | CG | −1.33 | 33.27 | 84.53 | 15.00 |
| 130 PRO | CD | −1.00 | 33.01 | 85.99 | 15.00 |
| 131 VAL | N | 3.32 | 32.57 | 84.15 | 15.00 |
| 131 VAL | CA | 4.72 | 32.96 | 84.13 | 15.00 |
| 131 VAL | C | 5.09 | 33.29 | 82.67 | 15.00 |
| 131 VAL | O | 4.48 | 32.77 | 81.73 | 15.00 |
| 131 VAL | CB | 5.63 | 31.83 | 84.73 | 15.00 |
| 131 VAL | CG1 | 5.57 | 30.58 | 83.89 | 15.00 |
| 131 VAL | CG2 | 7.07 | 32.28 | 84.86 | 15.00 |
| 132 SER | N | 6.03 | 34.23 | 82.49 | 15.00 |
| 132 SER | CA | 6.49 | 34.64 | 81.17 | 15.00 |
| 132 SER | C | 7.58 | 33.70 | 80.71 | 15.00 |
| 132 SER | O | 8.60 | 33.56 | 81.40 | 15.00 |
| 132 SER | CB | 7.08 | 36.05 | 81.25 | 15.00 |
| 132 SER | OG | 6.16 | 36.98 | 81.80 | 15.00 |
| 133 VAL | N | 7.39 | 33.03 | 79.58 | 15.00 |
| 133 VAL | CA | 8.39 | 32.10 | 79.03 | 15.00 |
| 133 VAL | C | 8.84 | 32.58 | 77.67 | 15.00 |
| 133 VAL | O | 8.20 | 33.43 | 77.06 | 15.00 |
| 133 VAL | CB | 7.86 | 30.66 | 78.87 | 15.00 |
| 133 VAL | CG1 | 8.20 | 29.83 | 80.07 | 15.00 |
| 133 VAL | CG2 | 6.37 | 30.65 | 78.66 | 15.00 |
| 134 ALA | N | 9.98 | 32.08 | 77.21 | 15.00 |
| 134 ALA | CA | 10.51 | 32.42 | 75.89 | 15.00 |
| 134 ALA | C | 10.71 | 31.08 | 75.20 | 15.00 |
| 134 ALA | O | 10.94 | 30.09 | 75.89 | 15.00 |
| 134 ALA | CB | 11.81 | 33.16 | 76.01 | 15.00 |

TABLE I-continued

Table of the orthogonal three dimensional coordinates in Ångstroms and B factors (Å²) for cathepsin K.

| Residue | Atom | X | Y | Z | B |
|---|---|---|---|---|---|
| 135 ILE | N | 10.58 | 31.02 | 73.88 | 15.00 |
| 135 ILE | CA | 10.74 | 29.75 | 73.17 | 15.00 |
| 135 ILE | C | 11.25 | 29.93 | 71.74 | 15.00 |
| 135 ILE | O | 11.54 | 31.04 | 71.29 | 15.00 |
| 135 ILE | CB | 9.39 | 29.00 | 73.05 | 15.00 |
| 135 ILE | CG1 | 8.32 | 29.93 | 72.47 | 15.00 |
| 135 ILE | CG2 | 8.98 | 28.39 | 74.37 | 15.00 |
| 135 ILE | CD1 | 7.01 | 29.26 | 72.13 | 15.00 |
| 136 ASP | N | 11.37 | 28.80 | 71.04 | 15.00 |
| 136 ASP | CA | 11.80 | 28.77 | 69.65 | 15.00 |
| 136 ASP | C | 10.54 | 28.58 | 68.80 | 15.00 |
| 136 ASP | O | 10.02 | 27.47 | 68.67 | 15.00 |
| 136 ASP | CB | 12.79 | 27.62 | 69.36 | 15.00 |
| 136 ASP | CG | 13.23 | 27.57 | 67.89 | 15.00 |
| 136 ASP | OD1 | 13.18 | 28.61 | 67.20 | 15.00 |
| 136 ASP | OD2 | 13.64 | 26.49 | 67.41 | 15.00 |
| 137 ALA | N | 10.05 | 29.68 | 68.24 | 15.00 |
| 137 ALA | CA | 8.87 | 29.65 | 67.41 | 15.00 |
| 137 ALA | C | 9.23 | 29.70 | 65.91 | 15.00 |
| 137 ALA | O | 8.38 | 30.00 | 65.07 | 15.00 |
| 137 ALA | CB | 7.97 | 30.81 | 67.79 | 15.00 |
| 138 SER | N | 10.47 | 29.35 | 65.57 | 15.00 |
| 138 SER | CA | 10.91 | 29.38 | 64.18 | 15.00 |
| 138 SER | C | 10.40 | 28.27 | 63.28 | 15.00 |
| 138 SER | O | 10.47 | 28.39 | 62.06 | 15.00 |
| 138 SER | CB | 12.43 | 29.40 | 64.10 | 15.00 |
| 138 SER | OG | 12.93 | 30.59 | 64.68 | 15.00 |
| 139 LEU | N | 9.85 | 27.22 | 63.87 | 15.00 |
| 139 LEU | CA | 9.36 | 26.07 | 63.12 | 15.00 |
| 139 LEU | C | 8.06 | 26.32 | 62.36 | 15.00 |
| 139 LEU | O | 7.07 | 26.74 | 62.94 | 15.00 |
| 139 LEU | CB | 9.17 | 24.86 | 64.04 | 15.00 |
| 139 LEU | CG | 10.27 | 24.49 | 65.02 | 15.00 |
| 139 LEU | CD1 | 11.61 | 24.35 | 64.30 | 15.00 |
| 139 LEU | CD2 | 10.33 | 25.54 | 66.14 | 15.00 |
| 140 THR | N | 8.06 | 26.00 | 61.06 | 15.00 |
| 140 THR | CA | 6.87 | 26.19 | 60.24 | 15.00 |
| 140 THR | C | 5.73 | 25.38 | 60.86 | 15.00 |
| 140 THR | O | 4.56 | 25.75 | 60.77 | 15.00 |
| 140 THR | CB | 7.09 | 25.72 | 58.78 | 15.00 |
| 140 THR | OG1 | 8.35 | 26.21 | 58.30 | 15.00 |
| 140 THR | CG2 | 6.00 | 26.29 | 57.88 | 15.00 |
| 141 SER | N | 6.11 | 24.29 | 61.54 | 15.00 |
| 141 SER | CA | 5.14 | 23.42 | 62.20 | 15.00 |
| 141 SER | C | 4.49 | 24.13 | 63.38 | 15.00 |
| 141 SER | O | 3.32 | 23.91 | 63.69 | 15.00 |
| 141 SER | CB | 5.83 | 22.12 | 62.64 | 15.00 |
| 141 SER | OG | 7.14 | 22.36 | 63.15 | 15.00 |
| 142 PHE | N | 5.25 | 25.01 | 64.02 | 15.00 |
| 142 PHE | CA | 4.74 | 25.76 | 65.15 | 15.00 |
| 142 PHE | C | 3.80 | 26.83 | 64.66 | 15.00 |
| 142 PHE | O | 2.78 | 27.12 | 65.30 | 15.00 |
| 142 PHE | CB | 5.88 | 26.41 | 65.94 | 15.00 |
| 142 PHE | CG | 5.41 | 27.24 | 67.09 | 15.00 |
| 142 PHE | CD1 | 5.07 | 28.58 | 66.91 | 15.00 |
| 142 PHE | CD2 | 5.31 | 26.70 | 68.37 | 15.00 |
| 142 PHE | CE1 | 4.64 | 29.36 | 67.97 | 15.00 |
| 142 PHE | CE2 | 4.89 | 27.47 | 69.44 | 15.00 |
| 142 PHE | CZ | 4.55 | 28.81 | 69.24 | 15.00 |
| 143 GLN | N | 4.13 | 27.43 | 63.52 | 15.00 |
| 143 GLN | CA | 3.31 | 28.49 | 62.99 | 15.00 |
| 143 GLN | C | 1.93 | 28.03 | 62.57 | 15.00 |
| 143 GLN | O | 0.95 | 28.72 | 62.84 | 15.00 |
| 143 GLN | CB | 4.05 | 29.25 | 61.89 | 15.00 |
| 143 GLN | CG | 5.12 | 30.14 | 62.48 | 15.00 |
| 143 GLN | CD | 6.22 | 30.52 | 61.51 | 15.00 |
| 143 GLN | OE1 | 5.97 | 31.14 | 60.47 | 15.00 |
| 143 GLN | NE2 | 7.45 | 30.19 | 61.86 | 15.00 |
| 144 PHE | N | 1.84 | 26.82 | 62.00 | 15.00 |
| 144 PHE | CA | 0.54 | 26.30 | 61.57 | 15.00 |
| 144 PHE | C | −0.14 | 25.30 | 62.52 | 15.00 |
| 144 PHE | O | −1.02 | 24.53 | 62.12 | 15.00 |
| 144 PHE | CB | 0.56 | 25.79 | 60.11 | 15.00 |
| 144 PHE | CG | 1.57 | 24.68 | 59.84 | 15.00 |
| 144 PHE | CD1 | 1.63 | 23.54 | 60.63 | 15.00 |
| 144 PHE | CD2 | 2.40 | 24.75 | 58.73 | 15.00 |
| 144 PHE | CE1 | 2.50 | 22.49 | 60.32 | 15.00 |
| 144 PHE | CE2 | 3.27 | 23.71 | 58.42 | 15.00 |
| 144 PHE | CZ | 3.32 | 22.58 | 59.22 | 15.00 |
| 145 TYR | N | 0.27 | 25.33 | 63.79 | 15.00 |
| 145 TYR | CA | −0.30 | 24.45 | 64.81 | 15.00 |
| 145 TYR | C | −1.80 | 24.73 | 64.93 | 15.00 |
| 145 TYR | O | −2.22 | 25.89 | 64.92 | 15.00 |
| 145 TYR | CB | 0.36 | 24.72 | 66.17 | 15.00 |
| 145 TYR | CG | −0.43 | 24.13 | 67.33 | 15.00 |
| 145 TYR | CD1 | −0.28 | 22.79 | 67.70 | 15.00 |
| 145 TYR | CD2 | −1.38 | 24.90 | 68.01 | 15.00 |
| 145 TYR | CE1 | −1.05 | 22.23 | 68.70 | 15.00 |
| 145 TYR | CE2 | −2.15 | 24.35 | 69.01 | 15.00 |
| 145 TYR | CZ | −1.99 | 23.01 | 69.35 | 15.00 |
| 145 TYR | OH | −2.76 | 22.46 | 70.34 | 15.00 |
| 146 SER | N | −2.60 | 23.68 | 65.08 | 15.00 |
| 146 SER | CA | −4.04 | 23.84 | 65.20 | 15.00 |
| 146 SER | C | −4.65 | 22.98 | 66.30 | 15.00 |
| 146 SER | O | −5.72 | 23.29 | 66.81 | 15.00 |
| 146 SER | CB | −4.74 | 23.59 | 63.84 | 15.00 |
| 146 SER | OG | −4.46 | 22.30 | 63.31 | 15.00 |
| 147 LYS | N | −3.96 | 21.91 | 66.67 | 15.00 |
| 147 LYS | CA | −4.48 | 21.04 | 67.73 | 15.00 |
| 147 LYS | C | −3.46 | 20.00 | 68.23 | 15.00 |
| 147 LYS | O | −2.52 | 19.67 | 67.51 | 15.00 |
| 147 LYS | CB | −5.79 | 20.37 | 67.27 | 15.00 |
| 147 LYS | CG | −5.76 | 19.70 | 65.88 | 15.00 |
| 147 LYS | CD | −7.11 | 19.05 | 65.50 | 15.00 |
| 147 LYS | CE | −7.19 | 18.65 | 64.01 | 15.00 |
| 147 LYS | NZ | −7.28 | 19.82 | 63.07 | 15.00 |
| 148 GLY | N | −3.63 | 19.55 | 69.48 | 15.00 |
| 148 GLY | CA | −2.75 | 18.55 | 70.07 | 15.00 |
| 148 GLY | C | −1.56 | 19.09 | 70.85 | 15.00 |
| 148 GLY | O | −1.43 | 20.29 | 71.06 | 15.00 |
| 149 VAL | N | −0.71 | 18.18 | 71.31 | 15.00 |
| 149 VAL | CA | 0.50 | 18.54 | 72.07 | 15.00 |
| 149 VAL | C | 1.66 | 18.70 | 71.06 | 15.00 |
| 149 VAL | O | 2.06 | 17.74 | 70.39 | 15.00 |
| 149 VAL | CB | 0.83 | 17.46 | 73.14 | 15.00 |
| 149 VAL | CG1 | 2.06 | 17.86 | 73.93 | 15.00 |
| 149 VAL | CG2 | −0.34 | 17.26 | 74.08 | 15.00 |
| 150 TYR | N | 2.21 | 19.90 | 70.99 | 15.00 |
| 150 TYR | CA | 3.25 | 20.21 | 70.03 | 15.00 |
| 150 TYR | C | 4.60 | 19.64 | 70.34 | 15.00 |
| 150 TYR | O | 5.26 | 20.08 | 71.28 | 15.00 |
| 150 TYR | CB | 3.39 | 21.72 | 69.86 | 15.00 |
| 150 TYR | CG | 4.42 | 22.11 | 68.81 | 15.00 |
| 150 TYR | CD1 | 4.39 | 21.53 | 67.54 | 15.00 |
| 150 TYR | CD2 | 5.44 | 23.02 | 69.11 | 15.00 |
| 150 TYR | CE1 | 5.36 | 21.85 | 66.58 | 15.00 |
| 150 TYR | CE2 | 6.41 | 23.33 | 68.15 | 15.00 |
| 150 TYR | CZ | 6.37 | 22.74 | 66.90 | 15.00 |
| 150 TYR | OH | 7.34 | 23.02 | 65.97 | 15.00 |
| 151 TYR | N | 5.03 | 18.69 | 69.53 | 15.00 |
| 151 TYR | CA | 6.35 | 18.11 | 69.70 | 15.00 |
| 151 TYR | C | 7.09 | 18.15 | 68.37 | 15.00 |
| 151 TYR | O | 6.65 | 17.56 | 67.39 | 15.00 |
| 151 TYR | CB | 6.30 | 16.68 | 70.20 | 15.00 |
| 151 TYR | CG | 7.67 | 16.22 | 70.63 | 15.00 |
| 151 TYR | CD1 | 8.45 | 17.02 | 71.46 | 15.00 |
| 151 TYR | CD2 | 8.20 | 15.02 | 70.17 | 15.00 |
| 151 TYR | CE1 | 9.74 | 16.65 | 71.82 | 15.00 |
| 151 TYR | CE2 | 9.50 | 14.63 | 70.52 | 15.00 |
| 151 TYR | CZ | 10.26 | 15.45 | 71.35 | 15.00 |
| 151 TYR | OH | 11.55 | 15.08 | 71.70 | 15.00 |
| 152 ASP | N | 8.21 | 18.85 | 68.35 | 15.00 |
| 152 ASP | CA | 8.98 | 18.96 | 67.12 | 15.00 |
| 152 ASP | C | 10.47 | 18.82 | 67.44 | 15.00 |
| 152 ASP | O | 11.08 | 19.72 | 68.03 | 15.00 |
| 152 ASP | CB | 8.70 | 20.31 | 66.45 | 15.00 |
| 152 ASP | CG | 9.22 | 20.37 | 65.03 | 15.00 |
| 152 ASP | OD1 | 8.48 | 19.96 | 64.12 | 15.00 |

TABLE I-continued

Table of the orthogonal three dimensional coordinates in Ångstroms and B factors (Å²) for cathepsin K.

| Residue | Atom | X | Y | Z | B |
|---|---|---|---|---|---|
| 152 ASP | OD2 | 10.37 | 20.82 | 64.82 | 15.00 |
| 153 GLU | N | 11.03 | 17.68 | 67.05 | 15.00 |
| 153 GLU | CA | 12.44 | 17.38 | 67.31 | 15.00 |
| 153 GLU | C | 13.40 | 18.37 | 66.69 | 15.00 |
| 153 GLU | O | 14.59 | 18.34 | 66.98 | 15.00 |
| 153 GLU | CB | 12.76 | 15.94 | 66.86 | 15.00 |
| 153 GLU | CG | 12.29 | 15.56 | 65.44 | 15.00 |
| 153 GLU | CD | 13.28 | 15.95 | 64.33 | 15.00 |
| 153 GLU | OE1 | 14.38 | 15.36 | 64.28 | 15.00 |
| 153 GLU | OE2 | 12.95 | 16.84 | 63.50 | 15.00 |
| 154 SER | N | 12.89 | 19.26 | 65.85 | 15.00 |
| 154 SER | CA | 13.75 | 20.24 | 65.20 | 15.00 |
| 154 SER | C | 13.86 | 21.54 | 66.01 | 15.00 |
| 154 SER | O | 14.71 | 22.38 | 65.71 | 15.00 |
| 154 SER | CB | 13.20 | 20.54 | 63.80 | 15.00 |
| 154 SER | OG | 14.08 | 21.32 | 63.02 | 15.00 |
| 155 CYS | N | 13.02 | 21.69 | 67.03 | 15.00 |
| 155 CYS | CA | 13.01 | 22.90 | 67.86 | 15.00 |
| 155 CYS | C | 14.34 | 23.17 | 68.55 | 15.00 |
| 155 CYS | O | 14.74 | 22.42 | 69.45 | 15.00 |
| 155 CYS | CB | 11.86 | 22.85 | 68.87 | 15.00 |
| 155 CYS | SG | 11.05 | 24.47 | 69.10 | 15.00 |
| 156 ASN | N | 15.02 | 24.23 | 68.14 | 15.00 |
| 156 ASN | CA | 16.33 | 24.57 | 68.70 | 15.00 |
| 156 ASN | C | 16.29 | 25.23 | 70.07 | 15.00 |
| 156 ASN | O | 16.21 | 26.46 | 70.19 | 15.00 |
| 156 ASN | CB | 17.16 | 25.40 | 67.73 | 15.00 |
| 156 ASN | CG | 18.54 | 25.71 | 68.28 | 15.00 |
| 156 ASN | OD1 | 18.89 | 26.86 | 68.48 | 15.00 |
| 156 ASN | ND2 | 19.32 | 24.66 | 68.57 | 15.00 |
| 157 SER | N | 16.46 | 24.39 | 71.09 | 15.00 |
| 157 SER | CA | 16.46 | 24.79 | 72.50 | 15.00 |
| 157 SER | C | 17.39 | 25.95 | 72.87 | 15.00 |
| 157 SER | O | 17.24 | 26.54 | 73.94 | 15.00 |
| 157 SER | CB | 16.79 | 23.56 | 73.34 | 15.00 |
| 157 SER | OG | 16.11 | 22.42 | 72.84 | 15.00 |
| 158 ASP | N | 18.34 | 26.27 | 71.99 | 15.00 |
| 158 ASP | CA | 19.29 | 27.35 | 72.24 | 15.00 |
| 158 ASP | C | 18.88 | 28.70 | 71.64 | 15.00 |
| 158 ASP | O | 19.31 | 29.76 | 72.09 | 15.00 |
| 158 ASP | CB | 20.69 | 26.96 | 71.75 | 15.00 |
| 158 ASP | CG | 21.57 | 26.39 | 72.87 | 15.00 |
| 158 ASP | OD1 | 21.02 | 25.82 | 73.85 | 15.00 |
| 158 ASP | OD2 | 22.82 | 26.53 | 72.78 | 15.00 |
| 159 ASN | N | 18.07 | 28.66 | 70.59 | 15.00 |
| 159 ASN | CA | 17.63 | 29.89 | 69.97 | 15.00 |
| 159 ASN | C | 16.22 | 30.22 | 70.46 | 15.00 |
| 159 ASN | O | 15.25 | 29.58 | 70.04 | 15.00 |
| 159 ASN | CB | 17.69 | 29.76 | 68.45 | 15.00 |
| 159 ASN | CG | 16.80 | 30.75 | 67.73 | 15.00 |
| 159 ASN | OD1 | 16.93 | 31.98 | 67.88 | 15.00 |
| 159 ASN | ND2 | 15.86 | 30.22 | 66.96 | 15.00 |
| 160 LEU | N | 16.13 | 31.16 | 71.39 | 15.00 |
| 160 LEU | CA | 14.83 | 31.58 | 71.93 | 15.00 |
| 160 LEU | C | 14.48 | 32.83 | 71.16 | 15.00 |
| 160 LEU | O | 15.25 | 33.79 | 71.14 | 15.00 |
| 160 LEU | CB | 14.90 | 31.88 | 73.44 | 15.00 |
| 160 LEU | CG | 15.29 | 30.75 | 74.43 | 15.00 |
| 160 LEU | CD1 | 15.63 | 31.34 | 75.78 | 15.00 |
| 160 LEU | CD2 | 14.20 | 29.70 | 74.54 | 15.00 |
| 161 ASN | N | 13.32 | 32.82 | 70.51 | 15.00 |
| 161 ASN | CA | 12.91 | 33.94 | 69.69 | 15.00 |
| 161 ASN | C | 11.44 | 34.33 | 69.76 | 15.00 |
| 161 ASN | O | 10.94 | 34.97 | 68.85 | 15.00 |
| 161 ASN | CB | 13.25 | 33.62 | 68.24 | 15.00 |
| 161 ASN | CG | 12.59 | 32.35 | 67.78 | 15.00 |
| 161 ASN | OD1 | 11.36 | 32.28 | 67.67 | 15.00 |
| 161 ASN | ND2 | 13.38 | 31.31 | 67.58 | 15.00 |
| 162 HIS | N | 10.72 | 33.90 | 70.78 | 15.00 |
| 162 HIS | CA | 9.33 | 34.31 | 70.87 | 15.00 |
| 162 HIS | C | 8.84 | 34.19 | 72.29 | 15.00 |
| 162 HIS | O | 8.74 | 33.09 | 72.84 | 15.00 |
| 162 HIS | CB | 8.45 | 33.51 | 69.91 | 15.00 |
| 162 HIS | CG | 7.10 | 34.12 | 69.68 | 15.00 |
| 162 HIS | ND1 | 6.93 | 35.47 | 69.42 | 15.00 |
| 162 HIS | CD2 | 5.86 | 33.58 | 69.66 | 15.00 |
| 162 HIS | CE1 | 5.64 | 35.72 | 69.24 | 15.00 |
| 162 HIS | NE2 | 4.97 | 34.59 | 69.38 | 15.00 |
| 163 ALA | N | 8.58 | 35.35 | 72.90 | 15.00 |
| 163 ALA | CA | 8.09 | 35.40 | 74.26 | 15.00 |
| 163 ALA | C | 6.63 | 34.98 | 74.30 | 15.00 |
| 163 ALA | O | 5.78 | 35.55 | 73.61 | 15.00 |
| 163 ALA | CB | 8.27 | 36.79 | 74.81 | 15.00 |
| 164 VAL | N | 6.36 | 33.96 | 75.09 | 15.00 |
| 164 VAL | CA | 5.02 | 33.43 | 75.28 | 15.00 |
| 164 VAL | C | 4.69 | 33.44 | 76.78 | 15.00 |
| 164 VAL | O | 5.54 | 33.79 | 77.60 | 15.00 |
| 164 VAL | CB | 4.95 | 32.00 | 74.70 | 15.00 |
| 164 VAL | CG1 | 5.97 | 31.10 | 75.37 | 15.00 |
| 164 VAL | CG2 | 3.57 | 31.44 | 74.89 | 15.00 |
| 165 LEU | N | 3.45 | 33.09 | 77.15 | 15.00 |
| 165 LEU | CA | 3.04 | 33.03 | 78.55 | 15.00 |
| 165 LEU | C | 2.46 | 31.67 | 78.88 | 15.00 |
| 165 LEU | O | 1.65 | 31.15 | 78.12 | 15.00 |
| 165 LEU | CB | 1.96 | 34.09 | 78.85 | 15.00 |
| 165 LEU | CG | 1.43 | 34.18 | 80.29 | 15.00 |
| 165 LEU | CD1 | 2.39 | 34.99 | 81.12 | 15.00 |
| 165 LEU | CD2 | 0.06 | 34.82 | 80.33 | 15.00 |
| 166 ALA | N | 2.87 | 31.11 | 80.01 | 15.00 |
| 166 ALA | CA | 2.35 | 29.81 | 80.46 | 15.00 |
| 166 ALA | C | 1.08 | 30.09 | 81.24 | 15.00 |
| 166 ALA | O | 1.06 | 30.96 | 82.11 | 15.00 |
| 166 ALA | CB | 3.36 | 29.12 | 81.34 | 15.00 |
| 167 VAL | N | 0.02 | 29.38 | 80.89 | 15.00 |
| 167 VAL | CA | −1.29 | 29.54 | 81.52 | 15.00 |
| 167 VAL | C | −1.67 | 28.28 | 82.34 | 15.00 |
| 167 VAL | O | −2.71 | 28.21 | 83.00 | 15.00 |
| 167 VAL | CB | −2.32 | 29.91 | 80.40 | 15.00 |
| 167 VAL | CG1 | −3.67 | 29.28 | 80.59 | 15.00 |
| 167 VAL | CG2 | −2.45 | 31.41 | 80.33 | 15.00 |
| 168 GLY | N | −0.76 | 27.32 | 82.38 | 15.00 |
| 168 GLY | CA | −0.99 | 26.12 | 83.13 | 15.00 |
| 168 GLY | C | −0.16 | 24.99 | 82.57 | 15.00 |
| 168 GLY | O | 0.86 | 25.22 | 81.93 | 15.00 |
| 169 TYR | N | −0.61 | 23.78 | 82.81 | 15.00 |
| 169 TYR | CA | 0.05 | 22.58 | 82.33 | 15.00 |
| 169 TYR | C | −1.02 | 21.51 | 82.42 | 15.00 |
| 169 TYR | O | −2.11 | 21.76 | 82.93 | 15.00 |
| 169 TYR | CB | 1.27 | 22.22 | 83.20 | 15.00 |
| 169 TYR | CG | 1.02 | 22.11 | 84.70 | 15.00 |
| 169 TYR | CD1 | 0.52 | 20.94 | 85.28 | 15.00 |
| 169 TYR | CD2 | 1.32 | 23.18 | 85.56 | 15.00 |
| 169 TYR | CE1 | 0.32 | 20.84 | 86.66 | 15.00 |
| 169 TYR | CE2 | 1.12 | 23.08 | 86.94 | 15.00 |
| 169 TYR | CZ | 0.62 | 21.91 | 87.48 | 15.00 |
| 169 TYR | OH | 0.44 | 21.83 | 88.85 | 15.00 |
| 170 GLY | N | −0.71 | 20.33 | 81.90 | 15.00 |
| 170 GLY | CA | −1.65 | 19.23 | 81.94 | 15.00 |
| 170 GLY | C | −1.16 | 18.11 | 81.05 | 15.00 |
| 170 GLY | O | −0.03 | 18.14 | 80.54 | 15.00 |
| 171 ILE | N | −2.04 | 17.15 | 80.81 | 15.00 |
| 171 ILE | CA | −1.78 | 15.98 | 79.97 | 15.00 |
| 171 ILE | C | −2.96 | 15.87 | 79.00 | 15.00 |
| 171 ILE | O | −3.95 | 16.60 | 79.14 | 15.00 |
| 171 ILE | CB | −1.62 | 14.73 | 80.86 | 15.00 |
| 171 ILE | CG1 | −1.47 | 13.46 | 80.02 | 15.00 |
| 171 ILE | CG2 | −2.76 | 14.65 | 81.87 | 15.00 |
| 171 ILE | CD1 | −1.03 | 12.22 | 80.81 | 15.00 |
| 172 GLN | N | −2.86 | 15.03 | 77.96 | 15.00 |
| 172 GLN | CA | −3.97 | 14.90 | 77.01 | 15.00 |
| 172 GLN | C | −4.16 | 13.50 | 76.45 | 15.00 |
| 172 GLN | O | −5.04 | 12.76 | 76.88 | 15.00 |
| 172 GLN | CB | −3.79 | 15.89 | 75.87 | 15.00 |
| 172 GLN | CG | −4.95 | 15.94 | 74.92 | 15.00 |
| 172 GLN | CD | −4.83 | 17.08 | 73.95 | 15.00 |
| 172 GLN | OE1 | −3.81 | 17.24 | 73.28 | 15.00 |
| 172 GLN | NE2 | −5.86 | 17.91 | 73.88 | 15.00 |
| 173 LYS | N | −3.39 | 13.15 | 75.44 | 15.00 |

TABLE I-continued

Table of the orthogonal three dimensional coordinates in Ångstroms and B factors (Å²) for cathepsin K.

| Residue | Atom | X | Y | Z | B |
|---|---|---|---|---|---|
| 173 LYS | CA | −3.51 | 11.81 | 74.89 | 15.00 |
| 173 LYS | C | −2.36 | 11.09 | 75.55 | 15.00 |
| 173 LYS | O | −1.55 | 10.43 | 74.90 | 15.00 |
| 173 LYS | CB | −3.36 | 11.82 | 73.36 | 15.00 |
| 173 LYS | CG | −4.57 | 12.39 | 72.60 | 15.00 |
| 173 LYS | CD | −5.81 | 11.53 | 72.82 | 15.00 |
| 173 LYS | CE | −7.06 | 12.17 | 72.19 | 15.00 |
| 173 LYS | NZ | −8.35 | 11.45 | 72.50 | 15.00 |
| 174 GLY | N | −2.29 | 11.24 | 76.87 | 15.00 |
| 174 GLY | CA | −1.20 | 10.64 | 77.60 | 15.00 |
| 174 GLY | C | 0.03 | 11.49 | 77.36 | 15.00 |
| 174 GLY | O | 1.17 | 11.08 | 77.62 | 15.00 |
| 175 ASN | N | −0.19 | 12.72 | 76.92 | 15.00 |
| 175 ASN | CA | 0.93 | 13.59 | 76.64 | 15.00 |
| 175 ASN | C | 1.02 | 14.78 | 77.57 | 15.00 |
| 175 ASN | O | 0.07 | 15.56 | 77.70 | 15.00 |
| 175 ASN | CB | 0.88 | 14.04 | 75.18 | 15.00 |
| 175 ASN | CG | 0.72 | 12.87 | 74.20 | 15.00 |
| 175 ASN | OD1 | −0.28 | 12.77 | 73.49 | 15.00 |
| 175 ASN | ND2 | 1.71 | 11.97 | 74.19 | 15.00 |
| 176 LYS | N | 2.15 | 14.88 | 78.27 | 15.00 |
| 176 LYS | CA | 2.42 | 15.97 | 79.20 | 15.00 |
| 176 LYS | C | 2.40 | 17.22 | 78.34 | 15.00 |
| 176 LYS | O | 2.76 | 17.17 | 77.16 | 15.00 |
| 176 LYS | CB | 3.83 | 15.84 | 79.78 | 15.00 |
| 176 LYS | CG | 4.38 | 14.45 | 79.93 | 15.00 |
| 176 LYS | CD | 4.27 | 13.97 | 81.36 | 15.00 |
| 176 LYS | CE | 4.98 | 12.63 | 81.55 | 15.00 |
| 176 LYS | NZ | 4.97 | 12.14 | 82.96 | 15.00 |
| 177 HIS | N | 2.01 | 18.36 | 78.91 | 15.00 |
| 177 HIS | CA | 1.99 | 19.58 | 78.13 | 15.00 |
| 177 HIS | C | 1.88 | 20.86 | 78.95 | 15.00 |
| 177 HIS | O | 1.47 | 20.84 | 80.12 | 15.00 |
| 177 HIS | CB | 0.88 | 19.53 | 77.06 | 15.00 |
| 177 HIS | CG | −0.52 | 19.66 | 77.59 | 15.00 |
| 177 HIS | ND1 | −1.43 | 18.63 | 77.56 | 15.00 |
| 177 HIS | CD2 | −1.16 | 20.71 | 78.16 | 15.00 |
| 177 HIS | CE1 | −2.57 | 19.03 | 78.08 | 15.00 |
| 177 HIS | NE2 | −2.44 | 20.29 | 78.45 | 15.00 |
| 178 TRP | N | 2.25 | 21.96 | 78.31 | 15.00 |
| 178 TRP | CA | 2.17 | 23.29 | 78.89 | 15.00 |
| 178 TRP | C | 1.16 | 24.04 | 78.03 | 15.00 |
| 178 TRP | O | 1.20 | 23.95 | 76.79 | 15.00 |
| 178 TRP | CB | 3.52 | 23.99 | 78.78 | 15.00 |
| 178 TRP | CG | 4.66 | 23.32 | 79.46 | 15.00 |
| 178 TRP | CD1 | 5.71 | 22.70 | 78.87 | 15.00 |
| 178 TRP | CD2 | 4.94 | 23.34 | 80.86 | 15.00 |
| 178 TRP | NE1 | 6.65 | 22.35 | 79.80 | 15.00 |
| 178 TRP | CE2 | 6.21 | 22.73 | 81.03 | 15.00 |
| 178 TRP | CE3 | 4.26 | 23.83 | 81.99 | 15.00 |
| 178 TRP | CZ2 | 6.80 | 22.60 | 82.29 | 15.00 |
| 178 TRP | CZ3 | 4.85 | 23.70 | 83.23 | 15.00 |
| 178 TRP | CH2 | 6.12 | 23.09 | 83.38 | 15.00 |
| 179 ILE | N | 0.22 | 24.75 | 78.66 | 15.00 |
| 179 ILE | CA | −0.79 | 25.51 | 77.92 | 15.00 |
| 179 ILE | C | −0.20 | 26.89 | 77.64 | 15.00 |
| 179 ILE | O | −0.07 | 27.71 | 78.54 | 15.00 |
| 179 ILE | CB | −2.08 | 25.66 | 78.74 | 15.00 |
| 179 ILE | CG1 | −2.67 | 24.27 | 79.03 | 15.00 |
| 179 ILE | CG2 | −3.07 | 26.56 | 78.02 | 15.00 |
| 179 ILE | CD1 | −3.80 | 24.25 | 80.04 | 15.00 |
| 180 ILE | N | 0.21 | 27.09 | 76.39 | 15.00 |
| 180 ILE | CA | 0.83 | 28.33 | 75.96 | 15.00 |
| 180 ILE | C | −0.17 | 29.28 | 75.34 | 15.00 |
| 180 ILE | O | −1.09 | 28.85 | 74.65 | 15.00 |
| 180 ILE | CB | 1.99 | 28.05 | 74.99 | 15.00 |
| 180 ILE | CG1 | 3.32 | 28.14 | 75.72 | 15.00 |
| 180 ILE | CG2 | 1.97 | 28.97 | 73.83 | 15.00 |
| 180 ILE | CD1 | 3.53 | 27.06 | 76.73 | 15.00 |
| 181 LYS | N | 0.00 | 30.57 | 75.64 | 15.00 |
| 181 LYS | CA | −0.85 | 31.66 | 75.14 | 15.00 |
| 181 LYS | C | −0.01 | 32.55 | 74.22 | 15.00 |
| 181 LYS | O | 0.91 | 33.23 | 74.68 | 15.00 |
| 181 LYS | CB | −1.38 | 32.51 | 76.30 | 15.00 |
| 181 LYS | CG | −2.27 | 33.66 | 75.84 | 15.00 |
| 181 LYS | CD | −2.51 | 34.72 | 76.91 | 15.00 |
| 181 LYS | CE | −3.38 | 35.84 | 76.37 | 15.00 |
| 181 LYS | NZ | −3.58 | 36.94 | 77.35 | 15.00 |
| 182 ASN | N | −0.32 | 32.56 | 72.93 | 15.00 |
| 182 ASN | CA | 0.44 | 33.36 | 71.97 | 15.00 |
| 182 ASN | C | −0.18 | 34.74 | 71.73 | 15.00 |
| 182 ASN | O | −1.29 | 35.00 | 72.17 | 15.00 |
| 182 ASN | CB | 0.55 | 32.59 | 70.66 | 15.00 |
| 182 ASN | CG | 1.83 | 32.87 | 69.93 | 15.00 |
| 182 ASN | OD1 | 2.41 | 33.95 | 70.05 | 15.00 |
| 182 ASN | ND2 | 2.31 | 31.89 | 69.17 | 15.00 |
| 183 SER | N | 0.55 | 35.64 | 71.08 | 15.00 |
| 183 SER | CA | 0.03 | 36.98 | 70.82 | 15.00 |
| 183 SER | C | −0.32 | 37.19 | 69.34 | 15.00 |
| 183 SER | O | −0.25 | 38.31 | 68.82 | 15.00 |
| 183 SER | CB | 1.03 | 38.04 | 71.25 | 15.00 |
| 183 SER | OG | 2.31 | 37.80 | 70.69 | 15.00 |
| 184 TRP | N | −0.74 | 36.12 | 68.68 | 15.00 |
| 184 TRP | CA | −1.05 | 36.18 | 67.26 | 15.00 |
| 184 TRP | C | −2.53 | 36.23 | 66.88 | 15.00 |
| 184 TRP | O | −2.87 | 36.09 | 65.71 | 15.00 |
| 184 TRP | CB | −0.36 | 35.01 | 66.55 | 15.00 |
| 184 TRP | CG | 1.12 | 35.12 | 66.54 | 15.00 |
| 184 TRP | CD1 | 1.85 | 36.23 | 66.82 | 15.00 |
| 184 TRP | CD2 | 2.05 | 34.09 | 66.23 | 15.00 |
| 184 TRP | CE1 | 3.18 | 35.97 | 66.69 | 15.00 |
| 184 TRP | CE2 | 3.34 | 34.66 | 66.33 | 15.00 |
| 184 TRP | CE3 | 1.94 | 32.75 | 65.87 | 15.00 |
| 184 TRP | CZ2 | 4.51 | 33.92 | 66.09 | 15.00 |
| 184 TRP | CZ3 | 3.10 | 32.01 | 65.63 | 15.00 |
| 184 TRP | CH2 | 4.37 | 32.60 | 65.74 | 15.00 |
| 185 GLY | N | −3.40 | 36.48 | 67.85 | 15.00 |
| 185 GLY | CA | −4.82 | 36.54 | 67.56 | 15.00 |
| 185 GLY | C | −5.46 | 35.18 | 67.75 | 15.00 |
| 185 GLY | O | −4.75 | 34.16 | 67.80 | 15.00 |
| 186 GLU | N | −6.78 | 35.15 | 67.86 | 15.00 |
| 186 GLU | CA | −7.54 | 33.91 | 68.07 | 15.00 |
| 186 GLU | C | −7.53 | 32.99 | 66.85 | 15.00 |
| 186 GLU | O | −7.65 | 31.78 | 67.00 | 15.00 |
| 186 GLU | CB | −8.98 | 34.24 | 68.44 | 15.00 |
| 186 GLU | CG | −9.10 | 35.32 | 69.49 | 15.00 |
| 186 GLU | CD | −10.45 | 36.03 | 69.45 | 15.00 |
| 186 GLU | OE1 | −10.66 | 36.84 | 68.51 | 15.00 |
| 186 GLU | OE2 | −11.29 | 35.77 | 70.34 | 15.00 |
| 187 ASN | N | −7.43 | 33.58 | 65.66 | 15.00 |
| 187 ASN | CA | −7.43 | 32.78 | 64.42 | 15.00 |
| 187 ASN | C | −6.14 | 31.97 | 64.30 | 15.00 |
| 187 ASN | O | −6.07 | 31.05 | 63.49 | 15.00 |
| 187 ASN | CB | −7.64 | 33.68 | 63.19 | 15.00 |
| 187 ASN | CG | −8.60 | 33.05 | 62.14 | 15.00 |
| 187 ASN | OD1 | −8.17 | 32.52 | 61.10 | 15.00 |
| 187 ASN | ND2 | −9.90 | 33.18 | 62.38 | 15.00 |
| 188 TRP | N | −5.12 | 32.31 | 65.10 | 15.00 |
| 188 TRP | CA | −3.87 | 31.57 | 65.07 | 15.00 |
| 188 TRP | C | −4.06 | 30.34 | 65.95 | 15.00 |
| 188 TRP | O | −4.78 | 30.41 | 66.95 | 15.00 |
| 188 TRP | CB | −2.71 | 32.38 | 65.64 | 15.00 |
| 188 TRP | CG | −1.45 | 31.59 | 65.56 | 15.00 |
| 188 TRP | CD1 | −0.68 | 31.41 | 64.46 | 15.00 |
| 188 TRP | CD2 | −0.89 | 30.74 | 66.58 | 15.00 |
| 188 TRP | NE1 | 0.30 | 30.49 | 64.71 | 15.00 |
| 188 TRP | CE2 | 0.20 | 30.06 | 66.00 | 15.00 |
| 188 TRP | CE3 | −1.21 | 30.49 | 67.92 | 15.00 |
| 188 TRP | CZ2 | 0.97 | 29.14 | 66.71 | 15.00 |
| 188 TRP | CZ3 | −0.44 | 29.57 | 68.62 | 15.00 |
| 188 TRP | CH2 | 0.64 | 28.92 | 68.02 | 15.00 |
| 189 GLY | N | −3.38 | 29.25 | 65.60 | 15.00 |
| 189 GLY | CA | −3.46 | 28.02 | 66.36 | 15.00 |
| 189 GLY | C | −4.84 | 27.67 | 66.87 | 15.00 |
| 189 GLY | O | −5.86 | 27.96 | 66.24 | 15.00 |
| 190 ASN | N | −4.87 | 27.07 | 68.04 | 15.00 |
| 190 ASN | CA | −6.10 | 26.65 | 68.68 | 15.00 |
| 190 ASN | C | −6.74 | 27.83 | 69.39 | 15.00 |

TABLE I-continued

Table of the orthogonal three dimensional coordinates in Ångstroms and B factors (Å²) for cathepsin K.

| Residue | Atom | X | Y | Z | B |
|---|---|---|---|---|---|
| 190 ASN | O | −6.67 | 27.92 | 70.61 | 15.00 |
| 190 ASN | CB | −5.76 | 25.58 | 69.71 | 15.00 |
| 190 ASN | CG | −6.97 | 24.84 | 70.19 | 15.00 |
| 190 ASN | OD1 | −8.11 | 25.26 | 69.96 | 15.00 |
| 190 ASN | ND2 | −6.73 | 23.72 | 70.87 | 15.00 |
| 191 LYS | N | −7.33 | 28.75 | 68.61 | 15.00 |
| 191 LYS | CA | −7.97 | 29.96 | 69.14 | 15.00 |
| 191 LYS | C | −7.01 | 30.82 | 69.95 | 15.00 |
| 191 LYS | O | −7.36 | 31.36 | 71.00 | 15.00 |
| 191 LYS | CB | −9.20 | 29.62 | 69.99 | 15.00 |
| 191 LYS | CG | −10.33 | 28.92 | 69.26 | 15.00 |
| 191 LYS | CD | −11.50 | 28.66 | 70.20 | 15.00 |
| 191 LYS | CE | −12.26 | 27.39 | 69.82 | 15.00 |
| 191 LYS | NZ | −11.42 | 26.16 | 70.01 | 15.00 |
| 192 GLY | N | −5.79 | 30.96 | 69.45 | 15.00 |
| 192 GLY | CA | −4.80 | 31.75 | 70.13 | 15.00 |
| 192 GLY | C | −3.88 | 30.93 | 70.99 | 15.00 |
| 192 GLY | O | −2.79 | 31.39 | 71.32 | 15.00 |
| 193 TYR | N | −4.28 | 29.72 | 71.35 | 15.00 |
| 193 TYR | CA | −3.43 | 28.86 | 72.18 | 15.00 |
| 193 TYR | C | −2.80 | 27.69 | 71.45 | 15.00 |
| 193 TYR | O | −3.25 | 27.27 | 70.39 | 15.00 |
| 193 TYR | CB | −4.21 | 28.31 | 73.39 | 15.00 |
| 193 TYR | CG | −4.63 | 29.36 | 74.36 | 15.00 |
| 193 TYR | CD1 | −3.77 | 29.78 | 75.37 | 15.00 |
| 193 TYR | CD2 | −5.85 | 30.00 | 74.22 | 15.00 |
| 193 TYR | CE1 | −4.12 | 30.82 | 76.22 | 15.00 |
| 193 TYR | CE2 | −6.21 | 31.05 | 75.06 | 15.00 |
| 193 TYR | CZ | −5.34 | 31.45 | 76.06 | 15.00 |
| 193 TYR | OH | −5.68 | 32.50 | 76.87 | 15.00 |
| 194 ILE | N | −1.73 | 27.17 | 72.05 | 15.00 |
| 194 ILE | CA | −1.01 | 26.02 | 71.53 | 15.00 |
| 194 ILE | C | −0.53 | 25.21 | 72.71 | 15.00 |
| 194 ILE | O | 0.04 | 25.75 | 73.66 | 15.00 |
| 194 ILE | CB | 0.20 | 26.40 | 70.62 | 15.00 |
| 194 ILE | CG1 | 1.05 | 25.15 | 70.32 | 15.00 |
| 194 ILE | CG2 | 1.04 | 27.49 | 71.24 | 15.00 |
| 194 ILE | CD1 | 2.33 | 25.42 | 69.60 | 15.00 |
| 195 LEU | N | −0.86 | 23.92 | 72.69 | 15.00 |
| 195 LEU | CA | −0.45 | 23.00 | 73.73 | 15.00 |
| 195 LEU | C | 0.90 | 22.46 | 73.34 | 15.00 |
| 195 LEU | O | 0.99 | 21.68 | 72.42 | 15.00 |
| 195 LEU | CB | −1.43 | 21.83 | 73.83 | 15.00 |
| 195 LEU | CG | −2.45 | 21.90 | 74.96 | 15.00 |
| 195 LEU | CD1 | −3.38 | 23.07 | 74.76 | 15.00 |
| 195 LEU | CD2 | −3.23 | 20.60 | 74.98 | 15.00 |
| 196 MET | N | 1.95 | 22.94 | 74.01 | 15.00 |
| 196 MET | CA | 3.31 | 22.50 | 73.75 | 15.00 |
| 196 MET | C | 3.70 | 21.30 | 74.64 | 15.00 |
| 196 MET | O | 2.97 | 20.96 | 75.57 | 15.00 |
| 196 MET | CB | 4.27 | 23.66 | 73.96 | 15.00 |
| 196 MET | CG | 4.16 | 24.69 | 72.88 | 15.00 |
| 196 MET | SD | 5.11 | 26.17 | 73.23 | 15.00 |
| 196 MET | CE | 6.79 | 25.64 | 72.90 | 15.00 |
| 197 ALA | N | 4.85 | 20.69 | 74.38 | 15.00 |
| 197 ALA | CA | 5.27 | 19.52 | 75.15 | 15.00 |
| 197 ALA | C | 5.99 | 19.75 | 76.49 | 15.00 |
| 197 ALA | O | 7.03 | 20.42 | 76.57 | 15.00 |
| 197 ALA | CB | 6.07 | 18.58 | 74.28 | 15.00 |
| 198 ARG | N | 5.43 | 19.14 | 77.54 | 15.00 |
| 198 ARG | CA | 5.99 | 19.22 | 78.88 | 15.00 |
| 198 ARG | C | 6.80 | 17.96 | 79.20 | 15.00 |
| 198 ARG | O | 6.41 | 16.84 | 78.86 | 15.00 |
| 198 ARG | CB | 4.89 | 19.44 | 79.92 | 15.00 |
| 198 ARG | CG | 5.35 | 19.32 | 81.39 | 15.00 |
| 198 ARG | CD | 4.48 | 20.12 | 82.35 | 15.00 |
| 198 ARG | NE | 3.08 | 19.72 | 82.36 | 15.00 |
| 198 ARG | CZ | 2.62 | 18.64 | 82.99 | 15.00 |
| 198 ARG | NH1 | 3.46 | 17.86 | 83.66 | 15.00 |
| 198 ARG | NH2 | 1.33 | 18.34 | 82.95 | 15.00 |
| 199 ASN | N | 7.96 | 18.18 | 79.83 | 15.00 |
| 199 ASN | CA | 8.87 | 17.11 | 80.24 | 15.00 |
| 199 ASN | C | 9.57 | 16.30 | 79.13 | 15.00 |
| 199 ASN | O | 10.36 | 15.40 | 79.43 | 15.00 |
| 199 ASN | CB | 8.21 | 16.18 | 81.28 | 15.00 |
| 199 ASN | CG | 8.15 | 16.81 | 82.68 | 15.00 |
| 199 ASN | OD1 | 7.06 | 17.06 | 83.21 | 15.00 |
| 199 ASN | ND2 | 9.31 | 17.07 | 83.27 | 15.00 |
| 200 LYS | N | 9.31 | 16.63 | 77.88 | 15.00 |
| 200 LYS | CA | 9.97 | 15.94 | 76.77 | 15.00 |
| 200 LYS | C | 11.29 | 16.67 | 76.54 | 15.00 |
| 200 LYS | O | 11.54 | 17.17 | 75.45 | 15.00 |
| 200 LYS | CB | 9.11 | 15.96 | 75.49 | 15.00 |
| 200 LYS | CG | 8.09 | 14.81 | 75.36 | 15.00 |
| 200 LYS | CD | 8.32 | 14.01 | 74.06 | 15.00 |
| 200 LYS | CE | 7.22 | 12.96 | 73.78 | 15.00 |
| 200 LYS | NZ | 5.87 | 13.49 | 73.41 | 15.00 |
| 201 ASN | N | 12.13 | 16.71 | 77.57 | 15.00 |
| 201 ASN | CA | 13.42 | 17.39 | 77.56 | 15.00 |
| 201 ASN | C | 13.27 | 18.81 | 77.00 | 15.00 |
| 201 ASN | O | 13.24 | 18.99 | 75.80 | 15.00 |
| 201 ASN | CB | 14.47 | 16.61 | 76.74 | 15.00 |
| 201 ASN | CG | 15.92 | 17.21 | 76.86 | 15.00 |
| 201 ASN | OD1 | 16.88 | 16.46 | 77.06 | 15.00 |
| 201 ASN | ND2 | 16.06 | 18.52 | 76.67 | 15.00 |
| 202 ASN | N | 13.15 | 19.80 | 77.89 | 15.00 |
| 202 ASN | CA | 13.04 | 21.22 | 77.54 | 15.00 |
| 202 ASN | C | 12.73 | 21.51 | 76.05 | 15.00 |
| 202 ASN | O | 13.56 | 22.10 | 75.34 | 15.00 |
| 202 ASN | CB | 14.35 | 21.92 | 77.95 | 15.00 |
| 202 ASN | CG | 14.13 | 23.30 | 78.56 | 15.00 |
| 202 ASN | OD1 | 13.04 | 23.64 | 79.00 | 15.00 |
| 202 ASN | ND2 | 15.18 | 24.09 | 78.60 | 15.00 |
| 203 ALA | N | 11.55 | 21.12 | 75.59 | 15.00 |
| 203 ALA | H | 11.67 | 20.72 | 76.05 | 15.00 |
| 203 ALA | CA | 11.15 | 21.27 | 74.19 | 15.00 |
| 203 ALA | CB | 10.97 | 20.66 | 73.61 | 15.00 |
| 203 ALA | C | 11.04 | 22.76 | 73.85 | 15.00 |
| 203 ALA | O | 10.23 | 23.49 | 74.41 | 15.00 |
| 204 CYS | N | 11.83 | 23.20 | 72.87 | 15.00 |
| 204 CYS | CA | 11.81 | 24.59 | 72.40 | 15.00 |
| 204 CYS | C | 12.38 | 25.57 | 73.42 | 15.00 |
| 204 CYS | O | 12.06 | 26.76 | 73.36 | 15.00 |
| 204 CYS | CB | 10.39 | 25.02 | 72.00 | 15.00 |
| 204 CYS | SG | 9.66 | 24.16 | 70.56 | 15.00 |
| 205 GLY | N | 13.21 | 25.07 | 74.33 | 15.00 |
| 205 GLY | CA | 13.84 | 25.89 | 75.36 | 15.00 |
| 205 GLY | C | 12.87 | 26.70 | 76.20 | 15.00 |
| 205 GLY | O | 13.17 | 27.80 | 76.64 | 15.00 |
| 206 ILE | N | 11.72 | 26.10 | 76.48 | 15.00 |
| 206 ILE | CA | 10.67 | 26.74 | 77.23 | 15.00 |
| 206 ILE | C | 11.05 | 27.11 | 78.67 | 15.00 |
| 206 ILE | O | 10.90 | 28.27 | 79.08 | 15.00 |
| 206 ILE | CB | 9.41 | 25.86 | 77.17 | 15.00 |
| 206 ILE | CG1 | 8.20 | 26.58 | 77.77 | 15.00 |
| 206 ILE | CG2 | 9.69 | 24.53 | 77.81 | 15.00 |
| 206 ILE | CD1 | 6.88 | 25.88 | 77.49 | 15.00 |
| 207 ALA | N | 11.62 | 26.17 | 79.41 | 15.00 |
| 207 ALA | CA | 12.03 | 26.40 | 80.79 | 15.00 |
| 207 ALA | C | 13.38 | 27.11 | 80.93 | 15.00 |
| 207 ALA | O | 13.98 | 27.10 | 82.01 | 15.00 |
| 207 ALA | CB | 12.05 | 25.09 | 81.54 | 15.00 |
| 208 ASN | N | 13.84 | 27.74 | 79.86 | 15.00 |
| 208 ASN | CA | 15.12 | 28.43 | 79.86 | 15.00 |
| 208 ASN | C | 15.08 | 29.92 | 80.08 | 15.00 |
| 208 ASN | O | 16.13 | 30.53 | 80.28 | 15.00 |
| 208 ASN | CB | 15.84 | 28.22 | 78.54 | 15.00 |
| 208 ASN | CG | 16.81 | 27.09 | 78.60 | 15.00 |
| 208 ASN | OD1 | 16.50 | 26.04 | 79.14 | 15.00 |
| 208 ASN | ND2 | 17.99 | 27.30 | 78.04 | 15.00 |
| 209 LEU | N | 13.91 | 30.54 | 79.98 | 15.00 |
| 209 LEU | CA | 13.84 | 31.98 | 80.18 | 15.00 |
| 209 LEU | C | 12.65 | 32.45 | 81.02 | 15.00 |
| 209 LEU | G | 12.23 | 33.63 | 80.94 | 15.00 |
| 209 LEU | CB | 13.89 | 32.69 | 78.83 | 15.00 |
| 209 LEU | CG | 14.33 | 34.16 | 78.81 | 15.00 |
| 209 LEU | CD1 | 15.60 | 34.32 | 79.63 | 15.00 |
| 209 LEU | CD2 | 14.56 | 34.61 | 77.37 | 15.00 |

TABLE I-continued

Table of the orthogonal three dimensional coordinates in Ångstroms and B factors (Å²) for cathepsin K.

| Residue | Atom | X | Y | Z | B |
|---|---|---|---|---|---|
| 210 ALA | N | 12.15 | 31.57 | 81.87 | 15.00 |
| 210 ALA | H | 12.50 | 30.94 | 81.70 | 15.00 |
| 210 ALA | CA | 10.99 | 31.87 | 82.71 | 15.00 |
| 210 ALA | CB | 10.41 | 31.04 | 83.16 | 15.00 |
| 210 ALA | C | 11.33 | 33.00 | 83.69 | 15.00 |
| 210 ALA | O | 12.46 | 33.21 | 84.13 | 15.00 |
| 211 SER | N | 10.26 | 33.74 | 84.06 | 15.00 |
| 211 SER | CA | 10.37 | 34.83 | 85.02 | 15.00 |
| 211 SER | C | 8.96 | 35.33 | 85.31 | 15.00 |
| 211 SER | O | 8.09 | 35.24 | 84.45 | 15.00 |
| 211 SER | CB | 11.22 | 35.98 | 84.46 | 15.00 |
| 211 SER | OG | 10.50 | 36.76 | 83.53 | 15.00 |
| 212 PHE | N | 8.72 | 35.78 | 86.53 | 15.00 |
| 212 PHE | CA | 7.42 | 36.30 | 86.88 | 15.00 |
| 212 PHE | C | 7.64 | 37.49 | 87.78 | 15.00 |
| 212 PHE | O | 8.68 | 37.61 | 88.42 | 15.00 |
| 212 PHE | CB | 6.57 | 35.23 | 87.56 | 15.00 |
| 212 PHE | CG | 7.23 | 34.60 | 88.75 | 15.00 |
| 212 PHE | CD1 | 7.39 | 35.31 | 89.94 | 15.00 |
| 212 PHE | CD2 | 7.68 | 33.28 | 88.69 | 15.00 |
| 212 PHE | CE1 | 7.99 | 34.73 | 91.05 | 15.00 |
| 212 PHE | CE2 | 8.28 | 32.68 | 89.78 | 15.00 |
| 212 PHE | CZ | 8.44 | 33.41 | 90.97 | 15.00 |
| 213 PRO | N | 6.69 | 38.43 | 87.80 | 15.00 |
| 213 PRO | CA | 6.84 | 39.62 | 88.65 | 15.00 |
| 213 PRO | C | 6.38 | 39.34 | 90.09 | 15.00 |
| 213 PRO | O | 5.56 | 38.44 | 90.33 | 15.00 |
| 213 PRO | CB | 5.93 | 40.62 | 87.97 | 15.00 |
| 213 PRO | CG | 4.79 | 39.75 | 87.52 | 15.00 |
| 213 PRO | CD | 5.47 | 38.52 | 86.97 | 15.00 |
| 214 LYS | N | 6.96 | 40.05 | 91.04 | 15.00 |
| 214 LYS | CA | 6.57 | 39.89 | 92.42 | 15.00 |
| 214 LYS | C | 5.65 | 41.06 | 92.68 | 15.00 |
| 214 LYS | O | 6.12 | 42.17 | 92.91 | 15.00 |
| 214 LYS | CB | 7.78 | 39.94 | 93.36 | 15.00 |
| 214 LYS | CG | 8.68 | 38.72 | 93.27 | 15.00 |
| 214 LYS | CD | 9.78 | 38.70 | 94.34 | 15.00 |
| 214 LYS | CE | 10.67 | 39.94 | 94.26 | 15.00 |
| 214 LYS | NZ | 11.94 | 39.80 | 95.03 | 15.00 |
| 215 MET | N | 4.36 | 40.85 | 92.51 | 15.00 |
| 215 MET | CA | 3.39 | 41.91 | 92.77 | 15.00 |
| 215 MET | C | 2.86 | 41.71 | 94.19 | 15.00 |
| 215 MET | CB | 2.25 | 41.86 | 91.76 | 15.00 |
| 215 MET | CG | 1.06 | 42.74 | 92.12 | 15.00 |
| 215 MET | SD | −0.32 | 42.54 | 90.98 | 15.00 |
| 215 MET | CE | 0.28 | 43.53 | 89.53 | 15.00 |

TABLE II

Table of the orthogonal three dimensional coordinates in Ångstroms and B factors (Å²) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 1 ALA | CB | −54.11 | −32.66 | 67.34 | 15.00 |
| 1 ALA | C | −54.02 | −32.71 | 64.82 | 15.00 |
| 1 ALA | O | −53.62 | −33.85 | 64.58 | 15.00 |
| 1 ALA | N | −56.02 | −33.44 | 65.99 | 15.00 |
| 1 ALA | CA | −54.90 | −32.46 | 66.05 | 15.00 |
| 2 PRO | N | −53.80 | −31.67 | 63.99 | 15.00 |
| 2 PRO | CD | −54.47 | −30.37 | 64.11 | 15.00 |
| 2 PRO | CA | −52.98 | −31.72 | 62.76 | 15.00 |
| 2 PRO | CB | −53.14 | −30.31 | 62.20 | 15.00 |
| 2 PRO | CG | −54.52 | −29.90 | 62.67 | 15.00 |
| 2 PRO | C | −51.51 | −32.06 | 62.95 | 15.00 |
| 2 PRO | O | −50.99 | −32.06 | 64.08 | 15.00 |
| 3 ASP | N | −50.81 | −32.33 | 61.85 | 15.00 |
| 3 ASP | CA | −49.39 | −32.67 | 61.91 | 15.00 |

TABLE II-continued

Table of the orthogonal three dimensional coordinates in Ångstroms and B factors (Å²) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 3 ASP | CB | −49.04 | −33.71 | 60.85 | 15.00 |
| 3 ASP | CG | −49.27 | −35.14 | 61.32 | 15.00 |
| 3 ASP | OD1 | −48.47 | −35.61 | 62.17 | 15.00 |
| 3 ASP | OD2 | −50.24 | −35.79 | 60.85 | 15.00 |
| 3 ASP | C | −48.52 | −31.44 | 61.73 | 15.00 |
| 3 ASP | O | −47.93 | −31.24 | 60.68 | 15.00 |
| 4 SER | N | −48.41 | −30.64 | 62.79 | 15.00 |
| 4 SER | CA | −47.62 | −29.41 | 62.75 | 15.00 |
| 4 SER | CB | −48.55 | −28.25 | 62.37 | 15.00 |
| 4 SER | OG | −47.82 | −27.08 | 62.01 | 15.00 |
| 4 SER | C | −47.01 | −29.13 | 64.12 | 15.00 |
| 4 SER | O | −47.59 | −29.49 | 65.15 | 15.00 |
| 5 VAL | N | −45.83 | −28.51 | 64.15 | 15.00 |
| 5 VAL | CA | −45.19 | −28.15 | 65.41 | 15.00 |
| 5 VAL | CB | −44.36 | −29.31 | 66.03 | 15.00 |
| 5 VAL | CG1 | −43.06 | −29.53 | 65.29 | 15.00 |
| 5 VAL | CG2 | −44.08 | −29.04 | 67.50 | 15.00 |
| 5 VAL | C | −44.34 | −26.88 | 65.24 | 15.00 |
| 5 VAL | O | −43.64 | −26.69 | 64.25 | 15.00 |
| 6 ASP | N | −44.48 | −25.96 | 66.20 | 15.00 |
| 6 ASP | CA | −43.78 | −24.69 | 66.19 | 15.00 |
| 6 ASP | CB | −44.75 | −23.59 | 65.74 | 15.00 |
| 6 ASP | CG | −44.11 | −22.19 | 65.67 | 15.00 |
| 6 ASP | OD1 | −42.99 | −21.99 | 66.18 | 15.00 |
| 6 ASP | OD2 | −44.75 | −21.27 | 65.13 | 15.00 |
| 6 ASP | C | −43.37 | −24.47 | 67.64 | 15.00 |
| 6 ASP | O | −44.19 | −24.09 | 68.48 | 15.00 |
| 7 TYR | N | −42.10 | −24.68 | 67.95 | 15.00 |
| 7 TYR | CA | −41.65 | −24.50 | 69.33 | 15.00 |
| 7 TYR | CB | −40.30 | −25.18 | 69.53 | 15.00 |
| 7 TYR | CG | −40.41 | −26.69 | 69.53 | 15.00 |
| 7 TYR | CD1 | −40.91 | −27.37 | 70.64 | 15.00 |
| 7 TYR | CE1 | −41.02 | −28.74 | 70.65 | 15.00 |
| 7 TYR | CD2 | −40.02 | −27.43 | 68.42 | 15.00 |
| 7 TYR | CE2 | −40.13 | −28.80 | 68.42 | 15.00 |
| 7 TYR | CZ | −40.63 | −29.45 | 69.53 | 15.00 |
| 7 TYR | OH | −40.70 | −30.82 | 69.53 | 15.00 |
| 7 TYR | C | −41.62 | −23.07 | 69.82 | 15.00 |
| 7 TYR | O | −41.41 | −22.81 | 71.00 | 15.00 |
| 8 ARG | N | −41.83 | −22.12 | 68.92 | 15.00 |
| 8 ARG | CA | −41.84 | −20.72 | 69.31 | 15.00 |
| 8 ARG | CB | −42.00 | −19.80 | 68.09 | 15.00 |
| 8 ARG | CG | −40.82 | −19.80 | 67.14 | 15.00 |
| 8 ARG | CD | −41.13 | −18.98 | 65.91 | 15.00 |
| 8 ARG | NE | −42.05 | −19.66 | 65.00 | 15.00 |
| 8 ARG | CZ | −42.68 | −19.07 | 64.00 | 15.00 |
| 8 ARG | NH1 | −42.49 | −17.78 | 63.77 | 15.00 |
| 8 ARG | NH2 | −43.50 | −19.77 | 63.22 | 15.00 |
| 8 ARG | C | −43.00 | −20.51 | 70.28 | 15.00 |
| 8 ARG | O | −42.87 | −19.79 | 71.28 | 15.00 |
| 9 LYS | N | −44.10 | −21.19 | 70.00 | 15.00 |
| 9 LYS | CA | −45.30 | −21.10 | 70.82 | 15.00 |
| 9 LYS | CB | −46.49 | −21.67 | 70.05 | 15.00 |
| 9 LYS | CG | −46.76 | −21.07 | 68.69 | 15.00 |
| 9 LYS | CD | −48.04 | −21.67 | 68.14 | 15.00 |
| 9 LYS | CE | −48.28 | −21.36 | 66.69 | 15.00 |
| 9 LYS | NZ | −49.49 | −22.07 | 66.19 | 15.00 |
| 9 LYS | C | −45.20 | −21.83 | 72.16 | 15.00 |
| 9 LYS | O | −46.13 | −21.78 | 72.97 | 15.00 |
| 10 LYS | N | −44.10 | −22.53 | 72.40 | 15.00 |
| 10 LYS | CA | −43.92 | −23.27 | 73.64 | 15.00 |
| 10 LYS | CB | −43.47 | −24.71 | 73.36 | 15.00 |
| 10 LYS | CG | −43.75 | −25.23 | 71.96 | 15.00 |
| 10 LYS | CD | −45.22 | −25.49 | 71.73 | 15.00 |
| 10 LYS | CE | −45.52 | −26.97 | 71.83 | 15.00 |
| 10 LYS | NZ | −45.21 | −27.50 | 73.19 | 15.00 |
| 10 LYS | C | −42.88 | −22.63 | 74.54 | 15.00 |
| 10 LYS | O | −42.67 | −23.06 | 75.67 | 15.00 |
| 11 GLY | N | −42.16 | −21.63 | 74.03 | 15.00 |
| 11 GLY | CA | −41.15 | −20.98 | 74.83 | 15.00 |
| 11 GLY | C | −39.79 | −21.63 | 74.68 | 15.00 |

TABLE II-continued

Table of the orthogonal three dimensional coordinates in Ångstroms and B factors (Å²) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 11 GLY | O | −38.90 | −21.42 | 75.50 | 15.00 |
| 12 TYR | N | −39.60 | −22.38 | 73.60 | 15.00 |
| 12 TYR | CA | −38.34 | −23.07 | 73.36 | 15.00 |
| 12 TYR | CB | −38.56 | −24.39 | 72.61 | 15.00 |
| 12 TYR | CG | −39.12 | −25.53 | 73.43 | 15.00 |
| 12 TYR | CD1 | −40.27 | −25.37 | 74.19 | 15.00 |
| 12 TYR | CE1 | −40.82 | −26.43 | 74.89 | 15.00 |
| 12 TYR | CD2 | −38.53 | −26.79 | 73.39 | 15.00 |
| 12 TYR | CE2 | −39.08 | −27.86 | 74.09 | 15.00 |
| 12 TYR | CZ | −40.23 | −27.67 | 74.84 | 15.00 |
| 12 TYR | OH | −40.79 | −28.71 | 75.55 | 15.00 |
| 12 TYR | C | −37.31 | −22.26 | 72.60 | 15.00 |
| 12 TYR | O | −36.14 | −22.61 | 72.57 | 15.00 |
| 13 VAL | N | −37.70 | −21.18 | 71.93 | 15.00 |
| 13 VAL | CA | −36.72 | −20.42 | 71.18 | 15.00 |
| 13 VAL | CB | −36.97 | −20.48 | 69.67 | 15.00 |
| 13 VAL | CG1 | −37.21 | −21.91 | 69.23 | 15.00 |
| 13 VAL | CG2 | −38.14 | −19.62 | 69.30 | 15.00 |
| 13 VAL | C | −36.63 | −18.98 | 71.64 | 15.00 |
| 13 VAL | O | −37.62 | −18.38 | 72.02 | 15.00 |
| 14 THR | N | −35.41 | −18.45 | 71.65 | 15.00 |
| 14 THR | CA | −35.16 | −17.08 | 72.07 | 15.00 |
| 14 THR | CB | −33.75 | 16.96 | 72.66 | 15.00 |
| 14 THR | OG1 | −32.79 | −17.40 | 71.71 | 15.00 |
| 14 THR | CG2 | −33.63 | −17.80 | 73.91 | 15.00 |
| 14 THR | C | −35.32 | −16.08 | 70.91 | 15.00 |
| 14 THR | O | −35.57 | −16.48 | 69.77 | 15.00 |
| 15 PRO | N | −35.24 | −14.77 | 71.20 | 15.00 |
| 15 PRO | CD | −35.20 | −14.14 | 72.53 | 15.00 |
| 15 PRO | CA | −35.37 | −13.75 | 70.15 | 15.00 |
| 15 PRO | CB | −35.25 | −12.44 | 70.93 | 15.00 |
| 15 PRO | CG | −35.83 | −12.79 | 72.26 | 15.00 |
| 15 PRO | C | −34.26 | −13.87 | 69.11 | 15.00 |
| 15 PRO | O | −33.13 | −14.23 | 69.44 | 15.00 |
| 16 VAL | N | −34.59 | −13.55 | 67.85 | 15.00 |
| 16 VAL | CA | −33.64 | −13.61 | 66.75 | 15.00 |
| 16 VAL | CB | −34.33 | −13.31 | 65.40 | 15.00 |
| 16 VAL | CG1 | −33.34 | −13.41 | 64.25 | 15.00 |
| 16 VAL | CG2 | −35.47 | −14.26 | 65.19 | 15.00 |
| 16 VAL | C | −32.48 | −12.65 | 66.96 | 15.00 |
| 16 VAL | O | −32.69 | −11.49 | 67.32 | 15.00 |
| 17 LYS | N | −31.28 | −13.13 | 66.71 | 15.00 |
| 17 LYS | CA | −30.07 | −12.35 | 66.86 | 15.00 |
| 17 LYS | CB | −29.12 | −13.04 | 67.84 | 15.00 |
| 17 LYS | CG | −29.68 | −13.07 | 69.24 | 15.00 |
| 17 LYS | CD | −28.91 | −14.03 | 70.13 | 15.00 |
| 17 LYS | CE | −29.54 | −14.07 | 71.53 | 15.00 |
| 17 LYS | NZ | −31.02 | −14.22 | 71.43 | 15.00 |
| 17 LYS | C | −29.39 | −12.14 | 65.52 | 15.00 |
| 17 LYS | O | −29.72 | −12.79 | 64.54 | 15.00 |
| 18 ASN | N | −28.42 | −11.23 | 65.50 | 15.00 |
| 18 ASN | CA | −27.68 | −10.87 | 64.29 | 15.00 |
| 18 ASN | CB | −27.77 | −9.36 | 64.10 | 15.00 |
| 18 ASN | CG | −27.26 | −8.90 | 62.75 | 15.00 |
| 18 ASN | OD1 | −26.16 | −9.25 | 62.32 | 15.00 |
| 18 ASN | ND2 | −28.07 | −8.10 | 62.08 | 15.00 |
| 18 ASN | C | −26.23 | −11.28 | 64.45 | 15.00 |
| 18 ASN | O | −25.55 | −10.79 | 65.35 | 15.00 |
| 19 GLN | N | −25.72 | −12.16 | 63.60 | 15.00 |
| 19 GLN | CA | −24.33 | −12.56 | 63.73 | 15.00 |
| 19 GLN | CB | −24.00 | −13.81 | 62.90 | 15.00 |
| 19 GLN | CG | −24.44 | −13.80 | 61.45 | 15.00 |
| 19 GLN | CD | −24.06 | −15.09 | 60.72 | 15.00 |
| 19 GLN | OE1 | −24.91 | −15.79 | 60.16 | 15.00 |
| 19 GLN | NE2 | −22.77 | −15.41 | 60.71 | 15.00 |
| 19 GLN | C | −23.40 | −11.40 | 63.39 | 15.00 |
| 19 GLN | O | −22.27 | −11.33 | 63.88 | 15.00 |
| 20 GLY | N | −23.91 | −10.46 | 62.60 | 15.00 |
| 20 GLY | CA | −23.14 | −9.30 | 62.21 | 15.00 |
| 20 GLY | C | −22.11 | −9.67 | 61.16 | 15.00 |
| 20 GLY | O | −22.39 | −10.50 | 60.28 | 15.00 |
| 21 GLN | N | −20.93 | −9.08 | 61.26 | 15.00 |
| 21 GLN | CA | −19.85 | −9.33 | 60.32 | 15.00 |
| 21 GLN | CB | −19.08 | −8.03 | 60.01 | 15.00 |
| 21 GLN | CG | −19.94 | −6.78 | 59.84 | 15.00 |
| 21 GLN | CD | −20.87 | −6.85 | 58.64 | 15.00 |
| 21 GLN | OE1 | −20.43 | −6.78 | 57.49 | 15.00 |
| 21 GLN | NE2 | −22.17 | −6.95 | 58.90 | 15.00 |
| 21 GLN | C | −18.91 | −10.35 | 60.98 | 15.00 |
| 21 GLN | O | −17.86 | −10.01 | 61.52 | 15.00 |
| 22 CYS | N | −19.31 | −11.61 | 60.97 | 15.00 |
| 22 CYS | CA | −18.53 | −12.68 | 61.58 | 15.00 |
| 22 CYS | C | −19.27 | −13.95 | 61.19 | 15.00 |
| 22 CYS | O | −20.48 | −14.03 | 61.36 | 15.00 |
| 22 CYS | CB | −18.50 | −12.50 | 63.11 | 15.00 |
| 22 CYS | SG | −17.85 | −13.86 | 64.14 | 15.00 |
| 23 GLY | N | −18.56 | −14.88 | 60.56 | 15.00 |
| 23 GLY | CA | −19.19 | −16.12 | 60.13 | 15.00 |
| 23 GLY | C | −19.43 | −17.05 | 61.30 | 15.00 |
| 23 GLY | O | −18.94 | −18.17 | 61.31 | 15.00 |
| 24 SER | N | −20.24 | −16.60 | 62.25 | 15.00 |
| 24 SER | CA | −20.56 | −17.36 | 63.44 | 15.00 |
| 24 SER | CB | −20.46 | −16.45 | 64.66 | 15.00 |
| 24 SER | OG | −21.23 | −15.30 | 64.42 | 15.00 |
| 24 SER | C | −21.95 | −17.97 | 63.37 | 15.00 |
| 24 SER | O | −22.54 | −18.31 | 64.40 | 15.00 |
| 25 CYS | N | −22.49 | −18.14 | 62.17 | 15.00 |
| 25 CYS | CA | −23.81 | −18.74 | 62.02 | 15.00 |
| 25 CYS | CB | −24.21 | −18.82 | 60.54 | 15.00 |
| 25 CYS | SG | −23.17 | −19.85 | 59.47 | 15.00 |
| 25 CYS | C | −23.88 | −20.12 | 62.68 | 15.00 |
| 25 CYS | O | −24.96 | −20.59 | 63.04 | 15.00 |
| 25 INH | C1 | −26.94 | −9.70 | 58.69 | 15.00 |
| 25 INH | C2 | −26.28 | −10.48 | 59.65 | 15.00 |
| 25 INH | C3 | −25.12 | −11.19 | 59.30 | 15.00 |
| 25 INH | C4 | −24.61 | −11.12 | 58.00 | 15.00 |
| 25 INH | C5 | −25.28 | −10.33 | 57.05 | 15.00 |
| 25 INH | C6 | −26.44 | −9.62 | 57.39 | 15.00 |
| 25 INH | C7 | −23.37 | −11.90 | 57.62 | 15.00 |
| 25 INH | O8 | −23.43 | −13.32 | 57.82 | 15.00 |
| 25 INH | C9 | −22.85 | −14.36 | 57.02 | 15.00 |
| 25 INH | O10 | −21.63 | −14.58 | 56.99 | 15.00 |
| 25 INH | C11 | −23.27 | −16.14 | 55.41 | 15.00 |
| 25 INH | C12 | −22.06 | −15.67 | 54.58 | 15.00 |
| 25 INH | C13 | −22.16 | −15.18 | 53.14 | 15.00 |
| 25 INH | C14 | −20.77 | −15.22 | 52.56 | 15.00 |
| 25 INH | C15 | −23.13 | −16.04 | 52.32 | 15.00 |
| 25 INH | C16 | −22.95 | −17.51 | 56.01 | 15.00 |
| 25 INH | O17 | −23.60 | −18.50 | 55.66 | 15.00 |
| 25 INH | N18 | −21.92 | −17.60 | 56.86 | 15.00 |
| 25 INH | C19 | −21.48 | −18.89 | 57.42 | 15.00 |
| 25 INH | C20 | −20.01 | −19.11 | 57.02 | 15.00 |
| 25 INH | C21 | −19.59 | −19.34 | 55.56 | 15.00 |
| 25 INH | C22 | −19.45 | −20.84 | 55.30 | 15.00 |
| 25 INH | C23 | −18.25 | −18.64 | 55.30 | 15.00 |
| 25 INH | N24 | −23.71 | −15.07 | 56.30 | 15.00 |
| 25 INH | C25 | −21.62 | −19.06 | 58.94 | 15.00 |
| 25 INH | O26 | −21.55 | −17.95 | 59.50 | 15.00 |
| 25 INH | C27 | −20.53 | −20.00 | 59.45 | 15.00 |
| 25 INH | O28 | −20.36 | −21.26 | 58.72 | 15.00 |
| 25 INH | C29 | −19.70 | −22.40 | 59.29 | 15.00 |
| 25 INH | C30 | −19.53 | −23.60 | 58.35 | 15.00 |
| 25 INH | C31 | −20.80 | −24.42 | 58.08 | 15.00 |
| 26 TRP | N | −22.73 | −20.75 | 62.90 | 15.00 |
| 26 TRP | CA | −22.65 | −22.06 | 63.54 | 15.00 |
| 26 TRP | CB | −21.30 | −22.75 | 63.25 | 15.00 |
| 26 TRP | CG | −20.09 | −22.04 | 63.79 | 15.00 |
| 26 TRP | CD2 | −19.48 | −22.23 | 65.08 | 15.00 |
| 26 TRP | CE2 | −18.36 | −21.38 | 65.14 | 15.00 |
| 26 TRP | CE3 | −19.77 | −23.04 | 66.19 | 15.00 |
| 26 TRP | CD1 | −19.33 | −21.11 | 63.15 | 15.00 |
| 26 TRP | NE1 | −18.29 | −20.70 | 63.95 | 15.00 |

TABLE II-continued

Table of the orthogonal three dimensional coordinates in Ångstroms and B factors (Å$^2$) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 26 TRP | CZ2 | −17.53 | −21.31 | 66.27 | 15.00 |
| 26 TRP | CZ3 | −18.94 | −22.97 | 67.31 | 15.00 |
| 26 TRP | CH2 | −17.83 | −22.11 | 67.33 | 15.00 |
| 26 TRP | C | −22.89 | −22.02 | 65.06 | 15.00 |
| 26 TRP | O | −23.59 | −22.87 | 65.61 | 15.00 |
| 27 ALA | N | −22.34 | −21.01 | 65.75 | 15.00 |
| 27 ALA | CA | −22.49 | −20.86 | 67.19 | 15.00 |
| 27 ALA | CB | −21.58 | −19.78 | 67.71 | 15.00 |
| 27 ALA | C | −23.93 | −20.53 | 67.54 | 15.00 |
| 27 ALA | O | −24.46 | −20.98 | 68.55 | 15.00 |
| 28 PHE | N | −24.55 | −19.71 | 66.70 | 15.00 |
| 28 PHE | CA | −25.93 | −19.33 | 66.91 | 15.00 |
| 28 PHE | CB | −26.33 | −18.21 | 65.94 | 15.00 |
| 28 PHE | CG | −25.73 | −16.88 | 66.28 | 15.00 |
| 28 PHE | CD1 | −24.51 | −16.49 | 65.73 | 15.00 |
| 28 PHE | CD2 | −26.34 | −16.04 | 67.19 | 15.00 |
| 28 PHE | CE1 | −23.92 | −15.30 | 66.11 | 15.00 |
| 28 PHE | CE2 | −25.75 | −14.85 | 67.57 | 15.00 |
| 28 PHE | CZ | −24.54 | −14.48 | 67.02 | 15.00 |
| 28 PHE | C | −26.82 | −20.55 | 66.75 | 15.00 |
| 28 PHE | O | −27.75 | −20.75 | 67.51 | 15.00 |
| 29 SER | N | −26.49 | −21.39 | 65.78 | 15.00 |
| 29 SER | CA | −27.25 | −22.61 | 65.53 | 15.00 |
| 29 SER | CB | −26.69 | −23.33 | 64.31 | 15.00 |
| 29 SER | OG | −27.48 | −24.45 | 63.98 | 15.00 |
| 29 SER | C | −27.16 | −23.52 | 66.74 | 15.00 |
| 29 SER | O | −28.17 | −23.93 | 67.30 | 15.00 |
| 30 SER | N | −25.92 | −23.82 | 67.14 | 15.00 |
| 30 SER | CA | −25.63 | −24.69 | 68.27 | 15.00 |
| 30 SER | CB | −24.13 | −24.77 | 68.46 | 15.00 |
| 30 SER | OG | −23.51 | −24.96 | 67.22 | 15.00 |
| 30 SER | C | −26.27 | −24.16 | 69.55 | 15.00 |
| 30 SER | O | −26.82 | −24.92 | 70.35 | 15.00 |
| 31 VAL | N | −26.17 | −22.85 | 69.75 | 15.00 |
| 31 VAL | CA | −26.75 | −22.24 | 70.93 | 15.00 |
| 31 VAL | CB | −26.25 | −20.78 | 71.09 | 15.00 |
| 31 VAL | CG1 | −27.32 | −19.87 | 71.63 | 15.00 |
| 31 VAL | CG2 | −25.06 | −20.75 | 72.01 | 15.00 |
| 31 VAL | C | −28.27 | −22.35 | 70.84 | 15.00 |
| 31 VAL | O | −28.94 | −22.62 | 71.82 | 15.00 |
| 32 GLY | N | −28.80 | −22.28 | 69.63 | 15.00 |
| 32 GLY | CA | −30.23 | −22.39 | 69.44 | 15.00 |
| 32 GLY | C | −30.80 | −23.73 | 69.86 | 15.00 |
| 32 GLY | O | −31.91 | −23.80 | 70.38 | 15.00 |
| 33 ALA | N | −30.05 | −24.80 | 69.59 | 15.00 |
| 33 ALA | CA | −30.46 | −26.15 | 69.95 | 15.00 |
| 33 ALA | CB | −29.65 | −27.18 | 69.17 | 15.00 |
| 33 ALA | C | −30.28 | −26.35 | 71.44 | 15.00 |
| 33 ALA | O | −31.16 | −26.89 | 72.11 | 15.00 |
| 34 LEU | N | −29.14 | −25.91 | 71.97 | 15.00 |
| 34 LEU | CA | −28.87 | −26.01 | 73.40 | 15.00 |
| 34 LEU | CB | −27.54 | −25.36 | 73.74 | 15.00 |
| 34 LEU | CG | −26.26 | −26.09 | 73.37 | 15.00 |
| 34 LEU | CD1 | −25.09 | −25.16 | 73.59 | 15.00 |
| 34 LEU | CD2 | −26.10 | −27.34 | 74.21 | 15.00 |
| 34 LEU | C | −29.98 | −25.32 | 74.18 | 15.00 |
| 34 LEU | O | −30.45 | −25.85 | 75.18 | 15.00 |
| 35 GLU | N | −30.43 | −24.16 | 73.69 | 15.00 |
| 35 GLU | CA | −31.51 | −23.39 | 74.33 | 15.00 |
| 35 GLU | CB | −31.65 | −22.03 | 73.66 | 15.00 |
| 35 GLU | CG | −30.44 | −21.12 | 73.81 | 15.00 |
| 35 GLU | CD | −30.54 | −19.82 | 73.03 | 15.00 |
| 35 GLU | OE1 | −31.35 | −19.71 | 72.09 | 15.00 |
| 35 GLU | OE2 | −29.77 | −18.91 | 73.35 | 15.00 |
| 35 GLU | C | −32.84 | −24.12 | 74.28 | 15.00 |
| 35 GLU | O | −33.67 | −24.00 | 75.19 | 15.00 |
| 36 GLY | N | −33.09 | −24.86 | 73.21 | 15.00 |
| 36 GLY | CA | −34.33 | −25.59 | 73.09 | 15.00 |
| 36 GLY | C | −34.37 | −26.71 | 74.11 | 15.00 |
| 36 GLY | O | −35.37 | −26.91 | 74.80 | 15.00 |
| 37 GLN | N | −33.26 | −27.43 | 74.25 | 15.00 |
| 37 GLN | CA | −33.18 | −28.52 | 75.20 | 15.00 |
| 37 GLN | CB | −31.92 | −29.34 | 74.98 | 15.00 |
| 37 GLN | CG | −31.94 | −30.12 | 73.69 | 15.00 |
| 37 GLN | CD | −33.17 | −31.00 | 73.57 | 15.00 |
| 37 GLN | OE1 | −33.42 | −31.85 | 74.43 | 15.00 |
| 37 GLN | NE2 | −33.95 | −30.79 | 72.53 | 15.00 |
| 37 GLN | C | −33.24 | −28.01 | 76.63 | 15.00 |
| 37 GLN | O | −33.97 | −28.56 | 77.47 | 15.00 |
| 38 LEU | N | −32.52 | −26.92 | 76.89 | 15.00 |
| 38 LEU | CA | −32.51 | −26.31 | 78.21 | 15.00 |
| 38 LEU | CB | −31.79 | −24.96 | 78.17 | 15.00 |
| 38 LEU | CG | −31.83 | −24.13 | 79.46 | 15.00 |
| 38 LEU | CD1 | −31.00 | −24.83 | 80.53 | 15.00 |
| 38 LEU | CD2 | −31.30 | −22.73 | 79.20 | 15.00 |
| 38 LEU | C | −33.94 | −26.11 | 78.69 | 15.00 |
| 38 LEU | O | −34.30 | −26.51 | 79.79 | 15.00 |
| 39 LYS | N | −34.77 | −25.51 | 77.85 | 15.00 |
| 39 LYS | CA | −36.16 | −25.26 | 78.20 | 15.00 |
| 39 LYS | CB | −36.85 | −24.43 | 77.11 | 15.00 |
| 39 LYS | CG | −38.06 | −23.64 | 77.59 | 15.00 |
| 39 LYS | CD | −39.32 | −24.48 | 77.65 | 15.00 |
| 39 LYS | CE | −40.53 | −23.66 | 78.07 | 15.00 |
| 39 LYS | NZ | −40.50 | −23.27 | 79.50 | 15.00 |
| 39 LYS | C | −36.89 | −26.59 | 78.36 | 15.00 |
| 39 LYS | O | −37.71 | −26.75 | 79.25 | 15.00 |
| 40 LYS | N | −36.57 | −27.57 | 77.53 | 15.00 |
| 40 LYS | CA | −37.25 | −28.86 | 77.63 | 15.00 |
| 40 LYS | CB | −36.85 | −29.79 | 76.48 | 15.00 |
| 40 LYS | CG | −37.77 | −31.00 | 76.39 | 15.00 |
| 40 LYS | CD | −37.48 | −31.90 | 75.22 | 15.00 |
| 40 LYS | CE | −38.53 | −32.99 | 75.17 | 15.00 |
| 40 LYS | NZ | −38.45 | −33.78 | 73.92 | 15.00 |
| 40 LYS | C | −36.98 | −29.55 | 78.95 | 15.00 |
| 40 LYS | O | −37.90 | −30.11 | 79.56 | 15.00 |
| 41 LYS | N | −35.74 | −29.45 | 79.42 | 15.00 |
| 41 LYS | CA | −35.35 | −30.09 | 80.66 | 15.00 |
| 41 LYS | CB | −33.87 | −30.48 | 80.61 | 15.00 |
| 41 LYS | CG | −33.50 | −31.39 | 79.43 | 15.00 |
| 41 LYS | CD | −34.48 | −32.55 | 79.32 | 15.00 |
| 41 LYS | CE | −34.33 | −33.33 | 78.02 | 15.00 |
| 41 LYS | NZ | −35.59 | −34.07 | 77.73 | 15.00 |
| 41 LYS | C | −35.67 | −29.31 | 81.94 | 15.00 |
| 41 LYS | O | −36.36 | −29.82 | 82.81 | 15.00 |
| 42 THR | N | −35.20 | −28.08 | 82.07 | 15.00 |
| 42 THR | CA | −35.45 | −27.32 | 83.29 | 15.00 |
| 42 THR | CB | −34.31 | −26.34 | 83.57 | 15.00 |
| 42 THR | OG1 | −34.40 | −25.23 | 82.67 | 15.00 |
| 42 THR | CG2 | −32.98 | −27.04 | 83.36 | 15.00 |
| 42 THR | C | −36.77 | −26.54 | 83.35 | 15.00 |
| 42 THR | O | −37.19 | −26.11 | 84.43 | 15.00 |
| 43 GLY | N | −37.42 | −26.34 | 82.21 | 15.00 |
| 43 GLY | CA | −38.67 | −25.60 | 82.16 | 15.00 |
| 43 GLY | C | −38.49 | −24.09 | 82.05 | 15.00 |
| 43 GLY | O | −39.45 | −23.33 | 81.92 | 15.00 |
| 44 LYS | N | −37.25 | −23.62 | 82.11 | 15.00 |
| 44 LYS | CA | −36.99 | −22.20 | 82.03 | 15.00 |
| 44 LYS | CB | −36.47 | −21.70 | 83.37 | 15.00 |
| 44 LYS | CG | −37.07 | −22.42 | 84.57 | 15.00 |
| 44 LYS | CD | −36.69 | −21.78 | 85.90 | 15.00 |
| 44 LYS | CE | −35.51 | −22.46 | 86.59 | 15.00 |
| 44 LYS | NZ | −35.95 | −23.54 | 87.52 | 15.00 |
| 44 LYS | C | −35.98 | −21.94 | 80.92 | 15.00 |
| 44 LYS | O | −34.92 | −22.58 | 80.87 | 15.00 |
| 45 LEU | N | −36.32 | −21.02 | 80.04 | 15.00 |
| 45 LEU | CA | −35.47 | −20.64 | 78.90 | 15.00 |
| 45 LEU | CB | −36.33 | −20.13 | 77.75 | 15.00 |
| 45 LEU | CG | −35.67 | −19.77 | 76.42 | 15.00 |
| 45 LEU | CD1 | −35.27 | −21.03 | 75.66 | 15.00 |
| 45 LEU | CD2 | −36.67 | −18.97 | 75.62 | 15.00 |
| 45 LEU | C | −34.47 | −19.58 | 79.29 | 15.00 |
| 45 LEU | O | −34.68 | −18.81 | 80.22 | 15.00 |

TABLE II-continued

Table of the orthogonal three dimensional coordinates in Ångstroms and B factors (Å$^2$) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 46 LEU | N | −33.38 | −19.50 | 78.54 | 15.00 |
| 46 LEU | CA | −32.33 | −18.54 | 78.81 | 15.00 |
| 46 LEU | CB | −31.43 | −19.09 | 79.91 | 15.00 |
| 46 LEU | CG | −30.45 | −18.17 | 80.63 | 15.00 |
| 46 LEU | CD1 | −31.17 | −16.89 | 81.03 | 15.00 |
| 46 LEU | CD2 | −29.91 | −18.88 | 81.84 | 15.00 |
| 46 LEU | C | −31.55 | −18.33 | 77.51 | 15.00 |
| 46 LEU | O | −31.62 | −19.14 | 76.60 | 15.00 |
| 47 ASN | N | −30.84 | −17.22 | 77.39 | 15.00 |
| 47 ASN | CA | −30.04 | −16.97 | 76.20 | 15.00 |
| 47 ASN | CB | −30.04 | −15.48 | 75.85 | 15.00 |
| 47 ASN | CG | −31.37 | −15.02 | 75.33 | 15.00 |
| 47 ASN | OD1 | −32.19 | −14.49 | 76.08 | 15.00 |
| 47 ASN | ND2 | −31.59 | −15.20 | 74.05 | 15.00 |
| 47 ASN | C | −28.62 | −17.42 | 76.46 | 15.00 |
| 47 ASN | O | −27.96 | −16.92 | 77.37 | 15.00 |
| 48 LEU | N | −28.15 | −18.40 | 75.69 | 15.00 |
| 48 LEU | CA | −26.80 | −18.91 | 75.86 | 15.00 |
| 48 LEU | CB | −26.74 | −20.39 | 75.53 | 15.00 |
| 48 LEU | CG | −27.64 | −21.29 | 76.40 | 15.00 |
| 48 LEU | CD1 | −27.37 | −22.73 | 76.07 | 15.00 |
| 48 LEU | CD2 | −27.39 | −21.05 | 77.86 | 15.00 |
| 48 LEU | C | −25.79 | −18.10 | 75.06 | 15.00 |
| 48 LEU | O | −26.16 | −17.33 | 74.17 | 15.00 |
| 49 SER | N | −24.51 | −18.27 | 75.36 | 15.00 |
| 49 SER | CA | −23.45 | −17.50 | 74.71 | 15.00 |
| 49 SER | CB | −22.34 | −17.20 | 75.73 | 15.00 |
| 49 SER | OG | −21.21 | −16.57 | 75.14 | 15.00 |
| 49 SER | C | −22.81 | −18.05 | 73.44 | 15.00 |
| 49 SER | O | −22.00 | −18.98 | 73.49 | 15.00 |
| 50 PRO | N | −23.17 | −17.49 | 72.28 | 15.00 |
| 50 PRO | CD | −24.25 | −16.53 | 71.99 | 15.00 |
| 50 PRO | CA | −22.56 | −17.98 | 71.04 | 15.00 |
| 50 PRO | CB | −23.40 | −17.29 | 69.95 | 15.00 |
| 50 PRO | CG | −23.89 | −16.05 | 70.62 | 15.00 |
| 50 PRO | C | −21.10 | −17.55 | 71.00 | 15.00 |
| 50 PRO | O | −20.25 | −18.21 | 70.41 | 15.00 |
| 51 GLN | N | −20.79 | −16.45 | 71.69 | 15.00 |
| 51 GLN | CA | −19.43 | −15.93 | 71.75 | 15.00 |
| 51 GLN | CB | −19.40 | −14.60 | 72.52 | 15.00 |
| 51 GLN | CG | −18.07 | −13.86 | 72.44 | 15.00 |
| 51 GLN | CD | −17.86 | −13.13 | 71.13 | 15.00 |
| 51 GLN | OE1 | −18.70 | −12.34 | 70.70 | 15.00 |
| 51 GLN | NE2 | −16.72 | −13.37 | 70.49 | 15.00 |
| 51 GLN | C | −18.52 | −16.94 | 72.44 | 15.00 |
| 51 GLN | O | −17.43 | −17.24 | 71.95 | 15.00 |
| 52 ASN | N | −18.97 | −17.50 | 73.56 | 15.00 |
| 52 ASN | CA | −18.21 | −18.49 | 74.31 | 15.00 |
| 52 ASN | CB | −19.13 | −19.10 | 75.38 | 15.00 |
| 52 ASN | CG | −18.41 | −20.00 | 76.37 | 15.00 |
| 52 ASN | OD1 | −18.80 | −20.05 | 77.53 | 15.00 |
| 52 ASN | ND2 | −17.40 | −20.73 | 75.93 | 15.00 |
| 52 ASN | C | −17.77 | −19.57 | 73.34 | 15.00 |
| 52 ASN | O | −16.66 | −29.11 | 73.43 | 15.00 |
| 53 LEU | N | −18.65 | −19.89 | 72.39 | 15.00 |
| 53 LEU | CA | −18.37 | −20.90 | 71.39 | 15.00 |
| 53 LEU | CB | −19.67 | −21.37 | 70.73 | 15.00 |
| 53 LEU | CG | −20.66 | −22.13 | 71.63 | 15.00 |
| 53 LEU | CD1 | −21.88 | −22.54 | 70.82 | 15.00 |
| 53 LEU | CD2 | −20.00 | −23.35 | 72.23 | 15.00 |
| 53 LEU | C | −17.40 | −20.39 | 70.35 | 15.00 |
| 53 LEU | O | −16.45 | −21.09 | 69.98 | 15.00 |
| 54 VAL | N | −17.59 | −19.15 | 69.91 | 15.00 |
| 54 VAL | CA | −16.73 | −18.54 | 68.89 | 15.00 |
| 54 VAL | CB | −17.24 | −17.11 | 68.51 | 15.00 |
| 54 VAL | CG1 | −16.31 | −16.45 | 67.49 | 15.00 |
| 54 VAL | CG2 | −18.63 | −17.19 | 67.92 | 15.00 |
| 54 VAL | C | −15.27 | −18.47 | 69.36 | 15.00 |
| 54 VAL | O | −14.36 | −18.89 | 68.64 | 15.00 |
| 55 ASP | N | −15.06 | −17.98 | 70.58 | 15.00 |
| 55 ASP | CA | −13.73 | −17.83 | 71.15 | 15.00 |
| 55 ASP | CB | −13.78 | −16.81 | 72.29 | 15.00 |
| 55 ASP | CG | −14.32 | −15.46 | 71.87 | 15.00 |
| 55 ASP | OD1 | −14.20 | −15.10 | 70.68 | 15.00 |
| 55 ASP | OD2 | −14.86 | −14.76 | 72.75 | 15.00 |
| 55 ASP | C | −13.05 | −19.09 | 71.70 | 15.00 |
| 55 ASP | O | −11.81 | −19.13 | 71.78 | 15.00 |
| 56 CYS | N | −13.81 | −20.12 | 72.07 | 15.00 |
| 56 CYS | CA | −13.22 | −21.32 | 72.67 | 15.00 |
| 56 CYS | C | −13.29 | −22.63 | 71.91 | 15.00 |
| 56 CYS | O | −12.56 | −23.59 | 72.23 | 15.00 |
| 56 CYS | CB | −13.83 | −21.53 | 74.05 | 15.00 |
| 56 CYS | SG | −14.01 | −20.02 | 75.04 | 15.00 |
| 57 VAL | N | −14.19 | −22.77 | 70.96 | 15.00 |
| 57 VAL | CA | −14.26 | −24.02 | 70.22 | 15.00 |
| 57 VAL | CB | −15.60 | −24.16 | 69.48 | 15.00 |
| 57 VAL | CG1 | −15.62 | −25.44 | 68.67 | 15.00 |
| 57 VAL | CG2 | −16.73 | −24.15 | 70.48 | 15.00 |
| 57 VAL | C | −13.09 | −24.06 | 69.25 | 15.00 |
| 57 VAL | O | −13.23 | −23.80 | 68.06 | 15.00 |
| 58 SER | N | −11.91 | −24.40 | 69.77 | 15.00 |
| 58 SER | CA | −10.67 | −24.46 | 69.00 | 15.00 |
| 58 SER | CB | −9.53 | −24.83 | 69.93 | 15.00 |
| 58 SER | OG | −10.02 | −25.66 | 70.98 | 15.00 |
| 58 SER | C | −10.66 | −25.38 | 67.79 | 15.00 |
| 58 SER | O | −9.70 | −25.38 | 67.02 | 15.00 |
| 59 GLU | N | −11.70 | −26.18 | 67.64 | 15.00 |
| 59 GLU | CA | −11.82 | −27.10 | 66.50 | 15.00 |
| 59 GLU | CB | −12.70 | −28.31 | 66.86 | 15.00 |
| 59 GLU | CG | −12.16 | −29.19 | 67.99 | 15.00 |
| 59 GLU | CD | −12.31 | −28.56 | 69.36 | 15.00 |
| 59 GLU | OE1 | −13.46 | −28.38 | 69.83 | 15.00 |
| 59 GLU | OE2 | −11.28 | −28.23 | 69.97 | 15.00 |
| 59 GLU | C | −12.44 | −26.34 | 65.33 | 15.00 |
| 59 GLU | O | −12.44 | −26.81 | 64.19 | 15.00 |
| 60 ASN | N | −13.03 | −25.19 | 65.61 | 15.00 |
| 60 ASN | CA | −13.64 | −24.37 | 64.58 | 15.00 |
| 60 ASN | CB | −15.08 | −23.98 | 64.97 | 15.00 |
| 60 ASN | CG | −16.03 | −25.16 | 64.95 | 15.00 |
| 60 ASN | OD1 | −17.08 | −25.12 | 65.58 | 15.00 |
| 60 ASN | ND2 | −15.68 | −26.20 | 64.22 | 15.00 |
| 60 ASN | C | −12.79 | −23.12 | 64.31 | 15.00 |
| 60 ASN | O | −11.88 | −22.80 | 65.06 | 15.00 |
| 61 ASP | N | −13.13 | −22.40 | 63.25 | 15.00 |
| 61 ASP | CA | −12.38 | −21.21 | 62.87 | 15.00 |
| 61 ASP | CB | −12.30 | −21.14 | 61.34 | 15.00 |
| 61 ASP | CG | −10.95 | −20.64 | 60.84 | 15.00 |
| 61 ASP | OD1 | −10.04 | −20.40 | 61.65 | 15.00 |
| 61 ASP | OD2 | −10.80 | −20.50 | 59.60 | 15.00 |
| 61 ASP | C | −12.97 | −19.91 | 63.44 | 15.00 |
| 61 ASP | O | −12.70 | −18.83 | 62.93 | 15.00 |
| 62 GLY | N | −13.78 | −19.99 | 64.49 | 15.00 |
| 62 GLY | CA | −14.37 | −18.79 | 65.05 | 15.00 |
| 62 GLY | C | −15.25 | −18.07 | 64.05 | 15.00 |
| 62 GLY | O | −16.26 | −18.59 | 63.58 | 15.00 |
| 63 CYS | N | −14.89 | −16.85 | 63.70 | 15.00 |
| 63 CYS | CA | −15.67 | −16.11 | 62.72 | 15.00 |
| 63 CYS | C | −15.48 | −16.70 | 61.33 | 15.00 |
| 63 CYS | O | −16.15 | −16.28 | 60.39 | 15.00 |
| 63 CYS | CB | −15.30 | −14.62 | 62.69 | 15.00 |
| 63 CYS | SG | −15.85 | −13.63 | 64.12 | 15.00 |
| 64 GLY | N | −14.54 | −17.62 | 61.19 | 15.00 |
| 64 GLY | CA | −14.29 | −18.25 | 59.90 | 15.00 |
| 64 GLY | C | −15.24 | −19.41 | 59.67 | 15.00 |
| 64 GLY | O | −15.32 | −19.97 | 58.57 | 15.00 |
| 65 GLY | N | −15.97 | −19.80 | 60.70 | 15.00 |
| 65 GLY | CA | −16.91 | −20.91 | 60.56 | 15.00 |
| 65 GLY | C | −16.55 | −22.16 | 61.33 | 15.00 |
| 65 GLY | O | −15.46 | −22.30 | 61.90 | 15.00 |
| 66 GLY | N | −17.47 | −23.10 | 61.38 | 15.00 |
| 66 GLY | CA | −17.25 | −24.34 | 62.07 | 15.00 |
| 66 GLY | C | −18.51 | −25.15 | 61.93 | 15.00 |

TABLE II-continued

Table of the orthogonal three dimensional coordinates in Ångstroms and B factors (Å$^2$) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 66 GLY | O | −19.46 | −24.72 | 61.29 | 15.00 |
| 67 TYR | N | −18.50 | −26.35 | 62.49 | 15.00 |
| 67 TYR | CA | −19.66 | −27.22 | 62.44 | 15.00 |
| 67 TYR | CB | −19.25 | −28.66 | 62.13 | 15.00 |
| 67 TYR | CG | −18.41 | −28.83 | 60.89 | 15.00 |
| 67 TYR | CD1 | −19.00 | −29.00 | 59.64 | 15.00 |
| 67 TYR | CE1 | −18.22 | −29.18 | 58.51 | 15.00 |
| 67 TYR | CD2 | −17.03 | −28.83 | 60.98 | 15.00 |
| 67 TYR | CE2 | −16.25 | −29.01 | 59.86 | 15.00 |
| 67 TYR | CZ | −16.84 | −29.18 | 58.63 | 15.00 |
| 67 TYR | OH | −16.03 | −29.34 | 57.52 | 15.00 |
| 67 TYR | C | −20.27 | −27.16 | 63.83 | 15.00 |
| 67 TYR | O | −19.59 | −26.85 | 64.80 | 15.00 |
| 68 MET | N | −21.55 | −27.48 | 63.93 | 15.00 |
| 68 MET | CA | −22.24 | −27.45 | 65.20 | 15.00 |
| 68 MET | CB | −23.75 | −27.51 | 65.00 | 15.00 |
| 68 MET | CG | −24.34 | −26.31 | 64.22 | 15.00 |
| 68 MET | SD | −23.95 | −26.25 | 62.46 | 15.00 |
| 68 MET | CE | −25.40 | −26.96 | 61.77 | 15.00 |
| 68 MET | C | −21.76 | −28.58 | 66.11 | 15.00 |
| 68 MET | O | −21.49 | −28.37 | 67.29 | 15.00 |
| 69 THR | N | −21.57 | −29.78 | 65.56 | 15.00 |
| 69 THR | CA | −21.13 | −30.94 | 66.33 | 15.00 |
| 69 THR | CB | −20.92 | −32.18 | 65.44 | 15.00 |
| 69 THR | OG1 | −20.10 | −31.83 | 64.31 | 15.00 |
| 69 THR | CG2 | −22.26 | −32.69 | 64.93 | 15.00 |
| 69 THR | C | −19.85 | −30.65 | 67.12 | 15.00 |
| 69 THR | O | −19.69 | −31.11 | 68.26 | 15.00 |
| 70 ASN | N | −18.95 | −29.84 | 66.55 | 15.00 |
| 70 ASN | CA | −17.71 | −29.46 | 67.22 | 15.00 |
| 70 ASN | CB | −16.73 | −28.81 | 66.24 | 15.00 |
| 70 ASN | CG | −15.97 | −29.81 | 65.39 | 15.00 |
| 70 ASN | OD1 | −15.41 | −29.45 | 64.37 | 15.00 |
| 70 ASN | ND2 | −15.92 | −31.06 | 65.83 | 15.00 |
| 70 ASN | C | −17.96 | −28.52 | 68.39 | 15.00 |
| 70 ASN | O | −17.14 | −28.42 | 69.30 | 15.00 |
| 71 ALA | N | −19.06 | −27.78 | 68.35 | 15.00 |
| 71 ALA | CA | −19.42 | −26.86 | 69.44 | 15.00 |
| 71 ALA | CB | −20.32 | −25.76 | 68.92 | 15.00 |
| 71 ALA | C | −20.12 | −27.66 | 70.53 | 15.00 |
| 71 ALA | O | −19.94 | −27.42 | 71.73 | 15.00 |
| 72 PHE | N | −20.96 | −28.60 | 70.13 | 15.00 |
| 72 PHE | CA | −21.67 | −29.44 | 71.08 | 15.00 |
| 72 PHE | CB | −22.56 | −30.44 | 70.34 | 15.00 |
| 72 PHE | CG | −23.74 | −29.82 | 69.63 | 15.00 |
| 72 PHE | CD1 | −24.33 | −28.66 | 70.11 | 15.00 |
| 72 PHE | CD2 | −24.27 | −30.43 | 68.50 | 15.00 |
| 72 PHE | CE1 | −25.45 | −28.12 | 69.48 | 15.00 |
| 72 PHE | CE2 | −25.39 | −29.90 | 67.87 | 15.00 |
| 72 PHE | CZ | −25.98 | −28.74 | 68.35 | 15.00 |
| 72 PHE | C | −20.60 | −30.19 | 71.89 | 15.00 |
| 72 PHE | O | −20.60 | −30.15 | 73.12 | 15.00 |
| 73 GLN | N | −19.64 | −30.81 | 71.21 | 15.00 |
| 73 GLN | CA | −18.58 | −31.56 | 71.87 | 15.00 |
| 73 GLN | CB | −17.64 | −32.18 | 70.82 | 15.00 |
| 73 GLN | CG | −16.55 | −33.13 | 71.36 | 15.00 |
| 73 GLN | CD | −17.07 | −34.54 | 71.69 | 15.00 |
| 73 GLN | OE1 | −17.16 | −34.93 | 72.87 | 15.00 |
| 73 GLN | NE2 | −17.37 | −35.32 | 70.65 | 15.00 |
| 73 GLN | C | −17.81 | −30.69 | 72.87 | 15.00 |
| 73 GLN | O | −17.46 | −31.13 | 73.96 | 15.00 |
| 74 TYR | N | −17.55 | −29.43 | 72.53 | 15.00 |
| 74 TYR | CA | −16.82 | −28.56 | 73.44 | 15.00 |
| 74 TYR | CB | −16.43 | −27.25 | 72.75 | 15.00 |
| 74 TYR | CG | −16.11 | −26.12 | 73.70 | 15.00 |
| 74 TYR | CD1 | −14.83 | −25.93 | 74.20 | 15.00 |
| 74 TYR | CE1 | −14.54 | −24.93 | 75.11 | 15.00 |
| 74 TYR | CD2 | −17.11 | −25.25 | 74.14 | 15.00 |
| 74 TYR | CE2 | −16.84 | −24.23 | 75.06 | 15.00 |
| 74 TYR | CZ | −15.55 | −24.08 | 75.53 | 15.00 |
| 74 TYR | OH | −15.28 | −23.08 | 76.45 | 15.00 |
| 74 TYR | C | −17.62 | −28.25 | 74.70 | 15.00 |
| 74 TYR | O | −17.05 | −28.00 | 75.76 | 15.00 |
| 75 VAL | N | −18.94 | −28.18 | 74.59 | 15.00 |
| 75 VAL | CA | −19.77 | −27.89 | 75.75 | 15.00 |
| 75 VAL | CB | −21.21 | −27.54 | 75.33 | 15.00 |
| 75 VAL | CG1 | −22.04 | −27.14 | 76.54 | 15.00 |
| 75 VAL | CG2 | −21.20 | −26.39 | 74.33 | 15.00 |
| 75 VAL | C | −19.74 | −29.11 | 76.68 | 15.00 |
| 75 VAL | O | −19.87 | −28.99 | 77.90 | 15.00 |
| 76 GLN | N | −19.50 | −30.29 | 76.09 | 15.00 |
| 76 GLN | CA | −19.43 | −31.54 | 76.84 | 15.00 |
| 76 GLN | CB | −19.51 | −32.72 | 75.88 | 15.00 |
| 76 GLN | CG | −19.44 | −34.10 | 76.53 | 15.00 |
| 76 GLN | CD | −19.41 | −35.21 | 75.50 | 15.00 |
| 76 GLN | OE1 | −20.45 | −35.67 | 75.05 | 15.00 |
| 76 GLN | NE2 | −18.23 | −35.64 | 75.12 | 15.00 |
| 76 GLN | C | −18.15 | −31.64 | 77.66 | 15.00 |
| 76 GLN | O | −18.20 | −31.71 | 78.89 | 15.00 |
| 77 LYS | N | −17.00 | −31.64 | 77.00 | 15.00 |
| 77 LYS | CA | −15.72 | −31.75 | 77.70 | 15.00 |
| 77 LYS | CB | −14.60 | −32.13 | 76.73 | 15.00 |
| 77 LYS | CG | −14.72 | −31.53 | 75.36 | 15.00 |
| 77 LYS | CD | −13.52 | −31.92 | 74.50 | 15.00 |
| 77 LYS | CE | −13.77 | −31.61 | 73.03 | 15.00 |
| 77 LYS | NZ | −14.25 | −30.21 | 72.83 | 15.00 |
| 77 LYS | C | −15.29 | −30.55 | 78.56 | 15.00 |
| 77 LYS | O | −14.36 | −30.63 | 79.36 | 15.00 |
| 78 ASN | N | −15.94 | −29.41 | 78.38 | 15.00 |
| 78 ASN | CA | −15.62 | −28.22 | 79.15 | 15.00 |
| 78 ASN | CB | −15.75 | −26.98 | 78.27 | 15.00 |
| 78 ASN | CG | −15.54 | −25.69 | 79.03 | 15.00 |
| 78 ASN | OD1 | −14.43 | −25.40 | 79.46 | 15.00 |
| 78 ASN | ND2 | −16.60 | −24.91 | 79.16 | 15.00 |
| 78 ASN | C | −16.60 | −28.14 | 80.32 | 15.00 |
| 78 ASN | O | −16.47 | −27.32 | 81.22 | 15.00 |
| 79 ARG | N | −17.60 | −29.01 | 80.27 | 15.00 |
| 79 ARG | CA | −18.63 | −29.08 | 81.29 | 15.00 |
| 79 ARG | CB | −18.06 | −29.64 | 82.60 | 15.00 |
| 79 ARG | CG | −17.45 | −31.04 | 82.42 | 15.00 |
| 79 ARG | CD | −17.13 | −31.71 | 83.75 | 15.00 |
| 79 ARG | NE | −18.34 | −32.20 | 84.40 | 15.00 |
| 79 ARG | CZ | −18.91 | −33.37 | 84.15 | 15.00 |
| 79 ARG | NH1 | −18.36 | −34.20 | 83.26 | 15.00 |
| 79 ARG | NH2 | −20.05 | −33.70 | 84.75 | 15.00 |
| 79 ARG | C | −19.36 | −27.77 | 81.50 | 15.00 |
| 79 ARG | O | −19.57 | −27.33 | 82.64 | 15.00 |
| 80 GLY | N | −19.75 | −27.14 | 80.39 | 15.00 |
| 80 GLY | CA | −20.48 | −25.89 | 80.49 | 15.00 |
| 80 GLY | C | −20.34 | −24.84 | 79.40 | 15.00 |
| 80 GLY | O | −19.34 | −24.78 | 78.67 | 15.00 |
| 81 ILE | N | −21.39 | −24.02 | 79.30 | 15.00 |
| 81 ILE | CA | −21.46 | −22.91 | 78.36 | 15.00 |
| 81 ILE | CB | −22.22 | −23.28 | 77.05 | 15.00 |
| 81 ILE | CG2 | −23.65 | −23.63 | 77.33 | 15.00 |
| 81 ILE | CG1 | −22.16 | −22.09 | 76.08 | 15.00 |
| 81 ILE | CD1 | −22.80 | −22.35 | 74.75 | 15.00 |
| 81 ILE | C | −22.15 | −21.75 | 79.07 | 15.00 |
| 81 ILE | O | −23.20 | −21.93 | 79.71 | 15.00 |
| 82 ASP | N | −21.51 | −20.59 | 79.03 | 15.00 |
| 82 ASP | CA | −22.01 | −19.37 | 79.65 | 15.00 |
| 82 ASP | CB | −20.99 | −18.24 | 79.46 | 15.00 |
| 82 ASP | CG | −19.78 | −18.37 | 80.35 | 15.00 |
| 82 ASP | OD1 | −18.71 | −17.88 | 79.95 | 15.00 |
| 82 ASP | OD2 | −19.91 | −18.93 | 81.47 | 15.00 |
| 82 ASP | C | −23.36 | −18.86 | 79.13 | 15.00 |
| 82 ASP | O | −23.86 | −19.29 | 78.09 | 15.00 |
| 83 SER | N | −23.91 | −17.90 | 79.86 | 15.00 |
| 83 SER | CA | −25.16 | −17.25 | 79.50 | 15.00 |
| 83 SER | CB | −25.99 | −16.98 | 80.76 | 15.00 |
| 83 SER | OG | −25.21 | −16.38 | 81.78 | 15.00 |
| 83 SER | C | −24.75 | −15.93 | 78.85 | 15.00 |

TABLE II-continued

Table of the orthogonal three dimensional coordinates in Ångstroms and B factors (Å²) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 83 SER | O | −23.63 | −15.45 | 79.05 | 15.00 |
| 84 GLU | N | −25.64 | −15.33 | 78.07 | 15.00 |
| 84 GLU | CA | −25.32 | −14.09 | 77.39 | 15.00 |
| 84 GLU | CB | −26.48 | −13.65 | 76.52 | 15.00 |
| 84 GLU | CG | −26.16 | −12.52 | 75.57 | 15.00 |
| 84 GLU | CD | −25.34 | −12.95 | 74.38 | 15.00 |
| 84 GLU | OE1 | −24.85 | −14.10 | 74.35 | 15.00 |
| 84 GLU | OE2 | −25.19 | −12.13 | 73.45 | 15.00 |
| 84 GLU | C | −24.88 | −12.96 | 78.31 | 15.00 |
| 84 GLU | O | −24.03 | −12.14 | 77.94 | 15.00 |
| 85 ASP | N | −25.44 | −12.87 | 79.52 | 15.00 |
| 85 ASP | CA | −25.03 | −11.81 | 80.45 | 15.00 |
| 85 ASP | CB | −25.92 | −11.77 | 81.71 | 15.00 |
| 85 ASP | CG | −25.48 | −10.69 | 82.73 | 15.00 |
| 85 ASP | OD1 | −24.60 | −9.85 | 82.41 | 15.00 |
| 85 ASP | OD2 | −26.00 | −10.66 | 83.87 | 15.00 |
| 85 ASP | C | −23.59 | −12.02 | 80.86 | 15.00 |
| 85 ASP | O | −22.83 | −11.07 | 81.00 | 15.00 |
| 86 ALA | N | −23.18 | −13.27 | 81.05 | 15.00 |
| 86 ALA | CA | −21.82 | −13.56 | 81.47 | 15.00 |
| 86 ALA | CB | −21.76 | −14.91 | 82.14 | 15.00 |
| 86 ALA | C | −20.78 | −13.48 | 80.36 | 15.00 |
| 86 ALA | O | −19.62 | −13.15 | 80.59 | 15.00 |
| 87 TYR | N | −21.18 | −13.74 | 79.12 | 15.00 |
| 87 TYR | CA | −20.23 | −13.71 | 78.02 | 15.00 |
| 87 TYR | CB | −19.79 | −15.15 | 77.74 | 15.00 |
| 87 TYR | CG | −18.44 | −15.33 | 77.08 | 15.00 |
| 87 TYR | CD1 | −17.91 | −14.37 | 76.21 | 15.00 |
| 87 TYR | CE1 | −16.69 | −14.59 | 75.57 | 15.00 |
| 87 TYR | CD2 | −17.72 | −16.51 | 77.28 | 15.00 |
| 87 TYR | CE2 | −16.50 | −16.73 | 76.64 | 15.00 |
| 87 TYR | CZ | −16.00 | −15.77 | 75.79 | 15.00 |
| 87 TYR | OH | −14.79 | −16.02 | 75.16 | 15.00 |
| 87 TYR | C | −20.92 | −13.13 | 76.79 | 15.00 |
| 87 TYR | O | −21.26 | −13.88 | 75.86 | 15.00 |
| 88 PRO | N | −21.19 | −11.80 | 76.79 | 15.00 |
| 88 PRO | CD | −21.02 | −10.93 | 77.96 | 15.00 |
| 88 PRO | CA | −21.85 | −11.07 | 75.70 | 15.00 |
| 88 PRO | CB | −21.91 | −9.64 | 76.23 | 15.00 |
| 88 PRO | CG | −22.06 | −9.86 | 77.72 | 15.00 |
| 88 PRO | C | −21.13 | −11.13 | 74.36 | 15.00 |
| 88 PRO | O | −19.90 | −11.11 | 74.31 | 15.00 |
| 89 TYR | N | −21.93 | −11.18 | 73.31 | 15.00 |
| 89 TYR | CA | −21.47 | −11.28 | 71.92 | 15.00 |
| 89 TYR | CB | −22.64 | −11.80 | 71.09 | 15.00 |
| 89 TYR | CG | −22.28 | −12.14 | 69.68 | 15.00 |
| 89 TYR | CD1 | −21.43 | −13.20 | 69.39 | 15.00 |
| 89 TYR | CE1 | −21.07 | −13.48 | 68.09 | 15.00 |
| 89 TYR | CD2 | −22.75 | −11.36 | 68.63 | 15.00 |
| 89 TYR | CE2 | −22.39 | −11.63 | 67.32 | 15.00 |
| 89 TYR | CZ | −21.55 | −12.69 | 67.06 | 15.00 |
| 89 TYR | OH | −21.15 | −12.93 | 65.77 | 15.00 |
| 89 TYR | C | −20.94 | −9.96 | 71.34 | 15.00 |
| 89 TYR | O | −21.71 | −9.04 | 71.08 | 15.00 |
| 90 VAL | N | −19.64 | −9.86 | 71.12 | 15.00 |
| 90 VAL | CA | −19.06 | −8.63 | 70.58 | 15.00 |
| 90 VAL | CB | −17.75 | −8.27 | 71.27 | 15.00 |
| 90 VAL | CG1 | −17.98 | −8.12 | 72.76 | 15.00 |
| 90 VAL | CG2 | −16.69 | −9.32 | 70.99 | 15.00 |
| 90 VAL | C | −18.87 | −8.65 | 69.07 | 15.00 |
| 90 VAL | O | −18.28 | −7.74 | 68.50 | 15.00 |
| 91 GLY | N | −19.30 | −9.73 | 68.44 | 15.00 |
| 91 GLY | CA | −19.20 | −9.84 | 67.00 | 15.00 |
| 91 GLY | C | −17.86 | −10.11 | 66.36 | 15.00 |
| 91 GLY | O | −17.67 | −9.84 | 65.18 | 15.00 |
| 92 GLN | N | −16.91 | −10.66 | 67.11 | 15.00 |
| 92 GLN | CA | −15.59 | −10.97 | 66.57 | 15.00 |
| 92 GLN | CB | −14.80 | −9.69 | 66.32 | 15.00 |
| 92 GLN | CG | −14.73 | −8.76 | 67.51 | 15.00 |
| 92 GLN | CD | −13.95 | −7.50 | 67.19 | 15.00 |
| 92 GLN | OE1 | −12.73 | −7.54 | 67.06 | 15.00 |
| 92 GLN | NE2 | −14.65 | −6.38 | 67.02 | 15.00 |
| 92 GLN | C | −14.83 | −11.87 | 67.53 | 15.00 |
| 92 GLN | O | −15.17 | −11.94 | 68.71 | 15.00 |
| 93 GLU | N | −13.80 | −12.53 | 67.04 | 15.00 |
| 93 GLU | CA | −13.02 | −13.45 | 67.85 | 15.00 |
| 93 GLU | CB | −12.36 | −14.52 | 66.98 | 15.00 |
| 93 GLU | CG | −11.54 | −13.97 | 65.80 | 15.00 |
| 93 GLU | CD | −11.57 | −14.90 | 64.59 | 15.00 |
| 93 GLU | OE1 | −10.51 | −15.16 | 63.98 | 15.00 |
| 93 GLU | OE2 | −12.67 | −15.36 | 64.22 | 15.00 |
| 93 GLU | C | −11.99 | −12.78 | 68.74 | 15.00 |
| 93 GLU | O | −11.29 | −11.86 | 68.33 | 15.00 |
| 94 GLU | N | −11.89 | −13.29 | 69.97 | 15.00 |
| 94 GLU | CA | −10.96 | −12.78 | 70.96 | 15.00 |
| 94 GLU | CB | −11.65 | −11.74 | 71.84 | 15.00 |
| 94 GLU | CG | −12.68 | −12.34 | 72.79 | 15.00 |
| 94 GLU | CD | −13.96 | −11.54 | 72.88 | 15.00 |
| 94 GLU | OE1 | −13.96 | −10.36 | 72.44 | 15.00 |
| 94 GLU | OE2 | −14.97 | −12.08 | 73.38 | 15.00 |
| 94 GLU | C | −10.54 | −13.98 | 71.82 | 15.00 |
| 94 GLU | O | −10.95 | −15.10 | 71.55 | 15.00 |
| 95 SER | N | −9.72 | −13.74 | 72.84 | 15.00 |
| 95 SER | CA | −9.26 | −14.80 | 73.73 | 15.00 |
| 95 SER | CB | −8.26 | −14.23 | 74.75 | 15.00 |
| 95 SER | OG | −7.14 | −13.65 | 74.09 | 15.00 |
| 95 SER | C | −10.41 | −15.51 | 74.46 | 15.00 |
| 95 SER | O | −11.34 | −14.87 | 74.95 | 15.00 |
| 96 CYS | N | −10.37 | −16.84 | 74.53 | 15.00 |
| 96 CYS | CA | −11.44 | −17.57 | 75.21 | 15.00 |
| 96 CYS | C | −11.55 | −17.03 | 76.62 | 15.00 |
| 96 CYS | O | −10.58 | −17.04 | 77.37 | 15.00 |
| 96 CYS | CB | −11.13 | −19.06 | 75.26 | 15.00 |
| 96 CYS | SG | −12.35 | −20.02 | 76.20 | 15.00 |
| 97 MET | N | −12.72 | −16.51 | 76.97 | 15.00 |
| 97 MET | CA | −12.95 | −15.95 | 78.31 | 15.00 |
| 97 MET | CB | −13.50 | −14.53 | 78.21 | 15.00 |
| 97 MET | CG | −12.65 | −13.51 | 77.52 | 15.00 |
| 97 MET | SD | −13.49 | −11.94 | 77.83 | 15.00 |
| 97 MET | CE | −14.95 | −12.05 | 76.75 | 15.00 |
| 97 MET | C | −13.95 | −16.74 | 79.15 | 15.00 |
| 97 MET | O | −14.60 | −16.15 | 80.02 | 15.00 |
| 98 TYR | N | −14.08 | −18.05 | 78.94 | 15.00 |
| 98 TYR | CA | −15.05 | −18.82 | 79.70 | 15.00 |
| 98 TYR | CB | −14.89 | −20.33 | 79.47 | 15.00 |
| 98 TYR | CG | −15.95 | −21.14 | 80.19 | 15.00 |
| 98 TYR | CD1 | −17.30 | −21.01 | 79.88 | 15.00 |
| 98 TYR | CE1 | −18.28 | −21.71 | 80.58 | 15.00 |
| 98 TYR | CD2 | −15.61 | −22.00 | 81.23 | 15.00 |
| 98 TYR | CE2 | −16.58 | −22.70 | 81.94 | 15.00 |
| 98 TYR | CZ | −17.91 | −22.55 | 81.62 | 15.00 |
| 98 TYR | OH | −18.86 | −23.22 | 82.33 | 15.00 |
| 98 TYR | C | −14.99 | −18.51 | 81.20 | 15.00 |
| 98 TYR | O | −13.92 | −18.32 | 81.77 | 15.00 |
| 99 ASN | N | −16.16 | −18.49 | 81.82 | 15.00 |
| 99 ASN | CA | −16.30 | −18.18 | 83.23 | 15.00 |
| 99 ASN | CB | −16.73 | −16.72 | 83.37 | 15.00 |
| 99 ASN | CG | −17.06 | −16.32 | 84.81 | 15.00 |
| 99 ASN | OD1 | −16.96 | −17.13 | 85.74 | 15.00 |
| 99 ASN | ND2 | −17.47 | −15.06 | 84.98 | 15.00 |
| 99 ASN | C | −17.34 | −19.10 | 83.86 | 15.00 |
| 99 ASN | O | −18.55 | −18.87 | 83.72 | 15.00 |
| 100 PRO | N | −16.89 | −20.13 | 84.60 | 15.00 |
| 100 PRO | CD | −15.46 | −20.39 | 84.86 | 15.00 |
| 100 PRO | CA | −17.73 | −21.12 | 85.29 | 15.00 |
| 100 PRO | CB | −16.74 | −21.80 | 86.22 | 15.00 |
| 100 PRO | CG | −15.49 | −21.81 | 85.41 | 15.00 |
| 100 PRO | C | −18.84 | −20.46 | 86.07 | 15.00 |
| 100 PRO | O | −19.93 | −21.02 | 86.20 | 15.00 |
| 101 THR | N | −18.58 | −19.26 | 86.58 | 15.00 |
| 101 THR | CA | −19.58 | −18.53 | 87.34 | 15.00 |
| 101 THR | CB | −18.99 | −17.20 | 87.84 | 15.00 |

TABLE II-continued

Table of the orthogonal three dimensional coordinates in Ångstroms and B factors (Å$^2$) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 101 THR | OG1 | −17.76 | −17.48 | 88.53 | 15.00 |
| 101 THR | CG2 | −19.95 | −16.50 | 88.80 | 15.00 |
| 101 THR | C | −20.78 | −18.25 | 86.46 | 15.00 |
| 101 THR | O | −21.93 | −18.29 | 86.93 | 15.00 |
| 102 GLY | N | −20.52 | −17.99 | 85.18 | 15.00 |
| 102 GLY | CA | −21.57 | −17.69 | 84.23 | 15.00 |
| 102 GLY | C | −22.29 | −18.89 | 83.62 | 15.00 |
| 102 GLY | O | −23.36 | −18.73 | 83.04 | 15.00 |
| 103 LYS | N | −21.70 | −20.07 | 83.72 | 15.00 |
| 103 LYS | CA | −22.30 | −21.29 | 83.17 | 15.00 |
| 103 LYS | CB | −21.60 | −22.52 | 83.76 | 15.00 |
| 103 LYS | CG | −22.34 | −23.84 | 83.55 | 15.00 |
| 103 LYS | CD | −21.59 | −24.99 | 84.23 | 15.00 |
| 103 LYS | CE | −22.56 | −26.02 | 84.79 | 15.00 |
| 103 LYS | NZ | −23.48 | −26.58 | 83.76 | 15.00 |
| 103 LYS | C | −23.81 | −21.37 | 83.41 | 15.00 |
| 103 LYS | O | −24.27 | −21.24 | 84.54 | 15.00 |
| 104 ALA | N | −24.58 | −21.60 | 82.35 | 15.00 |
| 104 ALA | CA | −26.04 | −21.70 | 82.45 | 15.00 |
| 104 ALA | CB | −26.69 | −20.52 | 81.78 | 15.00 |
| 104 ALA | C | −26.60 | −22.99 | 81.88 | 15.00 |
| 104 ALA | O | −27.76 | −23.32 | 82.12 | 15.00 |
| 105 ALA | N | −25.81 | −23.71 | 81.09 | 15.00 |
| 105 ALA | CA | −26.26 | −24.97 | 80.50 | 15.00 |
| 105 ALA | CB | −26.99 | −24.72 | 79.19 | 15.00 |
| 105 ALA | C | −25.10 | −25.92 | 80.28 | 15.00 |
| 105 ALA | O | −23.93 | −25.52 | 80.38 | 15.00 |
| 106 LYS | N | −25.41 | −27.18 | 79.98 | 15.00 |
| 106 LYS | CA | −24.40 | −28.19 | 79.72 | 15.00 |
| 106 LYS | CB | −23.77 | −28.66 | 81.03 | 15.00 |
| 106 LYS | CG | −24.73 | −29.25 | 82.04 | 15.00 |
| 106 LYS | CD | −24.01 | −29.56 | 83.33 | 15.00 |
| 106 LYS | CE | −22.75 | −30.37 | 83.07 | 15.00 |
| 106 LYS | NZ | −23.05 | −31.63 | 82.31 | 15.00 |
| 106 LYS | C | −25.06 | −29.34 | 78.99 | 15.00 |
| 106 LYS | O | −26.28 | −29.39 | 78.94 | 15.00 |
| 107 CYS | N | −24.27 | −30.21 | 78.38 | 15.00 |
| 107 CYS | CA | −24.83 | −31.36 | 77.65 | 15.00 |
| 107 CYS | CB | −25.14 | −30.97 | 76.20 | 15.00 |
| 107 CYS | SG | −23.71 | −31.01 | 75.11 | 15.00 |
| 107 CYS | C | −23.95 | −32.61 | 77.67 | 15.00 |
| 107 CYS | O | −22.73 | −32.53 | 77.81 | 15.00 |
| 108 ARG | N | −24.59 | −33.76 | 77.53 | 15.00 |
| 108 ARG | CA | −23.92 | −35.05 | 77.54 | 15.00 |
| 108 ARG | CB | −24.66 | −36.03 | 78.46 | 15.00 |
| 108 ARG | CG | −26.18 | −35.81 | 78.55 | 15.00 |
| 108 ARG | CD | −26.93 | −37.01 | 79.17 | 15.00 |
| 108 ARG | NE | −27.06 | −38.15 | 78.25 | 15.00 |
| 108 ARG | CZ | −28.19 | −38.49 | 77.62 | 15.00 |
| 108 ARG | NH1 | −29.31 | −37.79 | 77.80 | 15.00 |
| 108 ARG | NH2 | −28.22 | −39.56 | 76.84 | 15.00 |
| 108 ARG | C | −23.70 | −35.67 | 76.15 | 15.00 |
| 108 ARG | O | −23.77 | −36.88 | 75.98 | 15.00 |
| 109 GLY | N | −23.44 | −34.83 | 75.16 | 15.00 |
| 109 GLY | CA | −23.19 | −35.32 | 73.82 | 15.00 |
| 109 GLY | C | −24.08 | −34.73 | 72.75 | 15.00 |
| 109 GLY | O | −24.72 | −33.69 | 72.94 | 15.00 |
| 110 TYR | N | −24.15 | −35.41 | 71.61 | 15.00 |
| 110 TYR | CA | −24.97 | −34.95 | 70.50 | 15.00 |
| 110 TYR | CB | −24.19 | −33.91 | 69.71 | 15.00 |
| 110 TYR | CG | −22.97 | −34.46 | 68.99 | 15.00 |
| 110 TYR | CD1 | −21.71 | −34.43 | 69.59 | 15.00 |
| 110 TYR | CE1 | −20.59 | −34.90 | 68.91 | 15.00 |
| 110 TYR | CD2 | −23.07 | −34.99 | 67.71 | 15.00 |
| 110 TYR | CE2 | −21.97 | −35.45 | 67.03 | 15.00 |
| 110 TYR | CZ | −20.73 | −35.40 | 67.63 | 15.00 |
| 110 TYR | OH | −19.63 | −35.82 | 66.93 | 15.00 |
| 110 TYR | C | −25.31 | −36.11 | 69.57 | 15.00 |
| 110 TYR | O | −24.61 | −37.12 | 69.54 | 15.00 |
| 111 ARG | N | −26.35 | −35.94 | 68.76 | 15.00 |
| 111 ARG | CA | −26.74 | −36.97 | 67.82 | 15.00 |
| 111 ARG | CB | −28.02 | −37.68 | 68.29 | 15.00 |
| 111 ARG | CG | −27.87 | −38.44 | 69.61 | 15.00 |
| 111 ARG | CD | −29.17 | −39.16 | 70.00 | 15.00 |
| 111 ARG | NE | −29.49 | −40.25 | 69.07 | 15.00 |
| 111 ARG | CZ | −28.84 | −41.41 | 69.03 | 15.00 |
| 111 ARG | NH1 | −29.20 | −42.34 | 68.14 | 15.00 |
| 111 ARG | NH2 | −27.85 | −41.65 | 69.88 | 15.00 |
| 111 ARG | C | −27.00 | −36.34 | 66.45 | 15.00 |
| 111 ARG | O | −27.71 | −35.34 | 66.34 | 15.00 |
| 112 GLU | N | −26.39 | −36.90 | 65.42 | 15.00 |
| 112 GLU | CA | −26.57 | −36.42 | 64.06 | 15.00 |
| 112 GLU | CB | −25.27 | −36.56 | 63.27 | 15.00 |
| 112 GLU | CG | −24.17 | −35.62 | 63.74 | 15.00 |
| 112 GLU | CD | −22.80 | −35.91 | 63.12 | 15.00 |
| 112 GLU | OE1 | −22.22 | −34.99 | 62.47 | 15.00 |
| 112 GLU | OE2 | −22.29 | −37.05 | 63.30 | 15.00 |
| 112 GLU | C | −27.68 | −37.26 | 63.45 | 15.00 |
| 112 GLU | O | −27.84 | −38.43 | 63.80 | 15.00 |
| 113 ILE | N | −28.50 | −36.63 | 62.61 | 15.00 |
| 113 ILE | CA | −29.60 | −37.28 | 61.90 | 15.00 |
| 113 ILE | CB | −30.69 | −36.23 | 61.48 | 15.00 |
| 113 ILE | CG2 | −31.45 | −36.68 | 60.25 | 15.00 |
| 113 ILE | CG1 | −31.68 | −35.99 | 62.62 | 15.00 |
| 113 ILE | CD1 | −31.14 | −35.16 | 63.73 | 15.00 |
| 113 ILE | C | −29.00 | −37.94 | 60.66 | 15.00 |
| 113 ILE | O | −28.03 | −37.44 | 60.10 | 15.00 |
| 114 PRO | N | −29.54 | −39.09 | 60.23 | 15.00 |
| 114 PRO | CD | −30.62 | −39.89 | 60.83 | 15.00 |
| 114 PRO | CA | −29.00 | −39.75 | 59.04 | 15.00 |
| 114 PRO | CB | −30.00 | −40.89 | 58.81 | 15.00 |
| 114 PRO | CG | −30.41 | −41.24 | 60.19 | 15.00 |
| 114 PRO | C | −28.97 | −38.80 | 57.86 | 15.00 |
| 114 PRO | O | −29.98 | −38.20 | 57.52 | 15.00 |
| 115 GLU | N | −27.80 | −38.73 | 57.22 | 15.00 |
| 115 GLU | CA | −27.56 | −37.86 | 56.07 | 15.00 |
| 115 GLU | CB | −26.14 | −38.07 | 55.52 | 15.00 |
| 115 GLU | CG | −25.92 | −37.52 | 54.10 | 15.00 |
| 115 GLU | CD | −24.48 | −37.06 | 53.82 | 15.00 |
| 115 GLU | OE1 | −23.52 | −37.73 | 54.28 | 15.00 |
| 115 GLU | OE2 | −24.30 | −36.02 | 53.15 | 15.00 |
| 115 GLU | C | −28.55 | −38.00 | 54.93 | 15.00 |
| 115 GLU | O | −28.57 | −39.02 | 54.26 | 15.00 |
| 116 GLY | N | −29.31 | −36.94 | 54.69 | 15.00 |
| 116 GLY | CA | −30.27 | −36.94 | 53.60 | 15.00 |
| 116 GLY | C | −31.66 | −37.41 | 53.97 | 15.00 |
| 116 GLY | O | −32.57 | −37.40 | 53.14 | 15.00 |
| 117 ASN | N | −31.86 | −37.78 | 55.24 | 15.00 |
| 117 ASN | CA | −33.15 | −38.29 | 55.69 | 15.00 |
| 117 ASN | CB | −32.94 | −39.38 | 56.73 | 15.00 |
| 117 ASN | CG | −34.19 | −40.18 | 56.99 | 15.00 |
| 117 ASN | OD1 | −35.32 | −39.68 | 56.89 | 15.00 |
| 117 ASN | ND2 | −34.00 | −41.46 | 57.33 | 15.00 |
| 117 ASN | C | −34.07 | −37.22 | 56.27 | 15.00 |
| 117 ASN | O | −33.93 | −36.82 | 57.43 | 15.00 |
| 118 GLU | N | −35.06 | −36.79 | 55.50 | 15.00 |
| 118 GLU | CA | −35.97 | −35.78 | 55.99 | 15.00 |
| 118 GLU | CB | −36.70 | −35.07 | 54.85 | 15.00 |
| 118 GLU | CG | −36.04 | −33.77 | 54.42 | 15.00 |
| 118 GLU | CD | −36.91 | −32.99 | 53.45 | 15.00 |
| 118 GLU | OE1 | −36.81 | −33.22 | 52.23 | 15.00 |
| 118 GLU | OE2 | −37.72 | −32.15 | 53.91 | 15.00 |
| 118 GLU | C | −36.97 | −36.33 | 56.98 | 15.00 |
| 118 GLU | O | −37.46 | −35.59 | 57.83 | 15.00 |
| 119 LYS | N | −37.32 | −37.61 | 56.90 | 15.00 |
| 119 LYS | CA | −38.27 | −38.14 | 57.87 | 15.00 |
| 119 LYS | CB | −38.85 | −39.49 | 57.42 | 15.00 |
| 119 LYS | CG | −40.19 | −39.34 | 56.68 | 15.00 |
| 119 LYS | CD | −40.08 | −38.40 | 55.47 | 15.00 |
| 119 LYS | CE | −41.47 | −38.06 | 54.90 | 15.00 |
| 119 LYS | NZ | −42.26 | −37.19 | 55.83 | 15.00 |
| 119 LYS | C | −37.62 | −38.24 | 59.24 | 15.00 |

TABLE II-continued

Table of the orthogonal three dimensional coordinates in Ångstroms and B factors (Å$^2$) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 119 LYS | O | −38.23 | −37.90 | 60.26 | 15.00 |
| 120 ALA | N | −36.35 | −38.62 | 59.28 | 15.00 |
| 120 ALA | CA | −35.63 | −38.70 | 60.54 | 15.00 |
| 120 ALA | CB | −34.25 | −39.25 | 60.33 | 15.00 |
| 120 ALA | C | −35.55 | −37.30 | 61.16 | 15.00 |
| 120 ALA | O | −35.58 | −37.15 | 62.38 | 15.00 |
| 121 LEU | N | −35.45 | −36.27 | 60.32 | 15.00 |
| 121 LEU | CA | −35.38 | −34.89 | 60.82 | 15.00 |
| 121 LEU | CB | −34.93 | −33.91 | 59.73 | 15.00 |
| 121 LEU | CG | −34.80 | −32.45 | 60.19 | 15.00 |
| 121 LEU | CD1 | −33.77 | −32.34 | 61.30 | 15.00 |
| 121 LEU | CD2 | −34.42 | −31.56 | 59.03 | 15.00 |
| 121 LEU | C | −36.74 | −34.48 | 61.36 | 15.00 |
| 121 LEU | O | −36.83 | −33.80 | 62.38 | 15.00 |
| 122 LYS | N | −37.79 | −34.89 | 60.66 | 15.00 |
| 122 LYS | CA | −39.16 | −34.58 | 61.05 | 15.00 |
| 122 LYS | CB | −40.14 | −35.19 | 60.07 | 15.00 |
| 122 LYS | CG | −41.57 | −34.80 | 60.31 | 15.00 |
| 122 LYS | CD | −42.49 | −35.45 | 59.32 | 15.00 |
| 122 LYS | CE | −43.95 | −35.16 | 59.67 | 15.00 |
| 122 LYS | NZ | −44.88 | −35.66 | 58.60 | 15.00 |
| 122 LYS | C | −39.41 | −35.15 | 62.44 | 15.00 |
| 122 LYS | O | −39.87 | −34.44 | 63.33 | 15.00 |
| 123 ARG | N | −39.12 | −36.44 | 62.62 | 15.00 |
| 123 ARG | CA | −39.29 | −37.10 | 63.90 | 15.00 |
| 123 ARG | CB | −38.84 | −38.58 | 63.84 | 15.00 |
| 123 ARG | CG | −39.74 | −39.50 | 62.99 | 15.00 |
| 123 ARG | CD | −39.33 | −40.97 | 63.13 | 15.00 |
| 123 ARG | NE | −37.95 | −41.22 | 62.73 | 15.00 |
| 123 ARG | CZ | −37.42 | −42.43 | 62.51 | 15.00 |
| 123 ARG | NH1 | −38.15 | −43.53 | 62.66 | 15.00 |
| 123 ARG | NH2 | −36.17 | −42.53 | 62.08 | 15.00 |
| 123 ARG | C | −38.46 | −36.37 | 64.94 | 15.00 |
| 123 ARG | O | −39.01 | −35.82 | 65.89 | 15.00 |
| 124 ALA | N | −37.15 | −36.31 | 64.71 | 15.00 |
| 124 ALA | CA | −36.22 | −35.65 | 65.62 | 15.00 |
| 124 ALA | CB | −34.86 | −35.50 | 64.98 | 15.00 |
| 124 ALA | C | −36.70 | −34.29 | 66.11 | 15.00 |
| 124 ALA | O | −36.67 | −34.02 | 67.31 | 15.00 |
| 125 VAL | N | −37.16 | −33.45 | 65.19 | 15.00 |
| 125 VAL | CA | −37.66 | −32.13 | 65.55 | 15.00 |
| 125 VAL | CB | −38.00 | −31.28 | 64.27 | 15.00 |
| 125 VAL | CG1 | −38.50 | −29.89 | 64.64 | 15.00 |
| 125 VAL | CG2 | −36.77 | −31.11 | 63.41 | 15.00 |
| 125 VAL | C | −38.87 | −32.25 | 66.47 | 15.00 |
| 125 VAL | O | −39.03 | −31.46 | 67.41 | 15.00 |
| 126 ALA | N | −39.71 | −33.26 | 66.28 | 15.00 |
| 126 ALA | CA | −40.90 | −33.44 | 67.11 | 15.00 |
| 126 ALA | CB | −42.00 | −34.13 | 66.32 | 15.00 |
| 126 ALA | C | −40.64 | −34.18 | 68.44 | 15.00 |
| 126 ALA | O | −41.32 | −33.93 | 69.44 | 15.00 |
| 127 ARG | N | −39.67 | −35.09 | 68.46 | 15.00 |
| 127 ARG | CA | −39.36 | −35.83 | 69.68 | 15.00 |
| 127 ARG | CB | −38.79 | −37.22 | 69.36 | 15.00 |
| 127 ARG | CG | −39.80 | −38.34 | 69.36 | 15.00 |
| 127 ARG | CD | −40.24 | −38.71 | 67.96 | 15.00 |
| 127 ARG | NE | −39.78 | −40.04 | 67.58 | 15.00 |
| 127 ARG | CZ | −40.46 | −40.88 | 66.80 | 15.00 |
| 127 ARG | NH1 | −39.94 | −42.06 | 66.52 | 15.00 |
| 127 ARG | NH2 | −41.66 | −40.57 | 66.33 | 15.00 |
| 127 ARG | C | −38.36 | −35.09 | 70.56 | 15.00 |
| 127 ARG | O | −38.41 | −35.20 | 71.78 | 15.00 |
| 128 VAL | N | −37.44 | −34.37 | 69.94 | 15.00 |
| 128 VAL | CA | −36.42 | −33.64 | 70.68 | 15.00 |
| 128 VAL | CB | −35.07 | −33.78 | 69.99 | 15.00 |
| 128 VAL | CG1 | −33.97 | −33.24 | 70.88 | 15.00 |
| 128 VAL | CG2 | −34.81 | −35.23 | 69.64 | 15.00 |
| 128 VAL | C | −36.75 | −32.17 | 70.84 | 15.00 |
| 128 VAL | O | −36.91 | −31.68 | 71.94 | 15.00 |
| 129 GLY | N | −36.85 | −31.47 | 69.72 | 15.00 |
| 129 GLY | CA | −37.13 | −30.05 | 69.75 | 15.00 |
| 129 GLY | C | −36.29 | −29.43 | 68.64 | 15.00 |
| 129 GLY | O | −35.92 | −30.14 | 67.70 | 15.00 |
| 130 PRO | N | −35.92 | −28.15 | 68.76 | 15.00 |
| 130 PRO | CD | −36.24 | −27.22 | 69.86 | 15.00 |
| 130 PRO | CA | −35.11 | −27.49 | 67.75 | 15.00 |
| 130 PRO | CB | −34.80 | −26.14 | 68.39 | 15.00 |
| 130 PRO | CG | −36.01 | −25.88 | 69.20 | 15.00 |
| 130 PRO | C | −33.83 | −28.24 | 67.40 | 15.00 |
| 130 PRO | O | −33.02 | −28.57 | 68.28 | 15.00 |
| 131 VAL | N | −33.63 | −28.47 | 66.11 | 15.00 |
| 131 VAL | CA | −32.46 | −29.17 | 65.62 | 15.00 |
| 131 VAL | CB | −32.89 | −30.36 | 64.73 | 15.00 |
| 131 VAL | CG1 | −31.68 | −31.12 | 64.19 | 15.00 |
| 131 VAL | CG2 | −33.78 | −31.29 | 65.53 | 15.00 |
| 131 VAL | C | −31.59 | −28.20 | 64.81 | 15.00 |
| 131 VAL | O | −32.10 | −27.31 | 64.12 | 15.00 |
| 132 SER | N | −30.28 | −28.33 | 64.94 | 15.00 |
| 132 SER | CA | −29.35 | −27.48 | 64.21 | 15.00 |
| 132 SER | CB | −28.02 | −27.41 | 64.95 | 15.00 |
| 132 SER | OG | −28.18 | −26.80 | 66.21 | 15.00 |
| 132 SER | C | −29.16 | −28.09 | 62.83 | 15.00 |
| 132 SER | O | −28.84 | −29.27 | 62.71 | 15.00 |
| 133 VAL | N | −29.37 | −27.32 | 61.78 | 15.00 |
| 133 VAL | CA | −29.21 | −27.82 | 60.42 | 15.00 |
| 133 VAL | CB | −30.58 | −28.02 | 59.71 | 15.00 |
| 133 VAL | CG1 | −31.50 | −28.91 | 60.54 | 15.00 |
| 133 VAL | CG2 | −31.24 | −26.68 | 59.44 | 15.00 |
| 133 VAL | C | −28.37 | −26.84 | 59.60 | 15.00 |
| 133 VAL | O | −28.20 | −25.68 | 59.99 | 15.00 |
| 134 ALA | N | −27.82 | −27.30 | 58.48 | 15.00 |
| 134 ALA | CA | −27.00 | −26.45 | 57.62 | 15.00 |
| 134 ALA | CB | −25.58 | −26.95 | 57.57 | 15.00 |
| 134 ALA | C | −27.65 | −26.50 | 56.26 | 15.00 |
| 134 ALA | O | −28.14 | −27.55 | 55.86 | 15.00 |
| 135 ILE | N | −27.66 | −25.38 | 55.55 | 15.00 |
| 135 ILE | CA | −28.30 | −25.28 | 54.23 | 15.00 |
| 135 ILE | CB | −29.70 | −24.57 | 54.29 | 15.00 |
| 135 ILE | CG2 | −30.71 | −25.39 | 55.10 | 15.00 |
| 135 ILE | CG1 | −29.54 | −23.15 | 54.87 | 15.00 |
| 135 ILE | CD1 | −30.81 | −22.34 | 54.88 | 15.00 |
| 135 ILE | C | −27.46 | −24.44 | 53.29 | 15.00 |
| 135 ILE | O | −26.40 | −23.92 | 53.66 | 15.00 |
| 136 ASP | N | −27.97 | −24.32 | 52.07 | 15.00 |
| 136 ASP | CA | −27.34 | −23.50 | 51.04 | 15.00 |
| 136 ASP | CB | −27.56 | −24.11 | 49.65 | 15.00 |
| 136 ASP | CG | −27.02 | −23.23 | 48.53 | 15.00 |
| 136 ASP | OD1 | −27.80 | −22.84 | 47.64 | 15.00 |
| 136 ASP | OD2 | −25.83 | −22.91 | 48.54 | 15.00 |
| 136 ASP | C | −28.06 | −22.16 | 51.14 | 15.00 |
| 136 ASP | O | −29.21 | −22.03 | 50.74 | 15.00 |
| 137 ALA | N | −27.43 | −21.17 | 51.76 | 15.00 |
| 137 ALA | CA | −28.07 | −19.87 | 51.86 | 15.00 |
| 137 ALA | CB | −27.97 | −19.34 | 53.26 | 15.00 |
| 137 ALA | C | −27.47 | −18.89 | 50.85 | 15.00 |
| 137 ALA | O | −27.92 | −17.75 | 50.72 | 15.00 |
| 138 SER | N | −26.43 | −19.33 | 50.15 | 15.00 |
| 138 SER | CA | −25.79 | −18.51 | 49.14 | 15.00 |
| 138 SER | CB | −24.36 | −19.00 | 48.90 | 15.00 |
| 138 SER | OG | −23.55 | −18.75 | 50.04 | 15.00 |
| 138 SER | C | −26.61 | −18.61 | 47.87 | 15.00 |
| 138 SER | O | −26.41 | −19.53 | 47.07 | 15.00 |
| 139 LEU | N | −27.56 | −17.70 | 47.74 | 15.00 |
| 139 LEU | CA | −28.46 | −17.66 | 46.60 | 15.00 |
| 139 LEU | CB | −29.32 | −18.92 | 46.55 | 15.00 |
| 139 LEU | CG | −30.03 | −19.30 | 45.25 | 15.00 |
| 139 LEU | CD1 | −29.04 | −19.96 | 44.31 | 15.00 |
| 139 LEU | CD2 | −31.14 | −20.28 | 45.54 | 15.00 |
| 139 LEU | C | −29.35 | −16.43 | 46.82 | 15.00 |
| 139 LEU | O | −29.99 | −16.29 | 47.87 | 15.00 |
| 140 THR | N | −29.39 | −15.54 | 45.83 | 15.00 |
| 140 THR | CA | −30.17 | −14.30 | 45.90 | 15.00 |

TABLE II-continued

Table of the orthogonal three dimensional coordinates in Ångstroms and B factors (Å$^2$) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 140 THR | CB | −30.15 | −13.57 | 44.52 | 15.00 |
| 140 THR | OG1 | −29.95 | −14.53 | 43.47 | 15.00 |
| 140 THR | CG2 | −29.05 | −12.52 | 44.48 | 15.00 |
| 140 THR | C | −31.60 | −14.43 | 46.41 | 15.00 |
| 140 THR | O | −32.02 | −13.70 | 47.31 | 15.00 |
| 141 SER | N | −32.35 | −15.38 | 45.88 | 15.00 |
| 141 SER | CA | −33.74 | −15.58 | 46.27 | 15.00 |
| 141 SER | CB | −34.42 | −16.62 | 45.36 | 15.00 |
| 141 SER | OG | −33.62 | −17.78 | 45.21 | 15.00 |
| 141 SER | C | −33.92 | −15.96 | 47.74 | 15.00 |
| 141 SER | O | −34.99 | −15.74 | 48.33 | 15.00 |
| 142 PHE | N | −32.90 | −16.52 | 48.37 | 15.00 |
| 142 PHE | CA | −33.01 | −16.91 | 49.77 | 15.00 |
| 142 PHE | CB | −31.92 | −17.91 | 50.15 | 15.00 |
| 142 PHE | CG | −31.91 | −18.26 | 51.61 | 15.00 |
| 142 PHE | CD1 | −32.74 | −19.26 | 52.10 | 15.00 |
| 142 PHE | CD2 | −31.09 | −17.58 | 52.50 | 15.00 |
| 142 PHE | CE1 | −32.74 | −19.58 | 53.45 | 15.00 |
| 142 PHE | CE2 | −31.09 | −17.90 | 53.87 | 15.00 |
| 142 PHE | CZ | −31.92 | −18.89 | 54.34 | 15.00 |
| 142 PHE | C | −32.87 | −15.67 | 50.62 | 15.00 |
| 142 PHE | O | −33.64 | −15.45 | 51.55 | 15.00 |
| 143 GLN | N | −31.90 | −14.85 | 50.24 | 15.00 |
| 143 GLN | CA | −31.58 | −13.63 | 50.96 | 15.00 |
| 143 GLN | CB | −30.25 | −13.12 | 50.48 | 15.00 |
| 143 GLN | CG | −29.21 | −14.20 | 50.55 | 15.00 |
| 143 GLN | CD | −27.89 | −13.73 | 50.06 | 15.00 |
| 143 GLN | OE1 | −27.33 | −12.78 | 50.59 | 15.00 |
| 143 GLN | NE2 | −27.36 | −14.40 | 49.05 | 15.00 |
| 143 GLN | C | −32.63 | −12.53 | 50.92 | 15.00 |
| 143 GLN | O | −32.79 | −11.82 | 51.91 | 15.00 |
| 144 PHE | N | −33.31 | −12.35 | 49.79 | 15.00 |
| 144 PHE | CA | −34.36 | −11.32 | 49.70 | 15.00 |
| 144 PHE | CB | −34.28 | −10.50 | 48.39 | 15.00 |
| 144 PHE | CG | −34.49 | −11.30 | 47.11 | 15.00 |
| 144 PHE | CD1 | −33.53 | −11.26 | 46.11 | 15.00 |
| 144 PHE | CD2 | −35.66 | −12.02 | 46.88 | 15.00 |
| 144 PHE | CE1 | −33.74 | −11.93 | 44.90 | 15.00 |
| 144 PHE | CE2 | −35.88 | −12.69 | 45.67 | 15.00 |
| 144 PHE | CZ | −34.91 | −12.64 | 44.68 | 15.00 |
| 144 PHE | C | −35.77 | −11.88 | 49.96 | 15.00 |
| 144 PHE | O | −36.77 | −11.36 | 49.45 | 15.00 |
| 145 TYR | N | −35.82 | −12.95 | 50.76 | 15.00 |
| 145 TYR | CA | −37.05 | −13.64 | 51.13 | 15.00 |
| 145 TYR | CB | −36.69 | −14.96 | 51.83 | 15.00 |
| 145 TYR | CG | −37.83 | −15.59 | 52.60 | 15.00 |
| 145 TYR | CD1 | −38.64 | −16.56 | 52.01 | 15.00 |
| 145 TYR | CE1 | −39.71 | −17.11 | 52.70 | 15.00 |
| 145 TYR | CD2 | −38.11 | −15.20 | 53.91 | 15.00 |
| 145 TYR | CE2 | −39.18 | −15.74 | 54.60 | 15.00 |
| 145 TYR | CZ | −39.98 | −16.69 | 53.99 | 15.00 |
| 145 TYR | OH | −41.05 | −17.22 | 54.66 | 15.00 |
| 145 TYR | C | −37.79 | −12.74 | 52.10 | 15.00 |
| 145 TYR | O | −37.16 | −12.04 | 52.89 | 15.00 |
| 146 SER | N | −39.12 | −12.80 | 52.09 | 15.00 |
| 146 SER | CA | −39.93 | −11.97 | 52.99 | 15.00 |
| 146 SER | CB | −40.22 | −10.61 | 52.35 | 15.00 |
| 146 SER | OG | −40.75 | −10.75 | 51.05 | 15.00 |
| 146 SER | C | −41.25 | −12.62 | 53.43 | 15.00 |
| 146 SER | O | −41.83 | −12.21 | 54.43 | 15.00 |
| 147 LYN | N | −41.74 | −13.59 | 52.66 | 15.00 |
| 147 LYS | CA | −42.98 | −14.28 | 52.99 | 15.00 |
| 147 LYS | CB | −44.19 | −13.35 | 52.82 | 15.00 |
| 147 LYS | CG | −44.40 | −12.86 | 51.40 | 15.00 |
| 147 LYS | CD | −45.58 | −11.90 | 51.31 | 15.00 |
| 147 LYS | CE | −46.86 | −12.63 | 50.95 | 15.00 |
| 147 LYS | NZ | −48.03 | −11.69 | 50.96 | 15.00 |
| 147 LYS | C | −43.18 | −15.52 | 52.13 | 15.00 |
| 147 LYS | O | −42.61 | −15.62 | 51.04 | 15.00 |
| 148 GLY | N | −44.00 | −16.45 | 52.62 | 15.00 |
| 148 GLY | CA | −44.27 | −17.68 | 51.88 | 15.00 |
| 148 GLY | C | −43.30 | −18.81 | 52.16 | 15.00 |
| 148 GLY | O | −42.38 | −18.69 | 52.97 | 15.00 |
| 149 VAL | N | −43.52 | −19.94 | 51.51 | 15.00 |
| 149 VAL | CA | −42.66 | −21.10 | 51.68 | 15.00 |
| 149 VAL | CB | −43.47 | −22.41 | 51.46 | 15.00 |
| 149 VAL | CG1 | −42.59 | −23.63 | 51.61 | 15.00 |
| 149 VAL | CG2 | −44.62 | −22.47 | 52.45 | 15.00 |
| 149 VAL | C | −41.57 | −20.96 | 50.62 | 15.00 |
| 149 VAL | O | −41.84 | −20.56 | 49.50 | 15.00 |
| 150 TYR | N | −40.34 | −21.30 | 50.96 | 15.00 |
| 150 TYR | CA | −39.24 | −21.14 | 50.02 | 15.00 |
| 150 TYR | CB | −38.02 | −20.54 | 50.73 | 15.00 |
| 150 TYR | CG | −36.80 | −20.39 | 49.85 | 15.00 |
| 150 TYR | CD1 | −36.77 | −19.48 | 48.80 | 15.00 |
| 150 TYR | CE1 | −35.66 | −19.36 | 47.97 | 15.00 |
| 150 TYR | CD2 | −35.67 | −21.18 | 50.05 | 15.00 |
| 150 TYR | CE2 | −34.56 | −21.07 | 49.24 | 15.00 |
| 150 TYR | CZ | −34.56 | −20.16 | 48.20 | 15.00 |
| 150 TYR | OH | −33.45 | −20.04 | 47.40 | 15.00 |
| 150 TYR | C | −38.83 | −22.39 | 49.27 | 15.00 |
| 150 TYR | O | −38.66 | −23.45 | 49.85 | 15.00 |
| 151 TYR | N | −38.62 | −22.22 | 47.97 | 15.00 |
| 151 TYR | CA | −38.17 | −23.31 | 47.12 | 15.00 |
| 151 TYR | CB | −39.33 | −24.21 | 46.71 | 15.00 |
| 151 TYR | CG | −38.86 | −25.44 | 45.98 | 15.00 |
| 151 TYR | CD1 | −37.95 | −26.30 | 46.56 | 15.00 |
| 151 TYR | CE1 | −37.46 | −27.40 | 45.87 | 15.00 |
| 151 TYR | CD2 | −39.29 | −25.71 | 44.68 | 15.00 |
| 151 TYR | CE2 | −38.81 | −26.81 | 43.98 | 15.00 |
| 151 TYR | CZ | −37.89 | −27.65 | 44.58 | 15.00 |
| 151 TYR | OH | −37.37 | −28.73 | 43.90 | 15.00 |
| 151 TYR | C | −37.49 | −22.74 | 45.88 | 15.00 |
| 151 TYR | O | −37.97 | −21.79 | 45.28 | 15.00 |
| 152 ASP | N | −36.36 | −23.32 | 45.49 | 15.00 |
| 152 ASP | CA | −35.64 | −22.85 | 44.31 | 15.0G |
| 152 ASP | CB | −34.72 | −21.69 | 44.66 | 15.00 |
| 152 ASP | CG | −34.07 | −21.09 | 43.44 | 15.00 |
| 152 ASP | OD1 | −33.12 | −21.69 | 42.92 | 15.00 |
| 152 ASP | OD2 | −34.52 | −20.01 | 43.01 | 15.00 |
| 152 ASP | C | −34.83 | −23.96 | 43.66 | 15.00 |
| 152 ASP | O | −33.85 | −24.45 | 44.23 | 15.00 |
| 153 GLU | N | −35.21 | −24.32 | 42.44 | 15.00 |
| 153 GLU | CA | −34.53 | −25.36 | 41.69 | 15.00 |
| 153 GLU | CB | −34.98 | −25.36 | 40.21 | 15.00 |
| 153 GLU | CG | −35.22 | −23.98 | 39.55 | 15.00 |
| 153 GLU | CD | −33.95 | −23.34 | 38.93 | 15.00 |
| 153 GLU | OE1 | −33.38 | −22.41 | 39.56 | 15.00 |
| 153 GLU | OE2 | −33.56 | −23.73 | 37.80 | 15.00 |
| 153 GLU | C | −33.02 | −25.27 | 41.80 | 15.00 |
| 153 GLU | O | −32.36 | −26.29 | 42.00 | 15.00 |
| 154 SER | N | −32.48 | −24.05 | 41.74 | 15.00 |
| 154 SER | CA | −31.02 | −23.84 | 41.81 | 15.00 |
| 154 SER | CB | −30.65 | −22.45 | 41.31 | 15.00 |
| 154 SER | OG | −30.66 | −22.41 | 39.90 | 15.00 |
| 154 SER | C | −30.37 | −24.06 | 43.16 | 15.00 |
| 154 SER | O | −29.14 | −23.91 | 43.30 | 15.00 |
| 155 CYS | N | −31.15 | −24.39 | 44.19 | 15.00 |
| 155 CYS | CA | −30.56 | −24.61 | 45.49 | 15.00 |
| 155 CYS | C | −29.70 | −25.86 | 45.37 | 15.00 |
| 155 CYS | O | −30.17 | −26.88 | 44.86 | 15.00 |
| 155 CYS | CB | −31.63 | −24.79 | 46.55 | 15.GO |
| 155 CYS | SG | −31.06 | −24.07 | 48.11 | 15.00 |
| 156 ASN | N | −28.43 | −25.75 | 45.74 | 15.00 |
| 156 ASN | CA | −27.50 | −26.87 | 45.66 | 15.00 |
| 156 ASN | CB | −26.13 | −26.39 | 45.18 | 15.00 |
| 156 ASN | CG | −25.14 | −27.52 | 44.97 | 15.00 |
| 156 ASN | OD1 | −25.51 | −28.70 | 44.95 | 15.00 |
| 156 ASN | ND2 | −23.88 | −27.16 | 44.80 | 15.00 |
| 156 ASN | C | −27.34 | −27.66 | 46.95 | 15.00 |
| 156 ASN | O | −26.57 | −27.31 | 47.85 | 15.00 |
| 157 SER | N | −28.03 | −28.79 | 46.98 | 15.00 |

TABLE II-continued

Table of the orthogonal three dimensional coordinates in Ångstroms and B factors (Å²) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 157 SER | CA | −28.03 | −29.71 | 48.10 | 15.00 |
| 157 SER | CB | −28.72 | −31.00 | 47.65 | 15.00 |
| 157 SER | OG | −29.25 | −30.85 | 46.33 | 15.00 |
| 157 SER | C | −26.63 | −30.03 | 48.63 | 15.00 |
| 157 SER | O | −26.46 | −30.47 | 49.77 | 15.00 |
| 158 ASP | N | −25.61 | −29.83 | 47.80 | 15.00 |
| 158 ASP | CA | −24.23 | −30.12 | 48.18 | 15.00 |
| 158 ASP | CB | −23.50 | −30.73 | 47.00 | 15.00 |
| 158 ASP | CG | −23.99 | −32.13 | 46.66 | 15.00 |
| 158 ASP | OD1 | −24.82 | −32.27 | 45.74 | 15.00 |
| 158 ASP | OD2 | −23.57 | −33.09 | 47.34 | 15.00 |
| 158 ASP | C | −23.44 | −28.95 | 48.72 | 15.00 |
| 158 ASP | O | −22.48 | −29.13 | 49.48 | 15.00 |
| 159 ASN | N | −23.80 | −27.73 | 48.33 | 15.00 |
| 159 ASN | CA | −23.05 | −26.56 | 48.81 | 15.00 |
| 159 ASN | CB | −23.07 | −25.44 | 47.75 | 15.00 |
| 159 ASN | CG | −22.15 | −24.26 | 48.11 | 15.00 |
| 159 ASN | OD1 | −22.30 | −23.64 | 49.16 | 15.00 |
| 159 ASN | ND2 | −21.21 | −23.95 | 47.22 | 15.00 |
| 159 ASN | C | −23.63 | −26.08 | 50.13 | 15.00 |
| 159 ASN | O | −24.43 | −25.14 | 50.17 | 15.00 |
| 160 LEU | N | −23.27 | −26.74 | 51.23 | 15.00 |
| 160 LEU | CA | −23.78 | −26.33 | 52.55 | 15.00 |
| 160 LEU | CB | −23.76 | −27.50 | 53.53 | 15.00 |
| 160 LEU | CG | −24.57 | −28.73 | 53.10 | 15.00 |
| 160 LEU | CD1 | −24.08 | −29.96 | 53.84 | 15.00 |
| 160 LEU | CD2 | −26.06 | −28.51 | 53.32 | 15.00 |
| 160 LEU | C | −22.87 | −25.21 | 53.02 | 15.00 |
| 160 LEU | O | −21.70 | −25.45 | 53.29 | 15.00 |
| 161 ASN | N | −23.41 | −24.01 | 53.16 | 15.00 |
| 161 ASN | CA | −22.59 | −22.86 | 53.54 | 15.00 |
| 161 ASN | CB | −22.43 | −21.97 | 52.31 | 15.00 |
| 161 ASN | CG | −23.75 | −21.64 | 51.67 | 15.00 |
| 161 ASN | OD1 | −24.51 | −20.79 | 52.17 | 15.00 |
| 161 ASN | ND2 | −24.09 | −22.36 | 50.62 | 15.00 |
| 161 ASN | C | −23.07 | −22.00 | 54.70 | 15.00 |
| 161 ASN | O | −22.32 | −21.20 | 55.27 | 15.00 |
| 162 HIS | N | −24.34 | −22.10 | 55.06 | 15.00 |
| 162 HIS | CA | −24.87 | −21.31 | 56.16 | 15.00 |
| 162 HIS | CB | −25.90 | −20.34 | 55.60 | 15.00 |
| 162 HIS | CG | −26.42 | −19.36 | 56.60 | 15.00 |
| 162 HIS | CD2 | −27.67 | −19.00 | 56.94 | 15.00 |
| 162 HIS | ND1 | −25.58 | −18.61 | 57.40 | 15.00 |
| 162 HIS | CE1 | −26.30 | −17.82 | 58.18 | 15.00 |
| 162 HIS | NE2 | −27.57 | −18.05 | 57.92 | 15.00 |
| 162 HIS | C | −25.52 | −22.24 | 57.17 | 15.00 |
| 162 HIS | O | −26.26 | −23.14 | 56.80 | 15.00 |
| 163 ALA | N | −25.22 | −22.02 | 58.45 | 15.00 |
| 163 ALA | CA | −25.79 | −22.84 | 59.53 | 15.00 |
| 163 ALA | CB | −24.77 | −23.10 | 60.61 | 15.00 |
| 163 ALA | C | −27.00 | −22.13 | 60.10 | 15.00 |
| 163 ALA | O | −26.93 | −20.95 | 60.48 | 15.00 |
| 164 VAL | N | −28.10 | −22.85 | 60.20 | 15.00 |
| 164 VAL | CA | −29.34 | −22.30 | 60.70 | 15.00 |
| 164 VAL | CB | −30.25 | −22.02 | 59.52 | 15.00 |
| 164 VAL | CG1 | −31.04 | −23.26 | 59.13 | 15.00 |
| 164 VAL | CG2 | −31.11 | −20.83 | 59.80 | 15.00 |
| 164 VAL | C | −29.96 | −23.25 | 61.73 | 15.00 |
| 164 VAL | O | −29.32 | −24.21 | 62.14 | 15.00 |
| 165 LEU | N | −31.20 | −22.99 | 62.16 | 15.00 |
| 165 LEU | CA | −31.87 | −23.83 | 63.17 | 15.00 |
| 165 LEU | CB | −31.87 | −23.10 | 64.52 | 15.00 |
| 165 LEU | CG | −32.48 | −23.78 | 65.74 | 15.00 |
| 165 LEU | CD1 | −31.58 | −24.90 | 66.23 | 15.00 |
| 165 LEU | CD2 | −32.71 | −22.77 | 66.84 | 15.00 |
| 165 LEU | C | −33.31 | −24.16 | 62.81 | 15.00 |
| 165 LEU | O | −34.08 | −23.27 | 62.49 | 15.00 |
| 166 ALA | N | −33.69 | −25.43 | 62.90 | 15.00 |
| 166 ALA | CA | −35.06 | −25.86 | 62.59 | 15.00 |
| 166 ALA | CB | −35.05 | −27.27 | 62.00 | 15.00 |
| 166 ALA | C | −35.91 | −25.81 | 63.86 | 15.00 |
| 166 ALA | O | −35.69 | −26.57 | 64.80 | 15.00 |
| 167 VAL | N | −36.89 | −24.92 | 63.85 | 15.00 |
| 167 VAL | CA | −37.78 | −24.65 | 65.00 | 15.00 |
| 167 VAL | CB | −37.89 | −23.09 | 65.18 | 15.00 |
| 167 VAL | CG1 | −38.97 | −22.71 | 66.15 | 15.00 |
| 167 VAL | CG2 | −36.58 | −22.55 | 65.68 | 15.00 |
| 167 VAL | C | −39.16 | −25.32 | 64.93 | 15.00 |
| 167 VAL | O | −39.98 | −25.21 | 65.84 | 15.00 |
| 168 GLY | N | −39.43 | −26.06 | 63.87 | 15.00 |
| 168 GLY | CA | −40.71 | −26.72 | 63.75 | 15.00 |
| 168 GLY | C | −40.98 | −27.09 | 62.31 | 15.00 |
| 168 GLY | O | −40.05 | −27.10 | 61.49 | 15.00 |
| 169 TYR | N | −42.23 | −27.39 | 61.99 | 15.00 |
| 169 TYR | CA | −42.65 | −27.76 | 60.65 | 15.00 |
| 169 TYR | CB | −42.15 | −29.17 | 60.29 | 15.00 |
| 169 TYR | CG | −42.64 | −30.27 | 61.22 | 15.00 |
| 169 TYR | CD1 | −44.00 | −30.58 | 61.31 | 15.00 |
| 169 TYR | CE1 | −44.46 | −31.57 | 62.15 | 15.00 |
| 169 TYR | CD2 | −41.75 | −30.99 | 62.01 | 15.00 |
| 169 TYR | CE2 | −42.20 | −31.99 | 62.85 | 15.00 |
| 169 TYR | CZ | −43.56 | −32.28 | 62.91 | 15.00 |
| 169 TYR | OH | −44.04 | −33.28 | 63.71 | 15.00 |
| 169 TYR | C | −44.16 | −27.70 | 60.54 | 15.00 |
| 169 TYR | O | −44.85 | −27.38 | 61.52 | 15.00 |
| 170 GLY | N | −44.70 | −28.04 | 59.38 | 15.00 |
| 170 GLY | CA | −46.13 | −28.00 | 59.18 | 15.00 |
| 170 GLY | C | −46.49 | −27.76 | 57.73 | 15.00 |
| 170 GLY | O | −45.83 | −28.26 | 56.83 | 15.00 |
| 171 ILE | N | −47.48 | −26.92 | 57.48 | 15.00 |
| 171 ILE | CA | −47.95 | −26.63 | 56.13 | 15.00 |
| 171 ILE | CB | −49.03 | −27.66 | 55.72 | 15.00 |
| 171 ILE | CG2 | −50.01 | −27.09 | 54.71 | 15.00 |
| 171 ILE | CG1 | −48.36 | −28.95 | 55.21 | 15.00 |
| 171 ILE | CD1 | −49.35 | −30.05 | 54.82 | 15.00 |
| 171 ILE | C | −48.54 | −25.23 | 56.14 | 15.00 |
| 171 ILE | O | −48.91 | −24.71 | 57.20 | 15.00 |
| 172 GLN | N | −48.58 | −24.55 | 55.00 | 15.00 |
| 172 GLN | CA | −49.16 | −23.20 | 54.97 | 15.00 |
| 172 GLN | CB | −48.08 | −22.18 | 54.62 | 15.00 |
| 172 GLN | CG | −48.58 | −20.75 | 54.57 | 15.00 |
| 172 GLN | CD | −47.50 | −19.79 | 54.12 | 15.00 |
| 172 GLN | OE1 | −46.95 | −19.93 | 53.02 | 15.00 |
| 172 GLN | NE2 | −47.18 | −18.82 | 54.96 | 15.00 |
| 172 GLN | C | −50.29 | −23.15 | 53.96 | 15.00 |
| 172 GLN | O | −51.45 | −22.89 | 54.32 | 15.00 |
| 173 LYS | N | −49.96 | −23.36 | 52.68 | 15.00 |
| 173 LYS | CA | −50.96 | −23.38 | 51.61 | 15.00 |
| 173 LYS | CB | −50.84 | −22.14 | 50.69 | 15.00 |
| 173 LYS | CG | −51.09 | −20.78 | 51.36 | 15.00 |
| 173 LYS | CD | −52.40 | −20.72 | 52.16 | 15.00 |
| 173 LYS | CE | −53.63 | −20.91 | 51.29 | 15.00 |
| 173 LYS | NZ | −54.88 | −20.56 | 52.06 | 15.00 |
| 173 LYS | C | −50.66 | −24.63 | 50.81 | 15.00 |
| 173 LYS | O | −50.20 | −24.57 | 49.67 | 15.00 |
| 174 GLY | N | −50.86 | −25.77 | 51.45 | 15.00 |
| 174 GLY | CA | −50.60 | −27.04 | 50.79 | 15.00 |
| 174 GLY | C | −49.13 | −27.39 | 50.91 | 15.00 |
| 174 GLY | O | −48.77 | −28.52 | 51.28 | 15.00 |
| 175 ASN | N | −48.26 | −26.42 | 50.63 | 15.00 |
| 175 ASN | CA | −46.83 | −26.66 | 50.70 | 15.00 |
| 175 ASN | CB | −46.06 | −25.48 | 50.10 | 15.00 |
| 175 ASN | CG | −46.31 | −25.33 | 48.61 | 15.00 |
| 175 ASN | OD1 | −47.34 | −24.79 | 48.20 | 15.00 |
| 175 ASN | ND2 | −45.38 | −25.81 | 47.80 | 15.00 |
| 175 ASN | C | −46.33 | −26.96 | 52.11 | 15.00 |
| 175 ASN | O | −46.55 | −26.18 | 53.05 | 15.00 |
| 176 LYS | N | −45.69 | −28.13 | 52.25 | 15.00 |
| 176 LYS | CA | −45.13 | −28.55 | 53.53 | 15.00 |
| 176 LYS | CB | −44.68 | −30.01 | 53.48 | 15.00 |
| 176 LYS | CG | −45.77 | −31.03 | 53.17 | 15.00 |
| 176 LYS | CD | −45.27 | −32.45 | 53.44 | 15.00 |

TABLE II-continued

Table of the orthogonal three dimensional coordinates in Ångstroms and B factors ($Å^2$) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 176 LYS | CE | −46.19 | −33.50 | 52.85 | 15.00 |
| 176 LYS | NZ | −46.03 | −33.64 | 51.36 | 15.00 |
| 176 LYS | C | −43.92 | −27.66 | 53.74 | 15.00 |
| 176 LYS | O | −43.25 | −27.27 | 52.77 | 15.00 |
| 177 HIS | N | −43.57 | −27.37 | 54.99 | 15.00 |
| 177 HIS | CA | −42.44 | −26.49 | 55.22 | 15.00 |
| 177 HIS | CB | −42.90 | −25.04 | 55.10 | 15.00 |
| 177 HIS | CG | −43.81 | −24.59 | 56.20 | 15.00 |
| 177 HIS | CD2 | −43.59 | −24.40 | 57.52 | 15.00 |
| 177 HIS | ND1 | −45.13 | −24.24 | 55.98 | 15.00 |
| 177 HIS | CE1 | −45.67 | −23.85 | 57.12 | 15.00 |
| 177 HIS | NE2 | −44.76 | −23.93 | 58.07 | 15.00 |
| 177 HIS | C | −41.73 | −26.66 | 56.55 | 15.00 |
| 177 HIS | O | −42.31 | −27.17 | 57.50 | 15.00 |
| 178 TRP | N | −40.48 | −26.20 | 56.61 | 15.00 |
| 178 TRP | CA | −39.68 | −26.25 | 57.82 | 15.00 |
| 178 TRP | CB | −38.26 | −26.73 | 57.52 | 15.00 |
| 178 TRP | CG | −38.13 | −28.11 | 57.02 | 15.00 |
| 178 TRP | CD2 | −38.29 | −29.32 | 57.78 | 15.00 |
| 178 TRP | CE2 | −37.96 | −30.39 | 56.93 | 15.00 |
| 178 TRP | CE3 | −38.68 | −29.59 | 59.10 | 15.00 |
| 178 TRP | CD1 | −37.74 | −28.49 | 55.78 | 15.00 |
| 178 TRP | NE1 | −37.62 | −29.86 | 55.72 | 15.00 |
| 178 TRP | CZ2 | −38.00 | −31.71 | 57.35 | 15.00 |
| 178 TRP | CZ3 | −38.72 | −30.91 | 59.52 | 15.00 |
| 178 TRP | CH2 | −38.38 | −31.96 | 58.64 | 15.00 |
| 178 TRP | C | −39.60 | −24.81 | 58.34 | 15.00 |
| 178 TRP | O | −39.21 | −23.90 | 57.60 | 15.00 |
| 179 ILE | N | −39.96 | −24.57 | 59.59 | 15.00 |
| 179 ILE | CA | −39.89 | −23.23 | 60.17 | 15.00 |
| 179 ILE | CB | −40.79 | −23.11 | 61.41 | 15.00 |
| 179 ILE | CG2 | −40.66 | −21.74 | 62.03 | 15.00 |
| 179 ILE | CG1 | −42.24 | −23.42 | 61.02 | 15.00 |
| 179 ILE | CD1 | −43.21 | −23.40 | 62.15 | 15.00 |
| 179 ILE | C | −38.44 | −23.00 | 60.58 | 15.00 |
| 179 ILE | O | −37.97 | −23.57 | 61.56 | 15.00 |
| 180 ILE | N | −37.72 | −22.17 | 59.81 | 15.00 |
| 180 ILE | CA | −36.31 | −21.89 | 60.07 | 15.00 |
| 180 ILE | CB | −35.49 | −21.93 | 58.76 | 15.00 |
| 180 ILE | CG2 | −34.04 | −21.77 | 59.05 | 15.00 |
| 180 ILE | CG1 | −35.73 | −23.25 | 58.02 | 15.00 |
| 180 ILE | CD1 | −35.30 | −24.46 | 58.78 | 15.00 |
| 180 ILE | C | −36.03 | −20.55 | 60.77 | 15.00 |
| 180 ILE | O | −36.62 | −19.52 | 60.42 | 15.00 |
| 181 LYS | N | −35.13 | −20.57 | 61.74 | 15.00 |
| 181 LYS | CA | −34.73 | −19.40 | 62.50 | 15.00 |
| 181 LYS | CB | −34.63 | −19.75 | 63.99 | 15.00 |
| 181 LYS | CG | −34.15 | −18.60 | 64.87 | 15.00 |
| 181 LYS | CD | −33.79 | −19.04 | 66.29 | 15.00 |
| 181 LYS | CE | −33.65 | −17.84 | 67.19 | 15.00 |
| 181 LYS | NZ | −33.21 | −18.18 | 68.57 | 15.00 |
| 181 LYS | C | −33.36 | −19.00 | 62.01 | 15.00 |
| 181 LYS | O | −32.43 | −19.79 | 62.05 | 15.00 |
| 182 ASN | N | −33.20 | −17.77 | 61.53 | 15.00 |
| 182 ASN | CA | −31.90 | −17.34 | 61.04 | 15.00 |
| 182 ASN | CB | −32.07 | −16.64 | 59.69 | 15.00 |
| 182 ASN | CG | −30.84 | −16.74 | 58.82 | 15.00 |
| 182 ASN | OD1 | −29.75 | −17.06 | 59.30 | 15.00 |
| 182 ASN | ND2 | −31.01 | −16.50 | 57.53 | 15.00 |
| 182 ASN | C | −31.22 | −16.43 | 62.06 | 15.00 |
| 182 ASN | O | −31.77 | −16.14 | 63.11 | 15.00 |
| 183 SER | N | −30.00 | −15.98 | 61.77 | 15.00 |
| 183 SER | CA | −29.29 | −15.10 | 62.69 | 15.00 |
| 183 SER | CB | −28.07 | −15.81 | 63.25 | 15.00 |
| 183 SER | OG | −27.40 | −16.52 | 62.23 | 15.00 |
| 183 SER | C | −28.87 | −13.82 | 61.98 | 15.00 |
| 183 SER | O | −27.82 | −13.25 | 62.27 | 15.00 |
| 184 TRP | N | −29.70 | −13.35 | 61.06 | 15.00 |
| 184 TRP | CA | −29.40 | −12.13 | 60.34 | 15.00 |
| 184 TRP | CB | −29.58 | −12.36 | 58.83 | 15.00 |
| 184 TRP | CG | −28.57 | −13.29 | 58.22 | 15.00 |
| 184 TRP | CD2 | −28.61 | −13.87 | 56.90 | 15.00 |
| 184 TRP | CE2 | −27.40 | −14.58 | 56.72 | 15.00 |
| 184 TRP | CE3 | −29.54 | −13.84 | 55.86 | 15.00 |
| 184 TRP | CD1 | −27.39 | −13.69 | 58.76 | 15.00 |
| 184 TRP | NE1 | −26.68 | −14.46 | 57.87 | 15.00 |
| 184 TRP | CZ2 | −27.11 | −15.26 | 55.53 | 15.00 |
| 184 TRP | CZ3 | −29.25 | −14.52 | 54.67 | 15.00 |
| 184 TRP | CH2 | −28.04 | −15.22 | 54.52 | 15.00 |
| 184 TRP | C | −30.28 | −10.98 | 60.82 | 15.00 |
| 184 TRP | O | −30.61 | −10.09 | 60.04 | 15.00 |
| 185 GLY | N | −30.70 | −11.02 | 62.09 | 15.00 |
| 185 GLY | CA | −31.53 | −9.96 | 62.66 | 15.00 |
| 185 GLY | C | −33.03 | −10.14 | 62.46 | 15.00 |
| 185 GLY | O | −33.46 | −10.99 | 61.69 | 15.00 |
| 186 GLU | N | −33.84 | −9.34 | 63.17 | 15.00 |
| 186 GLU | CA | −35.30 | −9.44 | 63.04 | 15.00 |
| 186 GLU | CB | −36.00 | −8.71 | 64.19 | 15.00 |
| 186 GLU | CG | −35.52 | −9.13 | 65.56 | 15.00 |
| 186 GLU | CD | −36.52 | −8.85 | 66.68 | 15.00 |
| 186 GLU | OE1 | −36.30 | −9.38 | 67.80 | 15.00 |
| 186 GLU | OE2 | −37.51 | −8.13 | 66.46 | 15.00 |
| 186 GLU | C | −35.74 | −8.83 | 61.73 | 15.00 |
| 186 GLU | O | −36.83 | −9.11 | 61.22 | 15.00 |
| 187 ASN | N | −34.89 | −7.97 | 61.19 | 15.00 |
| 187 ASN | CA | −35.15 | −7.28 | 59.95 | 15.00 |
| 187 ASN | CB | −34.04 | −6.25 | 59.73 | 15.00 |
| 187 ASN | CG | −34.56 | −4.94 | 59.17 | 15.00 |
| 187 ASN | OD1 | −33.77 | −4.07 | 58.80 | 15.00 |
| 187 ASN | ND2 | −35.88 | −4.76 | 59.16 | 15.00 |
| 187 ASN | C | −35.21 | −8.22 | 58.75 | 15.00 |
| 187 ASN | O | −36.04 | −8.04 | 57.86 | 15.00 |
| 188 TRP | N | −34.33 | −9.22 | 58.73 | 15.00 |
| 188 TRP | CA | −34.26 | −10.18 | 57.64 | 15.00 |
| 188 TRP | CB | −33.03 | −11.07 | 57.79 | 15.00 |
| 188 TRP | CG | −32.85 | −12.02 | 56.65 | 15.00 |
| 188 TRP | CD2 | −33.28 | −13.38 | 56.57 | 15.00 |
| 188 TRP | CE2 | −32.98 | −13.85 | 55.28 | 15.00 |
| 188 TRP | CE3 | −33.90 | −14.26 | 57.48 | 15.00 |
| 188 TRP | CD1 | −32.31 | −11.72 | 55.44 | 15.00 |
| 188 TRP | NE1 | −32.39 | −12.81 | 54.61 | 15.00 |
| 188 TRP | CZ2 | −33.27 | −15.15 | 54.86 | 15.00 |
| 188 TRP | CZ3 | −34.20 | −15.55 | 57.06 | 15.00 |
| 188 TRP | CH2 | −33.88 | −15.98 | 55.77 | 15.00 |
| 188 TRP | C | −35.50 | −11.05 | 57.53 | 15.00 |
| 188 TRP | O | −36.10 | −11.42 | 58.55 | 15.00 |
| 189 GLY | N | −35.85 | −11.42 | 56.31 | 15.00 |
| 189 GLY | CA | −37.00 | −12.26 | 56.07 | 15.00 |
| 189 GLY | C | −38.21 | −11.92 | 56.90 | 15.00 |
| 189 GLY | O | −38.47 | −10.76 | 57.23 | 15.00 |
| 190 ASN | N | −38.97 | −12.94 | 57.27 | 15.00 |
| 190 ASN | CA | −40.16 | −12.73 | 58.07 | 15.00 |
| 190 ASN | CB | −41.17 | −13.86 | 57.83 | 15.00 |
| 190 ASN | CG | −42.55 | −13.53 | 58.36 | 15.00 |
| 190 ASN | OD1 | −42.70 | −12.88 | 59.39 | 15.00 |
| 190 ASN | ND2 | −43.57 | −13.99 | 57.65 | 15.00 |
| 190 ASN | C | −39.79 | −12.67 | 59.54 | 15.00 |
| 190 ASN | O | −39.85 | −13.66 | 60.25 | 15.00 |
| 191 LYS | N | −39.32 | −11.52 | 60.00 | 15.00 |
| 191 LYS | CA | −38.95 | −11.34 | 61.39 | 15.00 |
| 191 LYS | CB | −40.19 | −11.48 | 62.29 | 15.00 |
| 191 LYS | CG | −40.95 | −10.18 | 62.44 | 15.00 |
| 191 LYS | CD | −42.19 | −10.32 | 63.30 | 15.00 |
| 191 LYS | CE | −43.32 | −10.98 | 62.52 | 15.00 |
| 191 LYS | NZ | −43.71 | −10.21 | 61.31 | 15.00 |
| 191 LYS | C | −37.84 | −12.24 | 61.88 | 15.00 |
| 191 LYS | O | −37.77 | −12.55 | 63.06 | 15.00 |
| 192 GLY | N | −36.94 | −12.61 | 60.98 | 15.00 |
| 192 GLY | CA | −35.83 | −13.46 | 61.35 | 15.00 |
| 192 GLY | C | −36.05 | −14.91 | 60.98 | 15.00 |
| 192 GLY | O | −35.12 | −15.70 | 60.99 | 15.00 |
| 193 TYR | N | −37.29 | −15.27 | 60.65 | 15.00 |

TABLE II-continued

Table of the orthogonal three dimensional coordinates in Ångstroms and B factors (Å²) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 193 TYR | CA | −37.60 | −16.64 | 60.28 | 15.00 |
| 193 TYR | CB | −38.84 | −17.13 | 61.05 | 15.00 |
| 193 TYR | CG | −38.60 | −17.31 | 62.52 | 15.00 |
| 193 TYR | CD1 | −38.73 | −16.25 | 63.41 | 15.00 |
| 193 TYR | CE1 | −38.46 | −16.41 | 64.76 | 15.00 |
| 193 TYR | CD2 | −38.19 | −18.55 | 63.03 | 15.00 |
| 193 TYR | CE2 | −37.92 | −18.71 | 64.38 | 15.00 |
| 193 TYR | CZ | −38.05 | −17.64 | 65.23 | 15.00 |
| 193 TYR | OH | −37.77 | −17.80 | 66.56 | 15.00 |
| 193 TYR | C | −37.83 | −16.81 | 58.79 | 15.00 |
| 193 TYR | O | −38.02 | −15.82 | 58.08 | 15.00 |
| 194 ILE | N | −37.82 | −18.06 | 58.35 | 15.00 |
| 194 ILE | CA | −38.04 | −18.41 | 56.95 | 15.00 |
| 194 ILE | CB | −36.75 | −18.32 | 56.10 | 15.00 |
| 194 ILE | CG2 | −35.64 | −19.14 | 56.72 | 15.00 |
| 194 ILE | CG1 | −37.03 | −18.83 | 54.69 | 15.00 |
| 194 ILE | CD1 | −35.86 | −18.72 | 53.75 | 15.00 |
| 194 ILE | C | −38.61 | −19.81 | 56.83 | 15.00 |
| 194 ILE | O | −38.11 | −20.74 | 57.43 | 15.00 |
| 194 LEU | N | −39.72 | −19.92 | 56.10 | 15.00 |
| 194 LEU | CA | −40.38 | −21.19 | 55.85 | 15.00 |
| 195 LEU | CB | −41.88 | −20.96 | 55.65 | 15.00 |
| 195 LEU | CG | −42.82 | −20.84 | 56.86 | 15.00 |
| 195 LEU | CD1 | −42.19 | −20.08 | 58.01 | 15.00 |
| 195 LEU | CD2 | −44.12 | −20.18 | 56.42 | 15.00 |
| 195 LEU | C | −39.76 | −21.78 | 54.59 | 15.00 |
| 195 LEU | O | −39.79 | −21.16 | 53.53 | 15.00 |
| 196 MET | N | −39.11 | −22.93 | 54.71 | 15.00 |
| 196 MET | CA | −38.46 | −23.57 | 53.57 | 15.00 |
| 196 MET | CB | −37.03 | −23.97 | 53.96 | 15.00 |
| 196 MET | CG | −36.09 | −22.77 | 54.14 | 15.00 |
| 196 MET | SD | −34.43 | −23.18 | 54.74 | 15.00 |
| 196 MET | CE | −33.67 | −23.82 | 53.22 | 15.00 |
| 196 MET | C | −39.28 | −24.78 | 53.11 | 15.00 |
| 196 MET | O | −40.09 | −25.31 | 53.86 | 15.00 |
| 197 ALA | N | −39.08 | −25.23 | 51.87 | 15.00 |
| 197 ALA | CA | −39.83 | −26.37 | 51.32 | 15.00 |
| 197 ALA | CB | −39.62 | −26.47 | 49.82 | 15.00 |
| 197 ALA | C | −39.52 | −27.71 | 51.98 | 15.00 |
| 197 ALA | O | −38.37 | −28.15 | 51.98 | 15.00 |
| 198 ARG | N | −40.56 | −28.39 | 52.46 | 15.00 |
| 198 ARG | CA | −40.40 | −29.68 | 53.11 | 15.00 |
| 198 ARG | CB | −41.17 | −29.72 | 54.44 | 15.00 |
| 198 ARG | CG | −41.15 | −31.07 | 55.15 | 15.00 |
| 198 ARG | CD | −41.43 | −30.95 | 56.63 | 15.00 |
| 198 ARG | NE | −42.81 | −30.59 | 56.92 | 15.00 |
| 198 ARG | CZ | −43.79 | −31.47 | 57.10 | 15.00 |
| 198 ARG | NH1 | −43.54 | −32.78 | 57.01 | 15.00 |
| 198 ARG | NH2 | −45.01 | −31.05 | 57.42 | 15.00 |
| 198 ARG | C | −40.82 | −30.85 | 52.23 | 15.00 |
| 198 ARG | O | −41.86 | −30.80 | 51.57 | 15.00 |
| 199 ASN | N | −40.00 | −31.89 | 52.23 | 15.00 |
| 199 ASN | CA | −40.25 | −33.10 | 51.45 | 15.00 |
| 199 ASN | CB | −41.59 | −33.75 | 51.83 | 15.00 |
| 199 ASN | CG | −41.57 | −34.40 | 53.22 | 15.00 |
| 199 ASN | OD1 | −42.60 | −34.43 | 53.91 | 15.00 |
| 199 ASN | ND2 | −40.42 | −34.91 | 53.63 | 15.00 |
| 199 ASN | C | −40.15 | −32.94 | 49.94 | 15.00 |
| 199 ASN | O | −40.49 | −33.86 | 49.19 | 15.00 |
| 200 LYS | N | −39.67 | −31.77 | 49.49 | 15.00 |
| 200 LYS | CA | −39.50 | −31.55 | 48.05 | 15.00 |
| 200 LYS | CB | −39.77 | −30.09 | 47.65 | 15.00 |
| 200 LYS | CG | −41.23 | −29.79 | 47.39 | 15.00 |
| 200 LYS | CD | −41.42 | −28.49 | 46.63 | 15.00 |
| 200 LYS | CE | −42.88 | −28.03 | 46.65 | 15.00 |
| 200 LYS | NZ | −43.06 | −26.68 | 46.03 | 15.00 |
| 200 LYS | C | −38.09 | −31.95 | 47.69 | 15.00 |
| 200 LYS | O | −37.28 | −31.12 | 47.26 | 15.00 |
| 201 ASN | N | −37.80 | −33.22 | 47.95 | 15.00 |
| 201 ASN | CA | −36.50 | −33.81 | 47.65 | 15.00 |
| 201 ASN | CB | −36.24 | −33.83 | 46.13 | 15.00 |
| 201 ASN | CG | −37.32 | −34.57 | 45.35 | 15.00 |
| 201 ASN | OD1 | −37.09 | −35.68 | 44.87 | 15.00 |
| 201 ASN | ND2 | −38.46 | −33.92 | 45.15 | 15.00 |
| 201 ASN | C | −35.31 | −33.16 | 48.37 | 15.00 |
| 201 ASN | O | −34.31 | −32.84 | 47.74 | 15.00 |
| 202 ASN | N | −35.43 | −32.90 | 49.67 | 15.00 |
| 202 ASN | CA | −34.32 | −32.33 | 50.44 | 15.00 |
| 202 ASN | CB | −33.19 | −33.35 | 50.50 | 15.00 |
| 202 ASN | CG | −32.27 | −33.14 | 51.68 | 15.00 |
| 202 ASN | OD1 | −32.71 | −32.70 | 52.75 | 15.00 |
| 202 ASN | ND2 | −31.00 | −33.48 | 51.51 | 15.00 |
| 202 ASN | C | −33.81 | −30.99 | 49.89 | 15.00 |
| 202 ASN | O | −32.60 | −30.77 | 49.75 | 15.00 |
| 203 ALA | N | −34.73 | −30.09 | 49.59 | 15.00 |
| 203 ALA | H | −35.63 | −30.29 | 49.94 | 15.00 |
| 203 ALA | CA | −34.40 | −28.79 | 49.02 | 15.00 |
| 203 ALA | CB | −35.62 | −27.88 | 48.98 | 15.00 |
| 203 ALA | C | −33.35 | −28.09 | 49.90 | 15.00 |
| 203 ALA | O | −33.51 | −27.93 | 51.10 | 15.00 |
| 204 CYS | N | −32.27 | −27.66 | 49.25 | 15.00 |
| 204 CYS | CA | −31.18 | −26.94 | 49.91 | 15.00 |
| 204 CYS | C | −30.38 | −27.79 | 50.89 | 15.00 |
| 204 CYS | O | −29.60 | −27.25 | 51.68 | 15.00 |
| 204 CYS | CB | −31.71 | −25.68 | 50.59 | 15.00 |
| 204 CYS | SG | −32.51 | −24.48 | 49.47 | 15.00 |
| 205 GLY | N | −30.56 | −29.10 | 50.84 | 15.00 |
| 205 GLY | CA | −29.83 | −30.00 | 51.71 | 15.00 |
| 205 GLY | C | −30.11 | −29.81 | 53.19 | 15.00 |
| 205 GLY | O | −29.22 | −29.98 | 54.02 | 15.00 |
| 206 ILE | N | −31.35 | −29.51 | 53.52 | 15.00 |
| 206 ILE | CA | −31.77 | −29.30 | 54.89 | 15.00 |
| 206 ILE | CB | −33.30 | −29.10 | 54.96 | 15.00 |
| 206 ILE | CG2 | −34.02 | −30.31 | 54.38 | 15.00 |
| 206 ILE | CG1 | −33.76 | −28.86 | 56.41 | 15.00 |
| 206 ILE | CD1 | −33.48 | −27.47 | 56.92 | 15.00 |
| 206 ILE | C | −31.35 | −30.45 | 55.82 | 15.00 |
| 206 ILE | O | −30.94 | −30.23 | 56.97 | 15.00 |
| 207 ALA | N | −31.36 | −31.68 | 55.31 | 15.00 |
| 207 ALA | CA | −31.00 | −32.84 | 56.11 | 15.00 |
| 207 ALA | CB | −32.05 | −33.93 | 55.95 | 15.00 |
| 207 ALA | C | −29.61 | −33.42 | 55.88 | 15.00 |
| 207 ALA | O | −29.35 | −34.57 | 56.24 | 15.00 |
| 208 ASN | N | −28.68 | −32.65 | 55.31 | 15.00 |
| 208 ASN | CA | −27.33 | −33.15 | 55.05 | 15.00 |
| 208 ASN | CB | −26.76 | −32.53 | 53.77 | 15.00 |
| 208 ASN | CG | −27.34 | −33.15 | 52.51 | 15.00 |
| 208 ASN | OD1 | −28.21 | −34.02 | 52.57 | 15.00 |
| 208 ASN | ND2 | −26.89 | −32.67 | 51.36 | 15.00 |
| 208 ASN | C | −26.32 | −32.95 | 56.20 | 15.00 |
| 208 ASN | O | −25.17 | −33.40 | 56.12 | 15.00 |
| 209 LEU | N | −26.72 | −32.25 | 57.25 | 15.00 |
| 209 LEU | CA | −25.84 | −32.03 | 58.40 | 15.00 |
| 209 LEU | CB | −24.76 | −31.00 | 58.04 | 15.00 |
| 209 LEU | CG | −23.41 | −30.99 | 58.78 | 15.00 |
| 209 LEU | CD1 | −22.72 | −32.35 | 58.64 | 15.00 |
| 209 LEU | CD2 | −22.51 | −29.86 | 58.24 | 15.00 |
| 209 LEU | C | −26.67 | −31.60 | 59.63 | 15.00 |
| 209 LEU | O | −26.38 | −30.59 | 60.28 | 15.00 |
| 210 ALA | N | −27.72 | −32.37 | 59.95 | 15.00 |
| 210 ALA | H | −28.03 | −32.90 | 59.19 | 15.00 |
| 210 ALA | CA | −28.61 | −32.05 | 61.06 | 15.00 |
| 210 ALA | CB | −30.02 | −32.57 | 60.81 | 15.00 |
| 210 ALA | C | −28.10 | −32.73 | 62.34 | 15.00 |
| 210 ALA | O | −27.62 | −33.86 | 62.34 | 15.00 |
| 211 SER | N | −28.18 | −32.02 | 63.47 | 15.00 |
| 211 SER | CA | −27.75 | −32.59 | 64.74 | 15.00 |
| 211 SER | CB | −26.24 | −32.46 | 64.92 | 15.00 |
| 211 SER | OG | −25.84 | −31.12 | 65.06 | 15.00 |
| 211 SER | C | −28.45 | −31.88 | 65.88 | 15.00 |
| 211 SER | O | −29.03 | −30.80 | 65.71 | 15.00 |
| 212 PHE | N | −28.50 | −32.51 | 67.04 | 15.00 |

TABLE II-continued

Table of the orthogonal three dimensional coordinates in Ångstroms and B factors (Å$^2$) for the cathepsin K complex with inhibitor 3(S)-3-[(N-benzyloxycarbonyl)-L-leucinyl]amino-5-methyl-1-(1-propoxy)-2-hexanone.

| Residue | Atom | X | Y | Z | B |
|---|---|---|---|---|---|
| 212 PHE | CA | −29.11 | −31.91 | 68.21 | 15.00 |
| 212 PHE | CB | −30.59 | −32.31 | 68.33 | 15.00 |
| 212 PHE | CG | −30.81 | −33.79 | 68.43 | 15.00 |
| 212 PHE | CD1 | −31.11 | −34.54 | 67.30 | 15.00 |
| 212 PHE | CD2 | −30.72 | −34.44 | 69.66 | 15.00 |
| 212 PHE | CE1 | −31.32 | −35.91 | 67.39 | 15.00 |
| 212 PHE | CE2 | −30.92 | −35.81 | 69.77 | 15.00 |
| 212 PHE | CZ | −31.23 | −36.55 | 68.63 | 15.00 |
| 212 PHE | C | −28.30 | −32.39 | 69.40 | 15.00 |
| 212 PHE | O | −27.66 | −33.43 | 69.32 | 15.00 |
| 213 PRO | N | −28.24 | −31.58 | 70.46 | 15.00 |
| 213 PRO | CD | −28.77 | −30.21 | 70.54 | 15.00 |
| 213 PRO | CA | −27.48 | −31.92 | 71.67 | 15.00 |
| 213 PRO | CB | −27.21 | −30.55 | 72.28 | 15.00 |
| 213 PRO | CG | −28.47 | −29.82 | 71.97 | 15.00 |
| 213 PRO | C | −28.27 | −32.81 | 72.64 | 15.00 |
| 213 PRO | O | −29.50 | −32.76 | 72.69 | 15.00 |
| 214 LYS | N | −27.57 | −33.62 | 73.42 | 15.00 |
| 214 LYS | CA | −28.23 | −34.49 | 74.37 | 15.00 |
| 214 LYS | CB | −27.67 | −35.90 | 74.28 | 15.00 |
| 214 LYS | CG | −28.06 | −36.64 | 73.02 | 15.00 |
| 214 LYS | CD | −27.66 | −38.11 | 73.07 | 15.00 |
| 214 LYS | CE | −26.16 | −38.29 | 73.05 | 15.00 |
| 214 LYS | NZ | −25.79 | −39.70 | 72.73 | 15.00 |
| 214 LYS | C | −28.03 | −33.95 | 75.77 | 15.00 |
| 214 LYS | O | −26.90 | −33.70 | 76.18 | 15.00 |
| 215 MET | N | −29.12 | −33.69 | 76.47 | 15.00 |
| 215 MET | CA | −29.06 | −33.18 | 77.83 | 15.00 |
| 215 MET | CB | −29.71 | −31.80 | 77.93 | 15.00 |
| 215 MET | CG | −28.74 | −30.64 | 77.75 | 15.00 |
| 215 MET | SD | −29.45 | −29.00 | 78.06 | 15.00 |
| 215 MET | CE | −30.38 | −29.32 | 79.56 | 15.00 |
| 215 MET | C | −29.72 | −34.16 | 78.81 | 15.00 |
| 215 MET | OT1 | −30.39 | −35.12 | 78.35 | 15.00 |
| 215 MET | OT2 | −29.55 | −33.97 | 80.04 | 15.00 |
| 215 HOH | OH2 | −28.46 | −18.77 | 85.58 | 15.00 |
| 217 HOH | OH2 | −24.63 | −33.99 | 81.97 | 15.00 |
| 218 HOH | OH2 | −31.11 | −15.95 | 65.82 | 15.00 |
| 219 HOH | OH2 | −30.23 | −19.59 | 64.13 | 15.00 |
| 220 HOH | OH2 | −8.58 | −7.31 | 62.36 | 15.00 |
| 221 HOH | OH2 | −6.71 | −10.79 | 69.96 | 15.00 |
| 222 HOH | OH2 | −34.27 | −22.79 | 70.48 | 15.00 |
| 223 HOH | OH2 | −16.88 | −33.68 | 66.52 | 15.00 |
| 224 HOH | OH2 | −15.68 | −8.93 | 63.11 | 15.00 |
| 225 HOH | OH2 | −24.93 | −30.84 | 62.42 | 15.00 |
| 226 HOH | OH2 | −7.02 | −8.27 | 72.29 | 15.00 |
| 227 HOH | OH2 | −13.39 | −20.80 | 66.92 | 15.00 |
| 228 HOH | OH2 | −44.55 | −30.12 | 50.27 | 15.00 |
| 229 HOH | OH2 | −44.14 | −35.34 | 56.06 | 15.00 |
| 230 HOH | OH2 | −37.95 | −16.02 | 68.44 | 15.00 |
| 231 HOH | OH2 | −36.41 | −36.82 | 52.05 | 15.00 |
| 232 HOH | OH2 | −20.00 | −36.75 | 62.15 | 15.00 |
| 233 HOH | OH2 | −30.13 | −19.30 | 67.02 | 15.00 |
| 234 HOH | OH2 | −28.16 | −19.22 | 62.41 | 15.00 |
| 235 HOH | OH2 | −22.03 | −29.95 | 62.71 | 15.00 |
| 236 HOH | OH2 | −25.92 | −8.85 | 75.85 | 15.00 |
| 237 HOH | OH2 | −41.00 | −28.78 | 81.30 | 15.00 |
| 238 HOH | OH2 | −32.73 | −23.15 | 83.59 | 15.00 |
| 239 HOH | OH2 | −40.55 | −13.35 | 49.90 | 15.00 |
| 240 HOH | OH2 | −35.40 | −24.36 | 49.00 | 15.00 |
| 241 HOH | OH2 | −48.40 | −32.54 | 58.07 | 15.00 |
| 242 HOH | OH2 | −27.39 | −6.75 | 59.53 | 15.00 |
| 243 HOH | OH2 | −41.50 | −14.46 | 65.52 | 15.00 |
| 244 HOH | OH2 | −22.40 | −5.47 | 61.33 | 15.00 |
| 245 HOH | OH2 | −33.17 | −27.91 | 70.80 | 15.00 |
| 246 HOH | OH2 | −45.87 | −26.25 | 75.72 | 15.00 |
| 247 HOH | OH2 | −12.64 | −13.96 | 81.39 | 15.00 |
| 248 HOH | OH2 | −3.78 | −18.92 | 74.98 | 15.00 |
| 249 HOH | OH2 | −8.03 | −17.70 | 78.42 | 15.00 |
| 250 HOH | OH2 | −27.41 | −34.98 | 59.22 | 15.00 |
| 251 HOH | OH2 | −34.88 | −10.94 | 53.71 | 15.00 |
| 252 HOH | OH2 | −32.92 | −27.68 | 46.17 | 15.00 |
| 253 HOH | OH2 | −39.35 | −16.01 | 44.28 | 15.00 |
| 254 HOH | OH2 | −41.38 | −34.64 | 56.30 | 15.00 |
| 255 HOH | OH2 | −44.42 | −18.35 | 73.08 | 15.00 |
| 256 HOH | OH2 | −32.35 | −13.73 | 61.23 | 15.00 |
| 257 HOH | OH2 | −39.40 | −8.90 | 59.13 | 15.00 |
| 258 HOH | OH2 | −28.41 | −8.93 | 68.65 | 15.00 |
| 259 HOH | OH2 | −31.58 | −6.53 | 63.69 | 15.00 |
| 260 HOH | OH2 | −19.27 | −8.48 | 63.41 | 15.00 |
| 261 HOH | OH2 | −33.33 | −20.29 | 70.52 | 15.00 |
| 262 HOH | OH2 | −13.49 | −22.80 | 78.17 | 15.00 |
| 263 HOH | OH2 | −8.72 | −18.49 | 72.60 | 15.00 |
| 264 HOH | OH2 | −10.39 | −28.70 | 76.32 | 15.00 |
| 265 HOH | OH2 | −20.24 | −31.77 | 61.63 | 15.00 |
| 266 HOH | OH2 | −24.78 | −46.10 | 72.19 | 15.00 |
| 267 HOH | OH2 | −13.26 | −33.12 | 68.94 | 15.00 |
| 268 HOH | OH2 | −12.60 | −26.87 | 72.01 | 15.00 |
| 269 HOH | OH2 | −17.76 | −34.32 | 80.14 | 15.00 |
| 270 HOH | OH2 | −22.51 | −37.80 | 70.83 | 15.00 |
| 271 HOH | OH2 | −7.33 | −12.89 | 66.95 | 15.00 |
| 272 HOH | OH2 | −9.75 | −17.21 | 68.77 | 15.00 |
| 273 HOH | OH2 | −30.86 | −20.40 | 48.59 | 15.00 |
| 274 HOH | OH2 | −25.79 | −24.78 | 42.10 | 15.00 |
| 275 HOH | OH2 | −33.50 | −37.21 | 50.03 | 15.00 |
| 276 HOH | OH2 | −23.21 | −24.90 | 43.38 | 15.00 |
| 277 HOH | OH2 | −37.83 | −31.49 | 44.10 | 15.00 |
| 278 HOH | OH2 | −37.02 | −30.78 | 51.01 | 15.00 |

TABLE III

Table of the orthogonal three dimensional coordinates in Ångstroms and B factors (Å$^2$) for the cathepsin K complex with inhibitor bis-(cbz-leucinyl)-1,3-diamino-propan-2-one.

| Residue | Atom | X | Y | Z | B |
|---|---|---|---|---|---|
| 1 ALA | CB | −54.29 | −33.17 | 65.94 | 15.00 |
| 1 ALA | C | −53.88 | −32.69 | 63.50 | 15.00 |
| 1 ALA | O | −53.42 | −33.61 | 62.80 | 15.00 |
| 1 ALA | N | −55.60 | −34.28 | 64.17 | 15.00 |
| 1 ALA | CA | −54.93 | −33.01 | 64.57 | 15.00 |
| 2 PRO | N | −53.52 | −31.40 | 63.32 | 15.00 |
| 2 PRO | CD | −53.99 | −30.23 | 64.09 | 15.00 |
| 2 PRO | CA | −52.52 | −30.98 | 62.32 | 15.00 |
| 2 PRO | CB | −52.49 | −29.46 | 62.49 | 15.00 |
| 2 PRO | CG | −52.83 | −29.26 | 63.94 | 15.00 |
| 2 PRO | C | −51.13 | −31.59 | 62.52 | 15.00 |
| 2 PRO | O | −50.62 | −31.64 | 63.64 | 15.00 |
| 3 ASP | N | −50.53 | −32.08 | 61.44 | 15.00 |
| 3 ASP | CA | −49.19 | −32.65 | 61.51 | 15.00 |
| 3 ASP | CB | −48.89 | −33.49 | 60.27 | 15.00 |
| 3 ASP | CG | −49.53 | −34.88 | 60.32 | 15.00 |
| 3 ASP | OD1 | −49.43 | −35.55 | 61.39 | 15.00 |
| 3 ASP | OD2 | −50.12 | −35.29 | 59.28 | 15.00 |
| 3 ASP | C | −48.24 | −31.46 | 61.55 | 15.00 |
| 3 ASP | O | −47.60 | −31.14 | 60.54 | 15.00 |
| 4 SER | N | −48.16 | −30.78 | 62.68 | 15.00 |
| 4 SER | CA | −47.29 | −29.62 | 62.80 | 15.00 |
| 4 SER | CB | −47.99 | −28.35 | 62.27 | 15.00 |
| 4 SER | OG | −48.14 | −28.37 | 60.86 | 15.00 |
| 4 SER | C | −46.84 | −29.35 | 64.23 | 15.00 |
| 4 SER | O | −47.54 | −29.71 | 65.19 | 15.00 |
| 5 VAL | N | −45.68 | −28.72 | 64.36 | 15.00 |
| 5 VAL | CA | −45.14 | −28.35 | 65.65 | 15.00 |
| 5 VAL | CB | −44.25 | −29.47 | 66.25 | 15.00 |
| 5 VAL | CG1 | −43.09 | −29.81 | 65.33 | 15.00 |
| 5 VAL | CG2 | −43.75 | −29.04 | 67.62 | 15.00 |

TABLE III-continued

Table of the orthogonal three dimensional coordinates in Ångstroms and B factors (Å²) for the cathepsin K complex with inhibitor bis-(cbz-leucinyl)-1,3-diamino-propan-2-one.

| Residue Atom | X | Y | Z | B |
|---|---|---|---|---|
| 5 VAL C | −44.36 | −27.06 | 65.44 | 15.00 |
| 5 VAL O | −43.60 | −26.93 | 64.48 | 15.00 |
| 6 ASP N | −44.59 | −26.08 | 66.30 | 15.00 |
| 6 ASP CA | −43.94 | −24.79 | 66.20 | 15.00 |
| 6 ASP CB | −44.95 | −23.76 | 65.68 | 15.00 |
| 6 ASP CG | −44.35 | −22.38 | 65.47 | 15.00 |
| 6 ASP OD1 | −43.14 | −22.26 | 65.21 | 15.00 |
| 6 ASP OD2 | −45.11 | −21.39 | 65.56 | 15.00 |
| 6 ASP C | −43.47 | −24.45 | 67.60 | 15.00 |
| 6 ASP O | −44.25 | −24.02 | 68.45 | 15.00 |
| 7 TYR N | −42.18 | −24.61 | 67.86 | 15.00 |
| 7 TYR CA | −41.62 | −24.34 | 69.18 | 15.00 |
| 7 TYR CB | −40.24 | −24.98 | 69.29 | 15.00 |
| 7 TYR CG | −40.34 | −26.48 | 69.38 | 15.00 |
| 7 TYR CD1 | −40.73 | −27.10 | 70.57 | 15.00 |
| 7 TYR CE1 | −40.88 | −28.46 | 70.65 | 15.00 |
| 7 TYR CD2 | −40.08 | −27.28 | 68.27 | 15.00 |
| 7 TYR CE2 | −40.23 | −28.65 | 68.34 | 15.00 |
| 7 TYR CZ | −40.63 | −29.23 | 69.53 | 15.00 |
| 7 TYR OH | −40.78 | −30.58 | 69.62 | 15.00 |
| 7 TYR C | −41.58 | −22.91 | 69.65 | 15.00 |
| 7 TYR O | −41.37 | −22.64 | 70.84 | 15.00 |
| 8 ARG N | −41.80 | −21.97 | 68.74 | 15.00 |
| 8 ARG CA | −41.78 | −20.56 | 69.11 | 15.00 |
| 8 ARG CB | −41.99 | −19.67 | 67.87 | 15.00 |
| 8 ARG CG | −40.88 | −19.77 | 66.84 | 15.00 |
| 8 ARG CD | −41.23 | −19.01 | 65.57 | 15.00 |
| 8 ARG NE | −42.50 | −19.45 | 65.01 | 15.00 |
| 8 ARG CZ | −42.96 | −19.10 | 63.81 | 15.00 |
| 8 ARG NH1 | −42.24 | −18.30 | 63.03 | 15.00 |
| 8 ARG NH2 | −44.15 | −19.53 | 63.40 | 15.00 |
| 8 ARG C | −42.85 | −20.28 | 70.15 | 15.00 |
| 8 ARG O | −42.57 | −19.72 | 71.21 | 15.00 |
| 9 LYS N | −44.06 | −20.77 | 69.88 | 15.00 |
| 9 LYS CA | −45.18 | −20.55 | 70.78 | 15.00 |
| 9 LYS CB | −46.50 | −20.64 | 70.02 | 15.00 |
| 9 LYS CG | −46.63 | −21.81 | 69.10 | 15.00 |
| 9 LYS CD | −47.93 | −21.71 | 68.33 | 15.00 |
| 9 LYS CE | −48.22 | −22.99 | 67.54 | 15.00 |
| 9 LYS NZ | −49.52 | −22.90 | 66.80 | 15.00 |
| 9 LYS C | −45.22 | −21.43 | 72.02 | 15.00 |
| 9 LYS O | −46.25 | −21.56 | 72.67 | 15.00 |
| 10 LYS N | −44.08 | −22.02 | 72.38 | 15.00 |
| 10 LYS CA | −43.97 | −22.87 | 73.56 | 15.00 |
| 10 LYS CB | −43.66 | −24.32 | 73.16 | 15.00 |
| 10 LYS CG | −44.79 | −25.04 | 72.44 | 15.00 |
| 10 LYS CD | −44.37 | −26.46 | 72.08 | 15.00 |
| 10 LYS CE | −45.44 | −27.16 | 71.27 | 15.00 |
| 10 LYS NZ | −45.80 | −26.44 | 70.01 | 15.00 |
| 10 LYS C | −42.90 | −22.38 | 74.54 | 15.00 |
| 10 LYS O | −42.69 | −22.99 | 75.59 | 15.00 |
| 11 GLY N | −42.19 | −21.30 | 74.19 | 15.00 |
| 11 GLY CA | −41.15 | −20.78 | 75.05 | 15.00 |
| 11 GLY C | −39.83 | −21.52 | 74.90 | 15.00 |
| 11 GLY O | −38.95 | −21.41 | 75.74 | 15.00 |
| 12 TYR N | −39.69 | −22.25 | 73.79 | 15.00 |
| 12 TYR CA | −38.48 | −23.03 | 73.51 | 15.00 |
| 12 TYR CB | −38.82 | −24.26 | 72.67 | 15.00 |
| 12 TYR CG | −39.21 | −25.54 | 73.39 | 15.00 |
| 12 TYR CD1 | −40.43 | −25.65 | 74.06 | 15.00 |
| 12 TYR CE1 | −40.85 | −26.87 | 74.58 | 15.00 |
| 12 TYR CD2 | −38.41 | −26.68 | 73.27 | 15.00 |
| 12 TYR CE2 | −38.83 | −27.90 | 73.79 | 15.00 |
| 12 TYR CZ | −40.05 | −27.98 | 74.44 | 15.00 |
| 12 TYR OH | −40.47 | −29.19 | 74.93 | 15.00 |
| 12 TYR C | −37.45 | −22.25 | 72.72 | 15.00 |
| 12 TYR O | −36.33 | −22.72 | 72.54 | 15.00 |
| 13 VAL N | −37.85 | −21.09 | 72.19 | 15.00 |
| 13 VAL CA | −36.94 | −20.29 | 71.37 | 15.00 |
| 13 VAL CB | −37.40 | −20.32 | 69.88 | 15.00 |
| 13 VAL CG1 | −38.59 | −19.43 | 69.67 | 15.00 |
| 13 VAL CG2 | −36.26 | −19.93 | 68.97 | 15.00 |
| 13 VAL C | −36.77 | −18.86 | 71.87 | 15.00 |
| 13 VAL O | −37.69 | −18.26 | 72.43 | 15.00 |
| 14 THR N | −35.55 | −18.35 | 71.69 | 15.00 |
| 14 THR CA | −35.15 | −17.00 | 72.11 | 15.00 |
| 14 THR CB | −33.72 | −17.00 | 72.67 | 15.00 |
| 14 THR OG1 | −32.83 | −17.53 | 71.69 | 15.00 |
| 14 THR CG2 | −33.64 | −17.86 | 73.91 | 15.00 |
| 14 THR C | −35.21 | −15.98 | 70.97 | 15.00 |
| 14 THR O | −35.26 | −16.36 | 69.81 | 15.00 |
| 15 PRO N | −35.22 | −14.68 | 71.31 | 15.00 |
| 15 PRO CD | −35.25 | −14.08 | 72.65 | 15.00 |
| 15 PRO CA | −35.27 | −13.64 | 70.28 | 15.00 |
| 15 PRO CB | −35.03 | −12.35 | 71.08 | 15.00 |
| 15 PRO CG | −34.46 | −12.83 | 72.43 | 15.00 |
| 15 PRO C | −34.23 | −13.82 | 69.17 | 15.00 |
| 15 PRO O | −33.14 | −14.35 | 69.41 | 15.00 |
| 16 VAL N | −34.60 | −13.42 | 67.96 | 15.00 |
| 16 VAL CA | −33.72 | −13.53 | 66.81 | 15.00 |
| 16 VAL CB | −34.45 | −13.16 | 65.50 | 15.00 |
| 16 VAL CG1 | −33.63 | −13.60 | 64.31 | 15.00 |
| 16 VAL CG2 | −35.81 | −13.78 | 65.47 | 15.00 |
| 16 VAL C | −32.52 | −12.61 | 66.97 | 15.00 |
| 16 VAL O | −32.67 | −11.42 | 67.25 | 15.00 |
| 17 LYS N | −31.32 | −13.17 | 66.80 | 15.00 |
| 17 LYS CA | −30.09 | −12.42 | 66.91 | 15.00 |
| 17 LYS CB | −29.08 | −13.18 | 67.77 | 15.00 |
| 17 LYS CG | −29.01 | −12.72 | 69.22 | 15.00 |
| 17 LYS CD | −30.27 | −13.09 | 70.02 | 15.00 |
| 17 LYS CE | −30.18 | −14.48 | 70.64 | 15.00 |
| 17 LYS NZ | −29.12 | −14.54 | 71.68 | 15.00 |
| 17 LYS C | −29.49 | −12.15 | 65.54 | 15.00 |
| 17 LYS O | −29.82 | −12.81 | 64.56 | 15.00 |
| 18 ASN N | −28.62 | −11.15 | 65.49 | 15.00 |
| 18 ASN CA | −27.91 | −10.77 | 64.27 | 15.00 |
| 18 ASN CB | −28.01 | −9.26 | 64.05 | 15.00 |
| 18 ASN CG | −27.09 | −8.78 | 62.94 | 15.00 |
| 18 ASN OD1 | −26.98 | −9.42 | 61.89 | 15.00 |
| 18 ASN ND2 | −26.38 | −7.69 | 63.19 | 15.00 |
| 18 ASN C | −26.45 | −11.16 | 64.43 | 15.00 |
| 18 ASN O | −25.79 | −10.73 | 65.37 | 15.00 |
| 19 GLN N | −25.94 | −11.96 | 63.51 | 15.00 |
| 19 GLN CA | −24.56 | −12.40 | 63.60 | 15.00 |
| 19 GLN CB | −24.34 | −13.65 | 62.77 | 15.00 |
| 19 GLN CG | −24.88 | −13.58 | 61.37 | 15.00 |
| 19 GLN CD | −24.42 | −14.73 | 60.53 | 15.00 |
| 19 GLN OE1 | −25.17 | −15.28 | 59.73 | 15.00 |
| 19 GLN NE2 | −23.15 | −15.09 | 60.68 | 15.00 |
| 19 GLN C | −23.52 | −11.35 | 63.24 | 15.00 |
| 19 GLN O | −22.35 | −11.49 | 63.60 | 15.00 |
| 20 GLY N | −23.94 | −10.31 | 62.53 | 15.00 |
| 20 GLY CA | −23.02 | −9.26 | 62.14 | 15.00 |
| 20 GLY C | −22.10 | −9.67 | 61.00 | 15.00 |
| 20 GLY O | −22.51 | −10.40 | 60.11 | 15.00 |
| 21 GLN N | −20.85 | −9.20 | 61.04 | 15.00 |
| 21 GLN CA | −19.86 | −9.50 | 60.01 | 15.00 |
| 21 GLN CB | −18.92 | −8.30 | 59.78 | 15.00 |
| 21 GLN CG | −19.60 | −6.94 | 59.55 | 15.00 |
| 21 GLN CD | −20.68 | −6.99 | 58.49 | 15.00 |
| 21 GLN OE1 | −20.49 | −7.53 | 54.41 | 15.00 |
| 21 GLN NE2 | −21.85 | −6.43 | 58.81 | 15.00 |
| 21 GLN C | −19.03 | −10.74 | 60.38 | 15.00 |
| 21 GLN O | −18.02 | −11.06 | 59.74 | 15.00 |
| 22 CYS N | −19.41 | −11.42 | 61.44 | 15.00 |
| 22 CYS CA | −18.69 | −12.60 | 61.88 | 15.00 |
| 22 CYS C | −19.37 | −13.86 | 61.33 | 15.00 |
| 22 CYS O | −20.59 | −13.94 | 61.27 | 15.00 |
| 22 CYS CB | −18.63 | −12.61 | 63.41 | 15.00 |
| 22 CYS SG | −17.84 | −14.05 | 64.16 | 15.00 |
| 23 GLY N | −18.58 | −14.81 | 60.84 | 15.00 |
| 23 GLY CA | −19.15 | −16.03 | 60.30 | 15.00 |
| 23 GLY C | −19.41 | −17.03 | 61.41 | 15.00 |
| 23 GLY O | −18.90 | −18.15 | 61.38 | 15.00 |

TABLE III-continued

Table of the orthogonal three dimensional coordinates in Ångstroms and B factors (Å²) for the cathepsin K complex with inhibitor bis-(cbz-leucinyl)-1,3-diamino-propan-2-one.

| Residue Atom | X | Y | Z | B |
|---|---|---|---|---|
| 24 SER N | −20.22 | −16.62 | 62.37 | 15.00 |
| 24 SER CA | −20.56 | −17.43 | 63.53 | 15.00 |
| 24 SER CB | −20.36 | −16.59 | 64.79 | 15.00 |
| 24 SER OG | −21.14 | −15.41 | 64.68 | 15.00 |
| 24 SER C | −21.99 | −17.95 | 63.49 | 15.00 |
| 24 SER O | −22.60 | −18.20 | 64.53 | 15.00 |
| 25 CYS N | −22.55 | −18.14 | 62.30 | 15.00 |
| 25 CYS CA | −23.91 | −18.65 | 62.20 | 15.00 |
| 25 CYS CB | −24.41 | −18.63 | 60.75 | 15.00 |
| 25 CYS SG | −23.48 | −19.60 | 59.54 | 15.00 |
| 25 CYS C | −23.96 | −20.05 | 62.82 | 15.00 |
| 25 CYS O | −24.97 | −20.45 | 63.40 | 15.00 |
| 25 INH C1 | −27.24 | −9.28 | 57.72 | 15.00 |
| 25 INH C2 | −26.55 | −9.60 | 58.90 | 15.00 |
| 25 INH C3 | −25.31 | −10.22 | 58.84 | 15.00 |
| 25 INH C4 | −24.73 | −10.54 | 57.61 | 15.00 |
| 25 INH C5 | −25.43 | −10.21 | 56.44 | 15.00 |
| 25 INH C6 | −26.67 | −9.59 | 56.49 | 15.00 |
| 25 INH C7 | −23.41 | −11.26 | 57.54 | 15.00 |
| 25 INH O8 | −23.43 | −12.63 | 57.98 | 15.00 |
| 25 INH C9 | −22.90 | −13.56 | 57.08 | 15.00 |
| 25 INH O10 | −21.75 | −13.43 | 56.65 | 15.00 |
| 25 INH C11 | −23.40 | −15.62 | 55.77 | 15.00 |
| 25 INH C12 | −22.32 | −15.20 | 54.77 | 15.00 |
| 25 INH C13 | −22.79 | −14.65 | 53.42 | 15.00 |
| 25 INH C14 | −21.66 | −14.80 | 52.41 | 15.00 |
| 25 INH C15 | −24.07 | −15.33 | 52.91 | 15.00 |
| 25 INH C16 | −23.13 | −17.06 | 56.23 | 15.00 |
| 25 INH O17 | −23.79 | −17.98 | 55.74 | 15.00 |
| 25 INH N18 | −22.17 | −17.29 | 57.12 | 15.00 |
| 25 INH C19 | −21.81 | −18.63 | 57.60 | 15.00 |
| 25 INH N20 | −23.72 | −14.55 | 56.73 | 15.00 |
| 25 INH C21 | −21.96 | −18.81 | 59.10 | 15.00 |
| 25 INH O22 | −21.89 | −17.72 | 59.66 | 15.00 |
| 25 INH C23 | −19.42 | −29.07 | 54.27 | 15.00 |
| 25 INH C24 | −20.11 | −28.05 | 54.90 | 15.00 |
| 25 INH C25 | −19.45 | −26.88 | 55.23 | 15.00 |
| 25 INH C26 | −18.09 | −26.70 | 54.93 | 15.00 |
| 25 INH C27 | −17.41 | −27.74 | 54.30 | 15.00 |
| 25 INH C28 | −18.06 | −28.92 | 53.96 | 15.00 |
| 25 INH C29 | −17.39 | −25.41 | 55.26 | 15.00 |
| 25 INH O30 | −18.05 | −24.15 | 55.06 | 15.00 |
| 25 INH C31 | −19.20 | −23.80 | 55.81 | 15.00 |
| 25 INH O32 | −20.33 | −23.84 | 55.32 | 15.00 |
| 25 INH C33 | −20.15 | −23.05 | 57.92 | 15.00 |
| 25 INH C34 | −20.47 | −24.13 | 58.95 | 15.00 |
| 25 INH C35 | −21.49 | −25.18 | 58.56 | 15.00 |
| 25 INH C36 | −22.36 | −24.69 | 57.40 | 15.00 |
| 25 INH C37 | −20.73 | −26.42 | 58.16 | 15.00 |
| 25 INH C38 | −19.89 | −21.74 | 58.63 | 15.00 |
| 25 INH O39 | −18.75 | −21.39 | 58.90 | 15.00 |
| 25 INH N40 | −20.97 | −21.01 | 58.95 | 15.00 |
| 25 INH C41 | −20.91 | −19.72 | 59.64 | 15.00 |
| 25 INH N42 | −19.01 | −23.44 | 57.08 | 15.00 |
| 26 TRP N | −22.84 | −20.77 | 62.76 | 15.00 |
| 26 TRP CA | −22.76 | −22.11 | 63.33 | 15.00 |
| 26 TRP CB | −21.47 | −22.81 | 62.88 | 15.00 |
| 26 TRP CG | −20.24 | −22.16 | 63.40 | 15.00 |
| 26 TRF CD2 | −19.56 | −22.46 | 64.62 | 15.00 |
| 26 TRP CE2 | −18.51 | −21.53 | 64.75 | 15.00 |
| 26 TRP CE3 | −19.74 | −23.42 | 65.63 | 15.00 |
| 26 TRP CD1 | −19.59 | −21.11 | 62.84 | 15.00 |
| 26 TRP NE1 | −18.55 | −20.72 | 63.65 | 15.00 |
| 26 TRP CZ2 | −17.64 | −21.52 | 65.85 | 15.00 |
| 26 TRP CZ3 | −18.88 | −23.42 | 66.72 | 15.00 |
| 26 TRP CH2 | −17.84 | −22.47 | 66.82 | 15.00 |
| 26 TRP C | −22.82 | −22.02 | 64.87 | 15.00 |
| 26 TRP O | −23.31 | −22.93 | 65.53 | 15.00 |
| 27 ALA N | −22.34 | −20.92 | 65.44 | 15.00 |
| 27 ALA CA | −22.36 | −20.73 | 66.89 | 15.00 |
| 27 ALA CB | −21.43 | −19.61 | 67.30 | 15.00 |
| 27 ALA C | −23.79 | −20.43 | 67.32 | 15.00 |
| 27 ALA O | −24.29 | −21.00 | 68.29 | 15.00 |
| 28 PHE N | −24.48 | −19.57 | 66.58 | 15.00 |
| 28 PHE CA | −25.85 | −19.25 | 66.92 | 15.00 |
| 28 PHE CB | −26.38 | −18.14 | 66.01 | 15.00 |
| 28 PHE CG | −25.87 | −16.78 | 66.39 | 15.00 |
| 28 PHE CD1 | −24.63 | −16.33 | 65.94 | 15.00 |
| 28 PHE CD2 | −26.61 | −15.96 | 67.22 | 15.00 |
| 28 PHE CE1 | −24.14 | −15.10 | 66.33 | 15.00 |
| 28 PHE CE2 | −26.11 | −14.72 | 67.62 | 15.00 |
| 28 PHE CZ | −24.88 | −14.29 | 67.17 | 15.00 |
| 28 PHE C | −26.73 | −20.49 | 66.83 | 15.00 |
| 28 PHE O | −27.48 | −20.80 | 67.75 | 15.00 |
| 29 SER N | −26.60 | −21.24 | 65.74 | 15.00 |
| 29 SER CA | −27.36 | −22.46 | 65.54 | 15.00 |
| 29 SER CB | −26.91 | −23.14 | 64.25 | 15.00 |
| 29 SER OG | −27.55 | −24.39 | 64.08 | 15.00 |
| 29 SER C | −27.17 | −23.43 | 66.70 | 15.00 |
| 29 SER O | −28.14 | −23.89 | 67.30 | 15.00 |
| 30 SER N | −25.91 | −23.75 | 67.01 | 15.00 |
| 30 SER CA | −25.57 | −24.67 | 68.09 | 15.00 |
| 30 SER CB | −24.06 | −24.68 | 68.33 | 15.00 |
| 30 SER OG | −23.33 | −25.06 | 67.19 | 15.00 |
| 30 SER C | −26.28 | −24.24 | 69.38 | 15.00 |
| 30 SER O | −27.01 | −25.02 | 70.01 | 15.00 |
| 31 VAL N | −26.09 | −22.97 | 69.73 | 15.00 |
| 31 VAL CA | −26.67 | −22.39 | 70.93 | 15.00 |
| 31 VAL CB | −26.13 | −20.95 | 71.14 | 15.00 |
| 31 VAL CG1 | −27.14 | −20.07 | 71.79 | 15.00 |
| 31 VAL CG2 | −24.87 | −20.99 | 71.99 | 15.00 |
| 31 VAL C | −28.21 | −22.46 | 70.89 | 15.00 |
| 31 VAL O | −28.86 | −22.68 | 71.92 | 15.00 |
| 32 GLY N | −28.79 | −22.36 | 69.70 | 15.00 |
| 32 GLY CA | −30.23 | −22.42 | 69.58 | 15.00 |
| 32 GLY C | −30.77 | −23.77 | 69.99 | 15.00 |
| 32 GLY O | −31.84 | −23.88 | 70.58 | 15.00 |
| 33 ALA N | −30.04 | −24.83 | 69.66 | 15.00 |
| 33 ALA CA | −30.46 | −26.18 | 70.01 | 15.00 |
| 33 ALA CB | −29.67 | −27.20 | 69.23 | 15.00 |
| 33 ALA C | −30.27 | −26.36 | 71.50 | 15.00 |
| 33 ALA O | −31.10 | −26.99 | 72.17 | 15.00 |
| 34 LEU N | −29.20 | −25.80 | 72.04 | 15.00 |
| 34 LEU CA | −28.91 | −25.88 | 73.47 | 15.00 |
| 34 LEU CB | −27.55 | −25.25 | 73.77 | 15.00 |
| 34 LEU CG | −26.35 | −26.14 | 73.47 | 15.00 |
| 34 LEU CD1 | −25.07 | −25.37 | 73.60 | 15.00 |
| 34 LEU CD2 | −26.34 | −27.30 | 74.42 | 15.00 |
| 34 LEU C | −30.00 | −25.20 | 74.29 | 15.00 |
| 34 LEU O | −30.37 | −25.66 | 75.38 | 15.00 |
| 35 GLU N | −30.56 | −24.10 | 73.78 | 15.00 |
| 35 GLU CA | −31.61 | −23.39 | 74.49 | 15.00 |
| 35 GLU CB | −31.82 | −22.00 | 73.88 | 15.00 |
| 35 GLU CG | −30.62 | −21.08 | 74.05 | 15.00 |
| 35 GLU CD | −30.60 | −19.92 | 73.08 | 15.00 |
| 35 GLU OE1 | −31.49 | −19.83 | 72.21 | 15.00 |
| 35 GLU OE2 | −29.66 | −19.10 | 73.17 | 15.00 |
| 35 GLU C | −32.91 | −24.18 | 74.47 | 15.00 |
| 35 GLU O | −33.62 | −24.26 | 75.47 | 15.00 |
| 36 GLY N | −33.21 | −24.80 | 73.33 | 15.00 |
| 36 GLY CA | −34.43 | −25.58 | 73.22 | 15.00 |
| 36 GLY C | −34.49 | −26.72 | 74.22 | 15.00 |
| 36 GLY O | −35.52 | −26.94 | 74.86 | 15.00 |
| 37 GLN N | −33.38 | −27.43 | 74.36 | 15.00 |
| 37 GLN CA | −33.27 | −28.55 | 75.29 | 15.00 |
| 37 GLN CB | −31.99 | −29.34 | 75.02 | 15.00 |
| 37 GLN CG | −32.04 | −30.08 | 73.69 | 15.00 |
| 37 GLN CD | −33.27 | −30.95 | 73.58 | 15.00 |
| 37 GLN OE1 | −33.55 | −31.77 | 74.45 | 15.00 |
| 37 GLN NE2 | −34.04 | −30.77 | 72.52 | 15.00 |
| 37 GLN C | −33.31 | −28.07 | 76.74 | 15.00 |
| 37 GLN O | −33.94 | −28.69 | 77.60 | 15.00 |
| 38 LEU N | −32.66 | −26.94 | 77.00 | 15.00 |
| 38 LEU CA | −32.66 | −26.34 | 78.34 | 15.00 |

TABLE III-continued

Table of the orthogonal three dimensional coordinates in Ångstroms and B factors (Å²) for the cathepsin K complex with inhibitor bis-(cbz-leucinyl)-1,3-diamino-propan-2-one.

| Residue Atom | X | Y | Z | B |
|---|---|---|---|---|
| 38 LEU CB | −31.99 | −24.97 | 78.30 | 15.00 |
| 38 LEU CG | −31.70 | −24.28 | 79.63 | 15.00 |
| 38 LEU CD1 | −30.58 | −25.02 | 80.35 | 15.00 |
| 38 LEU CD2 | −31.32 | −22.84 | 79.40 | 15.00 |
| 38 LEU C | −34.11 | −26.19 | 78.79 | 15.00 |
| 38 LEU O | −34.52 | −26.71 | 79.82 | 15.00 |
| 39 LYS N | −34.91 | −25.51 | 77.97 | 15.00 |
| 39 LYS CA | −36.31 | −25.29 | 78.27 | 15.00 |
| 39 LYS CB | −36.98 | −24.53 | 77.12 | 15.00 |
| 39 LYS CG | −38.48 | −24.37 | 77.25 | 15.00 |
| 39 LYS CD | −38.89 | −23.62 | 78.49 | 15.00 |
| 39 LYS CE | −40.38 | −23.44 | 78.51 | 15.00 |
| 39 LYS NZ | −40.84 | −22.84 | 79.78 | 15.00 |
| 39 LYS C | −37.01 | −26.62 | 78.50 | 15.00 |
| 39 LYS O | −37.78 | −26.76 | 79.44 | 15.00 |
| 40 LYS N | −36.70 | −27.62 | 77.68 | 15.00 |
| 40 LYS CA | −37.32 | −28.93 | 77.83 | 15.00 |
| 40 LYS CB | −36.78 | −29.89 | 76.76 | 15.00 |
| 40 LYS CG | −37.56 | −31.18 | 76.57 | 15.00 |
| 40 LYS CD | −36.89 | −32.09 | 75.54 | 15.00 |
| 40 LYS CE | −37.73 | −33.32 | 75.24 | 15.00 |
| 40 LYS NZ | −39.05 | −32.97 | 74.63 | 15.00 |
| 40 LYS C | −37.07 | −29.52 | 79.22 | 15.00 |
| 40 LYS O | −38.00 | −29.92 | 79.93 | 15.00 |
| 41 LYS N | −35.80 | −29.51 | 79.64 | 15.00 |
| 41 LYS CA | −35.41 | −30.07 | 80.92 | 15.00 |
| 41 LYS CB | −33.92 | −30.40 | 80.91 | 15.00 |
| 41 LYS CG | −33.48 | −31.19 | 79.67 | 15.00 |
| 41 LYS CD | −34.36 | −32.41 | 79.42 | 15.00 |
| 41 LYS CE | −34.05 | −33.08 | 78.08 | 15.00 |
| 41 LYS NZ | −34.99 | −34.21 | 77.78 | 15.00 |
| 41 LYS C | −35.76 | −29.21 | 82.13 | 15.00 |
| 41 LYS O | −36.58 | −29.61 | 82.96 | 15.00 |
| 42 THR N | −35.17 | −28.02 | 82.25 | 15.00 |
| 42 THR CA | −35.41 | −27.14 | 83.39 | 15.00 |
| 42 THR CB | −34.27 | −26.12 | 83.52 | 15.00 |
| 42 THR OG1 | −34.29 | −25.25 | 82.38 | 15.00 |
| 42 THR CG2 | −32.94 | −26.82 | 83.57 | 15.00 |
| 42 THR C | −36.72 | −26.37 | 83.39 | 15.00 |
| 42 THR O | −37.10 | −25.79 | 84.41 | 15.00 |
| 43 GLY N | −37.40 | −26.33 | 82.25 | 15.00 |
| 43 GLY CA | −38.65 | −25.60 | 82.15 | 15.00 |
| 43 GLY C | −38.47 | −24.08 | 82.03 | 15.00 |
| 43 GLY O | −39.43 | −23.33 | 81.98 | 15.00 |
| 44 LYS N | −37.24 | −23.57 | 82.01 | 15.00 |
| 44 LYS CA | −37.05 | −22.13 | 81.89 | 15.00 |
| 44 LYS CB | −36.55 | −21.53 | 83.20 | 15.00 |
| 44 LYS CG | −37.49 | −21.67 | 84.38 | 15.00 |
| 44 LYS CD | −36.91 | −20.99 | 85.61 | 15.00 |
| 44 LYS CE | −35.68 | −21.70 | 86.11 | 15.00 |
| 44 LYS NZ | −36.03 | −23.03 | 86.65 | 15.00 |
| 44 LYS C | −36.05 | −21.83 | 80.80 | 15.00 |
| 44 LYS O | −35.00 | −22.48 | 80.70 | 15.00 |
| 45 LEU N | −36.39 | −20.84 | 79.97 | 15.00 |
| 45 LEU CA | −35.55 | −20.41 | 78.86 | 15.00 |
| 45 LEU CB | −36.43 | −19.88 | 77.73 | 15.00 |
| 45 LEU CG | −35.82 | −19.71 | 76.33 | 15.00 |
| 45 LEU CD1 | −35.62 | −21.08 | 75.69 | 15.00 |
| 45 LEU CD2 | −36.74 | −18.87 | 75.48 | 15.00 |
| 45 LEU C | −34.58 | −19.34 | 79.32 | 15.00 |
| 45 LEU O | −34.92 | −18.47 | 80.13 | 15.00 |
| 46 LEU N | −33.36 | −19.39 | 78.80 | 15.00 |
| 46 LEU CA | −32.32 | −18.44 | 79.15 | 15.00 |
| 46 LEU CB | −31.47 | −19.02 | 80.28 | 15.00 |
| 46 LEU CG | −30.58 | −18.14 | 81.17 | 15.00 |
| 46 LEU CD1 | −29.23 | −17.96 | 80.55 | 15.00 |
| 46 LEU CD2 | −31.23 | −16.81 | 81.44 | 15.00 |
| 46 LEU C | −31.51 | −18.26 | 77.86 | 15.00 |
| 46 LEU O | −31.48 | −19.15 | 77.01 | 15.00 |
| 47 ASN N | −30.92 | −17.08 | 77.67 | 15.00 |
| 47 ASN CA | −30.14 | −16.82 | 76.47 | 15.00 |
| 47 ASN CB | −30.22 | −15.35 | 76.06 | 15.00 |
| 47 ASN CG | −31.33 | −15.09 | 76.06 | 15.00 |
| 47 ASN OD1 | −32.44 | −14.74 | 75.43 | 15.00 |
| 47 ASN ND2 | −31.04 | −15.28 | 73.78 | 15.00 |
| 47 ASN C | −28.69 | −17.26 | 76.64 | 15.00 |
| 47 ASN O | −27.98 | −16.75 | 77.50 | 15.00 |
| 48 LEU N | −28.27 | −18.21 | 75.82 | 15.00 |
| 48 LEU CA | −26.92 | −18.73 | 75.89 | 15.00 |
| 48 LEU CB | −26.89 | −20.21 | 75.51 | 15.00 |
| 48 LEU CG | −27.53 | −21.15 | 76.55 | 15.00 |
| 48 LEU CD1 | −27.34 | −22.60 | 76.17 | 15.00 |
| 48 LEU CD2 | −26.88 | −20.92 | 77.88 | 15.00 |
| 48 LEU C | −25.93 | −17.89 | 75.07 | 15.00 |
| 48 LEU O | −26.32 | −17.11 | 74.20 | 15.00 |
| 49 SER N | −24.64 | −18.08 | 75.35 | 15.00 |
| 49 SER CA | −23.56 | −17.34 | 74.70 | 15.00 |
| 49 SER CB | −22.47 | −17.07 | 75.75 | 15.00 |
| 49 SER OG | −21.31 | −16.50 | 75.18 | 15.00 |
| 49 SER C | −22.92 | −17.91 | 73.43 | 15.00 |
| 49 SER O | −22.16 | −18.88 | 73.48 | 15.00 |
| 50 PRO N | −23.22 | −17.30 | 72.26 | 15.00 |
| 50 PRO CD | −24.28 | −16.31 | 72.02 | 15.00 |
| 50 PRO CA | −22.65 | −17.75 | 70.98 | 15.00 |
| 50 PRO CB | −23.42 | −16.92 | 69.95 | 15.00 |
| 50 PRO CG | −24.70 | −16.64 | 70.62 | 15.00 |
| 50 PRO C | −21.16 | −17.38 | 70.95 | 15.00 |
| 50 PRO O | −20.34 | −18.08 | 70.35 | 15.00 |
| 51 GLN N | −20.81 | −16.27 | 71.59 | 15.00 |
| 51 GLN CA | −19.43 | −15.80 | 71.65 | 15.00 |
| 51 GLN CB | −19.35 | −14.43 | 72.34 | 15.00 |
| 51 GLN CG | −17.95 | −13.79 | 72.39 | 15.00 |
| 51 GLN CD | −17.46 | −13.23 | 71.05 | 15.00 |
| 51 GLN OE1 | −18.21 | −12.62 | 70.30 | 15.00 |
| 51 GLN NE2 | −16.19 | −13.42 | 70.77 | 15.00 |
| 51 GLN C | −18.58 | −16.83 | 72.38 | 15.00 |
| 51 GLN O | −17.46 | −17.15 | 71.96 | 15.00 |
| 52 ASN N | −19.13 | −17.42 | 73.44 | 15.00 |
| 52 ASN CA | −18.41 | −18.42 | 74.24 | 15.00 |
| 52 ASN CB | −19.31 | −18.96 | 75.35 | 15.00 |
| 52 ASN CG | −18.59 | −19.90 | 76.31 | 15.00 |
| 52 ASN OD1 | −19.23 | −20.62 | 77.07 | 15.00 |
| 52 ASN ND2 | −17.27 | −19.89 | 76.28 | 15.00 |
| 52 ASN C | −17.91 | −19.55 | 73.35 | 15.00 |
| 52 ASN O | −16.84 | −20.12 | 73.59 | 15.00 |
| 53 LEU N | −18.67 | −19.86 | 72.31 | 15.00 |
| 53 LEU CA | −18.33 | −20.90 | 71.35 | 15.00 |
| 53 LEU CB | −19.58 | −21.37 | 70.60 | 15.00 |
| 53 LEU CG | −20.63 | −22.10 | 71.42 | 15.00 |
| 53 LEU CD1 | −21.81 | −22.44 | 70.55 | 15.00 |
| 53 LEU CD2 | −20.01 | −23.36 | 72.01 | 15.00 |
| 53 LEU C | −17.31 | −20.42 | 70.34 | 15.00 |
| 53 LEU O | −16.37 | −21.13 | 69.99 | 15.00 |
| 54 VAL N | −17.52 | −19.19 | 69.87 | 15.00 |
| 54 VAL CA | −16.66 | −18.57 | 68.87 | 15.00 |
| 54 VAL CB | −17.16 | −17.14 | 68.56 | 15.00 |
| 54 VAL CG1 | −16.22 | −16.45 | 67.59 | 15.00 |
| 54 VAL CG2 | −18.57 | −17.20 | 68.00 | 15.00 |
| 54 VAL C | −15.20 | −18.52 | 69.30 | 15.00 |
| 54 VAL O | −14.31 | −18.88 | 68.53 | 15.00 |
| 55 ASP N | −14.96 | −18.09 | 70.54 | 15.00 |
| 55 ASP CA | −13.61 | −17.98 | 71.07 | 15.00 |
| 55 ASP CB | −13.58 | −16.93 | 72.18 | 15.00 |
| 55 ASP CG | −14.14 | −15.59 | 71.76 | 15.00 |
| 55 ASP OD1 | −14.26 | −15.33 | 70.55 | 15.00 |
| 55 ASP OD2 | −14.45 | −14.78 | 72.67 | 15.00 |
| 55 ASP C | −13.02 | −19.26 | 71.65 | 15.00 |
| 55 ASP O | −11.80 | −19.39 | 71.72 | 15.00 |
| 56 CYS N | −13.86 | −20.19 | 72.09 | 15.00 |
| 56 CYS CA | −13.36 | −21.41 | 72.73 | 15.00 |
| 56 CYS C | −13.29 | −22.71 | 71.94 | 15.00 |
| 56 CYS O | −12.43 | −23.55 | 72.20 | 15.00 |
| 56 CYS CB | −14.10 | −21.61 | 74.04 | 15.00 |
| 56 CYS SG | −14.21 | −20.10 | 75.06 | 15.00 |

TABLE III-continued

Table of the orthogonal three dimensional coordinates in Ångstroms and B factors (Å²) for the cathepsin K complex with inhibitor bis-(cbz-leucinyl)-1,3-diamino-propan-2-one.

| Residue Atom | X | Y | Z | B |
|---|---|---|---|---|
| 57 VAL N | −14.17 | −22.93 | 70.96 | 15.00 |
| 57 VAL CA | −14.13 | −24.17 | 70.18 | 15.00 |
| 57 VAL CB | −15.44 | −24.43 | 69.39 | 15.00 |
| 57 VAL CG1 | −15.38 | −25.80 | 68.73 | 15.00 |
| 57 VAL CG2 | −16.63 | −24.33 | 70.30 | 15.00 |
| 57 VAL C | −12.97 | −24.10 | 69.19 | 15.00 |
| 57 VAL O | −13.17 | −23.81 | 68.02 | 15.00 |
| 58 SER N | −11.76 | −24.40 | 69.66 | 15.00 |
| 58 SER CA | −10.57 | −24.35 | 68.82 | 15.00 |
| 58 SER CB | −9.34 | −24.73 | 69.63 | 15.00 |
| 58 SER OG | −9.44 | −26.08 | 70.07 | 15.00 |
| 58 SER C | −10.65 | −25.25 | 67.61 | 15.00 |
| 58 SER O | −9.90 | −25.09 | 66.65 | 15.00 |
| 59 GLU N | −11.53 | −26.25 | 67.65 | 15.00 |
| 59 GLU CA | −11.69 | −27.16 | 66.53 | 15.00 |
| 59 GLU CB | −12.57 | −28.35 | 66.92 | 15.00 |
| 59 GLU CG | −12.00 | −29.23 | 68.00 | 15.00 |
| 59 GLU CD | −11.98 | −28.56 | 69.36 | 15.00 |
| 59 GLU OE1 | −13.00 | −27.95 | 69.73 | 15.00 |
| 59 GLU OE2 | −10.95 | −28.66 | 70.06 | 15.00 |
| 59 GLU C | −12.30 | −26.41 | 65.35 | 15.00 |
| 59 GLU O | −12.28 | −26.89 | 64.22 | 15.00 |
| 60 ASN N | −12.89 | −25.26 | 65.63 | 15.00 |
| 60 ASN CA | −13.53 | −24.45 | 64.61 | 15.00 |
| 60 ASN CB | −14.95 | −24.06 | 65.03 | 15.00 |
| 60 ASN CG | −15.92 | −25.21 | 64.90 | 15.00 |
| 60 ASN OD1 | −17.09 | −25.08 | 65.23 | 15.00 |
| 60 ASN ND2 | −15.45 | −26.34 | 64.38 | 15.00 |
| 60 ASN C | −12.71 | −23.22 | 64.26 | 15.00 |
| 60 ASN O | −11.73 | −22.92 | 64.93 | 15.00 |
| 61 ASP N | −13.13 | −22.50 | 63.23 | 15.00 |
| 61 ASP CA | −12.41 | −21.34 | 62.75 | 15.00 |
| 61 ASP CB | −12.53 | −21.28 | 61.22 | 15.00 |
| 61 ASP CG | −11.20 | −21.01 | 60.53 | 15.00 |
| 61 ASP OD1 | −10.34 | −20.32 | 61.12 | 15.00 |
| 61 ASP OD2 | −11.03 | −21.49 | 59.40 | 15.00 |
| 61 ASP C | −12.80 | −19.99 | 63.35 | 15.00 |
| 61 ASP O | −12.23 | −18.95 | 62.99 | 15.00 |
| 62 GLY N | −13.75 | −19.97 | 64.28 | 15.00 |
| 62 GLY CA | −14.17 | −18.71 | 64.87 | 15.00 |
| 62 GLY C | −15.12 | −18.03 | 63.91 | 15.00 |
| 62 GLY O | −16.13 | −18.61 | 63.51 | 15.00 |
| 63 CYS N | −14.80 | −16.81 | 63.48 | 15.00 |
| 63 CYS CA | −15.65 | −16.09 | 62.52 | 15.00 |
| 63 CYS C | −15.45 | −16.63 | 61.12 | 15.00 |
| 63 CYS O | −16.10 | −16.16 | 60.18 | 15.00 |
| 63 CYS CB | −15.34 | −14.59 | 62.52 | 15.00 |
| 63 CYS SG | −15.84 | −13.72 | 64.03 | 15.00 |
| 64 GLY N | −14.52 | −17.56 | 60.95 | 15.00 |
| 64 GLY CA | −14.26 | −18.14 | 59.65 | 15.00 |
| 64 GLY C | −15.17 | −19.33 | 59.40 | 15.00 |
| 64 GLY O | −15.50 | −19.67 | 58.26 | 15.00 |
| 65 GLY N | −15.60 | −19.99 | 60.48 | 15.00 |
| 65 GLY CA | −16.47 | −21.14 | 60.33 | 15.00 |
| 65 GLY C | −16.39 | −22.20 | 61.41 | 15.00 |
| 65 GLY O | −15.56 | −22.15 | 62.31 | 15.00 |
| 66 GLY N | −17.28 | −23.18 | 61.30 | 15.00 |
| 66 GLY CA | −17.31 | −24.25 | 62.27 | 15.00 |
| 66 GLY C | −18.50 | −25.16 | 62.14 | 15.00 |
| 66 GLY O | −19.48 | −24.83 | 61.48 | 15.00 |
| 67 TYR N | −18.43 | −26.32 | 62.78 | 15.00 |
| 67 TYR CA | −19.51 | −27.30 | 62.74 | 15.00 |
| 67 TYR CB | −18.97 | −28.70 | 62.45 | 15.00 |
| 67 TYR CG | −18.28 | −28.86 | 61.12 | 15.00 |
| 67 TYR CD1 | −19.02 | −29.00 | 59.94 | 15.00 |
| 67 TYR CE1 | −18.40 | −29.23 | 58.72 | 15.00 |
| 67 TYR CD2 | −16.90 | −28.94 | 61.04 | 15.00 |
| 67 TYR CE2 | −16.26 | −29.16 | 59.82 | 15.00 |
| 67 TYR CZ | −17.02 | −29.31 | 58.67 | 15.00 |
| 67 TYR OH | −16.39 | −29.51 | 57.46 | 15.00 |
| 67 TYR C | −20.17 | −27.29 | 64.10 | 15.00 |
| 67 TYR O | −19.48 | −27.14 | 65.12 | 15.00 |
| 68 MET N | −21.48 | −27.47 | 64.12 | 15.00 |
| 68 MET CA | −22.26 | −27.48 | 65.36 | 15.00 |
| 68 MET CB | −23.76 | −27.60 | 65.07 | 15.00 |
| 68 MET CG | −24.38 | −26.42 | 64.29 | 15.00 |
| 68 MET SD | −23.94 | −26.32 | 62.55 | 15.00 |
| 68 MET CE | −25.16 | −27.35 | 61.83 | 15.00 |
| 68 MET C | −21.81 | −28.62 | 66.27 | 15.00 |
| 68 MET O | −21.63 | −28.43 | 67.47 | 15.00 |
| 69 THR N | −21.58 | −29.79 | 65.68 | 15.00 |
| 69 THR CA | −21.15 | −30.96 | 66.43 | 15.00 |
| 69 THR CB | −20.90 | −32.18 | 65.50 | 15.00 |
| 69 THR OG1 | −20.04 | −31.81 | 64.42 | 15.00 |
| 69 THR CG2 | −22.21 | −32.71 | 64.94 | 15.00 |
| 69 THR C | −19.90 | −30.65 | 67.25 | 15.00 |
| 69 THR O | −19.80 | −31.06 | 68.41 | 15.00 |
| 70 ASN N | −18.98 | −29.86 | 66.69 | 15.00 |
| 70 ASN CA | −17.74 | −29.49 | 67.37 | 15.00 |
| 70 ASN CB | −16.79 | −28.76 | 66.42 | 15.00 |
| 70 ASN CG | −16.05 | −29.71 | 65.50 | 15.00 |
| 70 ASN OD1 | −14.84 | −29.64 | 65.39 | 15.00 |
| 70 ASN ND2 | −16.78 | −30.58 | 64.83 | 15.00 |
| 70 ASN C | −18.01 | −28.62 | 68.59 | 15.00 |
| 70 ASN O | −17.32 | −28.74 | 69.60 | 15.00 |
| 71 ALA N | −19.03 | −27.77 | 68.48 | 15.00 |
| 71 ALA CA | −19.43 | −26.88 | 69.56 | 15.00 |
| 71 ALA CB | −20.37 | −25.81 | 69.04 | 15.00 |
| 71 ALA C | −20.12 | −27.68 | 70.67 | 15.00 |
| 71 ALA O | −20.03 | −27.32 | 71.84 | 15.00 |
| 72 PHE N | −20.85 | −28.72 | 70.28 | 15.00 |
| 72 PHE CA | −21.54 | −29.59 | 71.22 | 15.00 |
| 72 PHE CB | −22.36 | −30.65 | 70.47 | 15.00 |
| 72 PHE CG | −23.54 | −30.11 | 69.74 | 15.00 |
| 72 PHE CD1 | −24.28 | −29.06 | 70.24 | 15.00 |
| 72 PHE CD2 | −23.91 | −30.66 | 68.53 | 15.00 |
| 72 PHE CE1 | −25.36 | −28.56 | 69.55 | 15.00 |
| 72 PHE CE2 | −25.00 | −30.17 | 67.83 | 15.00 |
| 72 PHE CZ | −25.72 | −29.12 | 68.34 | 15.00 |
| 72 PHE C | −20.46 | −30.29 | 72.05 | 15.00 |
| 72 PHE O | −20.43 | −30.18 | 73.28 | 15.00 |
| 73 GLN N | −19.58 | −30.98 | 71.34 | 15.00 |
| 73 GLN CA | −18.47 | −31.71 | 71.92 | 15.00 |
| 73 GLN CB | −17.53 | −32.13 | 70.78 | 15.00 |
| 73 GLN CG | −16.60 | −33.30 | 71.06 | 15.00 |
| 73 GLN CD | −17.31 | −34.63 | 71.03 | 15.00 |
| 73 GLN OE1 | −17.80 | −35.13 | 72.06 | 15.00 |
| 73 GLN NE2 | −17.35 | −35.25 | 69.85 | 15.00 |
| 73 GLN C | −17.74 | −30.81 | 72.93 | 15.00 |
| 73 GLN O | −17.27 | −31.26 | 73.97 | 15.00 |
| 74 TYR N | −17.66 | −29.51 | 72.63 | 15.00 |
| 74 TYR CA | −17.00 | −28.57 | 73.51 | 15.00 |
| 74 TYR CB | −16.75 | −27.21 | 72.81 | 15.00 |
| 74 TYR CG | −16.41 | −26.08 | 73.77 | 15.00 |
| 74 TYR CD1 | −15.19 | −26.05 | 74.43 | 15.00 |
| 74 TYR CE1 | −14.91 | −25.06 | 75.37 | 15.00 |
| 74 TYR CD2 | −17.34 | −25.09 | 74.06 | 15.00 |
| 74 TYR CE2 | −17.07 | −24.10 | 75.00 | 15.00 |
| 74 TYR CZ | −15.86 | −24.09 | 75.66 | 15.00 |
| 74 TYR OH | −15.60 | −23.15 | 76.63 | 15.00 |
| 74 TYR C | −17.75 | −28.36 | 74.82 | 15.00 |
| 74 TYR O | −17.14 | −28.37 | 75.89 | 15.00 |
| 75 VAL N | −19.07 | −28.16 | 74.78 | 15.00 |
| 75 VAL CA | −19.85 | −27.94 | 76.02 | 15.00 |
| 75 VAL CB | −21.30 | −27.45 | 75.73 | 15.00 |
| 75 VAL CG1 | −22.06 | −27.23 | 77.04 | 15.00 |
| 75 VAL CG2 | −21.27 | −26.15 | 74.92 | 15.00 |
| 75 VAL C | −19.87 | −29.20 | 76.91 | 15.00 |
| 75 VAL O | −20.07 | −29.13 | 78.12 | 15.00 |
| 76 GLN N | −19.65 | −30.35 | 76.29 | 15.00 |
| 76 GLN CA | −19.62 | −31.60 | 77.01 | 15.00 |
| 76 GLN CB | −19.93 | −32.73 | 76.04 | 15.00 |
| 76 GLN CG | −20.02 | −34.11 | 76.67 | 15.00 |
| 76 GLN CD | −19.74 | −35.20 | 75.68 | 15.00 |

TABLE III-continued

Table of the orthogonal three dimensional coordinates in Ångstroms and B factors (Å²) for the cathepsin K complex with inhibitor bis-(cbz-leucinyl)-1,3-diamino-propan-2-one.

| Residue Atom | X | Y | Z | B |
|---|---|---|---|---|
| 76 GLN OE1 | −20.14 | −35.11 | 74.52 | 15.00 |
| 76 GLN NE2 | −19.01 | −36.22 | 76.11 | 15.00 |
| 76 GLN C | −18.25 | −31.81 | 77.66 | 15.00 |
| 76 GLN O | −18.14 | −32.17 | 78.85 | 15.00 |
| 77 LYS N | −17.18 | −31.59 | 76.89 | 15.00 |
| 77 LYS CA | −15.82 | −31.78 | 77.39 | 15.00 |
| 77 LYS CB | −14.83 | −31.98 | 76.24 | 15.00 |
| 77 LYS CG | −14.56 | −30.75 | 75.41 | 15.00 |
| 77 LYS CD | −13.69 | −31.09 | 74.19 | 15.00 |
| 77 LYS CE | −14.41 | −32.05 | 73.24 | 15.00 |
| 77 LYS NZ | −13.62 | −32.45 | 72.02 | 15.00 |
| 77 LYS C | −15.34 | −30.65 | 78.29 | 15.00 |
| 77 LYS O | −14.37 | −30.81 | 79.01 | 15.00 |
| 78 ASN N | −15.97 | −29.49 | 78.22 | 15.00 |
| 78 ASN CA | −15.60 | −28.37 | 79.07 | 15.00 |
| 78 ASN CB | −15.58 | −27.07 | 78.27 | 15.00 |
| 78 ASN CG | −15.38 | −25.85 | 79.16 | 15.00 |
| 78 ASN OD1 | −14.28 | −25.58 | 79.64 | 15.00 |
| 78 ASN ND2 | −16.45 | −25.11 | 79.37 | 15.00 |
| 78 ASN C | −16.62 | −28.28 | 80.20 | 15.00 |
| 78 ASN O | −16.36 | −27.67 | 81.23 | 15.00 |
| 79 ARG N | −17.77 | −28.91 | 79.97 | 15.00 |
| 79 ARG CA | −18.89 | −28.98 | 80.92 | 15.00 |
| 79 ARG CB | −18.58 | −29.92 | 82.11 | 15.00 |
| 79 ARG CG | −17.47 | −29.49 | 83.06 | 15.00 |
| 79 ARG CD | −16.62 | −30.66 | 83.51 | 15.00 |
| 79 ARG NE | −17.44 | −31.76 | 84.00 | 15.00 |
| 79 ARB CZ | −17.90 | −32.75 | 83.23 | 15.00 |
| 79 ARG NH1 | −17.60 | −32.71 | 81.93 | 15.00 |
| 79 ARG NH2 | −18.73 | −33.66 | 83.74 | 15.00 |
| 79 ARG C | −19.45 | −27.65 | 81.39 | 15.00 |
| 79 ARG O | −19.42 | −27.31 | 82.57 | 15.00 |
| 80 GLY N | −20.00 | −26.92 | 80.44 | 15.00 |
| 80 GLY CA | −20.58 | −25.63 | 80.75 | 15.00 |
| 80 GLY C | −20.41 | −24.62 | 79.63 | 15.00 |
| 80 GLY O | −19.39 | −24.61 | 78.93 | 15.00 |
| 81 ILE N | −21.44 | −23.82 | 79.44 | 15.00 |
| 81 ILE CA | −21.45 | −22.77 | 78.45 | 15.00 |
| 81 ILE CB | −22.27 | −23.14 | 77.21 | 15.00 |
| 81 ILE CG2 | −23.71 | −23.46 | 77.59 | 15.00 |
| 81 ILE CG1 | −22.18 | −22.01 | 76.17 | 15.00 |
| 81 8LE CD1 | −22.74 | −22.34 | 74.79 | 15.00 |
| 81 ILE C | −22.09 | −21.59 | 79.18 | 15.00 |
| 81 ILE O | −23.08 | −21.77 | 79.89 | 15.00 |
| 82 ASP N | −21.48 | −20.42 | 79.06 | 15.00 |
| 82 ASP CA | −21.99 | −19.22 | 79.72 | 15.00 |
| 82 ASP CB | −20.95 | −18.10 | 79.68 | 15.00 |
| 82 ASP CG | −19.75 | −18.37 | 80.56 | 15.00 |
| 82 ASP OD1 | −18.66 | −17.89 | 80.20 | 15.00 |
| 82 ASP OD2 | −19.89 | −19.03 | 81.62 | 15.00 |
| 82 ASP C | −23.27 | −18.70 | 79.09 | 15.00 |
| 82 ASP O | −23.67 | −19.11 | 78.01 | 15.00 |
| 83 SER N | −23.91 | −17.78 | 79.79 | 15.00 |
| 83 SER CA | −25.12 | −17.15 | 79.30 | 15.00 |
| 83 SER CB | −26.03 | −16.79 | 80.46 | 15.00 |
| 83 SER OG | −25.32 | −16.05 | 81.44 | 15.00 |
| 83 SER C | −24.66 | −15.90 | 78.58 | 15.00 |
| 83 SER O | −23.49 | −15.51 | 78.67 | 15.00 |
| 84 GLU N | −25.57 | −15.24 | 77.87 | 15.00 |
| 84 GLU CA | −25.22 | −14.02 | 77.16 | 15.00 |
| 84 GLU CB | −26.40 | −13.50 | 76.35 | 15.00 |
| 84 GLU CG | −26.09 | −12.30 | 76.46 | 15.00 |
| 84 GLU CD | −25.06 | −12.58 | 74.36 | 15.00 |
| 84 GLU OE1 | −25.03 | −13.69 | 73.78 | 15.00 |
| 84 GLU OE2 | −24.28 | −11.66 | 74.06 | 15.00 |
| 84 GLU C | −24.70 | −12.95 | 78.14 | 15.00 |
| 84 GLU O | −23.64 | −12.37 | 77.92 | 15.00 |
| 85 ASP N | −25.41 | −12.69 | 79.23 | 15.00 |
| 85 ASP CA | −24.95 | −11.70 | 80.20 | 15.00 |
| 85 ASP CB | −25.99 | −11.46 | 81.31 | 15.00 |
| 85 ASP CG | −25.59 | −10.32 | 82.30 | 15.00 |
| 85 ASP OD1 | −26.24 | −10.19 | 83.38 | 15.00 |
| 85 ASP OD2 | −24.66 | −9.54 | 82.02 | 15.00 |
| 85 ASP C | −23.63 | −12.15 | 80.82 | 15.00 |
| 85 ASP O | −22.86 | −11.34 | 81.34 | 15.00 |
| 86 ALA N | −23.31 | −13.44 | 80.74 | 15.00 |
| 86 ALA CA | −22.07 | −13.91 | 81.32 | 15.00 |
| 86 ALA CB | −22.24 | −15.30 | 81.86 | 15.00 |
| 86 ALA C | −20.90 | −13.85 | 80.35 | 15.00 |
| 86 ALA O | −19.74 | −13.84 | 80.76 | 15.00 |
| 87 TYR N | −21.19 | −13.82 | 79.05 | 15.00 |
| 87 TYR CA | −20.14 | −13.77 | 78.03 | 15.00 |
| 87 TYR CB | −19.67 | −15.20 | 77.77 | 15.00 |
| 87 TYR CG | −18.31 | −15.36 | 77.13 | 15.00 |
| 87 TYR CD1 | −17.86 | −14.49 | 76.13 | 15.00 |
| 87 TYR CE1 | −16.64 | −14.70 | 75.51 | 15.00 |
| 87 TYR CD2 | −17.49 | −16.43 | 77.48 | 15.00 |
| 87 TYR CE2 | −16.27 | −16.64 | 76.86 | 15.00 |
| 87 TYR CZ | −15.85 | −15.78 | 75.88 | 15.00 |
| 87 TYR OH | −14.65 | −16.03 | 75.26 | 15.00 |
| 87 TYR C | −20.73 | −13.17 | 76.75 | 15.00 |
| 87 TYR O | −20.92 | −13.88 | 76.76 | 15.00 |
| 88 PRO N | −20.99 | −11.84 | 76.74 | 15.00 |
| 88 PRO CD | −20.79 | −10.92 | 77.87 | 15.00 |
| 88 PRO CA | −21.57 | −11.12 | 75.60 | 15.00 |
| 88 PRO CB | −21.52 | −9.66 | 76.07 | 15.00 |
| 88 PRO CG | −21.75 | −9.80 | 77.54 | 15.00 |
| 88 PRO C | −20.91 | −11.29 | 74.24 | 15.00 |
| 88 PRO O | −19.71 | −11.56 | 74.13 | 15.00 |
| 89 TYR N | −21.72 | −11.10 | 73.21 | 15.00 |
| 89 TYR CA | −21.30 | −11.23 | 71.83 | 15.00 |
| 89 TYR CB | −22.51 | −11.59 | 70.96 | 15.00 |
| 89 TYR CG | −22.16 | −12.03 | 69.56 | 15.00 |
| 89 TYR CD1 | −21.27 | −13.09 | 69.35 | 15.00 |
| 89 TYR CE1 | −20.90 | −13.46 | 68.07 | 15.00 |
| 89 TYR CD2 | −22.67 | −11.37 | 68.45 | 15.00 |
| 89 TYR CE2 | −22.31 | −11.74 | 67.17 | 15.00 |
| 89 TYR CZ | −21.42 | −12.78 | 66.98 | 15.00 |
| 89 TYR OH | −21.02 | −13.12 | 65.72 | 15.00 |
| 89 TYR C | −20.67 | −9.90 | 71.38 | 15.00 |
| 89 TYR O | −21.33 | −8.86 | 71.36 | 15.00 |
| 90 VAL N | −19.38 | −9.93 | 71.05 | 15.00 |
| 90 VAL CA | −18.66 | −8.73 | 70.61 | 15.00 |
| 90 VAL CB | −17.25 | −8.65 | 71.22 | 15.00 |
| 90 VAL CG1 | −17.32 | −8.67 | 72.73 | 15.00 |
| 90 VAL CG2 | −16.37 | −9.78 | 70.68 | 15.00 |
| 90 VAL C | −18.54 | −8.62 | 69.11 | 15.00 |
| 90 VAL O | −17.85 | −7.75 | 68.61 | 15.00 |
| 91 GLY N | −19.14 | −9.55 | 68.39 | 15.00 |
| 91 GLY CA | −19.10 | −9.49 | 66.94 | 15.00 |
| 91 GLY C | −17.76 | −9.77 | 66.31 | 15.00 |
| 91 GLY O | −17.52 | −9.39 | 65.15 | 15.00 |
| 92 GLN N | −16.88 | −10.44 | 67.03 | 15.00 |
| 92 GLN CA | −15.56 | −10.77 | 66.50 | 15.00 |
| 92 GLN CB | −14.74 | −9.51 | 66.31 | 15.00 |
| 92 GLN CG | −14.49 | −8.76 | 67.60 | 15.00 |
| 92 GLN CD | −13.93 | −7.40 | 67.35 | 15.00 |
| 92 GLN OE1 | −12.83 | −7.06 | 67.80 | 15.00 |
| 92 GLN NE2 | −14.67 | −6.59 | 66.60 | 15.00 |
| 92 GLN C | −14.81 | −11.73 | 67.41 | 15.00 |
| 92 GLN O | −15.19 | −11.95 | 68.57 | 15.00 |
| 93 GLU N | −13.72 | −12.26 | 66.89 | 15.00 |
| 93 GLU CA | −12.90 | −13.22 | 67.59 | 15.00 |
| 93 GLU CB | −12.01 | −13.95 | 66.59 | 15.00 |
| 93 GLU CG | −12.77 | −14.60 | 65.42 | 15.00 |
| 93 GLU CD | −11.84 | −15.07 | 64.31 | 15.00 |
| 93 GLU OE1 | −10.67 | −15.37 | 64.62 | 15.00 |
| 93 GLU OE2 | −12.27 | −15.13 | 63.13 | 15.00 |
| 93 GLU C | −12.05 | −12.56 | 68.66 | 15.00 |
| 93 GLU O | −11.53 | −11.46 | 68.49 | 15.00 |
| 94 GLU N | −11.92 | −13.25 | 69.78 | 15.00 |
| 94 GLU CA | −11.13 | −12.78 | 70.91 | 15.00 |
| 94 GLU CB | −11.93 | −11.79 | 71.76 | 15.00 |
| 94 GLU CG | −13.39 | −12.15 | 71.95 | 15.00 |

TABLE III-continued

Table of the orthogonal three dimensional coordinates in Ångstroms and B factors (Å²) for the cathepsin K complex with inhibitor bis-(cbz-leucinyl)-1,3-diamino-propan-2-one.

| Residue Atom | X | Y | Z | B |
|---|---|---|---|---|
| 94 GLU CD | −14.00 | −11.50 | 73.18 | 15.00 |
| 94 GLU OE1 | −14.15 | −10.26 | 73.18 | 15.00 |
| 94 GLU OE2 | −14.31 | −12.24 | 74.14 | 15.00 |
| 94 GLU C | −10.73 | −13.98 | 71.74 | 15.00 |
| 94 GLU O | −11.15 | −15.10 | 71.47 | 15.00 |
| 95 SER N | −9.88 | −13.75 | 72.73 | 15.00 |
| 95 SER CA | −9.40 | −14.80 | 73.61 | 15.00 |
| 95 SER CB | −8.39 | −14.21 | 74.60 | 15.00 |
| 95 SER OG | −7.22 | −13.77 | 73.94 | 15.00 |
| 95 SER C | −10.57 | −15.44 | 74.35 | 15.00 |
| 95 SER O | −11.48 | −14.73 | 74.82 | 15.00 |
| 96 CYS N | −10.55 | −16.77 | 74.42 | 15.00 |
| 96 CYS CA | −11.59 | −17.52 | 75.13 | 15.00 |
| 96 CYS C | −11.61 | −17.01 | 76.56 | 15.00 |
| 96 CYS O | −10.57 | −16.90 | 77.21 | 15.00 |
| 96 CYS CB | −11.31 | −19.03 | 75.08 | 15.00 |
| 96 CYS SG | −12.44 | −20.07 | 76.07 | 15.00 |
| 97 MET N | −12.80 | −16.65 | 77.03 | 15.00 |
| 97 MET CA | −12.96 | −16.09 | 78.36 | 15.00 |
| 97 MET CB | −13.24 | −14.58 | 78.26 | 15.00 |
| 97 MET CG | −12.05 | −13.75 | 77.73 | 15.00 |
| 97 MET SD | −12.56 | −12.29 | 76.76 | 15.00 |
| 97 MET CE | −13.48 | −11.34 | 78.03 | 15.00 |
| 97 MET C | −14.07 | −16.78 | 79.14 | 15.00 |
| 97 MET O | −14.87 | −16.11 | 79.82 | 15.00 |
| 98 TYR N | −14.13 | −18.10 | 79.07 | 15.00 |
| 98 TYR CA | −15.15 | −18.84 | 79.78 | 15.00 |
| 98 TYR CB | −15.00 | −20.35 | 79.61 | 15.00 |
| 98 TYR CG | −16.06 | −21.14 | 80.35 | 15.00 |
| 98 TYR CD1 | −17.39 | −21.10 | 79.94 | 15.00 |
| 98 TYR CE1 | −18.38 | −21.80 | 80.65 | 15.00 |
| 98 TYR CD2 | −15.74 | −21.90 | 81.48 | 15.00 |
| 98 TYR CE2 | −16.72 | −22.60 | 82.18 | 15.00 |
| 98 TYR CZ | −18.03 | −22.54 | 81.76 | 15.00 |
| 98 TYR OH | −19.00 | −23.23 | 82.44 | 15.00 |
| 98 TYR C | −15.08 | −18.52 | 81.26 | 15.00 |
| 98 TYR O | −14.04 | −18.68 | 81.89 | 15.00 |
| 99 ASN N | −16.19 | −18.01 | 81.79 | 15.00 |
| 99 ASN CA | −16.31 | −17.67 | 83.19 | 15.00 |
| 99 ASN CB | −16.96 | −16.29 | 83.38 | 15.00 |
| 99 ASN CG | −17.25 | −15.98 | 84.84 | 15.00 |
| 99 ASN OD1 | −16.67 | −16.58 | 85.75 | 15.00 |
| 99 ASN ND2 | −18.19 | −15.06 | 85.07 | 15.00 |
| 99 ASN C | −17.20 | −18.74 | 83.81 | 15.00 |
| 99 ASN O | −18.44 | −18.61 | 83.82 | 15.00 |
| 100 PRO N | −16.59 | −19.79 | 84.39 | 15.00 |
| 100 PRO CD | −15.15 | −19.84 | 84.68 | 15.00 |
| 100 PRO CA | −17.29 | −20.92 | 85.02 | 15.00 |
| 100 PRO CB | −16.19 | −21.58 | 85.86 | 15.00 |
| 100 PRO CG | −15.15 | −20.47 | 86.03 | 15.00 |
| 100 PRO C | −18.50 | −20.55 | 85.87 | 15.00 |
| 100 PRO O | −19.48 | −21.29 | 85.92 | 15.00 |
| 101 THR N | −18.46 | −19.40 | 86.53 | 15.00 |
| 101 THR CA | −19.58 | −19.00 | 87.37 | 15.00 |
| 101 THR CB | −19.22 | −17.77 | 88.22 | 15.00 |
| 101 THR OG1 | −18.93 | −16.65 | 87.36 | 15.00 |
| 101 THR CG2 | −17.99 | −18.06 | 89.08 | 15.00 |
| 101 THR C | −20.81 | −18.70 | 86.52 | 15.00 |
| 101 THR O | −21.94 | −19.07 | 86.88 | 15.00 |
| 102 GLY N | −20.59 | −18.06 | 85.37 | 15.00 |
| 102 GLY CA | −21.68 | −17.73 | 84.47 | 15.00 |
| 102 GLY C | −22.27 | −18.92 | 83.72 | 15.00 |
| 102 GLY O | −23.16 | −18.73 | 82.87 | 15.00 |
| 103 LYS N | −21.80 | −20.14 | 84.00 | 15.00 |
| 103 LYS CA | −22.32 | −21.34 | 83.33 | 15.00 |
| 103 LYS CB | −21.70 | −22.60 | 83.93 | 15.00 |
| 103 LYS CG | −22.23 | −23.88 | 83.33 | 15.00 |
| 103 LYS CD | −21.78 | −25.11 | 84.11 | 15.00 |
| 103 LYS CE | −22.56 | −25.26 | 85.40 | 15.00 |
| 103 LYS NZ | −24.02 | −25.47 | 85.12 | 15.00 |
| 103 LYS C | −23.83 | −21.42 | 83.45 | 15.00 |
| 103 LYS O | −24.39 | −21.26 | 84.53 | 15.00 |
| 104 ALA N | −24.50 | −21.68 | 82.34 | 15.00 |
| 104 ALA CA | −25.96 | −21.77 | 82.34 | 15.00 |
| 104 ALA CB | −26.56 | −20.57 | 81.61 | 15.00 |
| 104 ALA C | −26.48 | −23.97 | 81.73 | 15.00 |
| 104 ALA O | −27.69 | −23.30 | 81.71 | 15.00 |
| 105 ALA N | −25.59 | −23.92 | 81.24 | 15.00 |
| 105 ALA CA | −26.02 | −25.18 | 80.65 | 15.00 |
| 105 ALA CB | −26.71 | −24.94 | 79.31 | 15.00 |
| 105 ALA C | −24.89 | −26.20 | 80.49 | 15.00 |
| 105 ALA O | −23.72 | −25.84 | 80.50 | 15.00 |
| 106 LYS N | −25.28 | −27.46 | 80.37 | 15.00 |
| 106 LYS CA | −24.36 | −28.59 | 80.21 | 15.00 |
| 106 LYS CB | −24.28 | −29.40 | 81.51 | 15.00 |
| 106 LYS CG | −23.38 | −28.89 | 82.62 | 15.00 |
| 106 LYS CD | −23.65 | −29.73 | 83.87 | 15.00 |
| 106 LYS CE | −22.48 | −29.72 | 84.85 | 15.00 |
| 106 LYS NZ | −21.33 | −30.54 | 84.36 | 15.00 |
| 106 LYS C | −24.99 | −29.49 | 79.16 | 15.00 |
| 106 LYS O | −26.18 | −29.32 | 78.83 | 15.00 |
| 107 CYS N | −24.23 | −30.42 | 78.61 | 15.00 |
| 107 CYS CA | −24.77 | −31.37 | 77.64 | 15.00 |
| 107 CYS CB | −24.82 | −30.77 | 76.22 | 15.00 |
| 107 CYS SG | −23.38 | −31.03 | 75.18 | 15.00 |
| 107 CYS C | −23.93 | −32.64 | 77.72 | 15.00 |
| 107 CYS O | −22.76 | −32.59 | 78.10 | 15.00 |
| 108 ARG N | −24.54 | −33.78 | 77.45 | 15.00 |
| 108 ARG CA | −23.86 | −35.07 | 77.52 | 15.00 |
| 108 ARG CB | −24.60 | −35.99 | 78.50 | 15.00 |
| 108 ARG CG | −26.12 | −35.73 | 78.59 | 15.00 |
| 108 ARG CD | −26.86 | −36.86 | 79.28 | 15.00 |
| 108 ARG NE | −26.63 | −38.14 | 78.60 | 15.00 |
| 108 ARG CZ | −27.58 | −38.89 | 78.03 | 15.00 |
| 108 ARG NH1 | −28.85 | −38.51 | 78.05 | 15.00 |
| 108 ARG NH2 | −27.24 | −40.03 | 77.45 | 15.00 |
| 108 ARG C | −23.64 | −35.78 | 76.18 | 15.00 |
| 108 ARG O | −23.84 | −36.99 | 76.06 | 15.00 |
| 109 GLY N | −23.20 | −35.03 | 75.17 | 15.00 |
| 109 GLY CA | −22.97 | −35.63 | 73.87 | 15.00 |
| 109 GLY C | −23.82 | −34.99 | 72.80 | 15.00 |
| 109 GLY O | −24.27 | −33.85 | 72.95 | 15.00 |
| 110 TYR N | −24.09 | −35.72 | 71.72 | 15.00 |
| 110 TYR CA | −24.89 | −35.19 | 70.63 | 15.00 |
| 110 TYR CB | −24.12 | −34.08 | 69.91 | 15.00 |
| 110 TYR CG | −22.86 | −34.56 | 69.20 | 15.00 |
| 110 TYR CD1 | −21.64 | −34.62 | 69.87 | 15.00 |
| 110 TYR CE1 | −20.49 | −35.03 | 69.22 | 15.00 |
| 110 TYR CD2 | −22.90 | −34.93 | 67.85 | 15.00 |
| 110 TYR CE2 | −21.75 | −35.34 | 67.19 | 15.00 |
| 110 TYR CZ | −20.55 | −35.39 | 67.88 | 15.00 |
| 110 TYR OH | −19.39 | −35.77 | 67.23 | 15.00 |
| 110 TYR C | −25.22 | −36.28 | 69.62 | 15.00 |
| 110 TYR O | −24.44 | −37.21 | 69.43 | 15.00 |
| 111 ARG N | −26.34 | −36.11 | 68.92 | 15.00 |
| 111 ARG CA | −26.76 | −37.08 | 67.92 | 15.00 |
| 111 ARG CB | −28.02 | −37.81 | 68.38 | 15.00 |
| 111 ARG CG | −27.81 | −38.84 | 69.48 | 15.00 |
| 111 ARG CD | −28.75 | −40.03 | 69.33 | 15.00 |
| 111 ARG NE | −28.01 | −41.28 | 69.36 | 15.00 |
| 111 ARG CZ | −27.89 | −42.06 | 70.44 | 15.00 |
| 111 ARG NH1 | −27.18 | −43.18 | 70.36 | 15.00 |
| 111 ARG NH2 | −28.50 | −41.73 | 71.58 | 15.00 |
| 111 ARG C | −26.99 | −36.46 | 66.54 | 15.00 |
| 111 ARG O | −27.67 | −35.45 | 66.41 | 15.00 |
| 112 GLU N | −26.41 | −37.06 | 65.50 | 15.00 |
| 112 GLU CA | −26.56 | −36.57 | 64.14 | 15.00 |
| 112 GLU CB | −25.36 | −37.00 | 63.29 | 15.00 |
| 112 GLU CG | −24.03 | −36.42 | 63.76 | 15.00 |
| 112 GLU CD | −23.34 | −35.56 | 62.70 | 15.00 |
| 112 GLU OE1 | −23.95 | −34.57 | 62.22 | 15.00 |
| 112 GLU OE2 | −22.18 | −35.88 | 62.33 | 15.00 |
| 112 GLU C | −27.86 | −37.13 | 63.56 | 15.00 |

TABLE III-continued

Table of the orthogonal three dimensional coordinates in Ångstroms and B factors (Å²) for the cathepsin K complex with inhibitor bis-(cbz-leucinyl)-1,3-diamino-propan-2-one.

| Residue | Atom | X | Y | Z | B |
|---|---|---|---|---|---|
| 112 GLU | O | −28.64 | −37.75 | 64.27 | 15.00 |
| 113 ILE | N | −28.13 | −36.87 | 62.29 | 15.00 |
| 113 ILE | CA | −29.35 | −37.38 | 61.64 | 15.00 |
| 113 ILE | CB | −30.38 | −36.25 | 61.34 | 15.00 |
| 113 ILE | CG2 | −31.67 | −36.83 | 60.78 | 15.00 |
| 113 ILE | CG1 | −30.71 | −35.45 | 62.60 | 15.00 |
| 113 ILE | CD1 | −31.50 | −36.20 | 63.65 | 15.00 |
| 113 ILE | C | −28.85 | −37.98 | 60.33 | 15.00 |
| 113 ILE | O | −27.91 | −37.46 | 59.73 | 15.00 |
| 114 PRO | N | −29.41 | −39.13 | 59.92 | 15.00 |
| 114 PRO | CD | −30.48 | −39.91 | 60.57 | 15.00 |
| 114 PRO | CA | −28.98 | −39.77 | 58.68 | 15.00 |
| 114 PRO | CB | −30.10 | −40.78 | 58.43 | 15.00 |
| 114 PRO | CG | −30.41 | −41.23 | 59.83 | 15.00 |
| 114 PRO | C | −28.87 | −38.79 | 57.54 | 15.00 |
| 114 PRO | O | −29.84 | −38.12 | 57.20 | 15.00 |
| 115 GLU | N | −27.67 | −38.66 | 56.99 | 15.00 |
| 115 GLU | CA | −27.46 | −37.74 | 55.89 | 15.00 |
| 115 GLU | CB | −26.07 | −37.92 | 55.28 | 15.00 |
| 115 GLU | CG | −24.92 | −37.19 | 56.01 | 15.00 |
| 115 GLU | CD | −23.60 | −37.16 | 55.20 | 15.00 |
| 115 GLU | OE1 | −23.65 | −37.20 | 53.94 | 15.00 |
| 115 GLU | OE2 | −22.51 | −37.08 | 55.82 | 15.00 |
| 115 GLU | C | −28.53 | −37.91 | 54.82 | 15.00 |
| 115 GLU | O | −28.70 | −39.00 | 54.27 | 15.00 |
| 116 GLY | N | −29.27 | −36.83 | 54.59 | 15.00 |
| 116 GLY | CA | −30.30 | −36.78 | 53.57 | 15.00 |
| 116 GLY | C | −31.63 | −37.36 | 53.99 | 15.00 |
| 116 GLY | O | −32.46 | −37.66 | 53.13 | 15.00 |
| 117 ASN | N | −31.88 | −37.44 | 55.29 | 15.00 |
| 117 ASN | CA | −33.12 | −38.03 | 55.77 | 15.00 |
| 117 ASN | CB | −32.80 | −39.09 | 56.82 | 15.00 |
| 117 ASN | CG | −33.80 | −40.21 | 56.84 | 15.00 |
| 117 ASN | OD1 | −35.02 | −39.99 | 56.90 | 15.00 |
| 117 ASN | ND2 | −33.31 | −41.44 | 56.76 | 15.00 |
| 117 ASN | C | −34.17 | −37.06 | 56.31 | 15.00 |
| 117 ASN | O | −34.17 | −36.72 | 57.50 | 15.00 |
| 118 GLU | N | −35.12 | −36.66 | 55.48 | 15.00 |
| 118 GLU | CA | −36.15 | −35.72 | 55.91 | 15.00 |
| 118 GLU | CB | −36.86 | −35.08 | 54.72 | 15.00 |
| 118 GLU | CG | −36.09 | −33.98 | 54.02 | 15.00 |
| 118 GLU | CD | −36.99 | −33.14 | 53.15 | 15.00 |
| 118 GLU | OE1 | −36.58 | −32.75 | 52.04 | 15.00 |
| 118 GLU | OE2 | −38.13 | −32.87 | 53.57 | 15.00 |
| 118 GLU | C | −37.18 | −36.33 | 56.83 | 15.00 |
| 118 GLU | O | −37.76 | −35.64 | 57.66 | 15.00 |
| 119 LYS | N | −37.46 | −37.61 | 56.66 | 15.00 |
| 119 LYS | CA | −38.43 | −38.29 | 57.53 | 15.00 |
| 119 LYS | CB | −38.66 | −39.71 | 57.03 | 15.00 |
| 119 LYS | CG | −39.20 | −39.77 | 55.60 | 15.00 |
| 119 LYS | CD | −40.54 | −39.04 | 55.49 | 15.00 |
| 119 LYS | CE | −41.04 | −38.97 | 54.07 | 15.00 |
| 119 LYS | NZ | −40.26 | −38.00 | 53.26 | 15.00 |
| 119 LYS | C | −37.89 | −38.30 | 58.95 | 15.00 |
| 119 LYS | O | −38.55 | −37.86 | 59.89 | 15.00 |
| 120 ALA | N | −36.64 | −38.74 | 59.07 | 15.00 |
| 120 ALA | CA | −35.94 | −38.81 | 60.34 | 15.00 |
| 120 ALA | CB | −34.58 | −39.42 | 60.15 | 15.00 |
| 120 ALA | C | −35.81 | −37.43 | 60.97 | 15.00 |
| 120 ALA | O | −35.88 | −37.28 | 62.19 | 15.00 |
| 121 LEU | N | −35.56 | −36.42 | 60.14 | 15.00 |
| 121 LEU | CA | −35.43 | −35.06 | 60.66 | 15.00 |
| 121 LEU | CB | −34.96 | −34.10 | 59.56 | 15.00 |
| 121 LEU | CG | −34.93 | −32.61 | 59.96 | 15.00 |
| 121 LEU | CD1 | −33.81 | −32.34 | 60.93 | 15.00 |
| 121 LEU | CD2 | −34.78 | −31.76 | 58.72 | 15.00 |
| 121 LEU | C | −36.76 | −34.60 | 61.25 | 15.00 |
| 121 LEU | O | −36.81 | −33.98 | 62.31 | 15.00 |
| 122 LYS | N | −37.86 | −34.91 | 60.57 | 15.00 |
| 122 LYS | CA | −39.17 | −34.53 | 61.06 | 15.00 |
| 122 LYS | CB | −40.26 | −35.04 | 60.11 | 15.00 |
| 122 LYS | CG | −41.65 | −34.70 | 60.59 | 15.00 |
| 122 LYS | CD | −42.73 | −35.28 | 59.72 | 15.00 |
| 122 LYS | CE | −44.10 | −34.79 | 60.19 | 15.00 |
| 122 LYS | NZ | −45.21 | −35.17 | 59.28 | 15.00 |
| 122 LYS | C | −39.36 | −35.15 | 62.43 | 15.00 |
| 122 LYS | O | −39.79 | −34.47 | 63.36 | 15.00 |
| 123 ARG | N | −39.02 | −36.44 | 62.55 | 15.00 |
| 123 ARG | CA | −39.13 | −37.17 | 63.81 | 15.00 |
| 123 ARG | CB | −38.72 | −38.64 | 63.64 | 15.00 |
| 123 ARG | CG | −39.86 | −39.56 | 63.26 | 15.00 |
| 123 ARG | CD | −39.43 | −41.02 | 63.33 | 15.00 |
| 123 ARG | NE | −38.71 | −41.48 | 62.14 | 15.00 |
| 123 ARG | CZ | −37.42 | −41.79 | 62.12 | 15.00 |
| 123 ARG | NH1 | −36.68 | −41.70 | 63.21 | 15.00 |
| 123 ARG | NH2 | −36.87 | −42.22 | 60.99 | 15.00 |
| 123 ARG | C | −38.28 | −36.55 | 64.90 | 15.00 |
| 123 ARG | O | −38.69 | −36.51 | 66.05 | 15.00 |
| 124 ALA | N | −37.09 | −36.07 | 64.55 | 15.00 |
| 124 ALA | CA | −36.20 | −35.45 | 65.52 | 15.00 |
| 124 ALA | CB | −34.85 | −35.18 | 64.89 | 15.00 |
| 124 ALA | C | −36.81 | −34.15 | 66.03 | 15.00 |
| 124 ALA | O | −36.96 | −33.96 | 67.23 | 15.00 |
| 125 VAL | N | −37.17 | −33.25 | 65.12 | 15.00 |
| 125 VAL | CA | −37.77 | −31.97 | 65.50 | 15.00 |
| 125 VAL | CB | −38.07 | −31.11 | 64.25 | 15.00 |
| 125 VAL | CG1 | −38.97 | −29.94 | 64.59 | 15.00 |
| 125 VAL | CG2 | −36.78 | −30.59 | 63.67 | 15.00 |
| 125 VAL | C | −39.04 | −32.20 | 66.30 | 15.00 |
| 125 VAL | O | −39.36 | −31.43 | 67.20 | 15.00 |
| 126 ALA | N | −39.74 | −33.29 | 66.00 | 15.00 |
| 126 ALA | CA | −40.97 | −33.62 | 66.69 | 15.00 |
| 126 ALA | CB | −41.78 | −34.61 | 65.88 | 15.00 |
| 126 ALA | C | −40.72 | −34.17 | 68.09 | 15.00 |
| 126 ALA | O | −41.37 | −33.76 | 69.06 | 15.00 |
| 127 ARG | N | −39.77 | −35.10 | 68.19 | 15.00 |
| 127 ARG | CA | −39.41 | −35.74 | 69.44 | 15.00 |
| 127 ARG | CB | −38.71 | −37.07 | 69.18 | 15.00 |
| 127 ARG | CG | −39.58 | −38.30 | 69.27 | 15.00 |
| 127 ARG | CD | −40.17 | −38.70 | 67.94 | 15.00 |
| 127 ARG | NE | −39.87 | −40.09 | 67.60 | 15.00 |
| 127 ARG | CZ | −40.52 | −40.78 | 66.67 | 15.00 |
| 127 ARG | NH1 | −40.18 | −42.03 | 66.40 | 15.00 |
| 127 ARG | NH2 | −41.55 | −40.25 | 66.03 | 15.00 |
| 127 ARG | C | −38.52 | −34.91 | 70.35 | 15.00 |
| 127 ARG | O | −38.86 | −34.71 | 71.52 | 15.00 |
| 128 VAL | N | −37.37 | −34.50 | 69.82 | 15.00 |
| 128 VAL | CA | −36.36 | −33.72 | 70.56 | 15.00 |
| 128 VAL | CB | −34.95 | −33.91 | 69.94 | 15.00 |
| 128 VAL | CG1 | −33.88 | −33.45 | 70.91 | 15.00 |
| 128 VAL | CG2 | −34.73 | −35.35 | 69.57 | 15.00 |
| 128 VAL | C | −36.62 | −32.22 | 70.66 | 15.00 |
| 128 VAL | O | −36.44 | −31.61 | 71.71 | 15.00 |
| 129 GLY | N | −36.99 | −31.60 | 69.55 | 15.00 |
| 129 GLY | CA | −37.23 | −30.17 | 69.54 | 15.00 |
| 129 GLY | C | −36.29 | −29.54 | 68.53 | 15.00 |
| 129 GLY | O | −35.87 | −30.22 | 67.58 | 15.00 |
| 130 PRO | N | −35.94 | −28.25 | 68.71 | 15.00 |
| 130 PRO | CD | −36.46 | −27.38 | 69.78 | 15.00 |
| 130 PRO | CA | −35.04 | −27.50 | 67.83 | 15.00 |
| 130 PRO | CB | −34.80 | −26.22 | 68.62 | 15.00 |
| 130 PRO | CG | −36.12 | −26.00 | 69.26 | 15.00 |
| 130 PRO | C | −33.74 | −28.21 | 67.50 | 15.00 |
| 130 PRO | O | −32.90 | −28.46 | 68.37 | 15.00 |
| 131 VAL | N | −33.59 | −28.51 | 66.21 | 15.00 |
| 131 VAL | CA | −32.42 | −29.19 | 65.68 | 15.00 |
| 131 VAL | CB | −32.84 | −30.34 | 64.73 | 15.00 |
| 131 VAL | CG1 | −31.64 | −31.06 | 64.18 | 15.00 |
| 131 VAL | CG2 | −33.74 | −31.33 | 65.48 | 15.00 |
| 131 VAL | C | −31.57 | −28.19 | 64.90 | 15.00 |
| 131 VAL | O | −32.08 | −27.25 | 64.28 | 15.00 |
| 132 SER | N | −30.25 | −28.38 | 64.96 | 15.00 |
| 132 SER | CA | −29.32 | −27.53 | 64.26 | 15.00 |
| 132 SER | CB | −28.00 | −27.48 | 65.02 | 15.00 |

TABLE III-continued

Table of the orthogonal three dimensional coordinates in Ångstroms and B factors ($Å^2$) for the cathepsin K complex with inhibitor bis-(cbz-leucinyl)-1,3-diamino-propan-2-one.

| Residue Atom | X | Y | Z | B |
|---|---|---|---|---|
| 132 SER OG | −28.18 | −26.93 | 66.31 | 15.00 |
| 132 SER C | −29.08 | −28.14 | 62.88 | 15.00 |
| 132 SER O | −28.67 | −29.30 | 62.79 | 15.00 |
| 133 VAL N | −29.38 | −27.38 | 61.83 | 15.00 |
| 133 VAL CA | −29.21 | −27.83 | 60.44 | 15.00 |
| 133 VAL CB | −30.57 | −27.93 | 59.68 | 15.00 |
| 133 VAL CG1 | −31.55 | −28.81 | 60.43 | 15.00 |
| 133 VAL CG2 | −31.16 | −26.56 | 59.49 | 15.00 |
| 133 VAL C | −28.30 | −26.86 | 59.68 | 15.00 |
| 133 VAL O | −28.06 | −25.74 | 60.13 | 15.00 |
| 134 ALA N | −27.79 | −27.28 | 58.52 | 15.00 |
| 134 ALA CA | −26.94 | −26.44 | 57.69 | 15.00 |
| 134 ALA CB | −25.50 | −26.93 | 57.73 | 15.00 |
| 134 ALA C | −27.49 | −26.50 | 56.28 | 15.00 |
| 134 ALA O | −27.84 | −27.57 | 55.79 | 15.00 |
| 135 ILE N | −27.58 | −25.36 | 55.61 | 15.00 |
| 135 ILE CA | −28.14 | −25.32 | 54.27 | 15.00 |
| 135 ILE CB | −29.58 | −24.73 | 54.30 | 15.00 |
| 135 ILE CG2 | −30.49 | −25.57 | 55.19 | 15.00 |
| 135 ILE CG1 | −29.53 | −23.26 | 54.76 | 15.00 |
| 135 ILE CD1 | −30.88 | −22.58 | 54.88 | 15.00 |
| 135 ILE C | −27.33 | −24.44 | 53.32 | 15.00 |
| 135 ILE O | −26.33 | −23.82 | 53.72 | 15.00 |
| 136 ASP N | −27.75 | −24.41 | 52.05 | 15.00 |
| 136 ASP CA | −27.12 | −23.57 | 51.05 | 15.00 |
| 136 ASP CB | −27.25 | −24.16 | 49.65 | 15.00 |
| 136 ASP CG | −26.77 | −23.20 | 48.57 | 15.00 |
| 136 ASP OD1 | −27.27 | −23.28 | 47.43 | 15.00 |
| 136 ASP OD2 | −25.90 | −22.35 | 48.85 | 15.00 |
| 136 ASP C | −27.87 | −22.24 | 51.10 | 15.00 |
| 136 ASP O | −29.05 | −22.17 | 50.77 | 15.00 |
| 137 ALA N | −27.19 | −21.21 | 51.59 | 15.00 |
| 137 ALA CA | −27.80 | −19.89 | 51.68 | 15.00 |
| 137 ALA CB | −27.61 | −19.32 | 53.08 | 15.00 |
| 137 ALA C | −27.23 | −18.94 | 50.62 | 15.00 |
| 137 ALA O | −27.64 | −17.78 | 50.53 | 15.00 |
| 138 SER N | −26.26 | −19.43 | 49.84 | 15.00 |
| 138 SER CA | −25.66 | −18.65 | 48.77 | 15.00 |
| 138 SER CB | −24.30 | −19.22 | 48.37 | 15.00 |
| 138 SER OG | −23.28 | −18.86 | 49.30 | 15.00 |
| 138 SER C | −26.61 | −18.73 | 47.60 | 15.00 |
| 138 SER O | −26.51 | −19.65 | 46.80 | 15.00 |
| 139 LEU N | −27.54 | −17.77 | 47.57 | 15.00 |
| 139 LEU CA | −28.59 | −17.66 | 46.55 | 15.00 |
| 139 LEU CB | −29.53 | −18.86 | 46.65 | 15.00 |
| 139 LEU CG | −29.89 | −19.63 | 45.38 | 15.00 |
| 139 LEU CD1 | −28.66 | −20.27 | 44.80 | 15.00 |
| 139 LEU CD2 | −30.92 | −20.68 | 45.71 | 15.00 |
| 139 LEU C | −29.39 | −16.39 | 46.85 | 15.00 |
| 139 LEU O | −29.91 | −16.22 | 47.96 | 15.00 |
| 140 THR N | −29.52 | −15.49 | 45.87 | 15.00 |
| 140 THR CA | −30.23 | −14.23 | 46.08 | 15.00 |
| 140 THR CB | −30.06 | −13.28 | 44.87 | 15.00 |
| 140 THR OG1 | −29.05 | −13.81 | 43.99 | 15.00 |
| 140 THR CG2 | −29.62 | −11.89 | 45.34 | 15.00 |
| 140 THR C | −31.71 | −14.37 | 46.42 | 15.00 |
| 140 THR O | −32.23 | −13.63 | 47.24 | 15.00 |
| 141 SER N | −32.39 | −15.35 | 45.83 | 15.00 |
| 141 SER CA | −33.80 | −15.59 | 46.10 | 15.00 |
| 141 SER CB | −34.31 | −16.76 | 45.27 | 15.00 |
| 141 SER OG | −33.42 | −17.86 | 45.34 | 15.00 |
| 141 SER C | −34.00 | −15.89 | 47.57 | 15.00 |
| 141 SER O | −35.03 | −15.57 | 48.16 | 15.00 |
| 142 PHE N | −33.01 | −16.51 | 48.18 | 15.00 |
| 142 PHE CA | −33.07 | −16.86 | 49.59 | 15.00 |
| 142 PHE CB | −31.98 | −17.88 | 49.93 | 15.00 |
| 142 PHE CG | −31.93 | −18.24 | 51.39 | 15.00 |
| 142 PHE CD1 | −32.72 | −19.25 | 51.89 | 15.00 |
| 142 PHE CD2 | −31.10 | −17.54 | 52.25 | 15.00 |
| 142 PHE CE1 | −32.68 | −19.58 | 53.23 | 15.00 |
| 142 PHE CE2 | −31.05 | −17.85 | 53.60 | 15.00 |
| 142 PHE CZ | −31.85 | −18.87 | 54.09 | 15.00 |
| 142 PHE C | −32.88 | −15.61 | 50.43 | 15.00 |
| 142 PHE O | −33.66 | −15.33 | 51.34 | 15.00 |
| 143 GLN N | −31.86 | −14.84 | 50.09 | 15.00 |
| 143 GLN CA | −31.54 | −13.64 | 50.83 | 15.00 |
| 143 GLN CB | −30.25 | −13.06 | 50.30 | 15.00 |
| 143 GLN CG | −29.18 | −14.11 | 50.24 | 15.00 |
| 143 GLN CD | −27.84 | −13.53 | 49.97 | 15.00 |
| 143 GLN OE1 | −27.41 | −12.58 | 50.62 | 15.00 |
| 143 GLN NE2 | −27.15 | −14.10 | 48.99 | 15.00 |
| 143 GLN C | −32.63 | −12.59 | 50.89 | 15.00 |
| 143 GLN O | −32.90 | −12.05 | 51.95 | 15.00 |
| 144 PHE N | −33.29 | −12.29 | 49.77 | 15.00 |
| 144 PHE CA | −34.36 | −11.28 | 49.80 | 15.00 |
| 144 PHE CB | −34.33 | −10.38 | 48.55 | 15.00 |
| 144 PHE CG | −34.46 | −11.12 | 47.24 | 15.00 |
| 144 PHE CD1 | −33.45 | −11.04 | 46.30 | 15.00 |
| 144 PHE CD2 | −35.59 | −11.87 | 46.95 | 15.00 |
| 144 PHE CE1 | −33.56 | −11.71 | 45.09 | 15.00 |
| 144 PHE CE2 | −35.71 | −12.55 | 45.75 | 15.00 |
| 144 PHE CZ | −34.70 | −12.46 | 44.82 | 15.00 |
| 144 PHE C | −35.76 | −11.83 | 50.04 | 15.00 |
| 144 PHE O | −36.76 | −11.19 | 49.68 | 15.00 |
| 145 TYR N | −35.83 | −13.01 | 50.66 | 15.00 |
| 145 TYR CA | −37.09 | −13.68 | 50.97 | 15.00 |
| 145 TYR CB | −36.80 | −15.04 | 51.62 | 15.00 |
| 145 TYR CG | −37.95 | −15.65 | 52.36 | 15.00 |
| 145 TYR CD1 | −38.83 | −16.52 | 51.73 | 15.00 |
| 145 TYR CE1 | −39.93 | −17.05 | 52.41 | 15.00 |
| 145 TYR CD2 | −38.20 | −15.31 | 53.69 | 15.00 |
| 145 TYR CE2 | −39.28 | −15.83 | 54.38 | 15.00 |
| 145 TYR CZ | −40.14 | −16.69 | 53.73 | 15.00 |
| 145 TYR OH | −41.24 | −17.16 | 54.42 | 15.00 |
| 145 TYR C | −37.87 | −12.81 | 51.93 | 15.00 |
| 145 TYR O | −37.27 | −12.10 | 52.74 | 15.00 |
| 146 SER N | −39.20 | −12.88 | 51.89 | 15.00 |
| 146 SER CA | −40.01 | −12.07 | 52.78 | 15.00 |
| 146 SER CB | −40.45 | −10.78 | 52.10 | 15.00 |
| 146 SER OG | −41.31 | −11.05 | 51.01 | 15.00 |
| 146 SER C | −41.23 | −12.81 | 53.34 | 15.00 |
| 146 SER O | −41.69 | −12.52 | 54.45 | 15.00 |
| 147 LYS N | −41.77 | −13.75 | 52.58 | 15.00 |
| 147 LYS CA | −42.93 | −14.52 | 53.04 | 15.00 |
| 147 LYS CB | −44.16 | −13.62 | 53.21 | 15.00 |
| 147 LYS CG | −44.84 | −13.14 | 51.92 | 15.00 |
| 147 LYS CD | −45.64 | −11.86 | 52.19 | 15.00 |
| 147 LYS CE | −44.71 | −10.72 | 52.70 | 15.00 |
| 147 LYS NZ | −45.41 | −9.52 | 53.28 | 15.00 |
| 147 LYS C | −43.27 | −15.68 | 52.11 | 15.00 |
| 147 LYS O | −43.03 | −15.62 | 50.91 | 15.00 |
| 148 GLY N | −43.83 | −16.74 | 52.69 | 15.00 |
| 148 GLY CA | −44.21 | −17.90 | 51.90 | 15.00 |
| 148 GLY C | −43.31 | −19.08 | 52.16 | 15.00 |
| 148 GLY O | −42.50 | −19.07 | 53.08 | 15.00 |
| 149 VAL N | −43.46 | −20.12 | 51.35 | 15.00 |
| 149 VAL CA | −42.65 | −21.32 | 51.50 | 15.00 |
| 149 VAL CB | −43.52 | −22.60 | 51.39 | 15.00 |
| 149 VAL CG1 | −42.66 | −23.84 | 51.53 | 15.00 |
| 149 VAL CG2 | −44.59 | −22.59 | 52.45 | 15.00 |
| 149 VAL C | −41.57 | −21.27 | 50.42 | 15.00 |
| 149 VAL O | −41.84 | −21.44 | 49.24 | 15.00 |
| 150 TYR N | −40.34 | −21.01 | 50.84 | 15.00 |
| 150 TYR CA | −39.21 | −20.90 | 49.93 | 15.00 |
| 150 TYR CB | −37.98 | −20.37 | 50.67 | 15.00 |
| 150 TYR CG | −36.75 | −20.27 | 49.80 | 15.00 |
| 150 TYR CD1 | −36.73 | −19.44 | 48.68 | 15.00 |
| 150 TYR CE1 | −35.61 | −19.36 | 47.86 | 15.00 |
| 150 TYR CD2 | −35.61 | −21.03 | 50.09 | 15.00 |
| 150 TYR CE2 | −34.48 | −20.96 | 49.27 | 15.00 |
| 150 TYR CZ | −34.49 | −20.13 | 48.16 | 15.00 |
| 150 TYR OH | −33.41 | −20.06 | 47.32 | 15.00 |
| 150 TYR C | −38.81 | −22.16 | 49.19 | 15.00 |
| 150 TYR O | −38.56 | −23.19 | 49.80 | 15.00 |

TABLE III-continued

Table of the orthogonal three dimensional coordinates in Ångstroms and B factors (Å²) for the cathepsin K complex with inhibitor bis-(cbz-leucinyl)-1,3-diamino-propan-2-one.

| Residue Atom | X | Y | Z | B |
|---|---|---|---|---|
| 151 TYR N | −38.68 | −22.03 | 47.88 | 15.00 |
| 151 TYR CA | −38.24 | −23.13 | 47.02 | 15.00 |
| 151 TYR CB | −39.38 | −24.11 | 46.72 | 15.00 |
| 151 TYR CG | −38.89 | −25.32 | 45.96 | 15.00 |
| 151 TYR CD1 | −37.74 | −26.01 | 46.37 | 15.00 |
| 151 TYR CE1 | −37.23 | −27.06 | 45.63 | 15.00 |
| 151 TYR CD2 | −39.52 | −25.74 | 44.79 | 15.00 |
| 151 TYR CE2 | −39.01 | −26.80 | 44.03 | 15.00 |
| 151 TYR CZ | −37.87 | −27.45 | 44.46 | 15.00 |
| 151 TYR OH | −37.35 | −28.50 | 43.72 | 15.00 |
| 151 TYR C | −37.63 | −22.58 | 45.73 | 15.00 |
| 151 TYR O | −38.19 | −21.69 | 45.08 | 15.00 |
| 152 ASP N | −36.47 | −23.12 | 45.37 | 15.00 |
| 152 ASP CA | −35.74 | −22.69 | 44.19 | 15.00 |
| 152 ASP CB | −34.80 | −21.56 | 44.59 | 15.00 |
| 152 ASP CG | −34.09 | −20.92 | 43.42 | 15.00 |
| 152 ASP OD1 | −33.27 | −21.60 | 42.76 | 15.00 |
| 152 ASP OD2 | −34.35 | −19.73 | 43.17 | 15.00 |
| 152 ASP C | −34.93 | −23.88 | 43.70 | 15.00 |
| 152 ASP O | −33.98 | −24.30 | 44.37 | 15.00 |
| 153 GLU N | −35.23 | −24.36 | 42.51 | 15.00 |
| 153 GLU CA | −34.55 | −25.53 | 41.95 | 15.00 |
| 153 GLU CB | −35.15 | −25.91 | 40.59 | 15.00 |
| 153 GLU CG | −35.40 | −24.74 | 39.62 | 15.00 |
| 153 GLU CD | −34.12 | −24.02 | 39.16 | 15.00 |
| 153 GLU OE1 | −33.16 | −24.68 | 38.70 | 15.00 |
| 153 GLU OE2 | −34.09 | −22.76 | 39.27 | 15.00 |
| 153 GLU C | −33.03 | −25.50 | 41.88 | 15.00 |
| 153 GLU O | −32.40 | −26.49 | 41.49 | 15.00 |
| 154 SER N | −32.42 | −24.37 | 42.22 | 15.00 |
| 154 SER CA | −30.96 | −24.26 | 42.18 | 15.00 |
| 154 SER CB | −30.53 | −23.00 | 41.43 | 15.00 |
| 154 SER OG | −30.93 | −23.09 | 40.06 | 15.00 |
| 154 SER C | −30.27 | −24.34 | 43.55 | 15.00 |
| 154 SER O | −29.04 | −24.33 | 43.65 | 15.00 |
| 155 CYS N | −31.06 | −24.43 | 44.61 | 15.00 |
| 155 CYS CA | −30.49 | −24.54 | 45.95 | 15.00 |
| 155 CYS C | −29.66 | −25.81 | 45.88 | 15.00 |
| 155 CYS O | −30.16 | −26.88 | 45.54 | 15.00 |
| 155 CYS CB | −31.60 | −24.69 | 46.96 | 15.00 |
| 155 CYS SG | −31.20 | −23.89 | 48.53 | 15.00 |
| 156 ASN N | −28.36 | −25.70 | 46.16 | 15.00 |
| 156 ASN CA | −27.50 | −26.87 | 46.05 | 15.00 |
| 156 ASN CB | −26.20 | −26.49 | 45.36 | 15.00 |
| 156 ASN CG | −25.34 | −27.69 | 45.04 | 15.00 |
| 156 ASN OD1 | −25.83 | −28.82 | 44.97 | 15.00 |
| 156 ASN ND2 | −24.05 | −27.47 | 44.88 | 15.00 |
| 156 ASN C | −27.21 | −27.66 | 47.33 | 15.00 |
| 156 ASN O | −26.37 | −27.26 | 48.13 | 15.00 |
| 157 SER N | −27.82 | −28.83 | 47.43 | 15.00 |
| 157 SER CA | −27.66 | −29.72 | 48.57 | 15.00 |
| 157 SER CB | −28.41 | −31.03 | 48.33 | 15.00 |
| 157 SER OG | −29.78 | −30.78 | 48.03 | 15.00 |
| 157 SER C | −26.19 | −30.04 | 48.87 | 15.00 |
| 157 SER O | −25.86 | −30.54 | 49.96 | 15.00 |
| 158 ASP N | −25.31 | −29.75 | 47.92 | 15.00 |
| 158 ASP CA | −23.89 | −30.03 | 48.07 | 15.00 |
| 158 ASP CB | −23.30 | −30.43 | 46.71 | 15.00 |
| 157 ASP CG | −24.01 | −31.63 | 46.08 | 15.00 |
| 158 ASP OD1 | −25.23 | −31.53 | 45.79 | 15.00 |
| 158 ASP OD2 | −23.34 | −32.67 | 45.86 | 15.00 |
| 158 ASP C | −23.11 | −28.86 | 48.64 | 15.00 |
| 158 ASP O | −22.00 | −29.02 | 49.15 | 15.00 |
| 159 ASN N | −23.68 | −27.66 | 48.60 | 15.00 |
| 159 ASN CA | −22.98 | −26.49 | 49.11 | 15.00 |
| 159 ASN CB | −23.02 | −25.36 | 48.07 | 15.00 |
| 159 ASN CG | −21.95 | −24.29 | 48.31 | 15.00 |
| 159 ASN OD1 | −21.61 | −23.96 | 49.45 | 15.00 |
| 159 ASN ND2 | −21.43 | −23.72 | 47.22 | 15.00 |
| 159 ASN C | −23.59 | −26.01 | 50.41 | 15.00 |
| 159 ASN O | −24.34 | −25.03 | 50.44 | 15.00 |
| 160 LEU N | −23.31 | −26.69 | 51.52 | 15.00 |
| 160 LEU CA | −23.86 | −26.27 | 52.80 | 15.00 |
| 160 LEU CB | −23.99 | −27.45 | 53.77 | 15.00 |
| 160 LEU CG | −24.87 | −28.62 | 53.30 | 15.00 |
| 160 LEU CD1 | −25.08 | −29.56 | 54.47 | 15.00 |
| 160 LEU CD2 | −26.21 | −28.16 | 52.76 | 15.00 |
| 160 LEU C | −22.91 | −25.21 | 53.33 | 15.00 |
| 160 LEU O | −21.77 | −25.51 | 53.65 | 15.00 |
| 161 ASN N | −23.38 | −23.97 | 53.35 | 15.00 |
| 161 ASN CA | −22.55 | −22.84 | 53.78 | 15.00 |
| 161 ASN CB | −22.32 | −21.90 | 52.60 | 15.00 |
| 161 ASN CG | −23.61 | −21.59 | 51.84 | 15.00 |
| 161 ASN OD1 | −24.49 | −20.86 | 52.31 | 15.00 |
| 161 ASN ND2 | −23.75 | −22.18 | 50.66 | 15.00 |
| 161 ASN C | −23.10 | −22.04 | 54.94 | 15.00 |
| 161 ASN O | −22.37 | −21.29 | 55.58 | 15.00 |
| 162 HIS N | −24.38 | −22.20 | 55.24 | 15.00 |
| 162 HIS CA | −25.01 | −21.44 | 56.31 | 15.00 |
| 162 HIS CB | −26.00 | −20.43 | 55.72 | 15.00 |
| 162 HIS CG | −26.46 | −19.38 | 56.68 | 15.00 |
| 162 HIS CD2 | −27.69 | −18.91 | 56.97 | 15.00 |
| 162 HIS ND1 | −25.58 | −18.66 | 57.46 | 15.00 |
| 162 HIS CE1 | −26.25 | −17.79 | 58.19 | 15.00 |
| 162 HIS NE2 | −27.54 | −17.92 | 57.90 | 15.00 |
| 162 HIS C | −25.74 | −22.34 | 57.31 | 15.00 |
| 162 HIS O | −26.66 | −23.07 | 56.94 | 15.00 |
| 163 ALA N | −25.31 | −22.30 | 58.57 | 15.00 |
| 163 ALA CA | −25.93 | −23.09 | 59.63 | 15.00 |
| 163 ALA CB | −24.98 | −23.25 | 60.81 | 15.00 |
| 163 ALA C | −27.18 | −22.33 | 60.08 | 15.00 |
| 163 ALA O | −27.20 | −21.09 | 60.08 | 15.00 |
| 164 VAL N | −28.21 | −23.05 | 60.48 | 15.00 |
| 164 VAL CA | −29.44 | −22.43 | 60.91 | 15.00 |
| 164 VAL CB | −30.31 | −22.10 | 59.66 | 15.00 |
| 164 VAL CG1 | −31.25 | −23.23 | 59.31 | 15.00 |
| 164 VAL CG2 | −30.99 | −20.79 | 59.85 | 15.00 |
| 164 VAL C | −30.13 | −23.35 | 61.91 | 15.00 |
| 164 VAL O | −29.51 | −24.32 | 62.35 | 15.00 |
| 165 LEU N | −31.38 | −23.10 | 62.28 | 15.00 |
| 165 LEU CA | −32.05 | −23.93 | 63.28 | 15.00 |
| 165 LEU CB | −31.95 | −23.25 | 64.64 | 15.00 |
| 165 LEU CG | −32.41 | −23.97 | 65.90 | 15.00 |
| 165 LEU CD1 | −31.39 | −25.01 | 66.31 | 15.00 |
| 165 LEU CD2 | −32.58 | −22.96 | 67.00 | 15.00 |
| 165 LEU C | −33.51 | −24.20 | 62.98 | 15.00 |
| 165 LEU O | −34.30 | −23.27 | 62.86 | 15.00 |
| 166 ALA N | −33.88 | −25.48 | 62.93 | 15.00 |
| 166 ALA CA | −35.27 | −25.89 | 62.66 | 15.00 |
| 166 ALA CB | −35.30 | −27.31 | 62.15 | 15.00 |
| 166 ALA C | −36.07 | −25.78 | 63.95 | 15.00 |
| 166 ALA O | −35.74 | −26.40 | 64.95 | 15.00 |
| 167 VAL N | −37.14 | −24.99 | 63.93 | 15.00 |
| 167 VAL CA | −38.00 | −24.75 | 65.09 | 15.00 |
| 167 VAL CB | −38.22 | −23.21 | 65.30 | 15.00 |
| 167 VAL CG1 | −39.07 | −22.93 | 66.50 | 15.00 |
| 167 VAL CG2 | −36.88 | −22.50 | 65.47 | 15.00 |
| 167 VAL C | −39.35 | −25.46 | 64.93 | 15.00 |
| 167 VAL O | −40.25 | −25.34 | 65.77 | 15.00 |
| 168 GLY N | −39.51 | −26.21 | 63.85 | 15.00 |
| 168 GLY CA | −40.75 | −26.91 | 63.61 | 15.00 |
| 168 GLY C | −40.97 | −27.18 | 62.14 | 15.00 |
| 168 GLY O | −40.03 | −27.15 | 61.35 | 15.00 |
| 168 TYR N | −42.22 | −27.45 | 61.78 | 15.00 |
| 169 TYR CA | −42.63 | −27.75 | 60.41 | 15.00 |
| 169 TYR CB | −42.23 | −29.18 | 60.00 | 15.00 |
| 169 TYR CG | −42.72 | −30.27 | 60.93 | 15.00 |
| 169 TYR CD1 | −44.07 | −30.66 | 60.94 | 15.00 |
| 169 TYR CE1 | −44.52 | −31.66 | 61.81 | 15.00 |
| 169 TYR CD2 | −41.85 | −30.91 | 61.81 | 15.00 |
| 169 TYR CE2 | −42.29 | −31.91 | 62.68 | 15.00 |
| 169 TYR CZ | −43.63 | −32.27 | 62.68 | 15.00 |
| 169 TYR OH | −44.07 | −33.24 | 63.57 | 15.00 |
| 169 TYR C | −44.14 | −27.59 | 60.31 | 15.00 |

TABLE III-continued

Table of the orthogonal three dimensional coordinates in Ångstroms and B factors (Å$^2$) for the cathepsin K complex with inhibitor bis-(cbz-leucinyl)-1,3-diamino-propan-2-one.

| Residue Atom | X | Y | Z | B |
|---|---|---|---|---|
| 169 TYR O | −44.81 | −27.32 | 61.30 | 15.00 |
| 170 GLY N | −44.70 | −27.76 | 59.12 | 15.00 |
| 170 GLY CA | −46.14 | −27.63 | 58.97 | 15.00 |
| 170 GLY C | −46.56 | −27.53 | 57.52 | 15.00 |
| 170 GLY O | −45.85 | −27.94 | 56.61 | 15.00 |
| 171 ILE N | −47.74 | −26.97 | 57.30 | 15.00 |
| 171 ILE CA | −48.28 | −26.78 | 55.97 | 15.00 |
| 171 ILE CB | −49.43 | −27.78 | 55.69 | 15.00 |
| 171 ILE CG2 | −50.14 | −27.44 | 54.38 | 15.00 |
| 171 ILE CG1 | −48.91 | −29.22 | 55.69 | 15.00 |
| 171 ILE CD1 | −48.38 | −29.69 | 54.35 | 15.00 |
| 171 ILE C | −48.89 | −25.40 | 56.05 | 15.00 |
| 171 ILE O | −49.85 | −25.20 | 56.78 | 15.00 |
| 172 GLN N | −48.29 | −24.41 | 55.40 | 15.00 |
| 172 GLN CA | −48.86 | −23.07 | 55.47 | 15.00 |
| 172 GLN CB | −47.96 | −22.05 | 54.75 | 15.00 |
| 172 GLN CG | −48.37 | −20.59 | 54.97 | 15.00 |
| 172 GLN CD | −47.48 | −19.62 | 54.20 | 15.00 |
| 172 GLN OE1 | −46.94 | −19.96 | 53.14 | 15.00 |
| 172 GLN NE2 | −47.33 | −18.41 | 54.72 | 15.00 |
| 172 GLN C | −50.22 | −23.15 | 54.78 | 15.00 |
| 172 GLN O | −51.26 | −22.82 | 55.37 | 15.00 |
| 173 LYS N | −50.21 | −23.61 | 53.54 | 15.00 |
| 173 LYS CA | −51.45 | −23.77 | 52.79 | 15.00 |
| 173 LYS CB | −52.00 | −22.41 | 52.33 | 15.00 |
| 173 LYS CG | −53.53 | −22.35 | 52.25 | 15.00 |
| 173 LYS CD | −54.00 | −20.89 | 52.22 | 15.00 |
| 173 LYS CE | −55.51 | −20.75 | 52.34 | 15.00 |
| 173 LYS NZ | −55.91 | −19.31 | 52.33 | 15.00 |
| 173 LYS C | −51.07 | −24.63 | 51.61 | 15.00 |
| 173 LYS O | −50.50 | −24.16 | 50.63 | 15.00 |
| 174 GLY N | −51.28 | −25.93 | 51.80 | 15.00 |
| 174 GLY CA | −50.97 | −26.89 | 50.76 | 15.00 |
| 174 GLY C | −49.51 | −27.27 | 50.74 | 15.00 |
| 174 GLY O | −49.17 | −28.42 | 50.45 | 15.00 |
| 175 ASN N | −48.63 | −26.34 | 51.08 | 15.00 |
| 175 ASN CA | −47.20 | −26.64 | 51.05 | 15.00 |
| 175 ASN CB | −46.44 | −25.52 | 50.34 | 15.00 |
| 175 ASN CG | −46.88 | −25.35 | 48.88 | 15.00 |
| 175 ASN OD1 | −47.59 | −24.39 | 48.54 | 15.00 |
| 175 ASN ND2 | −46.49 | −26.29 | 48.03 | 15.00 |
| 175 ASN C | −46.52 | −26.98 | 52.38 | 15.00 |
| 175 ASN O | −46.58 | −26.21 | 53.35 | 15.00 |
| 176 LYS N | −45.88 | −28.15 | 52.40 | 15.00 |
| 176 LYS CA | −45.15 | −28.65 | 53.56 | 15.00 |
| 176 LYS CB | −44.68 | −30.09 | 53.34 | 15.00 |
| 176 LYS CG | −45.74 | −31.03 | 52.77 | 15.00 |
| 176 LYS CD | −45.35 | −32.49 | 52.97 | 15.00 |
| 176 LYS CE | −46.23 | −33.44 | 52.14 | 15.00 |
| 176 LYS NZ | −45.80 | −33.48 | 50.70 | 15.00 |
| 176 LYS C | −43.94 | −27.75 | 53.75 | 15.00 |
| 176 LYS O | −43.26 | −27.41 | 52.78 | 15.00 |
| 177 HIS N | −43.64 | −27.39 | 55.00 | 15.00 |
| 177 HIS CA | −42.51 | −26.50 | 55.25 | 15.00 |
| 177 HIS CB | −42.96 | −25.05 | 55.09 | 15.00 |
| 177 HIS CG | −43.85 | −24.56 | 56.20 | 15.00 |
| 177 HIS CD2 | −43.59 | −24.27 | 57.49 | 15.00 |
| 177 HIS ND1 | −45.16 | −24.20 | 55.99 | 15.00 |
| 177 HIS CE1 | −45.67 | −23.71 | 57.10 | 15.00 |
| 177 HIS NE2 | −44.74 | −23.75 | 58.03 | 15.00 |
| 177 HIS C | −41.82 | −26.66 | 56.59 | 15.00 |
| 177 HIS O | −42.44 | −27.05 | 57.57 | 15.00 |
| 178 TRP N | −40.52 | −26.34 | 56.60 | 15.00 |
| 178 TRP CA | −39.67 | −26.38 | 57.77 | 15.00 |
| 178 TRP CB | −38.26 | −26.80 | 57.38 | 15.00 |
| 178 TRP CG | −38.11 | −28.21 | 56.93 | 15.00 |
| 178 TRP CD2 | −38.28 | −29.38 | 57.73 | 15.00 |
| 178 TRP CE2 | −38.02 | −30.49 | 56.90 | 15.00 |
| 178 TRP CE3 | −38.62 | −29.60 | 59.08 | 15.00 |
| 178 TRP CD1 | −37.77 | −28.64 | 55.68 | 15.00 |
| 178 TRP NE1 | −37.71 | −30.01 | 55.65 | 15.00 |
| 178 TRP CZ2 | −38.09 | −31.80 | 57.37 | 15.00 |
| 178 TRP CZ3 | −38.69 | −30.89 | 59.54 | 15.00 |
| 178 TRP CH2 | −38.43 | −31.98 | 58.68 | 15.00 |
| 178 TRP C | −39.59 | −24.94 | 58.28 | 15.00 |
| 178 TRP O | −39.26 | −24.03 | 57.51 | 15.00 |
| 179 ILE N | −39.92 | −24.71 | 59.55 | 15.00 |
| 179 ILE CA | −39.85 | −23.36 | 60.09 | 15.00 |
| 179 ILE CB | −40.86 | −23.17 | 61.23 | 15.00 |
| 179 ILE CG2 | −40.80 | −21.75 | 61.74 | 15.00 |
| 179 ILE CG1 | −42.27 | −23.50 | 60.72 | 15.00 |
| 179 ILE CD1 | −43.38 | −23.28 | 61.70 | 15.00 |
| 179 ILE C | −38.42 | −23.13 | 60.55 | 15.00 |
| 179 ILE O | −37.94 | −23.79 | 61.47 | 15.00 |
| 180 ILE N | −37.73 | −22.22 | 59.88 | 15.00 |
| 180 ILE CA | −36.32 | −21.94 | 60.17 | 15.00 |
| 180 ILE CB | −35.50 | −22.02 | 58.86 | 15.00 |
| 180 ILE CG2 | −34.06 | −21.71 | 59.13 | 15.00 |
| 180 ILE CG1 | −35.63 | −23.40 | 58.22 | 15.00 |
| 180 ILE CD1 | −34.94 | −24.48 | 58.99 | 15.00 |
| 180 ILE C | −36.01 | −20.62 | 60.88 | 15.00 |
| 180 ILE O | −36.59 | −19.58 | 60.56 | 15.00 |
| 181 LYS N | −35.09 | −20.68 | 61.84 | 15.00 |
| 181 LYS CA | −34.67 | −19.51 | 62.60 | 15.00 |
| 181 LYS CB | −34.58 | −19.83 | 64.09 | 15.00 |
| 181 LYS CG | −34.19 | −18.62 | 64.93 | 15.00 |
| 181 LYS CD | −33.86 | −18.95 | 66.37 | 15.00 |
| 181 LYS CE | −33.68 | −17.66 | 67.16 | 15.00 |
| 181 LYS NZ | −33.07 | −17.85 | 68.50 | 15.00 |
| 181 LYS C | −33.30 | −19.10 | 62.12 | 15.00 |
| 181 LYS O | −33.31 | −19.74 | 62.48 | 15.00 |
| 182 ASN N | −33.22 | −18.04 | 61.32 | 15.00 |
| 182 ASN CA | −31.93 | −17.56 | 60.79 | 15.00 |
| 182 ASN CB | −32.17 | −16.80 | 59.48 | 15.00 |
| 182 ASN CG | −30.98 | −16.86 | 58.53 | 15.00 |
| 182 ASN OD1 | −29.87 | −17.20 | 58.92 | 15.00 |
| 182 ASN ND2 | −31.21 | −16.50 | 57.27 | 15.00 |
| 182 ASN C | −31.29 | −16.65 | 61.84 | 15.00 |
| 182 ASN O | −31.86 | −16.44 | 62.91 | 15.00 |
| 183 SER N | −30.11 | −16.11 | 61.56 | 15.00 |
| 183 SER CA | −29.44 | −15.21 | 62.52 | 15.00 |
| 183 SER CB | −28.26 | −15.93 | 63.18 | 15.00 |
| 183 SER OG | −27.41 | −16.54 | 62.21 | 15.00 |
| 183 SER C | −28.98 | −13.90 | 61.87 | 15.00 |
| 183 SER O | −27.84 | −13.44 | 62.08 | 15.00 |
| 184 TRP N | −29.85 | −13.26 | 61.11 | 15.00 |
| 184 TRP CA | −29.52 | −12.01 | 60.45 | 15.00 |
| 184 TRP CB | −29.70 | −12.14 | 58.84 | 15.00 |
| 184 TRP CG | −28.74 | −13.05 | 58.26 | 15.00 |
| 184 TRP CD2 | −28.89 | −13.61 | 56.96 | 15.00 |
| 184 TRP CE2 | −27.72 | −14.38 | 56.71 | 15.00 |
| 184 TRP CE3 | −29.87 | −13.53 | 55.98 | 15.00 |
| 184 TRP CD1 | −27.54 | −13.48 | 58.74 | 15.00 |
| 184 TRP NE1 | −26.92 | −14.29 | 57.81 | 15.00 |
| 184 TRP CZ2 | −27.53 | −15.07 | 55.51 | 15.00 |
| 184 TRP CZ3 | −29.68 | −14.22 | 54.78 | 15.00 |
| 184 TRP CH2 | −28.52 | −14.98 | 54.56 | 15.00 |
| 184 TRP C | −30.45 | −10.91 | 60.98 | 15.00 |
| 184 TRP O | −31.16 | −10.28 | 60.20 | 15.00 |
| 185 GLY N | −30.48 | −10.71 | 62.29 | 15.00 |
| 185 GLY CA | −31.34 | −9.69 | 62.86 | 15.00 |
| 185 GLY C | −32.79 | −10.02 | 62.61 | 15.00 |
| 185 GLY O | −33.09 | −11.01 | 61.96 | 15.00 |
| 186 GLU N | −33.73 | −9.25 | 63.14 | 15.00 |
| 186 GLU CA | −35.13 | −9.57 | 62.89 | 15.00 |
| 186 GLU CB | −36.01 | −9.41 | 64.14 | 15.00 |
| 186 GLU CG | −36.02 | −8.04 | 64.75 | 15.00 |
| 186 GLU CD | −37.04 | −7.92 | 65.87 | 15.00 |
| 186 GLU OE1 | −36.66 | −7.55 | 67.00 | 15.00 |
| 186 GLU OE2 | −38.23 | −8.21 | 65.61 | 15.00 |
| 186 GLU C | −35.67 | −8.78 | 61.72 | 15.00 |
| 186 GLU O | −36.84 | −8.91 | 61.34 | 15.00 |
| 187 ASN N | −34.80 | −7.96 | 61.13 | 15.00 |
| 187 ASN CA | −35.17 | −7.15 | 59.99 | 15.00 |

TABLE III-continued

Table of the orthogonal three dimensional coordinates in Ångstroms and B factors (Å²) for the cathepsin K complex with inhibitor bis-(cbz-leucinyl)-1,3-diamino-propan-2-one.

| Residue Atom | X | Y | Z | B |
|---|---|---|---|---|
| 187 ASN CB | −34.20 | −5.97 | 59.84 | 15.00 |
| 187 ASN CG | −34.83 | −4.76 | 59.13 | 15.00 |
| 187 ASN OD1 | −34.15 | −4.03 | 58.42 | 15.00 |
| 187 ASN ND2 | −36.12 | −4.54 | 59.36 | 15.00 |
| 187 ASN C | −35.15 | −8.03 | 58.74 | 15.00 |
| 187 ASN O | −35.75 | −7.72 | 57.72 | 15.00 |
| 187 TRP N | −34.45 | −9.16 | 58.81 | 15.00 |
| 188 TRP CA | −34.37 | −10.07 | 57.66 | 15.00 |
| 188 TRP CB | −33.13 | −10.97 | 57.77 | 15.00 |
| 188 TRP CG | −33.03 | −11.92 | 56.63 | 15.00 |
| 188 TRP CD2 | −33.46 | −13.29 | 56.62 | 15.00 |
| 188 TRP CE2 | −33.26 | −13.77 | 55.31 | 15.00 |
| 188 TRP CE3 | −34.00 | −14.15 | 57.58 | 15.00 |
| 188 TRP CD1 | −32.60 | −11.64 | 55.38 | 15.00 |
| 188 TRP NE1 | −32.73 | −12.74 | 54.58 | 15.00 |
| 188 TRP CZ2 | −33.58 | −15.08 | 54.93 | 15.00 |
| 188 TRP CZ3 | −34.31 | −15.45 | 57.20 | 15.00 |
| 188 TRP CH2 | −34.10 | −15.90 | 55.89 | 15.00 |
| 188 TRP C | −35.63 | −10.94 | 57.55 | 15.00 |
| 188 TRP O | −36.34 | −11.13 | 58.54 | 15.00 |
| 189 GLY N | −35.89 | −11.44 | 56.34 | 15.00 |
| 189 GLY CA | −37.04 | −12.29 | 56.09 | 15.00 |
| 189 GLY C | −38.26 | −11.99 | 56.92 | 15.00 |
| 189 GLY O | −38.56 | −10.84 | 57.23 | 15.00 |
| 190 ASN N | −38.99 | −13.02 | 57.32 | 15.00 |
| 190 ASN CA | −40.18 | −12.81 | 58.14 | 15.00 |
| 190 ASN CB | −41.17 | −13.96 | 57.97 | 15.00 |
| 190 ASN CG | −42.58 | −13.57 | 58.36 | 15.00 |
| 190 ADN OD1 | −43.53 | −13.95 | 57.69 | 15.00 |
| 190 ASN ND2 | −42.72 | −12.80 | 59.43 | 15.00 |
| 190 ASN C | −39.79 | −12.68 | 59.61 | 15.00 |
| 190 ASN O | −39.86 | −13.65 | 60.36 | 15.00 |
| 191 LYS N | −39.41 | −11.47 | 60.02 | 15.00 |
| 191 LYS CA | −39.01 | −11.18 | 61.41 | 15.00 |
| 191 LYS CB | −40.23 | −11.26 | 62.34 | 15.00 |
| 191 LYS CG | −41.41 | −10.38 | 61.96 | 15.00 |
| 191 LYS CD | −42.64 | −10.75 | 62.79 | 15.00 |
| 191 LYS CE | −43.93 | −10.18 | 62.20 | 15.00 |
| 191 LYS NZ | −45.15 | −10.69 | 62.91 | 15.00 |
| 191 LYS C | −37.94 | −12.14 | 61.90 | 15.00 |
| 191 LYS O | −38.00 | −12.62 | 63.03 | 15.00 |
| 192 GLY N | −36.97 | −12.45 | 61.05 | 15.00 |
| 192 GLY CA | −35.91 | −13.35 | 61.43 | 15.00 |
| 192 GLY C | −36.06 | −14.79 | 60.97 | 15.00 |
| 192 GLY O | −35.07 | −15.51 | 60.83 | 15.00 |
| 193 TYR N | −37.30 | −15.21 | 60.70 | 15.00 |
| 193 TYR CA | −37.56 | −16.59 | 60.27 | 15.00 |
| 193 TYR CB | −38.79 | −17.14 | 61.01 | 15.00 |
| 193 TYR CG | −38.57 | −17.28 | 62.49 | 15.00 |
| 193 TYR CD1 | −38.77 | −16.20 | 63.35 | 15.00 |
| 193 TYR CE1 | −38.49 | −16.30 | 64.70 | 15.00 |
| 193 TYR CD2 | −38.09 | −18.47 | 63.04 | 15.00 |
| 193 TYR CE2 | −37.81 | −18.58 | 64.40 | 15.00 |
| 193 TYR CZ | −38.00 | −17.48 | 65.22 | 15.00 |
| 193 TYR OH | −37.69 | −17.57 | 66.55 | 15.00 |
| 193 TYR C | −37.77 | −16.76 | 58.76 | 15.00 |
| 193 TYR O | −37.85 | −15.80 | 57.99 | 15.00 |
| 194 ILE N | −37.83 | −18.01 | 58.33 | 15.00 |
| 194 ILE CA | −38.06 | −18.34 | 56.94 | 15.00 |
| 194 ILE CB | −36.77 | −18.17 | 56.07 | 15.00 |
| 194 ILE CG2 | −35.64 | −19.02 | 56.60 | 15.00 |
| 194 ILE CG1 | −37.07 | −18.54 | 54.62 | 15.00 |
| 194 ILE CD1 | −35.87 | −18.54 | 53.71 | 15.00 |
| 194 ILE C | −38.59 | −19.77 | 56.84 | 15.00 |
| 194 ILE O | −38.12 | −20.68 | 57.53 | 15.00 |
| 195 LEU N | −39.65 | −19.93 | 56.06 | 15.00 |
| 195 LEU CA | −40.27 | −21.23 | 55.84 | 15.00 |
| 195 LEU CB | −41.76 | −21.08 | 55.61 | 15.00 |
| 195 LEU CG | −42.62 | −21.03 | 56.88 | 15.00 |
| 195 LEU CD1 | −41.90 | −20.32 | 58.01 | 15.00 |
| 195 LEU CD2 | −43.94 | −20.37 | 56.58 | 15.00 |
| 195 LEU C | −39.61 | −21.79 | 54.60 | 15.00 |
| 195 LEU O | −39.53 | −21.13 | 53.57 | 15.00 |
| 196 MET N | −39.08 | −23.00 | 54.71 | 15.00 |
| 196 MET CA | −38.42 | −23.63 | 53.58 | 15.00 |
| 196 MET CB | −36.96 | −23.90 | 53.93 | 15.00 |
| 196 MET CG | −36.13 | −22.63 | 54.11 | 15.00 |
| 196 MET SD | −34.43 | −22.96 | 54.57 | 15.00 |
| 196 MET CE | −33.85 | −23.77 | 53.09 | 15.00 |
| 196 MET C | −39.17 | −24.90 | 53.20 | 15.00 |
| 196 MET O | −39.74 | −25.58 | 54.05 | 15.00 |
| 197 ALA N | −39.23 | −25.22 | 51.91 | 15.00 |
| 197 ALA CA | −39.93 | −26.41 | 51.45 | 15.00 |
| 197 ALA CB | −39.79 | −26.55 | 49.94 | 15.00 |
| 197 ALA C | −39.51 | −27.70 | 52.15 | 15.00 |
| 197 ALA O | −38.32 | −27.92 | 52.41 | 15.00 |
| 198 ARG N | −40.50 | −28.53 | 52.47 | 15.00 |
| 198 ARG CA | −40.29 | −29.81 | 53.12 | 15.00 |
| 198 ARG CB | −40.95 | −29.84 | 54.50 | 15.00 |
| 198 ARG CG | −40.91 | −31.22 | 55.15 | 15.00 |
| 198 ARG CD | −41.22 | −31.19 | 56.63 | 15.00 |
| 198 ARG NE | −42.59 | −30.84 | 56.98 | 15.00 |
| 198 ARG CZ | −43.60 | −31.70 | 56.98 | 15.00 |
| 198 ARG NH1 | −43.40 | −32.96 | 56.63 | 15.00 |
| 198 ARG NH2 | −44.79 | −31.32 | 57.43 | 15.00 |
| 198 ARG C | −40.86 | −30.94 | 52.27 | 15.00 |
| 198 ARG O | −42.03 | −30.91 | 51.88 | 15.00 |
| 199 ASN N | −40.00 | −31.90 | 51.96 | 15.00 |
| 199 ASN CA | −40.33 | −33.08 | 51.17 | 15.00 |
| 199 ASN CB | −41.68 | −33.69 | 51.58 | 15.00 |
| 199 ASN CG | −41.66 | −34.26 | 53.00 | 15.00 |
| 199 ASN OD1 | −42.63 | −34.12 | 53.74 | 15.00 |
| 199 ASN ND2 | −40.55 | −34.91 | 53.38 | 15.00 |
| 199 ASN C | −40.22 | −32.89 | 49.66 | 15.00 |
| 199 ASN O | −40.46 | −33.83 | 48.89 | 15.00 |
| 200 LYS N | −39.80 | −31.71 | 49.23 | 15.00 |
| 200 LYS CA | −39.60 | −31.45 | 47.81 | 15.00 |
| 200 LYS CB | −39.83 | −29.98 | 47.45 | 15.00 |
| 200 LYS CG | −41.27 | −29.52 | 47.67 | 15.00 |
| 200 LYS CD | −41.61 | −28.27 | 46.88 | 15.00 |
| 200 LYS CE | −43.08 | −27.86 | 47.07 | 15.00 |
| 200 LYS NZ | −43.51 | −26.73 | 46.16 | 15.00 |
| 200 LYS C | −38.15 | −31.86 | 47.56 | 15.00 |
| 200 LYS O | −37.29 | −31.02 | 47.31 | 15.00 |
| 201 ASN N | −37.90 | −33.15 | 47.74 | 15.00 |
| 201 ASN CA | −36.58 | −33.74 | 47.55 | 15.00 |
| 201 ASN CB | −36.23 | −33.86 | 46.06 | 15.00 |
| 201 ASN CG | −37.27 | −34.62 | 45.25 | 15.00 |
| 201 ASN OD1 | −37.46 | −34.34 | 44.06 | 15.00 |
| 201 ASN ND2 | −37.96 | −35.58 | 45.88 | 15.00 |
| 201 ASN C | −35.48 | −32.95 | 48.24 | 15.00 |
| 201 ASN O | −34.88 | −32.07 | 47.64 | 15.00 |
| 202 ASN N | −35.27 | −33.23 | 49.53 | 15.00 |
| 202 ASN CA | −34.21 | −32.62 | 50.34 | 15.00 |
| 202 ASN CB | −33.01 | −33.56 | 50.33 | 15.00 |
| 202 ASN CG | −31.96 | −33.20 | 51.34 | 15.00 |
| 202 ASN OD1 | −32.27 | −32.76 | 52.45 | 15.00 |
| 202 ASN ND2 | −30.71 | −33.41 | 50.98 | 15.00 |
| 202 ASN C | −33.81 | −31.18 | 49.94 | 15.00 |
| 202 ASN O | −32.63 | −30.88 | 49.70 | 15.00 |
| 203 ALA N | −34.78 | −30.29 | 49.91 | 15.00 |
| 203 ALA H | −35.58 | −30.58 | 50.39 | 15.00 |
| 203 ALA CA | −34.60 | −28.89 | 49.49 | 15.00 |
| 203 ALA CB | −35.83 | −28.06 | 49.83 | 15.00 |
| 203 ALA C | −33.41 | −28.27 | 50.25 | 15.00 |
| 203 ALA O | −33.31 | −28.25 | 51.47 | 15.00 |
| 204 CYS N | −32.47 | −27.71 | 49.46 | 15.00 |
| 204 CYS CA | −31.31 | −27.02 | 50.02 | 15.00 |
| 204 CYC C | −30.43 | −27.87 | 50.92 | 15.00 |
| 204 CYS O | −29.53 | −27.34 | 51.59 | 15.00 |
| 204 CYS CB | −31.78 | −25.79 | 50.79 | 15.00 |
| 204 CYS SG | −32.67 | −24.58 | 49.75 | 15.00 |
| 205 GLY N | −30.64 | −29.19 | 50.92 | 15.00 |
| 205 GLY CA | −29.86 | −30.06 | 51.76 | 15.00 |

TABLE III-continued

Table of the orthogonal three dimensional coordinates in Ångstroms and B factors (Å$^2$) for the cathepsin K complex with inhibitor bis-(cbz-leucinyl)-1,3-diamino-propan-2-one.

| Residue Atom | X | Y | Z | B |
|---|---|---|---|---|
| 205 GLY C | −30.07 | −29.75 | 53.23 | 15.00 |
| 205 GLY O | −29.14 | −29.81 | 54.04 | 15.00 |
| 206 ILE N | −31.29 | −29.37 | 53.59 | 15.00 |
| 206 ILE CA | −31.60 | −29.06 | 54.98 | 15.00 |
| 206 ILE CB | −33.08 | −28.64 | 55.16 | 15.00 |
| 206 ILE CG2 | −34.01 | −29.71 | 54.60 | 15.00 |
| 206 ILE CG1 | −33.38 | −28.40 | 56.63 | 15.00 |
| 206 ILE CD1 | −34.65 | −27.65 | 56.89 | 15.00 |
| 206 ILE C | −31.30 | −30.24 | 55.91 | 15.00 |
| 206 ILE O | −30.92 | −30.05 | 57.07 | 15.00 |
| 207 ALA N | −31.42 | −31.46 | 55.39 | 15.00 |
| 207 ALA CA | −31.16 | −32.64 | 56.19 | 15.00 |
| 207 ALA CB | −32.30 | −33.64 | 56.03 | 15.00 |
| 207 ALA C | −29.82 | −33.31 | 55.92 | 15.00 |
| 207 ALA O | −29.71 | −34.52 | 55.99 | 15.00 |
| 208 ASN N | −28.75 | −32.54 | 55.69 | 15.00 |
| 208 ASN CA | −27.44 | −33.14 | 55.41 | 15.00 |
| 208 ASN CB | −26.91 | −32.66 | 54.07 | 15.00 |
| 208 ASN CG | −27.50 | −33.42 | 52.92 | 15.00 |
| 208 ASN OD1 | −28.69 | −33.32 | 52.66 | 15.00 |
| 208 ASN ND2 | −26.68 | −34.22 | 52.24 | 15.00 |
| 208 ASN C | −26.38 | −32.91 | 56.46 | 15.00 |
| 208 ASN O | −25.30 | −33.49 | 56.40 | 15.00 |
| 209 LEU N | −26.65 | −32.01 | 57.40 | 15.00 |
| 209 LEU CA | −25.71 | −31.72 | 58.47 | 15.00 |
| 209 LEU CB | −24.78 | −30.58 | 58.07 | 15.00 |
| 209 LEU CG | −23.44 | −30.57 | 58.80 | 15.00 |
| 209 LEU CD1 | −22.65 | −31.81 | 58.41 | 15.00 |
| 209 LEU CD2 | −22.65 | −29.33 | 58.46 | 15.00 |
| 209 LEU C | −26.52 | −31.34 | 59.69 | 15.00 |
| 209 LEU O | −26.24 | −30.34 | 60.34 | 15.00 |
| 210 ALA N | −27.55 | −32.13 | 59.94 | 15.00 |
| 210 ALA H | −27.87 | −32.61 | 59.15 | 15.00 |
| 210 ALA CA | −28.41 | −31.91 | 61.10 | 15.00 |
| 210 ALA CB | −29.82 | −32.45 | 60.85 | 15.00 |
| 210 ALA C | −27.84 | −32.66 | 62.31 | 15.00 |
| 210 ALA O | −27.12 | −33.64 | 62.12 | 15.00 |
| 211 SER N | −28.10 | −32.14 | 63.49 | 15.00 |
| 211 SER CA | −27.62 | −32.76 | 64.72 | 15.00 |
| 211 SER CB | −26.11 | −32.53 | 64.90 | 15.00 |
| 211 SER OG | −25.80 | −31.16 | 65.02 | 15.00 |
| 211 SER C | −28.35 | −32.12 | 65.88 | 15.00 |
| 211 SER O | −28.97 | −31.08 | 65.73 | 15.00 |
| 212 PHE N | −28.31 | −32.77 | 67.03 | 15.00 |
| 212 PHE CA | −28.95 | −32.21 | 68.21 | 15.00 |
| 212 PHE CB | −30.43 | −32.63 | 68.32 | 15.00 |
| 212 PHE CG | −30.66 | −34.13 | 68.43 | 15.00 |
| 212 PHE CD1 | −31.05 | −34.86 | 67.32 | 15.00 |
| 212 PHE CD2 | −30.55 | −34.79 | 69.67 | 15.00 |
| 212 PHE CE1 | −31.34 | −36.23 | 67.44 | 15.00 |
| 212 PHE CE2 | −30.83 | −36.15 | 69.79 | 15.00 |
| 212 PHE CZ | −31.23 | −36.86 | 68.67 | 15.00 |
| 212 PHE C | −28.14 | −32.62 | 69.42 | 15.00 |
| 212 PHE O | −27.50 | −33.67 | 69.42 | 15.00 |
| 213 PRO N | −28.02 | −31.73 | 70.40 | 15.00 |
| 213 PRO CD | −28.49 | −30.34 | 70.46 | 15.00 |
| 213 PRO CA | −27.25 | −32.08 | 71.59 | 15.00 |
| 213 PRO CB | −26.99 | −30.73 | 72.23 | 15.00 |
| 213 PRO CG | −28.24 | −29.98 | 71.91 | 15.00 |
| 213 PRO C | −28.08 | −32.96 | 72.51 | 15.00 |
| 213 PRO O | −29.31 | −32.92 | 72.48 | 15.00 |
| 214 LYS N | −27.43 | −33.79 | 73.30 | 15.00 |
| 214 LYS CA | −28.14 | −34.63 | 74.23 | 15.00 |
| 214 LYS CB | −27.49 | −36.02 | 74.28 | 15.00 |
| 214 LYS CG | −28.32 | −37.14 | 73.61 | 15.00 |
| 214 LYS CD | −27.43 | −38.10 | 72.81 | 15.00 |
| 214 LYS CE | −26.30 | −38.66 | 73.65 | 15.00 |
| 214 LYS NZ | −25.35 | −39.45 | 72.81 | 15.00 |
| 214 LYS C | −28.02 | −33.93 | 75.57 | 15.00 |
| 214 LYS O | −26.95 | −33.45 | 75.91 | 15.00 |
| 215 MET N | −29.11 | −33.79 | 76.30 | 15.00 |
| 215 MET CA | −29.01 | −33.15 | 77.60 | 15.00 |
| 215 MET CB | −29.60 | −31.73 | 77.56 | 15.00 |
| 215 MET CG | −28.77 | −30.73 | 78.36 | 15.00 |
| 215 MET SD | −29.41 | −29.06 | 78.37 | 15.00 |
| 215 MET CE | −30.41 | −29.07 | 79.82 | 15.00 |
| 215 MET C | −29.66 | −33.98 | 78.71 | 15.00 |
| 215 MET OT1 | −30.59 | −34.77 | 78.41 | 15.00 |
| 215 MET OT2 | −29.20 | −33.85 | 79.87 | 15.00 |
| 216 HOH OH2 | −28.05 | −18.06 | 84.86 | 15.00 |
| 217 HOH OH2 | −23.19 | −33.36 | 81.36 | 15.00 |
| 218 HOH OH2 | −31.64 | −15.80 | 65.41 | 15.00 |
| 219 HOH OH2 | −30.17 | −19.91 | 64.18 | 15.00 |
| 220 HOH OH2 | −13.36 | −11.60 | 62.86 | 15.00 |
| 221 HOH OH2 | −9.95 | −9.46 | 71.42 | 15.00 |
| 222 HOH OH2 | −34.59 | −22.68 | 70.30 | 15.00 |
| 223 HOH OH2 | −17.52 | −33.99 | 64.33 | 15.00 |
| 224 HOH OH2 | −15.72 | −11.02 | 61.35 | 15.00 |
| 225 HOH OH2 | −24.41 | −30.51 | 62.51 | 15.00 |
| 226 HOH OH2 | −10.27 | −5.38 | 68.19 | 15.00 |
| 227 HOH OH2 | −11.06 | −16.84 | 67.70 | 15.00 |
| 228 HOH OH2 | −44.88 | −30.73 | 49.92 | 15.00 |
| 229 HOH OH2 | −44.59 | −36.65 | 56.24 | 15.00 |
| 230 HOH OH2 | −37.78 | −15.40 | 68.33 | 15.00 |
| 231 HOH OH2 | −18.90 | −36.86 | 61.93 | 15.00 |
| 232 HOH OH2 | −18.90 | −36.86 | 51.51 | 15.00 |
| 233 HOH OH2 | −41.75 | −34.32 | 46.57 | 15.00 |
| 234 HOH OH2 | −28.01 | −19.38 | 62.11 | 15.00 |
| 235 HOH OH2 | −21.94 | −29.60 | 62.55 | 15.00 |
| 236 HOH OH2 | −26.15 | −8.89 | 74.53 | 15.00 |
| 237 HOH OH2 | −29.39 | −20.71 | 79.14 | 15.00 |
| 238 HOH OH2 | −30.20 | −22.42 | 84.30 | 15.00 |
| 239 HOH OH2 | −40.59 | −13.37 | 49.72 | 15.00 |
| 240 HOH OH2 | −36.04 | −24.57 | 49.50 | 15.00 |
| 241 HOH OH2 | −46.35 | −34.82 | 56.72 | 15.00 |
| 242 HOH OH2 | −24.71 | −3.06 | 61.99 | 15.00 |
| 243 HOH OH2 | −44.08 | −16.56 | 65.62 | 15.00 |
| 244 HOH OH2 | −25.57 | −5.90 | 65.10 | 15.00 |
| 245 HOH OH2 | −33.44 | −27.60 | 71.31 | 15.00 |
| 246 HOH OH2 | −47.48 | −27.33 | 77.05 | 15.00 |
| 247 HOH OH2 | −14.60 | −14.01 | 81.32 | 15.00 |
| 248 HOH OH2 | −7.93 | −18.05 | 73.48 | 15.00 |
| 249 HOH OH2 | −7.49 | −16.70 | 75.98 | 15.00 |
| 250 HOH OH2 | −26.27 | −35.42 | 59.26 | 15.00 |
| 251 HOH OH2 | −35.15 | −10.72 | 53.73 | 15.00 |
| 252 HOH OH2 | −33.62 | −27.20 | 46.10 | 15.00 |
| 253 HOH OH2 | −40.60 | −16.73 | 45.07 | 15.00 |
| 254 HOH OH2 | −41.25 | −34.55 | 55.94 | 15.00 |
| 255 HOH OH2 | −40.71 | −18.20 | 72.64 | 15.00 |
| 256 HOH OH2 | −32.67 | −13.41 | 60.76 | 15.00 |
| 257 HOH OH2 | −39.61 | −9.04 | 58.76 | 15.00 |
| 258 HOH OH2 | −31.33 | −8.54 | 65.90 | 15.00 |
| 259 HOH OH2 | −31.41 | −5.90 | 63.60 | 15.00 |
| 260 HOH OH2 | −19.54 | −8.02 | 63.36 | 15.00 |
| 261 HOH OH2 | −33.59 | −19.88 | 70.38 | 15.00 |
| 262 HOH OH2 | −32.78 | −42.12 | 66.81 | 15.00 |
| 263 HOH OH2 | −13.22 | −22.75 | 77.99 | 15.00 |
| 264 HOH OH2 | −8.15 | −22.46 | 73.27 | 15.00 |
| 265 HOH OH2 | −9.06 | −29.93 | 75.92 | 15.00 |
| 266 HOH OH2 | −20.77 | −33.56 | 62.36 | 15.00 |
| 267 HOH OH2 | −24.27 | −45.12 | 64.98 | 15.00 |
| 268 HOH OH2 | −11.63 | −32.82 | 70.13 | 15.00 |
| 269 HOH OH2 | −11.87 | −26.78 | 72.10 | 15.00 |
| 270 HOH OH2 | −19.16 | −34.47 | 79.41 | 15.00 |
| 271 HOH OH2 | −22.14 | −37.69 | 70.75 | 15.00 |
| 272 HOH OH2 | −34.50 | −24.81 | 88.02 | 15.00 |
| 273 HOH OH2 | −6.96 | −12.16 | 66.61 | 15.00 |
| 274 HOH OH2 | −7.05 | −22.45 | 69.94 | 15.00 |
| 275 HOH OH2 | −16.95 | −20.23 | 55.91 | 15.00 |
| 276 HOH OH2 | −29.20 | −20.58 | 48.90 | 15.00 |
| 277 HOH OH2 | −25.90 | −22.48 | 45.16 | 15.00 |
| 278 HOH OH2 | −35.36 | −37.73 | 52.91 | 15.00 |
| 279 HOH OH2 | −20.12 | −27.71 | 43.74 | 15.00 |
| 280 HOH OH2 | −38.87 | −31.38 | 41.99 | 15.00 |

TABLE III-continued

Table of the orthogonal three dimensional coordinates in Ångstroms and B factors (Å²) for the cathepsin K complex with inhibitor bis-(cbz-leucinyl)-1,3-diamino-propan-2-one.

| Residue Atom | X | Y | Z | B |
|---|---|---|---|---|
| 281 HOH OH2 | −38.13 | −30.43 | 51.07 | 15.00 |

TABLE IV

Table of the orthogonal three dimensional coordinates in Ångstroms and B factors (Å²) for the cathepsin K complex with inhibitor 2,2'-N,N'-bis-benzyloxycarbonyl-L-leucinylcarbohydrazide.

| Residue Atom | X | Y | Z | B |
|---|---|---|---|---|
| 1 ALA CB | −44.52 | −37.54 | 64.26 | 15.00 |
| 1 ALA C | −46.72 | −36.34 | 64.48 | 15.00 |
| 1 ALA O | −47.32 | −36.96 | 63.59 | 15.00 |
| 1 ALA N | −46.03 | −38.05 | 66.17 | 15.00 |
| 1 ALA CA | −45.55 | −36.98 | 65.24 | 15.00 |
| 2 PRO N | −47.09 | −35.10 | 64.86 | 15.00 |
| 2 PRO CD | −46.48 | −34.27 | 65.92 | 15.00 |
| 2 PRO CA | −48.19 | −34.39 | 64.20 | 15.00 |
| 2 PRO CB | −48.32 | −33.13 | 65.04 | 15.00 |
| 2 PRO CG | −46.89 | −32.89 | 65.50 | 15.00 |
| 2 PRO C | −47.85 | −34.05 | 62.76 | 15.00 |
| 2 PRO O | −46.73 | −34.29 | 62.29 | 15.00 |
| 3 ASP N | −48.84 | −33.52 | 62.05 | 15.00 |
| 3 ASP CA | −48.64 | −33.12 | 60.66 | 15.00 |
| 3 ASP CB | −49.97 | −33.13 | 59.91 | 15.00 |
| 3 ASP CG | −50.31 | −34.49 | 59.37 | 15.00 |
| 3 ASP OD1 | −50.61 | −34.58 | 58.16 | 15.00 |
| 3 ASP OD2 | −50.25 | −35.48 | 60.14 | 15.00 |
| 3 ASP C | −48.06 | −31.73 | 60.63 | 15.00 |
| 3 ASP O | −47.45 | −31.32 | 59.63 | 15.00 |
| 4 SER N | −48.18 | −31.03 | 61.75 | 15.00 |
| 4 SER CA | −47.72 | −29.67 | 61.87 | 15.00 |
| 4 SER CB | −48.86 | −28.74 | 61.51 | 15.00 |
| 4 SER OG | −48.48 | −27.37 | 61.57 | 15.00 |
| 4 SER C | −47.29 | −29.41 | 63.29 | 15.00 |
| 4 SER O | −47.89 | −29.91 | 64.23 | 15.00 |
| 5 VAL N | −46.20 | −28.66 | 63.43 | 15.00 |
| 5 VAL CA | −45.71 | −28.29 | 64.73 | 15.00 |
| 5 VAL CB | −44.98 | −29.44 | 65.47 | 15.00 |
| 5 VAL CG1 | −43.59 | −29.68 | 64.89 | 15.00 |
| 5 VAL CG2 | −44.88 | −29.11 | 66.96 | 15.00 |
| 5 VAL C | −44.81 | −27.08 | 64.62 | 15.00 |
| 5 VAL O | −44.04 | −26.93 | 63.66 | 15.00 |
| 6 ASP N | −44.96 | −26.20 | 65.59 | 15.00 |
| 6 ASP CA | −44.19 | −24.98 | 65.66 | 15.00 |
| 6 ASP CB | −45.08 | −23.81 | 65.22 | 15.00 |
| 6 ASP CG | −44.31 | −22.52 | 65.06 | 15.00 |
| 6 ASP OD1 | −43.13 | −22.45 | 65.49 | 15.00 |
| 6 ASP OD2 | −44.88 | −21.58 | 64.49 | 15.00 |
| 6 ASP C | −43.72 | −24.81 | 67.10 | 15.00 |
| 6 ASP O | −44.50 | −24.48 | 68.00 | 15.00 |
| 7 TYR N | −42.42 | −25.02 | 67.31 | 15.00 |
| 7 TYR CA | −41.83 | −24.90 | 68.64 | 15.00 |
| 7 TYR CB | −40.43 | −25.53 | 68.66 | 15.00 |
| 7 TYR CG | −40.49 | −27.05 | 68.76 | 15.00 |
| 7 TYR CD1 | −40.75 | −27.66 | 69.98 | 15.00 |
| 7 TYR CE1 | −40.88 | −29.04 | 70.08 | 15.00 |
| 7 TYR CD2 | −40.34 | −27.85 | 67.63 | 15.00 |
| 7 TYR CE2 | −40.47 | −29.24 | 67.72 | 15.00 |
| 7 TYR CZ | −40.74 | −29.83 | 68.95 | 15.00 |
| 7 TYR OH | −40.89 | −31.20 | 69.06 | 15.00 |
| 7 TYR C | −41.80 | −23.47 | 69.20 | 15.00 |
| 7 TYR O | −41.66 | −23.28 | 70.42 | 15.00 |
| 8 ARG N | −41.93 | −22.48 | 68.33 | 15.00 |
| 8 ARG CA | −41.95 | −21.08 | 68.77 | 15.00 |
| 8 ARG CB | −42.06 | −20.12 | 67.58 | 15.00 |
| 8 ARG CG | −40.92 | −20.21 | 66.57 | 15.00 |
| 8 ARG CD | −41.19 | −19.30 | 65.38 | 15.00 |
| 8 ARG NE | −42.23 | −19.84 | 64.51 | 15.00 |
| 8 ARG CZ | −42.66 | −19.26 | 63.38 | 15.00 |
| 8 ARG NH1 | −42.13 | −18.11 | 62.97 | 15.00 |
| 8 ARG NH2 | −43.61 | −19.84 | 62.66 | 15.00 |
| 8 ARG C | −43.20 | −20.93 | 69.64 | 15.00 |
| 8 ARG O | −43.18 | −20.25 | 70.68 | 15.00 |
| 9 LYS N | −44.28 | −21.58 | 69.21 | 15.00 |
| 9 LYS CA | −45.54 | −21.53 | 69.92 | 15.00 |
| 9 LYS CB | −46.66 | −22.14 | 69.08 | 15.00 |
| 9 LYS CG | −47.11 | −21.26 | 67.92 | 15.00 |
| 9 LYS CD | −47.98 | −22.07 | 66.95 | 15.00 |
| 9 LYS CE | −48.74 | −21.20 | 65.98 | 15.00 |
| 9 LYS NZ | −49.84 | −20.49 | 66.67 | 15.00 |
| 9 LYS C | −45.45 | −22.22 | 71.27 | 15.00 |
| 9 LYS O | −46.19 | −21.88 | 72.19 | 15.0OQ |
| 10 LYS N | −44.53 | −23.16 | 71.39 | 15.00 |
| 10 LYS CA | −44.30 | −23.91 | 72.63 | 15.00 |
| 10 LYS CB | −43.82 | −25.33 | 72.30 | 15.00 |
| 10 LYS CG | −44.90 | −26.25 | 71.75 | 15.00 |
| 10 LYS CD | −44.35 | −27.64 | 71.47 | 15.00 |
| 10 LYS CE | −45.48 | −28.63 | 71.20 | 15.00 |
| 10 LYS NZ | −44.99 | −30.01 | 70.87 | 15.00 |
| 10 LYS C | −43.28 | −23.22 | 73.53 | 15.00 |
| 10 LYS C | −42.94 | −23.73 | 74.60 | 15.00 |
| 11 GLY N | −42.75 | −22.09 | 73.09 | 15.00 |
| 11 GLY CA | −41.77 | −21.37 | 73.88 | 15.00 |
| 11 GLY C | −40.41 | −22.04 | 73.97 | 15.00 |
| 11 GLY O | −39.71 | −21.91 | 74.97 | 15.00 |
| 12 TYR N | −40.02 | −22.75 | 72.92 | 15.00 |
| 12 TYR CA | −38.73 | −23.41 | 72.89 | 15.00 |
| 12 TYR CB | −38.86 | −24.81 | 72.29 | 15.00 |
| 12 TYR CG | −39.47 | −25.86 | 73.18 | 15.00 |
| 12 TYR CD1 | −40.56 | −25.59 | 73.99 | 15.00 |
| 12 TYR CE1 | −41.12 | −26.56 | 74.81 | 15.00 |
| 12 TYR CD2 | −38.94 | −27.15 | 73.21 | 15.00 |
| 12 TYR CE2 | −39.49 | −28.14 | 74.02 | 15.00 |
| 12 TYR CZ | −40.58 | −27.84 | 74.82 | 15.00 |
| 12 TYR OH | −41.10 | −28.81 | 75.64 | 15.00 |
| 12 TYR C | −37.73 | −22.62 | 72.04 | 15.00 |
| 12 TYR C | −36.65 | −23.14 | 71.72 | 15.00 |
| 13 VAL N | −38.08 | −21.39 | 71.66 | 15.00 |
| 13 VAL CA | −37.21 | −20.59 | 70.80 | 15.00 |
| 13 VAL CB | −37.82 | −20.46 | 69.40 | 15.00 |
| 13 VAL CG1 | −36.75 | −20.07 | 68.38 | 15.00 |
| 13 VAL CG2 | −38.52 | −21.73 | 69.02 | 15.00 |
| 13 VAL C | −36.93 | −19.17 | 71.30 | 15.00 |
| 13 VAL O | −37.86 | −18.42 | 71.61 | 15.00 |
| 14 THR N | −35.66 | −18.79 | 71.34 | 15.00 |
| 14 THR CA | −35.29 | −17.45 | 71.78 | 15.00 |
| 14 THR CB | −33.84 | −17.40 | 72.32 | 15.00 |
| 14 THR OG1 | −32.91 | −17.76 | 71.28 | 15.00 |
| 14 THR CG2 | −33.67 | −18.33 | 73.52 | 15.00 |
| 14 THR C | −35.46 | −16.52 | 70.59 | 15.00 |
| 14 THR O | −35.55 | −16.96 | 69.46 | 15.00 |
| 15 PRO N | −35.49 | −15.20 | 70.84 | 15.00 |
| 15 PRO CD | −35.39 | −14.48 | 72.12 | 15.00 |
| 15 PRC CA | −35.65 | −14.27 | 69.72 | 15.00 |
| 15 PRO CB | −35.71 | −12.90 | 70.42 | 15.00 |
| 15 PRO CG | −34.93 | −13.12 | 71.67 | 15.00 |
| 15 PRO C | −34.54 | −14.35 | 68.69 | 15.00 |
| 15 PRO O | −33.45 | −14.89 | 68.95 | 15.00 |
| 16 VAL N | −34.85 | −13.85 | 67.50 | 15.00 |
| 16 VAL CA | −33.94 | −13.84 | 66.37 | 15.00 |
| 16 VAL CB | −34.68 | −13.41 | 65.08 | 15.00 |
| 16 VAL CG1 | −33.72 | −13.35 | 63.90 | 15.00 |
| 16 VAL CG2 | −35.82 | −14.39 | 64.78 | 15.00 |
| 16 VAL C | −32.71 | −12.94 | 66.61 | 15.00 |
| 16 VAL O | −32.84 | −11.79 | 67.04 | 15.00 |
| 17 LYS N | −31.54 | −13.50 | 66.33 | 15.00 |
| 17 LYS CA | −30.27 | −12.80 | 66.48 | 15.00 |
| 17 LYS CB | −29.26 | −13.70 | 67.22 | 15.00 |
| 17 LYS CG | −29.85 | −14.45 | 68.41 | 15.00 |

TABLE IV-continued

Table of the orthogonal three dimensional coordinates in Ångstroms and B factors (Å²) for the cathepsin K complex with inhibitor 2,2'-N,N'-bis-benzyloxycarbonyl-L-leucinylcarbohydrazide.

| Residue Atom | X | Y | Z | B |
|---|---|---|---|---|
| 17 LYS CD | −30.15 | −13.52 | 69.56 | 15.00 |
| 17 LYS CE | −31.10 | −14.14 | 70.58 | 15.00 |
| 17 LYS NZ | −30.73 | −15.52 | 70.94 | 15.00 |
| 17 LYS C | −29.70 | −12.43 | 65.09 | 15.00 |
| 17 LYS O | −30.25 | −12.81 | 64.05 | 15.00 |
| 18 ASN N | −28.59 | −11.71 | 65.10 | 15.00 |
| 18 ASN CA | −27.93 | −11.24 | 63.89 | 15.00 |
| 18 ASN CB | −28.25 | −9.75 | 63.69 | 15.00 |
| 18 ASN CG | −27.74 | −9.21 | 62.37 | 15.00 |
| 18 ASN OD1 | −27.34 | −9.95 | 61.49 | 15.00 |
| 18 ASN ND2 | −27.75 | −7.90 | 62.24 | 15.00 |
| 18 ASN C | −26.41 | −11.47 | 63.99 | 15.00 |
| 18 ASN O | −25.70 | −10.74 | 64.68 | 15.00 |
| 19 GLN N | −25.92 | −12.47 | 63.27 | 15.00 |
| 19 GLN CA | −24.50 | −12.81 | 63.27 | 15.00 |
| 19 GLN CB | −24.23 | −14.05 | 62.39 | 15.00 |
| 19 GLN CG | −24.59 | −13.91 | 60.91 | 15.00 |
| 19 GLN CD | −24.31 | −15.17 | 60.10 | 15.00 |
| 19 GLN OE1 | −25.15 | −16.06 | 60.00 | 15.00 |
| 19 GLN NE2 | −23.13 | −15.23 | 59.59 | 15.00 |
| 19 GLN C | −23.59 | −11.65 | 62.84 | 15.00 |
| 19 GLN O | −22.45 | −11.56 | 63.30 | 15.00 |
| 20 GLY N | −24.09 | −10.77 | 61.99 | 1S.00 |
| 20 GLY CA | −23.28 | −9.65 | 61.53 | 15.00 |
| 20 GLY C | −22.31 | −10.07 | 60.45 | 15.00 |
| 20 GLY O | −22.59 | −10.98 | 59.67 | 15.00 |
| 21 GLN N | −21.15 | −9.43 | 60.41 | 15.00 |
| 21 GLN CA | −20.14 | −9.75 | 59.41 | 15.00 |
| 21 GLN CB | −19.40 | −8.48 | 58.96 | 15.00 |
| 21 GLN CG | −20.22 | −7.59 | 58.06 | 15.00 |
| 21 GLN CD | −20.48 | −8.23 | 56.69 | 15.00 |
| 21 GLN OE1 | −19.88 | −9.26 | 56.33 | 15.00 |
| 21 GLN NE2 | −21.37 | −7.60 | 55.90 | 15.00 |
| 21 GLN C | −19.15 | −10.78 | 59.98 | 15.00 |
| 21 GLN O | −17.95 | −10.51 | 60.13 | 15.00 |
| 22 CYS N | −19.68 | −11.95 | 60.30 | 15.00 |
| 22 CYS CA | −18.90 | −13.04 | 60.86 | 15.00 |
| 22 CYS C | −19.59 | −14.32 | 60.46 | 15.00 |
| 22 CYS O | −20.82 | −14.40 | 60.50 | 15.00 |
| 22 CYS CB | −18.83 | −12.90 | 62.40 | 15.00 |
| 22 CYS SG | −18.13 | −14.32 | 63.33 | 15.00 |
| 23 GLY N | −18.81 | −15.30 | 60.03 | 15.00 |
| 23 GLY CA | −19.36 | −16.58 | 59.63 | 15.00 |
| 23 GLY C | −19.61 | −17.48 | 60.83 | 15.00 |
| 23 GLY O | −19.23 | −18.65 | 60.84 | 15.00 |
| 24 SER N | −20.32 | −16.94 | 61.82 | 15.00 |
| 24 SER CA | −20.63 | −17.67 | 63.03 | 15.00 |
| 24 SER CB | −20.58 | −16.71 | 64.22 | 15.00 |
| 24 SER OG | −21.38 | −15.58 | 64.00 | 15.00 |
| 24 SER C | −22.00 | −18.34 | 62.98 | 15.00 |
| 24 SER O | −22.52 | −18.78 | 64.01 | 15.00 |
| 25 CYS N | −22.59 | −18.45 | 61.79 | 15.00 |
| 25 CYS CA | −23.90 | −19.08 | 61.65 | 15.00 |
| 25 CYS CB | −24.31 | −19.15 | 60.17 | 15.00 |
| 25 CYS SG | −23.12 | −20.00 | 59.06 | 15.00 |
| 25 CYS C | −23.95 | −20.47 | 62.29 | 15.00 |
| 25 CYS O | −24.95 | −20.85 | 62.89 | 15.00 |
| 25 INH CT | −28.28 | −9.31 | 55.94 | 15.00 |
| 25 INH C2 | −28.07 | −9.03 | 57.30 | 15.00 |
| 25 INH C3 | −27.11 | −9.78 | 58.03 | 15.00 |
| 25 INH C4 | −26.37 | −10.78 | 57.40 | 15.00 |
| 25 INH C5 | −26.59 | −11.05 | 56.05 | 15.00 |
| 25 INH C6 | −27.54 | −10.32 | 55.31 | 15.00 |
| 25 INH C7 | −25.31 | −11.54 | 58.16 | 15.00 |
| 25 INH O8 | −24.19 | −11.68 | 57.24 | 15.00 |
| 25 INH C9 | −23.29 | −12.79 | 57.20 | 15.00 |
| 25 INH O10 | −22.50 | −12.99 | 58.13 | 15.00 |
| 25 INH C11 | −22.45 | −14.71 | 55.88 | 15.00 |
| 25 INH C12 | −21.05 | −14.47 | 56.48 | 15.00 |
| 25 INH C13 | −20.11 | −13.38 | 55.92 | 15.00 |
| 25 INH C14 | −19.15 | −12.91 | 57.01 | 15.00 |
| 25 INH C15 | −20.83 | −12.17 | 55.23 | 15.00 |
| 25 INH C16 | −23.00 | −16.06 | 56.34 | 15.00 |
| 25 INH O17 | −24.16 | −16.15 | 56.75 | 15.00 |
| 25 INH N18 | −22.19 | −17.17 | 56.30 | 15.00 |
| 25 INH N19 | −22.62 | −18.53 | 56.74 | 15.00 |
| 25 INH N20 | −23.34 | −13.55 | 56.10 | 15.00 |
| 25 INH C21 | −22.09 | −18.85 | 58.14 | 15.00 |
| 25 INH O22 | −22.10 | −17.80 | 58.75 | 15.00 |
| 25 INH C23 | −12.78 | −27.30 | 59.77 | 15.00 |
| 25 INH C24 | −13.75 | −26.80 | 60.62 | 15.00 |
| 25 INH C25 | −14.61 | −25.79 | 60.17 | 15.00 |
| 25 INH C26 | −14.52 | −25.29 | 58.88 | 15.00 |
| 25 INH C27 | −13.54 | −25.80 | 58.03 | 15.00 |
| 25 INH C28 | −12.67 | −26.81 | 58.47 | 15.00 |
| 25 INH C29 | −15.45 | −24.21 | 58.40 | 15.00 |
| 25 INH O30 | −16.52 | −24.58 | 57.49 | 15.00 |
| 25 INH C31 | −17.56 | −23.66 | 57.05 | 15.00 |
| 25 INH O32 | −47.32 | −22.74 | 56.27 | 15.00 |
| 25 INH C33 | −19.95 | −23.09 | 57.18 | 15.00 |
| 25 INH C34 | −21.23 | −23.90 | 57.35 | 15.00 |
| 25 INH C35 | −21.11 | −25.25 | 58.03 | 15.00 |
| 25 INH C36 | −22.32 | −25.59 | 58.89 | 15.00 |
| 25 INH C37 | −20.84 | −26.31 | 56.99 | 15.00 |
| 25 INH C38 | −20.07 | −21.83 | 58.03 | 15.00 |
| 25 INH O39 | −19.74 | −21.86 | 59.22 | 15.00 |
| 25 INH N40 | −20.56 | −20.70 | 57.43 | 15.00 |
| 25 INH N41 | −20.70 | −19.44 | 58.21 | 15.00 |
| 25 INH N42 | −18.78 | −23.90 | 57.54 | 15.00 |
| 26 TRP N | −22.83 | −21.19 | 62.21 | 15.00 |
| 26 TRP CA | −22.70 | −22.53 | 62.79 | 15.00 |
| 26 TRP CB | −21.33 | −23.13 | 62.41 | 15.00 |
| 26 TRP CG | −20.12 | −22.32 | 62.88 | 15.00 |
| 26 TRP CD2 | −19.43 | −22.44 | 64.14 | 15.00 |
| 26 TRP CE2 | −18.42 | −21.46 | 64.16 | 15.00 |
| 26 TRP CE3 | −19.58 | −23.27 | 65.26 | 15.00 |
| 26 TRP CD1 | −19.50 | −21.31 | 62.20 | 15.00 |
| 26 TRP NE1 | −18.48 | −20.79 | 62.96 | 15.00 |
| 26 TRP CZ2 | −17.56 | −21.29 | 65.25 | 15.00 |
| 26 TRP CZ3 | −18.73 | −23.10 | 66.34 | 15.00 |
| 26 TRP CH2 | −17.73 | −22.11 | 66.33 | 15.00 |
| 26 TRP C | −22.87 | −22.47 | 64.31 | 15.00 |
| 26 TRP O | −23.46 | −23.36 | 64.91 | 15.00 |
| 27 ALA N | −22.37 | −21.39 | 64.90 | 15.00 |
| 27 ALA CA | −22.43 | −21.17 | 66.34 | 15.00 |
| 27 ALA CB | −21.53 | −20.00 | 66.72 | 15.00 |
| 27 ALA C | −23.87 | −20.90 | 66.77 | 15.00 |
| 27 ALA O | −24.34 | −21.42 | 67.78 | 15.00 |
| 28 PHE N | −24.55 | −20.06 | 65.99 | 15.00 |
| 28 PHE CA | −25.94 | −19.71 | 66.23 | 15.00 |
| 28 PHE CB | −26.38 | −18.58 | 65.29 | 15.00 |
| 28 PHE CG | −25.85 | −17.23 | 65.70 | 15.00 |
| 28 PHE CD1 | −24.59 | −16.81 | 65.30 | 15.00 |
| 28 PHE CD2 | −26.60 | −16.39 | 66.52 | 15.00 |
| 28 PHE CE1 | −24.08 | −15.57 | 65.70 | 15.00 |
| 28 PHE CE2 | −26.09 | −15.15 | 66.93 | 15.00 |
| 28 PHE CZ | −24.83 | −14.74 | 66.52 | 15.00 |
| 28 PHE C | −26.86 | −20.93 | 66.07 | 15.00 |
| 28 PHE O | −27.82 | −21.10 | 66.82 | 15.00 |
| 29 SER N | −26.54 | −21.81 | 65.13 | 15.00 |
| 29 SER CA | −27.33 | −23.01 | 64.93 | 15.00 |
| 29 SER CB | −26.85 | −23.73 | 63.66 | 15.00 |
| 29 SER OG | −27.55 | −24.93 | 63.47 | 15.00 |
| 29 SER C | −27.19 | −23.93 | 66.16 | 15.00 |
| 29 SER O | −28.19 | −24.39 | 66.71 | 15.00 |
| 30 SER N | −25.95 | −24.16 | 66.59 | 15.00 |
| 30 SER CA | −25.63 | −25.00 | 67.75 | 15.00 |
| 30 SER CB | −24.12 | −24.97 | 68.04 | 15.00 |
| 30 SER OG | −23.34 | −25.28 | 66.91 | 15.00 |
| 30 SER C | −26.36 | −24.51 | 68.98 | 15.00 |
| 30 SER O | −27.02 | −25.26 | 69.69 | 15.00 |
| 31 VAL N | −26.16 | −23.23 | 69.26 | 15.00 |
| 31 VAL CA | −26.76 | −22.55 | 70.39 | 15.00 |
| 31 VAL CB | −26.31 | −21.07 | 70.38 | 15.00 |

TABLE IV-continued

Table of the orthogonal three dimensional coordinates in Ångstroms and B factors (Å²) for the cathepsin K complex with inhibitor 2,2'-N,N'-bis-benzyloxycarbonyl-L-leucinylcarbohydrazide.

| Residue Atom | X | Y | Z | B |
|---|---|---|---|---|
| 31 VAL CG1 | −27.42 | −20.13 | 70.84 | 15.00 |
| 31 VAL CG2 | −25.08 | −20.92 | 71.26 | 15.00 |
| 31 VAL C | −28.28 | −22.70 | 70.37 | 15.00 |
| 31 VAL O | −28.87 | −23.11 | 71.37 | 15.00 |
| 32 GLY N | −28.89 | −22.44 | 69.22 | 15.00 |
| 32 GLY CA | −30.32 | −22.56 | 69.08 | 15.00 |
| 32 GLY C | −30.79 | −23.96 | 69.45 | 15.00 |
| 32 GLY O | −31.80 | −24.12 | 70.14 | 15.00 |
| 33 ALA N | −30.03 | −24.96 | 69.01 | 15.00 |
| 33 ALA CA | −30.35 | −26.35 | 69.30 | 15.00 |
| 33 ALA CB | −29.44 | −27.29 | 68.48 | 15.00 |
| 33 ALA C | −30.24 | −26.64 | 70.80 | 15.00 |
| 33 ALA O | −31.11 | −27.29 | 71.38 | 15.00 |
| 34 LEU N | −29.17 | −26.15 | 71.42 | 15.00 |
| 34 LEU CA | −28.96 | −26.37 | 72.84 | 15.00 |
| 34 LEU CB | −27.61 | −25.82 | 73.28 | 15.00 |
| 34 LEU CG | −26.39 | −26.66 | 72.87 | 15.00 |
| 34 LEU CD1 | −25.12 | −25.82 | 72.89 | 15.00 |
| 34 LEU CD2 | −26.27 | −27.87 | 73.78 | 15.00 |
| 34 LEU C | −30.09 | −25.73 | 73.66 | 15.00 |
| 34 LEU O | −30.62 | −26.34 | 74.59 | 15.00 |
| 35 GLU N | −30.48 | −24.53 | 73.25 | 15.00 |
| 35 GLU CA | −31.55 | −23.78 | 73.90 | 15.00 |
| 35 GLU CB | −31.70 | −22.41 | 73.25 | 15.00 |
| 35 GLU CG | −30.49 | −21.53 | 73.41 | 15.00 |
| 35 GLU CD | −30.59 | −20.25 | 72.60 | 15.00 |
| 35 GLU OE1 | −31.42 | −20.17 | 71.67 | 15.00 |
| 35 CLU OE2 | −29.81 | −19.32 | 72.90 | 15.00 |
| 35 GLU C | −32.89 | −24.52 | 73.87 | 15.00 |
| 35 GLU O | −33.66 | −24.41 | 74.81 | 15.00 |
| 36 GLY N | −33.16 | −25.25 | 72.79 | 15.00 |
| 36 GLY CA | −34.41 | −25.97 | 72.72 | 15.00 |
| 36 GLY C | −34.42 | −27.05 | 73.78 | 15.00 |
| 36 GLY O | −35.32 | −27.13 | 74.61 | 15.00 |
| 37 GLN N | −33.35 | −27.86 | 73.77 | 15.00 |
| 37 GLN CA | −33.18 | −28.95 | 74.71 | 15.00 |
| 37 GLN CB | −31.95 | −29.77 | 74.32 | 15.00 |
| 37 GLN CG | −32.01 | −30.34 | 72.91 | 15.00 |
| 37 GLN CD | −33.22 | −31.25 | 72.69 | 15.00 |
| 37 GLN OE1 | −33.31 | −32.35 | 73.26 | 15.00 |
| 37 GLN NE2 | −34.16 | −30.78 | 71.87 | 15.00 |
| 37 GLN C | −33.10 | −28.48 | 76.17 | 15.00 |
| 37 GLN O | −33.70 | −29.09 | 77.06 | 15.00 |
| 38 LEU N | −32.38 | −27.39 | 76.40 | 15.00 |
| 38 LEU CA | −32.27 | −26.87 | 77.75 | 15.00 |
| 38 LEU CB | −31.39 | −25.63 | 77.79 | 15.00 |
| 38 LEU CG | −31.34 | −25.01 | 79.18 | 15.00 |
| 38 LEU CD1 | −30.49 | −25.87 | 80.11 | 15.00 |
| 38 LEU CD2 | −30.79 | −23.61 | 79.08 | 15.00 |
| 38 LEU C | −33.65 | −26.51 | 78.26 | 15.00 |
| 38 LEU O | −33.97 | −26.73 | 79.43 | 15.00 |
| 39 LYS N | −34.45 | −25.90 | 77.38 | 15.00 |
| 39 LYS CA | −35.81 | −25.51 | 77.72 | 15.00 |
| 39 LYS CB | −36.42 | −24.72 | 76.55 | 15.00 |
| 39 LYS CG | −37.63 | −23.88 | 76.91 | 15.00 |
| 39 LYS CD | −38.88 | −24.71 | 77.08 | 15.00 |
| 39 LYS CE | −39.79 | −24.14 | 78.15 | 15.00 |
| 39 LYS NZ | −39.99 | −22.66 | 78.01 | 15.00 |
| 39 LYS C | −36.61 | −26.78 | 78.00 | 15.00 |
| 39 LYS O | −37.28 | −26.89 | 79.04 | 15.00 |
| 40 LYS N | −36.48 | −27.75 | 77.11 | 15.00 |
| 40 LYS CA | −37.19 | −29.01 | 77.23 | 15.00 |
| 40 LYS CB | −36.93 | −29.90 | 76.01 | 15.00 |
| 40 LYS CG | −37.84 | −31.13 | 75.91 | 15.00 |
| 40 LYS CD | −37.59 | −31.87 | 74.60 | 15.00 |
| 40 LYS CE | −37.06 | −33.28 | 74.85 | 15.00 |
| 40 LYS NZ | −36.36 | −33.87 | 73.66 | 15.00 |
| 40 LYS C | −36.82 | −29.76 | 78.51 | 15.00 |
| 40 LYS O | −37.69 | −30.36 | 79.16 | 15.00 |
| 41 LYS N | −35.55 | −29.66 | 78.92 | 15.00 |
| 41 LYS CA | −35.08 | −30.37 | 80.10 | 15.00 |
| 41 LYS CB | −33.60 | −30.71 | 79.95 | 15.00 |
| 41 LYS CG | −33.12 | −31.74 | 80.95 | 15.00 |
| 41 LYS CD | −31.66 | −32.10 | 80.76 | 15.00 |
| 41 LYS CE | −31.18 | −33.02 | 81.87 | 15.00 |
| 41 LYS NZ | −31.86 | −34.35 | 81.80 | 15.00 |
| 41 LYS C | −35.32 | −29.68 | 81.45 | 15.00 |
| 41 LYS O | −35.76 | −30.32 | 82.40 | 15.00 |
| 42 THR N | −35.04 | −28.38 | 81.51 | 15.00 |
| 42 THR CA | −35.19 | −27.62 | 82.75 | 15.00 |
| 42 THR CB | −34.00 | −26.66 | 82.95 | 15.00 |
| 42 THR OG1 | −34.10 | −25.58 | 82.01 | 15.00 |
| 42 THR CG2 | −32.68 | −27.39 | 82.71 | 15.00 |
| 42 THR C | −36.46 | −26.78 | 82.86 | 15.00 |
| 42 THR O | −36.86 | −26.41 | 83.96 | 15.00 |
| 43 GLY N | −37.04 | −26.42 | 81.73 | 15.00 |
| 43 GLY CA | −38.24 | −25.60 | 81.75 | 15.00 |
| 43 GLY C | −37.95 | −24.12 | 81.59 | 15.00 |
| 43 GLY C | −38.88 | −23.31 | 81.62 | 15.00 |
| 44 LYS N | −36.67 | −23.75 | 81.48 | 15.00 |
| 44 LYS CA | −36.28 | −22.35 | 81.31 | 15.00 |
| 44 LYS CB | −35.14 | −21.96 | 82.26 | 15.00 |
| 44 LYS CG | −35.58 | −21.64 | 83.67 | 15.00 |
| 44 LYS CD | −35.80 | −22.90 | 84.47 | 15.00 |
| 44 LYS CE | −34.48 | −23.49 | 84.91 | 15.00 |
| 44 LYS NZ | −33.81 | −22.59 | 85.90 | 15.00 |
| 44 LYS C | −35.82 | −22.07 | 79.87 | 15.00 |
| 44 LYS O | −35.33 | −22.95 | 79.19 | 15.00 |
| 45 LEU N | −35.97 | −20.82 | 79.44 | 15.00 |
| 45 LEU CA | −35.56 | −20.40 | 78.11 | 15.00 |
| 45 LEU CB | −36.79 | −20.00 | 77.26 | 15.00 |
| 45 LEU CG | −36.54 | −19.61 | 75.80 | 15.00 |
| 45 LEU CD1 | −36.32 | −20.88 | 74.98 | 15.00 |
| 45 LEU CD2 | −37.71 | −18.81 | 75.22 | 15.00 |
| 45 LEU C | −34.65 | −19.18 | 78.26 | 15.00 |
| 45 LEU O | −35.09 | −18.11 | 78.69 | 15.00 |
| 46 LEU N | −33.36 | −19.38 | 78.00 | 15.00 |
| 46 LEU CA | −32.41 | −18.30 | 78.06 | 15.00 |
| 46 LEU CB | −31.64 | −18.25 | 79.40 | 15.00 |
| 46 LEU CG | −30.80 | −19.34 | 80.08 | 15.00 |
| 46 LEU CD1 | −31.61 | −20.01 | 81.15 | 15.00 |
| 46 LEU CD2 | −30.27 | −20.35 | 79.09 | 15.00 |
| 46 LEU C | −31.46 | −18.38 | 76.86 | 15.00 |
| 46 LEU C | −31.39 | −19.40 | 76.17 | 15.00 |
| 47 ASN N | −30.79 | −17.27 | 76.59 | 15.00 |
| 47 ASN CA | −29.86 | −17.18 | 75.47 | 15.00 |
| 47 ASN CB | −29.74 | −15.73 | 75.04 | 15.00 |
| 47 ASN CG | −31.07 | −15.14 | 74.66 | 15.00 |
| 47 ASN OD1 | −31.74 | −15.64 | 73.75 | 15.00 |
| 47 ASN ND2 | −31.50 | −14.13 | 75.39 | 15.00 |
| 47 ASN C | −28.51 | −17.75 | 75.81 | 15.00 |
| 47 ASN O | −27.91 | −17.37 | 76.81 | 15.00 |
| 48 LEU N | −28.07 | −18.74 | 75.05 | 15.00 |
| 48 LEU CA | −26.77 | −19.34 | 75.27 | 15.00 |
| 48 LEU CB | −26.81 | −20.84 | 74.95 | 15.00 |
| 48 LEU CG | −27.74 | −21.60 | 75.90 | 15.00 |
| 48 LEU CD1 | −27.67 | −23.09 | 75.67 | 15.00 |
| 48 LEU CD2 | −27.37 | −21.30 | 77.33 | 15.00 |
| 48 LEU C | −25.77 | −18.57 | 74.42 | 15.00 |
| 48 LEU O | −26.17 | −17.88 | 73.47 | 15.00 |
| 49 SER N | −24.50 | −18.67 | 74.76 | 15.00 |
| 49 SER CA | −23.45 | −17.92 | 74.09 | 15.00 |
| 49 SER CB | −22.32 | −17.62 | 75.08 | 15.00 |
| 49 SER OG | −21.28 | −16.87 | 74.48 | 15.00 |
| 49 SER C | −22.83 | −18.44 | 72.80 | 15.00 |
| 49 SER O | −22.08 | −19.40 | 72.82 | 15.00 |
| 50 PRO N | −23.10 | −17.78 | 71.67 | 15.00 |
| 50 PRO CD | −24.13 | −16.75 | 71.42 | 15.00 |
| 50 PRC CA | −22.50 | −18.23 | 70.41 | 15.00 |
| 50 PRO CB | −23.27 | −17.43 | 69.35 | 15.00 |
| 50 PRO CG | −24.58 | −17.10 | 70.04 | 15.00 |
| 50 PRO C | −21.01 | −17.85 | 70.42 | 15.00 |
| 50 PRC O | −20.16 | −18.58 | 69.92 | 15.00 |
| 51 GLN N | −20.70 | −16.70 | 71.03 | 15.00 |

TABLE IV-continued

Table of the orthogonal three dimensional coordinates in Ångstroms and B factors (Å²) for the cathepsin K complex with inhibitor 2,2'-N,N'-bis-benzyloxycarbonyl-L-leucinylcarbohydrazide.

| Residue Atom | X | Y | Z | B |
|---|---|---|---|---|
| 51 GLN CA | −19.34 | −16.20 | 71.12 | 15.00 |
| 51 GLN CB | −19.32 | −14.84 | 71.83 | 15.00 |
| 51 GLN CG | −18.00 | −14.10 | 71.73 | 15.00 |
| 51 GLN CD | −17.72 | −13.59 | 70.34 | 15.00 |
| 51 GLN OE1 | −18.55 | −12.90 | 69.73 | 15.00 |
| 51 GLN NE2 | −16.55 | −13.90 | 69.82 | 15.00 |
| 51 GLN C | −18.45 | −17.21 | 71.86 | 15.00 |
| 51 GLN O | −17.28 | −17.39 | 71.50 | 15.00 |
| 52 ASN N | −19.01 | −17.87 | 72.87 | 15.00 |
| 52 ASN CA | −18.28 | −18.88 | 73.62 | 15.00 |
| 52 ASN CB | −19.24 | −19.57 | 74.60 | 15.00 |
| 52 ASN CG | −18.54 | −20.47 | 75.63 | 15.00 |
| 52 ASN OD1 | −19.19 | −20.95 | 76.57 | 15.00 |
| 52 ASN ND2 | −17.24 | −20.70 | 75.48 | 15.00 |
| 52 ASN C | −17.74 | −19.88 | 72.59 | 15.00 |
| 52 ASN O | −16.55 | −20.22 | 72.60 | 15.00 |
| 53 LEU N | −18.60 | −20.31 | 71.68 | 15.00 |
| 53 LEU CA | −18.22 | −21.26 | 70.64 | 15.00 |
| 53 LEU CB | −19.47 | −21.70 | 69.86 | 15.00 |
| 53 LEU CG | −20.37 | −22.81 | 70.42 | 15.00 |
| 53 LEU CD1 | −20.05 | −23.13 | 71.87 | 15.00 |
| 53 LEU CD2 | −21.83 | −22.41 | 70.22 | 15.00 |
| 53 LEU C | −17.18 | −20.69 | 69.68 | 15.00 |
| 53 LEU O | −16.17 | −21.33 | 69.40 | 15.00 |
| 54 VAL N | −17.44 | −19.48 | 69.18 | 15.00 |
| 54 VAL CA | −16.55 | −18.82 | 68.23 | 15.00 |
| 54 VAL CB | −17.03 | −17.36 | 67.92 | 15.00 |
| 54 VAL CG1 | −15.96 | −16.58 | 67.19 | 15.00 |
| 54 VAL CG2 | −18.28 | −17.40 | 67.05 | 15.00 |
| 54 VAL C | −15.10 | −18.79 | 68.72 | 15.00 |
| 54 VAL O | −14.19 | −19.17 | 67.98 | 15.00 |
| 55 ASP N | −14.90 | −18.37 | 69.96 | 15.00 |
| 55 ASP CA | −13.56 | −18.26 | 70.51 | 15.00 |
| 55 ASP CB | −13.56 | −17.25 | 71.67 | 15.00 |
| 55 ASP CG | −14.04 | −15.87 | 71.27 | 15.00 |
| 55 ASP OD1 | −14.02 | −15.54 | 70.06 | 15.00 |
| 55 ASP OD2 | −14.43 | −15.10 | 72.18 | 15.00 |
| 55 ASP C | −12.93 | −19.55 | 71.04 | 15.00 |
| 55 ASP O | −11.72 | −19.70 | 71.00 | 15.00 |
| 56 CYS N | −13.76 | −20.47 | 71.50 | 15.00 |
| 56 CYS CA | −13.26 | −21.69 | 72.14 | 15.00 |
| 56 CYS C | −13.18 | −23.02 | 71.37 | 15.00 |
| 56 CYS O | −12.34 | −23.86 | 71.72 | 15.00 |
| 56 CYS CB | −14.03 | −21.89 | 73.45 | 15.00 |
| 56 CYS SG | −14.05 | −20.41 | 74.53 | 15.00 |
| 57 VAL N | −14.03 | −23.22 | 70.37 | 15.00 |
| 57 VAL CA | −14.00 | −24.47 | 69.62 | 15.00 |
| 57 VAL CB | −15.34 | −24.76 | 68.86 | 15.00 |
| 57 VAL CG1 | −15.38 | −26.20 | 68.38 | 15.00 |
| 57 VAL CG2 | −16.52 | −24.51 | 69.77 | 15.00 |
| 57 VAL C | −12.80 | −24.45 | 68.66 | 15.00 |
| 57 VAL O | −12.85 | −23.83 | 67.60 | 15.00 |
| 58 SER N | −11.72 | −25.10 | 69.08 | 15.00 |
| 58 SER CA | −10.48 | −25.16 | 68.32 | 15.00 |
| 58 SER CB | −9.34 | −25.68 | 69.21 | 15.00 |
| 58 SER OG | −9.70 | −26.91 | 69.82 | 15.00 |
| 58 SER C | −10.53 | −25.97 | 67.03 | 15.00 |
| 58 SER O | −9.67 | −25.81 | 66.17 | 15.00 |
| 59 GLU N | −11.4.9 | −26.88 | 66.92 | 15.00 |
| 59 GLU CA | −11.62 | −27.68 | 65.70 | 15.00 |
| 59 GLU CB | −12.33 | −29.00 | 65.99 | 15.00 |
| 59 GLU CG | −11.57 | −29.96 | 66.92 | 15.00 |
| 59 GLU CD | −11.66 | −29.59 | 68.40 | 15.00 |
| 59 GLU OE1 | −10.69 | −29.88 | 69.12 | 15.00 |
| 59 GLU OE2 | −12.69 | −29.03 | 68.85 | 15.00 |
| 59 GLU C | −12.37 | −26.89 | 64.62 | 15.00 |
| 59 GLU O | −12.48 | −27.34 | 63.49 | 15.00 |
| 60 ASN N | −12.91 | −25.73 | 64.98 | 15.00 |
| 60 ASN CA | −13.65 | −24.87 | 64.06 | 15.00 |
| 60 ASN CB | −14.99 | −24.44 | 64.66 | 15.00 |
| 60 ASN CG | −16.08 | −25.51 | 64.51 | 15.00 |
| 60 ASN OD1 | −17.16 | −25.38 | 65.08 | 15.00 |
| 60 ASN ND2 | −15.79 | −26.55 | 63.74 | 15.00 |
| 60 ASN C | −12.81 | −23.65 | 63.73 | 15.00 |
| 60 ASN O | −11.76 | −23.44 | 64.35 | 15.00 |
| 61 ASP N | −13.28 | −22.85 | 62.78 | 15.00 |
| 61 ASP CA | −12.53 | −21.67 | 62.38 | 15.00 |
| 61 ASP CB | −12.22 | −21.74 | 60.88 | 15.00 |
| 61 ASP CG | −11.54 | −23.04 | 60.50 | 15.00 |
| 61 ASP OD1 | −12.02 | −23.72 | 59.56 | 15.00 |
| 61 ASP OD2 | −10.54 | −23.41 | 61.16 | 15.00 |
| 61 ASP C | −13.13 | −20.31 | 62.74 | 15.00 |
| 61 ASP O | −12.89 | −19.32 | 62.04 | 15.00 |
| 62 GLY N | −13.88 | −20.27 | 63.83 | 15.00 |
| 62 GLY CA | −14.48 | −19.03 | 64.30 | 15.00 |
| 62 GLY C | −15.34 | −18.30 | 63.30 | 15.00 |
| 62 GLY O | −16.37 | −18.81 | 62.87 | 15.00 |
| 63 CYS N | −14.96 | −17.07 | 62.96 | 15.00 |
| 63 CYS CA | −15.71 | −16.28 | 61.99 | 15.00 |
| 63 CYS C | −15.49 | −16.79 | 60.56 | 15.00 |
| 63 CYS O | −16.19 | −16.39 | 59.63 | 15.00 |
| 63 CYS CB | −15.37 | −14.79 | 62.10 | 15.00 |
| 63 CYS SG | −16.14 | −13.94 | 63.53 | 15.00 |
| 64 GLY N | −14.55 | −17.71 | 60.41 | 15.00 |
| 64 GLY CA | −14.27 | −18.27 | 59.10 | 15.00 |
| 64 GLY C | −15.11 | −19.50 | 58.79 | 15.00 |
| 64 GLY O | −14.95 | −20.10 | 57.73 | 15.00 |
| 65 GLY N | −15.94 | −19.92 | 59.74 | 15.00 |
| 65 GLY CA | −16.78 | −21.08 | 59.52 | 15.00 |
| 65 GLY C | −16.54 | −22.20 | 60.51 | 15.00 |
| 65 GLY O | −15.54 | −22.20 | 61.24 | 15.00 |
| 66 GLY N | −17.44 | −23.18 | 60.52 | 15.00 |
| 66 GLY CA | −17.29 | −24.31 | 61.41 | 15.00 |
| 66 GLY C | −18.41 | −25.32 | 61.27 | 15.00 |
| 66 GLY O | −19.25 | −25.19 | 60.37 | 15.00 |
| 67 TYR N | −18.41 | −26.34 | 62.13 | 15.00 |
| 67 TYR CA | −19.42 | −27.39 | 62.15 | 15.00 |
| 67 TYR CB | −18.78 | −28.74 | 61.83 | 15.00 |
| 67 TYR CG | −18.30 | −28.84 | 60.41 | 15.00 |
| 67 TYR CD1 | −19.02 | −29.55 | 59.47 | 15.00 |
| 67 TYR CE1 | −18.62 | −29.59 | 58.13 | 15.00 |
| 67 TYR CD2 | −17.15 | −28.16 | 60.00 | 15.00 |
| 67 TYR CE2 | −16.74 | −28.19 | 58.67 | 15.00 |
| 67 TYR CZ | −17.48 | −28.90 | 57.74 | 15.00 |
| 67 TYR OH | −17.12 | −28.88 | 56.42 | 15.00 |
| 67 TYR C | −20.12 | −27.46 | 63.51 | 15.00 |
| 67 TYR O | −19.48 | −27.31 | 64.54 | 15.00 |
| 68 MET N | −21.43 | −27.73 | 63.50 | 15.00 |
| 68 MET CA | −22.22 | −27.81 | 64.73 | 15.00 |
| 68 MET CB | −23.72 | −27.83 | 64.41 | 15.00 |
| 68 MET CG | −24.26 | −26.60 | 63.63 | 15.00 |
| 68 MET SD | −24.05 | −26.62 | 61.79 | 15.00 |
| 68 MET CE | −25.42 | −27.66 | 61.31 | 15.00 |
| 68 MET C | −21.84 | −29.02 | 65.61 | 15.00 |
| 68 MET O | −21.89 | −28.95 | 66.84 | 15.00 |
| 69 THR N | −21.48 | −30.12 | 64.98 | 15.00 |
| 69 THR CA | −21.08 | −31.33 | 65.70 | 15.00 |
| 69 THR CB | −20.80 | −32.51 | 64.73 | 15.00 |
| 69 THR OG1 | −20.08 | −32.02 | 63.58 | 15.00 |
| 69 THR CG2 | −22.12 | −33.15 | 64.27 | 15.00 |
| 69 THR C | −19.82 | −31.05 | 66.53 | 15.00 |
| 69 THR O | −19.67 | −31.55 | 67.66 | 15.00 |
| 70 ASN N | −18.94 | −30.21 | 65.99 | 15.00 |
| 70 ASN CA | −17.72 | −29.85 | 66.69 | 15.00 |
| 70 ASN CB | −16.76 | −29.07 | 65.79 | 15.00 |
| 70 ASN CG | −15.89 | −29.97 | 64.95 | 15.00 |
| 70 ASN OD1 | −15.35 | −29.56 | 63.93 | 15.00 |
| 70 ASN ND2 | −15.72 | −31.21 | 65.39 | 15.00 |
| 70 ASN C | −18.08 | −29.02 | 67.91 | 15.00 |
| 70 ASN O | −17.57 | −29.25 | 69.00 | 15.00 |
| 71 ALA N | −19.02 | −28.09 | 67.71 | 15.00 |
| 71 ALA CA | −19.50 | −27.22 | 68.77 | 15.00 |
| 71 ALA CB | −20.49 | −26.20 | 68.21 | 15.00 |
| 71 ALA C | −20.14 | −28.02 | 69.90 | 15.00 |

TABLE IV-continued

Table of the orthogonal three dimensional coordinates in Ångstroms and B factors (Å²) for the cathepsin K complex with inhibitor 2,2'-N,N'-bis-benzyloxycarbonyl-L-leucinylcarbohydrazide.

| Residue Atom | X | Y | Z | B |
|---|---|---|---|---|
| 71 ALA O | −19.88 | −27.76 | 71.07 | 15.00 |
| 72 PHE N | −20.90 | −29.05 | 69.55 | 15.00 |
| 72 PHE CA | −21.56 | −29.89 | 70.55 | 15.00 |
| 72 PHE CB | −22.55 | −30.86 | 69.89 | 15.00 |
| 72 PHE CG | −23.72 | −30.18 | 69.24 | 15.00 |
| 72 PHE CD1 | −24.30 | −29.05 | 69.82 | 15.00 |
| 72 PHE CD2 | −24.23 | −30.65 | 68.04 | 15.00 |
| 72 PHE CE1 | −25.38 | −28.41 | 69.21 | 15.00 |
| 72 PHE CE2 | −25.31 | −30.01 | 67.42 | 15.00 |
| 72 PHE CZ | −25.89 | −28.89 | 68.01 | 15.00 |
| 72 PHE C | −20.53 | −30.68 | 71.37 | 15.00 |
| 72 PHE O | −20.66 | −30.76 | 72.60 | 15.00 |
| 73 GLN N | −19.55 | −31.27 | 70.69 | 15.00 |
| 73 GLN CA | −18.50 | −32.05 | 71.34 | 15.00 |
| 73 GLN CB | −17.52 | −32.66 | 70.34 | 15.00 |
| 73 GLN CG | −18.09 | −33.80 | 69.51 | 15.00 |
| 73 GLN CD | −17.03 | −34.63 | 68.79 | 15.00 |
| 73 GLN OE1 | −17.20 | −35.01 | 67.62 | 15.00 |
| 73 GLN NE2 | −15.95 | −34.94 | 69.49 | 15.00 |
| 73 GLN C | −17.75 | −31.16 | 72.30 | 15.00 |
| 73 GLN O | −17.35 | −31.61 | 73.38 | 15.00 |
| 74 TYR N | −17.55 | −29.89 | 71.92 | 15.00 |
| 74 TYR CA | −16.84 | −28.94 | 72.75 | 15.00 |
| 74 TYR CB | −16.75 | −27.57 | 72.08 | 15.00 |
| 74 TYR CG | −16.46 | −26.43 | 73.03 | 15.00 |
| 74 TYR CD1 | −15.18 | −26.26 | 73.58 | 15.00 |
| 74 TYR CE1 | −14.91 | −25.23 | 74.50 | 15.00 |
| 74 TYR CD2 | −17.46 | −25.54 | 73.42 | 15.00 |
| 74 TYR CE2 | −17.21 | −24.51 | 74.34 | 15.00 |
| 74 TYR CZ | −15.93 | −24.36 | 74.88 | 15.00 |
| 74 TYR OH | −15.69 | −23.36 | 75.78 | 15.00 |
| 74 TYR C | −17.58 | −28.81 | 74.06 | 15.00 |
| 74 TYR O | −17.02 | −29.09 | 75.12 | 15.00 |
| 75 VAL N | −18.84 | −28.39 | 73.99 | 15.00 |
| 75 VAL CA | −19.67 | −28.21 | 75.17 | 15.00 |
| 75 VAL CB | −21.14 | −27.89 | 74.77 | 15.00 |
| 75 VAL CG1 | −22.00 | −27.77 | 76.01 | 15.00 |
| 75 VAL CG2 | −21.20 | −26.59 | 73.96 | 15.00 |
| 75 VAL C | −19.61 | −29.43 | 76.09 | 15.00 |
| 75 VAL O | −19.55 | −29.27 | 77.31 | 15.00 |
| 76 GLN N | −19.56 | −30.63 | 75.51 | 15.00 |
| 76 GLN CA | −19.48 | −31.85 | 76.29 | 15.00 |
| 76 GLN CB | −19.68 | −33.09 | 75.42 | 15.00 |
| 76 GLN CG | −19.53 | −34.39 | 76.19 | 15.00 |
| 76 GLN CD | −19.73 | −35.63 | 75.35 | 15.00 |
| 76 GLN OE1 | −19.39 | −35.66 | 74.17 | 15.00 |
| 76 GLN NE2 | −20.27 | −36.67 | 75.97 | 15.00 |
| 76 GLN C | −18.15 | −31.96 | 77.03 | 15.00 |
| 76 GLN O | −18.14 | −32.20 | 78.23 | 15.00 |
| 77 LYS N | −17.05 | −31.81 | 76.30 | 15.00 |
| 77 LYS CA | −15.70 | −31.90 | 76.87 | 15.00 |
| 77 LYS CB | −14.63 | −31.71 | 75.79 | 15.00 |
| 77 LYS CG | −14.73 | −32.63 | 74.61 | 15.00 |
| 77 LYS CD | −14.44 | −34.07 | 74.97 | 15.00 |
| 77 LYS CE | −14.49 | −34.96 | 73.73 | 15.00 |
| 77 LYS NZ | −13.56 | −34.52 | 72.63 | 15.00 |
| 77 LYS C | −15.51 | −30.80 | 77.93 | 15.00 |
| 77 LYS O | −15.07 | −31.05 | 79.04 | 15.00 |
| 78 ASN N | −15.87 | −29.58 | 77.55 | 15.00 |
| 78 ASN CA | −15.78 | −28.42 | 78.42 | 15.00 |
| 78 ASN CB | −16.11 | −27.17 | 77.61 | 15.00 |
| 78 ASN CG | −15.75 | −25.90 | 78.33 | 15.00 |
| 78 ASN OD1 | −14.65 | −25.77 | 78.86 | 15.00 |
| 78 ASN ND2 | −16.66 | −24.93 | 78.33 | 15.00 |
| 78 ASN C | −16.76 | −28.55 | 79.61 | 15.00 |
| 78 ASN O | −16.66 | −27.82 | 80.59 | 15.00 |
| 79 ARG N | −17.70 | −29.48 | 79.47 | 15.00 |
| 79 ARG CA | −18.73 | −29.76 | 80.46 | 15.00 |
| 79 ARG CB | −18.11 | −30.22 | 81.77 | 15.00 |
| 79 ARC CG | −17.42 | −31.56 | 81.70 | 15.00 |
| 79 ARG CD | −16.95 | −31.93 | 83.08 | 15.00 |
| 79 ARG NE | −16.17 | −33.15 | 83.11 | 15.00 |
| 79 ARG CZ | −14.86 | −33.22 | 82.89 | 15.00 |
| 79 ARG NH1 | −14.17 | −32.13 | 82.58 | 15.00 |
| 79 ARG NH2 | −14.21 | −34.37 | 83.07 | 15.00 |
| 79 ARG C | −19.66 | −28.58 | 80.71 | 15.00 |
| 79 ARG O | −20.27 | −28.49 | 81.78 | 15.00 |
| 80 GLY N | −19.79 | −27.70 | 79.72 | 15.00 |
| 80 GLY CA | −20.65 | −26.55 | 79.87 | 15.00 |
| 80 GLY C | −20.48 | −25.48 | 78.81 | 15.00 |
| 80 GLY O | −19.54 | −25.52 | 78.01 | 15.00 |
| 81 ILE N | −21.41 | −24.53 | 78.80 | 15.00 |
| 81 ILE CA | −21.40 | −23.40 | 77.88 | 15.00 |
| 81 ILE CB | −22.23 | −23.68 | 76.58 | 15.00 |
| 81 ILE CG2 | −23.68 | −24.05 | 76.93 | 15.00 |
| 81 ILE CG1 | −22.19 | −22.46 | 75.64 | 15.00 |
| 81 ILE CD1 | −22.89 | −22.66 | 74.31 | 15.00 |
| 81 ILE C | −21.99 | −22.20 | 78.62 | 15.00 |
| 81 ILE O | −22.91 | −22.35 | 79.43 | 15.00 |
| 82 ASP N | −21.44 | −21.02 | 78.37 | 15.00 |
| 82 ASP CA | −21.91 | −19.81 | 79.01 | 15.00 |
| 82 ASP CB | −20.85 | −18.71 | 78.94 | 15.00 |
| 82 ASP CG | −19.73 | −18.92 | 79.95 | 15.00 |
| 82 ASP OD1 | −18.66 | −18.32 | 79.78 | 15.00 |
| 82 ASP OD2 | −19.93 | −19.69 | 80.91 | 15.00 |
| 82 ASP C | −23.21 | −19.25 | 78.45 | 15.00 |
| 82 ASP O | −23.63 | −19.58 | 77.33 | 15.00 |
| 83 SER N | −23.86 | −18.43 | 79.26 | 15.00 |
| 83 SER CA | −25.09 | −17.78 | 78.85 | 15.00 |
| 83 SER CB | −25.92 | −17.36 | 80.08 | 15.00 |
| 83 SER OG | −25.25 | −16.38 | 80.86 | 15.00 |
| 83 SER C | −24.65 | −16.55 | 78.06 | 15.00 |
| 83 SER O | −23.50 | −16.10 | 78.17 | 15.00 |
| 84 GLU N | −25.56 | −16.01 | 77.26 | 15.00 |
| 84 GLU CA | −25.27 | −14.83 | 76.47 | 15.00 |
| 84 GLU CB | −26.53 | −14.40 | 75.70 | 15.00 |
| 84 GLU CG | −26.39 | −13.10 | 74.93 | 15.00 |
| 84 GLU CD | −25.30 | −13.12 | 73.85 | 15.00 |
| 84 GLU OE1 | −24.76 | −12.04 | 73.52 | 15.00 |
| 84 GLU OE2 | −24.98 | −14.22 | 73.33 | 15.00 |
| 84 GLU C | −24.77 | −13.70 | 77.38 | 15.00 |
| 84 GLU O | −23.77 | −13.09 | 77.06 | 15.00 |
| 85 ASP N | −25.44 | −13.47 | 78.51 | 15.00 |
| 85 ASP CA | −25.05 | −12.41 | 79.46 | 15.00 |
| 85 ASP CB | −26.03 | −12.35 | 80.65 | 15.00 |
| 85 ASP CG | −27.20 | −11.39 | 80.42 | 15.00 |
| 85 ASP OD1 | −27.86 | −11.50 | 79.37 | 15.00 |
| 85 ASP OD2 | −27.47 | −10.53 | 81.29 | 15.00 |
| 85 ASP C | −23.62 | −12.54 | 79.98 | 15.00 |
| 85 ASP O | −22.89 | −11.55 | 80.07 | 15.00 |
| 86 ALA N | −23.23 | −13.77 | 80.27 | 15.00 |
| 86 ALA CA | −21.91 | −14.09 | 80.78 | 15.00 |
| 86 ALA CB | −21.95 | −15.45 | 81.49 | 15.00 |
| 86 ALA C | −20.79 | −14.09 | 79.71 | 15.00 |
| 86 ALA O | −19.61 | −14.21 | 80.04 | 15.00 |
| 87 TYR N | −21.16 | −13.98 | 78.44 | 15.00 |
| 87 TYR CA | −20.18 | −13.99 | 77.36 | 15.00 |
| 87 TYR CB | −19.75 | −15.44 | 77.09 | 15.00 |
| 87 TYR CG | −18.36 | −15.67 | 76.52 | 15.00 |
| 87 TYR CD1 | −17.82 | −14.83 | 75.54 | 15.00 |
| 87 TYR CE1 | −16.55 | −15.09 | 74.99 | 15.00 |
| 87 TYR CD2 | −17.60 | −16.76 | 76.94 | 15.00 |
| 87 TYR CE2 | −16.34 | −17.03 | 76.40 | 15.00 |
| 87 TYR CZ | −15.82 | −16.19 | 75.42 | 15.00 |
| 87 TYR OH | −14.59 | −16.49 | 74.88 | 15.00 |
| 87 TYR C | −20.90 | −13.42 | 76.14 | 15.00 |
| 87 TYR O | −21.25 | −14.15 | 75.22 | 15.00 |
| 88 PRO N | −21.09 | −12.09 | 76.11 | 15.00 |
| 88 PRO CD | −20.58 | −11.10 | 77.08 | 15.00 |
| 88 PRO CA | −21.77 | −11.42 | 75.00 | 15.00 |
| 88 PRO CB | −21.83 | −9.97 | 75.47 | 15.00 |
| 88 PRO CG | −20.62 | −9.82 | 76.28 | 15.00 |
| 88 PRO C | −21.13 | −11.58 | 73.62 | 15.00 |
| 88 PRO O | −19.92 | −11.77 | 73.47 | 15.00 |

TABLE IV-continued

Table of the orthogonal three dimensional coordinates in Ångstroms and B factors (Å²) for the cathepsin K complex with inhibitor 2,2'-N,N'-bis-benzyloxycarbonyl-L-leucinylcarbohydrazide.

| Residue Atom | X | Y | Z | B |
|---|---|---|---|---|
| 89 TYR N | -21.98 | -11.45 | 72.61 | 15.00 |
| 89 TYR CA | -21.56 | -11.59 | 71.22 | 15.00 |
| 89 TYR CB | -22.77 | -11.93 | 70.35 | 15.00 |
| 89 TYR CG | -22.41 | -12.26 | 68.92 | 15.00 |
| 89 TYR CD1 | -21.67 | -13.41 | 68.62 | 15.00 |
| 89 TYR CE1 | -21.30 | -13.71 | 67.32 | 15.00 |
| 89 TYR CD2 | -22.78 | -11.43 | 67.87 | 15.00 |
| 89 TYR CE2 | -22.41 | -11.72 | 66.56 | 15.00 |
| 89 TYR CZ | -21.68 | -12.87 | 66.30 | 15.00 |
| 89 TYR OH | -21.29 | -13.15 | 65.01 | 15.00 |
| 89 TYR C | -20.91 | -10.31 | 70.72 | 15.00 |
| 89 TYR C | -21.45 | -9.21 | 70.89 | 15.00 |
| 90 VAL N | -19.73 | -10.45 | 70.13 | 15.00 |
| 90 VAL CA | -19.01 | -9.31 | 69.58 | 15.00 |
| 90 VAL CB | -17.59 | -9.14 | 70.23 | 15.00 |
| 90 VAL CG1 | -17.71 | -8.96 | 71.73 | 15.00 |
| 90 VAL CG2 | -16.69 | -10.31 | 69.89 | 15.00 |
| 90 VAL C | -18.88 | -9.45 | 68.06 | 15.00 |
| 90 VAL O | -18.50 | -8.50 | 67.38 | 15.00 |
| 91 GLY N | -19.17 | -10.63 | 67.53 | 15.00 |
| 91 GLY CA | -19.08 | -10.82 | 66.09 | 15.00 |
| 91 GLY C | -17.67 | -10.74 | 65.55 | 15.00 |
| 91 GLY O | -17.44 | -10.33 | 64.40 | 15.00 |
| 92 GLN N | -16.71 | -11.14 | 66.37 | 15.00 |
| 92 GLN CA | -15.31 | -11.12 | 66.00 | 15.00 |
| 92 GLN CB | -14.73 | -9.72 | 66.26 | 15.00 |
| 92 GLN CG | -13.35 | -9.49 | 65.65 | 15.00 |
| 92 GLN CD | -12.71 | -8.19 | 66.08 | 15.00 |
| 92 GLN OE1 | -12.20 | -7.44 | 65.24 | 15.00 |
| 92 GLN NE2 | -12.73 | -7.92 | 67.39 | 15.00 |
| 92 GLN C | -14.60 | -12.19 | 66.82 | 15.00 |
| 92 GLN O | -15.02 | -12.50 | 67.94 | 15.00 |
| 93 GLU N | -13.54 | -12.78 | 66.26 | 15.00 |
| 93 GLU CA | -12.77 | -13.82 | 66.94 | 15.00 |
| 93 GLU CB | -11.86 | -14.56 | 65.94 | 15.00 |
| 93 GLU CG | -12.59 | -15.03 | 64.68 | 15.00 |
| 93 GLU CD | -11.65 | -15.50 | 63.57 | 15.00 |
| 93 GLU OE1 | -10.57 | -14.88 | 63.36 | 15.00 |
| 93 GLU OE2 | -12.02 | -16.49 | 62.88 | 15.00 |
| 93 GLU C | -11.92 | -13.20 | 68.04 | 15.00 |
| 93 GLU O | -11.31 | -12.14 | 67.84 | 15.00 |
| 94 GLU N | -11.90 | -13.84 | 69.20 | 15.00 |
| 94 GLU CA | -11.15 | -13.38 | 70.36 | 15.00 |
| 94 GLU CB | -12.03 | -12.49 | 71.25 | 15.00 |
| 94 GLU CG | -12.71 | -11.36 | 70.48 | 15.00 |
| 94 GLU CD | -13.30 | -10.28 | 71.35 | 15.00 |
| 94 GLU OE1 | -13.81 | -10.60 | 72.43 | 15.00 |
| 94 GLU OE2 | -13.27 | -9.10 | 70.94 | 15.00 |
| 94 GLU C | -10.70 | -14.63 | 71.11 | 15.00 |
| 94 GLU O | -11.13 | -15.74 | 70.77 | 15.00 |
| 95 SER N | -9.82 | -14.46 | 72.10 | 15.00 |
| 95 SER CA | -9.32 | -15.60 | 72.86 | 15.00 |
| 95 SER CB | -8.13 | -15.19 | 73.73 | 15.00 |
| 95 SER OG | -8.46 | -14.11 | 74.58 | 15.00 |
| 95 SER C | -10.40 | -16.21 | 73.74 | 15.00 |
| 95 SER O | -11.26 | -15.51 | 74.26 | 15.00 |
| 96 CYS N | -10.31 | -17.52 | 73.95 | 15.00 |
| 96 CYS CA | -11.30 | -18.20 | 74.78 | 15.00 |
| 96 CYS C | -11.28 | -17.68 | 76.21 | 15.00 |
| 96 CYS O | -10.25 | -17.71 | 76.89 | 15.00 |
| 96 CYS CB | -11.10 | -19.72 | 74.74 | 15.00 |
| 96 CYS SG | -12.37 | -20.66 | 75.65 | 15.00 |
| 97 MET N | -12.43 | -17.18 | 76.66 | 15.00 |
| 97 MET CA | -12.57 | -16.63 | 77.99 | 15.00 |
| 97 MET CB | -12.71 | -15.10 | 77.90 | 15.00 |
| 97 MET CG | -12.32 | -14.33 | 79.15 | 15.00 |
| 97 MET SD | -10.53 | -14.18 | 79.36 | 15.00 |
| 97 MET CE | -10.23 | -15.44 | 80.61 | 15.00 |
| 97 MET C | -13.83 | -17.23 | 78.62 | 15.00 |
| 97 MET O | -14.71 | -16.50 | 79.08 | 15.00 |
| 98 TYR N | -13.95 | -18.55 | 78.57 | 15.00 |
| 98 TYR CA | -15.11 | -19.23 | 79.14 | 15.00 |
| 98 TYR CB | -15.04 | -20.74 | 78.86 | 15.00 |
| 98 TYR CG | -16.04 | -21.57 | 79.65 | 15.00 |
| 98 TYR CD1 | -17.41 | -21.44 | 79.44 | 15.00 |
| 98 TYR CE1 | -18.32 | -22.23 | 80.14 | 15.00 |
| 98 TYR CD2 | -15.60 | -22.52 | 80.59 | 15.00 |
| 98 TYR CE2 | -16.51 | -23.31 | 81.29 | 15.00 |
| 98 TYR CZ | -17.87 | -23.16 | 81.06 | 15.00 |
| 98 TYR OH | -18.78 | -23.95 | 81.71 | 15.00 |
| 98 TYR C | -15.16 | -19.00 | 80.66 | 15.00 |
| 98 TYR O | -14.22 | -19.33 | 81.36 | 15.00 |
| 99 ASN N | -16.23 | -18.37 | 81.13 | 15.00 |
| 99 ASN CA | -16.39 | -18.12 | 82.56 | 15.00 |
| 99 ASN CB | -17.13 | -16.81 | 82.81 | 15.00 |
| 99 ASN CG | -17.36 | -16.54 | 84.30 | 15.00 |
| 99 ASN OD1 | -17.39 | -17.46 | 85.12 | 15.00 |
| 99 ASN ND2 | -17.54 | -15.27 | 84.65 | 15.00 |
| 99 ASN C | -17.18 | -19.27 | 83.16 | 15.00 |
| 99 ASN O | -18.38 | -19.39 | 82.93 | 15.00 |
| 100 PRO N | -16.53 | -20.09 | 83.98 | 15.00 |
| 100 PRO CD | -15.13 | -19.95 | 84.42 | 15.00 |
| 100 PRC CA | -17.17 | -21.24 | 84.63 | 15.00 |
| 100 PRO CB | -16.08 | -21.75 | 85.57 | 15.00 |
| 100 PRO CG | -14.80 | -21.33 | 84.89 | 15.00 |
| 100 PRO C | -18.43 | -20.86 | 85.40 | 15.00 |
| 100 PRO O | -19.41 | -21.59 | 85.40 | 15.00 |
| 101 THR N | -18.41 | -19.69 | 86.04 | 15.00 |
| 101 THR CA | -19.54 | -19.24 | 86.84 | 15.00 |
| 101 THR CB | -19.09 | -18.26 | 87.95 | 15.00 |
| 101 THR OG1 | -18.60 | -17.04 | 87.37 | 15.00 |
| 101 THR CG2 | -17.99 | -18.90 | 88.79 | 15.00 |
| 101 THR C | -20.73 | -18.68 | 86.08 | 15.00 |
| 101 THR O | -21.79 | -18.43 | 86.66 | 15.00 |
| 102 GLY N | -20.57 | -18.48 | 84.77 | 15.00 |
| 102 GLY CA | -21.68 | -17.98 | 83.97 | 15.00 |
| 102 GLY C | -22.30 | -19.14 | 83.21 | 15.00 |
| 102 GLY O | -23.13 | -18.94 | 82.32 | 15.00 |
| 103 LYS N | -21.88 | -20.35 | 83.54 | 15.00 |
| 103 LYS CA | -22.36 | -21.57 | 82.90 | 15.00 |
| 103 LYS CB | -21.73 | -22.79 | 83.58 | 15.00 |
| 103 LYS CG | -22.11 | -24.13 | 82.98 | 15.00 |
| 103 LYS CD | -21.50 | -25.25 | 83.81 | 15.00 |
| 103 LYS CE | -21.82 | -25.07 | 85.28 | 15.00 |
| 103 LYS NZ | -21.22 | -26.16 | 86.10 | 15.00 |
| 103 LYS C | -23.89 | -21.67 | 82.95 | 15.00 |
| 103 LYS O | -24.50 | -21.54 | 84.00 | 15.00 |
| 104 ALA N | -24.5O | -21.89 | 81.79 | 15.00 |
| 104 ALA CA | -25.95 | -21.97 | 81.72 | 15.00 |
| 104 ALA CB | -26.48 | -20.90 | 80.77 | 15.00 |
| 104 ALA C | -26.45 | -23.35 | 81.32 | 15.00 |
| 104 ALA O | -27.63 | -23.65 | 81.46 | 15.00 |
| 105 ALA N | -25.55 | -24.18 | 80.78 | 15.00 |
| 105 ALA CA | -25.91 | -25.53 | 80.36 | 15.00 |
| 105 ALA CB | -26.98 | -25.48 | 79.27 | 15.00 |
| 105 ALA C | -24.70 | -26.30 | 79.86 | 15.00 |
| 105 ALA O | -23.56 | -25.84 | 80.00 | 15.00 |
| 106 LYS N | -24.95 | -27.48 | 79.33 | 15.00 |
| 106 LYS CA | -23.93 | -28.36 | 78.78 | 15.00 |
| 106 LYS CB | -23.12 | -29.05 | 79.90 | 15.00 |
| 106 LYS CG | -23.87 | -30.12 | 80.70 | 15.00 |
| 106 LYS CD | -22.93 | -30.93 | 81.56 | 15.00 |
| 106 LYS CE | -23.66 | -31.74 | 82.65 | 15.00 |
| 106 LYS NZ | -24.38 | -32.97 | 82.21 | 15.00 |
| 106 LYS C | -24.70 | -29.41 | 77.99 | 15.00 |
| 106 LYS O | -25.89 | -29.23 | 77.73 | 15.00 |
| 107 CYS N | -24.03 | -30.47 | 77.57 | 15.00 |
| 107 CYS CA | -24.67 | -31.55 | 76.85 | 15.00 |
| 107 CYS CB | -24.96 | -31.18 | 75.39 | 15.00 |
| 107 CYS SG | -23.57 | -31.18 | 74.26 | 15.00 |
| 107 CYS C | -23.77 | -32.77 | 76.95 | 15.00 |
| 107 CYS O | -22.60 | -32.67 | 77.31 | 15.00 |
| 108 ARG N | -24.35 | -33.94 | 76.70 | 15.00 |
| 108 ARG CA | -23.62 | -35.19 | 76.78 | 15.00 |

TABLE IV-continued

Table of the orthogonal three dimensional coordinates in Ångstroms and B factors (Å²) for the cathepsin K complex with inhibitor 2,2'-N,N'-bis-benzyloxycarbonyl-L-leucinylcarbohydrazide.

| Residue Atom | X | Y | Z | B |
|---|---|---|---|---|
| 108 ARG CB | −24.30 | −36.10 | 77.80 | 15.00 |
| 108 ARG CG | −24.56 | −35.39 | 79.13 | 15.00 |
| 108 ARG CD | −24.78 | −36.37 | 80.25 | 15.00 |
| 108 ARG NE | −26.08 | −37.03 | 80.17 | 15.00 |
| 108 ARG CZ | −26.31 | −38.29 | 80.55 | 15.00 |
| 108 ARG NH1 | −25.34 | −39.05 | 81.03 | 15.00 |
| 108 ARG NH2 | −27.55 | −38.77 | 80.48 | 15.00 |
| 108 ARG C | −23.52 | −35.88 | 75.42 | 15.00 |
| 108 ARG O | −23.75 | −37.08 | 75.29 | 15.00 |
| 109 GLY N | −23.15 | −35.11 | 74.40 | 15.00 |
| 109 GLY CA | −23.01 | −35.66 | 73.07 | 15.00 |
| 109 GLY C | −23.96 | −35.04 | 72.06 | 15.00 |
| 109 GLY O | −24.53 | −33.97 | 72.30 | 15.00 |
| 110 TYR N | −24.12 | −35.71 | 70.92 | 15.00 |
| 110 TYR CA | −24.99 | −35.26 | 69.85 | 15.00 |
| 110 TYR CB | −24.28 | −34.21 | 68.99 | 15.00 |
| 110 TYR CG | −23.06 | −34.73 | 68.24 | 15.00 |
| 110 TYR CD1 | −21.77 | −34.40 | 68.67 | 15.00 |
| 110 TYR CE1 | −20.65 | −34.80 | 67.94 | 15.00 |
| 110 TYR CD2 | −23.19 | −35.48 | 67.08 | 15.00 |
| 110 TYR CE2 | −22.08 | −35.89 | 66.35 | 15.00 |
| 110 TYR CZ | −20.81 | −35.54 | 66.79 | 15.00 |
| 110 TYR OH | −19.71 | −35.91 | 66.03 | 15.00 |
| 110 TYR C | −25.41 | −36.44 | 68.98 | 15.00 |
| 110 TYR O | −24.81 | −37.52 | 69.04 | 15.00 |
| 111 ARG N | −26.39 | −36.20 | 68.12 | 15.00 |
| 111 ARG CA | −26.91 | −37.23 | 67.23 | 15.00 |
| 111 ARG CB | −28.22 | −37.78 | 67.83 | 15.00 |
| 111 ARG CG | −28.86 | −38.97 | 67.11 | 15.00 |
| 111 ARG CD | −29.48 | −38.54 | 65.78 | 15.00 |
| 111 ARG NE | −30.34 | −39.56 | 65.17 | 15.00 |
| 111 ARG CZ | −31.14 | −39.34 | 64.13 | 15.00 |
| 111 ARG NH1 | −31.19 | −38.13 | 63.58 | 15.00 |
| 111 ARG NH2 | −31.92 | −40.30 | 63.68 | 15.00 |
| 111 ARG C | −27.13 | −36.60 | 65.85 | 15.00 |
| 111 ARG O | −27.70 | −35.51 | 65.74 | 15.00 |
| 112 GLU N | −26.67 | −37.29 | 64.81 | 15.00 |
| 112 GLU CA | −26.82 | −36.82 | 63.43 | 15.00 |
| 112 GLU CB | −25.52 | −37.09 | 62.65 | 15.00 |
| 112 GLU CG | −24.30 | −36.39 | 63.23 | 15.00 |
| 112 GLU CD | −23.02 | −36.62 | 62.42 | 15.00 |
| 112 GLU OE1 | −22.60 | −35.70 | 61.69 | 15.00 |
| 112 GLU OE2 | −22.42 | −37.70 | 62.55 | 15.00 |
| 112 GLU C | −27.99 | −37.52 | 62.76 | 15.00 |
| 112 GLU O | −28.31 | −38.67 | 63.08 | 15.00 |
| 113 ILE N | −28.66 | −36.80 | 61.85 | 15.00 |
| 113 ILE CA | −29.79 | −37.35 | 61.11 | 15.00 |
| 113 ILE CB | −30.77 | −36.21 | 60.69 | 15.00 |
| 113 ILE CG2 | −31.67 | −36.67 | 59.56 | 15.00 |
| 113 ILE CG1 | −31.62 | −35.77 | 61.89 | 15.00 |
| 113 ILE CD1 | −30.84 | −35.23 | 63.06 | 15.00 |
| 113 ILE C | −29.26 | −38.07 | 59.87 | 15.00 |
| 113 ILE O | −28.26 | −37.65 | 59.27 | 15.00 |
| 114 PRO N | −29.88 | −39.21 | 59.49 | 15.00 |
| 114 PRO CD | −31.02 | −39.93 | 60.09 | 15.00 |
| 114 PRO CA | −29.39 | −39.90 | 58.30 | 15.00 |
| 114 PRO CB | −30.43 | −41.00 | 58.08 | 15.00 |
| 114 PRO CG | −30.91 | −41.30 | 59.46 | 15.00 |
| 114 PRO C | −29.36 | −38.89 | 57.15 | 15.00 |
| 114 PRO O | −30.36 | −38.22 | 56.87 | 15.00 |
| 115 GLU N | −28.18 | −38.70 | 56.57 | 15.00 |
| 115 GLU CA | −27.97 | −37.75 | 55.49 | 15.00 |
| 115 GLU CB | −26.55 | −37.89 | 54.96 | 15.00 |
| 115 GLU CG | −26.25 | −37.14 | 53.69 | 15.00 |
| 115 GLU CD | −24.98 | −37.66 | 53.04 | 15.00 |
| 115 GLU OE1 | −25.08 | −38.38 | 52.01 | 15.00 |
| 115 GLU OE2 | −23.89 | −37.37 | 53.58 | 15.00 |
| 115 GLU C | −28.99 | −37.89 | 54.35 | 15.00 |
| 115 GLU O | −29.14 | −38.97 | 53.79 | 15.00 |
| 116 GLY N | −29.66 | −36.78 | 54.03 | 15.00 |
| 116 GLY CA | −30.66 | −36.76 | 52.98 | 15.00 |
| 116 GLY C | −32.05 | −37.27 | 53.37 | 15.00 |
| 116 GLY O | −33.00 | −37.16 | 52.59 | 15.00 |
| 117 ASN N | −32.17 | −37.77 | 54.60 | 15.00 |
| 117 ASN CA | −33.43 | −38.32 | 55.09 | 15.00 |
| 117 ASN CB | −33.14 | −39.42 | 56.11 | 15.00 |
| 117 ASN CG | −34.25 | −40.47 | 56.18 | 15.00 |
| 117 ASN OD1 | −35.40 | −40.19 | 55.83 | 15.00 |
| 117 ASN ND2 | −33.91 | −41.67 | 56.64 | 15.00 |
| 117 ASN C | −34.36 | −37.28 | 55.72 | 15.00 |
| 117 ASN O | −34.34 | −37.10 | 56.93 | 15.00 |
| 118 GLU N | −35.19 | −36.64 | 54.89 | 15.00 |
| 118 GLU CA | −36.16 | −35.64 | 55.36 | 15.00 |
| 118 GLU CB | −36.86 | −34.94 | 54.19 | 15.00 |
| 118 GLU CG | −36.01 | −33.88 | 53.50 | 15.00 |
| 118 GLU CD | −36.83 | −32.98 | 52.60 | 15.00 |
| 118 GLU OE1 | −36.94 | −33.27 | 51.39 | 15.00 |
| 118 GLU OE2 | −37.37 | −31.97 | 53.11 | 15.00 |
| 118 GLU C | −37.21 | −36.24 | 56.30 | 15.00 |
| 118 GLU O | −37.72 | −35.57 | 57.19 | 15.00 |
| 119 LYS N | −37.53 | −37.52 | 56.08 | 15.00 |
| 119 LYS CA | −38.47 | −38.23 | 56.93 | 15.00 |
| 119 LYS CB | −38.64 | −39.66 | 56.41 | 15.00 |
| 119 LYS CG | −39.73 | −39.83 | 55.38 | 15.00 |
| 119 LYS CD | −39.53 | −41.10 | 54.58 | 15.00 |
| 119 LYS CE | −38.51 | −40.88 | 53.46 | 15.00 |
| 119 LYS NZ | −38.97 | −39.83 | 52.48 | 15.00 |
| 119 LYS C | −37.91 | −38.29 | 58.36 | 15.00 |
| 119 LYS O | −38.58 | −37.89 | 59.32 | 15.00 |
| 120 ALA N | −36.70 | −38.81 | 58.51 | 15.00 |
| 120 ALA CA | −36.06 | −38.92 | 59.81 | 15.00 |
| 120 ALA CB | −34.71 | −39.60 | 59.68 | 15.00 |
| 120 ALA C | −35.91 | −37.54 | 60.41 | 15.00 |
| 120 ALA O | −36.06 | −37.38 | 61.61 | 15.00 |
| 121 LEU N | −35.63 | −36.55 | 59.56 | 15.00 |
| 121 LEU CA | −35.48 | −35.17 | 60.05 | 15.00 |
| 121 LEU CB | −35.11 | −34.21 | 58.90 | 15.00 |
| 121 LEU CG | −34.87 | −32.75 | 59.33 | 15.00 |
| 121 LEU CD1 | −33.74 | −32.69 | 60.38 | 15.00 |
| 121 LEU CD2 | −34.53 | −31.88 | 58.12 | 15.00 |
| 121 LEU C | −36.78 | −34.71 | 60.72 | 15.00 |
| 121 LEU O | −36.75 | −34.17 | 61.83 | 15.00 |
| 122 LYS N | −37.91 | −34.94 | 60.05 | 15.00 |
| 122 LYS CA | −39.23 | −34.59 | 60.56 | 15.00 |
| 122 LYS CB | −40.31 | −35.02 | 59.58 | 15.00 |
| 122 LYS CG | −41.74 | −34.91 | 60.12 | 15.00 |
| 122 LYS CD | −42.72 | −35.57 | 59.17 | 15.00 |
| 122 LYS CE | −44.11 | −35.67 | 59.76 | 15.00 |
| 122 LYS NZ | −45.10 | −36.14 | 58.74 | 15.00 |
| 122 LYS C | −39.44 | −35.32 | 61.88 | 15.00 |
| 122 LYS O | −39.88 | −34.74 | 62.87 | 15.00 |
| 123 ARG N | −39.14 | −36.61 | 61.86 | 15.00 |
| 123 ARG CA | −39.28 | −37.46 | 63.03 | 15.00 |
| 123 ARG CB | −38.80 | −38.87 | 62.70 | 15.00 |
| 123 ARG CG | −38.84 | −39.87 | 63.86 | 15.00 |
| 123 ARG CD | −37.70 | −40.88 | 63.77 | 15.00 |
| 123 ARG NE | −37.37 | −41.20 | 62.38 | 15.00 |
| 123 ARG CZ | −36.78 | −42.32 | 61.98 | 15.00 |
| 123 ARG NH1 | −36.45 | −43.25 | 62.87 | 15.00 |
| 123 ARG NH2 | −36.53 | −42.51 | 60.69 | 15.00 |
| 123 ARG C | −38.46 | −36.88 | 64.19 | 15.00 |
| 123 ARG O | −38.93 | −36.84 | 65.32 | 15.00 |
| 124 ALA N | −37.25 | −36.42 | 63.89 | 15.00 |
| 124 ALA CA | −36.37 | −35.84 | 64.90 | 15.00 |
| 124 ALA CB | −34.98 | −35.61 | 64.35 | 15.00 |
| 124 ALA C | −36.95 | −34.53 | 65.45 | 15.00 |
| 124 ALA O | −37.02 | −34.33 | 66.66 | 15.00 |
| 125 VAL N | −37.41 | −33.66 | 64.57 | 15.00 |
| 125 VAL CA | −37.99 | −32.41 | 65.03 | 15.00 |
| 125 VAL CB | −38.35 | −31.48 | 63.87 | 15.00 |
| 125 VAL CG1 | −38.98 | −30.19 | 64.39 | 15.00 |
| 125 VAL CG2 | −37.09 | −31.17 | 63.06 | 15.00 |
| 125 VAL C | −39.23 | −32.65 | 65.89 | 15.00 |
| 125 VAL O | −39.46 | −31.94 | 66.87 | 15.00 |

TABLE IV-continued

Table of the orthogonal three dimensional coordinates in Ångstroms and B factors (Å²) for the cathepsin K complex with inhibitor 2,2'-N,N'-bis-benzyloxycarbonyl-L-leucinylcarbohydrazide.

| Residue Atom | X | Y | Z | B |
|---|---|---|---|---|
| 126 ALA N | −40.01 | −33.67 | 65.53 | 15.00 |
| 126 ALA CA | −41.22 | −34.03 | 66.25 | 15.00 |
| 126 ALA CB | −42.03 | −35.02 | 65.44 | 15.00 |
| 126 ALA C | −40.89 | −34.61 | 67.62 | 15.00 |
| 126 ALA O | −41.40 | −34.14 | 68.64 | 15.00 |
| 127 ARG N | −40.03 | −35.62 | 67.64 | 15.00 |
| 127 ARG CA | −39.61 | −36.29 | 68.86 | 15.00 |
| 127 ARG CB | −38.83 | −37.54 | 68.48 | 15.00 |
| 127 ARG CG | −38.45 | −38.44 | 69.64 | 15.00 |
| 127 ARG CD | −39.63 | −39.28 | 70.13 | 15.00 |
| 127 ARG NE | −40.15 | −40.18 | 69.10 | 15.00 |
| 127 ARG CZ | −41.18 | −39.90 | 68.31 | 15.00 |
| 127 ARG NH1 | −41.59 | −40.78 | 67.41 | 15.00 |
| 127 ARG NH2 | −41.81 | −38.73 | 68.42 | 15.00 |
| 127 ARG C | −38.75 | −35.47 | 69.83 | 15.00 |
| 127 ARG O | −39.05 | −35.36 | 71.01 | 15.00 |
| 128 VAL N | −37.64 | −34.94 | 69.31 | 15.00 |
| 128 VAL CA | −36.66 | −34.21 | 70.11 | 15.00 |
| 128 VAL CB | −35.23 | −34.54 | 69.59 | 15.00 |
| 128 VAL CG1 | −34.17 | −33.72 | 70.32 | 15.00 |
| 128 VAL CG2 | −34.95 | −36.02 | 69.74 | 15.00 |
| 128 VAL C | −36.82 | −32.70 | 70.26 | 15.00 |
| 128 VAL O | −36.73 | −32.17 | 71.36 | 15.00 |
| 129 GLY N | −37.00 | −32.01 | 69.14 | 15.00 |
| 129 GLY CA | −37.16 | −30.56 | 69.20 | 15.00 |
| 129 GLY C | −36.36 | −29.91 | 68.08 | 15.00 |
| 129 GLY O | −35.89 | −30.62 | 67.18 | 15.00 |
| 130 PRO N | −36.19 | −28.57 | 68.11 | 15.00 |
| 130 PRO CD | −36.66 | −27.66 | 69.17 | 15.00 |
| 130 PRO CA | −35.45 | −27.83 | 67.09 | 15.00 |
| 130 PRO CB | −35.23 | −26.47 | 67.74 | 15.00 |
| 130 PRO CG | −36.51 | −26.30 | 68.52 | 15.00 |
| 130 PRO C | −34.13 | −28.52 | 66.74 | 15.00 |
| 130 PRO O | −33.37 | −28.91 | 67.63 | 15.00 |
| 131 VAL N | −33.90 | −28.72 | 65.45 | 15.00 |
| 131 VAL CA | −32.71 | −29.40 | 64.97 | 15.00 |
| 131 VAL CB | −33.13 | −30.65 | 64.15 | 15.00 |
| 131 VAL CG1 | −31.93 | −31.36 | 63.57 | 15.00 |
| 131 VAL CG2 | −33.92 | −31.61 | 65.03 | 15.00 |
| 131 VAL C | −31.82 | −28.49 | 64.13 | 15.00 |
| 131 VAL O | −32.32 | −27.69 | 63.34 | 15.00 |
| 132 SER N | −30.51 | −28.59 | 64.32 | 15.00 |
| 132 SER CA | −29.56 | −27.79 | 63.55 | 15.00 |
| 132 SER CB | −28.18 | −27.83 | 64.22 | 15.00 |
| 132 SER OG | −28.20 | −27.34 | 65.55 | 15.00 |
| 132 SER C | −29.44 | −28.37 | 62.14 | 15.00 |
| 132 SER O | −29.41 | −29.59 | 61.96 | 15.00 |
| 133 VAL N | −29.39 | −27.50 | 61.13 | 15.00 |
| 133 VAL CA | −29.25 | −27.94 | 59.75 | 15.00 |
| 133 VAL CB | −30.63 | −28.07 | 59.03 | 15.00 |
| 133 VAL CG1 | −31.40 | −29.29 | 59.53 | 15.00 |
| 133 VAL CG2 | −31.45 | −26.80 | 59.20 | 15.00 |
| 133 VAL C | −28.37 | −27.00 | 58.94 | 15.00 |
| 133 VAL O | −28.12 | −25.87 | 59.34 | 15.00 |
| 134 ALA N | −27.86 | −27.50 | 57.82 | 15.00 |
| 134 ALA CA | −27.03 | −26.73 | 56.91 | 15.00 |
| 134 ALA CB | −25.65 | −27.34 | 56.76 | 15.00 |
| 134 ALA C | −27.75 | −26.73 | 55.57 | 15.00 |
| 134 ALA O | −28.29 | −27.76 | 55.14 | 15.00 |
| 135 ILE N | −27.80 | −25.58 | 54.94 | 15.00 |
| 135 ILE CA | −28.49 | −25.45 | 53.66 | 15.00 |
| 135 ILE CB | −29.82 | −24.68 | 53.82 | 15.00 |
| 135 ILE CG2 | −30.80 | −25.45 | 54.70 | 15.00 |
| 135 ILE CG1 | −29.52 | −23.28 | 54.38 | 15.00 |
| 135 ILE CD1 | −30.72 | −22.40 | 54.52 | 15.00 |
| 135 ILE C | −27.64 | −24.61 | 52.73 | 15.00 |
| 135 ILE O | −26.59 | −24.09 | 53.13 | 15.00 |
| 136 ASP N | −28.09 | −24.49 | 51.49 | 15.00 |
| 136 ASP CA | −27.42 | −23.66 | 50.51 | 15.00 |
| 136 ASP CB | −27.50 | −24.28 | 49.11 | 15.00 |
| 136 ASP CG | −27.02 | −23.32 | 48.02 | 15.00 |
| 136 ASP OD1 | −27.46 | −23.49 | 46.88 | 15.00 |
| 136 ASP OD2 | −26.22 | −22.40 | 48.29 | 15.00 |
| 136 ASP C | −28.19 | −22.36 | 50.54 | 15.00 |
| 136 ASP O | −29.34 | −22.29 | 50.10 | 15.00 |
| 137 ALA N | −27.58 | −21.33 | 51.11 | 15.00 |
| 137 ALA CA | −28.19 | −20.02 | 51.21 | 15.00 |
| 137 ALA CB | −28.14 | −19.54 | 52.65 | 15.00 |
| 137 ALA C | −27.47 | −19.04 | 50.30 | 15.00 |
| 137 ALA O | −27.42 | −17.85 | 50.60 | 15.00 |
| 138 SER N | −26.94 | −19.53 | 49.20 | 15.00 |
| 138 SER CA | −26.20 | −18.66 | 48.30 | 15.00 |
| 138 SER CB | −25.12 | −19.44 | 47.57 | 15.00 |
| 138 SER OG | −25.71 | −20.45 | 46.78 | 15.00 |
| 138 SER C | −27.06 | −17.91 | 47.29 | 15.00 |
| 138 SER O | −26.76 | −16.77 | 46.94 | 15.00 |
| 139 LEU N | −28.12 | −18.55 | 46.82 | 15.00 |
| 139 LEU CA | −28.99 | −17.95 | 45.82 | 15.00 |
| 139 LEU CB | −30.12 | −18.91 | 45.46 | 15.00 |
| 139 LEU CG | −29.76 | −20.02 | 44.48 | 15.00 |
| 139 LEU CD1 | −29.30 | −19.40 | 43.18 | 15.00 |
| 139 LEU CD2 | −28.67 | −20.89 | 45.03 | 15.00 |
| 139 LEU C | −29.56 | −16.58 | 46.18 | 15.00 |
| 139 LEU O | −29.93 | −16.32 | 47.33 | 15.00 |
| 140 THR N | −29.63 | −15.71 | 45.19 | 15.00 |
| 140 THR CA | −30.19 | −14.37 | 45.38 | 15.00 |
| 140 THR CB | −30.06 | −13.54 | 44.09 | 15.00 |
| 140 THR OG1 | −28.67 | −13.30 | 43.82 | 15.00 |
| 140 THR CG2 | −30.80 | −12.20 | 44.20 | 15.00 |
| 140 THR C | −31.65 | −14.43 | 45.86 | 15.00 |
| 140 THR O | −32.09 | −13.62 | 46.69 | 15.00 |
| 141 SER N | −32.38 | −15.45 | 45.40 | 15.00 |
| 141 SER CA | −33.77 | −15.63 | 45.79 | 15.00 |
| 141 SER CB | −34.39 | −16.77 | 44.99 | 15.00 |
| 141 SER OG | −33.78 | −18.00 | 45.32 | 15.00 |
| 141 SER C | −33.89 | −15.89 | 47.29 | 15.00 |
| 141 SER O | −34.94 | −15.63 | 47.90 | 15.00 |
| 142 PHE N | −32.82 | −16.43 | 47.89 | 15.00 |
| 142 PHE CA | −32.79 | −16.70 | 49.33 | 15.00 |
| 142 PHE CB | −31.71 | −17.72 | 49.67 | 15.00 |
| 142 PHE CG | −31.77 | −18.20 | 51.08 | 15.00 |
| 142 PHE CD1 | −32.45 | −19.38 | 51.39 | 15.00 |
| 142 PHE CD2 | −31.14 | −17.49 | 52.10 | 15.00 |
| 142 PHE CE1 | −32.51 | −19.85 | 52.70 | 15.00 |
| 142 PHE CE2 | −31.20 | −17.95 | 53.41 | 15.00 |
| 142 PHE CZ | −31.88 | −19.14 | 53.72 | 15.00 |
| 142 PHE C | −32.53 | −15.40 | 50.08 | 15.00 |
| 142 PHE O | −33.22 | −15.09 | 51.06 | 15.00 |
| 143 GLN N | −31.55 | −14.64 | 49.60 | 15.00 |
| 143 GLN CA | −31.19 | −13.38 | 50.22 | 15.00 |
| 143 GLN CB | −30.07 | −12.72 | 49.44 | 15.00 |
| 143 GLN CG | −29.68 | −11.32 | 49.94 | 15.00 |
| 143 GLN CD | −28.36 | −10.81 | 49.37 | 15.00 |
| 143 GLN OE1 | −28.05 | −9.62 | 49.47 | 15.00 |
| 143 GLN NE2 | −27.56 | −11.71 | 48.80 | 15.00 |
| 143 GLN C | −32.38 | −12.43 | 50.33 | 15.00 |
| 143 GLN O | −32.57 | −11.75 | 51.35 | 15.00 |
| 144 PHE N | −33.22 | −12.40 | 49.30 | 15.00 |
| 144 PHE CA | −34.36 | −11.50 | 49.31 | 15.00 |
| 144 PHE CB | −34.41 | −10.73 | 47.98 | 15.00 |
| 144 PHE CG | −33.22 | −9.85 | 47.75 | 15.00 |
| 144 PHE CD1 | −33.13 | −8.59 | 48.35 | 15.00 |
| 144 PHE CD2 | −32.17 | −10.27 | 46.94 | 15.00 |
| 144 PHE CE1 | −32.02 | −7.77 | 48.15 | 15.00 |
| 144 PHE CE2 | −31.05 | −9.46 | 46.73 | 15.00 |
| 144 PHE CZ | −30.98 | −8.21 | 47.34 | 15.00 |
| 144 PHE C | −35.73 | −12.13 | 49.64 | 15.00 |
| 144 PHE O | −36.77 | −11.52 | 49.38 | 15.00 |
| 145 TYR N | −35.72 | −13.30 | 50.26 | 15.00 |
| 145 TYR CA | −36.97 | −13.98 | 50.63 | 15.00 |
| 145 TYR CB | −36.68 | −15.35 | 51.26 | 15.00 |
| 145 TYR CG | −37.89 | −15.98 | 51.94 | 15.00 |
| 145 TYR CD1 | −38.72 | −16.89 | 51.26 | 15.00 |
| 145 TYR CE1 | −39.83 | −17.45 | 51.89 | 15.00 |

TABLE IV-continued

Table of the orthogonal three dimensional coordinates in Ångstroms and B factors (Å$^2$) for the cathepsin K complex with inhibitor 2,2'-N,N'-bis-benzyloxycarbonyl-L-leucinylcarbohydrazide.

| Residue Atom | X | Y | Z | B |
|---|---|---|---|---|
| 145 TYR CD2 | −38.21 | −15.66 | 53.26 | 15.00 |
| 145 TYR CE2 | −39.33 | −16.22 | 53.90 | 15.00 |
| 145 TYR CZ | −40.13 | −17.12 | 53.21 | 15.00 |
| 145 TYR OH | −41.21 | −17.68 | 53.85 | 15.00 |
| 145 TYR C | −37.81 | −13.16 | 51.62 | 15.00 |
| 145 TYR O | −37.27 | −12.49 | 52.50 | 15.00 |
| 146 SER N | −39.13 | −13.26 | 51.50 | 15.00 |
| 146 SER CA | −40.03 | −12.55 | 52.41 | 15.00 |
| 146 SER CB | −40.33 | −11.12 | 51.96 | 15.00 |
| 146 SER OG | −40.50 | −11.03 | 50.57 | 15.00 |
| 146 SER C | −41.31 | −13.30 | 52.73 | 15.00 |
| 146 SER O | −41.74 | −13.31 | 53.88 | 15.00 |
| 147 LYS N | −41.89 | −14.00 | 51.76 | 15.00 |
| 147 LYS CA | −43.13 | −14.74 | 51.99 | 15.00 |
| 147 LYS CB | −44.34 | −13.80 | 51.82 | 15.00 |
| 147 LYS CG | −44.60 | −12.90 | 53.05 | 15.00 |
| 147 LYS CD | −45.56 | −11.75 | 52.75 | 15.00 |
| 147 LYS CE | −45.63 | −10.76 | 53.91 | 15.00 |
| 147 LYS NZ | −46.25 | −11.32 | 55.15 | 15.00 |
| 147 LYS C | −43.30 | −15.99 | 51.13 | 15.00 |
| 147 LYS O | −42.68 | −16.13 | 50.07 | 15.00 |
| 148 GLY N | −44.12 | −16.92 | 51.60 | 15.00 |
| 148 GLY CA | −44.36 | −18.14 | 50.87 | 15.00 |
| 148 GLY C | −43.35 | −19.22 | 51.18 | 15.00 |
| 148 GLY O | −42.39 | −19.00 | 51.90 | 15.00 |
| 149 VAL N | −43.60 | −20.42 | 50.67 | 15.00 |
| 149 VAL CA | −42.69 | −21.53 | 50.90 | 15.00 |
| 149 VAL CB | −43.43 | −22.89 | 50.72 | 15.00 |
| 149 VAL CG1 | −42.46 | −24.05 | 50.79 | 15.00 |
| 149 VAL CG2 | −44.49 | −23.05 | 51.80 | 15.00 |
| 149 VAL C | −41.56 | −21.34 | 49.88 | 15.00 |
| 149 VAL O | −41.81 | −21.30 | 48.67 | 15.00 |
| 150 TYR N | −40.34 | −21.13 | 50.37 | 15.00 |
| 150 TYR CA | −39.19 | −20.92 | 49.50 | 15.00 |
| 150 TYR CB | −37.99 | −20.42 | 50.30 | 15.00 |
| 150 TYR CG | −36.72 | −20.27 | 49.46 | 15.00 |
| 150 TYR CD1 | −36.48 | −19.11 | 48.72 | 15.00 |
| 150 TYR CE1 | −35.31 | −18.98 | 47.96 | 15.00 |
| 150 TYR CD2 | −35.77 | −21.30 | 49.41 | 15.00 |
| 150 TYR CE2 | −34.59 | −21.17 | 48.65 | 15.00 |
| 150 TYR CZ | −34.37 | −20.01 | 47.93 | 15.00 |
| 15O TYR OH | −33.22 | −19.88 | 47.19 | 15.00 |
| 150 TYR C | −38.80 | −22.18 | 48.76 | 15.00 |
| 150 TYR O | −38.87 | −23.29 | 49.30 | 15.00 |
| 151 TYR N | −38.31 | −21.98 | 47.54 | 15.00 |
| 151 TYR CA | −37.87 | −23.07 | 46.68 | 15.00 |
| 151 TYR CB | −39.07 | −23.95 | 46.31 | 15.00 |
| 151 TYR CG | −38.80 | −25.01 | 45.27 | 15.00 |
| 151 TYR CD1 | −38.36 | −26.28 | 45.62 | 15.00 |
| 151 TYR CE1 | −38.19 | −27.27 | 44.66 | 15.00 |
| 151 TYR CD2 | −39.05 | −24.75 | 43.92 | 15.00 |
| 151 TYR CE2 | −38.88 | −25.73 | 42.96 | 15.00 |
| 151 TYR CZ | −38.46 | −26.98 | 43.33 | 15.00 |
| 151 TYR OH | −38.34 | −27.95 | 42.36 | 15.00 |
| 151 TYR C | −37.24 | −22.44 | 45.44 | 15.00 |
| 151 TYR O | −37.66 | −21.37 | 45.00 | 15.00 |
| 152 ASP N | −36.22 | −23.11 | 44.89 | 15.00 |
| 152 ASP CA | −35.52 | −22.62 | 43.70 | 15.00 |
| 152 ASP CB | −34.55 | −21.50 | 44.08 | 15.00 |
| 152 ASP CG | −33.97 | −20.77 | 42.87 | 15.00 |
| 152 ASP OD1 | −33.75 | −21.39 | 41.81 | 15.00 |
| 152 ASP OD2 | −33.72 | −19.56 | 42.99 | 15.00 |
| 152 ASP C | −34.75 | −23.77 | 43.07 | 15.00 |
| 152 ASP O | −33.90 | −24.38 | 43.73 | 15.00 |
| 153 GLU N | −35.01 | −24.02 | 41.79 | 15.00 |
| 153 GLU CA | −34.35 | −25.09 | 41.04 | 15.00 |
| 153 GLU CB | −34.78 | −25.06 | 39.56 | 15.00 |
| 153 GLU CG | −36.22 | −25.45 | 39.26 | 15.00 |
| 153 GLU CD | −36.59 | −25.21 | 37.78 | 15.00 |
| 153 GLU OE1 | −37.05 | −24.09 | 37.45 | 15.00 |
| 153 GLU OE2 | −36.40 | −26.14 | 36.96 | 15.00 |
| 153 GLU C | −32.84 | −24.95 | 41.09 | 15.00 |
| 153 CLU C | −32.12 | −25.93 | 40.99 | 15.00 |
| 154 SER N | −32.38 | −23.71 | 41.20 | 15.00 |
| 154 SER CA | −30.95 | −23.41 | 41.24 | 15.00 |
| 154 SER CB | −30.73 | −21.93 | 40.92 | 15.00 |
| 15A SER OG | −31.33 | −21.57 | 39.69 | 15.00 |
| 154 SER C | −30.25 | −23.78 | 42.55 | 15.00 |
| 154 SER O | −29.02 | −23.75 | 42.63 | 15.00 |
| 155 CYS N | −31.02 | −24.11 | 43.58 | 15.00 |
| 155 CYS CA | −30.44 | −24.46 | 44.87 | 15.00 |
| 155 CYS C | −29.58 | −25.72 | 44.76 | 15.00 |
| 155 CYS O | −29.98 | −26.72 | 44.17 | 15.00 |
| 155 CYS CB | −31.53 | −24.65 | 45.92 | 15.00 |
| 155 CYS SG | −31.12 | −23.81 | 47.48 | 15.00 |
| 156 ASN N | −28.40 | −25.67 | 45.35 | 15.00 |
| 156 ASN CA | −27.48 | −26.80 | 45.29 | 15.00 |
| 156 ASN CB | −26.09 | −26.28 | 44.91 | 15.00 |
| 156 ASN CG | −25.15 | −27.39 | 44.45 | 15.00 |
| 156 ASN OD1 | −25.21 | −28.54 | 44.94 | 15.00 |
| 156 ASN ND2 | −24.26 | −27.05 | 43.53 | 15.00 |
| 156 ASN C | −27.42 | −27.58 | 46.61 | 15.00 |
| 156 ASN O | −26.99 | −27.06 | 47.64 | 15.00 |
| 157 SER N | −27.80 | −28.85 | 46.54 | 15.00 |
| 157 SER CA | −27.82 | −29.72 | 47.71 | 15.00 |
| 157 SER CB | −28.66 | −30.98 | 47.45 | 15.00 |
| 157 SER OG | −28.07 | −31.81 | 46.47 | 15.00 |
| 157 SER C | −26.43 | −30.14 | 48.17 | 15.00 |
| 157 SER O | −26.27 | −30.76 | 49.23 | 15.00 |
| 158 ASP N | −25.42 | −29.82 | 47.37 | 15.00 |
| 158 ASP CA | −24.06 | −30.18 | 47.69 | 15.00 |
| 158 ASP CB | −23.44 | −30.99 | 46.55 | 15.00 |
| 158 ASP CG | −23.70 | −32.49 | 46.69 | 15.00 |
| 158 ASP OD1 | −24.30 | −33.11 | 45.78 | 15.00 |
| 158 ASP OD2 | −23.32 | −33.05 | 47.75 | 15.00 |
| 158 ASP C | −23.21 | −29.01 | 48.14 | 15.00 |
| 158 ASP O | −22.19 | −29.21 | 48.79 | 15.00 |
| 159 ASN N | −23.67 | −27.80 | 47.85 | 15.00 |
| 159 ASN CA | −22.95 | −26.60 | 48.28 | 15.00 |
| 159 ASN CB | −23.04 | −25.49 | 47.22 | 15.00 |
| 159 ASN CG | −22.27 | −24.23 | 47.61 | 15.00 |
| 159 ASN OD1 | −21.81 | −24.09 | 48.74 | 15.00 |
| 159 ASN ND2 | −22.14 | −23.31 | 46.67 | 15.00 |
| 159 ASN C | −23.55 | −26.10 | 49.61 | 15.00 |
| 159 ASN O | −24.20 | −25.06 | 49.67 | 15.00 |
| 160 LEU N | −23.38 | −26.89 | 50.68 | 15.00 |
| 160 LEU CA | −23.91 | −26.47 | 51.98 | 15.00 |
| 160 LEU CB | −23.83 | −27.61 | 52.99 | 15.00 |
| 160 LEU CG | −24.49 | −28.94 | 52.62 | 15.00 |
| 160 LEU CD1 | −24.41 | −29.89 | 53.81 | 15.00 |
| 160 LEU CD2 | −25.94 | −28.71 | 52.23 | 15.00 |
| 160 LEU C | −23.04 | −25.30 | 52.41 | 15.00 |
| 160 LEU O | −21.82 | −25.42 | 52.46 | 15.00 |
| 161 ASN N | −23.65 | −24.15 | 52.70 | 15.00 |
| 161 ASN CA | −22.86 | −22.98 | 53.07 | 15.00 |
| 161 ASN CB | −22.59 | −22.13 | 51.83 | 15.00 |
| 161 ASN CG | −23.82 | −21.92 | 50.98 | 15.00 |
| 161 ASN OD1 | −24.77 | −21.24 | 51.38 | 15.00 |
| 161 ASN ND2 | −23.83 | −22.51 | 49.81 | 15.00 |
| 161 ASN C | −23.40 | −22.10 | 54.20 | 15.00 |
| 161 ASN O | −22.80 | −21.07 | 54.54 | 15.00 |
| 162 HIS N | −24.47 | −22.55 | 54.85 | 15.00 |
| 162 HIS CA | −25.07 | −21.78 | 55.92 | 15.00 |
| 162 HIS CB | −26.12 | −20.83 | 55.33 | 15.00 |
| 162 HIS CG | −26.58 | −19.75 | 56.27 | 15.00 |
| 162 HIS CD2 | −27.81 | −19.22 | 56.48 | 15.00 |
| 162 HIS ND1 | −25.73 | −19.08 | 57.12 | 15.00 |
| 162 HIS CE1 | −26.41 | −18.20 | 57.83 | 15.00 |
| 162 HIS NE2 | −27.68 | −18.27 | 57.46 | 15.00 |
| 162 HIS C | −25.71 | −22.76 | 56.91 | 15.00 |
| 162 HIS O | −26.37 | −23.71 | 56.50 | 15.00 |
| 163 ALA N | −25.40 | −22.58 | 58.19 | 15.00 |
| 163 ALA CA | −25.96 | −23.43 | 59.24 | 15.00 |
| 163 ALA CB | −24.95 | −23.66 | 60.35 | 15.00 |

TABLE IV-continued

Table of the orthogonal three dimensional coordinates in Ångstroms and B factors (Å²) for the cathepsin K complex with inhibitor 2,2'-N,N'-bis-benzyloxycarbonyl-L-leucinylcarbohydrazide.

| Residue Atom | X | Y | Z | B |
|---|---|---|---|---|
| 163 ALA C | −27.17 | −22.65 | 59.74 | 15.00 |
| 163 ALA O | −27.10 | −21.42 | 59.92 | 15.00 |
| 164 VAL N | −28.27 | −23.34 | 59.96 | 15.00 |
| 164 VAL CA | −29.51 | −22.71 | 60.36 | 15.00 |
| 164 VAL CB | −30.30 | −22.38 | 59.08 | 15.00 |
| 164 VAL CG1 | −31.28 | −23.48 | 58.75 | 15.00 |
| 164 VAL CG2 | −30.90 | −20.99 | 59.15 | 15.00 |
| 164 VAL C | −30.30 | −23.60 | 61.34 | 15.00 |
| 164 VAL O | −29.89 | −24.73 | 61.62 | 15.00 |
| 165 LEU N | −31.40 | −23.09 | 61.89 | 15.00 |
| 165 LEU CA | −32.18 | −23.86 | 62.86 | 15.00 |
| 165 LEU CB | −32.27 | −23.11 | 64.20 | 15.00 |
| 165 LEU CG | −32.79 | −23.87 | 65.44 | 15.00 |
| 165 LEU CD1 | −31.76 | −24.89 | 65.90 | 15.00 |
| 165 LEU CD2 | −33.13 | −22.90 | 66.57 | 15.00 |
| 165 LEU C | −33.58 | −24.27 | 62.40 | 15.00 |
| 165 LEU O | −34.39 | −23.42 | 62.03 | 15.00 |
| 166 ALA N | −33.85 | −25.57 | 62.43 | 15.00 |
| 166 ALA CA | −35.15 | −26.11 | 62.05 | 15.00 |
| 166 ALA CB | −35.00 | −27.51 | 61.50 | 15.00 |
| 166 ALA C | −35.99 | −26.11 | 63.33 | 15.00 |
| 166 ALA O | −35.76 | −26.91 | 64.25 | 15.00 |
| 167 VAL N | −36.94 | −25.19 | 63.39 | 15.00 |
| 167 VAL CA | −37.80 | −25.06 | 64.55 | 15.00 |
| 167 VAL CB | −37.81 | −23.60 | 65.03 | 15.00 |
| 167 VAL CG1 | −38.83 | −22.75 | 64.24 | 15.00 |
| 167 VAL CG2 | −38.06 | −23.55 | 66.50 | 15.00 |
| 167 VAL C | −39.23 | −25.58 | 64.33 | 15.00 |
| 167 VAL O | −40.15 | −25.31 | 65.14 | 15.00 |
| 168 GLY N | −39.44 | −26.31 | 63.24 | 15.00 |
| 168 GLY CA | −40.76 | −26.84 | 62.97 | 15.00 |
| 168 GLY C | −40.97 | −27.25 | 61.53 | 15.00 |
| 168 GLY O | −40.02 | −27.37 | 60.74 | 15.00 |
| 169 TYR N | −42.23 | −27.48 | 61.20 | 15.00 |
| 169 TYR CA | −42.67 | −27.89 | 59.87 | 15.00 |
| 169 TYR CB | −42.21 | −29.33 | 59.54 | 15.00 |
| 169 TYR CC | −42.75 | −30.41 | 60.46 | 15.00 |
| 169 TYR CD1 | −43.94 | −31.09 | 60.16 | 15.00 |
| 169 TYR CE1 | −44.43 | −32.16 | 60.99 | 15.00 |
| 169 TYR CD2 | −42.06 | −30.79 | 61.61 | 15.00 |
| 169 TYR CE2 | −42.53 | −31.80 | 62.45 | 15.00 |
| 169 TYR CZ | −43.71 | −32.45 | 62.13 | 15.00 |
| 169 TYR OH | −44.15 | −33.47 | 62.94 | 15.00 |
| 169 TYR C | −44.18 | −27.80 | 59.84 | 15.00 |
| 169 TYR O | −44.84 | −27.82 | 60.88 | 15.00 |
| 170 GLY N | −44.73 | −27.73 | 58.64 | 15.00 |
| 170 GLY CA | −46.17 | −27.63 | 58.48 | 15.00 |
| 170 GLY C | −46.53 | −27.64 | 57.01 | 15.00 |
| 170 GLY O | −45.73 | −28.04 | 56.18 | 15.00 |
| 171 ILE N | −47.71 | −27.14 | 56.69 | 15.00 |
| 171 ILE CA | −48.16 | −27.09 | 55.30 | 15.00 |
| 171 ILE CB | −48.95 | −28.37 | 54.91 | 15.00 |
| 171 ILE CG2 | −50.04 | −28.69 | 55.91 | 15.00 |
| 171 ILE CG1 | −49.52 | −28.25 | 53.51 | 15.00 |
| 171 ILE CD1 | −50.20 | −29.53 | 53.05 | 15.00 |
| 171 ILE C | −48.97 | −25.82 | 55.09 | 15.00 |
| 171 ILE O | −49.84 | −25.48 | 55.89 | 15.00 |
| 172 GLN N | −48.59 | −25.07 | 54.05 | 15.00 |
| 172 GLN CA | −49.21 | −23.80 | 53.72 | 15.00 |
| 172 GLN CB | −48.19 | −22.67 | 53.89 | 15.00 |
| 172 GLN CG | −48.68 | −21.32 | 53.45 | 15.00 |
| 172 GLN CD | −47.73 | −20.20 | 53.84 | 15.00 |
| 172 GLN OE1 | −47.84 | −19.61 | 54.92 | 15.00 |
| 172 GLN NE2 | −46.78 | −19.89 | 52.96 | 15.00 |
| 172 GLN C | −49.73 | −23.81 | 52.29 | 15.00 |
| 172 GLN O | −48.96 | −23.96 | 51.33 | 15.00 |
| 173 LYS N | −51.04 | −23.64 | 52.17 | 15.00 |
| 173 LYS CA | −51.73 | −23.62 | 50.88 | 15.00 |
| 173 LYS CB | −51.37 | −22.35 | 50.09 | 15.00 |
| 173 LYS CG | −51.48 | −21.01 | 50.88 | 15.00 |
| 173 LYS CD | −52.85 | −20.77 | 51.55 | 15.00 |
| 173 LYS CE | −54.02 | −20.84 | 50.56 | 15.00 |
| 173 LYS NZ | −53.89 | −19.90 | 49.41 | 15.00 |
| 173 LYS C | −51.39 | −24.87 | 50.08 | 15.00 |
| 173 LYS O | −51.27 | −24.82 | 48.87 | 15.00 |
| 174 GLY N | −51.22 | −25.99 | 50.77 | 15.00 |
| 174 GLY CA | −50.91 | −27.24 | 50.10 | 15.00 |
| 174 GLY C | −49.43 | −27.58 | 50.06 | 15.00 |
| 174 GLY O | −49.07 | −28.71 | 49.74 | 15.00 |
| 175 ASN N | −48.59 | −26.65 | 50.48 | 15.00 |
| 175 ASN CA | −47.15 | −26.87 | 50.44 | 15.00 |
| 175 ASN CB | −46.44 | −25.64 | 49.88 | 15.00 |
| 175 ASN CG | −47.06 | −25.14 | 48.59 | 15.00 |
| 175 ASN OD1 | −47.08 | −25.86 | 47.58 | 15.00 |
| 175 ASN ND2 | −47.56 | −23.91 | 48.62 | 15.00 |
| 175 ASN C | −46.54 | −27.23 | 51.79 | 15.00 |
| 175 ASN O | −46.63 | −26.46 | 52.74 | 15.00 |
| 176 LYS N | −45.92 | −28.40 | 51.87 | 15.00 |
| 176 LYS CA | −45.28 | −28.84 | 53.09 | 15.00 |
| 176 LYS CB | −44.98 | −30.33 | 53.02 | 15.00 |
| 176 LYS CG | −46.23 | −31.18 | 52.84 | 15.00 |
| 176 LYS CD | −45.95 | −32.63 | 53.09 | 15.00 |
| 176 LYS CE | −47.17 | −33.48 | 52.82 | 15.00 |
| 176 LYS NZ | −46.84 | −34.93 | 52.78 | 15.00 |
| 176 LYS C | −44.00 | −28.03 | 53.20 | 15.00 |
| 176 LYS O | −43.37 | −27.73 | 52.19 | 15.00 |
| 177 HIS N | −43.59 | −27.60 | 54.42 | 15.00 |
| 177 HIS CA | −42.39 | −26.88 | 54.58 | 15.00 |
| 177 HIS CB | −42.76 | −25.39 | 54.51 | 15.00 |
| 177 HIS CG | −43.62 | −24.94 | 55.64 | 15.00 |
| 177 HIS CD2 | −43.32 | −24.68 | 56.94 | 15.00 |
| 177 HIS ND1 | −44.96 | −24.70 | 55.50 | 15.00 |
| 177 HIS CE1 | −45.46 | −24.31 | 56.66 | 15.00 |
| 177 HIS NE2 | −44.48 | −24.29 | 57.55 | 15.00 |
| 177 HIS C | −41.68 | −27.10 | 55.88 | 15.00 |
| 177 HIS O | −42.20 | −27.76 | 56.78 | 15.00 |
| 178 TRP N | −40.52 | −26.46 | 55.99 | 15.00 |
| 178 TRP CA | −39.69 | −26.51 | 57.18 | 15.00 |
| 178 TRP CB | −38.24 | −26.84 | 56.79 | 15.00 |
| 178 TRP CG | −38.01 | −28.23 | 56.31 | 15.00 |
| 178 TRP CD2 | −38.14 | −29.45 | 57.06 | 15.00 |
| 178 TRP CE2 | −37.73 | −30.50 | 56.22 | 15.00 |
| 178 TRP CE3 | −38.56 | −29.74 | 58.37 | 15.00 |
| 178 TRP CD1 | −37.55 | −28.59 | 55.07 | 15.00 |
| 178 TRP NE1 | −37.38 | −29.95 | 55.01 | 15.00 |
| 178 TRP CZ2 | −37.73 | −31.85 | 56.64 | 15.00 |
| 178 TRP CZ3 | −38.56 | −31.08 | 58.79 | 15.00 |
| 178 TRP CH2 | −38.14 | −32.12 | 57.92 | 15.00 |
| 178 TRP C | −39.73 | −25.11 | 57.74 | 15.00 |
| 178 TRP O | −39.68 | −24.14 | 56.97 | 15.00 |
| 179 ILE N | −39.90 | −24.97 | 59.05 | 15.00 |
| 179 ILE CA | −39.91 | −23.65 | 59.65 | 15.00 |
| 179 ILE CB | −40.89 | −23.55 | 60.84 | 15.00 |
| 179 ILE CG2 | −40.95 | −22.10 | 61.34 | 15.00 |
| 179 ILE CG1 | −42.29 | −24.02 | 60.43 | 15.00 |
| 179 ILE CD1 | −43.32 | −23.95 | 61.55 | 15.00 |
| 179 ILE C | −38.47 | −23.41 | 60.08 | 15.00 |
| 179 ILE O | −37.96 | −24.05 | 61.00 | 15.00 |
| 180 ILE N | −37.79 | −22.52 | 59.36 | 15.00 |
| 180 ILE CA | −36.40 | −22.23 | 59.61 | 15.00 |
| 180 ILE CB | −35.58 | −22.34 | 58.29 | 15.00 |
| 180 ILE CG2 | −34.14 | −21.97 | 58.52 | 15.00 |
| 180 ILE CG1 | −35.74 | −23.74 | 57.68 | 15.00 |
| 180 ILE CD1 | −35.52 | −24.88 | 58.66 | 15.00 |
| 180 ILE C | −36.13 | −20.88 | 60.25 | 15.00 |
| 180 ILE O | −36.68 | −19.85 | 59.84 | 15.00 |
| 181 LYS N | −35.24 | −20.90 | 61.25 | 15.00 |
| 181 LYS CA | −34.84 | −19.72 | 61.99 | 15.00 |
| 181 LYS CB | −34.77 | −20.06 | 63.48 | 15.00 |
| 181 LYS CG | −34.66 | −18.84 | 64.35 | 15.00 |
| 181 LYS CD | −34.34 | −19.17 | 65.79 | 15.00 |
| 181 LYS CE | −34.16 | −17.89 | 66.56 | 15.00 |
| 181 LYS NZ | −33.69 | −18.09 | 67.94 | 15.00 |
| 181 LYS C | −33.46 | −19.27 | 61.49 | 15.00 |

TABLE IV-continued

Table of the orthogonal three dimensional coordinates in Ångstroms and B factors (Å²) for the cathepsin K complex with inhibitor 2,2'-N,N'-bis-benzyloxycarbonyl-L-leucinylcarbohydrazide.

| Residue Atom | X | Y | Z | B |
|---|---|---|---|---|
| 181 LYS O | −32.50 | −20.03 | 61.56 | 15.00 |
| 182 ASN N | −33.37 | −18.05 | 60.98 | 15.00 |
| 182 ASN CA | −32.11 | −17.52 | 60.47 | 15.00 |
| 182 ASN CB | −32.33 | −16.76 | 59.15 | 15.00 |
| 182 ASN CG | −31.05 | −16.64 | 58.29 | 15.00 |
| 182 ASN OD1 | −30.00 | −17.21 | 58.60 | 15.00 |
| 182 ASN ND2 | −31.15 | −15.91 | 57.18 | 15.00 |
| 182 ASN C | −31.43 | −16.62 | 61.51 | 15.00 |
| 182 ASN O | −32.00 | −16.33 | 62.57 | 15.00 |
| 183 SER N | −30.18 | −16.25 | 61.24 | 15.00 |
| 183 SER CA | −29.43 | −15.38 | 62.14 | 15.00 |
| 183 SER CB | −28.25 | −16.13 | 62.75 | 15.00 |
| 183 SER OG | −27.48 | −16.78 | 61.76 | 15.00 |
| 183 SER C | −28.96 | −14.09 | 61.44 | 15.00 |
| 183 SER O | −27.85 | −13.63 | 61.66 | 15.00 |
| 184 TRP N | −29.82 | −13.52 | 60.59 | 15.00 |
| 184 TRP CA | −29.50 | −12.28 | 59.88 | 15.00 |
| 184 TRP CB | −29.69 | −12.45 | 58.37 | 15.00 |
| 184 TRP CG | −28.71 | −13.44 | 57.76 | 15.00 |
| 184 TRP CD2 | −28.74 | −13.98 | 56.44 | 15.00 |
| 184 TRP CE2 | −27.62 | −14.83 | 56.30 | 15.00 |
| 184 TRP CE3 | −29.60 | −13.83 | 55.34 | 15.00 |
| 184 TRP CD1 | −27.60 | −13.98 | 58.37 | 15.00 |
| 184 TRP NE1 | −26.95 | −14.81 | 57.50 | 15.00 |
| 184 TRP CZ2 | −27.34 | −15.53 | 55.13 | 15.00 |
| 184 TRP CZ3 | −29.33 | −14.52 | 54.17 | 15.00 |
| 184 TRP CH2 | −28.21 | −15.35 | 54.07 | 15.00 |
| 184 TRP C | −30.35 | −11.11 | 60.40 | 15.00 |
| 184 TRP O | −30.51 | −10.09 | 59.72 | 15.00 |
| 185 GLY N | −30.84 | −11.25 | 61.63 | 15.00 |
| 185 GLY CA | −31.67 | −10.22 | 62.24 | 15.00 |
| 185 GLY C | −33.14 | −10.43 | 61.94 | 15.00 |
| 185 GLY O | −33.49 | −11.18 | 61.03 | 15.00 |
| 186 GLU N | −33.99 | −9.73 | 62.68 | 15.00 |
| 186 GLU CA | −35.45 | −9.83 | 62.50 | 15.00 |
| 186 GLU CB | −36.17 | −9.31 | 63.74 | 15.00 |
| 186 GLU CG | −35.94 | −10.14 | 64.97 | 15.00 |
| 186 GLU CD | −37.15 | −10.15 | 65.89 | 15.00 |
| 186 GLU OE1 | −38.26 | −10.52 | 65.41 | 15.00 |
| 186 GLU OE2 | −37.01 | −9.81 | 67.09 | 15.00 |
| 186 GLU C | −36.05 | −9.15 | 61.27 | 15.00 |
| 186 GLU O | −37.10 | −9.56 | 60.78 | 15.00 |
| 187 ASN N | −35.38 | −8.12 | 60.76 | 15.00 |
| 187 ASN CA | −35.89 | −7.42 | 59.59 | 15.00 |
| 187 ASN CB | −35.32 | −6.00 | 59.52 | 15.00 |
| 187 ASN CG | −35.95 | −5.04 | 60.53 | 15.00 |
| 187 ASN OD1 | −35.82 | −3.83 | 60.39 | 15.00 |
| 187 ASN ND2 | −36.62 | −5.58 | 61.56 | 15.00 |
| 187 ASN C | −35.60 | −8.14 | 58.29 | 15.00 |
| 187 ASN O | −35.82 | −7.57 | 57.22 | 15.00 |
| 188 TRP N | −35.12 | −9.38 | 58.37 | 15.00 |
| 188 TRP CA | −34.81 | −10.18 | 57.17 | 15.00 |
| 188 TRP CB | −33.42 | −10.84 | 57.28 | 15.00 |
| 188 TRP CG | −33.16 | −11.85 | 56.18 | 15.00 |
| 188 TRP CD2 | −33.54 | −13.23 | 56.17 | 15.00 |
| 188 TRP CE2 | −33.19 | −13.75 | 54.89 | 15.00 |
| 188 TRP CE3 | −34.14 | −14.09 | 57.10 | 15.00 |
| 188 TRP CD1 | −32.60 | −11.59 | 54.97 | 15.00 |
| 188 TRP NE1 | −32.63 | −12.73 | 54.18 | 15.00 |
| 188 TRP CZ2 | −33.44 | −15.08 | 54.52 | 15.00 |
| 188 TRP CZ3 | −34.39 | −15.42 | 56.74 | 15.00 |
| 188 TRP CH2 | −34.03 | −15.90 | 55.46 | 15.00 |
| 188 TRP C | −35.88 | −11.27 | 57.03 | 15.00 |
| 188 TRP O | −36.45 | −11.71 | 58.04 | 15.00 |
| 189 GLY N | −36.14 | −11.69 | 55.79 | 15.00 |
| 189 GLY CA | −37.13 | −12.72 | 55.53 | 15.00 |
| 189 GLY C | −38.45 | −12.40 | 56.21 | 15.00 |
| 189 GLY O | −38.91 | −11.26 | 56.15 | 15.00 |
| 190 ASN N | −39.07 | −13.38 | 56.85 | 15.00 |
| 190 ASN CA | −40.33 | −13.14 | 57.55 | 15.00 |
| 190 ASN CB | −41.33 | −14.27 | 57.29 | 15.00 |
| 190 ASN CG | −42.74 | −13.89 | 57.69 | 15.00 |
| 190 ASN OD1 | −42.98 | −12.88 | 58.35 | 15.00 |
| 190 ASN ND2 | −43.69 | −14.70 | 57.26 | 15.00 |
| 190 ASN C | −40.03 | −13.04 | 59.04 | 15.00 |
| 190 ASN O | −40.09 | −14.04 | 59.76 | 15.00 |
| 191 LYS N | −39.68 | −11.83 | 59.49 | 15.00 |
| 191 LYS CA | −39.34 | −11.59 | 60.90 | 15.00 |
| 191 LYS CB | −40.57 | −11.79 | 61.81 | 15.00 |
| 191 LYS CG | −41.66 | −10.76 | 61.63 | 15.00 |
| 191 LYS CD | −42.98 | −11.23 | 62.27 | 15.00 |
| 191 LYS CE | −43.69 | −12.29 | 61.41 | 15.00 |
| 191 LYS NZ | −42.88 | −13.54 | 61.16 | 15.00 |
| 191 LYS C | −38.18 | −12.50 | 61.33 | 15.00 |
| 191 LYS O | −38.18 | −13.07 | 62.44 | 15.00 |
| 192 GLY N | −37.22 | −12.67 | 60.43 | 15.00 |
| 192 GLY CA | −36.06 | −13.51 | 60.71 | 15.00 |
| 192 GLY C | −36.27 | −14.99 | 60.45 | 15.00 |
| 192 GLY O | −35.41 | −15.81 | 60.78 | 15.00 |
| 193 TYR N | −37.40 | −15.34 | 59.87 | 15.00 |
| 193 TYR CA | −37.69 | −16.74 | 59.58 | 15.00 |
| 193 TYR CB | −38.93 | −17.20 | 60.33 | 15.00 |
| 193 TYR CG | −38.68 | −17.49 | 61.78 | 15.00 |
| 193 TYR CD1 | −38.81 | −16.48 | 62.74 | 15.00 |
| 193 TYR CE1 | −38.56 | −16.73 | 64.09 | 15.00 |
| 193 TYR CD2 | −38.31 | −18.77 | 62.20 | 15.00 |
| 193 TYR CE2 | −38.06 | −19.03 | 63.55 | 15.00 |
| 193 TYR CZ | −38.18 | −18.01 | 64.48 | 15.00 |
| 193 TYR OH | −37.91 | −18.26 | 65.81 | 15.00 |
| 193 TYR C | −37.92 | −16.95 | 58.10 | 15.00 |
| 193 TYR O | −38.22 | −16.01 | 57.36 | 15.00 |
| 194 ILE N | −37.81 | −18.21 | 57.68 | 15.00 |
| 194 ILE CA | −38.04 | −18.60 | 56.31 | 15.00 |
| 194 ILE CB | −36.73 | −18.55 | 55.43 | 15.00 |
| 194 ILE CG2 | −35.60 | −19.33 | 56.09 | 15.00 |
| 194 ILE CG1 | −37.01 | −19.10 | 54.03 | 15.00 |
| 194 ILE CD1 | −35.85 | −18.96 | 53.07 | 15.00 |
| 194 ILE C | −38.63 | −20.00 | 56.30 | 15.00 |
| 194 ILE O | −38.16 | −20.88 | 57.01 | 15.00 |
| 195 LEU N | −39.72 | −20.18 | 55.55 | 15.00 |
| 195 LEU CA | −40.34 | −21.49 | 55.42 | 15.00 |
| 195 LEU CB | −41.87 | −21.37 | 55.28 | 15.00 |
| 195 LEU CG | −42.73 | −20.47 | 56.17 | 15.00 |
| 195 LEU CD1 | −44.18 | −20.60 | 55.73 | 15.00 |
| 195 LEU CD2 | −42.58 | −20.81 | 57.65 | 15.00 |
| 195 LEU C | −39.76 | −22.05 | 54.13 | 15.00 |
| 195 LEU O | −39.93 | −21.45 | 53.06 | 15.00 |
| 196 MET N | −39.03 | −23.15 | 54.22 | 15.00 |
| 196 MET CA | −38.43 | −23.75 | 53.02 | 15.00 |
| 196 MET CB | −36.94 | −24.02 | 53.26 | 15.00 |
| 196 MET CG | −36.14 | −22.77 | 53.55 | 15.00 |
| 196 MET SD | −34.44 | −23.13 | 54.06 | 15.00 |
| 196 MET CE | −33.70 | −23.51 | 52.45 | 15.00 |
| 196 NET C | −39.16 | −25.05 | 52.64 | 15.00 |
| 196 MET O | −39.62 | −25.77 | 53.52 | 15.00 |
| 197 ALA N | −39.26 | −25.34 | 51.35 | 15.00 |
| 197 ALA CA | −39.95 | −26.53 | 50.86 | 15.00 |
| 197 ALA CB | −39.82 | −26.63 | 49.36 | 15.00 |
| 197 ALA C | −39.52 | −27.84 | 51.52 | 15.00 |
| 197 ALA O | −38.32 | −28.08 | 51.73 | 15.00 |
| 198 ARG N | −40.50 | −28.68 | 51.85 | 15.00 |
| 198 ARG CA | −40.27 | −29.98 | 52.48 | 15.00 |
| 198 ARG CB | −41.04 | −30.07 | 53.81 | 15.00 |
| 198 ARG CG | −41.06 | −31.45 | 54.43 | 15.00 |
| 198 ARG CD | −41.33 | −31.38 | 55.94 | 15.00 |
| 198 ARG NE | −42.61 | −30.75 | 56.26 | 15.00 |
| 198 ARG CZ | −43.75 | −31.42 | 56.44 | 15.00 |
| 198 ARG NH1 | −43.78 | −32.74 | 56.32 | 15.00 |
| 198 ARG NH2 | −44.87 | −30.76 | 56.70 | 15.00 |
| 198 ARG C | −40.73 | −31.09 | 51.56 | 15.00 |
| 198 ARG O | −41.79 | −31.00 | 50.96 | 15.00 |
| 199 ASN N | −39.95 | −32.17 | 51.52 | 15.00 |
| 199 ASN CA | −40.22 | −33.33 | 50.68 | 15.00 |
| 199 ASN CB | −41.58 | −33.97 | 50.99 | 15.00 |

TABLE IV-continued

Table of the orthogonal three dimensional coordinates in Ångstroms and B factors ($Å^2$) for the cathepsin K complex with inhibitor 2,2'-N,N'-bis-benzyloxycarbonyl-L-leucinylcarbohydrazide.

| Residue Atom | X | Y | Z | B |
|---|---|---|---|---|
| 199 ASN CG | −41.67 | −34.52 | 52.39 | 15.00 |
| 199 ASN OD1 | −40.69 | −34.50 | 53.14 | 15.00 |
| 199 ASN ND2 | −42.85 | −34.99 | 52.77 | 15.00 |
| 199 ASN C | −40.16 | −32.94 | 49.21 | 15.00 |
| 199 ASN O | −40.84 | −33.53 | 48.36 | 15.00 |
| 200 LYS N | −39.35 | −31.93 | 48.91 | 15.00 |
| 200 LYS CA | −39.21 | −31.49 | 47.55 | 15.00 |
| 200 LYS CB | −39.47 | −29.99 | 47.43 | 15.00 |
| 200 LYS CG | −40.30 | −29.64 | 46.22 | 15.00 |
| 200 LYS CD | −41.12 | −28.37 | 46.46 | 15.00 |
| 200 LYS CE | −42.16 | −28.18 | 45.36 | 15.00 |
| 200 LYS NZ | −41.56 | −28.02 | 43.99 | 15.00 |
| 200 LYS C | −37.78 | −31.85 | 47.17 | 15.00 |
| 200 LYS O | −36.94 | −30.98 | 46.93 | 15.00 |
| 201 ASN N | −37.51 | −33.15 | 47.20 | 15.00 |
| 201 ASN CA | −36.21 | −33.69 | 46.86 | 15.00 |
| 201 ASN CB | −35.94 | −33.51 | 45.37 | 15.00 |
| 201 ASN CG | −36.89 | −34.30 | 44.52 | 15.00 |
| 201 ASN OD1 | −37.20 | −35.46 | 44.81 | 15.00 |
| 201 ASN ND2 | −37.40 | −33.66 | 43.47 | 15.00 |
| 201 ASN C | −35.03 | −33.16 | 47.67 | 15.00 |
| 201 ASN O | −33.94 | −32.96 | 47.11 | 15.00 |
| 202 ASN N | −35.23 | −33.00 | 48.98 | 15.00 |
| 202 ASN CA | −34.18 | −32.51 | 49.89 | 15.00 |
| 202 ASN CB | −33.04 | −33.54 | 49.99 | 15.00 |
| 202 ASN CG | −32.05 | −33.23 | 51.10 | 15.00 |
| 202 ASN OD1 | −32.41 | −32.67 | 52.14 | 15.00 |
| 202 ASN ND2 | −30.79 | −33.59 | 50.89 | 15.00 |
| 202 ASN C | −33.66 | −31.16 | 49.41 | 15.00 |
| 202 ASN O | −32.46 | −30.95 | 49.27 | 15.00 |
| 203 ALA N | −34.57 | −30.23 | 49.18 | 15.00 |
| 203 ALA H | −35.42 | −30.45 | 49.60 | 15.00 |
| 203 ALA CA | −34.31 | −28.90 | 48.63 | 15.00 |
| 203 ALA CB | −35.55 | −28.01 | 48.72 | 15.00 |
| 203 ALA C | −33.20 | −28.21 | 49.44 | 15.00 |
| 203 ALA O | −33.27 | −28.01 | 50.64 | 15.00 |
| 204 CYS N | −32.19 | −27.72 | 48.68 | 15.00 |
| 204 CYS CA | −31.05 | −26.98 | 49.22 | 15.00 |
| 204 CYS C | −30.21 | −27.75 | 50.22 | 15.00 |
| 204 CYS O | −29.44 | −27.14 | 50.97 | 15.00 |
| 204 CYS CB | −31.51 | −25.67 | 49.86 | 15.00 |
| 204 CYS SG | −32.47 | −24.53 | 48.82 | 15.00 |
| 205 GLY N | −30.37 | −29.07 | 50.27 | 15.00 |
| 205 GLY CA | −29.60 | −29.89 | 51.20 | 15.00 |
| 205 GLY C | −30.01 | −29.85 | 52.66 | 15.00 |
| 206 GLY O | −29.23 | −30.21 | 53.55 | 15.00 |
| 206 ILE N | −31.27 | −29.50 | 52.90 | 15.00 |
| 206 ILE CA | −31.84 | −29.38 | 54.25 | 15.00 |
| 206 ILE CB | −33.38 | −29.05 | 54.17 | 15.00 |
| 206 ILE CG2 | −34.13 | −30.21 | 53.53 | 15.00 |
| 206 ILE CG1 | −33.94 | −28.69 | 55.54 | 15.00 |
| 206 ILE CD1 | −33.54 | −27.31 | 56.02 | 15.00 |
| 206 ILE C | −31.59 | −30.57 | 55.19 | 15.00 |
| 206 ILE O | −31.42 | −30.39 | 56.40 | 15.00 |
| 207 ALA N | −31.52 | −31.77 | 54.64 | 15.00 |
| 207 ALA CA | −31.27 | −32.95 | 55.49 | 15.00 |
| 207 ALA CB | −32.38 | −33.99 | 55.31 | 15.00 |
| 207 ALA C | −29.89 | −33.58 | 55.26 | 15.00 |
| 207 ALA O | −29.62 | −34.70 | 55.70 | 15.00 |
| 208 ASN N | −28.99 | −32.84 | 54.62 | 15.00 |
| 208 ASN CA | −27.66 | −33.36 | 54.34 | 15.00 |
| 208 ASN CB | −27.05 | −32.65 | 53.13 | 15.00 |
| 208 ASN CG | −27.49 | −33.27 | 51.83 | 15.00 |
| 208 ASN OD1 | −27.92 | −34.43 | 51.79 | 15.00 |
| 208 ASN ND2 | −27.39 | −32.51 | 50.75 | 15.00 |
| 208 ASN C | −26.67 | −33.32 | 55.51 | 15.00 |
| 208 ASN O | −25.80 | −34.19 | 55.61 | 15.00 |
| 209 LEU N | −26.82 | −32.35 | 56.40 | 15.00 |
| 209 LEU CA | −25.92 | −32.20 | 57.53 | 15.00 |
| 209 LEU CB | −24.79 | −31.22 | 57.16 | 15.00 |
| 209 LEU CG | −23.53 | −31.18 | 58.02 | 15.00 |
| 209 LEU CD1 | −22.72 | −32.44 | 57.77 | 15.00 |
| 209 LEU CD2 | −22.72 | −29.93 | 57.68 | 15.00 |
| 209 LEU C | −26.69 | −31.68 | 58.75 | 15.00 |
| 209 LEU O | −26.54 | −30.52 | 59.15 | 15.00 |
| 210 ALA N | −27.50 | −32.55 | 59.34 | 15.00 |
| 210 ALA H | −27.89 | −32.98 | 58.56 | 15.00 |
| 210 ALA CA | −28.32 | −32.12 | 60.48 | 15.00 |
| 210 ALA CB | −29.80 | −32.37 | 60.21 | 15.00 |
| 210 ALA C | −27.94 | −32.94 | 61.72 | 15.00 |
| 210 ALA O | −27.57 | −34.09 | 61.63 | 15.00 |
| 211 SER N | −28.10 | −32.29 | 62.88 | 15.00 |
| 211 SER CA | −27.80 | −32.92 | 64.15 | 15.00 |
| 211 SER CB | −26.28 | −32.97 | 64.37 | 15.00 |
| 211 SER OG | −25.71 | −31.66 | 64.34 | 15.00 |
| 211 SER C | −28.46 | −32.19 | 65.33 | 15.00 |
| 211 SER O | −29.01 | −31.09 | 65.17 | 15.00 |
| 212 PHE N | −28.43 | −32.83 | 66.50 | 15.00 |
| 212 PHE CA | −28.98 | −32.24 | 67.71 | 15.00 |
| 212 PHE CB | −30.46 | −32.59 | 67.86 | 15.00 |
| 212 PHE CG | −30.74 | −34.06 | 67.93 | 15.00 |
| 212 PHE CD1 | −31.03 | −34.79 | 66.77 | 15.00 |
| 212 PHE CD2 | −30.76 | −34.72 | 69.16 | 15.00 |
| 212 PHE CE1 | −31.34 | −36.13 | 66.83 | 15.00 |
| 212 PHE CE2 | −31.06 | −36.08 | 69.22 | 15.00 |
| 212 PHE CZ | −31.35 | −36.79 | 68.05 | 15.00 |
| 212 PHE C | −28.18 | −32.66 | 68.96 | 15.00 |
| 212 PHE O | −27.65 | −33.77 | 69.03 | 15.00 |
| 213 PRO N | −28.03 | −31.76 | 69.92 | 15.00 |
| 213 PRO CD | −28.51 | −30.37 | 69.98 | 15.00 |
| 213 PRO CA | −27.28 | −32.11 | 71.13 | 15.00 |
| 213 PRO CB | −27.07 | −30.76 | 71.79 | 15.00 |
| 213 PRO CG | −28.33 | −30.03 | 71.43 | 15.00 |
| 213 PRO C | −28.10 | −33.03 | 72.01 | 15.00 |
| 213 PRO O | −29.33 | −33.00 | 71.95 | 15.00 |
| 214 LYS N | −27.42 | −33.86 | 72.80 | 15.00 |
| 214 LYS CA | −28.08 | −34.78 | 73.73 | 15.00 |
| 214 LYS CB | −27.64 | −36.23 | 73.50 | 15.00 |
| 214 LYS CG | −27.92 | −36.75 | 72.10 | 15.00 |
| 214 LYS CD | −27.72 | −38.26 | 72.00 | 15.00 |
| 214 LYS CE | −26.29 | −38.66 | 72.30 | 15.00 |
| 214 LYS NZ | −26.00 | −39.99 | 71.69 | 15.00 |
| 214 LYS C | −27.60 | −34.34 | 75.10 | 15.00 |
| 214 LYS O | −26.43 | −34.00 | 75.26 | 15.00 |
| 215 MET N | −28.50 | −34.30 | 76.07 | 15.00 |
| 215 MET CA | −28.12 | −33.90 | 77.42 | 15.00 |
| 215 MET CB | −28.97 | −32.72 | 77.89 | 15.00 |
| 215 MET CG | −28.96 | −31.51 | 76.95 | 15.00 |
| 215 MET SD | −29.63 | −30.02 | 77.75 | 15.00 |
| 215 MET CE | −28.68 | −28.69 | 76.95 | 15.00 |
| 215 MET C | −28.26 | −35.09 | 78.36 | 15.00 |
| 215 MET OT1 | −27.93 | −34.95 | 79.55 | 15.00 |
| 215 MET OT2 | −28.65 | −36.17 | 77.89 | 15.00 |
| 216 HOH OH2 | −26.08 | −16.55 | 83.97 | 15.00 |
| 217 HOH OH2 | −20.53 | −32.33 | 79.43 | 15.00 |
| 218 HOH OH2 | −31.21 | −16.22 | 65.49 | 15.00 |
| 219 HOH OH2 | −30.95 | −18.19 | 68.23 | 15.00 |
| 220 HOH OH2 | −6.96 | −10.59 | 69.84 | 15.00 |
| 221 HOH OH2 | −15.23 | −12.63 | 73.08 | 15.00 |
| 222 HOH OH2 | −34.53 | −23.51 | 69.96 | 15.00 |
| 223 HOH OH2 | −13.78 | −33.08 | 69.63 | 15.00 |
| 224 HOH OH2 | −17.84 | −17.71 | 57.57 | 15.00 |
| 225 HOH OH2 | −24.92 | −31.02 | 61.65 | 15.00 |
| 226 HOH OH2 | −12.76 | −8.21 | 61.82 | 15.00 |
| 227 HOH OH2 | −14.16 | −21.69 | 66.48 | 15.00 |
| 228 HOH OH2 | −44.08 | −26.87 | 48.48 | 15.00 |
| 229 HOH OH2 | −44.49 | −35.40 | 55.40 | 15.00 |
| 230 HOH OH2 | −39.27 | −16.80 | 68.54 | 15.00 |
| 231 HOH OH2 | −24.12 | −35.40 | 48.13 | 15.00 |
| 232 HOH OH2 | −9.62 | −25.46 | 63.42 | 15.00 |
| 233 HOH OH2 | −46.02 | −25.14 | 44.36 | 15.00 |
| 234 HOH OH2 | −27.99 | −19.44 | 61.96 | 15.00 |
| 235 HOH OH2 | −22.10 | −30.02 | 61.67 | 15.00 |
| 236 HOH OH2 | −27.35 | −15.73 | 71.93 | 15.00 |

TABLE IV-continued

Table of the orthogonal three dimensional coordinates in Ångstroms and B factors (Å$^2$) for the cathepsin K complex with inhibitor 2,2'-N,N'-bis-benzyloxycarbonyl-L-leucinylcarbohydrazide.

| Residue | Atom | X | Y | Z | B |
|---|---|---|---|---|---|
| 237 HOH | OH2 | −29.19 | −17.48 | 70.74 | 15.00 |
| 238 HOH | OH2 | −29.55 | −22.69 | 83.52 | 15.00 |
| 239 HOH | OH2 | −35.73 | −26.96 | 51.77 | 15.00 |
| 240 HOH | OH2 | −36.27 | −24.64 | 49.31 | 15.00 |
| 241 HOH | OH2 | −46.67 | −33.01 | 57.38 | 15.00 |
| 242 HOH | OH2 | −27.40 | −10.90 | 68.66 | 15.00 |
| 243 HOH | OH2 | −42.01 | −15.97 | 60.76 | 15.00 |
| 244 HOH | OH2 | −18.00 | −3.18 | 62.85 | 15.00 |
| 245 HOH | OH2 | −33.49 | −28.43 | 70.56 | 15.00 |
| 246 HOH | OH2 | −44.87 | −25.33 | 75.86 | 15.00 |
| 247 HOH | OH2 | −17.32 | −10.85 | 74.90 | 15.00 |
| 248 HOH | OH2 | −11.45 | −17.84 | 66.51 | 15.00 |
| 249 HOH | OH2 | −11.56 | −21.89 | 82.27 | 15.00 |
| 250 HOH | OH2 | −28.01 | −35.21 | 58.24 | 15.00 |
| 251 HOH | OH2 | −35.05 | −10.64 | 53.00 | 15.00 |
| 252 HOH | OH2 | −31.64 | −28.63 | 46.10 | 15.00 |
| 253 HOH | OH2 | −35.04 | −24.79 | 46.85 | 15.00 |
| 254 HOH | OH2 | −41.38 | −35.11 | 55.81 | 15.00 |
| 255 HOH | OH2 | −40.44 | −19.77 | 71.52 | 15.00 |
| 256 HOH | OH2 | −43.66 | −16.34 | 65.70 | 15.00 |
| 257 HOH | OH2 | −39.00 | −11.99 | 70.39 | 15.00 |
| 258 HOH | OH2 | −30.92 | −9.07 | 66.51 | 15.00 |
| 259 HOH | OH2 | −32.51 | −6.89 | 60.41 | 15.00 |
| 260 HOH | OH2 | −19.20 | −8.29 | 62.91 | 15.00 |
| 261 HOH | OH2 | −33.67 | −20.84 | 69.78 | 15.00 |
| 262 HOH | OH2 | −32.87 | −44.92 | 73.87 | 15.00 |
| 263 HOH | OH2 | −13.20 | −24.01 | 76.81 | 15.00 |
| 264 HOH | OH2 | −8.83 | −25.26 | 60.26 | 15.00 |
| 265 HOH | OH2 | −17.23 | −39.22 | 57.64 | 15.00 |
| 266 HOH | OH2 | −21.10 | −32.62 | 61.09 | 15.00 |
| 267 HOH | OH2 | −24.50 | −33.44 | 60.85 | 15.00 |
| 268 HOH | OH2 | −6.37 | −28.13 | 76.25 | 15.00 |
| 269 HOH | OH2 | −10.20 | −38.51 | 65.40 | 15.00 |
| 270 HOH | OH2 | −21.41 | −37.76 | 78.27 | 15.00 |
| 271 HOH | OH2 | −22.56 | −38.95 | 69.33 | 15.00 |
| 272 HOH | OH2 | −30.18 | −25.13 | 93.77 | 15.00 |
| 273 HOH | OH2 | −12.08 | −12.20 | 63.63 | 15.00 |
| 274 HOH | OH2 | −1.36 | −9.62 | 67.96 | 15.00 |
| 275 HOH | OH2 | −28.39 | −30.26 | 56.30 | 15.00 |
| 276 HOH | OH2 | −29.74 | −20.19 | 48.42 | 15.00 |
| 277 HOH | OH2 | −26.12 | −23.01 | 44.41 | 15.00 |
| 278 HOH | OH2 | −29.92 | −34.21 | 47.42 | 15.00 |
| 279 HOH | OH2 | −26.24 | −33.39 | 47.92 | 15.00 |
| 280 HOH | OH2 | −32.19 | −28.29 | 42.42 | 15.00 |
| 281 HOH | OH2 | −37.49 | −30.33 | 50.55 | 15.00 |

TABLE V

Table of the orthogonal three dimensional coordinates in Ångstroms and B factors (Å$^2$) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 1 ALA | CB | −44.33 | −37.20 | 63.83 | 15.00 |
| 1 ALA | C | −46.76 | −36.62 | 63.83 | 15.00 |
| 1 ALA | O | −47.46 | −36.94 | 62.86 | 15.00 |
| 1 ALA | N | −46.07 | −38.96 | 63.89 | 15.00 |
| 1 ALA | CA | −45.70 | −37.59 | 64.36 | 15.00 |
| 2 PRO | N | −46.94 | −35.47 | 64.51 | 15.00 |
| 2 PRO | CD | −46.25 | −35.02 | 65.74 | 15.00 |
| 2 PRO | CA | −47.93 | −34.49 | 64.07 | 15.00 |
| 2 PRO | CB | −47.63 | −33.28 | 64.97 | 15.00 |
| 2 PRO | CG | −47.15 | −33.90 | 66.23 | 15.00 |
| 2 PRO | C | −47.63 | −34.15 | 62.63 | 15.00 |
| 2 PRO | O | −46.50 | −34.30 | 62.16 | 15.00 |
| 3 ASP | N | −48.65 | −33.74 | 61.88 | 15.00 |
| 3 ASP | CA | −48.39 | −33.36 | 60.52 | 15.00 |
| 3 ASP | CB | −49.60 | −33.60 | 59.63 | 15.00 |
| 3 ASP | CG | −49.78 | −35.10 | 59.29 | 15.00 |
| 3 ASP | OD1 | −50.65 | −35.42 | 58.45 | 15.00 |
| 3 ASP | OD2 | −49.05 | −35.95 | 59.86 | 15.00 |
| 3 ASP | C | −47.92 | −31.92 | 60.51 | 15.00 |
| 3 ASP | O | −47.44 | −31.42 | 59.49 | 15.00 |
| 4 SER | N | −47.94 | −31.30 | 61.69 | 15.00 |
| 4 SER | CA | −47.55 | −29.91 | 61.87 | 15.00 |
| 4 SER | CB | −48.70 | −28.98 | 61.49 | 15.00 |
| 4 SER | OG | −48.42 | −27.64 | 61.85 | 15.00 |
| 4 SER | C | −47.13 | −29.61 | 63.29 | 15.00 |
| 4 SER | O | −47.79 | −30.03 | 64.24 | 15.00 |
| 5 VAL | N | −46.04 | −28.86 | 63.45 | 15.00 |
| 5 VAL | CA | −45.60 | −28.47 | 64.78 | 15.00 |
| 5 VAL | CB | −44.86 | −29.61 | 65.53 | 15.00 |
| 5 VAL | CG1 | −43.46 | −29.81 | 64.97 | 15.00 |
| 5 VAL | CG2 | −44.83 | −29.31 | 67.02 | 15.00 |
| 5 VAL | C | −44.78 | −27.20 | 64.70 | 15.00 |
| 5 VAL | O | −44.00 | −26.98 | 63.77 | 15.00 |
| 6 ASP | N | −44.98 | −26.34 | 65.69 | 15.00 |
| 6 ASP | CA | −44.29 | −25.07 | 65.76 | 15.00 |
| 6 ASP | CB | −45.27 | −23.94 | 65.39 | 15.00 |
| 6 ASP | CG | −44.57 | −22.65 | 65.00 | 15.00 |
| 6 ASP | OD1 | −43.38 | −22.47 | 65.35 | 15.00 |
| 6 ASP | OD2 | −45.21 | −21.81 | 64.33 | 15.00 |
| 6 ASP | C | −43.72 | −24.87 | 67.16 | 15.00 |
| 6 ASP | O | −44.44 | −24.51 | 68.10 | 15.00 |
| 7 TYR | N | −42.41 | −25.07 | 67.29 | 15.00 |
| 7 TYR | CA | −41.75 | −24.90 | 68.58 | 15.00 |
| 7 TYR | CB | −40.35 | −25.51 | 68.57 | 15.00 |
| 7 TYR | CG | −40.39 | −27.00 | 68.75 | 15.00 |
| 7 TYR | CD1 | −40.49 | −27.57 | 70.02 | 15.00 |
| 7 TYR | CE1 | −40.58 | −28.94 | 70.20 | 15.00 |
| 7 TYR | CD2 | −40.38 | −27.87 | 67.65 | 15.00 |
| 7 TYR | CE2 | −40.47 | −29.25 | 67.81 | 15.00 |
| 7 TYR | CZ | −40.57 | −29.77 | 69.09 | 15.00 |
| 7 TYR | OH | −40.68 | −31.13 | 69.28 | 15.00 |
| 7 TYR | C | −41.75 | −23.46 | 69.08 | 15.00 |
| 7 TYR | O | −41.62 | −23.22 | 70.29 | 15.00 |
| 8 ARG | N | −41.91 | −22.51 | 68.17 | 15.00 |
| 8 ARG | CA | −41.98 | −21.10 | 68.55 | 15.00 |
| 8 ARG | CB | −42.05 | −20.19 | 67.33 | 15.00 |
| 8 ARG | CG | −40.91 | −20.36 | 66.38 | 15.00 |
| 8 ARG | CD | −41.09 | −19.45 | 65.19 | 15.00 |
| 8 ARG | NE | −42.20 | −19.81 | 64.32 | 15.00 |
| 8 ARG | CZ | −42.56 | −19.12 | 63.24 | 15.00 |
| 8 ARG | NH1 | −41.89 | −18.03 | 62.89 | 15.00 |
| 8 ARG | NH2 | −43.63 | −19.48 | 62.56 | 15.00 |
| 8 ARG | C | −43.22 | −20.92 | 69.42 | 15.00 |
| 8 ARG | O | −43.17 | −20.22 | 70.43 | 15.00 |
| 9 LYS | N | −44.31 | −21.59 | 69.04 | 15.00 |
| 9 LYS | CA | −45.55 | −21.53 | 69.81 | 15.00 |
| 9 LYS | CB | −46.77 | −21.98 | 68.99 | 15.00 |
| 9 LYS | CG | −47.20 | −21.00 | 67.88 | 15.00 |
| 9 LYS | CD | −48.52 | −21.46 | 67.22 | 15.00 |
| 9 LYS | CE | −48.99 | −20.55 | 66.08 | 15.00 |
| 9 LYS | NZ | −49.38 | −19.15 | 66.49 | 15.00 |
| 9 LYS | C | −45.44 | −22.32 | 71.13 | 15.00 |
| 9 LYS | O | −46.27 | −22.17 | 72.02 | 15.00 |
| 10 LYS | N | −44.41 | −23.16 | 71.23 | 15.00 |
| 10 LYS | CA | −44.17 | −23.94 | 72.43 | 15.00 |
| 10 LYS | CB | −43.58 | −25.32 | 72.11 | 15.00 |
| 10 LYS | CG | −44.58 | −26.34 | 71.57 | 15.00 |
| 10 LYS | CD | −43.93 | −27.72 | 71.47 | 15.00 |
| 10 LYS | CE | −44.97 | −28.81 | 71.25 | 15.00 |
| 10 LYS | NZ | −45.93 | −28.85 | 72.39 | 15.00 |
| 10 LYS | C | −43.25 | −23.20 | 73.40 | 15.00 |
| 10 LYS | O | −43.06 | −23.65 | 74.53 | 15.00 |

TABLE V-continued

Table of the orthogonal three dimensional coordinates in Ångstroms and B factors (Å²) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 11 GLY | N | −42.67 | −22.09 | 72.95 | 15.00 |
| 11 GLY | CA | −41.78 | −21.32 | 73.79 | 15.00 |
| 11 GLY | C | −40.38 | −21.91 | 73.87 | 15.00 |
| 11 GLY | O | −39.64 | −21.67 | 74.83 | 15.00 |
| 12 TYR | N | −40.01 | −22.66 | 72.84 | 15.00 |
| 12 TYR | CA | −38.73 | −23.31 | 72.77 | 15.00 |
| 12 TYR | CB | −38.80 | −24.65 | 72.05 | 15.00 |
| 12 TYR | CG | −39.27 | −25.80 | 72.87 | 15.00 |
| 12 TYR | CD1 | −40.41 | −25.71 | 73.66 | 15.00 |
| 12 TYR | CE1 | −40.84 | −26.79 | 74.42 | 15.00 |
| 12 TYR | CD2 | −38.57 | −27.00 | 72.85 | 15.00 |
| 12 TYR | CE2 | −38.99 | −28.09 | 73.59 | 15.00 |
| 12 TYR | CZ | −40.12 | −27.98 | 74.38 | 15.00 |
| 12 TYR | OH | −40.50 | −29.07 | 75.14 | 15.00 |
| 12 TYR | C | −37.64 | −22.48 | 72.08 | 15.00 |
| 12 TYR | O | −36.46 | −22.81 | 72.16 | 15.00 |
| 13 VAL | N | −38.06 | −21.44 | 71.37 | 15.00 |
| 13 VAL | CA | −37.14 | −20.62 | 70.58 | 15.00 |
| 13 VAL | CB | −37.66 | −20.50 | 69.13 | 15.00 |
| 13 VAL | CG1 | −36.66 | −19.77 | 68.25 | 15.00 |
| 13 VAL | CG2 | −37.95 | −21.87 | 68.56 | 15.00 |
| 13 VAL | C | −36.89 | −19.23 | 71.14 | 15.00 |
| 13 VAL | O | −37.84 | −18.50 | 71.45 | 15.00 |
| 14 THR | N | −35.63 | −18.84 | 71.23 | 15.00 |
| 14 THR | CA | −35.31 | −17.51 | 71.72 | 15.00 |
| 14 THR | CB | −33.91 | −17.47 | 72.36 | 15.00 |
| 14 THR | OG1 | −32.93 | −17.77 | 71.36 | 15.00 |
| 14 THR | CG2 | −33.80 | −18.49 | 73.47 | 15.00 |
| 14 THR | C | −35.44 | −16.50 | 70.56 | 15.00 |
| 14 THR | O | −35.63 | −16.89 | 69.40 | 15.00 |
| 15 PRO | N | −35.41 | −15.19 | 70.86 | 15.00 |
| 15 PRO | CD | −35.34 | −14.54 | 72.18 | 15.00 |
| 15 PRO | CA | −35.53 | −14.18 | 69.79 | 15.00 |
| 15 PRO | CB | −35.29 | −12.87 | 70.53 | 15.00 |
| 15 PRO | CG | −35.87 | −13.15 | 71.89 | 15.00 |
| 15 PRO | C | −34.52 | −14.37 | 68.66 | 15.00 |
| 15 PRO | O | −33.50 | −15.04 | 68.82 | 15.00 |
| 16 VAL | N | −34.82 | −13.76 | 67.52 | 15.00 |
| 16 VAL | CA | −33.93 | −13.83 | 66.37 | 15.00 |
| 16 VAL | CB | −34.62 | −13.31 | 65.09 | 15.00 |
| 16 VAL | CG1 | −33.61 | −13.11 | 63.98 | 15.00 |
| 16 VAL | CG2 | −35.68 | −14.31 | 64.65 | 15.00 |
| 16 VAL | C | −32.68 | −13.01 | 66.64 | 15.00 |
| 16 VAL | O | −32.76 | −11.88 | 67.11 | 15.00 |
| 17 LYS | N | −31.52 | −13.61 | 66.39 | 15.00 |
| 17 LYS | CA | −30.24 | −12.96 | 66.58 | 15.00 |
| 17 LYS | CB | −29.25 | −13.89 | 67.30 | 15.00 |
| 17 LYS | CG | −29.81 | −14.64 | 68.50 | 15.00 |
| 17 LYS | CD | −30.24 | −13.71 | 69.61 | 15.00 |
| 17 LYS | CE | −30.58 | −14.46 | 70.88 | 15.09 |
| 17 LYS | NZ | −31.75 | −15.34 | 70.73 | 15.00 |
| 17 LYS | C | −29.67 | −12.53 | 65.23 | 15.00 |
| 17 LYS | O | −30.20 | −12.88 | 64.17 | 15.00 |
| 18 ASN | N | −28.57 | −11.79 | 65.27 | 15.00 |
| 18 ASN | CA | −27.90 | −11.32 | 64.06 | 15.00 |
| 18 ASN | CB | −28.17 | −9.84 | 63.80 | 15.00 |
| 18 ASN | CG | −27.66 | −9.39 | 62.45 | 15.00 |
| 18 ASN | OD1 | −26.79 | −10.02 | 61.85 | 15.00 |
| 18 ASN | ND2 | −28.20 | −8.29 | 61.95 | 15.00 |
| 18 ASN | C | −26.41 | −11.58 | 64.19 | 15.00 |
| 18 ASN | O | −25.74 | −11.03 | 65.08 | 15.00 |
| 19 GLN | N | −25.89 | −12.42 | 63.30 | 15.00 |
| 19 GLN | CA | −24.48 | −12.75 | 63.31 | 15.00 |
| 19 GLN | CB | −24.20 | −14.02 | 62.48 | 15.00 |
| 19 GLN | CG | −24.56 | −13.94 | 61.00 | 15.00 |
| 19 GLN | CD | −24.28 | −15.24 | 60.27 | 15.00 |
| 19 GLN | OE1 | −25.14 | −15.79 | 59.60 | 15.00 |
| 19 GLN | NE2 | −23.06 | −15.74 | 60.40 | 15.00 |
| 19 GLN | C | −23.59 | −11.60 | 62.86 | 15.00 |
| 19 GLN | O | −22.43 | −11.51 | 63.27 | 15.00 |
| 20 GLY | N | −24.12 | −10.71 | 62.03 | 15.00 |
| 20 GLY | CA | −23.32 | −9.59 | 61.55 | 15.00 |
| 20 GLY | C | −22.33 | −10.05 | 60.49 | 15.00 |
| 20 GLY | O | −22.59 | −11.03 | 59.78 | 15.00 |
| 21 GLN | N | −21.19 | −9.38 | 60.40 | 15.00 |
| 21 GLN | CA | −20.18 | −9.73 | 59.39 | 15.00 |
| 21 GLN | CB | −19.51 | −8.48 | 58.81 | 15.00 |
| 21 GLN | CG | −20.42 | −7.63 | 57.93 | 15.00 |
| 21 GLN | CD | −20.79 | −8.33 | 56.62 | 15.00 |
| 21 GLN | OE1 | −20.02 | −9.12 | 56.07 | 15.00 |
| 21 GLN | NE2 | −21.97 | −8.02 | 56.11 | 15.00 |
| 21 GLN | C | −19.15 | −10.71 | 59.95 | 15.00 |
| 21 GLN | O | −17.96 | −10.40 | 60.02 | 15.00 |
| 22 CYS | N | −19.63 | −11.88 | 60.34 | 15.00 |
| 22 CYS | CA | −18.79 | −12.94 | 60.89 | 15.00 |
| 22 CYS | C | −19.49 | −14.24 | 60.53 | 15.00 |
| 22 CYS | O | −20.71 | −14.34 | 60.62 | 15.00 |
| 22 CYS | CB | −18.61 | −12.78 | 62.41 | 15.00 |
| 22 CYS | SG | −18.03 | −14.24 | 63.33 | 15.00 |
| 23 GLY | N | −18.73 | −15.19 | 60.00 | 15.00 |
| 23 GLY | CA | −19.29 | −16.48 | 59.66 | 15.00 |
| 23 GLY | C | −19.53 | −17.35 | 60.89 | 15.00 |
| 23 GLY | O | −19.04 | −18.48 | 60.98 | 15.00 |
| 24 SER | N | −20.36 | −16.86 | 61.81 | 15.00 |
| 24 SER | CA | −20.67 | −17.60 | 63.03 | 15.00 |
| 24 SER | CB | −20.61 | −16.66 | 64.22 | 15.00 |
| 24 SER | OG | −21.35 | −15.49 | 63.95 | 15.00 |
| 24 SER | C | −22.01 | −18.36 | 62.96 | 15.00 |
| 24 SER | O | −22.58 | −18.73 | 63.99 | 15.00 |
| 25 CYS | N | −22.50 | −18.58 | 61.74 | 15.00 |
| 25 CYS | CA | −23.76 | −19.28 | 61.52 | 15.00 |
| 25 CYS | CB | −23.98 | −19.51 | 60.01 | 15.00 |
| 25 CYS | SG | −22.57 | −20.30 | 59.15 | 15.00 |
| 25 CYS | C | −23.86 | −20.58 | 62.32 | 15.00 |
| 25 CYS | O | −24.84 | −20.82 | 63.02 | 15.00 |
| 25 INH | C1 | −28.50 | −9.52 | 55.70 | 15.00 |
| 25 INH | C2 | −28.63 | −9.33 | 57.08 | 15.00 |
| 25 INH | C3 | −27.56 | −9.63 | 57.94 | 15.00 |
| 25 INH | C4 | −26.35 | −10.11 | 57.43 | 15.00 |
| 25 INH | C5 | −26.23 | −10.29 | 56.05 | 15.00 |
| 25 INH | C6 | −27.29 | −10.00 | 55.19 | 15.00 |
| 25 INH | C7 | −25.20 | −10.40 | 58.35 | 15.00 |
| 25 INH | C8 | −24.73 | −11.77 | 58.36 | 15.00 |
| 25 INH | C9 | −24.03 | −12.42 | 57.30 | 15.00 |
| 25 INH | C10 | −24.33 | −12.23 | 56.10 | 15.00 |
| 25 INH | C11 | −22.27 | −14.01 | 56.70 | 15.00 |
| 25 INH | C12 | −20.77 | −13.63 | 56.80 | 15.00 |
| 25 INH | C13 | −20.18 | −12.60 | 55.82 | 15.00 |
| 25 INH | C14 | −19.01 | −11.83 | 56.47 | 15.00 |
| 25 INH | C15 | −21.22 | −11.63 | 55.23 | 15.00 |
| 25 INH | C16 | −22.50 | −15.59 | 56.80 | 15.00 |
| 25 INH | S17 | −23.78 | −16.32 | 55.92 | 15.00 |
| 25 INH | N18 | −21.80 | −16.55 | 57.50 | 15.00 |
| 25 INH | C19 | −22.21 | −17.87 | 57.39 | 15.00 |
| 25 INH | N20 | −23.05 | −13.25 | 57.68 | 15.00 |
| 25 INH | C21 | −23.27 | −17.88 | 56.55 | 15.00 |
| 25 INH | C22 | −21.58 | −19.10 | 58.24 | 15.00 |
| 25 INH | O23 | −21.37 | −18.39 | 59.17 | 15.00 |
| 25 INH | C24 | −13.79 | −23.51 | 54.96 | 15.00 |
| 25 INH | C25 | −14.23 | −22.84 | 56.08 | 15.00 |
| 25 INH | C26 | −14.83 | −23.54 | 57.12 | 15.00 |
| 25 INH | C27 | −15.00 | −24.93 | 57.04 | 15.00 |
| 25 INH | C28 | −14.54 | −25.60 | 55.91 | 15.00 |
| 25 INH | C29 | −13.94 | −24.90 | 54.87 | 15.00 |
| 25 INH | C30 | −15.72 | −25.67 | 58.14 | 15.00 |
| 25 INH | O31 | −17.10 | −25.93 | 57.71 | 15.00 |
| 25 INH | C32 | −17.91 | −25.03 | 56.96 | 15.00 |
| 25 INH | O33 | −17.69 | −24.81 | 55.77 | 15.00 |
| 25 INH | C34 | −19.82 | −23.49 | 57.00 | 15.00 |
| 25 INH | C35 | −21.22 | −24.12 | 56.84 | 15.00 |

TABLE V-continued

Table of the orthogonal three dimensional coordinates in Ångstroms and B factors (Å²) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 25 INH | C36 | −21.92 | −24.89 | 57.97 | 15.00 |
| 25 INH | C37 | −21.43 | −26.31 | 58.12 | 15.00 |
| 25 INH | C38 | −21.86 | −24.15 | 59.29 | 15.00 |
| 25 INH | C39 | −19.87 | −22.15 | 57.76 | 15.00 |
| 25 INH | O40 | −19.60 | −22.13 | 58.96 | 15.00 |
| 25 INH | N41 | −20.18 | −21.00 | 57.08 | 15.00 |
| 25 INH | N42 | −20.20 | −19.65 | 57.78 | 15.00 |
| 25 INH | N43 | −18.90 | −24.44 | 57.63 | 15.00 |
| 26 TRP | N | −22.80 | −21.38 | 62.25 | 15.00 |
| 26 TRP | CA | −22.73 | −22.65 | 62.97 | 15.00 |
| 26 TRP | CB | −21.39 | −23.33 | 62.67 | 15.00 |
| 26 TRP | CG | −20.19 | −22.46 | 62.98 | 15.00 |
| 26 TRP | CD2 | −19.41 | −22.45 | 64.19 | 15.00 |
| 26 TRP | CE2 | −18.44 | −21.44 | 64.05 | 15.00 |
| 26 TRP | CE3 | −19.43 | −23.21 | 65.37 | 15.00 |
| 26 TRP | CD1 | −19.67 | −21.48 | 62.19 | 15.00 |
| 26 TRP | NE1 | −18.62 | −20.86 | 62.82 | 15.00 |
| 26 TRP | CZ2 | −17.50 | −21.15 | 65.06 | 15.00 |
| 26 TRP | CZ3 | −18.50 | −22.92 | 66.37 | 15.00 |
| 26 TRP | CH2 | −17.55 | −21.91 | 66.21 | 15.00 |
| 26 TRP | C | −22.95 | −22.50 | 64.49 | 15.00 |
| 26 TRP | O | −23.65 | −23.30 | 65.10 | 15.00 |
| 27 ALA | N | −22.35 | −21.46 | 65.08 | 15.00 |
| 27 ALA | CA | −22.45 | −21.18 | 66.51 | 15.00 |
| 27 ALA | CB | −21.56 | −20.02 | 66.89 | 15.00 |
| 27 ALA | C | −23.90 | −20.90 | 66.88 | 15.00 |
| 27 ALA | O | −24.46 | −21.56 | 67.74 | 15.00 |
| 28 PHE | N | −24.53 | −19.94 | 66.19 | 15.00 |
| 28 PHE | CA | −25.93 | −19.58 | 66.41 | 15.00 |
| 28 PHE | CB | −26.36 | −18.44 | 65.48 | 15.00 |
| 28 PHE | CG | −25.83 | −17.09 | 65.88 | 15.00 |
| 28 PHE | CD1 | −24.66 | −16.59 | 65.32 | 15.00 |
| 28 PHE | CD2 | −26.48 | −16.32 | 66.84 | 15.00 |
| 28 PHE | CE1 | −24.14 | −15.37 | 65.71 | 15.00 |
| 28 PHE | CE2 | −25.97 | −15.09 | 67.24 | 15.00 |
| 28 PHE | CZ | −24.80 | −14.62 | 66.67 | 15.00 |
| 28 PHE | C | −26.87 | −20.78 | 66.23 | 15.00 |
| 28 PHE | O | −27.85 | −20.92 | 66.96 | 15.00 |
| 29 SER | N | −26.56 | −21.64 | 65.26 | 15.00 |
| 29 SER | CA | −27.35 | −22.83 | 64.99 | 15.00 |
| 29 SER | CB | −26.95 | −23.45 | 63.64 | 15.00 |
| 29 SER | OG | −27.68 | −24.63 | 63.36 | 15.00 |
| 29 SER | C | −27.21 | −23.84 | 66.13 | 15.00 |
| 29 SER | O | −28.19 | −24.49 | 66.50 | 15.00 |
| 30 SER | N | −26.01 | −23.96 | 66.69 | 15.00 |
| 30 SER | CA | −25.73 | −24.88 | 67.79 | 15.00 |
| 30 SER | CB | −24.23 | −25.10 | 68.00 | 15.00 |
| 30 SER | OG | −23.60 | −25.57 | 66.82 | 15.00 |
| 30 SER | C | −26.37 | −24.39 | 69.09 | 15.00 |
| 30 SER | O | −26.95 | −25.16 | 69.85 | 15.00 |
| 31 VAL | N | −26.23 | −23.09 | 69.33 | 15.00 |
| 31 VAL | CA | −26.80 | −22.45 | 70.51 | 15.00 |
| 31 VAL | CB | −26.39 | −20.95 | 70.55 | 15.00 |
| 31 VAL | CG1 | −27.42 | −20.12 | 71.24 | 15.00 |
| 31 VAL | CG2 | −25.07 | −20.81 | 71.26 | 15.00 |
| 31 VAL | C | −28.31 | −22.63 | 70.48 | 15.00 |
| 31 VAL | O | −28.91 | −22.92 | 71.51 | 15.00 |
| 32 GLY | N | −28.89 | −22.52 | 69.29 | 15.00 |
| 32 GLY | CA | −30.32 | −22.68 | 69.11 | 15.00 |
| 32 GLY | C | −30.78 | −24.09 | 69.45 | 15.00 |
| 32 GLY | O | −31.86 | −24.28 | 69.99 | 15.00 |
| 33 ALA | N | −29.97 | −25.08 | 69.09 | 15.00 |
| 33 ALA | CA | −30.29 | −26.47 | 69.38 | 15.00 |
| 33 ALA | CB | −29.33 | −27.39 | 68.65 | 15.00 |
| 33 ALA | C | −30.19 | −26.70 | 70.89 | 15.00 |
| 33 ALA | O | −31.08 | −27.30 | 71.50 | 15.00 |
| 34 LEU | N | −29.13 | −26.18 | 71.50 | 15.00 |
| 34 LEU | CA | −28.93 | −26.32 | 72.93 | 15.00 |
| 34 LEU | CB | −27.58 | −25.75 | 73.35 | 15.00 |
| 34 LEU | CG | −26.31 | −26.50 | 72.95 | 15.00 |
| 34 LEU | CD1 | −25.08 | −25.64 | 73.21 | 15.00 |
| 34 LEU | CD2 | −26.24 | −27.79 | 73.73 | 15.00 |
| 34 LEU | C | −30.07 | −25.65 | 73.69 | 15.00 |
| 34 LEU | O | −30.59 | −26.21 | 74.64 | 15.00 |
| 35 GLU | N | −30.47 | −24.47 | 73.22 | 15.00 |
| 35 GLU | CA | −31.55 | −23.70 | 73.82 | 15.00 |
| 35 GLU | CB | −31.77 | −22.39 | 73.08 | 15.00 |
| 35 GLU | CG | −30.84 | −21.28 | 73.54 | 15.00 |
| 35 GLU | CD | −30.76 | −20.13 | 72.55 | 15.00 |
| 35 GLU | OE1 | −31.51 | −20.14 | 71.54 | 15.00 |
| 35 GLU | OE2 | −29.93 | −19.22 | 72.76 | 15.00 |
| 35 GLU | C | −32.86 | −24.47 | 73.95 | 15.00 |
| 35 GLU | O | −33.52 | −24.39 | 75.00 | 15.00 |
| 36 GLY | N | −33.21 | −25.21 | 72.90 | 15.00 |
| 36 GLY | CA | −34.42 | −26.00 | 72.90 | 15.00 |
| 36 GLY | C | −34.35 | −27.13 | 73.91 | 15.00 |
| 36 GLY | O | −35.29 | −27.37 | 74.66 | 15.00 |
| 37 GLN | N | −33.22 | −27.82 | 73.95 | 15.00 |
| 37 GLN | CA | −33.04 | −28.92 | 74.90 | 15.00 |
| 37 GLN | CB | −31.77 | −29.71 | 74.56 | 15.00 |
| 37 GLN | CG | −31.84 | −30.38 | 73.19 | 15.00 |
| 37 GLN | CD | −33.17 | −31.11 | 72.97 | 15.00 |
| 37 GLN | OE1 | −33.60 | −31.90 | 73.81 | 15.00 |
| 37 GLN | NE2 | −33.82 | −30.83 | 71.85 | 15.00 |
| 37 GLN | C | −33.05 | −28.41 | 76.35 | 15.00 |
| 37 GLN | O | −33.63 | −29.04 | 77.23 | 15.00 |
| 38 LEU | N | −32.45 | −27.24 | 76.57 | 15.00 |
| 38 LEU | CA | −32.42 | −26.63 | 77.90 | 15.00 |
| 38 LEU | CB | −31.61 | −25.34 | 77.89 | 15.00 |
| 38 LEU | CG | −31.50 | −24.54 | 79.20 | 15.00 |
| 38 LEU | CD1 | −30.94 | −25.41 | 80.34 | 15.00 |
| 38 LEU | CD2 | −30.60 | −23.34 | 78.95 | 15.00 |
| 38 LEU | C | −33.85 | −26.35 | 78.35 | 15.00 |
| 38 LEU | O | −34.22 | −26.60 | 79.50 | 15.00 |
| 39 LYS | N | −34.66 | −25.84 | 77.42 | 15.00 |
| 39 LYS | CA | −36.06 | −25.56 | 77.68 | 15.00 |
| 39 LYS | CB | −36.71 | −24.85 | 76.49 | 15.00 |
| 39 LYS | CG | −38.21 | −24.62 | 76.62 | 15.00 |
| 39 LYS | CD | −38.52 | −23.64 | 77.74 | 15.00 |
| 39 LYS | CE | −40.03 | −23.47 | 77.92 | 15.00 |
| 39 LYS | NZ | −40.35 | −22.39 | 78.91 | 15.00 |
| 39 LYS | C | −36.83 | −26.83 | 78.04 | 15.00 |
| 39 LYS | O | −37.55 | −26.89 | 79.04 | 15.00 |
| 40 LYS | N | −36.65 | −27.87 | 77.23 | 15.00 |
| 40 LYS | CA | −37.33 | −29.14 | 77.44 | 15.00 |
| 40 LYS | CB | −37.06 | −30.09 | 76.28 | 15.00 |
| 40 LYS | CG | −37.54 | −31.50 | 76.53 | 15.00 |
| 40 LYS | CD | −37.53 | −32.32 | 75.26 | 15.00 |
| 40 LYS | CE | −38.47 | −31.72 | 74.22 | 15.00 |
| 40 LYS | NZ | −38.75 | −32.66 | 73.09 | 15.00 |
| 40 LYS | C | −37.01 | −29.80 | 78.78 | 15.00 |
| 40 LYS | O | −37.92 | −30.20 | 79.52 | 15.00 |
| 41 LYS | N | −35.73 | −29.90 | 79.11 | 15.00 |
| 41 LYS | CA | −35.29 | −30.52 | 80.36 | 15.00 |
| 41 LYS | CB | −33.84 | −31.02 | 80.22 | 15.00 |
| 41 LYS | CG | −33.70 | −32.50 | 79.87 | 15.00 |
| 41 LYS | CD | −34.49 | −32.90 | 78.62 | 15.00 |
| 41 LYS | CE | −33.58 | −33.12 | 77.41 | 15.00 |
| 41 LYS | NZ | −33.06 | −31.85 | 76.83 | 15.00 |
| 41 LYS | C | −35.47 | −29.73 | 81.68 | 15.00 |
| 41 LYS | O | −35.74 | −30.32 | 82.73 | 15.00 |
| 42 THR | N | −35.28 | −28.40 | 81.63 | 15.00 |
| 42 THR | CA | −35.41 | −27.57 | 82.83 | 15.00 |
| 42 THR | CB | −34.17 | −26.65 | 83.04 | 15.00 |
| 42 THR | OG1 | −34.20 | −25.57 | 82.10 | 15.00 |
| 42 THR | CG2 | −32.87 | −27.43 | 82.84 | 15.00 |
| 42 THR | C | −36.64 | −26.66 | 82.82 | 15.00 |
| 42 THR | O | −37.07 | −26.16 | 83.86 | 15.00 |
| 43 GLY | N | −37.17 | −26.41 | 81.63 | 15.00 |
| 43 GLY | CA | −38.33 | −25.55 | 81.52 | 15.00 |

TABLE V-continued

Table of the orthogonal three dimensional coordinates in Ångstroms and B factors (Å²) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 43 GLY | C | −37.93 | −24.10 | 81.41 | 15.00 |
| 43 GLY | O | −38.78 | −23.23 | 81.26 | 15.00 |
| 44 LYS | N | −36.63 | −23.82 | 81.53 | 15.00 |
| 44 LYS | CA | −36.11 | −22.46 | 81.41 | 15.00 |
| 44 LYS | CB | −34.91 | −22.24 | 82.33 | 15.00 |
| 44 LYS | CG | −35.25 | −22.15 | 83.79 | 15.00 |
| 44 LYS | CD | −34.06 | −21.63 | 84.59 | 15.00 |
| 44 LYS | CE | −33.69 | −20.18 | 84.17 | 15.00 |
| 44 LYS | NZ | −32.77 | −19.50 | 85.16 | 15.00 |
| 44 LYS | C | −35.72 | −22.17 | 79.96 | 15.00 |
| 44 LYS | O | −35.24 | −23.05 | 79.25 | 15.00 |
| 45 LEU | N | −35.91 | −20.93 | 79.54 | 15.00 |
| 45 LEU | CA | −35.56 | −20.52 | 78.19 | 15.00 |
| 45 LEU | CB | −36.80 | −20.28 | 77.31 | 15.00 |
| 45 LEU | CG | −36.49 | −19.86 | 75.87 | 15.00 |
| 45 LEU | CD1 | −36.01 | −21.07 | 75.08 | 15.00 |
| 45 LEU | CD2 | −37.69 | −19.23 | 75.17 | 15.00 |
| 45 LEU | C | −34.71 | −19.26 | 78.25 | 15.00 |
| 45 LEU | O | −35.22 | −18.17 | 78.53 | 15.00 |
| 46 LEU | N | −33.41 | −19.42 | 78.02 | 15.00 |
| 46 LEU | CA | −32.50 | −18.29 | 78.00 | 15.00 |
| 46 LEU | CB | −31.75 | −18.14 | 79.35 | 15.00 |
| 46 LEU | CG | −31.05 | −19.27 | 80.11 | 15.00 |
| 46 LEU | CD1 | −32.04 | −20.12 | 80.86 | 15.00 |
| 46 LEU | CD2 | −30.23 | −20.09 | 79.17 | 15.00 |
| 46 LEU | C | −31.54 | −18.34 | 76.80 | 15.00 |
| 46 LEU | O | −31.41 | −19.37 | 76.14 | 15.00 |
| 47 ASN | N | −30.93 | −17.20 | 76.48 | 15.00 |
| 47 ASN | CA | −30.00 | −17.12 | 75.36 | 15.00 |
| 47 ASN | CB | −29.88 | −15.69 | 74.84 | 15.00 |
| 47 ASN | CG | −31.21 | −15.12 | 74.46 | 15.00 |
| 47 ASN | OD1 | −31.91 | −15.66 | 73.60 | 15.00 |
| 47 ASN | ND2 | −31.59 | −14.04 | 75.11 | 15.00 |
| 47 ASN | C | −28.64 | −17.64 | 75.75 | 15.00 |
| 47 ASN | O | −28.10 | −17.24 | 76.78 | 15.00 |
| 48 LEU | N | −28.12 | −18.56 | 74.94 | 15.00 |
| 48 LEU | CA | −26.82 | −19.15 | 75.18 | 15.00 |
| 48 LEU | CB | −26.80 | −20.63 | 74.80 | 15.00 |
| 48 LEU | CG | −27.73 | −21.45 | 75.71 | 15.00 |
| 48 LEU | CD1 | −27.55 | −22.93 | 75.44 | 15.00 |
| 48 LEU | CD2 | −27.44 | −21.15 | 77.17 | 15.00 |
| 48 LEU | C | −25.73 | −18.36 | 74.47 | 15.00 |
| 48 LEU | O | −26.04 | −17.44 | 73.71 | 15.00 |
| 49 SER | N | −24.48 | −18.72 | 74.69 | 15.00 |
| 49 SER | CA | −23.36 | −18.00 | 74.12 | 15.00 |
| 49 SER | CB | −22.27 | −17.78 | 75.18 | 15.00 |
| 49 SER | OG | −21.19 | −17.01 | 74.69 | 15.00 |
| 49 SER | C | −22.73 | −18.50 | 72.83 | 15.00 |
| 49 SER | O | −21.93 | −19.43 | 72.84 | 15.00 |
| 50 PRO | N | −23.07 | −17.87 | 71.68 | 15.00 |
| 50 PRO | CD | −24.14 | −16.88 | 71.44 | 15.00 |
| 50 PRO | CA | −22.47 | −18.30 | 70.42 | 15.00 |
| 50 PRO | CB | −23.33 | −17.58 | 69.36 | 15.00 |
| 50 PRO | CG | −23.81 | −16.35 | 70.07 | 15.00 |
| 50 PRO | C | −21.00 | −17.83 | 70.39 | 15.00 |
| 50 PRO | O | −20.15 | −18.48 | 69.77 | 15.00 |
| 51 GLN | N | −20.70 | −16.73 | 71.10 | 15.00 |
| 51 GLN | CA | −19.34 | −16.18 | 71.19 | 15.00 |
| 51 GLN | CB | −19.35 | −14.78 | 71.82 | 15.00 |
| 51 GLN | CG | −18.06 | −13.96 | 71.66 | 15.00 |
| 51 GLN | CD | −17.76 | −13.49 | 70.22 | 15.00 |
| 51 GLN | OE1 | −18.60 | −12.89 | 69.54 | 15.00 |
| 51 GLN | NE2 | −16.54 | −13.74 | 69.77 | 15.00 |
| 51 GLN | C | −18.42 | −17.16 | 71.95 | 15.00 |
| 51 GLN | O | −17.25 | −17.33 | 71.59 | 15.00 |
| 52 ASN | N | −18.98 | −17.86 | 72.94 | 15.00 |
| 52 ASN | CA | −18.23 | −18.85 | 73.70 | 15.00 |
| 52 ASN | CB | −19.14 | −19.54 | 74.73 | 15.00 |
| 52 ASN | CG | −18.40 | −20.50 | 75.66 | 15.00 |
| 52 ASN | OD1 | −18.99 | −21.02 | 76.61 | 15.00 |
| 52 ASN | ND2 | −17.11 | −20.73 | 75.41 | 15.00 |
| 52 ASN | C | −17.68 | −19.86 | 72.70 | 15.00 |
| 52 ASN | O | −16.50 | −20.21 | 72.73 | 15.00 |
| 53 LEU | N | −18.55 | −20.28 | 71.78 | 15.00 |
| 53 LEU | CA | −1B.19 | −21.24 | 70.74 | 15.00 |
| 53 LEU | CB | −19.44 | −21.79 | 70.06 | 15.00 |
| 53 LEU | CG | −20.11 | −23.02 | 70.67 | 15.00 |
| 53 LEU | CD1 | −20.05 | −22.96 | 72.19 | 15.00 |
| 53 LEU | CD2 | −21.55 | −23.11 | 70.17 | 15.00 |
| 53 LEU | C | −17.21 | −20.66 | 69.72 | 15.00 |
| 53 LEU | O | −16.19 | −21.29 | 69.42 | 15.00 |
| 54 VAL | N | −17.51 | −19.46 | 69.21 | 15.00 |
| 54 VAL | CA | −16.65 | −18.82 | 68.22 | 15.00 |
| 54 VAL | CB | −17.39 | −17.39 | 67.85 | 15.00 |
| 54 VAL | CG1 | −16.22 | −16.73 | 66.85 | 15.00 |
| 54 VAL | CG2 | −18.56 | −17.47 | 67.25 | 15.00 |
| 54 VAL | C | −15.19 | −18.75 | 68.68 | 15.00 |
| 54 VAL | O | −14.28 | −19.13 | 67.94 | 15.00 |
| 55 ASP | N | −14.99 | −18.33 | 69.93 | 15.00 |
| 55 ASP | CA | −13.65 | −18.18 | 70.52 | 15.00 |
| 55 ASP | CB | −13.64 | −17.12 | 71.64 | 15.00 |
| 55 ASP | CG | −14.11 | −15.73 | 71.18 | 15.00 |
| 55 ASP | OD1 | −14.12 | −15.43 | 69.96 | 15.00 |
| 55 ASP | OD2 | −14.46 | −14.93 | 72.06 | 15.00 |
| 55 ASP | C | −12.98 | −19.44 | 71.08 | 15.00 |
| 55 ASP | O | −11.75 | −19.53 | 71.15 | 15.00 |
| 56 CYS | N | −13.79 | −20.43 | 71.47 | 15.00 |
| 56 CYS | CA | −13.26 | −21.63 | 72.12 | 15.00 |
| 56 CYS | C | −13.13 | −22.97 | 71.41 | 15.00 |
| 56 CYS | O | −12.36 | −23.82 | 71.86 | 15.00 |
| 56 CYS | CB | −13.97 | −21.81 | 73.45 | 15.00 |
| 56 CYS | SG | −13.91 | −20.34 | 74.55 | 15.00 |
| 57 VAL | N | −13.92 | −23.20 | 70.36 | 15.00 |
| 57 VAL | CA | −13.85 | −24.48 | 69.64 | 15.00 |
| 57 VAL | CB | −15.13 | −24.77 | 68.83 | 15.00 |
| 57 VAL | CG1 | −15.08 | −26.20 | 68.30 | 15.00 |
| 57 VAL | CG2 | −16.37 | −24.52 | 69.66 | 15.00 |
| 57 VAL | C | −12.67 | −24.45 | 68.68 | 15.00 |
| 57 VAL | O | −12.73 | −23.82 | 67.62 | 15.00 |
| 58 SER | N | −11.60 | −25.15 | 69.04 | 15.00 |
| 58 SER | CA | −10.40 | −25.18 | 68.22 | 15.00 |
| 58 SER | CB | −9.19 | −25.66 | 69.02 | 15.00 |
| 58 SER | OG | −9.56 | −26.66 | 69.95 | 15.00 |
| 58 SER | C | −10.54 | −25.93 | 66.91 | 15.00 |
| 58 SER | O | −9.71 | −25.75 | 66.02 | 15.00 |
| 59 GLU | N | −11.56 | −26.78 | 66.79 | 15.00 |
| 59 GLU | CA | −11.79 | −27.55 | 65.57 | 15.00 |
| 59 GLU | CB | −12.53 | −28.86 | 65.84 | 15.00 |
| 59 GLU | CG | −11.72 | −29.95 | 66.56 | 15.00 |
| 59 GLU | CD | −11.47 | −29.63 | 68.03 | 15.00 |
| 59 GLU | OE1 | −12.44 | −29.48 | 68.79 | 15.00 |
| 59 GLU | OE2 | −10.28 | −29.54 | 68.42 | 15.00 |
| 59 GLU | C | −12.51 | −26.74 | 64.50 | 15.00 |
| 59 GLU | O | −12.45 | −27.06 | 63.32 | 15.00 |
| 60 ASN | N | −13.22 | −25.69 | 64.92 | 15.00 |
| 60 ASN | CA | −13.91 | −24.83 | 63.98 | 15.00 |
| 60 ASN | CB | −15.29 | −24.45 | 64.49 | 15.00 |
| 60 ASN | CG | −16.25 | −25.62 | 64.51 | 15.00 |
| 60 ASN | OD1 | −17.17 | −25.66 | 65.32 | 15.00 |
| 60 ASN | ND2 | −16.04 | −26.59 | 63.62 | 15.00 |
| 60 ASN | C | −13.03 | −23.63 | 63.72 | 15.00 |
| 60 ASN | O | −12.01 | −23.46 | 64.39 | 15.00 |
| 61 ASP | N | −13.39 | −22.81 | 62.74 | 15.00 |
| 61 ASP | CA | −12.56 | −21.66 | 62.39 | 15.00 |
| 61 ASP | CB | −12.27 | −21.64 | 60.88 | 15.00 |
| 61 ASP | CG | −11.96 | −23.05 | 60.30 | 15.00 |
| 61 ASP | OD1 | −12.89 | −23.70 | 59.76 | 15.00 |
| 61 ASP | OD2 | −10.78 | −23.50 | 60.37 | 15.00 |
| 61 ASP | C | −13.12 | −20.30 | 62.86 | 15.00 |
| 61 ASP | O | −12.75 | −19.26 | 62.32 | 15.00 |

TABLE V-continued

Table of the orthogonal three dimensional coordinates in Ångstroms and B factors (Å²) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 62 GLY | N | −13.97 | −20.31 | 63.88 | 15.00 |
| 62 GLY | CA | −14.54 | −19.06 | 64.36 | 15.00 |
| 62 GLY | C | −15.40 | −18.39 | 63.30 | 15.00 |
| 62 GLY | O | −16.41 | −18.95 | 62.84 | 15.00 |
| 63 CYS | N | −15.00 | −17.18 | 62.90 | 15.00 |
| 63 CYS | CA | −15.71 | −16.43 | 61.88 | 15.00 |
| 63 CYS | C | −15.44 | −16.96 | 60.47 | 15.00 |
| 63 CYS | O | −16.00 | −16.47 | 59.49 | 15.00 |
| 63 CYS | CB | −15.39 | −14.94 | 61.97 | 15.00 |
| 63 CYS | SG | −16.00 | −14.06 | 63.45 | 15.00 |
| 64 GLY | N | −14.57 | −17.97 | 60.38 | 15.00 |
| 64 GLY | CA | −14.27 | −18.57 | 59.09 | 15.00 |
| 64 GLY | C | −15.01 | −19.88 | 58.84 | 15.00 |
| 64 GLY | O | −14.59 | −20.68 | 58.01 | 15.00 |
| 65 GLY | N | −16.09 | −20.12 | 59.59 | 15.00 |
| 65 GLY | CA | −16.86 | −21.34 | 59.42 | 15.00 |
| 65 GLY | C | −16.66 | −22.39 | 60.49 | 15.00 |
| 65 GLY | O | −15.77 | −22.30 | 61.34 | 15.00 |
| 66 GLY | N | −17.52 | −23.40 | 60.46 | 15.00 |
| 66 GLY | CA | −17.44 | −24.49 | 61.42 | 15.00 |
| 66 GLY | C | −18.61 | −25.44 | 61.32 | 15.00 |
| 66 GLY | O | −19.49 | −25.27 | 60.48 | 15.00 |
| 67 TYR | N | −18.62 | −26.44 | 62.18 | 15.00 |
| 67 TYR | CA | −19.68 | −27.44 | 62.21 | 15.00 |
| 67 TYR | CB | −19.14 | −28.83 | 61.87 | 15.00 |
| 67 TYR | CG | −18.68 | −28.95 | 60.44 | 15.00 |
| 67 TYR | CD1 | −19.58 | −29.32 | 59.44 | 15.00 |
| 67 TYR | CE1 | −19.18 | −29.39 | 58.11 | 15.00 |
| 67 TYR | CD2 | −17.37 | −28.64 | 60.07 | 15.00 |
| 67 TYR | CE2 | −16.96 | −28.70 | 58.75 | 15.00 |
| 67 TYR | CZ | −17.88 | −29.07 | 57.77 | 15.00 |
| 67 TYR | OH | −17.50 | −29.10 | 56.45 | 15.00 |
| 67 TYR | C | −20.36 | −27.48 | 63.56 | 15.00 |
| 67 TYR | O | −19.71 | −27.30 | 64.59 | 15.00 |
| 68 MET | N | −21.65 | −27.77 | 63.56 | 15.00 |
| 68 MET | CA | −22.44 | −27.85 | 64.78 | 15.00 |
| 68 MET | CB | −23.93 | −28.03 | 64.44 | 15.00 |
| 68 MET | CG | −24.58 | −26.86 | 63.66 | 15.00 |
| 68 MET | SD | −24.01 | −26.58 | 61.93 | 15.00 |
| 68 MET | CE | −25.23 | −27.50 | 61.01 | 15.00 |
| 68 MET | C | −21.91 | −28.98 | 65.68 | 15.00 |
| 68 MET | O | −21.68 | −28.77 | 66.87 | 15.00 |
| 69 THR | N | −21.68 | −30.16 | 65.08 | 15.00 |
| 69 THR | CA | −21.17 | −31.32 | 65.81 | 15.00 |
| 69 THR | CB | −20.89 | −32.54 | 64.87 | 15.00 |
| 69 THR | OG1 | −20.07 | −32.14 | 63.76 | 15.00 |
| 69 THR | CG2 | −22.20 | −33.12 | 64.35 | 15.00 |
| 69 THR | C | −19.91 | −31.01 | 66.64 | 15.00 |
| 69 THR | O | −19.80 | −31.46 | 67.78 | 15.00 |
| 70 ASN | N | −18.97 | −30.25 | 66.06 | 15.00 |
| 70 ASN | CA | −17.74 | −29.87 | 66.77 | 15.00 |
| 70 ASN | CB | −16.76 | −29.07 | 65.89 | 15.00 |
| 70 ASN | CG | −16.17 | −29.89 | 64.75 | 15.00 |
| 70 ASN | OD1 | −15.66 | −29.34 | 63.79 | 15.00 |
| 70 ASN | ND2 | −16.25 | −31.20 | 64.86 | 15.00 |
| 70 ASN | C | −18.11 | −29.01 | 67.98 | 15.00 |
| 70 ASN | O | −17.57 | −29.19 | 69.08 | 15.00 |
| 71 ALA | N | −19.02 | −28.07 | 67.74 | 15.00 |
| 71 ALA | CA | −19.50 | −27.16 | 68.77 | 15.00 |
| 71 ALA | CB | −20.44 | −26.11 | 68.16 | 15.00 |
| 71 ALA | C | −20.20 | −27.92 | 69.91 | 15.00 |
| 71 ALA | O | −20.03 | −27.59 | 71.08 | 15.00 |
| 72 PHE | N | −20.95 | −28.97 | 69.56 | 15.00 |
| 72 PHE | CA | −21.63 | −29.82 | 70.54 | 15.00 |
| 72 PHE | CB | −22.65 | −30.75 | 69.86 | 15.00 |
| 72 PHE | CG | −23.80 | −30.02 | 69.25 | 15.00 |
| 72 PHE | CD1 | −24.32 | −28.88 | 69.86 | 15.00 |
| 72 PHE | CD2 | −24.37 | −30.48 | 68.08 | 15.00 |
| 72 PHE | CE1 | −25.40 | −28.21 | 69.30 | 15.00 |
| 72 PHE | CE2 | −25.46 | −29.81 | 67.51 | 15.00 |
| 72 PHE | CZ | −25.97 | −28.67 | 68.13 | 15.00 |
| 72 PHE | C | −20.64 | −30.63 | 71.36 | 15.00 |
| 72 PHE | O | −20.69 | −30.66 | 72.59 | 15.00 |
| 73 GLN | N | −19.71 | −31.27 | 70.67 | 15.00 |
| 73 GLN | CA | −18.70 | −32.08 | 71.33 | 15.00 |
| 73 GLN | CB | −17.83 | −32.79 | 70.31 | 15.00 |
| 73 GLN | CG | −16.90 | −33.82 | 70.92 | 15.00 |
| 73 GLN | CD | −16.28 | −34.73 | 69.87 | 15.00 |
| 73 GLN | OE1 | −16.83 | −34.92 | 68.78 | 15.00 |
| 73 GLN | NE2 | −15.14 | −35.30 | 70.20 | 15.00 |
| 73 GLN | C | −17.87 | −31.21 | 72.25 | 15.00 |
| 73 GLN | O | −17.49 | −31.64 | 73.33 | 15.00 |
| 74 TYR | N | −17.60 | −29.98 | 71.82 | 15.00 |
| 74 TYR | CA | −16.83 | −29.03 | 72.62 | 15.00 |
| 74 TYR | CB | −16.61 | −27.69 | 71.89 | 15.00 |
| 74 TYR | CG | −16.39 | −26.51 | 72.83 | 15.00 |
| 74 TYR | CD1 | −15.18 | −26.35 | 73.51 | 15.00 |
| 74 TYR | CE1 | −15.02 | −25.35 | 74.47 | 15.00 |
| 74 TYR | CD2 | −17.43 | −25.63 | 73.12 | 15.00 |
| 74 TYR | CE2 | −17.28 | −24.64 | 74.08 | 15.00 |
| 74 TYR | CZ | −16.08 | −24.50 | 74.75 | 15.00 |
| 74 TYR | OH | −15.96 | −23.57 | 75.75 | 15.00 |
| 74 TYR | C | −17.55 | −28.79 | 73.94 | 15.00 |
| 74 TYR | O | −16.92 | −28.75 | 75.00 | 15.00 |
| 75 VAL | N | −18.87 | −28.62 | 73.86 | 15.00 |
| 75 VAL | CA | −19.70 | −28.36 | 75.04 | 15.00 |
| 75 VAL | CB | −21.11 | −27.88 | 74.63 | 15.00 |
| 75 VAL | CG1 | −21.96 | −27.66 | 75.85 | 15.00 |
| 75 VAL | CG2 | −21.00 | −26.57 | 73.83 | 15.00 |
| 75 VAL | C | −19.77 | −29.55 | 75.98 | 15.00 |
| 75 VAL | O | −19.91 | −29.38 | 77.19 | 15.00 |
| 76 GLN | N | −19.66 | −30.74 | 75.42 | 15.00 |
| 76 GLN | CA | −19.66 | −31.95 | 76.22 | 15.00 |
| 76 GLN | CB | −19.84 | −33.21 | 75.36 | 15.00 |
| 76 GLN | CG | −19.80 | −34.51 | 76.14 | 15.00 |
| 76 GLN | CD | −19.78 | −35.75 | 75.25 | 15.00 |
| 76 GLN | OE1 | −19.34 | −35.70 | 74.09 | 15.00 |
| 76 GLN | NE2 | −20.24 | −36.86 | 75.79 | 15.00 |
| 76 GLN | C | −18.34 | −32.00 | 77.00 | 15.00 |
| 76 GLN | O | −18.34 | −32.09 | 78.22 | 15.00 |
| 77 LYS | N | −17.22 | −31.90 | 76.29 | 15.00 |
| 77 LYS | CA | −15.89 | −31.95 | 76.91 | 15.00 |
| 77 LYS | CB | −14.79 | −32.01 | 75.85 | 15.00 |
| 77 LYS | CG | −14.77 | −33.29 | 75.01 | 15.00 |
| 77 LYS | CD | −13.80 | −33.14 | 73.84 | 15.00 |
| 77 LYS | CE | −13.62 | −34.44 | 73.09 | 15.00 |
| 77 LYS | NZ | −12.55 | −34.33 | 72.06 | 15.00 |
| 77 LYS | C | −15.63 | −30.80 | 77.87 | 15.00 |
| 77 LYS | O | −14.99 | −30.98 | 78.91 | 15.00 |
| 78 ASN | N | −16.09 | −29.61 | 77.50 | 15.00 |
| 78 ASN | CA | −15.91 | −28.43 | 78.32 | 15.00 |
| 78 ASN | CB | −16.18 | −27.16 | 77.51 | 15.00 |
| 78 ASN | CG | −15.95 | −25.89 | 78.31 | 15.00 |
| 78 ASN | OD1 | −14.90 | −25.69 | 78.92 | 15.00 |
| 78 ASN | ND2 | −16.93 | −24.99 | 78.28 | 15.00 |
| 78 ASN | C | −16.83 | −28.52 | 79.52 | 15.00 |
| 78 ASN | O | −16.64 | −27.81 | 80.49 | 15.00 |
| 79 ARG | N | −17.81 | −29.42 | 79.44 | 15.00 |
| 79 ARG | CA | −18.82 | −29.64 | 80.47 | 15.00 |
| 79 ARG | CB | −18.19 | −30.06 | 81.81 | 15.00 |
| 79 ARG | CG | −17.69 | −31.48 | 81.85 | 15.00 |
| 79 ARG | CD | −16.75 | −31.70 | 83.00 | 15.00 |
| 79 ARG | NE | −16.07 | −32.98 | 82.88 | 15.00 |
| 79 ARG | CZ | −14.79 | −33.13 | 82.56 | 15.00 |
| 79 ARG | NH1 | −14.02 | −32.08 | 82.33 | 15.00 |
| 79 ARG | NH2 | −14.28 | −34.36 | 82.41 | 15.00 |
| 79 ARG | C | −19.77 | −28.45 | 80.65 | 15.00 |
| 79 ARG | O | −20.43 | −28.32 | 81.69 | 15.00 |
| 80 GLY | N | −19.84 | −27.58 | 79.66 | 15.00 |
| 80 GLY | CA | −20.72 | −26.45 | 79.77 | 15.00 |

TABLE V-continued

Table of the orthogonal three dimensional coordinates in Ångstroms and B factors (Å²) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 80 GLY | C | −20.50 | −25.38 | 78.73 | 15.00 |
| 80 GLY | O | −19.60 | −25.49 | 77.89 | 15.00 |
| 81 ILE | N | −21.38 | −24.39 | 78.75 | 15.00 |
| 81 ILE | CA | −21.34 | −23.24 | 77.85 | 15.00 |
| 81 ILE | CB | −22.12 | −23.47 | 76.52 | 15.00 |
| 81 ILE | CG2 | −23.54 | −24.00 | 76.80 | 15.00 |
| 81 ILE | CG1 | −22.15 | −22.16 | 75.71 | 15.00 |
| 81 ILE | CD1 | −22.81 | −22.28 | 74.36 | 15.00 |
| 81 ILE | C | −21.98 | −22.09 | 78.60 | 15.00 |
| 81 ILE | O | −23.00 | −22.26 | 79.29 | 15.00 |
| 82 ASP | N | −21.37 | −20.92 | 78.48 | 15.00 |
| 82 ASP | CA | −21.88 | −19.75 | 79.15 | 15.00 |
| 82 ASP | CB | −20.83 | −18.66 | 79.19 | 15.00 |
| 82 ASP | CG | −19.68 | −19.00 | 80.10 | 15.00 |
| 82 ASP | OD1 | −18.57 | −18.52 | 79.85 | 15.00 |
| 82 ASP | OD2 | −19.91 | −19.76 | 81.07 | 15.00 |
| 82 ASP | C | −23.17 | −19.21 | 78.57 | 15.00 |
| 82 ASP | O | −23.56 | −19.54 | 77.45 | 15.00 |
| 83 SER | N | −23.85 | −18.42 | 79.39 | 15.00 |
| 83 SER | CA | −25.09 | −17.77 | 79.00 | 15.00 |
| 83 SER | CB | −25.89 | −17.34 | 80.22 | 15.00 |
| 83 SER | OG | −25.29 | −16.22 | 80.86 | 15.00 |
| 83 SER | C | −24.70 | −16.56 | 78.16 | 15.00 |
| 83 SER | O | −23.58 | −16.04 | 78.30 | 15.00 |
| 84 GLU | N | −25.59 | −16.10 | 77.30 | 15.00 |
| 84 GLU | CA | −25.30 | −14.93 | 76.49 | 15.00 |
| 84 GLU | CB | −26.55 | −14.46 | 75.73 | 15.00 |
| 84 GLU | CG | −26.40 | −13.12 | 75.04 | 15.00 |
| 84 GLU | CD | −25.37 | −13.12 | 73.92 | 15.00 |
| 84 GLU | OE1 | −24.73 | −12.07 | 73.72 | 15.00 |
| 84 GLU | OE2 | −25.20 | −14.15 | 73.23 | 15.00 |
| 84 GLU | C | −24.74 | −13.81 | 77.37 | 15.00 |
| 84 GLU | O | −23.72 | −13.20 | 77.06 | 15.00 |
| 85 ASP | N | −25.37 | −13.60 | 78.53 | 15.00 |
| 85 ASP | CA | −24.94 | −12.54 | 79.44 | 15.00 |
| 85 ASP | CB | −25.85 | −12.44 | 80.66 | 15.00 |
| 85 ASP | CG | −27.22 | −11.88 | 80.32 | 15.00 |
| 85 ASP | OD1 | −28.19 | −12.27 | 81.01 | 15.00 |
| 85 ASP | OD2 | −27.33 | −11.06 | 79.37 | 15.00 |
| 85 ASP | C | −23.49 | −12.60 | 79.87 | 15.00 |
| 85 ASP | O | −22.78 | −11.59 | 79.79 | 15.00 |
| 86 ALA | N | −23.05 | −13.79 | 80.28 | 15.00 |
| 86 ALA | CA | −21.67 | −14.00 | 80.73 | 15.00 |
| 86 ALA | CB | −21.59 | −15.24 | 81.59 | 15.00 |
| 86 ALA | C | −20.61 | −14.06 | 79.62 | 15.00 |
| 86 ALA | O | −19.42 | −14.18 | 79.92 | 15.00 |
| 87 TYR | N | −21.04 | −13.98 | 78.36 | 15.00 |
| 87 TYR | CA | −20.13 | −14.04 | 77.22 | 15.00 |
| 87 TYR | CB | −19.69 | −15.50 | 76.99 | 15.00 |
| 87 TYR | CG | −18.30 | −15.71 | 76.41 | 15.00 |
| 87 TYR | CD1 | −17.79 | −14.89 | 75.41 | 15.00 |
| 87 TYR | CE1 | −16.54 | −15.12 | 74.86 | 15.00 |
| 87 TYR | CD2 | −17.51 | −16.78 | 76.84 | 15.00 |
| 87 TYR | CE2 | −16.26 | −17.02 | 76.29 | 15.00 |
| 87 TYR | CZ | −15.78 | −16.18 | 75.30 | 15.00 |
| 87 TYR | OH | −14.54 | −16.42 | 74.76 | 15.00 |
| 87 TYR | C | −20.88 | −13.46 | 76.00 | 15.00 |
| 87 TYR | O | −21.14 | −14.15 | 75.02 | 15.00 |
| 88 PRO | N | −21.17 | −12.14 | 76.05 | 15.00 |
| 88 PRO | CD | −20.72 | −11.16 | 77.06 | 15.00 |
| 88 PRO | CA | −21.90 | −11.45 | 74.97 | 15.00 |
| 88 PRO | CB | −21.94 | −9.99 | 75.46 | 15.00 |
| 88 PRO | CG | −20.72 | −9.87 | 76.27 | 15.00 |
| 88 PRO | C | −21.30 | −11.57 | 73.58 | 15.00 |
| 88 PRO | O | −20.11 | −11.80 | 73.42 | 15.00 |
| 89 TYR | N | −22.15 | −11.39 | 72.58 | 15.00 |
| 89 TYR | CA | −21.74 | −11.48 | 71.18 | 15.00 |
| 89 TYR | CB | −22.93 | −11.78 | 70.27 | 15.00 |
| 89 TYR | CG | −22.53 | −12.08 | 68.84 | 15.00 |
| 89 TYR | CD1 | −21.82 | −13.23 | 68.54 | 15.00 |
| 89 TYR | CE1 | −21.40 | −13.50 | 67.25 | 15.00 |
| 89 TYR | CD2 | −22.83 | −11.20 | 67.81 | 15.00 |
| 89 TYR | CE2 | −22.40 | −11.46 | 66.50 | 15.00 |
| 89 TYR | CZ | −21.69 | −12.62 | 66.24 | 15.00 |
| 89 TYR | OH | −21.23 | −12.90 | 64.98 | 15.00 |
| 89 TYR | C | −21.04 | −10.21 | 70.71 | 15.00 |
| 89 TYR | O | −21.54 | −9.11 | 70.94 | 15.00 |
| 90 VAL | N | −19.88 | −10.36 | 70.08 | 15.00 |
| 90 VAL | CA | −19.15 | −9.21 | 69.55 | 15.00 |
| 90 VAL | CB | −17.81 | −8.94 | 70.27 | 15.00 |
| 90 VAL | CG1 | −18.06 | −8.15 | 71.55 | 15.00 |
| 90 VAL | CG2 | −17.08 | −10.23 | 70.56 | 15.00 |
| 90 VAL | C | −18.92 | −9.31 | 68.05 | 15.00 |
| 90 VAL | O | −18.60 | −8.32 | 67.40 | 15.00 |
| 91 GLY | N | −19.08 | −10.51 | 67.50 | 15.00 |
| 91 GLY | CA | −18.90 | −10.68 | 66.06 | 15.00 |
| 91 GLY | C | −17.46 | −10.67 | 65.56 | 15.00 |
| 91 GLY | O | −17.19 | −10.28 | 64.42 | 15.00 |
| 92 GLN | N | −16.54 | −11.10 | 66.41 | 15.00 |
| 92 GLN | CA | −15.14 | −11.17 | 66.04 | 15.00 |
| 92 GLN | CB | −14.46 | −9.80 | 66.11 | 15.00 |
| 92 GLN | CG | −14.41 | −9.16 | 67.49 | 15.00 |
| 92 GLN | CD | −14.16 | −7.65 | 67.45 | 15.00 |
| 92 GLN | OE1 | −14.60 | −6.91 | 68.33 | 15.00 |
| 92 GLN | NE2 | −13.46 | −7.18 | 66.42 | 15.00 |
| 92 GLN | C | −14.45 | −12.22 | 66.92 | 15.00 |
| 92 GLN | O | −14.82 | −12.42 | 68.07 | 15.00 |
| 93 GLU | N | −13.51 | −12.94 | 66.32 | 15.00 |
| 93 GLU | CA | −12.75 | −13.98 | 66.99 | 15.00 |
| 93 GLU | CB | −11.92 | −14.80 | 65.98 | 15.00 |
| 93 GLU | CG | −12.60 | −15.10 | 64.64 | 15.00 |
| 93 GLU | CD | −11.66 | −15.74 | 63.60 | 15.00 |
| 93 GLU | OE1 | −10.42 | −15.60 | 63.72 | 15.00 |
| 93 GLU | OE2 | −12.17 | −16.37 | 62.65 | 15.00 |
| 93 GLU | C | −11.83 | −13.34 | 68.03 | 15.00 |
| 93 GLU | O | −11.21 | −12.30 | 67.75 | 15.00 |
| 94 GLU | N | −11.73 | −13.97 | 69.20 | 15.00 |
| 94 GLU | CA | −10.88 | −13.49 | 70.30 | 15.00 |
| 94 GLU | CB | −11.58 | −12.42 | 71.15 | 45.00 |
| 94 GLU | CG | −11.71 | −11.07 | 70.44 | 15.00 |
| 94 GLU | CD | −12.53 | −10.04 | 71.21 | 15.00 |
| 94 GLU | OE1 | −13.43 | −10.42 | 71.98 | 15.00 |
| 94 GLU | OE2 | −12.26 | −8.84 | 71.02 | 15.00 |
| 94 GLU | C | −10.47 | −14.70 | 71.15 | 15.00 |
| 94 GLU | O | −10.92 | −15.82 | 70.89 | 15.00 |
| 95 SER | N | −9.61 | −14.49 | 72.13 | 15.00 |
| 95 SER | CA | −9.17 | −15.58 | 72.99 | 15.00 |
| 95 SER | CB | −7.98 | −15.16 | 73.87 | 15.00 |
| 95 SER | OG | −8.29 | −14.05 | 74.70 | 15.00 |
| 95 SER | C | −10.29 | −16.20 | 73.83 | 15.00 |
| 95 SER | O | −11.16 | −15.50 | 74.36 | 15.00 |
| 96 CYS | N | −10.27 | −17.53 | 73.93 | 15.00 |
| 96 CYS | CA | −11.26 | −18.23 | 74.72 | 15.00 |
| 96 CYS | C | −11.28 | −17.62 | 76.13 | 15.00 |
| 96 CYS | O | −10.26 | −17.58 | 76.83 | 15.00 |
| 96 CYS | CB | −10.97 | −19.73 | 74.75 | 15.00 |
| 96 CYS | SG | −12.23 | −20.69 | 75.64 | 15.00 |
| 97 MET | N | −12.44 | −17.08 | 76.50 | 15.00 |
| 97 MET | CA | −12.64 | −16.44 | 77.80 | 15.00 |
| 97 MET | CB | −12.80 | −14.93 | 77.61 | 15.00 |
| 97 MET | CG | −12.60 | −14.11 | 78.87 | 15.00 |
| 97 MET | SD | −10.92 | −14.28 | 79.50 | 15.00 |
| 97 MET | CE | −10.06 | −13;18 | 78.42 | 15.00 |
| 97 MET | C | −13.84 | −17.05 | 78.53 | 15.00 |
| 97 MET | O | −14.64 | −16.34 | 79.14 | 15.00 |
| 98 TYR | N | −13.96 | −18.37 | 78.44 | 15.00 |
| 98 TYR | CA | −15.04 | −19.09 | 79.10 | 15.00 |
| 98 TYR | CB | −15.03 | −20.57 | 78.73 | 15.00 |
| 98 TYR | CG | −15.99 | −21.40 | 79.55 | 15.00 |
| 98 TYR | CD1 | −17.36 | −21.36 | 79.31 | 15.00 |

TABLE V-continued

Table of the orthogonal three dimensional coordinates in Ångstroms and B factors (Å²) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 98 TYR | CE1 | −18.25 | −22.09 | 80.09 | 15.00 |
| 98 TYR | CD2 | −15.53 | −22.21 | 80.59 | 15.00 |
| 98 TYR | CE2 | −16.41 | −22.95 | 81.38 | 15.00 |
| 98 TYR | CZ | −17.77 | −22.88 | 81.13 | 15.00 |
| 98 TYR | OH | −18.64 | −23.57 | 81.93 | 15.00 |
| 98 TYR | C | −15.01 | −18.91 | 80.61 | 15.00 |
| 98 TYR | O | −14.00 | −19.18 | 81.26 | 15.00 |
| 99 ASN | N | −16.12 | −18.44 | 81.16 | 15.00 |
| 99 ASN | CA | −16.24 | −18.23 | 82.58 | 15.00 |
| 99 ASN | CB | −16.80 | −16.84 | 82.89 | 15.00 |
| 99 ASN | CG | −16.73 | −16.50 | 84.38 | 15.00 |
| 99 ASN | OD1 | −16.91 | −17.36 | 85.24 | 15.00 |
| 99 ASN | ND2 | −16.44 | −15.25 | 84.68 | 15.00 |
| 99 ASN | C | −17.14 | −19.31 | 83.15 | 15.00 |
| 99 ASN | O | −18.33 | −19.37 | 82.85 | 15.00 |
| 100 PRO | N | −16.59 | −20.19 | 83.99 | 15.00 |
| 100 PRO | CD | −15.16 | −20.25 | 84.37 | 15.00 |
| 100 PRO | CA | −17.34 | −21.29 | 84.62 | 15.00 |
| 100 PRO | CB | −16.27 | −21.98 | 85.47 | 15.00 |
| 100 PR6 | CG | −15.00 | −21.70 | 84.70 | 15.00 |
| 100 PRO | C | −18.52 | −20.82 | 85.48 | 15.00 |
| 100 PRO | O | −19.53 | −21.51 | 85.58 | 15.00 |
| 101 THR | N | −18.37 | −19.64 | 86.09 | 15.00 |
| 101 THR | CA | −19.42 | −19.05 | 86.93 | 15.00 |
| 101 THR | CB | −18.92 | −17.73 | 87.61 | 15.00 |
| 101 THR | OG1 | −17.73 | −17.97 | 88.38 | 15.00 |
| 101 THR | CG2 | −19.99 | −17.15 | 88.54 | 15.00 |
| 101 THR | C | −20.68 | −18.73 | 86.12 | 15.00 |
| 101 THR | O | −21.77 | −18.69 | 86.68 | 15.00 |
| 102 GLY | N | −20.52 | −18.51 | 84.81 | 15.00 |
| 102 GLY | CA | −21.67 | −18.18 | 83.97 | 15.00 |
| 102 GLY | C | −22.36 | −19.33 | 83.25 | 15.00 |
| 102 GLY | O | −23.34 | −19.12 | 82.53 | 15.00 |
| 103 LYS | N | −21.87 | −20.54 | 83.47 | 15.00 |
| 103 LYS | CA | −22.41 | −21.74 | 82.83 | 15.00 |
| 103 LYS | CB | −21.73 | −22.98 | 83.40 | 15.00 |
| 103 LYS | CG | −21.93 | −24.24 | 82.59 | 15.00 |
| 103 LYS | CD | −21.93 | −25.43 | 83.52 | 15.00 |
| 103 LYS | CE | −20.80 | −25.36 | 84.52 | 15.00 |
| 103 LYS | NZ | −21.18 | −26.01 | 85.80 | 15.00 |
| 103 LYS | C | −23.91 | −21.86 | 82.95 | 15.00 |
| 103 LYS | O | −24.44 | −21.97 | 84.05 | 15.00 |
| 104 ALA | N | −24.60 | −21.92 | 81.82 | 15.00 |
| 104 ALA | CA | −26.05 | −22.02 | 81.81 | 15.00 |
| 104 ALA | CB | −26.65 | −20.90 | 80.97 | 15.00 |
| 104 ALA | C | −26.59 | −23.38 | 81.35 | 15.00 |
| 104 ALA | O | −27.77 | −23.67 | 81.53 | 15.00 |
| 105 ALA | N | −25.72 | −24.20 | 80.77 | 15.00 |
| 105 ALA | CA | −26.11 | −25.53 | 80.29 | 15.00 |
| 105 ALA | CB | −27.03 | −25.41 | 79.07 | 15.00 |
| 105 ALA | C | −24.88 | −26.34 | 79.91 | 15.00 |
| 105 ALA | O | −23.75 | −25.83 | 79.94 | 15.00 |
| 106 LYS | N | −25.12 | −27.60 | 79.57 | 15.00 |
| 106 LYS | CA | −24.10 | −28.54 | 79.11 | 15.00 |
| 106 LYS | CB | −23.33 | −29.21 | 80.26 | 15.00 |
| 106 LYS | CG | −24.14 | −30.16 | 81.14 | 15.00 |
| 106 LYS | CD | −23.57 | −31.59 | 81.11 | 15.00 |
| 106 LYS | CE | −24.32 | −32.54 | 82.06 | 15.00 |
| 106 LYS | NZ | −25.78 | −32.68 | 81.70 | 15.00 |
| 106 LYS | C | −24.83 | −29.57 | 78.27 | 15.00 |
| 106 LYS | O | −26.05 | −29.54 | 78.19 | 15.00 |
| 107 CYS | N | −24.09 | −30.44 | 77.60 | 15.00 |
| 107 CYS | CA | −24.70 | −31.48 | 76.79 | 15.00 |
| 107 CYS | CB | −24.95 | −31.05 | 75.34 | 15.00 |
| 107 CYS | SG | −23.54 | −31.08 | 74.19 | 15.00 |
| 107 CYS | C | −23.84 | −32.72 | 76.88 | 15.00 |
| 107 CYS | O | −22.66 | −32.64 | 77.19 | 15.00 |
| 108 ARG | N | −24.45 | −33.87 | 76.68 | 15.00 |
| 108 ARG | CA | −23.73 | −35.13 | 76.74 | 15.00 |
| 108 ARG | CB | −24.36 | −36.04 | 77.78 | 15.00 |
| 108 ARG | CG | −24.14 | −35.57 | 79.21 | 15.00 |
| 108 ARG | CD | −24.54 | −36.64 | 80.19 | 15.00 |
| 108 ARG | NE | −25.96 | −36.93 | 80.10 | 15.00 |
| 108 ARG | CZ | −26.54 | −38.01 | 80.61 | 15.00 |
| 108 ARG | NH1 | −25.81 | −38.91 | 81.24 | 15.00 |
| 108 ARG | NH2 | −27.85 | −38.18 | 80.50 | 15.00 |
| 108 ARG | C | −23.58 | −35.82 | 75.39 | 15.00 |
| 108 ARG | O | −23.92 | −36.99 | 75.24 | 15.00 |
| 109 GLY | N | −23.09 | −35.08 | 74.41 | 15.00 |
| 109 GLY | CA | −22.90 | −35.66 | 73.10 | 15.00 |
| 109 GLY | C | −23.96 | −35.21 | 72.13 | 15.00 |
| 109 GLY | O | −24.80 | −34.38 | 72.48 | 15.00 |
| 110 TYR | N | −23.95 | −35.79 | 70.94 | 15.00 |
| 110 TYR | CA | −24.90 | −35.45 | 69.88 | 15.00 |
| 110 TYR | CB | −24.35 | −34.33 | 68.98 | 15.00 |
| 110 TYR | CG | −23.08 | −34.72 | 68.26 | 15.00 |
| 110 TYR | CD1 | −21.84 | −34.52 | 68.86 | 15.00 |
| 110 TYR | CE1 | −20.69 | −34.96 | 68.26 | 15.00 |
| 110 TYR | CD2 | −23.13 | −35.37 | 67.04 | 15.00 |
| 110 TYR | CE2 | −21.98 | −35.82 | 66.43 | 15.00 |
| 110 TYR | CZ | −20.76 | −35.62 | 67.05 | 15.00 |
| 110 TYR | OH | −19.61 | −36.09 | 66.45 | 15.00 |
| 110 TYR | C | −25.28 | −36.66 | 69.02 | 15.00 |
| 110 TYR | O | −24.66 | −37.72 | 69.09 | 15.00 |
| 111 ARG | N | −26.28 | −36.45 | 68.18 | 15.00 |
| 111 ARG | CA | −26.77 | −37.47 | 67.27 | 15.00 |
| 111 ARG | CB | −28.06 | −38.10 | 67.78 | 15.00 |
| 111 ARG | CG | −29.00 | −38.71 | 66.72 | 15.00 |
| 111 ARG | CD | −28.59 | −40.10 | 66.19 | 15.00 |
| 111 ARG | NE | −29.56 | −40.59 | 65.20 | 15.00 |
| 111 ARG | CZ | −29.24 | −41.12 | 64.02 | 15.00 |
| 111 ARG | NH1 | −27.97 | −41.25 | 63.65 | 15.00 |
| 111 ARG | NH2 | −30.20 | −41.45 | 63.15 | 15.00 |
| 111 ARG | C | −26.95 | −36.78 | 65.92 | 15.00 |
| 111 ARG | O | −27.32 | −35.60 | 65.85 | 15.00 |
| 112 GLU | N | −26.60 | −37.49 | 64.86 | 15.00 |
| 112 GLU | CA | −26.73 | −36.98 | 63.50 | 15.00 |
| 112 GLU | CB | −25.44 | −37.25 | 62.71 | 15.00 |
| 112 GLU | CG | −24.23 | −36.54 | 63.29 | 15.00 |
| 112 GLU | CD | −22.94 | −36.81 | 62.52 | 15.00 |
| 112 GLU | OE1 | −22.55 | −36.00 | 61.66 | 15.00 |
| 112 GLU | OE2 | −22.30 | −37.84 | 62.82 | 15.00 |
| 112 GLU | C | −27.95 | −37.64 | 62.84 | 15.00 |
| 112 GLU | O | −28.32 | −38.74 | 63.20 | 15.00 |
| 113 ILE | N | −28.60 | −36.94 | 61.93 | 15.00 |
| 113 ILE | CA | −29.75 | −37.51 | 61.24 | 15.00 |
| 113 ILE | CB | −30.79 | −36.40 | 60.90 | 15.00 |
| 113 ILE | CG2 | −31.82 | −36.90 | 59.89 | 15.00 |
| 113 ILE | CG1 | −31.47 | −35.89 | 62.17 | 15.00 |
| 113 ILE | CD1 | −32.11 | −36.98 | 63.00 | 15.00 |
| 113 ILE | C | −29.23 | −38.17 | 59.97 | 15.00 |
| 113 ILE | O | −28.24 | −37.70 | 59.39 | 15.00 |
| 114 PRO | N | −29.81 | −39.32 | 59.56 | 15.00 |
| 114 PRO | CD | −30.91 | −40.08 | 60.16 | 15.00 |
| 114 PRO | CA | −29.34 | −39.97 | 58.34 | 15.00 |
| 114 PRO | CB | −30.43 | −41.01 | 58.08 | 15.00 |
| 114 PRO | CG | −30.84 | −41.40 | 59.42 | 15.00 |
| 114 PRO | C | −29.30 | −38.94 | 57.22 | 15.00 |
| 114 PRO | O | −30.29 | −38.23 | 56.97 | 15.00 |
| 115 GLU | N | −28.14 | −38.81 | 56.59 | 15.00 |
| 115 GLU | CA | −27.95 | −37.85 | 55.52 | 15.00 |
| 115 GLU | CB | −26.52 | −37.88 | 55.00 | 15.00 |
| 115 GLU | CG | −26.24 | −36.84 | 53.95 | 15.00 |
| 115 GLU | CD | −24.87 | −36.97 | 53.34 | 15.00 |
| 115 GLU | OE1 | −24.73 | −37.74 | 52.35 | 15.00 |
| 115 GLU | OE2 | −23.94 | −36.29 | 53.84 | 15.00 |
| 115 GLU | C | −28.94 | −38.05 | 54.38 | 15.00 |
| 115 GLU | O | −29.14 | −39.17 | 53.91 | 15.00 |
| 116 GLY | N | −29.55 | −36.96 | 53.95 | 15.00 |
| 116 GLY | CA | −30.51 | −37.02 | 52.86 | 15.00 |

TABLE V-continued

Table of the orthogonal three dimensional coordinates in Ångstroms and B factors (Å²) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 116 GLY | C | −31.93 | −37.43 | 53.23 | 15.00 |
| 116 GLY | O | −32.85 | −37.23 | 52.44 | 15.00 |
| 117 ASN | N | −32.12 | −37.92 | 54.46 | 15.00 |
| 117 ASN | CA | −33.43 | −38.37 | 54.93 | 15.00 |
| 117 ASN | CB | −33.27 | −39.59 | 55.85 | 15.00 |
| 117 ASN | CG | −34.53 | −40.48 | 55.92 | 15.00 |
| 117 ASN | OD1 | −35.65 | −40.02 | 55.70 | 15.00 |
| 117 ASN | ND2 | −34.34 | −41.74 | 56.27 | 15.00 |
| 117 ASN | C | −34.30 | −37.30 | 55.60 | 15.00 |
| 117 ASN | O | −34.12 | −37.00 | 56.79 | 15.00 |
| 118 GLU | N | −35.26 | −36.75 | 54.86 | 15.00 |
| 118 GLU | CA | −36.18 | −35.73 | 55.38 | 15.00 |
| 118 GLU | CB | −36.91 | −34.98 | 54.26 | 15.00 |
| 118 GLU | CG | −36.01 | −34.11 | 53.37 | 15.00 |
| 118 GLU | CD | −36.78 | −33.09 | 52.55 | 15.00 |
| 118 GLU | OE1 | −36.86 | −33.26 | 51.32 | 15.00 |
| 118 GLU | OE2 | −37.30 | −32.11 | 53.13 | 15.00 |
| 118 GLU | C | −37.19 | −36.37 | 56.35 | 15.00 |
| 118 GLU | O | −37.57 | −35.76 | 57.35 | 15.00 |
| 119 LYS | N | −37.59 | −37.60 | 56.06 | 15.00 |
| 119 LYS | CA | −38.53 | −38.31 | 56.92 | 15.00 |
| 119 LYS | CB | −38.89 | −39.68 | 56.33 | 15.00 |
| 119 LYS | CG | −40.10 | −40.36 | 56.97 | 15.00 |
| 119 LYS | CD | −40.37 | −41.75 | 56.35 | 15.00 |
| 119 LYS | CE | −39.71 | −42.89 | 57.16 | 15.00 |
| 119 LYS | NZ | −39.80 | −44.23 | 56.47 | 15.00 |
| 119 LYS | C | −37.89 | −38.45 | 58.30 | 15.00 |
| 119 LYS | O | −38.53 | −38.23 | 59.33 | 15.00 |
| 120 ALA | N | −36.59 | −38.76 | 58.30 | 15.00 |
| 120 ALA | CA | −35.85 | −38.91 | 59.54 | 15.00 |
| 120 ALA | CB | −34.44 | −39.41 | 59.25 | 15.00 |
| 120 ALA | C | −35.78 | −37.58 | 60.26 | 15.00 |
| 120 ALA | O | −35.89 | −37.52 | 61.49 | 15.00 |
| 121 LEU | N | −35.61 | −36.51 | 59.48 | 15.00 |
| 121 LEU | CA | −35.52 | −35.16 | 60.02 | 15.00 |
| 121 LEU | CB | −35.02 | −34.18 | 58.94 | 15.00 |
| 121 LEU | CG | −34.84 | −32.68 | 59.23 | 15.00 |
| 121 LEU | CD1 | −33.98 | −32.43 | 60.46 | 15.00 |
| 121 LEU | CD2 | −34.25 | −32.02 | 57.99 | 15.00 |
| 121 LEU | C | −36.83 | −34.68 | 60.68 | 15.00 |
| 121 LEU | O | −36.79 | −34.05 | 61.74 | 15.00 |
| 122 LYS | N | −37.97 | −35.03 | 60.08 | 15.00 |
| 122 LYS | CA | −39.29 | −34.65 | 60.60 | 15.00 |
| 122 LYS | CB | −40.42 | −34.99 | 59.63 | 15.00 |
| 122 LYS | CG | −41.82 | −34.90 | 60.26 | 15.00 |
| 122 LYS | CD | −42.89 | −35.49 | 59.34 | 15.00 |
| 122 LYS | CE | −44.28 | −35.44 | 59.97 | 15.00 |
| 122 LYS | NZ | −45.36 | −35.91 | 59.03 | 15.00 |
| 122 LYS | C | −39.57 | −35.33 | 61.92 | 15.00 |
| 122 LYS | O | −40.03 | −34.70 | 62.88 | 15.00 |
| 123 ARG | N | −39.33 | −36.63 | 61.96 | 15.00 |
| 123 ARG | CA | −39.55 | −37.40 | 63.17 | 15.00 |
| 123 ARG | CB | −39.26 | −38.88 | 62.91 | 15.00 |
| 123 ARG | CG | −40.26 | −39.53 | 61.95 | 15.00 |
| 123 ARG | CD | −40.04 | −41.04 | 61.79 | 15.00 |
| 123 ARG | NE | −38.71 | −41.35 | 61.25 | 15.00 |
| 123 ARG | CZ | −37.76 | −42.03 | 61.89 | 15.00 |
| 123 ARG | NH1 | −37.99 | −42.51 | 63.12 | 15.00 |
| 123 ARG | NH2 | −36.57 | −42.20 | 61.33 | 15.00 |
| 123 ARG | C | −38.72 | −36.82 | 64.33 | 15.00 |
| 123 ARG | O | −39.21 | −36.72 | 65.46 | 15.00 |
| 124 ALA | N | −37.50 | −36.38 | 64.04 | 15.00 |
| 124 ALA | CA | −36.62 | −35.79 | 65.05 | 15.00 |
| 124 ALA | CB | −35.21 | −35.60 | 64.50 | 15.00 |
| 124 ALA | C | −37.17 | −34.46 | 65.58 | 15.00 |
| 124 ALA | O | −37.17 | −34.21 | 66.79 | 15.00 |
| 125 VAL | N | −37.64 | −33.61 | 64.68 | 15.00 |
| 125 VAL | CA | −38.20 | −32.33 | 65.09 | 15.00 |
| 125 VAL | CB | −38.57 | −31.44 | 63.87 | 15.00 |
| 125 VAL | CG1 | −39.39 | −30.23 | 64.31 | 15.00 |
| 125 VAL | CG2 | −37.30 | −30.97 | 63.15 | 15.00 |
| 125 VAL | C | −39.41 | −32.57 | 65.99 | 15.00 |
| 125 VAL | O | −39.53 | −31.99 | 67.07 | 15.00 |
| 126 ALA | N | −40.27 | −33.49 | 65.58 | 15.00 |
| 126 ALA | CA | −41.46 | −33.83 | 66.34 | 15.00 |
| 126 ALA | CB | −42.27 | −34.90 | 65.62 | 15.00 |
| 126 ALA | C | −41.15 | −34.29 | 67.77 | 15.00 |
| 126 ALA | O | −41.69 | −33.74 | 68.73 | 15.00 |
| 127 ARG | N | −40.26 | −35.26 | 67.93 | 15.00 |
| 127 ARG | CA | −39.95 | −35.76 | 69.27 | 15.00 |
| 127 ARG | CB | −39.99 | −37.28 | 69.30 | 15.00 |
| 127 ARG | CG | −38.95 | −37.98 | 68.45 | 15.00 |
| 127 ARG | CD | −39.08 | −39.48 | 68.63 | 15.00 |
| 127 ARG | NE | −40.43 | −39.95 | 68.30 | 15.00 |
| 127 ARG | CZ | −41.25 | −40.58 | 69.14 | 15.00 |
| 127 ARG | NH1 | −42.47 | −40.94 | 68.73 | 15.00 |
| 127 ARG | NH2 | −40.88 | −40.83 | 70.39 | 15.00 |
| 127 ARG | C | −38.72 | −35.26 | 70.01 | 15.00 |
| 127 ARG | O | −38.50 | −35.65 | 71.15 | 15.00 |
| 128 VAL | N | −37.91 | −34.42 | 69.40 | 15.00 |
| 128 VAL | CA | −36.72 | −33.94 | 70.07 | 15.00 |
| 128 VAL | CB | −35.46 | −34.31 | 69.27 | 15.00 |
| 128 VAL | CG1 | −34.25 | −33.52 | 69.74 | 15.00 |
| 128 VAL | CG2 | −35.18 | −35.79 | 69.42 | 15.00 |
| 128 VAL | C | −36.78 | −32.43 | 70.32 | 15.00 |
| 128 VAL | O | −36.54 | −31.96 | 71.43 | 15.00 |
| 129 GLY | N | −37.12 | −31.68 | 69.28 | 15.00 |
| 129 GLY | CA | −37.18 | −30.24 | 69.39 | 15.00 |
| 129 GLY | C | −36.41 | −29.69 | 68.22 | 15.00 |
| 129 GLY | O | −36.10 | −30.46 | 67.30 | 15.00 |
| 130 PRO | N | −36.09 | −28.39 | 68.19 | 15.00 |
| 130 PRO | CD | −36.46 | −27.40 | 69.22 | 15.00 |
| 130 PRO | CA | −35.34 | −27.75 | 67.11 | 15.00 |
| 130 PRO | CB | −35.01 | −26.38 | 67.70 | 15.00 |
| 130 PRO | CG | −36.23 | −26.08 | 68.51 | 15.00 |
| 130 PRO | C | −34.06 | −28.52 | 66.73 | 15.00 |
| 130 PRO | O | −33.35 | −29.05 | 67.61 | 15.00 |
| 131 VAL | N | −33.78 | −28.58 | 65.44 | 15.00 |
| 131 VAL | CA | −32.61 | −29.30 | 64.92 | 15.00 |
| 131 VAL | CB | −33.05 | −30.57 | 64.15 | 15.00 |
| 131 VAL | CG1 | −31.85 | −31.31 | 63.57 | 15.00 |
| 131 VAL | CG2 | −33.84 | −31.50 | 65.07 | 15.00 |
| 131 VAL | C | −31.71 | −28.42 | 64.02 | 15.00 |
| 131 VAL | O | −32.21 | −27.71 | 63.14 | 15.00 |
| 132 SER | N | −30.41 | −28.44 | 64.29 | 15.00 |
| 132 SER | CA | −29.40 | −27.69 | 63.53 | 15.00 |
| 132 SER | CB | −28.07 | −27.65 | 64.28 | 15.00 |
| 132 SER | OG | −28.22 | −27.17 | 65.59 | 15.00 |
| 132 SER | C | −29.19 | −28.31 | 62.13 | 15.00 |
| 132 SER | O | −28.82 | −29.48 | 62.02 | 15.00 |
| 133 VAL | N | −29.40 | −27.52 | 61.08 | 15.00 |
| 133 VAL | CA | −29.23 | −28.02 | 59.73 | 15.00 |
| 133 VAL | CB | −30.6O | −28.18 | 58.99 | 15.00 |
| 133 VAL | CG1 | −31.53 | −29.06 | 59.80 | 15.00 |
| 133 VAL | CG2 | −31.24 | −26.84 | 58.70 | 15.00 |
| 133 VAL | C | −28.35 | −27.10 | 58.89 | 15.00 |
| 133 VAL | O | −28.22 | −25.92 | 59.20 | 15.00 |
| 134 ALA | N | −27.74 | −27.66 | 57.85 | 15.00 |
| 134 ALA | CA | −26.88 | −26.90 | 56.95 | 15.00 |
| 134 ALA | CB | −25.50 | −27.56 | 56.83 | 15.00 |
| 134 ALA | C | −27.59 | −26.86 | 55.59 | 15.00 |
| 134 ALA | O | −28.15 | −27.87 | 55.15 | 15.00 |
| 135 ILE | N | −27.61 | −25.69 | 54.96 | 15.00 |
| 135 ILE | CA | −28.28 | −25.52 | 53.68 | 15.00 |
| 135 ILE | CB | −29.64 | −24.75 | 53.86 | 15.00 |
| 135 ILE | CG2 | −30.59 | −25.51 | 54.77 | 15.00 |
| 135 ILE | CG1 | −29.37 | −23.34 | 54.39 | 15.00 |
| 135 ILE | CD1 | −30.61 | −22.47 | 54.50 | 15.00 |
| 135 ILE | C | −27.45 | −24.69 | 52.71 | 15.00 |
| 135 ILE | O | −26.36 | −24.22 | 53.04 | 15.00 |

TABLE V-continued

Table of the orthogonal three dimensional coordinates in Ångstroms and B factors (Å²) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 136 ASP | N | −27.98 | −24.56 | 51.49 | 15.00 |
| 136 ASP | CA | −27.37 | −23.75 | 50.45 | 15.00 |
| 136 ASP | CB | −27.45 | −24.42 | 49.07 | 15.00 |
| 136 ASP | CG | −26.86 | −23.57 | 47.94 | 15.00 |
| 136 ASP | OD1 | −26.91 | −24.02 | 46.79 | 15.00 |
| 136 ASP | OD2 | −26.35 | −22.45 | 48.19 | 15.00 |
| 136 ASP | C | −28.21 | −22.46 | 50.50 | 15.00 |
| 136 ASP | O | −29.41 | −22.48 | 50.22 | 15.00 |
| 137 ALA | N | −27.58 | −21.38 | 50.92 | 15.00 |
| 137 ALA | CA | −28.23 | −20.08 | 51.04 | 15.00 |
| 137 ALA | CB | −28.30 | −19.68 | 52.49 | 15.00 |
| 137 ALA | C | −27.45 | −19.04 | 50.25 | 15.00 |
| 137 ALA | O | −27.31 | −17.91 | 50.69 | 15.00 |
| 138 SER | N | −26.97 | −19.44 | 49.08 | 15.00 |
| 138 SER | CA | −26.18 | −18.56 | 48.22 | 15.00 |
| 138 SER | CB | −25.05 | −19.36 | 47.56 | 15.00 |
| 138 SER | OG | −25.57 | −20.33 | 46.67 | 15.00 |
| 138 SER | C | −26.99 | −17.81 | 47.16 | 15.00 |
| 138 SER | O | −26.48 | −16.88 | 46.52 | 15.00 |
| 139 LEU | N | −28.23 | −18.24 | 46.97 | 15.00 |
| 139 LEU | CA | −29.11 | −17.68 | 45.97 | 15.00 |
| 139 LEU | CB | −30.17 | −18.70 | 45.55 | 15.00 |
| 139 LEU | CG | −29.68 | −19.89 | 44.71 | 15.00 |
| 139 LEU | CD1 | −28.41 | −20.51 | 45.27 | 15.00 |
| 139 LEU | CD2 | −30.78 | −20.93 | 44.65 | 15.00 |
| 139 LEU | C | −29.76 | −16.35 | 46.31 | 15.00 |
| 139 LEU | O | −30.20 | −16.13 | 47.44 | 15.00 |
| 140 THR | N | −29.82 | −15.48 | 45.31 | 15.00 |
| 140 THR | CA | −30.41 | −14.15 | 45.44 | 15.00 |
| 140 THR | CB | −30.31 | −13.40 | 44.07 | 15.00 |
| 140 THR | OG1 | −28.94 | −13.06 | 43.81 | 15.00 |
| 140 THR | CG2 | −31.17 | −12.14 | 44.06 | 15.00 |
| 140 THR | C | −31.87 | −14.27 | 45.91 | 15.00 |
| 140 THR | O | −32.36 | −13.41 | 46.66 | 15.00 |
| 141 SER | N | −32.55 | −15.34 | 45.50 | 15.00 |
| 141 SER | CA | −33.93 | −15.58 | 45.89 | 15.00 |
| 141 SER | CB | −34.47 | −16.84 | 45.23 | 15.00 |
| 141 SER | OG | −33.61 | −17.94 | 45.44 | 15.00 |
| 141 SER | C | −34.00 | −15.70 | 47.41 | 15.00 |
| 141 SER | O | −34.83 | −15.07 | 48.07 | 15.00 |
| 142 PHE | N | −33.07 | −16.47 | 47.97 | 15.00 |
| 142 PHE | CA | −32.99 | −16.70 | 49.40 | 15.00 |
| 142 PHE | CB | −31.94 | −17.76 | 49.73 | 15.00 |
| 142 PHE | CG | −31.90 | −18.15 | 51.17 | 15.00 |
| 142 PHE | CD1 | −32.77 | −19.12 | 51.66 | 15.00 |
| 142 PHE | CD2 | −31.02 | −17.55 | 52.05 | 15.00 |
| 142 PHE | CE1 | −32.75 | −19.48 | 53.00 | 15.00 |
| 142 PHE | CE2 | −31.00 | −17.90 | 53.39 | 15.00 |
| 142 PHE | CZ | −31.86 | −18.87 | 53.86 | 15.00 |
| 142 PHE | C | −32.73 | −15.42 | 50.16 | 15.00 |
| 142 PHE | O | −33.46 | −15.07 | 51.08 | 15.00 |
| 143 GLN | N | −31.67 | −14.71 | 49.76 | 15.00 |
| 143 GLN | CA | −31.30 | −13.45 | 50.40 | 15.00 |
| 143 GLN | CB | −30.10 | −12.81 | 49.70 | 15.00 |
| 143 GLN | CG | −29.69 | −11.45 | 50.28 | 15.00 |
| 143 GLN | CD | −28.34 | −10.91 | 49.77 | 15.00 |
| 143 GLN | OE1 | −27.73 | −10.04 | 50.40 | 15.00 |
| 143 GLN | NE2 | −27.85 | −11.46 | 48.64 | 15.00 |
| 143 GLN | C | −32.50 | −12.51 | 50.43 | 15.00 |
| 143 GLN | O | −32.76 | −11.85 | 51.44 | 15.00 |
| 144 PHE | N | −33.28 | −12.51 | 49.36 | 15.00 |
| 144 PHE | CA | −34.43 | −11.62 | 49.26 | 15.00 |
| 144 PHE | CB | −34.43 | −10.90 | 47.89 | 15.00 |
| 144 PHE | CG | −33.21 | −10.01 | 47.66 | 15.00 |
| 144 PHE | CD1 | −32.96 | −8.92 | 48.48 | 15.00 |
| 144 PHE | CD2 | −32.31 | −10.29 | 46.63 | 15.00 |
| 144 PHE | CE1 | −31.83 | −8.12 | 48.30 | 15.00 |
| 144 PHE | CE2 | −31.17 | −9.48 | 46.44 | 15.00 |
| 144 PHE | CZ | −30.94 | −8.40 | 47.27 | 15.00 |
| 144 PHE | C | −35.79 | −12.23 | 49.61 | 15.00 |
| 144 PHE | O | −36.83 | −11.62 | 49.35 | 15.00 |
| 145 TYR | N | −35.78 | −13.41 | 50.24 | 15.00 |
| 145 TYR | CA | −37.03 | −14.08 | 50.64 | 15.00 |
| 145 TYR | CB | −36.76 | −15.42 | 51.35 | 1S.00 |
| 145 TYR | CG | −37.96 | −16.00 | 52.08 | 15.00 |
| 145 TYR | CD1 | −38.82 | −16.92 | 51.46 | 15.00 |
| 145 TYR | CE1 | −39.93 | −17.45 | 52.13 | 15.00 |
| 145 TYR | CD2 | −38.26 | −15.62 | 53.38 | 15.00 |
| 145 TYR | CE2 | −39.37 | −16.13 | 54.05 | 15.00 |
| 145 TYR | CZ | −40.20 | −17.04 | 53.43 | 15.00 |
| 145 TYR | OH | −41.29 | −17.54 | 54.12 | 15.00 |
| 145 TYR | C | −37.90 | −13.18 | 51.52 | 15.00 |
| 145 TYR | O | −37.38 | −12.43 | 52.36 | 15.00 |
| 146 SER | N | −39.21 | −13.31 | 51.38 | 15.00 |
| 146 SER | CA | −40.13 | −12.49 | 52.15 | 15.00 |
| 146 SER | CB | −40.37 | −11.15 | 51.45 | 15.00 |
| 146 SER | OG | −40.91 | −11.35 | 50.15 | 15.00 |
| 146 SER | C | −41.46 | −13.15 | 52.51 | 15.00 |
| 146 SER | O | −41.95 | −12.96 | 53.62 | 15.00 |
| 147 LYS | N | −42.01 | −13.92 | 51.58 | 15.00 |
| 147 LYS | CA | −43.30 | −14.59 | 51.76 | 15.00 |
| 147 LYS | CB | −44.42 | −13.76 | 51.10 | 15.00 |
| 147 LYS | CG | −44.60 | −12.34 | 51.62 | 15.00 |
| 147 LYS | CD | −45.05 | −12.34 | 53.08 | 15.00 |
| 147 LYS | CE | −45.37 | −10.92 | 53.58 | 15.00 |
| 147 LYS | NZ | −46.00 | −10.90 | 54.93 | 15.00 |
| 147 LYS | C | −43.37 | −16.03 | 51.20 | 15.00 |
| 147 LYS | O | −42.63 | −16.39 | 50.27 | 15.00 |
| 148 GLY | N | −44.29 | −16.81 | 51.75 | 15.00 |
| 148 GLY | CA | −44.52 | −18.16 | 51.28 | 15.00 |
| 148 GLY | C | −43.46 | −19.22 | 51.49 | 15.00 |
| 148 GLY | O | −42.47 | −18.99 | 52.18 | 15.00 |
| 149 VAL | N | −43.70 | −20.41 | 50.95 | 15.00 |
| 149 VAL | CA | −42.78 | −21.53 | 51.07 | 15.00 |
| 149 VAL | CB | −43.53 | −22.90 | 50.95 | 15.00 |
| 149 VAL | CG1 | −42.55 | −24.07 | 50.90 | 15.00 |
| 149 VAL | CG2 | −44.47 | −23.08 | 52.14 | 15.00 |
| 149 VAL | C | −41.69 | −21.41 | 50.01 | 15.00 |
| 149 VAL | O | −41.94 | −21.55 | 48.82 | 15.00 |
| 150 TYR | N | −40.49 | −21.08 | 50.48 | 15.00 |
| 150 TYR | CA | −39.31 | −20.92 | 49.63 | 15.00 |
| 150 TYR | CB | −38.12 | −20.36 | 50.42 | 15.00 |
| 150 TYR | CG | −36.84 | −20.29 | 49.60 | 15.00 |
| 150 TYR | CD1 | −36.67 | −19.30 | 48.63 | 15.00 |
| 150 TYR | CE1 | −35.54 | −19.29 | 47.81 | 15.00 |
| 150 TYR | CD2 | −35.84 | −21.25 | 49.74 | 15.00 |
| 150 TYR | CE2 | −34.71 | −21.24 | 48.92 | 15.00 |
| 150 TYR | CZ | −34.57 | −20.26 | 47.96 | 15.00 |
| 150 TYR | OH | −33.48 | −20.27 | 47.12 | 15.00 |
| 150 TYR | C | −38.89 | −22.18 | 48.89 | 15.00 |
| 150 TYR | O | −38.88 | −23.28 | 49.45 | 15.00 |
| 151 TYR | N | −38.47 | −21.98 | 47.65 | 15.00 |
| 151 TYR | CA | −37.98 | −23.03 | 46.77 | 15.00 |
| 151 TYR | CB | −39.09 | −23.99 | 46.35 | 15.00 |
| 151 TYR | CG | −38.62 | −25.09 | 45.42 | 15.00 |
| 151 TYR | CD1 | −37.92 | −26.20 | 45.91 | 15.00 |
| 151 TYR | CE1 | −37.51 | −27.23 | 45.06 | 15.00 |
| 151 TYR | CD2 | −38.89 | −25.04 | 44.05 | 15.00 |
| 151 TYR | CE2 | −38.49 | −26.07 | 43.19 | 15.00 |
| 151 TYR | CZ | −37.80 | −27.16 | 43.70 | 15.00 |
| 151 TYR | OH | −37.46 | −28.21 | 42.87 | 15.00 |
| 151 TYR | C | −37.35 | −22.39 | 45.55 | 15.00 |
| 151 TYR | O | −37.80 | −21.33 | 45.07 | 15.00 |
| 152 ASP | N | −36.30 | −23.02 | 45.05 | 15.00 |
| 152 ASP | CA | −35.59 | −22.54 | 43.86 | 15.00 |
| 152 ASP | CB | −34.66 | −21.38 | 44.20 | 15.00 |
| 152 ASP | CG | −34.13 | −20.68 | 42.97 | 15.00 |
| 152 ASP | OD1 | −33.52 | −19.60 | 43.12 | 15.00 |
| 152 ASP | OD2 | −34.32 | −21.20 | 41.84 | 15.00 |
| 152 ASP | C | −34.83 | −23.70 | 43.25 | 15.00 |

TABLE V-continued

Table of the orthogonal three dimensional coordinates in Ångstroms and B factors (Å$^2$) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 152 ASP | O | −33.94 | −24.27 | 43.89 | 15.00 |
| 153 GLU | N | −35.15 | −24.04 | 42.01 | 15.00 |
| 153 GLU | CA | −34.50 | −25.15 | 41.34 | 15.00 |
| 153 GLU | CB | −35.16 | −25.45 | 40.00 | 15.00 |
| 153 GLU | CG | −34.95 | −24.38 | 38.96 | 15.00 |
| 153 GLU | CD | −35.39 | −24.81 | 37.56 | 15.00 |
| 153 GLU | OE1 | −35.72 | −26.00 | 37.37 | 15.00 |
| 153 GLU | OE2 | −35.40 | −23.94 | 36.66 | 15.00 |
| 153 GLU | C | −32.98 | −25.02 | 41.17 | 15.00 |
| 153 GLU | O | −32.30 | −26.01 | 40.92 | 15.00 |
| 154 SER | N | −32.46 | −23.80 | 41.32 | 15.00 |
| 154 SER | CA | −31.02 | −23.56 | 41.18 | 15.00 |
| 154 SER | CB | −30.77 | −22.15 | 40.66 | 15.00 |
| 154 SER | OG | −31.56 | −21.91 | 39.50 | 15.00 |
| 154 SER | C | −30.23 | −23.82 | 42.46 | 15.00 |
| 154 SER | O | −28.99 | −23.76 | 42.45 | 15.00 |
| 155 CYS | N | −30.94 | −24.13 | 43.53 | 15.00 |
| 155 CYS | CA | −30.35 | −24.39 | 44.84 | 15.00 |
| 155 CYS | C | −29.60 | −25.71 | 44.92 | 15.00 |
| 155 CYS | O | −30.20 | −26.78 | 44.85 | 15.00 |
| 155 CYS | CB | −31.43 | −24.32 | 45.91 | 15.00 |
| 155 CYS | SG | −30.84 | −23.76 | 47.53 | 15.00 |
| 156 ASN | N | −28.29 | −25.64 | 45.11 | 15.00 |
| 156 ASN | CA | −27.46 | −26.84 | 45.20 | 15.00 |
| 156 ASN | CB | −26.08 | −26.58 | 44.61 | 15.00 |
| 156 ASN | CG | −25.26 | −27.85 | 44.48 | 15.00 |
| 156 ASN | OD1 | −25.77 | −28.97 | 44.56 | 15.00 |
| 156 ASN | ND2 | −23.96 | −27.69 | 44.26 | 15.00 |
| 156 ASN | C | −27.33 | −27.51 | 46.58 | 15.00 |
| 156 ASN | O | −26.74 | −26.95 | 47.51 | 15.00 |
| 157 SER | N | −27.78 | −28.76 | 46.65 | 15.00 |
| 157 SER | CA | −27.73 | −29.53 | 47.88 | 15.00 |
| 157 SER | CB | −28.66 | −30.74 | 47.80 | 15.00 |
| 157 SER | OG | −28.22 | −31.64 | 46.80 | 15.00 |
| 157 SER | C | −26.33 | −29.97 | 48.29 | 15.00 |
| 157 SER | O | −26.16 | −30.58 | 49.35 | 15.00 |
| 158 ASP | N | −25.34 | −29.71 | 47.43 | 15.00 |
| 158 ASP | CA | −23.95 | −30.07 | 47.71 | 15.00 |
| 158 ASP | CB | −23.35 | −30.92 | 46.59 | 15.00 |
| 158 ASP | CG | −24.02 | −32.27 | 46.47 | 15.00 |
| 158 ASP | OD1 | −24.01 | −33.04 | 47.47 | 15.00 |
| 158 ASP | OD2 | −24.58 | −32.55 | 45.38 | 15.00 |
| 158 ASP | C | −23.09 | −28.84 | 47.97 | 15.00 |
| 158 ASP | O | −21.86 | −28.90 | 47.96 | 15.00 |
| 159 ASN | N | −23.76 | −27.70 | 48.14 | 15.00 |
| 159 ASN | CA | −23.08 | −26.45 | 48.42 | 15.00 |
| 159 ASN | CB | −23.32 | −25.45 | 47.30 | 15.00 |
| 159 ASN | CG | −22.57 | −24.14 | 47.51 | 15.00 |
| 159 ASN | OD1 | −21.74 | −24.00 | 48.41 | 15.00 |
| 159 ASN | ND2 | −22.86 | −23.16 | 46.67 | 15.00 |
| 159 ASN | C | −23.69 | −25.99 | 49.73 | 15.00 |
| 159 ASN | O | −24.50 | −25.06 | 49.75 | 15.00 |
| 160 LEU | N | −23.39 | −26.71 | 50.81 | 15.00 |
| 160 LEU | CA | −23.89 | −26.38 | 52.15 | 15.00 |
| 160 LEU | CB | −23.90 | −27.62 | 53.06 | 15.00 |
| 160 LEU | CG | −24.57 | −28.92 | 52.58 | 15.00 |
| 160 LEU | CD1 | −24.38 | −30.01 | 53.60 | 15.00 |
| 160 LEU | CD2 | −26.04 | −28.72 | 52.33 | 15.00 |
| 160 LEU | C | −23.01 | −25.25 | 52.70 | 15.00 |
| 160 LEU | O | −21.92 | −25.48 | 53.22 | 15.00 |
| 161 ASN | N | −23.52 | −24.02 | 52.60 | 15.00 |
| 161 ASN | CA | −22.76 | −22.83 | 53.00 | 15.00 |
| 161 ASN | CB | −22.57 | −21.92 | 51.79 | 15.00 |
| 161 ASN | CG | −23.88 | −21.63 | 51.05 | 15.00 |
| 161 ASN | OD1 | −24.76 | −20.95 | 51.55 | 15.00 |
| 161 ASN | ND2 | −24.00 | −22.18 | 49.86 | 15.00 |
| 161 ASN | C | −23.26 | −22.01 | 54.20 | 15.00 |
| 161 ASN | O | −22.55 | −21.12 | 54.69 | 15.00 |
| 162 HIS | N | −24.46 | −22.32 | 54.68 | 15.00 |
| 162 HIS | CA | −25.05 | −21.57 | 55.79 | 15.00 |
| 162 HIS | CB | −25.96 | −20.49 | 55.23 | 15.00 |
| 162 HIS | CG | −26.59 | −19.59 | 56.25 | 15.00 |
| 162 HIS | CD2 | −27.87 | −19.21 | 56.42 | 15.00 |
| 162 HIS | ND1 | −25.86 | −18.91 | 57.21 | 15.00 |
| 162 HIS | CE1 | −26.66 | −18.14 | 57.91 | 15.00 |
| 162 HIS | NE2 | −27.89 | −18.30 | 57.45 | 15.00 |
| 162 HIS | C | −25.78 | −22.50 | 56.78 | 15.00 |
| 162 HIS | O | −26.69 | −23.22 | 56.39 | 15.00 |
| 163 ALA | N | −25.32 | −22.55 | 58.02 | 15.00 |
| 163 ALA | CA | −25.96 | −23.37 | 59.05 | 15.00 |
| 163 ALA | CB | −24.98 | −23.74 | 60.15 | 15.00 |
| 163 ALA | C | −27.13 | −22.57 | 59.62 | 15.00 |
| 163 ALA | O | −26.96 | −21.42 | 60.03 | 15.00 |
| 164 VAL | N | −28.29 | −23.20 | 59.71 | 15.00 |
| 164 VAL | CA | −29.50 | −22.54 | 60.16 | 15.00 |
| 164 VAL | CB | −30.35 | −22.26 | 58.88 | 15.00 |
| 164 VAL | CG1 | −31.36 | −23.35 | 58.63 | 15.00 |
| 164 VAL | CG2 | −30.92 | −20.89 | 58.89 | 15.00 |
| 164 VAL | C | −30.20 | −23.45 | 61.21 | 15.00 |
| 164 VAL | O | −29.65 | −24.48 | 61.57 | 15.00 |
| 165 LEU | N | −31.35 | −23.06 | 61.74 | 15.00 |
| 165 LEU | CA | −32.05 | −23.90 | 62.72 | 15.00 |
| 165 LEU | CB | −32.05 | −23.25 | 64.11 | 15.00 |
| 165 LEU | CG | −32.78 | −23.96 | 65.26 | 15.00 |
| 165 LEU | CD1 | −32.01 | −25.18 | 65.72 | 15.00 |
| 165 LEU | CD2 | −32.97 | −22.99 | 66.42 | 15.00 |
| 165 LEU | C | −33.48 | −24.25 | 62.31 | 15.00 |
| 165 LEU | O | −34.26 | −23.36 | 61.97 | 15.00 |
| 166 ALA | N | −33.83 | −25.54 | 62.36 | 15.00 |
| 166 ALA | CA | −35.17 | −26.00 | 62.00 | 15.00 |
| 166 ALA | CB | −35.08 | −27.37 | 61.33 | 15.00 |
| 166 ALA | C | −36.09 | −26.07 | 63.23 | 15.00 |
| 166 ALA | O | −36.08 | −27.05 | 63.97 | 15.00 |
| 167 VAL | N | −36.92 | −25.04 | 63.39 | 15.00 |
| 167 VAL | CA | −37.82 | −24.95 | 64.54 | 15.00 |
| 167 VAL | CB | −37.90 | −23.48 | 65.05 | 15.00 |
| 167 VAL | CG1 | −36.52 | −22.98 | 65.43 | 15.00 |
| 167 VAL | CG2 | −38.52 | −22.57 | 64.00 | 15.00 |
| 1G7 VAL | C | −39.23 | −25.53 | 64.35 | 15.00 |
| 167 VAL | O | −40.12 | −25.32 | 65.18 | 15.00 |
| 168 GLY | N | −39.43 | −26.27 | 63.27 | 15.00 |
| 168 GLY | CA | −40.73 | −26.86 | 63.04 | 15.00 |
| 168 GLY | C | −40.94 | −27.30 | 61.61 | 15.00 |
| 168 GLY | O | −40.00 | −27.42 | 60.82 | 15.00 |
| 169 TYR | N | −42.21 | −27.55 | 61.29 | 15.00 |
| 169 TYR | CA | −42.63 | −28.00 | 59.98 | 15.00 |
| 169 TYR | CB | −42.14 | −29.44 | 59.67 | 15.00 |
| 169 TYR | CG | −42.65 | −30.54 | 60.59 | 15.00 |
| 169 TYR | CD1 | −43.92 | −31.12 | 60.41 | 15.00 |
| 169 TYR | CE1 | −44.37 | −32.15 | 61.25 | 15.00 |
| 169 TYR | CD2 | −41.86 | −31.02 | 61.63 | 15.00 |
| 169 TYR | CE2 | −42.31 | −32.06 | 62.47 | 15.00 |
| 169 TYR | CZ | −43.57 | −32.61 | 62.27 | 15.00 |
| 169 TYR | OH | −44.00 | −33.61 | 63.11 | 15.00 |
| 169 TYR | C | −44.14 | −27.91 | 59.91 | 15.00 |
| 169 TYR | O | −44.83 | −27.98 | 60.92 | 15.00 |
| 170 GLY | N | −44.65 | −27.78 | 58.70 | 15.00 |
| 170 GLY | CA | −46.08 | −27.68 | 58.51 | 15.00 |
| 170 GLY | C | −46.38 | −27.73 | 57.04 | 15.00 |
| 170 GLY | O | −45.57 | −28.17 | 56.24 | 15.00 |
| 171 ILE | N | −47.52 | −27.17 | 56.68 | 15.00 |
| 171 ILE | CA | −47.97 | −27.14 | 55.30 | 15.00 |
| 171 ILE | CB | −48.87 | −28.38 | 55.01 | 15.00 |
| 171 ILE | CG2 | −49.85 | −28.63 | 56.15 | 15.00 |
| 171 ILE | CG1 | −49.58 | −28.25 | 53.67 | 15.00 |
| 171 ILE | CD1 | −50.27 | −29.51 | 53.26 | 15.00 |
| 171 ILE | C | −48.71 | −25.83 | 55.06 | 15.00 |
| 171 ILE | O | −49.51 | −25.40 | 55.88 | 15.00 |
| 172 GLN | N | −48.35 | −25.13 | 53.99 | 15.00 |
| 172 GLN | CA | −48.99 | −23.87 | 53.65 | 15.00 |

TABLE V-continued

Table of the orthogonal three dimensional coordinates in Ångstroms and B factors (Å²) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 172 GLN | CB | −48.01 | −22.70 | 53.72 | 15.00 |
| 172 GLN | CG | −48.67 | −21.36 | 53.62 | 15.00 |
| 172 GLN | CD | −47.71 | −20.23 | 53.89 | 15.00 |
| 172 GLN | OE1 | −47.35 | −19.97 | 55.05 | 15.00 |
| 172 GLN | NE2 | −47.27 | −19.55 | 52.84 | 15.00 |
| 172 GLN | C | −49.60 | −24.00 | 52.25 | 15.00 |
| 172 GLN | O | −48.88 | −24.13 | 51.26 | 15.00 |
| 173 LYS | N | −50.93 | −23.99 | 52.20 | 15.00 |
| 173 LYS | CA | −51.68 | −24.15 | 50.97 | 15.00 |
| 173 LYS | CB | −51.66 | −22.89 | 50.10 | 15.00 |
| 173 LYS | CG | −52.38 | −23.03 | 48.72 | 15.00 |
| 173 LYS | CD | −53.92 | −23.15 | 48.79 | 15.00 |
| 173 LYS | CE | −54.45 | −24.44 | 49.47 | 15.00 |
| 173 LYS | NZ | −54.10 | −25.73 | 48.79 | 15.00 |
| 173 LYS | C | −51.15 | −25.34 | 50.20 | 15.00 |
| 173 LYS | O | −50.54 | −25.19 | 49.14 | 15.00 |
| 174 GLY | N | −51.31 | −26.53 | 50.77 | 15.00 |
| 174 GLY | CA | −50.84 | −27.73 | 50.10 | 15.00 |
| 174 GLY | C | −49.36 | −27.74 | 49.76 | 15.00 |
| 174 GLY | O | −48.95 | −28.42 | 48.82 | 15.00 |
| 175 ASN | N | −48.57 | −26.97 | 50.50 | 15.00 |
| 175 ASN | CA | −47.12 | −26.90 | 50.30 | 15.00 |
| 175 ASN | CB | −46.69 | −25.54 | 49.74 | 15.00 |
| 175 ASN | CG | −46.88 | −25.43 | 48.24 | 15.00 |
| 175 ASN | OD1 | −45.91 | −25.39 | 47.48 | 15.00 |
| 175 ASN | ND2 | −48.13 | −25.38 | 47.79 | 15.00 |
| 175 ASN | C | −46.40 | −27.18 | 51.61 | 15.00 |
| 175 ASN | O | −46.33 | −26.31 | 52.49 | 15.00 |
| 176 LYS | N | −45.91 | −28.41 | 51.76 | 15.00 |
| 176 LYS | CA | −45.18 | −28.82 | 52.97 | 15.00 |
| 176 LYS | CB | −44.88 | −30.32 | 52.95 | 15.00 |
| 176 LYS | CG | −46.14 | −31.18 | 52.92 | 15.00 |
| 176 LYS | CD | −45.83 | −32.64 | 52.63 | 15.00 |
| 176 LYS | CE | −47.08 | −33.51 | 52.74 | 15.00 |
| 176 LYS | NZ | −47.62 | −33.57 | 54.13 | 15.00 |
| 176 LYS | C | −43.90 | −28.00 | 53.08 | 15.00 |
| 176 LYS | O | −43.34 | −27.58 | 52.07 | 15.00 |
| 177 HIS | N | −43.42 | −27.80 | 54.30 | 15.00 |
| 177 HIS | CA | −42.23 | −26.99 | 54.52 | 15.00 |
| 177 HIS | CB | −42.58 | −25.51 | 54.38 | 15.00 |
| 177 HIS | CG | −43.53 | −25.04 | 55.43 | 15.00 |
| 177 HIS | CD2 | −43.36 | −24.83 | 56.76 | 15.00 |
| 177 HIS | ND1 | −44.87 | −24.83 | 55.18 | 15.00 |
| 177 HIS | CE1 | −45.48 | −24.50 | 56.31 | 15.00 |
| 177 HIS | NE2 | −44.59 | −24.50 | 57.28 | 15.00 |
| 177 HIS | C | −41.62 | −27.24 | 55.88 | 15.00 |
| 177 HIS | O | −42.21 | −27.92 | 56.71 | 15.00 |
| 178 TRP | N | −40.49 | −26.58 | 56.12 | 15.00 |
| 178 TRP | CA | −39.74 | −26.60 | 57.38 | 15.00 |
| 178 TRP | CB | −38.28 | −27.02 | 57.18 | 15.00 |
| 178 TRP | CG | −38.08 | −28.36 | 56.62 | 15.00 |
| 178 TRP | CD2 | −38.10 | −29.59 | 57.34 | 15.00 |
| 178 TRP | CE2 | −37.84 | −30.62 | 56.41 | 15.00 |
| 178 TRP | CE3 | −38.30 | −29.94 | 58.68 | 15.00 |
| 178 TRP | CD1 | −37.82 | −28.67 | 55.32 | 15.00 |
| 178 TRP | NE1 | −37.68 | −30.02 | 55.18 | 15.00 |
| 178 TRP | CZ2 | −37.79 | −31.98 | 56.77 | 15.00 |
| 178 TRP | CZ3 | −38.25 | −31.28 | 59.05 | 15.00 |
| 178 TRP | CH2 | −37.99 | −32.28 | 58.09 | 15.00 |
| 178 TRP | C | −39.76 | −25.15 | 57.89 | 15.00 |
| 178 TRP | O | −39.63 | −24.21 | 57.10 | 15.00 |
| 179 ILE | N | −39.96 | −24.95 | 59.18 | 15.00 |
| 179 ILE | CA | −39.96 | −23.60 | 59.72 | 15.00 |
| 179 ILE | CB | −40.92 | −23.46 | 60.92 | 15.00 |
| 179 ILE | CG2 | −41.00 | −22.01 | 61.38 | 15.00 |
| 179 ILE | CG1 | −42.33 | −23.91 | 60.50 | 15.00 |
| 179 ILE | CD1 | −43.31 | −23.94 | 61.64 | 15.00 |
| 179 ILE | C | −38.50 | −23.37 | 60.10 | 15.00 |
| 179 ILE | O | −37.97 | −24.03 | 61.00 | 15.00 |
| 180 ILE | N | −37.84 | −22.48 | 59.36 | 15.00 |
| 180 ILE | CA | −36.43 | −22.18 | 59.55 | 15.00 |
| 180 ILE | CB | −35.67 | −22.22 | 58.19 | 15.00 |
| 180 ILE | CG2 | −34.25 | −21.74 | 58.35 | 15.00 |
| 180 ILE | CG1 | −35.73 | −23.63 | 57.58 | 15.00 |
| 180 ILE | CD1 | −35.19 | −24.73 | 58.48 | 15.00 |
| 180 ILE | C | −36.14 | −20.84 | 60.22 | 15.00 |
| 180 ILE | O | −36.63 | −19.80 | 59.79 | 15.00 |
| 181 LYS | N | −35.33 | −20.88 | 61.27 | 15.00 |
| 181 LYS | CA | −34.93 | −19.68 | 62.01 | 15.00 |
| 181 LYS | CB | −34.89 | −19.94 | 63.51 | 15.00 |
| 181 LYS | CG | −34.35 | −18.76 | 64.31 | 15.00 |
| 181 LYS | CD | −34.18 | −19.11 | 65.77 | 15.00 |
| 181 LYS | CE | −33.68 | −17.92 | 66.56 | 15.00 |
| 181 LYS | NZ | −33.51 | −18.24 | 68.01 | 15.00 |
| 181 LYS | C | −33.55 | −19.25 | 61.51 | 15.00 |
| 181 LYS | O | −32.61 | −20.03 | 61.53 | 15.00 |
| 182 ASN | N | −33.43 | −18.00 | 61.07 | 15.00 |
| 182 ASN | CA | −32.16 | −17.49 | 60.56 | 15.00 |
| 182 ASN | CB | −32.35 | −16.82 | 59.19 | 15.00 |
| 182 ASN | CG | −31.05 | −16.69 | 58.41 | 15.00 |
| 182 ASN | OD1 | −30.02 | −17.26 | 58.78 | 15.00 |
| 182 ASN | ND2 | −31.09 | −15.95 | 57.31 | 15.00 |
| 182 ASN | C | −31.49 | −16.53 | 61.56 | 15.00 |
| 182 ASN | O | −32.12 | −16.09 | 62.52 | 15.00 |
| 183 SER | N | −30.20 | −16.28 | 61.35 | 15.00 |
| 183 SER | CA | −29.44 | −15.37 | 62.20 | 15.00 |
| 183 SER | CB | −28.30 | −16.09 | 62.93 | 15.00 |
| 183 SER | OG | −27.53 | −16.88 | 62.05 | 15.00 |
| 183 SER | C | −28.93 | −14.14 | 61.42 | 15.00 |
| 183 SER | O | −27.77 | −13.73 | 61.54 | 15.00 |
| 184 TRP | N | −29.81 | −13.60 | 60.57 | 15.00 |
| 184 TRP | CA | −29.50 | −12.41 | 59.78 | 15.00 |
| 184 TRP | CB | −29.71 | −12.65 | 58.29 | 15.00 |
| 184 TRP | CG | −28.64 | −13.47 | 57.67 | 15.00 |
| 184 TRP | CD2 | −28.66 | −14.06 | 56.37 | 15.00 |
| 184 TRP | CE2 | −27.47 | −14.81 | 56.23 | 15.00 |
| 184 TRP | CE3 | −29.58 | −14.04 | 55.31 | 15.00 |
| 184 TRP | CD1 | −27.46 | −13.86 | 58.25 | 15.00 |
| 184 TRP | NE1 | −26.76 | −14.67 | 57.39 | 15.00 |
| 184 TRP | CZ2 | −27.18 | −15.53 | 55.06 | 15.00 |
| 184 TRP | CZ3 | −29.29 | −14.76 | 54.16 | 15.00 |
| 184 TRP | CH2 | −28.09 | −15.49 | 54.04 | 15.00 |
| 184 TRP | C | −30.34 | −11.22 | 60.27 | 15.00 |
| 184 TRP | O | −30.59 | −10.27 | 59.53 | 15.00 |
| 185 GLY | N | −30.78 | −11.31 | 61.52 | 15.00 |
| 185 GLY | CA | −31.57 | −10.25 | 62.10 | 15.00 |
| 185 GLY | C | −33.05 | −10.45 | 61.90 | 15.00 |
| 185 GLY | O | −33.50 | −11.18 | 61.01 | 15.00 |
| 186 GLU | N | −33.81 | −9.76 | 62.75 | 15.00 |
| 186 GLU | CA | −35.27 | −9.78 | 62.74 | 15.00 |
| 186 GLU | CB | −35.81 | −9.15 | 64.05 | 15.00 |
| 186 GLU | CG | −37.34 | −9.12 | 64.18 | 15.00 |
| 186 GLU | CD | −37.84 | −9.82 | 65.44 | 15.00 |
| 186 GLU | OE1 | −37.53 | −9.33 | 66.55 | 15.00 |
| 186 GLU | OE2 | −38.54 | −10.87 | 65.33 | 15.00 |
| 186 GLU | C | −35.85 | −9.11 | 61.50 | 15.00 |
| 186 GLU | O | −36.99 | −9.36 | 61.12 | 15.00 |
| 187 ASN | N | −35.05 | −8.27 | 60.84 | 15.00 |
| 187 ASN | CA | −35.52 | −7.59 | 59.64 | 15.00 |
| 187 ASN | CB | −35.00 | −6.16 | 59.56 | 15.00 |
| 187 ASN | CG | −36.02 | −5.17 | 60.07 | 15.00 |
| 187 ASN | OD1 | −35.91 | −4.68 | 61.20 | 15.00 |
| 187 ASN | ND2 | −37.05 | −4.90 | 59.25 | 15.00 |
| 187 ASN | C | −35.23 | −8.31 | 58.33 | 15.00 |
| 187 ASN | O | −35.26 | −7.72 | 57.27 | 15.00 |
| 188 TRP | N | −34.94 | −9.60 | 58.43 | 15.00 |
| 188 TRP | CA | −34.68 | −10.39 | 57.25 | 15.00 |
| 188 TRP | CB | −33.32 | −11.10 | 57.33 | 15.00 |
| 188 TRP | CG | −33.12 | −12.00 | 56.19 | 15.00 |
| 188 TRP | CD2 | −33.49 | −13.38 | 56.12 | 15.00 |

TABLE V-continued

Table of the orthogonal three dimensional coordinates in Ångstroms and B factors (Å$^2$) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 188 TRP | CE2 | −33.22 | −13.81 | 54.80 | 15.00 |
| 188 TRP | CE3 | −34.04 | −14.29 | 57.03 | 15.00 |
| 188 TRP | CD1 | −32.64 | −11.66 | 54.96 | 15.00 |
| 188 TRP | NE1 | −32.71 | −12.74 | 54.12 | 15.00 |
| 188 TRP | CZ2 | −33.48 | −15.13 | 54.37 | 15.00 |
| 188 TRP | CZ3 | −34.30 | −15.60 | 56.60 | 15.00 |
| 188 TRP | CH2 | −34.02 | −16.00 | 55.28 | 15.00 |
| 188 TRP | C | −35.82 | −11.39 | 57.10 | 15.00 |
| 188 TRP | O | −36.41 | −11.81 | 58.09 | 15.00 |
| 189 GLY | N | −36.11 | −11.76 | 55.85 | 15.00 |
| 189 GLY | CA | −37.16 | −12.72 | 55.57 | 15.00 |
| 189 GLY | C | −38.43 | −12.37 | 56.32 | 15.00 |
| 189 GLY | O | −38.82 | −11.20 | 56.40 | 15.00 |
| 190 ASN | N | −39.08 | −13.38 | 56.89 | 15.00 |
| 190 ASN | CA | −40.30 | −13.15 | 57.64 | 15.00 |
| 190 ASN | CB | −41.37 | −14.19 | 57.30 | 15.00 |
| 190 ASN | CG | −42.78 | −13.73 | 57.68 | 15.00 |
| 190 ASN | OD1 | −43.76 | −14.38 | 57.34 | 15.00 |
| 190 ASN | ND2 | −42.88 | −12.59 | 58.37 | 15.00 |
| 190 ASN | C | −40.02 | −13.14 | 59.13 | 15.00 |
| 190 ASN | O | −40.22 | −14.15 | 59.80 | 15.00 |
| 191 LYS | N | −39.56 | −11.99 | 59.63 | 15.00 |
| 191 LYS | CA | −39.23 | −11.78 | 61.05 | 15.00 |
| 191 LYS | CB | −40.40 | −12.11 | 61.99 | 15.00 |
| 191 LYS | CG | −41.62 | −11.23 | 61.84 | 15.00 |
| 191 LYS | CD | −42.63 | −11.52 | 62.95 | 15.00 |
| 191 LYS | CE | −43.99 | −10.85 | 62.71 | 15.00 |
| 191 LYS | NZ | −44.94 | −11.70 | 61.92 | 15.00 |
| 191 LYS | C | −37.98 | −12.58 | 61.45 | 15.60 |
| 191 LYS | O | −37.79 | −12.95 | 62.61 | 15.00 |
| 192 GLY | N | −37.13 | −12.82 | 60.45 | 15.00 |
| 192 GLY | CA | −35.90 | −13.56 | 60.66 | 15.00 |
| 192 GLY | C | −36.13 | −15.04 | 60.40 | 15.00 |
| 192 GLY | O | −35.29 | −15.88 | 60.72 | 15.00 |
| 193 TYR | N | −37.28 | −15.34 | 59.80 | 15.00 |
| 193 TYR | CA | −37.66 | −16.70 | 59.49 | 15.00 |
| 193 TYR | CB | −38.91 | −17.11 | 60.25 | 15.00 |
| 193 TYR | CG | −38.66 | −17.45 | 61.68 | 15.00 |
| 193 TYR | CD1 | −38.59 | −16.46 | 62.66 | 15.00 |
| 193 TYR | CE1 | −38.33 | −16.78 | 63.98 | 15.00 |
| 193 TYR | CD2 | −38.48 | −18.78 | 62.07 | 15.00 |
| 193 TYR | CE2 | −38.22 | −19.11 | 63.38 | 15.00 |
| 193 TYR | CZ | −38.15 | −18.11 | 64.34 | 15.00 |
| 193 TYR | OH | −37.89 | −18.43 | 65.64 | 15.00 |
| 193 TYR | C | −37.86 | −16.93 | 58.01 | 15.00 |
| 193 TYR | O | −37.92 | −15.99 | 57.22 | 15.00 |
| 194 ILE | N | −37.97 | −18.20 | 57.65 | 15.00 |
| 194 ILE | CA | −38.20 | −18.60 | 56.28 | 15.00 |
| 194 ILE | CB | −36.88 | −18.58 | 55.44 | 15.00 |
| 194 ILE | CG2 | −35.81 | −19.44 | 56.08 | 15.00 |
| 194 ILE | CG1 | −37.16 | −19.03 | 54.00 | 15.00 |
| 194 ILE | CD1 | −36.05 | −18.68 | 53.02 | 15.00 |
| 194 ILE | C | −38.85 | −20.00 | 56.28 | 15.00 |
| 194 ILE | O | −38.54 | −20.83 | 57.14 | 15.00 |
| 195 LEU | N | −39.84 | −20.20 | 55.42 | 15.00 |
| 195 LEU | CA | −40.50 | −21.49 | 55.30 | 15.00 |
| 195 LEU | CB | −42.00 | −21.36 | 55.08 | 15.00 |
| 195 LEU | CG | −42.81 | −20.66 | 56.16 | 15.00 |
| 195 LEU | CD1 | −44.27 | −20.65 | 55.77 | 15.00 |
| 195 LEU | CD2 | −42.60 | −21.36 | 57.49 | 15.00 |
| 195 LEU | C | −39.83 | −22.09 | 54.09 | 15.00 |
| 195 LEU | O | −39.85 | −21.47 | 53.04 | 15.00 |
| 196 MET | N | −39.17 | −23.23 | 54.23 | 15.00 |
| 196 MET | CA | −38.49 | −23.84 | 53.10 | 15.00 |
| 196 MET | CB | −37.01 | −24.08 | 53.39 | 15.00 |
| 196 MET | CG | −36.15 | −22.83 | 53.37 | 15.0o |
| 196 MET | SD | −34.45 | −23.19 | 53.93 | 15.00 |
| 196 MET | CE | −33.63 | −23.67 | 52.36 | 15.00 |
| 196 MET | C | −39.17 | −25.14 | 52.72 | 15.00 |
| 196 MET | O | −39.59 | −25.89 | 53.59 | 15.00 |
| 197 ALA | N | −39.22 | −25.41 | 51.41 | 15.00 |
| 197 ALA | CA | −39.86 | −26.62 | 50.87 | 15.00 |
| 197 ALA | CB | −39.64 | −26.70 | 49.36 | 15.00 |
| 197 ALA | C | −39.42 | −27.93 | 51.53 | 15.00 |
| 197 ALA | O | −38.23 | −28.21 | 51.67 | 15.00 |
| 198 ARG | N | −40.41 | −28.73 | 51.91 | 15.00 |
| 198 ARG | CA | −40.18 | −30.01 | 52.57 | 15.00 |
| 198 ARG | CB | −40.77 | −30.03 | 53.98 | 15.00 |
| 198 ARG | CG | −40.78 | −31.39 | 54.66 | 15.00 |
| 198 ARG | CD | −41.18 | −31.28 | 56.12 | 15.00 |
| 198 ARG | NE | −42.52 | −30.73 | 56.31 | 15.00 |
| 198 ARG | CZ | −43.63 | −31.47 | 56.40 | 15.00 |
| 198 ARG | NH1 | −43.55 | −32.80 | 56.31 | 15.00 |
| 198 ARG | NH2 | −44.80 | −30.89 | 56.62 | 15.00 |
| 198 ARG | C | −40.74 | −31.13 | 51.71 | 15.00 |
| 198 ARG | O | −41.84 | −31.00 | 51.16 | 15.00 |
| 199 ASN | N | −39.98 | −32.21 | 51.61 | 15.00 |
| 199 ASN | CA | −40.35 | −33.37 | 50.81 | 15.00 |
| 199 ASN | CB | −41.72 | −33.92 | 51.23 | 15.00 |
| 199 ASN | CG | −41.71 | −34.55 | 52.61 | 15.00 |
| 199 ASN | OD1 | −40.67 | −34.60 | 53.26 | 15.00 |
| 199 ASN | ND2 | −42.87 | −35.01 | 53.07 | 15.00 |
| 199 ASN | C | −40.31 | −33.04 | 49.32 | 15.00 |
| 199 ASN | O | −41.18 | −33.43 | 48.57 | 15.00 |
| 200 LYS | N | −39.30 | −32.27 | 48.92 | 15.00 |
| 200 LYS | CA | −39.13 | −31.88 | 47.54 | 15.00 |
| 200 LYS | CB | −39.46 | −30.41 | 47.32 | 15.00 |
| 200 LYS | CG | −39.74 | −30.07 | 45.87 | 15.00 |
| 200 LYS | CD | −41.24 | −30.05 | 45.59 | 15.00 |
| 200 LYS | CE | −41.92 | −28.93 | 46.40 | 15.00 |
| 200 LYS | NZ | −43.41 | −28.84 | 46.21 | 15.00 |
| 200 LYS | C | −37.68 | −32.17 | 47.16 | 15.00 |
| 200 LYS | O | −36.89 | −31.26 | 46.91 | 15.00 |
| 201 ASN | N | −37.34 | −33.45 | 47.14 | 15.00 |
| 201 ASN | CA | −36.00 | −33.95 | 46.83 | 15.00 |
| 201 ASN | CB | −35.78 | −34.02 | 45.31 | 15.00 |
| 201 ASN | CG | −36.19 | −32.75 | 44.59 | 15.00 |
| 201 ASN | OD1 | −37.20 | −32.72 | 43.87 | 15.00 |
| 201 ASN | ND2 | −35.40 | −31.70 | 44.76 | 15.00 |
| 201 ASN | C | −34.84 | −33.24 | 47.54 | 15.00 |
| 201 ASN | O | −33.84 | −32.88 | 46.92 | 15.00 |
| 202 ASN | N | −34.98 | −33.11 | 48.86 | 15.00 |
| 202 ASN | CA | −33.97 | −32.49 | 49.74 | 15.00 |
| 202 ASN | CB | −32.74 | −33.42 | 49.89 | 15.00 |
| 202 ASN | CG | −31.91 | −33.12 | 51.13 | 15.00 |
| 202 ASN | OD1 | −32.36 | −32.48 | 52.07 | 15.00 |
| 202 ASN | ND2 | −30.67 | −33.60 | 51.13 | 15.00 |
| 202 ASN | C | −33.56 | −31.08 | 49.33 | 15.00 |
| 202 ASN | O | −32.39 | −30.82 | 49.02 | 15.00 |
| 203 ALA | N | −34.51 | −30.16 | 49.36 | 15.00 |
| 203 ALA | H | −35.31 | −30.45 | 49.85 | 15.00 |
| 203 ALA | CA | −34.34 | −28.77 | 48.93 | 15.00 |
| 203 ALA | CB | −35.57 | −27.93 | 49.27 | 15.00 |
| 203 ALA | C | −33.15 | −28.14 | 49.67 | 15.00 |
| 203 ALA | O | −33.11 | −27.98 | 50.89 | 15.00 |
| 204 CYS | N | −32.16 | −27.74 | 48.86 | 15.00 |
| 204 CYS | CA | −30.95 | −27.06 | 49.31 | 15.00 |
| 204 CYS | C | −30.08 | −27.85 | 50.28 | 15.00 |
| 204 CYS | O | −29.25 | −27.26 | 50.98 | 15.00 |
| 204 CYS | CB | −31.27 | −25.68 | 49.90 | 15.00 |
| 204 CYS | SG | −32.21 | −24.52 | 48.84 | 15.00 |
| 205 GLY | N | −30.24 | −29.17 | 50.32 | 15.00 |
| 205 GLY | CA | −29.45 | −29.99 | 51.22 | 15.00 |
| 205 GLY | C | −29.93 | −29.89 | 52.66 | 15.00 |
| 205 GLY | O | −29.14 | −30.07 | 53.60 | 15.00 |
| 206 ILE | N | −31.23 | −29.68 | 52.83 | 15.00 |
| 206 ILE | CA | −31.84 | −29.52 | 54.15 | 15.00 |
| 206 ILE | CB | −33.39 | −29.24 | 54.01 | 15.00 |
| 206 ILE | CG2 | −34.12 | −30.44 | 53.42 | 15.00 |
| 206 ILE | CG1 | −34.00 | −28.84 | 55.35 | 15.00 |

TABLE V-continued

Table of the orthogonal three dimensional coordinates in Ångstroms and B factors (Å²) for the cathepsin K complex with inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Residue | Atom | X | Y | Z | B |
|---|---|---|---|---|---|
| 206 ILE | CD1 | −33.66 | −27.44 | 55.81 | 15.00 |
| 206 ILE | C | −31.57 | −30.69 | 55.11 | 15.00 |
| 206 ILE | O | −31.39 | −30.47 | 56.31 | 15.00 |
| 207 ALA | N | −31.46 | −31.91 | 54.59 | 15.00 |
| 207 ALA | CA | −31.21 | −33.09 | 55.42 | 15.00 |
| 207 ALA | CB | −32.32 | −34.12 | 55.21 | 15.00 |
| 207 ALA | C | −29.83 | −33.73 | 55.24 | 15.00 |
| 207 ALA | O | −29.58 | −34.86 | 55.66 | 15.00 |
| 208 ASN | N | −28.92 | −32.98 | 54.65 | 15.00 |
| 208 ASN | CA | −27.58 | −33.50 | 54.42 | 15.00 |
| 208 ASN | CB | −26.91 | −32.79 | 53.25 | 15.00 |
| 208 ASN | CG | −27.23 | −33.43 | 51.92 | 15.00 |
| 208 ASN | OD1 | −27.61 | −34.59 | 51.86 | 15.00 |
| 208 ASN | ND2 | −27.06 | −32.67 | 50.84 | 15.00 |
| 208 ASN | C | −26.68 | −33.44 | 55.65 | 15.00 |
| 208 ASN | O | −25.80 | −34.29 | 55.81 | 15.00 |
| 209 LEU | N | −26.91 | −32.46 | 56.52 | 15.00 |
| 209 LEU | CA | −26.09 | −32.29 | 57.72 | 15.00 |
| 209 LEU | CB | −24.96 | −31.30 | 57.44 | 15.00 |
| 209 LEU | CG | −23.70 | −31.44 | 58.30 | 15.00 |
| 209 LEU | CD1 | −22.81 | −32.53 | 57.75 | 15.00 |
| 209 LEU | CD2 | −22.95 | −30.12 | 58.33 | 15.00 |
| 209 LEU | C | −26.86 | −31.91 | 58.99 | 15.00 |
| 209 LEU | O | −26.42 | −31.04 | 59.74 | 15.00 |
| 210 ALA | N | −27.99 | −32.56 | 59.23 | 15.00 |
| 210 ALA | H | −27.89 | −32.43 | 58.64 | 15.00 |
| 210 ALA | CA | −28.78 | −32.25 | 60.42 | 15.00 |
| 210 ALA | CB | −29.43 | −31.67 | 60.51 | 15.00 |
| 210 ALA | C | −28.24 | −33.03 | 61.63 | 15.00 |
| 210 ALA | O | −27.87 | −34.20 | 61.51 | 15.00 |
| 211 SER | N | −28.17 | −32.35 | 62.78 | 15.00 |
| 211 SER | CA | −27.71 | −32.98 | 64.03 | 15.00 |
| 211 SER | CB | −26.19 | −33.01 | 64.15 | 15.00 |
| 211 SER | OG | −25.65 | −31.71 | 64.29 | 15.00 |
| 211 SER | C | −28.32 | −32.28 | 65.24 | 15.00 |
| 211 SER | O | −28.93 | −31.20 | 65.11 | 15.00 |
| 212 PHE | N | −28.18 | −32.89 | 66.41 | 15.00 |
| 212 PHE | CA | −28.74 | −32.30 | 67.61 | 15.00 |
| 212 PHE | CB | −30.25 | −32.56 | 67.71 | 15.00 |
| 212 PHE | CG | −30.62 | −34.00 | 67.79 | 15.00 |
| 212 PHE | CD1 | −31.04 | −34.69 | 66.66 | 15.00 |
| 212 PHE | CD2 | −30.53 | −34.69 | 69.00 | 15.00 |
| 212 PHE | CE1 | −31.36 | −36.03 | 66.73 | 15.00 |
| 212 PHE | CE2 | −30.85 | −36.04 | 69.07 | 15.00 |
| 212 PHE | CZ | −31.27 | −36.71 | 67.94 | 15.00 |
| 212 PHE | C | −28.01 | −32.78 | 68.87 | 15.00 |
| 212 PHE | O | −27.55 | −33.94 | 68.95 | 15.00 |
| 213 PRO | N | −27.92 | −31.91 | 69.88 | 15.00 |
| 213 PRO | CD | −28.60 | −30.60 | 69.99 | 15.00 |
| 213 PRO | CA | −27.25 | −32.25 | 71.13 | 15.00 |
| 213 PRO | CB | −27.11 | −30.89 | 71.80 | 15.00 |
| 213 PRO | CG | −28.44 | −30.26 | 71.47 | 15.00 |
| 213 PRO | C | −28.13 | −33.17 | 71.96 | 15.00 |
| 213 PRO | O | −29.36 | −33.23 | 71.79 | 15.00 |
| 214 LYS | N | −27.48 | −33.94 | 72.82 | 15.00 |
| 214 LYS | CA | −28.19 | −34.82 | 73.72 | 15.00 |
| 214 LYS | CB | −27.71 | −36.27 | 73.59 | 15.00 |
| 214 LYS | CG | −27.91 | −36.90 | 72.23 | 15.00 |
| 214 LYS | CD | −27.28 | −38.29 | 72.16 | 15.00 |
| 214 LYS | CE | −25.79 | −38.27 | 72.50 | 15.00 |
| 214 LYS | NZ | −25.11 | −39.56 | 72.18 | 15.00 |
| 214 LYS | C | −27.84 | −34.26 | 75.07 | 15.00 |
| 214 LYS | O | −26.76 | −33.71 | 75.24 | 15.00 |
| 215 MET | N | −28.79 | −34.27 | 75.99 | 15.00 |
| 215 MET | CA | −28.55 | −33.78 | 77.34 | 15.00 |
| 215 MET | CB | −29.47 | −32.60 | 77.70 | 15.00 |
| 215 MET | CG | −29.12 | −31.30 | 76.96 | 15.00 |
| 215 MET | SD | −29.59 | −29.73 | 77.80 | 15.00 |
| 215 MET | CE | −28.68 | −28.54 | 76.81 | 15.00 |
| 215 MET | C | −28.66 | −34.93 | 78.34 | 15.00 |
| 215 MET | OT1 | −27.81 | −35.01 | 79.26 | 15.00 |
| 215 MET | OT2 | −29.54 | −35.80 | 78.16 | 15.00 |
| 216 HOH | OH2 | −40.32 | −20.86 | 90.40 | 15.00 |
| 217 HOH | OH2 | −20.71 | −32.43 | 79.67 | 15.00 |
| 218 HOH | OH2 | −31.33 | −16.38 | 65.47 | 15.00 |
| 219 HOH | OH2 | −29.76 | −17.63 | 70.42 | 15.00 |
| 220 HOH | OH2 | −7.13 | −18.39 | 66.48 | 15.00 |
| 221 HOH | OH2 | −15.45 | −12.55 | 73.01 | 15.00 |
| 222 HOH | OH2 | −34.69 | −23.23 | 69.94 | 15.00 |
| 223 HOH | OH2 | −11.03 | −30.64 | 72.74 | 15.00 |
| 224 HOH | OH2 | −30.92 | −18.33 | 68.20 | 15.00 |
| 225 HOH | OH2 | −24.49 | −30.79 | 61.59 | 15.00 |
| 226 HOH | OH2 | −15.06 | −10.95 | 61.61 | 15.00 |
| 227 HOH | OH2 | −14.14 | −21.84 | 66.38 | 15.00 |
| 228 HOH | OH2 | −45.46 | −29.94 | 49.49 | 15.00 |
| 229 HOH | OH2 | −45.53 | −34.98 | 55.75 | 15.00 |
| 230 HOH | OH2 | −37.47 | −12.36 | 67.54 | 15.00 |
| 231 HOH | OH2 | −32.59 | −13.97 | 60.21 | 15.00 |
| 232 HOH | OH2 | −23.45 | −33.51 | 51.76 | 15.00 |
| 233 HOH | OH2 | −9.95 | −25.41 | 63.34 | 15.00 |
| 234 HOH | OH2 | −57.83 | −31.91 | 39.28 | 15.00 |
| 235 HOH | OH2 | −30.05 | −20.10 | 63.45 | 15.00 |
| 236 HOH | OH2 | −22.11 | −29.91 | 61.97 | 15.00 |
| 237 HOH | OH2 | −26.54 | −11.16 | 68.27 | 15.00 |
| 238 HOH | OH2 | −28.19 | −16.14 | 71.94 | 15.00 |
| 239 HOH | OH2 | −26.07 | −26.03 | 83.66 | 15.00 |
| 240 HOH | OH2 | −35.84 | −27.16 | 51.26 | 15.00 |
| 241 HOH | OH2 | −35.66 | −24.80 | 49.57 | 15.00 |
| 242 HOH | OH2 | −46.96 | −32.65 | 56.91 | 15.00 |
| 243 HOH | OH2 | −25.39 | −9.00 | 77.82 | 15.00 |
| 244 HOH | OH2 | −41.61 | −14.85 | 64.38 | 15.00 |
| 245 HOH | OH2 | −18.39 | −3.01 | 63.15 | 15.00 |
| 246 HOH | OH2 | −33.49 | −28.51 | 70.47 | 15.00 |
| 247 HOH | OH2 | −48.24 | −19.58 | 79.27 | 15.00 |
| 248 HOH | OH2 | −17.16 | −11.08 | 74.86 | 15.00 |
| 249 HOH | OH2 | −7.77 | −18.99 | 72.85 | 15.00 |
| 250 HOH | OH2 | −12.50 | −24.63 | 81.88 | 15.00 |
| 251 HOH | OH2 | −28.11 | −35.31 | 58.10 | 15.00 |
| 252 HOH | OH2 | −35.24 | −11.03 | 53.39 | 15.00 |
| 253 HOH | OH2 | −31.85 | −28.95 | 46.18 | 15.00 |
| 254 HOH | OH2 | −35.11 | −24.97 | 46.75 | 15.00 |
| 255 HOH | OH2 | −42.46 | −38.44 | 54.37 | 15.00 |
| 256 HOH | OH2 | −37.82 | −16.40 | 67.58 | 15.00 |
| 257 HOH | OH2 | −43.11 | −16.23 | 66.45 | 15.00 |
| 258 HOH | OH2 | −36.79 | −9.70 | 73.69 | 15.00 |
| 259 HOH | OH2 | −34.92 | −15.40 | 75.95 | 15.00 |
| 260 HOH | OH2 | −32.03 | −7.39 | 60.30 | 15.00 |
| 261 HOH | OH2 | −19.94 | −8.07 | 62.81 | 15.00 |
| 262 HOH | OH2 | −33.79 | −20.76 | 69.68 | 15.00 |
| 263 HOH | OH2 | −33.86 | −45.02 | 74.42 | 15.00 |
| 264 HOH | OH2 | −11.97 | −27.02 | 71.08 | 15.00 |
| 265 HOH | OH2 | −8.26 | −25.33 | 61.28 | 15.00 |
| 266 HOH | OH2 | −19.53 | −42.28 | 58.81 | 15.00 |
| 267 HOH | OH2 | −20.68 | −32.75 | 61.19 | 15.00 |
| 268 HOH | OH2 | −24.87 | −33.89 | 60.62 | 15.00 |
| 269 HOH | OH2 | −2.83 | −32.79 | 71.85 | 15.00 |
| 270 HOH | OH2 | −14.43 | −40.52 | 59.53 | 15.00 |
| 271 HOH | OH2 | −21.46 | −37.41 | 78.35 | 15.00 |
| 272 HOH | OH2 | −19.79 | −36.03 | 71.33 | 15.00 |
| 273 HOH | OH2 | −28.57 | −35.40 | 88.70 | 15.00 |
| 274 HOH | OH2 | −13.04 | −12.02 | 63.26 | 15.00 |
| 275 HOH | OH2 | −8.63 | −11.89 | 72.80 | 15.00 |
| 276 HOH | OH2 | −28.58 | −30.13 | 56.41 | 15.00 |
| 277 HOH | OH2 | −29.86 | −20.69 | 48.27 | 15.00 |
| 278 HOH | OH2 | −26.77 | −22.94 | 44.37 | 15.00 |
| 279 HOH | OH2 | −25.17 | −36.24 | 49.68 | 15.00 |
| 280 HOH | OH2 | −19.40 | −31.57 | 49.99 | 15.00 |
| 281 HOH | OH2 | −34.95 | −29.42 | 45.52 | 15.00 |
| 282 HOH | OH2 | −37.69 | −30.43 | 50.51 | 15.00 |

TABLE VI

Table of the orthogonal three dimensional coordinates in Angstroms and B factors (Å²) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 1 ALA | CB | −53.28 | −28.69 | 64.46 | 15.00 |
| 1 ALA | C | −53.74 | −30.77 | 63.13 | 15.00 |
| 1 ALA | O | −54.17 | −31.71 | 63.79 | 15.00 |
| 1 ALA | N | −55.61 | −29.36 | 63.92 | 15.00 |
| 1 ALA | CA | −54.20 | −29.34 | 63.43 | 15.00 |
| 2 PRO | N | −52.92 | −30.93 | 62.07 | 15.00 |
| 2 PRO | CD | −52.55 | −29.87 | 61.11 | 15.00 |
| 2 PRO | CA | −52.38 | −32.23 | 61.65 | 15.00 |
| 2 PRO | CB | −52.22 | −32.03 | 60.15 | 15.00 |
| 2 PRO | CG | −51.68 | −30.61 | 60.09 | 15.00 |
| 2 PRO | C | −51.02 | −32.37 | 62.31 | 15.00 |
| 2 PRO | O | −50.88 | −32.09 | 63.50 | 15.00 |
| 3 ASP | N | −50.02 | −32.75 | 61.52 | 15.00 |
| 3 ASP | CA | −48.67 | −32.92 | 62.02 | 15.00 |
| 3 ASP | CB | −47.96 | −34.03 | 61.25 | 15.00 |
| 3 ASP | CG | −48.48 | −35.41 | 61.59 | 15.00 |
| 3 ASP | OD1 | −49.68 | −35.69 | 61.38 | 15.00 |
| 3 ASP | OD2 | −47.66 | −36.24 | 62.06 | 15.00 |
| 3 ASP | C | −47.93 | −31.60 | 61.84 | 15.00 |
| 3 ASP | O | −47.35 | −31.34 | 60.78 | 15.00 |
| 4 SER | N | −48.02 | −30.74 | 62.84 | 15.00 |
| 4 SER | CA | −47.34 | −29.45 | 62.82 | 15.00 |
| 4 SER | CB | −48.32 | −28.34 | 62.42 | 15.00 |
| 4 SER | OG | −48.91 | −28.65 | 61.17 | 15.00 |
| 4 SER | C | −46.76 | −29.17 | 64.20 | 15.00 |
| 4 SER | O | −47.33 | −29.58 | 65.22 | 15.00 |
| 5 VAL | N | −45.60 | −28.54 | 64.23 | 15.00 |
| 5 VAL | CA | −45.00 | −28.20 | 65.51 | 15.00 |
| 5 VAL | CB | −44.16 | −29.36 | 66.11 | 15.00 |
| 5 VAL | CG1 | −42.89 | −29.57 | 65.35 | 15.00 |
| 5 VAL | CG2 | −43.87 | −29.08 | 67.57 | 15.00 |
| 5 VAL | C | −44.21 | −26.91 | 65.37 | 15.00 |
| 5 VAL | O | −43.46 | −26.73 | 64.41 | 15.00 |
| 6 ASP | N | −44.48 | −25.98 | 66.27 | 15.00 |
| 6 ASP | CA | −43.81 | −24.70 | 66.29 | 15.00 |
| 6 ASP | CB | −44.76 | −23.60 | 65.80 | 15.00 |
| 6 ASP | CG | −44.06 | −22.25 | 65.59 | 15.00 |
| 6 ASP | OD1 | −42.88 | −22.10 | 65.94 | 15.00 |
| 6 ASP | OD2 | −44.73 | −21.33 | 65.08 | 15.00 |
| 6 ASP | C | −43.41 | −24.48 | 67.75 | 15.00 |
| 6 ASP | O | −44.26 | −24.33 | 68.63 | 15.00 |
| 7 TYR | N | −42.12 | −24.54 | 68.00 | 15.00 |
| 7 TYR | CA | −41.60 | −24.37 | 69.34 | 15.00 |
| 7 TYR | CB | −40.20 | −24.96 | 69.42 | 15.00 |
| 7 TYR | CG | −40.23 | −26.49 | 69.41 | 15.00 |
| 7 TYR | CD1 | −40.62 | −27.20 | 70.55 | 15.00 |
| 7 TYR | CE1 | −40.66 | −28.57 | 70.55 | 15.00 |
| 7 TYR | CD2 | −39.89 | −27.21 | 68.27 | 15.00 |
| 7 TYR | CE2 | −39.94 | −28.60 | 68.26 | 15.00 |
| 7 TYR | CZ | −40.32 | −29.27 | 69.41 | 15.00 |
| 7 TYR | OH | −40.40 | −30.63 | 69.42 | 15.00 |
| 7 TYR | C | −41.64 | −22.94 | 69.83 | 15.00 |
| 7 TYR | O | −41.52 | −22.68 | 71.03 | 15.00 |
| 8 ARG | N | −41.85 | −22.01 | 68.90 | 15.00 |
| 8 ARG | CA | −41.91 | −20.58 | 69.22 | 15.00 |
| 8 ARG | CB | −42.07 | −19.74 | 67.95 | 15.00 |
| 8 ARG | CG | −40.84 | −19.78 | 67.04 | 15.00 |
| 8 ARG | CD | −41.01 | −18.96 | 65.78 | 15.00 |
| 8 ARG | NE | −41.97 | −19.57 | 64.86 | 15.00 |
| 8 ARG | CZ | −42.43 | −18.97 | 63.77 | 15.00 |
| 8 ARG | NH1 | −42.03 | −17.75 | 63.46 | 15.00 |
| 8 ARG | NH2 | −43.30 | −19.60 | 62.98 | 15.00 |
| 8 ARG | C | −43.09 | −20.36 | 70.15 | 15.00 |
| 8 ARG | O | −42.95 | −19.71 | 71.18 | 15.00 |
| 9 LYS | N | −44.23 | −20.95 | 69.82 | 15.00 |
| 9 LYS | CA | −45.41 | −20.80 | 70.64 | 15.00 |
| 9 LYS | CB | −46.59 | −21.48 | 69.96 | 15.00 |
| 9 LYS | CG | −46.93 | −20.90 | 68.60 | 15.00 |
| 9 LYS | CD | −47.74 | −21.89 | 67.79 | 15.00 |
| 9 LYS | CE | −48.07 | −21.38 | 66.41 | 15.00 |
| 9 LYS | NZ | −48.46 | −22.50 | 65.49 | 15.00 |
| 9 LYS | C | −45.16 | −21.46 | 71.99 | 15.00 |
| 9 LYS | O | −45.70 | −21.01 | 73.01 | 15.00 |
| 10 LYS | N | −44.29 | −22.46 | 71.99 | 15.00 |
| 10 LYS | CA | −43.94 | −23.25 | 73.18 | 15.00 |
| 10 LYS | CB | −43.34 | −24.60 | 72.77 | 15.00 |
| 10 LYS | CG | −44.19 | −25.43 | 71.81 | 15.00 |
| 10 LYS | CD | −45.03 | −26.48 | 72.52 | 15.00 |
| 10 LYS | CE | −46.23 | −25.86 | 73.25 | 15.00 |
| 10 LYS | NZ | −47.28 | −25.31 | 72.33 | 15.00 |
| 10 LYS | C | −42.97 | −22.59 | 74.15 | 15.00 |
| 10 LYS | O | −42.91 | −22.97 | 75.32 | 15.00 |
| 11 GLY | N | −42.15 | −21.66 | 73.67 | 15.00 |
| 11 GLY | CA | −41.20 | −21.02 | 74.57 | 15.00 |
| 11 GLY | C | −39.83 | −21.68 | 74.55 | 15.00 |
| 11 GLY | O | −39.00 | −21.42 | 75.42 | 15.00 |
| 12 TYR | N | −39.57 | −22.49 | 73.53 | 15.00 |
| 12 TYR | CA | −38.29 | −23.18 | 73.39 | 15.00 |
| 12 TYR | CB | −38.48 | −24.53 | 72.68 | 15.00 |
| 12 TYR | CG | −39.09 | −25.67 | 73.49 | 15.00 |
| 12 TYR | CD1 | −40.24 | −25.49 | 74.27 | 15.00 |
| 12 TYR | CE1 | −40.82 | −26.55 | 74.95 | 15.00 |
| 12 TYR | CD2 | −38.55 | −26.95 | 73.42 | 15.00 |
| 12 TYR | CE2 | −39.13 | −28.01 | 74.09 | 15.00 |
| 12 TYR | CZ | −40.26 | −27.81 | 74.85 | 15.00 |
| 12 TYR | OH | −40.86 | −28.88 | 75.47 | 15.00 |
| 12 TYR | C | −37.31 | −22.37 | 72.55 | 15.00 |
| 12 TYR | O | −36.15 | −22.73 | 72.44 | 15.00 |
| 13 VAL | N | −37.78 | −21.29 | 71.94 | 15.00 |
| 13 VAL | CA | −36.94 | −20.46 | 71.07 | 15.00 |
| 13 VAL | CB | −37.56 | −20.37 | 69.65 | 15.00 |
| 13 VAL | CG1 | −36.60 | −19.70 | 68.68 | 15.00 |
| 13 VAL | CG2 | −37.91 | −21.76 | 69.16 | 15.00 |
| 13 VAL | C | −36.75 | −19.06 | 71.62 | 15.00 |
| 13 VAL | O | −37.70 | −18.41 | 72.02 | 15.00 |
| 14 THR | N | −35.51 | −18.61 | 71.66 | 15.00 |
| 14 THR | CA | −35.21 | −17.27 | 72.15 | 15.00 |
| 14 THR | CB | −33.80 | −17.21 | 72.74 | 15.00 |
| 14 THR | OG1 | −32.85 | −17.58 | 71.74 | 15.00 |
| 14 THR | CG2 | −33.69 | −18.13 | 73.92 | 15.00 |
| 14 THR | C | −35.31 | −16.23 | 71.02 | 15.00 |
| 14 THR | O | −35.46 | −16.59 | 69.85 | 15.00 |
| 15 PRO | N | −35.25 | −14.94 | 71.35 | 15.00 |
| 15 PRO | CD | −35.15 | −14.35 | 72.71 | 15.00 |
| 15 PRO | CA | −35.34 | −13.89 | 70.34 | 15.00 |
| 15 PRO | CB | −35.15 | −12.62 | 71.16 | 15.00 |
| 15 PRO | CG | −35.72 | −12.99 | 72.50 | 15.00 |
| 15 PRO | C | −34.26 | −14.00 | 69.25 | 15.00 |
| 15 PRO | O | −33.13 | −14.41 | 69.53 | 15.00 |
| 16 VAL | N | −34.61 | −13.62 | 68.02 | 15.00 |
| 16 VAL | CA | −33.69 | −13.67 | 66.89 | 15.00 |
| 16 VAL | CB | −34.39 | −13.43 | 65.54 | 15.00 |
| 16 VAL | CG1 | −33.36 | −13.27 | 64.43 | 15.00 |
| 16 VAL | CG2 | −35.29 | −14.58 | 65.20 | 15.00 |
| 16 VAL | C | −32.56 | −12.66 | 67.05 | 15.00 |
| 16 VAL | O | −32.79 | −11.47 | 67.28 | 15.00 |
| 17 LYS | N | −31.34 | −13.17 | 66.92 | 15.00 |
| 17 LYS | CA | −30.15 | −12.36 | 67.04 | 15.00 |
| 17 LYS | CB | −29.13 | −13.09 | 67.91 | 15.00 |
| 17 LYS | CG | −29.67 | −13.49 | 69.27 | 15.00 |
| 17 LYS | CD | −30.28 | −12.30 | 69.96 | 15.00 |
| 17 LYS | CE | −30.93 | −12.65 | 71.28 | 15.00 |
| 17 LYS | NZ | −31.68 | −11.47 | 71.83 | 15.00 |
| 17 LYS | C | −29.58 | −12.08 | 65.65 | 15.00 |
| 17 LYS | O | −30.13 | −12.52 | 64.64 | 15.00 |
| 18 ASN | N | −28.48 | −11.33 | 65.60 | 15.00 |
| 18 ASN | CA | −27.82 | −10.98 | 64.34 | 15.00 |
| 18 ASN | CB | −28.02 | −9.49 | 64.05 | 15.00 |
| 18 ASN | CG | −27.42 | −9.05 | 62.72 | 15.00 |
| 18 ASN | OD1 | −26.35 | −9.49 | 62.32 | 15.00 |
| 18 ASN | ND2 | −28.11 | −8.15 | 62.03 | 15.00 |
| 18 ASN | C | −26.32 | −11.27 | 64.49 | 15.00 |

TABLE VI-continued

Table of the orthogonal three dimensional coordinates in Angstroms and B factors (Å²) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 18 ASN | O | −25.67 | −10.71 | 65.37 | 15.00 |
| 19 GLN | N | −25.79 | −12.14 | 63.63 | 15.00 |
| 19 GLN | CA | −24.38 | −12.49 | 63.68 | 15.00 |
| 19 GLN | CB | −24.08 | −13.76 | 62.87 | 15.00 |
| 19 GLN | CG | −24.55 | −13.74 | 61.41 | 15.00 |
| 19 GLN | CD | −24.19 | −15.02 | 60.65 | 15.00 |
| 19 GLN | OE1 | −25.06 | −15.85 | 60.37 | 15.00 |
| 19 GLN | NE2 | −22.92 | −15.16 | 60.28 | 15.00 |
| 19 GLN | C | −23.43 | −11.34 | 63.29 | 15.00 |
| 19 GLN | O | −22.26 | −11.34 | 63.67 | 15.00 |
| 20 GLY | N | −23.92 | −10.39 | 62.50 | 15.00 |
| 20 GLY | CA | −23.11 | −9.25 | 62.11 | 15.00 |
| 20 GLY | C | −22.23 | −9.49 | 60.91 | 15.00 |
| 20 GLY | O | −22.71 | −9.92 | 59.87 | 15.00 |
| 21 GLN | N | −20.96 | −9.14 | 61.02 | 15.00 |
| 21 GLN | CA | −20.02 | −9.34 | 59.92 | 15.00 |
| 21 GLN | CB | −19.11 | −8.11 | 59.75 | 15.00 |
| 21 GLN | CG | −19.78 | −6.87 | 59.13 | 15.00 |
| 21 GLN | CD | −20.32 | −7.11 | 57.72 | 15.00 |
| 21 GLN | OE1 | −19.57 | −7.44 | 56.79 | 15.00 |
| 21 GLN | NE2 | −21.62 | −6.95 | 57.55 | 15.00 |
| 21 GLN | C | −19.18 | −10.59 | 60.17 | 15.00 |
| 21 GLN | O | −18.39 | −11.01 | 59.33 | 15.00 |
| 22 CYS | N | −19.34 | −11.17 | 61.36 | 15.00 |
| 22 CYS | CA | −18.63 | −12.38 | 61.75 | 15.00 |
| 22 CYS | C | −19.40 | −13.60 | 61.22 | 15.00 |
| 22 CYS | O | −20.64 | −13.58 | 61.15 | 15.00 |
| 22 CYS | CB | −18.52 | −12.41 | 63.27 | 15.00 |
| 22 CYS | SG | −17.94 | −13.95 | 64.05 | 15.00 |
| 23 GLY | N | −18.68 | −14.63 | 60.78 | 15.00 |
| 23 GLY | CA | −19.32 | −15.82 | 60.25 | 15.00 |
| 23 GLY | C | −19.52 | −16.87 | 61.32 | 15.00 |
| 23 GLY | O | −19.06 | −18.00 | 61.18 | 15.00 |
| 24 SER | N | −20.24 | −16.49 | 62.37 | 15.00 |
| 24 SER | CA | −20.52 | −17.34 | 63.52 | 15.00 |
| 24 SER | CB | −20.42 | −16.49 | 64.77 | 15.00 |
| 24 SER | OG | −21.27 | −15.36 | 64.65 | 15.00 |
| 24 SER | C | −21.92 | −17.95 | 63.44 | 15.00 |
| 24 SER | O | −22.54 | −18.24 | 64.47 | 15.00 |
| 25 CYS | N | −22.40 | −18.17 | 62.23 | 15.00 |
| 25 CYS | CA | −23.72 | −18.75 | 62.04 | 15.00 |
| 25 CYS | CB | −24.08 | −18.74 | 60.55 | 15.00 |
| 25 CYS | SG | −23.06 | −19.79 | 59.52 | 15.00 |
| 25 CYS | C | −23.81 | −20.15 | 62.66 | 15.00 |
| 25 CYS | O | −24.90 | −20.59 | 63.05 | 15.00 |
| 25 INH | C1 | −27.01 | −9.79 | 58.47 | 15.00 |
| 25 INH | C2 | −26.33 | −10.46 | 59.49 | 15.00 |
| 25 INH | C3 | −25.12 | −11.10 | 59.22 | 15.00 |
| 25 INH | C4 | −24.57 | −11.08 | 57.94 | 15.00 |
| 25 INH | C5 | −25.26 | −10.40 | 56.92 | 15.00 |
| 25 INH | C6 | −26.47 | −9.76 | 57.18 | 15.00 |
| 25 INH | C7 | −23.25 | −11.75 | 57.65 | 15.00 |
| 25 INH | O8 | −23.16 | −13.18 | 57.51 | 15.00 |
| 25 INH | C9 | −22.82 | −13.83 | 56.29 | 15.00 |
| 25 INH | C10 | −22.10 | −13.30 | 55.22 | 15.00 |
| 25 INH | C11 | −23.03 | −15.93 | 55.08 | 15.00 |
| 25 INH | C12 | −22.32 | −15.39 | 54.01 | 15.00 |
| 25 INH | C13 | −21.85 | −14.07 | 54.07 | 15.00 |
| 25 INH | C14 | −23.54 | −17.29 | 55.29 | 15.00 |
| 25 INH | O15 | −24.49 | −17.82 | 54.70 | 15.00 |
| 25 INH | N16 | −22.71 | −17.77 | 56.29 | 15.00 |
| 25 INH | N17 | −22.76 | −19.07 | 56.92 | 15.00 |
| 25 INH | C18 | −23.27 | −15.13 | 56.20 | 15.00 |
| 25 INH | C19 | −22.05 | −19.01 | 58.26 | 15.00 |
| 25 INH | O20 | −21.78 | −17.83 | 58.57 | 15.00 |
| 25 INH | C21 | −21.27 | −30.33 | 52.84 | 15.00 |
| 25 INH | C22 | −20.95 | −30.49 | 54.19 | 15.00 |
| 25 INH | C23 | −20.34 | −29.44 | 54.89 | 15.00 |
| 25 INH | C24 | −20.03 | −28.23 | 54.25 | 15.00 |
| 25 INH | C25 | −20.35 | −28.09 | 52.90 | 15.00 |
| 25 INH | C26 | −20.96 | −29.12 | 52.19 | 15.00 |
| 25 INH | C27 | −19.35 | −27.11 | 55.01 | 15.00 |
| 25 INH | O28 | −20.01 | −25.85 | 55.20 | 15.00 |
| 25 INH | C29 | −20.09 | −25.30 | 56.50 | 15.00 |
| 25 INH | O30 | −19.34 | −25.70 | 57.40 | 15.00 |
| 25 INH | C31 | −21.28 | −23.64 | 57.93 | 15.00 |
| 25 INH | C32 | −21.14 | −24.56 | 59.14 | 15.00 |
| 25 INH | C33 | −22.16 | −25.68 | 59.35 | 15.00 |
| 25 INH | C34 | −23.25 | −25.62 | 58.28 | 15.00 |
| 25 INH | C35 | −21.45 | −27.01 | 59.33 | 15.00 |
| 25 INH | C36 | −20.52 | −22.34 | 58.22 | 15.00 |
| 25 INH | O37 | −19.37 | −22.35 | 58.66 | 15.00 |
| 25 INH | N38 | −21.23 | −21.24 | 57.98 | 15.00 |
| 25 INH | N39 | −20.81 | −19.86 | 58.17 | 15.00 |
| 25 INH | N40 | −21.01 | −24.34 | 56.66 | 15.00 |
| 26 TRP | N | −22.67 | −20.83 | 62.82 | 15.00 |
| 26 TRP | CA | −22.65 | −22.16 | 63.44 | 15.00 |
| 26 TRP | CB | −21.35 | −22.91 | 63.12 | 15.00 |
| 26 TRP | CG | −20.11 | −22.22 | 63.59 | 15.00 |
| 26 TRP | CD2 | −19.48 | −22.37 | 64.87 | 15.00 |
| 26 TRP | CE2 | −18.42 | −21.44 | 64.92 | 15.00 |
| 26 TRP | CE3 | −19.71 | −23.18 | 65.98 | 15.00 |
| 26 TRP | CD1 | −19.41 | −21.27 | 62.93 | 15.00 |
| 26 TRP | NE1 | −18.40 | −20.78 | 63.72 | 15.00 |
| 26 TRP | CZ2 | −17.59 | −21.30 | 66.03 | 15.00 |
| 26 TRP | CZ3 | −18.88 | −23.05 | 67.10 | 15.00 |
| 26 TRP | CH2 | −17.84 | −22.11 | 67.11 | 15.00 |
| 26 TRP | C | −22.85 | −22.06 | 64.96 | 15.00 |
| 26 TRP | O | −23.57 | −22.86 | 65.55 | 15.00 |
| 27 ALA | N | −22.24 | −21.04 | 65.57 | 15.00 |
| 27 ALA | CA | −22.33 | −20.83 | 67.01 | 15.00 |
| 27 ALA | CB | −21.35 | −19.78 | 67.46 | 15.00 |
| 27 ALA | C | −23.74 | −20.47 | 67.45 | 15.00 |
| 27 ALA | O | −24.21 | −20.91 | 68.50 | 15.00 |
| 28 PHE | N | −24.42 | −19.66 | 66.66 | 15.00 |
| 28 PHE | CA | −25.79 | −19.27 | 66.96 | 15.00 |
| 28 PHE | CB | −26.23 | −18.10 | 66.07 | 15.00 |
| 28 PHE | CG | −25.67 | −16.77 | 66.49 | 15.00 |
| 28 PHE | CD1 | −24.46 | −16.32 | 65.99 | 15.00 |
| 28 PHE | CD2 | −26.35 | −15.98 | 67.42 | 15.00 |
| 28 PHE | CE1 | −23.92 | −15.11 | 66.41 | 15.00 |
| 28 PHE | CE2 | −25.81 | −14.78 | 67.84 | 15.00 |
| 28 PHE | CZ | −24.60 | −14.35 | 67.34 | 15.00 |
| 28 PHE | C | −26.74 | −20.47 | 66.82 | 15.00 |
| 28 PHE | O | −27.62 | −20.68 | 67.66 | 15.00 |
| 29 SER | N | −26.56 | −21.25 | 65.78 | 15.00 |
| 29 SER | CA | −27.40 | −22.41 | 65.55 | 15.00 |
| 29 SER | CB | −27.05 | −23.08 | 64.23 | 15.00 |
| 29 SER | OG | −27.68 | −24.35 | 64.15 | 15.00 |
| 29 SER | C | −27.28 | −23.44 | 66.66 | 15.00 |
| 29 SER | O | −28.27 | −24.06 | 67.03 | 15.00 |
| 30 SER | N | −26.06 | −23.65 | 67.16 | 15.00 |
| 30 SER | CA | −25.79 | −24.61 | 68.22 | 15.00 |
| 30 SER | CB | −24.29 | −24.72 | 68.44 | 15.00 |
| 30 SER | OG | −23.64 | −25.04 | 67.22 | 15.00 |
| 30 SER | C | −26.44 | −24.15 | 69.51 | 15.00 |
| 30 SER | O | −27.07 | −24.93 | 70.25 | 15.00 |
| 31 VAL | N | −26.25 | −22.87 | 69.80 | 15.00 |
| 31 VAL | CA | −26.81 | −22.23 | 70.98 | 15.00 |
| 31 VAL | CB | −26.39 | −20.75 | 71.00 | 15.00 |
| 31 VAL | CG1 | −27.52 | −19.85 | 71.44 | 15.00 |
| 31 VAL | CG2 | −25.18 | −20.58 | 71.92 | 15.00 |
| 31 VAL | C | −28.32 | −22.41 | 70.92 | 15.00 |
| 31 VAL | O | −28.95 | −22.72 | 71.94 | 15.00 |
| 32 GLY | N | −28.89 | −22.27 | 69.73 | 15.00 |
| 32 GLY | CA | −30.32 | −22.44 | 69.56 | 15.00 |
| 32 GLY | C | −30.76 | −23.83 | 69.97 | 15.00 |
| 32 GLY | O | −31.77 | −24.00 | 70.65 | 15.00 |
| 33 ALA | N | −30.00 | −24.83 | 69.55 | 15.00 |
| 33 ALA | CA | −30.28 | −26.21 | 69.89 | 15.00 |
| 33 ALA | CB | −29.29 | −27.14 | 69.22 | 15.00 |
| 33 ALA | C | −30.20 | −26.34 | 71.42 | 15.00 |

TABLE VI-continued

Table of the orthogonal three dimensional coordinates in Angstroms and B factors (Å²) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 33 ALA | O | −31.19 | −26.70 | 72.06 | 15.00 |
| 34 LEU | N | −29.06 | −25.98 | 71.99 | 15.00 |
| 34 LEU | CA | −28.87 | −26.06 | 73.44 | 15.00 |
| 34 LEU | CB | −27.55 | −25.42 | 73.85 | 15.00 |
| 34 LEU | CG | −26.25 | −26.10 | 73.41 | 15.00 |
| 34 LEU | CD1 | −25.07 | −25.21 | 73.74 | 15.00 |
| 34 LEU | CD2 | −26.11 | −27.45 | 74.08 | 15.00 |
| 34 LEU | C | −30.02 | −25.41 | 74.21 | 15.00 |
| 34 LEU | O | −30.59 | −26.01 | 75.13 | 15.00 |
| 35 GLU | N | −30.39 | −24.20 | 73.80 | 15.00 |
| 35 GLU | CA | −31.46 | −23.44 | 74.44 | 15.00 |
| 35 GLU | CB | −31.63 | −22.08 | 73.77 | 15.00 |
| 35 GLU | CG | −30.41 | −21.18 | 73.87 | 15.00 |
| 35 GLU | CD | −30.58 | −19.86 | 73.15 | 15.00 |
| 35 GLU | OE1 | −31.46 | −19.76 | 72.27 | 15.00 |
| 35 GLU | OE2 | −29.83 | −18.92 | 73.46 | 15.00 |
| 35 GLU | C | −32.79 | −24.17 | 74.42 | 15.00 |
| 35 GLU | O | −33.51 | −24.18 | 75.42 | 15.00 |
| 36 GLY | N | −33.11 | −24.77 | 73.27 | 15.00 |
| 36 GLY | CA | −34.35 | −25.52 | 73.13 | 15.00 |
| 36 GLY | C | −34.42 | −26.67 | 74.11 | 15.00 |
| 36 GLY | O | −35.48 | −26.98 | 74.65 | 15.00 |
| 37 GLN | N | −33.28 | −27.30 | 74.37 | 15.00 |
| 37 GLN | CA | −33.21 | −28.42 | 75.29 | 15.00 |
| 37 GLN | CB | −31.94 | −29.22 | 75.05 | 15.00 |
| 37 GLN | CG | −32.00 | −30.06 | 73.80 | 15.00 |
| 37 GLN | CD | −33.19 | −31.00 | 73.80 | 15.00 |
| 37 GLN | OE1 | −33.32 | −31.84 | 74.69 | 15.00 |
| 37 GLN | NE2 | −34.07 | −30.83 | 72.84 | 15.00 |
| 37 GLN | C | −33.28 | −27.96 | 76.74 | 15.00 |
| 37 GLN | O | −33.94 | −28.58 | 77.58 | 15.00 |
| 38 LEU | N | −32.64 | −26.83 | 77.01 | 15.00 |
| 38 LEU | CA | −32.62 | −26.25 | 78.35 | 15.00 |
| 38 LEU | CB | −31.77 | −24.98 | 78.37 | 15.00 |
| 38 LEU | CG | −31.54 | −24.37 | 79.75 | 15.00 |
| 38 LEU | CD1 | −30.73 | −25.34 | 80.61 | 15.00 |
| 38 LEU | CD2 | −30.82 | −23.05 | 79.63 | 15.00 |
| 38 LEU | C | −34.04 | −25.95 | 78.83 | 15.00 |
| 38 LEU | O | −34.31 | −25.95 | 80.02 | 15.00 |
| 39 LYS | N | −34.94 | −25.65 | 77.90 | 15.00 |
| 39 LYS | CA | −36.32 | −25.38 | 78.26 | 15.00 |
| 39 LYS | CB | −37.04 | −24.66 | 77.12 | 15.00 |
| 39 LYS | CG | −38.53 | −24.45 | 77.32 | 15.00 |
| 39 LYS | CD | −38.85 | −23.47 | 78.43 | 15.00 |
| 39 LYS | CE | −40.35 | −23.46 | 78.70 | 15.00 |
| 39 LYS | NZ | −40.71 | −22.74 | 79.94 | 15.00 |
| 39 LYS | C | −36.98 | −26.72 | 78.54 | 15.00 |
| 39 LYS | O | −37.63 | −26.90 | 79.57 | 15.00 |
| 40 LYS | N | −36.73 | −27.68 | 77.65 | 15.00 |
| 40 LYS | CA | −37.28 | −29.03 | 77.72 | 15.00 |
| 40 LYS | CB | −36.61 | −29.90 | 76.66 | 15.00 |
| 40 LYS | CG | −37.25 | −31.25 | 76.41 | 15.00 |
| 40 LYS | CD | −38.51 | −31.10 | 75.61 | 15.00 |
| 40 LYS | CE | −39.15 | −32.44 | 75.34 | 15.00 |
| 40 LYS | NZ | −38.32 | −33.29 | 74.44 | 15.00 |
| 40 LYS | C | −37.07 | −29.66 | 79.08 | 15.00 |
| 40 LYS | O | −37.99 | −30.28 | 79.63 | 15.00 |
| 41 LYS | N | −35.87 | −29.50 | 79.64 | 15.00 |
| 41 LYS | CA | −35.54 | −30.10 | 80.93 | 15.00 |
| 41 LYS | CB | −34.07 | −30.55 | 80.94 | 15.00 |
| 41 LYS | CG | −33.59 | −31.28 | 79.68 | 15.00 |
| 41 LYS | CD | −34.50 | −32.44 | 79.28 | 15.00 |
| 41 LYS | CE | −34.05 | −33.08 | 77.96 | 15.00 |
| 41 LYS | NZ | −35.06 | −34.05 | 77.42 | 15.00 |
| 41 LYS | C | −35.79 | −29.20 | 82.14 | 15.00 |
| 41 LYS | O | −36.48 | −29.59 | 83.09 | 15.00 |
| 42 THR | N | −35.20 | −28.01 | 82.11 | 15.00 |
| 42 THR | CA | −35.30 | −27.03 | 83.19 | 15.00 |
| 42 THR | CB | −34.20 | −25.98 | 82.99 | 15.00 |
| 42 THR | OG1 | −32.95 | −26.64 | 82.85 | 15.00 |
| 42 THR | CG2 | −34.13 | −25.03 | 84.17 | 15.00 |
| 42 THR | C | −36.64 | −26.32 | 83.38 | 15.00 |
| 42 THR | O | −36.96 | −25.86 | 84.48 | 15.00 |
| 43 GLY | N | −37.43 | −26.23 | 82.31 | 15.00 |
| 43 GLY | CA | −38.70 | −25.53 | 82.38 | 15.00 |
| 43 GLY | C | −38.52 | −24.01 | 82.29 | 15.00 |
| 43 GLY | O | −39.48 | −23.25 | 82.34 | 15.00 |
| 44 LYS | N | −37.27 | −23.57 | 82.16 | 15.00 |
| 44 LYS | CA | −36.94 | −22.15 | 82.05 | 15.00 |
| 44 LYS | CB | −36.25 | −21.65 | 83.33 | 15.00 |
| 44 LYS | CG | −37.19 | −21.45 | 84.50 | 15.00 |
| 44 LYS | CD | −36.45 | −21.05 | 85.78 | 15.00 |
| 44 LYS | CE | −35.71 | −22.21 | 86.39 | 15.00 |
| 44 LYS | NZ | −36.62 | −23.38 | 86.62 | 15.00 |
| 44 LYS | C | −35.98 | −21.98 | 80.87 | 15.00 |
| 44 LYS | O | −35.10 | −22.82 | 80.66 | 15.00 |
| 45 LEU | N | −36.17 | −20.92 | 80.10 | 15.00 |
| 45 LEU | CA | −35.33 | −20.65 | 78.93 | 15.00 |
| 45 LEU | CB | −36.23 | −20.21 | 77.77 | 15.00 |
| 45 LEU | CG | −35.64 | −20.07 | 76.38 | 15.00 |
| 45 LEU | CD1 | −35.28 | −21.42 | 75.82 | 15.00 |
| 45 LEU | CD2 | −36.67 | −19.42 | 75.52 | 15.00 |
| 45 LEU | C | −34.33 | −19.56 | 79.25 | 15.00 |
| 45 LEU | O | −34.59 | −18.70 | 80.09 | 15.00 |
| 46 LEU | N | −33.18 | −19.57 | 78.58 | 15.00 |
| 46 LEU | CA | −32.16 | −18.56 | 78.80 | 15.00 |
| 46 LEU | CB | −31.30 | −18.93 | 80.01 | 15.00 |
| 46 LEU | CG | −30.51 | −17.78 | 80.61 | 15.00 |
| 46 LEU | CD1 | −31.46 | −16.70 | 81.06 | 15.00 |
| 46 LEU | CD2 | −29.69 | −18.27 | 81.78 | 15.00 |
| 46 LEU | C | −31.27 | −18.40 | 77.56 | 15.00 |
| 46 LEU | O | −31.02 | −19.36 | 76.85 | 15.00 |
| 47 ASN | N | −30.83 | −17.17 | 77.29 | 15.00 |
| 47 ASN | CA | −29.98 | −16.89 | 76.13 | 15.00 |
| 47 ASN | CB | −29.92 | −15.38 | 75.84 | 15.00 |
| 47 ASN | CG | −31.27 | −14.80 | 75.53 | 15.00 |
| 47 ASN | OD1 | −31.93 | −14.22 | 76.41 | 15.00 |
| 47 ASN | ND2 | −31.71 | −14.94 | 74.29 | 15.00 |
| 47 ASN | C | −28.57 | −17.36 | 76.39 | 15.00 |
| 47 ASN | O | −27.91 | −16.86 | 77.30 | 15.00 |
| 48 LEU | N | −28.10 | −18.32 | 75.61 | 15.00 |
| 48 LEU | CA | −26.75 | −18.84 | 75.78 | 15.00 |
| 48 LEU | CB | −26.70 | −20.31 | 75.39 | 15.00 |
| 48 LEU | CG | −27.60 | −21.19 | 76.26 | 15.00 |
| 48 LEU | CD1 | −27.18 | −22.64 | 76.10 | 15.00 |
| 48 LEU | CD2 | −27.50 | −20.77 | 77.73 | 15.00 |
| 48 LEU | C | −25.77 | −18.04 | 74.98 | 15.00 |
| 48 LEU | O | −26.14 | −17.34 | 74.04 | 15.00 |
| 49 SER | N | −24.50 | −18.13 | 75.34 | 15.00 |
| 49 SER | CA | −23.47 | −17.36 | 74.67 | 15.00 |
| 49 SER | CB | −22.34 | −17.06 | 75.64 | 15.00 |
| 49 SER | OG | −21.34 | −16.25 | 75.03 | 15.00 |
| 49 SER | C | −22.89 | −17.98 | 73.40 | 15.00 |
| 49 SER | O | −22.29 | −19.06 | 73.45 | 15.00 |
| 50 PRO | N | −23.07 | −17.31 | 72.24 | 15.00 |
| 50 PRO | CD | −24.05 | −16.24 | 72.05 | 15.00 |
| 50 PRO | CA | −22.55 | −17.77 | 70.95 | 15.00 |
| 50 PRO | CB | −23.37 | −16.96 | 69.95 | 15.00 |
| 50 PRO | CG | −24.61 | −16.59 | 70.71 | 15.00 |
| 50 PRO | C | −21.09 | −17.37 | 70.86 | 15.00 |
| 50 PRO | O | −20.29 | −18.01 | 70.19 | 15.00 |
| 51 GLN | N | −20.74 | −16.27 | 71.52 | 15.00 |
| 51 GLN | CA | −19.37 | −15.78 | 71.56 | 15.00 |
| 51 GLN | CB | −19.30 | −14.45 | 72.33 | 15.00 |
| 51 GLN | CG | −17.93 | −13.77 | 72.34 | 15.00 |
| 51 GLN | CD | −17.55 | −13.17 | 71.00 | 15.00 |
| 51 GLN | OE1 | −18.39 | −12.57 | 70.31 | 15.00 |
| 51 GLN | NE2 | −16.29 | −13.29 | 70.64 | 15.00 |
| 51 GLN | C | −18.53 | −16.82 | 72.26 | 15.00 |
| 51 GLN | O | −17.45 | −17.17 | 71.80 | 15.00 |
| 52 ASN | N | −19.03 | −17.33 | 73.38 | 15.00 |
| 52 ASN | CA | −18.30 | −18.34 | 74.14 | 15.00 |

TABLE VI-continued

Table of the orthogonal three dimensional coordinates in Angstroms and B factors (Å$^2$) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 52 ASN | CB | −19.20 | −18.91 | 75.24 | 15.00 |
| 52 ASN | CG | −18.51 | −19.98 | 76.10 | 15.00 |
| 52 ASN | OD1 | −19.13 | −20.54 | 76.99 | 15.00 |
| 52 ASN | ND2 | −17.23 | −20.22 | 75.86 | 15.00 |
| 52 ASN | C | −17.86 | −19.45 | 73.19 | 15.00 |
| 52 ASN | O | −16.70 | −19.87 | 73.22 | 15.00 |
| 53 LEU | N | −18.76 | −19.88 | 72.32 | 15.00 |
| 53 LEU | CA | −18.42 | −20.92 | 71.38 | 15.00 |
| 53 LEU | CB | −19.66 | −21.39 | 70.63 | 15.00 |
| 53 LEU | CG | −20.68 | −22.14 | 71.49 | 15.00 |
| 53 LEU | CD1 | −21.63 | −22.88 | 70.59 | 15.00 |
| 53 LEU | CD2 | −19.98 | −23.13 | 72.38 | 15.00 |
| 53 LEU | C | −17.35 | −20.41 | 70.42 | 15.00 |
| 53 LEU | O | −16.28 | −21.02 | 70.31 | 15.00 |
| 54 VAL | N | −17.61 | −19.27 | 69.79 | 15.00 |
| 54 VAL | CA | −16.68 | −18.63 | 68.86 | 15.00 |
| 54 VAL | CB | −17.16 | −17.18 | 68.52 | 15.00 |
| 54 VAL | CG1 | −16.02 | −16.35 | 67.96 | 15.00 |
| 54 VAL | CG2 | −18.31 | −17.21 | 67.54 | 15.00 |
| 54 VAL | C | −15.24 | −18.57 | 69.37 | 15.00 |
| 54 VAL | O | −14.31 | −18.91 | 68.66 | 15.00 |
| 55 ASP | N | −15.07 | −18.14 | 70.61 | 15.00 |
| 55 ASP | CA | −13.75 | −18.00 | 71.21 | 15.00 |
| 55 ASP | CB | −13.78 | −16.96 | 72.33 | 15.00 |
| 55 ASP | CG | −14.29 | −15.61 | 71.87 | 15.00 |
| 55 ASP | OD1 | −14.16 | −15.30 | 70.67 | 15.00 |
| 55 ASP | OD2 | −14.79 | −14.85 | 72.72 | 15.00 |
| 55 ASP | C | −13.10 | −19.26 | 71.77 | 15.00 |
| 55 ASP | O | −11.88 | −19.33 | 71.86 | 15.00 |
| 56 CYS | N | −13.89 | −20.25 | 72.17 | 15.00 |
| 56 CYS | CA | −13.31 | −21.45 | 72.77 | 15.00 |
| 56 CYS | C | −13.25 | −22.75 | 71.96 | 15.00 |
| 56 CYS | O | −12.44 | −23.62 | 72.27 | 15.00 |
| 56 CYS | CB | −13.98 | −21.73 | 74.11 | 15.00 |
| 56 CYS | SG | −14.30 | −20.24 | 75.11 | 15.00 |
| 57 VAL | N | −14.09 | −22.89 | 70.94 | 15.00 |
| 57 VAL | CA | −14.08 | −24.13 | 70.16 | 15.00 |
| 57 VAL | CB | −15.43 | −24.34 | 69.42 | 15.00 |
| 57 VAL | CG1 | −15.47 | −25.73 | 68.80 | 15.00 |
| 57 VAL | CG2 | −16.59 | −24.17 | 70.38 | 15.00 |
| 57 VAL | C | −12.91 | −24.19 | 69.18 | 15.00 |
| 57 VAL | O | −13.08 | −24.04 | 67.98 | 15.00 |
| 58 SER | N | −11.71 | −24.46 | 69.70 | 15.00 |
| 58 SER | CA | −10.50 | −24.55 | 68.89 | 15.00 |
| 58 SER | CB | −9.34 | −25.09 | 69.72 | 15.00 |
| 58 SER | OG | −9.08 | −24.27 | 70.85 | 15.00 |
| 58 SER | C | −10.61 | −25.37 | 67.62 | 15.00 |
| 58 SER | O | −9.84 | −25.18 | 66.70 | 15.00 |
| 59 GLU | N | −11.57 | −26.29 | 67.56 | 15.00 |
| 59 GLU | CA | −11.71 | −27.13 | 66.38 | 15.0b |
| 59 GLU | CB | −12.49 | −28.41 | 66.73 | 15.00 |
| 59 GLU | CG | −11.81 | −29.30 | 67.75 | 15.00 |
| 59 GLU | CD | −11.90 | −28.75 | 69.16 | 15.00 |
| 59 GLU | OE1 | −12.96 | −28.18 | 69.51 | 15.00 |
| 59 GLU | OE2 | −10.92 | −28.91 | 69.91 | 15.00 |
| 59 GLU | C | −12.39 | −26.41 | 65.23 | 15.00 |
| 59 GLU | O | −12.46 | −26.91 | 64.11 | 15.00 |
| 60 ASN | N | −12.93 | −25.24 | 65.53 | 15.00 |
| 60 ASN | CA | −13.61 | −24.41 | 64.53 | 15.00 |
| 60 ASN | CB | −14.99 | −24.01 | 65.03 | 15.00 |
| 60 ASN | CG | −15.97 | −25.16 | 65.02 | 15.00 |
| 60 ASN | OD1 | −17.03 | −25.09 | 65.63 | 15.00 |
| 60 ASN | ND2 | −15.62 | −26.23 | 64.31 | 15.00 |
| 60 ASN | C | −12.75 | −23.19 | 64.27 | 15.00 |
| 60 ASN | O | −11.79 | −22.94 | 64.98 | 15.00 |
| 61 ASP | N | −13.12 | −22.41 | 63.25 | 15.00 |
| 61 ASP | CA | −12.36 | −21.23 | 62.88 | 15.00 |
| 61 ASP | CB | −12.21 | −21.20 | 61.35 | 15.00 |
| 61 ASP | CG | −10.99 | −20.43 | 60.90 | 15.00 |
| 61 ASP | OD1 | −10.38 | −19.70 | 61.71 | 15.00 |
| 61 ASP | OD2 | −10.63 | −20.55 | 59.71 | 15.00 |
| 61 ASP | C | −12.92 | −19.89 | 63.39 | 15.00 |
| 61 ASP | O | −12.71 | −18.86 | 62.76 | 15.00 |
| 62 GLY | N | −13.61 | −19.89 | 64.52 | 15.00 |
| 62 GLY | CA | −14.16 | −18.66 | 65.06 | 15.00 |
| 62 GLY | C | −15.11 | −17.97 | 64.10 | 15.00 |
| 62 GLY | O | −16.17 | −18.50 | 63.79 | 15.00 |
| 63 CYS | N | −14.73 | −16.79 | 63.62 | 15.00 |
| 63 CYS | CA | −15.56 | −16.06 | 62.67 | 15.00 |
| 63 CYS | C | −15.39 | −16.55 | 61.24 | 15.00 |
| 63 CYS | O | −16.01 | −16.03 | 60.31 | 15.00 |
| 63 CYS | CB | −15.28 | −14.56 | 62.73 | 15.00 |
| 63 CYS | SG | −15.94 | −13.72 | 64.20 | 15.00 |
| 64 GLY | N | −14.52 | −17.54 | 61.06 | 15.00 |
| 64 GLY | CA | −14.28 | −18.09 | 59.74 | 15.00 |
| 64 GLY | C | −15.24 | −19.23 | 59.47 | 15.00 |
| 64 GLY | O | −15.42 | −19.63 | 58.32 | 15.00 |
| 65 GLY | N | −15.85 | −19.77 | 60.52 | 15.00 |
| 65 GLY | CA | −16.79 | −20.86 | 60.33 | 15.00 |
| 65 GLY | C | −16.54 | −22.03 | 61.25 | 15.00 |
| 65 GLY | O | −15.56 | −22.04 | 62.00 | 15.00 |
| 66 GLY | N | −17.42 | −23.02 | 61.19 | 15.00 |
| 66 GLY | CA | −17.29 | −24.19 | 62.03 | 15.00 |
| 66 GLY | C | −18.50 | −25.10 | 61.96 | 15.00 |
| 66 GLY | O | −19.48 | −24.76 | 61.32 | 15.00 |
| 67 TYR | N | −18.43 | −26.25 | 62.62 | 15.00 |
| 67 TYR | CA | −19.53 | −27.20 | 62.62 | 15.00 |
| 67 TYR | CB | −19.02 | −28.60 | 62.32 | 15.00 |
| 67 TYR | CG | −18.35 | −28.77 | 60.99 | 15.00 |
| 67 TYR | CD1 | −19.08 | −29.16 | 59.86 | 15.00 |
| 67 TYR | CE1 | −18.46 | −29.38 | 58.65 | 15.00 |
| 67 TYR | CD2 | −16.98 | −28.59 | 60.86 | 15.00 |
| 67 TYR | CE2 | −16.36 | −28.81 | 59.65 | 15.00 |
| 67 TYR | CZ | −17.10 | −29.20 | 58.55 | 15.00 |
| 67 TYR | OH | −16.46 | −29.41 | 57.35 | 15.00 |
| 67 TYR | C | −20.23 | −27.22 | 63.97 | 15.00 |
| 67 TYR | O | −19.59 | −27.04 | 65.00 | 15.00 |
| 68 MET | N | −21.52 | −27.51 | 63.96 | 15.00 |
| 68 MET | CA | −22.31 | −27.57 | 65.19 | 15.00 |
| 68 MET | CB | −23.81 | −27.69 | 64.91 | 15.00 |
| 68 MET | CG | −24.46 | −26.48 | 64.23 | 15.00 |
| 68 MET | SD | −24.10 | −26.27 | 62.47 | 15.00 |
| 68 MET | CE | −25.07 | −27.56 | 61.75 | 15.00 |
| 68 MET | C | −21.86 | −28.72 | 66.09 | 15.00 |
| 68 MET | O | −21.76 | −28.56 | 67.30 | 15.00 |
| 69 THR | N | −21.54 | −29.86 | 65.49 | 15.00 |
| 69 THR | CA | −21.10 | −31.02 | 66.26 | 15.00 |
| 69 THR | CB | −20.78 | −32.22 | 65.35 | 15.00 |
| 69 THR | OG1 | −20.01 | −31.77 | 64.24 | 15.00 |
| 69 THR | CG2 | −22.06 | −32.86 | 64.85 | 15.00 |
| 69 THR | C | −19.88 | −30.71 | 67.11 | 15.00 |
| 69 THR | O | −19.77 | −31.19 | 68.25 | 15.00 |
| 70 ASN | N | −18.97 | −29.89 | 66.59 | 15.00 |
| 70 ASN | CA | −17.77 | −29.52 | 67.33 | 15.00 |
| 70 ASN | CB | −16.79 | −28.76 | 66.46 | 15.00 |
| 70 ASN | CG | −15.98 | −29.65 | 65.58 | 15.00 |
| 70 ASN | OD1 | −15.42 | −29.19 | 64.60 | 15.00 |
| 70 ASN | ND2 | −15.89 | −30.93 | 65.92 | 15.00 |
| 70 ASN | C | −18.11 | −28.66 | 68.55 | 15.00 |
| 70 ASN | O | −17.46 | −28.77 | 69.59 | 15.00 |
| 71 ALA | N | −19.12 | −27.80 | 68.40 | 15.00 |
| 71 ALA | CA | −19.57 | −26.91 | 69.47 | 15.00 |
| 71 ALA | CB | −20.58 | −25.91 | 68.94 | 15.00 |
| 71 ALA | C | −20.15 | −27.71 | 70.63 | 15.00 |
| 71 ALA | O | −19.80 | −27.50 | 71.78 | 15.00 |
| 72 PHE | N | −21.03 | −28.66 | 70.31 | 15.00 |
| 72 PHE | CA | −21.64 | −29.51 | 71.33 | 15.00 |
| 72 PHE | CB | −22.57 | −30.54 | 70.69 | 15.00 |
| 72 PHE | CG | −23.72 | −29.93 | 69.96 | 15.00 |
| 72 PHE | CD1 | −24.28 | −28.73 | 70.39 | 15.00 |
| 72 PHE | CD2 | −24.24 | −30.55 | 68.84 | 15.00 |
| 72 PHE | CE1 | −25.33 | −28.16 | 69.70 | 15.00 |

TABLE VI-continued

Table of the orthogonal three dimensional coordinates in Angstroms and B factors (Å²) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 72 PHE | CE2 | −25.30 | −29.98 | 68.15 | 15.00 |
| 72 PHE | CZ | −25.84 | −28.78 | 68.58 | 15.00 |
| 72 PHE | C | −20.53 | −30.25 | 72.07 | 15.00 |
| 72 PHE | O | −20.43 | −30.18 | 73.31 | 15.00 |
| 73 GLN | N | −19.67 | −30.90 | 71.31 | 15.00 |
| 73 GLN | CA | −18.56 | −31.66 | 71.86 | 15.00 |
| 73 GLN | CB | −17.68 | −32.20 | 70.72 | 15.00 |
| 73 GLN | CG | −16.78 | −33.40 | 71.09 | 15.00 |
| 73 GLN | CD | −17.54 | −34.73 | 71.21 | 15.00 |
| 73 GLN | OE1 | −17.47 | −35.58 | 70.31 | 15.00 |
| 73 GLN | NE2 | −18.21 | −34.94 | 72.35 | 15.00 |
| 73 GLN | C | −17.76 | −30.78 | 72.84 | 15.00 |
| 73 GLN | O | −17.33 | −31.25 | 73.89 | 15.00 |
| 74 TYR | N | −17.62 | −29.50 | 72.53 | 15.00 |
| 74 TYR | CA | −16.89 | −28.59 | 73.40 | 15.00 |
| 74 TYR | CB | −16.70 | −27.22 | 72.75 | 15.00 |
| 74 TYR | CG | −16.35 | −26.13 | 73.74 | 15.00 |
| 74 TYR | CD1 | −15.09 | −26.05 | 74.30 | 15.00 |
| 74 TYR | CE1 | −14.77 | −25.07 | 75.22 | 15.00 |
| 74 TYR | CD2 | −17.30 | −25.18 | 74.12 | 15.00 |
| 74 TYR | CE2 | −17.00 | −24.19 | 75.04 | 15.00 |
| 74 TYR | CZ | −15.73 | −24.14 | 75.59 | 15.00 |
| 74 TYR | OH | −15.42 | −23.15 | 76.51 | 15.00 |
| 74 TYR | C | −17.58 | −28.38 | 74.73 | 15.00 |
| 74 TYR | O | −16.93 | −28.39 | 75.78 | 15.00 |
| 75 VAL | N | −18.88 | −28.12 | 74.67 | 15.00 |
| 75 VAL | CA | −19.68 | −27.89 | 75.88 | 15.00 |
| 75 VAL | CB | −21.15 | −27.58 | 75.52 | 15.00 |
| 75 VAL | CG1 | −21.95 | −27.27 | 76.78 | 15.00 |
| 75 VAL | CG2 | −21.22 | −26.39 | 74.55 | 15.00 |
| 75 VAL | C | −19.62 | −29.10 | 76.80 | 15.00 |
| 75 VAL | O | −19.60 | −28.96 | 78.03 | 15.00 |
| 76 GLN | N | −19.59 | −30.29 | 76.21 | 15.00 |
| 76 GLN | CA | −19.51 | −31.51 | 76.98 | 15.00 |
| 76 GLN | CB | −19.75 | −32.69 | 76.05 | 15.00 |
| 76 GLN | CG | −19.79 | −34.05 | 76.69 | 15.00 |
| 76 GLN | CD | −19.56 | −35.13 | 75.66 | 15.00 |
| 76 GLN | OE1 | −20.03 | −35.04 | 74.53 | 15.00 |
| 76 GLN | NE2 | −18.78 | −36.13 | 76.03 | 15.00 |
| 76 GLN | C | −18.14 | −31.60 | 77.64 | 15.00 |
| 76 GLN | O | −18.03 | −31.59 | 78.86 | 15.00 |
| 77 LYS | N | −17.08 | −31.61 | 76.84 | 15.00 |
| 77 LYS | CA | −15.72 | −31.70 | 77.36 | 15.00 |
| 77 LYS | CB | −14.70 | −31.55 | 76.22 | 15.00 |
| 77 LYS | CG | −13.27 | −31.34 | 76.69 | 15.00 |
| 77 LYS | CD | −12.32 | −31.10 | 75.51 | 15.00 |
| 77 LYS | CE | −10.89 | −30.81 | 75.97 | 15.00 |
| 77 LYS | NZ | −10.30 | −31.95 | 76.76 | 15.00 |
| 77 LYS | C | −15.45 | −30.64 | 78.42 | 15.00 |
| 77 LYS | O | −14.81 | −30.91 | 79.45 | 15.00 |
| 78 ASN | N | −15.92 | −29.42 | 78.17 | 15.00 |
| 78 ASN | CA | −15.74 | −28.29 | 79.06 | 15.00 |
| 78 ASN | CB | −15.98 | −27.00 | 78.28 | 15.00 |
| 78 ASN | CG | −15.69 | −25.76 | 79.10 | 15.00 |
| 78 ASN | OD1 | −14.58 | −25.59 | 79.62 | 15.00 |
| 78 ASN | ND2 | −16.67 | −24.87 | 79.19 | 15.00 |
| 78 ASN | C | −16.68 | −28.34 | 80.25 | 15.00 |
| 78 ASN | O | −16.42 | −27.72 | 81.28 | 15.00 |
| 79 ARG | N | −17.79 | −29.06 | 80.11 | 15.00 |
| 79 ARG | CA | −18.78 | −29.18 | 81.16 | 15.00 |
| 79 ARG | CB | −18.14 | −29.76 | 82.43 | 15.00 |
| 79 ARG | CG | −17.67 | −31.20 | 82.26 | 15.00 |
| 79 ARG | CD | −16.65 | −31.59 | 83.33 | 15.00 |
| 79 ARG | NE | −17.15 | −31.38 | 84.68 | 15.00 |
| 79 ARG | CZ | −18.16 | −32.06 | 85.22 | 15.00 |
| 79 ARG | NH1 | −18.78 | −33.03 | 84.55 | 15.00 |
| 79 ARG | NH2 | −18.62 | −31.70 | 86.43 | 15.00 |
| 79 ARG | C | −19.45 | −27.84 | 81.45 | 15.00 |
| 79 ARG | O | −19.31 | −27.30 | 82.55 | 15.00 |
| 80 GLY | N | −20.13 | −27.28 | 80.45 | 15.00 |
| 80 GLY | CA | −20.82 | −26.02 | 80.66 | 15.00 |
| 80 GLY | C | −20.62 | −24.91 | 79.64 | 15.00 |
| 80 GLY | O | −19.56 | −24.82 | 79.00 | 15.00 |
| 81 ILE | N | −21.64 | −24.08 | 79.48 | 15.00 |
| 81 ILE | CA | −21.59 | −22.95 | 78.57 | 15.00 |
| 81 ILE | CB | −22.30 | −23.23 | 77.22 | 15.00 |
| 81 ILE | CG2 | −23.77 | −23.52 | 77.45 | 15.00 |
| 81 ILE | CG1 | −22.10 | −22.05 | 76.27 | 15.00 |
| 81 ILE | CD1 | −22.84 | −22.16 | 74.96 | 15.00 |
| 81 ILE | C | −22.24 | −21.75 | 79.25 | 15.00 |
| 81 ILE | O | −23.28 | −21.89 | 79.90 | 15.00 |
| 82 ASP | N | −21.61 | −20.59 | 79.11 | 15.00 |
| 82 ASP | CA | −22.11 | −19.37 | 79.71 | 15.00 |
| 82 ASP | CB | −21.03 | −18.29 | 79.64 | 15.00 |
| 82 ASP | CG | −19.90 | −18.53 | 80.58 | 15.00 |
| 82 ASP | OD1 | −18.82 | −17.98 | 80.34 | 15.00 |
| 82 ASP | OD2 | −20.09 | −19.26 | 81.58 | 15.00 |
| 82 ASP | C | −23.36 | −18.81 | 79.09 | 15.00 |
| 82 ASP | O | −23.69 | −19.07 | 77.93 | 15.00 |
| 83 SER | N | −24.07 | −18.02 | 79.89 | 15.00 |
| 83 SER | CA | −25.27 | −17.36 | 79.44 | 15.00 |
| 83 SER | CB | −26.09 | −16.90 | 80.64 | 15.00 |
| 83 SER | OG | −25.27 | −16.23 | 81.59 | 15.00 |
| 83 SER | C | −24.75 | −16.15 | 78.66 | 15.00 |
| 83 SER | O | −23.57 | −15.79 | 78.79 | 15.00 |
| 84 GLU | N | −25.61 | −15.54 | 77.86 | 15.00 |
| 84 GLU | CA | −25.25 | −14.36 | 77.07 | 15.00 |
| 84 GLU | CB | −26.46 | −13.84 | 76.31 | 15.00 |
| 84 GLU | CG | −26.17 | −12.64 | 75.43 | 15.00 |
| 84 GLU | CD | −25.31 | −12.99 | 74.24 | 15.00 |
| 84 GLU | OE1 | −24.08 | −12.98 | 74.38 | 15.00 |
| 84 GLU | OE2 | −25.87 | −13.29 | 73.17 | 15.00 |
| 84 GLU | C | −24.70 | −13.27 | 77.99 | 15.00 |
| 84 GLU | O | −23.53 | −12.89 | 77.88 | 15.00 |
| 85 ASP | N | −25.51 | −12.82 | 78.94 | 15.00 |
| 85 ASP | CA | −25.09 | −11.79 | 79.87 | 15.00 |
| 85 ASP | CB | −26.13 | −11.60 | 80.99 | 15.00 |
| 85 ASP | CG | −25.66 | −10.63 | 82.08 | 15.00 |
| 85 ASP | OD1 | −25.92 | −10.88 | 83.29 | 15.00 |
| 85 ASP | OD2 | −25.03 | −9.60 | 81.73 | 15.00 |
| 85 ASP | C | −23.72 | −12.09 | 80.49 | 15.00 |
| 85 ASP | O | −22.91 | −11.18 | 80.65 | 15.00 |
| 86 ALA | N | −23.45 | −13.34 | 80.81 | 15.00 |
| 86 ALA | CA | −22.18 | −13.67 | 81.44 | 15.00 |
| 86 ALA | CB | −22.25 | −15.05 | 82.03 | 15.00 |
| 86 ALA | C | −21.01 | −13.56 | 80.47 | 15.00 |
| 86 ALA | O | −19.91 | −13.17 | 80.86 | 15.00 |
| 87 TYR | N | −21.26 | −13.89 | 79.21 | 15.00 |
| 87 TYR | CA | −20.23 | −13.85 | 78.18 | 15.00 |
| 87 TYR | CB | −19.77 | −15.27 | 77.87 | 15.00 |
| 87 TYR | CG | −18.42 | −15.39 | 77.19 | 15.00 |
| 87 TYR | CD1 | −17.96 | −14.41 | 76.30 | 15.00 |
| 87 TYR | CE1 | −16.74 | −14.56 | 75.65 | 15.00 |
| 87 TYR | CD2 | −17.62 | −16.52 | 77.40 | 15.00 |
| 87 TYR | CE2 | −16.40 | −16.67 | 76.76 | 15.00 |
| 87 TYR | CZ | −15.96 | −15.69 | 75.88 | 15.00 |
| 87 TYR | OH | −14.75 | −15.83 | 75.25 | 15.00 |
| 87 TYR | C | −20.93 | −13.23 | 76.97 | 15.00 |
| 87 TYR | O | −21.57 | −13.94 | 76.19 | 15.00 |
| 88 PRO | N | −20.90 | −11.90 | 76.86 | 15.00 |
| 88 PRO | CD | −20.42 | −10.97 | 77.90 | 15.00 |
| 88 PRO | CA | −21.52 | −11.15 | 75.78 | 15.00 |
| 88 PRO | CB | −21.33 | −9.70 | 76.23 | 15.00 |
| 88 PRO | CG | −21.34 | −9.81 | 77.71 | 15.00 |
| 88 PRO | C | −20.91 | −11.38 | 74.39 | 15.00 |
| 88 PRO | O | −19.74 | −11.74 | 74.25 | 15.00 |
| 89 TYR | N | −21.73 | −11.12 | 73.38 | 15.00 |
| 89 TYR | CA | −21.35 | −11.29 | 71.99 | 15.00 |
| 89 TYR | CB | −22.56 | −11.78 | 71.18 | 15.00 |
| 89 TYR | CG | −22.24 | −12.15 | 69.76 | 15.00 |
| 89 TYR | CD1 | −21.38 | −13.20 | 69.47 | 15.00 |
| 89 TYR | CE1 | −21.06 | −13.53 | 68.17 | 15.00 |

TABLE VI-continued

Table of the orthogonal three dimensional coordinates in Angstroms and B factors (Å²) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 89 TYR | CD2 | −22.78 | −11.44 | 68.70 | 15.00 |
| 89 TYR | CE2 | −22.47 | −11.76 | 67.39 | 15.00 |
| 89 TYR | CZ | −21.61 | −12.79 | 67.13 | 15.00 |
| 89 TYR | OH | −21.27 | −13.08 | 65.83 | 15.00 |
| 89 TYR | C | −20.85 | −9.95 | 71.48 | 15.00 |
| 89 TYR | O | −21.52 | −8.92 | 71.64 | 15.00 |
| 90 VAL | N | −19.65 | −9.94 | 70.91 | 15.00 |
| 90 VAL | CA | −19.07 | −8.71 | 70.39 | 15.00 |
| 90 VAL | CB | −17.75 | −8.36 | 71.12 | 15.00 |
| 90 VAL | CG1 | −17.97 | −8.36 | 72.62 | 15.00 |
| 90 VAL | CG2 | −16.65 | −9.33 | 70.74 | 15.00 |
| 90 VAL | C | −18.88 | −8.78 | 68.87 | 15.00 |
| 90 VAL | O | −18.54 | −7.78 | 68.23 | 15.00 |
| 91 GLY | N | −19.08 | −9.96 | 68.30 | 15.00 |
| 91 GLY | CA | −18.95 | −10.12 | 66.86 | 15.00 |
| 91 GLY | C | −17.55 | −10.23 | 66.27 | 15.00 |
| 91 GLY | O | −17.34 | −9.87 | 65.12 | 15.00 |
| 92 GLN | N | −16.61 | −10.80 | 67.01 | 15.00 |
| 92 GLN | CA | −15.24 | −10.95 | 66.50 | 15.00 |
| 92 GLN | CB | −14.56 | −9.58 | 66.41 | 15.00 |
| 92 GLN | CG | −14.68 | −8.72 | 67.67 | 15.00 |
| 92 GLN | CD | −13.59 | −7.67 | 67.79 | 15.00 |
| 92 GLN | OE1 | −12.77 | −7.72 | 68.72 | 15.00 |
| 92 GLN | NE2 | −13.56 | −6.72 | 66.85 | 15.00 |
| 92 GLN | C | −14.45 | −11.86 | 67.43 | 15.00 |
| 92 GLN | O | −14.78 | −11.97 | 68.62 | 15.00 |
| 93 GLU | N | −13.43 | −12.52 | 66.89 | 15.00 |
| 93 GLU | CA | −12.64 | −13.42 | 67.71 | 15.00 |
| 93 GLU | CB | −11.68 | −14.28 | 66.89 | 15.00 |
| 93 GLU | CG | −12.31 | −15.10 | 65.78 | 15.00 |
| 93 GLU | CD | −11.63 | −14.87 | 64.44 | 15.00 |
| 93 GLU | OE1 | −11.94 | −15.61 | 63.48 | 15.00 |
| 93 GLU | OE2 | −10.78 | −13.94 | 64.33 | 15.00 |
| 93 GLU | C | −11.84 | −12.62 | 68.71 | 15.00 |
| 93 GLU | O | −11.41 | −11.49 | 68.44 | 15.00 |
| 94 GLU | N | −11.61 | −13.26 | 69.85 | 15.00 |
| 94 GLU | CA | −10.88 | −12.70 | 70.98 | 15.00 |
| 94 GLU | CB | −11.81 | −11.81 | 71.79 | 15.00 |
| 94 GLU | CG | −13.19 | −12.42 | 71.93 | 15.00 |
| 94 GLU | CD | −14.06 | −11.70 | 72.92 | 15.00 |
| 94 GLU | OE1 | −13.99 | −10.45 | 72.96 | 15.00 |
| 94 GLU | OE2 | −14.83 | −12.38 | 73.64 | 15.00 |
| 94 GLU | C | −10.52 | −13.92 | 71.80 | 15.00 |
| 94 GLU | O | −10.89 | −15.02 | 71.45 | 15.00 |
| 95 SER | N | −9.81 | −13.73 | 72.91 | 15.00 |
| 95 SER | CA | −9.43 | −14.85 | 73.75 | 15.00 |
| 95 SER | CB | −8.32 | −14.42 | 74.71 | 15.00 |
| 95 SER | OG | −7.20 | −13.94 | 73.98 | 15.00 |
| 95 SER | C | −10.62 | −15.42 | 74.52 | 15.00 |
| 95 SER | O | −11.48 | −14.67 | 75.02 | 15.00 |
| 96 CYS | N | −10.69 | −16.75 | 74.57 | 15.00 |
| 96 CYS | CA | −11.76 | −17.45 | 75.28 | 15.00 |
| 96 CYS | C | −11.74 | −16.96 | 76.71 | 15.00 |
| 96 CYS | O | −10.73 | −17.09 | 77.42 | 15.00 |
| 96 CYS | CB | −11.53 | −18.97 | 75.20 | 15.00 |
| 96 CYS | SG | −12.62 | −20.03 | 76.22 | 15.00 |
| 97 MET | N | −12.85 | −16.38 | 77.14 | 15.00 |
| 97 MET | CA | −12.96 | −15.85 | 78.49 | 15.00 |
| 97 MET | CB | −13.32 | −14.36 | 78.39 | 15.00 |
| 97 MET | CG | −12.29 | −13.51 | 77.69 | 15.00 |
| 97 MET | SD | −13.01 | −11.98 | 77.03 | 15.00 |
| 97 MET | CE | −14.07 | −11.44 | 78.40 | 15.00 |
| 97 MET | C | −14.03 | −16.60 | 79.28 | 15.00 |
| 97 MET | O | −14.87 | −15.99 | 79.96 | 15.00 |
| 98 TYR | N | −13.98 | −17.93 | 79.21 | 15.00 |
| 98 TYR | CA | −14.96 | −18.74 | 79.91 | 15.00 |
| 98 TYR | CB | −14.69 | −20.23 | 79.71 | 15.00 |
| 98 TYR | CG | −15.74 | −21.10 | 80.34 | 15.00 |
| 98 TYR | CD1 | −17.08 | −20.99 | 79.97 | 15.00 |
| 98 TYR | CE1 | −18.07 | −21.74 | 80.59 | 15.00 |
| 98 TYR | CD2 | −15.41 | −22.00 | 81.36 | 15.00 |
| 98 TYR | CE2 | −16.40 | −22.76 | 81.98 | 15.00 |
| 98 TYR | CZ | −17.72 | −22.62 | 81.60 | 15.00 |
| 98 TYR | OH | −18.70 | −23.34 | 82.23 | 15.00 |
| 98 TYR | C | −15.03 | −18.43 | 81.39 | 15.00 |
| 98 TYR | O | −14.01 | −18.38 | 82.08 | 15.00 |
| 99 ASN | N | −16.25 | −18.27 | 81.88 | 15.00 |
| 99 ASN | CA | −16.49 | −17.97 | 83.28 | 15.00 |
| 99 ASN | CB | −17.29 | −16.66 | 83.38 | 15.00 |
| 99 ASN | CG | −17.66 | −16.33 | 84.80 | 15.00 |
| 99 ASN | OD1 | −16.88 | −16.57 | 85.74 | 15.00 |
| 99 ASN | ND2 | −18.85 | −15.79 | 84.99 | 15.00 |
| 99 ASN | C | −17.28 | −19.10 | 83.92 | 15.00 |
| 99 ASN | O | −18.51 | −19.16 | 83.78 | 15.00 |
| 100 PRO | N | −16.60 | −19.99 | 84.67 | 15.00 |
| 100 PRO | CD | −15.22 | −19.88 | 85.16 | 15.00 |
| 100 PRO | CA | −17.29 | −21.11 | 85.32 | 15.00 |
| 100 PRO | CB | −16.20 | −21.72 | 86.20 | 15.00 |
| 100 PRO | CG | −15.31 | −20.55 | 86.51 | 15.00 |
| 100 PRO | C | −18.45 | −20.63 | 86.16 | 15.00 |
| 100 PRO | O | −19.51 | −21.24 | 86.15 | 15.00 |
| 101 THR | N | −18.28 | −19.50 | 86.84 | 15.00 |
| 101 THR | CA | −19.33 | −18.95 | 87.68 | 15.00 |
| 101 THR | CB | −18.86 | −17.68 | 88.45 | 15.00 |
| 101 THR | OG1 | −18.71 | −16.57 | 87.55 | 15.00 |
| 101 THR | CG2 | −17.51 | −17.93 | 89.13 | 15.00 |
| 101 THR | C | −20.55 | −18.59 | 86.82 | 15.00 |
| 101 THR | O | −21.68 | −18.56 | 87.32 | 15.00 |
| 102 GLY | N | −20.32 | −18.34 | 85.54 | 15.00 |
| 102 GLY | CA | −21.40 | −17.98 | 84.64 | 15.00 |
| 102 GLY | C | −22.06 | −19.12 | 83.88 | 15.00 |
| 102 GLY | O | −22.92 | −18.86 | 83.03 | 15.00 |
| 103 LYS | N | −21.65 | −20.36 | 84.12 | 15.00 |
| 103 LYS | CA | −22.24 | −21.50 | 83.42 | 15.00 |
| 103 LYS | CB | −21.72 | −22.83 | 83.98 | 15.00 |
| 103 LYS | CG | −22.32 | −24.05 | 83.29 | 15.00 |
| 103 LYS | CD | −22.10 | −25.33 | 84.06 | 15.00 |
| 103 LYS | CE | −22.96 | −25.41 | 85.35 | 15.00 |
| 103 LYS | NZ | −24.41 | −25.79 | 85.14 | 15.00 |
| 103 LYS | C | −23.75 | −21.49 | 83.57 | 15.00 |
| 103 LYS | O | −24.26 | −21.26 | 84.67 | 15.00 |
| 104 ALA | N | −24.47 | −21.73 | 82.48 | 15.00 |
| 104 ALA | CA | −25.93 | −21.75 | 82.53 | 15.00 |
| 104 ALA | CB | −26.51 | −20.51 | 81.87 | 15.00 |
| 104 ALA | C | −26.52 | −22.99 | 81.89 | 15.00 |
| 104 ALA | O | −27.73 | −23.15 | 81.87 | 15.00 |
| 105 ALA | N | −25.66 | −23.87 | 81.38 | 15.00 |
| 105 ALA | CA | −26.11 | −25.10 | 80.75 | 15.00 |
| 105 ALA | CB | −26.84 | −24.78 | 79.44 | 15.00 |
| 105 ALA | C | −24.95 | −26.03 | 80.46 | 15.00 |
| 105 ALA | O | −23.79 | −25.67 | 80.62 | 15.00 |
| 106 LYS | N | −25.28 | −27.26 | 80.07 | 15.00 |
| 106 LYS | CA | −24.29 | −28.25 | 79.70 | 15.00 |
| 106 LYS | CB | −23.55 | −28.80 | 80.92 | 15.00 |
| 106 LYS | CG | −24.41 | −29.35 | 82.04 | 15.00 |
| 106 LYS | CD | −23.54 | −29.64 | 83.27 | 15.00 |
| 106 LYS | CE | −22.40 | −30.62 | 82.95 | 15.00 |
| 106 LYS | NZ | −21.34 | −30.67 | 84.03 | 15.00 |
| 106 LYS | C | −24.99 | −29.36 | 78.93 | 15.00 |
| 106 LYS | O | −26.21 | −29.30 | 78.75 | 15.00 |
| 107 CYS | N | −24.23 | −30.30 | 78.39 | 15.00 |
| 107 CYS | CA | −24.82 | −31.40 | 77.64 | 15.00 |
| 107 CYS | CB | −25.06 | −30.99 | 76.19 | 15.00 |
| 107 CYS | SG | −23.58 | −30.95 | 75.18 | 15.00 |
| 107 CYS | C | −23.91 | −32.61 | 77.68 | 15.00 |
| 107 CYS | O | −22.75 | −32.49 | 78.06 | 15.00 |
| 108 ARG | N | −24.43 | −33.77 | 77.32 | 15.00 |
| 108 ARG | CA | −23.64 | −35.00 | 77.33 | 15.00 |
| 108 ARG | CB | −24.12 | −35.97 | 78.42 | 15.00 |
| 108 ARG | CG | −25.63 | −36.03 | 78.64 | 15.00 |
| 108 ARG | CD | −26.27 | −37.28 | 78.04 | 15.00 |
| 108 ARG | NE | −27.73 | −37.21 | 78.14 | 15.00 |

TABLE VI-continued

Table of the orthogonal three dimensional coordinates in Angstroms and B factors (Å$^2$) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 108 ARG | CZ | −28.57 | −38.06 | 77.54 | 15.00 |
| 108 ARG | NH1 | −28.09 | −39.05 | 76.80 | 15.00 |
| 108 ARG | NH2 | −29.88 | −37.94 | 77.72 | 15.00 |
| 108 ARG | C | −23.55 | −35.70 | 75.97 | 15.00 |
| 108 ARG | O | −23.77 | −36.91 | 75.85 | 15.00 |
| 109 GLY | N | −23.19 | −34.93 | 74.94 | 15.00 |
| 109 GLY | CA | −23.06 | −35.50 | 73.61 | 15.00 |
| 109 GLY | C | −24.08 | −34.95 | 72.65 | 15.00 |
| 109 GLY | O | −24.81 | −34.01 | 72.97 | 15.00 |
| 110 TYR | N | −24.16 | −35.57 | 71.48 | 15.00 |
| 110 TYR | CA | −25.07 | −35.16 | 70.42 | 15.00 |
| 110 TYR | CB | −24.41 | −34.09 | 69.55 | 15.00 |
| 110 TYR | CG | −23.10 | −34.53 | 68.92 | 15.00 |
| 110 TYR | CD1 | −21.91 | −34.49 | 69.64 | 15.00 |
| 110 TYR | CE1 | −20.71 | −34.90 | 69.08 | 15.00 |
| 110 TYR | CD2 | −23.06 | −34.99 | 67.62 | 15.00 |
| 110 TYR | CE2 | −21.87 | −35.41 | 67.04 | 15.00 |
| 110 TYR | CZ | −20.70 | −35.35 | 67.77 | 15.00 |
| 110 TYR | OH | −19.52 | −35.75 | 67.18 | 15.00 |
| 110 TYR | C | −25.39 | −36.37 | 69.57 | 15.00 |
| 110 TYR | O | −24.80 | −37.44 | 69.77 | 15.00 |
| 111 ARG | N | −26.29 | −36.20 | 68.61 | 15.00 |
| 111 ARG | CA | −26.69 | −37.28 | 67.73 | 15.00 |
| 111 ARG | CB | −27.96 | −37.95 | 68.26 | 15.00 |
| 111 ARG | CG | −27.84 | −38.48 | 69.67 | 15.00 |
| 111 ARG | CD | −29.18 | −39.01 | 70.20 | 15.00 |
| 111 ARG | NE | −29.77 | −40.08 | 69.39 | 15.00 |
| 111 ARG | CZ | −29.16 | −41.20 | 69.02 | 15.00 |
| 111 ARG | NH1 | −29.81 | −42.09 | 68.27 | 15.00 |
| 111 ARG | NH2 | −27.91 | −41.45 | 69.40 | 15.00 |
| 111 ARG | C | −26.98 | −36.73 | 66.35 | 15.00 |
| 111 ARG | O | −27.99 | −36.05 | 66.17 | 15.00 |
| 112 GLU | N | −26.10 | −36.96 | 65.39 | 15.00 |
| 112 GLU | CA | −26.32 | −36.48 | 64.03 | 15.00 |
| 112 GLU | CB | −25.09 | −36.71 | 63.15 | 15.00 |
| 112 GLU | CG | −23.91 | −35.81 | 63.46 | 15.00 |
| 112 GLU | CD | −23.40 | −35.09 | 62.22 | 15.00 |
| 112 GLU | OE1 | −24.13 | −34.21 | 61.69 | 15.00 |
| 112 GLU | OE2 | −22.27 | −35.41 | 61.77 | 15.00 |
| 112 GLU | C | −27.50 | −37.23 | 63.45 | 15.00 |
| 112 GLU | O | −27.70 | −38.41 | 63.76 | 15.00 |
| 113 ILE | N | −28.29 | −36.55 | 62.64 | 15.00 |
| 113 ILE | CA | −29.46 | −37.15 | 62.02 | 15.00 |
| 113 ILE | CB | −30.51 | −36.04 | 61.71 | 15.00 |
| 113 ILE | CG2 | −31.75 | −36.60 | 61.05 | 15.00 |
| 113 ILE | CG1 | −30.92 | −35.38 | 63.02 | 15.00 |
| 113 ILE | CD1 | −31.95 | −34.32 | 62.87 | 15.00 |
| 113 ILE | C | −28.95 | −37.84 | 60.75 | 15.00 |
| 113 ILE | O | −27.93 | −37.44 | 60.20 | 15.00 |
| 114 PRO | N | −29.60 | −38.95 | 60.34 | 15.00 |
| 114 PRO | CD | −30.69 | −39.67 | 61.02 | 15.00 |
| 114 PRO | CA | −29.17 | −39.68 | 59.14 | 15.00 |
| 114 PRO | CB | −30.28 | −40.72 | 58.97 | 15.00 |
| 114 PRO | CG | −30.62 | −41.05 | 60.38 | 15.00 |
| 114 PRO | C | −29.04 | −38.79 | 57.93 | 15.00 |
| 114 PRO | O | −30.00 | −38.17 | 57.47 | 15.00 |
| 115 GLU | N | −27.82 | −38.75 | 57.41 | 15.00 |
| 115 GLU | CA | −27.50 | −37.92 | 56.26 | 15.00 |
| 115 GLU | CB | −26.12 | −38.30 | 55.74 | 15.00 |
| 115 GLU | CG | −25.58 | −37.36 | 54.68 | 15.00 |
| 115 GLU | CD | −24.19 | −37.76 | 54.22 | 15.00 |
| 115 GLU | OE1 | −23.20 | −37.34 | 54.86 | 15.00 |
| 115 GLU | OE2 | −24.10 | −38.51 | 53.22 | 15.00 |
| 115 GLU | C | −28.52 | −38.00 | 55.14 | 15.00 |
| 115 GLU | O | −28.72 | −39.05 | 54.56 | 15.00 |
| 116 GLY | N | −29.21 | −36.89 | 54.90 | 15.00 |
| 116 GLY | CA | −30.18 | −36.81 | 53.83 | 15.00 |
| 116 GLY | C | −31.55 | −37.41 | 54.07 | 15.00 |
| 116 GLY | O | −32.34 | −37.53 | 53.14 | 15.00 |
| 117 ASN | N | −31.86 | −37.73 | 55.32 | 15.00 |
| 117 ASN | CA | −33.15 | −38.34 | 55.65 | 15.00 |
| 117 ASN | CB | −32.91 | −39.54 | 56.56 | 15.00 |
| 117 ASN | CG | −34.17 | −40.32 | 56.84 | 15.00 |
| 117 ASN | OD1 | −35.26 | −39.75 | 56.98 | 15.00 |
| 117 ASN | ND2 | −34.04 | −41.64 | 56.94 | 15.00 |
| 117 ASN | C | −34.11 | −37.34 | 56.30 | 15.00 |
| 117 ASN | O | −34.16 | −37.23 | 57.52 | 15.00 |
| 118 GLU | N | −34.90 | −36.66 | 55.48 | 15.00 |
| 118 GLU | CA | −35.85 | −35.67 | 55.98 | 15.00 |
| 118 GLU | CB | −36.67 | −35.08 | 54.85 | 15.00 |
| 118 GLU | CG | −35.91 | −34.08 | 54.01 | 15.00 |
| 118 GLU | CD | −36.80 | −32.98 | 53.50 | 15.00 |
| 118 GLU | OE1 | −37.51 | −32.38 | 54.32 | 15.00 |
| 118 GLU | OE2 | −36.79 | −32.73 | 52.29 | 15.00 |
| 118 GLU | C | −36.80 | −36.20 | 57.04 | 15.00 |
| 118 GLU | O | −37.05 | −35.54 | 58.04 | 15.00 |
| 119 LYS | N | −37.34 | −37.38 | 56.81 | 15.00 |
| 119 LYS | CA | −38.28 | −37.95 | 57.77 | 15.00 |
| 119 LYS | CB | −38.87 | −39.24 | 57.21 | 15.00 |
| 119 LYS | CG | −39.46 | −39.06 | 55.80 | 15.00 |
| 119 LYS | CD | −40.57 | −38.01 | 55.77 | 15.00 |
| 119 LYS | CE | −41.82 | −38.49 | 56.49 | 15.00 |
| 119 LYS | NZ | −42.97 | −37.55 | 56.32 | 15.00 |
| 119 LYS | C | −37.66 | −38.15 | 59.15 | 15.00 |
| 119 LYS | O | −38.29 | −37.87 | 60.16 | 15.00 |
| 120 ALA | N | −36.39 | −38.56 | 59.19 | 15.00 |
| 120 ALA | CA | −35.73 | −38.76 | 60.48 | 15.00 |
| 120 ALA | CB | −34.39 | −39.43 | 60.30 | 15.00 |
| 120 ALA | C | −35.56 | −37.41 | 61.15 | 15.00 |
| 120 ALA | O | −35.40 | −37.34 | 62.37 | 15.00 |
| 121 LEU | N | −35.58 | −36.35 | 60.34 | 15.00 |
| 121 LEU | CA | −35.45 | −34.99 | 60.83 | 15.00 |
| 121 LEU | CB | −35.03 | −34.03 | 59.71 | 15.00 |
| 121 LEU | CG | −34.92 | −32.51 | 59.96 | 15.00 |
| 121 LEU | CD1 | −33.98 | −32.21 | 61.11 | 15.00 |
| 121 LEU | CD2 | −34.45 | −31.82 | 58.71 | 15.00 |
| 121 LEU | C | −36.78 | −34.54 | 61.43 | 15.00 |
| 121 LEU | O | −36.80 | −33.96 | 62.51 | 15.00 |
| 122 LYS | N | −37.89 | −34.84 | 60.76 | 15.00 |
| 122 LYS | CA | −39.20 | −34.44 | 61.28 | 15.00 |
| 122 LYS | CB | −40.34 | −34.86 | 60.35 | 15.00 |
| 122 LYS | CG | −41.71 | −34.49 | 60.95 | 15.00 |
| 122 LYS | CD | −42.90 | −34.72 | 60.02 | 15.00 |
| 122 LYS | CE | −43.21 | −36.19 | 59.84 | 15.00 |
| 122 LYS | NZ | −42.13 | −36.87 | 59.07 | 15.00 |
| 122 LYS | C | −39.43 | −35.03 | 62.67 | 15.00 |
| 122 LYS | O | −40.00 | −34.38 | 63.54 | 15.00 |
| 123 ARG | N | 39.02 | −36.28 | 62.85 | 15.00 |
| 123 ARG | CA | −39.18 | −36.96 | 64.12 | 15.00 |
| 123 ARG | CB | −38.90 | −38.45 | 63.95 | 15.00 |
| 123 ARG | CG | −40.04 | −39.22 | 63.30 | 15.00 |
| 123 ARG | CD | −39.53 | −40.52 | 62.67 | 15.00 |
| 123 ARG | NE | −38.42 | −41.08 | 63.44 | 15.00 |
| 123 ARG | CZ | −37.46 | −41.85 | 62.92 | 15.00 |
| 123 ARG | NH1 | −37.47 | −42.16 | 61.62 | 15.00 |
| 123 ARG | NH2 | −36.45 | −42.23 | 63.68 | 15.00 |
| 123 ARG | C | −38.24 | −36.34 | 65.14 | 15.00 |
| 123 ARG | O | −38.65 | −36.04 | 66.25 | 15.00 |
| 124 ALA | N | −36.99 | −36.12 | 64.76 | 15.00 |
| 124 ALA | CA | −36.05 | −35.51 | 65.68 | 15.00 |
| 124 ALA | CB | −34.70 | −35.31 | 65.02 | 15.00 |
| 124 ALA | C | −36.60 | −34.17 | 66.19 | 15.00 |
| 124 ALA | O | −36.55 | −33.91 | 67.39 | 15.00 |
| 125 VAL | N | −37.14 | −33.34 | 65.30 | 15.00 |
| 125 VAL | CA | −37.68 | −32.06 | 65.76 | 15.00 |
| 125 VAL | CB | −38.01 | −31.03 | 64.60 | 15.00 |
| 125 VAL | CG1 | −36.78 | −30.27 | 64.19 | 15.00 |
| 125 VAL | CG2 | −38.58 | −31.72 | 63.39 | 15.00 |
| 125 VAL | C | −38.94 | −32.28 | 66.58 | 15.00 |
| 125 VAL | O | −39.21 | −31.52 | 67.50 | 15.00 |
| 126 ALA | N | −39.69 | −33.32 | 66.27 | 15.00 |
| 126 ALA | CA | −40.93 | −33.60 | 66.98 | 15.00 |

TABLE VI-continued

Table of the orthogonal three dimensional coordinates in Angstroms and B factors (Å$^2$) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 126 ALA | CB | −41.81 | −34.52 | 66.16 | 15.00 |
| 126 ALA | C | −40.75 | −34.16 | 68.38 | 15.00 |
| 126 ALA | O | −41.53 | −33.84 | 69.28 | 15.00 |
| 127 ARG | N | −39.73 | −35.00 | 68.55 | 15.00 |
| 127 ARG | CA | −39.42 | −35.68 | 69.81 | 15.00 |
| 127 ARG | CB | −39.04 | −37.14 | 69.54 | 15.00 |
| 127 ARG | CG | −40.20 | −37.95 | 69.00 | 15.00 |
| 127 ARG | CD | −39.78 | −39.23 | 68.27 | 15.00 |
| 127 ARG | NE | −40.95 | −39.80 | 67.60 | 15.00 |
| 127 ARG | CZ | −40.95 | −40.88 | 66.83 | 15.00 |
| 127 ARG | NH1 | −42.09 | −41.30 | 66.28 | 15.00 |
| 127 ARG | NH2 | −39.84 | −41.56 | 66.63 | 15.00 |
| 127 ARG | C | −38.33 | −35.04 | 70.66 | 15.00 |
| 127 ARG | O | −38.25 | −35.30 | 71.86 | 15.00 |
| 128 VAL | N | −37.48 | −34.22 | 70.04 | 15.00 |
| 128 VAL | CA | −36.40 | −33.54 | 70.75 | 15.00 |
| 128 VAL | CB | −35.03 | −33.81 | 70.10 | 15.00 |
| 128 VAL | CG1 | −33.92 | −33.34 | 71.02 | 15.00 |
| 128 VAL | CG2 | −34.87 | −35.29 | 69.78 | 15.00 |
| 128 VAL | C | −36.58 | −32.02 | 70.88 | 15.00 |
| 128 VAL | O | −36.43 | −31.46 | 71.95 | 15.00 |
| 129 GLY | N | −36.89 | −31.35 | 69.77 | 15.00 |
| 129 GLY | CA | −37.08 | −29.91 | 69.81 | 15.00 |
| 129 GLY | C | −36.26 | −29.29 | 68.69 | 15.00 |
| 129 GLY | O | −36.02 | −29.96 | 67.68 | 15.00 |
| 130 PRO | N | −35.83 | −28.02 | 68.81 | 15.00 |
| 130 PRO | CD | −36.20 | −27.06 | 69.86 | 15.00 |
| 130 PRO | CA | −35.04 | −27.37 | 67.77 | 15.00 |
| 130 PRO | CB | −34.67 | −26.05 | 68.43 | 15.00 |
| 139 PRO | CG | −35.92 | −25.74 | 69.18 | 15.00 |
| 130 PRO | C | −33.81 | −28.17 | 67.39 | 15.00 |
| 130 PRO | O | −33.07 | −28.64 | 68.26 | 15.00 |
| 131 VAL | N | −33.60 | −28.33 | 66.09 | 15.00 |
| 131 VAL | CA | −32.46 | −29.08 | 65.58 | 15.00 |
| 131 VAL | CB | −32.94 | −30.26 | 64.68 | 15.00 |
| 131 VAL | CG1 | −31.76 | −31.03 | 64.14 | 15.00 |
| 131 VAL | CG2 | −33.82 | −31.20 | 65.46 | 15.00 |
| 131 VAL | C | −31.50 | −28.20 | 64.77 | 15.00 |
| 131 VAL | O | −31.93 | −27.35 | 63.99 | 15.00 |
| 132 SER | N | −30.20 | −28.39 | 64.96 | 15.00 |
| 132 SER | CA | −29.23 | −27.61 | 64.22 | 15.00 |
| 132 SER | CB | −27.88 | −27.61 | 64.94 | 15.00 |
| 132 SER | OG | −28.00 | −26.96 | 66.20 | 15.00 |
| 132 SER | C | −29.08 | −28.21 | 62.82 | 15.00 |
| 132 SER | O | −28.83 | −29.41 | 62.68 | 15.00 |
| 133 VAL | N | −29.31 | −27.39 | 61.80 | 15.00 |
| 133 VAL | CA | −29.22 | −27.82 | 60.40 | 15.00 |
| 133 VAL | CB | −30.60 | −27.81 | 59.68 | 15.00 |
| 133 VAL | CG1 | −31.51 | −28.90 | 60.23 | 15.00 |
| 133 VAL | CG2 | −31.27 | −26.45 | 59.80 | 15.00 |
| 133 VAL | C | −28.26 | −26.93 | 59.62 | 15.00 |
| 133 VAL | O | −27.88 | −25.85 | 60.08 | 15.00 |
| 134 ALA | N | −27.93 | −27.36 | 58.41 | 15.00 |
| 134 ALA | CA | −27.02 | −26.64 | 57.54 | 15.00 |
| 134 ALA | CB | −25.69 | −27.35 | 57.48 | 15.00 |
| 134 ALA | C | −27.64 | −26.61 | 56.16 | 15.00 |
| 134 ALA | O | −27.92 | −27.66 | 55.60 | 15.00 |
| 135 ILE | N | −27.84 | −25.43 | 55.60 | 15.00 |
| 135 ILE | CA | −28.45 | −25.31 | 54.28 | 15.00 |
| 135 ILE | CB | −29.84 | −24.62 | 54.36 | 15.00 |
| 135 ILE | CG2 | −30.82 | −25.47 | 55.15 | 15.00 |
| 135 ILE | CG1 | −29.70 | −23.24 | 55.00 | 15.00 |
| 135 ILE | CD1 | −30.95 | −22.42 | 54.97 | 15.00 |
| 135 ILE | C | −27.59 | −24.49 | 53.32 | 15.00 |
| 135 ILE | O | −26.49 | −24.04 | 53.66 | 15.00 |
| 136 ASP | N | −28.09 | −24.33 | 52.10 | 15.00 |
| 136 ASP | CA | −27.45 | −23.52 | 51.07 | 15.00 |
| 136 ASP | CB | −27.50 | −24.23 | 49.72 | 15.00 |
| 136 ASP | CG | −27.09 | −23.32 | 48.57 | 15.00 |
| 136 ASP | OD1 | −27.71 | −23.40 | 47.49 | 15.00 |
| 136 ASP | OD2 | −26.15 | −22.50 | 48.73 | 15.00 |
| 136 ASP | C | −28.22 | −22.21 | 50.99 | 15.00 |
| 136 ASP | O | −29.36 | −22.17 | 50.52 | 15.00 |
| 137 ALA | N | −27.61 | −21.13 | 51.46 | 15.00 |
| 137 ALA | CA | −28.26 | −19.83 | 51.42 | 15.00 |
| 137 ALA | CB | −28.42 | −19.30 | 52.83 | 15.00 |
| 137 ALA | C | −27.46 | −18.84 | 50.56 | 15.00 |
| 137 ALA | O | −27.34 | −17.66 | 50.89 | 15.00 |
| 138 SER | N | −26.92 | −19.34 | 49.45 | 15.00 |
| 138 SER | CA | −26.12 | −18.53 | 48.53 | 15.00 |
| 138 SER | CB | −25.09 | −19.42 | 47.83 | 15.00 |
| 138 SER | OG | −25.71 | −20.52 | 47.19 | 15.00 |
| 138 SER | C | −26.97 | −17.80 | 47.49 | 15.00 |
| 138 SER | O | −26.60 | −16.72 | 47.01 | 15.00 |
| 139 LEU | N | −28.12 | −18.36 | 47.17 | 15.00 |
| 139 LEU | CA | −29.02 | −17.79 | 46.19 | 15.00 |
| 139 LEU | CB | −30.07 | −18.84 | 45.80 | 15.00 |
| 139 LEU | CG | −29.49 | −20.25 | 45.62 | 15.00 |
| 139 LEU | CD1 | −30.58 | −21.21 | 45.21 | 15.00 |
| 139 LEU | CD2 | −28.37 | −20.28 | 44.61 | 15.00 |
| 139 LEU | C | −29.70 | −16.52 | 46.70 | 15.00 |
| 139 LEU | O | −30.06 | −16.43 | 47.88 | 15.00 |
| 140 THR | N | −29.90 | −15.54 | 45.81 | 15.00 |
| 140 THR | CA | −30.54 | −14.29 | 46.18 | 15.00 |
| 140 THR | CB | −30.46 | −13.21 | 45.07 | 15.00 |
| 140 THR | OG1 | −30.85 | −13.77 | 43.82 | 15.00 |
| 140 THR | CG2 | −29.05 | −12.66 | 44.96 | 15.00 |
| 140 THR | C | −32.00 | −14.49 | 46.57 | 15.00 |
| 140 THR | O | −32.50 | −13.79 | 47.45 | 15.00 |
| 141 SER | N | −32.68 | −15.45 | 45.95 | 15.00 |
| 141 SER | CA | −34.08 | −15.70 | 46.30 | 15.00 |
| 141 SER | CB | −34.66 | −16.86 | 45.50 | 15.00 |
| 141 SER | OG | −33.72 | −17.92 | 45.39 | 15.00 |
| 141 SER | C | −34.19 | −15.94 | 47.79 | 15.00 |
| 141 SER | O | −35.04 | −15.37 | 48.46 | 15.00 |
| 142 PHE | N | −33.27 | −16.72 | 48.33 | 15.00 |
| 142 PHE | CA | −33.28 | −17.01 | 49.76 | 15.00 |
| 142 PHE | CB | −32.21 | −18.05 | 50.11 | 15.00 |
| 142 PHE | CG | −32.17 | −18.41 | 51.57 | 15.00 |
| 142 PHE | CD1 | −32.97 | −19.43 | 52.08 | 15.00 |
| 142 PHE | CD2 | −31.34 | −17.72 | 52.45 | 15.00 |
| 142 PHE | CE1 | −32.94 | −19.75 | 53.43 | 15.00 |
| 142 PHE | CE2 | −31.31 | −18.04 | 53.80 | 15.00 |
| 142 PHE | CZ | −32.11 | −19.05 | 54.29 | 15.00 |
| 142 PHE | C | −33.01 | −15.75 | 50.54 | 15.00 |
| 142 PHE | O | −33.66 | −15.45 | 51.52 | 15.00 |
| 143 GLN | N | −32.01 | −15.00 | 50.09 | 15.00 |
| 143 GLN | CA | −31.61 | −13.79 | 50.78 | 15.00 |
| 143 GLN | CB | −30.30 | −13.26 | 50.21 | 15.00 |
| 143 GLN | CG | −29.18 | −14.29 | 50.23 | 15.00 |
| 143 GLN | CD | −27.85 | −13.72 | 49.81 | 15.00 |
| 143 GLN | OE1 | −27.29 | −12.84 | 50.48 | 15.00 |
| 143 GLN | NE2 | −27.31 | −14.22 | 48.70 | 15.00 |
| 143 GLN | C | −32.67 | −12.70 | 50.84 | 15.00 |
| 143 GLN | O | −32.79 | −12.04 | 51.86 | 15.00 |
| 144 PHE | N | −33.45 | −12.51 | 49.78 | 15.00 |
| 144 PHE | CA | −34.50 | −11.48 | 49.83 | 15.00 |
| 144 PHE | CB | −34.57 | −10.60 | 48.55 | 15.00 |
| 144 PHE | CG | −34.78 | −11.35 | 47.27 | 15.00 |
| 144 PHE | CD1 | −33.92 | −11.14 | 46.19 | 15.00 |
| 144 PHE | CD2 | −35.84 | −12.24 | 47.12 | 15.00 |
| 144 PHE | CE1 | −34.11 | −11.81 | 44.99 | 15.00 |
| 144 PHE | CE2 | −36.04 | −12.92 | 45.91 | 15.00 |
| 144 PHE | CZ | −35.18 | −12.71 | 44.85 | 15.00 |
| 144 PHE | C | −35.88 | −12.04 | 50.20 | 15.00 |
| 144 PHE | O | −36.90 | −11.36 | 50.02 | 15.00 |
| 145 TYR | N | −35.89 | −13.28 | 50.71 | 15.00 |
| 145 TYR | CA | −37.12 | −13.95 | 51.12 | 15.00 |
| 145 TYR | CB | −36.80 | −15.21 | 51.94 | 15.00 |
| 145 TYR | CG | −37.98 | −15.77 | 52.70 | 15.00 |
| 145 TYR | CD1 | −38.84 | −16.69 | 52.12 | 15.00 |
| 145 TYR | CE1 | −39.96 | −17.15 | 52.80 | 15.00 |

TABLE VI-continued

Table of the orthogonal three dimensional coordinates in Angstroms and B factors (Å$^2$) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 145 TYR | CD2 | −38.27 | −15.32 | 53.99 | 15.00 |
| 145 TYR | CE2 | −39.40 | −15.78 | 54.67 | 15.00 |
| 145 TYR | CZ | −40.24 | −16.69 | 54.07 | 15.00 |
| 145 TYR | OH | −41.38 | −17.11 | 54.73 | 15.00 |
| 145 TYR | C | −37.90 | −12.98 | 51.97 | 15.00 |
| 145 TYR | O | −37.32 | −12.24 | 52.74 | 15.00 |
| 146 SER | N | −39.21 | −13.02 | 51.84 | 15.00 |
| 146 SER | CA | −40.07 | −12.13 | 52.59 | 15.00 |
| 146 SER | CB | −40.63 | −11.07 | 51.63 | 15.00 |
| 146 SER | OG | −41.38 | −10.08 | 52.30 | 15.00 |
| 146 SER | C | −41.21 | −12.89 | 53.24 | 15.00 |
| 146 SER | O | −41.48 | −12.72 | 54.43 | 15.00 |
| 147 LYS | N | −41.86 | −13.77 | 52.48 | 15.00 |
| 147 LYS | CA | −42.98 | −14.54 | 53.01 | 15.00 |
| 147 LYS | CB | −44.25 | −13.71 | 53.04 | 15.00 |
| 147 LYS | CG | −44.62 | −13.11 | 51.70 | 15.00 |
| 147 LYS | CD | −46.07 | −12.67 | 51.68 | 15.00 |
| 147 LYS | CE | −46.47 | −12.13 | 50.31 | 15.00 |
| 147 LYS | NZ | −47.97 | −12.11 | 50.14 | 15.00 |
| 147 LYS | C | −43.21 | −15.79 | 52.19 | 15.00 |
| 147 LYS | O | −42.55 | −16.01 | 51.17 | 15.00 |
| 148 GLY | N | −44.16 | −16.61 | 52.64 | 15.00 |
| 148 GLY | CA | −44.49 | −17.85 | 51.95 | 15.00 |
| 148 GLY | C | −43.47 | −18.95 | 52.16 | 15.00 |
| 148 GLY | O | −42.52 | −18.79 | 52.93 | 15.00 |
| 149 VAL | N | −43.64 | −20.04 | 51.43 | 15.00 |
| 149 VAL | CA | −42.75 | −21.19 | 51.52 | 15.00 |
| 149 VAL | CB | −43.57 | −22.51 | 51.47 | 15.00 |
| 149 VAL | CG1 | −42.66 | −23.71 | 51.33 | 15.00 |
| 149 VAL | CG2 | −44.41 | −22.65 | 52.72 | 15.00 |
| 149 VAL | C | −41.67 | −21.17 | 50.43 | 15.00 |
| 149 VAL | O | −41.96 | −21.34 | 49.24 | 15.00 |
| 150 TYR | N | −40.43 | −20.96 | 50.84 | 15.00 |
| 150 TYR | CA | −39.30 | −20.91 | 49.91 | 15.00 |
| 150 TYR | CB | −38.04 | −20.41 | 50.64 | 15.00 |
| 150 TYR | CG | −36.82 | −20.29 | 49.75 | 15.00 |
| 150 TYR | CD1 | −36.78 | −19.38 | 48.69 | 15.00 |
| 150 TYR | CE1 | −35.67 | −19.27 | 47.88 | 15.00 |
| 150 TYR | CD2 | −35.69 | −21.07 | 49.97 | 15.00 |
| 150 TYR | CE2 | −34.56 | −20.96 | 49.16 | 15.00 |
| 150 TYR | CZ | −34.56 | −20.06 | 48.11 | 15.00 |
| 150 TYR | OH | −33.45 | −19.93 | 47.32 | 15.00 |
| 150 TYR | C | −39.03 | −22.26 | 49.27 | 15.00 |
| 150 TYR | O | −39.23 | −23.31 | 49.88 | 15.00 |
| 151 TYR | N | −38.55 | −22.22 | 48.03 | 15.00 |
| 151 TYR | CA | −38.21 | −23.42 | 47.28 | 15.00 |
| 151 TYR | CB | −39.45 | −24.26 | 46.99 | 15.00 |
| 151 TYR | CG | −39.15 | −25.46 | 46.11 | 15.00 |
| 151 TYR | CD1 | −38.22 | −26.42 | 46.51 | 15.00 |
| 151 TYR | CE1 | −37.94 | −27.53 | 45.71 | 15.00 |
| 151 TYR | CD2 | −39.79 | −25.63 | 44.89 | 15.00 |
| 151 TYR | CE2 | −39.52 | −26.74 | 44.08 | 15.00 |
| 151 TYR | CZ | −38.59 | −27.69 | 44.50 | 15.00 |
| 151 TYR | OH | −38.36 | −28.83 | 43.75 | 15.00 |
| 151 TYR | C | −37.60 | −23.00 | 45.97 | 15.00 |
| 151 TYR | O | −38.29 | −22.44 | 45.11 | 15.00 |
| 152 ASP | N | −36.31 | −23.25 | 45.80 | 15.00 |
| 152 ASP | CA | −35.66 | −22.90 | 44.55 | 15.00 |
| 152 ASP | CB | −34.74 | −21.69 | 44.71 | 15.00 |
| 152 ASP | CG | −34.02 | −21.34 | 43.43 | 15.00 |
| 152 ASP | OD1 | −34.60 | −21.55 | 42.34 | 15.00 |
| 152 ASP | OD2 | −32.87 | −20.86 | 43.49 | 15.00 |
| 152 ASP | C | −34.87 | −24.07 | 44.02 | 15.00 |
| 152 ASP | O | −33.84 | −24.43 | 44.56 | 15.00 |
| 153 GLU | N | −35.33 | −24.60 | 42.90 | 15.00 |
| 153 GLU | CA | −34.70 | −25.74 | 42.26 | 15.00 |
| 153 GLU | CB | −35.49 | −26.18 | 41.03 | 15.00 |
| 153 GLU | CG | −35.79 | −25.08 | 40.01 | 15.00 |
| 153 GLU | CD | −37.17 | −24.43 | 40.19 | 15.00 |
| 153 GLU | OE1 | −38.12 | −24.84 | 39.48 | 15.00 |
| 153 GLU | OE2 | −37.29 | −23.50 | 41.02 | 15.00 |
| 153 GLU | C | −33.22 | −25.56 | 41.91 | 15.00 |
| 153 GLU | O | −32.59 | −26.50 | 41.44 | 15.00 |
| 154 SER | N | −32.66 | −24.37 | 42.12 | 15.00 |
| 154 SER | CA | −31.24 | −24.12 | 41.82 | 15.00 |
| 154 SER | CB | −31.02 | −22.70 | 41.29 | 15.00 |
| 154 SER | OG | −32.05 | −22.32 | 40.40 | 15.00 |
| 154 SER | C | −30.40 | −24.30 | 43.08 | 15.00 |
| 154 SER | O | −29.17 | −24.21 | 43.04 | 15.00 |
| 155 CYS | N | −31.08 | −24.48 | 44.22 | 15.00 |
| 155 CYS | CA | −30.41 | −24.66 | 45.49 | 15.00 |
| 155 CYS | C | −29.57 | −25.91 | 45.40 | 15.00 |
| 155 CYS | O | −30.00 | −2&.91 | 44.82 | 15.00 |
| 155 CYS | CB | −31.44 | −24.79 | 46.62 | 15.00 |
| 155 CYS | SG | −30.90 | −24.05 | 48.19 | 15.00 |
| 156 ASN | N | −28.36 | −25.87 | 45.94 | 15.00 |
| 156 ASN | CA | −27.47 | −27.01 | 45.87 | 15.00 |
| 156 ASN | CB | −26.18 | −26.59 | 45.19 | 15.00 |
| 156 ASN | CG | −25.28 | −27.76 | 44.91 | 15.00 |
| 156 ASN | OD1 | −25.73 | −28.91 | 44.88 | 15.00 |
| 156 ASN | ND2 | −23.99 | −27.49 | 44.73 | 15.00 |
| 156 ASN | C | −27.20 | −27.67 | 47.23 | 15.00 |
| 156 ASN | O | −26.43 | −27.16 | 48.05 | 15.00 |
| 157 SER | N | −27.79 | −28.85 | 47.41 | 15.00 |
| 157 SER | CA | −27.67 | −29.64 | 48.62 | 15.00 |
| 157 SER | CB | −28.48 | −30.92 | 48.45 | 15.00 |
| 157 SER | OG | −29.83 | −30.63 | 48.13 | 15.00 |
| 157 SER | C | −26.24 | −30.00 | 49.04 | 15.00 |
| 157 SER | O | −26.01 | −30.36 | 50.19 | 15.00 |
| 158 ASP | N | −25.30 | −29.93 | 48.10 | 15.00 |
| 158 ASP | CA | −23.89 | −30.24 | 48.35 | 15.00 |
| 158 ASP | CB | −23.21 | −30.69 | 47.07 | 15.00 |
| 158 ASP | CG | −23.72 | −32.01 | 46.57 | 15.00 |
| 158 ASP | OD1 | −24.95 | −32.15 | 46.33 | 15.00 |
| 158 ASP | OD2 | −22.86 | −32.91 | 46.38 | 15.00 |
| 158 ASP | C | −23.14 | −29.02 | 48.87 | 15.00 |
| 158 ASP | O | −22.11 | −29.15 | 49.53 | 15.00 |
| 159 ASN | N | −23.62 | −27.84 | 48.51 | 15.00 |
| 159 ASN | CA | −22.98 | −26.62 | 48.94 | 15.00 |
| 159 ASN | CB | −23.10 | −25.57 | 47.84 | 15.00 |
| 159 ASN | CG | −22.14 | −24.40 | 48.03 | 15.00 |
| 159 ASN | OD1 | −21.43 | −24.30 | 49.04 | 15.00 |
| 159 ASN | ND2 | −22.10 | −23.51 | 47.04 | 15.00 |
| 159 ASN | C | −23.68 | −26.14 | 50.20 | 15.00 |
| 159 ASN | O | −24.63 | −25.37 | 50.12 | 15.00 |
| 160 LEU | N | −23.25 | −26.64 | 51.36 | 15.00 |
| 160 LEU | CA | −23.84 | −26.23 | 52.63 | 15.00 |
| 160 LEU | CB | −23.88 | −27.42 | 53.60 | 15.00 |
| 160 LEU | CG | −24.59 | −28.72 | 53.22 | 15.00 |
| 160 LEU | CD1 | −24.45 | −29.70 | 54.37 | 15.00 |
| 160 LEU | CD2 | −26.06 | −28.49 | 52.89 | 15.00 |
| 160 LEU | C | −22.98 | −25.11 | 53.22 | 15.00 |
| 160 LEU | O | −21.91 | −25.35 | 53.78 | 15.00 |
| 161 ASN | N | −23.47 | −23.89 | 53.16 | 15.00 |
| 161 ASN | CA | −22.70 | −22.75 | 53.65 | 15.00 |
| 161 ASN | CB | −22.58 | −21.73 | 52.53 | 15.00 |
| 161 ASN | CG | −23.89 | −21.51 | 51.84 | 15.00 |
| 161 ASN | OD1 | −24.74 | −20.76 | 52.33 | 15.00 |
| 161 ASN | ND2 | −24.10 | −22.23 | 50.75 | 15.00 |
| 161 ASN | C | −23.23 | −22.05 | 54.89 | 15.00 |
| 161 ASN | O | −22.45 | −21.62 | 55.73 | 15.00 |
| 162 HIS | N | −24.54 | −21.93 | 55.01 | 15.00 |
| 162 HIS | CA | −25.13 | −21.27 | 56.16 | 15.00 |
| 162 HIS | CB | −26.18 | −20.27 | 55.67 | 15.00 |
| 162 HIS | CG | −26.55 | −19.22 | 56.67 | 15.00 |
| 162 HIS | CD2 | −27.72 | −18.61 | 56.93 | 15.00 |
| 162 HIS | ND1 | −25.63 | −18.66 | 57.53 | 15.00 |
| 162 HIS | CE1 | −26.22 | −17.74 | 58.27 | 15.00 |
| 162 HIS | NE2 | −27.49 | −17.69 | 57.93 | 15.00 |
| 162 HIS | C | −25.76 | −22.27 | 57.12 | 15.00 |
| 162 HIS | O | −26.47 | −23.19 | 56.69 | 15.00 |
| 163 ALA | N | −25.47 | −22.12 | 58.41 | 15.00 |

TABLE VI-continued

Table of the orthogonal three dimensional coordinates in Angstroms and B factors (Å²) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 163 ALA | CA | −26.01 | −23.00 | 59.45 | 15.00 |
| 163 ALA | CB | −24.93 | −23.33 | 60.47 | 15.00 |
| 163 ALA | C | −27.15 | −22.28 | 60.13 | 15.00 |
| 163 ALA | O | −27.00 | −21.13 | 60.54 | 15.00 |
| 164 VAL | N | −28.30 | −22.94 | 60.24 | 15.00 |
| 164 VAL | CA | −29.48 | −22.34 | 60.86 | 15.00 |
| 164 VAL | CB | −30.54 | −21.99 | 59.79 | 15.00 |
| 164 VAL | CG1 | −30.11 | −20.79 | 58.99 | 15.00 |
| 164 VAL | CG2 | −30.75 | −23.16 | 58.86 | 15.00 |
| 164 VAL | C | −30.05 | −23.28 | 61.91 | 15.00 |
| 164 VAL | O | −29.37 | −24.21 | 62.33 | 15.00 |
| 165 LEU | N | −31.31 | −23.07 | 62.30 | 15.00 |
| 165 LEU | CA | −31.97 | −23.88 | 63.33 | 15.00 |
| 165 LEU | CB | −32.00 | −23.11 | 64.64 | 15.00 |
| 165 LEU | CG | −32.59 | −23.77 | 65.88 | 15.00 |
| 165 LEU | CD1 | −31.53 | −24.65 | 66.49 | 15.00 |
| 165 LEU | CD2 | −33.04 | −22.71 | 66.87 | 15.00 |
| 165 LEU | C | −33.40 | −24.17 | 62.94 | 15.00 |
| 165 LEU | O | −34.16 | −23.24 | 62.72 | 15.00 |
| 166 ALA | N | −33.79 | −25.44 | 62.92 | 15.00 |
| 166 ALA | CA | −35.15 | −25.82 | 62.56 | 15.00 |
| 166 ALA | CB | −35.16 | −27.19 | 61.92 | 15.00 |
| 166 ALA | C | −36.03 | −25.80 | 63.80 | 15.00 |
| 166 ALA | O | −35.93 | −26.66 | 64.66 | 15.00 |
| 167 VAL | N | −36.89 | −24.80 | 63.88 | 15.00 |
| 167 VAL | CA | −37.79 | −24.62 | 65.01 | 15.00 |
| 167 VAL | CB | −38.11 | −23.11 | 65.18 | 15.00 |
| 167 VAL | CG1 | −39.35 | −22.88 | 66.00 | 15.00 |
| 167 VAL | CG2 | −36.94 | −22.42 | 65.84 | 15.00 |
| 167 VAL | C | −39.06 | −25.46 | 64.92 | 15.00 |
| 167 VAL | O | −39.83 | −25.56 | 65.87 | 15.00 |
| 168 GLY | N | −39.28 | −26.10 | 63.78 | 15.00 |
| 168 GLY | CA | −40.48 | −26.91 | 63.65 | 15.00 |
| 168 GLY | C | −40.77 | −27.29 | 62.23 | 15.00 |
| 168 GLY | O | −39.85 | −27.36 | 61.41 | 15.00 |
| 169 TYR | N | −42.04 | −27.55 | 61.95 | 15.00 |
| 169 TYR | CA | −42.50 | −27.93 | 60.62 | 15.00 |
| 169 TYR | CB | −42.09 | −29.38 | 60.30 | 15.00 |
| 169 TYR | CG | −42.61 | −30.41 | 61.28 | 15.00 |
| 169 TYR | CD1 | −43.94 | −30.82 | 61.25 | 15.00 |
| 169 TYR | CE1 | −44.42 | −31.76 | 62.13 | 15.00 |
| 169 TYR | CD2 | −41.77 | −30.98 | 62.23 | 15.00 |
| 169 TYR | CE2 | −42.24 | −31.93 | 63.13 | 15.00 |
| 169 TYR | CZ | −43.57 | −32.31 | 63.07 | 15.00 |
| 169 TYR | OH | −44.04 | −33.26 | 63.95 | 15.00 |
| 169 TYR | C | −44.02 | −27.78 | 60.54 | 15.00 |
| 169 TYR | O | −44.70 | −27.74 | 61.57 | 15.00 |
| 170 GLY | N | −44.55 | −27.71 | 59.33 | 15.00 |
| 170 GLY | CA | −45.98 | −27.55 | 59.16 | 15.00 |
| 170 GLY | C | −46.42 | −27.49 | 57.72 | 15.00 |
| 170 GLY | O | −45.69 | −27.89 | 56.82 | 15.00 |
| 171 ILE | N | −47.61 | −26.95 | 57.49 | 15.00 |
| 171 ILE | CA | −48.20 | −26.83 | 56.16 | 15.00 |
| 171 ILE | CB | −49.51 | −27.69 | 56.06 | 15.00 |
| 171 ILE | CG2 | −50.16 | −27.55 | 54.70 | 15.00 |
| 171 ILE | CG1 | −49.20 | −29.18 | 56.27 | 15.00 |
| 171 ILE | CD1 | −48.97 | −29.59 | 57.73 | 15.00 |
| 171 ILE | C | −48.55 | −25.36 | 55.90 | 15.00 |
| 171 ILE | O | −48.58 | −24.55 | 56.84 | 15.00 |
| 172 GLN | N | −48.73 | −25.00 | 54.63 | 15.00 |
| 172 GLN | CA | −49.10 | −23.64 | 54.25 | 15.00 |
| 172 GLN | CB | −47.90 | −22.90 | 53.68 | 15.00 |
| 172 GLN | CG | −47.16 | −22.04 | 54.69 | 15.00 |
| 172 GLN | CD | −47.81 | −20.68 | 54.87 | 15.00 |
| 172 GLN | OE1 | −47.24 | −19.66 | 54.49 | 15.00 |
| 172 GLN | NE2 | −49.00 | −20.66 | 55.47 | 15.00 |
| 172 GLN | C | −50.24 | −23.71 | 53.24 | 15.00 |
| 172 GLN | O | −51.31 | −24.23 | 53.55 | 15.00 |
| 173 LYS | N | −50.05 | −23.17 | 52.05 | 15.00 |
| 173 LYS | CA | −51.11 | −23.24 | 51.05 | 15.00 |
| 173 LYS | CB | −51.04 | −22.05 | 50.08 | 15.00 |
| 173 LYS | CG | −S1.15 | −20.70 | 50.77 | 15.00 |
| 173 LYS | CD | −50.94 | −19.57 | 49.77 | 15.00 |
| 173 LYS | CE | −50.57 | −18.27 | 50.50 | 15.00 |
| 173 LYS | NZ | −49.28 | −18.39 | S1.26 | 15.00 |
| 173 LYS | C | −50.82 | −24.55 | 50.34 | 15.00 |
| 173 LYS | O | −50.33 | −24.58 | 49.21 | 15.00 |
| 174 GLY | N | −51.02 | −25.63 | 51.08 | 15.00 |
| 174 GLY | CA | −50.77 | −26.96 | 50.56 | 15.00 |
| 174 GLY | C | −49.30 | −27.32 | 50.59 | 15.00 |
| 174 GLY | O | −48.95 | −28.47 | 50.31 | 15.00 |
| 175 ASN | N | −48.44 | −26.35 | 50.92 | 15.00 |
| 175 ASN | CA | −47.00 | −26.60 | 50.98 | 15.00 |
| 175 ASN | CB | −46.20 | −25.39 | 50.47 | 15.00 |
| 175 ASN | CG | −46.70 | −24.86 | 49.14 | 15.00 |
| 175 ASN | OD1 | −47.33 | −23.79 | 49.08 | 15.00 |
| 175 ASN | ND2 | −46.41 | −25.58 | 48.06 | 15.00 |
| 175 ASN | C | −46.49 | −26.95 | 52.38 | 15.00 |
| 175 ASN | O | −46.66 | −26.16 | 53.33 | 15.00 |
| 176 LYS | N | −45.90 | −28.13 | 52.53 | 15.00 |
| 176 LYS | CA | −45.33 | −28.50 | 53.82 | 15.00 |
| 176 LYS | CB | −44.94 | −29.98 | 53.84 | 15.00 |
| 176 LYS | CG | −46.10 | −30.95 | 53.63 | 15.00 |
| 176 LYS | CD | −45.67 | −32.36 | 53.98 | 15.00 |
| 176 LYS | CE | −46.71 | −33.40 | 53.61 | 15.00 |
| 176 LYS | NZ | −46.36 | −34.11 | 52.34 | 15.00 |
| 176 LYS | C | −44.08 | −27.63 | 53.94 | 15.00 |
| 176 LYS | O | −43.52 | −27.21 | 52.92 | 15.00 |
| 177 HIS | N | −43.62 | −27.37 | 55.16 | 15.00 |
| 177 HIS | CA | −42.44 | −26.52 | 55.34 | 15.00 |
| 177 HIS | CB | −42.84 | −25.05 | 55.23 | 15.00 |
| 177 HIS | CG | −43.71 | −24.59 | 56.35 | 15.00 |
| 177 HIS | CD2 | −43.41 | −24.18 | 57.61 | 15.00 |
| 177 HIS | ND1 | −45.09 | −24.52 | 56.26 | 15.00 |
| 177 HIS | CE1 | −45.59 | −24.10 | 57.40 | 15.00 |
| 177 HIS | NE2 | −44.59 | −23.89 | 58.24 | 15.00 |
| 177 HIS | C | −41.74 | −26.73 | 56.67 | 15.00 |
| 177 HIS | O | −42.32 | −27.24 | 57.62 | 15.00 |
| 178 TRP | N | −40.49 | −26.28 | 56.73 | 15.00 |
| 178 TRP | CA | −39.64 | −26.34 | 57.91 | 15.00 |
| 178 TRP | CB | −38.24 | −26.82 | 57.54 | 15.00 |
| 178 TRP | CG | −38.16 | −28.22 | 57.08 | 15.00 |
| 178 TRP | CD2 | −38.28 | −29.41 | 57.88 | 15.00 |
| 178 TRP | CE2 | −38.08 | −30.51 | 57.03 | 15.00 |
| 178 TRP | CE3 | −38.52 | −29.64 | 59.24 | 15.00 |
| 178 TRP | CD1 | −37.92 | −28.65 | 55.81 | 15.00 |
| 178 TRP | NE1 | −37.87 | −30.02 | 55.77 | 15.00 |
| 178 TRP | CZ2 | −38.13 | −31.83 | 57.48 | 15.00 |
| 178 TRP | CZ3 | −38.57 | −30.95 | 59.70 | 15.00 |
| 178 TRP | CH2 | −38.37 | −32.03 | 58.83 | 15.00 |
| 178 TRP | C | −39.53 | −24.91 | 58.39 | 15.00 |
| 178 TRP | O | −39.15 | −24.04 | 57.61 | 15.00 |
| 179 ILE | N | −39.89 | −24.63 | 59.63 | 15.00 |
| 179 ILE | CA | −39.79 | −23.28 | 60.16 | 15.00 |
| 179 ILE | CB | −40.65 | −23.09 | 61.42 | 15.00 |
| 179 ILE | CG2 | −40.61 | −21.64 | 61.85 | 15.00 |
| 179 ILE | CG1 | −42.09 | −23.52 | 61.15 | 15.00 |
| 179 ILE | CD1 | −42.97 | −23.45 | 62.38 | 15.00 |
| 179 ILE | C | −38.32 | −23.04 | 60.52 | 15.00 |
| 179 ILE | O | −37.80 | −23.66 | 61.45 | 15.00 |
| 180 ILE | N | −37.67 | −22.16 | 59.78 | 15.00 |
| 180 ILE | CA | −36.27 | −21.87 | 60.01 | 15.00 |
| 180 ILE | CB | −35.46 | −22.00 | 58.70 | 15.00 |
| 180 ILE | CG2 | −34.01 | −21.64 | 58.91 | 15.00 |
| 180 ILE | CG1 | −35.57 | −23.42 | 58.16 | 15.00 |
| 180 ILE | CD1 | −34.96 | −24.46 | 59.08 | 15.00 |
| 180 ILE | C | −36.01 | −20.52 | 60.69 | 15.00 |
| 180 ILE | O | −36.70 | −19.53 | 60.44 | 15.00 |
| 181 LYS | N | −35.02 | −20.53 | 61.58 | 15.00 |
| 181 LYS | CA | −34.60 | −19.36 | 62.34 | 15.00 |
| 181 LYS | CB | −34.59 | −19.69 | 63.84 | 15.00 |
| 181 LYS | CG | −34.02 | −18.59 | 64.70 | 15.00 |

TABLE VI-continued

Table of the orthogonal three dimensional coordinates in Angstroms and B factors (Å²) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 181 LYS | CD | −33.87 | −19.04 | 66.14 | 15.00 |
| 181 LYS | CE | −33.58 | −17.85 | 67.01 | 15.00 |
| 181 LYS | NZ | −33.52 | −18.17 | 68.45 | 15.00 |
| 181 LYS | C | −33.19 | −19.02 | 61.91 | 15.00 |
| 181 LYS | O | −32.28 | −19.85 | 62.04 | 15.00 |
| 182 ASN | N | −33.00 | −17.82 | 61.37 | 15.00 |
| 182 ASN | CA | −31.68 | −17.42 | 60.93 | 15.00 |
| 182 ASN | CB | −31.77 | −16.80 | 59.54 | 15.00 |
| 182 ASN | CG | −30.45 | −16.80 | 58.83 | 15.00 |
| 182 ASN | OD1 | −29.40 | −16.99 | 59.44 | 15.00 |
| 182 ASN | ND2 | −30.48 | −16.62 | 57.51 | 15.00 |
| 182 ASN | C | −31.10 | −16.42 | 61.92 | 15.00 |
| 182 ASN | O | −31.81 | −15.94 | 62.79 | 15.00 |
| 183 SER | N | −29.81 | −16.14 | 61.82 | 15.00 |
| 183 SER | CA | −29.19 | −15.20 | 62.74 | 15.00 |
| 183 SER | CB | −27.97 | −15.85 | 63.38 | 15.00 |
| 183 SER | CG | −27.30 | −16.66 | 62.44 | 15.00 |
| 183 SER | C | −28.79 | −13.90 | 62.04 | 15.00 |
| 183 SER | O | −27.68 | −13.40 | 62.23 | 15.00 |
| 184 TRP | N | −29.70 | −13.34 | 61.25 | 15.00 |
| 184 TRP | CA | −29.44 | −12.11 | 60.52 | 15.00 |
| 184 TRP | CB | −29.77 | −12.29 | 59.03 | 15.00 |
| 184 TRP | CG | −28.79 | −13.14 | 58.29 | 15.00 |
| 184 TRP | CD2 | −28.97 | −13.73 | 57.01 | 15.00 |
| 184 TRP | CE2 | −27.80 | −14.45 | 56.71 | 15.00 |
| 184 TRP | CE3 | −30.01 | −13.74 | 56.08 | 15.00 |
| 184 TRP | CD1 | −27.55 | −13.50 | 58.71 | 15.00 |
| 184 TRP | NE1 | −26.94 | −14.28 | 57.77 | 15.00 |
| 184 TRP | CZ2 | −27.64 | −15.17 | 55.52 | 15.00 |
| 184 TRP | CZ3 | −29.85 | −14.46 | 54.90 | 15.00 |
| 184 TRP | CH2 | −28.67 | −15.16 | 54.63 | 15.00 |
| 184 TRP | C | −30.23 | −10.93 | 61.07 | 15.00 |
| 184 TRP | O | −30.32 | −9.88 | 60.43 | 15.00 |
| 185 GLY | N | −30.78 | −11.07 | 62.27 | 15.00 |
| 185 GLY | CA | −31.54 | −9.98 | 62.83 | 15.00 |
| 185 GLY | C | −33.02 | −10.16 | 62.62 | 15.00 |
| 185 GLY | O | −33.46 | −11.00 | 61.84 | 15.00 |
| 186 GLU | N | −33.80 | −9.35 | 63.33 | 15.00 |
| 186 GLU | CA | −35.26 | −9.39 | 63.27 | 15.00 |
| 186 GLU | CB | −35.79 | −8.71 | 64.53 | 15.00 |
| 186 GLU | CG | −37.29 | −8.65 | 64.70 | 15.00 |
| 186 GLU | CD | −37.71 | −8.03 | 66.04 | 15.00 |
| 186 GLU | OE1 | −36.83 | −7.61 | 66.83 | 15.00 |
| 186 GLU | OE2 | −38.93 | −7.98 | 66.31 | 15.00 |
| 186 GLU | C | −35.73 | −8.65 | 62.03 | 15.00 |
| 186 GLU | O | −36.89 | −8.73 | 61.64 | 15.00 |
| 187 ASN | N | −34.78 | −8.02 | 61.36 | 15.00 |
| 187 ASN | CA | −35.02 | −7.21 | 60.18 | 15.00 |
| 187 ASN | CB | −34.03 | −6.03 | 60.25 | 15.00 |
| 187 ASN | CG | −34.42 | −4.86 | 59.37 | 15.00 |
| 187 ASN | OD1 | −33.58 | −4.33 | 58.64 | 15.00 |
| 187 ASN | ND2 | −35.67 | −4.40 | 59.48 | 15.00 |
| 187 ASN | C | −34.86 | −7.97 | 58.86 | 15.00 |
| 187 ASN | O | −34.92 | −7.36 | 57.80 | 15.00 |
| 188 TRP | N | −34.62 | −9.28 | 58.92 | 15.00 |
| 188 TRP | CA | −34.47 | −10.08 | 57.70 | 15.00 |
| 188 TRP | CB | −33.20 | −10.94 | 57.77 | 15.00 |
| 188 TRP | CG | −33.05 | −11.85 | 56.60 | 15.00 |
| 188 TRP | CD2 | −33.41 | −13.23 | 56.52 | 15.00 |
| 188 TRP | CE2 | −33.18 | −13.66 | 55.20 | 15.00 |
| 188 TRP | CE3 | −33.92 | −14.16 | 57.45 | 15.00 |
| 188 TRP | CD1 | −32.61 | −11.50 | 55.36 | 15.00 |
| 188 TRP | NE1 | −32.69 | −12.58 | 54.51 | 15.00 |
| 188 TRP | CZ2 | −33.45 | −14.96 | 54.76 | 15.00 |
| 188 TRP | CZ3 | −34.18 | −15.46 | 57.02 | 15.00 |
| 188 TRP | CH2 | −33.94 | −15.85 | 55.69 | 15.00 |
| 188 TRP | C | −35.66 | −11.00 | 57.51 | 15.00 |
| 188 TRP | O | −36.23 | −11.48 | 58.49 | 15.00 |
| 189 GLY | N | −36.02 | −11.29 | 56.27 | 15.00 |
| 189 GLY | CA | −37.14 | −12.17 | 56.00 | 15.00 |
| 189 GLY | C | −38.37 | −11.86 | 56.84 | 15.00 |
| 189 GLY | O | −38.70 | −10.69 | 57.08 | 15.00 |
| 190 ASN | N | −39.02 | −12.91 | 57.32 | 15.00 |
| 190 ASN | CA | −40.22 | −12.78 | 58.13 | 15.00 |
| 190 ASN | CB | −41.13 | −14.00 | 57.93 | 15.00 |
| 190 ASN | CG | −42.58 | −13.74 | 58.32 | 15.00 |
| 190 ASN | OD1 | −42.87 | −13.07 | 59.31 | 15.00 |
| 190 ASN | ND2 | −43.50 | −14.27 | 57.53 | 15.00 |
| 190 ASN | C | −39.86 | −12.63 | 59.61 | 15.00 |
| 190 ASN | O | −39.81 | −13.61 | 60.35 | 15.00 |
| 191 LYS | N | −39.55 | −11.41 | 60.02 | 15.00 |
| 191 LYS | CA | −39.19 | −11.14 | 61.41 | 15.00 |
| 191 LYS | CB | −40.43 | −11.19 | 62.29 | 15.00 |
| 191 LYS | CG | −41.44 | −10.10 | 61.96 | 15.00 |
| 191 LYS | CD | −40.92 | −8.71 | 62.35 | 15.00 |
| 191 LYS | CE | −41.18 | −7.63 | 61.27 | 15.00 |
| 191 LYS | NZ | −40.19 | −7.69 | 60.13 | 15.00 |
| 191 LYS | C | −38.10 | −12.07 | 61.94 | 15.00 |
| 191 LYS | O | −38.11 | −12.46 | 63.11 | 15.00 |
| 192 GLY | N | −37.15 | −12.41 | 61.07 | 15.00 |
| 192 GLY | CA | −36.04 | −13.26 | 61.47 | 15.00 |
| 192 GLY | C | −36.15 | −14.73 | 61.13 | 15.00 |
| 192 GLY | O | −35.19 | −15.48 | 61.32 | 15.00 |
| 193 TYR | N | −37.30 | −15.16 | 60.63 | 15.00 |
| 193 TYR | CA | −37.50 | −16.56 | 60.28 | 15.00 |
| 193 TYR | CB | −38.69 | −17.14 | 61.04 | 15.00 |
| 193 TYR | CG | −38.47 | −17.29 | 62.51 | 15.00 |
| 193 TYR | CD1 | −38.57 | −16.19 | 63.36 | 15.00 |
| 193 TYR | CE1 | −38.34 | −16.32 | 64.72 | 15.00 |
| 193 TYR | CD2 | −38.13 | −18.51 | 63.06 | 15.00 |
| 193 TYR | CE2 | −37.91 | −18.65 | 64.42 | 15.00 |
| 193 TYR | CZ | −38.01 | −17.55 | 65.24 | 15.00 |
| 193 TYR | OH | −37.78 | −17.71 | 66.59 | 15.00 |
| 193 TYR | C | −37.76 | −16.73 | 58.80 | 15.00 |
| 193 TYR | O | −37.97 | −15.76 | 58.08 | 15.00 |
| 194 ILE | N | −37.78 | −17.99 | 58.37 | 15.00 |
| 194 ILE | CA | −38.03 | −18.32 | 56.99 | 15.00 |
| 194 ILE | CB | −36.75 | −18.27 | 56.13 | 15.00 |
| 194 ILE | CG2 | −35.65 | −19.10 | 56.76 | 15.00 |
| 194 ILE | CG1 | −37.06 | −18.74 | 54.72 | 15.00 |
| 194 ILE | CD1 | −35.95 | −18.54 | 53.75 | 15.00 |
| 194 ILE | C | −38.65 | −19.70 | 56.88 | 15.00 |
| 194 ILE | O | −38.20 | −20.64 | 57.S1 | 15.00 |
| 195 LEU | N | −39.71 | −19.79 | 56.09 | 15.00 |
| 195 LEU | CA | −40.40 | −21.04 | 55.87 | 15.00 |
| 195 LEU | CB | −41.91 | −20.78 | 55.71 | 15.00 |
| 195 LEU | CG | −42.77 | −20.89 | 56.98 | 15.00 |
| 195 LEU | CD1 | −42.08 | −20.31 | 58.19 | 15.00 |
| 195 LEU | CD2 | −44.09 | −20.19 | 56.75 | 15.00 |
| 195 LEU | C | −39.83 | −21.68 | 54.62 | 15.00 |
| 195 LEU | O | −40.04 | −21.19 | 53.51 | 15.00 |
| 196 MET | N | −39.05 | −22.73 | 54.81 | 15.00 |
| 196 MET | CA | −38.44 | −23.44 | 53.70 | 15.00 |
| 196 MET | CB | −37.01 | −23.80 | 54.04 | 15.00 |
| 196 MET | CG | −36.11 | −22.58 | 54.16 | 15.00 |
| 196 MET | SD | −34.46 | −22.98 | 54.73 | 15.00 |
| 196 MET | CE | −33.78 | −23.75 | 53.28 | 15.00 |
| 196 MET | C | −39.27 | −24.68 | 53.38 | 15.00 |
| 196 MET | O | −40.03 | −25.14 | 54.23 | 15.00 |
| 197 ALA | N | −39.15 | −25.19 | 52.16 | 15.00 |
| 197 ALA | CA | −39.91 | −26.36 | 51.72 | 15.00 |
| 197 ALA | CB | −39.86 | −26.48 | 50.19 | 15.00 |
| 197 ALA | C | −39.51 | −27.69 | 52.36 | 15.00 |
| 197 ALA | O | −38.33 | −28.00 | 52.50 | 15.00 |
| 198 ARG | N | −40.52 | −28.50 | 52.67 | 15.00 |
| 198 ARG | CA | −40.32 | −29.81 | 53.28 | 15.00 |
| 198 ARG | CB | −41.08 | −29.90 | 54.60 | 15.00 |
| 198 ARG | CG | −41.09 | −31.28 | 55.23 | 15.00 |
| 198 ARG | CD | −41.40 | −31.21 | 56.71 | 15.00 |
| 198 ARG | NE | −42.71 | −30.64 | 57.00 | 15.00 |
| 198 ARG | CZ | −43.83 | −31.35 | 57.04 | 15.00 |
| 198 ARG | NH1 | −43.80 | −32.66 | 56.80 | 15.00 |

TABLE VI-continued

Table of the orthogonal three dimensional coordinates in Angstroms and B factors (Å$^2$) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 198 ARG | NH2 | −44.97 | −30.76 | 57.34 | 15.00 |
| 198 ARG | C | −40.79 | −30.90 | 52.34 | 15.00 |
| 198 ARG | O | −41.87 | −30.81 | 51.76 | 15.00 |
| 199 ASN | N | −39.97 | −31.93 | 52.20 | 15.00 |
| 199 ASN | CA | −40.28 | −33.07 | 51.33 | 15.00 |
| 199 ASN | CB | −41.68 | −33.62 | 51.60 | 15.00 |
| 199 ASN | CG | −41.76 | −34.41 | 52.90 | 15.00 |
| 199 ASN | OD1 | −42.80 | −34.44 | 53.57 | 15.00 |
| 199 ASN | ND2 | −40.65 | −35.05 | 53.28 | 15.00 |
| 199 ASN | C | −40.08 | −32.78 | 49.85 | 15.00 |
| 199 ASN | O | −40.45 | −33.59 | 48.99 | 15.00 |
| 200 LYS | N | −39.47 | −31.65 | 49.54 | 15.00 |
| 200 LYS | CA | −39.18 | −31.30 | 48.16 | 15.00 |
| 200 LYS | CB | −39.18 | −29.77 | 47.95 | 15.00 |
| 200 LYS | CG | −40.55 | −29.15 | 47.76 | 15.00 |
| 200 LYS | CD | −41.24 | −29.74 | 46.54 | 15.00 |
| 200 LYS | CE | −42.64 | −29.19 | 46.34 | 15.00 |
| 200 LYS | NZ | −43.39 | −29.98 | 45.32 | 15.00 |
| 200 LYS | C | −37.80 | −31.87 | 47.84 | 15.00 |
| 200 LYS | O | −36.86 | −31.13 | 47.56 | 15.00 |
| 201 ASN | N | −37.66 | −33.19 | 48.01 | 15.00 |
| 201 ASN | CA | −36.40 | −33.87 | 47.72 | 15.00 |
| 201 ASN | CB | −36.24 | −33.99 | 46.19 | 15.00 |
| 201 ASN | CG | −35.16 | −35.00 | 45.77 | 15.00 |
| 201 ASN | OD1 | −35.27 | −35.62 | 44.69 | 15.00 |
| 201 ASN | ND2 | −34.11 | −35.15 | 46.58 | 15.00 |
| 201 ASN | C | −35.18 | −33.16 | 48.34 | 15.00 |
| 201 ASN | O | −34.28 | −32.70 | 47.62 | 15.00 |
| 202 ASN | N | −35.16 | −33.09 | 49.67 | 15.00 |
| 202 ASN | CA | −34.05 | −32.47 | 50.41 | 15.00 |
| 202 ASN | CB | −32.86 | −33.43 | 50.47 | 15.00 |
| 202 ASN | CG | −31.99 | −33.22 | 51.69 | 15.00 |
| 202 ASN | OD1 | −32.43 | −32.60 | 52.67 | 15.00 |
| 202 ASN | ND2 | −30.77 | −33.72 | 51.66 | 15.00 |
| 202 ASN | C | −33.61 | −31.11 | 49.86 | 15.00 |
| 202 ASN | O | −32.42 | −30.87 | 49.62 | 15.00 |
| 203 ALA | N | −34.58 | −30.22 | 49.72 | 15.00 |
| 203 ALA | H | −35.43 | −30.48 | 50.10 | 15.00 |
| 203 ALA | CA | −34.36 | −28.88 | 49.17 | 15.00 |
| 203 ALA | CB | −35.62 | −28.06 | 49.20 | 15.00 |
| 203 ALA | C | −33.31 | −28.14 | 50.00 | 15.00 |
| 203 ALA | O | −33.47 | −27.92 | 51.19 | 15.00 |
| 204 CYS | N | −32.23 | −27.75 | 49.33 | 15.00 |
| 204 CYS | CA | −31.15 | −27.01 | 49.98 | 15.00 |
| 204 CYS | C | −30.39 | −27.80 | 51.03 | 15.00 |
| 204 CYS | O | −29.68 | −27.21 | 51.83 | 15.00 |
| 204 CYS | CB | −31.68 | −25.71 | 50.61 | 15.00 |
| 204 CYS | SG | −32.40 | −24.49 | 49.47 | 15.00 |
| 205 GLY | N | −30.51 | −29.13 | 51.01 | 15.00 |
| 205 GLY | CA | −29.80 | −29.96 | 51.97 | 15.00 |
| 205 GLY | C | −30.19 | −29.78 | 53.44 | 15.00 |
| 205 GLY | O | −29.39 | −30.02 | 54.34 | 15.00 |
| 206 ILE | N | −31.43 | −29.40 | 53.67 | 15.00 |
| 206 ILE | CA | −31.94 | −29.18 | 55.01 | 15.00 |
| 206 ILE | CB | −33.46 | −28.88 | 54.98 | 15.00 |
| 206 ILE | CG2 | −34.18 | −29.93 | 54.15 | 15.00 |
| 206 ILE | CG1 | −34.03 | −28.79 | 56.39 | 15.00 |
| 206 ILE | CD1 | −33.55 | −27.60 | 57.17 | 15.00 |
| 206 ILE | C | −31.63 | −30.32 | 55.98 | 15.00 |
| 206 ILE | O | −31.31 | −30.07 | 57.15 | 15.00 |
| 207 ALA | N | −31.68 | −31.56 | 55.50 | 15.00 |
| 207 ALA | CA | −31.40 | −32.72 | 56.36 | 15.00 |
| 207 ALA | CB | −32.50 | −33.74 | 56.24 | 15.00 |
| 207 ALA | C | −30.07 | −33.37 | 56.02 | 15.00 |
| 207 ALA | O | −29.89 | −34.56 | 56.21 | 15.00 |
| 208 ASN | N | −29.11 | −32.58 | 55.55 | 15.00 |
| 208 ASN | CA | −27.81 | −33.10 | 55.16 | 15.00 |
| 208 ASN | CB | −27.34 | −32.39 | 53.88 | 15.00 |
| 208 ASN | CG | −27.15 | −33.35 | 52.72 | 15.00 |
| 208 ASN | OD1 | −28.12 | −33.85 | 52.15 | 15.00 |
| 208 ASN | ND2 | −25.90 | −33.60 | 52.36 | 15.00 |
| 208 ASN | C | −26.72 | −33.00 | 56.22 | 15.00 |
| 208 ASN | O | −25.66 | −33.62 | 56.10 | 15.00 |
| 209 LEU | N | −26.96 | −32.22 | 57.27 | 15.00 |
| 209 LEU | CA | −25.96 | −32.06 | 58.31 | 15.00 |
| 209 LEU | CB | −24.98 | −30.96 | 57.89 | 15.00 |
| 209 LEU | CG | −23.69 | −30.69 | 58.67 | 15.00 |
| 209 LEU | CD1 | −22.77 | −31.90 | 58.61 | 15.00 |
| 209 LEU | CD2 | −22.99 | −29.49 | 58.09 | 15.00 |
| 209 LEU | C | −26.63 | −31.70 | 59.63 | 15.00 |
| 209 LEU | O | −26.11 | −30.91 | 60.41 | 15.00 |
| 210 ALA | N | −27.79 | −32.31 | 59.90 | 15.00 |
| 210 ALA | H | −28.15 | −32.83 | 59.17 | 15.00 |
| 210 ALA | CA | −28.56 | −32.01 | 61.10 | 15.00 |
| 210 ALA | CB | −29.98 | −32.52 | 60.98 | 15.00 |
| 210 ALA | C | −27.93 | −32.71 | 62.32 | 15.00 |
| 210 ALA | O | −27.23 | −33.70 | 62.23 | 15.00 |
| 211 SER | N | −28.20 | −32.12 | 63.50 | 15.00 |
| 211 SER | CA | −27.73 | −32.66 | 64.78 | 15.00 |
| 211 SER | CB | −26.21 | −32.55 | 64.89 | 15.00 |
| 211 SER | OG | −25.79 | −31.20 | 64.98 | 15.00 |
| 211 SER | C | −28.38 | −31.89 | 65.92 | 15.00 |
| 211 SER | O | −28.93 | −30.80 | 65.72 | 15.00 |
| 212 PHE | N | −28.35 | −32.47 | 67.11 | 15.00 |
| 212 PHE | CA | −28.93 | −31.84 | 68.28 | 15.00 |
| 212 PHE | CB | −30.43 | −32.16 | 68.36 | 15.00 |
| 212 PHE | CG | −30.75 | −33.63 | 68.34 | 15.00 |
| 212 PHE | CD1 | −31.28 | −34.23 | 67.20 | 15.00 |
| 212 PHE | CD2 | −30.55 | −34.43 | 69.48 | 15.00 |
| 212 PHE | CE1 | −31.61 | −35.57 | 67.19 | 15.00 |
| 212 PHE | CE2 | −30.87 | −35.79 | 69.48 | 15.00 |
| 212 PHE | CZ | −31.40 | −36.35 | 68.33 | 15.00 |
| 212 PHE | C | −28.17 | −32.36 | 69.50 | 15.00 |
| 212 PHE | O | −27.66 | −33.48 | 69.48 | 15.00 |
| 213 PRO | N | −28.03 | −31.54 | 70.55 | 15.00 |
| 213 PRO | CD | −28.53 | −30.16 | 70.68 | 15.00 |
| 213 PRO | CA | −27.32 | −31.95 | 71.76 | 15.00 |
| 213 PRO | CB | −26.95 | −30.61 | 72.38 | 15.00 |
| 213 PRO | CG | −28.16 | −29.81 | 72.11 | 15.00 |
| 213 PRO | C | −28.20 | −32.77 | 72.70 | 15.00 |
| 213 PRO | O | −29.42 | −32.64 | 72.69 | 15.00 |
| 214 LYS | N | −27.58 | −33.60 | 73.53 | 15.00 |
| 214 LYS | CA | −28.32 | −34.41 | 74.49 | 15.00 |
| 214 LYS | CB | −27.85 | −35.85 | 74.47 | 15.00 |
| 214 LYS | CG | −28.28 | −36.60 | 73.23 | 15.00 |
| 214 LYS | CD | −27.98 | −38.09 | 73.30 | 15.00 |
| 214 LYS | CE | −26.48 | −38.39 | 73.31 | 15.00 |
| 214 LYS | NZ | −25.86 | −38.24 | 74.66 | 15.00 |
| 214 LYS | C | −28.17 | −33.84 | 75.89 | 15.00 |
| 214 LYS | O | −27.07 | −33.47 | 76.29 | 15.00 |
| 215 MET | N | −29.28 | −33.75 | 76.61 | 15.00 |
| 215 MET | CA | −29.29 | −33.24 | 77.98 | 15.00 |
| 215 MET | CB | −30.27 | −32.08 | 78.11 | 15.00 |
| 215 MET | CG | −29.79 | −30.79 | 77.48 | 15.00 |
| 215 MET | SD | −28.97 | −29.73 | 78.67 | 15.00 |
| 215 MET | CE | −30.38 | −28.92 | 79.43 | 15.00 |
| 215 MET | C | −29.67 | −34.33 | 78.99 | 15.00 |
| 215 MET | OT1 | −30.25 | −35.37 | 78.59 | 15.00 |
| 215 MET | OT2 | −29.39 | −34.13 | 80.20 | 15.00 |
| 216 HOH | OH2 | −21.96 | −40.63 | 81.12 | 15.00 |
| 217 HOH | OH2 | −30.77 | −17.16 | 67.86 | 15.00 |
| 218 HOH | OH2 | −30.16 | −20.07 | 64.02 | 15.00 |
| 219 HOH | OH2 | −3.64 | −10.82 | 59.75 | 15.00 |
| 220 HOH | OH2 | −13.18 | −7.77 | 71.57 | 15.00 |
| 221 HOH | OH2 | −34.51 | −22.61 | 70.17 | 15.00 |
| 222 HOH | OH2 | −18.02 | −34.44 | 65.29 | 15.00 |
| 223 HOH | OH2 | −17.01 | −5.28 | 69.42 | 15.00 |
| 224 HOH | OH2 | −24.38 | −30.77 | 62.26 | 15.00 |
| 225 HOH | OH2 | 0.36 | −5.40 | 64.98 | 15.00 |
| 226 HOH | OH2 | −13.68 | −21.42 | 66.86 | 15.00 |
| 227 HOH | OH2 | −46.72 | −29.80 | 50.41 | 15.00 |
| 228 HOH | OH2 | −45.10 | −36.23 | 56.40 | 15.00 |

TABLE VI-continued

Table of the orthogonal three dimensional coordinates in Ångstroms and B factors (Å²) for the cathepsin K complex with inhibitor 2-[N-(3-benzyloxybenzoyl)]-2'-[N'-(N-benzyloxycarbonyl-L-leucinyl)]carbohydrazide.

| Residue | Atom | X | Y | Z | B |
|---|---|---|---|---|---|
| 229 HOH | OH2 | −39.09 | −12.35 | 65.48 | 15.00 |
| 230 HOH | OH2 | −35.85 | −37.05 | 52.41 | 15.00 |
| 231 HOH | OH2 | −19.20 | −39.14 | 66.78 | 15.00 |
| 232 HOH | OH2 | −30.09 | −19.72 | 66.64 | 15.00 |
| 233 HOH | OH2 | −27.95 | −19.50 | 62.38 | 15.00 |
| 234 HOH | OH2 | −21.75 | −30.29 | 62.28 | 15.00 |
| 235 HOH | OH2 | −30.30 | −2.55 | 77.57 | 15.00 |
| 236 HOH | OH2 | −33.08 | −28.99 | 86.45 | 15.00 |
| 237 HOH | OH2 | −30.07 | −22.68 | 84.37 | 15.00 |
| 238 HOH | OH2 | −39.83 | −16.82 | 48.34 | 15.00 |
| 239 HOH | OH2 | −34.57 | −24.95 | 47.01 | 15.00 |
| 240 HOH | OH2 | −46.44 | −34.07 | 57.12 | 15.00 |
| 241 HOH | OH2 | −26.91 | −7.02 | 56.22 | 15.00 |
| 242 HOH | OH2 | −42.10 | −15.05 | 61.98 | 15.00 |
| 243 HOH | OH2 | −24.27 | −7.11 | 65.05 | 15.00 |
| 244 HOH | OH2 | −33.44 | −27.69 | 70.80 | 15.00 |
| 245 HOH | OH2 | −40.50 | −27.38 | 80.61 | 15.00 |
| 246 HOH | OH2 | −14.45 | −17.44 | 86.64 | 15.00 |
| 247 HOH | OH2 | −4.86 | −12.23 | 73.56 | 15.00 |
| 248 HOH | OH2 | −10.86 | −20.50 | 79.87 | 15.00 |
| 249 HOH | OH2 | −27.43 | −35.04 | S9.25 | 15.00 |
| 250 HOH | OH2 | −35.26 | −10.90 | 53.73 | 15.00 |
| 251 HOH | OH2 | −31.84 | −29.20 | 46.92 | 15.00 |
| 252 HOH | OH2 | −42.75 | −9.71 | 40.49 | 15.00 |
| 253 HOH | OH2 | −41.27 | −34.56 | 56.25 | 15.00 |
| 254 HOH | OH2 | −44.55 | −15.65 | 65.22 | 15.00 |
| 255 HOH | OH2 | −32.52 | −13.49 | 60.73 | 15.00 |
| 256 HOH | OH2 | −39.73 | −4.62 | 63.34 | 15.00 |
| 257 HOH | OH2 | −25.69 | −11.84 | 70.98 | 15.00 |
| 258 HOH | OH2 | −31.93 | −6.64 | 63.98 | 15.00 |
| 259 HOH | OH2 | −19.62 | −7.72 | 62.94 | 15.00 |
| 260 HOH | OH2 | −33.42 | −20.20 | 70.53 | 15.00 |
| 261 HOH | OH2 | −12.62 | −24.00 | 79.04 | 15.00 |
| 262 HOH | OH2 | −9.78 | −21.46 | 77.40 | 15.00 |
| 263 HOH | OH2 | −6.71 | −27.36 | 80.84 | 15.00 |
| 264 HOH | OH2 | −21.06 | −35.71 | 57.19 | 15.00 |
| 265 HOH | OH2 | −26.47 | −48.97 | 59.68 | 15.00 |
| 266 HOH | OH2 | −14.22 | −32.57 | 69.97 | 15.00 |
| 267 HOH | OH2 | −11.69 | −25.57 | 76.63 | 15.00 |
| 268 HOH | OH2 | −17.38 | −27.79 | 86.86 | 15.00 |
| 269 HOH | OH2 | −22.39 | −37.94 | 70.91 | 15.00 |
| 270 HOH | OH2 | −10.44 | −11.32 | 63.69 | 15.00 |
| 271 HOH | OH2 | −8.66 | −22.33 | 72.95 | 15.00 |
| 272 HOH | OH2 | −29.93 | −20.17 | 48.73 | 15.00 |
| 273 HOH | OH2 | −22.92 | −30.27 | 39.30 | 15.00 |
| 274 HOH | OH2 | −33.19 | −37.20 | 49.46 | 15.00 |
| 275 HOH | OH2 | −28.10 | −25.82 | 41.06 | 15.00 |
| 276 HOH | OH2 | −35.93 | −29.91 | 44.54 | 15.00 |
| 277 HOH | OH2 | −37.76 | −30.41 | 51.24 | 15.00 |

TABLE VII

Table of the orthogonal three dimensional coordinates in Ångstroms and B factors (Å²) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| | Residue | Atom | X | Y | Z | B |
|---|---|---|---|---|---|---|
| 1 | ALA | CB | −46.25 | −39.17 | 62.96 | 30.60 |
| 1 | ALA | C | −47.93 | −37.51 | 63.80 | 29.74 |
| 1 | ALA | O | −49.14 | −37.57 | 63.58 | 32.13 |
| 1 | ALA | N | −48.18 | −39.83 | 64.36 | 28.23 |
| 1 | ALA | CA | −47.15 | −38.78 | 64.13 | 28.86 |
| 2 | PRO | N | −47.26 | −36.34 | 63.80 | 27.19 |
| 2 | PRO | CD | −45.94 | −36.10 | 64.40 | 26.45 |

TABLE VII-continued

Table of the orthogonal three dimensional coordinates in Ångstroms and B factors (Å²) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| | Residue | Atom | X | Y | Z | B |
|---|---|---|---|---|---|---|
| 2 | PRO | CA | −47.92 | −35.06 | 63.50 | 27.01 |
| 2 | PRO | CB | −47.28 | −34.10 | 64.52 | 26.65 |
| 2 | PRO | CG | −46.25 | −34.95 | 65.31 | 27.69 |
| 2 | PRO | C | −47.73 | −34.52 | 62.09 | 26.37 |
| 2 | PRO | O | −46.67 | −34.70 | 61.50 | 26.53 |
| 3 | ASP | N | −48.76 | −33.86 | 61.58 | 26.63 |
| 3 | ASP | CA | −48.73 | −33.23 | 60.26 | 24.49 |
| 3 | ASP | CB | −50.14 | −33.03 | 59.69 | 23.94 |
| 3 | ASP | CG | −50.75 | −34.32 | 59.17 | 24.73 |
| 3 | ASP | OD1 | −50.19 | −34.88 | 58.21 | 31.10 |
| 3 | ASP | OD2 | −51.79 | −34.76 | 59.71 | 23.79 |
| 3 | ASP | C | −48.03 | −31.88 | 60.39 | 24.62 |
| 3 | ASP | O | −47.08 | −31.59 | 59.67 | 23.92 |
| 4 | SER | N | −48.55 | −31.04 | 61.28 | 24.05 |
| 4 | SER | CA | −47.98 | −29.72 | 61.55 | 22.83 |
| 4 | SER | CB | −49.04 | −28.62 | 61.52 | 23.29 |
| 4 | SER | OG | −49.84 | −28.70 | 60.36 | 24.54 |
| 4 | SER | C | −47.30 | −29.75 | 62.91 | 23.31 |
| 4 | SER | O | −47.71 | −30.51 | 63.79 | 26.63 |
| 5 | VAL | N | −46.27 | −28.92 | 63.09 | 24.43 |
| 5 | VAL | CA | −45.52 | −28.80 | 64.34 | 22.41 |
| 5 | VAL | CB | −44.44 | −29.91 | 64.50 | 24.60 |
| 5 | VAL | CG1 | −43.39 | −29.50 | 65.53 | 19.58 |
| 5 | VAL | CG2 | −45.09 | −31.22 | 64.94 | 26.54 |
| 5 | VAL | C | −44.80 | −27.45 | 64.30 | 22.72 |
| 5 | VAL | O | −44.23 | −27.09 | 63.27 | 24.78 |
| 6 | ASP | N | −44.80 | −26.74 | 65.41 | 22.25 |
| 6 | ASP | CA | −44.17 | −25.43 | 65.48 | 20.13 |
| 6 | ASP | CB | −45.15 | −24.34 | 65.04 | 20.94 |
| 6 | ASP | CG | −44.49 | −22.99 | 64.81 | 19.46 |
| 6 | ASP | OD1 | −43.28 | −22.84 | 65.12 | 15.02 |
| 6 | ASP | OD2 | −45.20 | −22.09 | 64.31 | 15.42 |
| 6 | ASP | C | −43.67 | −25.17 | 66.88 | 20.15 |
| 6 | ASP | O | −44.45 | −24.78 | 67.74 | 26.96 |
| 7 | TYR | N | −42.37 | −25.32 | 67.10 | 20.70 |
| 7 | TYR | CA | −41.82 | −25.08 | 68.42 | 19.50 |
| 7 | TYR | CB | −40.44 | −25.71 | 68.58 | 22.46 |
| 7 | TYR | CG | −40.51 | −27.21 | 68.76 | 22.69 |
| 7 | TYR | CD1 | −40.50 | −27.78 | 70.03 | 24.39 |
| 7 | TYR | CE1 | −40.61 | −29.16 | 70.20 | 23.01 |
| 7 | TYR | CD2 | −40.62 | −28.05 | 67.66 | 17.84 |
| 7 | TYR | CE2 | −40.72 | −29.42 | 67.82 | 17.55 |
| 7 | TYR | CZ | −40.72 | −29.97 | 69.08 | 16.70 |
| 7 | TYR | OH | −40.84 | −31.33 | 69.22 | 21.92 |
| 7 | TYR | C | −41.77 | −23.62 | 68.78 | 18.59 |
| 7 | TYR | O | −41.12 | −23.25 | 69.75 | 23.10 |
| 8 | ARG | N | −42.39 | −22.78 | 67.96 | 16.73 |
| 8 | ARG | CA | −42.44 | −21.36 | 68.25 | 17.40 |
| 8 | ARG | CB | −42.56 | −20.52 | 66.98 | 19.28 |
| 8 | ARG | CG | −41.27 | −20.40 | 66.17 | 22.66 |
| 8 | ARG | CD | −41.41 | −19.48 | 64.98 | 14.98 |
| 8 | ARG | NE | −42.40 | −19.99 | 64.04 | 17.92 |
| 8 | ARG | CZ | −42.59 | −19.53 | 62.81 | 22.05 |
| 8 | ARG | NH1 | −41.85 | −18.52 | 62.36 | 24.53 |
| 8 | ARG | NH2 | −43.50 | −20.10 | 62.03 | 26.01 |
| 8 | ARG | C | −43.64 | −21.14 | 69.17 | 15.35 |
| 8 | ARG | O | −43.52 | −20.55 | 70.24 | 14.09 |
| 9 | LYS | N | −44.77 | −21.73 | 68.79 | 13.90 |
| 9 | LYS | CA | −46.01 | −21.63 | 69.54 | 13.24 |
| 9 | LYS | CB | −47.21 | −21.84 | 68.62 | 10.93 |
| 9 | LYS | CG | −47.27 | −20.83 | 67.48 | 16.03 |
| 9 | LYS | CD | −48.31 | −21.19 | 66.44 | 13.55 |
| 9 | LYS | CE | −49.69 | −21.20 | 67.04 | 17.52 |
| 9 | LYS | NZ | −50.71 | −21.24 | 65.97 | 18.86 |
| 9 | LYS | C | −46.01 | −22.61 | 70.70 | 15.37 |
| 9 | LYS | O | −47.06 | −23.10 | 71.14 | 15.03 |
| 10 | LYS | N | −44.81 | −22.90 | 71.19 | 17.15 |
| 10 | LYS | CA | −44.58 | −23.82 | 72.31 | 14.97 |
| 10 | LYS | CB | −44.10 | −25.19 | 71.81 | 13.68 |
| 10 | LYS | CG | −45.15 | −26.06 | 71.14 | 17.87 |

TABLE VII-continued

Table of the orthogonal three dimensional coordinates in Ångstroms and B factors (Å²) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| Residue | Atom |  | X | Y | Z | B |
|---|---|---|---|---|---|---|
| 10 | LYS | CD | −44.58 | −27.44 | 70.87 | 17.96 |
| 10 | LYS | CE | −45.67 | −28.49 | 70.71 | 22.08 |
| 10 | LYS | NZ | −45.07 | −29.82 | 70.35 | 25.39 |
| 10 | LYS | C | −43.52 | −23.20 | 73.23 | 10.83 |
| 10 | LYS | O | −43.08 | −23.82 | 74.19 | 9.39 |
| 11 | GLY | N | −43.07 | −22.01 | 72.88 | 11.15 |
| 11 | GLY | CA | −42.08 | −21.35 | 73.70 | 14.48 |
| 11 | GLY | C | −40.71 | −21.99 | 73.69 | 15.75 |
| 11 | GLY | O | −39.92 | −21.75 | 74.60 | 16.24 |
| 12 | TYR | N | −40.41 | −22.80 | 72.67 | 16.05 |
| 12 | TYR | CA | −39.09 | −23.44 | 72.59 | 15.26 |
| 12 | TYR | CB | −39.18 | −24.83 | 71.96 | 16.85 |
| 12 | TYR | CG | −39.84 | −25.90 | 72.80 | 12.79 |
| 12 | TYR | CD1 | −41.22 | −26.04 | 72.82 | 12.72 |
| 12 | TYR | CE1 | −41.82 | −27.07 | 73.52 | 16.82 |
| 12 | TYR | CD2 | −39.08 | −26.82 | 73.50 | 18.15 |
| 12 | TYR | CE2 | −39.67 | −27.86 | 74.20 | 21.62 |
| 12 | TYR | CZ | −41.04 | −27.98 | 74.20 | 19.19 |
| 12 | TYR | OH | −41.63 | −29.03 | 74.89 | 22.22 |
| 12 | TYR | C | −38.08 | −22.61 | 71.81 | 16.45 |
| 12 | TYR | O | −36.89 | −22.92 | 71.82 | 18.97 |
| 13 | VAL | N | −38.55 | −21.55 | 71.16 | 16.26 |
| 13 | VAL | CA | −37.67 | −20.71 | 70.34 | 17.11 |
| 13 | VAL | CB | −38.25 | −20.58 | 68.90 | 17.86 |
| 13 | VAL | CG1 | −37.20 | −20.07 | 67.96 | 18.97 |
| 13 | VAL | CG2 | −38.77 | −21.92 | 68.41 | 19.17 |
| 13 | VAL | C | −37.37 | −19.31 | 70.89 | 16.02 |
| 13 | VAL | O | −38.27 | −18.51 | 71.14 | 16.61 |
| 14 | THR | N | −36.08 | −19.01 | 71.03 | 15.90 |
| 14 | THR | CA | −35.65 | −17.71 | 71.53 | 20.92 |
| 14 | THR | CB | −34.21 | −17.77 | 72.04 | 22.63 |
| 14 | THR | OG1 | −33.33 | −18.11 | 70.97 | 28.59 |
| 14 | THR | CG2 | −34.09 | −18.78 | 73.17 | 23.81 |
| 14 | THR | C | −35.73 | −16.67 | 70.41 | 25.69 |
| 14 | THR | O | −36.01 | −17.02 | 69.26 | 28.47 |
| 15 | PRO | N | −35.50 | −15.37 | 70.73 | 28.26 |
| 15 | PRO | CD | −35.15 | −14.82 | 72.05 | 27.19 |
| 15 | PRO | CA | −35.56 | −14.29 | 69.73 | 23.60 |
| 15 | PRO | CB | −35.29 | −13.04 | 70.58 | 24.84 |
| 15 | PRO | CG | −34.43 | −13.55 | 71.68 | 26.75 |
| 15 | PRO | C | −34.53 | −14.44 | 68.62 | 19.41 |
| 15 | PRO | O | −33.43 | −14.94 | 68.84 | 15.67 |
| 16 | VAL | N | −34.90 | −13.96 | 67.43 | 16.42 |
| 16 | VAL | CA | −34.03 | −14.06 | 66.27 | 12.13 |
| 16 | VAL | CB | −34.77 | −13.71 | 64.95 | 9.20 |
| 16 | VAL | CG1 | −33.84 | −13.89 | 63.77 | 7.84 |
| 16 | VAL | CG2 | −36.01 | −14.56 | 64.78 | 6.59 |
| 16 | VAL | C | −32.81 | −13.16 | 66.39 | 11.22 |
| 16 | VAL | O | −32.93 | −11.94 | 66.44 | 11.47 |
| 17 | LYS | N | −31.65 | −13.79 | 66.45 | 10.35 |
| 17 | LYS | CA | −30.39 | −13.07 | 66.55 | 9.97 |
| 17 | LYS | CB | −29.31 | −13.93 | 67.22 | 14.75 |
| 17 | LYS | CG | −29.17 | −13.71 | 68.75 | 10.18 |
| 17 | LYS | CD | −30.45 | −14.02 | 69.52 | 5.48 |
| 17 | LYS | CE | −30.69 | −15.51 | 69.66 | 15.18 |
| 17 | LYS | NZ | −29.75 | −16.23 | 70.59 | 13.03 |
| 17 | LYS | C | −29.98 | −12.57 | 65.16 | 9.61 |
| 17 | LYS | O | −30.72 | −12.73 | 64.20 | 9.93 |
| 18 | ASN | N | −28.76 | −12.05 | 65.05 | 8.91 |
| 18 | ASN | CA | −28.28 | −11.47 | 63.80 | 8.23 |
| 18 | ASN | CB | −28.78 | −10.03 | 63.72 | 10.88 |
| 18 | ASN | CG | −28.51 | −9.36 | 62.39 | 13.91 |
| 18 | ASN | OD1 | −27.51 | −9.63 | 61.72 | 9.48 |
| 18 | ASN | ND2 | −29.40 | −8.44 | 62.03 | 13.48 |
| 18 | ASN | C | −26.75 | −11.54 | 63.75 | 8.02 |
| 18 | ASN | O | −26.07 | −10.64 | 64.22 | 13.56 |
| 19 | GLN | N | −26.22 | −12.59 | 63.14 | 7.59 |
| 19 | GLN | CA | −24.78 | −12.81 | 63.06 | 9.07 |
| 19 | GLN | CB | −24.50 | −14.08 | 62.26 | 11.76 |
| 19 | GLN | CG | −24.91 | −14.00 | 60.81 | 10.58 |
| 19 | GLN | CD | −24.73 | −15.33 | 60.11 | 10.05 |
| 19 | GLN | OE1 | −25.69 | −16.07 | 59.88 | 8.08 |
| 19 | GLN | NE2 | −23.49 | −15.66 | 59.80 | 3.31 |
| 19 | GLN | C | −23.84 | −11.70 | 62.60 | 12.84 |
| 19 | GLN | O | −22.65 | −11.71 | 62.95 | 14.67 |
| 20 | GLY | N | −24.33 | −10.75 | 61.81 | 9.97 |
| 20 | GLY | CA | −23.45 | −9.68 | 61.35 | 9.75 |
| 20 | GLY | C | −22.40 | −10.16 | 60.37 | 9.12 |
| 20 | GLY | O | −22.56 | −11.21 | 59.74 | 14.46 |
| 21 | GLN | N | −21.32 | −9.40 | 60.20 | 10.42 |
| 21 | GLN | CA | −20.28 | −9.80 | 59.25 | 13.95 |
| 21 | GLN | CB | −19.55 | −8.58 | 58.66 | 13.14 |
| 21 | GLN | CG | −20.40 | −7.79 | 57.65 | 12.44 |
| 21 | GLN | CD | −20.73 | −8.61 | 56.41 | 13.48 |
| 21 | GLN | OE1 | −19.84 | −9.15 | 55.76 | 14.90 |
| 21 | GLN | NE2 | −22.02 | −8.71 | 56.08 | 9.41 |
| 21 | GLN | C | −19.30 | −10.83 | 59.81 | 15.26 |
| 21 | GLN | O | −18.08 | −10.64 | 59.79 | 16.33 |
| 22 | CYS | N | −19.86 | −11.93 | 60.29 | 17.72 |
| 22 | CYS | CA | −19.10 | −13.04 | 60.86 | 16.36 |
| 22 | CYS | C | −19.82 | −14.31 | 60.40 | 16.07 |
| 22 | CYS | O | −21.05 | −14.39 | 60.44 | 8.26 |
| 22 | CYS | CB | −19.02 | −12.91 | 62.40 | 16.53 |
| 22 | CYS | SG | −18.36 | −14.33 | 63.35 | 15.48 |
| 23 | GLY | N | −19.04 | −15.25 | 59.83 | 16.86 |
| 23 | GLY | CA | −19.59 | −16.52 | 59.35 | 14.89 |
| 23 | GLY | C | −19.67 | −17.49 | 60.52 | 13.50 |
| 23 | GLY | O | −18.91 | −18.45 | 60.61 | 11.64 |
| 24 | SER | N | −20.61 | −17.20 | 61.41 | 13.66 |
| 24 | SER | CA | −20.82 | −17.99 | 62.61 | 14.12 |
| 24 | SER | CB | −20.65 | −17.10 | 63.84 | 17.06 |
| 24 | SER | OG | −21.37 | −15.88 | 63.67 | 19.58 |
| 24 | SER | C | −22.18 | −18.67 | 62.64 | 14.42 |
| 24 | SER | O | −22.63 | −19.12 | 63.69 | 15.12 |
| 25 | CYS | N | −22.83 | −18.77 | 61.48 | 15.74 |
| 25 | CYS | CA | −24.16 | −19.38 | 61.40 | 12.45 |
| 25 | CYS | CB | −24.61 | −19.48 | 59.92 | 17.82 |
| 25 | CYS | SG | −23.46 | −20.34 | 58.77 | 15.84 |
| 25 | CYS | C | −24.23 | −20.73 | 62.12 | 12.21 |
| 25 | CYS | O | −25.27 | −21.09 | 62.66 | 8.88 |
| 25 | INH | C1 | −26.76 | −10.18 | 57.23 | 37.63 |
| 25 | INH | C2 | −25.50 | −10.64 | 57.58 | 37.16 |
| 25 | INH | C3 | −24.85 | −11.61 | 56.79 | 34.05 |
| 25 | INH | C4 | −25.45 | −12.12 | 55.64 | 32.87 |
| 25 | INH | C5 | −26.72 | −11.65 | 55.30 | 36.05 |
| 25 | INH | C6 | −27.38 | −10.68 | 56.09 | 37.28 |
| 25 | INH | C7 | −24.76 | −13.16 | 54.79 | 31.70 |
| 25 | INH | O8 | −24.07 | −14.24 | 55.46 | 33.18 |
| 25 | INH | C9 | −24.20 | −15.65 | 55.36 | 32.90 |
| 25 | INH | O10 | −24.83 | −16.33 | 56.19 | 27.65 |
| 25 | INH | C11 | −23.57 | −17.64 | 54.11 | 33.43 |
| 25 | INH | C12 | −23.56 | −17.98 | 52.63 | 29.93 |
| 25 | INH | C13 | −24.79 | −17.58 | 51.82 | 30.09 |
| 25 | INH | C14 | −24.84 | −16.08 | 51.57 | 28.76 |
| 25 | INH | C15 | −24.70 | −18.31 | 50.53 | 33.84 |
| 25 | INH | C16 | −22.36 | −18.24 | 54.80 | 34.35 |
| 25 | INH | O17 | −21.26 | −18.25 | 54.27 | 39.78 |
| 25 | INH | N18 | −22.58 | −18.72 | 56.02 | 35.16 |
| 25 | INH | C19 | −21.64 | −19.29 | 56.85 | 29.32 |
| 25 | INH | N20 | −23.57 | −16.20 | 54.33 | 34.33 |
| 25 | INH | C21 | −21.16 | −20.68 | 56.54 | 29.68 |
| 25 | INH | C22 | −22.10 | −19.32 | 58.29 | 26.25 |
| 25 | INH | O23 | −22.30 | −18.20 | 58.72 | 26.33 |
| 25 | INH | C24 | −13.39 | −26.50 | 60.06 | 25.12 |
| 25 | INH | C25 | −13.12 | −25.19 | 59.68 | 26.39 |
| 25 | INH | C26 | −14.04 | −24.48 | 58.91 | 25.10 |
| 25 | INH | C27 | −15.23 | −25.07 | 58.52 | 23.88 |
| 25 | INH | C28 | −15.49 | −26.37 | 58.90 | 24.81 |
| 25 | INH | C29 | −14.58 | −27.09 | 59.67 | 23.22 |
| 25 | INH | C30 | −16.20 | −24.31 | 57.66 | 25.64 |

TABLE VII-continued

Table of the orthogonal three dimensional coordinates in Ångstroms and B factors (Å²) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| Residue | Atom | X | Y | Z | B |
|---|---|---|---|---|---|
| 25 | INH | O31 | −16.99 | −24.94 | 56.63 | 26.66 |
| 25 | INH | C32 | −18.41 | −24.84 | 56.56 | 24.33 |
| 25 | INH | O33 | −19.08 | −25.66 | 55.96 | 24.89 |
| 25 | INH | C34 | −20.39 | −23.56 | 57.26 | 25.72 |
| 25 | INH | C35 | −21.15 | −24.78 | 57.78 | 22.12 |
| 25 | INH | C36 | −21.80 | −25.75 | 56.80 | 16.61 |
| 25 | INH | C37 | −23.15 | −25.25 | 56.41 | 15.08 |
| 25 | INH | C38 | −21.91 | −27.08 | 57.47 | 16.77 |
| 25 | INH | C39 | −20.56 | −22.41 | 58.25 | 28.82 |
| 25 | INH | O40 | −20.39 | −22.62 | 59.45 | 37.25 |
| 25 | INH | N41 | −20.88 | −21.18 | 57.82 | 28.59 |
| 25 | INH | C42 | −21.00 | −20.17 | 58.81 | 27.26 |
| 25 | INH | N43 | −18.95 | −23.81 | 57.20 | 25.99 |
| 26 | TRP | N | −23.11 | −21.45 | 62.14 | 14.10 |
| 26 | TRP | CA | −23.02 | −22.74 | 62.82 | 15.29 |
| 26 | TRP | CB | −21.66 | −23.38 | 62.56 | 12.22 |
| 26 | TRP | CG | −20.53 | −22.49 | 62.90 | 15.74 |
| 26 | TRP | CD2 | −19.74 | −22.52 | 64.10 | 17.65 |
| 26 | TRP | CE2 | −18.76 | −21.51 | 63.98 | 15.49 |
| 26 | TRP | CE3 | −19.77 | −23.30 | 65.27 | 18.53 |
| 26 | TRP | CD1 | −20.02 | −21.49 | 62.14 | 16.57 |
| 26 | TRP | NE1 | −18.95 | −20.90 | 62.77 | 17.92 |
| 26 | TRP | CZ2 | −17.82 | −21.26 | 64.98 | 13.72 |
| 26 | TRP | CZ3 | −18.83 | −23.05 | 66.26 | 16.53 |
| 26 | TRP | CH2 | −17.87 | −22.04 | 66.11 | 15.09 |
| 26 | TRP | C | −23.24 | −22.55 | 64.32 | 19.46 |
| 26 | TRP | O | −24.09 | −23.21 | 64.92 | 24.77 |
| 27 | ALA | N | −22.52 | −21.59 | 64.90 | 19.49 |
| 27 | ALA | CA | −22.61 | −21.25 | 66.31 | 12.94 |
| 27 | ALA | CB | −21.77 | −20.01 | 66.61 | 12.05 |
| 27 | ALA | C | −24.07 | −20.99 | 66.64 | 8.35 |
| 27 | ALA | O | −24.61 | −21.54 | 67.60 | 6.75 |
| 28 | PHE | N | −24.72 | −20.18 | 65.80 | 8.07 |
| 28 | PHE | CA | −26.13 | −19.83 | 65.95 | 9.51 |
| 28 | PHE | CB | −26.51 | −18.67 | 65.04 | 7.62 |
| 28 | PHE | CG | −25.96 | −17.35 | 65.48 | 4.72 |
| 28 | PHE | CD1 | −24.74 | −16.91 | 65.01 | 4.11 |
| 28 | PHE | CD2 | −26.66 | −16.56 | 66.38 | 2.92 |
| 28 | PHE | CE1 | −24.22 | −15.69 | 65.41 | 4.53 |
| 28 | PHE | CE2 | −26.16 | −15.33 | 66.79 | 2.38 |
| 28 | PHE | CZ | −24.93 | −14.89 | 66.31 | 2.00 |
| 28 | PHE | C | −27.07 | −21.01 | 65.72 | 10.66 |
| 28 | PHE | O | −28.18 | −21.04 | 66.26 | 14.07 |
| 29 | SER | N | −26.64 | −21.96 | 64.89 | 10.83 |
| 29 | SER | CA | −27.44 | −23.15 | 64.62 | 8.54 |
| 29 | SER | CB | −26.92 | −23.88 | 63.37 | 2.45 |
| 29 | SER | OG | −27.80 | −24.93 | 62.97 | 2.00 |
| 29 | SER | C | −27.40 | −24.05 | 65.86 | 7.86 |
| 29 | SER | O | −28.44 | −24.46 | 66.38 | 6.37 |
| 30 | SER | N | −26.19 | −24.29 | 66.36 | 5.14 |
| 30 | SER | CA | −26.00 | −25.14 | 67.52 | 7.65 |
| 30 | SER | CB | −24.52 | −25.27 | 67.84 | 10.56 |
| 30 | SER | OG | −23.81 | −25.61 | 66.67 | 14.28 |
| 30 | SER | C | −26.76 | −24.61 | 68.73 | 6.72 |
| 30 | SER | O | −27.57 | −25.32 | 69.34 | 8.64 |
| 31 | VAL | N | −26.50 | −23.35 | 69.06 | 6.44 |
| 31 | VAL | CA | −27.15 | −22.71 | 70.19 | 6.61 |
| 31 | VAL | CB | −26.73 | −21.23 | 70.25 | 6.76 |
| 31 | VAL | CG1 | −27.74 | −20.40 | 71.03 | 9.71 |
| 31 | VAL | CG2 | −25.35 | −21.14 | 70.90 | 2.00 |
| 31 | VAL | C | −28.67 | −22.86 | 70.18 | 9.86 |
| 31 | VAL | O | −29.25 | −23.30 | 71.17 | 13.64 |
| 32 | GLY | N | −29.30 | −22.56 | 69.05 | 12.98 |
| 32 | GLY | CA | −30.75 | −22.68 | 68.94 | 9.41 |
| 32 | GLY | C | −31.27 | −24.10 | 69.19 | 10.59 |
| 32 | GLY | O | −32.42 | −24.29 | 69.59 | 8.20 |
| 33 | ALA | N | −30.44 | −25.10 | 68.91 | 11.42 |
| 33 | ALA | CA | −30.82 | −26.50 | 69.12 | 13.15 |
| 33 | ALA | CB | −29.82 | −27.42 | 68.47 | 10.51 |
| 33 | ALA | C | −30.86 | −26.73 | 70.64 | 14.58 |
| 33 | ALA | O | −31.87 | −27.19 | 71.19 | 12.75 |
| 34 | LEU | N | −29.75 | −26.39 | 71.29 | 12.77 |
| 34 | LEU | CA | −29.62 | −26.51 | 72.73 | 12.38 |
| 34 | LEU | CB | −28.26 | −26.01 | 73.20 | 4.32 |
| 34 | LEU | CG | −27.04 | −26.64 | 72.57 | 4.80 |
| 34 | LEU | CD1 | −25.82 | −25.86 | 72.95 | 6.27 |
| 34 | LEU | CD2 | −26.92 | −28.09 | 73.01 | 4.63 |
| 34 | LEU | C | −30.73 | −25.73 | 73.43 | 16.38 |
| 34 | LEU | O | −31.32 | −26.22 | 74.39 | 18.32 |
| 35 | GLU | N | −31.00 | −24.53 | 72.95 | 15.34 |
| 35 | GLU | CA | −32.03 | −23.71 | 73.54 | 15.20 |
| 35 | GLU | CB | −32.17 | −22.38 | 72.81 | 12.21 |
| 35 | GLU | CG | −30.92 | −21.55 | 72.88 | 18.17 |
| 35 | GLU | CD | −31.07 | −20.22 | 72.17 | 21.50 |
| 35 | GLU | OE1 | −31.87 | −20.14 | 71.21 | 23.90 |
| 35 | GLU | OE2 | −30.40 | −19.25 | 72.57 | 22.09 |
| 35 | GLU | C | −33.37 | −24.43 | 73.60 | 18.81 |
| 35 | GLU | O | −34.06 | −24.37 | 74.62 | 23.06 |
| 36 | GLY | N | −33.73 | −25.11 | 72.52 | 19.33 |
| 36 | GLY | CA | −35.00 | −25.83 | 72.48 | 19.77 |
| 36 | GLY | C | −34.96 | −27.02 | 73.42 | 21.74 |
| 36 | GLY | O | −35.97 | −27.38 | 74.05 | 18.02 |
| 37 | GLN | N | −33.79 | −27.63 | 73.53 | 23.70 |
| 37 | GLN | CA | −33.61 | −28.77 | 74.41 | 23.25 |
| 37 | GLN | CB | −32.27 | −29.48 | 74.15 | 22.37 |
| 37 | GLN | CG | −32.08 | −29.98 | 72.71 | 26.26 |
| 37 | GLN | CD | −33.38 | −30.28 | 71.94 | 30.06 |
| 37 | GLN | OE1 | −34.20 | −31.11 | 72.36 | 29.64 |
| 37 | GLN | NE2 | −33.58 | −29.57 | 70.83 | 31.26 |
| 37 | GLN | C | −33.73 | −28.32 | 75.86 | 24.67 |
| 37 | GLN | O | −34.51 | −28.89 | 76.62 | 25.08 |
| 38 | LEU | N | −32.99 | −27.27 | 76.22 | 22.29 |
| 38 | LEU | CA | −33.04 | −26.73 | 77.57 | 23.08 |
| 38 | LEU | CB | −32.20 | −25.46 | 77.70 | 21.38 |
| 38 | LEU | CG | −32.11 | −24.78 | 79.07 | 17.48 |
| 38 | LEU | CD1 | −31.77 | −25.77 | 80.17 | 13.71 |
| 38 | LEU | CD2 | −31.07 | −23.68 | 78.99 | 17.90 |
| 38 | LEU | C | −34.47 | −26.46 | 77.99 | 24.35 |
| 38 | LEU | O | −34.92 | −26.97 | 79.01 | 26.24 |
| 39 | LYS | N | −35.20 | −25.71 | 77.17 | 26.25 |
| 39 | LYS | CA | −36.59 | −25.41 | 77.47 | 28.16 |
| 39 | LYS | CB | −37.25 | −24.61 | 76.34 | 28.65 |
| 39 | LYS | CG | −38.35 | −23.65 | 76.81 | 27.61 |
| 39 | LYS | CD | −39.60 | −24.37 | 77.25 | 27.20 |
| 39 | LYS | CE | −40.68 | −23.40 | 77.70 | 26.81 |
| 39 | LYS | NZ | −41.94 | −24.12 | 78.05 | 28.10 |
| 39 | LYS | C | −37.37 | −26.69 | 77.76 | 26.01 |
| 39 | LYS | O | −38.28 | −26.70 | 78.60 | 25.82 |
| 40 | LYS | N | −37.00 | −27.77 | 77.11 | 26.61 |
| 40 | LYS | CA | −37.69 | −29.03 | 77.34 | 27.03 |
| 40 | LYS | CB | −37.64 | −29.93 | 76.11 | 28.30 |
| 40 | LYS | CG | −38.65 | −31.06 | 76.16 | 29.91 |
| 40 | LYS | CD | −38.79 | −31.77 | 74.82 | 29.72 |
| 40 | LYS | CE | −37.74 | −32.83 | 74.61 | 26.31 |
| 40 | LYS | NZ | −38.04 | −33.61 | 73.37 | 31.45 |
| 40 | LYS | C | −37.09 | −29.72 | 78.56 | 25.36 |
| 40 | LYS | O | −37.81 | −30.32 | 79.35 | 23.91 |
| 41 | LYS | N | −35.78 | −29.57 | 78.73 | 25.39 |
| 41 | LYS | CA | −35.06 | −30.20 | 79.84 | 25.65 |
| 41 | LYS | CB | −33.55 | −30.06 | 79.66 | 24.57 |
| 41 | LYS | CG | −32.72 | −30.84 | 80.67 | 20.75 |
| 41 | LYS | CD | −32.89 | −32.34 | 80.50 | 26.88 |
| 41 | LYS | CE | −31.76 | −33.13 | 81.15 | 28.72 |
| 41 | LYS | NZ | −31.63 | −32.85 | 82.61 | 29.46 |
| 41 | LYS | C | −35.50 | −29.67 | 81.19 | 25.70 |
| 41 | LYS | O | −35.92 | −30.44 | 82.06 | 23.51 |
| 42 | THR | N | −35.42 | −28.35 | 81.34 | 26.91 |
| 42 | THR | CA | −35.76 | −27.67 | 82.58 | 25.94 |
| 42 | THR | CB | −34.61 | −26.77 | 83.03 | 26.05 |
| 42 | THR | OG1 | −34.60 | −25.58 | 82.23 | 27.18 |

TABLE VII-continued

Table of the orthogonal three dimensional coordinates in Ångstroms and B factors (Å²) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| Residue | | Atom | X | Y | Z | B |
|---|---|---|---|---|---|---|
| 42 | THR | CG2 | −33.28 | −27.49 | 82.85 | 28.99 |
| 42 | THR | C | −37.00 | −26.78 | 82.52 | 25.00 |
| 42 | THR | O | −37.57 | −26.43 | 83.55 | 28.90 |
| 43 | GLY | N | −37.38 | −26.35 | 81.32 | 24.41 |
| 43 | GLY | CA | −38.54 | −25.48 | 81.19 | 21.01 |
| 43 | GLY | C | −38.09 | −24.02 | 81.13 | 19.83 |
| 43 | GLY | O | −38.92 | −23.10 | 81.08 | 14.91 |
| 44 | LYS | N | −36.78 | −23.82 | 81.15 | 22.11 |
| 44 | LYS | CA | −36.16 | −22.50 | 81.10 | 24.14 |
| 44 | LYS | CB | −35.06 | −22.38 | 82.17 | 26.33 |
| 44 | LYS | CG | −35.61 | −22.19 | 83.60 | 25.46 |
| 44 | LYS | CD | −34.54 | −22.37 | 84.69 | 26.23 |
| 44 | LYS | CE | −33.36 | −21.39 | 84.56 | 26.78 |
| 44 | LYS | NZ | −32.26 | −21.89 | 83.66 | 25.35 |
| 44 | LYS | C | −35.63 | −22.16 | 79.70 | 22.98 |
| 44 | LYS | O | −34.86 | −22.92 | 79.12 | 25.51 |
| 45 | LEU | N | −36.06 | −21.02 | 79.17 | 20.83 |
| 45 | LEU | CA | −35.68 | −20.55 | 77.84 | 14.37 |
| 45 | LEU | CB | −36.93 | −20.19 | 77.03 | 6.57 |
| 45 | LEU | CG | −36.73 | −19.98 | 75.54 | 7.56 |
| 45 | LEU | CD1 | −36.34 | −21.28 | 74.88 | 7.35 |
| 45 | LEU | CD2 | −38.01 | −19.44 | 74.92 | 7.68 |
| 45 | LEU | C | −34.73 | −19.36 | 77.92 | 12.93 |
| 45 | LEU | O | −35.17 | −18.22 | 78.02 | 12.18 |
| 46 | LEU | N | −33.43 | −19.62 | 77.91 | 12.78 |
| 46 | LEU | CA | −32.45 | −18.55 | 77.99 | 16.27 |
| 46 | LEU | CB | −31.57 | −18.68 | 79.23 | 17.06 |
| 46 | LEU | CG | −32.20 | −18.84 | 80.61 | 22.73 |
| 46 | LEU | CD1 | −33.29 | −17.80 | 80.80 | 27.00 |
| 46 | LEU | CD2 | −32.76 | −20.25 | 80.75 | 24.49 |
| 46 | LEU | C | −31.59 | −18.55 | 76.75 | 19.40 |
| 46 | LEU | O | −31.38 | −19.61 | 76.15 | 22.78 |
| 47 | ASN | N | −31.05 | −17.39 | 76.39 | 19.21 |
| 47 | ASN | CA | −30.18 | −17.27 | 75.21 | 16.88 |
| 47 | ASN | CB | −30.12 | −15.82 | 74.70 | 17.63 |
| 47 | ASN | CG | −31.41 | −15.38 | 74.02 | 19.44 |
| 47 | ASN | OD1 | −32.47 | −15.31 | 74.64 | 24.63 |
| 47 | ASN | ND2 | −31.33 | −15.04 | 72.74 | 18.95 |
| 47 | ASN | C | −28.78 | −17.79 | 75.50 | 14.05 |
| 47 | ASN | O | −28.08 | −17.23 | 76.36 | 11.81 |
| 48 | LEU | N | −28.39 | −18.87 | 74.83 | 12.40 |
| 48 | LEU | CA | −27.05 | −19.46 | 74.97 | 13.22 |
| 48 | LEU | CB | −27.02 | −20.94 | 74.58 | 14.23 |
| 48 | LEU | CG | −27.64 | −22.02 | 75.50 | 16.25 |
| 48 | LEU | CD1 | −26.96 | −22.02 | 76.87 | 20.21 |
| 48 | LEU | CD2 | −29.13 | −21.80 | 75.67 | 14.71 |
| 48 | LEU | C | −26.08 | −18.63 | 74.14 | 13.45 |
| 48 | LEU | O | −26.51 | −17.85 | 73.29 | 17.95 |
| 49 | SER | N | −24.78 | −18.80 | 74.36 | 15.33 |
| 49 | SER | CA | −23.79 | −17.98 | 73.65 | 13.70 |
| 49 | SER | CB | −22.77 | −17.41 | 74.65 | 14.72 |
| 49 | SER | OG | −21.73 | −16.68 | 74.02 | 13.12 |
| 49 | SER | C | −23.05 | −18.50 | 72.42 | 14.35 |
| 49 | SER | O | −22.14 | −19.33 | 72.52 | 15.35 |
| 50 | PRO | N | −23.38 | −17.93 | 71.24 | 13.10 |
| 50 | PRO | CD | −24.49 | −16.99 | 71.00 | 13.10 |
| 50 | PRO | CA | −22.73 | −18.30 | 69.99 | 8.82 |
| 50 | PRO | CB | −23.41 | −17.39 | 68.98 | 10.23 |
| 50 | PRO | CG | −24.79 | −17.23 | 69.54 | 10.20 |
| 50 | PRO | C | −21.25 | −17.95 | 70.09 | 7.83 |
| 50 | PRO | O | −20.40 | −18.65 | 69.56 | 7.76 |
| 51 | GLN | N | −20.96 | −16.86 | 70.80 | 8.14 |
| 51 | GLN | CA | −19.59 | −16.38 | 70.97 | 8.89 |
| 51 | GLN | CB | −19.58 | −14.99 | 71.62 | 12.14 |
| 51 | GLN | CG | −18.31 | −14.16 | 71.33 | 13.72 |
| 51 | GLN | CD | −18.18 | −13.71 | 69.87 | 12.95 |
| 51 | GLN | OE1 | −19.12 | −13.18 | 69.27 | 10.44 |
| 51 | GLN | NE2 | −16.99 | −13.89 | 69.30 | 6.01 |
| 51 | GLN | C | −18.70 | −17.34 | 71.74 | 8.59 |
| 51 | GLN | O | −17.49 | −17.46 | 71.45 | 8.17 |
| 52 | ASN | N | −19.27 | −18.03 | 72.72 | 6.61 |
| 52 | ASN | CA | −18.50 | −19.01 | 73.49 | 6.19 |
| 52 | ASN | CB | −19.36 | −19.58 | 74.62 | 6.41 |
| 52 | ASN | CG | −18.70 | −20.74 | 75.34 | 7.63 |
| 52 | ASN | OD1 | −19.39 | −21.64 | 75.81 | 9.07 |
| 52 | ASN | ND2 | −17.39 | −20.70 | 75.48 | 4.94 |
| 52 | ASN | C | −18.04 | −20.09 | 72.50 | 9.66 |
| 52 | ASN | O | −16.89 | −20.56 | 72.54 | 9.03 |
| 53 | LEU | N | −18.94 | −20.43 | 71.58 | 10.50 |
| 53 | LEU | CA | −18.69 | −21.42 | 70.54 | 7.20 |
| 53 | LEU | CB | −20.01 | −21.83 | 69.89 | 6.76 |
| 53 | LEU | CG | −20.74 | −23.04 | 70.49 | 12.00 |
| 53 | LEU | CD1 | −20.47 | −23.19 | 71.98 | 14.61 |
| 53 | LEU | CD2 | −22.22 | −22.93 | 70.21 | 8.55 |
| 53 | LEU | C | −17.69 | −20.92 | 69.49 | 6.03 |
| 53 | LEU | O | −16.75 | −21.63 | 69.14 | 4.01 |
| 54 | VAL | N | −17.87 | −19.70 | 69.01 | 2.00 |
| 54 | VAL | CA | −16.99 | −19.14 | 68.00 | 6.81 |
| 54 | VAL | CB | −17.34 | −17.67 | 67.64 | 7.05 |
| 54 | VAL | CG1 | −16.27 | −17.07 | 66.74 | 13.23 |
| 54 | VAL | CG2 | −18.66 | −17.58 | 66.93 | 5.36 |
| 54 | VAL | C | −15.55 | −19.15 | 68.47 | 12.15 |
| 54 | VAL | O | −14.66 | −19.63 | 67.76 | 16.44 |
| 55 | ASP | N | −15.32 | −18.59 | 69.65 | 15.93 |
| 55 | ASP | CA | −13.98 | −18.48 | 70.22 | 17.26 |
| 55 | ASP | CB | −13.98 | −17.47 | 71.37 | 19.77 |
| 55 | ASP | CG | −14.33 | −16.06 | 70.94 | 22.96 |
| 55 | ASP | OD1 | −14.48 | −15.78 | 69.72 | 24.84 |
| 55 | ASP | OD2 | −14.44 | −15.21 | 71.84 | 23.39 |
| 55 | ASP | C | −13.37 | −19.78 | 70.72 | 18.42 |
| 55 | ASP | O | −12.18 | −20.06 | 70.49 | 12.75 |
| 56 | CYS | N | −14.18 | −20.55 | 71.43 | 20.14 |
| 56 | CYS | CA | −13.75 | −21.79 | 72.06 | 19.35 |
| 56 | CYS | C | −13.66 | −23.12 | 71.30 | 16.79 |
| 56 | CYS | O | −13.00 | −24.05 | 71.77 | 19.07 |
| 56 | CYS | CB | −14.52 | −21.96 | 73.37 | 17.64 |
| 56 | CYS | SG | −14.48 | −20.45 | 74.39 | 15.52 |
| 57 | VAL | N | −14.31 | −23.23 | 70.14 | 14.99 |
| 57 | VAL | CA | −14.24 | −24.47 | 69.38 | 12.09 |
| 57 | VAL | CB | −15.48 | −24.72 | 68.51 | 9.25 |
| 57 | VAL | CG1 | −15.37 | −26.09 | 67.85 | 2.60 |
| 57 | VAL | CG2 | −16.75 | −24.62 | 69.34 | 5.09 |
| 57 | VAL | C | −13.02 | −24.48 | 68.47 | 12.69 |
| 57 | VAL | O | −13.04 | −23.91 | 67.39 | 15.30 |
| 58 | SER | N | −11.96 | −25.14 | 68.92 | 15.12 |
| 58 | SER | CA | −10.72 | −25.21 | 68.15 | 18.94 |
| 58 | SER | CB | −9.59 | −25.78 | 69.00 | 21.08 |
| 58 | SER | OG | −9.92 | −27.07 | 69.49 | 20.89 |
| 58 | SER | C | −10.84 | −25.98 | 66.83 | 19.38 |
| 58 | SER | O | −10.00 | −25.81 | 65.94 | 21.21 |
| 59 | GLU | N | −11.83 | −26.87 | 66.74 | 21.74 |
| 59 | GLU | CA | −12.04 | −27.68 | 65.53 | 20.63 |
| 59 | GLU | CB | −12.88 | −28.94 | 65.82 | 20.59 |
| 59 | GLU | CG | −12.48 | −29.76 | 67.06 | 21.89 |
| 59 | GLU | CD | −13.08 | −29.21 | 68.37 | 21.83 |
| 59 | GLU | OE1 | −14.32 | −29.11 | 68.47 | 25.51 |
| 59 | GLU | OE2 | −12.31 | −28.90 | 69.30 | 26.68 |
| 59 | GLU | C | −12.69 | −26.87 | 64.41 | 19.86 |
| 59 | GLU | O | −12.56 | −27.21 | 63.23 | 21.27 |
| 60 | ASN | N | −13.43 | −25.83 | 64.79 | 16.86 |
| 60 | ASN | CA | −14.11 | −24.97 | 63.83 | 10.64 |
| 60 | ASN | CB | −15.49 | −24.61 | 64.33 | 2.00 |
| 60 | ASN | CG | −16.43 | −25.78 | 64.27 | 6.50 |
| 60 | ASN | CD1 | −17.46 | −25.83 | 64.96 | 3.71 |
| 60 | ASN | ND2 | −16.09 | −26.75 | 63.42 | 3.21 |
| 60 | ASN | C | −13.27 | −23.76 | 63.49 | 13.09 |
| 60 | ASN | O | −12.25 | −23.51 | 64.13 | 14.35 |
| 61 | ASP | N | −13.67 | −23.01 | 62.46 | 14.85 |
| 61 | ASP | CA | −12.90 | −21.86 | 62.02 | 15.28 |
| 61 | ASP | CB | −12.74 | −21.86 | 60.51 | 21.27 |

TABLE VII-continued

Table of the orthogonal three dimensional coordinates in Ångstroms and B factors (Å²) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| Residue | | Atom | X | Y | Z | B |
|---|---|---|---|---|---|---|
| 61 | ASP | CG | −11.30 | −22.08 | 60.07 | 23.24 |
| 61 | ASP | OD1 | −10.60 | −21.08 | 59.84 | 26.41 |
| 61 | ASP | OD2 | −10.88 | −23.25 | 59.97 | 20.64 |
| 61 | ASP | C | −13.36 | −20.50 | 62.51 | 15.18 |
| 61 | ASP | O | −12.89 | −19.47 | 62.01 | 13.47 |
| 62 | GLY | N | −14.26 | −20.50 | 63.48 | 15.64 |
| 62 | GLY | CA | −14.75 | −19.25 | 64.03 | 15.74 |
| 62 | GLY | C | −15.68 | −18.55 | 63.07 | 17.26 |
| 62 | GLY | O | −16.72 | −19.10 | 62.72 | 19.72 |
| 63 | CYS | N | −15.30 | −17.35 | 62.64 | 19.00 |
| 63 | CYS | CA | −16.14 | −16.62 | 61.70 | 18.17 |
| 63 | CYS | C | −16.00 | −17.19 | 60.29 | 19.74 |
| 63 | CYS | O | −16.79 | −16.86 | 59.41 | 22.59 |
| 63 | CYS | CB | −15.85 | −15.11 | 61.73 | 16.37 |
| 63 | CYS | SG | −16.32 | −14.21 | 63.25 | 14.06 |
| 64 | GLY | N | −15.00 | −18.05 | 60.09 | 17.99 |
| 64 | GLY | CA | −14.81 | −18.67 | 58.79 | 15.84 |
| 64 | GLY | C | −15.66 | −19.92 | 58.60 | 17.59 |
| 64 | GLY | O | −15.50 | −20.66 | 57.63 | 19.05 |
| 65 | GLY | N | −16.59 | −20.15 | 59.53 | 18.26 |
| 65 | GLY | CA | −17.46 | −21.31 | 59.44 | 12.24 |
| 65 | GLY | C | −17.03 | −22.45 | 60.34 | 10.78 |
| 65 | GLY | O | −15.90 | −22.47 | 60.83 | 9.37 |
| 66 | GLY | N | −17.94 | −23.40 | 60.53 | 8.77 |
| 66 | GLY | CA | −17.68 | −24.56 | 61.36 | 8.46 |
| 66 | GLY | C | −18.83 | −25.55 | 61.24 | 10.14 |
| 66 | GLY | O | −19.79 | −25.29 | 60.51 | 9.60 |
| 67 | TYR | N | −18.69 | −26.70 | 61.88 | 12.33 |
| 67 | TYR | CA | −19.74 | −27.73 | 61.84 | 14.13 |
| 67 | TYR | CB | −19.18 | −29.12 | 61.49 | 14.00 |
| 67 | TYR | CG | −18.53 | −29.22 | 60.13 | 16.82 |
| 67 | TYR | CD1 | −19.29 | −29.29 | 58.96 | 19.29 |
| 67 | TYR | CE1 | −18.68 | −29.37 | 57.70 | 19.34 |
| 67 | TYR | CD2 | −17.15 | −29.24 | 60.02 | 17.85 |
| 67 | TYR | CE2 | −16.53 | −29.32 | 58.77 | 21.15 |
| 67 | TYR | CZ | −17.30 | −29.39 | 57.61 | 22.41 |
| 67 | TYR | OH | −16.66 | −29.42 | 56.38 | 22.94 |
| 67 | TYR | C | −20.44 | −27.77 | 63.20 | 12.95 |
| 67 | TYR | O | −19.80 | −27.61 | 64.23 | 14.93 |
| 68 | MET | N | −21.75 | −27.98 | 63.19 | 14.10 |
| 68 | MET | CA | −22.51 | −28.01 | 64.44 | 11.02 |
| 68 | MET | CB | −24.02 | −28.04 | 64.18 | 7.28 |
| 68 | MET | CG | −24.57 | −26.75 | 63.53 | 12.57 |
| 68 | MET | SD | −24.82 | −26.81 | 61.72 | 9.43 |
| 68 | MET | CE | −23.29 | −26.23 | 61.15 | 5.50 |
| 68 | MET | C | −22.07 | −29.15 | 65.34 | 10.25 |
| 68 | MET | O | −21.98 | −28.98 | 66.55 | 9.78 |
| 69 | THR | N | −21.74 | −30.30 | 64.76 | 11.11 |
| 69 | THR | CA | −21.31 | −31.45 | 65.54 | 9.38 |
| 69 | THR | CB | −21.06 | −32.69 | 64.65 | 7.39 |
| 69 | THR | OG1 | −20.19 | −32.36 | 63.55 | 6.10 |
| 69 | THR | CG2 | −22.39 | −33.24 | 64.11 | 6.49 |
| 69 | THR | C | −20.08 | −31.11 | 66.39 | 8.98 |
| 69 | THR | O | −20.06 | −31.41 | 67.57 | 15.86 |
| 70 | ASN | N | −19.09 | −30.44 | 65.81 | 5.69 |
| 70 | ASN | CA | −17.89 | −30.06 | 66.55 | 7.38 |
| 70 | ASN | CB | −16.87 | −29.34 | 65.67 | 9.34 |
| 70 | ASN | CG | −16.43 | −30.17 | 64.49 | 11.35 |
| 70 | ASN | OD1 | −16.13 | −29.63 | 63.43 | 13.75 |
| 70 | ASN | ND2 | −16.38 | −31.48 | 64.66 | 13.26 |
| 70 | ASN | C | −18.26 | −29.15 | 67.71 | 9.60 |
| 70 | ASN | O | −17.68 | −29.25 | 68.79 | 10.75 |
| 71 | ALA | N | −19.24 | −28.28 | 67.47 | 12.80 |
| 71 | ALA | CA | −19.72 | −27.33 | 68.48 | 15.69 |
| 71 | ALA | CB | −20.62 | −26.29 | 67.84 | 12.87 |
| 71 | ALA | C | −20.48 | −28.04 | 69.59 | 16.01 |
| 71 | ALA | O | −20.50 | −27.56 | 70.72 | 18.32 |
| 72 | PHE | N | −21.14 | −29.14 | 69.25 | 15.89 |
| 72 | PHE | CA | −21.91 | −29.90 | 70.23 | 15.72 |
| 72 | PHE | CB | −22.88 | −30.85 | 69.53 | 12.85 |
| 72 | PHE | CG | −24.07 | −30.17 | 68.91 | 10.89 |
| 72 | PHE | CD1 | −24.61 | −29.03 | 69.48 | 13.23 |
| 72 | PHE | CD2 | −24.69 | −30.70 | 67.78 | 13.69 |
| 72 | PHE | CE1 | −25.75 | −28.43 | 68.93 | 14.17 |
| 72 | PHE | CE2 | −25.83 | −30.10 | 67.23 | 11.57 |
| 72 | PHE | CZ | −26.36 | −28.96 | 67.80 | 8.27 |
| 72 | PHE | C | −20.93 | −30.66 | 71.11 | 17.93 |
| 72 | PHE | O | −20.98 | −30.59 | 72.34 | 16.27 |
| 73 | GLN | N | −20.01 | −31.36 | 70.44 | 19.40 |
| 73 | GLN | CA | −18.97 | −32.16 | 71.08 | 19.37 |
| 73 | GLN | CB | −18.09 | −32.78 | 70.00 | 17.22 |
| 73 | GLN | CG | −16.99 | −33.70 | 70.46 | 19.79 |
| 73 | GLN | CD | −16.30 | −34.36 | 69.27 | 20.51 |
| 73 | GLN | OE1 | −16.73 | −35.40 | 68.78 | 22.61 |
| 73 | GLN | NE2 | −15.24 | −33.72 | 68.75 | 18.71 |
| 73 | GLN | C | −18.15 | −31.29 | 72.03 | 20.01 |
| 73 | GLN | O | −17.74 | −31.75 | 73.10 | 20.37 |
| 74 | TYR | N | −17.92 | −30.04 | 71.65 | 18.39 |
| 74 | TYR | CA | −17.16 | −29.12 | 72.48 | 15.45 |
| 74 | TYR | CB | −16.90 | −27.79 | 71.73 | 13.54 |
| 74 | TYR | CG | −16.82 | −26.58 | 72.63 | 12.20 |
| 74 | TYR | CD1 | −15.63 | −26.22 | 73.26 | 10.63 |
| 74 | TYR | CE1 | −15.59 | −25.18 | 74.18 | 11.99 |
| 74 | TYR | CD2 | −17.97 | −25.84 | 72.93 | 9.97 |
| 74 | TYR | CE2 | −17.94 | −24.79 | 73.84 | 7.22 |
| 74 | TYR | CZ | −16.75 | −24.47 | 74.47 | 11.24 |
| 74 | TYR | OH | −16.74 | −23.48 | 75.43 | 17.85 |
| 74 | TYR | C | −17.93 | −28.93 | 73.80 | 12.38 |
| 74 | TYR | O | −17.38 | −29.14 | 74.87 | 15.74 |
| 75 | VAL | N | −19.21 | −28.60 | 73.71 | 11.39 |
| 75 | VAL | CA | −20.05 | −28.38 | 74.88 | 11.24 |
| 75 | VAL | CB | −21.50 | −28.06 | 74.44 | 8.02 |
| 75 | VAL | CG1 | −22.42 | −27.95 | 75.64 | 6.92 |
| 75 | VAL | CG2 | −21.54 | −26.76 | 73.66 | 9.76 |
| 75 | VAL | C | −20.05 | −29.59 | 75.83 | 16.34 |
| 75 | VAL | O | −20.35 | −29.45 | 77.03 | 11.43 |
| 76 | GLN | N | −19.74 | −30.76 | 75.28 | 18.49 |
| 76 | GLN | CA | −19.69 | −32.02 | 76.03 | 17.15 |
| 76 | GLN | CB | −19.98 | −33.22 | 75.11 | 16.55 |
| 76 | GLN | CG | −19.90 | −34.60 | 75.78 | 17.80 |
| 76 | GLN | CD | −20.05 | −35.78 | 74.81 | 16.42 |
| 76 | GLN | OE1 | −19.33 | −35.89 | 73.81 | 12.60 |
| 76 | GLN | NE2 | −20.98 | −36.68 | 75.12 | 11.09 |
| 76 | GLN | C | −18.33 | −32.15 | 76.71 | 17.72 |
| 76 | GLN | O | −18.25 | −32.28 | 77.92 | 19.51 |
| 77 | LYS | N | −17.25 | −32.04 | 75.94 | 18.51 |
| 77 | LYS | CA | −15.91 | −32.16 | 76.50 | 18.56 |
| 77 | LYS | CB | −14.84 | −32.18 | 75.41 | 18.21 |
| 77 | LYS | CG | −14.75 | −33.47 | 74.62 | 18.16 |
| 77 | LYS | CD | −13.48 | −33.47 | 73.77 | 21.11 |
| 77 | LYS | CE | −13.38 | −34.69 | 72.84 | 22.51 |
| 77 | LYS | NZ | −12.02 | −34.81 | 72.23 | 21.73 |
| 77 | LYS | C | −15.58 | −31.08 | 77.52 | 20.04 |
| 77 | LYS | O | −14.76 | −31.29 | 78.42 | 21.61 |
| 78 | ASN | N | −16.20 | −29.91 | 77.36 | 20.45 |
| 78 | ASN | CA | −15.96 | −28.79 | 78.27 | 19.68 |
| 78 | ASN | CB | −15.88 | −27.47 | 77.50 | 18.78 |
| 78 | ASN | CG | −15.19 | −26.36 | 78.30 | 19.30 |
| 78 | ASN | OD1 | −13.97 | −26.34 | 78.44 | 16.41 |
| 78 | ASN | ND2 | −15.98 | −25.40 | 78.79 | 20.55 |
| 78 | ASN | C | −17.03 | −28.73 | 79.35 | 18.44 |
| 78 | ASN | O | −17.03 | −27.83 | 80.18 | 20.10 |
| 79 | ARG | N | −17.96 | −29.68 | 79.32 | 16.26 |
| 79 | ARG | CA | −19.04 | −29.74 | 80.30 | 16.53 |
| 79 | ARG | CB | −18.53 | −30.31 | 81.63 | 16.34 |
| 79 | ARG | CG | −17.65 | −31.54 | 81.47 | 17.65 |
| 79 | ARG | CD | −16.99 | −31.93 | 82.78 | 19.26 |
| 79 | ARG | NE | −16.03 | −33.01 | 82.58 | 21.25 |
| 79 | ARG | CZ | −14.74 | −32.82 | 82.27 | 24.36 |
| 79 | ARG | NH1 | −14.27 | −31.59 | 82.11 | 27.69 |

TABLE VII-continued

Table of the orthogonal three dimensional coordinates in Ångstroms and B factors (Å²) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| Residue | Atom |   | X | Y | Z | B |
|---|---|---|---|---|---|---|
| 79 | ARG | NH2 | -13.93 | -33.86 | 82.13 | 18.73 |
| 79 | ARG | C | -19.74 | -28.39 | 80.51 | 14.94 |
| 79 | ARG | O | -19.91 | -27.95 | 81.64 | 14.77 |
| 80 | GLY | N | -20.12 | -27.73 | 79.42 | 16.45 |
| 80 | GLY | CA | -20.82 | -26.46 | 79.56 | 14.39 |
| 80 | GLY | C | -20.59 | -25.34 | 78.56 | 13.10 |
| 80 | GLY | O | -19.49 | -25.18 | 78.00 | 10.43 |
| 81 | ILE | N | -21.64 | -24.54 | 78.38 | 9.15 |
| 81 | ILE | CA | -21.62 | -23.39 | 77.50 | 7.25 |
| 81 | ILE | CB | -22.39 | -23.68 | 76.19 | 6.85 |
| 81 | ILE | CG2 | -23.87 | -23.89 | 76.48 | 4.07 |
| 81 | ILE | CG1 | -22.16 | -22.55 | 75.18 | 8.21 |
| 81 | ILE | CD1 | -23.07 | -22.63 | 73.97 | 11.83 |
| 81 | ILE | C | -22.27 | -22.21 | 78.25 | 8.64 |
| 81 | ILE | O | -23.29 | -22.38 | 78.94 | 9.51 |
| 82 | ASP | N | -21.68 | -21.03 | 78.13 | 11.32 |
| 82 | ASP | CA | -22.20 | -19.84 | 78.81 | 12.61 |
| 82 | ASP | CB | -21.14 | -18.75 | 78.92 | 10.86 |
| 82 | ASP | CG | -19.95 | -19.18 | 79.72 | 10.55 |
| 82 | ASP | OD1 | -18.81 | -18.86 | 79.31 | 8.90 |
| 82 | ASP | OD2 | -20.14 | -19.86 | 80.74 | 14.89 |
| 82 | ASP | C | -23.46 | -19.26 | 78.19 | 12.50 |
| 82 | ASP | O | -23.92 | -19.70 | 77.14 | 15.36 |
| 83 | SER | N | -24.03 | -18.28 | 78.87 | 11.91 |
| 83 | SER | CA | -25.23 | -17.61 | 78.39 | 12.55 |
| 83 | SER | CB | -26.14 | -17.24 | 79.55 | 18.80 |
| 83 | SER | OG | -25.48 | -16.36 | 80.45 | 22.70 |
| 83 | SER | C | -24.78 | -16.35 | 77.64 | 9.20 |
| 83 | SER | O | -23.59 | -16.01 | 77.64 | 5.74 |
| 84 | GLU | N | -25.71 | -15.67 | 76.99 | 9.19 |
| 84 | GLU | CA | -25.33 | -14.43 | 76.31 | 14.72 |
| 84 | GLU | CB | -26.47 | -13.88 | 75.45 | 13.64 |
| 84 | GLU | CG | -26.29 | -14.13 | 73.96 | 13.53 |
| 84 | GLU | CD | -25.09 | -13.41 | 73.36 | 12.40 |
| 84 | GLU | OE1 | -24.88 | -12.23 | 73.68 | 14.45 |
| 84 | GLU | OE2 | -24.38 | -14.02 | 72.56 | 16.00 |
| 84 | GLU | C | -24.86 | -13.42 | 77.35 | 15.76 |
| 84 | GLU | O | -23.85 | -12.75 | 77.16 | 15.77 |
| 85 | ASP | N | -25.57 | -13.36 | 78.49 | 18.15 |
| 85 | ASP | CA | -25.21 | -12.45 | 79.58 | 18.14 |
| 85 | ASP | CB | -26.05 | -12.73 | 80.84 | 21.42 |
| 85 | ASP | CG | -27.47 | -12.20 | 80.72 | 27.07 |
| 85 | ASP | OD1 | -28.43 | -12.97 | 80.98 | 25.69 |
| 85 | ASP | OD2 | -27.63 | -11.01 | 80.38 | 28.79 |
| 85 | ASP | C | -23.73 | -12.56 | 79.90 | 20.03 |
| 85 | ASP | O | -22.98 | -11.59 | 79.78 | 24.76 |
| 86 | ALA | N | -23.32 | -13.77 | 80.28 | 17.91 |
| 86 | ALA | CA | -21.93 | -14.08 | 80.62 | 16.67 |
| 86 | ALA | CB | -21.87 | -15.44 | 81.30 | 15.93 |
| 86 | ALA | C | -20.99 | -14.07 | 79.41 | 19.50 |
| 86 | ALA | O | -19.76 | -14.03 | 79.57 | 22.48 |
| 87 | TYR | N | -21.56 | -14.13 | 78.21 | 16.64 |
| 87 | TYR | CA | -20.72 | -14.15 | 77.01 | 16.44 |
| 87 | TYR | CB | -20.31 | -15.59 | 76.69 | 12.21 |
| 87 | TYR | CG | -18.90 | -15.72 | 76.20 | 5.93 |
| 87 | TYR | CD1 | -18.37 | -14.81 | 75.28 | 6.36 |
| 87 | TYR | CE1 | -17.08 | -14.96 | 74.80 | 2.57 |
| 87 | TYR | CD2 | -18.10 | -16.78 | 76.62 | 7.25 |
| 87 | TYR | CE2 | -16.81 | -16.93 | 76.14 | 3.11 |
| 87 | TYR | CZ | -16.31 | -16.01 | 75.23 | 2.00 |
| 87 | TYR | OH | -15.04 | -16.18 | 74.72 | 8.83 |
| 87 | TYR | C | -21.41 | -13.49 | 75.82 | 16.77 |
| 87 | TYR | O | -21.87 | -14.18 | 74.91 | 22.23 |
| 88 | PRO | N | -21.48 | -12.15 | 75.80 | 15.42 |
| 88 | PRO | CD | -20.91 | -11.18 | 76.74 | 12.94 |
| 88 | PRO | CA | -22.13 | -11.44 | 74.70 | 13.08 |
| 88 | PRO | CB | -21.96 | -9.97 | 75.08 | 12.38 |
| 88 | PRO | CG | -21.82 | -10.00 | 76.55 | 9.35 |
| 88 | PRO | C | -21.49 | -11.72 | 73.35 | 14.00 |
| 88 | PRO | O | -20.33 | -12.14 | 73.27 | 15.05 |
| 89 | TYR | N | -22.25 | -11.52 | 72.28 | 13.57 |
| 89 | TYR | CA | -21.77 | -11.73 | 70.93 | 14.96 |
| 89 | TYR | CB | -22.90 | -12.16 | 69.99 | 16.79 |
| 89 | TYR | CG | -22.46 | -12.46 | 68.56 | 19.46 |
| 89 | TYR | CD1 | -21.64 | -13.54 | 68.28 | 17.96 |
| 89 | TYR | CE1 | -21.26 | -13.85 | 66.98 | 20.62 |
| 89 | TYR | CD2 | -22.90 | -11.67 | 67.49 | 17.49 |
| 89 | TYR | CE2 | -22.53 | -11.96 | 66.17 | 17.03 |
| 89 | TYR | CZ | -21.70 | -13.06 | 65.92 | 17.44 |
| 89 | TYR | OH | -21.28 | -13.36 | 64.65 | 16.20 |
| 89 | TYR | C | -21.11 | -10.47 | 70.39 | 14.19 |
| 89 | TYR | O | -21.79 | -9.45 | 70.23 | 14.43 |
| 90 | VAL | N | -19.80 | -10.50 | 70.18 | 11.92 |
| 90 | VAL | CA | -19.15 | -9.33 | 69.61 | 12.81 |
| 90 | VAL | CB | -17.69 | -9.13 | 70.09 | 11.22 |
| 90 | VAL | CG1 | -17.68 | -8.76 | 71.57 | 19.09 |
| 90 | VAL | CG2 | -16.84 | -10.35 | 69.83 | 10.92 |
| 90 | VAL | C | -19.21 | -9.39 | 68.09 | 14.23 |
| 90 | VAL | O | -19.09 | -8.36 | 67.42 | 14.19 |
| 91 | GLY | N | -19.44 | -10.58 | 67.53 | 14.09 |
| 91 | GLY | CA | -19.52 | -10.72 | 66.09 | 15.26 |
| 91 | GLY | C | -18.16 | -10.68 | 65.44 | 18.32 |
| 91 | GLY | O | -18.01 | -10.38 | 64.24 | 16.36 |
| 92 | GLN | N | -17.16 | -11.06 | 66.23 | 20.31 |
| 92 | GLN | CA | -15.78 | -11.06 | 65.81 | 20.17 |
| 92 | GLN | CB | -15.16 | -9.69 | 66.09 | 23.65 |
| 92 | GLN | CG | -13.83 | -9.44 | 65.42 | 28.99 |
| 92 | GLN | CD | -13.36 | -8.00 | 65.62 | 34.47 |
| 92 | GLN | OE1 | -14.10 | -7.15 | 66.15 | 34.75 |
| 92 | GLN | NE2 | -12.14 | -7.72 | 65.19 | 37.63 |
| 92 | GLN | C | -15.09 | -12.17 | 66.60 | 20.89 |
| 92 | GLN | O | -15.53 | -12.53 | 67.70 | 18.43 |
| 93 | GLU | N | -14.04 | -12.73 | 66.03 | 22.82 |
| 93 | GLU | CA | -13.31 | -13.81 | 66.69 | 24.92 |
| 93 | GLU | CB | -12.63 | -14.74 | 65.66 | 27.98 |
| 93 | GLU | CG | -12.23 | -16.10 | 66.22 | 29.38 |
| 93 | GLU | CD | -12.00 | -17.17 | 65.15 | 34.25 |
| 93 | GLU | OE1 | -12.30 | -16.93 | 63.95 | 35.80 |
| 93 | GLU | OE2 | -11.52 | -18.26 | 65.52 | 34.14 |
| 93 | GLU | C | -12.31 | -13.29 | 67.71 | 24.19 |
| 93 | GLU | O | -11.61 | -12.31 | 67.45 | 24.56 |
| 94 | GLU | N | -12.28 | -13.94 | 68.87 | 23.61 |
| 94 | GLU | CA | -11.38 | -13.58 | 69.96 | 24.32 |
| 94 | GLU | CB | -12.02 | -12.55 | 70.90 | 22.62 |
| 94 | GLU | CG | -12.23 | -11.20 | 70.27 | 23.90 |
| 94 | GLU | CD | -12.86 | -10.23 | 71.21 | 24.44 |
| 94 | GLU | OE1 | -12.18 | -9.26 | 71.60 | 29.56 |
| 94 | GLU | OE2 | -14.04 | -10.43 | 71.57 | 23.54 |
| 94 | GLU | C | -10.99 | -14.84 | 70.73 | 23.80 |
| 94 | GLU | O | -11.64 | -15.89 | 70.59 | 21.98 |
| 95 | SER | N | -9.95 | -14.73 | 71.55 | 20.75 |
| 95 | SER | CA | -9.47 | -15.86 | 72.36 | 19.71 |
| 95 | SER | CB | -8.26 | -15.46 | 73.19 | 20.00 |
| 95 | SER | OG | -8.57 | -14.41 | 74.09 | 24.28 |
| 95 | SER | C | -10.60 | -16.38 | 73.25 | 20.63 |
| 95 | SER | O | -11.48 | -15.60 | 73.65 | 22.33 |
| 96 | CYS | N | -10.56 | -17.66 | 73.58 | 17.74 |
| 96 | CYS | CA | -11.60 | -18.26 | 74.42 | 18.66 |
| 96 | CYS | C | -11.59 | -17.72 | 75.85 | 19.92 |
| 96 | CYS | O | -10.58 | -17.79 | 76.56 | 21.50 |
| 96 | CYS | CB | -11.51 | -19.78 | 74.41 | 16.39 |
| 96 | CYS | SG | -12.75 | -20.61 | 75.44 | 19.58 |
| 97 | MET | N | -12.72 | -17.14 | 76.26 | 17.89 |
| 97 | MET | CA | -12.88 | -16.59 | 77.60 | 18.67 |
| 97 | MET | CB | -12.86 | -15.07 | 77.57 | 17.60 |
| 97 | MET | CG | -12.76 | -14.43 | 78.94 | 18.29 |
| 97 | MET | SD | -11.15 | -13.66 | 79.17 | 26.40 |
| 97 | MET | CE | -9.99 | -15.01 | 78.76 | 19.16 |
| 97 | MET | C | -14.18 | -17.09 | 78.20 | 21.66 |
| 97 | MET | O | -15.07 | -16.31 | 78.52 | 25.61 |

TABLE VII-continued

Table of the orthogonal three dimensional coordinates in Ångstroms and B factors ($Å^2$) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| Residue | | Atom | X | Y | Z | B |
|---|---|---|---|---|---|---|
| 98 | TYR | N | −14.30 | −18.41 | 78.29 | 23.47 |
| 98 | TYR | CA | −15.49 | −19.06 | 78.83 | 23.75 |
| 98 | TYR | CB | −15.58 | −20.50 | 78.30 | 21.70 |
| 98 | TYR | CG | −16.39 | −21.46 | 79.13 | 18.51 |
| 98 | TYR | CD1 | −17.74 | −21.64 | 78.90 | 18.20 |
| 98 | TYR | CE1 | −18.49 | −22.49 | 79.70 | 19.99 |
| 98 | TYR | CD2 | −15.80 | −22.16 | 80.17 | 16.39 |
| 98 | TYR | CE2 | −16.53 | −23.01 | 80.97 | 12.68 |
| 98 | TYR | CZ | −17.87 | −23.17 | 80.74 | 16.90 |
| 98 | TYR | OH | −18.60 | −23.99 | 81.57 | 22.57 |
| 98 | TYR | C | −15.48 | −19.01 | 80.37 | 26.07 |
| 98 | TYR | O | −14.44 | −19.23 | 80.99 | 27.32 |
| 99 | ASN | N | −16.63 | −18.67 | 80.96 | 28.21 |
| 99 | ASN | CA | −16.76 | −18.59 | 82.42 | 27.40 |
| 99 | ASN | CB | −17.24 | −17.20 | 82.85 | 30.57 |
| 99 | ASN | CG | −17.89 | −17.21 | 84.22 | 33.86 |
| 99 | ASN | OD1 | −19.06 | −16.84 | 84.36 | 33.41 |
| 99 | ASN | ND2 | −17.16 | −17.66 | 85.24 | 34.39 |
| 99 | ASN | C | −17.67 | −19.66 | 83.03 | 25.48 |
| 99 | ASN | O | −18.88 | −19.64 | 82.82 | 25.31 |
| 100 | PRO | N | −17.12 | −20.53 | 83.87 | 22.21 |
| 100 | PRO | CD | −15.70 | −20.60 | 84.27 | 21.06 |
| 100 | PRO | CA | −17.89 | −21.60 | 84.50 | 19.72 |
| 100 | PRO | CB | −16.89 | −22.18 | 85.49 | 21.18 |
| 100 | PRO | CG | −15.58 | −22.01 | 84.75 | 22.13 |
| 100 | PRO | C | −19.14 | −21.08 | 85.22 | 19.80 |
| 100 | PRO | O | −20.22 | −21.65 | 85.09 | 15.82 |
| 101 | THR | N | −18.98 | −19.97 | 85.92 | 22.73 |
| 101 | THR | CA | −20.07 | −19.36 | 86.68 | 23.85 |
| 101 | THR | CB | −19.53 | −18.25 | 87.60 | 22.86 |
| 101 | THR | OG1 | −18.13 | −18.47 | 87.87 | 20.58 |
| 101 | THR | CG2 | −20.28 | −18.26 | 88.92 | 21.48 |
| 101 | THR | C | −21.22 | −18.80 | 85.82 | 24.75 |
| 101 | THR | O | −22.30 | −18.46 | 86.33 | 22.15 |
| 102 | GLY | N | −20.96 | −18.70 | 84.51 | 25.15 |
| 102 | GLY | CA | −21.96 | −18.20 | 83.59 | 21.81 |
| 102 | GLY | C | −22.72 | −19.34 | 82.94 | 19.11 |
| 102 | GLY | O | −23.78 | −19.12 | 82.36 | 19.57 |
| 103 | LYS | N | −22.15 | −20.55 | 83.03 | 18.20 |
| 103 | LYS | CA | −22.73 | −21.77 | 82.47 | 16.81 |
| 103 | LYS | CB | −22.08 | −23.02 | 83.07 | 16.94 |
| 103 | LYS | CG | −22.90 | −24.30 | 82.93 | 15.32 |
| 103 | LYS | CD | −22.03 | −25.53 | 83.10 | 18.87 |
| 103 | LYS | CE | −21.32 | −25.57 | 84.46 | 21.19 |
| 103 | LYS | NZ | −20.02 | −26.34 | 84.40 | 20.74 |
| 103 | LYS | C | −24.24 | −21.83 | 82.62 | 17.92 |
| 103 | LYS | O | −24.78 | −21.68 | 83.72 | 18.81 |
| 104 | ALA | N | −24.92 | −22.05 | 81.50 | 17.95 |
| 104 | ALA | CA | −26.38 | −22.11 | 81.49 | 17.78 |
| 104 | ALA | CB | −26.93 | −21.14 | 80.47 | 21.54 |
| 104 | ALA | C | −26.84 | −23.52 | 81.18 | 18.07 |
| 104 | ALA | O | −27.99 | −23.88 | 81.47 | 16.81 |
| 105 | ALA | N | −25.95 | −24.31 | 80.58 | 15.87 |
| 105 | ALA | CA | −26.27 | −25.69 | 80.23 | 13.04 |
| 105 | ALA | CB | −27.41 | −25.72 | 79.22 | 10.01 |
| 105 | ALA | C | −25.05 | −26.40 | 79.66 | 11.95 |
| 105 | ALA | O | −23.94 | −25.86 | 79.68 | 8.46 |
| 106 | LYS | N | −25.27 | −27.63 | 79.20 | 12.25 |
| 106 | LYS | CA | −24.24 | −28.45 | 78.57 | 18.76 |
| 106 | LYS | CB | −23.26 | −29.07 | 79.58 | 23.73 |
| 106 | LYS | CG | −23.89 | −30.02 | 80.60 | 26.39 |
| 106 | LYS | CD | −22.88 | −31.05 | 81.09 | 29.44 |
| 106 | LYS | CE | −23.54 | −32.05 | 82.06 | 33.28 |
| 106 | LYS | NZ | −24.76 | −32.74 | 81.51 | 24.10 |
| 106 | LYS | C | −24.95 | −29.54 | 77.77 | 18.52 |
| 106 | LYS | O | −26.18 | −29.49 | 77.64 | 16.87 |
| 107 | CYS | N | −24.21 | −30.50 | 77.22 | 19.97 |
| 107 | CYS | CA | −24.81 | −31.59 | 76.45 | 21.83 |
| 107 | CYS | CB | −25.13 | −31.16 | 75.00 | 23.15 |
| 107 | CYS | SG | −23.72 | −30.88 | 73.87 | 21.75 |
| 107 | CYS | C | −23.98 | −32.87 | 76.48 | 22.08 |
| 107 | CYS | O | −22.75 | −32.84 | 76.60 | 21.41 |
| 108 | ARG | N | −24.66 | −34.00 | 76.40 | 22.61 |
| 108 | ARG | CA | −23.96 | −35.28 | 76.44 | 25.98 |
| 108 | ARG | CB | −24.57 | −36.18 | 77.53 | 25.00 |
| 108 | ARG | CG | −24.76 | −35.44 | 78.85 | 19.33 |
| 108 | ARG | CD | −25.24 | −36.32 | 79.99 | 17.89 |
| 108 | ARG | NE | −26.61 | −36.80 | 79.81 | 10.20 |
| 108 | ARG | CZ | −27.00 | −38.02 | 80.15 | 9.00 |
| 108 | ARG | NH1 | −26.12 | −38.88 | 80.68 | 6.62 |
| 108 | ARG | NH2 | −28.26 | −38.39 | 79.99 | 10.32 |
| 108 | ARG | C | −23.91 | −35.98 | 75.08 | 23.86 |
| 108 | ARG | O | −24.38 | −37.10 | 74.94 | 25.08 |
| 109 | GLY | N | −23.34 | −35.29 | 74.10 | 23.61 |
| 109 | GLY | CA | −23.21 | −35.84 | 72.76 | 20.68 |
| 109 | GLY | C | −24.30 | −35.35 | 71.82 | 18.95 |
| 109 | GLY | O | −25.15 | −34.56 | 72.22 | 19.25 |
| 110 | TYR | N | −24.29 | −35.85 | 70.58 | 18.18 |
| 110 | TYR | CA | −25.27 | −35.46 | 69.57 | 17.03 |
| 110 | TYR | CB | −24.72 | −34.38 | 68.64 | 14.76 |
| 110 | TYR | CG | −23.48 | −34.81 | 67.90 | 12.25 |
| 110 | TYR | CD1 | −22.21 | −34.48 | 68.37 | 14.76 |
| 110 | TYR | CE1 | −21.06 | −34.95 | 67.75 | 14.89 |
| 110 | TYR | CD2 | −23.56 | −35.61 | 66.78 | 12.73 |
| 110 | TYR | CE2 | −22.41 | −36.08 | 66.14 | 15.02 |
| 110 | TYR | CZ | −21.17 | −35.75 | 66.64 | 17.33 |
| 110 | TYR | OH | −20.03 | −36.26 | 66.03 | 22.26 |
| 110 | TYR | C | −25.70 | −36.67 | 68.75 | 16.81 |
| 110 | TYR | O | −25.01 | −37.69 | 68.73 | 19.27 |
| 111 | ARG | N | −26.83 | −36.53 | 68.07 | 16.77 |
| 111 | ARG | CA | −27.34 | −37.57 | 67.19 | 18.25 |
| 111 | ARG | CB | −28.73 | −38.08 | 67.60 | 20.39 |
| 111 | ARG | CG | −29.51 | −38.81 | 66.48 | 21.92 |
| 111 | ARG | CD | −28.94 | −40.20 | 66.16 | 26.51 |
| 111 | ARG | NE | −29.54 | −40.85 | 64.98 | 25.17 |
| 111 | ARG | CZ | −28.83 | −41.49 | 64.03 | 26.40 |
| 111 | ARG | NH1 | −27.50 | −41.55 | 64.12 | 21.95 |
| 111 | ARG | NH2 | −29.45 | −42.10 | 63.02 | 18.73 |
| 111 | ARG | C | −27.43 | −36.92 | 65.81 | 20.54 |
| 111 | ARG | O | −27.88 | −35.77 | 65.69 | 23.20 |
| 112 | GLU | N | −26.95 | −37.62 | 64.79 | 17.24 |
| 112 | GLU | CA | −27.01 | −37.12 | 63.42 | 13.69 |
| 112 | GLU | CB | −25.70 | −37.34 | 62.69 | 12.60 |
| 112 | GLU | CG | −24.59 | −36.38 | 63.05 | 10.04 |
| 112 | GLU | CD | −23.25 | −36.92 | 62.62 | 11.35 |
| 112 | GLU | OE1 | −22.50 | −36.23 | 61.89 | 10.65 |
| 112 | GLU | OE2 | −22.97 | −38.06 | 63.01 | 14.44 |
| 112 | GLU | C | −28.15 | −37.85 | 62.72 | 15.47 |
| 112 | GLU | O | −28.49 | −38.97 | 63.09 | 17.83 |
| 113 | ILE | N | −28.72 | −37.25 | 61.70 | 17.43 |
| 113 | ILE | CA | −29.82 | −37.87 | 60.96 | 14.32 |
| 113 | ILE | CB | −30.99 | −36.87 | 60.90 | 13.01 |
| 113 | ILE | CG2 | −32.04 | −37.32 | 59.87 | 11.54 |
| 113 | ILE | CG1 | −31.55 | −36.70 | 62.33 | 10.24 |
| 113 | ILE | CD1 | −32.35 | −35.44 | 62.57 | 7.36 |
| 113 | ILE | C | −29.38 | −38.34 | 59.57 | 12.75 |
| 113 | ILE | O | −28.59 | −37.68 | 58.91 | 11.81 |
| 114 | PRO | N | −29.83 | −39.53 | 59.13 | 15.44 |
| 114 | PRO | CD | −30.82 | −40.40 | 59.80 | 19.88 |
| 114 | PRO | CA | −29.47 | −40.08 | 57.81 | 15.21 |
| 114 | PRO | CB | −30.54 | −41.13 | 57.59 | 15.21 |
| 114 | PRO | CG | −30.79 | −41.66 | 58.96 | 16.85 |
| 114 | PRO | C | −29.53 | −39.00 | 56.73 | 18.58 |
| 114 | PRO | O | −30.52 | −38.27 | 56.64 | 21.69 |
| 115 | GLU | N | −28.49 | −38.91 | 55.91 | 17.93 |
| 115 | GLU | CA | −28.45 | −37.90 | 54.87 | 18.15 |
| 115 | GLU | CB | −27.12 | −37.95 | 54.11 | 21.41 |
| 115 | GLU | CG | −27.04 | −39.05 | 53.06 | 28.55 |
| 115 | GLU | CD | −25.73 | −39.04 | 52.26 | 34.52 |
| 115 | GLU | OE1 | −25.24 | −37.94 | 51.90 | 34.27 |

TABLE VII-continued

Table of the orthogonal three dimensional coordinates in Ångstroms and B factors (Å$^2$) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| Residue | | Atom | X | Y | Z | B |
|---|---|---|---|---|---|---|
| 115 | GLU | OE2 | −25.21 | −40.14 | 51.99 | 34.99 |
| 115 | GLU | C | −29.63 | −37.99 | 53.90 | 20.57 |
| 115 | GLU | O | −30.10 | −39.08 | 53.56 | 20.47 |
| 116 | GLY | N | −30.13 | −36.82 | 53.51 | 21.25 |
| 116 | GLY | CA | −31.24 | −36.73 | 52.58 | 19.05 |
| 116 | GLY | C | −32.59 | −37.14 | 53.12 | 19.97 |
| 116 | GLY | O | −33.62 | −36.74 | 52.56 | 24.15 |
| 117 | ASN | N | −32.62 | −37.87 | 54.23 | 17.37 |
| 117 | ASN | CA | −33.90 | −38.33 | 54.77 | 15.93 |
| 117 | ASN | CB | −33.73 | −39.57 | 55.64 | 10.26 |
| 117 | ASN | CG | −35.03 | −40.34 | 55.79 | 12.00 |
| 117 | ASN | OD1 | −36.12 | −39.76 | 55.79 | 10.30 |
| 117 | ASN | ND2 | −34.92 | −41.66 | 55.91 | 13.10 |
| 117 | ASN | C | −34.73 | −37.30 | 55.49 | 17.41 |
| 117 | ASN | O | −34.57 | −37.09 | 56.70 | 18.71 |
| 118 | GLU | N | −35.66 | −36.70 | 54.77 | 15.53 |
| 118 | GLU | CA | −36.56 | −35.71 | 55.34 | 15.33 |
| 118 | GLU | CB | −37.27 | −34.93 | 54.25 | 15.94 |
| 118 | GLU | CG | −36.37 | −34.00 | 53.46 | 22.20 |
| 118 | GLU | CD | −37.14 | −33.16 | 52.46 | 21.94 |
| 118 | GLU | OE1 | −37.27 | −33.58 | 51.29 | 25.99 |
| 118 | GLU | OE2 | −37.64 | −32.08 | 52.85 | 25.26 |
| 118 | GLU | C | −37.57 | −36.30 | 56.33 | 18.60 |
| 118 | GLU | O | −38.02 | −35.60 | 57.23 | 23.43 |
| 119 | LYS | N | −37.93 | −37.57 | 56.17 | 19.21 |
| 119 | LYS | CA | −38.89 | −38.21 | 57.08 | 17.16 |
| 119 | LYS | CB | −39.39 | −39.55 | 56.54 | 18.23 |
| 119 | LYS | CG | −40.29 | −39.44 | 55.34 | 23.03 |
| 119 | LYS | CD | −41.48 | −38.55 | 55.62 | 24.88 |
| 119 | LYS | CE | −41.85 | −37.77 | 54.36 | 33.17 |
| 119 | LYS | NZ | −40.65 | −37.00 | 53.78 | 35.51 |
| 119 | LYS | C | −38.30 | −38.39 | 58.44 | 13.83 |
| 119 | LYS | O | −38.99 | −38.27 | 59.45 | 14.48 |
| 120 | ALA | N | −37.02 | −38.74 | 58.47 | 11.43 |
| 120 | ALA | CA | −36.30 | −38.93 | 59.71 | 11.35 |
| 120 | ALA | CB | −34.91 | −39.44 | 59.43 | 12.94 |
| 120 | ALA | C | −36.23 | −37.57 | 60.34 | 14.11 |
| 120 | ALA | O | −36.49 | −37.41 | 61.53 | 20.36 |
| 121 | LEU | N | −35.94 | −36.57 | 59.52 | 14.09 |
| 121 | LEU | CA | −35.84 | −35.19 | 59.98 | 14.37 |
| 121 | LEU | CB | −35.35 | −34.28 | 58.86 | 11.45 |
| 121 | LEU | CG | −35.11 | −32.82 | 59.20 | 13.53 |
| 121 | LEU | CD1 | −34.22 | −32.69 | 60.44 | 17.91 |
| 121 | LEU | CD2 | −34.49 | −32.13 | 57.98 | 13.43 |
| 121 | LEU | C | −37.17 | −34.71 | 60.57 | 14.14 |
| 121 | LEU | O | −37.19 | −34.08 | 61.63 | 17.50 |
| 122 | LYS | N | −38.28 | −35.01 | 59.90 | 14.51 |
| 122 | LYS | CA | −39.61 | −34.63 | 60.36 | 14.97 |
| 122 | LYS | CB | −40.67 | −34.97 | 59.32 | 15.25 |
| 122 | LYS | CG | −42.09 | −34.67 | 59.75 | 15.73 |
| 122 | LYS | CD | −43.09 | −35.54 | 59.00 | 15.63 |
| 122 | LYS | CE | −44.48 | −35.36 | 59.56 | 22.12 |
| 122 | LYS | NZ | −45.45 | −36.35 | 59.02 | 25.27 |
| 122 | LYS | C | −39.93 | −35.32 | 61.69 | 17.92 |
| 122 | LYS | O | −40.58 | −34.74 | 62.58 | 15.41 |
| 123 | ARG | N | −39.51 | −36.57 | 61.80 | 20.19 |
| 123 | ARG | CA | −39.71 | −37.36 | 63.00 | 24.53 |
| 123 | ARG | CB | −39.36 | −38.82 | 62.76 | 26.04 |
| 123 | ARG | CG | −40.37 | −39.57 | 61.92 | 29.94 |
| 123 | ARG | CD | −39.79 | −40.87 | 61.39 | 33.27 |
| 123 | ARG | NE | −38.98 | −41.56 | 62.39 | 38.93 |
| 123 | ARG | CZ | −37.67 | −41.79 | 62.26 | 38.64 |
| 123 | ARG | NH1 | −37.03 | −41.37 | 61.18 | 39.92 |
| 123 | ARG | NH2 | −37.00 | −42.45 | 63.20 | 34.71 |
| 123 | ARG | C | −38.89 | −36.77 | 64.14 | 25.64 |
| 123 | ARG | C | −39.33 | −36.76 | 65.30 | 25.72 |
| 124 | ALA | N | −37.70 | −36.26 | 63.80 | 23.74 |
| 124 | ALA | CA | −36.80 | −35.64 | 64.77 | 25.05 |
| 124 | ALA | CB | −35.49 | −35.23 | 64.09 | 22.46 |
| 124 | ALA | C | −37.48 | −34.41 | 65.37 | 24.90 |
| 124 | ALA | O | −37.50 | −34.23 | 66.59 | 25.58 |
| 125 | VAL | N | −38.02 | −33.57 | 64.50 | 25.44 |
| 125 | VAL | CA | −38.69 | −32.35 | 64.92 | 24.60 |
| 125 | VAL | CB | −39.08 | −31.46 | 63.72 | 20.30 |
| 125 | VAL | CG1 | −39.85 | −30.23 | 64.19 | 13.27 |
| 125 | VAL | CG2 | −37.80 | −31.05 | 62.95 | 19.58 |
| 125 | VAL | C | −39.93 | −32.66 | 65.73 | 24.17 |
| 125 | VAL | O | −40.19 | −32.01 | 66.73 | 26.08 |
| 126 | ALA | N | −40.69 | −33.66 | 65.32 | 25.26 |
| 126 | ALA | CA | −41.90 | −34.00 | 66.05 | 26.85 |
| 126 | ALA | CB | −42.65 | −35.08 | 65.34 | 27.49 |
| 126 | ALA | C | −41.59 | −34.41 | 67.50 | 28.51 |
| 126 | ALA | O | −42.22 | −33.91 | 68.43 | 29.45 |
| 127 | ARG | N | −40.60 | −35.30 | 67.68 | 27.15 |
| 127 | ARG | CA | −40.20 | −35.80 | 69.01 | 26.50 |
| 127 | ARG | CB | −39.52 | −37.17 | 68.92 | 25.80 |
| 127 | ARG | CG | −40.36 | −38.31 | 68.39 | 29.17 |
| 127 | ARG | CD | −41.39 | −38.82 | 69.38 | 30.20 |
| 127 | ARG | NE | −42.01 | −40.06 | 68.90 | 31.67 |
| 127 | ARG | CZ | −43.14 | −40.57 | 69.38 | 31.87 |
| 127 | ARG | NH1 | −43.62 | −41.70 | 68.87 | 32.34 |
| 127 | ARG | NH2 | −43.80 | −39.97 | 70.36 | 33.34 |
| 127 | ARG | C | −39.30 | −34.88 | 69.83 | 26.63 |
| 127 | ARG | O | −39.61 | −34.54 | 70.98 | 29.49 |
| 128 | VAL | N | −38.13 | −34.58 | 69.27 | 24.07 |
| 128 | VAL | CA | −37.14 | −33.75 | 69.93 | 20.27 |
| 128 | VAL | CB | −35.74 | −33.96 | 69.29 | 17.18 |
| 128 | VAL | CG1 | −34.73 | −33.00 | 69.87 | 16.62 |
| 128 | VAL | CG2 | −35.27 | −35.40 | 69.51 | 16.17 |
| 128 | VAL | C | −37.51 | −32.28 | 69.92 | 19.91 |
| 128 | VAL | O | −38.00 | −31.75 | 70.91 | 21.31 |
| 129 | GLY | N | −37.26 | −31.63 | 68.79 | 21.40 |
| 129 | GLY | CA | −37.56 | −30.22 | 68.67 | 18.08 |
| 129 | GLY | C | −36.62 | −29.60 | 67.67 | 17.76 |
| 129 | GLY | O | −36.22 | −30.27 | 66.71 | 14.46 |
| 130 | PRO | N | −36.25 | −28.33 | 67.86 | 18.11 |
| 130 | PRO | CD | −36.68 | −27.44 | 68.96 | 20.59 |
| 130 | PRO | CA | −35.35 | −27.64 | 66.94 | 17.36 |
| 130 | PRO | CB | −35.03 | −26.36 | 67.70 | 17.67 |
| 130 | PRO | CG | −36.33 | −26.07 | 68.41 | 19.12 |
| 130 | PRO | C | −34.10 | −28.47 | 66.69 | 18.18 |
| 130 | PRO | O | −33.43 | −28.92 | 67.63 | 21.49 |
| 131 | VAL | N | −33.81 | −28.71 | 65.41 | 14.71 |
| 131 | VAL | CA | −32.64 | −29.47 | 64.99 | 10.15 |
| 131 | VAL | CB | −33.09 | −30.69 | 64.16 | 13.09 |
| 131 | VAL | CG1 | −31.88 | −31.39 | 63.55 | 14.17 |
| 131 | VAL | CG2 | −33.88 | −31.63 | 65.02 | 19.95 |
| 131 | VAL | C | −31.80 | −28.60 | 64.10 | 10.57 |
| 131 | VAL | O | −32.33 | −27.86 | 63.27 | 13.19 |
| 132 | SER | N | −30.49 | −28.71 | 64.25 | 7.45 |
| 132 | SER | CA | −29.59 | −27.93 | 63.42 | 7.72 |
| 132 | SER | CB | −28.23 | −27.81 | 64.07 | 9.68 |
| 132 | SER | OG | −28.37 | −27.45 | 65.44 | 20.96 |
| 132 | SER | C | −29.48 | −28.55 | 62.02 | 6.88 |
| 132 | SER | O | −29.18 | −29.74 | 61.86 | 4.58 |
| 133 | VAL | N | −29.75 | −27.75 | 61.00 | 7.92 |
| 133 | VAL | CA | −29.68 | −28.20 | 59.62 | 6.47 |
| 133 | VAL | CB | −31.09 | −28.35 | 59.00 | 6.27 |
| 133 | VAL | CG1 | −31.92 | −29.35 | 59.80 | 5.31 |
| 133 | VAL | CG2 | −31.80 | −27.00 | 58.93 | 2.32 |
| 133 | VAL | C | −28.88 | −27.20 | 58.78 | 6.11 |
| 133 | VAL | O | −28.93 | −25.99 | 59.01 | 4.92 |
| 134 | ALA | N | −28.09 | −27.71 | 57.85 | 8.55 |
| 134 | ALA | CA | −27.29 | −26.90 | 56.94 | 10.56 |
| 134 | ALA | CB | −25.90 | −27.49 | 56.80 | 10.48 |
| 134 | ALA | C | −28.01 | −26.89 | 55.59 | 11.28 |
| 134 | ALA | O | −28.61 | −27.91 | 55.19 | 10.70 |
| 135 | ILE | N | −28.00 | −25.75 | 54.91 | 5.87 |
| 135 | ILE | CA | −28.65 | −25.64 | 53.61 | 9.02 |
| 135 | ILE | CB | −30.05 | −25.04 | 53.75 | 9.82 |

TABLE VII-continued

Table of the orthogonal three dimensional coordinates in Ångstroms and B factors (Å²) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| Residue | | Atom | X | Y | Z | B |
|---|---|---|---|---|---|---|
| 135 | ILE | CG2 | −30.96 | −25.98 | 54.52 | 8.18 |
| 135 | ILE | CG1 | −29.97 | −23.67 | 54.42 | 7.95 |
| 135 | ILE | CD1 | −31.24 | −22.87 | 54.30 | 5.36 |
| 135 | ILE | C | −27.84 | −24.75 | 52.67 | 10.58 |
| 135 | ILE | O | −26.82 | −24.17 | 53.08 | 11.83 |
| 136 | ASP | N | −28.27 | −24.67 | 51.41 | 14.26 |
| 136 | ASP | CA | −27.64 | −23.83 | 50.39 | 12.77 |
| 136 | ASP | CB | −27.59 | −24.54 | 49.03 | 11.56 |
| 136 | ASP | CG | −27.29 | −23.58 | 47.87 | 11.70 |
| 136 | ASP | OD1 | −27.82 | −23.80 | 46.77 | 16.82 |
| 136 | ASP | OD2 | −26.54 | −22.61 | 48.06 | 6.89 |
| 136 | ASP | C | −28.44 | −22.53 | 50.29 | 11.76 |
| 136 | ASP | O | −29.51 | −22.50 | 49.69 | 12.86 |
| 137 | ALA | N | −27.90 | −21.45 | 50.83 | 12.10 |
| 137 | ALA | CA | −28.63 | −20.19 | 50.80 | 14.12 |
| 137 | ALA | CB | −28.77 | −19.64 | 52.22 | 16.96 |
| 137 | ALA | C | −28.02 | −19.14 | 49.87 | 15.39 |
| 137 | ALA | O | −28.27 | −17.94 | 50.04 | 11.83 |
| 138 | SER | N | −27.20 | −19.57 | 48.91 | 16.46 |
| 138 | SER | CA | −26.56 | −18.66 | 47.96 | 16.14 |
| 138 | SER | CB | −25.45 | −19.36 | 47.17 | 13.20 |
| 138 | SER | OG | −25.91 | −20.60 | 46.65 | 11.80 |
| 138 | SER | C | −27.54 | −17.97 | 47.02 | 17.22 |
| 138 | SER | O | −27.42 | −16.77 | 46.74 | 16.85 |
| 139 | LEU | N | −28.50 | −18.75 | 46.53 | 11.84 |
| 139 | LEU | CA | −29.51 | −18.24 | 45.62 | 10.88 |
| 139 | LEU | CB | −30.62 | −19.27 | 45.41 | 10.28 |
| 139 | LEU | CG | −30.39 | −20.25 | 44.25 | 7.79 |
| 139 | LEU | CD1 | −28.98 | −20.81 | 44.28 | 16.09 |
| 139 | LEU | CD2 | −31.39 | −21.35 | 44.31 | 6.66 |
| 139 | LEU | C | −30.07 | −16.90 | 46.07 | 10.95 |
| 139 | LEU | O | −30.56 | −16.77 | 47.18 | 10.84 |
| 140 | THR | N | −29.98 | −15.89 | 45.20 | 12.65 |
| 140 | THR | CA | −30.48 | −14.56 | 45.55 | 10.04 |
| 140 | THR | CB | −30.04 | −13.47 | 44.54 | 8.74 |
| 140 | THR | OG1 | −30.71 | −13.68 | 43.29 | 16.41 |
| 140 | THR | CG2 | −28.52 | −13.50 | 44.33 | 5.90 |
| 140 | THR | C | −31.98 | −14.51 | 45.76 | 7.53 |
| 140 | THR | O | −32.51 | −13.48 | 46.16 | 7.86 |
| 141 | SER | N | −32.69 | −15.60 | 45.48 | 7.62 |
| 141 | SER | CA | −34.13 | −15.60 | 45.71 | 10.59 |
| 141 | SER | CB | −34.81 | −16.69 | 44.90 | 7.78 |
| 141 | SER | OG | −34.14 | −17.92 | 45.09 | 10.19 |
| 141 | SER | C | −34.32 | −15.81 | 47.21 | 14.46 |
| 141 | SER | O | −35.31 | −15.38 | 47.80 | 15.07 |
| 142 | PHE | N | −33.33 | −16.47 | 47.81 | 16.29 |
| 142 | PHE | CA | −33.32 | −16.75 | 49.24 | 18.29 |
| 142 | PHE | CB | −32.26 | −17.80 | 49.57 | 19.91 |
| 142 | PHE | CG | −32.23 | −18.22 | 51.01 | 19.34 |
| 142 | PHE | CD1 | −32.83 | −19.42 | 51.40 | 19.10 |
| 142 | PHE | CD2 | −31.58 | −17.44 | 51.96 | 17.86 |
| 142 | PHE | CE1 | −32.77 | −19.84 | 52.72 | 18.29 |
| 142 | PHE | CE2 | −31.52 | −17.86 | 53.29 | 16.09 |
| 142 | PHE | CZ | −32.12 | −19.06 | 53.67 | 17.03 |
| 142 | PHE | C | −33.04 | −15.46 | 49.98 | 18.87 |
| 142 | PHE | O | −33.70 | −15.13 | 50.96 | 20.82 |
| 143 | GLN | N | −32.06 | −14.71 | 49.48 | 17.89 |
| 143 | GLN | CA | −31.69 | −13.46 | 50.11 | 17.94 |
| 143 | GLN | CB | −30.35 | −12.98 | 49.56 | 20.86 |
| 143 | GLN | CG | −29.29 | −14.07 | 49.66 | 27.97 |
| 143 | GLN | CD | −27.96 | −13.66 | 49.06 | 35.25 |
| 143 | GLN | OE1 | −27.88 | −12.65 | 48.36 | 42.66 |
| 143 | GLN | NE2 | −26.91 | −14.44 | 49.35 | 32.14 |
| 143 | GLN | C | −32.77 | −12.40 | 49.97 | 16.38 |
| 143 | GLN | O | −32.78 | −11.43 | 50.72 | 21.06 |
| 144 | PHE | N | −33.71 | −12.62 | 49.07 | 16.70 |
| 144 | PHE | CA | −34.81 | −11.68 | 48.86 | 16.93 |
| 144 | PHE | CB | −34.83 | −11.16 | 47.42 | 14.35 |
| 144 | PHE | CG | −33.63 | −10.34 | 47.06 | 9.94 |
| 144 | PHE | CD1 | −33.23 | −9.28 | 47.87 | 7.40 |
| 144 | PHE | CD2 | −32.87 | −10.63 | 45.94 | 11.47 |
| 144 | PHE | CE1 | −32.09 | −8.54 | 47.58 | 2.23 |
| 144 | PHE | CE2 | −31.73 | −9.89 | 45.63 | 11.16 |
| 144 | PHE | CZ | −31.34 | −8.85 | 46.45 | 5.01 |
| 144 | PHE | C | −36.15 | −12.29 | 49.26 | 19.07 |
| 144 | PHE | O | −37.21 | −11.75 | 48.94 | 23.82 |
| 145 | TYR | N | −36.10 | −13.42 | 49.95 | 21.54 |
| 145 | TYR | CA | −37.31 | −14.10 | 50.39 | 20.66 |
| 145 | TYR | CB | −36.98 | −15.43 | 51.09 | 19.50 |
| 145 | TYR | CG | −38.13 | −16.04 | 51.85 | 20.41 |
| 145 | TYR | CD1 | −38.96 | −16.98 | 51.25 | 22.31 |
| 145 | TYR | CE1 | −40.05 | −17.51 | 51.93 | 23.37 |
| 145 | TYR | CD2 | −38.43 | −15.64 | 53.15 | 19.98 |
| 145 | TYR | CE2 | −39.52 | −16.16 | 53.84 | 20.51 |
| 145 | TYR | CZ | −40.33 | −17.09 | 53.22 | 22.20 |
| 145 | TYR | OH | −41.42 | −17.60 | 53.89 | 24.45 |
| 145 | TYR | C | −38.13 | −13.18 | 51.31 | 19.31 |
| 145 | TYR | O | −37.57 | −12.41 | 52.09 | 16.29 |
| 146 | SER | N | −39.44 | −13.29 | 51.23 | 19.16 |
| 146 | SER | CA | −40.31 | −12.46 | 52.05 | 18.38 |
| 146 | SER | CB | −40.69 | −11.17 | 51.33 | 21.74 |
| 146 | SER | OG | −41.24 | −11.45 | 50.05 | 25.62 |
| 146 | SER | C | −41.55 | −13.21 | 52.52 | 17.33 |
| 146 | SER | O | −41.87 | −13.19 | 53.70 | 17.00 |
| 147 | LYS | N | −42.21 | −13.90 | 51.60 | 15.30 |
| 147 | LYS | CA | −43.42 | −14.63 | 51.94 | 16.47 |
| 147 | LYS | CB | −44.65 | −13.72 | 51.85 | 21.13 |
| 147 | LYS | CG | −45.98 | −14.43 | 52.13 | 26.90 |
| 147 | LYS | CD | −47.15 | −13.75 | 51.41 | 31.88 |
| 147 | LYS | CE | −48.38 | −14.69 | 51.35 | 38.13 |
| 147 | LYS | NZ | −49.45 | −14.23 | 50.41 | 36.35 |
| 147 | LYS | C | −43.61 | −15.88 | 51.09 | 16.19 |
| 147 | LYS | O | −43.21 | −15.91 | 49.92 | 18.85 |
| 148 | GLY | N | −44.20 | −16.91 | 51.69 | 14.07 |
| 148 | GLY | CA | −44.47 | −18.14 | 50.98 | 13.24 |
| 148 | GLY | C | −43.46 | −19.26 | 51.17 | 12.23 |
| 148 | GLY | O | −42.39 | −19.05 | 51.74 | 11.43 |
| 149 | VAL | N | −43.82 | −20.45 | 50.71 | 9.32 |
| 149 | VAL | CA | −42.95 | −21.61 | 50.81 | 8.20 |
| 149 | VAL | CB | −43.70 | −22.96 | 50.60 | 5.83 |
| 149 | VAL | CG1 | −42.72 | −24.11 | 50.73 | 2.00 |
| 149 | VAL | CG2 | −44.82 | −23.12 | 51.61 | 4.34 |
| 149 | VAL | C | −41.92 | −21.43 | 49.70 | 11.54 |
| 149 | VAL | O | −42.25 | −21.45 | 48.50 | 12.48 |
| 150 | TYR | N | −40.68 | −21.21 | 50.13 | 12.91 |
| 150 | TYR | CA | −39.55 | −21.02 | 49.24 | 10.42 |
| 150 | TYR | CB | −38.33 | −20.58 | 50.03 | 4.78 |
| 150 | TYR | CG | −37.10 | −20.42 | 49.19 | 8.23 |
| 150 | TYR | CD1 | −36.83 | −19.21 | 48.55 | 10.09 |
| 150 | TYR | CE1 | −35.68 | −19.06 | 47.77 | 11.54 |
| 150 | TYR | CD2 | −36.21 | −21.47 | 49.02 | 8.80 |
| 150 | TYR | CE2 | −35.07 | −21.33 | 48.24 | 9.65 |
| 150 | TYR | CZ | −34.81 | −20.13 | 47.62 | 10.30 |
| 150 | TYR | OH | −33.67 | −19.97 | 46.88 | 18.73 |
| 150 | TYR | C | −39.27 | −22.30 | 48.46 | 14.00 |
| 150 | TYR | O | −39.45 | −23.40 | 48.96 | 16.63 |
| 151 | TYR | N | −38.79 | −22.13 | 47.24 | 15.66 |
| 151 | TYR | CA | −38.48 | −23.25 | 46.37 | 17.45 |
| 151 | TYR | CB | −39.74 | −24.04 | 46.01 | 21.54 |
| 151 | TYR | CG | −39.53 | −25.25 | 45.13 | 23.93 |
| 151 | TYR | CD1 | −38.93 | −26.42 | 45.64 | 28.17 |
| 151 | TYR | CE1 | −38.74 | −27.54 | 44.83 | 29.69 |
| 151 | TYR | CD2 | −39.94 | −25.25 | 43.80 | 26.78 |
| 151 | TYR | CE2 | −39.76 | −26.36 | 42.99 | 29.59 |
| 151 | TYR | CZ | −39.16 | −27.50 | 43.51 | 32.44 |
| 151 | TYR | OH | −38.99 | −28.60 | 42.70 | 37.61 |
| 151 | TYR | C | −37.85 | −22.60 | 45.15 | 18.03 |
| 151 | TYR | O | −38.32 | −21.56 | 44.68 | 16.75 |
| 152 | ASP | N | −36.76 | −23.17 | 44.68 | 19.75 |
| 152 | ASP | CA | −36.05 | −22.64 | 43.52 | 21.69 |

TABLE VII-continued

Table of the orthogonal three dimensional coordinates in Ångstroms and B factors (Å²) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| Residue | Atom | X | Y | Z | B |
|---|---|---|---|---|---|
| 152 | ASP | CB | −35.07 | −21.53 | 43.91 | 21.35 |
| 152 | ASP | CG | −34.48 | −20.80 | 42.70 | 22.73 |
| 152 | ASP | OD1 | −34.58 | −19.56 | 42.63 | 20.20 |
| 152 | ASP | OD2 | −33.90 | −21.46 | 41.82 | 23.61 |
| 152 | ASP | C | −35.33 | −23.85 | 42.96 | 25.58 |
| 152 | ASP | O | −34.67 | −24.57 | 43.72 | 28.85 |
| 153 | GLU | N | −35.50 | −24.09 | 41.66 | 26.65 |
| 153 | GLU | CA | −34.86 | −25.25 | 41.03 | 26.63 |
| 153 | GLU | CB | −35.52 | −25.57 | 39.69 | 30.19 |
| 153 | GLU | CG | −36.09 | −24.38 | 38.92 | 34.99 |
| 153 | GLU | CD | −35.04 | −23.61 | 38.15 | 37.99 |
| 153 | GLU | OE1 | −34.95 | −22.38 | 38.34 | 40.14 |
| 153 | GLU | OE2 | −34.31 | −24.24 | 37.34 | 40.23 |
| 153 | GLU | C | −33.34 | −25.20 | 40.91 | 24.39 |
| 153 | GLU | O | −32.71 | −26.22 | 40.70 | 23.54 |
| 154 | SER | N | −32.75 | −24.02 | 41.11 | 23.15 |
| 154 | SER | CA | −31.30 | −23.83 | 41.04 | 25.05 |
| 154 | SER | CB | −30.95 | −22.35 | 40.85 | 24.11 |
| 154 | SER | OG | −31.81 | −21.71 | 39.91 | 26.07 |
| 154 | SER | C | −30.53 | −24.38 | 42.26 | 25.62 |
| 154 | SER | O | −29.37 | −24.78 | 42.15 | 26.42 |
| 155 | CYS | N | −31.19 | −24.33 | 43.43 | 24.27 |
| 155 | CYS | CA | −30.63 | −24.77 | 44.71 | 19.73 |
| 155 | CYS | C | −29.88 | −26.08 | 44.59 | 17.05 |
| 155 | CYS | O | −30.44 | −27.08 | 44.16 | 14.86 |
| 155 | CYS | CB | −31.72 | −24.87 | 45.79 | 20.11 |
| 155 | CYS | SG | −31.27 | −24.12 | 47.40 | 19.94 |
| 156 | ASN | N | −28.61 | −26.07 | 44.99 | 19.11 |
| 156 | ASN | CA | −27.76 | −27.26 | 44.92 | 21.62 |
| 156 | ASN | CB | −26.37 | −26.87 | 44.41 | 19.84 |
| 156 | ASN | CG | −25.47 | −28.06 | 44.20 | 20.15 |
| 156 | ASN | OD1 | −25.86 | −29.20 | 44.44 | 15.60 |
| 156 | ASN | ND2 | −24.23 | −27.80 | 43.77 | 19.95 |
| 156 | ASN | C | −27.67 | −28.05 | 46.24 | 22.71 |
| 156 | ASN | O | −27.08 | −27.58 | 47.21 | 23.56 |
| 157 | SER | N | −28.20 | −29.28 | 46.23 | 22.09 |
| 157 | SER | CA | −28.22 | −30.17 | 47.40 | 16.83 |
| 157 | SER | CB | −28.93 | −31.49 | 47.06 | 14.81 |
| 157 | SER | OG | −30.26 | −31.26 | 46.66 | 19.44 |
| 157 | SER | C | −26.86 | −30.49 | 48.02 | 17.43 |
| 157 | SER | O | −26.78 | −31.10 | 49.10 | 16.02 |
| 158 | ASP | N | −25.79 | −30.19 | 47.30 | 17.73 |
| 158 | ASP | CA | −24.46 | −30.46 | 47.80 | 20.40 |
| 158 | ASP | CB | −23.70 | −31.42 | 46.88 | 24.69 |
| 158 | ASP | CG | −24.27 | −32.82 | 46.89 | 27.15 |
| 158 | ASP | OD1 | −24.93 | −33.19 | 45.88 | 26.00 |
| 158 | ASP | OD2 | −24.08 | −33.55 | 47.90 | 26.52 |
| 158 | ASP | C | −23.68 | −29.19 | 48.00 | 20.27 |
| 158 | ASP | O | −22.46 | −29.22 | 48.16 | 20.24 |
| 159 | ASN | N | −24.39 | −28.07 | 47.97 | 17.11 |
| 159 | ASN | CA | −23.72 | −26.81 | 48.19 | 16.88 |
| 159 | ASN | CB | −24.01 | −25.79 | 47.10 | 18.24 |
| 159 | ASN | CG | −23.00 | −24.66 | 47.10 | 21.17 |
| 159 | ASN | OD1 | −21.83 | −24.86 | 47.42 | 16.98 |
| 159 | ASN | ND2 | −23.46 | −23.46 | 46.75 | 22.38 |
| 159 | ASN | C | −24.12 | −26.28 | 49.55 | 17.56 |
| 159 | ASN | O | −24.64 | −25.17 | 49.67 | 19.13 |
| 160 | LEU | N | −23.93 | −27.12 | 50.57 | 12.99 |
| 160 | LEU | CA | −24.23 | −26.73 | 51.94 | 8.24 |
| 160 | LEU | CB | −24.00 | −27.89 | 52.89 | 4.68 |
| 160 | LEU | CG | −25.09 | −28.95 | 53.11 | 5.66 |
| 160 | LEU | CD1 | −25.96 | −29.16 | 51.89 | 3.96 |
| 160 | LEU | CD2 | −24.43 | −30.24 | 53.54 | 6.24 |
| 160 | LEU | C | −23.28 | −25.58 | 52.23 | 8.29 |
| 160 | LEU | O | −22.07 | −25.75 | 52.11 | 8.75 |
| 161 | ASN | N | −23.83 | −24.41 | 52.54 | 9.39 |
| 161 | ASN | CA | −23.02 | −23.23 | 52.83 | 10.51 |
| 161 | ASN | CB | −22.74 | −22.43 | 51.56 | 14.18 |
| 161 | ASN | CG | −24.01 | −22.01 | 50.85 | 10.89 |
| 161 | ASN | OD1 | −24.80 | −21.22 | 51.35 | 14.49 |
| 161 | ASN | ND2 | −24.21 | −22.56 | 49.67 | 16.31 |
| 161 | ASN | C | −23.56 | −22.29 | 53.92 | 12.43 |
| 161 | ASN | C | −23.02 | −21.20 | 54.14 | 13.86 |
| 162 | HIS | N | −24.62 | −22.69 | 54.60 | 11.27 |
| 162 | HIS | CA | −25.19 | −21.85 | 55.64 | 10.37 |
| 162 | HIS | CB | −26.13 | −20.82 | 55.00 | 5.69 |
| 162 | HIS | CG | −26.80 | −19.89 | 55.96 | 6.06 |
| 162 | HIS | CD2 | −28.10 | −19.79 | 56.33 | 6.15 |
| 162 | HIS | ND1 | −26.14 | −18.85 | 56.61 | 11.02 |
| 162 | HIS | CE1 | −27.01 | −18.16 | 57.33 | 5.27 |
| 162 | HIS | NE2 | −28.20 | −18.71 | 57.17 | 6.68 |
| 162 | HIS | C | −25.92 | −22.76 | 56.61 | 11.99 |
| 162 | HIS | O | −26.68 | −23.63 | 56.20 | 15.71 |
| 163 | ALA | N | −25.59 | −22.65 | 57.89 | 14.09 |
| 163 | ALA | CA | −26.22 | −23.48 | 58.91 | 10.89 |
| 163 | ALA | CB | −25.26 | −23.79 | 60.01 | 12.33 |
| 163 | ALA | C | −27.38 | −22.67 | 59.43 | 8.08 |
| 163 | ALA | O | −27.24 | −21.48 | 59.69 | 7.93 |
| 164 | VAL | N | −28.52 | −23.33 | 59.61 | 8.61 |
| 164 | VAL | CA | −29.73 | −22.67 | 60.06 | 9.19 |
| 164 | VAL | CB | −30.58 | −22.36 | 58.82 | 13.42 |
| 164 | VAL | CG1 | −31.55 | −23.51 | 58.50 | 8.48 |
| 164 | VAL | CG2 | −31.22 | −21.00 | 58.93 | 12.71 |
| 164 | VAL | C | −30.45 | −23.60 | 61.06 | 9.94 |
| 164 | VAL | O | −29.95 | −24.69 | 61.35 | 11.85 |
| 165 | LEU | N | −31.59 | −23.20 | 61.61 | 5.74 |
| 165 | LEU | CA | −32.29 | −24.07 | 62.58 | 6.61 |
| 165 | LEU | CB | −32.27 | −23.43 | 63.97 | 3.31 |
| 165 | LEU | CG | −32.85 | −24.20 | 65.15 | 2.00 |
| 165 | LEU | CD1 | −31.81 | −25.14 | 65.69 | 3.91 |
| 165 | LEU | CD2 | −33.27 | −23.20 | 66.22 | 3.66 |
| 165 | LEU | C | −33.71 | −24.47 | 62.20 | 8.12 |
| 165 | LEU | O | −34.52 | −23.62 | 61.80 | 12.38 |
| 166 | ALA | N | −34.04 | −25.75 | 62.36 | 6.76 |
| 166 | ALA | CA | −35.37 | −26.25 | 62.02 | 6.92 |
| 166 | ALA | CB | −35.28 | −27.67 | 61.50 | 5.38 |
| 166 | ALA | C | −36.29 | −26.20 | 63.24 | 9.15 |
| 166 | ALA | O | −36.23 | −27.07 | 64.10 | 12.12 |
| 167 | VAL | N | −37.15 | −25.19 | 63.30 | 10.50 |
| 167 | VAL | CA | −38.06 | −25.06 | 64.42 | 10.11 |
| 167 | VAL | CB | −38.16 | −23.60 | 64.93 | 9.38 |
| 167 | VAL | CG1 | −36.79 | −23.07 | 65.35 | 2.39 |
| 167 | VAL | CG2 | −38.82 | −22.71 | 63.88 | 7.39 |
| 167 | VAL | C | −39.47 | −25.56 | 64.11 | 10.07 |
| 167 | VAL | O | −40.44 | −25.13 | 64.73 | 12.94 |
| 168 | GLY | N | −39.60 | −26.47 | 63.16 | 9.76 |
| 168 | GLY | CA | −40.93 | −26.97 | 62.85 | 7.51 |
| 168 | GLY | C | −41.09 | −27.55 | 61.46 | 8.86 |
| 168 | GLY | O | −40.11 | −27.88 | 60.80 | 7.84 |
| 169 | TYR | N | −42.34 | −27.71 | 61.06 | 10.03 |
| 169 | TYR | CA | −42.70 | −28.24 | 59.76 | 12.55 |
| 169 | TYR | CB | −42.20 | −29.67 | 59.56 | 12.27 |
| 169 | TYR | CG | −42.79 | −30.71 | 60.51 | 12.03 |
| 169 | TYR | CD1 | −44.13 | −31.06 | 60.43 | 9.03 |
| 169 | TYR | CE1 | −44.67 | −32.02 | 61.26 | 9.87 |
| 169 | TYR | CD2 | −42.00 | −31.35 | 61.45 | 11.40 |
| 169 | TYR | CE2 | −42.54 | −32.31 | 62.30 | 8.77 |
| 169 | TYR | CZ | −43.87 | −32.64 | 62.19 | 6.67 |
| 169 | TYR | OH | −44.45 | −33.58 | 63.00 | 8.74 |
| 169 | TYR | C | −44.21 | −28.15 | 59.68 | 15.32 |
| 169 | TYR | O | −44.88 | −28.12 | 60.72 | 19.66 |
| 170 | GLY | N | −44.77 | −28.10 | 58.47 | 15.75 |
| 170 | GLY | CA | −46.21 | −28.00 | 58.36 | 13.53 |
| 170 | GLY | C | −46.70 | −28.03 | 56.94 | 14.99 |
| 170 | GLY | O | −46.13 | −28.72 | 56.09 | 14.31 |
| 171 | ILE | N | −47.70 | −27.21 | 56.66 | 17.47 |
| 171 | ILE | CA | −48.28 | −27.14 | 55.33 | 23.06 |
| 171 | ILE | CB | −49.37 | −28.23 | 55.17 | 25.40 |
| 171 | ILE | CG2 | −50.56 | −27.93 | 56.06 | 30.02 |
| 171 | ILE | CG1 | −49.86 | −28.31 | 53.73 | 33.16 |

TABLE VII-continued

Table of the orthogonal three dimensional coordinates in Ångstroms and B factors (Å$^2$) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| Residue | | Atom | X | Y | Z | B |
|---|---|---|---|---|---|---|
| 171 | ILE | CD1 | −49.86 | −29.73 | 53.19 | 37.53 |
| 171 | ILE | C | −48.86 | −25.75 | 55.07 | 21.85 |
| 171 | ILE | O | −49.14 | −25.02 | 56.01 | 26.83 |
| 172 | GLN | N | −48.95 | −25.33 | 53.81 | 24.21 |
| 172 | GLN | CA | −49.52 | −24.03 | 53.46 | 24.63 |
| 172 | GLN | CB | −48.53 | −22.88 | 53.66 | 22.98 |
| 172 | GLN | CG | −49.13 | −21.50 | 53.34 | 24.04 |
| 172 | GLN | CD | −48.15 | −20.35 | 53.49 | 25.53 |
| 172 | GLN | OE1 | −47.37 | −20.30 | 54.45 | 30.09 |
| 172 | GLN | NE2 | −48.17 | −19.42 | 52.55 | 28.42 |
| 172 | GLN | C | −50.02 | −24.03 | 52.02 | 25.83 |
| 172 | GLN | O | −49.24 | −24.28 | 51.09 | 28.71 |
| 173 | LYS | N | −51.32 | −23.80 | 51.83 | 23.80 |
| 173 | LYS | CA | −51.91 | −23.78 | 50.49 | 22.33 |
| 173 | LYS | CB | −51.58 | −22.46 | 49.78 | 22.26 |
| 173 | LYS | CG | −52.35 | −21.23 | 50.29 | 26.56 |
| 173 | LYS | CD | −53.81 | −21.23 | 49.80 | 30.52 |
| 173 | LYS | CE | −54.48 | −19.85 | 49.89 | 29.44 |
| 173 | LYS | NZ | −54.64 | −19.30 | 51.27 | 28.52 |
| 173 | LYS | C | −51.45 | −24.98 | 49.66 | 21.89 |
| 173 | LYS | O | −51.02 | −24.84 | 48.52 | 22.66 |
| 174 | GLY | N | −51.49 | −26.16 | 50.27 | 21.87 |
| 174 | GLY | CA | −51.08 | −27.38 | 49.61 | 20.01 |
| 174 | GLY | C | −49.59 | −27.70 | 49.71 | 19.12 |
| 174 | GLY | O | −49.18 | −28.85 | 49.49 | 14.08 |
| 175 | ASN | N | −48.79 | −26.71 | 50.06 | 19.25 |
| 175 | ASN | CA | −47.34 | −26.90 | 50.16 | 22.03 |
| 175 | ASN | CB | −46.59 | −25.65 | 49.70 | 23.43 |
| 175 | ASN | CG | −47.13 | −25.08 | 48.40 | 26.87 |
| 175 | ASN | OD1 | −46.80 | −25.56 | 47.31 | 24.31 |
| 175 | ASN | ND2 | −47.96 | −24.04 | 48.52 | 27.46 |
| 175 | ASN | C | −46.85 | −27.30 | 51.56 | 22.36 |
| 175 | ASN | O | −46.95 | −26.52 | 52.51 | 22.73 |
| 176 | LYS | N | −46.34 | −28.52 | 51.69 | 18.82 |
| 176 | LYS | CA | −45.79 | −28.98 | 52.95 | 18.15 |
| 176 | LYS | CB | −45.64 | −30.50 | 52.97 | 19.27 |
| 176 | LYS | CG | −46.95 | −31.32 | 53.07 | 21.41 |
| 176 | LYS | CD | −46.63 | −32.84 | 52.96 | 17.01 |
| 176 | LYS | CE | −47.83 | −33.72 | 53.27 | 21.32 |
| 176 | LYS | NZ | −48.07 | −33.97 | 54.73 | 17.44 |
| 176 | LYS | C | −44.42 | −28.30 | 53.03 | 20.70 |
| 176 | LYS | O | −43.56 | −28.53 | 52.17 | 21.72 |
| 177 | HIS | N | −44.19 | −27.51 | 54.08 | 18.91 |
| 177 | HIS | CA | −42.93 | −26.78 | 54.26 | 13.73 |
| 177 | HIS | CB | −43.18 | −25.28 | 54.19 | 16.90 |
| 177 | HIS | CG | −44.04 | −24.76 | 55.30 | 17.13 |
| 177 | HIS | CD2 | −43.77 | −24.55 | 56.62 | 20.36 |
| 177 | HIS | ND1 | −45.37 | −24.39 | 55.13 | 20.15 |
| 177 | HIS | CE1 | −45.87 | −23.99 | 56.28 | 21.57 |
| 177 | HIS | NE2 | −44.92 | −24.08 | 57.20 | 21.14 |
| 177 | HIS | C | −42.20 | −27.08 | 55.56 | 13.57 |
| 177 | HIS | O | −42.71 | −27.80 | 56.42 | 15.98 |
| 178 | TRP | N | −41.05 | −26.45 | 55.74 | 11.27 |
| 178 | TRP | CA | −40.27 | −26.56 | 56.97 | 10.08 |
| 178 | TRP | CB | −38.80 | −26.95 | 56.72 | 13.29 |
| 178 | TRP | CG | −38.53 | −28.36 | 56.29 | 9.82 |
| 178 | TRP | CD2 | −38.48 | −29.53 | 57.12 | 13.57 |
| 178 | TRP | CE2 | −38.10 | −30.61 | 56.30 | 13.92 |
| 178 | TRP | CE3 | −38.73 | −29.77 | 58.48 | 15.49 |
| 178 | TRP | CD1 | −38.19 | −28.77 | 55.04 | 12.10 |
| 178 | TRP | NE1 | −37.93 | −30.12 | 55.03 | 13.58 |
| 178 | TRP | CZ2 | −37.95 | −31.92 | 56.79 | 14.49 |
| 178 | TRP | CZ3 | −38.58 | −31.07 | 58.97 | 16.39 |
| 178 | TRP | CH2 | −38.19 | −32.13 | 58.12 | 16.81 |
| 178 | TRP | C | −40.31 | −25.13 | 57.51 | 10.66 |
| 178 | TRP | O | −40.55 | −24.19 | 56.75 | 11.76 |
| 179 | ILE | N | −40.13 | −24.95 | 58.82 | 11.11 |
| 179 | ILE | CA | −40.11 | −23.61 | 59.41 | 9.30 |
| 179 | ILE | CB | −40.99 | −23.50 | 60.66 | 11.02 |
| 179 | ILE | CG2 | −40.96 | −22.10 | 61.21 | 3.09 |
| 179 | ILE | CG1 | −42.44 | −23.88 | 60.33 | 9.87 |
| 179 | ILE | CD1 | −43.38 | −23.79 | 61.52 | 10.20 |
| 179 | ILE | C | −38.66 | −23.46 | 59.79 | 10.91 |
| 179 | ILE | O | −38.13 | −24.27 | 60.55 | 13.14 |
| 180 | ILE | N | −38.01 | −22.45 | 59.23 | 12.47 |
| 180 | ILE | CA | −36.60 | −22.25 | 59.48 | 10.39 |
| 180 | ILE | CB | −35.84 | −22.35 | 58.14 | 4.50 |
| 180 | ILE | CG2 | −34.41 | −21.90 | 58.27 | 4.54 |
| 180 | ILE | CG1 | −35.91 | −23.78 | 57.61 | 6.63 |
| 180 | ILE | CD1 | −35.21 | −24.85 | 58.48 | 10.08 |
| 180 | ILE | C | −36.27 | −20.95 | 60.18 | 12.35 |
| 180 | ILE | O | −36.73 | −19.88 | 59.76 | 18.36 |
| 181 | LYS | N | −35.50 | −21.05 | 61.27 | 9.02 |
| 181 | LYS | CA | −35.06 | −19.88 | 62.03 | 6.93 |
| 181 | LYS | CB | −34.92 | −20.19 | 63.52 | 8.20 |
| 181 | LYS | CG | −34.55 | −18.99 | 64.39 | 4.18 |
| 181 | LYS | CD | −34.21 | −19.41 | 65.80 | 5.00 |
| 181 | LYS | CE | −33.83 | −18.23 | 66.69 | 2.00 |
| 181 | LYS | NZ | −33.38 | −18.69 | 68.03 | 2.00 |
| 181 | LYS | C | −33.71 | −19.45 | 61.47 | 6.56 |
| 181 | LYS | O | −32.76 | −20.23 | 61.51 | 9.50 |
| 182 | ASN | N | −33.63 | −18.25 | 60.93 | 6.31 |
| 182 | ASN | CA | −32.38 | −17.79 | 60.36 | 7.51 |
| 182 | ASN | CB | −32.62 | −17.18 | 58.97 | 12.34 |
| 182 | ASN | CG | −31.37 | −17.16 | 58.12 | 13.66 |
| 182 | ASN | OD1 | −30.38 | −17.83 | 58.43 | 13.80 |
| 182 | ASN | ND2 | −31.40 | −16.41 | 57.03 | 14.20 |
| 182 | ASN | C | −31.67 | −16.80 | 61.27 | 8.95 |
| 182 | ASN | O | −32.29 | −16.18 | 62.12 | 9.35 |
| 183 | SER | N | −30.37 | −16.65 | 61.07 | 12.23 |
| 183 | SER | CA | −29.55 | −15.74 | 61.87 | 12.33 |
| 183 | SER | CB | −28.41 | −16.50 | 62.54 | 11.14 |
| 183 | SER | OG | −27.51 | −17.06 | 61.60 | 2.83 |
| 183 | SER | C | −29.03 | −14.56 | 61.05 | 17.18 |
| 183 | SER | O | −27.84 | −14.23 | 61.12 | 14.11 |
| 184 | TRP | N | −29.92 | −13.92 | 60.30 | 20.03 |
| 184 | TRP | CA | −29.59 | −12.77 | 59.45 | 17.75 |
| 184 | TRP | CB | −29.94 | −13.03 | 57.99 | 17.44 |
| 184 | TRP | CG | −28.96 | −13.87 | 57.26 | 11.74 |
| 184 | TRP | CD2 | −29.09 | −14.40 | 55.93 | 10.49 |
| 184 | TRP | CE2 | −27.91 | −15.11 | 55.65 | 11.82 |
| 184 | TRP | CE3 | −30.09 | −14.34 | 54.96 | 7.76 |
| 184 | TRP | CD1 | −27.75 | −14.27 | 57.71 | 13.64 |
| 184 | TRP | NE1 | −27.11 | −15.01 | 56.76 | 18.22 |
| 184 | TRP | CZ2 | −27.70 | −15.76 | 54.44 | 8.06 |
| 184 | TRP | CZ3 | −29.88 | −14.99 | 53.75 | 8.86 |
| 184 | TRP | CH2 | −28.70 | −15.69 | 53.50 | 6.44 |
| 184 | TRP | C | −30.30 | −11.51 | 59.91 | 18.70 |
| 184 | TRP | O | −30.21 | −10.47 | 59.27 | 18.61 |
| 185 | GLY | N | −31.05 | −11.62 | 61.01 | 19.92 |
| 185 | GLY | CA | −31.75 | −10.48 | 61.55 | 17.99 |
| 185 | GLY | C | −33.25 | −10.62 | 61.47 | 21.34 |
| 185 | GLY | O | −33.78 | −11.41 | 60.68 | 24.20 |
| 186 | GLU | N | −33.94 | −9.85 | 62.30 | 25.86 |
| 186 | GLU | CA | −35.39 | −9.85 | 62.34 | 28.63 |
| 186 | GLU | CB | −35.92 | −9.06 | 63.55 | 33.72 |
| 186 | GLU | CG | −37.35 | −9.41 | 64.01 | 33.62 |
| 186 | GLU | CD | −37.39 | −10.59 | 64.97 | 33.61 |
| 186 | GLU | OE1 | −36.64 | −10.57 | 65.96 | 35.89 |
| 186 | GLU | OE2 | −38.18 | −11.54 | 64.74 | 33.82 |
| 186 | GLU | C | −35.93 | −9.26 | 61.04 | 27.44 |
| 186 | GLU | O | −37.08 | −9.48 | 60.68 | 29.63 |
| 187 | ASN | N | −35.09 | −8.50 | 60.33 | 28.18 |
| 187 | ASN | CA | −35.54 | −7.88 | 59.08 | 30.53 |
| 187 | ASN | CB | −35.10 | −6.41 | 58.99 | 33.02 |
| 187 | ASN | CG | −36.04 | −5.57 | 58.12 | 36.45 |
| 187 | ASN | OD1 | −35.65 | −4.51 | 57.62 | 41.13 |
| 187 | ASN | ND2 | −37.28 | −6.03 | 57.95 | 34.46 |
| 187 | ASN | C | −35.20 | −8.65 | 57.79 | 29.17 |
| 187 | ASN | O | −35.12 | −8.08 | 56.69 | 26.38 |

TABLE VII-continued

Table of the orthogonal three dimensional coordinates in Ångstroms and B factors (Å²) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| Residue | | Atom | X | Y | Z | B |
|---|---|---|---|---|---|---|
| 188 | TRP | N | -34.95 | -9.94 | 57.93 | 26.78 |
| 188 | TRP | CA | -34.69 | -10.76 | 56.76 | 22.32 |
| 188 | TRP | CB | -33.39 | -11.54 | 56.84 | 20.90 |
| 188 | TRP | CG | -33.28 | -12.47 | 55.69 | 18.19 |
| 188 | TRP | CD2 | -33.78 | -13.82 | 55.64 | 20.16 |
| 188 | TRP | CE2 | -33.53 | -14.30 | 54.34 | 16.93 |
| 188 | TRP | CE3 | -34.43 | -14.65 | 56.56 | 15.73 |
| 188 | TRP | CD1 | -32.75 | -12.21 | 54.46 | 12.09 |
| 188 | TRP | NE1 | -32.90 | -13.31 | 53.64 | 17.84 |
| 188 | TRP | CZ2 | -33.90 | -15.58 | 53.94 | 18.81 |
| 188 | TRP | CZ3 | -34.79 | -15.92 | 56.17 | 18.58 |
| 188 | TRP | CH2 | -34.53 | -16.38 | 54.87 | 19.87 |
| 188 | TRP | C | -35.87 | -11.70 | 56.68 | 21.57 |
| 188 | TRP | O | -36.40 | -12.11 | 57.72 | 19.48 |
| 189 | GLY | N | -36.28 | -12.04 | 55.46 | 22.26 |
| 189 | GLY | CA | -37.41 | -12.93 | 55.26 | 19.03 |
| 189 | GLY | C | -38.59 | -12.53 | 56.12 | 16.83 |
| 189 | GLY | O | -38.70 | -11.37 | 56.51 | 16.64 |
| 190 | ASN | N | -39.44 | -13.48 | 56.47 | 19.64 |
| 190 | ASN | CA | -40.60 | -13.17 | 57.30 | 21.04 |
| 190 | ASN | CB | -41.76 | -14.13 | 57.02 | 18.69 |
| 190 | ASN | CG | -43.09 | -13.58 | 57.49 | 20.80 |
| 190 | ASN | OD1 | -43.14 | -12.58 | 58.20 | 25.63 |
| 190 | ASN | ND2 | -44.18 | -14.23 | 57.09 | 16.08 |
| 190 | ASN | C | -40.20 | -13.18 | 58.78 | 20.26 |
| 190 | ASN | O | -40.08 | -14.23 | 59.39 | 21.80 |
| 191 | LYS | N | -39.91 | -11.99 | 59.31 | 19.09 |
| 191 | LYS | CA | -39.51 | -11.81 | 60.71 | 17.89 |
| 191 | LYS | CB | -40.69 | -11.99 | 61.66 | 19.60 |
| 191 | LYS | CG | -41.88 | -11.07 | 61.39 | 20.04 |
| 191 | LYS | CD | -43.02 | -11.37 | 62.36 | 17.35 |
| 191 | LYS | CE | -44.34 | -10.84 | 61.84 | 16.88 |
| 191 | LYS | NZ | -45.47 | -11.13 | 62.77 | 17.42 |
| 191 | LYS | C | -38.33 | -12.71 | 61.12 | 14.97 |
| 191 | LYS | O | -38.28 | -13.22 | 62.23 | 11.80 |
| 192 | GLY | N | -37.38 | -12.87 | 60.20 | 16.54 |
| 192 | GLY | CA | -36.20 | -13.67 | 60.47 | 10.79 |
| 192 | GLY | C | -36.40 | -15.14 | 60.19 | 12.10 |
| 192 | GLY | O | -35.53 | -15.94 | 60.52 | 14.29 |
| 193 | TYR | N | -37.53 | -15.50 | 59.59 | 15.02 |
| 193 | TYR | CA | -37.82 | -16.91 | 59.26 | 15.85 |
| 193 | TYR | CB | -39.02 | -17.45 | 60.08 | 19.04 |
| 193 | TYR | CG | -38.75 | -17.68 | 61.55 | 20.49 |
| 193 | TYR | CD1 | -38.79 | -16.64 | 62.45 | 23.39 |
| 193 | TYR | CE1 | -38.52 | -16.84 | 63.79 | 24.79 |
| 193 | TYR | CD2 | -38.43 | -18.95 | 62.02 | 21.17 |
| 193 | TYR | CE2 | -38.15 | -19.17 | 63.36 | 22.23 |
| 193 | TYR | CZ | -38.19 | -18.11 | 64.24 | 24.79 |
| 193 | TYR | OH | -37.88 | -18.29 | 65.56 | 25.50 |
| 193 | TYR | C | -38.11 | -17.13 | 57.77 | 14.84 |
| 193 | TYR | O | -38.58 | -16.22 | 57.07 | 11.51 |
| 194 | ILE | N | -37.90 | -18.36 | 57.33 | 16.12 |
| 194 | ILE | CA | -38.16 | -18.78 | 55.96 | 14.70 |
| 194 | ILE | CB | -36.84 | -18.88 | 55.15 | 17.12 |
| 194 | ILE | CG2 | -35.85 | -19.82 | 55.81 | 13.78 |
| 194 | ILE | CG1 | -37.11 | -19.29 | 53.70 | 15.67 |
| 194 | ILE | CD1 | -35.97 | -18.96 | 52.77 | 13.44 |
| 194 | ILE | C | -38.92 | -20.12 | 55.97 | 12.70 |
| 194 | ILE | O | -38.59 | -21.02 | 56.73 | 11.58 |
| 195 | LEU | N | -39.99 | -20.21 | 55.18 | 12.52 |
| 195 | LEU | CA | -40.79 | -21.43 | 55.09 | 12.23 |
| 195 | LEU | CB | -42.27 | -21.12 | 54.93 | 12.99 |
| 195 | LEU | CG | -42.88 | -20.23 | 55.99 | 16.19 |
| 195 | LEU | CD1 | -44.36 | -20.05 | 55.68 | 16.70 |
| 195 | LEU | CD2 | -42.69 | -20.87 | 57.36 | 17.95 |
| 195 | LEU | C | -40.36 | -22.30 | 53.93 | 10.25 |
| 195 | LEU | O | -41.15 | -22.59 | 53.05 | 15.85 |
| 196 | MET | N | -39.12 | -22.76 | 53.96 | 9.10 |
| 196 | MET | CA | -38.58 | -23.59 | 52.89 | 9.39 |
| 196 | MET | CB | -37.15 | -23.99 | 53.20 | 8.97 |
| 196 | MET | CG | -36.23 | -22.80 | 53.29 | 8.78 |
| 196 | MET | SD | -34.62 | -23.28 | 53.80 | 18.24 |
| 196 | MET | CE | -33.88 | -23.71 | 52.24 | 8.14 |
| 196 | MET | C | -39.43 | -24.79 | 52.52 | 10.25 |
| 196 | MET | O | -40.21 | -25.27 | 53.33 | 13.91 |
| 197 | ALA | N | -39.26 | -25.28 | 51.30 | 11.72 |
| 197 | ALA | CA | -40.03 | -26.42 | 50.82 | 12.43 |
| 197 | ALA | CB | -39.92 | -26.52 | 49.30 | 7.27 |
| 197 | ALA | C | -39.62 | -27.73 | 51.49 | 13.38 |
| 197 | ALA | O | -38.45 | -27.92 | 51.85 | 11.55 |
| 198 | ARG | N | -40.58 | -28.64 | 51.65 | 11.95 |
| 198 | ARG | CA | -40.38 | -29.92 | 52.30 | 13.06 |
| 198 | ARG | CB | -41.05 | -29.94 | 53.69 | 14.09 |
| 198 | ARG | CG | -41.05 | -31.27 | 54.39 | 5.88 |
| 198 | ARG | CD | -41.44 | -31.09 | 55.84 | 6.02 |
| 198 | ARG | NE | -42.82 | -30.68 | 56.02 | 3.48 |
| 198 | ARG | CZ | -43.85 | -31.52 | 56.05 | 6.84 |
| 198 | ARG | NH1 | -43.64 | -32.82 | 55.89 | 2.00 |
| 198 | ARG | NH2 | -45.07 | -31.08 | 56.35 | 2.52 |
| 198 | ARG | C | -40.94 | -31.02 | 51.43 | 12.96 |
| 198 | ARG | O | -41.97 | -30.84 | 50.78 | 15.58 |
| 199 | ASN | N | -40.29 | -32.18 | 51.47 | 12.90 |
| 199 | ASN | CA | -40.66 | -33.34 | 50.66 | 13.45 |
| 199 | ASN | CB | -42.17 | -33.57 | 50.63 | 17.26 |
| 199 | ASN | CG | -42.69 | -34.17 | 51.91 | 22.47 |
| 199 | ASN | OD1 | -42.08 | -35.09 | 52.47 | 20.71 |
| 199 | ASN | ND2 | -43.83 | -33.68 | 52.36 | 26.83 |
| 199 | ASN | C | -40.12 | -33.20 | 49.24 | 12.34 |
| 199 | ASN | O | -39.63 | -34.18 | 48.69 | 12.85 |
| 200 | LYS | N | -40.22 | -32.00 | 48.68 | 10.89 |
| 200 | LYS | CA | -39.73 | -31.64 | 47.34 | 8.22 |
| 200 | LYS | CB | -39.86 | -30.13 | 47.11 | 8.55 |
| 200 | LYS | CG | -41.26 | -29.57 | 47.04 | 5.90 |
| 200 | LYS | CD | -41.97 | -30.04 | 45.79 | 9.80 |
| 200 | LYS | CE | -43.07 | -29.09 | 45.40 | 9.34 |
| 200 | LYS | NZ | -42.51 | -27.88 | 44.72 | 10.27 |
| 200 | LYS | C | -38.29 | -32.09 | 47.02 | 7.56 |
| 200 | LYS | O | -37.43 | -31.27 | 46.71 | 5.62 |
| 201 | ASN | N | -38.05 | -33.39 | 47.07 | 9.28 |
| 201 | ASN | CA | -36.76 | -33.99 | 46.79 | 10.44 |
| 201 | ASN | CB | -36.58 | -34.11 | 45.28 | 12.24 |
| 201 | ASN | CG | -37.80 | -34.72 | 44.61 | 16.00 |
| 201 | ASN | OD1 | -38.18 | -35.86 | 44.91 | 12.64 |
| 201 | ASN | ND2 | -38.47 | -33.93 | 43.78 | 14.00 |
| 201 | ASN | C | -35.55 | -33.38 | 47.47 | 10.11 |
| 201 | ASN | O | -34.60 | -32.95 | 46.82 | 11.93 |
| 202 | ASN | N | -35.59 | -33.36 | 48.80 | 11.90 |
| 202 | ASN | CA | -34.50 | -32.83 | 49.61 | 9.85 |
| 202 | ASN | CB | -33.31 | -33.79 | 49.55 | 13.31 |
| 202 | ASN | CG | -32.38 | -33.63 | 50.72 | 13.23 |
| 202 | ASN | OD1 | -32.82 | -33.40 | 51.84 | 16.24 |
| 202 | ASN | ND2 | -31.09 | -33.81 | 50.47 | 7.73 |
| 202 | ASN | C | -34.09 | -31.43 | 49.19 | 10.35 |
| 202 | ASN | O | -32.90 | -31.12 | 49.17 | 13.84 |
| 203 | ALA | N | -35.05 | -30.59 | 48.88 | 15.00 |
| 203 | ALA | H | -35.55 | -31.01 | 49.01 | 15.00 |
| 203 | ALA | CA | -34.83 | -29.22 | 48.41 | 15.00 |
| 203 | ALA | CB | -35.54 | -28.63 | 48.10 | 15.00 |
| 203 | ALA | C | -33.66 | -28.58 | 49.16 | 15.00 |
| 203 | ALA | O | -33.48 | -28.72 | 50.36 | 18.81 |
| 204 | CYS | N | -32.82 | -27.85 | 48.40 | 16.60 |
| 204 | CYS | CA | -31.68 | -27.12 | 48.94 | 13.11 |
| 204 | CYS | C | -30.69 | -27.92 | 49.78 | 13.70 |
| 204 | CYS | O | -29.77 | -27.35 | 50.36 | 13.59 |
| 204 | CYS | CB | -32.14 | -25.88 | 49.70 | 11.09 |
| 204 | CYS | SG | -32.81 | -24.55 | 48.65 | 21.00 |
| 205 | GLY | N | -30.86 | -29.23 | 49.82 | 15.46 |
| 205 | GLY | CA | -29.96 | -30.07 | 50.60 | 17.31 |
| 205 | GLY | C | -30.16 | -29.87 | 52.09 | 18.03 |
| 205 | GLY | O | -29.21 | -29.94 | 52.87 | 16.28 |

TABLE VII-continued

Table of the orthogonal three dimensional coordinates in Ångstroms and B factors (Å²) for the cathepsin K complex with inhibitor 4-[N-[(phenylmethoxy)carbonyl]-L-leucyl]-1-[N-[(phenylmethoxy)carbonyl]-L-leucyl]-3-pyrrolidinone

| Residue | Atom | X | Y | Z | B |
|---|---|---|---|---|---|
| 206 | ILE | N | −31.42 | −29.72 | 52.49 | 18.33 |
| 206 | ILE | CA | −31.76 | −29.48 | 53.88 | 18.94 |
| 206 | ILE | CB | −33.23 | −28.93 | 54.04 | 19.06 |
| 206 | ILE | CG2 | −34.22 | −29.85 | 53.34 | 18.93 |
| 206 | ILE | CG1 | −33.59 | −28.78 | 55.52 | 14.65 |
| 206 | ILE | CD1 | −34.76 | −27.88 | 55.75 | 16.36 |
| 206 | ILE | C | −31.52 | −30.66 | 54.82 | 21.37 |
| 206 | ILE | O | −31.03 | −30.47 | 55.94 | 21.08 |
| 267 | ALA | N | −31.79 | −31.88 | 54.34 | 20.23 |
| 207 | ALA | CA | −31.63 | −33.08 | 55.16 | 19.58 |
| 207 | ALA | CB | −32.79 | −34.05 | 54.92 | 20.40 |
| 207 | ALA | C | −30.29 | −33.82 | 55.03 | 17.00 |
| 207 | ALA | O | −30.18 | −34.98 | 55.38 | 15.14 |
| 208 | ASN | N | −29.26 | −33.13 | 54.55 | 17.17 |
| 208 | ASN | CA | −27.97 | −33.79 | 54.42 | 16.44 |
| 208 | ASN | CB | −27.26 | −33.40 | 53.11 | 16.56 |
| 208 | ASN | CG | −27.95 | 33.93 | 51.86 | 12.14 |
| 208 | ASN | OD1 | −28.79 | −34.83 | 51.91 | 6.67 |
| 208 | ASN | ND2 | −27.58 | −33.36 | 50.72 | 12.22 |
| 208 | ASN | C | −27.01 | −33.56 | 55.59 | 16.20 |
| 208 | ASN | O | −26.14 | −34.39 | 55.83 | 19.88 |
| 209 | LEU | N | −27.14 | −32.44 | 56.30 | 11.98 |
| 209 | LEU | CA | −26.22 | −32.16 | 57.40 | 12.42 |
| 209 | LEU | CB | −25.19 | −31.10 | 56.96 | 11.33 |
| 209 | LEU | CG | −23.81 | −31.03 | 57.61 | 6.60 |
| 209 | LEU | CD1 | −23.24 | −32.42 | 57.81 | 6.26 |
| 209 | LEU | CD2 | −22.89 | −30.23 | 56.73 | 6.70 |
| 209 | LEU | C | −26.87 | −31.77 | 58.73 | 14.26 |
| 209 | LEU | O | −26.32 | −30.96 | 59.48 | 15.18 |
| 210 | ALA | N | −27.99 | −32.44 | 59.08 | 15.00 |
| 210 | ALA | H | −28.41 | −32.84 | 58.30 | 15.00 |
| 210 | ALA | CA | −28.76 | −32.10 | 60.27 | 15.00 |
| 210 | ALA | CB | −30.25 | −32.37 | 60.06 | 15.00 |
| 210 | ALA | C | −28.31 | −32.97 | 61.45 | 15.00 |
| 210 | ALA | O | −28.07 | −34.16 | 61.40 | 11.82 |
| 211 | SER | N | −28.32 | −32.32 | 62.66 | 12.69 |
| 211 | SER | CA | −27.97 | −33.00 | 63.90 | 11.35 |
| 211 | SER | CB | −26.47 | −33.22 | 64.03 | 10.79 |
| 211 | SER | OG | −25.80 | −32.01 | 64.32 | 5.14 |
| 211 | SER | C | −28.50 | −32.25 | 65.11 | 11.89 |
| 211 | SER | O | −28.51 | −31.01 | 65.14 | 11.91 |
| 212 | PHE | N | −28.97 | −32.99 | 66.09 | 12.57 |
| 212 | PHE | CA | −29.47 | −32.38 | 67.31 | 11.64 |
| 212 | PHE | CB | −30.95 | −32.69 | 67.51 | 12.77 |
| 212 | PHE | CG | −31.27 | −34.12 | 67.44 | 11.84 |
| 212 | PHE | CD1 | −31.61 | −34.70 | 66.24 | 10.42 |
| 212 | PHE | CD2 | −31.23 | −34.91 | 68.58 | 14.45 |
| 212 | PHE | CE1 | −31.91 | −36.03 | 66.17 | 16.06 |
| 212 | PHE | CE2 | −31.53 | −36.24 | 68.53 | 15.41 |
| 212 | PHE | CZ | −31.87 | −36.81 | 67.32 | 16.55 |
| 212 | PHE | C | −28.61 | −32.83 | 68.48 | 12.10 |
| 212 | PHE | O | −27.91 | −33.85 | 68.41 | 12.03 |
| 213 | PRO | N | −28.60 | −32.05 | 69.57 | 12.99 |
| 213 | PRO | CD | −29.24 | −30.73 | 69.77 | 10.69 |
| 213 | PRO | CA | −27.79 | −32.41 | 70.74 | 12.29 |
| 213 | PRO | CB | −27.41 | −31.05 | 71.29 | 11.67 |
| 213 | PRO | CG | −28.70 | −30.29 | 71.12 | 14.62 |
| 213 | PRO | C | −28.56 | −33.23 | 71.75 | 12.17 |
| 213 | PRO | O | −29.78 | −33.11 | 71.88 | 2.00 |
| 214 | LYS | N | −27.82 | −34.09 | 72.45 | 14.45 |
| 214 | LYS | CA | −28.39 | −34.94 | 73.50 | 19.77 |
| 214 | LYS | CB | −27.80 | −31.34 | 73.46 | 20.65 |
| 214 | LYS | CG | −28.06 | −37.08 | 72.17 | 24.16 |
| 214 | LYS | CD | −27.54 | −38.52 | 72.24 | 29.93 |
| 214 | LYS | CE | −26.02 | −38.57 | 72.40 | 33.14 |
| 214 | LYS | NZ | −25.49 | −39.97 | 72.44 | 35.37 |
| 214 | LYS | C | −28.15 | −34.26 | 74.84 | 21.45 |
| 214 | LYS | O | −27.02 | −33.92 | 75.20 | 16.74 |
| 215 | MET | N | −29.23 | −34.05 | 75.57 | 22.65 |
| 215 | MET | CA | −29.16 | −33.38 | 76.85 | 25.38 |
| 215 | MET | CB | −30.04 | −32.13 | 76.79 | 27.81 |
| 215 | MET | CG | −29.77 | −31.09 | 77.85 | 26.22 |
| 215 | MET | SD | −30.44 | −29.54 | 77.29 | 25.84 |
| 215 | MET | CE | −28.92 | −28.76 | 76.63 | 23.17 |
| 215 | MET | C | −29.56 | −34.30 | 77.99 | 25.33 |
| 215 | MET | OT1 | −28.65 | −34.77 | 78.71 | 27.00 |
| 215 | MET | OT2 | −30.77 | −34.58 | 78.12 | 23.48 |
| 216 | HOH | OH2 | −31.11 | −16.42 | 65.02 | 14.43 |
| 217 | HOH | OH2 | −29.30 | −20.25 | 62.17 | 18.73 |
| 218 | HOH | OH2 | −10.67 | −12.22 | 63.70 | 43.10 |
| 219 | HOH | OH2 | −16.45 | −12.20 | 72.96 | 5.87 |
| 220 | HOH | OH2 | −35.12 | −23.55 | 69.64 | 9.44 |
| 221 | HOH | OH2 | −24.01 | −30.97 | 61.16 | 4.73 |
| 222 | HOH | OH2 | −13.01 | −8.39 | 61.94 | 32.49 |
| 223 | HOH | OH2 | −14.66 | −21.66 | 66.41 | 2.00 |
| 224 | HOH | OH2 | −43.65 | −26.52 | 48.92 | 29.00 |
| 225 | HOH | OH2 | −45.60 | −35.43 | 55.56 | 13.84 |
| 226 | HOH | OH2 | −40.92 | −17.45 | 68.90 | 12.03 |
| 227 | HOH | OH2 | −43.72 | −25.26 | 44.65 | 38.82 |
| 228 | HOH | OH2 | −24.12 | −5.83 | 68.94 | 43.50 |
| 229 | HOH | OH2 | −30.71 | −18.60 | 67.86 | 32.89 |
| 230 | HOH | OH2 | −35.05 | −26.71 | 51.39 | 30.11 |
| 231 | HOH | OH2 | −36.74 | −24.80 | 49.94 | 8.69 |
| 232 | HOH | OH2 | −46.77 | −33.25 | 57.36 | 12.67 |
| 233 | HOH | OH2 | −28.91 | −10.19 | 75.44 | 15.32 |
| 234 | HOH | OH2 | −36.31 | −14.76 | 75.60 | 16.14 |
| 235 | HOH | OH2 | −16.18 | −4.92 | 68.62 | 27.92 |
| 236 | HOH | OH2 | −16.52 | −8.98 | 75.02 | 28.63 |
| 237 | HOH | OH2 | −10.50 | −18.37 | 70.18 | 39.29 |
| 238 | HOH | OH2 | −9.29 | −19.89 | 78.20 | 29.36 |
| 239 | HOH | OH2 | −45.95 | −16.45 | 54.42 | 32.47 |
| 240 | HOH | OH2 | −33.98 | −29.86 | 44.88 | 32.74 |
| 241 | HOH | OH2 | −36.55 | −38.18 | 52.42 | 11.87 |
| 242 | HOH | OH2 | −41.73 | −34.84 | 55.47 | 18.73 |
| 243 | HOH | OH2 | −41.21 | −19.79 | 71.20 | 12.36 |
| 244 | HOH | OH2 | −47.90 | −19.78 | 72.76 | 27.97 |
| 245 | HOH | OH2 | −42.20 | −14.92 | 70.78 | 34.65 |
| 246 | HOH | OH2 | −26.14 | −8.98 | 67.92 | 37.03 |
| 247 | HOH | OH2 | −32.81 | −7.84 | 63.95 | 35.20 |
| 248 | HOH | OH2 | −19.95 | −7.54 | 63.08 | 32.69 |
| 249 | HOH | OH2 | −16.19 | −10.67 | 61.92 | 30.22 |
| 250 | HOH | OH2 | −35.01 | −39.74 | 65.90 | 10.75 |
| 251 | HOH | OH2 | −13.63 | −24.17 | 76.67 | 16.76 |
| 252 | HOH | OH2 | −8.21 | −25.68 | 60.56 | 19.27 |
| 253 | HOH | OH2 | −20.14 | −27.62 | 51.69 | 32.97 |
| 254 | HOH | OH2 | −25.01 | −33.27 | 60.23 | 25.95 |
| 255 | HOH | OH2 | −13.56 | −29.77 | 72.49 | 36.07 |
| 256 | HOH | OH2 | −33.43 | −40.03 | 63.75 | 25.23 |
| 257 | HOH | OH2 | −20.84 | −23.81 | 87.06 | 28.06 |
| 258 | HOH | OH2 | −13.50 | −12.46 | 62.97 | 41.75 |
| 259 | HOH | OH2 | −28.41 | −30.03 | 56.55 | 11.99 |
| 260 | HOH | OH2 | −28.87 | −16.56 | 42.17 | 23.76 |
| 261 | HOH | OH2 | −25.56 | −19.23 | 42.44 | 8.60 |
| 262 | HOH | OH2 | −32.08 | −33.98 | 47.05 | 47.25 |
| 263 | HOH | OH2 | −22.35 | −31.23 | 43.22 | 18.34 |
| 264 | HOH | OH2 | −32.62 | −28.89 | 42.32 | 42.83 |
| 265 | HOH | OH2 | −38.09 | −30.05 | 50.12 | 38.26 |

TABLE VIII

Table of the orthogonal three dimensional coordinates in Ångstroms and B factors (Å$^2$) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue |  | Atom | X | Y | Z | B |
|---|---|---|---|---|---|---|
| 1 | ALA | CB | −46.30 | −38.07 | 64.13 | 15.00 |
| 1 | ALA | C | −48.64 | −37.16 | 64.46 | 15.00 |
| 1 | ALA | O | −49.53 | −37.68 | 63.79 | 15.00 |
| 1 | ALA | N | −48.10 | −39.41 | 65.31 | 15.00 |
| 1 | ALA | CA | −47.55 | −38.03 | 65.08 | 15.00 |
| 2 | PRO | N | −48.69 | −35.88 | 64.81 | 15.00 |
| 2 | PRO | CD | −48.06 | −35.33 | 66.02 | 15.00 |
| 2 | PRO | CA | −49.67 | −34.93 | 64.29 | 15.00 |
| 2 | PRO | CB | −49.53 | −33.73 | 65.24 | 15.00 |
| 2 | PRO | CG | −48.13 | −33.85 | 65.77 | 15.00 |
| 2 | PRO | C | −49.42 | −34.53 | 62.86 | 15.00 |
| 2 | PRO | O | −48.34 | −34.77 | 62.28 | 15.00 |
| 3 | ASP | N | −50.40 | −33.85 | 62.30 | 15.00 |
| 3 | ASP | CA | −50.29 | −33.37 | 60.93 | 15.00 |
| 3 | ASP | CB | −51.65 | −33.42 | 60.27 | 15.00 |
| 3 | ASP | CG | −52.12 | −34.84 | 60.00 | 15.00 |
| 3 | ASP | OD1 | −52.02 | −35.30 | 58.84 | 15.00 |
| 3 | ASP | OD2 | −52.59 | −35.51 | 60.95 | 15.00 |
| 3 | ASP | C | −49.76 | −31.93 | 61.01 | 15.00 |
| 3 | ASP | O | −49.44 | −31.32 | 59.99 | 15.00 |
| 4 | SER | N | −49.58 | −31.45 | 62.24 | 15.00 |
| 4 | SER | CA | −49.13 | −30.09 | 62.51 | 15.00 |
| 4 | SER | CB | −50.32 | −29.14 | 62.52 | 15.00 |
| 4 | SER | OG | −50.86 | −29.02 | 61.20 | 15.00 |
| 4 | SER | C | −48.39 | −29.96 | 63.84 | 15.00 |
| 4 | SER | O | −48.74 | −30.63 | 64.84 | 15.00 |
| 5 | VAL | N | −47.34 | −29.15 | 63.84 | 15.00 |
| 5 | VAL | CA | −46.50 | −28.91 | 64.99 | 15.00 |
| 5 | VAL | CB | −45.35 | −29.97 | 65.11 | 15.00 |
| 5 | VAL | CG1 | −44.17 | −29.43 | 65.89 | 15.00 |
| 5 | VAL | CG2 | −45.84 | −31.21 | 65.74 | 15.00 |
| 5 | VAL | C | −45.86 | −27.57 | 64.80 | 15.00 |
| 5 | VAL | O | −45.37 | −27.25 | 63.70 | 15.00 |
| 6 | ASP | N | −45.84 | −26.80 | 65.89 | 15.00 |
| 6 | ASP | CA | −45.22 | −25.50 | 65.92 | 15.00 |
| 6 | ASP | CB | −46.16 | −24.37 | 65.46 | 15.00 |
| 6 | ASP | CG | −45.40 | −23.07 | 65.15 | 15.00 |
| 6 | ASP | OD1 | −44.21 | −22.96 | 65.51 | 15.00 |
| 6 | ASP | OD2 | −45.98 | −22.17 | 64.51 | 15.00 |
| 6 | ASP | C | −44.81 | −25.27 | 67.34 | 15.00 |
| 6 | ASP | O | −45.65 | −24.96 | 68.17 | 15.00 |
| 7 | TYR | N | −43.51 | −25.35 | 67.61 | 15.00 |
| 7 | TYR | CA | −43.00 | −25.14 | 68.94 | 15.00 |
| 7 | TYR | CB | −41.63 | −25.80 | 69.13 | 15.00 |
| 7 | TYR | CG | −41.68 | −27.30 | 69.31 | 15.00 |
| 7 | TYR | CD1 | −41.55 | −27.88 | 70.57 | 15.00 |
| 7 | TYR | CE1 | −41.60 | −29.29 | 70.74 | 15.00 |
| 7 | TYR | CD2 | −41.86 | −28.14 | 68.22 | 15.00 |
| 7 | TYR | CE2 | −41.91 | −29.55 | 68.38 | 15.00 |
| 7 | TYR | CZ | −41.79 | −30.10 | 69.64 | 15.00 |
| 7 | TYR | OH | −41.91 | −31.46 | 69.83 | 15.00 |
| 7 | TYR | C | −42.85 | −23.70 | 69.30 | 15.00 |
| 7 | TYR | O | −42.16 | −23.39 | 70.26 | 15.00 |
| 8 | ARG | N | −43.40 | −22.80 | 68.50 | 15.00 |
| 8 | ARG | CA | −43.31 | −21.39 | 68.80 | 15.00 |
| 8 | ARG | CB | −43.55 | −20.55 | 67.56 | 15.00 |
| 8 | ARG | CG | −42.37 | −20.55 | 66.60 | 15.00 |
| 8 | ARG | CD | −42.57 | −19.68 | 65.38 | 15.00 |
| 8 | ARG | NE | −43.64 | −20.20 | 64.53 | 15.00 |
| 8 | ARG | CZ | −43.88 | −19.78 | 63.29 | 15.00 |
| 8 | ARG | NH1 | −43.09 | −18.84 | 62.77 | 15.00 |
| 8 | ARG | NH2 | −44.92 | −20.26 | 62.60 | 15.00 |
| 8 | ARG | C | −44.37 | −21.14 | 69.84 | 15.00 |
| 8 | ARG | O | −44.09 | −20.64 | 70.93 | 15.00 |
| 9 | LYS | N | −45.58 | −21.65 | 69.54 | 15.00 |
| 9 | LYS | CA | −46.73 | −21.55 | 70.42 | 15.00 |
| 9 | LYS | CB | −47.95 | −22.19 | 69.75 | 15.00 |
| 9 | LYS | CC | −48.42 | −21.37 | 68.55 | 15.00 |
| 9 | LYS | CD | −48.71 | −22.24 | 67.29 | 15.00 |
| 9 | LYS | CE | −49.41 | −21.46 | 66.17 | 15.00 |
| 9 | LYS | NZ | −50.87 | −21.36 | 66.45 | 15.00 |
| 9 | LYS | C | −46.44 | −22.17 | 71.79 | 15.00 |
| 9 | LYS | O | −46.36 | −21.45 | 72.77 | 15.00 |
| 10 | LYS | N | −46.15 | −23.46 | 71.83 | 15.00 |
| 10 | LYS | CA | −45.85 | −24.13 | 73.10 | 15.00 |
| 10 | LYS | CB | −45.43 | −25.57 | 72.86 | 15.00 |
| 10 | LYS | CG | −46.52 | −26.39 | 72.25 | 15.00 |
| 10 | LYS | CD | −46.05 | −27.76 | 71.89 | 15.00 |
| 10 | LYS | CE | −46.89 | −28.35 | 70.81 | 15.00 |
| 10 | LYS | NZ | −48.31 | −27.94 | 70.92 | 15.00 |
| 10 | LYS | C | −44.81 | −23.41 | 73.94 | 15.00 |
| 10 | LYS | O | −44.74 | −23.62 | 75.14 | 15.00 |
| 11 | GLY | N | −43.95 | −22.63 | 73.30 | 15.00 |
| 11 | GLY | CA | −42.94 | −21.90 | 74.05 | 15.00 |
| 11 | GLY | C | −41.53 | −22.43 | 74.01 | 15.00 |
| 11 | GLY | O | −40.78 | −22.24 | 74.97 | 15.00 |
| 12 | TYR | N | −41.13 | −23.07 | 72.91 | 15.00 |
| 12 | TYR | CA | −39.76 | −23.60 | 72.84 | 15.00 |
| 12 | TYR | CB | −39.78 | −24.98 | 72.15 | 15.00 |
| 12 | TYR | CG | −40.42 | −26.09 | 72.97 | 15.00 |
| 12 | TYR | CD1 | −41.76 | −26.06 | 73.35 | 15.00 |
| 12 | TYR | CE1 | −42.34 | −27.10 | 74.13 | 15.00 |
| 12 | TYR | CD2 | −39.66 | −27.18 | 73.39 | 15.00 |
| 12 | TYR | CE2 | −40.21 | −28.21 | 74.17 | 15.00 |
| 12 | TYR | CZ | −41.55 | −28.17 | 74.53 | 15.00 |
| 12 | TYR | OH | −42.10 | −29.21 | 75.25 | 15.00 |
| 12 | TYR | C | −38.82 | −22.68 | 72.08 | 15.00 |
| 12 | TYR | O | −37.64 | −22.97 | 71.90 | 15.00 |
| 13 | VAL | N | −39.37 | −21.59 | 71.56 | 15.00 |
| 13 | VAL | CA | −38.56 | −20.71 | 70.75 | 15.0D |
| 13 | VAL | CB | −39.14 | −20.70 | 69.33 | 15.00 |
| 13 | VAL | CG1 | −38.15 | −20.04 | 68.35 | 15.00 |
| 13 | VAL | CG2 | −39.49 | −22.09 | 68.92 | 15.00 |
| 13 | VAL | C | −38.31 | −19.27 | 71.23 | 15.00 |
| 13 | VAL | O | −39.24 | −18.52 | 71.45 | 15.00 |
| 14 | THR | N | −37.03 | −18.90 | 71.32 | 15.00 |
| 14 | THR | CA | −36.64 | −17.56 | 71.76 | 15.00 |
| 14 | THR | CB | −35.17 | −17.57 | 72.25 | 15.00 |
| 14 | THR | OG1 | −34.33 | −18.03 | 71.18 | 15.00 |
| 14 | THR | CG2 | −35.01 | −18.43 | 73.50 | 15.00 |
| 14 | THR | C | −36.70 | −16.58 | 70.60 | 15.00 |
| 14 | THR | O | −37.20 | −16.92 | 69.53 | 15.00 |
| 15 | PRO | N | −36.27 | −15.32 | 70.83 | 15.00 |
| 15 | PRO | CD | −36.21 | −14.64 | 72.14 | 15.00 |
| 15 | PRO | CA | −36.29 | −14.32 | 69.76 | 15.00 |
| 15 | PRO | CB | −35.98 | −13.04 | 70.49 | 15.00 |
| 15 | PRO | CG | −36.64 | −13.24 | 71.83 | 15.00 |
| 15 | PRO | C | −35.23 | −14.60 | 68.72 | 15.00 |
| 15 | PRO | O | −34.20 | −15.21 | 69.02 | 15.00 |
| 16 | VAL | N | −35.48 | −14.05 | 67.52 | 15.00 |
| 16 | VAL | CA | −34.61 | −14.19 | 66.36 | 15.00 |
| 16 | VAL | CB | −35.37 | −13.74 | 65.10 | 15.00 |
| 16 | VAL | CG1 | −34.43 | −13.61 | 63.92 | 15.00 |
| 16 | VAL | CG2 | −36.44 | −14.72 | 64.78 | 15.00 |
| 16 | VAL | C | −33.40 | −13.33 | 66.56 | 15.00 |
| 16 | VAL | O | −33.47 | −12.33 | 67.23 | 15.00 |
| 17 | LYS | N | −32.24 | −13.78 | 66.10 | 15.00 |
| 17 | LYS | CA | −31.04 | −12.97 | 66.26 | 15.00 |
| 17 | LYS | CB | −29.96 | −13.71 | 67.06 | 15.00 |
| 17 | LYS | CG | −30.45 | −14.44 | 68.35 | 15.00 |
| 17 | LYS | CD | −30.63 | −13.52 | 69.54 | 15.00 |
| 17 | LYS | CE | −30.89 | −14.30 | 70.82 | 15.00 |
| 17 | LYS | NZ | −32.14 | −15.10 | 70.83 | 15.00 |
| 17 | LYS | C | −30.46 | −12.58 | 64.91 | 15.00 |
| 17 | LYS | O | −31.06 | −12.84 | 63.87 | 15.00 |
| 18 | ASN | N | −29.30 | −11.94 | 64.94 | 15.00 |
| 18 | ASN | CA | −28.58 | −11.48 | 63.75 | 15.00 |
| 18 | ASN | CB | −28.58 | −9.96 | 63.69 | 15.00 |
| 18 | ASN | CG | −29.93 | −9.39 | 63.96 | 15.00 |
| 18 | ASN | OD1 | −30.89 | −9.75 | 63.32 | 15.00 |

TABLE VIII-continued

Table of the orthogonal three dimensional coordinates in Ångstroms and B factors (Å²) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue | Atom | X | Y | Z | B |
|---|---|---|---|---|---|
| 18 ASN | ND2 | −30.02 | −8.56 | 64.97 | 15.00 |
| 18 ASN | C | −27.16 | −11.93 | 63.99 | 15.00 |
| 18 ASN | O | −26.58 | −11.59 | 65.03 | 15.00 |
| 19 GLN | N | −26.59 | −12.69 | 63.06 | 15.00 |
| 19 GLN | CA | −25.22 | −13.13 | 63.22 | 15.00 |
| 19 GLN | CB | −24.96 | −14.41 | 62.43 | 15.00 |
| 19 GLN | CG | −25.34 | −14.25 | 60.98 | 15.00 |
| 19 GLN | CD | −25.10 | −15.49 | 60.16 | 15.00 |
| 19 GLN | OE1 | −26.04 | −16.20 | 59.82 | 15.00 |
| 19 GLN | NE2 | −23.86 | −15.72 | 59.77 | 15.00 |
| 19 GLN | C | −24.24 | −12.02 | 62.83 | 15.00 |
| 19 GLN | O | −23.05 | −12.15 | 63.08 | 15.00 |
| 20 GLY | N | −24.72 | −11.01 | 62.11 | 15.00 |
| 20 GLY | CA | −23.86 | −9.91 | 61.69 | 15.00 |
| 20 GLY | C | −22.83 | −10.31 | 60.65 | 15.00 |
| 20 GLY | O | −23.08 | −11.26 | 59.94 | 15.00 |
| 21 GLN | N | −21.69 | −9.61 | 60.49 | 15.00 |
| 21 GLN | CA | −20.72 | −10.02 | 59.43 | 15.00 |
| 21 GLN | CB | −20.01 | −8.83 | 58.75 | 15.00 |
| 21 GLN | CG | −20.87 | −8.13 | 57.66 | 15.00 |
| 21 GLN | CD | −21.58 | −9.06 | 56.63 | 15.00 |
| 21 GLN | OE1 | −20.99 | −10.02 | 56.16 | 15.00 |
| 21 GLN | NE2 | −22.84 | −8.74 | 56.29 | 15.00 |
| 21 GLN | C | −19.72 | −11.10 | 59.87 | 15.00 |
| 21 GLN | O | −18.50 | −11.01 | 59.66 | 15.00 |
| 22 CYS | N | −20.32 | −12.22 | 60.26 | 15.00 |
| 22 CYS | CA | −19.59 | −13.37 | 60.72 | 15.00 |
| 22 CYS | C | −20.26 | −14.68 | 60.30 | 15.00 |
| 22 CYS | O | −21.48 | −14.80 | 60.28 | 15.00 |
| 22 CYS | CB | −19.48 | −13.22 | 62.25 | 15.00 |
| 22 CYS | SG | −19.02 | −14.67 | 63.24 | 15.00 |
| 23 GLY | N | −19.45 | −15.65 | 59.90 | 15.00 |
| 23 GLY | CA | −20.01 | −16.93 | 59.52 | 15.00 |
| 23 GLY | C | −20.27 | −17.81 | 60.75 | 15.00 |
| 23 GLY | O | −19.73 | −18.91 | 60.83 | 15.00 |
| 24 SER | N | −21.20 | −17.40 | 61.61 | 15.00 |
| 24 SER | CA | −21.49 | −18.12 | 62.84 | 15.00 |
| 24 SER | CB | −21.32 | −17.21 | 64.08 | 15.00 |
| 24 SER | OG | −22.22 | −16.10 | 64.07 | 15.00 |
| 24 SER | C | −22.89 | −18.73 | 62.86 | 15.00 |
| 24 SER | O | −23.44 | −19.03 | 63.90 | 15.00 |
| 25 CYS | N | −23.46 | −18.96 | 61.69 | 15.00 |
| 25 CYS | CA | −24.78 | −19.55 | 61.56 | 15.00 |
| 25 CYS | CB | −25.18 | −19.59 | 60.07 | 15.00 |
| 25 CYS | SG | −24.19 | −20.73 | 59.02 | 15.00 |
| 25 CYS | C | −24.80 | −20.92 | 62.24 | 15.00 |
| 25 CYS | O | −25.77 | −21.25 | 62.88 | 15.00 |
| 25 INH | C1 | −14.75 | −27.52 | 59.81 | 15.00 |
| 25 INH | C2 | −15.58 | −26.77 | 58.94 | 15.00 |
| 25 INH | C3 | −15.24 | −25.44 | 58.65 | 15.00 |
| 25 INH | C4 | −14.06 | −24.88 | 59.25 | 15.00 |
| 25 INH | C5 | −13.21 | −25.64 | 60.14 | 15.00 |
| 25 INH | C6 | −13.57 | −26.96 | 60.42 | 15.00 |
| 25 INH | C7 | −16.11 | −24.63 | 57.72 | 15.00 |
| 25 INH | O8 | −17.39 | −25.29 | 57.48 | 15.00 |
| 25 INH | C9 | −18.43 | −24.53 | 57.00 | 15.00 |
| 25 INH | O10 | −18.33 | −23.63 | 56.17 | 15.00 |
| 25 INH | N11 | −19.57 | −24.86 | 57.54 | 15.00 |
| 25 INH | C12 | −20.88 | −24.22 | 57.23 | 15.00 |
| 25 INH | C13 | −21.31 | −23.29 | 58.42 | 15.00 |
| 25 INH | N14 | −21.06 | −21.86 | 58.16 | 15.00 |
| 25 INH | C15 | −21.68 | −21.41 | 56.87 | 15.00 |
| 25 INH | C16 | −21.59 | −21.00 | 59.27 | 15.00 |
| 25 INH | C17 | −22.57 | −20.07 | 58.55 | 15.00 |
| 25 INH | C18 | −22.15 | −19.99 | 57.10 | 15.00 |
| 25 INH | C19 | −21.87 | −25.40 | 57.01 | 15.00 |
| 25 INH | C20 | −22.73 | −25.74 | 58.21 | 15.00 |
| 25 INH | C21 | −22.94 | −27.22 | 58.28 | 15.00 |
| 25 INH | C22 | −24.00 | −25.01 | 57.98 | 15.00 |
| 25 INH | N23 | −23.18 | −19.45 | 56.18 | 15.00 |
| 25 INH | C24 | −23.12 | −18.15 | 55.84 | 15.00 |
| 25 INH | O25 | −22.20 | −17.42 | 56.28 | 15.00 |
| 25 INH | C26 | −24.25 | −17.59 | 54.91 | 15.00 |
| 25 INH | C27 | −24.00 | −18.05 | 53.43 | 15.00 |
| 25 INH | C28 | −25.22 | −18.05 | 52.51 | 15.00 |
| 25 INH | C29 | −25.14 | −19.24 | 51.66 | 15.00 |
| 25 INH | C30 | −25.25 | −16.77 | 51.69 | 15.00 |
| 25 INH | N31 | −24.30 | −16.10 | 54.92 | 15.00 |
| 25 INH | C32 | −24.85 | −15.34 | 55.87 | 15.00 |
| 25 INH | O33 | −25.40 | −15.84 | 56.83 | 15.00 |
| 25 INH | O34 | −24.72 | −13.96 | 55.64 | 15.00 |
| 25 INH | C35 | −24.74 | −13.12 | 56.80 | 15.00 |
| 25 INH | C36 | −25.68 | −11.91 | 56.62 | 15.00 |
| 25 INH | C37 | −25.21 | −10.60 | 56.86 | 15.00 |
| 25 INH | C38 | −26.09 | −9.52 | 56.74 | 15.00 |
| 25 INH | N39 | −27.37 | −9.73 | 56.40 | 15.00 |
| 25 INH | C40 | −27.85 | −10.96 | 56.16 | 15.00 |
| 25 INH | C41 | −27.03 | −12.08 | 56.26 | 15.00 |
| 25 INH | O42 | −22.66 | −18.72 | 58.88 | 15.00 |
| 26 TRP | N | −23.72 | −21.69 | 62.15 | 15.00 |
| 26 TRP | CA | −23.64 | −23.01 | 62.85 | 15.00 |
| 26 TRP | CB | −22.30 | −23.65 | 62.59 | 15.00 |
| 26 TRP | CG | −21.18 | −22.75 | 63.06 | 15.00 |
| 26 TRP | CD2 | −20.40 | −22.85 | 64.28 | 15.00 |
| 26 TRP | CE2 | −19.44 | −21.79 | 64.22 | 15.00 |
| 26 TRP | CE3 | −20.41 | −23.71 | 65.38 | 15.00 |
| 26 TRP | CD1 | −20.71 | −21.70 | 62.39 | 15.00 |
| 26 TRP | NE1 | −19.66 | −21.12 | 63.05 | 15.00 |
| 26 TRP | CZ2 | −18.49 | −21.56 | 65.24 | 15.00 |
| 26 TRP | CZ3 | −19.48 | −23.49 | 66.41 | 15.00 |
| 26 TRP | CH2 | −18.52 | −22.41 | 66.33 | 15.00 |
| 26 TRP | C | −23.72 | −22.83 | 64.40 | 15.00 |
| 26 TRP | O | −23.97 | −23.79 | 65.16 | 15.00 |
| 27 ALA | N | −23.39 | −21.64 | 64.91 | 15.00 |
| 27 ALA | CA | −23.50 | −21.43 | 66.36 | 15.00 |
| 27 ALA | CB | −22.70 | −20.24 | 66.80 | 15.00 |
| 27 ALA | C | −24.98 | −21.21 | 66.72 | 15.00 |
| 27 ALA | O | −25.52 | −21.89 | 67.60 | 15.00 |
| 28 PHE | N | −25.63 | −20.27 | 66.03 | 15.00 |
| 28 PHE | CA | −27.02 | −19.90 | 66.31 | 15.00 |
| 28 PHE | CB | −27.46 | −18.71 | 65.44 | 15.00 |
| 28 PHE | CG | −26.88 | −17.40 | 65.85 | 15.00 |
| 28 PHE | CD1 | −25.73 | −16.87 | 65.27 | 15.00 |
| 28 PHE | CD2 | −27.47 | −16.73 | 66.88 | 15.00 |
| 28 PHE | CE1 | −25.16 | −15.71 | 65.70 | 15.00 |
| 28 PHE | CE2 | −26.92 | −15.57 | 67.33 | 15.00 |
| 28 PHE | CZ | −25.75 | −15.04 | 66.75 | 15.00 |
| 28 PHE | C | −27.93 | −21.09 | 66.06 | 15.00 |
| 28 PHE | O | −29.08 | −21.05 | 66.44 | 15.00 |
| 29 SER | N | −27.44 | −22.09 | 65.33 | 15.00 |
| 29 SER | CA | −28.24 | −23.28 | 65.05 | 15.00 |
| 29 SER | CB | −27.74 | −23.99 | 63.81 | 15.00 |
| 29 SER | OG | −28.44 | −25.21 | 63.58 | 15.00 |
| 29 SER | C | −28.13 | −24.15 | 66.27 | 15.00 |
| 29 SER | 0 | −29.14 | −24.63 | 66.79 | 15.00 |
| 30 SER | N | −26.90 | −24.31 | 66.76 | 15.00 |
| 30 SER | CA | −26.64 | −25.13 | 67.94 | 15.00 |
| 30 SER | CB | −25.14 | −25.24 | 68.21 | 15.00 |
| 30 SER | OG | −24.40 | −25.67 | 67.06 | 15.00 |
| 30 SER | C | −27.29 | −24.63 | 69.21 | 15.00 |
| 30 SER | C | −27.66 | −25.40 | 70.08 | 15.00 |
| 31 VAL | N | −27.31 | −23.32 | 69.35 | 15.00 |
| 31 VAL | CA | −27.89 | −22.67 | 70.51 | 15.00 |
| 31 VAL | CB | −27.39 | −21.19 | 70.58 | 15.00 |
| 31 VAL | CG1 | −28.13 | −20.34 | 71.59 | 15.00 |
| 31 VAL | CG2 | −25.91 | −21.19 | 70.86 | 15.00 |
| 31 VAL | C | −29.41 | −22.80 | 70.55 | 15.00 |
| 31 VAL | O | −30.02 | −22.96 | 71.63 | 15.00 |
| 32 GLY | N | −29.99 | −22.81 | 69.35 | 15.00 |
| 32 GLY | CA | −31.43 | −22.91 | 69.21 | 15.00 |

TABLE VIII-continued

Table of the orthogonal three dimensional coordinates in Ångstroms and B factors (Å$^2$) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue | Atom | X | Y | Z | B |
|---|---|---|---|---|---|
| 32 GLY | C | −31.90 | −24.26 | 69.66 | 15.00 |
| 32 GLY | O | −32.81 | −24.39 | 70.47 | 15.00 |
| 33 ALA | N | −31.22 | −25.29 | 69.17 | 15.00 |
| 33 ALA | CA | −31.51 | −26.66 | 69.53 | 15.00 |
| 33 ALA | CB | −30.58 | −27.55 | 68.80 | 15.00 |
| 33 ALA | C | −31.38 | −26.86 | 71.06 | 15.00 |
| 33 ALA | O | −32.23 | −27.54 | 71.68 | 15.00 |
| 34 LEU | N | −30.29 | −26.34 | 71.63 | 15.00 |
| 34 LEU | CA | −30.03 | −26.45 | 73.05 | 15.00 |
| 34 LEU | CB | −28.72 | −25.82 | 73.41 | 15.00 |
| 34 LEU | CG | −27.43 | −26.58 | 73.17 | 15.00 |
| 34 LEU | CD1 | −26.28 | −25.63 | 73.53 | 15.00 |
| 34 LEU | CD2 | −27.38 | −27.85 | 74.05 | 15.00 |
| 34 LEU | C | −31.12 | −25.73 | 73.83 | 15.00 |
| 34 LEU | O | −31.65 | −26.29 | 74.80 | 15.00 |
| 35 GLU | N | −31.47 | −24.51 | 73.44 | 15.00 |
| 35 GLU | CA | −32.54 | −23.76 | 74.12 | 15.00 |
| 35 GLU | CB | −32.78 | −22.42 | 73.41 | 15.00 |
| 35 GLU | CG | −31.67 | −21.39 | 73.64 | 15.00 |
| 35 GLU | CD | −31.63 | −20.29 | 72.57 | 15.00 |
| 35 GLU | OE1 | −32.41 | −20.37 | 71.57 | 15.00 |
| 35 GLU | OE2 | −30.81 | −19.35 | 72.71 | 15.00 |
| 35 GLU | C | −33.83 | −24.57 | 74.20 | 15.00 |
| 35 GLU | O | −34.34 | −24.83 | 75.31 | 15.00 |
| 36 GLY | N | −34.26 | −25.10 | 73.05 | 15.00 |
| 36 GLY | CA | −35.48 | −25.91 | 72.99 | 15.00 |
| 36 GLY | C | −35.58 | −27.11 | 73.93 | 15.00 |
| 36 GLY | O | −36.67 | −27.47 | 74.37 | 15.00 |
| 37 GLN | N | −34.44 | −27.72 | 74.24 | 15.00 |
| 37 GLN | CA | −34.40 | −28.87 | 75.12 | 15.00 |
| 37 GLN | CB | −33.06 | −29.60 | 74.95 | 15.00 |
| 37 GLN | CG | −32.79 | −30.19 | 73.58 | 15.00 |
| 37 GLN | CD | −33.83 | −31.19 | 73.19 | 15.00 |
| 37 GLN | OE1 | −33.99 | −32.23 | 73.84 | 15.00 |
| 37 GLN | NE2 | −34.56 | −30.89 | 72.11 | 15.00 |
| 37 GLN | C | −34.52 | −28.38 | 76.55 | 15.00 |
| 37 GLN | O | −35.01 | −29.10 | 77.43 | 15.00 |
| 38 LEU | N | −33.98 | −27.18 | 76.79 | 15.00 |
| 38 LEU | CA | −34.03 | −26.60 | 78.12 | 15.00 |
| 38 LEU | CB | −33.30 | −25.26 | 78.14 | 15.00 |
| 38 LEU | CG | −33.24 | −24.54 | 79.47 | 15.00 |
| 38 LEU | CD1 | −32.61 | −25.51 | 80.46 | 15.00 |
| 38 LEU | CD2 | −32.41 | −23.30 | 79.36 | 15.00 |
| 38 LEU | C | −35.46 | −26.45 | 78.60 | 15.00 |
| 38 LEU | O | −35.86 | −27.10 | 79.58 | 15.00 |
| 39 LYS | N | −36.26 | −25.70 | 77.84 | 15.00 |
| 39 LYS | CA | −37.68 | −25.45 | 78.15 | 15.00 |
| 39 LYS | CB | −38.34 | −24.71 | 76.97 | 15.00 |
| 39 LYS | CG | −39.49 | −23.74 | 77.33 | 15.00 |
| 39 LYS | CD | −40.74 | −24.43 | 77.83 | 15.00 |
| 39 LYS | CE | −41.85 | −23.45 | 78.12 | 15.00 |
| 39 LYS | NZ | −41.65 | −22.78 | 79.42 | 15.00 |
| 39 LYS | C | −38.42 | −26.78 | 78.46 | 15.00 |
| 39 LYS | O | −39.33 | −26.82 | 79.30 | 15.00 |
| 40 LYS | N | −38.04 | −27.84 | 77.77 | 15.00 |
| 40 LYS | CA | −38.66 | −29.14 | 77.99 | 15.00 |
| 40 LYS | CB | −38.41 | −30.07 | 76.81 | 15.00 |
| 40 LYS | CG | −39.57 | −31.02 | 76.53 | 15.00 |
| 40 LYS | CD | −39.10 | −32.29 | 75.82 | 15.00 |
| 40 LYS | CE | −40.02 | −32.72 | 74.68 | 15.00 |
| 40 LYS | NZ | −40.21 | −31.65 | 73.65 | 15.00 |
| 40 LYS | C | −38.08 | −29.74 | 79.27 | 15.00 |
| 40 LYS | O | −38.79 | −30.27 | 80.12 | 15.00 |
| 41 LYS | N | −36.77 | −29.60 | 79.41 | 15.00 |
| 41 LYS | CA | −36.05 | −30.13 | 80.55 | 15.00 |
| 41 LYS | CB | −34.53 | −29.93 | 80.33 | 15.00 |
| 41 LYS | CG | −33.63 | −30.86 | 81.11 | 15.00 |
| 41 LYS | CD | −33.79 | −32.26 | 80.55 | 15.00 |
| 41 LYS | CE | −33.13 | −33.31 | 81.42 | 15.00 |
| 41 LYS | NZ | −33.45 | −34.68 | 80.86 | 15.00 |
| 41 LYS | C | −36.49 | −29.45 | 81.84 | 15.00 |
| 41 LYS | O | −37.34 | −29.97 | 82.61 | 15.00 |
| 42 THR | N | −35.96 | −28.25 | 82.04 | 15.00 |
| 42 THR | CA | −36.22 | −27.48 | 83.24 | 15.00 |
| 42 THR | CB | −34.87 | −26.94 | 83.78 | 15.00 |
| 42 THR | OG1 | −34.35 | −25.91 | 82.92 | 15.00 |
| 42 THR | CG2 | −33.86 | −28.07 | 83.79 | 15.00 |
| 42 THR | C | −37.16 | −26.30 | 83.02 | 15.00 |
| 42 THR | O | −36.86 | −25.20 | 83.45 | 15.00 |
| 43 GLY | N | −38.28 | −26.52 | 82.34 | 15.00 |
| 43 GLY | CA | −39.26 | −25.47 | 82.12 | 15.00 |
| 43 GLY | C | −38.87 | −24.03 | 81.79 | 15.00 |
| 43 GLY | O | −39.77 | −23.21 | 81.54 | 15.00 |
| 44 LYS | N | −37.56 | −23.75 | 81.75 | 15.00 |
| 44 LYS | CA | −37.02 | −22.41 | 81.49 | 15.00 |
| 44 LYS | CB | −35.84 | −22.13 | 82.44 | 15.00 |
| 44 LYS | CG | −36.25 | −21.41 | 83.72 | 15.00 |
| 44 LYS | CD | −35.09 | −21.25 | 84.67 | 15.00 |
| 44 LYS | CE | −35.50 | −20.36 | 85.86 | 15.00 |
| 44 LYS | NZ | −36.56 | −20.99 | 86.66 | 15.00 |
| 44 LYS | C | −36.56 | −22.13 | 80.06 | 15.00 |
| 44 LYS | O | −35.71 | −22.83 | 79.51 | 15.00 |
| 45 LEU | N | −37.07 | −21.04 | 79.50 | 15.00 |
| 45 LEU | CA | −36.70 | −20.66 | 78.14 | 15.00 |
| 45 LEU | CB | −37.93 | −20.08 | 77.46 | 15.00 |
| 45 LEU | CG | −38.06 | −19.92 | 75.94 | 15.00 |
| 45 LEU | CD1 | −37.93 | −21.25 | 75.26 | 15.00 |
| 45 LEU | CD2 | −39.40 | −19.29 | 75.63 | 15.00 |
| 45 LEU | C | −35.66 | −19.57 | 78.35 | 15.00 |
| 45 LEU | O | −36.00 | −18.46 | 78.71 | 15.00 |
| 46 LEU | N | −34.40 | −19.94 | 78.29 | 15.00 |
| 46 LEU | CA | −33.30 | −18.99 | 78.50 | 15.00 |
| 46 LEU | CB | −32.23 | −19.62 | 79.41 | 15.00 |
| 46 LEU | CG | −31.90 | −18.84 | 80.70 | 15.00 |
| 46 LEU | CD1 | −32.48 | −19.56 | 81.88 | 15.00 |
| 46 LEU | CD2 | −30.35 | −18.72 | 80.89 | 15.00 |
| 46 LEU | C | −32.68 | −18.70 | 77.13 | 15.00 |
| 46 LEU | O | −32.93 | −19.45 | 76.19 | 15.00 |
| 47 ASN | N | −31.92 | −17.61 | 76.99 | 15.00 |
| 47 ASN | CA | −31.23 | −17.30 | 75.73 | 15.00 |
| 47 ASN | CB | −31.29 | −15.79 | 75.44 | 15.00 |
| 47 ASN | CG | −32.61 | −15.36 | 74.77 | 15.00 |
| 47 ASN | OD1 | −32.68 | −15.24 | 73.55 | 15.00 |
| 47 ASN | ND2 | −33.63 | −15.06 | 75.58 | 15.00 |
| 47 ASN | C | −29.74 | −17.70 | 75.90 | 15.00 |
| 47 ASN | O | −29.01 | −16.99 | 76.58 | 15.00 |
| 48 LEU | N | −29.28 | −18.80 | 75.29 | 15.00 |
| 48 LEU | CA | −27.88 | −19.20 | 75.45 | 15.00 |
| 48 LEU | CB | −27.67 | −20.68 | 75.16 | 15.00 |
| 48 LEU | CG | −28.05 | −21.69 | 76.27 | 15.00 |
| 48 LEU | CD1 | −27.81 | −21.07 | 77.65 | 15.00 |
| 48 LEU | CD2 | −29.49 | −22.12 | 76.12 | 15.00 |
| 48 LEU | C | −26.85 | −18.34 | 74.73 | 15.00 |
| 48 LEU | O | −27.20 | −17.31 | 74.23 | 15.00 |
| 49 SER | N | −25.58 | −18.70 | 74.74 | 15.00 |
| 49 SER | CA | −24.59 | −17.83 | 74.11 | 15.00 |
| 49 SER | CB | −23.51 | −17.50 | 75.14 | 15.00 |
| 49 SER | OG | −22.32 | −17.09 | 74.51 | 15.00 |
| 49 SER | C | −23.93 | −18.37 | 72.87 | 15.00 |
| 49 SER | O | −23.08 | −19.27 | 72.98 | 15.00 |
| 50 PRO | N | −24.29 | −17.86 | 71.67 | 15.00 |
| 50 PRO | CD | −25.31 | −16.83 | 71.34 | 15.00 |
| 50 PRO | CA | −23.66 | −18.36 | 70.45 | 15.00 |
| 50 PRO | CB | −24.47 | −17.67 | 69.35 | 15.00 |
| 50 PRO | CG | −24.96 | −16.44 | 69.97 | 15.00 |
| 50 PRO | C | −22.18 | −17.94 | 70.44 | 15.00 |
| 50 PRO | O | −21.36 | −18.62 | 69.86 | 15.00 |
| 51 GLN | N | −21.82 | −16.87 | 71.13 | 15.00 |
| 51 GLN | CA | −20.43 | −16.41 | 71.17 | 15.00 |
| 51 GLN | CB | −20.39 | −14.98 | 71.74 | 15.00 |

TABLE VIII-continued

Table of the orthogonal three dimensional coordinates in Ångstroms and B factors (Å$^2$) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue | Atom | X | Y | Z | B |
|---|---|---|---|---|---|
| 51 GLN | CG | −19.02 | −14.25 | 71.69 | 15.00 |
| 51 GLN | CD | −18.76 | −13.61 | 70.35 | 15.00 |
| 51 GLN | OE1 | −19.65 | −12.97 | 69.76 | 15.00 |
| 51 GLN | NE2 | −17.54 | −13.79 | 69.84 | 15.00 |
| 51 GLN | C | −19.46 | −17.34 | 71.94 | 15.00 |
| 51 GLN | O | −18.31 | −17.50 | 71.53 | 15.00 |
| 52 ASN | N | −19.90 | −17.99 | 73.02 | 15.00 |
| 52 ASN | CA | −19.02 | −18.91 | 73.78 | 15.00 |
| 52 ASN | CB | −19.79 | −19.58 | 74.91 | 15.00 |
| 52 ASN | CG | −18.92 | −20.56 | 75.72 | 15.00 |
| 52 ASN | OD1 | −19.45 | −21.25 | 76.60 | 15.00 |
| 52 ASN | ND2 | −17.61 | −20.58 | 75.49 | 15.00 |
| 52 ASN | C | −18.54 | −19.96 | 72.80 | 15.00 |
| 52 ASN | O | −17.34 | −20.22 | 72.69 | 15.00 |
| 53 LEU | N | −19.50 | −20.50 | 72.05 | 15.00 |
| 53 LEU | CA | −19.28 | −21.52 | 71.00 | 15.00 |
| 53 LEU | CB | −20.62 | −21.86 | 70.33 | 15.00 |
| 53 LEU | CG | −21.43 | −23.10 | 70.69 | 15.00 |
| 53 LEU | CD1 | −21.19 | −23.59 | 72.12 | 15.00 |
| 53 LEU | CD2 | −22.91 | −22.80 | 70.38 | 15.00 |
| 53 LEU | C | −18.28 | −21.04 | 69.94 | 15.00 |
| 53 LEU | O | −17.34 | −21.76 | 69.60 | 15.00 |
| 54 VAL | N | −18.48 | −19.82 | 69.46 | 15.00 |
| 54 VAL | CA | −17.63 | −19.27 | 68.44 | 15.00 |
| 54 VAL | CB | −18.01 | −17.82 | 68.09 | 15.00 |
| 54 VAL | CG1 | −16.94 | −17.17 | 67.25 | 15.00 |
| 54 VAL | CG2 | −19.32 | −17.76 | 67.40 | 15.00 |
| 54 VAL | C | −16.18 | −19.32 | 68.84 | 15.00 |
| 54 VAL | O | −15.36 | −19.90 | 68.11 | 15.00 |
| 55 ASP | N | −15.88 | −18.75 | 70.02 | 15.00 |
| 55 ASP | CA | −14.53 | −18.65 | 70.58 | 15.00 |
| 55 ASP | CB | −14.49 | −17.73 | 71.81 | 15.00 |
| 55 ASP | CG | −14.86 | −16.30 | 71.52 | 15.00 |
| 55 ASP | OD1 | −14.87 | −15.89 | 70.35 | 15.00 |
| 55 ASP | OD2 | −15.13 | −15.56 | 72.49 | 15.00 |
| 55 ASP | C | −13.87 | −19.93 | 71.08 | 15.00 |
| 55 ASP | O | −12.65 | −20.14 | 70.82 | 15.00 |
| 56 CYS | N | −14.62 | −20.75 | 71.81 | 15.00 |
| 56 CYS | CA | −14.06 | −21.94 | 72.42 | 15.00 |
| 56 CYS | C | −14.14 | −23.23 | 71.62 | 15.00 |
| 56 CYS | O | −13.36 | −24.15 | 71.85 | 15.00 |
| 56 CYS | CB | −14.74 | −22.17 | 73.76 | 15.00 |
| 56 CYS | SG | −14.67 | −20.81 | 74.99 | 15.00 |
| 57 VAL | N | −15.00 | −23.30 | 70.62 | 15.00 |
| 57 VAL | CA | −15.09 | −24.53 | 69.88 | 15.00 |
| 57 VAL | CB | −16.51 | −24.71 | 69.30 | 15.00 |
| 57 VAL | CG1 | −16.66 | −26.03 | 68.70 | 15.00 |
| 57 VAL | CG2 | −17.56 | −24.53 | 70.42 | 15.00 |
| 57 VAL | C | −13.92 | −24.66 | 68.88 | 15.00 |
| 57 VAL | O | −14.05 | −24.47 | 67.68 | 15.00 |
| 58 SER | N | −12.79 | −25.08 | 69.43 | 15.00 |
| 58 SER | CA | −11.51 | −25.26 | 68.71 | 15.00 |
| 58 SER | CB | −10.43 | −25.78 | 69.66 | 15.00 |
| 58 SER | OG | −9.18 | −25.96 | 68.99 | 15.00 |
| 58 SER | C | −11.53 | −26.13 | 67.45 | 15.00 |
| 58 SER | O | −10.66 | −26.01 | 66.58 | 15.00 |
| 59 GLU | N | −12.54 | −26.98 | 67.36 | 15.00 |
| 59 GLU | CA | −12.67 | −27.86 | 66.21 | 15.00 |
| 59 GLU | CB | −13.47 | −29.12 | 66.60 | 15.00 |
| 59 GLU | CG | −13.12 | −29.70 | 68.00 | 15.00 |
| 59 GLU | CD | −14.02 | −29.15 | 69.13 | 15.00 |
| 59 GLU | OE1 | −15.16 | −29.68 | 69.29 | 15.00 |
| 59 GLU | OE2 | −13.56 | −28.20 | 69.84 | 15.00 |
| 59 GLU | C | −13.30 | −27.07 | 65.05 | 15.00 |
| 59 GLU | O | −13.21 | −27.46 | 63.91 | 15.00 |
| 60 ASN | N | −13.91 | −25.93 | 65.35 | 15.00 |
| 60 ASN | CA | −14.50 | −25.14 | 64.28 | 15.00 |
| 60 ASN | CB | −15.92 | −24.71 | 64.63 | 15.00 |
| 60 ASN | CG | −16.96 | −25.87 | 64.48 | 15.00 |
| 60 ASN | OD1 | −17.94 | −25.95 | 65.23 | 15.00 |
| 60 ASN | ND2 | −16.75 | −26.74 | 63.50 | 15.00 |
| 60 ASN | C | −13.60 | −23.94 | 63.89 | 15.00 |
| 60 ASN | O | −12.43 | −23.91 | 64.25 | 15.00 |
| 61 ASP | N | −14.11 | −23.06 | 63.02 | 15.00 |
| 61 ASP | CA | −13.36 | −21.90 | 62.53 | 15.00 |
| 61 ASP | CB | −13.29 | −21.96 | 61.02 | 15.00 |
| 61 ASP | CG | −11.96 | −22.46 | 60.52 | 15.00 |
| 61 ASP | OD1 | −11.41 | −23.42 | 61.13 | 15.00 |
| 61 ASP | OD2 | −11.48 | −21.91 | 59.50 | 15.00 |
| 61 ASP | C | −13.89 | −20.55 | 62.98 | 15.00 |
| 61 ASP | O | −13.38 | −19.49 | 62.62 | 15.00 |
| 62 GLY | N | −14.94 | −20.59 | 63.77 | 15.00 |
| 62 GLY | CA | −15.48 | −19.35 | 64.30 | 15.00 |
| 62 GLY | C | −16.16 | −18.55 | 63.21 | 15.00 |
| 62 GLY | O | −17.14 | −19.03 | 62.59 | 15.00 |
| 63 CYS | N | −15.70 | −17.33 | 62.93 | 15.00 |
| 63 CYS | CA | −16.40 | −16.58 | 61.91 | 15.00 |
| 63 CYS | C | −16.18 | −17.07 | 60.50 | 15.00 |
| 63 CYS | O | −16.75 | −16.57 | 59.55 | 15.00 |
| 63 CYS | CB | −16.13 | −15.11 | 62.08 | 15.00 |
| 63 CYS | SG | −17.00 | −14.35 | 63.54 | 15.00 |
| 64 GLY | N | −15.46 | −18.19 | 60.41 | 15.00 |
| 64 GLY | CA | −15.19 | −18.79 | 59.11 | 15.00 |
| 64 GLY | C | −16.12 | −19.97 | 58.83 | 15.00 |
| 64 GLY | O | −16.19 | −20.49 | 57.72 | 15.00 |
| 65 GLY | N | −16.79 | −20.46 | 59.86 | 15.00 |
| 65 GLY | CA | −17.70 | −21.56 | 59.62 | 15.00 |
| 65 GLY | C | −17.39 | −22.81 | 60.42 | 15.00 |
| 65 GLY | O | −16.24 | −23.13 | 60.74 | 15.00 |
| 66 GLY | N | −18.43 | −23.62 | 60.61 | 15.00 |
| 66 GLY | CA | −18.29 | −24.85 | 61.37 | 15.00 |
| 66 GLY | C | −19.48 | −25.78 | 61.43 | 15.00 |
| 66 GLY | O | −20.57 | −25.37 | 61.00 | 15.00 |
| 67 TYR | N | −19.31 | −26.94 | 62.06 | 15.00 |
| 67 TYR | CA | −20.37 | −27.91 | 62.16 | 15.00 |
| 67 TYR | CB | −19.83 | −29.31 | 61.82 | 15.00 |
| 67 TYR | CG | −19.28 | −29.38 | 60.43 | 15.00 |
| 67 TYR | CD1 | −20.08 | −29.14 | 59.33 | 15.00 |
| 67 TYR | CE1 | −19.54 | −29.09 | 58.03 | 15.00 |
| 67 TYR | CD2 | −17.93 | −29.57 | 60.21 | 15.00 |
| 67 TYR | CE2 | −17.39 | −29.52 | 58.91 | 15.00 |
| 67 TYR | CZ | −18.20 | −29.27 | 57.84 | 15.00 |
| 67 TYR | OH | −17.70 | −29.21 | 56.59 | 15.00 |
| 67 TYR | C | −21.11 | −27.86 | 63.49 | 15.00 |
| 67 TYR | O | −20.55 | −27.52 | 64.52 | 15.00 |
| 68 MET | N | −22.40 | −28.13 | 63.48 | 15.00 |
| 68 MET | CA | −23.12 | −28.14 | 64.76 | 15.00 |
| 68 MET | CB | −24.62 | −28.23 | 64.56 | 15.00 |
| 68 MET | CG | −25.11 | −27.02 | 63.82 | 15.00 |
| 68 MET | SD | −24.76 | −27.31 | 62.04 | 15.00 |
| 68 MET | CE | −26.39 | −28.14 | 61.56 | 15.00 |
| 68 MET | C | −22.66 | −29.31 | 65.63 | 15.00 |
| 68 MET | O | −22.63 | −29.21 | 66.83 | 15.00 |
| 69 THR | N | −22.32 | −30.42 | 64.99 | 15.00 |
| 69 THR | CA | −21.87 | −31.57 | 65.74 | 15.00 |
| 69 THR | CB | −21.55 | −32.78 | 64.81 | 15.00 |
| 69 THR | OG1 | −20.68 | −32.38 | 63.72 | 15.00 |
| 69 THR | CG2 | −22.82 | −33.41 | 64.29 | 15.00 |
| 69 THR | C | −20.65 | −31.21 | 66.61 | 15.00 |
| 69 THR | O | −20.61 | −31.62 | 67.76 | 15.00 |
| 70 ASN | N | −19.74 | −30.38 | 66.11 | 15.00 |
| 70 ASN | CA | −18.56 | −30.05 | 66.91 | 15.00 |
| 70 ASN | CB | −17.53 | −29.28 | 66.07 | 15.00 |
| 70 ASN | CG | −16.83 | −30.17 | 65.02 | 15.00 |
| 70 ASN | OD1 | −17.07 | −31.39 | 64.94 | 15.00 |
| 70 ASN | ND2 | −16.02 | −29.55 | 64.17 | 15.00 |
| 70 ASN | C | −18.99 | −29.22 | 68.11 | 15.00 |
| 70 ASN | O | −18.59 | −29.49 | 69.21 | 15.00 |
| 71 ALA | N | −19.95 | −28.33 | 67.87 | 15.00 |
| 71 ALA | CA | −20.42 | −27.44 | 68.91 | 15.00 |

TABLE VIII-continued

Table of the orthogonal three dimensional coordinates in Ångstroms and B factors (Å²) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue | Atom | X | Y | Z | B |
|---|---|---|---|---|---|
| 71 ALA | CB | −21.27 | −26.35 | 68.33 | 15.00 |
| 71 ALA | C | −21.15 | −28.13 | 70.05 | 15.00 |
| 71 ALA | O | −21.13 | −27.69 | 71.20 | 15.00 |
| 72 PHE | N | −21.84 | −29.22 | 69.71 | 15.00 |
| 72 PHE | CA | −22.53 | −29.99 | 70.74 | 15.00 |
| 72 PHE | CB | −23.59 | −30.93 | 70.13 | 15.00 |
| 72 PHE | CG | −24.75 | −30.22 | 69.47 | 15.00 |
| 72 PHE | CD1 | −25.59 | −29.41 | 70.21 | 15.00 |
| 72 PHE | CD2 | −25.05 | −30.41 | 68.12 | 15.00 |
| 72 PHE | CE1 | −26.70 | −28.82 | 69.63 | 15.00 |
| 72 PHE | CE2 | −26.16 | −29.82 | 67.55 | 15.00 |
| 72 PHE | CZ | −26.97 | −29.03 | 68.31 | 15.00 |
| 72 PHE | C | −21.49 | −30.80 | 71.51 | 15.00 |
| 72 PHE | O | −21.54 | −30.91 | 72.73 | 15.00 |
| 73 GLN | N | −20.55 | −31.39 | 70.78 | 15.00 |
| 73 GLN | CA | −19.50 | −32.16 | 71.39 | 15.00 |
| 73 GLN | CB | −18.48 | −32.63 | 70.34 | 15.00 |
| 73 GLN | CG | −17.59 | −33.74 | 70.84 | 15.00 |
| 73 GLN | CD | −17.19 | −34.69 | 69.73 | 15.00 |
| 73 GLN | OE1 | −17.48 | −35.89 | 69.18 | 15.00 |
| 73 GLN | NE2 | −16.52 | −34.16 | 68.72 | 15.00 |
| 73 GLN | C | −18.81 | −31.26 | 72.43 | 15.00 |
| 73 GLN | O | −18.64 | −31.64 | 73.59 | 15.00 |
| 74 TYR | N | −18.39 | −30.06 | 72.02 | 15.00 |
| 74 TYR | CA | −17.70 | −29.17 | 72.97 | 15.00 |
| 74 TYR | CB | −17.27 | −27.85 | 72.29 | 15.00 |
| 74 TYR | CG | −17.25 | −26.64 | 73.21 | 15.00 |
| 74 TYR | CD1 | −16.09 | −26.24 | 73.83 | 15.00 |
| 74 TYR | CE1 | −16.11 | −25.21 | 74.74 | 15.00 |
| 74 TYR | CD2 | −18.43 | −25.98 | 73.51 | 15.00 |
| 74 TYR | CE2 | −18.46 | −24.94 | 74.43 | 15.00 |
| 74 TYR | CZ | −17.30 | −24.57 | 75.05 | 15.00 |
| 74 TYR | OH | −17.27 | −23.57 | 76.01 | 15.00 |
| 74 TYR | C | −18.51 | −28.95 | 74.27 | 15.00 |
| 74 TYR | O | −18.01 | −29.19 | 75.35 | 15.00 |
| 75 VAL | N | −19.77 | −28.61 | 74.13 | 15.00 |
| 75 VAL | CA | −20.68 | −28.40 | 75.27 | 15.00 |
| 75 VAL | CB | −22.10 | −28.09 | 74.67 | 15.00 |
| 75 VAL | CG1 | −23.21 | −28.24 | 75.71 | 15.00 |
| 75 VAL | CG2 | −22.09 | −26.67 | 74.09 | 15.00 |
| 75 VAL | C | −20.70 | −29.59 | 76.29 | 15.00 |
| 75 VAL | O | −21.29 | −29.50 | 77.38 | 15.00 |
| 76 GLN | N | −20.09 | −30.71 | 75.88 | 15.00 |
| 76 GLN | CA | −20.03 | −31.93 | 76.68 | 15.00 |
| 76 GLN | CB | −20.30 | −33.15 | 75.77 | 15.00 |
| 76 GLN | CG | −20.03 | −34.52 | 76.35 | 15.00 |
| 76 GLN | CD | −20.70 | −35.58 | 75.54 | 15.00 |
| 76 GLN | OE1 | −21.76 | −36.09 | 75.93 | 15.00 |
| 76 GLN | NE2 | −20.15 | −35.88 | 74.37 | 15.00 |
| 76 GLN | C | −18.70 | −32.10 | 77.39 | 15.00 |
| 76 GLN | O | −18.66 | −32.13 | 78.61 | 15.00 |
| 77 LYS | N | −17.61 | −32.20 | 76.65 | 15.09 |
| 77 LYS | CA | −16.31 | −32.37 | 77.28 | 15.00 |
| 77 LYS | CB | −15.24 | −32.65 | 76.24 | 15.00 |
| 77 LYS | CG | −15.60 | −33.84 | 75.35 | 15.00 |
| 77 LYS | CD | −14.38 | −34.57 | 74.81 | 15.00 |
| 77 LYS | CE | −13.52 | −33.71 | 73.91 | 15.00 |
| 77 LYS | NZ | −12.57 | −34.54 | 73.09 | 15.00 |
| 77 LYS | C | −15.94 | −31.16 | 78.15 | 15.00 |
| 77 LYS | O | −15.31 | −31.32 | 79.19 | 15.00 |
| 78 ASN | N | −16.35 | −29.96 | 77.75 | 15.00 |
| 78 ASN | CA | −16.09 | −28.77 | 78.57 | 15.00 |
| 78 ASN | CB | −16.09 | −27.49 | 77.72 | 15.00 |
| 78 ASN | CG | −16.13 | −26.22 | 78.58 | 15.00 |
| 78 ASN | OD1 | −15.14 | −25.84 | 79.17 | 15.00 |
| 78 ASN | ND2 | −17.32 | −25.64 | 78.72 | 15.00 |
| 78 ASN | C | −17.17 | −28.68 | 79.66 | 15.00 |
| 78 ASN | O | −17.18 | −27.77 | 80.49 | 15.00 |
| 79 ARG | N | −18.08 | −29.64 | 79.64 | 15.00 |
| 79 ARG | CA | −19.18 | −29.69 | 80.60 | 15.00 |
| 79 ARG | CB | −18.69 | −30.15 | 81.98 | 15.00 |
| 79 ARG | CG | −18.36 | −31.63 | 82.12 | 15.00 |
| 79 ARG | CD | −17.79 | −31.93 | 83.52 | 15.00 |
| 79 ARG | NE | −16.63 | −32.84 | 83.47 | 15.00 |
| 79 ARG | CZ | −15.39 | −32.46 | 83.15 | 15.00 |
| 79 ARG | NH1 | −15.15 | −31.19 | 82.86 | 15.00 |
| 79 ARG | NH2 | −14.38 | −33.34 | 83.16 | 15.00 |
| 79 ARG | C | −20.00 | −28.40 | 89.78 | 15.00 |
| 79 ARG | O | −20.27 | −27.99 | 81.91 | 15.00 |
| 80 GLY | N | −20.32 | −27.70 | 79.70 | 15.00 |
| 80 GLY | CA | −21.14 | −26.50 | 79.88 | 15.00 |
| 80 GLY | C | −21.02 | −25.34 | 78.91 | 15.00 |
| 80 GLY | O | −19.94 | −25.13 | 78.31 | 15.00 |
| 81 ILE | N | −22.13 | −24.60 | 78.78 | 15.00 |
| 81 ILE | CA | −22.27 | −23.43 | 77.92 | 15.00 |
| 81 ILE | CB | −23.18 | −23.77 | 76.69 | 15.00 |
| 81 ILE | CG2 | −24.60 | −24.14 | 77.13 | 15.00 |
| 81 ILE | CG1 | −23.28 | −22.57 | 75.76 | 15.00 |
| 81 ILE | CD1 | −24.04 | −22.84 | 74.48 | 15.00 |
| 81 ILE | C | −22.91 | −22.32 | 78.75 | 15.00 |
| 81 ILE | O | −23.73 | −22.62 | 79.63 | 15.00 |
| 82 ASP | N | −22.58 | −21.05 | 78.48 | 15.00 |
| 82 ASP | CA | −23.13 | −19.92 | 79.28 | 15.00 |
| 82 ASP | CB | −22.13 | −18.77 | 79.29 | 15.00 |
| 82 ASP | CG | −20.88 | −19.11 | 80.02 | 15.00 |
| 82 ASP | OD1 | −19.80 | −18.87 | 79.48 | 15.00 |
| 82 ASP | OD2 | −20.96 | −19.62 | 81.14 | 15.00 |
| 82 ASP | C | −24.47 | −19.36 | 78.83 | 15.00 |
| 82 ASP | O | −25.10 | −19.90 | 77.94 | 15.00 |
| 83 SER | N | −24.92 | −18.31 | 79.51 | 15.00 |
| 83 SER | CA | −26.12 | −17.57 | 79.18 | 15.00 |
| 83 SER | CB | −26.70 | −16.97 | 80.48 | 15.00 |
| 83 SER | OG | −25.68 | −16.38 | 81.28 | 15.00 |
| 83 SER | C | −25.55 | −16.45 | 78.27 | 15.00 |
| 83 SER | O | −24.33 | −16.24 | 78.28 | 15.00 |
| 84 GLU | N | −26.35 | −15.82 | 77.39 | 15.00 |
| 84 GLU | CA | −25.85 | −14.72 | 76.54 | 15.00 |
| 84 GLU | CB | −27.00 | −13.88 | 75.94 | 15.00 |
| 84 GLU | CG | −27.12 | −13.72 | 74.39 | 15.00 |
| 84 GLU | CD | −25.97 | −12.97 | 73.70 | 15.00 |
| 84 GLU | OE1 | −25.80 | −11.74 | 73.90 | 15.00 |
| 84 GLU | OE2 | −25.23 | −13.64 | 72.93 | 15.00 |
| 84 GLU | C | −25.15 | −13.79 | 77.53 | 15.00 |
| 84 GLU | O | −24.00 | −13.44 | 77.37 | 15.00 |
| 85 ASP | N | −25.85 | −13.43 | 78.61 | 15.00 |
| 85 ASP | CA | −25.31 | −12.53 | 79.65 | 15.00 |
| 85 ASP | CB | −26.08 | −12.68 | 80.98 | 15.00 |
| 85 ASP | CG | −27.48 | −12.06 | 80.94 | 15.00 |
| 85 ASP | OD1 | −28.41 | −12.76 | 81.40 | 15.00 |
| 85 ASP | OD2 | −27.63 | −10.90 | 80.45 | 15.00 |
| 85 ASP | C | −23.80 | −12.67 | 79.97 | 15.00 |
| 85 ASP | O | −23.07 | −11.67 | 80.00 | 15.00 |
| 86 ALA | N | −23.36 | −13.90 | 80.22 | 15.00 |
| 86 ALA | CA | −21.96 | −14.21 | 80.59 | 15.00 |
| 86 ALA | CB | −21.89 | −15.55 | 81.31 | 15.00 |
| 86 ALA | C | −21.00 | −14.20 | 79.40 | 15.00 |
| 86 ALA | O | −19.76 | −14.22 | 79.57 | 15.00 |
| 87 TYR | N | −21.55 | −14.11 | 78.20 | 15.00 |
| 87 TYR | CA | −20.74 | −14.13 | 76.99 | 15.00 |
| 87 TYR | CB | −20.41 | −15.60 | 76.66 | 15.00 |
| 87 TYR | CG | −18.96 | −15.90 | 76.36 | 15.00 |
| 87 TYR | CD1 | −18.23 | −15.14 | 75.50 | 15.00 |
| 87 TYR | CE1 | −16.93 | −15.44 | 75.21 | 15.00 |
| 87 TYR | CD2 | −18.34 | −16.98 | 76.94 | 15.00 |
| 87 TYR | CE2 | −17.04 | −17.27 | 76.65 | 15.00 |
| 87 TYR | CZ | −16.35 | −16.52 | 75.79 | 15.00 |
| 87 TYR | OH | −15.09 | −16.87 | 75.41 | 15.00 |
| 87 TYR | C | −21.57 | −13.50 | 75.86 | 15.00 |
| 87 TYR | O | −21.88 | −14.19 | 74.89 | 15.00 |
| 88 PRO | N | −21.98 | −12.22 | 75.98 | 15.00 |

TABLE VIII-continued

Table of the orthogonal three dimensional coordinates in Ångstroms and B factors (Å²) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue | Atom | X | Y | Z | B |
|---|---|---|---|---|---|
| 88 PRO | CD | −21.70 | −11.28 | 77.08 | 15.00 |
| 88 PRO | CA | −22.78 | −11.57 | 74.93 | 15.00 |
| 88 PRO | CB | −22.84 | −10.11 | 75.41 | 15.00 |
| 88 PRO | CG | −22.78 | −10.21 | 76.93 | 15.00 |
| 88 PRO | C | −22.14 | −11.72 | 73.54 | 15.00 |
| 88 PRO | O | −20.91 | −11.95 | 73.44 | 15.00 |
| 89 TYR | N | −22.97 | −11.62 | 72.49 | 15.00 |
| 89 TYR | CA | −22.50 | −11.76 | 71.11 | 15.00 |
| 89 TYR | CB | −23.64 | −12.25 | 70.22 | 15.00 |
| 89 TYR | CG | −23.22 | −12.67 | 68.82 | 15.00 |
| 89 TYR | CD1 | −22.42 | −13.82 | 68.64 | 15.00 |
| 89 TYR | CE1 | −22.03 | −14.24 | 67.35 | 15.00 |
| 89 TYR | CD2 | −23.62 | −11.92 | 67.68 | 15.00 |
| 89 TYR | CE2 | −23.24 | −12.31 | 66.41 | 15.00 |
| 89 TYR | CZ | −22.44 | −13.47 | 66.24 | 15.00 |
| 89 TYR | OH | −22.00 | −13.78 | 64.96 | 15.00 |
| 89 TYR | C | −21.91 | −10.45 | 70.58 | 15.00 |
| 89 TYR | O | −22.53 | −9.40 | 70.70 | 15.00 |
| 90 VAL | N | −20.67 | −10.51 | 70.08 | 15.00 |
| 90 VAL | CA | −19.98 | −9.36 | 69.50 | 15.00 |
| 90 VAL | CB | −18.74 | −8.92 | 70.32 | 15.00 |
| 90 VAL | CG1 | −19.17 | −8.55 | 71.75 | 15.00 |
| 90 VAL | CG2 | −17.66 | −9.99 | 70.28 | 15.00 |
| 90 VAL | C | −19.58 | −9.60 | 68.03 | 15.00 |
| 90 VAL | O | −18.77 | −8.86 | 67.47 | 15.00 |
| 91 GLY | N | −20.12 | −10.65 | 67.43 | 15.00 |
| 91 GLY | CA | −19.85 | −10.97 | 66.03 | 15.00 |
| 91 GLY | C | −18.40 | −10.89 | 65.56 | 15.00 |
| 91 GLY | O | −18.09 | −10.75 | 64.36 | 15.00 |
| 92 GLN | N | −17.49 | −11.02 | 66.50 | 15.00 |
| 92 GLN | CA | −16.08 | −10.99 | 66.22 | 15.00 |
| 92 GLN | CB | −15.44 | −9.73 | 66.78 | 15.00 |
| 92 GLN | CG | −14.07 | −9.49 | 66.26 | 15.00 |
| 92 GLN | CD | −13.74 | −8.01 | 66.30 | 15.00 |
| 92 GLN | OE1 | −13.84 | −7.29 | 65.30 | 15.00 |
| 92 GLN | NE2 | −13.35 | −7.54 | 67.49 | 15.00 |
| 92 GLN | C | −15.63 | −12.18 | 67.00 | 15.00 |
| 92 GLN | O | −16.16 | −12.45 | 68.08 | 15.00 |
| 93 GLU | N | −14.75 | −12.96 | 66.42 | 15.00 |
| 93 GLU | CA | −14.27 | −14.11 | 67.13 | 15.00 |
| 93 GLU | CB | −13.67 | −15.14 | 66.19 | 15.00 |
| 93 GLU | CG | −13.54 | −16.51 | 66.82 | 15.00 |
| 93 GLU | CD | −12.31 | −17.23 | 66.33 | 15.00 |
| 93 GLU | OE1 | −11.79 | −18.11 | 67.03 | 15.00 |
| 93 GLU | OE2 | −11.86 | −16.90 | 65.23 | 15.00 |
| 93 GLU | C | −13.17 | −13.56 | 68.00 | 15.00 |
| 93 GLU | O | −12.58 | −12.52 | 67.67 | 15.00 |
| 94 GLU | N | −12.98 | −14.19 | 69.17 | 15.00 |
| 94 GLU | CA | −11.95 | −13.83 | 70.12 | 15.00 |
| 94 GLU | CB | −12.45 | −12.76 | 71.08 | 15.00 |
| 94 GLU | CG | −13.44 | −11.78 | 70.55 | 15.00 |
| 94 GLU | CD | −13.36 | −10.49 | 71.28 | 15.00 |
| 94 GLU | OE1 | −12.35 | −9.77 | 71.16 | 15.00 |
| 94 GLU | OE2 | −14.28 | −10.18 | 72.03 | 15.00 |
| 94 GLU | C | −11.52 | −15.03 | 70.95 | 15.00 |
| 94 GLU | O | −12.21 | −16.05 | 71.03 | 15.00 |
| 95 SER | N | −10.46 | −14.79 | 71.73 | 15.00 |
| 95 SER | CA | −9.89 | −15.79 | 72.60 | 15.00 |
| 95 SER | CB | −8.61 | −15.24 | 73.23 | 15.00 |
| 95 SER | OG | −7.71 | −14.80 | 72.23 | 15.00 |
| 95 SER | C | −10.92 | −16.24 | 73.63 | 15.00 |
| 95 SER | O | −11.66 | −15.42 | 74.18 | 15.00 |
| 96 CYS | N | −10.99 | −17.55 | 73.82 | 15.00 |
| 96 CYS | CA | −11.94 | −18.19 | 74.74 | 15.00 |
| 96 CYS | C | −11.83 | −17.70 | 76.17 | 15.00 |
| 96 CYS | O | −10.75 | −17.73 | 76.79 | 15.00 |
| 96 CYS | CB | −11.80 | −19.73 | 74.68 | 15.00 |
| 96 CYS | SG | −12.78 | −20.81 | 75.78 | 15.00 |
| 97 MET | N | −12.97 | −17.26 | 76.69 | 15.00 |
| 97 MET | CA | −13.10 | −16.73 | 78.03 | 15.00 |
| 97 MET | CB | −13.17 | −15.20 | 78.02 | 15.00 |
| 97 MET | CG | −12.67 | −14.49 | 79.27 | 15.00 |
| 97 MET | SD | −10.82 | −14.26 | 79.19 | 15.00 |
| 97 MET | CE | −10.31 | −15.40 | 80.50 | 15.00 |
| 97 MET | C | −14.34 | −17.32 | 78.74 | 15.00 |
| 97 MET | O | −15.06 | −16.60 | 79.42 | 15.00 |
| 98 TYR | N | −14.60 | −18.61 | 78.59 | 15.00 |
| 98 TYR | CA | −15.74 | −19.28 | 79.24 | 15.00 |
| 98 TYR | CB | −15.63 | −20.78 | 79.00 | 15.00 |
| 98 TYR | CG | −16.63 | −21.59 | 79.77 | 15.00 |
| 98 TYR | CD1 | −17.98 | −21.47 | 79.50 | 15.00 |
| 98 TYR | CE1 | −18.91 | −22.15 | 80.24 | 15.00 |
| 98 TYR | CD2 | −16.22 | −22.44 | 80.82 | 15.00 |
| 98 TYR | CE2 | −17.15 | −23.16 | 81.58 | 15.00 |
| 98 TYR | CZ | −18.51 | −22.99 | 81.27 | 15.00 |
| 98 TYR | OH | −19.51 | −23.63 | 81.97 | 15.00 |
| 98 TYR | C | −15.85 | −19.00 | 80.73 | 15.00 |
| 98 TYR | O | −14.85 | −18.70 | 81.38 | 15.00 |
| 99 ASN | N | −17.06 | −19.08 | 81.26 | 15.00 |
| 99 ASN | CA | −17.25 | −18.79 | 82.67 | 15.00 |
| 99 ASN | CB | −17.77 | −17.37 | 82.86 | 15.00 |
| 99 ASN | CG | −17.78 | −16.95 | 84.33 | 15.00 |
| 99 ASN | OD1 | −18.62 | −17.40 | 85.11 | 15.00 |
| 99 ASN | ND2 | −16.82 | −16.11 | 84.70 | 15.00 |
| 99 ASN | C | −18.13 | −19.73 | 83.47 | 15.00 |
| 99 ASN | O | −19.36 | −19.70 | 83.36 | 15.00 |
| 100 PRO | N | −17.51 | −20.60 | 84.28 | 15.00 |
| 100 PRO | CD | −16.06 | −20.90 | 84.34 | 15.00 |
| 100 PRO | CA | −18.26 | −21.55 | 85.10 | 15.00 |
| 100 PRO | CB | −17.25 | −21.89 | 86.20 | 15.00 |
| 100 PRO | CG | −15.98 | −22.00 | 85.45 | 15.00 |
| 100 PRO | C | −19.56 | −21.03 | 85.71 | 15.00 |
| 100 PRO | O | −20.61 | −21.68 | 85.55 | 15.00 |
| 101 THR | N | −19.48 | −19.89 | 86.41 | 15.00 |
| 101 THR | CA | −20.63 | −19.30 | 87.10 | 15.00 |
| 101 THR | CB | −20.18 | −18.20 | 88.13 | 15.00 |
| 101 THR | OG1 | −19.04 | −17.45 | 87.66 | 15.00 |
| 101 THR | CG2 | −19.82 | −18.87 | 89.46 | 15.00 |
| 101 THR | C | −21.77 | −18.86 | 86.17 | 15.00 |
| 101 THR | O | −22.95 | −18.78 | 86.56 | 15.00 |
| 102 GLY | N | −21.40 | −18.68 | 84.91 | 15.00 |
| 102 GLY | CA | −22.35 | −18.33 | 83.88 | 15.00 |
| 102 GLY | C | −23.27 | −19.50 | 83.58 | 15.00 |
| 102 GLY | O | −24.47 | −19.30 | 83.42 | 15.00 |
| 103 LYS | N | −22.68 | −20.69 | 83.38 | 15.00 |
| 103 LYS | CA | −23.39 | −21.95 | 83.13 | 15.00 |
| 103 LYS | CB | −22.95 | −23.01 | 84.16 | 15.00 |
| 103 LYS | CG | −23.73 | −24.31 | 84.12 | 15.00 |
| 103 LYS | CD | −23.11 | −25.38 | 85.05 | 15.00 |
| 103 LYS | CE | −21.69 | −25.76 | 84.61 | 15.00 |
| 103 LYS | NZ | −21.01 | −26.68 | 85.56 | 15.00 |
| 103 LYS | C | −24.90 | −21.82 | 83.20 | 15.00 |
| 103 LYS | O | −25.45 | −21.45 | 84.23 | 15.00 |
| 104 ALA | N | −25.58 | −22.16 | 82.10 | 15.00 |
| 104 ALA | CA | −27.05 | −22.11 | 82.04 | 15.00 |
| 104 ALA | CB | −27.54 | −20.84 | 81.26 | 15.00 |
| 104 ALA | C | −27.64 | −23.39 | 81.42 | 15.00 |
| 104 ALA | O | −28.85 | −23.61 | 81.42 | 15.00 |
| 105 ALA | N | −26.79 | −24.26 | 80.92 | 15.00 |
| 105 ALA | CA | −27.24 | −25.50 | 80.30 | 15.00 |
| 105 ALA | CB | −28.05 | −25.22 | 79.03 | 15.00 |
| 105 ALA | C | −26.03 | −26.35 | 79.97 | 15.00 |
| 105 ALA | O | −24.88 | −25.90 | 80.04 | 15.00 |
| 106 LYS | N | −26.32 | −27.59 | 79.60 | 15.00 |
| 106 LYS | CA | −25.32 | −28.57 | 79.25 | 15.00 |
| 106 LYS | CB | −24.74 | −29.13 | 80.55 | 15.00 |
| 106 LYS | CG | −23.71 | −30.22 | 80.42 | 15.00 |
| 106 LYS | CD | −23.54 | −30.96 | 81.75 | 15.00 |
| 106 LYS | CE | −24.85 | −31.60 | 82.15 | 15.00 |
| 106 LYS | NZ | −24.61 | −32.90 | 82.82 | 15.00 |

TABLE VIII-continued

Table of the orthogonal three dimensional coordinates in Ångstroms and B factors (Å²) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue | Atom | X | Y | Z | B |
|---|---|---|---|---|---|
| 106 LYS | C | −26.09 | −29.63 | 78.43 | 15.00 |
| 106 LYS | O | −27.32 | −29.62 | 78.34 | 15.00 |
| 107 CYS | N | −25.36 | −30.51 | 77.77 | 15.00 |
| 107 CYS | CA | −26.00 | −31.54 | 76.97 | 15.00 |
| 107 CYS | CB | −26.06 | −31.11 | 75.50 | 15.00 |
| 107 CYS | SG | −24.54 | −31.49 | 74.55 | 15.00 |
| 107 CYS | C | −25.07 | −32.72 | 77.10 | 15.00 |
| 107 CYS | O | −23.85 | −32.54 | 77.25 | 15.00 |
| 108 ARG | N | −25.62 | −33.92 | 77.06 | 15.00 |
| 108 ARG | CA | −24.80 | −35.12 | 77.17 | 15.00 |
| 108 ARG | CB | −25.28 | −36.03 | 78.28 | 15.00 |
| 108 ARG | CG | −25.35 | −35.42 | 79.64 | 15.00 |
| 108 ARG | CD | −25.75 | −36.49 | 80.66 | 15.00 |
| 108 ARG | NE | −27.18 | −36.72 | 80.71 | 15.00 |
| 108 ARG | CZ | −27.75 | −37.86 | 81.09 | 15.00 |
| 108 ARG | NH1 | −27.00 | −38.90 | 81.43 | 15.00 |
| 108 ARG | NH2 | −29.07 | −37.94 | 81.22 | 15.00 |
| 108 ARG | C | −24.85 | −35.89 | 75.85 | 15.00 |
| 108 ARG | O | −25.59 | −36.87 | 75.72 | 15.00 |
| 109 GLY | N | −24.11 | −35.40 | 74.87 | 15.00 |
| 109 GLY | CA | −24.05 | −36.03 | 73.57 | 15.00 |
| 109 GLY | C | −24.99 | −35.44 | 72.55 | 15.00 |
| 109 GLY | O | −25.58 | −34.38 | 72.78 | 15.00 |
| 110 TYR | N | −25.00 | −36.06 | 71.36 | 15.00 |
| 110 TYR | CA | −25.86 | −35.67 | 70.23 | 15.00 |
| 110 TYR | CB | −25.19 | −34.54 | 69.43 | 15.00 |
| 110 TYR | CG | −23.92 | −34.95 | 68.76 | 15.00 |
| 110 TYR | CD1 | −22.72 | −34.87 | 69.39 | 15.00 |
| 110 TYR | CE1 | −21.60 | −35.34 | 68.80 | 15.00 |
| 110 TYR | CD2 | −23.95 | −35.49 | 67.52 | 15.00 |
| 110 TYR | CE2 | −22.82 | −35.97 | 66.92 | 15.00 |
| 110 TYR | CZ | −21.64 | −35.90 | 67.55 | 15.00 |
| 110 TYR | OH | −20.45 | −36.35 | 66.94 | 15.00 |
| 110 TYR | C | −26.23 | −36.85 | 69.29 | 15.00 |
| 110 TYR | O | −25.46 | −37.79 | 69.07 | 15.00 |
| 111 ARG | N | −27.40 | −36.72 | 68.69 | 15.00 |
| 111 ARG | CA | −27.92 | −37.70 | 67.75 | 15.00 |
| 111 ARG | CB | −29.27 | −38.26 | 68.26 | 15.00 |
| 111 ARG | CG | −29.50 | −39.79 | 68.03 | 15.00 |
| 111 ARG | CD | −28.98 | −40.22 | 66.68 | 15.00 |
| 111 ARG | NE | −29.52 | −41.47 | 66.17 | 15.00 |
| 111 ARG | CZ | −30.81 | −41.70 | 65.92 | 15.00 |
| 111 ARG | NH1 | −31.74 | −40.77 | 66.15 | 15.00 |
| 111 ARG | NH2 | −31.18 | −42.86 | 65.41 | 15.00 |
| 111 ARG | C | −28.09 | −37.07 | 66.36 | 15.00 |
| 111 ARG | O | −28.58 | −35.94 | 66.20 | 15.00 |
| 112 GLU | N | −27.59 | −37.78 | 65.36 | 15.00 |
| 112 GLU | CA | −27.69 | −37.35 | 63.96 | 15.00 |
| 112 GLU | CB | −26.37 | −37.55 | 63.21 | 15.00 |
| 112 GLU | CG | −25.23 | −36.68 | 63.74 | 15.00 |
| 112 GLU | CD | −23.92 | −36.94 | 63.06 | 15.00 |
| 112 GLU | OE1 | −23.53 | −36.15 | 62.19 | 15.00 |
| 112 GLU | OE2 | −23.25 | −37.90 | 63.42 | 15.00 |
| 112 GLU | C | −28.84 | −38.09 | 63.31 | 15.00 |
| 112 GLU | O | −29.00 | −39.31 | 63.50 | 15.00 |
| 113 ILE | N | −29.66 | −37.35 | 62.57 | 15.00 |
| 113 ILE | CA | −30.83 | −37.86 | 61.85 | 15.00 |
| 113 ILE | CB | −31.89 | −36.74 | 61.73 | 15.00 |
| 113 ILE | CG2 | −32.92 | −37.06 | 60.63 | 15.00 |
| 113 ILE | CG1 | −32.57 | −36.51 | 63.08 | 15.00 |
| 113 ILE | CD1 | −33.32 | −35.23 | 63.13 | 15.00 |
| 113 ILE | C | −30.46 | −38.42 | 60.45 | 15.00 |
| 113 ILE | O | −29.74 | −37.79 | 59.70 | 15.00 |
| 114 PRO | N | −30.93 | −39.62 | 60.13 | 15.00 |
| 114 PRO | CD | −31.77 | −40.50 | 60.95 | 15.00 |
| 114 PRO | CA | −30.66 | −40.27 | 58.84 | 15.00 |
| 114 PRO | CB | −31.85 | −41.21 | 58.73 | 15.00 |
| 114 PRO | CG | −31.86 | −41.77 | 60.07 | 15.00 |
| 114 PRO | C | −30.61 | −39.34 | 57.65 | 15.00 |
| 114 PRO | O | −31.62 | −38.83 | 57.20 | 15.00 |
| 115 GLU | N | −29.44 | −39.26 | 57.05 | 15.00 |
| 115 GLU | CA | −29.18 | −38.44 | 55.87 | 15.00 |
| 115 GLU | CB | −27.80 | −38.78 | 55.30 | 15.00 |
| 115 GLU | CG | −27.56 | −38.41 | 53.84 | 15.00 |
| 115 GLU | CD | −26.48 | −39.24 | 53.21 | 15.00 |
| 115 GLU | OE1 | −26.78 | −40.40 | 52.85 | 15.00 |
| 115 GLU | OE2 | −25.33 | −38.75 | 53.12 | 15.00 |
| 115 GLU | C | −30.20 | −38.50 | 54.78 | 15.00 |
| 115 GLU | O | −30.37 | −39.53 | 54.16 | 15.00 |
| 116 GLY | N | −30.90 | −37.40 | 54.58 | 15.00 |
| 116 GLY | CA | −31.88 | −37.30 | 53.52 | 15.00 |
| 116 GLY | C | −33.29 | −37.78 | 53.79 | 15.00 |
| 116 GLY | O | −34.11 | −37.73 | 52.87 | 15.00 |
| 117 ASN | N | −33.56 | −38.25 | 55.01 | 15.00 |
| 117 ASN | CA | −34.89 | −38.73 | 55.36 | 15.00 |
| 117 ASN | CB | −34.76 | −40.00 | 56.22 | 15.00 |
| 117 ASN | CG | −36.06 | −40.77 | 56.33 | 15.00 |
| 117 ASN | OD1 | −37.13 | −40.29 | 55.89 | 15.00 |
| 117 ASN | ND2 | −35.99 | −41.96 | 56.91 | 15.00 |
| 117 ASN | C | −35.76 | −37.69 | 56.07 | 15.00 |
| 117 ASN | O | −35.55 | −37.38 | 57.23 | 15.00 |
| 118 GLU | N | −36.72 | −37.13 | 55.34 | 15.00 |
| 118 GLU | CA | −37.65 | −36.15 | 55.89 | 15.00 |
| 118 GLU | CB | −38.29 | −35.34 | 54.78 | 15.00 |
| 118 GLU | CG | −37.31 | −34.44 | 54.07 | 15.00 |
| 118 GLU | CD | −38.00 | −33.61 | 53.01 | 15.00 |
| 118 GLU | OE1 | −38.09 | −34.08 | 51.85 | 15.00 |
| 118 GLU | OE2 | −38.48 | −32.51 | 53.32 | 15.00 |
| 118 GLU | C | −38.73 | −36.78 | 56.75 | 15.00 |
| 118 GLU | O | −39.42 | −36.09 | 57.50 | 15.00 |
| 119 LYS | N | −38.84 | −38.11 | 56.68 | 15.00 |
| 119 LYS | CA | −39.82 | −38.82 | 57.49 | 15.00 |
| 119 LYS | CB | −40.11 | −40.20 | 56.91 | 15.00 |
| 119 LYS | CG | −40.84 | −41.15 | 57.86 | 15.00 |
| 119 LYS | CD | −41.21 | −42.46 | 57.19 | 15.00 |
| 119 LYS | CE | −39.98 | −43.29 | 56.80 | 15.00 |
| 119 LYS | NZ | −38.99 | −43.60 | 57.92 | 15.00 |
| 119 LYS | C | −39.24 | −38.95 | 58.88 | 15.00 |
| 119 LYS | O | −39.97 | −38.92 | 59.86 | 15.00 |
| 120 ALA | N | −37.92 | −39.06 | 58.95 | 15.00 |
| 120 ALA | CA | −37.26 | −39.21 | 60.24 | 15.00 |
| 120 ALA | CB | −35.86 | −39.73 | 60.05 | 15.00 |
| 120 ALA | C | −37.20 | −37.84 | 60.87 | 15.00 |
| 120 ALA | O | −37.26 | −37.70 | 62.09 | 15.00 |
| 121 LEU | N | −37.08 | −36.82 | 60.03 | 15.00 |
| 121 LEU | CA | −36.98 | −35.45 | 60.51 | 15.00 |
| 121 LEU | CB | −36.44 | −34.53 | 59.41 | 15.00 |
| 121 LEU | CG | −36.17 | −33.05 | 59.73 | 15.00 |
| 121 LEU | CD1 | −35.09 | −32.86 | 60.74 | 15.00 |
| 121 LEU | CD2 | −35.74 | −32.40 | 58.46 | 15.00 |
| 121 LEU | C | −38.30 | −34.95 | 61.07 | 15.00 |
| 121 LEU | O | −38.33 | −34.36 | 62.16 | 15.00 |
| 122 LYS | N | −39.40 | −35.27 | 60.39 | 15.00 |
| 122 LYS | CA | −40.71 | −34.88 | 60.89 | 15.00 |
| 122 LYS | CB | −41.80 | −35.31 | 59.90 | 15.00 |
| 122 LYS | CG | −43.25 | −35.03 | 60.34 | 15.00 |
| 122 LYS | CD | −44.28 | −35.77 | 59.47 | 15.00 |
| 122 LYS | CE | −45.67 | −35.70 | 60.08 | 15.00 |
| 122 LYS | NZ | −46.60 | −36.58 | 59.32 | 15.00 |
| 122 LYS | C | −40.88 | −35.54 | 62.26 | 15.00 |
| 122 LYS | O | −41.33 | −34.90 | 63.22 | 15.00 |
| 123 ARG | N | −40.48 | −36.81 | 62.38 | 15.00 |
| 123 ARG | CA | −40.58 | −37.50 | 63.65 | 15.00 |
| 123 ARG | CB | −40.25 | −38.98 | 63.52 | 15.00 |
| 123 ARG | CG | −41.30 | −39.84 | 62.88 | 15.00 |
| 123 ARG | CD | −41.30 | −41.21 | 63.51 | 15.00 |
| 123 ARG | NE | −39.95 | −41.78 | 63.60 | 15.00 |
| 123 ARG | CZ | −39.25 | −42.23 | 62.56 | 15.00 |
| 123 ARG | NH1 | −39.75 | −42.19 | 61.32 | 15.00 |
| 123 ARG | NH2 | −38.05 | −42.77 | 62.77 | 15.00 |

TABLE VIII-continued

Table of the orthogonal three dimensional coordinates in Ångstroms and B factors (Å$^2$) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue | Atom | X | Y | Z | B |
|---|---|---|---|---|---|
| 123 ARG | C | −39.70 | −36.88 | 64.73 | 15.00 |
| 123 ARG | O | −40.18 | −36.62 | 65.83 | 15.00 |
| 124 ALA | N | −38.45 | −36.57 | 64.41 | 15.00 |
| 124 ALA | CA | −37.57 | −35.99 | 65.43 | 15.00 |
| 124 ALA | CB | −36.19 | −35.74 | 64.86 | 15.00 |
| 124 ALA | C | −38.12 | −34.71 | 66.02 | 15.00 |
| 124 ALA | O | −38.00 | −34.46 | 67.22 | 15.00 |
| 125 VAL | N | −38.77 | −33.92 | 65.17 | 15.00 |
| 125 VAL | CA | −39.36 | −32.62 | 65.52 | 15.00 |
| 125 VAL | CB | −39.54 | −31.74 | 64.24 | 15.00 |
| 125 VAL | CG1 | −40.40 | −30.50 | 64.54 | 15.00 |
| 125 VAL | CG2 | −38.15 | −31.36 | 63.70 | 15.00 |
| 125 VAL | C | −40.70 | −32.75 | 66.24 | 15.00 |
| 125 VAL | O | −41.14 | −31.81 | 66.92 | 15.00 |
| 126 ALA | N | −41.40 | −33.85 | 66.02 | 15.00 |
| 126 ALA | CA | −42.67 | −34.05 | 66.68 | 15.00 |
| 126 ALA | CB | −43.57 | −35.00 | 65.86 | 15.00 |
| 126 ALA | C | −42.42 | −34.59 | 68.08 | 15.00 |
| 126 ALA | O | −42.99 | −34.11 | 69.06 | 15.00 |
| 127 ARG | N | −41.47 | −35.52 | 68.18 | 15.00 |
| 127 ARG | CA | −41.15 | −36.15 | 69.47 | 15.00 |
| 127 ARG | CB | −40.71 | −37.61 | 69.26 | 15.00 |
| 127 ARG | CG | −41.77 | −38.56 | 68.76 | 15.00 |
| 127 ARG | CD | −42.88 | −38.82 | 69.77 | 15.00 |
| 127 ARG | NE | −43.75 | −39.92 | 69.33 | 15.00 |
| 127 ARG | CZ | −44.83 | −40.35 | 69.98 | 15.00 |
| 127 ARG | NH1 | −45.54 | −41.36 | 69.47 | 15.00 |
| 127 ARG | NH2 | −45.21 | −39.78 | 71.13 | 15.00 |
| 127 ARG | C | −40.13 | −35.44 | 70.36 | 15.00 |
| 127 ARG | O | −40.28 | −35.42 | 71.58 | 15.00 |
| 128 VAL | N | −39.07 | −34.89 | 69.76 | 15.00 |
| 128 VAL | CA | −37.97 | −34.24 | 70.49 | 15.00 |
| 128 VAL | CB | −36.63 | −34.58 | 69.81 | 15.00 |
| 128 VAL | CG1 | −35.45 | −34.03 | 70.61 | 15.00 |
| 128 VAL | CG2 | −36.48 | −36.07 | 69.66 | 15.00 |
| 128 VAL | C | −38.10 | −32.73 | 70.56 | 15.00 |
| 128 VAL | O | −37.92 | −32.12 | 71.63 | 15.00 |
| 129 GLY | N | −38.44 | −32.14 | 69.42 | 15.00 |
| 129 GLY | CA | −38.57 | −30.70 | 69.33 | 15.00 |
| 129 GLY | C | −37.60 | −30.09 | 68.33 | 15.00 |
| 129 GLY | O | −37.12 | −30.79 | 67.45 | 15.00 |
| 130 PRO | N | −37.31 | −28.77 | 68.42 | 15.00 |
| 130 PRO | CD | −37.83 | −27.89 | 69.47 | 15.00 |
| 130 PRO | CA | −36.40 | −28.02 | 67.54 | 15.00 |
| 130 PRO | CB | −36.13 | −26.77 | 68.34 | 15.00 |
| 130 PRO | CG | −37.40 | −26.52 | 68.98 | 15.00 |
| 130 PRO | C | −35.13 | −28.78 | 67.19 | 15.00 |
| 130 PRO | O | −34.38 | −29.24 | 68.05 | 15.00 |
| 131 VAL | N | −34.91 | −28.91 | 65.89 | 15.00 |
| 131 VAL | CA | −33.78 | −29.63 | 65.37 | 15.00 |
| 131 VAL | CB | −34.27 | −30.83 | 64.56 | 15.00 |
| 131 VAL | CG1 | −33.10 | −31.52 | 63.87 | 15.00 |
| 131 VAL | CG2 | −35.02 | −31.76 | 65.47 | 15.00 |
| 131 VAL | C | −32.91 | −28.75 | 64.48 | 15.00 |
| 131 VAL | O | −33.43 | −28.02 | 63.65 | 15.00 |
| 132 SER | N | −31.60 | −28.85 | 64.68 | 15.00 |
| 132 SER | CA | −30.59 | −28.13 | 63.91 | 15.00 |
| 132 SER | CB | −29.21 | −28.32 | 64.54 | 15.00 |
| 132 SER | OG | −28.89 | −27.37 | 65.52 | 15.00 |
| 132 SER | C | −30.50 | −28.73 | 62.50 | 15.00 |
| 132 SER | O | −30.34 | −29.94 | 62.34 | 15.00 |
| 133 VAL | N | −30.47 | −27.87 | 61.50 | 15.00 |
| 133 VAL | CA | −30.38 | −28.36 | 60.13 | 15.00 |
| 133 VAL | CB | −31.75 | −28.35 | 59.45 | 15.00 |
| 133 VAL | CG1 | −32.73 | −29.24 | 60.17 | 15.00 |
| 133 VAL | CG2 | −32.30 | −26.98 | 59.41 | 15.00 |
| 133 VAL | C | −29.52 | −27.41 | 59.35 | 15.00 |
| 133 VAL | O | −29.29 | −26.29 | 59.79 | 15.00 |
| 134 ALA | N | −29.14 | −27.85 | 58.15 | 15.00 |
| 134 ALA | CA | −28.32 | −27.08 | 57.22 | 15.00 |
| 134 ALA | CB | −26.99 | −27.75 | 56.97 | 15.00 |
| 134 ALA | C | −29.14 | −27.06 | 55.95 | 15.00 |
| 134 ALA | O | −29.99 | −27.92 | 55.71 | 15.00 |
| 135 ILE | N | −28.79 | −26.11 | 55.09 | 15.00 |
| 135 ILE | CA | −29.49 | −25.93 | 53.83 | 15.00 |
| 135 ILE | CB | −30.82 | −25.12 | 54.04 | 15.00 |
| 135 ILE | CG2 | −31.90 | −26.00 | 54.64 | 15.00 |
| 135 ILE | CG1 | −30.57 | −23.83 | 54.85 | 15.00 |
| 135 ILE | CD1 | −31.76 | −22.91 | 54.86 | 15.00 |
| 135 ILE | C | −28.69 | −25.16 | 52.82 | 15.00 |
| 135 ILE | O | −27.58 | −24.73 | 53.10 | 15.00 |
| 136 ASP | N | −29.20 | −25.10 | 51.61 | 15.00 |
| 136 ASP | CA | −28.56 | −24.32 | 50.56 | 15.00 |
| 136 ASP | CB | −28.74 | −24.95 | 49.18 | 15.00 |
| 136 ASP | CG | −28.23 | −24.06 | 48.08 | 15.00 |
| 136 ASP | OD1 | −28.28 | −24.45 | 46.91 | 15.00 |
| 136 ASP | OD2 | −27.73 | −22.96 | 48.35 | 15.00 |
| 136 ASP | C | −29.32 | −23.01 | 50.62 | 15.00 |
| 136 ASP | O | −30.51 | −22.93 | 50.35 | 15.00 |
| 137 ALA | N | −28.59 | −21.94 | 50.84 | 15.00 |
| 137 ALA | CA | −29.23 | −20.64 | 50.97 | 15.00 |
| 137 ALA | CB | −29.22 | −20.22 | 52.43 | 15.00 |
| 137 ALA | C | −28.65 | −19.55 | 50.07 | 15.00 |
| 137 ALA | O | −28.89 | −18.38 | 50.30 | 15.00 |
| 138 SER | N | −27.97 | −19.97 | 49.00 | 15.00 |
| 138 SER | CA | −27.34 | −19.06 | 48.03 | 15.00 |
| 138 SER | CB | −26.28 | −19.80 | 47.23 | 15.00 |
| 138 SER | OG | −26.71 | −21.14 | 47.02 | 15.00 |
| 138 SER | C | −28.32 | −18.41 | 47.07 | 15.00 |
| 138 SER | O | −28.09 | −17.29 | 46.57 | 15.00 |
| 139 LEU | N | −29.42 | −19.14 | 46.81 | 15.00 |
| 139 LEU | CA | −30.44 | −18.68 | 45.87 | 15.00 |
| 139 LEU | CB | −31.60 | −19.68 | 45.83 | 15.00 |
| 139 LEU | CG | −31.57 | −20.77 | 44.76 | 15.00 |
| 139 LEU | CD1 | −31.68 | −20.14 | 43.39 | 15.00 |
| 139 LEU | CD2 | −30.29 | −21.58 | 44.84 | 15.00 |
| 139 LEU | C | −30.95 | −17.30 | 46.25 | 15.00 |
| 139 LEU | O | −31.39 | −17.09 | 47.37 | 15.00 |
| 140 THR | N | −30.99 | −16.39 | 45.28 | 15.00 |
| 140 THR | CA | −31.41 | −15.04 | 45.54 | 15.00 |
| 140 THR | CB | −31.16 | −14.10 | 44.30 | 15.00 |
| 140 THR | OG1 | −30.83 | −14.87 | 43.13 | 15.00 |
| 140 THR | CG2 | −30.00 | −13.22 | 44.59 | 15.00 |
| 140 THR | C | −32.86 | −14.97 | 46.00 | 15.00 |
| 140 THR | O | −33.25 | −14.00 | 46.66 | 15.00 |
| 141 SER | N | −33.65 | −15.99 | 45.68 | 15.00 |
| 141 SER | CA | −35.05 | −16.03 | 46.09 | 15.00 |
| 141 SER | CB | −35.80 | −17.14 | 45.35 | 15.00 |
| 141 SER | OG | −34.95 | −18.27 | 45.17 | 15.00 |
| 141 SER | C | −35.15 | −16.16 | 47.60 | 15.00 |
| 141 SER | O | −35.95 | −15.48 | 48.25 | 15.00 |
| 142 PHE | N | −34.23 | −16.95 | 48.15 | 15.00 |
| 142 PHE | CA | −34.11 | −17.19 | 49.58 | 15.00 |
| 142 PHE | CB | −32.92 | −18.13 | 49.84 | 15.00 |
| 142 PHE | CG | −32.94 | −18.73 | 51.21 | 15.00 |
| 142 PHE | CD1 | −33.41 | −20.03 | 51.41 | 15.00 |
| 142 PHE | CD2 | −32.54 | −17.97 | 52.34 | 15.00 |
| 142 PHE | CE1 | −33.50 | −20.55 | 52.67 | 15.00 |
| 142 PHE | CE2 | −32.63 | −18.49 | 53.60 | 15.00 |
| 142 PHE | CZ | −33.10 | −19.77 | 53.78 | 15.00 |
| 142 PHE | C | −33.90 | −15.87 | 50.34 | 15.00 |
| 142 PHE | O | −34.57 | −15.60 | 51.33 | 15.00 |
| 143 GLN | N | −33.02 | −15.01 | 49.84 | 15.00 |
| 143 GLN | CA | −32.74 | −13.74 | 50.49 | 15.00 |
| 143 GLN | CB | −31.45 | −13.14 | 49.95 | 15.00 |
| 143 GLN | CG | −30.34 | −14.15 | 49.75 | 15.00 |
| 143 GLN | CD | −29.07 | −13.49 | 49.24 | 15.00 |
| 143 GLN | OE1 | −29.02 | −12.26 | 49.08 | 15.00 |
| 143 GLN | NE2 | −28.02 | −14.29 | 49.00 | 15.00 |
| 143 GLN | C | −33.90 | −12.76 | 50.35 | 15.00 |

TABLE VIII-continued

Table of the orthogonal three dimensional coordinates in Ångstroms and B factors (Å²) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue | Atom | X | Y | Z | B |
|---|---|---|---|---|---|
| 143 GLN | O | −34.20 | −12.02 | 51.29 | 15.00 |
| 144 PHE | N | −34.58 | −12.77 | 49.20 | 15.00 |
| 144 PHE | CA | −35.72 | −11.87 | 49.00 | 15.00 |
| 144 PHE | CB | −35.76 | −11.31 | 47.56 | 15.00 |
| 144 PHE | CG | −34.56 | −10.48 | 47.21 | 15.00 |
| 144 PHE | CD1 | −34.12 | −9.49 | 48.08 | 15.00 |
| 144 PHE | CD2 | −33.89 | −10.69 | 46.02 | 15.00 |
| 144 PHE | CE1 | −33.03 | −8.71 | 47.77 | 15.00 |
| 144 PHE | CE2 | −32.80 | −9.92 | 45.68 | 15.00 |
| 144 PHE | CZ | −32.36 | −8.93 | 46.55 | 15.00 |
| 144 PHE | C | −37.07 | −12.48 | 49.36 | 15.00 |
| 144 PHE | O | −38.09 | −11.81 | 49.24 | 15.00 |
| 145 TYR | N | −37.08 | −13.74 | 49.80 | 15.00 |
| 145 TYR | CA | −38.31 | −14.45 | 50.22 | 15.00 |
| 145 TYR | CB | −37.94 | −15.77 | 50.96 | 15.00 |
| 145 TYR | CG | −39.07 | −16.36 | 51.80 | 15.00 |
| 145 TYR | CD1 | −39.94 | −17.34 | 51.29 | 15.00 |
| 145 TYR | CE1 | −41.00 | −17.82 | 52.05 | 15.00 |
| 145 TYR | CD2 | −39.30 | −15.88 | 53.10 | 15.00 |
| 145 TYR | CE2 | −40.33 | −16.32 | 53.86 | 15.00 |
| 145 TYR | CZ | −41.19 | −17.29 | 53.34 | 15.00 |
| 145 TYR | OH | −42.25 | −17.67 | 54.16 | 15.00 |
| 145 TYR | C | −39.14 | −13.55 | 51.14 | 15.00 |
| 145 TYR | O | −38.60 | −12.81 | 51.97 | 15.00 |
| 146 SER | N | −40.45 | −13.64 | 51.02 | 15.00 |
| 146 SER | CA | −41.31 | −12.83 | 51.88 | 15.00 |
| 146 SER | CB | −41.74 | −11.55 | 51.16 | 15.00 |
| 146 SER | OG | −40.94 | −10.40 | 51.51 | 15.00 |
| 146 SER | C | −42.53 | −13.55 | 52.45 | 15.00 |
| 146 SER | O | −42.89 | −13.33 | 53.61 | 15.00 |
| 147 LYS | N | −43.15 | −14.44 | 51.68 | 15.00 |
| 147 LYS | CA | −44.33 | −15.12 | 52.17 | 15.00 |
| 147 LYS | CB | −45.53 | −14.22 | 51.94 | 15.00 |
| 147 LYS | CG | −45.80 | −13.23 | 53.02 | 15.00 |
| 147 LYS | CD | −46.76 | −12.13 | 52.55 | 15.00 |
| 147 LYS | CE | −47.91 | −12.66 | 51.67 | 15.00 |
| 147 LYS | NZ | −48.65 | −13.77 | 52.35 | 15.00 |
| 147 LYS | C | −44.63 | −16.41 | 51.41 | 15.00 |
| 147 LYS | O | −44.45 | −16.45 | 50.20 | 15.00 |
| 148 GLY | N | −45.09 | −17.43 | 52.10 | 15.00 |
| 148 GLY | CA | −45.45 | −18.66 | 51.42 | 15.00 |
| 148 GLY | C | −44.53 | −19.82 | 51.65 | 15.00 |
| 148 GLY | O | −43.56 | −19.73 | 52.41 | 15.00 |
| 149 VAL | N | −44.79 | −20.91 | 50.92 | 15.00 |
| 149 VAL | CA | −43.99 | −22.13 | 50.98 | 15.00 |
| 149 VAL | CB | −44.85 | −23.39 | 50.69 | 15.00 |
| 149 VAL | CG1 | −43.98 | −24.66 | 50.78 | 15.00 |
| 149 VAL | CG2 | −45.98 | −23.43 | 51.62 | 15.00 |
| 149 VAL | C | −42.91 | −22.02 | 49.90 | 15.00 |
| 149 VAL | O | −43.22 | −22.06 | 48.72 | 15.00 |
| 150 TYR | N | −41.68 | −21.79 | 50.34 | 15.00 |
| 150 TYR | CA | −40.49 | −21.66 | 49.49 | 15.00 |
| 150 TYR | CB | −39.31 | −21.17 | 50.33 | 15.00 |
| 150 TYR | CG | −38.07 | −21.02 | 49.48 | 15.00 |
| 150 TYR | CD1 | −37.90 | −19.91 | 48.65 | 15.00 |
| 150 TYR | CE1 | −36.75 | −19.75 | 47.90 | 15.00 |
| 150 TYR | CD2 | −37.05 | −21.97 | 49.52 | 15.00 |
| 150 TYR | CE2 | −35.89 | −21.82 | 48.77 | 15.00 |
| 150 TYR | CZ | −35.75 | −20.71 | 47.97 | 15.00 |
| 150 TYR | OH | −34.59 | −20.55 | 47.26 | 15.00 |
| 150 TYR | C | −40.04 | −22.89 | 48.73 | 15.00 |
| 150 TYR | O | −39.72 | −23.95 | 49.29 | 15.00 |
| 151 TYR | N | −39.88 | −22.68 | 47.44 | 15.00 |
| 151 TYR | CA | −39.46 | −23.73 | 46.54 | 15.00 |
| 151 TYR | CB | −40.63 | −24.64 | 46.18 | 15.00 |
| 151 TYR | CG | −40.18 | −25.91 | 45.48 | 15.00 |
| 151 TYR | CD1 | −39.56 | −26.99 | 46.24 | 15.00 |
| 151 TYR | CE1 | −39.05 | −28.12 | 45.59 | 15.00 |
| 151 TYR | CD2 | −40.31 | −25.99 | 44.05 | 15.00 |
| 151 TYR | CE2 | −39.83 | −27.07 | 43.37 | 15.00 |
| 151 TYR | CZ | −39.19 | −28.15 | 44.13 | 15.00 |
| 151 TYR | OH | −38.66 | −29.25 | 43.41 | 15.00 |
| 151 TYR | C | −38.86 | −23.09 | 45.29 | 15.00 |
| 151 TYR | O | −39.45 | −22.21 | 44.68 | 15.00 |
| 152 ASP | N | −37.66 | −23.52 | 44.96 | 15.00 |
| 152 ASP | CA | −36.90 | −23.04 | 43.81 | 15.00 |
| 152 ASP | CB | −35.90 | −21.97 | 44.26 | 15.00 |
| 152 ASP | CG | −35.26 | −21.25 | 43.08 | 15.00 |
| 152 ASP | OD1 | −35.42 | −20.01 | 42.99 | 15.00 |
| 152 ASP | OD2 | −34.63 | −21.92 | 42.23 | 15.00 |
| 152 ASP | C | −36.16 | −24.28 | 43.31 | 15.00 |
| 152 ASP | O | −35.56 | −25.00 | 44.09 | 15.00 |
| 153 GLU | N | −36.16 | −24.49 | 42.00 | 15.00 |
| 153 GLU | CA | −35.56 | −25.67 | 41.38 | 15.00 |
| 153 GLU | CB | −36.09 | −25.74 | 39.97 | 15.00 |
| 153 GLU | CG | −35.94 | −24.42 | 39.26 | 15.00 |
| 153 GLU | CD | −36.44 | −24.48 | 37.83 | 15.00 |
| 153 GLU | OE1 | −35.63 | −24.12 | 36.94 | 15.00 |
| 153 GLU | OE2 | −37.62 | −24.87 | 37.62 | 15.00 |
| 153 GLU | C | −34.04 | −25.70 | 41.31 | 15.00 |
| 153 GLU | O | −33.47 | −26.73 | 40.99 | 15.00 |
| 154 SER | N | −33.39 | −24.59 | 41.60 | 15.00 |
| 154 SER | CA | −31.95 | −24.48 | 41.56 | 15.00 |
| 154 SER | CB | −31.59 | −23.07 | 41.09 | 15.00 |
| 154 SER | OG | −32.22 | −22.78 | 39.85 | 15.00 |
| 154 SER | C | −31.28 | −24.79 | 42.91 | 15.00 |
| 154 SER | O | −30.07 | −24.67 | 43.03 | 15.00 |
| 155 CYS | N | −32.08 | −25.19 | 43.90 | 15.00 |
| 155 CYS | CA | −31.55 | −25.49 | 45.23 | 15.00 |
| 155 CYS | C | −30.88 | −26.84 | 45.21 | 15.00 |
| 155 CYS | O | −31.52 | −27.87 | 45.08 | 15.00 |
| 155 CYS | CB | −32.63 | −25.43 | 46.33 | 15.00 |
| 155 CYS | SG | −32.25 | −24.44 | 47.82 | 15.00 |
| 156 ASN | N | −29.57 | −26.79 | 45.39 | 15.00 |
| 156 ASN | CA | −28.70 | −27.97 | 45.38 | 15.00 |
| 156 ASN | CB | −27.30 | −27.52 | 44.99 | 15.00 |
| 156 ASN | CG | −26.51 | −28.59 | 44.35 | 15.00 |
| 156 ASN | OD1 | −26.70 | −29.78 | 44.62 | 15.00 |
| 156 ASN | ND2 | −25.58 | −28.18 | 43.51 | 15.00 |
| 156 ASN | C | −28.63 | −28.71 | 46.72 | 15.00 |
| 156 ASN | O | −28.12 | −28.19 | 47.70 | 15.00 |
| 157 SER | N | −29.09 | −29.96 | 46.73 | 15.00 |
| 157 SER | CA | −29.09 | −30.77 | 47.95 | 15.00 |
| 157 SER | CB | −29.77 | −32.11 | 47.70 | 15.00 |
| 157 SER | OG | −31.03 | −31.95 | 47.10 | 15.00 |
| 157 SER | C | −27.68 | −31.08 | 48.43 | 15.00 |
| 157 SER | O | −27.48 | −31.52 | 49.54 | 15.00 |
| 158 ASP | N | −26.71 | −30.93 | 47.55 | 15.00 |
| 158 ASP | CA | −25.34 | −31.23 | 47.91 | 15.00 |
| 158 ASP | CB | −24.69 | −32.07 | 46.78 | 15.00 |
| 158 ASP | CG | −25.32 | −33.44 | 46.67 | 15.00 |
| 158 ASP | OD1 | −26.15 | −33.63 | 45.75 | 15.00 |
| 158 ASP | OD2 | −25.05 | −34.30 | 47.55 | 15.00 |
| 158 ASP | C | −24.46 | −30.07 | 48.28 | 15.00 |
| 158 ASP | O | −23.27 | −30.25 | 48.57 | 15.00 |
| 159 ASN | N | −25.05 | −28.88 | 48.29 | 15.00 |
| 159 ASN | CA | −24.30 | −27.69 | 48.61 | 15.00 |
| 159 ASN | CB | −24.34 | −26.74 | 47.42 | 15.00 |
| 159 ASN | CG | −23.51 | −25.49 | 47.62 | 15.00 |
| 159 ASN | OD1 | −22.35 | −25.55 | 48.00 | 15.00 |
| 159 ASN | ND2 | −24.12 | −24.33 | 47.38 | 15.00 |
| 159 ASN | C | −24.93 | −27.03 | 49.82 | 15.00 |
| 159 ASN | O | −25.67 | −26.05 | 49.68 | 15.00 |
| 160 LEU | N | −24.68 | −27.59 | 50.99 | 15.00 |
| 160 LEU | CA | −25.16 | −27.07 | 52.24 | 15.00 |
| 160 LEU | CB | −25.06 | −28.15 | 53.29 | 15.00 |
| 160 LEU | CG | −25.72 | −29.45 | 52.83 | 15.00 |
| 160 LEU | CD1 | −25.24 | −30.64 | 53.62 | 15.00 |
| 160 LEU | CD2 | −27.22 | −29.26 | 52.91 | 15.00 |
| 160 LEU | C | −24.22 | −25.95 | 52.63 | 15.00 |

TABLE VIII-continued

Table of the orthogonal three dimensional coordinates in Ångstroms and B factors (Å$^2$) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue | Atom | X | Y | Z | B |
|---|---|---|---|---|---|
| 160 LEU | O | −23.06 | −26.21 | 52.92 | 15.00 |
| 161 ASN | N | −24.73 | −24.74 | 52.74 | 15.00 |
| 161 ASN | CA | −23.91 | −23.58 | 53.10 | 15.00 |
| 161 ASN | CB | −23.61 | −22.78 | 51.83 | 15.00 |
| 161 ASN | CG | −24.84 | −22.55 | 50.93 | 15.00 |
| 161 ASN | OD1 | −25.71 | −21.74 | 51.22 | 15.00 |
| 161 ASN | ND2 | −24.92 | −23.31 | 49.84 | 15.00 |
| 161 ASN | C | −24.42 | −22.67 | 54.23 | 15.00 |
| 161 ASN | O | −23.75 | −21.70 | 54.59 | 15.00 |
| 162 HIS | N | −25.60 | −22.96 | 54.76 | 15.00 |
| 162 HIS | CA | −26.13 | −22.19 | 55.86 | 15.00 |
| 162 HIS | CB | −27.12 | −21.15 | 55.35 | 15.00 |
| 162 HIS | CG | −27.63 | −20.21 | 56.41 | 15.00 |
| 162 HIS | CD2 | −28.89 | −19.99 | 56.84 | 15.00 |
| 162 HIS | ND1 | −26.82 | −19.39 | 57.16 | 15.00 |
| 162 HIS | CE1 | −27.56 | −18.68 | 57.99 | 15.00 |
| 162 HIS | NE2 | −28.82 | −19.03 | 57.82 | 15.00 |
| 162 HIS | C | −26.80 | −23.11 | 56.86 | 15.00 |
| 162 HIS | O | −27.41 | −24.10 | 56.49 | 15.00 |
| 163 ALA | N | −26.61 | −22.84 | 58.14 | 15.00 |
| 163 ALA | CA | −27.27 | −23.63 | 59.17 | 15.00 |
| 163 ALA | CB | −26.35 | −23.90 | 60.32 | 15.00 |
| 163 ALA | C | −28.47 | −22.85 | 59.65 | 15.00 |
| 163 ALA | O | −28.43 | −21.62 | 59.83 | 15.00 |
| 164 VAL | N | −29.53 | −23.57 | 59.97 | 15.00 |
| 164 VAL | CA | −30.75 | −22.92 | 60.40 | 15.00 |
| 164 VAL | CB | −31.54 | −22.58 | 59.10 | 15.00 |
| 164 VAL | CG1 | −32.42 | −23.71 | 58.68 | 15.00 |
| 164 VAL | CG2 | −32.27 | −21.27 | 59.22 | 15.00 |
| 164 VAL | C | −31.49 | −23.77 | 61.47 | 15.00 |
| 164 VAL | O | −31.01 | −24.81 | 61.87 | 15.00 |
| 165 LEU | N | −32.64 | −23.32 | 61.97 | 15.00 |
| 165 LEU | CA | −33.33 | −24.10 | 62.98 | 15.00 |
| 165 LEU | CB | −33.27 | −23.41 | 64.32 | 15.00 |
| 165 LEU | CG | −33.72 | −24.12 | 65.58 | 15.00 |
| 165 LEU | CD1 | −32.59 | −24.89 | 66.21 | 15.00 |
| 165 LEU | CD2 | −34.18 | −23.05 | 66.52 | 15.00 |
| 165 LEU | C | −34.76 | −24.44 | 62.63 | 15.00 |
| 165 LEU | O | −35.55 | −23.56 | 62.28 | 15.00 |
| 166 ALA | N | −35.05 | −25.73 | 62.66 | 15.00 |
| 166 ALA | CA | −36.37 | −26.25 | 62.37 | 15.00 |
| 166 ALA | CB | −36.25 | −27.61 | 61.71 | 15.00 |
| 166 ALA | C | −37.09 | −26.35 | 63.69 | 15.00 |
| 166 ALA | O | −36.63 | −27.02 | 64.62 | 15.00 |
| 167 VAL | N | −38.24 | −25.69 | 63.76 | 15.00 |
| 167 VAL | CA | −39.08 | −25.64 | 64.97 | 15.00 |
| 167 VAL | CB | −39.16 | −24.22 | 65.61 | 15.00 |
| 167 VAL | CG1 | −37.79 | −23.68 | 65.96 | 15.00 |
| 167 VAL | CG2 | −39.89 | −23.25 | 64.67 | 15.00 |
| 167 VAL | C | −40.52 | −26.07 | 64.76 | 15.00 |
| 167 VAL | O | −41.40 | −25.61 | 65.46 | 15.00 |
| 168 GLY | N | −40.78 | −26.91 | 63.77 | 15.00 |
| 168 GLY | CA | −42.15 | −27.34 | 63.56 | 15.00 |
| 168 GLY | C | −42.35 | −27.62 | 62.09 | 15.00 |
| 168 GLY | O | −41.42 | −27.58 | 61.31 | 15.00 |
| 169 TYR | N | −43.58 | −27.95 | 61.73 | 15.00 |
| 169 TYR | CA | −43.99 | −28.29 | 60.36 | 15.00 |
| 169 TYR | CB | −43.51 | −29.71 | 59.99 | 15.00 |
| 169 TYR | CG | −44.07 | −30.82 | 60.89 | 15.00 |
| 169 TYR | CD1 | −45.33 | −31.41 | 60.61 | 15.00 |
| 169 TYR | CE1 | −45.86 | −32.39 | 61.43 | 15.00 |
| 169 TYR | CD2 | −43.34 | −31.27 | 62.02 | 15.00 |
| 169 TYR | CE2 | −43.88 | −32.28 | 62.86 | 15.00 |
| 169 TYR | CZ | −45.12 | −32.81 | 62.55 | 15.00 |
| 169 TYR | OH | −45.63 | −33.71 | 63.41 | 15.00 |
| 169 TYR | C | −45.53 | −28.26 | 60.32 | 15.00 |
| 169 TYR | O | −46.20 | −28.25 | 61.37 | 15.00 |
| 170 GLY | N | −46.09 | −28.23 | 59.12 | 15.00 |
| 170 GLY | CA | −47.54 | −28.17 | 58.95 | 15.00 |
| 170 GLY | C | −47.93 | −28.06 | 57.48 | 15.00 |
| 170 GLY | O | −47.12 | −28.35 | 56.61 | 15.00 |
| 171 ILE | N | −49.14 | −27.61 | 57.17 | 15.00 |
| 171 ILE | CA | −49.55 | −27.54 | 55.77 | 15.00 |
| 171 ILE | CB | −50.30 | −28.85 | 55.41 | 15.00 |
| 171 ILE | CG2 | −51.37 | −29.17 | 56.40 | 15.00 |
| 171 ILE | CG1 | −50.79 | −28.82 | 53.99 | 15.00 |
| 171 ILE | CD1 | −51.11 | −30.20 | 53.45 | 15.00 |
| 171 ILE | C | −50.38 | −26.29 | 55.43 | 15.00 |
| 171 ILE | O | −51.37 | −26.02 | 56.10 | 15.00 |
| 172 GLN | N | −49.93 | −25.52 | 54.44 | 15.00 |
| 172 GLN | CA | −50.64 | −24.31 | 54.01 | 15.00 |
| 172 GLN | CB | −49.68 | −23.10 | 54.05 | 15.00 |
| 172 GLN | CG | −50.30 | −21.69 | 53.87 | 15.00 |
| 172 GLN | CD | −49.27 | −20.56 | 53.75 | 15.00 |
| 172 GLN | OE1 | −48.07 | −20.77 | 53.89 | 15.00 |
| 172 GLN | NE2 | −49.74 | −19.35 | 53.49 | 15.00 |
| 172 GLN | C | −51.25 | −24.41 | 52.63 | 15.00 |
| t72 GLN | O | −50.56 | −24.19 | 51.64 | 15.00 |
| 173 LYS | N | −52.55 | −24.75 | 52.57 | 15.00 |
| 173 LYS | CA | −53.33 | −24.85 | 51.32 | 15.00 |
| 173 LYS | CB | −53.40 | −23.48 | 50.61 | 15.00 |
| 173 LYS | CG | −54.16 | −22.39 | 51.36 | 15.00 |
| 173 LYS | CD | −53.57 | −22.02 | 52.75 | 15.00 |
| 173 LYS | CE | −54.37 | −22.65 | 53.92 | 15.00 |
| 173 LYS | NZ | −54.04 | −22.06 | 55.23 | 15.00 |
| 173 LYS | C | −52.85 | −25.93 | 50.36 | 15.00 |
| 173 LYS | O | −52.73 | −25.69 | 49.15 | 15.00 |
| 174 GLY | N | −52.61 | −27.11 | 50.90 | 15.00 |
| 174 GLY | CA | −52.15 | −28.21 | 50.08 | 15.00 |
| 174 GLY | C | −50.64 | −28.26 | 50.03 | 15.00 |
| 174 GLY | O | −50.08 | −29.23 | 49.53 | 15.00 |
| 175 ASN | N | −49.97 | −27.25 | 50.58 | 15.00 |
| 175 ASN | CA | −48.52 | −27.27 | 50.57 | 15.00 |
| 175 ASN | CB | −47.92 | −26.00 | 49.95 | 15.00 |
| 175 ASN | CG | −48.48 | −25.73 | 48.57 | 15.00 |
| 175 ASN | OD1 | −48.53 | −26.61 | 47.73 | 15.00 |
| 175 ASN | ND2 | −48.96 | −24.51 | 48.37 | 15.00 |
| 175 ASN | C | −47.94 | −27.50 | 51.94 | 15.00 |
| 175 ASN | O | −48.04 | −26.66 | 52.86 | 15.00 |
| 176 LYS | N | −47.37 | −28.69 | 52.07 | 15.00 |
| 176 LYS | CA | −46.71 | −29.13 | 53.27 | 15.00 |
| 176 LYS | CB | −46.28 | −30.61 | 53.08 | 15.00 |
| 176 LYS | CG | −47.40 | −31.59 | 52.68 | 15.00 |
| 176 LYS | CD | −47.20 | −32.92 | 53.41 | 15.00 |
| 176 LYS | CE | −48.36 | −33.85 | 53.17 | 15.00 |
| 176 LYS | NZ | −48.49 | −34.80 | 54.30 | 15.00 |
| 176 LYS | C | −45.51 | −28.18 | 53.48 | 15.00 |
| 176 LYS | O | −45.12 | −27.49 | 52.55 | 15.00 |
| 177 HIS | N | −44.94 | −28.15 | 54.68 | 15.00 |
| 177 HIS | CA | −43.82 | −27.26 | 54.97 | 15.00 |
| 177 HIS | CB | −44.23 | −25.79 | 54.78 | 15.00 |
| 177 HIS | CG | −45.19 | −25.25 | 55.82 | 15.00 |
| 177 HIS | CD2 | −45.07 | −25.11 | 57.17 | 15.00 |
| 177 HIS | ND1 | −46.37 | −24.62 | 55.49 | 15.00 |
| 177 HIS | CE1 | −46.93 | −24.11 | 56.58 | 15.00 |
| 177 HIS | NE2 | −46.16 | −24.40 | 57.61 | 15.00 |
| 177 HIS | C | −43.08 | −27.42 | 56.30 | 15.00 |
| 177 HIS | O | −43.62 | −27.92 | 57.28 | 15.00 |
| 178 TRP | N | −41.81 | −27.01 | 56.29 | 15.00 |
| 178 TRP | CA | −40.97 | −27.01 | 57.48 | 15.00 |
| 178 TRP | CB | −39.52 | −27.41 | 57.16 | 15.00 |
| 178 TRP | CG | −39.34 | −28.83 | 56.89 | 15.00 |
| 178 TRP | CD2 | −39.46 | −29.91 | 57.82 | 15.00 |
| 178 TRP | CE2 | −39.29 | −31.11 | 57.09 | 15.00 |
| 178 TRP | CE3 | −39.70 | −29.97 | 59.20 | 15.00 |
| 178 TRP | CD1 | −39.09 | −29.39 | 55.68 | 15.00 |
| 178 TRP | NE1 | −39.07 | −30.76 | 55.78 | 15.00 |
| 178 TRP | CZ2 | −39.34 | −32.38 | 57.67 | 15.00 |
| 178 TRP | CZ3 | −39.76 | −31.22 | 59.78 | 15.00 |
| 178 TRP | CH2 | −39.58 | −32.42 | 59.b1 | 15.00 |

TABLE VIII-continued

Table of the orthogonal three dimensional coordinates in Ångstroms and B factors (Å$^2$) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue | Atom | X | Y | Z | B |
|---|---|---|---|---|---|
| 178 TRP | C | −41.00 | −25.55 | 57.95 | 15.00 |
| 178 TRP | O | −41.12 | −24.64 | 57.14 | 15.00 |
| 179 ILE | N | −41.04 | −25.34 | 59.26 | 15.00 |
| 179 ILE | CA | −41.05 | −23.98 | 59.78 | 15.00 |
| 179 ILE | CB | −41.99 | −23.89 | 60.97 | 15.00 |
| 179 ILE | CG2 | −41.90 | −22.54 | 61.61 | 15.00 |
| 179 ILE | CG1 | −43.42 | −24.18 | 60.51 | 15.00 |
| 179 ILE | CD1 | −44.37 | −24.29 | 61.63 | 15.00 |
| 179 ILE | C | −39.62 | −23.75 | 60.20 | 15.00 |
| 179 ILE | O | −39.07 | −24.45 | 61.07 | 15.00 |
| 180 ILE | N | −38.99 | −22.78 | 59.57 | 15.00 |
| 180 ILE | CA | −37.58 | −22.52 | 59.86 | 15.00 |
| 180 ILE | CB | −36.79 | −22.59 | 58.57 | 15.00 |
| 180 ILE | CG2 | −35.36 | −22.38 | 58.83 | 15.00 |
| 180 ILE | CG1 | −36.99 | −23.93 | 57.91 | 15.00 |
| 180 ILE | CD1 | −36.41 | −25.01 | 58.75 | 15.00 |
| 180 ILE | C | −37.25 | −21.18 | 60.52 | 15.00 |
| 180 ILE | O | −37.82 | −20.13 | 60.17 | 15.00 |
| 181 LYS | N | −36.35 | −21.19 | 61.49 | 15.00 |
| 181 LYS | CA | −35.97 | −19.95 | 62.16 | 15.00 |
| 181 LYS | CB | −35.83 | −20.19 | 63.65 | 15.00 |
| 181 LYS | CG | −35.49 | −18.92 | 64.45 | 15.00 |
| 181 LYS | CD | −35.36 | −19.25 | 65.93 | 15.00 |
| 181 LYS | CE | −35.01 | −18.04 | 66.76 | 15.00 |
| 181 LYS | NZ | −34.86 | −18.51 | 68.16 | 15.00 |
| 181 LYS | C | −34.64 | −19.50 | 61.61 | 15.00 |
| 181 LYS | O | −33.72 | −20.32 | 61.54 | 15.00 |
| 182 ASN | N | −34.49 | −18.23 | 61.27 | 15.00 |
| 182 ASN | CA | −33.22 | −17.79 | 60.71 | 15.00 |
| 182 ASN | CB | −33.45 | −17.10 | 59.34 | 15.00 |
| 182 ASN | CG | −32.32 | −17.37 | 58.34 | 15.00 |
| 182 ASN | OD1 | −31.30 | −18.02 | 58.65 | 15.00 |
| 182 ASN | ND2 | −32.53 | −16.89 | 57.09 | 15.00 |
| 182 ASN | C | −32.54 | −16.84 | 61.68 | 15.00 |
| 182 ASN | O | −33.16 | −16.31 | 62.60 | 15.00 |
| 183 SER | N | −31.25 | −16.64 | 61.45 | 15.00 |
| 183 SER | CA | −30.40 | −15.74 | 62.23 | 15.00 |
| 183 SER | CB | −29.16 | −16.50 | 62.75 | 15.00 |
| 183 SER | OG | −28.52 | −17.33 | 61.76 | 15.00 |
| 183 SER | C | −29.95 | −14.52 | 61.41 | 15.00 |
| 183 SER | O | −28.81 | −14.06 | 61.56 | 15.00 |
| 184 TRP | N | −30.82 | −13.98 | 60.55 | 15.00 |
| 184 TRP | CA | −30.50 | −12.82 | 59.71 | 15.00 |
| 184 TRP | CB | −30.71 | −13.10 | 58.22 | 15.00 |
| 184 TRP | CG | −29.79 | −14.06 | 57.58 | 15.00 |
| 184 TRP | CD2 | −29.90 | −14.58 | 56.26 | 15.00 |
| 184 TRP | CE2 | −28.80 | −15.45 | 56.05 | 15.00 |
| 184 TRP | CE3 | −30.82 | −14.38 | 55.22 | 15.00 |
| 184 TRP | CD1 | −28.66 | −14.61 | 58.11 | 15.00 |
| 184 TRP | NE1 | −28.06 | −15.46 | 57.20 | 15.00 |
| 184 TRP | CZ2 | −28.59 | −16.14 | 54.84 | 15.00 |
| 184 TRP | CZ3 | −30.63 | −15.04 | 54.04 | 15.00 |
| 184 TRP | CH2 | −29.52 | −15.92 | 53.84 | 15.00 |
| 184 TRP | C | −31.34 | −11.59 | 60.02 | 15.00 |
| 184 TRP | O | −31.41 | −10.70 | 59.18 | 15.00 |
| 185 GLY | N | −31.95 | −11.51 | 61.20 | 15.00 |
| 185 GLY | CA | −32.75 | −10.34 | 61.52 | 15.00 |
| 185 GLY | C | −34.24 | −10.61 | 61.41 | 15.00 |
| 185 GLY | O | −34.63 | −11.61 | 60.82 | 15.00 |
| 186 GLU | N | −35.09 | −9.75 | 61.96 | 15.00 |
| 186 GLU | CA | −36.52 | −10.00 | 61.83 | 15.00 |
| 186 GLU | CB | −37.32 | −9.44 | 63.01 | 15.00 |
| 186 GLU | CG | −36.65 | −9.45 | 64.34 | 15.00 |
| 186 GLU | CD | −37.34 | −8.56 | 65.32 | 15.00 |
| 186 GLU | OE1 | −36.68 | −8.08 | 66.25 | 15.00 |
| 186 GLU | OE2 | −38.55 | −8.32 | 65.21 | 15.00 |
| 186 GLU | C | −36.99 | −9.30 | 60.56 | 15.00 |
| 186 GLU | O | −38.10 | −9.52 | 60.08 | 15.00 |
| 187 ASN | N | −36.14 | −8.44 | 60.02 | 15.00 |
| 187 ASN | CA | −36.46 | −7.68 | 58.83 | 15.00 |
| 187 ASN | CB | −35.60 | −6.42 | 58.79 | 15.00 |
| 187 ASN | CG | −35.84 | −5.51 | 59.97 | 15.00 |
| 187 ASN | OD1 | −34.92 | −4.82 | 60.44 | 15.00 |
| 187 ASN | ND2 | −37.10 | −5.46 | 60.45 | 15.00 |
| 187 ASN | C | −36.21 | −8.52 | 57.60 | 15.00 |
| 187 ASN | O | −36.21 | −8.00 | 56.49 | 15.00 |
| 188 TRP | N | −35.89 | −9.79 | 57.81 | 15.00 |
| 188 TRP | CA | −35.66 | −10.68 | 56.68 | 15.00 |
| 188 TRP | CB | −34.39 | −11.49 | 56.84 | 15.00 |
| 188 TRP | CG | −34.20 | −12.53 | 55.78 | 15.00 |
| 188 TRP | CD2 | −34.69 | −13.89 | 55.77 | 15.00 |
| 188 TRP | CE2 | −34.21 | −14.49 | 54.59 | 15.00 |
| 188 TRP | CE3 | −35.48 | −14.67 | 56.67 | 15.00 |
| 188 TRP | CD1 | −33.48 | −12.37 | 54.63 | 15.00 |
| 188 TRP | NE1 | −33.48 | −13.54 | 53.91 | 15.00 |
| 188 TRP | CZ2 | −34.50 | −15.83 | 54.26 | 15.00 |
| 188 TRP | CZ3 | −35.76 | −15.96 | 56.35 | 15.00 |
| 188 TRP | CH2 | −35.28 | −16.55 | 55.16 | 15.00 |
| 188 TRP | C | −36.80 | −11.63 | 56.71 | 15.00 |
| 188 TRP | O | −37.29 | −11.96 | 57.78 | 15.00 |
| 189 GLY | N | −37.22 | −12.09 | 55.53 | 15.00 |
| 189 GLY | CA | −38.30 | −13.05 | 55.42 | 15.00 |
| 189 GLY | C | −39.53 | −12.66 | 56.18 | 15.00 |
| 189 GLY | O | −39.85 | −11.50 | 56.32 | 15.00 |
| 190 ASN | N | −40.23 | −13.64 | 56.73 | 15.00 |
| 190 ASN | CA | −41.43 | −13.31 | 57.46 | 15.00 |
| 190 ASN | CB | −42.42 | −14.44 | 57.30 | 15.00 |
| 190 ASN | CG | −43.81 | −14.05 | 57.76 | 15.00 |
| 190 ASN | OD1 | −44.10 | −12.89 | 58.14 | 15.00 |
| 190 ASN | ND2 | −44.72 | −15.00 | 57.62 | 15.00 |
| 190 ASN | C | −41.04 | −13.20 | 58.90 | 15.00 |
| 190 ASN | O | −40.92 | −14.22 | 59.57 | 15.00 |
| 191 LYS | N | −40.80 | −11.98 | 59.38 | 15.00 |
| 191 LYS | CA | −40.39 | −11.79 | 60.76 | 15.00 |
| 191 LYS | CB | −41.62 | −11.71 | 61.67 | 15.00 |
| 191 LYS | CG | −42.53 | −10.45 | 61.51 | 15.00 |
| 191 LYS | CD | −43.64 | −10.73 | 60.48 | 15.00 |
| 191 LYS | CE | −44.65 | −9.57 | 60.22 | 15.00 |
| 191 LYS | NZ | −44.60 | −8.96 | 58.86 | 15.00 |
| 191 LYS | C | −39.36 | −12.83 | 61.26 | 15.00 |
| 191 LYS | O | −39.58 | −13.50 | 62.27 | 15.00 |
| 192 GLY | N | −38.25 | −12.96 | 60.52 | 15.00 |
| 192 GLY | CA | −37.17 | −13.89 | 60.87 | 15.00 |
| 192 GLY | C | −37.47 | −15.35 | 60.56 | 15.00 |
| 192 GLY | O | −36.64 | −16.20 | 60.86 | 15.00 |
| 193 TYR | N | −38.59 | −15.63 | 59.91 | 15.00 |
| 193 TYR | CA | −38.89 | −17.04 | 59.63 | 15.00 |
| 193 TYR | CB | −40.12 | −17.53 | 60.44 | 15.00 |
| 193 TYR | CG | −39.91 | −17.72 | 61.94 | 15.00 |
| 193 TYR | CD1 | −39.96 | −16.63 | 62.83 | 15.00 |
| 193 TYR | CE1 | −39.79 | −16.81 | 64.19 | 15.00 |
| 193 TYR | CD2 | −39.69 | −18.99 | 62.47 | 15.00 |
| 193 TYR | CE2 | −39.52 | −19.20 | 63.79 | 15.00 |
| 193 TYR | CZ | −39.56 | −18.12 | 64.67 | 15.00 |
| 193 TYR | OH | −39.33 | −18.34 | 66.03 | 15.00 |
| 193 TYR | C | −39.11 | −17.29 | 58.14 | 15.00 |
| 193 TYR | O | −39.23 | −16.35 | 57.35 | 15.00 |
| 194 ILE | N | −39.08 | −18.56 | 57.75 | 15.00 |
| 194 ILE | CA | −39.32 | −18.92 | 56.37 | 15.00 |
| 194 ILE | CB | −37.98 | −18.83 | 55.52 | 15.00 |
| 194 ILE | CG2 | −36.90 | −19.78 | 56.01 | 15.00 |
| 194 ILE | CG1 | −38.23 | −19.04 | 54.02 | 15.00 |
| 194 ILE | CD1 | −36.98 | −19.00 | 53.22 | 15.00 |
| 194 ILE | C | −39.99 | −20.30 | 56.33 | 15.00 |
| 194 ILE | O | −39.67 | −21.16 | 57.18 | 15.00 |
| 195 LEU | N | −41.01 | −20.45 | 55.48 | 15.00 |
| 195 LEU | CA | −41.71 | −21.72 | 55.30 | 15.00 |
| 195 LEU | CB | −43.20 | −21.48 | 55.00 | 15.00 |
| 195 LEU | CG | −43.96 | −20.94 | 56.22 | 15.00 |
| 195 LEU | CD1 | −45.35 | −20.46 | 55.85 | 15.00 |

TABLE VIII-continued

Table of the orthogonal three dimensional coordinates in Ångstroms and B factors (Å$^2$) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue | Atom | X | Y | Z | B |
|---|---|---|---|---|---|
| 195 LEU | CD2 | −44.03 | −22.03 | 57.28 | 15.00 |
| 195 LEU | C | −41.08 | −22.46 | 54.14 | 15.00 |
| 195 LEU | O | −41.24 | −22.03 | 52.99 | 15.00 |
| 196 MET | N | −40.38 | −23.55 | 54.41 | 15.00 |
| 196 MET | CA | −39.73 | −24.28 | 53.34 | 15.00 |
| 196 MET | CB | −38.30 | −24.61 | 53.74 | 15.00 |
| 196 MET | CG | −37.40 | −23.37 | 53.79 | 15.00 |
| 196 MET | SD | −35.72 | −23.74 | 54.33 | 15.00 |
| 196 MET | CE | −35.19 | −24.86 | 53.02 | 15.00 |
| 196 MET | C | −40.45 | −25.54 | 52.91 | 15.00 |
| 196 MET | O | −40.92 | −26.29 | 53.76 | 15.00 |
| 197 ALA | N | −40.52 | −25.77 | 51.61 | 15.00 |
| 197 ALA | CA | −41.19 | −26.95 | 51.06 | 15.00 |
| 197 ALA | CB | −40.98 | −26.99 | 49.58 | 15.00 |
| 197 ALA | C | −40.77 | −28.28 | 51.69 | 15.00 |
| 197 ALA | O | −39.59 | −28.51 | 51.93 | 15.00 |
| 198 ARG | N | −41.77 | −29.13 | 51.96 | 15.00 |
| 198 ARG | CA | −41.53 | −30.45 | 52.55 | 15.00 |
| 198 ARG | CB | −42.18 | −30.53 | 53.94 | 15.00 |
| 198 ARG | CG | −42.26 | −31.94 | 54.56 | 15.00 |
| 198 ARG | CD | −42.45 | −31.86 | 56.05 | 15.00 |
| 198 ARG | NE | −43.59 | −31.03 | 56.41 | 15.00 |
| 198 ARG | CZ | −44.85 | −31.46 | 56.47 | 15.00 |
| 198 ARG | NH1 | −45.11 | −32.72 | 56.19 | 15.00 |
| 198 ARG | NH2 | −45.84 | −30.65 | 56.84 | 15.00 |
| 198 ARG | C | −42.05 | −31.55 | 51.67 | 15.00 |
| 198 ARG | O | −43.07 | −31.41 | 50.99 | 15.00 |
| 199 ASN | N | −41.39 | −32.69 | 51.77 | 15.00 |
| 199 ASN | CA | −41.70 | −33.89 | 51.02 | 15.00 |
| 199 ASN | CB | −43.17 | −34.27 | 51.14 | 15.00 |
| 199 ASN | CG | −43.54 | −34.74 | 52.54 | 15.00 |
| 199 ASN | OD1 | −42.66 | −34.97 | 53.39 | 15.00 |
| 199 ASN | ND2 | −44.84 | −34.86 | 52.79 | 15.00 |
| 199 ASN | C | −41.32 | −33.73 | 49.56 | 15.00 |
| 199 ASN | O | −41.24 | −34.72 | 48.84 | 15.00 |
| 200 LYS | N | −41.04 | −32.51 | 49.14 | 15.00 |
| 200 LYS | CA | −40.66 | −32.31 | 47.77 | 15.00 |
| 200 LYS | CB | −40.98 | −30.88 | 47.33 | 15.00 |
| 200 LYS | CG | −42.41 | −30.50 | 47.40 | 15.00 |
| 200 LYS | CD | −42.69 | −29.14 | 46.77 | 15.00 |
| 200 LYS | CE | −42.63 | −29.16 | 45.28 | 15.00 |
| 200 LYS | NZ | −43.85 | −29.82 | 44.77 | 15.00 |
| 200 LYS | C | −39.20 | −32.67 | 47.45 | 15.00 |
| 200 LYS | O | −38.40 | −31.81 | 47.09 | 15.00 |
| 201 ASN | N | −38.85 | −33.95 | 47.62 | 15.00 |
| 201 ASN | CA | −37.50 | −34.49 | 47.34 | 15.00 |
| 201 ASN | CB | −37.30 | −34.62 | 45.82 | 15.00 |
| 201 ASN | CG | −38.27 | −35.59 | 45.16 | 15.00 |
| 201 ASN | OD1 | −37.88 | −36.36 | 44.27 | 15.00 |
| 201 ASN | ND2 | −39.56 | −35.52 | 45.54 | 15.00 |
| 201 ASN | C | −36.34 | −33.71 | 47.95 | 15.00 |
| 201 ASN | O | −35.58 | −33.08 | 47.22 | 15.00 |
| 202 ASN | N | −36.22 | −33.75 | 49.28 | 15.00 |
| 202 ASN | CA | −35.14 | −33.08 | 50.02 | 15.00 |
| 202 ASN | CB | −33.88 | −33.93 | 49.92 | 15.00 |
| 202 ASN | CG | −33.05 | −33.91 | 51.18 | 15.00 |
| 202 ASN | OD1 | −33.57 | −33.92 | 52.30 | 15.00 |
| 202 ASN | ND2 | −31.73 | −33.90 | 51.01 | 15.00 |
| 202 ASN | C | −34.85 | −31.68 | 49.53 | 15.00 |
| 202 ASN | O | −33.72 | −31.35 | 49.20 | 15.00 |
| 203 ALA | N | −35.85 | −30.82 | 49.54 | 15.00 |
| 203 ALA | H | −36.60 | −31.08 | 50.11 | 15.00 |
| 203 ALA | CA | −35.72 | −29.46 | 49.02 | 15.00 |
| 203 ALA | CB | −36.91 | −28.60 | 49.43 | 15.00 |
| 203 ALA | C | −34.46 | −28.80 | 49.61 | 15.00 |
| 203 ALA | O | −34.31 | −28.70 | 50.79 | 15.00 |
| 204 CYS | N | −33.59 | −28.31 | 48.74 | 15.00 |
| 204 CYS | CA | −32.40 | −27.62 | 49.21 | 15.00 |
| 204 CYS | C | −31.47 | −28.47 | 50.07 | 15.00 |
| 204 CYS | O | −30.40 | −28.02 | 50.45 | 15.00 |
| 204 CYS | CB | −32.76 | −26.38 | 50.00 | 15.00 |
| 204 CYS | SG | −33.64 | −25.09 | 49.12 | 15.00 |
| 205 GLY | N | −31.91 | −29.64 | 50.49 | 15.00 |
| 205 GLY | CA | −31.04 | −30.48 | 51.28 | 15.00 |
| 205 GLY | C | −31.30 | −30.32 | 52.77 | 15.00 |
| 205 GLY | O | −30.40 | −30.54 | 53.58 | 15.00 |
| 206 ILE | N | −32.52 | −29.94 | 53.13 | 15.00 |
| 206 ILE | CA | −32.90 | −29.75 | 54.52 | 15.00 |
| 206 ILE | CB | −34.33 | −29.12 | 54.62 | 15.00 |
| 206 ILE | CG2 | −35.41 | −30.09 | 54.17 | 15.00 |
| 206 ILE | CG1 | −34.60 | −28.70 | 56.06 | 15.00 |
| 206 ILE | CD1 | −35.73 | −27.69 | 56.23 | 15.00 |
| 206 ILE | C | −32.75 | −31.00 | 55.45 | 15.00 |
| 206 ILE | O | −32.59 | −30.85 | 56.66 | 15.00 |
| 207 ALA | N | −32.81 | −32.22 | 54.92 | 15.00 |
| 207 ALA | CA | −32.67 | −33.38 | 55.79 | 15.00 |
| 207 ALA | CB | −33.80 | −34.33 | 55.58 | 15.00 |
| 207 ALA | C | −31.34 | −34.09 | 55.63 | 15.00 |
| 207 ALA | O | −31.17 | −35.20 | 56.13 | 15.00 |
| 208 ASN | N | −30.36 | −33.45 | 55.00 | 15.00 |
| 208 ASN | CA | −29.04 | −34.07 | 54.76 | 15.00 |
| 208 ASN | CB | −28.34 | −33.45 | 53.52 | 15.00 |
| 208 ASN | CG | −28.78 | −34.07 | 52.18 | 15.00 |
| 208 ASN | OD1 | −29.25 | −35.21 | 52.11 | 15.00 |
| 208 ASN | ND2 | −28.60 | −33.31 | 51.12 | 15.00 |
| 208 ASN | C | −28.08 | −34.01 | 55.94 | 15.00 |
| 208 ASN | O | −27.28 | −34.93 | 56.15 | 15.00 |
| 209 LEU | N | −28.08 | −32.88 | 56.64 | 15.00 |
| 209 LEU | CA | −27.19 | −32.64 | 57.78 | 15.00 |
| 209 LEU | CB | −26.07 | −31.64 | 57.40 | 15.00 |
| 209 LEU | CG | −24.73 | −31.69 | 58.15 | 15.00 |
| 209 LEU | CD1 | −24.11 | −33.07 | 58.09 | 15.00 |
| 209 LEU | CD2 | −23.76 | −30.66 | 57.52 | 15.00 |
| 209 LEU | C | −27.97 | −32.12 | 59.02 | 15.00 |
| 209 LEU | O | −27.72 | −30.99 | 59.50 | 15.00 |
| 210 ALA | N | −28.79 | −32.99 | 59.65 | 15.00 |
| 210 ALA | H | −29.19 | −33.47 | 58.90 | 15.00 |
| 210 ALA | CA | −29.59 | −32.51 | 60.77 | 15.00 |
| 210 ALA | CB | −31.08 | −32.79 | 60.54 | 15.00 |
| 210 ALA | C | −29.19 | −33.24 | 62.06 | 15.00 |
| 210 ALA | O | −28.91 | −34.44 | 62.09 | 15.00 |
| 211 SER | N | −29.24 | −32.48 | 63.17 | 15.00 |
| 211 SER | CA | −28.94 | −33.06 | 64.47 | 15.00 |
| 211 SER | CB | −27.44 | −33.22 | 64.70 | 15.00 |
| 211 SER | OG | −26.78 | −31.96 | 64.75 | 15.00 |
| 211 SER | C | −29.57 | −32.31 | 65.62 | 15.00 |
| 211 SER | O | −30.17 | −31.24 | 65.41 | 15.00 |
| 212 PHE | N | −29.43 | −32.92 | 66.81 | 15.00 |
| 212 PHE | CA | −29.96 | −32.40 | 68.07 | 15.00 |
| 212 PHE | CB | −31.46 | −32.75 | 68.27 | 15.00 |
| 212 PHE | CG | −31.78 | −34.22 | 68.27 | 15.00 |
| 212 PHE | CD1 | −32.33 | −34.84 | 67.14 | 15.00 |
| 212 PHE | CD2 | −31.61 | −34.97 | 69.41 | 15.00 |
| 212 PHE | CE1 | −32.71 | −36.19 | 67.17 | 15.00 |
| 212 PHE | CE2 | −31.98 | −36.30 | 69.45 | 15.00 |
| 212 PHE | CZ | −32.54 | −36.91 | 68.33 | 15.00 |
| 212 PHE | C | −29.16 | −32.88 | 69.27 | 15.00 |
| 212 PHE | O | −28.56 | −33.95 | 69.23 | 15.00 |
| 213 PRO | N | −29.11 | −32.06 | 70.33 | 15.00 |
| 213 PRO | CD | −29.69 | −30.71 | 70.50 | 15.00 |
| 213 PRO | CA | −28.36 | −32.43 | 71.53 | 15.00 |
| 213 PRO | CB | −28.14 | −31.08 | 72.20 | 15.00 |
| 213 PRO | CG | −29.45 | −30.47 | 72.01 | 15.00 |
| 213 PRO | C | −29.19 | −33.38 | 72.46 | 15.00 |
| 213 PRO | O | −30.42 | −33.47 | 72.36 | 15.00 |
| 214 LYS | N | −28.53 | −34.16 | 73.30 | 15.00 |
| 214 LYS | CA | −29.24 | −35.05 | 74.22 | 15.00 |
| 214 LYS | CB | −28.57 | −36.43 | 74.20 | 15.00 |
| 214 LYS | CG | −28.79 | −37.24 | 72.91 | 15.00 |
| 214 LYS | CD | −28.01 | −38.56 | 72.92 | 15.00 |

TABLE VIII-continued

Table of the orthogonal three dimensional coordinates in Ångstroms and B factors (Å$^2$) for the cathepsin K complex with inhibitor 4-[N-[(4-pyridylmethoxy)carbonyl]-L-leucyl]-1-[N-[(phenylmethoxy)carbonyl]-L-leucyl]-3-pyrrolidinone.

| Residue | Atom | X | Y | Z | B |
|---|---|---|---|---|---|
| 214 LYS | CE | −28.46 | −39.53 | 71.81 | 15.00 |
| 214 LYS | NZ | −27.39 | −40.57 | 71.71 | 15.00 |
| 214 LYS | C | −29.05 | −34.34 | 75.56 | 15.00 |
| 214 LYS | O | −27.98 | −33.76 | 75.79 | 15.00 |
| 215 MET | N | −30.08 | −34.35 | 76.41 | 15.00 |
| 215 MET | CA | −29.99 | −33.65 | 77.70 | 15.00 |
| 215 MET | CB | −31.12 | −32.61 | 77.90 | 15.00 |
| 215 MET | CG | −30.96 | −31.28 | 77.20 | 15.00 |
| 215 MET | SD | −29.93 | −30.01 | 77.96 | 15.00 |
| 215 MET | CE | −31.16 | −28.81 | 78.53 | 15.00 |
| 215 MET | C | −29.93 | −34.56 | 78.90 | 15.00 |
| 215 MET | OT1 | −28.98 | −34.44 | 79.69 | 15.00 |
| 215 MET | OT2 | −30.83 | −35.40 | 79.08 | 15.00 |
| 216 HOH | OH2 | −32.26 | −16.46 | 65.37 | 15.00 |
| 217 HOH | OH2 | −29.10 | −19.91 | 62.23 | 15.00 |
| 218 HOH | OH2 | −10.46 | −12.34 | 64.01 | 15.00 |
| 219 HOH | OH2 | −16.64 | −12.04 | 73.86 | 15.00 |
| 220 HOH | OH2 | −35.65 | −23.61 | 70.00 | 15.00 |
| 221 HOH | OH2 | −30.42 | −35.41 | 58.75 | 15.00 |
| 222 HOH | OH2 | −31.55 | −20.39 | 66.10 | 15.00 |
| 223 HOH | OH2 | −25.68 | −31.53 | 62.01 | 15.00 |
| 224 HOH | OH2 | −12.63 | −8.84 | 62.20 | 15.00 |
| 225 HOH | OH2 | −14.75 | −22.14 | 66.35 | 15.00 |
| 226 HOH | OH2 | −44.50 | −27.54 | 49.50 | 15.00 |
| 227 HOH | OH2 | −46.66 | −35.25 | 56.37 | 15.00 |
| 228 HOH | OH2 | −41.69 | −17.81 | 69.13 | 15.00 |
| 229 HOH | OH2 | −31.65 | −20.57 | 63.48 | 15.00 |
| 230 HOH | OH2 | −19.45 | −17.08 | 56.43 | 15.00 |
| 231 HOH | OH2 | −14.47 | −31.20 | 62.15 | 15.00 |
| 232 HOH | OH2 | −44.49 | −25.37 | 44.32 | 15.00 |
| 233 HOH | OH2 | −23.11 | −31.07 | 62.02 | 15.00 |
| 234 HOH | OH2 | −24.80 | −4.69 | 68.36 | 15.00 |
| 235 HOH | OH2 | −31.22 | −18.66 | 68.39 | 15.00 |
| 236 HOH | OH2 | −37.21 | −27.28 | 51.82 | 15.00 |
| 237 HOH | OH2 | −37.54 | −25.42 | 49.65 | 15.00 |
| 238 HOH | OH2 | −48.22 | −33.37 | 57.46 | 15.00 |
| 239 HOH | OH2 | −29.06 | −10.11 | 76.59 | 15.00 |
| 240 HOH | OH2 | −35.53 | −14.09 | 77.20 | 15.00 |
| 241 HOH | OH2 | −16.66 | −4.74 | 70.29 | 15.00 |
| 242 HOH | OH2 | −17.42 | −8.40 | 75.32 | 15.00 |
| 243 HOH | OH2 | −10.92 | −18.14 | 70.16 | 15.00 |
| 244 HOH | OH2 | −9.58 | −20.04 | 78.06 | 15.00 |
| 245 HOH | OH2 | −46.35 | −17.06 | 54.42 | 15.00 |
| 246 HOH | OH2 | −34.19 | −29.40 | 45.76 | 15.00 |
| 247 HOH | OH2 | −36.78 | −37.90 | 52.62 | 15.00 |
| 248 HOH | OH2 | −42.43 | −35.18 | 56.19 | 15.00 |
| 249 HOH | OH2 | −41.62 | −19.52 | 71.38 | 15.00 |
| 250 HOH | OH2 | −48.81 | −19.01 | 73.95 | 15.00 |
| 251 HOH | OH2 | −41.55 | −15.71 | 71.06 | 15.00 |
| 252 HOH | OH2 | −26.21 | −9.24 | 68.97 | 15.00 |
| 253 HOH | OH2 | −33.78 | −8.96 | 64.11 | 15.00 |
| 254 HOH | OH2 | −20.04 | −8.25 | 62.53 | 15.00 |
| 255 HOH | OH2 | −17.20 | −6.33 | 64.20 | 15.00 |
| 256 HOH | OH2 | −35.58 | −40.12 | 65.37 | 15.00 |
| 257 HOH | OH2 | −13.46 | −24.38 | 76.78 | 15.00 |
| 258 HOH | OH2 | −8.00 | −25.77 | 61.24 | 15.00 |
| 259 HOH | OH2 | −21.06 | −27.44 | 51.53 | 15.00 |
| 260 HOH | OH2 | −25.94 | −34.05 | 61.10 | 15.00 |
| 261 HOH | OH2 | −12.35 | −29.04 | 72.99 | 15.00 |
| 262 HOH | OH2 | −33.29 | −40.38 | 63.87 | 15.00 |
| 263 HOH | OH2 | −20.24 | −23.70 | 87.14 | 15.00 |
| 264 HOH | OH2 | −13.21 | −12.02 | 62.79 | 15.00 |
| 265 HOH | OH2 | −21.34 | −33.08 | 61.27 | 15.00 |
| 266 HOH | OH2 | −29.60 | −16.68 | 41.72 | 15.00 |
| 267 HOH | OH2 | −25.80 | −19.25 | 42.13 | 15.00 |
| 268 HOH | OH2 | −32.98 | −34.45 | 47.05 | 15.00 |
| 269 HOH | OH2 | −23.16 | −31.07 | 42.89 | 15.00 |
| 270 HOH | OH2 | −34.03 | −29.11 | 42.28 | 15.00 |
| 271 HOH | OH2 | −36.71 | −26.01 | 46.91 | 15.00 |

TABLE IX

Table of the orthogonal three dimensional coordinates in Ångstroms and B factors (Å$^2$) for the cathepsin K complex with inhibitor 4-[N-[(phenylmethoxy)carbonyl]-L-leucyl]-1-N[N-(methyl)-L-leucyl)]-3-pyrrolidinone

| Residue | Atom | X | Y | Z | B |
|---|---|---|---|---|---|
| 1 ALA | CB | −54.23 | −33.20 | 65.64 | 15.00 |
| 1 ALA | C | −53.54 | −33.00 | 63.24 | 15.00 |
| 1 ALA | O | −52.73 | −33.83 | 62.79 | 15.00 |
| 1 ALA | N | −54.89 | −34.90 | 63.97 | 15.00 |
| 1 ALA | CA | −54.65 | −33.45 | 64.19 | 15.00 |
| 2 PRO | N | −53.49 | −31.70 | 62.91 | 15.00 |
| 2 PRO | CD | −54.26 | −30.56 | 63.46 | 15.00 |
| 2 PRO | CA | −52.44 | −31.22 | 62.00 | 15.00 |
| 2 PRO | CB | −52.58 | −29.69 | 62.07 | 15.00 |
| 2 PRO | CG | −53.25 | −29.45 | 63.41 | 15.00 |
| 2 PRO | C | −51.07 | −31.68 | 62.50 | 15.00 |
| 2 PRO | O | −50.74 | −31.50 | 63.67 | 15.00 |
| 3 ASP | N | −50.31 | −32.35 | 61.64 | 15.00 |
| 3 ASP | CA | −48.98 | −32.84 | 62.01 | 15.00 |
| 3 ASP | CB | −48.55 | −33.98 | 61.08 | 15.00 |
| 3 ASP | CG | −47.66 | −35.01 | 61.77 | 15.00 |
| 3 ASP | OD1 | −46.52 | −34.66 | 62.18 | 15.00 |
| 3 ASP | OD2 | −48.10 | −36.17 | 61.89 | 15.00 |
| 3 ASP | C | −48.00 | −31.68 | 61.94 | 15.00 |
| 3 ASP | O | −47.13 | −31.65 | 61.06 | 15.00 |
| 4 SER | N | −48.12 | −30.72 | 62.85 | 15.00 |
| 4 SER | CA | −47.23 | −29.56 | 62.86 | 15.00 |
| 4 SER | CB | −47.87 | −28.37 | 62.15 | 15.00 |
| 4 SER | OG | −49.05 | −27.95 | 62.82 | 15.00 |
| 4 SER | C | −46.76 | −29.14 | 64.25 | 15.00 |
| 4 SER | O | −47.54 | −29.19 | 65.22 | 15.00 |
| 5 VAL | N | −45.50 | −28.70 | 64.35 | 15.00 |
| 5 VAL | CA | −44.91 | −28.26 | 65.61 | 15.00 |
| 5 VAL | CB | −43.77 | −29.21 | 66.10 | 15.00 |
| 5 VAL | CG1 | −43.35 | −28.82 | 67.51 | 15.00 |
| 5 VAL | CG2 | −44.19 | −30.65 | 66.04 | 15.00 |
| 5 VAL | C | −44.29 | −26.87 | 65.45 | 15.00 |
| 5 VAL | O | −43.47 | −26.65 | 64.55 | 15.00 |
| 6 ASP | N | −44.64 | −25.95 | 66.33 | 15.00 |
| 6 ASP | CA | −44.10 | −24.60 | 66.28 | 15.00 |
| 6 ASP | CB | −45.17 | −23.57 | 65.90 | 15.00 |
| 6 ASP | CG | −44.59 | −22.26 | 65.40 | 15.00 |
| 6 ASP | OD1 | −43.41 | −21.95 | 65.68 | 15.00 |
| 6 ASP | OD2 | −45.34 | −21.52 | 64.73 | 15.00 |
| 6 ASP | C | −43.52 | −24.32 | 67.66 | 15.00 |
| 6 ASP | O | −44.20 | −23.78 | 68.53 | 15.00 |
| 7 TYR | N | −42.27 | −24.69 | 67.85 | 15.00 |
| 7 TYR | CA | −41.62 | −24.50 | 69.13 | 15.00 |
| 7 TYR | CB | −40.20 | −25.08 | 69.12 | 15.00 |
| 7 TYR | CG | −40.20 | −26.58 | 69.20 | 15.00 |
| 7 TYR | CD1 | −40.68 | −27.24 | 70.33 | 15.00 |
| 7 TYR | CE1 | −40.76 | −28.62 | 70.38 | 15.00 |
| 7 TYR | CD2 | −39.81 | −27.36 | 68.11 | 15.00 |
| 7 TYR | CE2 | −39.89 | −28.74 | 68.15 | 15.00 |
| 7 TYR | CZ | −40.37 | −29.36 | 69.29 | 15.00 |
| 7 TYR | OH | −40.51 | −30.72 | 69.31 | 15.00 |
| 7 TYR | C | −41.63 | −23.07 | 69.62 | 15.00 |
| 7 TYR | O | −41.57 | −22.84 | 70.83 | 15.00 |
| 8 ARG | N | −41.74 | −22.11 | 68.70 | 15.00 |
| 8 ARG | CA | −41.77 | −20.68 | 69.08 | 15.00 |
| 8 ARG | CB | −41.86 | −19.77 | 67.84 | 15.00 |
| 8 ARG | CG | −40.77 | −19.98 | 66.80 | 15.00 |
| 8 ARG | CD | −41.01 | −19.12 | 65.58 | 15.00 |
| 8 ARG | NE | −42.34 | −19.33 | 65.02 | 15.00 |
| 8 ARG | CZ | −42.70 | −18.96 | 63.80 | 15.00 |
| 8 ARG | NH1 | −41.83 | −18.36 | 63.00 | 15.00 |
| 8 ARG | NH2 | −43.94 | −19.18 | 63.38 | 15.00 |
| 8 ARG | C | −42.94 | −20.39 | 70.02 | 15.00 |
| 8 ARG | O | −42.79 | −19.67 | 71.02 | 15.00 |
| 9 LYS | N | −44.10 | −20.98 | 69.72 | 15.00 |
| 9 LYS | CA | −45.29 | −20.80 | 70.53 | 15.00 |
| 9 LYS | CB | −46.53 | −21.26 | 69.78 | 15.00 |
| 9 LYS | CG | −46.84 | −20.43 | 68.56 | 15.00 |
| 9 LYS | CD | −48.15 | −20.86 | 67.92 | 15.00 |
| 9 LYS | CE | −48.39 | −20.11 | 66.62 | 15.00 |
| 9 LYS | NZ | −49.58 | −20.62 | 65.88 | 15.00 |

TABLE IX-continued

Table of the orthogonal three dimensional coordinates in Ångstroms and B factors (Å²) for the cathepsin K complex with inhibitor 4-[N-[(phenylmethoxy)carbonyl]-L-leucyl]-1-N[N-(methyl)-L-leucyl)]-3-pyrrolidinone

| Residue | Atom | X | Y | Z | B |
|---|---|---|---|---|---|
| 9 LYS | C | −45.18 | −21.53 | 71.85 | 15.00 |
| 9 LYS | O | −45.95 | −21.29 | 72.77 | 15.00 |
| 10 LYS | N | −44.18 | −22.40 | 71.95 | 15.00 |
| 10 LYS | CA | −43.99 | −23.17 | 73.16 | 15.00 |
| 10 LYS | CB | −43.71 | −24.63 | 72.80 | 15.00 |
| 10 LYS | CG | −44.67 | −25.19 | 71.78 | 15.00 |
| 10 LYS | CD | −44.34 | −26.64 | 71.49 | 15.00 |
| 10 LYS | CE | −44.42 | −27.48 | 72.76 | 15.00 |
| 10 LYS | NZ | −45.74 | −27.26 | 73.43 | 15.00 |
| 10 LYS | C | −42.92 | −22.65 | 74.11 | 15.00 |
| 10 LYS | O | −42.70 | −23.25 | 75.15 | 15.00 |
| 11 GLY | N | −42.24 | −21.57 | 73.73 | 15.00 |
| 11 GLY | CA | −41.21 | −21.00 | 74.58 | 15.00 |
| 11 GLY | C | −39.83 | −21.65 | 74.47 | 15.00 |
| 11 GLY | O | −38.92 | −21.31 | 75.21 | 15.00 |
| 12 TYR | N | −39.68 | −22.56 | 73.52 | 15.00 |
| 12 TYR | CA | −38.41 | −23.26 | 73.31 | 15.00 |
| 12 TYR | CB | −38.63 | −24.56 | 72.54 | 15.00 |
| 12 TYR | CG | −39.27 | −25.70 | 73.30 | 15.00 |
| 12 TYR | CD1 | −40.37 | −25.50 | 74.13 | 15.00 |
| 12 TYR | CE1 | −40.97 | −26.57 | 74.82 | 15.00 |
| 12 TYR | CD2 | −38.78 | −27.00 | 73.17 | 15.00 |
| 12 TYR | CE2 | −39.37 | −28.07 | 73.84 | 15.00 |
| 12 TYR | CZ | −40.45 | −27.85 | 74.66 | 15.00 |
| 12 TYR | OH | −41.02 | −28.91 | 75.33 | 15.00 |
| 12 TYR | C | −37.36 | −22.43 | 72.56 | 15.00 |
| 12 TYR | O | −36.22 | −22.86 | 72.46 | 15.00 |
| 13 VAL | N | −37.76 | −21.27 | 72.03 | 15.00 |
| 13 VAL | CA | −36.86 | −20.43 | 71.23 | 15.00 |
| 13 VAL | CB | −37.38 | −20.33 | 69.78 | 15.00 |
| 13 VAL | CG1 | −36.34 | −19.72 | 68.89 | 15.00 |
| 13 VAL | CG2 | −37.75 | −21.69 | 69.26 | 15.00 |
| 13 VAL | C | −36.62 | −19.00 | 71.75 | 15.00 |
| 13 VAL | O | −37.55 | −18.32 | 72.18 | 15.00 |
| 14 THR | N | −35.38 | −18.53 | 71.67 | 15.00 |
| 14 THR | CA | −35.04 | −17.18 | 72.11 | 15.00 |
| 14 THR | CB | −33.58 | −17.11 | 72.54 | 15.00 |
| 14 THR | OG1 | −32.76 | −17.76 | 71.55 | 15.00 |
| 14 THR | CG2 | −33.39 | −17.76 | 73.88 | 15.00 |
| 14 THR | C | −35.25 | −16.15 | 70.99 | 15.00 |
| 14 THR | O | −35.59 | −16.51 | 69.86 | 15.00 |
| 15 PRO | N | −35.10 | −14.85 | 71.31 | 15.00 |
| 15 PRO | CD | −35.02 | −14.21 | 72.63 | 15.00 |
| 15 PRO | CA | −35.29 | −13.83 | 70.27 | 15.00 |
| 15 PRO | CB | −35.03 | −12.54 | 71.03 | 15.00 |
| 15 PRO | CG | −35.58 | −12.84 | 72.37 | 15.00 |
| 15 PRO | C | −34.27 | −14.02 | 69.14 | 15.00 |
| 15 PRO | O | −33.20 | −14.57 | 69.36 | 15.00 |
| 16 VAL | N | −34.63 | −13.62 | 67.92 | 15.00 |
| 16 VAL | CA | −33.72 | −13.74 | 66.79 | 15.00 |
| 16 VAL | CB | −34.41 | −13.41 | 65.45 | 15.00 |
| 16 VAL | CG1 | −33.40 | −13.43 | 64.31 | 15.00 |
| 16 VAL | CG2 | −35.52 | −14.40 | 65.18 | 15.00 |
| 16 VAL | C | −32.53 | −12.82 | 67.01 | 15.00 |
| 16 VAL | O | −32.69 | −11.69 | 67.46 | 15.00 |
| 17 LYS | N | −31.34 | −13.30 | 66.69 | 15.00 |
| 17 LYS | CA | −30.16 | −12.50 | 66.88 | 15.00 |
| 17 LYS | CB | −29.27 | −13.11 | 67.95 | 15.00 |
| 17 LYS | CG | −29.97 | −13.18 | 69.30 | 15.00 |
| 17 LYS | CD | −29.17 | −13.95 | 70.33 | 15.00 |
| 17 LYS | CE | −29.96 | −14.12 | 71.61 | 15.00 |
| 17 LYS | NZ | −31.23 | −14.87 | 71.36 | 15.00 |
| 17 LYS | C | −29.41 | −12.30 | 65.58 | 15.00 |
| 17 LYS | O | −29.51 | −13.11 | 64.66 | 15.00 |
| 18 ASN | N | −28.68 | −11.18 | 65.51 | 15.00 |
| 18 ASN | CA | −27.89 | −10.84 | 64.33 | 15.00 |
| 18 ASN | CB | −28.01 | −9.37 | 63.99 | 15.00 |
| 18 ASN | CG | −27.30 | −9.03 | 62.72 | 15.00 |
| 18 ASN | OD1 | −27.10 | −9.90 | 61.88 | 15.00 |
| 18 ASN | ND2 | −26.89 | −7.78 | 62.57 | 15.00 |
| 18 ASN | C | −26.42 | −11.21 | 64.52 | 15.00 |
| 18 ASN | O | −25.77 | −10.70 | 65.43 | 15.00 |
| 19 GLN | N | −25.89 | −12.04 | 63.63 | 15.00 |
| 19 GLN | CA | −24.50 | −12.46 | 63.73 | 15.00 |
| 19 GLN | CB | −24.24 | −13.75 | 62.96 | 15.00 |
| 19 GLN | CG | −24.32 | −13.63 | 61.47 | 15.00 |
| 19 GLN | CD | −24.07 | −14.96 | 60.80 | 15.00 |
| 19 GLN | OE1 | −25.01 | −15.66 | 60.43 | 15.00 |
| 19 GLN | NE2 | −22.81 | −15.32 | 60.65 | 15.00 |
| 19 GLN | C | −23.48 | −11.40 | 63.36 | 15.00 |
| 19 GLN | O | −22.32 | −11.48 | 63.76 | 15.00 |
| 20 GLY | N | −23.90 | −10.40 | 62.59 | 15.00 |
| 20 GLY | CA | −22.99 | −9.33 | 62.22 | 15.00 |
| 20 GLY | C | −21.93 | −9.72 | 61.22 | 15.00 |
| 20 GLY | O | −22.06 | −10.71 | 60.52 | 15.00 |
| 21 GLN | N | −20.86 | −8.94 | 61.15 | 15.00 |
| 21 GLN | CA | −19.79 | −9.22 | 60.22 | 15.00 |
| 21 GLN | CB | −19.10 | −7.92 | 59.77 | 15.00 |
| 21 GLN | CG | −20.08 | −6.82 | 59.31 | 15.00 |
| 21 GLN | CD | −21.21 | −7.35 | 58.42 | 15.00 |
| 21 GLN | OE1 | −20.98 | −7.83 | 57.31 | 15.00 |
| 21 GLN | NE2 | −22.44 | −7.28 | 58.92 | 15.00 |
| 21 GLN | C | −18.81 | −10.21 | 60.83 | 15.00 |
| 21 GLN | O | −17.67 | −9.87 | 61.14 | 15.00 |
| 22 CYS | N | −19.29 | −11.45 | 61.00 | 15.00 |
| 22 CYS | CA | −18.53 | −12.54 | 61.60 | 15.00 |
| 22 CYS | C | −19.20 | −13.84 | 61.19 | 15.00 |
| 22 CYS | O | −20.43 | −13.93 | 61.23 | 15.00 |
| 22 CYS | CB | −18.48 | −12.40 | 63.13 | 15.00 |
| 22 CYS | SG | −18.13 | −13.92 | 64.07 | 15.00 |
| 23 GLY | N | −18.42 | −14.83 | 60.76 | 15.00 |
| 23 GLY | CA | −19.01 | −16.09 | 60.33 | 15.00 |
| 23 GLY | C | −19.33 | −17.04 | 61.47 | 15.00 |
| 23 GLY | O | −18.80 | −18.16 | 61.54 | 15.00 |
| 24 SER | N | −20.21 | −16.60 | 62.36 | 15.00 |
| 24 SER | CA | −20.58 | −17.40 | 63.52 | 15.00 |
| 24 SER | CB | −20.34 | −16.63 | 64.80 | 15.00 |
| 24 SER | OG | −21.04 | −15.40 | 64.76 | 15.00 |
| 24 SER | C | −22.00 | −17.93 | 63.45 | 15.00 |
| 24 SER | O | −22.68 | −18.02 | 64.46 | 15.00 |
| 25 CYS | N | −22.46 | −18.32 | 62.28 | 15.00 |
| 25 CYS | CA | −23.80 | −18.84 | 62.17 | 15.00 |
| 25 CYS | CB | −24.25 | −18.85 | 60.71 | 15.00 |
| 25 CYS | SG | −23.19 | −19.72 | 59.59 | 15.00 |
| 25 CYS | C | −23.89 | −20.22 | 62.84 | 15.00 |
| 25 CYS | O | −24.95 | −20.62 | 63.34 | 15.00 |
| 25 INH | C1 | −26.58 | −9.77 | 58.47 | 15.00 |
| 25 INH | C2 | −26.25 | −10.40 | 57.28 | 15.00 |
| 25 INH | C3 | −25.06 | −11.13 | 57.18 | 15.00 |
| 25 INH | C4 | −24.20 | −11.22 | 58.27 | 15.00 |
| 25 INH | C5 | −24.54 | −10.58 | 59.46 | 15.00 |
| 25 INH | C6 | −25.72 | −9.86 | 59.56 | 15.00 |
| 25 INH | C7 | −22.95 | −12.04 | 58.18 | 15.00 |
| 25 INH | O8 | −22.93 | −12.74 | 56.96 | 15.00 |
| 25 INH | C9 | −23.31 | −14.09 | 56.78 | 15.00 |
| 25 INH | O10 | −24.36 | −14.56 | 57.24 | 15.00 |
| 25 INH | C11 | −22.67 | −16.23 | 55.81 | 15.00 |
| 25 INH | C12 | −22.36 | −16.56 | 54.34 | 15.00 |
| 25 INH | C13 | −23.44 | −17.20 | 53.45 | 15.00 |
| 25 INH | C14 | −24.11 | −18.35 | 54.17 | 15.00 |
| 25 INH | C15 | −24.46 | −16.19 | 52.94 | 15.00 |
| 25 INH | C16 | −21.76 | −17.01 | 56.78 | 15.00 |
| 25 INH | O17 | −20.87 | −16.42 | 57.43 | 15.00 |
| 25 INH | N18 | −21.99 | −18.32 | 56.91 | 15.00 |
| 25 INH | C19 | −21.15 | −18.98 | 57.84 | 15.00 |
| 25 INH | N20 | −22.45 | −14.81 | 56.08 | 15.00 |
| 25 INH | C21 | −20.81 | −20.41 | 57.54 | 15.00 |
| 25 INH | C22 | −21.63 | −18.99 | 59.30 | 15.00 |
| 25 INH | O23 | −21.62 | −17.88 | 59.81 | 15.00 |
| 25 INH | C24 | −17.90 | −23.12 | 57.09 | 15.00 |
| 25 INH | C25 | −20.20 | −23.31 | 57.89 | 15.00 |
| 25 INH | C26 | −21.15 | −24.49 | 58.06 | 15.00 |

TABLE IX-continued

Table of the orthogonal three dimensional coordinates in Ångstroms and B factors (Å²) for the cathepsin K complex with inhibitor 4-[N-[(phenylmethoxy)carbonyl]-L-leucyl]-1-N[N-(methyl)-L-leucyl)]-3-pyrrolidinone

| Residue | Atom | X | Y | Z | B |
|---|---|---|---|---|---|
| 25 | INH | C27 | −21.28 | −25.45 | 56.87 | 15.00 |
| 25 | INH | C28 | −19.93 | −25.80 | 56.26 | 15.00 |
| 25 | INH | C29 | −22.00 | −26.71 | 57.30 | 15.00 |
| 25 | INH | C30 | −20.37 | −22.34 | 59.06 | 15.00 |
| 25 | INH | O31 | −20.24 | −22.76 | 60.20 | 15.00 |
| 25 | INH | N32 | −20.66 | −21.04 | 58.80 | 15.00 |
| 25 | INH | C33 | −20.82 | −20.11 | 59.89 | 15.00 |
| 25 | INH | N34 | −18.81 | −23.74 | 57.85 | 15.00 |
| 26 | TRP | N | −22.76 | −20.93 | 62.89 | 15.00 |
| 26 | TRP | CA | −22.67 | −22.24 | 63.53 | 15.00 |
| 26 | TRP | CB | −21.35 | −22.95 | 63.19 | 15.00 |
| 26 | TRP | CG | −20.14 | −22.22 | 63.67 | 15.00 |
| 26 | TRP | CD2 | −19.45 | −22.41 | 64.92 | 15.00 |
| 26 | TRP | CE2 | −18.44 | −21.43 | 65.00 | 15.00 |
| 26 | TRP | CE3 | −19.61 | −23.30 | 65.99 | 15.00 |
| 26 | TRP | CD1 | −19.51 | −21.18 | 63.05 | 15.00 |
| 26 | TRP | NE1 | −18.50 | −20.70 | 63.84 | 15.00 |
| 26 | TRP | CZ2 | −17.59 | −21.32 | 66.10 | 15.00 |
| 26 | TRP | CZ3 | −18.76 | −23.19 | 67.08 | 15.00 |
| 26 | TRP | CH2 | −17.76 | −22.21 | 67.13 | 15.00 |
| 26 | TRP | C | −22.83 | −22.09 | 65.05 | 15.00 |
| 26 | TRP | O | −23.50 | −22.90 | 65.69 | 15.00 |
| 27 | ALA | N | −22.22 | −21.05 | 65.60 | 15.00 |
| 27 | ALA | CA | −22.28 | −20.76 | 67.03 | 15.00 |
| 27 | ALA | CB | −21.34 | −19.64 | 67.37 | 15.00 |
| 27 | ALA | C | −23.71 | −20.40 | 67.41 | 15.00 |
| 27 | ALA | O | −24.15 | −20.67 | 68.53 | 15.00 |
| 28 | PHE | N | −24.44 | −19.79 | 66.48 | 15.00 |
| 28 | PHE | CA | −25.83 | −19.42 | 66.72 | 15.00 |
| 28 | PHE | CB | −26.28 | −18.29 | 65.81 | 15.00 |
| 28 | PHE | CG | −25.77 | −16.95 | 66.24 | 15.00 |
| 28 | PHE | CD1 | −24.53 | −16.50 | 65.83 | 15.00 |
| 28 | PHE | CD2 | −26.52 | −16.16 | 67.11 | 15.00 |
| 28 | PHE | CE1 | −24.03 | −15.31 | 66.28 | 15.00 |
| 28 | PHE | CE2 | −26.02 | −14.96 | 67.56 | 15.00 |
| 28 | PHE | CZ | −24.78 | −14.53 | 67.15 | 15.00 |
| 28 | PHE | C | −26.76 | −20.62 | 66.63 | 15.00 |
| 28 | PHE | O | −27.71 | −20.74 | 67.40 | 15.00 |
| 29 | SER | N | −26.51 | −21.50 | 65.67 | 15.00 |
| 29 | SER | CA | −27.33 | −22.69 | 65.53 | 15.00 |
| 29 | SER | CB | −26.88 | −23.54 | 64.35 | 15.00 |
| 29 | SER | OG | −27.59 | −24.76 | 64.31 | 15.00 |
| 29 | SER | C | −27.22 | −23.49 | 66.82 | 15.00 |
| 29 | SER | O | −28.20 | −23.61 | 67.54 | 15.00 |
| 30 | SER | N | −26.01 | −23.95 | 67.12 | 15.00 |
| 30 | SER | CA | −25.70 | −24.75 | 68.32 | 15.00 |
| 30 | SER | CB | −24.19 | −24.86 | 68.50 | 15.00 |
| 30 | SER | OG | −23.53 | −25.04 | 67.27 | 15.00 |
| 30 | SER | C | −26.34 | −24.24 | 69.61 | 15.00 |
| 30 | SER | O | −26.97 | −25.00 | 70.37 | 15.00 |
| 31 | VAL | N | −26.15 | −22.96 | 69.88 | 15.00 |
| 31 | VAL | CA | −26.71 | −22.32 | 71.06 | 15.00 |
| 31 | VAL | CB | −26.23 | −20.85 | 71.13 | 15.00 |
| 31 | VAL | CG1 | −27.15 | −20.01 | 71.98 | 15.00 |
| 31 | VAL | CG2 | −24.83 | −20.81 | 71.69 | 15.00 |
| 31 | VAL | C | −28.23 | −22.44 | 71.03 | 15.00 |
| 31 | VAL | O | −28.86 | −22.74 | 72.04 | 15.00 |
| 32 | GLY | N | −28.82 | −22.26 | 69.85 | 15.00 |
| 32 | GLY | CA | −30.26 | −22.36 | 69.72 | 15.00 |
| 32 | GLY | C | −30.78 | −23.75 | 70.03 | 15.00 |
| 32 | GLY | O | −31.86 | −23.89 | 70.62 | 15.00 |
| 33 | ALA | N | −30.07 | −24.78 | 69.61 | 15.00 |
| 33 | ALA | CA | −30.50 | −26.14 | 69.90 | 15.00 |
| 33 | ALA | CB | −29.65 | −27.14 | 69.16 | 15.00 |
| 33 | ALA | C | −30.37 | −26.36 | 71.40 | 15.00 |
| 33 | ALA | O | −31.29 | −26.85 | 72.05 | 15.00 |
| 34 | LEU | N | −29.24 | −25.92 | 71.96 | 15.00 |
| 34 | LEU | CA | −28.96 | −26.04 | 73.40 | 15.00 |
| 34 | LEU | CB | −27.57 | −25.50 | 73.75 | 15.00 |
| 34 | LEU | CG | −26.28 | −26.23 | 73.40 | 15.00 |
| 34 | LEU | CD1 | −25.11 | −25.32 | 73.73 | 15.00 |
| 34 | LEU | CD2 | −26.17 | −27.53 | 74.19 | 15.00 |
| 34 | LEU | C | −30.00 | −25.35 | 74.28 | 15.00 |
| 34 | LEU | O | −30.28 | −25.81 | 75.38 | 15.00 |
| 35 | GLU | N | −30.49 | −24.21 | 73.82 | 15.00 |
| 35 | GLU | CA | −31.50 | −23.44 | 74.55 | 15.00 |
| 35 | GLU | CB | −31.65 | −22.02 | 74.01 | 15.00 |
| 35 | GLU | CG | −30.41 | −21.16 | 74.08 | 15.00 |
| 35 | GLU | CD | −30.48 | −19.98 | 73.14 | 15.00 |
| 35 | GLU | OE1 | −31.23 | −20.04 | 72.14 | 15.00 |
| 35 | GLU | OE2 | −29.79 | −18.98 | 73.39 | 15.00 |
| 35 | GLU | C | −32.84 | −24.14 | 74.47 | 15.00 |
| 35 | GLU | O | −33.60 | −24.12 | 75.44 | 15.00 |
| 36 | GLY | N | −33.13 | −24.71 | 73.31 | 15.00 |
| 36 | GLY | CA | −34.38 | −25.43 | 73.12 | 15.00 |
| 36 | GLY | C | −34.45 | −26.58 | 74.11 | 15.00 |
| 36 | GLY | O | −35.47 | −26.75 | 74.79 | 15.00 |
| 37 | GLN | N | −33.35 | −27.32 | 74.22 | 15.00 |
| 37 | GLN | CA | −33.25 | −28.43 | 75.15 | 15.00 |
| 37 | GLN | CB | −32.05 | −29.31 | 74.83 | 15.00 |
| 37 | GLN | CG | −32.27 | −30.21 | 73.64 | 15.00 |
| 37 | GLN | CD | −33.50 | −31.08 | 73.81 | 15.00 |
| 37 | GLN | OE1 | −33.74 | −31.63 | 74.88 | 15.00 |
| 37 | GLN | NE2 | −34.28 | −31.20 | 72.75 | 15.00 |
| 37 | GLN | C | −33.22 | −27.96 | 76.60 | 15.00 |
| 37 | GLN | O | −33.78 | −28.61 | 77.48 | 15.00 |
| 38 | LEU | N | −32.60 | −26.81 | 76.84 | 15.00 |
| 38 | LEU | CA | −32.52 | −26.23 | 78.19 | 15.00 |
| 38 | LEU | CB | −31.72 | −24.94 | 78.20 | 15.00 |
| 38 | LEU | CG | −31.57 | −24.25 | 79.55 | 15.00 |
| 38 | LEU | CD1 | −30.61 | −25.04 | 80.42 | 15.00 |
| 38 | LEU | CD2 | −31.08 | −22.82 | 79.38 | 15.00 |
| 38 | LEU | C | −33.94 | −26.00 | 78.70 | 15.00 |
| 38 | LEU | O | −34.27 | −26.33 | 79.83 | 15.00 |
| 39 | LYS | N | −34.78 | −25.42 | 77.86 | 15.00 |
| 39 | LYS | CA | −36.17 | −25.16 | 78.19 | 15.00 |
| 39 | LYS | CB | −36.85 | −24.36 | 77.08 | 15.00 |
| 39 | LYS | CG | −38.38 | −24.43 | 77.06 | 15.00 |
| 39 | LYS | CD | −39.03 | −23.68 | 78.21 | 15.00 |
| 39 | LYS | CE | −40.52 | −23.93 | 78.24 | 15.00 |
| 39 | LYS | NZ | −41.17 | −23.27 | 79.40 | 15.00 |
| 39 | LYS | C | −36.89 | −26.48 | 78.42 | 15.00 |
| 39 | LYS | O | −37.73 | −26.59 | 79.30 | 15.00 |
| 40 | LYS | N | −36.56 | −27.49 | 77.63 | 15.00 |
| 40 | LYS | CA | −37.20 | −28.78 | 77.78 | 15.00 |
| 40 | LYS | CB | −36.83 | −29.73 | 76.64 | 15.00 |
| 40 | LYS | CG | −37.74 | −30.93 | 76.59 | 15.00 |
| 40 | LYS | CD | −37.39 | −31.91 | 75.51 | 15.00 |
| 40 | LYS | CE | −38.47 | −32.98 | 75.42 | 15.00 |
| 40 | LYS | NZ | −38.17 | −34.02 | 74.40 | 15.00 |
| 40 | LYS | C | −36.89 | −29.42 | 79.13 | 15.00 |
| 40 | LYS | O | −37.79 | −29.93 | 79.80 | 15.00 |
| 41 | LYS | N | −35.62 | −29.36 | 79.53 | 15.00 |
| 41 | LYS | CA | −35.17 | −29.95 | 80.79 | 15.00 |
| 41 | LYS | CB | −33.65 | −30.16 | 80.81 | 15.00 |
| 41 | LYS | CG | −33.08 | −30.87 | 79.59 | 15.00 |
| 41 | LYS | CD | −33.91 | −32.09 | 79.21 | 15.00 |
| 41 | LYS | CE | −33.34 | −32.77 | 77.99 | 15.00 |
| 41 | LYS | NZ | −34.29 | −33.81 | 77.44 | 15.00 |
| 41 | LYS | C | −35.59 | −29.16 | 82.02 | 15.00 |
| 41 | LYS | O | −36.42 | −29.61 | 82.81 | 15.00 |
| 42 | THR | N | −35.01 | −27.98 | 82.17 | 15.00 |
| 42 | THR | CA | −35.26 | −27.11 | 83.32 | 15.00 |
| 42 | THR | CB | −34.10 | −26.13 | 83.49 | 15.00 |
| 42 | THR | OG1 | −34.11 | −25.20 | 82.40 | 15.00 |
| 42 | THR | CG2 | −32.77 | −26.87 | 83.51 | 15.00 |
| 42 | THR | C | −36.58 | −26.34 | 83.35 | 15.00 |
| 42 | THR | O | −36.92 | −25.75 | 84.37 | 15.00 |
| 43 | GLY | N | −37.30 | −26.30 | 82.24 | 15.00 |
| 43 | GLY | CA | −38.56 | −25.58 | 82.19 | 15.00 |
| 43 | GLY | C | −38.44 | −24.08 | 82.03 | 15.00 |
| 43 | GLY | O | −39.45 | −23.39 | 81.86 | 15.00 |

TABLE IX-continued

Table of the orthogonal three dimensional coordinates in Ångstroms and B factors (Å²) for the cathepsin K complex with inhibitor 4-[N-[(phenylmethoxy)carbonyl]-L-leucyl]-1-N[N-(methyl)-L-leucyl)]-3-pyrrolidinone

| Residue | Atom | X | Y | Z | B |
|---|---|---|---|---|---|
| 44 | LYS | N | −37.22 | −23.56 | 82.10 | 15.00 |
| 44 | LYS | CA | −36.96 | −22.13 | 81.97 | 15.00 |
| 44 | LYS | CB | −36.42 | −21.56 | 83.28 | 15.00 |
| 44 | LYS | CG | −37.47 | −21.47 | 84.38 | 15.00 |
| 44 | LYS | CD | −36.85 | −21.18 | 85.72 | 15.00 |
| 44 | LYS | CE | −36.08 | −22.36 | 86.23 | 15.00 |
| 44 | LYS | NZ | −37.00 | −23.52 | 86.37 | 15.00 |
| 44 | LYS | C | −35.99 | −21.90 | 80.82 | 15.00 |
| 44 | LYS | O | −35.12 | −22.73 | 80.57 | 15.00 |
| 45 | LEU | N | −36.16 | −20.79 | 80.10 | 15.00 |
| 45 | LEU | CA | −35.31 | −20.46 | 78.95 | 15.00 |
| 45 | LEU | CB | −36.19 | −20.14 | 77.73 | 15.00 |
| 45 | LEU | CG | −35.60 | −19.92 | 76.34 | 15.00 |
| 45 | LEU | CD1 | −35.30 | −21.23 | 75.64 | 15.00 |
| 45 | LEU | CD2 | −36.62 | −19.13 | 75.55 | 15.00 |
| 45 | LEU | C | −34.32 | −19.32 | 79.23 | 15.00 |
| 45 | LEU | O | −34.65 | −18.34 | 79.89 | 15.00 |
| 46 | LEU | N | −33.11 | −19.46 | 78.68 | 15.00 |
| 46 | LEU | CA | −32.02 | −18.47 | 78.83 | 15.00 |
| 46 | LEU | CB | −30.97 | −18.94 | 79.82 | 15.00 |
| 46 | LEU | CG | −30.95 | −18.53 | 81.29 | 15.00 |
| 46 | LEU | CD1 | −29.80 | −19.23 | 81.98 | 15.00 |
| 46 | LEU | CD2 | −30.80 | −17.02 | 81.38 | 15.00 |
| 46 | LEU | C | −31.33 | −18.24 | 77.48 | 15.00 |
| 46 | LEU | O | −31.36 | −19.10 | 76.62 | 15.00 |
| 47 | ASN | N | −30.68 | −17.09 | 77.32 | 15.00 |
| 47 | ASN | CA | −29.95 | −16.81 | 76.10 | 15.00 |
| 47 | ASN | CB | −29.88 | −15.32 | 75.78 | 15.00 |
| 47 | ASN | CG | −31.23 | −14.72 | 75.46 | 15.00 |
| 47 | ASN | OD1 | −31.79 | −13.96 | 76.25 | 15.00 |
| 47 | ASN | ND2 | −31.74 | −15.03 | 74.28 | 15.00 |
| 47 | ASN | C | −28.56 | −17.33 | 76.35 | 15.00 |
| 47 | ASN | O | −27.87 | −16.81 | 77.23 | 15.00 |
| 48 | LEU | N | −28.16 | −18.41 | 75.67 | 15.00 |
| 48 | LEU | CA | −26.81 | −18.95 | 75.85 | 15.00 |
| 48 | LEU | CB | −26.75 | −20.44 | 75.51 | 15.00 |
| 48 | LEU | CG | −27.61 | −21.41 | 76.33 | 15.00 |
| 48 | LEU | CD1 | −27.10 | −22.82 | 76.11 | 15.00 |
| 48 | LEU | CD2 | −27.55 | −21.06 | 77.80 | 15.00 |
| 48 | LEU | C | −25.82 | −18.14 | 75.02 | 15.00 |
| 48 | LEU | O | −26.22 | −17.32 | 74.19 | 15.00 |
| 49 | SER | N | −24.53 | −18.38 | 75.23 | 15.00 |
| 49 | SER | CA | −23.48 | −17.62 | 74.55 | 15.00 |
| 49 | SER | CB | −22.43 | −17.16 | 75.56 | 15.00 |
| 49 | SER | OG | −21.36 | −16.51 | 74.91 | 15.00 |
| 49 | SER | C | −22.77 | −18.19 | 73.33 | 15.00 |
| 49 | SER | O | −21.87 | −19.03 | 73.46 | 15.00 |
| 50 | PRO | N | −23.11 | −17.69 | 72.12 | 15.00 |
| 50 | PRO | CD | −24.26 | −16.83 | 71.79 | 15.00 |
| 50 | PRO | CA | −22.46 | −18.17 | 70.90 | 15.00 |
| 50 | PRO | CB | −23.32 | −17.56 | 69.80 | 15.00 |
| 50 | PRO | CG | −23.89 | −16.34 | 70.43 | 15.00 |
| 50 | PRO | C | −21.01 | −17.66 | 70.85 | 15.00 |
| 50 | PRO | O | −20.16 | −18.22 | 70.16 | 15.00 |
| 51 | GLN | N | −20.74 | −16.59 | 71.61 | 15.00 |
| 51 | GLN | CA | −19.41 | −15.98 | 71.71 | 15.00 |
| 51 | GLN | CB | −19.50 | −14.57 | 72.29 | 15.00 |
| 51 | GLN | CG | −18.18 | −13.80 | 72.34 | 15.00 |
| 51 | GLN | CD | −17.66 | −13.43 | 70.96 | 15.00 |
| 51 | GLN | OE1 | −18.33 | −12.73 | 70.19 | 15.00 |
| 51 | GLN | NE2 | −16.45 | −13.88 | 70.65 | 15.00 |
| 51 | GLN | C | −18.50 | −16.86 | 72.56 | 15.00 |
| 51 | GLN | O | −17.27 | −16.82 | 72.42 | 15.00 |
| 52 | ASN | N | −19.11 | −17.64 | 73.44 | 15.00 |
| 52 | ASN | CA | −18.38 | −18.58 | 74.30 | 15.00 |
| 52 | ASN | CB | −19.35 | −19.26 | 75.26 | 15.00 |
| 52 | ASN | CG | −18.67 | −20.14 | 76.30 | 15.00 |
| 52 | ASN | OD1 | −18.91 | −19.99 | 77.51 | 15.00 |
| 52 | ASN | ND2 | −17.88 | −21.11 | 75.85 | 15.00 |
| 52 | ASN | C | −17.74 | −19.57 | 73.32 | 15.00 |
| 52 | ASN | O | −16.55 | −19.90 | 73.41 | 15.00 |
| 53 | LEU | N | −18.55 | −20.00 | 72.36 | 15.00 |
| 53 | LEU | CA | −18.11 | −20.96 | 71.35 | 15.00 |
| 53 | LEU | CB | −19.32 | −21.52 | 70.61 | 15.00 |
| 53 | LEU | CG | −20.38 | −22.09 | 71.55 | 15.00 |
| 53 | LEU | CD1 | −21.65 | −22.44 | 70.79 | 15.00 |
| 53 | LEU | CD2 | −19.83 | −23.30 | 72.25 | 15.00 |
| 53 | LEU | C | −17.06 | −20.37 | 70.39 | 15.00 |
| 53 | LEU | O | −15.94 | −20.89 | 70.28 | 15.00 |
| 54 | VAL | N | −17.43 | −19.27 | 69.73 | 15.00 |
| 54 | VAL | CA | −16.55 | −18.58 | 68.78 | 15.00 |
| 54 | VAL | CB | −17.06 | −17.14 | 68.52 | 15.00 |
| 54 | VAL | CG1 | −16.12 | −16.40 | 67.60 | 15.00 |
| 54 | VAL | CG2 | −18.46 | −17.18 | 67.91 | 15.00 |
| 54 | VAL | C | −15.12 | −18.49 | 69.29 | 15.00 |
| 54 | VAL | O | −14.16 | −18.6S | 68.55 | 15.00 |
| 55 | ASP | N | −15.00 | −18.21 | 70.58 | 15.00 |
| 55 | ASP | CA | −13.71 | −18.08 | 71.23 | 15.00 |
| 55 | ASP | CB | −13.82 | −17.19 | 72.49 | 15.00 |
| 55 | ASP | CG | −14.16 | −15.76 | 72.16 | 15.00 |
| 55 | ASP | OD1 | −13.98 | −15.35 | 71.00 | 15.00 |
| 55 | ASP | OD2 | −14.62 | −15.03 | 73.06 | 15.00 |
| 55 | ASP | C | −13.05 | −19.41 | 71.60 | 15.00 |
| 55 | ASP | O | −11.98 | −19.76 | 71.08 | 15.00 |
| 56 | CYS | N | −13.74 | −20.18 | 72.43 | 15.00 |
| 56 | CYS | CA | −13.21 | −21.42 | 72.96 | 15.00 |
| 56 | CYS | C | −13.19 | −22.70 | 72.14 | 15.00 |
| 56 | CYS | O | −12.40 | −23.59 | 72.45 | 15.00 |
| 56 | CYS | CB | −13.84 | −21.68 | 74.32 | 15.00 |
| 56 | CYS | SG | −14.09 | −20.14 | 75.26 | 15.00 |
| 57 | VAL | N | −14.06 | −22.83 | 71.15 | 15.00 |
| 57 | VAL | CA | −14.11 | −24.04 | 70.33 | 15.00 |
| 57 | VAL | CB | −15.47 | −24.21 | 69.61 | 15.00 |
| 57 | VAL | CG1 | −15.58 | −25.61 | 69.01 | 15.00 |
| 57 | VAL | CG2 | −16.61 | −23.97 | 70.58 | 15.00 |
| 57 | VAL | C | −12.98 | −24.06 | 69.30 | 15.00 |
| 57 | VAL | O | −13.18 | −23.78 | 68.12 | 15.00 |
| 58 | SER | N | −11.80 | −24.45 | 69.76 | 15.00 |
| 58 | SER | CA | −10.60 | −24.55 | 68.94 | 15.00 |
| 58 | SER | CB | −9.45 | −25.07 | 69.79 | 15.00 |
| 58 | SER | OG | −9.53 | −24.53 | 71.10 | 15.00 |
| 58 | SER | C | −10.73 | −25.37 | 67.67 | 15.00 |
| 58 | SER | O | −9.99 | −25.17 | 66.72 | 15.00 |
| 59 | GLU | N | −11.61 | −26.36 | 67.70 | 15.00 |
| 59 | GLU | CA | −11.83 | −27.23 | 66.55 | 15.00 |
| 59 | GLU | CB | −12.73 | −28.41 | 66.92 | 15.00 |
| 59 | GLU | CG | −12.20 | −29.30 | 68.03 | 15.00 |
| 59 | GLU | CD | −12.38 | −28.71 | 69.41 | 15.00 |
| 59 | GLU | OE1 | −13.54 | −28.51 | 69.82 | 15.00 |
| 59 | GLU | OE2 | −11.37 | −28.43 | 70.06 | 15.00 |
| 59 | GLU | C | −12.41 | −26.48 | 65.37 | 15.00 |
| 59 | GLU | O | −12.37 | −26.95 | 64.23 | 15.00 |
| 60 | ASN | N | −13.03 | −25.34 | 65.65 | 15.00 |
| 60 | ASN | CA | −13.65 | −24.52 | 64.62 | 15.00 |
| 60 | ASN | CB | −15.10 | −24.18 | 64.99 | 15.00 |
| 60 | ASN | CG | −16.04 | −25.37 | 64.87 | 15.00 |
| 60 | ASN | OD1 | −17.24 | −25.24 | 65.03 | 15.00 |
| 60 | ASN | ND2 | −15.49 | −26.53 | 64.55 | 15.00 |
| 60 | ASN | C | −12.83 | −23.26 | 64.38 | 15.00 |
| 60 | ASN | O | −11.82 | −23.03 | 65.05 | 15.00 |
| 61 | ASP | N | −13.28 | −22.43 | 63.44 | 15.00 |
| 61 | ASP | CA | −12.56 | −21.22 | 63.09 | 15.00 |
| 61 | ASP | CB | −12.53 | −21.05 | 61.57 | 15.00 |
| 61 | ASP | CG | −11.12 | −20.82 | 61.03 | 15.00 |
| 61 | ASP | OD1 | −10.18 | −20.65 | 61.83 | 15.00 |
| 61 | ASP | OD2 | −10.96 | −20.82 | 59.79 | 15.00 |
| 61 | ASP | C | −13.09 | −19.95 | 63.76 | 15.00 |
| 61 | ASP | O | −12.67 | −18.85 | 63.43 | 15.00 |
| 62 | GLY | N | −14.00 | −20.09 | 64.72 | 15.00 |
| 62 | GLY | CA | −14.55 | −18.91 | 65.36 | 15.00 |
| 62 | GLY | C | −15.40 | −18.19 | 64.33 | 15.00 |
| 62 | GLY | O | −16.39 | −18.75 | 63.85 | 15.00 |

TABLE IX-continued

Table of the orthogonal three dimensional coordinates in Ångstroms and B factors (Å²) for the cathepsin K complex with inhibitor 4-[N-[(phenylmethoxy)carbonyl]-L-leucyl]-1-N[N-(methyl)-L-leucyl)]-3-pyrrolidinone

| Residue | Atom | X | Y | Z | B |
|---|---|---|---|---|---|
| 63 | CYS | N | −14.98 | −16.99 | 63.94 | 15.00 |
| 63 | CYS | CA | −15.70 | −16.19 | 62.94 | 15.00 |
| 63 | CYS | C | −15.40 | −16.66 | 61.53 | 15.00 |
| 63 | CYS | O | −15.88 | −16.07 | 60.57 | 15.00 |
| 63 | CYS | CB | −15.39 | −14.70 | 63.02 | 15.00 |
| 63 | CYS | SG | −16.14 | −13.86 | 64.44 | 15.00 |
| 64 | GLY | N | −14.57 | −17.68 | 61.40 | 1s.00 |
| 64 | GLY | CA | −14.26 | −18.20 | 60.08 | 15.00 |
| 64 | GLY | C | −15.21 | −19.31 | 59.69 | 15.00 |
| 64 | GLY | O | −15.23 | −19.74 | 58.53 | 15.00 |
| 65 | GLY | N | −15.99 | −19.80 | 60.65 | 15.00 |
| 65 | GLY | CA | −16.93 | −20.87 | 60.37 | 15.00 |
| 65 | GLY | C | −16.62 | −22.14 | 61.14 | 15.00 |
| 65 | GLY | O | −15.48 | −22.38 | 61.54 | 15.00 |
| 66 | GLY | N | −17.64 | −22.95 | 61.35 | 15.00 |
| 66 | GLY | CA | −17.45 | −24.19 | 62.08 | 15.00 |
| 66 | GLY | C | −18.56 | −25.20 | 61.92 | 15.00 |
| 66 | GLY | O | −19.38 | −25.12 | 61.00 | 15.00 |
| 67 | TYR | N | −18.56 | −26.18 | 62.81 | 15.00 |
| 67 | TYR | CA | −19.55 | −27.25 | 62.80 | 15.00 |
| 67 | TYR | CB | −18.89 | −28.59 | 62.62 | 15.00 |
| 67 | TYR | CG | −18.09 | −28.77 | 61.37 | 15.00 |
| 67 | TYR | CD1 | −18.68 | −28.65 | 60.11 | 15.00 |
| 67 | TYR | CE1 | −17.97 | −28.95 | 58.95 | 15.00 |
| 67 | TYR | CD2 | −16.77 | −29.18 | 61.44 | 15.00 |
| 67 | TYR | CE2 | −16.05 | −29.48 | 60.30 | 15.00 |
| 67 | TYR | CZ | −16.65 | −29.37 | 59.06 | 15.00 |
| 67 | TYR | OH | −15.93 | −29.71 | 57.94 | 15.00 |
| 67 | TYR | C | −20.31 | −27.25 | 64.11 | 15.00 |
| 67 | TYR | O | −19.73 | −26.97 | 65.15 | 15.00 |
| 68 | MET | N | −21.60 | −27.57 | 64.06 | 15.00 |
| 68 | MET | CA | −22.40 | −27.64 | 65.27 | 15.00 |
| 68 | MET | CB | −23.88 | −27.79 | 64.94 | 15.00 |
| 68 | MET | CG | −24.47 | −26.62 | 64.20 | 15.00 |
| 68 | MET | SD | −23.93 | −26.55 | 62.51 | 15.00 |
| 68 | MET | CE | −25.32 | −27.25 | 61.69 | 15.00 |
| 68 | MET | C | −21.91 | −28.78 | 66.17 | 15.00 |
| 68 | MET | O | −21.81 | −28.64 | 67.39 | 15.00 |
| 69 | THR | N | −21.56 | −29.90 | 65.54 | 15.00 |
| 69 | THR | CA | −21.07 | −31.07 | 66.27 | 15.00 |
| 69 | THR | CB | −20.66 | −32.20 | 65.31 | 15.00 |
| 69 | THR | OG1 | −19.57 | −31.77 | 64.48 | 15.00 |
| 69 | THR | CG2 | −21.84 | −32.58 | 64.45 | 15.00 |
| 69 | THR | C | −19.91 | −30.70 | 67.18 | 15.00 |
| 69 | THR | O | −19.94 | −31.00 | 68.37 | 15.00 |
| 70 | ASN | N | −18.92 | −30.00 | 66.64 | 15.00 |
| 70 | ASN | CA | −17.77 | −29.54 | 67.42 | 15.00 |
| 70 | ASN | CB | −16.75 | −28.84 | 66.55 | 15.00 |
| 70 | ASN | CG | −15.86 | −29.80 | 65.85 | 15.00 |
| 70 | ASN | OD1 | −15.33 | −30.72 | 66.46 | 15.00 |
| 70 | ASN | ND2 | −15.68 | −29.61 | 64.55 | 15.00 |
| 70 | ASN | C | −18.17 | −28.63 | 68.60 | 15.00 |
| 70 | ASN | O | −17.53 | −28. 66 | 69.66 | 15.00 |
| 71 | ALA | N | −19.20 | −27.82 | 68.40 | 15.00 |
| 71 | ALA | CA | −19.67 | −26.91 | 69.44 | 15.00 |
| 71 | ALA | CB | −20.66 | −25.91 | 68.86 | 15.00 |
| 71 | ALA | C | −20.33 | −27.72 | 70.55 | 15.00 |
| 71 | ALA | O | −20.26 | −27.37 | 71.72 | 15.00 |
| 72 | PHE | N | −20.96 | −28.83 | 70.16 | 15.00 |
| 72 | PHE | CA | −21.61 | −29.70 | 71.13 | 15.00 |
| 72 | PHE | CB | −22.57 | −30.66 | 70.43 | 15.00 |
| 72 | PHE | CG | −23.73 | −29.98 | 69.79 | 15.00 |
| 72 | PHE | CD1 | −24.28 | −28.84 | 70.36 | 15.00 |
| 72 | PHE | CD2 | −24.29 | −30.48 | 68.63 | 15.00 |
| 72 | PHE | CE1 | −25.35 | −28.21 | 69.79 | 15.00 |
| 72 | PHE | CE2 | −25.37 | −29.87 | 68.04 | 15.00 |
| 72 | PHE | CZ | −25.91 | −28.72 | 68.62 | 15.00 |
| 72 | PHE | C | −20.59 | −30.46 | 71.96 | 15.00 |
| 72 | PHE | O | −20.79 | −30.69 | 73.15 | 15.00 |
| 73 | GLN | N | −19.48 | −30.82 | 71.33 | 15.00 |
| 73 | GLN | CA | −18.43 | −31.54 | 72.03 | 15.00 |
| 73 | GLN | CB | −17.46 | −32.17 | 71.04 | 15.00 |
| 73 | GLN | CG | −16.71 | −33.36 | 71.59 | 15.00 |
| 73 | GLN | CD | −16.83 | −34.56 | 70.67 | 15.00 |
| 73 | GLN | OE1 | −17.35 | −35.61 | 71.07 | 15.00 |
| 73 | GLN | NE2 | −16.37 | −34.41 | 69.44 | 15.00 |
| 73 | GLN | C | −17.70 | −30.62 | 72.99 | 15.00 |
| 73 | GLN | O | −17.18 | −31.07 | 74.02 | 15.00 |
| 74 | TYR | N | −17.64 | −29.34 | 72.65 | 15.00 |
| 74 | TYR | CA | −16.96 | −28.38 | 73.52 | 15.00 |
| 74 | TYR | CB | −16.74 | −27.03 | 72.81 | 15.00 |
| 74 | TYR | CG | −16.38 | −25.93 | 73.78 | 15.00 |
| 74 | TYR | CD1 | −15.16 | −25.95 | 74.45 | 15.00 |
| 74 | TYR | CE1 | −14.87 | −25.02 | 75.40 | 15.00 |
| 74 | TYR | CD2 | −17.30 | −24.94 | 74.11 | 15.00 |
| 74 | TYR | CE2 | −17.01 | −24.00 | 75.07 | 15.00 |
| 74 | TYR | CZ | −15.79 | −24.05 | 75.71 | 15.00 |
| 74 | TYR | OH | −15.47 | −23.11 | 76.67 | 15.00 |
| 74 | TYR | C | −17.69 | −28.17 | 74.84 | 15.00 |
| 74 | TYR | O | −17.07 | −28.14 | 75.89 | 15.00 |
| 75 | VAL | N | −19.00 | −27.98 | 74.77 | 15.00 |
| 75 | VAL | CA | −19.82 | −27.78 | 75.97 | 15.00 |
| 75 | VAL | CB | −21.29 | −27.47 | 75.58 | 15.00 |
| 75 | VAL | CG1 | −22.13 | −27.23 | 76.82 | 15.00 |
| 75 | VAL | CG2 | −21.34 | −26.25 | 74.67 | 15.00 |
| 75 | VAL | C | −19.73 | −29.01 | 76.87 | 15.00 |
| 75 | VAL | O | −19.82 | −28.91 | 78.10 | 15.00 |
| 76 | GLN | N | −19.47 | −30.16 | 76.26 | 15.00 |
| 76 | GLN | CA | −19.33 | −31.42 | 76.97 | 15.00 |
| 76 | GLN | CB | −19.57 | −32.58 | 76.01 | 15.00 |
| 76 | GLN | CG | −19.54 | −33.95 | 76.62 | 15.00 |
| 76 | GLN | CD | −19.67 | −35.03 | 75.58 | 15.00 |
| 76 | GLN | OE1 | −20.73 | −35.62 | 75.41 | 15.00 |
| 76 | GLN | NE2 | −18.60 | −35.28 | 74.86 | 15.00 |
| 76 | GLN | C | −17.96 | −31.55 | 77.68 | 15.00 |
| 76 | GLN | O | −17.91 | −31.76 | 78.89 | 15.00 |
| 77 | LYS | N | −16.87 | −31.41 | 76.94 | 15.00 |
| 77 | LYS | CA | −15.53 | −31.51 | 77.53 | 15.00 |
| 77 | LYS | CB | −14.43 | −31.56 | 76.46 | 15.00 |
| 77 | LYS | CG | −14.07 | −30.18 | 75.87 | 15.00 |
| 77 | LYS | CD | −12.80 | −30.21 | 75.01 | 15.00 |
| 77 | LYS | CE | −13.01 | −30.90 | 73.67 | 15.00 |
| 77 | LYS | NZ | −14.16 | −30.32 | 72.90 | 15.00 |
| 77 | LYS | C | −15.26 | −30.36 | 78.49 | 15.00 |
| 77 | LYS | O | −14.45 | −30.49 | 79.41 | 15.00 |
| 78 | ASN | N | −15.89 | −29.22 | 78.22 | 15.00 |
| 78 | ASN | CA | −15.73 | −28.04 | 79.05 | 15.00 |
| 78 | ASN | CB | −16.05 | −26.77 | 78.27 | 15.00 |
| 78 | ASN | CG | −15.64 | −25.51 | 79.00 | 15.00 |
| 78 | ASN | OD1 | −14.49 | −25.35 | 79.40 | 15.00 |
| 78 | ASN | ND2 | −16.57 | −24.59 | 79.14 | 15.00 |
| 78 | ASN | C | −16.64 | −28.15 | 80.26 | 15.00 |
| 78 | ASN | O | −16.46 | −27.45 | 81.25 | 15.00 |
| 79 | ARG | N | −17.63 | −29.04 | 80.16 | 15.00 |
| 79 | ARG | CA | −18.61 | −29.26 | 81.22 | 15.00 |
| 79 | ARG | CB | −17.95 | −29.71 | 82.54 | 15.00 |
| 79 | ARG | CG | −17.19 | −31.05 | 82.52 | 15.00 |
| 79 | ARG | CD | −18.12 | −32.28 | 82.55 | 15.00 |
| 79 | ARG | NE | −18.94 | −32.34 | 83.76 | 15.00 |
| 79 | ARG | CZ | −20.14 | −32.92 | 83.84 | 15.00 |
| 79 | ARG | NH1 | −20.69 | −33.51 | 82.78 | 15.00 |
| 79 | ARG | NH2 | −20.82 | −32.88 | 84.99 | 15.00 |
| 79 | ARG | C | −19.47 | −28.02 | 81.44 | 15.00 |
| 79 | ARG | O | −19.86 | −27.74 | 82.57 | 15.00 |
| 80 | GLY | N | −19.75 | −27.27 | 80.38 | 15.00 |
| 80 | GLY | CA | −20.58 | −26.08 | 80.52 | 15.00 |
| 80 | GLY | C | −20.38 | −24.97 | 79.49 | 15.00 |
| 80 | GLY | O | −19.36 | −24.93 | 78.78 | 15.00 |
| 81 | ILE | N | −21.37 | −24.08 | 79.41 | 15.00 |
| 81 | ILE | CA | −21.35 | −22.92 | 78.50 | 15.00 |
| 81 | ILE | CB | −22.14 | −23.20 | 77.17 | 15.00 |
| 81 | ILE | CG2 | −23.59 | −23.57 | 77.46 | 15.00 |

TABLE IX-continued

Table of the orthogonal three dimensional coordinates in Ångstroms and B factors (Å²) for the cathepsin K complex with inhibitor 4-[N-[(phenylmethoxy)carbonyl]-L-leucyl]-1-N[N-(methyl)-L-leucyl)]-3-pyrrolidinone

| Residue | Atom | X | Y | Z | B |
|---|---|---|---|---|---|
| 81 | ILE | CG1 | −22.11 | −21.97 | 76.25 | 15.00 |
| 81 | ILE | CD1 | −22.75 | −22.19 | 74.90 | 15.00 |
| 81 | ILE | C | −22.00 | −21.76 | 79.25 | 15.00 |
| 81 | ILE | O | −22.86 | −21.98 | 80.11 | 15.00 |
| 82 | ASP | N | −21.56 | −20.54 | 78.96 | 15.00 |
| 82 | ASP | CA | −22.09 | −19.34 | 79.61 | 15.00 |
| 82 | ASP | CB | −21.08 | −18.20 | 79.59 | 15.00 |
| 82 | ASP | CG | −19.89 | −18.44 | 80.48 | 15.00 |
| 82 | ASP | OD1 | −18.82 | −17.87 | 80.21 | 15.00 |
| 82 | ASP | OD2 | −20.03 | −19.18 | 81.47 | 15.00 |
| 82 | ASP | C | −23.40 | −18.85 | 79.02 | 15.00 |
| 82 | ASP | O | −23.89 | −19.36 | 78.02 | 15.00 |
| 83 | SER | N | −23.96 | −17.84 | 79.68 | 15.00 |
| 83 | SER | CA | −25.19 | −17.20 | 79.27 | 15.00 |
| 83 | SER | CB | −26.03 | −16.83 | 80.49 | 15.00 |
| 83 | SER | OG | −25.19 | −16.35 | 81.52 | 15.00 |
| 83 | SER | C | −24.76 | −15.96 | 78.49 | 15.00 |
| 83 | SER | O | −23.59 | −15.58 | 78.53 | 15.00 |
| 84 | GLU | N | −25.68 | −15.29 | 77.81 | 15.00 |
| 84 | GLU | CA | −25.29 | −14.13 | 77.03 | 15.00 |
| 84 | GLU | CB | −26.39 | −13.59 | 76.13 | 15.00 |
| 84 | GLU | CG | −25.83 | −12.69 | 75.03 | 15.00 |
| 84 | GLU | CD | −24.85 | −13.42 | 74.11 | 1500 |
| 84 | GLU | OE1 | −25.26 | −13.79 | 72.99 | 15.00 |
| 84 | GLU | OE2 | −23.68 | −13.64 | 74.49 | 15.00 |
| 84 | GLU | C | −24.73 | −13.05 | 77.92 | 15.00 |
| 84 | GLU | O | −23.52 | −12.84 | 77.90 | 15.00 |
| 85 | ASP | N | −25.56 | −12.36 | 78.69 | 15.00 |
| 85 | ASP | CA | −25.00 | −11.32 | 79.55 | 15.00 |
| 85 | ASP | CB | −26.06 | −10.32 | 80.06 | 15.00 |
| 85 | ASP | CG | −25.45 | −8.93 | 80.42 | 15.00 |
| 85 | ASP | OD1 | −26.14 | −8.14 | 81.10 | 15.00 |
| 85 | ASP | OD2 | −24.30 | −8.62 | 80.02 | 15.00 |
| 85 | ASP | C | −24.32 | −12.06 | 80.68 | 15.00 |
| 85 | ASP | O | −24.91 | −12.29 | 81.73 | 15.00 |
| 86 | ALA | N | −23.11 | −12.51 | 80.37 | 15.00 |
| 86 | ALA | CA | −22.20 | −13.27 | 81.22 | 15.00 |
| 86 | ALA | CB | −22.80 | −14.62 | 81.60 | 15.00 |
| 86 | ALA | C | −20.96 | −13.46 | 80.33 | 15.00 |
| 86 | ALA | O | −19.83 | −13.52 | 80.81 | 15.00 |
| 87 | TYR | N | −21.21 | −13.59 | 79.03 | 15.00 |
| 87 | TYR | CA | −20.18 | −13.73 | 78.00 | 15.00 |
| 87 | TYR | CB | −19.74 | −15.19 | 77.86 | 15.00 |
| 87 | TYR | CG | −18.39 | −15.40 | 77.19 | 15.00 |
| 87 | TYR | CD1 | −17.78 | −14.58 | 76.45 | 15.00 |
| 87 | TYR | CE1 | −16.54 | −14.59 | 75.84 | 15.00 |
| 87 | TYR | CD2 | −17.73 | −16.61 | 77.31 | 15.00 |
| 87 | TYR | CE2 | −16.49 | −16.82 | 76.72 | 15.00 |
| 87 | TYR | CZ | −15.90 | −15.80 | 75.98 | 15.00 |
| 87 | TYR | OH | −14.67 | −15.99 | 75.42 | 15.00 |
| 87 | TYR | C | −20.88 | −13.21 | 76.73 | 15.00 |
| 87 | TYR | O | −21.25 | −13.98 | 75.86 | 15.00 |
| 88 | PRO | N | −21.07 | −11.89 | 76.64 | 15.00 |
| 88 | PRO | CD | −20.61 | −10.92 | 77.65 | 15.00 |
| 88 | PRO | CA | −21.72 | −11.18 | 75.54 | 15.00 |
| 88 | PRO | CB | −21.69 | −9.73 | 76.00 | 15.00 |
| 88 | PRO | CG | −21.61 | −9.83 | 77.49 | 15.00 |
| 88 | PRO | C | −21.11 | −11.32 | 74.15 | 15.00 |
| 88 | PRO | O | −19.90 | −11.51 | 74.00 | 15.00 |
| 89 | TYR | N | −21.95 | −11.12 | 73.14 | 15.00 |
| 89 | TYR | CA | −21.55 | −11.21 | 71.74 | 15.00 |
| 89 | TYR | CB | −22.75 | −11.61 | 70.87 | 15.00 |
| 89 | TYR | CG | −22.36 | −12.04 | 69.48 | 15.00 |
| 89 | TYR | CD1 | −21.49 | −13.11 | 69.29 | 15.00 |
| 89 | TYR | CE1 | −21.07 | −13.47 | 68.02 | 15.00 |
| 89 | TYR | CD2 | −22.82 | −11.36 | 68.36 | 15.00 |
| 89 | TYR | CE2 | −22.41 | −11.72 | 67.10 | 15.00 |
| 89 | TYR | CZ | −21.53 | −12.77 | 66.94 | 15.00 |
| 89 | TYR | OH | −21.09 | −13.11 | 65.69 | 15.00 |
| 89 | TYR | C | −20.90 | −9.91 | 71.24 | 15.00 |
| 89 | TYR | O | −21.59 | −8.91 | 71.03 | 15.00 |
| 90 | VAL | N | −19.58 | −9.92 | 71.08 | 15.00 |
| 90 | VAL | CA | −18.87 | −8.73 | 70.61 | 15.00 |
| 90 | VAL | CB | −17.41 | −8.68 | 71.09 | 15.00 |
| 90 | VAL | CG1 | −17.35 | −8.79 | 72.60 | 15.00 |
| 90 | VAL | CG2 | −16.59 | −9.77 | 70.43 | 15.00 |
| 90 | VAL | c | −18.89 | −8.68 | 69.08 | 15.00 |
| 90 | VAL | O | −18.92 | −7.61 | 68.49 | 15.00 |
| 91 | GLY | N | −18.98 | −9.84 | 68.45 | 15.00 |
| 91 | GLY | CA | −19.04 | −9.87 | 67.01 | 15.00 |
| 91 | GLY | C | −17.71 | −10.16 | 66.36 | 15.00 |
| 91 | GLY | O | −17.56 | −9.93 | 65.16 | 15.00 |
| 92 | GLN | N | −16.76 | −10.69 | 67.13 | 15.00 |
| 92 | GLN | CA | −15.43 | −11.01 | 66.62 | 15.00 |
| 92 | GLN | CB | −14.62 | −9.75 | 66.38 | 15.00 |
| 92 | GLN | CG | −14.24 | −9.09 | 67.68 | 15.00 |
| 92 | GLN | CD | −13.83 | −7.66 | 67.52 | 15.00 |
| 92 | GLN | OE1 | −12.91 | −7.19 | 68.19 | 15.00 |
| 92 | GLN | NE2 | −14.53 | −6.93 | 66.64 | 15.00 |
| 92 | GLN | C | −14.67 | −11.92 | 67.58 | 15.00 |
| 92 | GLN | O | −14.91 | −11.91 | 68.79 | 15.00 |
| 93 | GLU | N | −13.72 | −12.66 | 67.02 | 15.00 |
| 93 | GLU | CA | −12.89 | −13.59 | 67.78 | 15.00 |
| 93 | GLU | CB | −11.95 | −14.35 | 66.85 | 15.00 |
| 93 | GLU | CG | −12.64 | −15.06 | 65.69 | 15.00 |
| 93 | GLU | CD | −11.68 | −15.45 | 64.57 | 15.00 |
| 93 | GLU | OE1 | −10.56 | −15.94 | 64.87 | 15.00 |
| 93 | GLU | OE2 | −12.03 | −15.24 | 63.39 | 15.00 |
| 93 | GLU | C | −12.11 | −12.86 | 68.86 | 15.00 |
| 93 | GLU | O | −11.54 | −11.79 | 68.61 | 15.00 |
| 94 | GLU | N | −12.08 | −13.46 | 70.05 | 15.00 |
| 94 | GLU | CA | −11.38 | −12.93 | 71.22 | 15.00 |
| 94 | GLU | CB | −12.31 | −12.19 | 72.16 | 15.00 |
| 94 | GLU | CG | −12.77 | −10.82 | 71.71 | 15.00 |
| 94 | GLU | CD | −13.69 | −10.18 | 72.74 | 15.00 |
| 94 | GLU | OE1 | −13.59 | −8.95 | 72.97 | 15.00 |
| 94 | GLU | OE2 | −14.50 | −10.92 | 73.33 | 15.00 |
| 94 | GLU | C | −10.77 | −14.12 | 71.96 | 15.00 |
| 94 | GLU | O | −11.15 | −15.26 | 71.71 | 15.00 |
| 95 | SER | N | −9.87 | −13.85 | 72.90 | 15.00 |
| 95 | SER | CA | −9.24 | −14.91 | 73.69 | 15.00 |
| 95 | SER | CB | −8.09 | −14.36 | 74.52 | 15.00 |
| 95 | SER | OG | −8.52 | −13.24 | 75.28 | 15.00 |
| 95 | SER | C | −10.32 | −15.52 | 74.59 | 15.00 |
| 95 | SER | O | −11.03 | −14.78 | 75.28 | 15.00 |
| 96 | CYS | N | −10.42 | −16.84 | 74.58 | 15.00 |
| 96 | CYS | CA | −11.43 | −17.54 | 75.38 | 15.00 |
| 96 | CYS | C | −11.55 | −17.08 | 76.82 | 15.00 |
| 96 | CYS | O | −10.69 | −17.37 | 77.66 | 15.00 |
| 96 | CYS | CB | −11.24 | −19.06 | 75.31 | 15.00 |
| 96 | CYS | SG | −12.40 | −19.98 | 76.37 | 15.00 |
| 97 | MET | N | −12.60 | −16.32 | 77.10 | 15.00 |
| 97 | MET | CA | −12.86 | −15.80 | 78.44 | 15.00 |
| 97 | MET | CB | −13.16 | −14.29 | 78.41 | 15.00 |
| 97 | MET | CG | −11.97 | −13.37 | 78.13 | 15.00 |
| 97 | MET | SD | −12.05 | −12.55 | 76.50 | 15.00 |
| 97 | MET | CE | −13.66 | −11.72 | 76.66 | 15.00 |
| 97 | MET | C | −13.99 | −16.57 | 79.13 | 15.00 |
| 97 | MET | O | −14.93 | −15.96 | 79.66 | 15.00 |
| 98 | TYR | N | −13.91 | −17.90 | 79.15 | 15.00 |
| 98 | TYR | CA | −14.96 | −18.68 | 79.80 | 15.00 |
| 98 | TYR | CB | −14.79 | −20.17 | 79.54 | 15.00 |
| 98 | TYR | CG | −15.85 | −21.01 | 80.24 | 15.00 |
| 98 | TYR | CD1 | −17.20 | −20.84 | 79.95 | 15.00 |
| 98 | TYR | CE1 | −18.17 | −21.59 | 80.59 | 15.00 |
| 98 | TYR | CD2 | −15.50 | −21.96 | 81.19 | 15.00 |
| 98 | TYR | CE2 | −16.48 | −22.73 | 81.83 | 15.00 |
| 98 | TYR | CZ | −17.80 | −22.53 | 81.53 | 15.00 |
| 98 | TYR | OH | −18.77 | −23.27 | 82.16 | 15.00 |
| 98 | TYR | C | −15.11 | −18.42 | 81.29 | 15.00 |
| 98 | TYR | O | −14.28 | −18.80 | 82.11 | 15.00 |
| 99 | ASN | N | −16.21 | −17.74 | 81.62 | 15.00 |

TABLE IX-continued

Table of the orthogonal three dimensional coordinates in Ångstroms and B factors (Å²) for the cathepsin K complex with inhibitor 4-[N-[(phenylmethoxy)carbonyl]-L-leucyl]-1-N[N-(methyl)-L-leucyl)]-3-pyrrolidinone

| Residue | Atom | X | Y | Z | B |
|---|---|---|---|---|---|
| 99 | ASN | CA | −16.59 | −17.38 | 82.98 | 15.00 |
| 99 | ASN | CB | −17.52 | −16.16 | 82.93 | 15.00 |
| 99 | ASN | CG | −17.93 | −15.66 | 84.29 | 15.00 |
| 99 | ASN | OD1 | −17.61 | −16.27 | 85.32 | 15.00 |
| 99 | ASN | ND2 | −18.65 | −14.53 | 84.32 | 15.00 |
| 99 | ASN | C | −17.30 | −18.62 | 83.57 | 15.00 |
| 99 | ASN | O | −18.50 | −18.81 | 83.35 | 15.00 |
| 100 | PRO | N | −16.59 | −19.46 | 84.35 | 15.00 |
| 100 | PRO | CD | −15.20 | −19.31 | 84.81 | 15.00 |
| 100 | PRO | CA | −17.20 | −20.67 | 84.94 | 15.00 |
| 100 | PRO | CB | −16.06 | −21.26 | 85.77 | 15.00 |
| 100 | PRO | CG | −14.82 | −20.73 | 85.09 | 15.00 |
| 100 | PRO | C | −18.40 | −20.36 | 85.82 | 15.00 |
| 100 | PRO | O | −19.33 | −21.16 | 85.93 | 15.00 |
| 101 | THR | N | −18.37 | −19.19 | 86.44 | 15.00 |
| 101 | THR | CA | −19.44 | −18.75 | 87.32 | 15.00 |
| 101 | THR | CB | −19.06 | −17.44 | 88.03 | 15.00 |
| 101 | THR | OG1 | −17.64 | −17.23 | 87.93 | 15.00 |
| 101 | THR | CG2 | −19.46 | −17.51 | 89.50 | 15.00 |
| 101 | THR | C | −20.74 | −18.53 | 86.56 | 15.00 |
| 101 | THR | O | −21.82 | −18.83 | 87.07 | 15.00 |
| 102 | GLY | N | −20.64 | −18.01 | 85.35 | 15.00 |
| 102 | GLY | CA | −21.85 | −17.75 | 84.58 | 15.00 |
| 102 | GLY | C | −22.38 | −18.91 | 83.77 | 15.00 |
| 102 | GLY | O | −23.27 | −18.70 | 82.94 | 15.00 |
| 103 | LYS | N | −21.85 | −20.12 | 83.98 | 15.00 |
| 103 | LYS | CA | −22.32 | −21.28 | 83.21 | 15.00 |
| 103 | LYS | CB | −21.62 | −22.56 | 83.63 | 15.00 |
| 103 | LYS | CG | −22.20 | −23.22 | 84.86 | 15.00 |
| 103 | LYS | CD | −21.67 | −24.63 | 85.01 | 15.00 |
| 103 | LYS | CE | −22.02 | −25.45 | 83.79 | 15.00 |
| 103 | LYS | NZ | −23.49 | −25.45 | 83.60 | 15.00 |
| 103 | LYS | C | −23.83 | −21.40 | 83.35 | 15.00 |
| 103 | LYS | O | −24.37 | −21.25 | 84.45 | 15.00 |
| 104 | ALA | N | −24.51 | −21.65 | 82.24 | 15.00 |
| 104 | ALA | CA | −25.96 | −21.74 | 82.28 | 15.00 |
| 104 | ALA | CB | −26.57 | −20.48 | 81.67 | 15.00 |
| 104 | ALA | C | −26.55 | −22.97 | 81.62 | 15.00 |
| 104 | ALA | O | −27.76 | −23.22 | 81.72 | 15.00 |
| 105 | ALA | N | −25.70 | −23.76 | 80.97 | 15.00 |
| 105 | ALA | CA | −26.17 | −24.96 | 80.31 | 15.00 |
| 105 | ALA | CB | −26.66 | −24.65 | 78.91 | 15.00 |
| 105 | ALA | C | −25.10 | −26.02 | 80.24 | 15.00 |
| 105 | ALA | O | −23.91 | −25.72 | 80.09 | 15.00 |
| 106 | LYS | N | −25.53 | −27.26 | 80.40 | 15.00 |
| 106 | LYS | CA | −24.65 | −28.41 | 80.36 | 15.00 |
| 106 | LYS | CB | −24.77 | −29.23 | 81.64 | 15.00 |
| 106 | LYS | CG | −24.05 | −28.65 | 82.83 | 15.00 |
| 106 | LYS | CD | −22.56 | −28.96 | 82.80 | 15.00 |
| 106 | LYS | CE | −22.28 | −30.46 | 82.89 | 15.00 |
| 106 | LYS | NZ | −22.56 | −31.21 | 81.62 | 15.00 |
| 106 | LYS | C | −25.08 | −29.23 | 79.17 | 15.00 |
| 106 | LYS | O | −26.18 | −29.04 | 78.65 | 15.00 |
| 107 | CYS | N | −24.23 | −30.15 | 78.76 | 15.00 |
| 107 | CYS | CA | −24.52 | −31.01 | 77.62 | 15.00 |
| 107 | CYS | CB | −24.00 | −30.36 | 76.33 | 15.00 |
| 107 | CYS | SG | −24.10 | −31.36 | 74.81 | 15.00 |
| 107 | CYS | C | −23.81 | −32.31 | 77.94 | 15.00 |
| 107 | CYS | O | −22.94 | −32.34 | 78.81 | 15.00 |
| 108 | ARG | N | −24.23 | −33.40 | 77.30 | 15.00 |
| 108 | ARG | CA | −23.60 | −34.70 | 77.51 | 15.00 |
| 108 | ARG | CB | −24.27 | −35.46 | 78.66 | 15.00 |
| 108 | ARG | CG | −25.67 | −35.93 | 78.35 | 15.00 |
| 108 | ARG | CD | −26.16 | −36.95 | 79.38 | 15.00 |
| 108 | ARG | NE | −27.36 | −37.64 | 78.90 | 15.00 |
| 108 | ARG | CZ | −27.34 | −38.78 | 78.20 | 15.00 |
| 108 | ARG | NH1 | −26.18 | −39.37 | 77.92 | 15.00 |
| 108 | ARG | NH2 | −28.48 | −39.29 | 77.75 | 15.00 |
| 108 | ARG | C | −23.57 | −35.53 | 76.23 | 15.00 |
| 108 | ARG | O | −23.71 | −36.76 | 76.27 | 15.00 |
| 109 | GLY | N | −23.37 | −34.87 | 75.10 | 15.00 |
| 109 | GLY | CA | −23.30 | −35.59 | 73.85 | 15.00 |
| 109 | GLY | C | −24.02 | −34.85 | 72.75 | 15.00 |
| 109 | GLY | O | −24.50 | −33.73 | 72.95 | 15.00 |
| 110 | TYR | N | −24.10 | −35.48 | 71.59 | 15.00 |
| 110 | TYR | CA | −24.77 | −34.92 | 70.44 | 15.00 |
| 110 | TYR | CB | −23.91 | −33.89 | 69.74 | 15.00 |
| 110 | TYR | CG | −22.68 | −34.45 | 69.05 | 15.00 |
| 110 | TYR | CD1 | −21.45 | −34.47 | 69.70 | 15.00 |
| 110 | TYR | CE1 | −20.31 | −34.89 | 69.04 | 15.00 |
| 110 | TYR | CD2 | −22.74 | −34.88 | 67.73 | 15.00 |
| 110 | TYR | CE2 | −21.61 | −35.30 | 67.07 | 15.00 |
| 110 | TYR | CZ | −20.39 | −35.30 | 67.72 | 15.00 |
| 110 | TYR | OH | −19.24 | −35.68 | 67.05 | 15.00 |
| 110 | TYR | C | −25.16 | −36.02 | 69.48 | 15.00 |
| 110 | TYR | O | −24.41 | −36.99 | 69.31 | 15.00 |
| 111 | ARG | N | −26.32 | −35.87 | 68.86 | 15.00 |
| 111 | ARG | CA | −26.83 | −36.84 | 67.91 | 15.00 |
| 111 | ARG | CB | −28.14 | −37.43 | 68.41 | 15.00 |
| 111 | ARG | CG | −28.01 | −38.15 | 69.74 | 15.00 |
| 111 | ARG | CD | −28.52 | −39.57 | 69.65 | 15.00 |
| 111 | ARG | NE | −27.97 | −40.28 | 68.49 | 15.00 |
| 111 | ARG | CZ | −28.38 | −41.48 | 68.10 | 15.00 |
| 111 | ARG | NH1 | −27.83 | −42.06 | 67.03 | 15.00 |
| 111 | ARG | NH2 | −29.32 | −42.12 | 68.78 | 15.00 |
| 111 | ARG | C | −27.01 | −36.25 | 66.52 | 15.00 |
| 111 | ARG | O | −27.32 | −35.07 | 66.39 | 15.00 |
| 112 | GLU | N | −26.81 | −37.06 | 65.50 | 15.00 |
| 112 | GLU | CA | −26.94 | −36.62 | 64.12 | 15.00 |
| 112 | GLU | CB | −25.68 | −36.90 | 63.30 | 15.00 |
| 112 | GLU | CG | −24.42 | −36.10 | 63.68 | 15.00 |
| 112 | GLU | CD | −23.23 | −36.42 | 62.77 | 15.00 |
| 112 | GLU | OE1 | −22.07 | −36.07 | 63.13 | 15.00 |
| 112 | GLU | OE2 | −23.44 | −37.01 | 61.69 | 15.00 |
| 112 | GLU | C | −28.14 | −37.26 | 63.44 | 15.00 |
| 112 | GLU | O | −28.60 | −38.33 | 63.84 | 15.00 |
| 113 | ILE | N | −28.61 | −36.60 | 62.39 | 15.00 |
| 113 | ILE | CA | −29.74 | −37.06 | 61.60 | 15.00 |
| 113 | ILE | CB | −30.51 | −35.84 | 61.05 | 15.00 |
| 113 | ILE | CG2 | −31.61 | −36.25 | 60.09 | 15.00 |
| 113 | ILE | CG1 | −31.10 | −35.06 | 62.22 | 15.00 |
| 113 | ILE | CD1 | −32.01 | −35.89 | 63.07 | 15.00 |
| 113 | ILE | C | −29.15 | −37.84 | 60.43 | 15.00 |
| 113 | ILE | O | −28.13 | −37.44 | 59.88 | 15.00 |
| 114 | PRO | N | −29.74 | −38.99 | 60.08 | 15.00 |
| 114 | PRO | CD | −30.93 | −39.67 | 60.65 | 15.00 |
| 114 | PRO | CA | −29.19 | −39.76 | 58.95 | 15.00 |
| 114 | PRO | CB | −30.23 | −40.86 | 58.75 | 15.00 |
| 114 | PRO | CG | −30.78 | −41.07 | 60.12 | 15.00 |
| 114 | PRO | C | −29.18 | −38.82 | 57.75 | 15.00 |
| 114 | PRO | O | −30.23 | −38.35 | 57.30 | 15.00 |
| 115 | GLU | N | −27.98 | −38.53 | 57.25 | 15.00 |
| 115 | GLU | CA | −27.81 | −37.64 | 56.11 | 15.00 |
| 115 | GLU | CB | −26.36 | −37.71 | 55.63 | 15.00 |
| 115 | GLU | CG | −26.00 | −38.96 | 54.84 | 15.00 |
| 115 | GLU | CD | −26.11 | −38.74 | 53.34 | 15.00 |
| 11s | GLU | OE1 | −26.79 | −39.55 | 52.65 | 15.00 |
| 115 | GLU | OE2 | −25.52 | −37.74 | 52.85 | 15.00 |
| 11s | GLU | C | −28.81 | −37.80 | 54.96 | 15.00 |
| 11s | GLU | O | −28.93 | −38.86 | 54.37 | 15.00 |
| 116 | GLY | N | −29.54 | −36.73 | 54.67 | 15.00 |
| 116 | GLY | CA | −30.51 | −36.71 | 53.59 | 15.00 |
| 116 | GLY | C | −31.88 | −37.25 | 53.92 | 15.00 |
| 116 | GLY | O | −32.76 | −37.31 | 53.05 | 15.00 |
| 117 | ASN | N | −32.09 | −37.61 | 55.18 | 15.00 |
| 117 | ASN | CA | −33.37 | −38.18 | 55.61 | 15.00 |
| 117 | ASN | CB | −33.13 | −39.38 | 56.52 | 15.00 |
| 117 | ASN | CG | −34.42 | −40.02 | 57.01 | 15.00 |
| 117 | ASN | OD1 | −35.53 | −39.60 | 56.65 | 15.00 |
| 117 | ASN | ND2 | −34.28 | −41.06 | 57.83 | 15.00 |
| 117 | ASN | C | −34.32 | −37.19 | 56.27 | 15.00 |
| 117 | ASN | O | −34.40 | −37.10 | 57.50 | 15.00 |

TABLE IX-continued

Table of the orthogonal three dimensional coordinates in Ångstroms and B factors (Å²) for the cathepsin K complex with inhibitor 4-[N-[(phenylmethoxy)carbonyl]-L-leucyl]-1-N[N-(methyl)-L-leucyl)]-3-pyrrolidinone

| Residue | | Atom | X | Y | Z | B |
|---|---|---|---|---|---|---|
| 118 | GLU | N | −35.10 | −36.50 | 55.45 | 15.00 |
| 118 | GLU | CA | −36.05 | −35.52 | 55.96 | 15.00 |
| 118 | GLU | CB | −36.81 | −34.85 | 54.83 | 15.00 |
| 118 | GLU | CG | −36.06 | −33.74 | 54.15 | 15.00 |
| 118 | GLU | CD | −36.96 | −32.95 | 53.26 | 15.00 |
| 118 | GLU | OE1 | −37.20 | −33.39 | 52.11 | 15.00 |
| 118 | GLU | OE2 | −37.46 | −31.91 | 53.72 | 15.00 |
| 118 | GLU | C | −37.03 | −36.09 | 56.96 | 15.00 |
| 118 | GLU | O | −37.48 | −35.39 | 57.88 | 15.00 |
| 119 | LYS | N | −37.39 | −37.36 | 56.79 | 15.00 |
| 119 | LYS | CA | −38.33 | −37.99 | 57.71 | 15.00 |
| 119 | LYS | CB | −38.85 | −39.30 | 57.15 | 15.00 |
| 119 | LYS | CG | −40.37 | −39.34 | 57.05 | 15.00 |
| 119 | LYS | CD | −40.95 | −38.10 | 56.34 | 15.00 |
| 119 | LYS | CE | −42.47 | −38.10 | 56.44 | 15.00 |
| 119 | LYS | NZ | −43.07 | −36.84 | 55.99 | 15.00 |
| 119 | LYS | C | −37.71 | −38.16 | 59.09 | 15.00 |
| 119 | LYS | O | −38.36 | −37.86 | 60.09 | 15.00 |
| 120 | ALA | N | −36.45 | −38.57 | 59.15 | 15.00 |
| 120 | ALA | CA | −35.77 | −38.75 | 60.44 | 15.00 |
| 120 | ALA | CB | −34.45 | −39.45 | 60.27 | 15.00 |
| 120 | ALA | C | −35.56 | −37.40 | 61.08 | 15.00 |
| 120 | ALA | O | −35.41 | −37.31 | 62.30 | 15.00 |
| 121 | LEU | N | −35.52 | −36.34 | 60.26 | 15.00 |
| 121 | LEU | CA | −35.37 | −34.98 | 60.78 | 15.00 |
| 121 | LEU | CB | −34.93 | −33.98 | 59.69 | 15.00 |
| 121 | LEU | CG | −34.71 | −32.55 | 60.19 | 15.00 |
| 121 | LEU | CD1 | −33.44 | −32.47 | 61.03 | 15.00 |
| 121 | LEU | CD2 | −34.62 | −31.58 | 59.02 | 15.00 |
| 121 | LEU | C | −36.70 | −34.57 | 61.37 | 15.00 |
| 121 | LEU | O | −36.77 | −34.00 | 62.45 | 15.00 |
| 122 | LYS | N | −37.77 | −34.88 | 60.65 | 15.00 |
| 122 | LYS | CA | −39.12 | −34.58 | 61.09 | 15.00 |
| 122 | LYS | CB | −40.14 | −35.16 | 60.12 | 15.00 |
| 122 | LYS | CG | −41.58 | −34.91 | 60.49 | 15.00 |
| 122 | LYS | CD | −42.51 | −35.55 | 59.48 | 15.00 |
| 122 | LYS | CE | −43.96 | −35.15 | 59.73 | 15.00 |
| 122 | LYS | NZ | −44.83 | −35.53 | 58.58 | 15.00 |
| 122 | LYS | C | −39.29 | −35.19 | 62.48 | 15.00 |
| 122 | LYS | O | −39.68 | −34.50 | 63.42 | 15.00 |
| 123 | ARG | N | −38.95 | −36.47 | 62.59 | 15.00 |
| 123 | ARG | CA | −39.04 | −37.19 | 63.86 | 15.00 |
| 123 | ARG | CB | −38.64 | −38.65 | 63.70 | 15.00 |
| 123 | ARG | CG | −39.66 | −39.49 | 62.94 | 15.00 |
| 123 | ARG | CD | −39.69 | −40.93 | 63.45 | 15.00 |
| 123 | ARG | NE | −38.49 | −41.71 | 63.12 | 15.00 |
| 123 | ARG | CZ | −38.54 | −42.87 | 62.47 | 15.00 |
| 123 | ARG | NH1 | −39.71 | −43.37 | 62.09 | 15.00 |
| 123 | ARG | NH2 | −37.42 | −43.54 | 62.20 | 15.00 |
| 123 | ARG | C | −38.19 | −36.51 | 64.93 | 15.00 |
| 123 | ARG | O | −38.63 | −36.34 | 66.05 | 15.00 |
| 124 | ALA | N | −36.98 | −36.12 | 64.57 | 15.00 |
| 124 | ALA | CA | −36.09 | −35.45 | 65.50 | 15.00 |
| 124 | ALA | CB | −34.77 | −35.16 | 64.86 | 15.00 |
| 124 | ALA | C | −36.70 | −34.15 | 66.00 | 15.00 |
| 124 | ALA | O | −36.77 | −33.93 | 67.21 | 15.00 |
| 125 | VAL | N | −37.14 | −33.31 | 65.08 | 15.00 |
| 125 | VAL | CA | −37.72 | −32.03 | 65.45 | 15.00 |
| 125 | VAL | CB | −38.13 | −31.20 | 64.21 | 15.00 |
| 125 | VAL | CG1 | −38.87 | −29.94 | 64.63 | 15.00 |
| 125 | VAL | CG2 | −36.90 | −30.81 | 63.41 | 15.00 |
| 125 | VAL | C | −38.90 | −32.21 | 66.39 | 15.00 |
| 125 | VAL | O | −39.02 | −31.48 | 67.36 | 15.00 |
| 126 | ALA | N | −39.75 | −33.20 | 66.13 | 15.00 |
| 126 | ALA | CA | −40.92 | −33.43 | 66.99 | 15.00 |
| 126 | ALA | CB | −41.96 | −34.25 | 66.25 | 15.00 |
| 126 | ALA | C | −40.58 | −34.09 | 68.33 | 15.00 |
| 126 | ALA | O | −41.09 | −33.68 | 69.38 | 15.00 |
| 127 | ARG | N | −39.75 | −35.12 | 68.30 | 15.00 |
| 127 | ARG | CA | −39.38 | −35.83 | 69.52 | 15.00 |
| 127 | ARG | CB | −38.82 | −37.21 | 69.20 | 15.00 |
| 127 | ARG | CG | −39.74 | −38.08 | 68.36 | 15.00 |
| 127 | ARG | CD | −39.22 | −39.50 | 68.39 | 15.00 |
| 127 | ARG | NE | −39.68 | −40.36 | 67.30 | 15.00 |
| 127 | ARG | CZ | −40.95 | −40.55 | 66.96 | 15.00 |
| 127 | ARG | NH1 | −41.25 | −41.36 | 65.96 | 15.00 |
| 127 | ARG | NH2 | −41.92 | −39.90 | 67.59 | 15.00 |
| 127 | ARG | C | −38.41 | −35.07 | 70.40 | 15.00 |
| 127 | ARG | O | −38.63 | −34.94 | 71.60 | 15.00 |
| 128 | VAL | N | −37.33 | −34.58 | 69.81 | 15.00 |
| 128 | VAL | CA | −36.30 | −33.85 | 70.54 | 15.00 |
| 128 | VAL | CB | −34.95 | −33.96 | 69.83 | 15.00 |
| 128 | VAL | CG1 | −33.89 | −33.20 | 70.59 | 15.00 |
| 128 | VAL | CG2 | −34.56 | −35.42 | 69.68 | 15.00 |
| 128 | VAL | C | −36.62 | −32.39 | 70.77 | 15.00 |
| 128 | VAL | O | −36.73 | −31.94 | 71.90 | 15.00 |
| 129 | GLY | N | −36.70 | −31.64 | 69.68 | 15.00 |
| 129 | GLY | CA | −36.98 | −30.21 | 69.76 | 15.00 |
| 129 | GLY | C | −36.20 | −29.51 | 68.66 | 15.00 |
| 129 | GLY | O | −35.93 | −30.12 | 67.63 | 15.00 |
| 130 | PRO | N | −35.81 | −28.24 | 68.86 | 15.00 |
| 130 | PRO | CD | −36.15 | −27.39 | 70.00 | 15.00 |
| 130 | PRO | CA | −35.06 | −27.48 | 67.86 | 15.00 |
| 130 | PRO | CB | −34.77 | −26.18 | 68.58 | 15.00 |
| 130 | PRO | CG | −36.00 | −26.00 | 69.41 | 15.00 |
| 130 | PRO | C | −33.78 | −28.20 | 67.49 | 15.00 |
| 130 | PRO | O | −32.98 | −28.51 | 68.37 | 15.00 |
| 131 | VAL | N | −33.60 | −28.46 | 66.19 | 15.00 |
| 131 | VAL | CA | −32.42 | −29.16 | 65.69 | 15.00 |
| 131 | VAL | CB | −32.80 | −30.40 | 64.82 | 15.00 |
| 131 | VAL | CG1 | −31.55 | −31.10 | 64.33 | 15.00 |
| 131 | VAL | CG2 | −33.66 | −31.37 | 65.60 | 15.00 |
| 131 | VAL | C | −31.54 | −28.26 | 64.83 | 15.00 |
| 131 | VAL | O | −32.02 | −27.54 | 63.96 | 15.00 |
| 132 | SER | N | −30.24 | −28.35 | 65.05 | 15.00 |
| 132 | SER | CA | −29.27 | −27.55 | 64.31 | 15.00 |
| 132 | SER | CB | −27.93 | −27.54 | 65.04 | 15.00 |
| 132 | SER | OG | −28.09 | −27.80 | 66.43 | 15.00 |
| 132 | SER | C | −29.11 | −28.11 | 62.90 | 15.00 |
| 132 | SER | O | −28.80 | −29.29 | 62.74 | 15.00 |
| 133 | VAL | N | −29.34 | −27.29 | 61.88 | 15.00 |
| 133 | VAL | CA | −29.20 | −27.74 | 60.49 | 15.00 |
| 133 | VAL | CB | −30.57 | −27.83 | 59.76 | 15.00 |
| 133 | VAL | CG1 | −31.29 | −29.10 | 60.15 | 15.00 |
| 133 | VAL | CG2 | −31.42 | −26.63 | 60.06 | 15.00 |
| 133 | VAL | C | −28.26 | −26.86 | 59.67 | 15.00 |
| 133 | VAL | O | −27.82 | −25.81 | 60.14 | 15.00 |
| 134 | ALA | N | −27.93 | −27.29 | 58.46 | 15.00 |
| 134 | ALA | CA | −27.05 | −26.53 | 57.59 | 15.00 |
| 134 | ALA | CB | −25.65 | −27.10 | 57.62 | 15.00 |
| 134 | ALA | C | −27.62 | −26.60 | 56.18 | 15.00 |
| 134 | ALA | O | −27.92 | −27.68 | 55.69 | 15.00 |
| 135 | ILE | N | −27.80 | −25.44 | 55.56 | 15.00 |
| 135 | ILE | CA | −28.36 | −25.36 | 54.21 | 15.00 |
| 135 | ILE | CB | −29.74 | −24.70 | 54.21 | 15.00 |
| 135 | ILE | CG2 | −30.76 | −25.58 | 54.87 | 15.00 |
| 135 | ILE | CG1 | −29.64 | −23.31 | 54.87 | 15.00 |
| 135 | ILE | CD1 | −30.91 | −22.52 | 54.84 | 15.00 |
| 135 | ILE | C | −27.51 | −24.50 | 53.29 | 15.00 |
| 135 | ILE | O | −26.46 | −23.99 | 53.67 | 15.00 |
| 136 | ASP | N | −28.04 | −24.32 | 52.09 | 15.00 |
| 136 | ASP | CA | −27.44 | −23.50 | 51.05 | 15.00 |
| 136 | ASP | CB | −27.56 | −24.20 | 49.70 | 15.00 |
| 136 | ASP | CG | −27.01 | −23.38 | 48.56 | 15.00 |
| 136 | ASP | OD1 | −27.62 | −23.39 | 47.48 | 15.00 |
| 136 | ASP | CD2 | −25.96 | −22.75 | 48.73 | 15.00 |
| 136 | ASP | C | −28.17 | −22.15 | 51.05 | 15.00 |
| 136 | ASP | O | −29.30 | −22.07 | 50.57 | 15.00 |
| 137 | ALA | N | −27.56 | −21.12 | 51.62 | 15.00 |
| 137 | ALA | CA | −28.19 | −19.81 | 51.68 | 15.00 |
| 137 | ALA | CB | −28.23 | −19.33 | 53.12 | 15.00 |
| 137 | ALA | C | −27.52 | −18.76 | 50.80 | 15.00 |

TABLE IX-continued

Table of the orthogonal three dimensional coordinates in Ångstroms and B factors (Å$^2$) for the cathepsin K complex with inhibitor 4-[N-[(phenylmethoxy)carbonyl]-L-leucyl]-1-N[N-(methyl)-L-leucyl)]-3-pyrrolidinone

| Residue | | Atom | X | Y | Z | B |
|---|---|---|---|---|---|---|
| 137 | ALA | C | −27.74 | −17.56 | 50.97 | 15.00 |
| 138 | SER | N | −26.72 | −19.22 | 49.84 | 15.00 |
| 138 | SER | CA | −26.00 | −18.34 | 48.92 | 15.00 |
| 138 | SER | CB | −24.80 | −19.07 | 48.33 | 15.00 |
| 138 | SER | OG | −25.20 | −20.25 | 47.66 | 15.00 |
| 138 | SER | C | −26.85 | −17.71 | 47.82 | 15.00 |
| 138 | SER | O | −26.50 | −16.66 | 47.27 | 15.00 |
| 139 | LEU | N | −27.96 | −18.36 | 47.45 | 15.00 |
| 139 | LEU | CA | −28.85 | −17.84 | 46.42 | 15.00 |
| 139 | LEU | CB | −29.97 | −18.82 | 46.10 | 15.00 |
| 139 | LEU | CG | −29.63 | −20.08 | 45.32 | 15.00 |
| 139 | LEU | CD1 | −30.91 | −20.89 | 45.13 | 15.00 |
| 139 | LEU | CD2 | −29.04 | −19.71 | 43.97 | 15.00 |
| 139 | LEU | C | −29.45 | −16.51 | 46.85 | 15.00 |
| 139 | LEU | O | −29.82 | −16.33 | 48.00 | 15.00 |
| 140 | THR | N | −29.61 | −15.59 | 45.90 | 15.00 |
| 140 | THR | CA | −30.17 | −14.28 | 46.20 | 15.00 |
| 140 | THR | CB | −29.95 | −13.25 | 45.03 | 15.00 |
| 140 | THR | OG1 | −29.88 | −13.93 | 43.77 | 15.00 |
| 140 | THR | CG2 | −28.67 | −12.47 | 45.23 | 15.00 |
| 140 | THR | C | −31.65 | −14.34 | 46.59 | 15.00 |
| 140 | THR | O | −32.12 | −13.52 | 47.37 | 15.00 |
| 141 | SER | N | −32.37 | −15.35 | 46.10 | 15.00 |
| 141 | SER | CA | −33.79 | −15.49 | 46.43 | 15.00 |
| 141 | SER | CB | −34.47 | −16.53 | 45.55 | 15.00 |
| 141 | SER | OG | −33.70 | −17.71 | 45.45 | 15.00 |
| 141 | SER | C | −34.00 | −15.80 | 47.91 | 15.00 |
| 141 | SER | O | −34.99 | −15.38 | 48.50 | 15.00 |
| 142 | PHE | N | −33.07 | −16.54 | 48.49 | 15.00 |
| 142 | PHE | CA | −33.13 | −16.89 | 49.91 | 15.00 |
| 142 | PHE | CB | −32.01 | −17.88 | 50.28 | 15.00 |
| 142 | PHE | CG | −31.93 | −18.18 | 51.75 | 15.00 |
| 142 | PHE | CD1 | −32.67 | −19.22 | 52.31 | 15.00 |
| 142 | PHE | CD2 | −31.12 | −17.42 | 52.59 | 15.00 |
| 142 | PHE | CE1 | −32.62 | −19.48 | 53.68 | 15.00 |
| 142 | PHE | CE2 | −31.06 | −17.68 | 53.95 | 15.00 |
| 142 | PHE | CZ | −31.81 | −18.71 | 54.51 | 15.00 |
| 142 | PHE | C | −33.00 | −15.60 | 50.70 | 15.00 |
| 142 | PHE | O | −33.80 | −15.30 | 51.59 | 15.00 |
| 143 | GLN | N | −32.00 | −14.81 | 50.30 | 15.00 |
| 143 | GLN | CA | −31.67 | −13.54 | 50.93 | 15.00 |
| 143 | GLN | CB | −30.35 | −13.03 | 50.36 | 15.00 |
| 143 | GLN | CG | −29.20 | −13.96 | 50.70 | 15.00 |
| 143 | GLN | CD | −27.93 | −13.71 | 49.91 | 15.00 |
| 143 | GLN | OE1 | −27.22 | −12.73 | 50.12 | 15.00 |
| 143 | GLN | NE2 | −27.63 | −14.63 | 49.01 | 15.00 |
| 143 | GLN | C | −32.77 | −12.47 | 50.94 | 15.00 |
| 143 | GLN | O | −32.99 | −11.82 | 51.97 | 15.00 |
| 144 | PHE | N | −33.47 | −12.27 | 49.82 | 15.0a |
| 144 | PHE | CA | −34.54 | −11.27 | 49.79 | 15.00 |
| 144 | PHE | CB | −34.55 | −10.47 | 48.49 | 15.00 |
| 144 | PHE | CG | −34.68 | −11.30 | 47.25 | 15.00 |
| 144 | PHE | CD1 | −33.69 | −11.28 | 46.28 | 15.00 |
| 144 | PHE | CD2 | −35.81 | −12.07 | 47.03 | 15.00 |
| 144 | PHE | CE1 | −33.82 | −12.00 | 45.10 | 15.00 |
| 144 | PHE | CE2 | −35.95 | −12.79 | 45.85 | 15.00 |
| 144 | PHE | CZ | −34.95 | −12.76 | 44.89 | 15.00 |
| 144 | PHE | C | −35.92 | −11.84 | 50.10 | 15.00 |
| 144 | PHE | O | −36.95 | −11.28 | 49.70 | 15.00 |
| 145 | TYR | N | −35.94 | −12.99 | 50.77 | 15.00 |
| 145 | TYR | CA | −37.17 | −13.65 | 51.15 | 15.00 |
| 145 | TYR | CB | −36.88 | −15.04 | 51.74 | 15.00 |
| 145 | TYR | CG | −38.04 | −15.65 | 52.51 | 15.00 |
| 145 | TYR | CD1 | −38.88 | −16.58 | 51.91 | 15.00 |
| 145 | TYR | CE1 | −39.95 | −17.13 | 52.62 | 15.00 |
| 145 | TYR | CD2 | −38.29 | −15.28 | 53.83 | 15.00 |
| 145 | TYR | CE2 | −39.35 | −15.82 | 54.53 | 15.00 |
| 145 | TYR | CZ | −40.17 | −16.74 | 53.93 | 15.00 |
| 145 | TYR | OH | −41.23 | −17.25 | 54.64 | 15.00 |
| 145 | TYR | C | −37.88 | −12.76 | 52.15 | 15.00 |
| 145 | TYR | O | −37.25 | −12.09 | 52.96 | 15.00 |
| 146 | SER | N | −39.21 | −12.78 | 52.12 | 15.00 |
| 146 | SER | CA | −40.01 | −12.00 | 53.04 | 15.00 |
| 146 | SER | CB | −40.30 | −10.61 | 52.47 | 15.00 |
| 146 | SER | OG | −40.96 | −10.71 | 51.22 | 15.00 |
| 146 | SER | C | −41.29 | −12.72 | 53.43 | 15.00 |
| 146 | SER | O | −41.83 | −12.48 | 54.51 | 15.00 |
| 147 | LYS | N | −41.76 | −13.63 | 52.58 | 15.00 |
| 147 | LYS | CA | −42.98 | −14.39 | 52.86 | 15.00 |
| 147 | LYS | CB | −44.22 | −13.50 | 52.79 | 15.00 |
| 147 | LYS | CG | −44.61 | −13.04 | 51.39 | 15.00 |
| 147 | LYS | CD | −45.75 | −12.03 | 51.44 | 15.00 |
| 147 | LYS | CE | −45.98 | −11.35 | 50.09 | 15.00 |
| 147 | LYS | NZ | −47.01 | −10.28 | 50.19 | 15.00 |
| 147 | LYS | C | −43.16 | −15.60 | 51.95 | 15.00 |
| 147 | LYS | O | −42.49 | −15.70 | 50.92 | 15.00 |
| 148 | GLY | N | −44.05 | −16.50 | 52.36 | 15.00 |
| 148 | GLY | CA | −44.34 | −17.71 | 51.60 | 15.00 |
| 148 | GLY | C | −43.51 | −18.90 | 52.07 | 15.00 |
| 148 | GLY | O | −42.99 | −18.90 | 53.18 | 15.00 |
| 149 | VAL | N | −43.43 | −19.92 | 51.22 | 15.00 |
| 149 | VAL | CA | −42.66 | −21.12 | 51.51 | 15.00 |
| 149 | VAL | CB | −43.53 | −22.39 | 51.40 | 15.00 |
| 149 | VAL | CG1 | −42.69 | −23.64 | 51.56 | 15.00 |
| 149 | VAL | CG2 | −44.62 | −22.35 | 52.45 | 15.00 |
| 149 | VAL | C | −41.53 | −21.16 | 59.47 | 15.00 |
| 149 | VAL | O | −41.75 | −21.48 | 49.30 | 15.00 |
| 150 | TYR | N | −40.33 | −20.80 | 50.90 | 15.00 |
| 150 | TYR | CA | −39.19 | −20.78 | 50.01 | 15.00 |
| 150 | TYR | CB | −37.96 | −20.25 | 50.75 | 15.00 |
| 150 | TYR | CG | −36.72 | −20.12 | 49.90 | 15.00 |
| 150 | TYR | CD1 | −36.64 | −19.13 | 48.91 | 15.00 |
| 150 | TYR | CE1 | −35.51 | −19.02 | 48.09 | 15.00 |
| 150 | TYR | CD2 | −35.64 | −20.99 | 50.05 | 15.00 |
| 150 | TYR | CE2 | −34.51 | −20.89 | 49.24 | 15.00 |
| 150 | TYR | CZ | −34.45 | −19.91 | 48.26 | 15.00 |
| 150 | TYR | OH | −33.36 | −19.82 | 47.42 | 15.00 |
| 150 | TYR | C | −38.89 | −22.11 | 49.33 | 15.00 |
| 150 | TYR | O | −38.81 | −23.15 | 49.98 | 15.00 |
| 151 | TYR | N | −38.77 | −22.06 | 48.01 | 15.00 |
| 151 | TYR | CA | −38.39 | −23.22 | 47.21 | 15.00 |
| 151 | TYR | CB | −39.55 | −24.11 | 46.79 | 15.00 |
| 151 | TYR | CG | −39.06 | −25.31 | 45.98 | 15.00 |
| 151 | TYR | CD1 | −37.99 | −26.08 | 46.43 | 15.00 |
| 151 | TYR | CE1 | −37.47 | −27.12 | 45.66 | 15.00 |
| 151 | TYR | CD2 | −39.60 | −25.61 | 44.73 | 15.00 |
| 151 | TYR | CE2 | −39.09 | −26.64 | 43.95 | 15.00 |
| 151 | TYR | CZ | −38.02 | −27.39 | 44.43 | 15.00 |
| 151 | TYR | OH | −37.46 | −28.37 | 43.65 | 15.00 |
| 151 | TYR | C | −37.65 | −22.71 | 45.98 | 15.00 |
| 151 | TYR | O | −38.13 | −21.81 | 45.29 | 15.00 |
| 152 | ASP | N | −36.50 | −23.30 | 45.71 | 15.00 |
| 152 | ASP | CA | −35.69 | −22.88 | 44.58 | 15.00 |
| 152 | ASP | CB | −34.92 | −21.62 | 44.94 | 15.00 |
| 152 | ASP | CG | −34.31 | −20.95 | 43.75 | 15.00 |
| 152 | ASP | OD1 | −33.30 | −21.46 | 43.24 | 15.00 |
| 152 | ASP | OD2 | −34.83 | −19.90 | 43.34 | 15.00 |
| 152 | ASP | C | −34.74 | −24.00 | 44.16 | 15.00 |
| 152 | ASP | O | −33.67 | −24.16 | 44.74 | 15.00 |
| 153 | GLU | N | −35.12 | −24.77 | 43.14 | 15.00 |
| 153 | GLU | CA | −34.30 | −25.88 | 42.66 | 15.00 |
| 153 | GLU | CB | −34.99 | −26.68 | 41.55 | 15.00 |
| 153 | GLU | CG | −35.86 | −25.85 | 40.61 | 15.00 |
| 153 | GLU | CD | −35.20 | −24.55 | 40.21 | 15.00 |
| 153 | GLU | OE1 | −35.85 | −23.49 | 40.40 | 15.00 |
| 153 | GLU | OE2 | −34.05 | −24.58 | 39.73 | 15.00 |
| 153 | GLU | C | −32.88 | −25.53 | 42.24 | 15.00 |
| 153 | GLU | O | −32.12 | −26.41 | 41.84 | 15.00 |
| 154 | SER | N | −32.56 | −24.24 | 42.24 | 15.00 |
| 154 | SER | CA | −31.21 | −23.81 | 41.87 | 15.00 |
| 154 | SER | CB | −31.23 | −22.38 | 41.29 | 15.00 |
| 154 | SER | OG | −29.99 | −22.04 | 40.68 | 15.00 |

TABLE IX-continued

Table of the orthogonal three dimensional coordinates in Ångstroms and B factors (Å²) for the cathepsin K complex with inhibitor 4-[N-[(phenylmethoxy)carbonyl]-L-leucyl]-1-N[N-(methyl)-L-leucyl)]-3-pyrrolidinone

| Residue | Atom | X | Y | Z | B |
|---|---|---|---|---|---|
| 154 | SER | C | −30.32 | −23.92 | 43.11 | 15.00 |
| 154 | SER | O | −29.08 | −23.86 | 43.03 | 15.00 |
| 155 | CYS | N | −30.95 | −24.11 | 44.26 | 15.00 |
| 155 | CYS | CA | −30.25 | −24.27 | 45.52 | 15.00 |
| 155 | CYS | C | −29.46 | −25.57 | 45.44 | 15.00 |
| 155 | CYS | O | −30.01 | −26.60 | 45.04 | 15.00 |
| 155 | CYS | CB | −31.24 | −24.29 | 46.67 | 15.00 |
| 155 | CYS | SG | −30.52 | −24.05 | 48.32 | 15.00 |
| 156 | ASN | N | −28.18 | −25.54 | 45.80 | 15.00 |
| 156 | ASN | CA | −27.32 | −26.73 | 45.73 | 15.00 |
| 156 | ASN | CB | −25.94 | −26.34 | 45.18 | 15.00 |
| 156 | ASN | CG | −25.00 | −27.52 | 45.10 | 15.00 |
| 156 | ASN | OD1 | −25.41 | −28.68 | 45.25 | 15.00 |
| 156 | ASN | ND2 | −23.72 | −27.24 | 44.86 | 15.00 |
| 156 | ASN | C | −27.17 | −27.54 | 47.03 | 15.00 |
| 156 | ASN | O | −26.43 | −27.15 | 47.94 | 15.00 |
| 157 | SER | N | −27.79 | −28.71 | 47.05 | 15.00 |
| 157 | SER | CA | −27.75 | −29.59 | 48.22 | 15.00 |
| 157 | SER | CB | −28.54 | −30.87 | 47.97 | 15.00 |
| 157 | SER | OG | −29.86 | −30.55 | 47.53 | 15.00 |
| 157 | SER | C | −26.34 | −29.93 | 48.65 | 15.00 |
| 157 | SER | O | −26.09 | −30.17 | 49.82 | 15.00 |
| 158 | ASP | N | −25.42 | −29.97 | 47.69 | 15.00 |
| 158 | ASP | CA | −24.04 | −30.32 | 47.98 | 15.00 |
| 158 | ASP | CB | −23.39 | −30.98 | 46.77 | 15.00 |
| 158 | ASP | CG | −24.30 | −32.01 | 46.10 | 15.00 |
| 158 | ASP | OD1 | −25.16 | −31.59 | 45.30 | 15.00 |
| 158 | ASP | OD2 | −24.16 | −33.22 | 46.38 | 15.00 |
| 158 | ASP | C | −23.23 | −29.12 | 48.47 | 15.00 |
| 158 | ASP | O | −22.07 | −29.26 | 48.88 | 15.00 |
| 159 | ASN | N | −23.84 | −27.94 | 48.44 | 15.00 |
| 159 | ASN | CA | −23.16 | −26.74 | 48.87 | 15.00 |
| 159 | ASN | CB | −23.23 | −25.65 | 47.79 | 15.00 |
| 159 | ASN | CG | −22.43 | −24.40 | 48.16 | 15.00 |
| 159 | ASN | OD1 | −21.20 | −24.43 | 48.25 | 15.00 |
| 159 | ASN | ND2 | −23.13 | −23.30 | 48.37 | 15.00 |
| 159 | ASN | C | −23.72 | −26.25 | 50.20 | 15.00 |
| 159 | ASN | O | −24.52 | −25.31 | 50.24 | 15.00 |
| 160 | LEU | N | −23.32 | −26.89 | 51.29 | 15.00 |
| 160 | LEU | CA | −23.78 | −26.48 | 52.62 | 15.00 |
| 160 | LEU | CB | −23.80 | −27.66 | 53.59 | 15.00 |
| 160 | LEU | CG | −24.71 | −28.86 | 53.26 | 15.00 |
| 160 | LEU | CD1 | −24.59 | −29.92 | 54.34 | 15.00 |
| 160 | LEU | CD2 | −26.15 | −28.43 | 53.10 | 15.00 |
| 160 | LEU | C | −22.89 | −25.34 | 53.12 | 15.00 |
| 160 | LEU | O | −21.71 | −25.55 | 53.43 | 15.00 |
| 161 | ASN | N | −23.46 | −24.15 | 53.23 | 15.00 |
| 161 | ASN | CA | −22.70 | −22.98 | 53.65 | 15.00 |
| 161 | ASN | CB | −22.49 | −22.04 | 52.46 | 15.00 |
| 161 | ASN | CG | −23.80 | −21.60 | 51.80 | 15.00 |
| 161 | ASN | OD1 | −24.62 | −20.89 | 52.40 | 15.00 |
| 161 | ASN | ND2 | −24.02 | −22.04 | 50.57 | 15.00 |
| 161 | ASN | C | −23.24 | −22.19 | 54.82 | 15.00 |
| 161 | ASN | O | −22.50 | −21.41 | 55.44 | 15.00 |
| 162 | HIS | N | −24.50 | −22.38 | 55.16 | 15.00 |
| 162 | HIS | CA | −25.09 | −21.63 | 56.25 | 15.00 |
| 162 | HIS | CB | −26.09 | −20.60 | 55.70 | 15.00 |
| 162 | HIS | CG | −26.36 | −19.45 | 56.63 | 15.00 |
| 162 | HIS | CD2 | −27.52 | −18.88 | 57.02 | 15.00 |
| 162 | HIS | ND1 | −25.35 | −18.74 | 57.27 | 15.00 |
| 162 | HIS | CE1 | −25.89 | −17.79 | 58.01 | 15.00 |
| 162 | HIS | NE2 | −27.20 | −17.85 | 57.88 | 15.00 |
| 162 | HIS | C | −25.73 | −22.52 | 57.32 | 15.00 |
| 162 | HIS | O | −26.57 | −23.36 | 57.03 | 15.00 |
| 163 | ALA | N | −25.29 | −22.33 | 58.56 | 15.00 |
| 163 | ALA | CA | −25.82 | −23.08 | 59.68 | 15.00 |
| 163 | ALA | CB | −24.83 | −23.11 | 60.82 | 15.00 |
| 163 | ALA | C | −27.09 | −22.35 | 60.10 | 15.00 |
| 163 | ALA | O | −27.17 | −21.12 | 60.04 | 15.00 |
| 164 | VAL | N | −28.07 | −23.10 | 60.57 | 15.00 |
| 164 | VAL | CA | −29.33 | −22.51 | 60.95 | 15.00 |
| 164 | VAL | CB | −30.15 | −22.28 | 59.67 | 15.00 |
| 164 | VAL | CG1 | −30.99 | −23.50 | 59.31 | 15.00 |
| 164 | VAL | CG2 | −30.94 | −21.02 | 59.76 | 15.00 |
| 164 | VAL | C | −30.02 | −23.41 | 62.00 | 15.00 |
| 164 | VAL | O | −29.40 | −24.32 | 62.53 | 15.00 |
| 165 | LEU | N | −31.28 | −23.14 | 62.31 | 15.00 |
| 165 | LEU | CA | −31.97 | −23.95 | 63.31 | 15.00 |
| 165 | LEU | CB | −31.89 | −23.27 | 64.69 | 15.00 |
| 165 | LEU | CG | −32.54 | −23.86 | 65.94 | 15.00 |
| 165 | LEU | CD1 | −31.64 | −24.89 | 66.56 | 1500 |
| 165 | LEU | CD2 | −32.80 | −22.75 | 66.92 | 15.00 |
| 165 | LEU | C | −33.42 | −24.23 | 62.94 | 15.00 |
| 165 | LEU | O | −34.17 | −23.31 | 62.68 | 15.00 |
| 166 | ALA | N | −33.78 | −25.51 | 62.87 | 15.00 |
| 166 | ALA | CA | −35.16 | −25.91 | 62.55 | 15.00 |
| 166 | ALA | CB | −35.20 | −27.32 | 62.01 | 15.00 |
| 166 | ALA | C | −35.95 | −25.80 | 63.83 | 15.00 |
| 166 | ALA | O | −35.67 | −26.47 | 64.81 | 15.00 |
| 167 | VAL | N | −36.93 | −24.91 | 63.82 | 15.00 |
| 167 | VAL | CA | −37.77 | −24.62 | 64.97 | 15.00 |
| 167 | VAL | CB | −37.87 | −23.05 | 65.10 | 15.00 |
| 167 | VAL | CG1 | −39.11 | −22.60 | 65.81 | 15.00 |
| 167 | VAL | CG2 | −36.64 | −22.53 | 65.82 | 15.00 |
| 167 | VAL | C | −39.14 | −25.30 | 64.88 | 15.00 |
| 167 | VAL | O | −39.98 | −25.17 | 65.77 | 15.00 |
| 168 | GLY | N | −39.36 | −26.05 | 63.81 | 15.00 |
| 168 | GLY | CA | −40.63 | −26.73 | 63.66 | 15.00 |
| 168 | GLY | C | −40.88 | −27.11 | 62.23 | 15.00 |
| 168 | GLY | O | −39.96 | −27.09 | 61.41 | 15.00 |
| 169 | TYR | N | −42.12 | −27.45 | 61.92 | 15.00 |
| 169 | TYR | CA | −42.52 | −27.84 | 60.57 | 15.00 |
| 169 | TYR | CB | −41.99 | −29.24 | 60.21 | 15.00 |
| 169 | TYR | CG | −42.49 | −30.37 | 61.09 | 15.00 |
| 169 | TYR | CD1 | −43.82 | −30.80 | 61.01 | 15.00 |
| 169 | TYR | CE1 | −44.30 | −31.81 | 61.82 | 15.00 |
| 169 | TYR | CD2 | −41.66 | −30.99 | 62.01 | 15.00 |
| 169 | TYR | CE2 | −42.13 | −32.01 | 62.83 | 15.00 |
| 169 | TYR | CZ | −43.46 | −32.41 | 62.73 | 15.00 |
| 169 | TYR | OH | −43.96 | −33.41 | 63.53 | 15.00 |
| 169 | TYR | C | −44.03 | −27.76 | 60.48 | 15.00 |
| 169 | TYR | O | −44.71 | −27.65 | 61.49 | 15.00 |
| 170 | GLY | N | −44.57 | −27.80 | 59.26 | 15.00 |
| 170 | GLY | CA | −46.01 | −27.72 | 59.11 | 15.00 |
| 170 | GLY | C | −46.48 | −27.54 | 57.68 | 15.00 |
| 170 | GLY | O | −45.85 | −28.04 | 56.75 | 15.00 |
| 171 | ILE | N | −47.55 | −26.79 | 57.50 | 15.00 |
| 171 | ILE | CA | −48.11 | −26.53 | 56.18 | 15.00 |
| 171 | ILE | CB | −49.30 | −27.48 | 55.85 | 15.00 |
| 171 | ILE | CG2 | −48.79 | −28.88 | 55.55 | 15.00 |
| 171 | ILE | CG1 | −50.29 | −27.53 | 57.02 | 15.00 |
| 171 | ILE | CD1 | −51.40 | −26.48 | 56.97 | 15.00 |
| 171 | ILE | C | −48.63 | −25.10 | 56.07 | 15.00 |
| 171 | ILE | O | −48.87 | −24.44 | 57.08 | 15.00 |
| 172 | GLN | N | −48.75 | −24.62 | 54.84 | 15.00 |
| 172 | GLN | CA | −49.27 | −23.28 | 54.60 | 15.00 |
| 172 | GLN | CB | −48.22 | −22.34 | 54.00 | 15.00 |
| 172 | GLN | CG | −48.63 | −20.86 | 53.96 | 15.00 |
| 172 | GLN | CD | −47.49 | −19.92 | 54.36 | 15.00 |
| 172 | GLN | OE1 | −47.54 | −19.28 | 55.40 | 15.00 |
| 172 | GLN | NE2 | −46.46 | −19.83 | 53.52 | 15.00 |
| 172 | GLN | C | −50.46 | −23.45 | 53.67 | 15.00 |
| 172 | GLN | O | −51.49 | −24.00 | 54.07 | 15.00 |
| 173 | LYS | N | −50.30 | −23.07 | 52.41 | 15.00 |
| 173 | LYS | CA | −51.38 | −23.21 | 51.46 | 15.00 |
| 173 | LYS | CB | −51.36 | −22.10 | 50.42 | 15.00 |
| 173 | LYS | CG | −51.38 | −20.70 | 51.04 | 15.00 |
| 173 | LYS | CD | −52.68 | −20.45 | 51.78 | 15.00 |
| 173 | LYS | CE | −53.81 | −20.28 | 50.78 | 15.00 |
| 173 | LYS | NZ | −53.58 | −19.10 | 49.88 | 15.00 |
| 173 | LYS | C | −51.15 | −24.57 | 50.86 | 15.00 |
| 173 | LYS | O | −50.84 | −24.70 | 49.68 | 15.00 |

TABLE IX-continued

Table of the orthogonal three dimensional coordinates in Ångstroms and B factors (Å²) for the cathepsin K complex with inhibitor 4-[N-[(phenylmethoxy)carbonyl]-L-leucyl]-1-N[N-(methyl)-L-leucyl)]-3-pyrrolidinone

| Residue | Atom | X | Y | Z | B |
|---|---|---|---|---|---|
| 174 GLY | N | -51.19 | -25.57 | 51.73 | 15.00 |
| 174 GLY | CA | -50.98 | -26.94 | 51.31 | 15.00 |
| 174 GLY | C | -49.52 | -27.32 | 51.13 | 15.00 |
| 174 GLY | O | -49.20 | -28.49 | 50.87 | 15.00 |
| 175 ASN | N | -48.63 | -26.35 | 51.27 | 15.00 |
| 175 ASN | CA | -47.21 | -26.62 | 51.11 | 15.00 |
| 175 ASN | CB | -46.45 | -25.42 | 50.56 | 15.00 |
| 175 ASN | CG | -47.23 | -24.69 | 49.49 | 15.00 |
| 175 ASN | OD1 | -48.07 | -23.83 | 49.80 | 15.00 |
| 175 ASN | ND2 | -46.97 | -25.03 | 48.24 | 15.00 |
| 175 ASN | C | -46.60 | -27.05 | 52.42 | 15.00 |
| 175 ASN | O | -46.82 | -26.41 | 53.46 | 15.00 |
| 176 LYS | N | -45.87 | -28.16 | 52.38 | 15.00 |
| 176 LYS | CA | -45.20 | -28.68 | 53.57 | 15.00 |
| 176 LYS | CB | -44.69 | -30.10 | 53.34 | 15.00 |
| 176 LYS | CG | -45.74 | -31.11 | 52.86 | 15.00 |
| 176 LYS | CD | -46.88 | -31.26 | 53.85 | 15.00 |
| 176 LYS | CE | -47.97 | -32.21 | 53.34 | 15.00 |
| 176 LYS | NZ | -48.80 | -31.66 | 52.19 | 15.00 |
| 176 LYS | C | -44.05 | -27.71 | 53.76 | 15.00 |
| 176 LYS | O | -43.63 | -27.08 | 52.80 | 15.00 |
| 177 HIS | N | -43.57 | -27.54 | 54.99 | 15.00 |
| 177 HIS | CA | -42.45 | -26.64 | 55.21 | 15.00 |
| 177 HIS | CB | -42.88 | -25.18 | 54.99 | 15.00 |
| 177 HIS | CG | -43.82 | -24.66 | 56.02 | 15.00 |
| 177 HIS | CD2 | -43.66 | -24.45 | 57.35 | 15.00 |
| 177 HIS | ND1 | -45.10 | -24.21 | 55.71 | 15.00 |
| 177 HIS | CE1 | -45.67 | -23.75 | 56.81 | 15.00 |
| 177 HIS | NE2 | -44.82 | -23.88 | 57.81 | 15.00 |
| 177 HIS | C | -41.71 | -26.78 | 56.53 | 15.00 |
| 177 HIS | O | -42.23 | -27.35 | 57.50 | 15.00 |
| 178 TRP | N | -40.49 | -26.24 | 56.54 | 15.00 |
| 178 TRP | CA | -39.60 | -26.23 | 57.69 | 15.00 |
| 178 TRP | CB | -38.19 | -26.64 | 57.31 | 15.00 |
| 178 TRP | CG | -37.99 | -28.06 | 56.96 | 15.00 |
| 178 TRP | CD2 | -38.07 | -29.18 | 57.84 | 15.00 |
| 178 TRP | CE2 | -37.75 | -30.33 | 57.09 | 15.00 |
| 178 TRP | CE3 | -38.38 | -29.33 | 59.20 | 15.00 |
| 178 TRP | CD1 | -37.64 | -28.56 | 55.74 | 15.00 |
| 178 TRP | NE1 | -37.49 | -29.92 | 55.81 | 15.00 |
| 178 TRP | CZ2 | -37.73 | -31.61 | 57.65 | 15.00 |
| 178 TRP | CZ3 | -38.37 | -30.60 | 59.76 | 15.00 |
| 178 TRP | CH2 | -38.05 | -31.72 | 58.98 | 15.00 |
| 178 TRP | C | -39.54 | -24.81 | 58.28 | 15.00 |
| 178 TRP | O | -39.17 | -23.88 | 57.58 | 15.00 |
| 179 ILE | N | -39.90 | -24.63 | 59.55 | 15.00 |
| 179 ILE | CA | -39.78 | -23.31 | 60.15 | 15.00 |
| 179 ILE | CB | -40.56 | -23.19 | 61.47 | 15.00 |
| 179 ILE | CG2 | -40.42 | -21.80 | 62.04 | 15.00 |
| 179 ILE | CG1 | -42.03 | -23.55 | 61.26 | 15.00 |
| 179 ILE | CD1 | -42.83 | -23.54 | 62.53 | 15.00 |
| 179 ILE | C | -38.30 | -23.20 | 60.48 | 15.00 |
| 179 ILE | O | -37.76 | -24.02 | 61.22 | 15.00 |
| 180 ILE | N | -37.61 | -22.23 | 59.88 | 15.00 |
| 180 ILE | CA | -36.18 | -22.05 | 60.12 | 15.00 |
| 180 ILE | CB | -35.39 | -22.09 | 58.78 | 15.00 |
| 180 ILE | CG2 | -33.93 | -21.75 | 58.98 | 15.00 |
| 180 ILE | CG1 | -35.49 | -23.48 | 58.17 | 15.00 |
| 180 ILE | CD1 | -35.01 | -24.57 | 59.10 | 15.00 |
| 180 ILE | C | -35.91 | -20.73 | 60.84 | 15.00 |
| 180 ILE | O | -36.58 | -19.74 | 60.60 | 15.00 |
| 181 LYS | N | -34.98 | -20.76 | 61.79 | 15.00 |
| 181 LYS | CA | -34.59 | -19.57 | 62.52 | 15.00 |
| 181 LYS | CB | -34.57 | -19.82 | 64.03 | 15.00 |
| 181 LYS | CG | -34.13 | -18.62 | 64.86 | 15.00 |
| 181 LYS | CD | -33.87 | -19.01 | 66.30 | 15.00 |
| 181 LYS | CE | -33.59 | -17.80 | 67.13 | 15.00 |
| 181 LYS | NZ | -33.32 | -18.14 | 68.55 | 15.00 |
| 181 LYS | C | -33.19 | -19.24 | 62.02 | 15.00 |
| 181 LYS | O | -32.27 | -20.05 | 62.15 | 15.00 |
| 182 ASN | N | -33.04 | -18.08 | 61.38 | 15.00 |
| 182 ASN | CA | -31.75 | -17.66 | 60.85 | 15.00 |
| 182 ASN | CB | -31.93 | -16.90 | 59.53 | 15.00 |
| 182 ASN | CG | -30.71 | -16.97 | 58.64 | 15.00 |
| 182 ASN | OD1 | -29.58 | -17.07 | 59.11 | 15.00 |
| 182 ASN | ND2 | -30.94 | -16.92 | 57.33 | 15.00 |
| 182 ASN | C | -31.07 | -16.80 | 61.91 | 15.00 |
| 182 ASN | O | -31.52 | -16.75 | 63.05 | 15.00 |
| 183 SER | N | -29.98 | -16.13 | 61.55 | 15.00 |
| 183 SER | CA | -29.28 | -15.27 | 62.49 | 15.00 |
| 183 SER | CB | -28.10 | -16.00 | 63.13 | 15.00 |
| 183 SER | OG | -27.27 | -16.59 | 62.15 | 15.00 |
| 183 SER | C | -28.83 | -13.99 | 61.81 | 15.00 |
| 183 SER | O | -27.65 | -13.66 | 61.82 | 15.00 |
| 184 TRP | N | -29.77 | -13.30 | 61.17 | 15.00 |
| 184 TRP | CA | -29.49 | -12.05 | 60.48 | 15.00 |
| 184 TRP | CB | -29.61 | -12.22 | 58.96 | 15.00 |
| 184 TRP | CG | -28.60 | -13.15 | 58.37 | 15.00 |
| 184 TRP | CD2 | -28.66 | -13.78 | 57.08 | 15.00 |
| 184 TRP | CE2 | -27.49 | -14.55 | 56.94 | 15.00 |
| 184 TRP | CE3 | -29.60 | -13.77 | 56.03 | 15.00 |
| 184 TRP | CD1 | -27.43 | -13.56 | 58.93 | 15.00 |
| 184 TRP | NE1 | -26.76 | -14.39 | 58.08 | 15.00 |
| 184 TRP | CZ2 | -27.22 | -15.31 | 55.78 | 15.00 |
| 184 TRP | CZ3 | -29.33 | -14.53 | 54.89 | 15.00 |
| 184 TRP | CH2 | -28.15 | -15.29 | 54.78 | 15.00 |
| 184 TRP | C | -30.42 | -10.97 | 61.00 | 15.00 |
| 184 TRP | O | -30.89 | -10.12 | 60.25 | 15.00 |
| 185 GLY | N | -30.70 | -11.03 | 62.30 | 15.00 |
| 185 GLY | CA | -31.58 | -10.07 | 62.94 | 15.00 |
| 185 GLY | C | -33.02 | -10.33 | 62.57 | 15.00 |
| 185 GLY | O | -33.31 | -11.05 | 61.62 | 15.00 |
| 186 GLU | N | -33.94 | -9.76 | 63.35 | 15.00 |
| 186 GLU | CA | -35.36 | -9.93 | 63.07 | 15.00 |
| 186 GLU | CB | -36.22 | -9.59 | 64.28 | 15.00 |
| 186 GLU | CG | -36.03 | -8.21 | 64.80 | 15.00 |
| 186 GLU | CD | -36.84 | -7.96 | 66.04 | 15.00 |
| 186 GLU | OE1 | -37.97 | -8.49 | 66.13 | 15.00 |
| 186 GLU | OE2 | -36.35 | -7.22 | 66.93 | 15.00 |
| 186 GLU | C | -35.77 | -9.12 | 61.86 | 15.00 |
| 186 GLU | O | -36.90 | -9.24 | 61.38 | 15.00 |
| 187 ASN | N | -34.84 | -8.32 | 61.36 | 15.00 |
| 187 ASN | CA | -35.06 | -7.47 | 60.20 | 15.00 |
| 187 ASN | CB | -34.05 | -6.32 | 60.16 | 15.00 |
| 187 ASN | CG | -34.41 | -5.27 | 59.11 | 15.00 |
| 187 ASN | OD1 | -35.57 | -5.16 | 58.70 | 15.00 |
| 187 ASN | ND2 | -33.41 | -4.49 | 58.69 | 15.00 |
| 187 ASN | C | -35.00 | -8.26 | 58.94 | 15.00 |
| 187 ASN | O | -35.44 | -7.79 | 57.86 | 15.00 |
| 188 TRP | N | -34.42 | -9.46 | 58.97 | 15.00 |
| 188 TRP | CA | -34.30 | -10.30 | 57.80 | 15.00 |
| 188 TRP | CB | -33.01 | -11.12 | 57.86 | 15.00 |
| 188 TRP | CG | -32.84 | -11.99 | 56.71 | 15.00 |
| 188 TRP | CD2 | -33.26 | -13.36 | 56.60 | 15.00 |
| 188 TRP | CE2 | -32.96 | -13.77 | 55.29 | 15.00 |
| 188 TRP | CE3 | -33.86 | -14.26 | 57.48 | 15.00 |
| 188 TRP | CD1 | -32.32 | -11.65 | 55.51 | 15.00 |
| 188 TRP | NE1 | -32.39 | -12.71 | 54.64 | 15.00 |
| 188 TRP | CZ2 | -33.24 | -15.07 | 54.83 | 15.00 |
| 188 TRP | CZ3 | -34.15 | -15.55 | 57.02 | 15.00 |
| 188 TRP | CH2 | -33.84 | -15.94 | 55.72 | 15.00 |
| 188 TRP | C | -35.50 | -11.21 | 57.63 | 15.00 |
| 188 TRP | O | -36.05 | -11.71 | 58.61 | 15.00 |
| 189 GLY | N | -35.92 | -11.43 | 56.38 | 15.00 |
| 189 GLY | CA | -37.05 | -12.30 | 56.10 | 15.00 |
| 189 GLY | C | -38.29 | -11.99 | 56.92 | 15.00 |
| 189 GLY | O | -38.61 | -10.83 | 57.20 | 15.00 |
| 190 ASN | N | -39.01 | -13.04 | 57.31 | 15.00 |
| 190 ASN | CA | -40.21 | -12.85 | 58.11 | 15.00 |
| 190 ASN | CB | -41.21 | -13.98 | 57.90 | 15.00 |
| 190 ASN | CG | -42.58 | -13.65 | 58.45 | 15.00 |
| 190 ASN | OD1 | -42.74 | -12.81 | 59.33 | 15.00 |

TABLE IX-continued

Table of the orthogonal three dimensional coordinates in Ångstroms and B factors (Å²) for the cathepsin K complex with inhibitor 4-[N-[(phenylmethoxy)carbonyl]-L-leucyl]-1-N[N-(methyl)-L-leucyl)]-3-pyrrolidinone

| Residue | Atom | X | Y | Z | B |
|---|---|---|---|---|---|
| 190 | ASN | ND2 | −43.60 | −14.32 | 57.92 | 15.00 |
| 190 | ASN | C | −39.77 | −12.74 | 59.56 | 15.00 |
| 190 | ASN | O | −39.83 | −13.72 | 60.30 | 15.00 |
| 191 | LYS | N | −39.24 | −11.59 | 59.94 | 15.00 |
| 191 | LYS | CA | −38.80 | −11.39 | 61.31 | 15.00 |
| 191 | LYS | CB | −40.02 | −11.23 | 62.23 | 15.00 |
| 191 | LYS | CG | −40.86 | −10.00 | 61.87 | 15.00 |
| 191 | LYS | CD | −42.05 | −9.79 | 62.79 | 15.00 |
| 191 | LYS | CE | −43.16 | −10.79 | 62.51 | 15.00 |
| 191 | LYS | NZ | −43.76 | −10.63 | 61.14 | 15.00 |
| 191 | LYS | C | −37.83 | −12.46 | 61.81 | 15.00 |
| 191 | LYS | O | −38.02 | −13.08 | 62.86 | 15.00 |
| 192 | GLY | N | −36.77 | −12.65 | 61.03 | 15.00 |
| 192 | GLY | CA | −35.73 | −13.62 | 61.37 | 15.00 |
| 192 | GLY | C | −35.96 | −15.05 | 60.91 | 15.00 |
| 192 | GLY | O | −35.00 | −15.80 | 60.72 | 15.00 |
| 193 | TYR | N | −37.21 | −15.43 | 60.71 | 15.00 |
| 193 | TYR | CA | −37.53 | −16.78 | 60.30 | 15.00 |
| 193 | TYR | CB | −38.71 | −17.32 | 61.10 | 15.00 |
| 193 | TYR | CG | −38.44 | −17.47 | 62.58 | 15.00 |
| 193 | TYR | CD1 | −38.48 | −16.39 | 63.44 | 15.00 |
| 193 | TYR | CE1 | −38.21 | −16.54 | 64.79 | 15.00 |
| 193 | TYR | CD2 | −38.12 | −18.72 | 63.11 | 15.00 |
| 193 | TYR | CE2 | −37.84 | −18.88 | 64.46 | 15.00 |
| 193 | TYR | CZ | −37.89 | −17.79 | 65.29 | 15.00 |
| 193 | TYR | OH | −37.62 | −17.95 | 66.63 | 15.00 |
| 193 | TYR | C | −37.78 | −16.91 | 58.82 | 15.00 |
| 193 | TYR | O | −38.05 | −15.93 | 58.14 | 15.00 |
| 194 | ILE | N | −37.72 | −18.14 | 58.33 | 15.00 |
| 194 | ILE | CA | −37.95 | −18.43 | 56.92 | 15.00 |
| 194 | ILE | CB | −36.63 | −18.38 | 56.07 | 15.00 |
| 194 | ILE | CG2 | −35.63 | −19.42 | 56.55 | 15.00 |
| 194 | ILE | CG1 | −36.94 | −18.61 | 54.60 | 15.00 |
| 194 | ILE | CD1 | −35.75 | −18.49 | 53.69 | 15.00 |
| 194 | ILE | C | −38.57 | −19.82 | 56.79 | 15.00 |
| 194 | ILE | O | −38.12 | −20.78 | 57.42 | 15.00 |
| 195 | LEU | N | −39.65 | −19.91 | 56.03 | 15.00 |
| 195 | LEU | CA | −40.34 | −21.17 | 55.80 | 15.00 |
| 195 | LEU | CB | −41.84 | −20.95 | 55.67 | 15.00 |
| 195 | LEU | CG | −42.72 | −21.15 | 56.90 | 15.00 |
| 195 | LEU | CD1 | −42.11 | −20.50 | 58.14 | 15.00 |
| 195 | LEU | CD2 | −44.10 | −20.59 | 56.59 | 15.00 |
| 195 | LEU | C | −39.79 | −21.84 | 54.56 | 15.00 |
| 195 | LEU | O | −40.17 | −21.50 | 53.45 | 15.00 |
| 196 | MET | N | −38.86 | −22.76 | 54.75 | 15.00 |
| 196 | MET | CA | −38.25 | −23.48 | 53.63 | 15.00 |
| 196 | MET | CB | −36.83 | −23.91 | 53.98 | 15.00 |
| 196 | MET | CG | −35.91 | −22.73 | 54.21 | 15.00 |
| 196 | MET | SD | −34.18 | −23.17 | 54.37 | 15.00 |
| 196 | MET | CE | −33.94 | −24.05 | 52.84 | 15.00 |
| 196 | MET | C | −39.13 | −24.66 | 53.22 | 15.00 |
| 196 | MET | O | −40.03 | −25.06 | 53.97 | 15.00 |
| 197 | ALA | N | −38.87 | −25.24 | 52.05 | 15.00 |
| 197 | ALA | CA | −39.67 | −26.35 | 51.54 | 15.00 |
| 197 | ALA | CB | −39.50 | −26.46 | 50.04 | 15.00 |
| 197 | ALA | C | −39.40 | −27.70 | 52.18 | 15.00 |
| 197 | ALA | O | −38.26 | −28.15 | 52.25 | 15.00 |
| 198 | ARG | N | −40.47 | −28.36 | 52.62 | 15.00 |
| 198 | ARG | CA | −40.35 | −29.67 | 53.24 | 15.00 |
| 198 | ARG | CB | −41.11 | −29.71 | 54.57 | 15.00 |
| 198 | ARG | CG | −41.08 | −31.06 | 55.27 | 15.00 |
| 198 | ARG | CD | −41.32 | −30.93 | 56.75 | 15.00 |
| 198 | ARG | NE | −42.61 | −30.32 | 57.06 | 15.00 |
| 198 | ARG | CZ | −43.76 | −30.98 | 57.14 | 15.00 |
| 198 | ARG | NH1 | −43.79 | −32.29 | 56.95 | 15.00 |
| 198 | ARG | NH2 | −44.88 | −30.33 | 57.45 | 15.00 |
| 198 | ARG | C | −40.82 | −30.77 | 52.30 | 15.00 |
| 198 | ARG | O | −41.91 | −30.70 | 51.73 | 15.00 |
| 199 | ASN | N | −39.97 | −31.76 | 52.12 | 15.00 |
| 199 | ASN | CA | −40.27 | −32.90 | 51.25 | 15.00 |
| 199 | ASN | CB | −41.62 | −33.54 | 51.63 | 15.00 |
| 199 | ASN | CG | −41.53 | −34.36 | 52.90 | 15.00 |
| 199 | ASN | OD1 | −42.42 | −34.31 | 53.75 | 15.00 |
| 199 | ASN | ND2 | −40.45 | −35.13 | 53.05 | 15.00 |
| 199 | ASN | C | −40.21 | −32.59 | 49.76 | 15.00 |
| 199 | ASN | O | −40.78 | −33.32 | 48.94 | 15.00 |
| 200 | LYS | N | −39.48 | −31.54 | 49.41 | 15.00 |
| 200 | LYS | CA | −39.31 | −31.17 | 48.01 | 15.00 |
| 200 | LYS | CB | −39.31 | −29.66 | 47.81 | 15.00 |
| 200 | LYS | CG | −40.70 | −29.02 | 47.77 | 15.00 |
| 200 | LYS | CD | −41.37 | −29.23 | 46.42 | 15.00 |
| 200 | LYS | CE | −42.76 | −28.59 | 46.37 | 15.00 |
| 200 | LYS | NZ | −42.73 | −27.14 | 46.73 | 15.00 |
| 200 | LYS | C | −37.98 | −31.78 | 47.60 | 15.00 |
| 200 | LYS | O | −37.11 | −31.09 | 47.06 | 15.00 |
| 201 | ASN | N | −37.81 | −33.06 | 47.93 | 15.00 |
| 201 | ASN | CA | −36.58 | −33.78 | 47.62 | 15.00 |
| 201 | ASN | CB | −36.41 | −33.93 | 46.11 | 15.00 |
| 201 | ASN | CG | −37.15 | −35.13 | 45.56 | 15.00 |
| 201 | ASN | OD1 | −36.68 | −35.78 | 44.63 | 15.00 |
| 201 | ASN | ND2 | −38.3.2 | −35.42 | 46.13 | 15.00 |
| 201 | ASN | C | −35.33 | −33.22 | 48.27 | 15.00 |
| 201 | ASN | O | −34.27 | −33.16 | 47.66 | 15.00 |
| 202 | ASN | N | −35.46 | −32.84 | 49.54 | 15.00 |
| 202 | ASN | CA | −34.37 | −32.30 | 50.35 | 15.00 |
| 202 | ASN | CB | −33.25 | −33.34 | 50.49 | 15.00 |
| 202 | ASN | CG | −32.20 | −32.93 | 51.48 | 15.00 |
| 202 | ASN | OD1 | −32.51 | −32.44 | 52.56 | 15.00 |
| 202 | ASN | ND2 | −30.94 | −33.14 | 51.13 | 15.00 |
| 202 | ASN | C | −33.83 | −30.96 | 49.85 | 15.00 |
| 202 | ASN | O | −32.62 | −30.77 | 49.68 | 15.00 |
| 203 | ALA | N | −34.73 | −30.00 | 49.69 | 15.00 |
| 203 | ALA | H | −35.60 | −30.20 | 50.07 | 15.00 |
| 203 | ALA | CA | −34.39 | −28.68 | 49.18 | 15.00 |
| 203 | ALA | CB | −35.57 | −27.74 | 49.24 | 15.00 |
| 203 | ALA | C | −33.27 | −28.06 | 50.04 | 15.00 |
| 203 | ALA | O | −33.33 | −28.03 | 51.26 | 15.00 |
| 204 | CYS | N | −32.23 | −27.56 | 49.35 | 15.00 |
| 204 | CYS | CA | −31.11 | −26.89 | 50.02 | 15.00 |
| 204 | CYS | C | −30.29 | −27.71 | 51.00 | 15.00 |
| 204 | CYS | O | −29.50 | −27.14 | 51.76 | 15.00 |
| 204 | CYS | CB | −31.58 | −25.60 | 50.69 | 15.00 |
| 204 | CYS | SG | −32.12 | −24.29 | 49.55 | 15.00 |
| 205 | GLY | N | −30.43 | −29.03 | 50.98 | 15.00 |
| 205 | GLY | CA | −29.68 | −29.88 | 51.90 | 15.00 |
| 205 | GLY | C | −30.10 | −29.71 | 53.35 | 15.00 |
| 205 | GLY | O | −29.31 | −29.92 | 54.27 | 15.00 |
| 206 | ILE | N | −31.37 | −29.38 | 53.54 | 15.00 |
| 206 | ILE | CA | −31.95 | −29.16 | 54.85 | 15.00 |
| 206 | ILE | CB | −33.46 | −28.92 | 54.73 | 15.00 |
| 206 | ILE | CG2 | −34.13 | −30.13 | 54.12 | 15.00 |
| 206 | ILE | CG1 | −34.06 | −28.55 | 56.10 | 15.00 |
| 206 | ILE | CD1 | −33.76 | −27.15 | 56.54 | 15.00 |
| 206 | ILE | C | −31.71 | −30.29 | 55.85 | 15.00 |
| 206 | ILE | O | −31.47 | −30.04 | 57.03 | 15.00 |
| 207 | ALA | N | −31.79 | −31.54 | 55.38 | 15.00 |
| 207 | ALA | CA | −31.58 | −32.69 | 56.25 | 15.00 |
| 207 | ALA | CB | −32.72 | −33.68 | 56.08 | 15.00 |
| 207 | ALA | C | −30.25 | −33.35 | 55.94 | 15.00 |
| 207 | ALA | O | −30.15 | −34.57 | 55.95 | 15.00 |
| 208 | ASN | N | −29.24 | −32.54 | 55.67 | 15.00 |
| 208 | ASN | CA | −27.91 | −33.04 | 55.33 | 15.00 |
| 208 | ASN | CB | −27.41 | −32.42 | 54.03 | 15.00 |
| 208 | ASN | CG | −27.70 | −33.30 | 52.84 | 15.00 |
| 208 | ASN | OD1 | −28.85 | −33.50 | 52.47 | 15.00 |
| 208 | ASN | ND2 | −26.65 | −33.86 | 52.26 | 15.00 |
| 208 | ASN | C | −26.85 | −32.89 | 56.41 | 15.00 |
| 208 | ASN | O | −25.80 | −33.53 | 56.35 | 15.00 |
| 209 | LEU | N | −27.08 | −32.00 | 57.36 | 15.00 |
| 209 | LEU | CA | −26.10 | −31.82 | 58.42 | 15.00 |
| 209 | LEU | CB | −25.07 | −30.77 | 58.03 | 15.00 |
| 209 | LEU | CG | −23.69 | −31.04 | 58.63 | 15.00 |

TABLE IX-continued

Table of the orthogonal three dimensional coordinates in Ångstroms and B factors (Å$^2$) for the cathepsin K complex with inhibitor 4-[N-[(phenylmethoxy)carbonyl]-L-leucyl]-1-N[N-(methyl)-L-leucyl)]-3-pyrrolidinone

| Residue | Atom | X | Y | Z | B |
|---|---|---|---|---|---|
| 209 | LEU | CD1 | −23.08 | −32.21 | 57.88 | 15.00 |
| 209 | LEU | CD2 | −22.82 | −29.81 | 58.52 | 15.00 |
| 209 | LEU | C | −26.77 | −31.46 | 59.73 | 15.00 |
| 209 | LEU | O | −26.25 | −30.66 | 60.51 | 15.00 |
| 210 | ALA | N | −27.91 | −32.08 | 59.97 | 15.00 |
| 210 | ALA | H | −27.81 | −31.90 | 59.38 | 15.00 |
| 210 | ALA | CA | −28.67 | −31.80 | 61.19 | 15.00 |
| 210 | ALA | CB | −29.27 | −31.17 | 61.33 | 15.00 |
| 210 | ALA | C | −28.06 | −32.58 | 62.37 | 15.00 |
| 210 | ALA | O | −27.58 | −33.69 | 62.23 | 15.00 |
| 211 | SER | N | −28.08 | −31.93 | 63.53 | 15.00 |
| 211 | SER | CA | −27.60 | −32.53 | 64.76 | 15.00 |
| 211 | SER | CB | −26.07 | −32.52 | 64.86 | 15.00 |
| 211 | SER | OG | −25.53 | −31.21 | 64.89 | 15.00 |
| 211 | SER | C | −28.25 | −31.80 | 65.93 | 15.00 |
| 211 | SER | O | −28.68 | −30.65 | 65.78 | 15.00 |
| 212 | PHE | N | −28.44 | −32.51 | 67.03 | 15.00 |
| 212 | PHE | CA | −29.04 | −31.94 | 68.23 | 15.00 |
| 212 | PHE | CB | −30.53 | −32.29 | 68.37 | 15.00 |
| 212 | PHE | CC | −30.81 | −33.77 | 68.41 | 15.00 |
| 212 | PHE | CD1 | −31.04 | −34.48 | 67.24 | 15.00 |
| 212 | PHE | CD2 | −30.85 | −34.45 | 69.62 | 15.00 |
| 212 | PHE | CE1 | −31.30 | −35.84 | 67.27 | 15.00 |
| 212 | PHE | CE2 | −31.11 | −35.82 | 69.67 | 15.00 |
| 212 | PHE | CZ | −31.33 | −36.51 | 68.48 | 15.00 |
| 212 | PHE | C | −28.22 | −32.41 | 69.43 | 15.00 |
| 212 | PHE | O | −27.54 | −33.43 | 69.36 | 15.00 |
| 213 | PRO | N | −28.19 | −31.63 | 70.50 | 15.00 |
| 213 | PRO | CD | −28.56 | −30.21 | 70.63 | 15.00 |
| 213 | PRO | CA | −27.41 | −32.07 | 71.65 | 15.00 |
| 213 | PRO | CB | −26.98 | −30.75 | 72.28 | 15.00 |
| 213 | PRO | CG | −28.17 | −29.90 | 72.06 | 15.00 |
| 213 | PRO | C | −28.21 | −32.91 | 72.65 | 15.00 |
| 213 | PRO | O | −29.45 | −32.81 | 72.72 | 15.00 |
| 214 | LYS | N | −27.50 | −33.77 | 73.38 | 15.00 |
| 214 | LYS | CA | −28.12 | −34.59 | 74.42 | 15.00 |
| 214 | LYS | CB | −27.50 | −35.97 | 74.52 | 15.00 |
| 214 | LYS | CG | −28.01 | −37.00 | 73.53 | 15.00 |
| 214 | LYS | CD | −27.20 | −38.28 | 73.68 | 15.00 |
| 214 | LYS | CE | −27.79 | −39.45 | 72.93 | 15.00 |
| 214 | LYS | NZ | −27.00 | −40.67 | 73.21 | 15.00 |
| 214 | LYS | C | −27.86 | −33.84 | 75.70 | 15.00 |
| 214 | LYS | O | −26.73 | −33.45 | 75.98 | 15.00 |
| 215 | MET | N | −28.90 | −33.63 | 76.49 | 15.00 |
| 215 | MET | CA | −28.73 | −32.91 | 77.73 | 15.00 |
| 215 | MET | CB | −29.47 | −31.58 | 77.67 | 15.00 |
| 215 | MET | CG | −28.62 | −30.45 | 78.17 | 15.00 |
| 215 | MET | SD | −29.49 | −28.92 | 78.17 | 15.00 |
| 215 | MET | CE | −30.02 | −28.81 | 79.89 | 15.00 |
| 215 | MET | C | −29.15 | −33.74 | 78.95 | 15.00 |
| 215 | MET | OT1 | −30.12 | −34.53 | 78.84 | 15.00 |
| 215 | MET | OT2 | −28.49 | −33.59 | 80.01 | 15.00 |
| 216 | HOH | OH2 | −28.59 | −18.05 | 86.43 | 15.00 |
| 217 | HOH | OH2 | −24.24 | −33.32 | 82.08 | 15.00 |
| 218 | HOH | OH2 | −30.97 | −16.19 | 65.69 | 15.00 |
| 219 | HOH | OH2 | −30.10 | −20.71 | 63.47 | 15.00 |
| 220 | HOH | OH2 | −13.66 | −11.12 | 63.10 | 15.00 |
| 221 | HOH | OH2 | −9.67 | −9.48 | 64.25 | 15.00 |
| 222 | HOH | OH2 | −34.55 | −23.08 | 70.24 | 15.00 |
| 223 | HOH | OH2 | −14.15 | −32.13 | 69.51 | 15.00 |
| 224 | HOH | OH2 | −11.90 | −8.52 | 62.51 | 15.00 |
| 225 | HOH | OH2 | −24.25 | −30.66 | 62.17 | 15.00 |
| 226 | HOH | OH2 | −10.58 | −2.52 | 79.25 | 15.00 |
| 227 | HOH | OH2 | −14.05 | −21.32 | 67.22 | 15.00 |
| 228 | HOH | OH2 | −44.68 | −30.63 | 50.04 | 15.00 |
| 229 | HOH | OH2 | −45.38 | −36.05 | 56.05 | 15.00 |
| 230 | HOH | OH2 | −39.65 | −13.31 | 65.32 | 15.00 |
| 231 | HOH | OH2 | −35.12 | −36.60 | 49.29 | 15.00 |
| 232 | HOH | OH2 | −17.36 | −34.13 | 65.07 | 15.00 |
| 233 | HOH | OH2 | −30.35 | −19.53 | 65.73 | 15.00 |
| 234 | HOH | OH2 | −27.89 | −19.53 | 62.51 | 15.00 |
| 235 | HOH | OH2 | −21.85 | −29.55 | 62.34 | 15.00 |
| 236 | HOH | OH2 | −30.14 | 3.73 | 67.17 | 15.00 |
| 237 | HOH | OH2 | −40.50 | −29.62 | 80.16 | 15.00 |
| 238 | HOH | OH2 | −27.85 | −23.15 | 86.33 | 15.00 |
| 239 | HOH | OH2 | −38.29 | −13.95 | 44.87 | 15.00 |
| 240 | HOH | OH2 | −36.58 | −24.59 | 50.05 | 15.00 |
| 241 | HOH | OH2 | −46.68 | −34.18 | 57.37 | 15.00 |
| 242 | HOH | OH2 | −26.77 | −6.82 | 59.79 | 15.00 |
| 243 | HOH | OH2 | −43.58 | −17.40 | 60.45 | 15.00 |
| 244 | HOH | OH2 | −23.22 | −6.13 | 61.38 | 15.00 |
| 245 | HOH | OH2 | −33.13 | −28.30 | 71.09 | 15.00 |
| 246 | HOH | OH2 | −46.57 | −25.22 | 78.97 | 15.00 |
| 247 | HOH | OH2 | −14.51 | −7.76 | 88.79 | 15.00 |
| 248 | HOH | OH2 | −3.26 | −20.73 | 74.76 | 15.00 |
| 249 | HOH | OH2 | 0.44 | −15.91 | 75.31 | 15.00 |
| 250 | HOH | OH2 | −19.71 | −34.82 | 58.63 | 15.00 |
| 251 | HOH | OH2 | −34.91 | −11.28 | 53.79 | 15.00 |
| 252 | HOH | OH2 | −32.46 | −28.27 | 46.13 | 15.00 |
| 253 | HOH | OH2 | −38.20 | −15.68 | 37.93 | 15.00 |
| 254 | HOH | OH2 | −41.44 | −34.28 | 56.30 | 15.00 |
| 255 | HOH | OH2 | −46.93 | −13.62 | 73.92 | 15.00 |
| 256 | HOH | OH2 | −32.58 | −13.60 | 60.68 | 15.00 |
| 257 | HOH | OH2 | −35.46 | −6.38 | 55.50 | 15.00 |
| 258 | HOH | OH2 | −24.79 | −7.91 | 66.67 | 15.00 |
| 259 | HOH | OH2 | −32.06 | −6.48 | 63.77 | 15.00 |
| 260 | HOH | OH2 | −17.19 | −5.30 | 66.67 | 15.00 |
| 261 | HOH | OH2 | −33.68 | −20.47 | 70.17 | 15.00 |
| 262 | HOH | OH2 | −13.42 | −23.06 | 78.55 | 15.00 |
| 263 | HOH | OH2 | −8.54 | −20.70 | 73.58 | 15.00 |
| 264 | HOH | OH2 | −8.22 | −29.32 | 76.42 | 15.00 |
| 265 | HOH | OH2 | −25.08 | −33.76 | 60.84 | 15.00 |
| 266 | HOH | OH2 | −23.92 | −37.99 | 66.66 | 15.00 |
| 267 | HOH | OH2 | −14.04 | −33.08 | 66.81 | 15.00 |
| 268 | HOH | OH2 | −12.79 | −27.03 | 71.88 | 15.00 |
| 269 | HOH | OH2 | −18.55 | −42.19 | 77.34 | 15.00 |
| 270 | HOH | OH2 | −22.19 | −37.43 | 71.34 | 15.00 |
| 271 | HOH | OH2 | −3.79 | −11.43 | 71.45 | 15.00 |
| 272 | HOH | OH2 | −10.91 | −19.86 | 67.02 | 15.00 |
| 273 | HOH | OH2 | −30.22 | −20.12 | 49.07 | 15.00 |
| 274 | HOH | OH2 | −25.88 | −18.93 | 42.52 | 15.00 |
| 275 | HOH | OH2 | −36.21 | −36.23 | 51.70 | 15.00 |
| 276 | HOH | OH2 | −20.20 | −20.55 | 47.99 | 15.00 |
| 277 | HOH | OH2 | −38.35 | −31.19 | 41.44 | 15.00 |
| 278 | HOH | OH2 | −37.29 | −30.41 | 51.12 | 15.00 |

TABLE X

Table of the orthogonal three dimensional coordinates in Ångstroms and B factors (Å$^2$) for the cathepsin K complex with inhibitor 1-N-(N-imidazole acetyl-leucinyl)-amino-3-N-(4-phenoxy-phenyl-sulfonyl)-amino-propan-2-one

| Residue | Atom | X | Y | Z | B |
|---|---|---|---|---|---|
| 1 | ALA | CB | −8.26 | 15.35 | 87.29 | 15.00 |
| 1 | ALA | C | −6.43 | 14.73 | 88.90 | 15.00 |
| 1 | ALA | O | −6.17 | 15.27 | 89.97 | 15.00 |
| 1 | ALA | N | −8.92 | 14.74 | 89.58 | 15.00 |
| 1 | ALA | CA | −7.91 | 14.50 | 88.49 | 15.00 |
| 2 | PRO | N | −5.47 | 14.25 | 88.09 | 15.00 |
| 2 | PRO | CD | −5.62 | 13.29 | 86.98 | 15.00 |
| 2 | PRO | CA | −4.05 | 14.45 | 88.44 | 15.00 |
| 2 | PRO | CB | −3.32 | 13.49 | 87.50 | 15.00 |
| 2 | PRO | CG | −4.27 | 13.38 | 86.30 | 15.00 |
| 2 | PRO | C | −3.55 | 15.87 | 88.27 | 15.00 |
| 2 | PRO | O | −4.33 | 16.79 | 88.21 | 15.00 |
| 3 | ASP | N | −2.23 | 16.02 | 88.20 | 15.00 |

TABLE X-continued

Table of the orthogonal three dimensional coordinates in Ångstroms and B factors (Å$^2$) for the cathepsin K complex with inhibitor 1-N-(N-imidazole acetyl-leucinyl)-amino-3-N-(4-phenoxy-phenyl-sulfonyl)-amino-propan-2-one

| Residue | Atom | X | Y | Z | B |
|---|---|---|---|---|---|
| 3 | ASP | CA | -1.59 | 17.30 | 88.03 | 15.00 |
| 3 | ASP | CB | -0.07 | 17.14 | 88.15 | 15.00 |
| 3 | ASP | CG | 0.45 | 17.62 | 89.50 | 15.00 |
| 3 | ASP | OD1 | -0.04 | 17.07 | 90.52 | 15.00 |
| 3 | ASP | OD2 | 1.29 | 18.57 | 89.55 | 15.00 |
| 3 | ASP | C | -1.90 | 18.00 | 86.73 | 15.00 |
| 3 | ASP | O | -1.71 | 17.44 | 85.64 | 15.00 |
| 4 | SER | N | -2.32 | 19.26 | 86.85 | 15.00 |
| 4 | SER | CA | -2.67 | 20.16 | 85.75 | 15.00 |
| 4 | SER | CB | -3.63 | 19.49 | 84.75 | 15.00 |
| 4 | SER | OG | -4.80 | 19.03 | 85.40 | 15.00 |
| 4 | SER | C | -3.32 | 21.45 | 86.30 | 15.00 |
| 4 | SER | O | -3.83 | 21.46 | 87.42 | 15.00 |
| 5 | VAL | N | -3.30 | 22.53 | 85.53 | 15.00 |
| 5 | VAL | CA | -3.93 | 23.80 | 85.94 | 15.00 |
| 5 | VAL | CB | -3.00 | 24.65 | 86.90 | 15.00 |
| 5 | VAL | CG1 | -1.73 | 25.13 | 86.17 | 15.00 |
| 5 | VAL | CG2 | -3.76 | 25.89 | 87.45 | 15.00 |
| 5 | VAL | C | -4.21 | 24.62 | 84.69 | 15.00 |
| 5 | VAL | O | -3.43 | 24.58 | 83.75 | 15.00 |
| 6 | ASP | N | -5.38 | 25.23 | 84.60 | 15.00 |
| 6 | ASP | CA | -5.68 | 26.09 | 83.46 | 15.00 |
| 6 | ASP | CB | -6.83 | 25.51 | 82.64 | 15.00 |
| 6 | ASP | CG | -7.00 | 26.20 | 81.28 | 15.00 |
| 6 | ASP | OD1 | -6.01 | 26.77 | 80.80 | 15.00 |
| 6 | ASP | OD2 | -8.12 | 26.17 | 80.72 | 15.00 |
| 6 | ASP | C | -6.08 | 27.42 | 84.03 | 15.00 |
| 6 | ASP | O | -7.06 | 27.49 | 84.72 | 15.00 |
| 7 | TYR | N | -5.27 | 28.45 | 83.88 | 15.00 |
| 7 | TYR | CA | -5.62 | 29.77 | 84.41 | 15.00 |
| 7 | TYR | CB | -4.36 | 30.64 | 84.56 | 15.00 |
| 7 | TYR | CG | -3.46 | 30.18 | 85.71 | 15.00 |
| 7 | TYR | CD1 | -3.91 | 30.31 | 87.05 | 15.00 |
| 7 | TYR | CE1 | -3.20 | 29.78 | 88.07 | 15.00 |
| 7 | TYR | CD2 | -2.23 | 29.50 | 85.46 | 15.00 |
| 7 | TYR | CE2 | -1.52 | 28.98 | 86.45 | 15.00 |
| 7 | TYR | CZ | -2.00 | 29.10 | 87.79 | 15.00 |
| 7 | TYR | OH | -1.35 | 28.46 | 88.84 | 15.00 |
| 7 | TYR | C | -6.71 | 30.50 | 83.66 | 15.00 |
| 7 | TYR | O | -7.24 | 31.48 | 84.14 | 15.00 |
| 8 | ARG | N | -7.05 | 29.98 | 82.49 | 15.00 |
| 8 | ARG | CA | -8.10 | 30.59 | 81.68 | 15.00 |
| 8 | ARG | CB | -8.09 | 30.02 | 80.26 | 15.00 |
| 8 | ARG | CG | -6.79 | 30.28 | 79.56 | 15.00 |
| 8 | ARG | CD | -6.68 | 29.59 | 78.25 | 15.00 |
| 8 | ARG | NE | -6.70 | 28.13 | 78.38 | 15.00 |
| 8 | ARG | CZ | -6.78 | 27.29 | 77.36 | 15.00 |
| 8 | ARG | NH1 | -6.85 | 27.73 | 76.13 | 15.00 |
| 8 | ARG | NH2 | -6.72 | 25.99 | 77.58 | 15.00 |
| 8 | ARG | C | -9.44 | 30.40 | 82.35 | 15.00 |
| 8 | ARG | O | -10.24 | 31.34 | 82.45 | 15.00 |
| 9 | LYS | N | -9.68 | 29.21 | 82.87 | 15.00 |
| 9 | LYS | CA | -10.94 | 28.95 | 83.54 | 15.00 |
| 9 | LYS | CB | -11.17 | 27.45 | 83.73 | 15.00 |
| 9 | LYS | CG | -11.06 | 26.59 | 82.48 | 15.00 |
| 9 | LYS | CD | -11.19 | 25.12 | 82.85 | 15.00 |
| 9 | LYS | CE | -11.10 | 24.18 | 81.67 | 15.00 |
| 9 | LYS | NZ | -11.53 | 22.81 | 82.08 | 15.00 |
| 9 | LYS | C | -10.96 | 29.61 | 84.91 | 15.00 |
| 9 | LYS | O | -12.02 | 29.58 | 85.59 | 15.00 |
| 10 | LYS | N | -9.86 | 30.26 | 85.31 | 15.00 |
| 10 | LYS | CA | -9.84 | 30.86 | 86.64 | 15.00 |
| 10 | LYS | CB | -8.57 | 30.42 | 87.38 | 15.00 |
| 10 | LYS | CG | -8.45 | 28.89 | 87.51 | 15.00 |
| 10 | LYS | CD | -7.03 | 28.46 | 87.81 | 15.00 |
| 10 | LYS | CE | -6.43 | 29.14 | 89.04 | 15.00 |
| 10 | LYS | NZ | -7.24 | 28.91 | 90.30 | 15.00 |
| 10 | LYS | C | -9.98 | 32.40 | 86.61 | 15.00 |
| 10 | LYS | O | -10.16 | 33.04 | 87.64 | 15.00 |
| 11 | GLY | N | -9.85 | 32.98 | 85.41 | 15.00 |
| 11 | GLY | CA | -9.94 | 34.41 | 85.22 | 15.00 |
| 11 | GLY | C | -8.63 | 35.17 | 85.27 | 15.00 |
| 11 | GLY | O | -8.61 | 36.39 | 85.26 | 15.00 |
| 12 | TYR | N | -7.54 | 34.42 | 85.20 | 15.00 |
| 12 | TYR | CA | -6.21 | 34.98 | 85.26 | 15.00 |
| 12 | TYR | CB | -5.24 | 33.95 | 85.84 | 15.00 |
| 12 | TYR | CG | -5.32 | 33.72 | 87.35 | 15.00 |
| 12 | TYR | CD1 | -6.52 | 33.50 | 87.99 | 15.00 |
| 12 | TYR | CE1 | -6.58 | 33.26 | 89.37 | 15.00 |
| 12 | TYR | CD2 | -4.18 | 33.66 | 88.13 | 15.00 |
| 12 | TYR | CE2 | -4.23 | 33.42 | 89.47 | 15.00 |
| 12 | TYR | CZ | -5.42 | 33.23 | 90.06 | 15.00 |
| 12 | TYR | OH | -5.43 | 33.02 | 91.43 | 15.00 |
| 12 | TYR | C | -5.68 | 35.43 | 83.90 | 15.00 |
| 12 | TYR | O | -4.68 | 36.17 | 83.83 | 15.00 |
| 13 | VAL | N | -6.34 | 35.06 | 82.81 | 15.00 |
| 13 | VAL | CA | -5.82 | 35.45 | 81.50 | 15.00 |
| 13 | VAL | CB | -5.54 | 34.18 | 80.66 | 15.00 |
| 13 | VAL | CG1 | -4.93 | 34.52 | 79.31 | 15.00 |
| 13 | VAL | CG2 | -4.58 | 33.24 | 81.42 | 15.00 |
| 13 | VAL | C | -6.76 | 36.37 | 80.72 | 15.00 |
| 13 | VAL | O | -7.95 | 36.17 | 80.78 | 15.00 |
| 14 | THR | N | -6.24 | 37.41 | 80.08 | 15.00 |
| 14 | THR | CA | -7.06 | 38.29 | 79.27 | 15.00 |
| 14 | THR | CB | -6.41 | 39.67 | 79.12 | 15.00 |
| 14 | THR | OG1 | -5.06 | 39.53 | 78.69 | 15.00 |
| 14 | THR | CG2 | -6.48 | 40.43 | 80.39 | 15.00 |
| 14 | THR | C | -7.20 | 37.68 | 77.89 | 15.00 |
| 14 | THR | O | -6.41 | 36.81 | 77.48 | 15.00 |
| 15 | PRO | N | -8.14 | 38.18 | 77.09 | 15.00 |
| 15 | PRO | CD | -9.11 | 39.26 | 77.34 | 15.00 |
| 15 | PRO | CA | -8.33 | 37.64 | 75.75 | 15.00 |
| 15 | PRO | CB | -9.51 | 38.47 | 75.23 | 15.00 |
| 15 | PRO | CG | -9.35 | 39.77 | 75.97 | 15.00 |
| 15 | PRO | C | -7.09 | 37.85 | 74.89 | 15.00 |
| 15 | PRO | O | -6.26 | 38.73 | 75.17 | 15.00 |
| 16 | VAL | N | -6.96 | 37.00 | 73.87 | 15.00 |
| 16 | VAL | CA | -5.81 | 37.05 | 73.00 | 15.00 |
| 16 | VAL | CB | -5.74 | 35.80 | 72.11 | 15.00 |
| 16 | VAL | CG1 | -4.42 | 35.77 | 71.35 | 15.00 |
| 16 | VAL | CG2 | -5.84 | 34.56 | 72.97 | 15.00 |
| 16 | VAL | C | -5.76 | 38.30 | 72.12 | 15.00 |
| 16 | VAL | O | -6.70 | 38.61 | 71.37 | 15.00 |
| 17 | LYS | N | -4.58 | 38.91 | 72.12 | 15.00 |
| 17 | LYS | CA | -4.36 | 40.08 | 71.32 | 15.00 |
| 17 | LYS | CB | -3.75 | 41.20 | 72.15 | 15.00 |
| 17 | LYS | CG | -4.73 | 42.01 | 72.95 | 15.00 |
| 17 | LYS | CD | -5.27 | 41.23 | 74.12 | 15.00 |
| 17 | LYS | CE | -5.71 | 42.11 | 75.23 | 15.00 |
| 17 | LYS | NZ | -5.93 | 41.40 | 76.53 | 15.00 |
| 17 | LYS | C | -3.45 | 39.72 | 70.16 | 15.00 |
| 17 | LYS | O | -2.83 | 38.63 | 70.16 | 15.00 |
| 18 | ASN | N | -3.32 | 40.68 | 69.24 | 15.00 |
| 18 | ASN | CA | -2.51 | 40.54 | 68.03 | 15.00 |
| 18 | ASN | CB | -3.37 | 40.84 | 66.84 | 15.00 |
| 18 | ASN | CG | -2.76 | 40.33 | 65.56 | 15.00 |
| 18 | ASN | OD1 | -1.57 | 40.56 | 65.29 | 15.00 |
| 18 | ASN | ND2 | -3.55 | 39.60 | 64.78 | 15.00 |
| 18 | ASN | C | -1.33 | 41.51 | 68.00 | 15.00 |
| 18 | ASN | O | -1.50 | 42.73 | 67.86 | 15.00 |
| 19 | GLN | N | -0.15 | 40.93 | 68.03 | 15.00 |
| 19 | GLN | CA | 1.12 | 41.67 | 68.01 | 15.00 |
| 19 | GLN | CB | 2.23 | 40.66 | 67.93 | 15.00 |
| 19 | GLN | CG | 3.64 | 41.21 | 67.96 | 15.00 |
| 19 | GLN | CD | 4.65 | 40.13 | 68.03 | 15.00 |
| 19 | GLN | OE1 | 4.35 | 39.00 | 68.42 | 15.00 |
| 19 | GLN | NE2 | 5.86 | 40.47 | 67.64 | 15.00 |
| 19 | GLN | C | 1.22 | 42.69 | 66.88 | 15.00 |
| 19 | GLN | O | 1.75 | 43.75 | 67.04 | 15.00 |
| 20 | GLY | N | 0.66 | 42.38 | 65.74 | 15.00 |
| 20 | GLY | CA | 0.66 | 43.27 | 64.59 | 15.00 |
| 20 | GLY | C | 1.84 | 42.90 | 63.73 | 15.00 |

TABLE X-continued

Table of the orthogonal three dimensional coordinates in Ångstroms and B factors (Å²) for the cathepsin K complex with inhibitor 1-N-(N-imidazole acetyl-leucinyl)-amino-3-N-(4-phenoxy-phenyl-sulfonyl)-amino-propan-2-one

| Residue | | Atom | X | Y | Z | B |
|---|---|---|---|---|---|---|
| 20 | GLY | O | 1.98 | 41.74 | 63.33 | 15.00 |
| 21 | GLN | N | 2.67 | 43.89 | 63.43 | 15.00 |
| 21 | GLN | CA | 3.88 | 43.70 | 62.61 | 15.00 |
| 21 | GLN | CB | 3.90 | 44.62 | 61.39 | 15.00 |
| 21 | GLN | CG | 2.90 | 44.23 | 60.27 | 15.00 |
| 21 | GLN | CD | 3.33 | 43.03 | 59.44 | 15.00 |
| 21 | GLN | OE1 | 4.25 | 43.10 | 58.59 | 15.00 |
| 21 | GLN | NE2 | 2.58 | 41.95 | 59.58 | 15.00 |
| 21 | GLN | C | 5.05 | 44.09 | 63.52 | 15.00 |
| 21 | GLN | O | 6.20 | 43.88 | 63.19 | 15.00 |
| 22 | CYS | N | 4.74 | 44.77 | 64.60 | 15.00 |
| 22 | CYS | CA | 5.74 | 45.22 | 65.53 | 15.00 |
| 22 | CYS | C | 6.26 | 44.01 | 66.35 | 15.00 |
| 22 | CYS | O | 5.48 | 43.07 | 66.60 | 15.00 |
| 22 | CYS | CB | 5.08 | 46.25 | 66.43 | 15.00 |
| 22 | CYS | SG | 6.07 | 46.62 | 67.91 | 15.00 |
| 23 | GLY | N | 7.57 | 43.99 | 66.68 | 15.00 |
| 23 | GLY | CA | 8.16 | 42.91 | 67.47 | 15.00 |
| 23 | GLY | C | 8.07 | 43.16 | 68.96 | 15.00 |
| 23 | GLY | O | 9.08 | 43.15 | 69.68 | 15.00 |
| 24 | SER | N | 6.82 | 43.29 | 69.42 | 15.00 |
| 24 | SER | CA | 6.47 | 43.55 | 70.79 | 15.00 |
| 24 | SER | CB | 5.45 | 44.66 | 70.86 | 15.00 |
| 24 | SER | OG | 4.31 | 44.30 | 70.15 | 15.00 |
| 24 | SER | C | 5.97 | 42.28 | 71.46 | 15.00 |
| 24 | SER | O | 5.26 | 42.34 | 72.45 | 15.00 |
| 25 | CYS | N | 6.43 | 41.13 | 70.98 | 15.00 |
| 25 | CYS | CA | 6.06 | 39.87 | 71.53 | 15.00 |
| 25 | CYS | CB | 6.61 | 38.78 | 70.65 | 15,00 |
| 25 | CYS | SG | 8.41 | 38.83 | 70.46 | 15.00 |
| 25 | CYS | C | 6.49 | 39.79 | 73.01 | 15.00 |
| 25 | CYS | O | 5.74 | 39.28 | 73.84 | 15.00 |
| 25 | INH | C1 | 3.24 | 39.22 | 63.40 | 15.00 |
| 25 | INH | C2 | 2.86 | 38.72 | 62.13 | 15.00 |
| 25 | INH | C3 | 1.57 | 38.27 | 61.89 | 15.00 |
| 25 | INH | C4 | 0.62 | 38.31 | 62.90 | 15.00 |
| 25 | INH | C5 | 0.94 | 38.79 | 64.16 | 15.00 |
| 25 | INH | C6 | 2.25 | 39.24 | 64.42 | 15.00 |
| 25 | INH | O7 | 4.57 | 39.75 | 63.63 | 15.00 |
| 25 | INH | C8 | 5.72 | 39.02 | 63.91 | 15.00 |
| 25 | INH | C9 | 5.62 | 38.42 | 65.17 | 15.00 |
| 25 | INH | C10 | 6.58 | 37.50 | 65.60 | 15.00 |
| 25 | INH | C11 | 7.65 | 37.17 | 64.78 | 15.00 |
| 25 | INH | C12 | 7.79 | 37.78 | 63.51 | 15.00 |
| 25 | INH | C13 | 6.82 | 38.71 | 63.08 | 15.00 |
| 25 | INH | S14 | 8.67 | 35.93 | 65.55 | 15.00 |
| 25 | INH | O15 | 7.93 | 34.70 | 65.54 | 15.00 |
| 25 | INH | O16 | 9.92 | 35.97 | 64.82 | 15.00 |
| 25 | INH | N17 | 8.95 | 36.39 | 67.18 | 15.00 |
| 25 | INH | C18 | 9.50 | 37.7.0 | 67.57 | 15.00 |
| 25 | INH | C19 | 9.05 | 38.78 | 68.64 | 15.00 |
| 25 | INH | O20 | 8.53 | 39.68 | 67.70 | 15.00 |
| 25 | INH | C21 | 10.52 | 39.34 | 69.16 | 15.00 |
| 25 | INH | N22 | 11.1& | 38.50 | 70.20 | 15.00 |
| 25 | INH | C23 | 12.14 | 38.91 | 71.00 | 15.00 |
| 25 | INH | O24 | 12.59 | 40.07 | 70.97 | 15.00 |
| 25 | INH | C25 | 12.61 | 37.92 | 72.07 | 15.00 |
| 25 | INH | C26 | 11.69 | 38.19 | 73.25 | 15.00 |
| 25 | INH | C27 | 11.80 | 37.33 | 74.48 | 15.00 |
| 25 | INH | C28 | 12.06 | 35.90 | 74.03 | 15.00 |
| 25 | INH | C29 | 12.95 | 37.84 | 75.32 | 15.00 |
| 25 | INH | N30 | 14.03 | 38.09 | 72.47 | 15.00 |
| 25 | INH | C31 | 14.92 | 37.10 | 72.44 | 15.00 |
| 25 | INH | O32 | 14.63 | 35.96 | 72.06 | 15.00 |
| 25 | INH | C33 | 16.36 | 37.38 | 72.94 | 15.00 |
| 25 | INH | C34 | 17.21 | 36.17 | 73.26 | 15.00 |
| 25 | INH | C35 | 17.54 | 35.58 | 74.44 | 15.00 |
| 25 | INH | N36 | 18.35 | 34.51 | 74.16 | 15.00 |
| 25 | INH | C37 | 18.52 | 34.43 | 72.85 | 15.00 |
| 25 | INH | N38 | 17.85 | 35.42 | 72.28 | 15.00 |
| 26 | TRP | N | 7.57 | 40.50 | 73.34 | 15.00 |
| 26 | TRP | CA | 8.08 | 40.58 | 74.69 | 15.00 |
| 26 | TRP | CB | 9.55 | 41.06 | 74.66 | 15.00 |
| 26 | TRP | CG | 9.72 | 42.45 | 74.12 | 15.00 |
| 26 | TRP | CD2 | 9.74 | 43.67 | 74.85 | 15.00 |
| 26 | TRP | CE2 | 9.80 | 44.74 | 73.89 | 15.00 |
| 26 | TRP | CE3 | 9.72 | 43.99 | 76.22 | 15.00 |
| 26 | TRP | CD1 | 9.78 | 42.79 | 72.83 | 15.00 |
| 26 | TRP | NE1 | 9.82 | 44.15 | 72.67 | 15.00 |
| 26 | TRP | CZ2 | 9.83 | 46.10 | 74.25 | 15.00 |
| 26 | TRP | CZ3 | 9.75 | 45.31 | 76.58 | 15.00 |
| 26 | TRP | CH2 | 9.81 | 46.37 | 75.59 | 15.00 |
| 26 | TRP | C | 7.21 | 41.51 | 75.60 | 15.00 |
| 26 | TRP | O | 7.08 | 41.27 | 76.81 | 15.00 |
| 27 | ALA | N | 6.58 | 42.54 | 75.01 | 15.00 |
| 27 | ALA | CA | 5.77 | 43.48 | 75.79 | 15.00 |
| 27 | ALA | CB | 5.51 | 44.71 | 74.96 | 15.00 |
| 27 | ALA | C | 4.47 | 42.75 | 76.05 | 15.00 |
| 27 | ALA | O | 3.88 | 42.85 | 71.12 | 15.00 |
| 28 | PHE | N | 4.07 | 41.90 | 75.13 | 15.00 |
| 28 | PHE | CA | 2.81 | 41.20 | 75.33 | 15.00 |
| 28 | PHE | CB | 2.29 | 40.66 | 73.99 | 15.00 |
| 28 | PHE | CG | 1.55 | 41.68 | 73.15 | 15.00 |
| 28 | PHE | CD1 | 2.23 | 42.39 | 72.20 | 15.00 |
| 28 | PHE | CD2 | 0.19 | 41.92 | 73.31 | 15.00 |
| 28 | PHE | CE1 | 1.57 | 43.34 | 71.43 | 15.00 |
| 28 | PHE | CE2 | −0.46 | 42.87 | 72.55 | 15.00 |
| 28 | PHE | CZ | 0.23 | 43.58 | 71.61 | 15.00 |
| 28 | PHE | C | 2.87 | 40.12 | 76.46 | 15.00 |
| 28 | PHE | O | 1.92 | 39.99 | 77.26 | 15.00 |
| 29 | SER | N | 3.97 | 39.39 | 76.54 | 15.00 |
| 29 | SER | CA | 4.16 | 38.37 | 77.55 | 15.00 |
| 29 | SER | CB | 5.40 | 37.55 | 77.18 | 15.00 |
| 29 | SER | OG | 5.72 | 36.66 | 78.21 | 15.00 |
| 29 | SER | C | 4.28 | 38.96 | 78.94 | 15.00 |
| 29 | SER | O | 3.68 | 38.47 | 79.91 | 15.00 |
| 30 | SER | N | 5.04 | 40.05 | 79.02 | 15.00 |
| 30 | SER | CA | 5.25 | 40.76 | 80.28 | 15.00 |
| 30 | SER | CB | 6.13 | 41.95 | 80.06 | 15.00 |
| 30 | SER | OG | 7.38 | 41.52 | 79.59 | 15.00 |
| 30 | SER | C | 3.96 | 41.22 | 80.96 | 15.00 |
| 30 | SER | O | 3.72 | 40.99 | 82.17 | 15.00 |
| 31 | VAL | N | 3.13 | 41.85 | 80.14 | 15.00 |
| 31 | VAL | CA | 1.83 | 42.35 | 80.51 | 15.00 |
| 31 | VAL | CB | 1.33 | 43.26 | 79.35 | 15.00 |
| 31 | VAL | CG1 | −0.15 | 43.27 | 79.23 | 15.00 |
| 31 | VAL | CG2 | 1.86 | 44.66 | 79.52 | 15.00 |
| 31 | VAL | C | 0.91 | 41.16 | 80.90 | 15.00 |
| 31 | VAL | O | 0.02 | 41.32 | 81.77 | 15.00 |
| 32 | GLY | N | 1.16 | 39.98 | 80.31 | 15.00 |
| 32 | GLY | CA | 0.35 | 38.81 | 80.61 | 15.00 |
| 32 | GLY | C | 0.70 | 38.25 | 81.97 | 15.00 |
| 32 | GLY | O | −0.17 | 37.79 | 82.70 | 15.00 |
| 33 | ALA | N | 1.98 | 38.30 | 82.34 | 15.00 |
| 33 | ALA | CA | 2.47 | 37.84 | 83.63 | 15.00 |
| 33 | ALA | CB | 3.98 | 37.93 | 83.67 | 15.00 |
| 33 | ALA | C | 1.84 | 38.86 | 84.60 | 15.00 |
| 33 | ALA | O | 1.09 | 38.48 | 85.52 | 15.00 |
| 34 | LEU | N | 2.09 | 40.15 | 84.37 | 15.00 |
| 34 | LEU | CA | 1.54 | 41.22 | 85.20 | 15.00 |
| 34 | LEU | CB | 1.88 | 42.56 | 84.56 | 15.00 |
| 34 | LEU | CG | 3.30 | 43.17 | 84.66 | 15.00 |
| 34 | LEU | CD1 | 3.26 | 44.56 | 84.13 | 15.00 |
| 34 | LEU | CD2 | 3.76 | 43.24 | 86.11 | 15.00 |
| 34 | LEU | C | 0.02 | 41.13 | 85.45 | 15.00 |
| 34 | LEU | O | −0.47 | 41.28 | 86.60 | 15.00 |
| 35 | GLU | N | −0.70 | 40.80 | 84.39 | 15.00 |
| 35 | GLU | CA | −2.16 | 40.62 | 84.49 | 15.00 |
| 35 | GLU | CB | −2.77 | 40.37 | 83.11 | 15.00 |
| 35 | GLU | CG | −2.92 | 41.61 | 82.27 | 15.00 |
| 35 | GLU | CD | −3.06 | 41.33 | 80.78 | 15.00 |
| 35 | GLU | OE1 | −2.97 | 40.14 | 80.38 | 15.00 |

TABLE X-continued

Table of the orthogonal three dimensional coordinates in Ångstroms and B factors (Å$^2$) for the cathepsin K complex with inhibitor 1-N-(N-imidazole acetyl-leucinyl)-amino-3-N-(4-phenoxy-phenyl-sulfonyl)-amino-propan-2-one

| Residue | | Atom | X | Y | Z | B |
|---|---|---|---|---|---|---|
| 35 | GLU | OE2 | -3.31 | 42.29 | 80.00 | 15.00 |
| 35 | GLU | C | -2.60 | 39.51 | 85.47 | 15.00 |
| 35 | GLU | O | -3.31 | 39.78 | 86.45 | 15.00 |
| 36 | GLY | N | -2.11 | 38.29 | 85.24 | 15.00 |
| 36 | GLY | CA | -2.42 | 37.14 | 86.06 | 15.00 |
| 36 | GLY | C | -2.20 | 37.38 | 87.56 | 15.00 |
| 36 | GLY | O | -2.96 | 36.89 | 88.40 | 15.00 |
| 37 | GLN | N | -1.13 | 38.09 | 87.89 | 15.00 |
| 37 | GLN | CA | -0.78 | 38.39 | 89.27 | 15.00 |
| 37 | GLN | CB | 0.64 | 38.96 | 89.35 | 15.00 |
| 37 | GLN | CG | 1.72 | 37.92 | 89.12 | 15.00 |
| 37 | GLN | CD | 1.50 | 36.73 | 90.00 | 15.00 |
| 37 | GLN | OE1 | 1.69 | 36.81 | 91.20 | 15.00 |
| 37 | GLN | NE2 | 1.12 | 35.61 | 89.42 | 15.00 |
| 37 | GLN | C | -1.78 | 39.38 | 89.83 | 15.00 |
| 37 | GLN | O | -2.30 | 39.19 | 90.94 | 15.00 |
| 38 | LEU | N | -2.10 | 40.38 | 89.02 | 15.00 |
| 38 | LEU | CA | -3.04 | 41.41 | 89.38 | 15.00 |
| 38 | LEU | CB | -3.28 | 42.29 | 88.15 | 15.00 |
| 38 | LEU | CG | -4.10 | 43.56 | 88.33 | 15.00 |
| 38 | LEU | CD1 | -3.72 | 44.25 | 89.66 | 15.00 |
| 38 | LEU | CD2 | -3.95 | 44.48 | 87.16 | 15.00 |
| 38 | LEU | C | -4.32 | 40.75 | 89.82 | 15.00 |
| 38 | LEU | O | -4.90 | 41.05 | 90.86 | 15.00 |
| 39 | LYS | N | -4.75 | 39.78 | 89.04 | 15.00 |
| 39 | LYS | CA | -5.95 | 39.07 | 89.36 | 15.00 |
| 39 | LYS | CB | -6.29 | 38.15 | 88.20 | 15.00 |
| 39 | LYS | CG | -7.34 | 37.13 | 88.56 | 15.00 |
| 39 | LYS | CD | -8.65 | 37.80 | 88.80 | 15.00 |
| 39 | LYS | CE | -9.71 | 36.74 | 88.86 | 15.00 |
| 39 | LYS | NZ | -10.82 | 37.33 | 89.61 | 15.00 |
| 39 | LYS | C | -5.78 | 38.28 | 90.67 | 15.00 |
| 39 | LYS | O | -6.62 | 38.34 | 91.53 | 15.00 |
| 40 | LYS | N | -4.66 | 37.59 | 90.83 | 15.00 |
| 40 | LYS | CA | -4.40 | 36.83 | 92.03 | 15.00 |
| 40 | LYS | CB | -3.01 | 36.20 | 91.96 | 15.00 |
| 40 | LYS | CG | -2.68 | 35.31 | 93.16 | 15.00 |
| 40 | LYS | CD | -1.38 | 34.53 | 93.00 | 15.00 |
| 40 | LYS | CE | -1.10 | 33.63 | 94.23 | 15.00 |
| 40 | LYS | NZ | -0.27 | 32.41 | 93.89 | 15.00 |
| 40 | LYS | C | -4.50 | 37.71 | 93.27 | 15.00 |
| 40 | LYS | O | -5.26 | 37.42 | 94.20 | 15.00 |
| 41 | LYS | N | -3.86 | 38.87 | 93.18 | 15.00 |
| 41 | LYS | CA | -3.77 | 39.84 | 94.28 | 15.00 |
| 41 | LYS | CB | -2.31 | 40.32 | 94.41 | 15.00 |
| 41 | LYS | CG | -1.28 | 39.21 | 94.20 | 15.00 |
| 41 | LYS | CD | -0.04 | 39.35 | 95.07 | 15.00 |
| 41 | LYS | CE | 0.68 | 38.01 | 95.15 | 15.00 |
| 41 | LYS | NZ | -0.14 | 36.86 | 95.66 | 15.00 |
| 41 | LYS | C | -4.64 | 41.07 | 94.09 | 15.00 |
| 41 | LYS | O | -4.15 | 42.18 | 94.26 | 15.00 |
| 42 | THR | N | -5.91 | 40.88 | 93.78 | 15.00 |
| 42 | THR | CA | -6.80 | 42.01 | 93.60 | 15.00 |
| 42 | THR | CB | -6.50 | 42.75 | 92.28 | 15.00 |
| 42 | THR | OG1 | -5.17 | 43.26 | 92.28 | 15.00 |
| 42 | THR | CG2 | -7.48 | 43.85 | 92.07 | 15.00 |
| 42 | THR | C | -8.22 | 41.47 | 93.50 | 15.00 |
| 42 | THR | O | -9.17 | 42.02 | 94.07 | 15.00 |
| 43 | GLY | N | -8.37 | 40.40 | 92.74 | 15.00 |
| 43 | GLY | CA | -9.67 | 39.80 | 92.56 | 15.00 |
| 43 | GLY | C | -10.28 | 40.20 | 91.22 | 15.00 |
| 43 | GLY | O | -11.22 | 39.57 | 90.74 | 15.00 |
| 44 | LYS | N | -9.65 | 41.19 | 90.58 | 15.00 |
| 44 | LYS | CA | -10.13 | 41.70 | 89.32 | 15.00 |
| 44 | LYS | CB | -10.71 | 43.10 | 89.52 | 15.00 |
| 44 | LYS | CG | -11.95 | 43.16 | 90.39 | 15.00 |
| 44 | LYS | CD | -12.36 | 44.57 | 90.76 | 15.00 |
| 44 | LYS | CE | -11.43 | 45.21 | 91.78 | 15.00 |
| 44 | LYS | NZ | -11.50 | 44.47 | 93.08 | 15.00 |
| 44 | LYS | C | -9.02 | 41.76 | 88.30 | 15.00 |
| 44 | LYS | O | -7.91 | 42.20 | 88.61 | 15.00 |
| 45 | LEU | N | -9.35 | 41.40 | 87.07 | 15.00 |
| 45 | LEU | CA | -8.38 | 41.39 | 85.99 | 15.00 |
| 45 | LEU | CB | -8.61 | 40.14 | 85.13 | 15.00 |
| 45 | LEU | CG | -7.85 | 39.77 | 83.85 | 15.00 |
| 45 | LEU | CD1 | -6.47 | 39.23 | 84.16 | 15.00 |
| 45 | LEU | CD2 | -8.67 | 38.72 | 83.14 | 15.00 |
| 45 | LEU | C | -8.55 | 42.68 | 85.16 | 15.00 |
| 45 | LEU | O | -9.55 | 43.36 | 85.27 | 15.00 |
| 46 | LEU | N | -7.57 | 43.04 | 84.37 | 15.00 |
| 46 | LEU | CA | -7.65 | 44.23 | 83.55 | 15.00 |
| 46 | LEU | CB | -7.27 | 45.46 | 84.35 | 15.00 |
| 46 | LEU | CG | -7.82 | 46.76 | 83.83 | 15.00 |
| 46 | LEU | CD1 | -9.28 | 46.67 | 83.92 | 15.00 |
| 46 | LEU | CD2 | -7.33 | 47.91 | 84.71 | 15.00 |
| 46 | LEU | C | -6.63 | 44.03 | 82.45 | 15.00 |
| 46 | LEU | O | -5.67 | 43.30 | 82.61 | 15.00 |
| 47 | ASN | N | -6.80 | 44.76 | 81.36 | 15.00 |
| 47 | ASN | CA | -5.90 | 44.66 | 80.25 | 15.00 |
| 47 | ASN | CB | -6.61 | 45.08 | 78.95 | 15.00 |
| 47 | ASN | CG | -7.47 | 43.98 | 78.39 | 15.00 |
| 47 | ASN | OD1 | -7.52 | 42.88 | 78.93 | 15.00 |
| 47 | ASN | ND2 | -8.19 | 44.28 | 77.33 | 15.00 |
| 47 | ASN | C | -4.77 | 45.63 | 80.52 | 15.00 |
| 47 | ASN | O | -5.02 | 46.82 | 80.64 | 15.00 |
| 48 | LEU | N | -3.54 | 45.17 | 80.66 | 15.00 |
| 48 | LEU | CA | -2.44 | 46.13 | 80.87 | 15.00 |
| 48 | LEU | CB | -1.29 | 45.54 | 81.75 | 15.00 |
| 48 | LEU | CG | -1.76 | 45.23 | 83.19 | 15.00 |
| 48 | LEU | CD1 | -0.62 | 44.99 | 84.10 | 15.00 |
| 48 | LEU | CD2 | -2.69 | 46.29 | 83.75 | 15.00 |
| 48 | LEU | C | -1.96 | 46.66 | 79.51 | 15.00 |
| 48 | LEU | O | -2.40 | 46.14 | 78.46 | 15.00 |
| 49 | SER | N | -1.12 | 47.70 | 79.52 | 15.00 |
| 49 | SER | CA | -0.63 | 48.29 | 78.28 | 15.00 |
| 49 | SER | CB | -0.70 | 49.82 | 78.41 | 15.00 |
| 49 | SER | OG | 0.06 | 50.46 | 77.43 | 15.00 |
| 49 | SER | C | 0.75 | 47.87 | 77.84 | 15.00 |
| 49 | SER | O | 1.75 | 48.29 | 78.43 | 15.00 |
| 50 | PRO | N | 0.81 | 47.08 | 76.75 | 15.00 |
| 50 | PRO | CD | -0.34 | 46.48 | 76.03 | 15.00 |
| 50 | PRO | CA | 2.10 | 46.61 | 76.22 | 15.00 |
| 50 | PRO | CB | 1.68 | 45.45 | 75.34 | 15.00 |
| 50 | PRO | CG | 0.33 | 45.96 | 74.79 | 15.00 |
| 50 | PRO | C | 2.77 | 47.79 | 75.45 | 15.00 |
| 50 | PRO | O | 3.99 | 47.96 | 75.47 | 15.00 |
| 51 | GLN | N | 1.96 | 48.67 | 74.86 | 15.00 |
| 51 | GLN | CA | 2.48 | 49.87 | 74.18 | 15.00 |
| 51 | GLN | CB | 1.37 | 50.77 | 73.66 | 15.00 |
| 51 | GLN | CG | 2.00 | 51.92 | 72.85 | 15.00 |
| 51 | GLN | CD | 2.33 | 51.51 | 71.46 | 15.00 |
| 51 | GLN | OE1 | 1.83 | 50.49 | 70.97 | 15.00 |
| 51 | GLN | NE2 | 3.19 | 52.26 | 70.81 | 15.00 |
| 51 | GLN | C | 3.29 | 50.70 | 75.17 | 15.00 |
| 51 | GLN | O | 4.21 | 51.38 | 74.79 | 15.00 |
| 52 | ASN | N | 2.93 | 50.65 | 76.45 | 15.00 |
| 52 | ASN | CA | 3.62 | 51.40 | 77.47 | 15.00 |
| 52 | ASN | CB | 2.96 | 51.15 | 78.82 | 15.00 |
| 52 | ASN | CG | 3.52 | 52.04 | 79.91 | 15.00 |
| 52 | ASN | OD1 | 4.31 | 52.93 | 79.64 | 15.00 |
| 52 | ASN | ND2 | 3.09 | 51.81 | 81.14 | 15.00 |
| 52 | ASN | C | 5.04 | 50.91 | 77.52 | 15.00 |
| 52 | ASN | O | 5.98 | 51.71 | 77.54 | 15.00 |
| 53 | LEU | N | 5.19 | 49.60 | 77.57 | 15.00 |
| 53 | LEU | CA | 6.53 | 49.05 | 77.64 | 15.00 |
| 53 | LEU | CB | 6.40 | 47.59 | 77.98 | 15.00 |
| 53 | LEU | CG | 5.80 | 47.51 | 79.34 | 15.00 |
| 53 | LEU | CD1 | 5.66 | 46.07 | 79.79 | 15.00 |
| 53 | LEU | CD2 | 6.65 | 48.34 | 80.33 | 15.00 |
| 53 | LEU | C | 7.25 | 49.26 | 76.30 | 15.00 |
| 53 | LEU | O | 8.43 | 49.52 | 76.27 | 15.00 |
| 54 | VAL | N | 6.53 | 49.17 | 75.19 | 15.00 |

TABLE X-continued

Table of the orthogonal three dimensional coordinates in Ångstroms and B factors (Å²) for the cathepsin K complex with inhibitor 1-N-(N-imidazole acetyl-leucinyl)-amino-3-N-(4-phenoxy-phenyl-sulfonyl)-amino-propan-2-one

| Residue | | Atom | X | Y | Z | B |
|---|---|---|---|---|---|---|
| 54 | VAL | CA | 7.19 | 49.34 | 73.89 | 15.00 |
| 54 | VAL | CB | 6.25 | 49.16 | 72.69 | 15.00 |
| 54 | VAL | CG1 | 6.98 | 49.50 | 71.41 | 15.00 |
| 54 | VAL | CG2 | 5.83 | 47.75 | 72.63 | 15.00 |
| 54 | VAL | C | 7.89 | 50.66 | 73.74 | 15.00 |
| 54 | VAL | O | 9.06 | 50.71 | 73.32 | 15.00 |
| 55 | ASP | N | 7.28 | 51.70 | 74.27 | 15.00 |
| 55 | ASP | CA | 7.87 | 53.05 | 74.15 | 15.00 |
| 55 | ASP | CB | 6.76 | 54.08 | 73.93 | 15.00 |
| 55 | ASP | CG | 5.70 | 53.58 | 72.94 | 15.00 |
| 55 | ASP | OD1 | 5.95 | 52.76 | 72.00 | 15.00 |
| 55 | ASP | OD2 | 4.60 | 54.09 | 73.02 | 15.00 |
| 55 | ASP | C | 8.68 | 53.42 | 75.33 | 15.00 |
| 55 | ASP | O | 9.58 | 54.23 | 75.23 | 15.00 |
| 56 | CYS | N | 8.38 | 52.90 | 76.50 | 15.00 |
| 56 | CYS | CA | 9.13 | 53.37 | 77.67 | 15.00 |
| 56 | CYS | C | 10.33 | 52.59 | 78.21 | 15.00 |
| 56 | CYS | O | 11.25 | 53.15 | 78.82 | 15.00 |
| 56 | CYS | CB | 8.16 | 53.80 | 78.81 | 15.00 |
| 56 | CYS | SG | 6.73 | 54.73 | 78.24 | 15.00 |
| 57 | VAL | N | 10.39 | 51.31 | 77.97 | 15.00 |
| 57 | VAL | CA | 11.49 | 50.47 | 78.46 | 15.00 |
| 57 | VAL | CB | 11.10 | 48.99 | 78.38 | 15.00 |
| 57 | VAL | CG1 | 12.15 | 48.16 | 78.95 | 15.00 |
| 57 | VAL | CG2 | 9.83 | 48.77 | 79.11 | 15.00 |
| 57 | VAL | C | 12.66 | 50.67 | 77.55 | 15.00 |
| 57 | VAL | O | 12.94 | 49.87 | 76.66 | 15.00 |
| 58 | SER | N | 13.40 | 51.73 | 77.79 | 15.00 |
| 58 | SER | CA | 14.54 | 52.04 | 76.91 | 15.00 |
| 58 | SER | CB | 15.13 | 53.44 | 77.26 | 15.00 |
| 58 | SER | OG | 15.02 | 53.68 | 78.65 | 15.00 |
| 58 | SER | C | 15.61 | 50.98 | 76.86 | 15.00 |
| 58 | SER | O | 16.39 | 50.92 | 75.91 | 15.00 |
| 59 | GLU | N | 15.66 | 50.15 | 77.91 | 15.00 |
| 59 | GLU | CA | 16.66 | 49.07 | 78.00 | 15.00 |
| 59 | GLU | CB | 16.59 | 48.34 | 79.35 | 15.00 |
| 59 | GLU | CG | 16.98 | 49.19 | 80.58 | 15.00 |
| 59 | GLU | CD | 15.98 | 50.33 | 80.88 | 15.00 |
| 59 | GLU | OE1 | 14.75 | 50.10 | 80.81 | 15.00 |
| 59 | GLU | OE2 | 16.46 | 51.46 | 81.17 | 15.00 |
| 59 | GLU | C | 16.48 | 48.04 | 76.89 | 15.00 |
| 59 | GLU | O | 17.36 | 47.20 | 76.67 | 15.00 |
| 60 | ASN | N | 15.31 | 48.07 | 76.27 | 15.00 |
| 60 | ASN | CA | 15.00 | 47.16 | 75.19 | 15.00 |
| 60 | ASN | CB | 13.64 | 46.51 | 75.47 | 15.00 |
| 60 | ASN | CG | 13.69 | 45.49 | 76.59 | 15.00 |
| 60 | ASN | OD1 | 12.76 | 45.39 | 77.36 | 15.00 |
| 60 | ASN | ND2 | 14.76 | 44.68 | 76.63 | 15.00 |
| 60 | ASN | C | 14.98 | 47.89 | 73.85 | 15.00 |
| 60 | ASN | O | 15.26 | 49.09 | 73.79 | 15.00 |
| 61 | ASP | N | 14.67 | 47.16 | 72.79 | 15.00 |
| 61 | ASP | CA | 14.64 | 47.72 | 71.44 | 15.00 |
| 61 | ASP | CB | 15.38 | 46.80 | 70.48 | 15.00 |
| 61 | ASP | CG | 16.10 | 47.57 | 69.36 | 15.00 |
| 61 | ASP | OD1 | 16.04 | 48.81 | 69.34 | 15.00 |
| 61 | ASP | OD2 | 16.76 | 46.92 | 68.52 | 15.00 |
| 61 | ASP | C | 13.28 | 48.07 | 70.81 | 15.00 |
| 61 | ASP | O | 13.13 | 48.13 | 69.60 | 15.00 |
| 62 | GLY | N | 12.31 | 48.40 | 71.63 | 15.00 |
| 62 | GLY | CA | 10.98 | 48.67 | 71.11 | 15.00 |
| 62 | GLY | C | 10.49 | 47.51 | 70.24 | 15.00 |
| 62 | GLY | O | 10.64 | 46.38 | 70.57 | 15.00 |
| 63 | CYS | N | 9.98 | 47.80 | 69.05 | 15.00 |
| 63 | CYS | CA | 9.47 | 46.79 | 68.11 | 15.00 |
| 63 | CYS | C | 10.61 | 45.95 | 67.62 | 15.00 |
| 63 | CYS | O | 10.41 | 45.05 | 66.81 | 15.00 |
| 63 | CYS | CB | 8.71 | 47.45 | 66.95 | 15.00 |
| 63 | CYS | SG | 7.16 | 48.19 | 67.39 | 15.00 |
| 64 | GLY | N | 11.82 | 46.25 | 68.06 | 15.00 |
| 64 | GLY | CA | 12.94 | 45.47 | 67.59 | 15.00 |
| 64 | GLY | C | 13.32 | 44.36 | 68.55 | 15.00 |
| 64 | GLY | O | 14.37 | 43.74 | 68.40 | 15.00 |
| 65 | GLY | N | 12.48 | 44.12 | 69.55 | 15.00 |
| 65 | GLY | CA | 12.76 | 43.06 | 70.49 | 15.00 |
| 65 | GLY | C | 13.11 | 43.58 | 71.88 | 15.00 |
| 65 | GLY | O | 13.33 | 44.80 | 72.13 | 15.00 |
| 66 | GLY | N | 13.21 | 42.63 | 72.80 | 15.00 |
| 66 | GLY | CA | 13.50 | 43.00 | 74.18 | 15.00 |
| 66 | GLY | C | 13.34 | 41.82 | 75.15 | 15.00 |
| 66 | GLY | O | 12.91 | 40.73 | 74.72 | 15.00 |
| 67 | TYR | N | 13.65 | 42.02 | 76.42 | 15.00 |
| 67 | TYR | CA | 13.55 | 40.94 | 77.37 | 15.00 |
| 67 | TYR | CB | 14.85 | 40.83 | 78.19 | 15.00 |
| 67 | TYR | CG | 16.13 | 40.41 | 77.42 | 15.00 |
| 67 | TYR | CD1 | 16.31 | 39.16 | 76.96 | 15.00 |
| 67 | TYR | CE1 | 17.51 | 38.77 | 76.29 | 15.00 |
| 67 | TYR | CD2 | 17.13 | 41.25 | 77.20 | 15.00 |
| 67 | TYR | CE2 | 18.32 | 40.83 | 76.53 | 15.00 |
| 67 | TYR | CZ | 18.49 | 39.61 | 76.08 | 15.00 |
| 67 | TYR | OH | 19.63 | 39.12 | 75.47 | 15.00 |
| 67 | TYR | C | 12.41 | 41.24 | 78.31 | 15.00 |
| 67 | TYR | O | 12.00 | 42.40 | 78.46 | 15.00 |
| 68 | MET | N | 11.84 | 40.20 | 78.88 | 15.00 |
| 68 | MET | CA | 10.72 | 40.40 | 79.78 | 15.00 |
| 68 | MET | CB | 10.01 | 39.09 | 80.00 | 15.00 |
| 68 | MET | CG | 9.14 | 38.63 | 78.85 | 15.00 |
| 68 | MET | SD | 10.15 | 37.92 | 77.61 | 15.00 |
| 68 | MET | CE | 10.37 | 36.10 | 78.19 | 15.00 |
| 68 | MET | C | 11.20 | 41.05 | 81.10 | 15.00 |
| 68 | MET | O | 10.55 | 41.92 | 81.68 | 15.00 |
| 69 | THR | N | 12.33 | 40.56 | 81.59 | 15.00 |
| 69 | THR | CA | 12.91 | 41.02 | 82.85 | 15.00 |
| 69 | THR | CB | 14.24 | 40.26 | 83.21 | 15.00 |
| 69 | THR | OG1 | 15.16 | 40.38 | 82.12 | 15.00 |
| 69 | THR | CG2 | 13.99 | 38.77 | 83.56 | 15.00 |
| 69 | THR | C | 13.15 | 42.55 | 82.80 | 15.00 |
| 69 | THR | O | 13.15 | 43.20 | 83.83 | 15.00 |
| 70 | ASN | N | 13.42 | 43.10 | 81.63 | 15.00 |
| 70 | ASN | CA | 13.61 | 44.55 | 81.51 | 15.00 |
| 70 | ASN | CB | 14.23 | 44.95 | 80.15 | 15.00 |
| 70 | ASN | CG | 15.73 | 44.64 | 80.08 | 15.00 |
| 70 | ASN | OD1 | 16.28 | 44.44 | 78.98 | 15.00 |
| 70 | ASN | ND2 | 16.41 | 44.61 | 81.22 | 15.00 |
| 70 | ASN | C | 12.27 | 45.27 | 81.66 | 15.00 |
| 70 | ASN | O | 12.24 | 46.42 | 82.08 | 15.00 |
| 71 | ALA | N | 11.20 | 44.62 | 81.19 | 15.00 |
| 71 | ALA | CA | 9.84 | 45.13 | 81.24 | 15.00 |
| 71 | ALA | CB | 8.96 | 44.17 | 80.50 | 15.00 |
| 71 | ALA | C | 9.39 | 45.23 | 82.69 | 15.00 |
| 71 | ALA | O | 8.79 | 46.23 | 83.13 | 15.00 |
| 72 | PHE | N | 9.72 | 44.17 | 83.43 | 15.00 |
| 72 | PHE | CA | 9.39 | 44.09 | 84.87 | 15.00 |
| 72 | PHE | CB | 9.67 | 42.66 | 85.39 | 15.00 |
| 72 | PHE | CG | 8.80 | 41.59 | 84.75 | 15.00 |
| 72 | PHE | CD1 | 7.52 | 41.87 | 84.33 | 15.00 |
| 72 | PHE | CD2 | 9.28 | 40.32 | 84.57 | 15.00 |
| 72 | PHE | CE1 | 6.73 | 40.91 | 83.73 | 15.00 |
| 72 | PHE | CE2 | 8.50 | 39.35 | 83.98 | 15.00 |
| 72 | PHE | CZ | 7.23 | 39.64 | 83.56 | 15.00 |
| 72 | PHE | C | 10.19 | 45.09 | 85.71 | 15.00 |
| 72 | PHE | O | 9.73 | 45.60 | 86.72 | 15.00 |
| 73 | GLN | N | 11.41 | 45.38 | 85.28 | 15.00 |
| 73 | GLN | CA | 12.27 | 46.36 | 85.97 | 15.00 |
| 73 | GLN | CB | 13.74 | 46.30 | 85.47 | 15.00 |
| 73 | GLN | CG | 14.74 | 46.94 | 86.38 | 15.00 |
| 73 | GLN | CD | 14.58 | 46.42 | 87.78 | 15.00 |
| 73 | GLN | OE1 | 14.18 | 45.26 | 87.96 | 15.00 |
| 73 | GLN | NE2 | 14.76 | 47.28 | 88.79 | 15.00 |
| 73 | GLN | C | 11.74 | 47.79 | 85.84 | 15.00 |
| 73 | GLN | O | 11.83 | 48.57 | 86.78 | 15.00 |
| 74 | TYR | N | 11.23 | 48.14 | 84.67 | 15.00 |
| 74 | TYR | CA | 10.67 | 49.45 | 84.41 | 15.00 |

TABLE X-continued

Table of the orthogonal three dimensional coordinates in Ångstroms and B factors (Å²) for the cathepsin K complex with inhibitor 1-N-(N-imidazole acetyl-leucinyl)-amino-3-N-(4-phenoxy-phenyl-sulfonyl)-amino-propan-2-one

| Residue | | Atom | X | Y | Z | B |
|---|---|---|---|---|---|---|
| 74 | TYR | CB | 10.48 | 49.62 | 82.93 | 15.00 |
| 74 | TYR | CG | 9.52 | 50.72 | 82.59 | 15.00 |
| 74 | TYR | CD1 | 9.90 | 51.97 | 82.44 | 15.00 |
| 74 | TYR | CE1 | 8.98 | 53.00 | 82.06 | 15.00 |
| 74 | TYR | CD2 | 8.25 | 50.50 | 82.38 | 15.00 |
| 74 | TYR | CE2 | 7.39 | 51.55 | 82.01 | 15.00 |
| 74 | TYR | CZ | 7.74 | 52.77 | 81.85 | 15.00 |
| 74 | TYR | OH | 6.87 | 53.67 | 81.39 | 15.00 |
| 74 | TYR | C | 9.35 | 49.64 | 85.16 | 15.00 |
| 74 | TYR | O | 9.04 | 50.74 | 85.58 | 15.00 |
| 75 | VAL | N | 8.60 | 48.58 | 85.39 | 15.00 |
| 75 | VAL | CA | 7.35 | 48.70 | 86.13 | 15.00 |
| 75 | VAL | CB | 6.46 | 47.47 | 85.92 | 15.00 |
| 75 | VAL | CG1 | 5.15 | 47.64 | 86.74 | 15.00 |
| 75 | VAL | CG2 | 6.10 | 47.32 | 84.44 | 15.00 |
| 75 | VAL | C | 7.63 | 48.95 | 87.62 | 15.00 |
| 75 | VAL | O | 6.92 | 49.76 | 88.26 | 15.00 |
| 76 | GLN | N | 8.69 | 48.31 | 88.13 | 15.00 |
| 76 | GLN | CA | 9.12 | 48.47 | 89.51 | 15.00 |
| 76 | GLN | CB | 10.10 | 47.35 | 89.89 | 15.00 |
| 76 | GLN | CG | 10.55 | 47.31 | 91.38 | 15.00 |
| 76 | GLN | CD | 11.76 | 46.4r | 91.65 | 15.00 |
| 76 | GLN | OE1 | 12.14 | 46.22 | 92.80 | 15.00 |
| 76 | GLN | NE2 | 12.37 | 45.85 | 90.59 | 15.00 |
| 76 | GLN | C | 9.78 | 49.88 | 89.59 | 15.00 |
| 76 | GLN | O | 9.37 | 50.72 | 90.39 | 15.00 |
| 77 | LYS | N | 10.72 | 50.19 | 88.69 | 15.00 |
| 77 | LYS | CA | 11.40 | 51.49 | 88.72 | 15.00 |
| 77 | LYS | CB | 12.56 | 51.50 | 87.72 | 15.00 |
| 77 | LYS | CG | 13.20 | 52.85 | 87.44 | 15.00 |
| 77 | LYS | CD | 14.22 | 52.70 | 86.33 | 15.00 |
| 77 | LYS | CE | 15.18 | 51.56 | 86.62 | 15.00 |
| 77 | LYS | NZ | 16.20 | 51.34 | 85.56 | 15.00 |
| 77 | LYS | C | 10.51 | 52.71 | 88.55 | 15.00 |
| 77 | LYS | O | 10.73 | 53.76 | 89.17 | 15.00 |
| 78 | ASN | N | 9.50 | 52.55 | 87.70 | 15.00 |
| 78 | ASN | CA | 8.51 | 53.59 | 87.37 | 15.00 |
| 78 | ASN | CB | 7.84 | 53.25 | 86.04 | 15.00 |
| 78 | ASN | CG | 7.15 | 54.42 | 85.42 | 15.00 |
| 78 | ASN | OD1 | 7.70 | 55.49 | 85.36 | 15.00 |
| 78 | ASN | ND2 | 5.93 | 54.22 | 84.95 | 15.00 |
| 78 | ASN | C | 7.44 | 53.69 | 88.42 | 15.00 |
| 78 | ASN | O | 6.89 | 54.77 | 88.64 | 15.00 |
| 79 | ARG | N | 7.15 | 52.56 | 89.05 | 15.00 |
| 79 | ARG | CA | 6.14 | 52.48 | 90.08 | 15.00 |
| 79 | ARG | CB | 6.27 | 53.65 | 91.07 | 15.00 |
| 79 | ARG | CG | 7.58 | 53.69 | 91.85 | 15.00 |
| 79 | ARG | CD | 7.76 | 55.00 | 92.63 | 15.00 |
| 79 | ARG | NE | 6.66 | 55.34 | 93.55 | 15.00 |
| 79 | ARG | CZ | 6.30 | 54.65 | 94.63 | 15.00 |
| 79 | ARG | NH1 | 6.95 | 53.54 | 94.96 | 15.00 |
| 79 | ARG | NH2 | 5.21 | 55.01 | 95.31 | 15.00 |
| 79 | ARG | C | 4.77 | 52.46 | 89.43 | 15.00 |
| 79 | ARG | O | 3.80 | 52.99 | 90.00 | 15.00 |
| 80 | GLY | N | 4.66 | 51.78 | 88.30 | 15.00 |
| 80 | GLY | CA | 3.39 | 51.70 | 87.64 | 15.00 |
| 80 | GLY | C | 3.39 | 51.50 | 86.16 | 15.00 |
| 80 | GLY | O | 4.32 | 51.90 | 85.43 | 15.00 |
| 81 | ILE | N | 2.30 | 50.87 | 85.73 | 15.00 |
| 81 | ILE | CA | 2.03 | 50.55 | 84.34 | 15.00 |
| 81 | ILE | CB | 2.38 | 49.06 | 83.98 | 15.00 |
| 81 | ILE | CG2 | 1.41 | 48.10 | 84.64 | 15.00 |
| 81 | ILE | CG1 | 2.48 | 48.88 | 82.46 | 15.00 |
| 81 | ILE | CD1 | 2.67 | 47.47 | 82.00 | 15.00 |
| 81 | ILE | C | 0.57 | 50.92 | 84.01 | 15.00 |
| 81 | ILE | O | −0.33 | 50.73 | 84.82 | 15.00 |
| 82 | ASP | N | 0.35 | 51.53 | 82.85 | 15.00 |
| 82 | ASP | CA | −1.01 | 51.93 | 82.43 | 15.00 |
| 82 | ASP | CB | −0.91 | 52.93 | 81.27 | 15.00 |
| 82 | ASP | CG | −0.45 | 54.32 | 81.71 | 15.00 |
| 82 | ASP | OD1 | 0.52 | 54.88 | 81.14 | 15.00 |
| 82 | ASP | OD2 | −1.08 | 54.84 | 82.64 | 15.00 |
| 82 | ASP | C | −1.87 | 50.76 | 82.00 | 15.00 |
| 82 | ASP | O | −1.39 | 49.64 | 81.87 | 15.00 |
| 83 | SER | N | −3.16 | 51.03 | 81.87 | 15.00 |
| 83 | SER | CA | −4.11 | 50.02 | 81.42 | 15.00 |
| 83 | SER | CB | −5.54 | 50.23 | 82.00 | 15.00 |
| 83 | SER | OG | −5.97 | 51.58 | 81.87 | 15.00 |
| 83 | SER | C | −4.14 | 50.20 | 79.91 | 15.00 |
| 83 | SER | O | −3.48 | 51.11 | 79.34 | 15.00 |
| 84 | GLU | N | −4.79 | 49.26 | 79.24 | 15.00 |
| 84 | GLU | CA | −4.92 | 49.33 | 77.79 | 15.00 |
| 84 | GLU | CB | −5.77 | 48.16 | 77.25 | 15.00 |
| 84 | GLU | CG | −5.57 | 47.95 | 75.77 | 15.00 |
| 84 | GLU | CD | −4.09 | 47.91 | 75.42 | 15.00 |
| 84 | GLU | OE1 | −3.52 | 48.88 | 74.89 | 15.00 |
| 84 | GLU | OE2 | −3.46 | 46.90 | 75.73 | 15.00 |
| 84 | GLU | C | −5.65 | 50.62 | 77.45 | 15.00 |
| 84 | GLU | O | −5.13 | 51.48 | 76.76 | 15.00 |
| 85 | ASP | N | −6.84 | 50.77 | 78.03 | 15.00 |
| 85 | ASP | CA | −7.68 | 51.96 | 77.78 | 15.00 |
| 85 | ASP | CB | −9.03 | 51.85 | 78.51 | 15.00 |
| 85 | ASP | CG | −9.94 | 53.12 | 78.30 | 15.00 |
| 85 | ASP | OD1 | −10.32 | 53.78 | 79.30 | 15.00 |
| 85 | ASP | OD2 | −10.26 | 53.46 | 77.15 | 15.00 |
| 85 | ASP | C | −7.01 | 53.27 | 78.08 | 15.00 |
| 85 | ASP | O | −7.29 | 54.29 | 77.43 | 15.00 |
| 86 | ALA | N | −6.11 | 53.26 | 79.05 | 15.00 |
| 86 | ALA | CA | −5.41 | 54.47 | 79.38 | 15.00 |
| 86 | ALA | CB | −4.88 | 54.38 | 80.80 | 15.00 |
| 86 | ALA | C | −4.27 | 54.73 | 78.39 | 15.00 |
| 86 | ALA | O | −4.00 | 55.89 | 78.07 | 15.00 |
| 87 | TYR | N | −3.69 | 53.66 | 77.83 | 15.00 |
| 87 | TYR | CA | −2.57 | 53.78 | 76.88 | 15.00 |
| 87 | TYR | CB | −1.24 | 53.68 | 77.66 | 15.00 |
| 87 | TYR | CG | 0.04 | 54.14 | 77.00 | 15.00 |
| 87 | TYR | CD1 | 0.10 | 54.44 | 75.56 | 15.00 |
| 87 | TYR | CE1 | 1.32 | 54.83 | 74.98 | 15.00 |
| 87 | TYR | CD2 | 1.21 | 54.26 | 77.84 | 15.00 |
| 87 | TYR | CE2 | 2.42 | 54.65 | 77.33 | 15.00 |
| 87 | TYR | CZ | 2.49 | 54.94 | 75.86 | 15.00 |
| 87 | TYR | OH | 3.71 | 55.29 | 75.29 | 15.00 |
| 87 | TYR | C | −2.68 | 52.66 | 75.83 | 15.00 |
| 87 | TYR | O | −2.00 | 51.63 | 75.92 | 15.00 |
| 88 | PRO | N | −3.51 | 52.90 | 74.79 | 15.00 |
| 88 | PRO | CD | −4.53 | 53.97 | 74.75 | 15.00 |
| 88 | PRO | CA | −3.75 | 51.94 | 73.71 | 15.00 |
| 88 | PRO | CB | −4.87 | 52.62 | 72.90 | 15.00 |
| 88 | PRO | CG | −5.64 | 53.31 | 73.98 | 15.00 |
| 88 | PRO | C | −2.52 | 51.62 | 72.84 | 15.00 |
| 88 | PRO | O | −1.59 | 52.42 | 72.70 | 15.00 |
| 89 | TYR | N | −2.58 | 50.42 | 72.24 | 15.00 |
| 89 | TYR | CA | −1.54 | 49.87 | 71.38 | 15.00 |
| 89 | TYR | CB | −1.64 | 48.34 | 71.47 | 15.00 |
| 89 | TYR | CG | −0.54 | 47.59 | 70.84 | 15.00 |
| 89 | TYR | CD1 | 0.79 | 47.78 | 71.31 | 15.00 |
| 89 | TYR | CE1 | 1.83 | 47.13 | 70.72 | 15.00 |
| 89 | TYR | CD2 | −0.80 | 46.69 | 69.76 | 15.00 |
| 89 | TYR | CE2 | 0.20 | 46.03 | 69.15 | 15.00 |
| 89 | TYR | CZ | 1.53 | 46.24 | 69.61 | 15.00 |
| 89 | TYR | OH | 2.55 | 45.63 | 68.93 | 15.00 |
| 89 | TYR | C | −1.73 | 50.30 | 69.92 | 15.00 |
| 89 | TYR | O | −2.81 | 50.16 | 69.38 | 15.00 |
| 90 | VAL | N | −0.65 | 50.73 | 69.28 | 15.00 |
| 90 | VAL | CA | −0.69 | 51.22 | 67.88 | 15.00 |
| 90 | VAL | CB | −0.15 | 52.67 | 67.77 | 15.00 |
| 90 | VAL | CG1 | −0.81 | 53.58 | 68.80 | 15.00 |
| 90 | VAL | CG2 | 1.34 | 52.68 | 67.96 | 15.00 |
| 90 | VAL | C | 0.11 | 50.36 | 66.90 | 15.00 |
| 90 | VAL | O | −0.09 | 50.40 | 65.68 | 15.00 |
| 91 | GLY | N | 1.05 | 49.58 | 67.43 | 15.00 |
| 91 | GLY | CA | 1.85 | 48.75 | 66.55 | 15.00 |

TABLE X-continued

Table of the orthogonal three dimensional coordinates in Ångstroms and B factors (Å²) for the cathepsin K complex with inhibitor 1-N-(N-imidazole acetyl-leucinyl)-amino-3-N-(4-phenoxy-phenyl-sulfonyl)-amino-propan-2-one

| Residue | | Atom | X | Y | Z | B |
|---|---|---|---|---|---|---|
| 91 | GLY | C | 3.14 | 49.42 | 66.11 | 15.00 |
| 91 | GLY | O | 3.81 | 48.92 | 65.19 | 15.00 |
| 92 | GLN | N | 3.51 | 50.52 | 66.75 | 15.00 |
| 92 | GLN | CA | 4.75 | 51.17 | 66.39 | 15.00 |
| 92 | GLN | CB | 4.53 | 52.11 | 65.23 | 15.00 |
| 92 | GLN | CG | 3.31 | 52.97 | 65.48 | 15.00 |
| 92 | GLN | CD | 3.44 | 54.31 | 64.81 | 15.00 |
| 92 | GLN | OE1 | 2.68 | 54.64 | 63.92 | 15.00 |
| 92 | GLN | NE2 | 4.41 | 55.10 | 65.25 | 15.00 |
| 92 | GLN | C | 5.34 | 51.97 | 67.53 | 15.00 |
| 92 | GLN | O | 4.72 | 52.25 | 68.53 | 15.00 |
| 93 | GLU | N | 6.57 | 52.40 | 67.30 | 15.00 |
| 93 | GLU | CA | 7.33 | 53.20 | 68.25 | 15.00 |
| 93 | GLU | CB | 8.81 | 53.08 | 67.91 | 15.00 |
| 93 | GLU | CG | 9.33 | 51.65 | 68.15 | 15.00 |
| 93 | GLU | CD | 10.59 | 51.29 | 67.38 | 15.00 |
| 93 | GLU | OE1 | 10.87 | 51.94 | 66.34 | 15.00 |
| 93 | GLU | OE2 | 11.31 | 50.35 | 67.80 | 15.00 |
| 93 | GLU | C | 6.85 | 54.66 | 68.26 | 15.00 |
| 93 | GLU | O | 6.48 | 55.24 | 67.24 | 15.00 |
| 94 | GLU | N | 6.79 | 55.20 | 69.46 | 15.00 |
| 94 | GLU | CA | 6.36 | 56.56 | 69.67 | 15.00 |
| 94 | GLU | CB | 4.83 | 56.70 | 69.62 | 15.00 |
| 94 | GLU | CG | 4.07 | 55.48 | 70.04 | 15.00 |
| 94 | GLU | CD | 2.76 | 55.78 | 70.70 | 15.00 |
| 94 | GLU | OE1 | 1.99 | 56.60 | 70.14 | 15.00 |
| 94 | GLU | OE2 | 2.51 | 55.26 | 71.81 | 15.00 |
| 94 | GLU | C | 6.86 | 56.98 | 71.01 | 15.00 |
| 94 | GLU | O | 7.15 | 56.12 | 71.84 | 15.00 |
| 95 | SER | N | 6.98 | 58.29 | 71.23 | 15.00 |
| 95 | SER | CA | 7.47 | 58.78 | 72.52 | 15.00 |
| 95 | SER | CB | 7.26 | 6.0.29 | 72.63 | 15.00 |
| 95 | SER | CG | 6.14 | 60.73 | 71.85 | 15.00 |
| 95 | SER | C | 6.78 | 58.06 | 73.70 | 15.00 |
| 95 | SER | O | 5.61 | 57.59 | 73.59 | 15.00 |
| 96 | CYS | N | 7.52 | 57.90 | 74.80 | 15.00 |
| 96 | CYS | CA | 6.93 | 57.30 | 75.96 | 15.00 |
| 96 | CYS | C | 5.80 | 58.23 | 76.33 | 15.00 |
| 96 | CYS | O | 6.00 | 59.44 | 76.37 | 15.00 |
| 96 | CYS | CB | 7.95 | 57.27 | 77.09 | 15.00 |
| 96 | CYS | SG | 7.32 | 56.63 | 78.67 | 15.00 |
| 97 | MET | N | 4.58 | 57.73 | 76.42 | 15.00 |
| 97 | MET | CA | 3.46 | 58.59 | 76.84 | 15.00 |
| 97 | MET | CB | 2.40 | 5&.64 | 75.75 | 15.00 |
| 97 | MET | CG | 2.95 | 58.79 | 74.35 | 15.00 |
| 97 | MET | SD | 1.74 | 59.21 | 73.09 | 15.00 |
| 97 | MET | CE | 0.27 | 58.48 | 73.83 | 15.00 |
| 97 | MET | C | 2.79 | 58.10 | 78.14 | 15.00 |
| 97 | MET | O | 1.57 | 58.06 | 78.24 | 15.00 |
| 98 | TYR | N | 3.59 | 57.79 | 79.15 | 15.00 |
| 98 | TYR | CA | 3.09 | 57.31 | 80.45 | 15.00 |
| 98 | TYR | CB | 4.25 | 56.91 | 81.37 | 15.00 |
| 98 | TYR | CG | 3.71 | 56.31 | 82.64 | 15.00 |
| 98 | TYR | CD1 | 2.99 | 55.13 | 82.59 | 15.00 |
| 98 | TYR | CE1 | 2.42 | 54.60 | 83.75 | 15.00 |
| 98 | TYR | CD2 | 3.86 | 56.96 | 83.88 | 15.00 |
| 98 | TYR | CE2 | 3.30 | 56.45 | 85.03 | 15.00 |
| 98 | TYR | CZ | 2.59 | 55.27 | 84.95 | 15.00 |
| 98 | .TYR | OH | 1.99 | 54.70 | 86.05 | 15.00 |
| 98 | TYR | C | 2.17 | 58.29 | 81.19 | 15.00 |
| 98 | TYR | O | 2.56 | 59.42 | 81.48 | 15.00 |
| 99 | ASN | N | 0.97 | 57.85 | 81.49 | 15.00 |
| 99 | ASN | CA | −0.01 | 58.66 | 82.21 | 15.00 |
| 99 | ASN | CB | −1.39 | 58.64 | 81.52 | 15.00 |
| 99 | ASN | CG | −2.41 | 59.49 | 82.25 | 15.00 |
| 99 | ASN | OD1 | −2.15 | 59.98 | 83.35 | 15.00 |
| 99 | ASN | ND2 | −3.60 | 59.65 | 81.65 | 15.00 |
| 99 | ASN | C | −0.17 | 58.09 | 83.63 | 15.00 |
| 99 | ASN | O | −0.87 | 57.05 | 83.81 | 15.00 |
| 100 | PRO | N | 0.31 | 58.85 | 84.66 | 15.00 |
| 100 | PRO | CD | 0.81 | 60.23 | 84.63 | 15.00 |
| 100 | PRO | CA | 0.20 | 58.38 | 86.04 | 15.00 |
| 100 | PRO | CB | 0.80 | 59.53 | 86.83 | 15.00 |
| 100 | PRO | CG | 1.64 | 60.28 | 85.79 | 15.00 |
| 100 | PRO | C | −1.25 | 58.14 | 86.50 | 15.00 |
| 100 | PRO | O | −1.49 | 57.37 | 87.41 | 15.00 |
| 101 | THR | N | −2.22 | 58.73 | 85.82 | 15.00 |
| 101 | THR | CA | −3.61 | 58.53 | 86.23 | 15.00 |
| 101 | THR | CB | −4.58 | 59.63 | 85.74 | 15.00 |
| 101 | THR | OG1 | −5.12 | 59.28 | 84.45 | 15.00 |
| 101 | THR | CG2 | −3.91 | 60.96 | 85.67 | 15.00 |
| 101 | THR | C | −4.09 | 57.21 | 85.69 | 15.00 |
| 101 | THR | O | −5.05 | 56.64 | 86.24 | 15.00 |
| 102 | GLY | N | −3.50 | 56.77 | 84.58 | 15.00 |
| 102 | GLY | CA | −3.90 | 55.51 | 83.98 | 15.00 |
| 102 | GLY | C | −3.31 | 54.30 | 84.66 | 15.00 |
| 102 | GLY | O | −3.63 | 53.16 | 84.25 | 15.00 |
| 103 | LYS | N | −2.50 | 54.52 | 85.70 | 15.00 |
| 103 | LYS | CA | −1.87 | 53.41 | 86.40 | 15.00 |
| 103 | LYS | CB | −1.06 | 53.93 | 87.58 | 15.00 |
| 103 | LYS | CG | −0.26 | 52.86 | 88.29 | 15.00 |
| 103 | LYS | CD | −0.09 | 53.20 | 89.77 | 15.00 |
| 103 | LYS | CE | −1.41 | 52.95 | 90.56 | 15.00 |
| 103 | LYS | NZ | −1.62 | 51.48 | 90.82 | 15.00 |
| 103 | LYS | C | −2.90 | 52.38 | 86.85 | 15.00 |
| 103 | LYS | O | −3.84 | 52.70 | 87.56 | 15.00 |
| 104 | ALA | N | −2.70 | 51.13 | 86.45 | 15.00 |
| 104 | ALA | CA | −3.60 | 50.03 | 86.82 | 15.00 |
| 104 | ALA | CB | −4.23 | 49.45 | 85.59 | 15.00 |
| 104 | ALA | C | −2.81 | 48.95 | 87.53 | 15.00 |
| 104 | ALA | O | −3.37 | 48.03 | 88.10 | 15.00 |
| 105 | ALA | N | −1.49 | 49.07 | 87.52 | 15.00 |
| 105 | ALA | CA | −0.72 | 48.05 | 88.20 | 15.00 |
| 105 | ALA | CB | −0.65 | 46.80 | 87.34 | 15.00 |
| 105 | ALA | C | 0.66 | 48.46 | 88.70 | 15.00 |
| 105 | ALA | O | 1.21 | 49.47 | 88.26 | 15.00 |
| 106 | LYS | N | 1.18 | 47.64 | 89.63 | 15.00 |
| 106 | LYS | CA | 2.49 | 47.81 | 90.27 | 15.00 |
| 106 | LYS | CB | 2.33 | 48.37 | 91.70 | 15.00 |
| 106 | LYS | CG | 1.94 | 49.82 | 91.78 | 15.00 |
| 106 | LYS | CD | 2.39 | 50.49 | 93.08 | 15.00 |
| 106 | LYS | CE | 3.90 | 50.73 | 93.15 | 15.00 |
| 106 | LYS | NZ | 4.68 | 49.45 | 93.03 | 15.00 |
| 106 | LYS | C | 3.31 | 46.52 | 90.33 | 15.00 |
| 106 | LYS | O | 2.78 | 45.42 | 90.25 | 15.00 |
| 107 | CYS | N | 4.58 | 46.66 | 90.67 | 15.00 |
| 107 | CYS | CA | 5.44 | 45.50 | 90.73 | 15.00 |
| 107 | CYS | CB | 5.96 | 45.28 | 89.31 | 15.00 |
| 107 | CYS | SG | 7.11 | 43.91 | 89.12 | 15.00 |
| 107 | CYS | C | 6.58 | 45.74 | 91.71 | 15.00 |
| 107 | CYS | O | 7.13 | 46.84 | 91.75 | 15.00 |
| 108 | ARG | N | 6.93 | 44.73 | 92.50 | 15.00 |
| 108 | ARG | CA | 8.03 | 44.94 | 93.42 | 15.00 |
| 108 | ARG | CB | 7.57 | 44.79 | 94.87 | 15.00 |
| 108 | ARG | CG | 7.03 | 43.41 | 95.26 | 15.00 |
| 108 | ARG | CD | 6.66 | 43.37 | 96.77 | 15.00 |
| 108 | ARG | NE | 6.16 | 42.05 | 97.15 | 15.00 |
| 108 | ARG | CZ | 6.83 | 40.90 | 96.99 | 15.00 |
| 108 | ARG | NH1 | 8.05 | 40.88 | 96.47 | 15.00 |
| 108 | ARG | NH2 | 6.25 | 39.76 | 97.31 | 15.00 |
| 108 | ARG | C | 9.24 | 44.06 | 93.14 | 15.00 |
| 108 | ARG | O | 9.94 | 43.63 | 94.07 | 15.00 |
| 109 | GLY | N | 9.47 | 43.78 | 91.85 | 15.00 |
| 109 | GLY | CA | 10.58 | 42.92 | 91.49 | 15.00 |
| 109 | GLY | C | 10.15 | 41.85 | 90.50 | 15.00 |
| 109 | GLY | O | 9.05 | 41.91 | 89.95 | 15.00 |
| 110 | TYR | N | 10.97 | 40.81 | 90.37 | 15.00 |
| 110 | TYR | CA | 10.68 | 39.71 | 89.47 | 15.00 |
| 110 | TYR | CB | 10.79 | 40.15 | 88.01 | 15.00 |
| 110 | TYR | CG | 12.20 | 40.50 | 87.61 | 15.00 |
| 110 | TYR | CD1 | 12.66 | 41.85 | 87.79 | 15.00 |
| 110 | TYR | CE1 | 13.95 | 42.21 | 87.41 | 15.00 |

TABLE X-continued

Table of the orthogonal three dimensional coordinates in Ångstroms and B factors (Å$^2$) for the cathepsin K complex with inhibitor 1-N-(N-imidazole acetyl-leucinyl)-amino-3-N-(4-phenoxy-phenyl-sulfonyl)-amino-propan-2-one

| Residue | | Atom | X | Y | Z | B |
|---|---|---|---|---|---|---|
| 110 | TYR | CD2 | 13.08 | 39.49 | 87.02 | 15.00 |
| 110 | TYR | CE2 | 14.35 | 39.80 | 86.64 | 15.00 |
| 110 | TYR | CZ | 14.80 | 41.19 | 86.83 | 15.00 |
| 110 | TYR | OH | 16.07 | 41.57 | 86.47 | 15.00 |
| 110 | TYR | C | 11.67 | 38.57 | 89.72 | 15.00 |
| 110 | TYR | O | 12.72 | 38.78 | 90.34 | 15.00 |
| 111 | ARG | N | 11.36 | 37.37 | 89.26 | 15.00 |
| 111 | ARG | CA | 12.26 | 36.23 | 89.43 | 15.00 |
| 111 | ARG | CB | 11.86 | 35.41 | 90.67 | 15.00 |
| 111 | ARG | CG | 11.78 | 36.26 | 91.34 | 15.00 |
| 111 | ARG | CD | 12.04 | 35.36 | 93.15 | 15.00 |
| 111 | ARG | NE | 13.43 | 34.92 | 93.18 | 15.00 |
| 111 | ARG | CZ | 13.89 | 33.89 | 93.89 | 15.00 |
| 111 | ARG | NH1 | 15.19 | 33.60 | 93.83 | 15.00 |
| 111 | ARG | NH2 | 13.04 | 33.14 | 94.59 | 15.00 |
| 111 | ARG | C | 12.24 | 35.31 | 88.24 | 15.00 |
| 111 | ARG | O | 11.17 | 35.05 | 87.66 | 15.00 |
| 112 | GLU | N | 13.43 | 34.83 | 87.90 | 15.00 |
| 112 | GLU | CA | 13.63 | 33.90 | 86.82 | 15.00 |
| 112 | GLU | CB | 15.09 | 33.97 | 86.40 | 15.00 |
| 112 | GLU | CG | 15.46 | 35.25 | 85.64 | 15.00 |
| 112 | GLU | CD | 15.38 | 35.07 | 84.12 | 15.00 |
| 112 | GLU | OE1 | 14.25 | 35.12 | 83.56 | 15.00 |
| 112 | GLU | OE2 | 16.47 | 34.88 | 83.50 | 15.00 |
| 112 | GLU | C | 13.36 | 32.48 | 87.30 | 15.00 |
| 112 | GLU | O | 13.00 | 32.27 | 88.44 | 15.00 |
| 113 | ILE | N | 13.55 | 31.53 | 86.41 | 15.00 |
| 113 | ILE | CA | 13.36 | 30.12 | 86.72 | 15.00 |
| 113 | ILE | CB | 12.20 | 29.54 | 85.92 | 15.00 |
| 113 | ILE | CG2 | 12.22 | 28.02 | 85.90 | 15.00 |
| 113 | ILE | CG1 | 10.91 | 30.06 | 86.51 | 15.00 |
| 113 | ILE | CD1 | 9.69 | 29.82 | 85.68 | 15.00 |
| 113 | ILE | C | 14.68 | 29.49 | 86.33 | 15.00 |
| 113 | ILE | O | 15.33 | 29.97 | 85.44 | 15.00 |
| 114 | PRO | N | 15.20 | 28.55 | 87.13 | 15.00 |
| 114 | PRO | CD | 14.60 | 28.07 | 88.38 | 15.00 |
| 114 | PRO | CA | 16.49 | 27.87 | 86.88 | 15.00 |
| 114 | PRO | CB | 16.38 | 26.62 | 87.77 | 15.00 |
| 114 | PRO | CG | 15.73 | 27.17 | 88.97 | 15.00 |
| 114 | PRO | C | 16.69 | 27.54 | 85.40 | 15.00 |
| 114 | PRO | O | 15.93 | 26.78 | 84.83 | 15.00 |
| 115 | GLU | N | 17.71 | 28.13 | 84.80 | 15.00 |
| 115 | GLU | CA | 18.03 | 28.00 | 83.38 | 15.00 |
| 115 | GLU | CB | 19.41 | 28.59 | 83.11 | 15.00 |
| 115 | GLU | CG | 19.58 | 29.05 | 81.64 | 15.00 |
| 115 | GLU | CD | 20.85 | 29.87 | 81.42 | 15.00 |
| 115 | GLU | OE1 | 20.80 | 31.11 | 81.48 | 15.00 |
| 115 | GLU | OE2 | 21.91 | 29.28 | 81.19 | 15.00 |
| 115 | GLU | C | 17.96 | 26.62 | 82.77 | 15.00 |
| 115 | GLU | O | 18.99 | 25.96 | 82.65 | 15.00 |
| 116 | GLY | N | 16.78 | 26.24 | 82.28 | 15.00 |
| 116 | GLY | CA | 16.64 | 24.93 | 81.66 | 15.00 |
| 116 | GLY | C | 15.95 | 23.89 | 82.52 | 15.00 |
| 116 | GLY | O | 15.82 | 22.73 | 82.13 | 15.00 |
| 117 | ASN | N | 15.49 | 24.30 | 83.70 | 15.00 |
| 117 | ASN | CA | 14.84 | 23.38 | 84.61 | 15.00 |
| 117 | ASN | CB | 15.29 | 23.66 | 86.03 | 15.00 |
| 117 | ASN | CG | 14.55 | 22.85 | 87.06 | 15.00 |
| 117 | ASN | OD1 | 13.47 | 22.36 | 86.81 | 15.00 |
| 117 | ASN | ND2 | 15.14 | 22.73 | 88.25 | 15.00 |
| 117 | ASN | C | 13.34 | 23.50 | 84.47 | 15.00 |
| 117 | ASN | O | 12.71 | 24.37 | 85.05 | 15.00 |
| 118 | GLU | N | 12.78 | 22.55 | 83.74 | 15.00 |
| 118 | GLU | CA | 11.35 | 22.52 | 83.45 | 15.00 |
| 118 | GLU | CB | 11.10 | 21.52 | 82.33 | 15.00 |
| 118 | GLU | CG | 10.04 | 21.91 | 81.37 | 15.00 |
| 118 | GLU | CD | 9.94 | 20.95 | 80.16 | 15.00 |
| 118 | GLU | OE1 | 8.82 | 20.50 | 79.88 | 15.00 |
| 118 | GLU | OE2 | 10.96 | 20.58 | 79.52 | 15.00 |
| 118 | GLU | C | 10.45 | 22.18 | 84.64 | 15.00 |
| 118 | GLU | O | 9.30 | 22.61 | 84.67 | 15.00 |
| 119 | LYS | N | 10.97 | 21.46 | 85.63 | 15.00 |
| 119 | LYS | CA | 10.15 | 21.13 | 86.77 | 15.00 |
| 119 | LYS | CB | 10.74 | 19.95 | 87.52 | 15.00 |
| 119 | LYS | CG | 9.69 | 19.04 | 88.07 | 15.00 |
| 119 | LYS | CD | 8.84 | 18.47 | 86.94 | 15.00 |
| 119 | LYS | CE | 7.78 | 17:54 | 87.45 | 15.00 |
| 119 | LYS | NZ | 7.03 | 17.08 | 86.28 | 15.00 |
| 119 | LYS | C | 10.02 | 22.33 | 87.69 | 15.00 |
| 119 | LYS | O | 9.02 | 22.45 | 88.42 | 15.00 |
| 120 | ALA | N | 11.01 | 23.22 | 87.66 | 15.00 |
| 120 | ALA | CA | 10.99 | 24.43 | 88.48 | 15.00 |
| 120 | ALA | CB | 12.36 | 25.05 | 88.46 | 15.00 |
| 120 | ALA | C | 9.95 | 25.39 | 87.87 | 15.00 |
| 120 | ALA | O | 9.39 | 26.27 | 88.57 | 15.00 |
| 121 | LEU | N | 9.79 | 25.27 | 86.55 | 15.00 |
| 121 | LEU | CA | 8.83 | 26.05 | 85.78 | 15.00 |
| 121 | LEU | CB | 9.06 | 25.87 | 84.28 | 15.00 |
| 121 | LEU | CG | 8.06 | 26.54 | 83.31 | 15.00 |
| 121 | LEU | CD1 | 8.05 | 28.02 | 83.54 | 15.00 |
| 121 | LEU | CD2 | 8.42 | 26.24 | 81.90 | 15.00 |
| 121 | LEU | C | 7.43 | 25.59 | 86.13 | 15.00 |
| 121 | LEU | O | 6.59 | 26.43 | 86.46 | 15.00 |
| 122 | LYS | N | 7.17 | 24.28 | 86.10 | 15.00 |
| 122 | LYS | CA | 5.83 | 23.74 | 86.40 | 15.00 |
| 122 | LYS | CB | 5.81 | 22.20 | 86.25 | 15.00 |
| 122 | LYS | CG | 4.49 | 21.54 | 86.59 | 15.00 |
| 122 | LYS | CD | 4.61 | 20.10 | 86.92 | 15.00 |
| 122 | LYS | CE | 5.26 | 19.90 | 88.29 | 15.00 |
| 122 | LYS | NZ | 5.14 | 18.48 | 88.78 | 15.00 |
| 122 | LYS | C | 5.34 | 24.13 | 87.78 | 15.00 |
| 122 | LYS | O | 4.13 | 24.20 | 87.99 | 15.00 |
| 123 | ARG | N | 6.27 | 24.36 | 88.71 | 15.00 |
| 123 | ARG | CA | 5.90 | 24.16 | 90.06 | 15.00 |
| 123 | ARG | CB | 6.95 | 24.36 | 91.07 | 15.00 |
| 123 | ARG | CG | 7.05 | 22.94 | 91.45 | 15.00 |
| 123 | ARG | CD | 8.15 | 22.86 | 92.43 | 15.00 |
| 123 | ARG | NE | 9.44 | 23.25 | 91.82 | 15.00 |
| 123 | ARG | CZ | 10.56 | 23.53 | 92.50 | 15.00 |
| 123 | ARG | NH1 | 10.58 | 23.50 | 93.81 | 15.00 |
| 123 | ARG | NH2 | 11.71 | 23.76 | 91.85 | 15.00 |
| 123 | ARG | C | 5.71 | 26.25 | 90.17 | 15.00 |
| 123 | ARG | O | 5.12 | 26.72 | 91.13 | 15.00 |
| 124 | ALA | N | 6.31 | 27.00 | 89.25 | 15.00 |
| 124 | ALA | CA | 6.16 | 28.42 | 89.30 | 15.00 |
| 124 | ALA | CB | 7.22 | 29.12 | 88.43 | 15.00 |
| 124 | ALA | C | 4.78 | 28.73 | 88.81 | 15.00 |
| 124 | ALA | O | 4.06 | 29.46 | 89.47 | 15.00 |
| 125 | VAL | N | 4.37 | 28.09 | 87.72 | 15.00 |
| 125 | VAL | CA | 3.06 | 28.41 | 87.21 | 15.00 |
| 125 | VAL | CB | 2.82 | 27.94 | 85.72 | 15.00 |
| 125 | VAL | CG1 | 4.09 | 27.54 | 85.00 | 15.00 |
| 125 | VAL | CG2 | 1.70 | 26.88 | 85.60 | 15.00 |
| 125 | VAL | C | 2.03 | 27.82 | 88.15 | 15.00 |
| 125 | VAL | O | 0.89 | 28.28 | 88.17 | 15.00 |
| 126 | ALA | N | 2.42 | 26.86 | 88.98 | 15.00 |
| 126 | ALA | CA | 1.47 | 26.25 | 89.89 | 15.00 |
| 126 | ALA | CB | 1.94 | 24.91 | 90.29 | 15.00 |
| 126 | ALA | C | 1.32 | 27.11 | 91.12 | 15.00 |
| 126 | ALA | O | 0.22 | 27.27 | 91.63 | 15.00 |
| 127 | ARG | N | 2.42 | 27.71 | 91.55 | 15.00 |
| 127 | ARG | CA | 2.42 | 28.50 | 92.77 | 15.00 |
| 127 | ARG | CB | 3.67 | 28.22 | 93.60 | 15.00 |
| 127 | ARG | CG | 3.74 | 26.79 | 94.07 | 15.00 |
| 127 | ARG | CD | 5.07 | 26.45 | 94.67 | 15.00 |
| 127 | ARG | NE | 5.02 | 25.01 | 94.96 | 15.00 |
| 127 | ARG | CZ | 6.03 | 24.24 | 95.34 | 15.00 |
| 127 | ARG | NH1 | 5.84 | 22.94 | 95.55 | 15.00 |
| 127 | ARG | NH2 | 7.24 | 24.73 | 95.54 | 15.00 |
| 127 | ARG | C | 2.30 | 29.98 | 92.61 | 15.00 |
| 127 | ARG | O | 2.15 | 30.68 | 93.60 | 15.00 |
| 128 | VAL | N | 2.46 | 30.47 | 91.38 | 15.00 |

TABLE X-continued

Table of the orthogonal three dimensional coordinates in Ångstroms and B factors (Å²) for the cathepsin K complex with inhibitor 1-N-(N-imidazole acetyl-leucinyl)-amino-3-N-(4-phenoxy-phenyl-sulfonyl)-amino-propan-2-one

| Residue | Atom | X | Y | Z | B |
|---|---|---|---|---|---|
| 128 VAL | CA | 2.37 | 31.91 | 91.11 | 15.00 |
| 128 VAL | CB | 3.70 | 32.49 | 90.59 | 15.00 |
| 128 VAL | CG1 | 3.62 | 33.98 | 90.47 | 15.00 |
| 128 VAL | CG2 | 4.87 | 32.10 | 91.53 | 15.00 |
| 128 VAL | C | 1.29 | 32.25 | 90.10 | 15.00 |
| 128 VAL | O | 0.47 | 33.10 | 90.36 | 15.00 |
| 129 GLY | N | 1.30 | 31.60 | 88.94 | 15.00 |
| 129 GLY | CA | 0.31 | 31.85 | 87.91 | 15.00 |
| 129 GLY | C | 1.10 | 32.00 | 86.61 | 15.00 |
| 129 GLY | O | 2.27 | 31.60 | 86.57 | 15.00 |
| 130 PRO | N | 0.52 | 32.56 | 85.53 | 15.00 |
| 130 PRO | CD | −0.89 | 32.96 | 85.30 | 15.00 |
| 130 PRO | CA | 1.27 | 32.70 | 84.30 | 15.00 |
| 130 PRO | CB | 0.38 | 33.61 | 83.50 | 15.00 |
| 130 PRO | CG | −0.98 | 33.09 | 83.81 | 15.00 |
| 139 PRO | O | 2.68 | 33.24 | 84.44 | 15.00 |
| 130 PRO | O | 2.93 | 34.17 | 85.20 | 15.00 |
| 131 VAL | N | 3.59 | 32.56 | 83.75 | 15.00 |
| 131 VAL | CA | 5.01 | 32.88 | 83.76 | 15.00 |
| 131 VAL | CB | 5.79 | 31.64 | 84.27 | 15.00 |
| 131 VAL | CG1 | 7.25 | 31.88 | 84.32 | 15.00 |
| 131 VAL | CG2 | 5.29 | 31.20 | 85.62 | 15.00 |
| 131 VAL | C | 5.46 | 33.28 | 82.34 | 15.00 |
| 131 VAL | O | 4.93 | 32.82 | 81.36 | 15.00 |
| 132 SER | N | 6.29 | 34.30 | 82.27 | 15.00 |
| 132 SER | CA | 6.77 | 34.75 | 80.98 | 15.00 |
| 132 SER | CB | 7.15 | 36.24 | 81.04 | 15.00 |
| 132 SER | OG | 5.98 | 36.98 | 81.39 | 15.00 |
| 132 SER | C | 7.92 | 33.89 | 80.48 | 15.00 |
| 132 SER | O | 9.01 | 33.83 | 81.08 | 15.00 |
| 133 VAL | N | 7.65 | 33.20 | 79.38 | 15.00 |
| 133 VAL | CA | 8.65 | 32.34 | 78.76 | 15.00 |
| 133 VAL | CB | 8.09 | 30.90 | 78.61 | 15.00 |
| 133 VAL | CG1 | 7.58 | 30.35 | 79.92 | 15.00 |
| 133 VAL | CG2 | 6.97 | 30.91 | 77.61 | 15.00 |
| 133 VAL | C | 9.05 | 32.84 | 77.37 | 15.00 |
| 133 VAL | O | 8.48 | 33.81 | 76.85 | 15.00 |
| 134 ALA | N | 10.08 | 32.21 | 76.81 | 15.00 |
| 134 ALA | CA | 10.60 | 32.51 | 75.49 | 15.00 |
| 134 ALA | CB | 11.89 | 33.29 | 75.59 | 15.00 |
| 134 ALA | C | 10.85 | 31.16 | 74.84 | 15.00 |
| 134 ALA | O | 11.46 | 30.30 | 75.47 | 15.00 |
| 135 ILE | N | 10.35 | 30.97 | 73.62 | 15.00 |
| 135 ILE | CA | 10.52 | 29.73 | 72.86 | 15.00 |
| 135 ILE | CB | 9.18 | 28.95 | 72.80 | 15.00 |
| 135 ILE | CG2 | 8.71 | 28.60 | 74.21 | 15.00 |
| 135 ILE | CG1 | 8.13 | 29.80 | 72.09 | 15.00 |
| 135 ILE | CD1 | 6.78 | 29.14 | 72.00 | 15.00 |
| 135 ILE | C | 11.04 | 30.04 | 71.44 | 15.00 |
| 135 ILE | O | 11.30 | 31.20 | 71.08 | 15.00 |
| 136 ASP | N | 11.28 | 28.98 | 70.67 | 15.00 |
| 136 ASP | CA | 11.71 | 29.13 | 69.30 | 15.00 |
| 136 ASP | CB | 12.68 | 28.01 | 68.94 | 15.00 |
| 136 ASP | CG | 13.21 | 28.11 | 67.50 | 15.00 |
| 136 ASP | OD1 | 13.77 | 27.12 | 67.00 | 15.00 |
| 136 ASP | OD2 | 13.08 | 29.18 | 66.88 | 15.00 |
| 136 ASP | C | 10.45 | 28.94 | 68.51 | 15.00 |
| 136 ASP | O | 9.90 | 27.82 | 68.48 | 15.00 |
| 137 ALA | N | 9.98 | 30.01 | 67.87 | 15.00 |
| 137 ALA | CA | 8.78 | 29.93 | 67.06 | 15.00 |
| 137 ALA | CB | 7.74 | 30.91 | 67.56 | 15.00 |
| 137 ALA | C | 9.09 | 30.18 | 65.58 | 15.00 |
| 137 ALA | O | 8.27 | 30.79 | 64.88 | 15.00 |
| 138 SER | N | 10.22 | 29.67 | 65.10 | 15.00 |
| 138 SER | CA | 10.66 | 29.83 | 63.72 | 15.00 |
| 138 SER | CB | 12.18 | 29.81 | 63.63 | 15.00 |
| 138 SER | OG | 12.67 | 28.54 | 64.01 | 15.00 |
| 138 SER | C | 10.15 | 28.77 | 62.77 | 15.00 |
| 138 SER | O | 9.81 | 29.07 | 61.62 | 15.00 |
| 139 LEU | N | 10.12 | 27.53 | 63.26 | 15.00 |
| 139 LEU | CA | 9.66 | 26.42 | 62.45 | 15.00 |
| 139 LEU | CB | 9.74 | 25.13 | 63.29 | 15.00 |
| 139 LEU | CG | 11.05 | 24.33 | 63.34 | 15.00 |
| 139 LEU | CD1 | 12.24 | 25.24 | 63.67 | 15.00 |
| 139 LEU | CD2 | 10.92 | 23.21 | 64.38 | 15.00 |
| 139 LEU | C | 8.24 | 26.59 | 61.88 | 15.00 |
| 139 LEU | O | 7.32 | 26.95 | 62.60 | 15.00 |
| 140 THR | N | 8.08 | 26.30 | 60.58 | 15.00 |
| 140 THR | CA | 6.80 | 26.39 | 59.88 | 15.00 |
| 140 THR | CB | 6.88 | 25.76 | 58.50 | 15.00 |
| 140 THR | OG1 | 8.18 | 25.97 | 57.94 | 15.00 |
| 140 THR | CG2 | 5.86 | 26.37 | 57.60 | 15.00 |
| 140 THR | C | 5.76 | 25.62 | 60.67 | 15.00 |
| 140 THR | O | 4.67 | 26.12 | 60.88 | 15.00 |
| 141 SER | N | 6.13 | 24.45 | 61.17 | 15.00 |
| 141 SER | CA | 5.20 | 23.63 | 61.94 | 15.00 |
| 141 SER | CB | 5.79 | 22.28 | 62.28 | 15.00 |
| 141 SER | OG | 7.00 | 22.40 | 62.97 | 15.00 |
| 141 SER | C | 4.65 | 24.28 | 63.18 | 15.00 |
| 141 SER | O | 3.60 | 23.89 | 63.66 | 15.00 |
| 142 PHE | N | 5.35 | 25.26 | 63.72 | 15.00 |
| 142 PHE | CA | 4.82 | 25.94 | 64.90 | 15.00 |
| 142 PHE | CB | 5.94 | 26.71 | 65.64 | 15.00 |
| 142 PHE | CG | 5.46 | 27.49 | 66.86 | 15.00 |
| 142 PHE | CD1 | 5.60 | 26.99 | 68.12 | 15.00 |
| 142 PHE | CD2 | 4.89 | 28.74 | 66.71 | 15.00 |
| 142 PHE | CE1 | 5.15 | 27.76 | 69.25 | 15.00 |
| 142 PHE | CE2 | 4.46 | 29.49 | 67.82 | 15.00 |
| 142 PHE | CZ | 4.59 | 29.00 | 69.07 | 15.00 |
| 142 PHE | C | 3.74 | 26.88 | 64.42 | 15.00 |
| 142 PHE | O | 2.63 | 26.88 | 64.93 | 15.00 |
| 143 GLN | N | 4.08 | 27.58 | 63.36 | 15.00 |
| 143 GLN | CA | 3.24 | 28.59 | 62.73 | 15.00 |
| 143 GLN | CB | 4.04 | 29.36 | 61.69 | 15.00 |
| 143 GLN | CG | 5.38 | 29.87 | 62.23 | 15.00 |
| 143 GLN | CD | 6.19 | 30.64 | 61.16 | 15.00 |
| 143 GLN | OE1 | 5.83 | 31.75 | 60.75 | 15.00 |
| 143 GLN | NE2 | 7.25 | 30.01 | 60.64 | 15.00 |
| 143 GLN | C | 1.95 | 28.10 | 62.12 | 15.00 |
| 143 GLN | O | 0.99 | 28.86 | 62.08 | 15.00 |
| 144 PHE | N | 1.91 | 26.90 | 61.55 | 15.00 |
| 144 PHE | CA | 0.61 | 26.44 | 61.01 | 15.00 |
| 144 PHE | CB | 0.73 | 25.77 | 59.63 | 15.00 |
| 144 PHE | CG | 1.72 | 24.62 | 59.58 | 15.00 |
| 144 PHE | CD1 | 2.76 | 24.61 | 58.69 | 15.00 |
| 144 PHE | CD2 | 1.58 | 23.50 | 60.36 | 15.00 |
| 144 PHE | CE1 | 3.60 | 23.51 | 58.60 | 15.00 |
| 144 PHE | CE2 | 2.47 | 22.41 | 60.22 | 15.00 |
| 144 PHE | CZ | 3.44 | 22.44 | 59.35 | 15.00 |
| 144 PHE | C | −0.14 | 25.50 | 61.98 | 15.00 |
| 144 PHE | O | −1.10 | 24.82 | 61.59 | 15.00 |
| 145 TYR | N | 0.31 | 25.47 | 63.24 | 15.00 |
| 145 TYR | CA | −0.31 | 24.65 | 64.26 | 15.00 |
| 145 TYR | CB | 0.32 | 24.91 | 65.65 | 15.00 |
| 145 TYR | CG | −0.47 | 24.34 | 66.81 | 15.00 |
| 145 TYR | CD1 | −0.26 | 23.01 | 67.22 | 15.00 |
| 145 TYR | CE1 | −0.98 | 22.48 | 68.28 | 15.00 |
| 145 TYR | CD2 | −1.42 | 25.12 | 67.48 | 15.00 |
| 145 TYR | CE2 | −2.15 | 24.61 | 68.54 | 15.00 |
| 145 TYR | CZ | −1.93 | 23.28 | 68.94 | 15.00 |
| 145 TYR | OH | −2.67 | 22.83 | 70.02 | 15.00 |
| 145 TYR | C | −1.80 | 24.98 | 64.30 | 15.00 |
| 145 TYR | C | −2.24 | 26.10 | 64.03 | 15.00 |
| 146 SER | N | −2.60 | 24.00 | 64.69 | 15.00 |
| 146 SER | CA | −4.06 | 24.19 | 64.77 | 15.00 |
| 146 SER | CB | −4.67 | 23.67 | 63.48 | 15.00 |
| 146 SER | OG | −4.29 | 22.33 | 63.27 | 15.00 |
| 146 SER | C | −4.67 | 23.42 | 65.95 | 15.00 |
| 146 SER | O | −5.59 | 23.89 | 66.62 | 15.00 |
| 147 LYS | N | −4.20 | 22.20 | 66.13 | 15.00 |
| 147 LYS | CA | −4.67 | 21.36 | 67.20 | 15.00 |
| 147 LYS | CB | −5.96 | 20.64 | 66.83 | 15.00 |

TABLE X-continued

Table of the orthogonal three dimensional coordinates in Ångstroms and B factors (Å²) for the cathepsin K complex with inhibitor 1-N-(N-imidazole acetyl-leucinyl)-amino-3-N-(4-phenoxy-phenyl-sulfonyl)-amino-propan-2-one

| Residue | | Atom | X | Y | Z | B |
|---|---|---|---|---|---|---|
| 147 | LYS | CG | −5.81 | 19.47 | 65.90 | 15.00 |
| 147 | LYS | CD | −7.06 | 18.58 | 65.92 | 15.00 |
| 147 | LYS | CE | −6.91 | 17.41 | 64.96 | 15.00 |
| 147 | LYS | NZ | −8.13 | 16.56 | 64.99 | 15.00 |
| 147 | LYS | C | −3.60 | 20.36 | 67.62 | 15.00 |
| 147 | LYS | O | −2.62 | 20.16 | 66.90 | 15.00 |
| 148 | GLY | N | −3.82 | 19.73 | 68.78 | 15.00 |
| 148 | GLY | CA | −2.88 | 18.75 | 69.30 | 15.00 |
| 148 | GLY | C | −1.76 | 19.26 | 70.20 | 15.00 |
| 148 | GLY | O | −1.75 | 20.39 | 70.59 | 15.00 |
| 149 | VAL | N | −0.79 | 18.40 | 70.52 | 15.00 |
| 149 | VAL | CA | 0.33 | 18.81 | 71.35 | 15.00 |
| 149 | VAL | CB | 0.58 | 17.89 | 72.57 | 15.00 |
| 149 | VAL | CG1 | 1.74 | 18.42 | 73.41 | 15.00 |
| 149 | VAL | CG2 | −0.68 | 17.75 | 73.42 | 15.00 |
| 149 | VAL | C | 1.59 | 18.86 | 70.48 | 15.00 |
| 149 | VAL | O | 2.06 | 17.84 | 69.96 | 15.00 |
| 150 | TYR | N | 2.13 | 20.07 | 70.35 | 15.00 |
| 150 | TYR | CA | 3.32 | 20.33 | 69.53 | 15.00 |
| 150 | TYR | CB | 3.50 | 21.83 | 69.29 | 15.00 |
| 150 | TYR | CG | 4.59 | 22.21 | 68.31 | 15.00 |
| 150 | TYR | CD1 | 4.47 | 22.01 | 66.95 | 15.00 |
| 150 | TYR | CE1 | 5.48 | 22.37 | 66.04 | 15.00 |
| 150 | TYR | CD2 | 5.74 | 22.78 | 68.72 | 15.00 |
| 150 | TYR | CE2 | 6.75 | 23.13 | 67.81 | 15.00 |
| 150 | TYR | CZ | 6.61 | 22.93 | 66.48 | 15.00 |
| 150 | TYR | OH | 7.57 | 23.30 | 65.60 | 15.00 |
| 150 | TYR | C | 4.60 | 19.72 | 70.12 | 15.00 |
| 150 | TYR | O | 4.76 | 19.60 | 71.37 | 15.00 |
| 151 | TYR | N | 5.44 | 19.24 | 69.21 | 15.00 |
| 151 | TYR | CA | 6.74 | 18.68 | 69.55 | 15.00 |
| 151 | TYR | CB | 6.62 | 17.30 | 70.22 | 15.00 |
| 151 | TYR | CG | 7.96 | 16.61 | 70.42 | 15.00 |
| 151 | TYR | CD1 | 9.15 | 17.34 | 70.60 | 15.00 |
| 151 | TYR | CE1 | 10.41 | 16.67 | 70.84 | 15.00 |
| 151 | TYR | CD2 | 8.02 | 15.21 | 70.47 | 15.00 |
| 151 | TYR | CE2 | 9.24 | 14.52 | 70.71 | 15.00 |
| 151 | TYR | CZ | 10.43 | 15.27 | 70.89 | 15.00 |
| 151 | TYR | OH | 11.60 | 14.61 | 71.14 | 15.00 |
| 151 | TYR | C | 7.38 | 18.53 | 68.19 | 15.00 |
| 151 | TYR | O | 6.82 | 17.86 | 67.31 | 15.00 |
| 152 | ASP | N | 8.47 | 19.26 | 67.98 | 15.00 |
| 152 | ASP | CA | 9.18 | 19.22 | 66.71 | 15.00 |
| 152 | ASP | CB | 8.83 | 20.40 | 65.81 | 15.00 |
| 152 | ASP | CG | 9.30 | 20.18 | 64.37 | 15.00 |
| 152 | ASP | OD1 | 10.54 | 20.06 | 64.18 | 15.00 |
| 152 | ASP | OD2 | 8.42 | 20.06 | 63.48 | 15.00 |
| 152 | ASP | C | 10.69 | 19.18 | 66.97 | 15.00 |
| 152 | ASP | O | 11.34 | 20.21 | 67.14 | 15.00 |
| 153 | GLU | N | 11.24 | 17.97 | 66.94 | 15.00 |
| 153 | GLU | CA | 12.64 | 17.77 | 67.18 | 15.00 |
| 153 | GLU | CB | 13.00 | 16.30 | 66.88 | 15.00 |
| 153 | GLU | CG | 12.45 | 15.71 | 65.61 | 15.00 |
| 153 | GLU | CD | 11.10 | 15.02 | 65.83 | 15.00 |
| 153 | GLU | OE1 | 11.10 | 13.96 | 66.53 | 15.00 |
| 153 | GLU | OE2 | 10.06 | 15.52 | 65.30 | 15.00 |
| 153 | GLU | C | 13.60 | 18.73 | 66.48 | 15.00 |
| 153 | GLU | O | 14.75 | 18.90 | 66.91 | 15.00 |
| 154 | SER | N | 13.17 | 19.30 | 65.35 | 15.00 |
| 154 | SER | CA | 14.02 | 20.24 | 64.60 | 15.00 |
| 154 | SER | CB | 13.49 | 20.49 | 63.17 | 15.00 |
| 154 | SER | OG | 13.06 | 19.29 | 62.54 | 15.00 |
| 154 | SER | C | 14.13 | 21.57 | 65.34 | 15.00 |
| 154 | SER | O | 14.95 | 22.40 | 65.00 | 15.00 |
| 155 | CYS | N | 13.37 | 21.72 | 66.43 | 15.00 |
| 155 | CYS | CA | 13.33 | 22.98 | 67.21 | 15.00 |
| 155 | CYS | C | 14.64 | 23.18 | 67.97 | 15.00 |
| 155 | CYS | O | 15.25 | 22.21 | 68.44 | 15.00 |
| 155 | CYS | CB | 12.15 | 22.99 | 68.17 | 15.00 |
| 155 | CYS | SG | 11.63 | 24.66 | 68.64 | 15.00 |
| 156 | ASN | N | 15.04 | 24.44 | 68.16 | 15.00 |
| 156 | ASN | CA | 16.31 | 24.74 | 68.81 | 15.00 |
| 156 | ASN | CB | 17.20 | 25.46 | 67.80 | 15.00 |
| 156 | ASN | CG | 18.46 | 26.05 | 68.41 | 15.00 |
| 156 | ASN | OD1 | 18.80 | 25.83 | 69.59 | 15.00 |
| 156 | ASN | ND2 | 19.18 | 26.80 | 67.59 | 15.00 |
| 156 | ASN | C | 16.22 | 25.55 | 70.11 | 15.00 |
| 156 | ASN | O | 16.12 | 26.80 | 70.09 | 15.00 |
| 157 | SER | N | 16.27 | 24.83 | 71.22 | 15.00 |
| 157 | SER | CA | 16.22 | 25.44 | 72.55 | 15.00 |
| 157 | SER | CB | 16.51 | 24.37 | 73.60 | 15.00 |
| 157 | SER | OG | 15.49 | 23.40 | 73.56 | 15.00 |
| 157 | SER | C | 17.22 | 26.59 | 72.72 | 15.00 |
| 157 | SER | O | 16.99 | 27.51 | 73.49 | 15.00 |
| 158 | ASP | N | 18.35 | 26.52 | 72.02 | 15.00 |
| 158 | ASP | CA | 19.40 | 27.52 | 72.06 | 15.00 |
| 158 | ASP | CB | 20.71 | 26.91 | 71.57 | 15.00 |
| 158 | ASP | CG | 20.91 | 25.47 | 72.03 | 15.00 |
| 158 | ASP | OD1 | 21.16 | 24.60 | 71.16 | 15.00 |
| 158 | ASP | OD2 | 20.81 | 25.18 | 73.26 | 15.00 |
| 158 | ASP | C | 19.05 | 28.77 | 71.26 | 15.00 |
| 158 | ASP | O | 19.69 | 29.81 | 71.37 | 15.00 |
| 159 | ASN | N | 18.04 | 28.67 | 70.40 | 15.00 |
| 159 | ASN | CA | 17.64 | 29.82 | 69.62 | 15.00 |
| 159 | ASN | CB | 17.77 | 29.53 | 68.12 | 15.00 |
| 159 | ASN | CG | 17.54 | 30.78 | 67.23 | 15.00 |
| 159 | ASN | OD1 | 17.33 | 30.67 | 66.00 | 15.00 |
| 159 | ASN | ND2 | 17.63 | 31.96 | 67.83 | 15.00 |
| 159 | ASN | C | 16.22 | 30.27 | 69.99 | 15.00 |
| 159 | ASN | O | 15.23 | 29.87 | 69.36 | 15.00 |
| 160 | LEU | N | 16.12 | 31.10 | 71.03 | 15.00 |
| 160 | LEU | CA | 14.84 | 31.64 | 71.49 | 15.00 |
| 160 | LEU | CB | 14.88 | 31.87 | 73.00 | 15.00 |
| 160 | LEU | CG | 15.40 | 30.70 | 73.88 | 15.00 |
| 160 | LEU | CD1 | 15.23 | 31.09 | 75.33 | 15.00 |
| 160 | LEU | CD2 | 14.68 | 29.38 | 73.59 | 15.00 |
| 160 | LEU | C | 14.66 | 32.96 | 70.75 | 15.00 |
| 160 | LEU | O | 15.56 | 33.76 | 70.75 | 15.00 |
| 161 | ASN | N | 13.52 | 33.17 | 70.11 | 15.00 |
| 161 | ASN | CA | 13.28 | 34.40 | 69.36 | 15.00 |
| 161 | ASN | CB | 13.53 | 34.18 | 67.85 | 15.00 |
| 161 | ASN | CG | 12.91 | 32.90 | 67.32 | 15.00 |
| 161 | ASN | OD1 | 11.68 | 32.70 | 67.33 | 15.00 |
| 161 | ASN | ND2 | 13.78 | 32.01 | 66.83 | 15.00 |
| 161 | ASN | C | 11.86 | 34.98 | 69.54 | 15.00 |
| 161 | ASN | O | 11.57 | 36.09 | 69.09 | 15.00 |
| 162 | HIS | N | 10.99 | 34.28 | 70.26 | 15.00 |
| 162 | HIS | CA | 9.66 | 34.79 | 70.41 | 15.00 |
| 162 | HIS | CB | 8.74 | 34.04 | 69.45 | 15.00 |
| 162 | HIS | CG | 7.37 | 34.62 | 69.35 | 15.00 |
| 162 | HIS | CD2 | 6.94 | 35.88 | 69.10 | 15.00 |
| 162 | HIS | ND1 | 6.24 | 33.84 | 69.45 | 15.00 |
| 162 | HIS | CE1 | 5.17 | 34.59 | 69.25 | 15.00 |
| 162 | HIS | NE2 | 5.57 | 35.83 | 69.03 | 15.00 |
| 162 | HIS | C | 9.28 | 34.53 | 71.85 | 15.00 |
| 162 | HIS | O | 9.61 | 33.48 | 72.39 | 15.00 |
| 163 | ALA | N | 8.70 | 35.56 | 72.47 | 15.00 |
| 163 | ALA | CA | 8.26 | 35.51 | 73.85 | 15.00 |
| 163 | ALA | CD | 8.50 | 36.80 | 74.53 | 15.00 |
| 163 | ALA | C | 6.78 | 35.24 | 73.87 | 15.00 |
| 163 | ALA | O | 6.02 | 35.80 | 73.09 | 15.00 |
| 164 | VAL | N | 6.39 | 34.38 | 74.78 | 15.00 |
| 164 | VAL | CA | 5.01 | 34.03 | 74.97 | 15.00 |
| 164 | VAL | CB | 4.69 | 32.69 | 74.29 | 15.00 |
| 164 | VAL | CG1 | 4.67 | 32.84 | 72.75 | 15.00 |
| 164 | VAL | CG2 | 5.73 | 31.64 | 74.69 | 15.00 |
| 164 | VAL | C | 4.72 | 33.94 | 76.48 | 15.00 |
| 164 | VAL | O | 5.55 | 34.42 | 77.30 | 15.00 |
| 165 | LEU | N | 3.60 | 33.31 | 76.85 | 15.00 |
| 165 | LEU | CA | 3.27 | 33.21 | 78.26 | 15.00 |
| 165 | LEU | CB | 2.31 | 34.36 | 78.60 | 15.00 |
| 165 | LEU | CG | 1.52 | 34.51 | 79.93 | 15.00 |

TABLE X-continued

Table of the orthogonal three dimensional coordinates in Ångstroms and B factors (Å²) for the cathepsin K complex with inhibitor 1-N-(N-imidazole acetyl-leucinyl)-amino-3-N-(4-phenoxy-phenyl-sulfonyl)-amino-propan-2-one

| Residue | | Atom | X | Y | Z | B |
|---|---|---|---|---|---|---|
| 165 | LEU | CD1 | 2.25 | 35.21 | 81.00 | 15.00 |
| 165 | LEU | CD2 | 0.26 | 35.25 | 79.65 | 15.00 |
| 165 | LEU | C | 2.65 | 31.88 | 78.63 | 15.00 |
| 165 | LEU | O | 1.68 | 31.50 | 77.98 | 15.00 |
| 166 | ALA | N | 3.25 | 31.15 | 79.57 | 15.00 |
| 166 | ALA | CA | 2.73 | 29.85 | 80.03 | 15.00 |
| 166 | ALA | CB | 3.79 | 29.05 | 80.72 | 15.00 |
| 166 | ALA | C | 1.57 | 30.12 | 80.98 | 15.00 |
| 166 | ALA | O | 1.76 | 30.63 | 82.05 | 15.00 |
| 167 | VAL | N | 0.38 | 29.73 | 80.56 | 15.00 |
| 167 | VAL | CA | −0.88 | 29.95 | 81.26 | 15.00 |
| 167 | VAL | CD | −1.94 | 30.48 | 80.19 | 15.00 |
| 167 | VAL | CG1 | −3.36 | 30.02 | 80.45 | 15.00 |
| 167 | VAL | CG2 | −1.88 | 32.03 | 80.10 | 15.00 |
| 167 | VAL | C | −1.36 | 28.70 | 82.03 | 15.00 |
| 167 | VAL | O | −2.35 | 28.75 | 82.70 | 15.00 |
| 168 | GLY | N | −0.67 | 27.57 | 81.88 | 15.00 |
| 168 | GLY | CA | −1.07 | 26.35 | 82.56 | 15.00 |
| 168 | GLY | C | −0.36 | 25.13 | 82.00 | 15.00 |
| 168 | GLY | O | 0.52 | 25.29 | 81.17 | 15.00 |
| 169 | TYR | N | −0.68 | 23.94 | 82.49 | 15.00 |
| 169 | TYR | CA | −0.03 | 22.73 | 81.98 | 15.00 |
| 169 | TYR | CB | 1.33 | 22.45 | 82.69 | 15.00 |
| 169 | TYR | CG | 1.24 | 22.33 | 84.21 | 15.00 |
| 169 | TYR | CD1 | 0.66 | 21.21 | 84.82 | 15.00 |
| 169 | TYR | CE1 | 0.51 | 21.16 | 86.19 | 15.00 |
| 169 | TYR | CD2 | 1.67 | 23.36 | 85.02 | 15.00 |
| 169 | TYR | CE2 | 1.53 | 23.30 | 86.36 | 15.00 |
| 169 | TYR | CZ | 0.94 | 22.20 | 86.95 | 15.00 |
| 169 | TYR | OH | 0.76 | 22.18 | 88.32 | 15.00 |
| 169 | TYR | C | −0.97 | 21.62 | 82.29 | 15.00 |
| 169 | TYR | O | −1.89 | 21.79 | 83.08 | 15.00 |
| 170 | GLY | N | −0.71 | 20.47 | 81.70 | 15.00 |
| 170 | GLY | CA | −1.54 | 19.31 | 81.93 | 15.00 |
| 170 | GLY | C | −1.19 | 18.20 | 80.97 | 15.00 |
| 170 | GLY | O | −0.05 | 18.05 | 80.56 | 15.00 |
| 171 | ILE | N | −2.19 | 17.42 | 80.63 | 15.00 |
| 171 | ILE | CA | −1.99 | 16.31 | 79.71 | 15.00 |
| 171 | ILE | CB | −1.71 | 14.98 | 80.49 | 15.00 |
| 171 | ILE | CG2 | −2.84 | 14.65 | 81.48 | 15.00 |
| 171 | ILE | CG1 | −1.47 | 13.80 | 79.57 | 15.00 |
| 171 | ILE | CD1 | −1.37 | 12.49 | 80.30 | 15.00 |
| 171 | ILE | C | −3.23 | 16.19 | 78.81 | 15.00 |
| 171 | ILE | O | −4.29 | 16.77 | 79.10 | 15.00 |
| 172 | GLN | N | −3.09 | 15.50 | 77.69 | 15.00 |
| 172 | GLN | CA | −4.21 | 15.35 | 76.77 | 15.00 |
| 172 | GLN | CB | −3.96 | 16.16 | 75.48 | 15.00 |
| 172 | GLN | CG | −5.15 | 16.20 | 74.49 | 15.00 |
| 172 | GLN | CD | −5.05 | 17.33 | 73.50 | 15.00 |
| 172 | GLN | OE1 | −4.76 | 18.47 | 73.87 | 15.00 |
| 172 | GLN | NE2 | −5.27 | 17.03 | 72.22 | 15.00 |
| 172 | GLN | C | −4.51 | 13.86 | 76.49 | 15.00 |
| 172 | GLN | O | −5.23 | 13.22 | 77.27 | 15.00 |
| 173 | LYS | N | −4.00 | 13.30 | 75.41 | 15.00 |
| 173 | LYS | CA | −4.27 | 11.89 | 75.22 | 15.00 |
| 173 | LYS | CB | −4.76 | 11.64 | 73.81 | 15.00 |
| 173 | LYS | CG | −6.07 | 12.36 | 73.52 | 15.00 |
| 173 | LYS | CD | −6.45 | 12.30 | 72.03 | 15.00 |
| 173 | LYS | CE | −5.44 | 13.01 | 71.15 | 15.00 |
| 173 | LYS | NZ | −5.85 | 12.96 | 69.72 | 15.00 |
| 173 | LYS | C | −2.97 | 11.18 | 75.51 | 15.00 |
| 173 | LYS | O | −2.29 | 10.72 | 74.59 | 15.00 |
| 174 | GLY | N | −2.59 | 11.22 | 76.78 | 15.00 |
| 174 | GLY | CA | −1.36 | 10.60 | 77.21 | 15.00 |
| 174 | GLY | C | −0.18 | 11.54 | 77.14 | 15.00 |
| 174 | GLY | O | 0.88 | 11.27 | 77.72 | 15.00 |
| 175 | ASN | N | −0.34 | 12.66 | 76.42 | 15.00 |
| 175 | ASN | CA | 0.75 | 13.62 | 76.27 | 15.00 |
| 175 | ASN | CB | 0.84 | 14.07 | 74.82 | 15.00 |
| 175 | ASN | CG | 1.30 | 12.97 | 73.90 | 15.00 |
| 175 | ASN | OD1 | 2.46 | 12.52 | 73.96 | 15.00 |
| 175 | ASN | ND2 | 0.38 | 12.50 | 73.05 | 15.00 |
| 175 | ASN | C | 0.75 | 14.84 | 77.17 | 15.00 |
| 175 | ASN | O | −0.24 | 15.61 | 77.23 | 15.00 |
| 176 | LYS | N | 1.91 | 15.07 | 77.78 | 15.00 |
| 176 | LYS | CA | 2.12 | 16.20 | 78.66 | 15.00 |
| 176 | LYS | CB | 3.36 | 15.99 | 79.53 | 15.00 |
| 176 | LYS | CG | 3.19 | 14.86 | 80.52 | 15.00 |
| 176 | LYS | CD | 4.24 | 14.85 | 81.66 | 15.00 |
| 176 | LYS | CE | 4.17 | 13.51 | 82.41 | 15.00 |
| 176 | LYS | NZ | 2.95 | 13.37 | 83.28 | 15.00 |
| 176 | LYS | C | 2.25 | 17.46 | 77.85 | 15.00 |
| 176 | LYS | O | 2.71 | 17.42 | 76.71 | 15.00 |
| 177 | HIS | N | 1.74 | 18.56 | 78.38 | 15.00 |
| 177 | HIS | CA | 1.85 | 19.81 | 77.66 | 15.00 |
| 177 | HIS | CB | 0.73 | 19.92 | 76.63 | 15.00 |
| 177 | HIS | CG | −0.62 | 20.17 | 77.21 | 15.00 |
| 177 | HIS | CD2 | −1.20 | 21.32 | 77.65 | 15.00 |
| 177 | HIS | ND1 | −1.56 | 19.18 | 77.38 | 15.00 |
| 177 | HIS | CE1 | −2.67 | 19.70 | 77.89 | 15.00 |
| 177 | HIS | NE2 | −2.47 | 21.00 | 78.06 | 15.00 |
| 177 | HIS | C | 1.83 | 21.03 | 78.53 | 15.00 |
| 177 | HIS | O | 1.38 | 20.97 | 79.68 | 15.00 |
| 178 | TRP | N | 2.20 | 22.13 | 77.89 | 15.00 |
| 178 | TRP | CA | 2.21 | 23.47 | 78.45 | 15.00 |
| 178 | TRP | CB | 3.57 | 24.15 | 78.26 | 15.00 |
| 178 | TRP | CG | 4.71 | 23.55 | 78.98 | 15.00 |
| 178 | TRP | CD2 | 4.98 | 23.62 | 80.41 | 15.00 |
| 178 | TRP | CE2 | 6.14 | 22.88 | 80.64 | 15.00 |
| 178 | TRP | CE3 | 4.33 | 24.22 | 81.52 | 15.00 |
| 178 | TRP | CD1 | 5.70 | 22.82 | 78.45 | 15.00 |
| 178 | TRP | NE1 | 6.56 | 22.40 | 79.44 | 15.00 |
| 178 | TRP | CZ2 | 6.67 | 22.72 | 81.91 | 15.00 |
| 178 | TRP | CZ3 | 4.86 | 24.05 | 82.17 | 15.00 |
| 178 | TRP | CH2 | 6.01 | 23.31 | 82.96 | 15.00 |
| 178 | TRP | C | 1.18 | 24.24 | 77.64 | 15.00 |
| 178 | TRP | O | 1.14 | 24.11 | 76.42 | 15.00 |
| 179 | ILE | N | 0.33 | 25.01 | 78.30 | 15.00 |
| 179 | ILE | CA | −0.64 | 25.81 | 77.55 | 15.00 |
| 179 | ILE | CB | −1.90 | 26.08 | 78.34 | 15.00 |
| 179 | ILE | CG2 | −2.77 | 27.07 | 77.61 | 15.00 |
| 179 | ILE | CG1 | −2.54 | 24.73 | 78.71 | 15.00 |
| 179 | ILE | CD1 | −3.79 | 24.79 | 79.53 | 15.00 |
| 179 | ILE | C | 0.03 | 27.14 | 77.31 | 15.00 |
| 179 | ILE | O | 0.36 | 27.82 | 78.27 | 15.00 |
| 180 | ILE | N | 0.23 | 27.49 | 76.05 | 15.00 |
| 180 | ILE | CA | 0.89 | 28.72 | 75.68 | 15.00 |
| 180 | ILE | CB | 2.09 | 28.49 | 74.78 | 15.00 |
| 180 | ILE | CG2 | 2.73 | 29.81 | 74.51 | 15.00 |
| 180 | ILE | CG1 | 3.09 | 27.57 | 75.46 | 15.00 |
| 180 | ILE | CD1 | 3.92 | 28.26 | 76.47 | 15.00 |
| 180 | ILE | C | −0.04 | 29.69 | 75.03 | 15.00 |
| 180 | ILE | O | −0.88 | 29.33 | 74.22 | 15.00 |
| 181 | LYS | N | 0.06 | 30.94 | 75.44 | 15.00 |
| 181 | LYS | CA | −0.80 | 31.95 | 74.91 | 15.00 |
| 181 | LYS | CB | −1.26 | 32.84 | 76.03 | 15.00 |
| 181 | LYS | CG | −1.94 | 34.09 | 75.52 | 15.00 |
| 181 | LYS | CD | −2.47 | 34.90 | 76.67 | 15.00 |
| 181 | LYS | CE | −2.92 | 36.22 | 76.11 | 15.00 |
| 181 | LYS | NZ | −3.47 | 37.09 | 77.17 | 15.00 |
| 181 | LYS | C | 0.15 | 32.72 | 74.03 | 15.00 |
| 181 | LYS | O | 1.19 | 33.15 | 74.52 | 15.00 |
| 182 | ASN | N | −0.15 | 32.81 | 72.75 | 15.00 |
| 182 | ASN | CA | 0.73 | 33.49 | 71.81 | 15.00 |
| 182 | ASN | CB | 0.96 | 32.61 | 70.59 | 15.00 |
| 182 | ASN | CG | 1.97 | 33.17 | 69.65 | 15.00 |
| 182 | ASN | OD1 | 2.31 | 34.34 | 69.73 | 15.00 |
| 182 | ASN | ND2 | 2.42 | 32.35 | 68.71 | 15.00 |
| 182 | ASN | C | 0.01 | 34.76 | 71.38 | 15.00 |
| 182 | ASN | O | −1.21 | 34.83 | 71.39 | 15.00 |
| 183 | SER | N | 0.75 | 35.80 | 71.01 | 15.00 |
| 183 | SER | CA | 0.09 | 37.03 | 70.61 | 15.00 |

TABLE X-continued

Table of the orthogonal three dimensional coordinates in Ångstroms and B factors (Å²) for the cathepsin K complex with inhibitor 1-N-(N-imidazole acetyl-leucinyl)-amino-3-N-(4-phenoxy-phenyl-sulfonyl)-amino-propan-2-one

| Residue | | Atom | X | Y | Z | B |
|---|---|---|---|---|---|---|
| 183 | SER | CB | 0.81 | 38.23 | 71.20 | 15.00 |
| 183 | SER | OG | 2.19 | 38.09 | 71.04 | 15.00 |
| 183 | SER | C | −0.09 | 37.18 | 69.10 | 15.00 |
| 183 | SER | O | 0.19 | 38.25 | 68.56 | 15.00 |
| 184 | TRP | N | −0.58 | 36.16 | 68.41 | 15.00 |
| 184 | TRP | CA | −0.73 | 36.29 | 66.97 | 15.00 |
| 184 | TRP | CB | 0.00 | 35.18 | 66.21 | 15.00 |
| 184 | TRP | CG | 1.47 | 35.38 | 66.20 | 15.00 |
| 184 | TRP | CD2 | 2.44 | 34.39 | 65.92 | 15.00 |
| 184 | TRP | CE2 | 3.69 | 35.01 | 65.97 | 15.00 |
| 184 | TRP | CE3 | 2.38 | 33.02 | 65.61 | 15.00 |
| 184 | TRP | CD1 | 2.13 | 36.54 | 66.41 | 15.00 |
| 184 | TRP | NE1 | 3.47 | 36.33 | 66.27 | 15.00 |
| 184 | TRP | CZ2 | 4.88 | 34.32 | 65.74 | 15.00 |
| 184 | TRP | CZ3 | 3.56 | 32.33 | 65.37 | 15.00 |
| 184 | TRP | CH2 | 4.79 | 32.98 | 65.44 | 15.00 |
| 184 | TRP | C | −2.17 | 36.42 | 66.57 | 15.00 |
| 184 | TRP | O | −2.53 | 36.20 | 65.42 | 15.00 |
| 185 | GLY | N | −2.97 | 36.92 | 67.51 | 15.00 |
| 185 | GLY | CA | −4.37 | 37.14 | 67.23 | 15.00 |
| 185 | GLY | C | −5.06 | 35.83 | 67.50 | 15.00 |
| 185 | GLY | O | −4.46 | 34.76 | 67.64 | 15.00 |
| 186 | GLU | N | −6.37 | 35.94 | 67.57 | 15.00 |
| 186 | GLU | CA | −7.23 | 34.80 | 67.84 | 15.00 |
| 186 | GLU | CB | −8.63 | 35.32 | 68.26 | 15.00 |
| 186 | GLU | CG | −9.57 | 34.27 | 68.68 | 15.00 |
| 186 | GLU | CD | −10.89 | 34.86 | 69.09 | 15.00 |
| 186 | GLU | OE1 | −11.68 | 35.25 | 68.20 | 15.00 |
| 186 | GLU | OE2 | −11.14 | 34.91 | 70.31 | 15.00 |
| 186 | GLU | C | −7.36 | 33.76 | 66.75 | 15.00 |
| 186 | GLU | O | −7.74 | 32.62 | 67.03 | 15.00 |
| 187 | ASN | N | −7.00 | 34.14 | 65.52 | 15.00 |
| 187 | ASN | CA | −7.11 | 33.25 | 64.36 | 15.00 |
| 187 | ASN | CB | −7.33 | 34.07 | 63.08 | 15.00 |
| 187 | ASN | CG | −8.45 | 33.50 | 62.21 | 15.00 |
| 187 | ASN | OD1 | −8.22 | 33.17 | 61.07 | 15.00 |
| 187 | ASN | ND2 | −9.66 | 33.42 | 62.75 | 15.00 |
| 187 | ASN | C | −5.92 | 32.36 | 64.14 | 15.00 |
| 187 | ASN | O | −5.90 | 31.63 | 63.13 | 15.00 |
| 188 | TRP | N | −4.89 | 32.50 | 64.96 | 15.00 |
| 188 | TRP | CA | −3.73 | 31.66 | 64.83 | 15.00 |
| 188 | TRP | CB | −2.53 | 32.41 | 65.32 | 15.00 |
| 188 | TRP | CG | −1.34 | 31.51 | 65.25 | 15.00 |
| 188 | TRP | CD2 | −0.66 | 30.87 | 66.35 | 15.00 |
| 188 | TRP | CE2 | 0.34 | 30.12 | 65.83 | 15.00 |
| 188 | TRP | CE3 | −0.81 | 30.87 | 67.72 | 15.00 |
| 188 | TRP | CD1 | −0.72 | 31.11 | 64.13 | 15.00 |
| 188 | TRP | NE1 | 0.30 | 30.26 | 64.46 | 15.00 |
| 188 | TRP | CZ2 | 1.18 | 29.39 | 66.64 | 15.00 |
| 188 | TRP | CZ3 | 0.04 | 30.13 | 68.52 | 15.00 |
| 188 | TRP | CH2 | 0.98 | 29.43 | 68.01 | 15.00 |
| 188 | TRP | C | −3.93 | 30.46 | 65.72 | 15.00 |
| 188 | TRP | O | −4.69 | 30.59 | 66.69 | 15.00 |
| 189 | GLY | N | −3.29 | 29.33 | 65.40 | 15.00 |
| 189 | GLY | CA | −3.42 | 28.14 | 66.22 | 15.00 |
| 189 | GLY | C | −4.80 | 27.88 | 66.77 | 15.00 |
| 189 | GLY | O | −5.82 | 28.15 | 66.15 | 15.00 |
| 190 | ASN | N | −4.87 | 27.38 | 67.98 | 15.00 |
| 190 | ASN | CA | −6.16 | 27.08 | 68.58 | 15.00 |
| 190 | ASN | CB | −6.04 | 25.89 | 69.53 | 15.00 |
| 190 | ASN | CG | −7.37 | 25.28 | 69.86 | 15.00 |
| 190 | ASN | OD1 | −8.42 | 25.95 | 69.81 | 15.00 |
| 190 | ASN | ND2 | −7.34 | 24.00 | 70.23 | 15.00 |
| 190 | ASN | C | −6.70 | 28.34 | 69.26 | 15.00 |
| 190 | ASN | O | −6.57 | 28.50 | 70.46 | 15.00 |
| 191 | LYS | N | −7.23 | 29.26 | 68.47 | 15.00 |
| 191 | LYS | CA | −7.79 | 30.49 | 68.99 | 15.00 |
| 191 | LYS | CB | −9.10 | 30.17 | 69.71 | 15.00 |
| 191 | LYS | CG | −10.01 | 29.28 | 68.87 | 15.00 |
| 191 | LYS | CD | −10.50 | 29.93 | 67.53 | 15.00 |
| 191 | LYS | CE | −9.41 | 30.19 | 66.45 | 15.00 |
| 191 | LYS | NZ | −8.63 | 28.95 | 66.03 | 15.00 |
| 191 | LYS | C | −6.81 | 31.27 | 69.84 | 15.00 |
| 191 | LYS | O | −7.13 | 31.73 | 70.96 | 15.00 |
| 192 | GLY | N | −5.60 | 31.43 | 69.30 | 15.00 |
| 192 | GLY | CA | −4.58 | 32.18 | 70.01 | 15.00 |
| 192 | GLY | C | −3.63 | 31.36 | 70.87 | 15.00 |
| 192 | GLY | O | −2.54 | 31.86 | 71.19 | 15.00 |
| 193 | TYR | N | −4.03 | 30.16 | 71.27 | 15.00 |
| 193 | TYR | CA | −3.20 | 29.32 | 72.12 | 15.00 |
| 193 | TYR | CB | −4.03 | 28.72 | 73.28 | 15.00 |
| 193 | TYR | CG | −4.53 | 29.79 | 74.21 | 15.00 |
| 193 | TYR | CD1 | −5.69 | 30.50 | 73.91 | 15.00 |
| 193 | TYR | CE1 | −6.13 | 31.53 | 74.73 | 15.00 |
| 193 | TYR | CD2 | −3.81 | 30.13 | 75.36 | 15.00 |
| 193 | TYR | CE2 | −4.22 | 31.14 | 76.20 | 15.00 |
| 193 | TYR | CZ | −5.37 | 31.84 | 75.89 | 15.00 |
| 193 | TYR | OH | −5.74 | 32.89 | 76.71 | 15.00 |
| 193 | TYR | C | −2.54 | 28.21 | 71.35 | 15.00 |
| 193 | TYR | O | −2.85 | 27.94 | 70.17 | 15.00 |
| 194 | ILE | N | −1.68 | 27.50 | 72.06 | 15.00 |
| 194 | ILE | CA | −0.99 | 26.35 | 71.50 | 15.00 |
| 194 | ILE | CB | 0.26 | 26.72 | 70.64 | 15.00 |
| 194 | ILE | CG2 | 1.18 | 27.65 | 71.44 | 15.00 |
| 194 | ILE | CG1 | 1.03 | 25.47 | 70.15 | 15.00 |
| 194 | ILE | CD1 | 2.16 | 25.76 | 69.14 | 15.00 |
| 194 | ILE | C | −0.54 | 25.54 | 72.70 | 15.00 |
| 194 | ILE | O | −0.28 | 26.08 | 73.75 | 15.00 |
| 195 | LEU | N | −0.56 | 24.23 | 72.57 | 15.00 |
| 195 | LEU | CA | −0.12 | 23.30 | 73.59 | 15.00 |
| 195 | LEU | CB | −1.11 | 22.15 | 73.67 | 15.00 |
| 195 | LEU | CG | −2.34 | 22.29 | 74.58 | 15.00 |
| 195 | LEU | CD1 | −2.88 | 23.70 | 74.67 | 15.00 |
| 195 | LEU | CD2 | −3.41 | 21.38 | 74.05 | 15.00 |
| 195 | LEU | C | 1.21 | 22.81 | 73.09 | 15.00 |
| 195 | LEU | O | 1.31 | 22.26 | 71.99 | 15.00 |
| 196 | MET | N | 2.25 | 23.13 | 73.83 | 15.00 |
| 196 | MET | CA | 3.58 | 22.69 | 73.45 | 15.00 |
| 196 | MET | CB | 4.57 | 23.83 | 73.65 | 15.00 |
| 196 | MET | CG | 4.29 | 24.99 | 72.69 | 15.00 |
| 196 | MET | SD | 5.56 | 26.26 | 72.94 | 15.00 |
| 196 | MET | CE | 7.08 | 25.68 | 71.98 | 15.00 |
| 196 | MET | C | 3.97 | 21.45 | 74.27 | 15.00 |
| 196 | MET | O | 3.31 | 21.15 | 75.28 | 15.00 |
| 197 | ALA | N | 4.97 | 20.70 | 73.81 | 15.00 |
| 197 | ALA | CA | 5.38 | 19.48 | 74.52 | 15.00 |
| 197 | ALA | CB | 6.32 | 18.63 | 73.67 | 15.00 |
| 197 | ALA | C | 6.01 | 19.71 | 75.90 | 15.00 |
| 197 | ALA | O | 6.93 | 20.50 | 76.02 | 15.00 |
| 198 | ARG | N | 5.56 | 19.01 | 76.94 | 15.00 |
| 198 | ARG | CA | 6.13 | 19.21 | 78.27 | 15.00 |
| 198 | ARG | CB | 5.05 | 19.61 | 79.26 | 15.00 |
| 198 | ARG | CG | 5.46 | 19.52 | 80.76 | 15.00 |
| 198 | ARG | CD | 4.45 | 20.21 | 81.65 | 15.00 |
| 198 | ARG | NE | 3.20 | 19.48 | 81.76 | 15.00 |
| 198 | ARG | CZ | 3.00 | 18.51 | 82.64 | 15.00 |
| 198 | ARG | NH1 | 3.99 | 18.18 | 83.47 | 15.00 |
| 198 | ARG | NH2 | 1.80 | 17.95 | 82.78 | 15.00 |
| 198 | ARG | C | 6.82 | 17.93 | 78.72 | 15.00 |
| 198 | ARG | O | 6.19 | 16.88 | 78.82 | 15.00 |
| 199 | ASN | N | 8.13 | 18.02 | 78.90 | 15.00 |
| 199 | ASN | CA | 8.99 | 16.89 | 79.34 | 15.00 |
| 199 | ASN | CB | 8.28 | 15.93 | 80.33 | 15.00 |
| 199 | ASN | CG | 8.26 | 16.47 | 81.77 | 15.00 |
| 199 | ASN | OD1 | 7.22 | 16.83 | 82.31 | 15.00 |
| 199 | ASN | ND2 | 9.45 | 16.55 | 82.38 | 15.00 |
| 199 | ASN | C | 9.79 | 16.12 | 78.28 | 15.00 |
| 199 | ASN | O | 10.49 | 15.17 | 78.61 | 15.00 |
| 200 | LYS | N | 9.77 | 16.62 | 77.05 | 15.00 |
| 200 | LYS | CA | 10.56 | 16.06 | 75.94 | 15.00 |
| 200 | LYS | CB | 9.83 | 16.23 | 74.61 | 15.00 |
| 200 | LYS | CG | 8.82 | 15.14 | 74.28 | 15.00 |

TABLE X-continued

Table of the orthogonal three dimensional coordinates in Ångstroms and B factors (Å²) for the cathepsin K complex with inhibitor 1-N-(N-imidazole acetyl-leucinyl)-amino-3-N-(4-phenoxy-phenyl-sulfonyl)-amino-propan-2-one

| Residue | | Atom | X | Y | Z | B |
|---|---|---|---|---|---|---|
| 200 | LYS | CD | 7.48 | 15.29 | 74.99 | 15.00 |
| 200 | LYS | CE | 6.27 | 15.00 | 74.07 | 15.00 |
| 200 | LYS | NZ | 6.29 | 13.60 | 73.43 | 15.00 |
| 200 | LYS | C | 11.87 | 16.86 | 75.92 | 15.00 |
| 200 | LYS | O | 12.15 | 17.61 | 74.99 | 15.00 |
| 201 | ASN | N | 12.64 | 16.70 | 76.99 | 15.00 |
| 201 | ASN | CA | 13.91 | 17.41 | 77.22 | 15.00 |
| 201 | ASN | CB | 15.14 | 16.71 | 76.60 | 15.00 |
| 201 | ASN | CG | 15.48 | 15.43 | 77.29 | 15.00 |
| 201 | ASN | OD1 | 15.33 | 14.36 | 76.70 | 15.00 |
| 201 | ASN | ND2 | 15.91 | 15.52 | 78.56 | 15.00 |
| 201 | ASN | C | 13.91 | 18.86 | 76.81 | 15.00 |
| 201 | ASN | O | 14.74 | 19.28 | 76.01 | 15.00 |
| 202 | ASN | N | 13.02 | 19.62 | 77.41 | 15.00 |
| 202 | ASN | CA | 12.87 | 21.05 | 77.17 | 15.00 |
| 202 | ASN | CB | 13.98 | 21.82 | 77.88 | 15.00 |
| 202 | ASN | CG | 13.66 | 23.27 | 78.07 | 15.00 |
| 202 | ASN | OD1 | 12.53 | 23.63 | 78.38 | 15.00 |
| 202 | ASN | ND2 | 14.63 | 24.12 | 77.83 | 15.00 |
| 202 | ASN | C | 12.73 | 21.47 | 75.69 | 15.00 |
| 202 | ASN | O | 13.48 | 22.28 | 75.16 | 15.00 |
| 203 | ALA | N | 11.66 | 21.00 | 75.05 | 15.00 |
| 203 | ALA | H | 11.06 | 20.52 | 75.65 | 15.00 |
| 203 | ALA | CA | 11.34 | 21.22 | 73.64 | 15.00 |
| 203 | ALA | CB | 10.03 | 20.53 | 73.27 | 15.00 |
| 203 | ALA | C | 11.16 | 22.72 | 73.38 | 15.00 |
| 203 | ALA | O | 10.25 | 23.38 | 73.78 | 15.00 |
| 204 | CYS | N | 11.98 | 23.21 | 72.42 | 15.00 |
| 204 | CYS | CA | 12.00 | 24.60 | 72.00 | 15.00 |
| 204 | CYS | C | 12.56 | 25.58 | 73.01 | 15.00 |
| 204 | CYS | O | 12.50 | 26.79 | 72.81 | 15.00 |
| 204 | CYS | CB | 10.64 | 25.06 | 71.56 | 15.00 |
| 204 | CYS | SG | 10.05 | 24.34 | 69.96 | 15.00 |
| 205 | GLY | N | 13.03 | 25.04 | 74.13 | 15.00 |
| 205 | GLY | CA | 13.63 | 25.86 | 75.14 | 15.00 |
| 205 | GLY | C | 12.69 | 26.61 | 76.01 | 15.00 |
| 205 | GLY | O | 13.03 | 27.59 | 76.63 | 15.00 |
| 206 | ILE | N | 11.50 | 26.08 | 76.12 | 15.00 |
| 206 | ILE | CA | 10.47 | 26.69 | 76.92 | 15.00 |
| 206 | ILE | CB | 9.30 | 25.69 | 77.08 | 15.00 |
| 206 | ILE | CG2 | 9.78 | 24.44 | 77.78 | 15.00 |
| 206 | ILE | CG1 | 8.15 | 26.33 | 77.87 | 15.00 |
| 206 | ILE | CD1 | 7.20 | 27.12 | 77.00 | 15.00 |
| 206 | ILE | C | 10.95 | 27.11 | 78.33 | 15.00 |
| 206 | ILE | O | 10.50 | 28.12 | 78.86 | 15.00 |
| 207 | ALA | N | 11.85 | 26.34 | 78.95 | 15.00 |
| 207 | ALA | CA | 12.32 | 26.67 | 80.30 | 15.00 |
| 207 | ALA | CB | 12.30 | 25.45 | 81.18 | 15.00 |
| 207 | ALA | C | 13.68 | 27.35 | 80.43 | 15.00 |
| 207 | ALA | O | 14.20 | 27.46 | 81.56 | 15.00 |
| 208 | ASN | N | 14.21 | 27.84 | 79.31 | 15.00 |
| 208 | ASN | CA | 15.51 | 28.52 | 79.26 | 15.00 |
| 208 | ASN | CB | 16.13 | 28.39 | 77.88 | 15.00 |
| 208 | ASN | CG | 16.75 | 27.01 | 77.59 | 15.00 |
| 208 | ASN | OD1 | 16.26 | 25.96 | 78.00 | 15.00 |
| 208 | ASN | ND2 | 17.86 | 27.03 | 76.88 | 15.00 |
| 208 | ASN | C | 15.37 | 30.02 | 79.55 | 15.00 |
| 208 | ASN | O | 16.37 | 30.73 | 79.73 | 15.00 |
| 209 | LEU | N | 14.16 | 30.55 | 79.48 | 15.00 |
| 209 | LEU | CA | 13.97 | 31.98 | 79.73 | 15.00 |
| 209 | LEU | CB | 14.05 | 32.79 | 78.43 | 15.00 |
| 209 | LEU | CG | 14.45 | 34.26 | 78.52 | 15.00 |
| 209 | LEU | CD1 | 15.95 | 34.30 | 78.78 | 15.00 |
| 209 | LEU | CD2 | 14.12 | 35.06 | 77.23 | 15.00 |
| 209 | LEU | C | 12.71 | 32.35 | 80.51 | 15.00 |
| 209 | LEU | O | 12.13 | 33.44 | 80.31 | 15.00 |
| 210 | ALA | N | 12.37 | 31.55 | 81.52 | 15.00 |
| 210 | ALA | H | 12.79 | 30.67 | 81.51 | 15.00 |
| 210 | ALA | CA | 11.14 | 31.81 | 82.27 | 15.00 |
| 210 | ALA | CB | 10.61 | 30.53 | 82.92 | 15.00 |
| 210 | ALA | C | 11.43 | 32.81 | 83.41 | 15.00 |
| 210 | ALA | O | 12.41 | 32.78 | 84.11 | 15.00 |
| 211 | SER | N | 10.44 | 33.74 | 83.58 | 15.00 |
| 211 | SER | CA | 10.44 | 34.68 | 84.69 | 15.00 |
| 211 | SER | CB | 11.25 | 35.95 | 84.38 | 15.00 |
| 211 | SER | OG | 10.66 | 36.74 | 83.37 | 15.00 |
| 211 | SER | C | 8.97 | 35.02 | 85.03 | 15.00 |
| 211 | SER | O | 8.07 | 34.77 | 84.22 | 15.00 |
| 212 | PHE | N | 8.74 | 35.50 | 86.25 | 15.00 |
| 212 | PHE | CA | 7.44 | 35.96 | 86.75 | 15.00 |
| 212 | PHE | CB | 6.68 | 34.87 | 87.53 | 15.00 |
| 212 | PHE | CG | 7.43 | 34.30 | 88.72 | 15.00 |
| 212 | PHE | CD1 | 8.34 | 33.31 | 88.54 | 15.00 |
| 212 | PHE | CD2 | 7.26 | 34.79 | 90.01 | 15.00 |
| 212 | PHE | CE1 | 9.08 | 32.83 | 89.64 | 15.00 |
| 212 | PHE | CE1 | 8.00 | 34.30 | 91.08 | 15.00 |
| 212 | PHE | CZ | 8.90 | 33.33 | 90.90 | 15.00 |
| 212 | PHE | C | 7.65 | 37.23 | 87.63 | 15.00 |
| 212 | PHE | O | 8.64 | 37.35 | 88.34 | 15.00 |
| 213 | PRO | N | 6.79 | 38.23 | 87.46 | 15.00 |
| 213 | PRO | CD | 5.64 | 38.27 | 86.55 | 15.00 |
| 213 | PRO | CA | 6.88 | 39.49 | 88.23 | 15.00 |
| 213 | PRO | CB | 6.03 | 40.48 | 87.41 | 15.00 |
| 213 | PRO | CG | 4.96 | 39.59 | 87.00 | 15.00 |
| 213 | PRO | C | 6.30 | 39.32 | 89.66 | 15.00 |
| 213 | PRO | O | 5.25 | 38.68 | 89.88 | 15.00 |
| 214 | LYS | N | 6.99 | 39.82 | 90.67 | 15.00 |
| 214 | LYS | CA | 6.40 | 39.71 | 92.01 | 15.00 |
| 214 | LYS | CB | 7.46 | 39.54 | 93.11 | 15.00 |
| 214 | LYS | CG | 8.31 | 38.28 | 92.90 | 15.00 |
| 214 | LYS | CD | 8.81 | 37.72 | 94.19 | 15.00 |
| 214 | LYS | CE | 9.63 | 38.73 | 94.95 | 15.00 |
| 214 | LYS | NZ | 10.60 | 39.41 | 94.05 | 15.00 |
| 214 | LYS | C | 5.57 | 40.96 | 92.27 | 15.00 |
| 214 | LYS | O | 5.99 | 42.07 | 91.94 | 15.00 |
| 215 | MET | N | 4.33 | 40.78 | 92.72 | 15.00 |
| 215 | MET | CA | 3.47 | 41.93 | 92.99 | 15.00 |
| 215 | MET | CB | 2.11 | 41.74 | 92.32 | 15.00 |
| 215 | MET | CG | 1.57 | 43.08 | 91.85 | 15.00 |
| 215 | MET | SD | 0.31 | 43.10 | 90.56 | 15.00 |
| 215 | MET | CE | −1.09 | 43.67 | 91.53 | 15.00 |
| 215 | MET | C | 3.31 | 42.16 | 94.50 | 15.00 |
| 215 | MET | OT1 | 3.48 | 41.21 | 95.29 | 15.00 |
| 215 | MET | OT2 | 3.17 | 43.33 | 94.89 | 15.00 |
| 216 | HOH | OH2 | 8.87 | 46.84 | 97.48 | 15.00 |
| 217 | HOH | OH2 | −2.18 | 37.97 | 73.56 | 15.00 |
| 218 | HOH | OH2 | 1.71 | 36.04 | 75.21 | 15.00 |
| 219 | HOH | OH2 | 9.44 | 52.65 | 61.91 | 15.00 |
| 220 | HOH | OH2 | 0.80 | 56.90 | 67.17 | 15.00 |
| 221 | HOH | OH2 | −2.51 | 36.41 | 82.35 | 15.00 |
| 222 | HOH | OH2 | 17.40 | 43.23 | 83.47 | 15.00 |
| 223 | HOH | OH2 | −1.57 | 52.44 | 64.46 | 15.00 |
| 224 | HOH | OH2 | 12.41 | 35.91 | 80.62 | 15.00 |
| 225 | HOH | OH2 | 11.65 | 62.93 | 58.36 | 15.00 |
| 226 | HOH | OH2 | 11.38 | 48.93 | 74.41 | 15.00 |
| 227 | HOH | OH2 | 5.00 | 12.95 | 78.69 | 15.00 |
| 228 | HOH | OH2 | 4.86 | 15.66 | 86.17 | 15.00 |
| 229 | HOH | OH2 | −9.01 | 32.96 | 72.96 | 15.00 |
| 230 | HOH | OH2 | 14.02 | 19.79 | 82.02 | 15.00 |
| 231 | HOH | OH2 | 18.09 | 36.59 | 88.86 | 15.00 |
| 232 | HOH | OH2 | 0.22 | 37.62 | 76.69 | 15.00 |
| 233 | HOH | OH2 | 3.45 | 36.52 | 73.19 | 15.00 |
| 234 | HOH | OH2 | 13.53 | 38.17 | 80.00 | 15.00 |
| 235 | HOH | OH2 | −15.93 | 48.59 | 69.63 | 15.00 |
| 236 | HOH | OH2 | −5.38 | 44.85 | 97.00 | 15.00 |
| 237 | HOH | OH2 | −7.89 | 45.15 | 89.13 | 15.00 |
| 238 | HOH | OH2 | 2.43 | 19.39 | 65.70 | 15.00 |
| 239 | HOH | OH2 | 7.43 | 21.65 | 71.07 | 15.00 |
| 240 | HOH | OH2 | 2.41 | 16.41 | 85.78 | 15.00 |
| 241 | HOH | OH2 | −0.33 | 36.99 | 59.82 | 15.00 |
| 242 | HOH | OH2 | −7.54 | 26.54 | 72.89 | 15.00 |
| 243 | HOH | OH2 | −3.03 | 44.85 | 65.86 | 15.00 |

TABLE X-continued

Table of the orthogonal three dimensional coordinates in Ångstroms and B factors (Å²) for the cathepsin K complex with inhibitor 1-N-(N-imidazole acetyl-leucinyl)-amino-3-N-(4-phenoxy-phenyl-sulfonyl)-amino-propan-2-one

| Residue | Atom | X | Y | Z | B |
|---|---|---|---|---|---|
| 244 | HOH | OH2 | 0.80 | 35.69 | 86.28 | 15.00 |
| 245 | HOH | OH2 | −9.57 | 36.85 | 95.54 | 15.00 |
| 246 | HOH | OH2 | −1.06 | 62.37 | 83.93 | 15.00 |
| 247 | HOH | OH2 | 7.72 | 62.09 | 69.81 | 15.00 |
| 248 | HOH | OH2 | 4.95 | 60.85 | 80.90 | 15.00 |
| 249 | HOH | OH2 | 14.51 | 30.92 | 83.13 | 15.00 |
| 250 | HOH | OH2 | −1.50 | 28.47 | 63.31 | 15.00 |
| 251 | HOH | OH2 | 15.32 | 22.32 | 71.31 | 15.00 |
| 252 | HOH | OH2 | −1.00 | 14.71 | 55.75 | 15.00 |
| 253 | HOH | OH2 | 6.77 | 18.87 | 84.05 | 15.00 |
| 254 | HOH | OH2 | −9.65 | 32.88 | 79.27 | 15.00 |
| 255 | HOH | OH2 | −2.32 | 34.26 | 69.09 | 15.00 |
| 256 | HOH | OH2 | −11.12 | 32.20 | 64.94 | 15.00 |
| 257 | HOH | OH2 | −3.80 | 45.19 | 72.07 | 15.00 |
| 258 | HOH | OH2 | −7.43 | 38.35 | 65.10 | 15.00 |
| 259 | HOH | OH2 | 1.41 | 46.77 | 63.08 | 15.00 |
| 260 | HOH | OH2 | −3.18 | 37.41 | 80.05 | 15.00 |
| 261 | HOH | OH2 | 7.12 | 59.13 | 81.53 | 15.00 |
| 262 | HOH | OH2 | 9.18 | 59.65 | 79.58 | 15.00 |
| 263 | HOH | OH2 | 8.43 | 57.49 | 83.56 | 15.00 |
| 264 | HOH | OH2 | 22.06 | 33.25 | 80.24 | 15.00 |
| 265 | HOH | OH2 | 20.66 | 27.84 | 95.17 | 15.00 |
| 266 | HOH | OH2 | 17.09 | 49.08 | 84.72 | 15.00 |
| 267 | HOH | OH2 | 12.06 | 54.25 | 84.82 | 15.00 |
| 268 | HOH | OH2 | 9.93 | 50.78 | 92.92 | 15.00 |
| 269 | HOH | OH2 | 13.59 | 41.50 | 91.19 | 15.00 |
| 270 | HOH | OH2 | 11.18 | 49.64 | 64.47 | 15.00 |
| 271 | HOH | OH2 | 12.14 | 55.71 | 75.81 | 15.00 |
| 272 | HOH | OH2 | 9.07 | 26.37 | 66.15 | 15.00 |
| 273 | HOH | OH2 | 24.27 | 24.31 | 64.11 | 15.00 |
| 274 | HOH | OH2 | 18.35 | 21.16 | 79.19 | 15.00 |
| 275 | HOH | OH2 | 20.62 | 28.49 | 61.87 | 15.00 |
| 276 | HOH | OH2 | 13.58 | 15.19 | 72.83 | 15.00 |
| 277 | HOH | OH2 | 9.33 | 19.74 | 77.14 | 15.00 |

TABLE XI

Table of angles between atoms of the inhibitor and protein for all protein atoms within 5 Ångstroms of the inhibitor 3(S)-3-[(N-benzyloxycarbonyl)-L-leucinyl] amino-5-methyl-1-(1-propoxy)-2-hexanone.

| Atom 1 | Atom 2 | Atom 3 | Angle | Atom 1 | Atom 2 | Atom 3 | Angle |
|---|---|---|---|---|---|---|---|
| 242OH2 | 25C1 | 18OD1 | 69.66 | 242OH2 | 25C1 | 18ND2 | 48.33 |
| 242OH2 | 25C1 | 184O | 82.25 | 242OH2 | 25C1 | 18CG | 62.66 |
| 242OH2 | 25C1 | 184C | 92.20 | 18OD1 | 25C1 | 184CA | 78.01 |
| 18OD1 | 25C1 | 18ND2 | 33.84 | 18OD1 | 25C1 | 184O | 82.68 |
| 18OD1 | 25C1 | 184CD1 | 97.11 | 18OD1 | 25C1 | 18CG | 16.91 |
| 18OD1 | 25C1 | 184C | 73.04 | 18OD1 | 25C1 | 20O | 60.56 |
| 184CB | 25C1 | 184CA | 23.31 | 184CB | 25C1 | 18ND2 | 93.14 |
| 184CB | 25C1 | 184O | 42.27 | 184CB | 25C1 | 184CG | 22.32 |
| 184CB | 25C1 | 184CD1 | 38.40 | 184CB | 25C1 | 18CG | 92.58 |
| 184CB | 25C1 | 184C | 36.61 | 184CB | 25C1 | 184CD2 | 32.79 |
| 184CB | 25C1 | 184NE1 | 49.18 | 184CA | 25C1 | 18ND2 | 72.65 |
| 184CA | 25C1 | 184O | 35.91 | 184CA | 25C1 | 184CG | 38.24 |
| 184CA | 25C1 | 184CD1 | 44.79 | 184CA | 25C1 | 18CG | 69.61 |
| 184CA | 25C1 | 184C | 21.48 | 184CA | 25C1 | 184CD2 | 52.43 |
| 184CA | 25C1 | 184NE1 | 58.86 | 18ND2 | 25C1 | 184O | 58.28 |
| 18ND2 | 25C1 | 18CG | 18.49 | 18ND2 | 25C1 | 184C | 56.82 |
| 18ND2 | 25C1 | 20O | 92.88 | 184O | 25C1 | 184CG | 64.55 |
| 184O | 25C1 | 184CD1 | 78.02 | 184O | 25C1 | 18CG | 67.10 |
| 184O | 25C1 | 184C | 17.17 | 184O | 25C1 | 184CD2 | 73.76 |
| 184O | 25C1 | 184NE1 | 90.68 | 184CG | 25C1 | 184CD1 | 19.59 |
| 184CG | 25C1 | 184C | 56.91 | 184CG | 25C1 | 184CD2 | 15.07 |
| 184CG | 25C1 | 184NE1 | 27.32 | 184CD1 | 25C1 | 18CG | 99.42 |
| 184CD1 | 25C1 | 184C | 66.13 | 184CD1 | 25C1 | 184CD2 | 27.32 |
| 184CD1 | 25C1 | 184NE1 | 14.36 | 184CD1 | 25C1 | 20O | 86.22 |
| 18CG | 25C1 | 184C | 59.85 | 18CG | 25C1 | 20O | 77.46 |
| 184C | 25C1 | 184CD2 | 69.30 | 184C | 25C1 | 184NE1 | 80.01 |
| 184CD2 | 25C1 | 184NE1 | 26.78 | 184NE1 | 25C1 | 20O | 80.98 |
| 18OD1 | 25C2 | 184CA | 93.13 | 18OD1 | 25C2 | 18CG | 18.16 |

TABLE XI-continued

Table of angles between atoms of the inhibitor and protein for all protein atoms within 5 Ångstroms of the inhibitor 3(S)-3-[(N-benzyloxycarbonyl)-L-leucinyl] amino-5-methyl-1-(1-propoxy)-2-hexanone.

| Atom 1 | Atom 2 | Atom 3 | Angle | Atom 1 | Atom 2 | Atom 3 | Angle |
|---|---|---|---|---|---|---|---|
| 18OD1 | 25C2 | 20N | 42.62 | 18OD1 | 25C2 | 18ND2 | 35.44 |
| 18OD1 | 25C2 | 242OH2 | 68.83 | 18OD1 | 25C2 | 20O | 79.33 |
| 18OD1 | 25C2 | 183O | 73.73 | 18OD1 | 25C2 | 184C | 80.63 |
| 18OD1 | 25C2 | 19CG | 85.64 | 18OD1 | 25C2 | 20CA | 45.72 |
| 18OD1 | 25C2 | 19N | 47.90 | 18OD1 | 25C2 | 184O | 85.52 |
| 18OD1 | 25C2 | 20C | 65.28 | 18OD1 | 25C2 | 184N | 90.71 |
| 18OD1 | 25C2 | 19C | 49.49 | 18OD1 | 25C2 | 18CB | 22.83 |
| 18OD1 | 25C2 | 183C | 82.72 | 18OD1 | 25C2 | 18CA | 34.96 |
| 18OD1 | 25C2 | 18C | 34.23 | 18OD1 | 25C2 | 19CA | 54.26 |
| 184CD1 | 25C2 | 184CA | 49.90 | 184CD1 | 25C2 | 184CB | 40.27 |
| 184CD1 | 25C2 | 184CG | 20.32 | 184CD1 | 25C2 | 183O | 55.01 |
| 184CD1 | 25C2 | 184C | 70.22 | 184CD1 | 25C2 | 19CG | 61.53 |
| 184CD1 | 25C2 | 19N | 85.18 | 184CD1 | 25C2 | 184O | 78.11 |
| 184CD1 | 25C2 | 184NE1 | 15.62 | 184CD1 | 25C2 | 184N | 44.48 |
| 184CD1 | 25C2 | 183C | 47.20 | 184CD1 | 25C2 | 18CA | 94.36 |
| 184CD1 | 25C2 | 18C | 95.90 | 184CD1 | 25C2 | 184CD2 | 23.77 |
| 184CD1 | 25C2 | 19CA | 87.00 | 184CA | 25C2 | 18CG | 78.59 |
| 184CA | 25C2 | 18ND2 | 76.16 | 184CA | 25C2 | 184CB | 23.25 |
| 184CA | 25C2 | 184CG | 39.72 | 184CA | 25C2 | 183O | 40.92 |
| 184CA | 25C2 | 184C | 20.77 | 184CA | 25C2 | 19CG | 86.38 |
| 184CA | 25C2 | 19N | 76.16 | 184CA | 25C2 | 184O | 33.25 |
| 184CA | 25C2 | 184NE1 | 65.31 | 184CA | 25C2 | 184N | 13.46 |
| 184CA | 25C2 | 18CB | 70.34 | 184CA | 25C2 | 183C | 28.93 |
| 184CA | 25C2 | 18CA | 61.99 | 184CA | 25C2 | 18C | 75.30 |
| 184CA | 25C2 | 184CD2 | 51.97 | 184CA | 25C2 | 19CA | 89.58 |
| 18CG | 25C2 | 20N | 59.81 | 18CG | 25C2 | 18ND2 | 20.07 |
| 18CG | 25C2 | 184CB | 99.39 | 18CG | 25C2 | 242OH2 | 62.04 |
| 18CG | 25C2 | 20O | 97.48 | 18CG | 25C2 | 183O | 69.32 |
| 18CG | 25C2 | 184C | 63.66 | 18CG | 25C2 | 19CG | 95.51 |
| 18CG | 25C2 | 20CA | 63.78 | 18CG | 25C2 | 19N | 54.69 |
| 18CG | 25C2 | 184O | 67.41 | 18CG | 25C2 | 20C | 83.28 |
| 18CG | 25C2 | 184N | 79.10 | 18CG | 25C2 | 19C | 65.07 |
| 18CG | 25C2 | 18CB | 12.54 | 18CG | 25C2 | 183C | 75.08 |
| 18CG | 25C2 | 18CA | 30.58 | 18CG | 25C2 | 18C | 39.48 |
| 18CG | 25C2 | 19CA | 65.54 | 20N | 25C2 | 18ND2 | 78.04 |
| 20N | 25C2 | 20O | 42.02 | 20N | 25C2 | 183O | 74.98 |
| 20N | 25C2 | 19CG | 52.80 | 20N | 25C2 | 20CA | 19.88 |
| 20N | 25C2 | 19N | 37.71 | 20N | 25C2 | 20C | 32.71 |
| 20N | 25C2 | 19C | 11.44 | 20N | 25C2 | 18CB | 58.04 |
| 20N | 25C2 | 183C | 87.83 | 20N | 25C2 | 18CA | 55.70 |
| 20N | 25C2 | 18C | 39.13 | 20N | 25C2 | 19CA | 28.06 |
| 18ND2 | 25C2 | 184CB | 92.26 | 18ND2 | 25C2 | 242OH2 | 45.09 |
| 18ND2 | 25C2 | 183O | 80.83 | 18ND2 | 25C2 | 184C | 57.03 |
| 18ND2 | 25C2 | 20CA | 77.75 | 18ND2 | 25C2 | 19N | 73.94 |
| 18ND2 | 25C2 | 184O | 55.05 | 18ND2 | 25C2 | 20C | 96.02 |
| 18ND2 | 25C2 | 184N | 81.33 | 18ND2 | 25C2 | 19C | 84.52 |
| 18ND2 | 25C2 | 18CB | 29.48 | 18ND2 | 25C2 | 183C | 82.74 |
| 18ND2 | 25C2 | 18CA | 46.57 | 18ND2 | 25C2 | 18C | 58.80 |
| 18ND2 | 25C2 | 19CA | 85.56 | 184CB | 25C2 | 184CG | 22.40 |
| 184CB | 25C2 | 183O | 59.35 | 184CB | 25C2 | 184C | 36.03 |
| 184CB | 25C2 | 19CG | 94.64 | 184CB | 25C2 | 19N | 96.61 |
| 184CB | 25C2 | 184O | 38.77 | 184CB | 25C2 | 184NE1 | 52.96 |
| 184CB | 25C2 | 184N | 31.46 | 184CB | 25C2 | 18CB | 92.63 |
| 184CB | 25C2 | 183C | 46.49 | 184CB | 25C2 | 18CA | 85.24 |
| 184CB | 25C2 | 18C | 97.95 | 184CB | 25C2 | 184CD2 | 31.97 |
| 242OH2 | 25C2 | 184C | 81.46 | 242OH2 | 25C2 | 20CA | 87.88 |
| 242OH2 | 25C2 | 184O | 68.50 | 242OH2 | 25C2 | 20C | 95.83 |
| 242OH2 | 25C2 | 18CB | 73.69 | 242OH2 | 25C2 | 18CA | 91.46 |
| 184CG | 25C2 | 183O | 61.89 | 184CG | 25C2 | 184C | 57.17 |
| 184CG | 25C2 | 19CG | 81.07 | 184CG | 25C2 | 19N | 97.59 |
| 184CG | 25C2 | 184O | 61.14 | 184CG | 25C2 | 184NE1 | 30.80 |
| 184CG | 25C2 | 184N | 40.66 | 184CG | 25C2 | 183C | 50.54 |
| 184CG | 25C2 | 18CA | 97.12 | 184CG | 25C2 | 184CD2 | 12.85 |
| 20O | 25C2 | 19CG | 59.65 | 20O | 25C2 | 20CA | 33.80 |
| 20O | 25C2 | 19N | 73.93 | 20O | 25C2 | 184NE1 | 98.68 |
| 20O | 25C2 | 20C | 15.00 | 20O | 25C2 | 19C | 44.20 |
| 20O | 25C2 | 18CB | 98.94 | 20O | 25C2 | 18CA | 97.51 |
| 20O | 25C2 | 18C | 80.19 | 20O | 25C2 | 19CA | 58.60 |
| 183O | 25C2 | 184C | 52.11 | 183O | 25C2 | 19CG | 50.15 |
| 183O | 25C2 | 20CA | 94.61 | 183O | 25C2 | 19N | 37.44 |
| 183O | 25C2 | 184O | 68.46 | 183O | 25C2 | 184NE1 | 67.20 |
| 183O | 25C2 | 184N | 28.51 | 183O | 25C2 | 19C | 66.39 |

TABLE XI-continued

Table of angles between atoms of the inhibitor and protein for all protein atoms within 5 Ångstroms of the inhibitor 3(S)-3-[(N-benzyloxycarbonyl)-L-leucinyl] amino-5-methyl-1-(1-propoxy)-2-hexanone.

| Atom 1 | Atom 2 | Atom 3 | Angle | Atom 1 | Atom 2 | Atom 3 | Angle |
|---|---|---|---|---|---|---|---|
| 183O | 25C2 | 18CB | 56.86 | 183O | 25C2 | 183C | 12.86 |
| 183O | 25C2 | 18CA | 39.61 | 183O | 25C2 | 18C | 42.74 |
| 183O | 25C2 | 184CD2 | 73.55 | 183O | 25C2 | 19CA | 48.97 |
| 184C | 25C2 | 19N | 79.88 | 184C | 25C2 | 184O | 16.37 |
| 184C | 25C2 | 184NE1 | 85.33 | 184C | 25C2 | 184N | 31.43 |
| 184C | 25C2 | 18CB | 58.56 | 184C | 25C2 | 183C | 43.26 |
| 184C | 25C2 | 18CA | 56.66 | 184C | 25C2 | 18C | 73.56 |
| 184C | 25C2 | 184CD2 | 67.95 | 184C | 25C2 | 19CA | 95.56 |
| 19CG | 25C2 | 20CA | 68.54 | 19CG | 25C2 | 19N | 41.00 |
| 19CG | 25C2 | 184NE1 | 59.71 | 19CG | 25C2 | 20C | 65.93 |
| 19CG | 25C2 | 184N | 72.99 | 19CG | 25C2 | 19C | 41.61 |
| 19CG | 25C2 | 18CB | 85.55 | 19CG | 25C2 | 183C | 58.81 |
| 19CG | 25C2 | 18CA | 69.73 | 19CG | 25C2 | 18C | 56.16 |
| 19CG | 25C2 | 184CD2 | 84.49 | 19CG | 25C2 | 19CA | 31.40 |
| 20CA | 25C2 | 19N | 57.18 | 20CA | 25C2 | 20C | 19.60 |
| 20CA | 25C2 | 19C | 30.27 | 20CA | 25C2 | 18CB | 66.65 |
| 20CA | 25C2 | 18CA | 70.02 | 20CA | 25C2 | 18C | 55.87 |
| 20CA | 25C2 | 19CA | 47.75 | 19N | 25C2 | 184O | 94.75 |
| 19N | 25C2 | 184NE1 | 91.69 | 19N | 25C2 | 20C | 69.08 |
| 19N | 25C2 | 184N | 65.26 | 19N | 25C2 | 19C | 30.47 |
| 19N | 25C2 | 18CB | 44.60 | 19N | 25C2 | 183C | 50.23 |
| 19N | 25C2 | 18CA | 30.19 | 19N | 25C2 | 18C | 15.21 |
| 19N | 25C2 | 19CA | 16.11 | 184O | 25C2 | 184NE1 | 91.68 |
| 184O | 25C2 | 184N | 45.89 | 184O | 25C2 | 18CB | 65.91 |
| 184O | 25C2 | 183C | 59.15 | 184O | 25C2 | 18CA | 68.65 |
| 184O | 25C2 | 18C | 86.43 | 184O | 25C2 | 184CD2 | 69.23 |
| 184NE1 | 25C2 | 184N | 60.01 | 184NE1 | 25C2 | 183C | 61.27 |
| 184NE1 | 25C2 | 184CD2 | 26.96 | 184NE1 | 25C2 | 19CA | 89.32 |
| 20C | 25C2 | 19C | 38.71 | 20C | 25C2 | 18CB | 86.12 |
| 20C | 25C2 | 18CA | 87.75 | 20C | 25C2 | 18C | 71.80 |
| 20C | 25C2 | 19CA | 55.73 | 184N | 25C2 | 19C | 94.86 |
| 184N | 25C2 | 18CB | 68.81 | 184N | 25C2 | 183C | 15.92 |
| 184N | 25C2 | 18CA | 56.71 | 184N | 25C2 | 18C | 67.03 |
| 184N | 25C2 | 184CD2 | 53.50 | 184N | 25C2 | 19CA | 77.48 |
| 19C | 25C2 | 18CB | 66.71 | 19C | 25C2 | 183C | 79.19 |
| 19C | 25C2 | 18CA | 54.22 | 19C | 25C2 | 18C | 36.38 |
| 19C | 25C2 | 19CA | 17.76 | 18CB | 25C2 | 183C | 63.21 |
| 18CB | 25C2 | 18CA | 18.13 | 18CB | 25C2 | 18C | 29.64 |
| 18CB | 25C2 | 19CA | 57.42 | 183C | 25C2 | 18CA | 47.76 |
| 183C | 25C2 | 18C | 54.26 | 183C | 25C2 | 184CD2 | 62.80 |
| 183C | 25C2 | 19CA | 61.67 | 18CA | 25C2 | 18C | 17.97 |
| 18CA | 25C2 | 19CA | 45.40 | 18C | 25C2 | 19CA | 28.26 |
| 20O | 25C3 | 19CG | 77.70 | 20O | 25C3 | 20N | 48.86 |
| 20O | 25C3 | 18OD1 | 82.41 | 20O | 25C3 | 20C | 15.02 |
| 20O | 25C3 | 20CA | 36.52 | 20O | 25C3 | 19CD | 82.71 |
| 20O | 25C3 | 19C | 49.69 | 20O | 25C3 | 19N | 81.60 |
| 20O | 25C3 | 19CB | 69.52 | 20O | 25C3 | 18CG | 93.56 |
| 20O | 25C3 | 19OE1 | 97.10 | 20O | 25C3 | 19CA | 66.55 |
| 184CD1 | 25C3 | 19CG | 70.95 | 184CD1 | 25C3 | 184NE1 | 20.32 |
| 184CD1 | 25C3 | 184CG | 17.18 | 184CD1 | 25C3 | 19CD | 63.15 |
| 184CD1 | 25C3 | 19N | 84.37 | 184CD1 | 25C3 | 184CA | 41.74 |
| 184CD1 | 25C3 | 183O | 51.08 | 184CD1 | 25C3 | 19CB | 82.21 |
| 184CD1 | 25C3 | 184CB | 33.05 | 184CD1 | 25C3 | 18CG | 99.94 |
| 184CD1 | 25C3 | 19OE1 | 48.60 | 184CD1 | 25C3 | 19CA | 92.55 |
| 184CD1 | 25C3 | 184CE2 | 24.46 | 19CG | 25C3 | 20N | 60.87 |
| 19CG | 25C3 | 18OD1 | 86.79 | 19CG | 25C3 | 20C | 80.83 |
| 19CG | 25C3 | 184NE1 | 70.80 | 19CG | 25C3 | 20CA | 78.71 |
| 19CG | 25C3 | 184CG | 86.74 | 19CG | 25C3 | 19CD | 19.15 |
| 19CG | 25C3 | 19C | 46.56 | 19CG | 25C3 | 19N | 42.15 |
| 19CG | 25C3 | 184CA | 83.50 | 19CG | 25C3 | 183O | 50.42 |
| 19CG | 25C3 | 19CB | 14.34 | 19CG | 25C3 | 184CB | 93.55 |
| 19CG | 25C3 | 18CG | 90.03 | 19CG | 25C3 | 19OE1 | 29.89 |
| 19CG | 25C3 | 19CA | 32.74 | 19CG | 25C3 | 184CE2 | 83.95 |
| 20N | 25C3 | 18OD1 | 40.95 | 20N | 25C3 | 20C | 38.02 |
| 20N | 25C3 | 20CA | 21.15 | 20N | 25C3 | 19CD | 78.19 |
| 20N | 25C3 | 19C | 14.72 | 20N | 25C3 | 19N | 36.90 |
| 20N | 25C3 | 184CA | 98.63 | 20N | 25C3 | 183O | 71.83 |
| 20N | 25C3 | 19CB | 46.57 | 20N | 25C3 | 18CG | 51.19 |
| 20N | 25C3 | 19OE1 | 90.75 | 20N | 25C3 | 19CA | 30.28 |
| 20N | 25C3 | 242OH2 | 86.06 | 18OD1 | 25C3 | 20C | 67.75 |
| 18CD1 | 25C3 | 20CA | 45.89 | 18OD1 | 25C3 | 19C | 52.30 |
| 18OD1 | 25C3 | 19N | 45.18 | 18OD1 | 25C3 | 184CA | 70.04 |

TABLE XI-continued

Table of angles between atoms of the inhibitor and protein for all protein atoms within 5 Ångstroms of the inhibitor 3(S)-3-[(N-benzyloxycarbonyl)-L-leucinyl] amino-5-methyl-1-(1-propoxy)-2-hexanone.

| Atom 1 | Atom 2 | Atom 3 | Angle | Atom 1 | Atom 2 | Atom 3 | Angle |
|---|---|---|---|---|---|---|---|
| 18OD1 | 25C3 | 18O | 62.55 | 18OD1 | 25C3 | 19CB | 74.34 |
| 18OD1 | 25C3 | 184CB | 86.92 | 18OD1 | 25C3 | 18CG | 11.19 |
| 18OD1 | 25C3 | 19CA | 55.77 | 18OD1 | 25C3 | 242OH2 | 51.35 |
| 20C | 25C3 | 20CA | 22.11 | 20C | 25C3 | 19CD | 90.19 |
| 20C | 25C3 | 19C | 43.18 | 20C | 25C3 | 19N | 73.89 |
| 20C | 25C3 | 19CB | 69.80 | 20C | 25C3 | 18CG | 78.83 |
| 20C | 25C3 | 19CA | 61.77 | 20C | 25C3 | 242OH2 | 89.06 |
| 184NE1 | 25C3 | 184CG | 32.04 | 184NE1 | 25C3 | 19CD | 56.99 |
| 184NE1 | 25C3 | 19N | 96.67 | 184NE1 | 25C3 | 184CA | 61.92 |
| 184NE1 | 25C3 | 18O | 67.54 | 184NE1 | 25C3 | 19CB | 84.48 |
| 184NE1 | 25C3 | 184CB | 50.65 | 184NE1 | 25C3 | 19OE1 | 42.30 |
| 184NE1 | 25C3 | 19CA | 99.57 | 184NE1 | 25C3 | 184CE2 | 13.16 |
| 20CA | 25C3 | 19CD | 93.68 | 20CA | 25C3 | 19C | 32.85 |
| 20CA | 25C3 | 19N | 57.68 | 20CA | 25C3 | 18O | 91.89 |
| 20CA | 25C3 | 19CB | 64.99 | 20CA | 25C3 | 18CG | 57.06 |
| 20CA | 25C3 | 19CA | 50.80 | 20CA | 25C3 | 242OH2 | 76.89 |
| 184CG | 25C3 | 19CD | 80.27 | 184CG | 25C3 | 19N | 91.72 |
| 184CG | 25C3 | 184CA | 34.06 | 184CG | 25C3 | 18O | 56.45 |
| 184CG | 25C3 | 19CB | 96.63 | 184CG | 25C3 | 184CB | 18.84 |
| 184CG | 25C3 | 18CG | 93.58 | 184CG | 25C3 | 19OE1 | 65.78 |
| 184CG | 25C3 | 184CE2 | 28.26 | 184CG | 25C3 | 242OH2 | 94.95 |
| 19CD | 25C3 | 19C | 63.50 | 19CD | 25C3 | 19N | 60.85 |
| 19CD | 25C3 | 184CA | 88.20 | 19CD | 25C3 | 18O | 60.91 |
| 19CD | 25C3 | 19CB | 32.82 | 19CD | 25C3 | 184CB | 92.35 |
| 19CD | 25C3 | 19OE1 | 14.96 | 19CD | 25C3 | 19CA | 51.66 |
| 19CD | 25C3 | 184CE2 | 69.81 | 19C | 25C3 | 19N | 31.91 |
| 19C | 25C3 | 184CA | 98.36 | 19C | 25C3 | 18O | 66.62 |
| 19C | 25C3 | 19CB | 32.43 | 19C | 25C3 | 18CG | 61.26 |
| 19C | 25C3 | 19OE1 | 76.35 | 19C | 25C3 | 19CA | 18.84 |
| 19N | 25C3 | 184CA | 66.70 | 19N | 25C3 | 18O | 35.29 |
| 19N | 25C3 | 19CB | 31.75 | 19N | 25C3 | 184CB | 85.03 |
| 19N | 25C3 | 18CG | 47.94 | 19N | 25C3 | 19OE1 | 67.18 |
| 19N | 25C3 | 19CA | 17.97 | 19N | 25C3 | 242OH2 | 95.18 |
| 184CA | 25C3 | 18O | 35.33 | 184CA | 25C3 | 19CB | 86.05 |
| 184CA | 25C3 | 184CB | 19.26 | 184CA | 25C3 | 18CG | 59.77 |
| 184CA | 25C3 | 19OE1 | 78.16 | 184CA | 25C3 | 19CA | 83.25 |
| 184CA | 25C3 | 184CE2 | 61.84 | 184CA | 25C3 | 242OH2 | 75.15 |
| 18O | 25C3 | 19CB | 50.84 | 18O | 25C3 | 184CB | 51.32 |
| 18O | 25C3 | 18CG | 57.48 | 18O | 25C3 | 19OE1 | 57.08 |
| 18O | 25C3 | 19CA | 49.31 | 18O | 25C3 | 184CE2 | 75.42 |
| 18O | 25C3 | 242OH2 | 96.01 | 19CB | 25C3 | 184CB | 99.69 |
| 19CB | 25C3 | 18CG | 79.10 | 19CB | 25C3 | 19OE1 | 44.22 |
| 19CB | 25C3 | 19CA | 18.92 | 19CB | 25C3 | 184CE2 | 97.58 |
| 184CB | 25C3 | 18CG | 76.03 | 184CB | 25C3 | 19OE1 | 79.22 |
| 184CB | 25C3 | 184CE2 | 46.73 | 184CB | 25C3 | 242OH2 | 78.05 |
| 18CG | 25C3 | 19CA | 61.53 | 18CG | 25C3 | 242OH2 | 47.27 |
| 19OE1 | 25C3 | 19CA | 62.05 | 19OE1 | 25C3 | 184CE2 | 55.29 |
| 20O | 25C4 | 20C | 10.43 | 20O | 25C4 | 19CG | 62.30 |
| 20O | 25C4 | 20N | 35.25 | 20O | 25C4 | 20CA | 26.32 |
| 20O | 25C4 | 19CD | 71.57 | 20O | 25C4 | 21NE2 | 50.82 |
| 20O | 25C4 | 18OD1 | 61.89 | 184CD1 | 25C4 | 184NE1 | 20.27 |
| 184CD1 | 25C4 | 19CG | 57.56 | 184CD1 | 25C4 | 184CG | 16.41 |
| 184CD1 | 25C4 | 184CE2 | 28.68 | 184CD1 | 25C4 | 20N | 90.35 |
| 184CD1 | 25C4 | 19CD | 54.84 | 184CD1 | 25C4 | 18OD1 | 81.65 |
| 184CD1 | 25C4 | 184CD2 | 25.56 | 184NE1 | 25C4 | 19CG | 61.65 |
| 184NE1 | 25C4 | 184CG | 29.79 | 184NE1 | 25C4 | 184CE2 | 15.87 |
| 184NE1 | 25C4 | 19CD | 51.78 | 184NE1 | 25C4 | 184CD2 | 25.93 |
| 20C | 25C4 | 19CG | 66.50 | 20C | 25C4 | 20N | 31.03 |
| 20C | 25C4 | 20CA | 17.90 | 20C | 25C4 | 19CD | 78.21 |
| 20C | 25C4 | 21NE2 | 44.60 | 20C | 25C4 | 18OD1 | 53.90 |
| 19CG | 25C4 | 184CG | 72.66 | 19CG | 25C4 | 184CE2 | 77.52 |
| 19CG | 25C4 | 20N | 46.19 | 19CG | 25C4 | 20CA | 61.94 |
| 19CG | 25C4 | 19CD | 18.17 | 19CG | 25C4 | 18OD1 | 63.67 |
| 19CG | 25C4 | 184CD2 | 82.38 | 184CG | 25C4 | 184CE2 | 28.98 |
| 184CG | 25C4 | 20N | 98.65 | 184CG | 25C4 | 19CD | 71.23 |
| 184CG | 25C4 | 18OD1 | 82.35 | 184CG | 25C4 | 184CD2 | 16.48 |
| 184CE2 | 25C4 | 19CD | 67.12 | 184CE2 | 25C4 | 184CD2 | 16.42 |
| 20N | 25C4 | 20CA | 17.47 | 20N | 25C4 | 19CD | 63.14 |
| 20N | 25C4 | 21NE2 | 68.18 | 20N | 25C4 | 18OD1 | 30.69 |
| 20CA | 25C4 | 19CD | 77.50 | 20CA | 25C4 | 21NE2 | 50.79 |
| 20CA | 25C4 | 18OD1 | 36.03 | 19CD | 25C4 | 18OD1 | 81.70 |
| 19CD | 25C4 | 184CD2 | 76.27 | 21NE2 | 25C4 | 18OD1 | 71.09 |

TABLE XI-continued

Table of angles between atoms of the inhibitor and protein for all protein atoms within 5 Ångstroms of the inhibitor 3(S)-3-[(N-benzyloxycarbonyl)-L-leucinyl] amino-5-methyl-1-(1-propoxy)-2-hexanone.

| Atom 1 | Atom 2 | Atom 3 | Angle | Atom 1 | Atom 2 | Atom 3 | Angle |
|---|---|---|---|---|---|---|---|
| 18OD1 | 25C4 | 184CD2 | 98.63 | 184CD1 | 25C5 | 20O | 89.99 |
| 184CD1 | 25C5 | 184NE1 | 17.97 | 184CD1 | 25C5 | 184CG | 17.29 |
| 184CD1 | 25C5 | 184CE2 | 27.88 | 184CD1 | 25C5 | 242OH2 | 99.26 |
| 184CD1 | 25C5 | 184CD2 | 27.37 | 20O | 25C5 | 184NE1 | 92.08 |
| 20O | 25C5 | 242OH2 | 86.50 | 20O | 25C5 | 21NE2 | 47.88 |
| 184NE1 | 25C5 | 184CG | 28.79 | 184NE1 | 25C5 | 184CE2 | 16.62 |
| 184NE1 | 25C5 | 184CD2 | 27.40 | 184CG | 25C5 | 184CE2 | 28.30 |
| 184CG | 25C5 | 242OH2 | 92.08 | 184CG | 25C5 | 184CD2 | 17.13 |
| 184CE2 | 25C5 | 184CD2 | 16.84 | 242OH2 | 25C5 | 21NE2 | 65.12 |
| 242OH2 | 25C6 | 184CB | 96.30 | 242OH2 | 25C6 | 184CA | 83.88 |
| 242OH2 | 25C6 | 18OD1 | 51.77 | 242OH2 | 25C6 | 184O | 63.15 |
| 184CG | 25C6 | 184CD1 | 17.92 | 184CG | 25C6 | 184CB | 19.89 |
| 184CG | 25C6 | 184CD2 | 17.11 | 184CG | 25C6 | 184NE1 | 27.45 |
| 184CG | 25C6 | 184CA | 31.62 | 184CG | 25C6 | 18OD1 | 84.34 |
| 184CG | 25C6 | 184O | 53.51 | 184CD1 | 25C6 | 184CB | 33.90 |
| 184CD1 | 25C6 | 184CD2 | 27.70 | 184CD1 | 25C6 | 184NE1 | 16.02 |
| 184CD1 | 25C6 | 184CA | 37.26 | 184CD1 | 25C6 | 18OD1 | 76.75 |
| 184CD1 | 25C6 | 184O | 64.28 | 184CB | 25C6 | 184CD2 | 32.92 |
| 184CB | 25C6 | 184NE1 | 46.79 | 184CB | 25C6 | 184CA | 18.16 |
| 184CB | 25C6 | 18OD1 | 76.20 | 184CB | 25C6 | 184O | 33.78 |
| 184CD2 | 25C6 | 184NE1 | 26.79 | 184CD2 | 25C6 | 184CA | 47.98 |
| 184CD2 | 25C6 | 184O | 65.87 | 184NE1 | 25C6 | 184CA | 53.03 |
| 184NE1 | 25C6 | 18OD1 | 88.79 | 184NE1 | 25C6 | 184O | 79.21 |
| 184CA | 25C6 | 18OD1 | 58.04 | 184CA | 25C6 | 184O | 28.15 |
| 18OD1 | 25C6 | 184O | 61.50 | 20O | 25C7 | 20C | 4.43 |
| 20O | 25C7 | 19CG | 62.28 | 20O | 25C7 | 19CD | 77.38 |
| 20O | 25C7 | 19NE2 | 74.82 | 20O | 25C7 | 19OE1 | 90.67 |
| 184NE1 | 25C7 | 19CG | 59.54 | 184NE1 | 25C7 | 19CD | 53.46 |
| 184NE1 | 25C7 | 184CD1 | 17.49 | 184NE1 | 25C7 | 19NE2 | 66.80 |
| 184NE1 | 25C7 | 19OE1 | 40.08 | 184NE1 | 25C7 | 184CE2 | 14.60 |
| 20C | 25C7 | 19CG | 65.46 | 20C | 25C7 | 19CD | 81.18 |
| 20C | 25C7 | 19NE2 | 79.11 | 20C | 25C7 | 19OE1 | 94.22 |
| 19CG | 25C7 | 19CD | 19.72 | 19CG | 25C7 | 184CD1 | 52.93 |
| 19CG | 25C7 | 19NE2 | 30.67 | 19CG | 25C7 | 19OE1 | 29.47 |
| 19CG | 25C7 | 184CE2 | 74.12 | 19CD | 25C7 | 184CD1 | 53.97 |
| 19CD | 25C7 | 19NE2 | 16.35 | 19CD | 25C7 | 19OE1 | 14.31 |
| 19CD | 25C7 | 184CE2 | 67.37 | 19NE2 | 25C7 | 19OE1 | 69.74 |
| 184CD1 | 25C7 | 19OE1 | 43.73 | 184CD1 | 25C7 | 184CE2 | 26.87 |
| 19NE2 | 25C7 | 19OE1 | 26.90 | 19NE2 | 25C7 | 184CE2 | 79.58 |
| 19OE1 | 25C7 | 184CE2 | 53.50 | 184NE1 | 25O8 | 19CD | 69.28 |
| 184NE1 | 25O8 | 19NE2 | 88.26 | 184NE1 | 25O8 | 19OE1 | 52.70 |
| 184NE1 | 25O8 | 19CG | 72.15 | 184NE1 | 25O8 | 184CD1 | 18.62 |
| 184NE1 | 25O8 | 184CE2 | 15.78 | 184NE1 | 25O8 | 184CZ2 | 30.82 |
| 19CD | 25O8 | 19NE2 | 21.45 | 19CD | 25O8 | 19OE1 | 19.40 |
| 19CD | 25O8 | 19CG | 23.73 | 19CD | 25O8 | 20O | 83.60 |
| 19CD | 25O8 | 184CD1 | 65.36 | 19CD | 25O8 | 184CE2 | 84.12 |
| 19CD | 25O8 | 22O | 53.07 | 19CD | 25O8 | 184CZ2 | 93.15 |
| 19NE2 | 25O8 | 19OE1 | 35.59 | 19NE2 | 25O8 | 19CG | 38.13 |
| 19NE2 | 25O8 | 20O | 82.17 | 19NE2 | 25O8 | 184CD1 | 86.56 |
| 19NE2 | 25O8 | 22O | 36.04 | 19OE1 | 25O8 | 19CG | 37.46 |
| 19OE1 | 25O8 | 184CD1 | 53.61 | 19OE1 | 25O8 | 184CE2 | 66.40 |
| 19OE1 | 25O8 | 22O | 70.80 | 19OE1 | 25O8 | 184CZ2 | 73.99 |
| 19CG | 25O8 | 20O | 63.71 | 19CG | 25O8 | 184CD1 | 60.70 |
| 19CG | 25O8 | 184CE2 | 87.89 | 19CG | 25O8 | 22O | 54.69 |
| 20C | 25O8 | 22O | 57.31 | 184CD1 | 25O8 | 184CE2 | 30.67 |
| 184CD1 | 25O8 | 184CZ2 | 47.47 | 184CE2 | 25O8 | 184CZ2 | 16.93 |
| 19NE2 | 25C9 | 184NE1 | 78.75 | 19NE2 | 25C9 | 19CD | 19.52 |
| 19NE2 | 25C9 | 19OE1 | 33.07 | 19NE2 | 25C9 | 184CE2 | 94.10 |
| 19NE2 | 25C9 | 19CG | 30.70 | 19NE2 | 25C9 | 184CD1 | 73.44 |
| 19NE2 | 25C9 | 22O | 33.46 | 184NE1 | 25C9 | 19CD | 59.66 |
| 184NE1 | 25C9 | 19OE1 | 47.23 | 184NE1 | 25C9 | 184CE2 | 16.38 |
| 184NE1 | 25C9 | 184CZ2 | 33.08 | 184NE1 | 25C9 | 19CG | 58.24 |
| 184NE4 | 25C9 | 184CD1 | 12.56 | 19CD | 25C9 | 19OE1 | 17.75 |
| 19CD | 25C9 | 184CE2 | 75.46 | 19CD | 25C9 | 184CZ2 | 89.07 |
| 19CD | 25C9 | 19CG | 17.50 | 19CD | 25C9 | 184CD1 | 53.92 |
| 19CD | 25C9 | 22O | 48.71 | 19OE1 | 25C9 | 184CE2 | 61.55 |
| 19OE1 | 25C9 | 184CZ2 | 73.08 | 19OE1 | 25C9 | 19CG | 30.61 |
| 19OE1 | 25C9 | 184CD1 | 45.28 | 19OE1 | 25C9 | 22O | 65.42 |
| 184CE2 | 25C9 | 184CZ2 | 17.56 | 184CE2 | 25C9 | 19CG | 74.59 |
| 184CE2 | 25C9 | 184CD1 | 26.94 | 184CZ2 | 25C9 | 19CG | 90.93 |
| 184CZ2 | 25C9 | 184CD1 | 44.43 | 19CG | 25C9 | 184CD1 | 48.87 |
| 19CG | 25C9 | 22O | 48.21 | 184CD1 | 25C9 | 22O | 97.02 |

TABLE XI-continued

Table of angles between atoms of the inhibitor and protein for all protein atoms within 5 Ångstroms of the inhibitor 3(S)-3-[(N-benzyloxycarbonyl)-L-leucinyl] amino-5-methyl-1-(1-propoxy)-2-hexanone.

| Atom 1 | Atom 2 | Atom 3 | Angle | Atom 1 | Atom 2 | Atom 3 | Angle |
|---|---|---|---|---|---|---|---|
| 19NE2 | 25O10 | 23CA | 53.09 | 19NE2 | 25O10 | 19CD | 16.71 |
| 19NE2 | 25O10 | 22O | 36.83 | 19NE2 | 25O10 | 23N | 57.66 |
| 19NE2 | 25O10 | 19OE1 | 28.25 | 19NE2 | 25O10 | 22C | 50.13 |
| 23CA | 25O10 | 19CD | 69.80 | 23CA | 25O10 | 22O | 36.05 |
| 23CA | 25O10 | 23N | 17.68 | 23CA | 25O10 | 19OE1 | 79.02 |
| 23CA | 25O10 | 22C | 29.83 | 19CD | 25O10 | 22O | 49.55 |
| 19CD | 25O10 | 23N | 73.42 | 19CD | 25O10 | 19OE1 | 15.11 |
| 19CD | 25O10 | 22C | 63.87 | 22O | 25O10 | 23N | 27.96 |
| 22O | 25O10 | 19CE1 | 63.96 | 22O | 25O10 | 22C | 14.56 |
| 23N | 25O10 | 19OE1 | 85.79 | 23N | 25O10 | 22C | 15.87 |
| 19OE1 | 25O10 | 22C | 77.94 | 162ND1 | 25C11 | 184CZ2 | 63.39 |
| 162ND1 | 25C11 | 162CE1 | 16.78 | 162ND1 | 25C11 | 184NE1 | 61.01 |
| 162ND1 | 25C11 | 184CE2 | 62.72 | 162ND1 | 25C11 | 162CG | 15.67 |
| 162ND1 | 25C11 | 184CH2 | 68.93 | 162ND1 | 25C11 | 162CB | 30.11 |
| 184CZ2 | 25C11 | 162CE1 | 53.21 | 184CZ2 | 25C11 | 184NE1 | 33.69 |
| 184CZ2 | 25C11 | 184CE2 | 16.65 | 184CZ2 | 25C11 | 162CG | 59.25 |
| 184CZ2 | 25C11 | 184CH2 | 12.22 | 184CZ2 | 25C11 | 162CB | 70.77 |
| 162CE1 | 25C11 | 184NE1 | 44.59 | 162CE1 | 25C11 | 184CE2 | 48.65 |
| 162CE1 | 25C11 | 162CG | 27.93 | 162CE1 | 25C11 | 184CH2 | 61.58 |
| 162CE1 | 25C11 | 162CB | 44.93 | 184NE1 | 25C11 | 184CE2 | 17.24 |
| 184NE1 | 25C11 | 162CG | 67.01 | 184NE1 | 25C11 | 184CH2 | 45.73 |
| 184NE1 | 25C11 | 162CB | 83.92 | 184CE2 | 25C11 | 162CG | 63.63 |
| 184CE2 | 25C11 | 184CH2 | 28.52 | 184CE2 | 25C11 | 162CB | 78.45 |
| 162CG | 25C11 | 184CH2 | 61.52 | 162CG | 25C11 | 162CB | 17.47 |
| 184CH2 | 25C11 | 162CB | 69.67 | 138OG | 25C15 | 138CB | 12.25 |
| 138OG | 25C15 | 138CA | 28.90 | 138OG | 25C15 | 161OD1 | 38.49 |
| 138CB | 25C15 | 138CA | 18.42 | 138CB | 25C15 | 161OD1 | 45.39 |
| 138CA | 25C15 | 161OD1 | 48.24 | 162ND1 | 25C16 | 161O | 83.50 |
| 162ND1 | 25C16 | 162CG | 18.14 | 162ND1 | 25C16 | 162CE1 | 16.51 |
| 162ND1 | 25C16 | 162CB | 37.71 | 162ND1 | 25C16 | 25SG | 53.12 |
| 162ND1 | 25C16 | 162CA | 45.79 | 162ND1 | 25C16 | 161C | 76.59 |
| 162ND1 | 25C16 | 184CZ2 | 58.80 | 162ND1 | 25C16 | 25CB | 44.47 |
| 162ND1 | 25C16 | 162N | 61.56 | 162ND1 | 25C16 | 19OE1 | 54.44 |
| 161O | 25C16 | 162CG | 73.87 | 161O | 25C16 | 162CE1 | 99.61 |
| 161O | 25C16 | 162CB | 55.47 | 161O | 25C16 | 25SG | 68.22 |
| 161O | 25C16 | 162CA | 38.54 | 161O | 25C16 | 161C | 12.03 |
| 161O | 25C16 | 25CB | 87.95 | 161O | 25C16 | 162N | 25.97 |
| 162CG | 25C16 | 162CE1 | 32.06 | 162CG | 25C16 | 162CB | 21.17 |
| 162CG | 25C16 | 25SG | 64.52 | 162CG | 25C16 | 162CA | 35.58 |
| 162CG | 25C16 | 161C | 64.63 | 162CG | 25C16 | 184CZ2 | 58.11 |
| 162CG | 25C16 | 25CB | 60.75 | 162CG | 25C16 | 162N | 48.98 |
| 162CG | 25C16 | 19OE1 | 71.80 | 162CE1 | 25C16 | 162CB | 53.00 |
| 162CE1 | 25C16 | 25SG | 57.54 | 162CE1 | 25C16 | 162CA | 62.27 |
| 162CE1 | 25C16 | 161C | 93.08 | 162CE1 | 25C16 | 184CZ2 | 50.19 |
| 162CE1 | 25C16 | 25CB | 42.26 | 162CE1 | 25C16 | 162N | 78.06 |
| 162CE1 | 25C16 | 19OE1 | 40.00 | 162CB | 25C16 | 25SG | 70.05 |
| 162CB | 25C16 | 162CA | 20.87 | 162CB | 25C16 | 161C | 44.96 |
| 162CB | 25C16 | 184CZ2 | 71.73 | 162CB | 25C16 | 25CB | 73.86 |
| 162CB | 25C16 | 162N | 29.56 | 162CB | 25C16 | 19OE1 | 92.15 |
| 25SG | 25C16 | 162CA | 56.57 | 25SG | 25C16 | 161C | 72.16 |
| 25SG | 25C16 | 25CB | 21.35 | 25SG | 25C16 | 162N | 67.66 |
| 25SG | 25C16 | 19OE1 | 58.28 | 162CA | 25C16 | 161C | 30.81 |
| 162CA | 25C16 | 184CZ2 | 91.78 | 162CA | 25C16 | 25CB | 67.26 |
| 162CA | 25C16 | 162N | 16.41 | 162CA | 25C16 | 19OE1 | 95.96 |
| 161C | 25C16 | 25CB | 89.77 | 161C | 25C16 | 162N | 15.65 |
| 184CZ2 | 25C16 | 25CB | 89.70 | 184CZ2 | 25C16 | 19OE1 | 64.53 |
| 25CB | 25C16 | 162N | 81.65 | 25CB | 25C16 | 19OE1 | 37.30 |
| 162ND1 | 25O17 | 162CB | 53.19 | 162ND1 | 25O17 | 162CG | 26.33 |
| 162ND1 | 25O17 | 162CA | 63.48 | 162ND1 | 25O17 | 162N | 85.18 |
| 162ND1 | 25O17 | 162CE1 | 12.84 | 162ND1 | 25O17 | 25SG | 56.41 |
| 162ND1 | 25O17 | 162CD2 | 24.16 | 162ND1 | 25O17 | 162C | 54.50 |
| 162ND1 | 25O17 | 162NE2 | 14.17 | 162ND1 | 25O17 | 184CZ2 | 59.71 |
| 162ND1 | 25O17 | 163N | 47.86 | 162ND1 | 25O17 | 25CB | 41.51 |
| 162CB | 25O17 | 161O | 76.56 | 162CB | 25O17 | 162CG | 28.45 |
| 162CB | 25O17 | 162CA | 28.85 | 162CB | 25O17 | 161C | 60.68 |
| 162CB | 25O17 | 162N | 40.36 | 162CB | 25O17 | 162CE1 | 64.12 |
| 162CB | 25O17 | 25SG | 83.81 | 162CB | 25O17 | 161OD1 | 58.91 |
| 162CB | 25O17 | 162CD2 | 36.23 | 162CB | 25O17 | 162C | 31.62 |
| 162CB | 25O17 | 162NE2 | 52.83 | 162CB | 25O17 | 184CZ2 | 81.36 |
| 162CB | 25O17 | 163N | 44.40 | 162CB | 25O17 | 25CB | 83.22 |
| 162CB | 25O17 | 161CA | 66.51 | 162CB | 25O17 | 161CB | 74.63 |
| 161O | 25O17 | 162CA | 52.04 | 161O | 25O17 | 161C | 18.10 |

TABLE XI-continued

Table of angles between atoms of the inhibitor and protein for all protein atoms within 5 Ångstroms of the inhibitor 3(S)-3-[(N-benzyloxycarbonyl)-L-leucinyl] amino-5-methyl-1-(1-propoxy)-2-hexanone.

| Atom 1 | Atom 2 | Atom 3 | Angle | Atom 1 | Atom 2 | Atom 3 | Angle |
|---|---|---|---|---|---|---|---|
| 161O | 25O17 | 162N | 36.49 | 161O | 25O17 | 25SG | 77.20 |
| 161O | 25O17 | 161OD1 | 60.19 | 161O | 25O17 | 162C | 58.32 |
| 161O | 25O17 | 163N | 63.78 | 161O | 25O17 | 25CB | 97.03 |
| 161O | 25O17 | 161CA | 21.34 | 161O | 25O17 | 161CB | 35.39 |
| 162CG | 25O17 | 162CA | 48.03 | 162CG | 25O17 | 161C | 86.77 |
| 162CG | 25O17 | 162N | 66.31 | 162CG | 25O17 | 162CE1 | 35.94 |
| 162CG | 25O17 | 25SG | 73.55 | 162CG | 25O17 | 161OD1 | 84.63 |
| 162CG | 25O17 | 162CD2 | 9.57 | 162CG | 25O17 | 162C | 43.30 |
| 162CG | 25O17 | 162NE2 | 24.46 | 162CG | 25O17 | 184CZ2 | 61.90 |
| 162CG | 25O17 | 163N | 46.12 | 162CG | 25O17 | 25CB | 64.34 |
| 162CG | 25O17 | 161CA | 94.08 | 162CA | 25O17 | 161C | 40.53 |
| 162CA | 25O17 | 162N | 22.22 | 162CA | 25O17 | 162CE1 | 76.31 |
| 162CA | 25O17 | 25SG | 66.07 | 162CA | 25O17 | 161OD1 | 63.93 |
| 162CA | 25O17 | 162CD2 | 57.57 | 162CA | 25O17 | 162C | 11.05 |
| 162CA | 25O17 | 162NE2 | 70.12 | 162CA | 25O17 | 163N | 26.62 |
| 162CA | 25O17 | 25CB | 74.60 | 162CA | 25O17 | 161CA | 50.08 |
| 162CA | 25O17 | 161CB | 64.72 | 161C | 25O17 | 162N | 20.53 |
| 161C | 25O17 | 25SG | 84.94 | 161C | 25O17 | 161OD1 | 45.99 |
| 161C | 25O17 | 162CD2 | 95.86 | 161C | 25O17 | 162C | 49.50 |
| 161C | 25O17 | 163N | 59.81 | 161C | 25O17 | 161CA | 11.07 |
| 161C | 25O17 | 161CB | 28.61 | 162N | 25O17 | 162CE1 | 97.92 |
| 162N | 25O17 | 25SG | 81.29 | 162N | 25O17 | 161OD1 | 46.28 |
| 162N | 25O17 | 162CD2 | 75.34 | 162N | 25O17 | 162C | 32.79 |
| 162N | 25O17 | 162NE2 | 90.12 | 162N | 25O17 | 163N | 46.59 |
| 162N | 25O17 | 25CB | 94.05 | 162N | 25O17 | 161CA | 28.47 |
| 162N | 25O17 | 161CB | 42.50 | 162CE1 | 25O17 | 25SG | 60.41 |
| 162CE1 | 25O17 | 162CD2 | 30.63 | 162CE1 | 25O17 | 162C | 67.29 |
| 162CE1 | 25O17 | 162NE2 | 14.05 | 162CE1 | 25O17 | 184CZ2 | 50.87 |
| 162CE1 | 25O17 | 163N | 59.73 | 162CE1 | 25O17 | 25CB | 42.09 |
| 25SG | 25O17 | 162CD2 | 77.38 | 25SG | 25O17 | 162C | 56.56 |
| 25SG | 25O17 | 162NE2 | 70.26 | 25SG | 25O17 | 163N | 40.80 |
| 25SG | 25O17 | 25CB | 20.52 | 25SG | 25O17 | 161CA | 94.97 |
| 161OD1 | 25O17 | 162CD2 | 88.85 | 161OD1 | 25O17 | 162C | 74.74 |
| 161OD1 | 25O17 | 163N | 90.55 | 161OD1 | 25O17 | 161CA | 38.88 |
| 161OD1 | 25O17 | 161CB | 28.90 | 162CD2 | 25O17 | 162C | 52.76 |
| 162CD2 | 25O17 | 162NE2 | 17.33 | 162CD2 | 25O17 | 184CZ2 | 52.52 |
| 162CD2 | 25O17 | 163N | 54.44 | 162CD2 | 25O17 | 25CB | 65.18 |
| 162C | 25O17 | 162NE2 | 62.89 | 162C | 25O17 | 163N | 16.06 |
| 162C | 25O17 | 25CB | 63.70 | 162C | 25O17 | 161CA | 59.72 |
| 162C | 25O17 | 161CB | 75.18 | 162NE2 | 25O17 | 184CZ2 | 46.51 |
| 162NE2 | 25O17 | 163N | 59.43 | 162NE2 | 25O17 | 25CB | 53.98 |
| 184CZ2 | 25O17 | 25CB | 88.90 | 163N | 25O17 | 25CB | 48.07 |
| 163N | 25O17 | 161CA | 70.75 | 163N | 25O17 | 161CB | 87.59 |
| 161CA | 25O17 | 161CB | 17.64 | 25SG | 25N18 | 162ND1 | 54.05 |
| 25SG | 25N18 | 161O | 72.12 | 25SG | 25N18 | 25CB | 22.85 |
| 25SG | 25N18 | 19NE2 | 68.04 | 25SG | 25N18 | 23CA | 83.69 |
| 25SG | 25N18 | 162CE1 | 55.83 | 25SG | 25N18 | 162CA | 54.53 |
| 25SG | 25N18 | 19OE1 | 61.94 | 25SG | 25N18 | 162CG | 59.80 |
| 25SG | 25N18 | 162CB | 64.56 | 162ND1 | 25N18 | 161O | 73.75 |
| 162ND1 | 25N18 | 25CB | 47.82 | 162ND1 | 25N18 | 19NE2 | 80.11 |
| 162ND1 | 25N18 | 162CE1 | 14.94 | 162ND1 | 25N18 | 162CA | 39.62 |
| 162ND1 | 25N18 | 19OE1 | 53.76 | 162ND1 | 25N18 | 162CG | 12.62 |
| 162ND1 | 25N18 | 162CB | 29.54 | 161O | 25N18 | 25CB | 91.76 |
| 161O | 25N18 | 162CE1 | 88.51 | 161O | 25N18 | 162CA | 34.27 |
| 161O | 25N18 | 162CG | 63.44 | 161O | 25N18 | 162CB | 47.06 |
| 25CB | 25N18 | 19NE2 | 48.54 | 25CB | 25N18 | 23CA | 78.61 |
| 25CB | 25N18 | 162CE1 | 42.68 | 25CB | 25N18 | 162CA | 66.30 |
| 25CB | 25N18 | 19OE1 | 39.11 | 25CB | 25N18 | 162CG | 58.13 |
| 25CB | 25N18 | 162CB | 69.62 | 19NE2 | 25N18 | 23CA | 48.32 |
| 19NE2 | 25N18 | 162CE1 | 66.29 | 19NE2 | 25N18 | 19OE1 | 27.62 |
| 19NE2 | 25N18 | 162CG | 92.70 | 23CA | 25N18 | 19OE1 | 75.78 |
| 162CE1 | 25N18 | 162CA | 54.27 | 162CE1 | 25N18 | 19OE1 | 39.27 |
| 162CE1 | 25N18 | 162CG | 26.90 | 162CE1 | 25N18 | 162CB | 44.19 |
| 162CA | 25N18 | 19OE1 | 90.56 | 162CA | 25N18 | 162CG | 30.46 |
| 162CA | 25N18 | 162CB | 17.73 | 19OE1 | 25N18 | 162CG | 66.12 |
| 19OE1 | 25N18 | 162CB | 83.30 | 162CG | 25N18 | 162CB | 17.35 |
| 25SG | 25C19 | 161O | 94.77 | 25SG | 25C19 | 162ND1 | 55.31 |
| 25SG | 25C19 | 25CB | 20.96 | 25SG | 25C19 | 162CA | 63.69 |
| 25SG | 25C19 | 161C | 89.52 | 25SG | 25C19 | 23CA | 94.30 |
| 25SG | 25C19 | 23O | 76.83 | 25SG | 25C19 | 23C | 78.19 |
| 25SG | 25C19 | 162N | 77.13 | 25SG | 25C19 | 25N | 39.34 |
| 25SG | 25C19 | 19NE2 | 66.56 | 25SG | 25C19 | 163N | 35.68 |

TABLE XI-continued

Table of angles between atoms of the inhibitor and protein for all protein atoms within 5 Ångstroms of the inhibitor 3(S)-3-[(N-benzyloxycarbonyl)-L-leucinyl] amino-5-methyl-1-(1-propoxy)-2-hexanone.

| Atom 1 | Atom 2 | Atom 3 | Angle | Atom 1 | Atom 2 | Atom 3 | Angle |
|---|---|---|---|---|---|---|---|
| 25SG | 25C19 | 162CE1 | 52.07 | 25SG | 25C19 | 162CB | 68.67 |
| 161O | 25C19 | 162ND1 | 77.82 | 161O | 25C19 | 162CA | 38.27 |
| 161O | 25C19 | 161C | 6.45 | 161O | 25C19 | 162N | 21.62 |
| 161O | 25C19 | 163N | 59.92 | 161O | 25C19 | 162CE1 | 90.20 |
| 161O | 25C19 | 162CB | 47.78 | 162ND1 | 25C19 | 25CB | 49.17 |
| 162ND1 | 25C19 | 162CA | 42.28 | 162ND1 | 25C19 | 161C | 71.68 |
| 162ND1 | 25C19 | 162N | 57.38 | 162ND1 | 25C19 | 25N | 77.84 |
| 162ND1 | 25C19 | 19NE2 | 72.32 | 162ND1 | 25C19 | 163N | 45.25 |
| 162ND1 | 25C19 | 162CE1 | 12.42 | 162ND1 | 25C19 | 162CB | 30.12 |
| 25CB | 25C19 | 162CA | 73.53 | 25CB | 25C19 | 23CA | 82.52 |
| 25CB | 25C19 | 23C | 74.24 | 25CB | 25C19 | 23C | 70.22 |
| 25CB | 25C19 | 162N | 89.39 | 25CB | 25C19 | 25N | 30.03 |
| 25CB | 25C19 | 19NE2 | 46.97 | 25CB | 25C19 | 163N | 50.32 |
| 25CB | 25C19 | 162CE1 | 41.12 | 25CB | 25C19 | 162CB | 72.32 |
| 162CA | 25C19 | 161C | 31.82 | 162CA | 25C19 | 162N | 16.65 |
| 162CA | 25C19 | 163N | 29.20 | 162CA | 25C19 | 162CE1 | 53.97 |
| 162CA | 25C19 | 162CB | 17.00 | 161C | 25C19 | 162N | 15.17 |
| 161C | 25C19 | 163N | 54.26 | 161C | 25C19 | 162CE1 | 84.02 |
| 161C | 25C19 | 162CB | 41.75 | 23CA | 25C19 | 23O | 29.88 |
| 23CA | 25C19 | 23C | 18.55 | 23CA | 25C19 | 25N | 55.13 |
| 23CA | 25C19 | 19NE2 | 45.62 | 23O | 25C19 | 23C | 14.86 |
| 23O | 25C19 | 25N | 44.51 | 23O | 25C19 | 19NE2 | 58.93 |
| 23C | 25C19 | 25N | 40.60 | 23C | 25C19 | 19NE2 | 45.52 |
| 162N | 25C19 | 163N | 41.46 | 162N | 25C19 | 162CE1 | 69.54 |
| 162N | 25C19 | 162CB | 28.25 | 25N | 25C19 | 19NE2 | 36.78 |
| 25N | 25C19 | 163N | 74.96 | 25N | 25C19 | 162CE1 | 67.79 |
| 19NE2 | 25C19 | 163N | 96.25 | 19NE2 | 25C19 | 162CE1 | 59.92 |
| 163N | 25C19 | 162CE1 | 51.59 | 163N | 25C19 | 162CB | 39.57 |
| 162CE1 | 25C19 | 162CB | 42.53 | 161O | 25C20 | 25SG | 71.78 |
| 161O | 25C20 | 161C | 1.07 | 25SG | 25C20 | 23CA | 80.86 |
| 25SG | 25C20 | 23O | 69.40 | 25SG | 25C20 | 23C | 68.41 |
| 25SG | 25C20 | 161C | 71.72 | 23CA | 25C20 | 23O | 30.94 |
| 23CA | 25C20 | 23C | 18.34 | 23O | 25C20 | 23C | 14.77 |
| 161C | 25C21 | 161C | 6.69 | 161O | 25C22 | 161C | 13.34 |
| 161C | 25C22 | 161CA | 34.90 | 161O | 25C22 | 161CB | 44.27 |
| 161C | 25C22 | 161CA | 21.77 | 161C | 25C22 | 161CB | 34.39 |
| 161CA | 25C22 | 161CB | 20.42 | 184NE1 | 25N24 | 184CZ2 | 42.68 |
| 184NE1 | 25N24 | 184CE2 | 21.38 | 184NE1 | 25N24 | 19OE1 | 49.07 |
| 184NE1 | 25N24 | 162ND1 | 68.83 | 184NE1 | 25N24 | 162CE1 | 51.55 |
| 184NE1 | 25N24 | 19CD | 58.30 | 184NE1 | 25N24 | 19NE2 | 75.34 |
| 184NE1 | 25N24 | 184CD1 | 9.07 | 184NE1 | 25N24 | 184CH2 | 51.38 |
| 184CZ2 | 25N24 | 184CE2 | 21.94 | 184CZ2 | 25N24 | 19OE1 | 85.09 |
| 184CZ2 | 25N24 | 162ND1 | 64.71 | 184CZ2 | 25N24 | 162CE1 | 57.67 |
| 184CZ2 | 25N24 | 19CD | 98.31 | 184CZ2 | 25N24 | 184CD1 | 50.33 |
| 184CZ2 | 25N24 | 184CH2 | 9.57 | 184CE2 | 25N24 | 19OE1 | 68.35 |
| 184CE2 | 25N24 | 162ND1 | 68.77 | 184CE2 | 25N24 | 162CE1 | 55.33 |
| 184CE2 | 25N24 | 19CD | 79.25 | 184CE2 | 25N24 | 19NE2 | 96.20 |
| 184CE2 | 25N24 | 184CD1 | 28.46 | 184CE2 | 25N24 | 184CH2 | 30.12 |
| 19OE1 | 25N24 | 162ND1 | 58.04 | 19OE1 | 25N24 | 162CE1 | 44.62 |
| 19OE1 | 25N24 | 19CD | 16.03 | 19OE1 | 25N24 | 19NE2 | 29.68 |
| 19OE1 | 25N24 | 184CD1 | 47.21 | 19OE1 | 25N24 | 184CH2 | 94.65 |
| 162ND1 | 25N24 | 162CE1 | 18.14 | 162ND1 | 25N24 | 19CD | 72.35 |
| 162ND1 | 25N24 | 19NE2 | 76.87 | 162ND1 | 25N24 | 184CD1 | 75.84 |
| 162ND1 | 25N24 | 184CH2 | 69.90 | 162CE1 | 25N24 | 19CD | 60.33 |
| 162CE1 | 25N24 | 19NE2 | 69.25 | 162CE1 | 25N24 | 184CD1 | 58.03 |
| 162CE1 | 25N24 | 184CH2 | 65.20 | 19CD | 25N24 | 19NE2 | 17.04 |
| 19CD | 25N24 | 184CD1 | 53.84 | 19NE2 | 25N24 | 184CD1 | 70.73 |
| 184CD1 | 25N24 | 184CH2 | 58.50 | 25SG | 25C25 | 25CB | 32.75 |
| 25SG | 25C25 | 25N | 68.12 | 25SG | 25C25 | 25CA | 46.11 |
| 25SG | 25C25 | 19NE2 | 91.26 | 25SG | 25C25 | 162ND1 | 50.45 |
| 25SG | 25C25 | 161O | 83.98 | 25SG | 25C25 | 26N | 50.26 |
| 25SG | 25C25 | 25C | 39.24 | 25SG | 25C25 | 24C | 75.91 |
| 25SG | 25C25 | 163N | 26.06 | 25SG | 25C25 | 19OE1 | 68.77 |
| 25SG | 25C25 | 162CA | 52.77 | 25SG | 25C25 | 162CE1 | 48.87 |
| 25SG | 25C25 | 24CA | 93.64 | 25SG | 25C25 | 19CD | 79.92 |
| 25CB | 25C25 | 25N | 43.75 | 25CB | 25C25 | 25CA | 22.80 |
| 25CB | 25C25 | 23C | 96.85 | 25CB | 25C25 | 19NE2 | 58.71 |
| 25CB | 25C25 | 162ND1 | 52.80 | 25CB | 25C25 | 24N | 79.85 |
| 25CB | 25C25 | 26N | 49.57 | 25CB | 25C25 | 25C | 32.45 |
| 25CB | 25C25 | 24C | 53.95 | 25CB | 25C25 | 163N | 56.86 |
| 25CB | 25C25 | 19OE1 | 39.72 | 25CB | 25C25 | 162CA | 76.70 |
| 25CB | 25C25 | 162CE1 | 41.55 | 25CB | 25C25 | 24CA | 71.02 |

TABLE XI-continued

Table of angles between atoms of the inhibitor and protein for all protein atoms within 5 Ångstroms of the inhibitor 3(S)-3-[(N-benzyloxycarbonyl)-L-leucinyl] amino-5-methyl-1-(1-propoxy)-2-hexanone.

| Atom 1 | Atom 2 | Atom 3 | Angle | Atom 1 | Atom 2 | Atom 3 | Angle |
|---|---|---|---|---|---|---|---|
| 25CB | 25C25 | 19CD | 48.30 | 25N | 25C25 | 23O | 61.20 |
| 25N | 25C25 | 25CA | 22.53 | 25N | 25C25 | 23C | 54.87 |
| 25N | 25C25 | 23CA | 71.33 | 25N | 25C25 | 19NE2 | 46.58 |
| 25N | 25C25 | 162ND1 | 94.33 | 25N | 25C25 | 24N | 38.82 |
| 25N | 25C25 | 26N | 37.62 | 25N | 25C25 | 25C | 32.96 |
| 25N | 25C25 | 24C | 10.58 | 25N | 25C25 | 163N | 94.01 |
| 25N | 25C25 | 19OE1 | 53.89 | 25N | 25C25 | 162CE1 | 80.69 |
| 25N | 25C25 | 24CA | 27.34 | 25N | 25C25 | 19CD | 48.28 |
| 23O | 25C25 | 25CA | 82.78 | 23O | 25C25 | 23C | 18.78 |
| 23O | 25C25 | 23CA | 35.84 | 23O | 25C25 | 19NE2 | 73.70 |
| 23O | 25C25 | 24N | 31.06 | 23O | 25C25 | 26N | 72.39 |
| 23O | 25C25 | 25C | 83.36 | 23O | 25C25 | 24C | 51.02 |
| 23O | 25C25 | 19OE1 | 99.77 | 23O | 25C25 | 24CA | 34.14 |
| 23O | 25C25 | 19CD | 86.19 | 25CA | 25C25 | 23C | 77.38 |
| 25CA | 25C25 | 23CA | 92.63 | 25CA | 25C25 | 19NE2 | 55.22 |
| 25CA | 25C25 | 162ND1 | 75.50 | 25CA | 25C25 | 24N | 61.07 |
| 25CA | 25C25 | 26N | 33.30 | 25CA | 25C25 | 25C | 18.88 |
| 25CA | 25C25 | 24C | 31.91 | 25CA | 25C25 | 163N | 72.17 |
| 25CA | 25C25 | 19OE1 | 48.70 | 25CA | 25C25 | 162CA | 96.87 |
| 25CA | 25C25 | 162CE1 | 63.50 | 25CA | 25C25 | 24CA | 49.61 |
| 25CA | 25C25 | 19CD | 50.26 | 23C | 25C25 | 23CA | 22.22 |
| 23C | 25C25 | 19NE2 | 55.76 | 23C | 25C25 | 24N | 17.04 |
| 23C | 25C25 | 26N | 77.83 | 23C | 25C25 | 25C | 83.98 |
| 23C | 25C25 | 24C | 46.58 | 23C | 25C25 | 19OE1 | 82.85 |
| 23C | 25C25 | 24CA | 28.93 | 23C | 25C25 | 19CD | 68.78 |
| 23CA | 25C25 | 19NE2 | 53.36 | 23CA | 25C25 | 24N | 33.27 |
| 23CA | 25C25 | 26N | 99.45 | 23CA | 25C25 | 24C | 65.16 |
| 23CA | 25C25 | 19OE1 | 80.77 | 23CA | 25C25 | 24CA | 48.92 |
| 23CA | 25C25 | 19CD | 66.76 | 19NE2 | 25C25 | 162ND1 | 78.91 |
| 19NE2 | 25C25 | 24N | 43.72 | 19NE2 | 25C25 | 26N | 83.54 |
| 19NE2 | 25C25 | 25C | 73.61 | 19NE2 | 25C25 | 24C | 50.86 |
| 19NE2 | 25C25 | 19OE1 | 27.88 | 19NE2 | 25C25 | 162CE1 | 65.60 |
| 19NE2 | 25C25 | 24CA | 51.46 | 19NE2 | 25C25 | 19CD | 13.57 |
| 162ND1 | 25C25 | 161O | 66.11 | 162ND1 | 25C25 | 26N | 97.49 |
| 162ND1 | 25C25 | 25C | 81.90 | 162ND1 | 25C25 | 163N | 47.00 |
| 162ND1 | 25C25 | 19OE1 | 52.01 | 162ND1 | 25C25 | 162CA | 38.64 |
| 162ND1 | 25C25 | 162CE1 | 14.60 | 162ND1 | 25C25 | 19CD | 65.91 |
| 161O | 25C25 | 163N | 58.15 | 161O | 25C25 | 162CA | 33.71 |
| 161O | 25C25 | 162CE1 | 80.71 | 24N | 25C25 | 26N | 67.35 |
| 24N | 25C25 | 25C | 70.00 | 24N | 25C25 | 24C | 31.89 |
| 24N | 25C25 | 19OE1 | 68.76 | 24N | 25C25 | 24CA | 16.51 |
| 24N | 25C25 | 19CD | 55.45 | 26N | 25C25 | 25C | 17.11 |
| 26N | 25C25 | 24C | 37.71 | 26N | 25C25 | 163N | 70.13 |
| 26N | 25C25 | 19OE1 | 81.99 | 26N | 25C25 | 162CA | 99.71 |
| 26N | 25C25 | 162CE1 | 89.75 | 26N | 25C25 | 24CA | 50.94 |
| 26N | 25C25 | 19CD | 82.06 | 25C | 25C25 | 24C | 38.11 |
| 25C | 25C25 | 163N | 63.33 | 25C | 25C25 | 19OE1 | 66.63 |
| 25C | 25C25 | 162CA | 91.85 | 25C | 25C25 | 162CE1 | 73.03 |
| 25C | 25C25 | 24CA | 55.12 | 25C | 25C25 | 19CD | 69.13 |
| 24C | 25C25 | 19OE1 | 62.72 | 24C | 25C25 | 162CE1 | 91.22 |
| 24C | 25C25 | 24CA | 17.90 | 24C | 25C25 | 19CD | 55.23 |
| 163N | 25C25 | 19OE1 | 86.02 | 163N | 25C25 | 162CA | 29.58 |
| 163N | 25C25 | 162CE1 | 53.83 | 163N | 25C25 | 19CD | 99.46 |
| 19OE1 | 25C25 | 162CA | 90.22 | 19OE1 | 25C25 | 162CE1 | 38.06 |
| 19OE1 | 25C25 | 24CA | 71.30 | 19OE1 | 25C25 | 19CD | 14.33 |
| 162CA | 25C25 | 162CE1 | 52.16 | 162CE1 | 25C25 | 19CD | 52.25 |
| 24CA | 25C25 | 19CD | 60.28 | 25SG | 25O26 | 25N | 75.08 |
| 25SG | 25O26 | 25CB | 37.30 | 25SG | 25O26 | 25CA | 54.02 |
| 25SG | 25O26 | 24C | 86.45 | 25SG | 25O26 | 19CD | 97.95 |
| 25SG | 25O26 | 19OE1 | 82.42 | 25SG | 25O26 | 25C | 45.95 |
| 25SG | 25O26 | 26N | 51.16 | 25SG | 25O26 | 162ND1 | 46.91 |
| 25SG | 25O26 | 162CE1 | 52.51 | 25N | 25O26 | 23C | 71.27 |
| 25N | 25O26 | 25CB | 49.91 | 25N | 25O26 | 23CA | 95.71 |
| 25N | 25O26 | 19NE2 | 63.43 | 25N | 25O26 | 23O | 74.28 |
| 25N | 25O26 | 24N | 51.65 | 25N | 25O26 | 25CA | 24.00 |
| 25N | 25O26 | 24C | 13.92 | 25N | 25O26 | 19CD | 63.32 |
| 25N | 25O26 | 19OE1 | 66.78 | 25N | 25O26 | 24CA | 35.47 |
| 25N | 25O26 | 23N | 92.49 | 25N | 25O26 | 22O | 75.23 |
| 25N | 25O26 | 25C | 29.57 | 25N | 25O26 | 26N | 34.00 |
| 25N | 25O26 | 162ND1 | 97.43 | 25N | 25O26 | 22C | 83.38 |
| 25N | 25O26 | 162CE1 | 86.18 | 23C | 25O26 | 23CA | 29.24 |
| 23C | 25O26 | 19NE2 | 77.74 | 23C | 25O26 | 23O | 22.63 |

TABLE XI-continued

Table of angles between atoms of the inhibitor and protein for all protein atoms within 5 Ångstroms of the inhibitor 3(S)-3-[(N-benzyloxycarbonyl)-L-leucinyl] amino-5-methyl-1-(1-propoxy)-2-hexanone.

| Atom 1 | Atom 2 | Atom 3 | Angle | Atom 1 | Atom 2 | Atom 3 | Angle |
|---|---|---|---|---|---|---|---|
| 23C | 25O26 | 24N | 23.28 | 23C | 25O26 | 25CA | 95.23 |
| 23C | 25O26 | 24C | 57.44 | 23C | 25O26 | 19CD | 92.50 |
| 23C | 25O26 | 24CA | 35.81 | 23C | 25O26 | 23N | 31.40 |
| 23C | 25O26 | 22O | 45.44 | 23C | 25O26 | 25C | 94.92 |
| 23C | 25O26 | 26N | 85.14 | 23C | 25O26 | 22C | 36.80 |
| 25CB | 25O26 | 19NE2 | 75.38 | 25CB | 25O26 | 25CA | 26.07 |
| 25CB | 25O26 | 24C | 63.79 | 25CB | 25O26 | 19CD | 62.61 |
| 25CB | 25O26 | 19OE1 | 50.03 | 25CB | 25O26 | 24CA | 85.37 |
| 25CB | 25O26 | 25C | 32.00 | 25CB | 25O26 | 26N | 48.03 |
| 25CB | 25O26 | 162ND1 | 48.42 | 25CB | 25O26 | 162CE1 | 40.75 |
| 23CA | 25O26 | 19NE2 | 74.13 | 23CA | 25O26 | 23O | 44.84 |
| 23CA | 25O26 | 24N | 44.10 | 23CA | 25O26 | 24C | 82.84 |
| 23CA | 25O26 | 19CD | 89.48 | 23CA | 25O26 | 24CA | 61.85 |
| 23CA | 25O26 | 23N | 7.91 | 23CA | 25O26 | 22O | 37.03 |
| 23CA | 25O26 | 22C | 22.99 | 19NE2 | 25O26 | 23O | 99.02 |
| 19NE2 | 25O26 | 24N | 59.57 | 19NE2 | 25O26 | 25CA | 69.12 |
| 19NE2 | 25O26 | 24C | 64.61 | 19NE2 | 25O26 | 19CD | 15.61 |
| 19NE2 | 25O26 | 23N | 66.26 | 19NE2 | 25O26 | 22O | 37.24 |
| 19NE2 | 25O26 | 25C | 85.04 | 19NE2 | 25O26 | 26N | 96.39 |
| 19NE2 | 25O26 | 162ND1 | 87.10 | 19NE2 | 25O26 | 22C | 51.16 |
| 19NE2 | 25O26 | 162CE1 | 72.58 | 23O | 25O26 | 24N | 40.19 |
| 23O | 25O26 | 25CA | 95.80 | 23O | 25O26 | 24C | 61.05 |
| 23O | 25O26 | 24CA | 42.72 | 23O | 25O26 | 23N | 49.93 |
| 23O | 25O26 | 22O | 68.06 | 23O | 25O26 | 25C | 89.22 |
| 23O | 25O26 | 26N | 75.10 | 23O | 25O26 | 22C | 58.63 |
| 24N | 25O26 | 25CA | 75.32 | 24N | 25O26 | 24C | 38.83 |
| 24N | 25O26 | 19CD | 72.68 | 24N | 25O26 | 19OE1 | 88.39 |
| 24N | 25O26 | 24CA | 19.05 | 24N | 25O26 | 23N | 41.71 |
| 24N | 25O26 | 22O | 37.44 | 24N | 25O26 | 25C | 79.23 |
| 24N | 25O26 | 26N | 74.55 | 24N | 25O26 | 22C | 37.15 |
| 25CA | 25O26 | 24C | 37.79 | 25CA | 25O26 | 19CD | 62.07 |
| 25CA | 25O26 | 19OE1 | 57.50 | 25CA | 25O26 | 24CA | 59.43 |
| 25CA | 25O26 | 22O | 92.92 | 25CA | 25O26 | 25C | 16.48 |
| 25CA | 25O26 | 26N | 31.94 | 25CA | 25O26 | 162ND1 | 74.28 |
| 25CA | 25O26 | 162CE1 | 64.77 | 24C | 25O26 | 19CD | 68.53 |
| 24C | 25O26 | 19OE1 | 75.73 | 24C | 25O26 | 24CA | 21.65 |
| 24C | 25O26 | 23N | 80.40 | 24C | 25O26 | 22O | 67.31 |
| 24C | 25O26 | 25C | 40.54 | 24C | 25O26 | 26N | 39.44 |
| 24C | 25O26 | 22C | 73.15 | 24C | 25O26 | 162CE1 | 99.55 |
| 19CD | 25O26 | 19OE1 | 17.61 | 19CD | 25O26 | 24CA | 75.72 |
| 19CD | 25O26 | 23N | 81.58 | 19CD | 25O26 | 22O | 52.77 |
| 19CD | 25O26 | 25C | 78.56 | 19CD | 25O26 | 26N | 92.72 |
| 19CD | 25O26 | 162ND1 | 71.98 | 19CD | 25O26 | 22C | 66.59 |
| 19CD | 25O26 | 162CE1 | 57.18 | 19OE1 | 25O26 | 24CA | 87.94 |
| 19OE1 | 25O26 | 23N | 98.65 | 19OE1 | 25O26 | 22O | 70.22 |
| 19OE1 | 25O26 | 25C | 73.17 | 19OE1 | 25O26 | 26N | 89.43 |
| 19OE1 | 25O26 | 162ND1 | 54.76 | 19OE1 | 25O26 | 22C | 83.88 |
| 19OE1 | 25O26 | 162CE1 | 39.72 | 24CA | 25O26 | 23N | 60.38 |
| 24CA | 25O26 | 22O | 54.26 | 24CA | 25O26 | 25C | 60.91 |
| 24CA | 25O26 | 26N | 55.50 | 24CA | 25O26 | 22C | 56.01 |
| 23N | 25O26 | 22O | 29.27 | 23N | 25O26 | 22C | 15.20 |
| 22O | 25O26 | 22C | 14.07 | 25C | 25O26 | 26N | 16.90 |
| 25C | 25O26 | 162ND1 | 78.47 | 25C | 25O26 | 162CE1 | 72.68 |
| 26N | 25O26 | 162ND1 | 91.53 | 26N | 25O26 | 162CE1 | 88.05 |
| 162ND1 | 25O26 | 162CE1 | 15.41 | 25SG | 25C27 | 25N | 57.08 |
| 25SG | 25C27 | 25CB | 21.02 | 25SG | 25C27 | 26N | 58.38 |
| 25SG | 25C27 | 25CA | 39.38 | 25SG | 25C27 | 24N | 91.00 |
| 25SG | 25C27 | 24C | 70.32 | 25SG | 25C27 | 25C | 43.75 |
| 25SG | 25C27 | 161O | 68.95 | 25SG | 25C27 | 26CB | 82.20 |
| 25SG | 25C27 | 24CA | 87.49 | 25SG | 25C27 | 26CG | 96.26 |
| 23C | 25C27 | 23C | 18.46 | 23O | 25C27 | 25N | 62.85 |
| 23O | 25C27 | 65CA | 58.88 | 23O | 25C27 | 25CB | 97.75 |
| 23O | 25C27 | 26CD1 | 56.83 | 23O | 25C27 | 26N | 82.95 |
| 23O | 25C27 | 23CA | 34.44 | 23O | 25C27 | 25CA | 81.88 |
| 23O | 25C27 | 24N | 28.16 | 23O | 25C27 | 24C | 51.85 |
| 23O | 25C27 | 25C | 88.07 | 23O | 25C27 | 65N | 46.70 |
| 23O | 25C27 | 26CB | 86.79 | 23O | 25C27 | 66N | 79.07 |
| 23O | 25C27 | 24CA | 33.37 | 23O | 25C27 | 26CG | 69.96 |
| 23O | 25C27 | 65C | 66.97 | 23C | 25C27 | 25N | 53.34 |
| 23C | 25C27 | 65CA | 76.45 | 23C | 25C27 | 25CB | 84.25 |
| 23C | 25C27 | 26CD1 | 70.76 | 23C | 25C27 | 26N | 83.38 |
| 23C | 25C27 | 23CA | 21.08 | 23C | 25C27 | 25CA | 72.15 |

TABLE XI-continued

Table of angles between atoms of the inhibitor and protein for all protein atoms within 5 Ångstroms of the inhibitor 3(S)-3-[(N-benzyloxycarbonyl)-L-leucinyl] amino-5-methyl-1-(1-propoxy)-2-hexanone.

| Atom 1 | Atom 2 | Atom 3 | Angle | Atom 1 | Atom 2 | Atom 3 | Angle |
|---|---|---|---|---|---|---|---|
| 23C | 25C27 | 24N | 15.52 | 23C | 25C27 | 24C | 46.42 |
| 23C | 25C27 | 25C | 83.42 | 23C | 25C27 | 65N | 62.90 |
| 23C | 25C27 | 26CB | 96.45 | 23C | 25C27 | 66N | 97.46 |
| 23C | 25C27 | 24CA | 29.98 | 23C | 25C27 | 26CG | 81.94 |
| 23C | 25C27 | 65C | 85.36 | 25N | 25C27 | 25CB | 36.48 |
| 25N | 25C27 | 26CD1 | 68.71 | 25N | 25C27 | 26N | 39.49 |
| 25N | 25C27 | 23CA | 66.25 | 25N | 25C27 | 25CA | 19.15 |
| 25N | 25C27 | 24N | 37.84 | 25N | 25C27 | 24C | 14.42 |
| 25N | 25C27 | 25C | 31.97 | 25N | 25C27 | 26CB | 68.32 |
| 25N | 25C27 | 24CA | 30.42 | 25N | 25C27 | 26CG | 67.30 |
| 65CA | 25C27 | 26CD1 | 53.12 | 65CA | 25C27 | 23CA | 82.66 |
| 65CA | 25C27 | 24N | 86.51 | 65CA | 25C27 | 24C | 98.45 |
| 65CA | 25C27 | 65N | 15.90 | 65CA | 25C27 | 26CB | 77.82 |
| 65CA | 25C27 | 66N | 30.25 | 65CA | 25C27 | 24CA | 84.16 |
| 65CA | 25C27 | 26CG | 63.87 | 65CA | 25C27 | 65C | 14.85 |
| 25CB | 25C27 | 26CD1 | 96.07 | 25CB | 25C27 | 26N | 48.98 |
| 25CB | 25C27 | 23CA | 88.62 | 25CB | 25C27 | 25CA | 20.65 |
| 25CB | 25C27 | 24N | 70.19 | 25CB | 25C27 | 24C | 50.31 |
| 25CB | 25C27 | 25C | 32.85 | 25CB | 25C27 | 161O | 88.13 |
| 25CB | 25C27 | 26CB | 78.77 | 25CB | 25C27 | 24CA | 66.76 |
| 25CB | 25C27 | 26CG | 88.03 | 26CD1 | 25C27 | 26N | 49.41 |
| 26CD1 | 25C27 | 23CA | 90.70 | 26CD1 | 25C27 | 25CA | 76.35 |
| 26CD1 | 25C27 | 24N | 67.23 | 26CD1 | 25C27 | 24C | 55.82 |
| 26CD1 | 25C27 | 25C | 64.70 | 26CD1 | 25C27 | 65N | 58.91 |
| 26CD1 | 25C27 | 26CB | 32.69 | 26CD1 | 25C27 | 66N | 42.33 |
| 26CD1 | 25C27 | 24CA | 52.50 | 26CD1 | 25C27 | 26CG | 14.60 |
| 26CD1 | 25C27 | 65C | 44.57 | 26N | 25C27 | 25CA | 33.28 |
| 26N | 25C27 | 24N | 69.36 | 26N | 25C27 | 24C | 38.31 |
| 26N | 25C27 | 25C | 16.13 | 26N | 25C27 | 26CB | 31.48 |
| 26N | 25C27 | 66N | 83.54 | 26N | 25C27 | 24CA | 53.43 |
| 26N | 25C27 | 26CG | 39.23 | 26N | 25C27 | 65C | 91.88 |
| 23CA | 25C27 | 25CA | 82.90 | 23CA | 25C27 | 24N | 32.54 |
| 23CA | 25C27 | 24C | 63.47 | 23CA | 25C27 | 25C | 98.17 |
| 25CA | 25C27 | 65N | 67.00 | 23CA | 25C27 | 24CA | 49.60 |
| 23CA | 25C27 | 65C | 95.04 | 25CA | 25C27 | 24N | 56.77 |
| 25CA | 25C27 | 24C | 31.07 | 25CA | 25C27 | 25C | 19.16 |
| 25CA | 25C27 | 26CB | 64.76 | 25CA | 25C27 | 24CA | 48.93 |
| 25CA | 25C27 | 26CG | 70.17 | 24N | 25C27 | 24C | 31.48 |
| 24N | 25C27 | 25C | 68.08 | 24N | 25C27 | 65N | 74.86 |
| 24N | 25C27 | 26CB | 87.15 | 24N | 25C27 | 24CA | 17.56 |
| 24N | 25C27 | 26CG | 75.54 | 24N | 25C27 | 65C | 92.54 |
| 24C | 25C27 | 25C | 37.23 | 24C | 25C27 | 65N | 93.14 |
| 24C | 25C27 | 26CB | 61.81 | 24C | 25C27 | 66N | 98.06 |
| 24C | 25C27 | 24CA | 18.48 | 24C | 25C27 | 26CG | 56.79 |
| 24C | 25C27 | 65C | 96.78 | 25C | 25C27 | 26CB | 46.70 |
| 25C | 25C27 | 66N | 99.53 | 25C | 25C27 | 24CA | 55.28 |
| 25C | 25C27 | 26CG | 55.30 | 65N | 25C27 | 26CB | 88.24 |
| 65N | 25C27 | 66N | 45.67 | 65N | 25C27 | 24CA | 76.36 |
| 65N | 25C27 | 26CG | 72.00 | 65N | 25C27 | 65C | 30.06 |
| 26CB | 25C27 | 66N | 53.44 | 26CB | 25C27 | 24CA | 69.63 |
| 26CB | 25C27 | 26CG | 18.09 | 26CB | 25C27 | 65C | 64.59 |
| 66N | 25C27 | 24CA | 91.56 | 66N | 25C27 | 26CG | 45.61 |
| 66N | 25C27 | 65C | 15.61 | 24CA | 25C27 | 26CG | 58.92 |
| 24CA | 25C27 | 65C | 85.96 | 26CG | 25C27 | 65C | 52.65 |
| 25SG | 25O28 | 161O | 76.60 | 25SG | 25O28 | 23O | 80.25 |
| 25SG | 25O28 | 26CD1 | 87.41 | 25SG | 25O28 | 26N | 47.59 |
| 25SG | 25O28 | 26CB | 75.36 | 25SG | 25O28 | 161C | 77.06 |
| 25SG | 25O28 | 25CB | 9.94 | 25SG | 25O28 | 163N | 39.01 |
| 65CA | 25O28 | 23O | 50.13 | 65CA | 25O28 | 66N | 33.41 |
| 65CA | 25O28 | 66O | 67.54 | 65CA | 25O28 | 26CD1 | 48.79 |
| 65CA | 25O28 | 65C | 17.37 | 65CA | 25O28 | 26N | 90.83 |
| 65CA | 25O28 | 26CB | 76.12 | 161O | 25O28 | 161C | 10.43 |
| 161O | 25O28 | 25CB | 85.93 | 161O | 25O28 | 163N | 57.90 |
| 23O | 25O28 | 66N | 73.33 | 23O | 25O28 | 66O | 98.34 |
| 23O | 25O28 | 26CD1 | 46.36 | 23O | 25O28 | 65C | 62.14 |
| 23O | 25O28 | 26N | 63.88 | 23O | 25O28 | 26CB | 73.66 |
| 23O | 25O28 | 25CB | 70.99 | 66N | 25O28 | 66O | 34.18 |
| 66N | 25O28 | 26CD1 | 42.77 | 66N | 25O28 | 65C | 16.09 |
| 66N | 25O28 | 26N | 80.82 | 66N | 25O28 | 26CB | 55.05 |
| 66O | 25O28 | 26CD1 | 53.93 | 66O | 25O28 | 65C | 50.27 |
| 66O | 25O28 | 26N | 71.20 | 66O | 25O28 | 26CB | 41.80 |
| 66O | 25O28 | 163N | 96.32 | 26CD1 | 25O28 | 65C | 44.16 |

TABLE XI-continued

Table of angles between atoms of the inhibitor and protein for
all protein atoms within 5 Ångstroms of the inhibitor 3(S)-3-
[(N-benzyloxycarbonyl)-L-leucinyl] amino-5-methyl-1-(1-propoxy)-
2-hexanone.

| Atom 1 | Atom 2 | Atom 3 | Angle | Atom 1 | Atom 2 | Atom 3 | Angle |
|---|---|---|---|---|---|---|---|
| 26CD1 | 25O28 | 26N | 42.70 | 26CD1 | 25O28 | 26CB | 31.40 |
| 26CD1 | 25O28 | 25CB | 78.43 | 65C | 25O28 | 26N | 86.36 |
| 65C | 25O28 | 26CB | 65.21 | 26N | 25O28 | 26CB | 29.67 |
| 26N | 25O28 | 25CB | 40.69 | 26N | 25O28 | 163N | 65.13 |
| 26CB | 25O28 | 25CB | 69.78 | 26CB | 25O28 | 163N | 79.13 |
| 161C | 25O28 | 25CB | 86.86 | 161C | 25O28 | 163N | 52.19 |
| 25CB | 25O28 | 163N | 47.47 | 66O | 25C29 | 66N | 48.91 |
| 66O | 25C29 | 65CA | 91.41 | 66O | 25C29 | 65C | 68.29 |
| 66O | 25C29 | 66C | 13.27 | 66O | 25C29 | 26CD1 | 67.50 |
| 66O | 25C29 | 66CA | 34.11 | 66O | 25C29 | 26CB | 50.71 |
| 66O | 25C29 | 26CG | 54.55 | 66O | 25C29 | 65N | 99.08 |
| 66O | 25C29 | 65O | 66.95 | 66O | 25C29 | 26N | 80.09 |
| 66N | 25C29 | 65CA | 42.87 | 66N | 25C29 | 65C | 19.38 |
| 66N | 25C29 | 66C | 36.24 | 66N | 25C29 | 26CD1 | 51.44 |
| 66N | 25C29 | 66CA | 15.57 | 66N | 25C29 | 26CB | 68.44 |
| 66N | 25C29 | 26CG | 54.31 | 66N | 25C29 | 23O | 78.55 |
| 66N | 25C29 | 65N | 50.66 | 66N | 25C29 | 65O | 18.11 |
| 66N | 25C29 | 26N | 91.42 | 65CA | 25C29 | 65C | 23.73 |
| 65CA | 25C29 | 66C | 79.07 | 65CA | 25C29 | 26CD1 | 55.65 |
| 65CA | 25C29 | 66CA | 58.35 | 65CA | 25C29 | 26CB | 89.86 |
| 65CA | 25C29 | 26CG | 70.46 | 65CA | 25C29 | 23O | 47.25 |
| 65CA | 25C29 | 65N | 7.81 | 65CA | 25C29 | 65O | 25.70 |
| 65CA | 25C29 | 26N | 94.75 | 65C | 25C29 | 66C | 55.59 |
| 65C | 25C29 | 26CD1 | 52.52 | 65C | 25C29 | 66CA | 34.70 |
| 65C | 25C29 | 26CB | 79.47 | 65C | 25C29 | 26CG | 61.82 |
| 65C | 25C29 | 23O | 65.09 | 65C | 25C29 | 65N | 31.53 |
| 65C | 25C29 | 65O | 2.78 | 65C | 25C29 | 26N | 95.49 |
| 66C | 25C29 | 26CD1 | 64.26 | 66C | 25C29 | 66CA | 21.04 |
| 66C | 25C29 | 26CB | 56.28 | 66C | 25C29 | 26CG | 54.75 |
| 66C | 25C29 | 65N | 86.84 | 66C | 25C29 | 65O | 54.09 |
| 66C | 25C29 | 26N | 86.08 | 26CD1 | 25C29 | 66CA | 57.66 |
| 26CD1 | 25C29 | 26CB | 35.62 | 26CD1 | 25C29 | 25SG | 81.23 |
| 26CD1 | 25C29 | 26CG | 17.23 | 26CD1 | 25C29 | 23O | 45.73 |
| 26CD1 | 25C29 | 65N | 58.39 | 26CD1 | 25C29 | 65O | 54.62 |
| 26CD1 | 25C29 | 26N | 42.97 | 66CA | 25C29 | 26CB | 64.36 |
| 66CA | 25C29 | 26CG | 54.97 | 66CA | 25C29 | 23O | 92.04 |
| 66CA | 25C29 | 65N | 66.15 | 66CA | 25C29 | 65O | 33.08 |
| 66CA | 25C29 | 26N | 91.66 | 26CB | 25C29 | 25SG | 73.09 |
| 26CB | 25C29 | 26CG | 19.41 | 26CB | 25C29 | 23O | 74.83 |
| 26CB | 25C29 | 65N | 93.60 | 26CB | 25C29 | 65O | 80.55 |
| 26CB | 25C29 | 26N | 29.84 | 25SG | 25C29 | 26CG | 81.03 |
| 25SG | 25C29 | 23O | 65.42 | 25SG | 25C29 | 161O | 57.72 |
| 25SG | 25C29 | 26N | 44.40 | 26CG | 25C29 | 23O | 61.35 |
| 26CG | 25C29 | 65N | 74.27 | 26CG | 25C29 | 65O | 63.28 |
| 26CG | 25C29 | 26N | 37.32 | 23O | 25C29 | 65N | 42.49 |
| 23O | 25C29 | 65O | 67.82 | 23O | 25C29 | 26N | 59.60 |
| 65N | 25C29 | 65O | 33.46 | 65N | 25C29 | 26N | 94.60 |
| 65O | 25C29 | 26N | 97.54 | 66O | 25C30 | 66N | 43.16 |
| 66O | 25C30 | 66C | 13.69 | 66O | 25C30 | 65CA | 74.47 |
| 66O | 25C30 | 66CA | 31.15 | 66O | 25C30 | 65C | 58.33 |
| 66N | 25C30 | 66C | 35.28 | 66N | 25C30 | 65CA | 33.44 |
| 66N | 25C30 | 66CA | 17.60 | 66N | 25C30 | 65C | 15.22 |
| 66C | 25C30 | 65CA | 68.55 | 66C | 25C30 | 66CA | 19.80 |
| 66C | 25C30 | 65C | 50.23 | 65CA | 25C30 | 66CA | 50.69 |
| 65CA | 25C30 | 65C | 19.75 | 66CA | 25C30 | 65C | 31.38 |
| 66O | 25C31 | 66C | 9.16 | 66O | 25C31 | 66N | 30.51 |
| 66O | 25C31 | 163CB | 81.88 | 161O | 25C30 | 161C | 15.04 |
| 161O | 25C31 | 163CB | 81.82 | 161O | 25C31 | 160O | 59.31 |
| 66C | 25C31 | 66N | 28.88 | 66C | 25C31 | 163CB | 90.84 |
| 161C | 25C31 | 163CB | 80.88 | 161C | 25C31 | 160O | 48.22 |
| 66N | 25C31 | 163CB | 97.56 | | | | |

TABLE XII

Table of angles between atoms of the inhibitor and protein for all protein atoms within 5 Ångstroms of the inhibitor bis-(Cbz-leucinyl)-1,3-diamino-propan-2-one

| Atom 1 | Atom 2 | Atom 3 | Angle | Atom 1 | Atom 2 | Atom 3 | Angle |
|---|---|---|---|---|---|---|---|
| 184CB | 25C1 | 184CG | 21.22 | 184CB | 25C1 | 18OD1 | 72.94 |
| 184CB | 25C1 | 184CD1 | 35.50 | 184CB | 25C1 | 184CA | 19.59 |
| 184CB | 25C1 | 184CD2 | 33.67 | 184CB | 25C1 | 184O | 34.28 |
| 184CB | 25C1 | 184C | 30.67 | 184CG | 25C1 | 18OD1 | 81.92 |
| 184CG | 25C1 | 184CD1 | 18.31 | 184CG | 25C1 | 184CA | 34.17 |
| 184CG | 25C1 | 184CD2 | 16.99 | 184CG | 25C1 | 184O | 55.47 |
| 184CG | 25C1 | 184C | 50.07 | 18OD1 | 25C1 | 184CD1 | 74.79 |
| 18OD1 | 25C1 | 184CA | 53.36 | 18OD1 | 25C1 | 184CD2 | 98.79 |
| 18OD1 | 25C1 | 184O | 61.42 | 18OD1 | 25C1 | 184C | 50.27 |
| 184CD1 | 25C1 | 184CA | 39.83 | 184CD1 | 25C1 | 184CD2 | 28.30 |
| 184CD1 | 25C1 | 184O | 67.35 | 184CD1 | 25C1 | 184C | 57.99 |
| 184CA | 25C1 | 184CD2 | 50.19 | 184CA | 25C1 | 184O | 29.82 |
| 184CA | 2SC1 | 184C | 18.22 | 184CD2 | 25C1 | 184O | 66.46 |
| 184CD2 | 2SC1 | 184C | 64.29 | 184O | 25C1 | 184C | 14.58 |
| 18OD1 | 25C2 | 184CD1 | 93.56 | 18OD1 | 25C2 | 184CB | 85.20 |
| 18OD1 | 25C2 | 184CA | 63.93 | 18OD1 | 25C2 | 184CG | 97.27 |
| 18OD1 | 25C2 | 18CG | 7.95 | 18OD1 | 25C2 | 20O | 82.27 |
| 18OD1 | 25C2 | 20N | 45.49 | 18OD1 | 25C2 | 184C | 56.77 |
| 18OD1 | 25C2 | 18ND2 | 22.89 | 18OD1 | 25C2 | 20CA | 55.50 |
| 18OD1 | 25C2 | 184O | 66.85 | 18OD1 | 25C2 | 20C | 72.94 |
| 18OD1 | 25C2 | 19CG | 66.66 | 184CD1 | 25C2 | 184CB | 36.96 |
| 184CD1 | 25C2 | 184CA | 43.35 | 184CD1 | 25C2 | 184CG | 19.17 |
| 184CD1 | 25C2 | 20O | 93.58 | 184CD1 | 25C2 | 20N | 91.27 |
| 184CD1 | 25C2 | 184C | 62.15 | 184CD1 | 25C2 | 184NE1 | 14.42 |
| 184CD1 | 25C2 | 184O | 68.85 | 184CD1 | 25C2 | 19CG | 47.81 |
| 184CB | 25C2 | 184CA | 21.51 | 184CB | 25C2 | 184CG | 20.93 |
| 184CB | 25C2 | 18CG | 90.69 | 184CB | 25C2 | 184C | 32.58 |
| 184CB | 25C2 | 184NE1 | 48.17 | 184CB | 25C2 | 184O | 33.58 |
| 184CB | 25C2 | 19CG | 75.81 | 184CA | 25C2 | 184CG | 35.93 |
| 184CA | 25C2 | 18CG | 69.84 | 184CA | 25C2 | 20N | 91.24 |
| 184CA | 25C2 | 184C | 19.09 | 184CA | 25C2 | 18ND2 | 85.37 |
| 184CA | 25C2 | 184NE1 | 57.50 | 184CA | 25C2 | 184O | 29.61 |
| 184CA | 25C2 | 19CG | 65.69 | 184CG | 25C2 | 184C | 51.91 |
| 184CG | 25C2 | 184NE1 | 27.66 | 184CG | 25C2 | 184O | 54.51 |
| 184CG | 25C2 | 19CG | 65.63 | 18CG | 25C2 | 20O | 83.37 |
| 18CG | 25C2 | 20N | 47.67 | 18CG | 25C2 | 184C | 60.57 |
| 18CG | 25C2 | 18ND2 | 15.73 | 18CG | 25C2 | 20CA | 54.96 |
| 18CG | 25C2 | 184O | 69.03 | 18CG | 25C2 | 20C | 72.82 |
| 18CG | 25C2 | 19CG | 73.59 | 20O | 25C2 | 20N | 37.03 |
| 20O | 25C2 | 18ND2 | 77.52 | 20O | 25C2 | 20CA | 29.71 |
| 20O | 25C2 | 184NE1 | 87.40 | 20O | 25C2 | 20C | 13.14 |
| 20O | 25C2 | 19CG | 52.69 | 20N | 25C2 | 184C | 94.70 |
| 20N | 25C2 | 18ND2 | 46.43 | 20N | 25C2 | 20CA | 17.58 |
| 20N | 25C2 | 184NE1 | 94.15 | 20N | 25C2 | 20C | 29.99 |
| 20N | 25C2 | 19CG | 44.09 | 184C | 25C2 | 18ND2 | 74.66 |
| 184C | 25C2 | 184NE1 | 76.04 | 184C | 25C2 | 184O | 14.64 |
| 184C | 25C2 | 19CG | 80.33 | 18ND2 | 25C2 | 20CA | 47.82 |
| 18ND2 | 25C2 | 184O | 81.12 | 18ND2 | 25C2 | 20C | 65.32 |
| 18ND2 | 25C2 | 19CG | 81.86 | 20CA | 25C2 | 20C | 17.90 |
| 20CA | 25C2 | 19CG | 58.30 | 184NE1 | 25C2 | 184O | 81.39 |
| 184NE1 | 25C2 | 20C | 98.78 | 184NE1 | 25C2 | 19CG | 50.29 |
| 184O | 25C2 | 19CG | 94.21 | 20C | 25C2 | 19CG | 58.17 |
| 20O | 25C3 | 18OD1 | 94.92 | 20O | 25C3 | 20C | 14.93 |
| 20O | 25C3 | 20N | 45.22 | 20O | 25C3 | 20CA | 34.91 |
| 20O | 25C3 | 19CG | 67.31 | 20O | 25C3 | 18CG | 90.10 |
| 20O | 25C3 | 19C | 44.11 | 20O | 25C3 | 19CD | 68.85 |
| 18OD1 | 25C3 | 20C | 83.09 | 18OD1 | 25C3 | 20N | 50.73 |
| 18OD1 | 25C3 | 184CD1 | 86.70 | 18OD1 | 25C3 | 20CA | 61.59 |
| 18OD1 | 25C3 | 19CG | 73.40 | 18OD1 | 25C3 | 184CG | 83.83 |
| 18OD1 | 25C3 | 18CG | 7.01 | 18OD1 | 25C3 | 184CB | 69.00 |
| 18OD1 | 25C3 | 184CA | 52.51 | 18OD1 | 25C3 | 19C | 56.82 |
| 18OD1 | 25C3 | 19CD | 89.80 | 20C | 25C3 | 20N | 36.79 |
| 20C | 25C3 | 20CA | 21.55 | 20C | 25C3 | 19CG | 72.42 |
| 20C | 25C3 | 18CG | 77.56 | 20C | 25C3 | 19C | 39.99 |
| 20C | 25C3 | 19CD | 77.92 | 20N | 25C3 | 20CA | 20.57 |
| 20N | 25C3 | 19CG | 52.06 | 20N | 25C3 | 18CG | 47.19 |
| 20N | 25C3 | 184CA | 88.94 | 20N | 25C3 | 19C | 12.18 |
| 20N | 25C3 | 19CD | 65.92 | 184CD1 | 25C3 | 19CG | 54.41 |
| 184CD1 | 25C3 | 184CG | 17.14 | 184CD1 | 25C3 | 184NE1 | 17.22 |
| 184CD1 | 25C3 | 18CG | 93.47 | 184CD1 | 25C3 | 184CB | 32.16 |
| 184CD1 | 25C3 | 184CA | 38.24 | 184CD1 | 25C3 | 19C | 92.25 |
| 184CD1 | 25C3 | 19CD | 49.63 | 20CA | 25C3 | 19CG | 69.55 |
| 20CA | 25C3 | 18CG | 56.01 | 20CA | 25C3 | 19C | 29.66 |

TABLE XII-continued

Table of angles between atoms of the inhibitor and protein
for all protein atoms within 5 Ångstroms of the inhibitor
bis-(Cbz-leucinyl)-1,3-diamino-propan-2-one

| Atom 1 | Atom 2 | Atom 3 | Angle | Atom 1 | Atom 2 | Atom 3 | Angle |
|---|---|---|---|---|---|---|---|
| 20CA | 25C3 | 19CD | 80.70 | 19CG | 25C3 | 184CG | 69.80 |
| 19CG | 25C3 | 184NE1 | 57.02 | 19CG | 25C3 | 18CG | 76.04 |
| 19CG | 25C3 | 184CB | 76.30 | 19CG | 25C3 | 184CA | 66.22 |
| 19CG | 25C3 | 19C | 40.46 | 19CG | 25C3 | 19CD | 16.92 |
| 184CG | 25C3 | 184NE1 | 28.96 | 184CG | 25C3 | 18CG | 90.83 |
| 184CG | 25C3 | 184CB | 18.06 | 184CG | 25C3 | 184CA | 31.35 |
| 184CG | 25C3 | 19CD | 66.65 | 184NE1 | 25C3 | 184CB | 46.68 |
| 184NE1 | 25C3 | 184CA | 55.31 | 184NE1 | 25C3 | 19C | 97.43 |
| 184NE1 | 25C3 | 19CD | 46.53 | 18CG | 25C3 | 184CB | 75.84 |
| 18CG | 25C3 | 184CA | 59.51 | 18CG | 25C3 | 19C | 54.70 |
| 18CG | 25C3 | 19CD | 92.81 | 184CB | 25C3 | 184CA | 18.20 |
| 184CB | 25C3 | 19CD | 77.96 | 184CA | 25C3 | 19C | 86.12 |
| 184CA | 25C3 | 19CD | 72.78 | 19C | 25C3 | 19CD | 53.79 |
| 20O | 25C4 | 20C | 9.86 | 20O | 25C4 | 19CG | 57.67 |
| 20O | 25C4 | 18OD1 | 69.35 | 20O | 25C4 | 20N | 32.43 |
| 184CD1 | 25C4 | 184NE1 | 18.35 | 184CD1 | 25C4 | 184CG | 15.96 |
| 184CD1 | 25C4 | 19CG | 48.28 | 184CD1 | 25C4 | 184CE2 | 26.62 |
| 184CD1 | 25C4 | 18OD1 | 68.05 | 184CD1 | 25C4 | 20N | 82.80 |
| 184NE1 | 25C4 | 184CG | 27.99 | 184NE1 | 25C4 | 19CG | 53.65 |
| 184NE1 | 25C4 | 184CE2 | 15.20 | 184NE1 | 25C4 | 18OD1 | 85.79 |
| 184NE1 | 25C4 | 20N | 94.26 | 20C | 25C4 | 19CG | 62.70 |
| 20C | 25C4 | 18OD1 | 63.89 | 20C | 25C4 | 20N | 29.77 |
| 184CG | 25C4 | 19CG | 62.53 | 184CG | 25C4 | 184CE2 | 27.11 |
| 184CG | 25C4 | 18OD1 | 67.71 | 184CG | 25C4 | 20N | 91.33 |
| 19CG | 25C4 | 184CE2 | 68.70 | 19CG | 25C4 | 18OD1 | 57.18 |
| 19CG | 25C4 | 20N | 42.85 | 184CE2 | 25C4 | 18OD1 | 93.39 |
| 18OD1 | 25C4 | 20N | 37.93 | 184CD1 | 25C5 | 184NE1 | 17.38 |
| 184CD1 | 25C5 | 20O | 82.23 | 184CD1 | 25C5 | 184CG | 16.75 |
| 184CD1 | 25C5 | 184CE2 | 27.59 | 184CD1 | 25C5 | 184CD2 | 27.17 |
| 184NE1 | 25C5 | 20O | 86.19 | 184NE1 | 25C5 | 184CG | 27.91 |
| 184NE1 | 25C5 | 184CE2 | 16.68 | 184NE1 | 25C5 | 184CD2 | 27.27 |
| 20O | 25C5 | 184CG | 96.36 | 184CG | 25C5 | 184CE2 | 27.86 |
| 184CG | 25C5 | 184CD2 | 16.99 | 184CE2 | 25C5 | 184CD2 | 16.85 |
| 184CG | 25C6 | 184CD1 | 17.30 | 184CG | 25C6 | 184CD2 | 18.02 |
| 184CG | 25C6 | 184CB | 18.64 | 184CG | 25C6 | 184NE1 | 27.34 |
| 184CG | 25C6 | 184CE2 | 27.75 | 184CD1 | 25C6 | 184CD2 | 28.13 |
| 184CD1 | 25C6 | 184CB | 32.10 | 184CD1 | 25C6 | 184NE1 | 16.25 |
| 184CD1 | 25C6 | 184CE2 | 26.86 | 184CD2 | 25C6 | 184CB | 32.59 |
| 184CD2 | 25C6 | 184NE1 | 27.14 | 184CD2 | 25C6 | 184CE2 | 16.75 |
| 184CB | 25C6 | 184NE1 | 45.42 | 184CB | 25C6 | 184CE2 | 45.85 |
| 184NE1 | 25C6 | 184CE2 | 16.05 | 20O | 25C7 | 20C | 5.96 |
| 20O | 25C7 | 21CA | 34.09 | 20O | 25C7 | 19CD | 73.49 |
| 20O | 25C7 | 19CG | 60.92 | 20O | 25C7 | 21OE1 | 66.16 |
| 20O | 25C7 | 21N | 17.58 | 20O | 25C7 | 19OE1 | 87.57 |
| 20O | 25C7 | 19NE2 | 69.26 | 20C | 25C7 | 21CA | 31.76 |
| 20C | 25C7 | 19CD | 79.31 | 20C | 25C7 | 19CG | 66.28 |
| 20C | 25C7 | 21OE1 | 60.89 | 20C | 25C7 | 21N | 14.18 |
| 20C | 25C7 | 19OE1 | 93.30 | 20C | 25C7 | 19NE2 | 75.21 |
| 184NE1 | 25C7 | 19CD | 47.01 | 184NE1 | 25C7 | 19CG | 52.85 |
| 184NE1 | 25C7 | 184CD1 | 16.44 | 184NE1 | 25C7 | 19OE1 | 33.68 |
| 184NE1 | 25C7 | 19NE2 | 59.90 | 21CA | 25C7 | 19CD | 96.04 |
| 21CA | 25C7 | 19CG | 89.60 | 21CA | 25C7 | 21OE1 | 41.39 |
| 21CA | 25C7 | 21N | 17.76 | 21CA | 25C7 | 19NE2 | 85.25 |
| 19CD | 25C7 | 19CG | 18.31 | 19CD | 25C7 | 21N | 88.09 |
| 19CD | 25C7 | 184CD1 | 47.08 | 19CD | 25C7 | 19OE1 | 14.53 |
| 19CD | 25C7 | 19NE2 | 15.43 | 19CG | 25C7 | 21N | 77.54 |
| 19CG | 25C7 | 184CD1 | 46.14 | 19CG | 25C7 | 19OE1 | 28.58 |
| 19CG | 25C7 | 19NE2 | 28.52 | 21OE1 | 25C7 | 21N | 49.85 |
| 21N | 25C7 | 19NE2 | 80.92 | 184CD1 | 25C7 | 19OE1 | 37.45 |
| 184CD1 | 25C7 | 19NE2 | 62.12 | 19OE1 | 25C7 | 19NE2 | 26.24 |
| 20O | 25O8 | 19CD | 90.86 | 20O | 25O8 | 19NE2 | 87.53 |
| 20O | 25O8 | 19CG | 72.09 | 20O | 25O8 | 20C | 2.00 |
| 20O | 25O8 | 22O | 62.72 | 20O | 25O8 | 19CB | 63.81 |
| 19CD | 25O8 | 19OE1 | 19.87 | 19CD | 25O8 | 19NE2 | 21.15 |
| 19CD | 25O8 | 19CG | 23.15 | 19CD | 25O8 | 184NE1 | 60.87 |
| 19CD | 25O8 | 184CD1 | 58.07 | 19CD | 25O8 | 20C | 89.41 |
| 19CD | 25O8 | 22O | 57.75 | 19CD | 25O8 | 184CE2 | 73.67 |
| 19CD | 25O8 | 19CB | 27.32 | 19OE1 | 25O8 | 19NE2 | 35.82 |
| 19OE1 | 25O8 | 19CG | 37.30 | 19OE1 | 25O8 | 184NE1 | 43.39 |
| 19OE1 | 25O8 | 184CD1 | 45.88 | 19OE1 | 25O8 | 22O | 74.89 |
| 19OE1 | 25O8 | 184CE2 | 55.38 | 19OE1 | 25O8 | 19CB | 45.39 |
| 19NE2 | 25O8 | 19CG | 37.34 | 19NE2 | 25O8 | 184NE1 | 79.21 |
| 19NE2 | 25O8 | 184CD1 | 78.91 | 19NE2 | 25O8 | 20C | 85.68 |

TABLE XII-continued

Table of angles between atoms of the inhibitor and protein
for all protein atoms within 5 Ångstroms of the inhibitor
bis-(Cbz-leucinyl)-1,3-diamino-propan-2-one

| Atom 1 | Atom 2 | Atom 3 | Angle | Atom 1 | Atom 2 | Atom 3 | Angle |
|---|---|---|---|---|---|---|---|
| 19NE2 | 25O8 | 22O | 39.13 | 19NE2 | 25O8 | 184CE2 | 91.05 |
| 19NE2 | 25O8 | 19CB | 33.61 | 19CG | 25O8 | 184NE1 | 65.75 |
| 19CG | 25O8 | 184CD1 | 54.97 | 19CG | 25O8 | 20C | 71.02 |
| 19CG | 25O8 | 22O | 61.28 | 19CG | 25O8 | 184CE2 | 78.82 |
| 19CG | 25O8 | 19CB | 12.33 | 184NE1 | 25O8 | 184CD1 | 18.60 |
| 184NE1 | 25O8 | 184CE2 | 13.25 | 184NE1 | 25O8 | 19CB | 77.87 |
| 184CD1 | 25O8 | 184CE2 | 27.58 | 184CD1 | 25O8 | 19CB | 67.24 |
| 20C | 25O8 | 22O | 60.75 | 20C | 25O8 | 19CB | 62.46 |
| 22O | 25O8 | 19CB | 49.98 | 184CE2 | 25O8 | 19CB | 91.01 |
| 19OE1 | 25C9 | 19NE2 | 33.38 | 19OE1 | 25C9 | 19CD | 18.07 |
| 19OE1 | 25C9 | 184NE1 | 40.26 | 19OE1 | 25C9 | 20O | 84.29 |
| 19OE1 | 25C9 | 19CG | 30.18 | 19OE1 | 25C9 | 22O | 69.67 |
| 19OE1 | 25C9 | 184CE2 | 53.38 | 19OE1 | 25C9 | 184CD1 | 39.42 |
| 19NE2 | 25C9 | 19CD | 19.36 | 19NE2 | 25C9 | 184NE1 | 73.02 |
| 19NE2 | 25C9 | 20O | 69.77 | 19NE2 | 25C9 | 19CG | 30.40 |
| 19NE2 | 25C9 | 22O | 36.73 | 19NE2 | 25C9 | 184CE2 | 86.66 |
| 19NE2 | 25C9 | 184CD1 | 68.70 | 19CD | 25C9 | 184NE1 | 54.70 |
| 19CD | 25C9 | 20O | 69.22 | 19CD | 25C9 | 19CG | 17.06 |
| 19CD | 25C9 | 22O | 53.02 | 19CD | 25C9 | 184CE2 | 68.86 |
| 19CD | 25C9 | 184CD1 | 49.36 | 184NE1 | 25C9 | 20O | 95.14 |
| 184NE1 | 25C9 | 19CG | 55.54 | 184NE1 | 25C9 | 184CE2 | 14.51 |
| 184NE1 | 25C9 | 184CD1 | 14.36 | 20O | 25C9 | 19CG | 54.13 |
| 20O | 25C9 | 22O | 54.06 | 20O | 25C9 | 184CD1 | 80.80 |
| 19CG | 25C9 | 22O | 53.71 | 19CG | 25C9 | 184CE2 | 69.95 |
| 19CG | 25C9 | 184CD1 | 45.63 | 22O | 25C9 | 184CD1 | 99.26 |
| 184CE2 | 25C9 | 184CD1 | 26.16 | 19NE2 | 25O10 | 20O | 62.12 |
| 19NE2 | 25O10 | 22O | 35.56 | 19NE2 | 25O10 | 19CD | 15.61 |
| 19NE2 | 25O10 | 19OE1 | 26.78 | 20O | 25O10 | 22O | 52.61 |
| 20O | 25O10 | 19CD | 59.60 | 20O | 25O10 | 19OE1 | 70.63 |
| 22O | 25O10 | 19CD | 48.47 | 22O | 25O10 | 19OE1 | 61.86 |
| 19CD | 25O10 | 19OE1 | 14.34 | 162ND1 | 25C11 | 184CZ2 | 66.42 |
| 162ND1 | 2SC11 | 184NE1 | 66.34 | 162ND1 | 25C11 | 162CE1 | 17.78 |
| 162ND1 | 25C11 | 19OE1 | 57.83 | 162ND1 | 25C11 | 184CE2 | 67.52 |
| 162ND1 | 25C11 | 162CG | 14.11 | 162ND1 | 25C11 | 19NE2 | 72.38 |
| 162ND1 | 25C11 | 19CD | 68.15 | 184CZ2 | 25C11 | 184NE1 | 34.50 |
| 184CZ2 | 25C11 | 162CE1 | 56.59 | 184CZ2 | 25C11 | 19OE1 | 69.19 |
| 184CZ2 | 2SC11 | 184CE2 | 17.54 | 184CZ2 | 25C11 | 162CG | 60.04 |
| 184CZ2 | 25C11 | 19NE2 | 95.66 | 184CZ2 | 25C11 | 19CD | 80.47 |
| 184NE1 | 2SC11 | 162CE1 | 49.27 | 184NE1 | 25C11 | 19OE1 | 37.54 |
| 184NE1 | 25C11 | 184CE2 | 17.27 | 184NE1 | 25C11 | 162CG | 68.99 |
| 184NE1 | 25C11 | 19NE2 | 62.26 | 184NE1 | 25C11 | 19CD | 46.90 |
| 162CE1 | 25C11 | 19OE1 | 42.46 | 162CE1 | 25C11 | 184CE2 | 53.20 |
| 162CE1 | 25C11 | 162CG | 26.53 | 162CE1 | 25C11 | 19NE2 | 62.11 |
| 162CE1 | 25C11 | 19CD | 54.33 | 19OE1 | 25C11 | 184CE2 | 53.84 |
| 19OE1 | 25C11 | 162CG | 68.94 | 19OE1 | 25C11 | 19NE2 | 26.94 |
| 19OE1 | 25C11 | 19CD | 13.30 | 184CE2 | 25C11 | 162CG | 65.59 |
| 184CE2 | 25C11 | 19NE2 | 79.38 | 184CE2 | 25C11 | 19CD | 64.03 |
| 162CG | 2SC11 | 19NE2 | 86.02 | 162CG | 25C11 | 19CD | 80.39 |
| 19NE2 | 25C11 | 19CD | 15.36 | 184CZ2 | 25C15 | 184CH2 | 16.48 |
| 184CZ2 | 25C15 | 143OE1 | 72.66 | 184CZ2 | 25C15 | 137O | 75.04 |
| 184CH2 | 25C15 | 143OE1 | 58.91 | 184CH2 | 25C15 | 137O | 61.89 |
| 143OE1 | 25C15 | 137O | 63.98 | 162ND1 | 25C16 | 162CE1 | 19.73 |
| 162ND1 | 25C16 | 162CG | 16.60 | 162ND1 | 25C16 | 25SG | 47.39 |
| 162ND1 | 25C16 | 161O | 72.64 | 162ND1 | 25C16 | 19OE1 | 62.63 |
| 162ND1 | 25C16 | 162CB | 33.51 | 162ND1 | 25C16 | 162CA | 39.24 |
| 162ND1 | 25C16 | 162NE2 | 20.67 | 162ND1 | 25C16 | 19NE2 | 81.12 |
| 162ND1 | 25C16 | 184CZ2 | 64.44 | 162ND1 | 25C16 | 25CB | 44.50 |
| 162ND1 | 25C16 | 184NE1 | 64.44 | 162ND1 | 25C16 | 162CD2 | 17.81 |
| 162CE1 | 25C16 | 162CG | 32.31 | 162CE1 | 25C16 | 25SG | 53.22 |
| 162CE1 | 25C16 | 161O | 91.93 | 162CE1 | 25C16 | 19OE1 | 44.18 |
| 162CE1 | 25C16 | 162CB | 51.51 | 162CE1 | 25C16 | 162CA | 58.97 |
| 162CE1 | 25C16 | 162NE2 | 11.09 | 162CE1 | 25C16 | 19NE2 | 66.33 |
| 162CE1 | 25C16 | 184CZ2 | 53.67 | 162CE1 | 25C16 | 25CB | 41.27 |
| 162CE1 | 25C16 | 184NE1 | 46.11 | 162CE1 | 25C16 | 162CD2 | 24.34 |
| 162CG | 25C16 | 25SG | 59.98 | 162CG | 25C16 | 161O | 66.72 |
| 162CG | 25C16 | 19OE1 | 76.48 | 162CG | 25C16 | 162CB | 19.50 |
| 162CG | 25C16 | 162CA | 32.20 | 162CG | 25C16 | 162NE2 | 27.13 |
| 162CG | 25C16 | 19NE2 | 97.24 | 162CG | 25C16 | 184CZ2 | 60.98 |
| 162CG | 25C16 | 25CB | 60.57 | 162CG | 25C16 | 184NE1 | 70.16 |
| 162CG | 25C16 | 162CD2 | 12.90 | 25SG | 25C16 | 161O | 62.69 |
| 25SG | 25C16 | 19OE1 | 65.19 | 25SG | 25C16 | 162CB | 65.02 |
| 25SG | 25C16 | 162CA | 52.80 | 25SG | 25C16 | 162NE2 | 62.49 |
| 25SG | 25C16 | 19NE2 | 61.43 | 25SG | 25C16 | 25CB | 20.75 |

TABLE XII-continued

Table of angles between atoms of the inhibitor and protein
for all protein atoms within 5 Ångstroms of the inhibitor
bis-(Cbz-leucinyl)-1,3-diamino-propan-2-one

| Atom 1 | Atom 2 | Atom 3 | Angle | Atom 1 | Atom 2 | Atom 3 | Angle |
|---|---|---|---|---|---|---|---|
| 25SG | 25C16 | 184NE1 | 91.34 | 25SG | 25C16 | 162CD2 | 65.19 |
| 161O | 25C16 | 162CB | 50.15 | 161O | 25C16 | 162CA | 34.64 |
| 161O | 25C16 | 162NE2 | 92.16 | 161O | 25C16 | 25CB | 82.66 |
| 161O | 25C16 | 162CD2 | 79.61 | 19OE1 | 25C16 | 162CB | 95.63 |
| 19OE1 | 25C16 | 162CA | 99.99 | 19OE1 | 25C16 | 162NE2 | 51.09 |
| 19OE1 | 25C16 | 19NE2 | 27.38 | 19OE1 | 25C16 | 184CZ2 | 62.46 |
| 19OE1 | 25C16 | 25CB | 44.47 | 19OE1 | 25C16 | 184NE1 | 33.86 |
| 19OE1 | 25C16 | 162CD2 | 67.06 | 162CB | 25C16 | 162CA | 18.75 |
| 162CB | 25C16 | 162NE2 | 46.53 | 162CB | 25C16 | 184CZ2 | 73.28 |
| 162CB | 25C16 | 25CB | 72.45 | 162CB | 25C16 | 184NE1 | 88.17 |
| 162CB | 25C16 | 162CD2 | 31.28 | 162CA | 25C16 | 162NE2 | 57.73 |
| 162CA | 25C16 | 184CZ2 | 91.31 | 162CA | 25C16 | 25CB | 65.83 |
| 162CA | 25C16 | 162CD2 | 45.08 | 162NE2 | 25C16 | 19NE2 | 75.48 |
| 162NE2 | 25C16 | 184CZ2 | 45.32 | 162NE2 | 25C16 | 25CB | 52.16 |
| 162NE2 | 25C16 | 184NE1 | 44.44 | 162NE2 | 25C16 | 162CD2 | 16.02 |
| 19NE2 | 25C16 | 184CZ2 | 88.09 | 19NE2 | 25C16 | 25CB | 44.94 |
| 19NE2 | 25C16 | 184NE1 | 58.55 | 19NE2 | 25C16 | 162CD2 | 90.64 |
| 184CZ2 | 25C16 | 25CB | 91.81 | 184CZ2 | 25C16 | 184NE1 | 29.55 |
| 184CZ2 | 25C16 | 162CD2 | 49.38 | 25CB | 25C16 | 184NE1 | 71.82 |
| 25CB | 25C16 | 162CD2 | 60.66 | 184NE1 | 25C16 | 162CD2 | 57.37 |
| 162ND1 | 25O17 | 162CG | 25.38 | 162ND1 | 25O17 | 162CB | 48.94 |
| 162ND1 | 25O17 | 162CE1 | 18.45 | 162ND1 | 25O17 | 161O | 93.58 |
| 162ND1 | 25O17 | 162CA | 54.76 | 162ND1 | 25O17 | 25SG | 48.39 |
| 162ND1 | 25O17 | 161C | 89.31 | 162ND1 | 25O17 | 162CD2 | 25.71 |
| 162ND1 | 25O17 | 162N | 73.99 | 162ND1 | 25O17 | 162NE2 | 21.11 |
| 162ND1 | 25O17 | 184CZ2 | 69.27 | 162ND1 | 25O17 | 137CB | 75.37 |
| 162CG | 25O17 | 162CB | 26.64 | 162CG | 25O17 | 162CE1 | 38.41 |
| 162CG | 25O17 | 161O | 86.53 | 162CG | 25O17 | 162CA | 42.50 |
| 162CG | 25O17 | 25SG | 67.49 | 162CG | 25O17 | 161C | 76.51 |
| 162CG | 25O17 | 162CD2 | 13.63 | 162CG | 25O17 | 162N | 58.79 |
| 162CG | 25O17 | 162NE2 | 29.02 | 162CG | 25O17 | 161OD1 | 79.16 |
| 162CG | 25O17 | 184CZ2 | 67.73 | 162CG | 25O17 | 137CB | 51.32 |
| 162CB | 25O17 | 162CE1 | 64.60 | 162CB | 25O17 | 161O | 65.36 |
| 162CB | 25O17 | 162CA | 24.38 | 162CB | 25O17 | 25SG | 76.49 |
| 162CB | 25O17 | 161C | 52.48 | 162CB | 25O17 | 162CD2 | 38.18 |
| 162CB | 25O17 | 162N | 34.58 | 162CB | 25O17 | 162NE2 | 55.49 |
| 162CB | 25O17 | 161OD1 | 54.52 | 162CB | 25O17 | 184CZ2 | 85.85 |
| 162CB | 25O17 | 137CB | 42.56 | 162CE1 | 25O17 | 162CA | 73.15 |
| 162CE1 | 25O17 | 25SG | 55.22 | 162CE1 | 25O17 | 162CD2 | 31.50 |
| 162CE1 | 25O17 | 162N | 92.28 | 162CE1 | 25O17 | 162NE2 | 14.96 |
| 162CE1 | 25O17 | 184CZ2 | 56.06 | 162CE1 | 25O17 | 137CB | 81.03 |
| 161O | 25O17 | 162CA | 44.07 | 161O | 25O17 | 25SG | 69.63 |
| 161O | 25O17 | 161C | 15.96 | 161O | 25O17 | 162N | 31.46 |
| 161O | 25O17 | 161OD1 | 56.32 | 161O | 25O17 | 137CB | 91.92 |
| 162CA | 25O17 | 25SG | 61.24 | 162CA | 25O17 | 161C | 35.13 |
| 162CA | 25O17 | 162CD2 | 56.09 | 162CA | 25O17 | 162N | 19.37 |
| 162CA | 25O17 | 162NE2 | 69.58 | 162CA | 25O17 | 161OD1 | 58.28 |
| 162CA | 25O17 | 137CB | 64.45 | 25SG | 25O17 | 161C | 77.58 |
| 25SG | 25O17 | 162CD2 | 73.41 | 25SG | 25O17 | 162N | 74.60 |
| 25SG | 25O17 | 162NE2 | 67.15 | 161C | 25O17 | 162CD2 | 89.68 |
| 161C | 25O17 | 162N | 17.96 | 161C | 25O17 | 161OD1 | 42.82 |
| 161C | 25O17 | 137CB | 75.96 | 162CD2 | 25O17 | 162N | 71.80 |
| 162CD2 | 25O17 | 162NE2 | 18.45 | 162CD2 | 25O17 | 161OD1 | 86.33 |
| 162CD2 | 25O17 | 184CZ2 | 54.40 | 162CD2 | 25O17 | 137CB | 50.73 |
| 162N | 25O17 | 162NE2 | 87.31 | 162N | 25O17 | 161OD1 | 42.68 |
| 162N | 25O17 | 137CB | 63.55 | 162NE2 | 25O17 | 184CZ2 | 48.21 |
| 162NE2 | 25O17 | 137CB | 66.23 | 161OD1 | 25O17 | 137CB | 44.42 |
| 184CZ2 | 25O17 | 137CB | 61.47 | 25SG | 25N18 | 162ND1 | 50.41 |
| 25SG | 25N18 | 162CE1 | 53.56 | 25SG | 25N18 | 161O | 67.92 |
| 25SG | 25N18 | 19NE2 | 71.90 | 25SG | 25N18 | 19OE1 | 69.62 |
| 25SG | 25N18 | 25CB | 22.82 | 25SG | 25N18 | 23CA | 87.13 |
| 25SG | 25N18 | 162CG | 56.99 | 25SG | 25N18 | 19CD | 72.29 |
| 162ND1 | 25N18 | 162CE1 | 17.36 | 162ND1 | 25N18 | 161O | 69.09 |
| 162ND1 | 25N18 | 19NE2 | 84.51 | 162ND1 | 25N18 | 19OE1 | 59.48 |
| 162ND1 | 25N18 | 25CB | 49.58 | 162ND1 | 25N18 | 162CG | 11.34 |
| 162ND1 | 25N18 | 19CD | 72.69 | 162CE1 | 25N18 | 161O | 86.28 |
| 162CE1 | 25N18 | 19NE2 | 68.55 | 162CE1 | 25N18 | 19OE1 | 42.23 |
| 162CE1 | 25N18 | 25CB | 43.96 | 162CE1 | 25N18 | 162CG | 27.38 |
| 162CE1 | 25N18 | 19CD | 55.80 | 161O | 25N18 | 25CB | 89.34 |
| 161O | 25N18 | 162CG | 61.14 | 19NE2 | 25N18 | 19OE1 | 29.63 |
| 19NE2 | 25N18 | 25CB | 50.72 | 19NE2 | 25N18 | 23CA | 55.49 |
| 19NE2 | 25N18 | 162CG | 95.57 | 19NE2 | 25N18 | 19CD | 15.35 |
| 19OE1 | 25N18 | 25CB | 47.37 | 19OE1 | 25N18 | 23CA | 85.11 |

TABLE XII-continued

Table of angles between atoms of the inhibitor and protein for all protein atoms within 5 Ångstroms of the inhibitor bis-(Cbz-leucinyl)-1,3-diamino-propan-2-one

| Atom 1 | Atom 2 | Atom 3 | Angle | Atom 1 | Atom 2 | Atom 3 | Angle |
|---|---|---|---|---|---|---|---|
| 19OE1 | 25N18 | 162CG | 69.47 | 19OE1 | 25N18 | 19CD | 14.61 |
| 25CB | 25N18 | 23CA | 81.33 | 25CB | 25N18 | 162CG | 59.74 |
| 25CB | 25N18 | 19CD | 49.52 | 23CA | 25N18 | 19CD | 70.70 |
| 162CG | 25N18 | 19CD | 83.18 | 25SG | 25C19 | 161O | 92.47 |
| 25SG | 25C19 | 162ND1 | 54.14 | 25SG | 25C19 | 25CB | 20.86 |
| 25SG | 25C19 | 162CA | 62.74 | 25SG | 25C19 | 161C | 88.58 |
| 25SG | 25C19 | 162CE1 | 51.71 | 25SG | 25C19 | 23CA | 97.99 |
| 25SG | 25C19 | 25N | 41.07 | 25SG | 25C19 | 23C | 82.10 |
| 25SG | 25C19 | 23O | 81.30 | 25SG | 25C19 | 162CG | 59.31 |
| 25SG | 25C19 | 19NE2 | 69.11 | 25SG | 25C19 | 162CB | 67.82 |
| 25SG | 25C19 | 162N | 76.57 | 161O | 25C19 | 162ND1 | 78.79 |
| 161O | 25C19 | 162CA | 38.01 | 161O | 25C19 | 161C | 7.13 |
| 161O | 25C19 | 162CE1 | 93.42 | 161O | 25C19 | 162CG | 66.49 |
| 161O | 25C19 | 162CB | 49.06 | 161O | 25C19 | 162N | 21.75 |
| 162ND1 | 25C19 | 25CB | 52.62 | 162ND1 | 25C19 | 162CA | 42.73 |
| 162ND1 | 25C19 | 161C | 71.68 | 162ND1 | 25C19 | 162CE1 | 14.66 |
| 162ND1 | 25C19 | 25N | 83.32 | 162ND1 | 25C19 | 162CG | 12.47 |
| 162ND1 | 25C19 | 19NE2 | 75.83 | 162ND1 | 25C19 | 162CB | 30.03 |
| 162ND1 | 25C19 | 162N | 57.42 | 25CB | 25C19 | 162CA | 76.45 |
| 25CB | 25C19 | 162CE1 | 44.02 | 25CB | 25C19 | 23CA | 85.20 |
| 25CB | 25C19 | 25N | 31.12 | 25CB | 25C19 | 23C | 72.96 |
| 25CB | 25C19 | 23O | 77.28 | 25CB | 25C19 | 162CG | 62.09 |
| 25CB | 25C19 | 19NE2 | 48.58 | 25CB | 25C19 | 162CB | 75.75 |
| 25CB | 25C19 | 162N | 92.17 | 162CA | 25C19 | 161C | 31.40 |
| 162CA | 25C19 | 162CE1 | 56.83 | 162CA | 25C19 | 162CG | 31.62 |
| 162CA | 25C19 | 162CB | 17.87 | 162CA | 25C19 | 162N | 16.50 |
| 161C | 25C19 | 162CE1 | 86.32 | 161C | 25C19 | 162CG | 59.37 |
| 161C | 25C19 | 162CB | 41.93 | 161C | 25C19 | 162N | 14.94 |
| 162CE1 | 25C19 | 25N | 72.85 | 162CE1 | 25C19 | 162CG | 27.09 |
| 162CE1 | 25C19 | 19NE2 | 61.17 | 162CE1 | 25C19 | 162CB | 44.66 |
| 162CE1 | 25C19 | 162N | 71.95 | 23CA | 25C19 | 25N | 56.99 |
| 23CA | 25C19 | 23C | 18.49 | 23CA | 25C19 | 23O | 29.45 |
| 23CA | 25C19 | 19NE2 | 51.58 | 25N | 25C19 | 23C | 42.38 |
| 25N | 25C19 | 23O | 46.35 | 25N | 25C19 | 162CG | 93.20 |
| 25N | 25C19 | 19NE2 | 42.58 | 23C | 25C19 | 23O | 14.74 |
| 23C | 25C19 | 19NE2 | 52.68 | 23O | 25C19 | 19NE2 | 66.29 |
| 162CG | 25C19 | 19NE2 | 88.25 | 162CG | 25C19 | 162CB | 17.57 |
| 162CG | 25C19 | 162N | 45.36 | 162CB | 25C19 | 162N | 28.45 |
| 184NE1 | 25N20 | 19OE1 | 48.31 | 184NE1 | 25N20 | 19CD | 61.42 |
| 184NE1 | 25N20 | 184CE2 | 19.07 | 184NE1 | 25N20 | 19NE2 | 80.38 |
| 184NE1 | 25N20 | 184CZ2 | 38.30 | 184NE1 | 25N20 | 162CE1 | 53.42 |
| 184NE1 | 25N20 | 184CD1 | 12.98 | 184NE1 | 25N20 | 162ND1 | 68.69 |
| 184NE1 | 25N20 | 19CG | 57.21 | 19OE1 | 25N20 | 19CD | 18.12 |
| 19OE1 | 25N20 | 184CE2 | 65.80 | 19OE1 | 25N20 | 19NE2 | 33.85 |
| 19OE1 | 25N20 | 184CZ2 | 80.73 | 19OE1 | 25N20 | 162CE1 | 45.71 |
| 19OE1 | 25N20 | 184CD1 | 44.65 | 19OE1 | 25N20 | 162ND1 | 59.71 |
| 19OE1 | 25N20 | 19CG | 26.58 | 19CD | 25N20 | 184CE2 | 80.19 |
| 19CD | 25N20 | 19NE2 | 19.18 | 19CD | 25N20 | 184CZ2 | 97.13 |
| 19CD | 25N20 | 162CE1 | 62.24 | 19CD | 25N20 | 184CD1 | 54.10 |
| 19CD | 25N20 | 162ND1 | 74.29 | 19CD | 25N20 | 19CG | 14.62 |
| 184CE2 | 25N20 | 19NE2 | 98.89 | 184CE2 | 25N20 | 184CZ2 | 20.04 |
| 184CE2 | 25N20 | 162CE1 | 56.95 | 184CE2 | 25N20 | 184CD1 | 30.00 |
| 184CE2 | 25N20 | 162ND1 | 68.56 | 184CE2 | 25N20 | 19CG | 76.21 |
| 19NE2 | 25N20 | 162CE1 | 69.93 | 19NE2 | 25N20 | 184CD1 | 73.25 |
| 19NE2 | 25N20 | 162ND1 | 77.40 | 19NE2 | 25N20 | 19CG | 29.26 |
| 184CZ2 | 25N20 | 162CE1 | 57.21 | 184CZ2 | 25N20 | 184CD1 | 49.98 |
| 184CZ2 | 25N20 | 162ND1 | 63.26 | 184CZ2 | 25N20 | 19CG | 95.28 |
| 162CE1 | 25N20 | 184CD1 | 61.93 | 162CE1 | 25N20 | 162ND1 | 16.79 |
| 162CE1 | 25N20 | 19CG | 72.21 | 184CD1 | 25N20 | 162ND1 | 78.20 |
| 184CD1 | 25N20 | 19CG | 47.15 | 162ND1 | 25N20 | 19CG | 86.13 |
| 25SG | 25C21 | 25CB | 34.64 | 25SG | 25C21 | 25N | 72.39 |
| 25SG | 25C21 | 25CA | 49.66 | 25SG | 25C21 | 162ND1 | 48.43 |
| 25SG | 25C21 | 19NE2 | 93.26 | 25SG | 25C21 | 26N | 53.17 |
| 25SG | 25C21 | 161O | 82.24 | 25SG | 25C21 | 25C | 43.41 |
| 25SG | 25C21 | 24C | 80.54 | 25SG | 25C21 | 162CE1 | 48.10 |
| 25SG | 25C21 | 19OE1 | 73.78 | 25SG | 25C21 | 24CA | 98.55 |
| 25SG | 25C21 | 163N | 27.76 | 25SG | 25C21 | 162CA | 50.66 |
| 25SG | 25C21 | 19CD | 82.46 | 25SG | 25C21 | 26CD1 | 90.92 |
| 25CB | 25C21 | 25N | 45.83 | 25CB | 25C21 | 25CA | 23.90 |
| 25CB | 25C21 | 162ND1 | 58.24 | 25CB | 25C21 | 19NE2 | 60.12 |
| 25CB | 25C21 | 26N | 51.36 | 25CB | 25C21 | 24N | 83.08 |
| 25CB | 25C21 | 25C | 33.89 | 25CB | 25C21 | 24C | 55.62 |
| 25CB | 25C21 | 162CE1 | 46.38 | 25CB | 25C21 | 19OE1 | 47.87 |

TABLE XII-continued

Table of angles between atoms of the inhibitor and protein
for all protein atoms within 5 Ångstroms of the inhibitor
bis-(Cbz-leucinyl)-1,3-diamino-propan-2-one

| Atom 1 | Atom 2 | Atom 3 | Angle | Atom 1 | Atom 2 | Atom 3 | Angle |
|---|---|---|---|---|---|---|---|
| 25CB | 25C21 | 24CA | 73.29 | 25CB | 25C21 | 163N | 62.27 |
| 25CB | 25C21 | 162CA | 80.47 | 25CB | 25C21 | 19CD | 51.61 |
| 25CB | 25C21 | 26CD1 | 90.22 | 25N | 25C21 | 25CA | 23.31 |
| 25N | 25C21 | 23O | 62.57 | 25N | 25C21 | 23C | 56.71 |
| 25N | 25C21 | 23CA | 72.88 | 25N | 25C21 | 19NE2 | 53.88 |
| 25N | 25C21 | 26N | 39.27 | 25N | 25C21 | 24N | 40.31 |
| 25N | 25C21 | 25C | 33.06 | 25N | 25C21 | 24C | 9.89 |
| 25N | 25C21 | 162CE1 | 88.84 | 25N | 25C21 | 19OE1 | 66.88 |
| 25N | 25C21 | 24CA | 27.62 | 25N | 25C21 | 163N | 97.26 |
| 25N | 25C21 | 19CD | 57.91 | 25N | 25C21 | 26CD1 | 57.03 |
| 25CA | 25C21 | 23O | 85.08 | 25CA | 25C21 | 23C | 79.97 |
| 25CA | 25C21 | 162ND1 | 82.14 | 25CA | 25C21 | 23CA | 94.92 |
| 25CA | 25C21 | 19NE2 | 59.55 | 25CA | 25C21 | 26N | 34.96 |
| 25CA | 25C21 | 24N | 63.21 | 25CA | 25C21 | 25C | 19.25 |
| 25CA | 25C21 | 24C | 32.60 | 25CA | 25C21 | 162CE1 | 69.83 |
| 25CA | 25C21 | 19OE1 | 60.15 | 25CA | 25C21 | 24CA | 50.80 |
| 25CA | 25C21 | 163N | 75.98 | 25CA | 25C21 | 19CD | 57.10 |
| 25CA | 25C21 | 26CD1 | 68.81 | 23O | 25C21 | 23C | 18.23 |
| 23O | 25C21 | 23CA | 34.62 | 23O | 25C21 | 19NE2 | 81.51 |
| 23O | 25C21 | 26N | 74.70 | 23O | 25C21 | 24N | 31.37 |
| 23O | 25C21 | 25C | 84.83 | 23O | 25C21 | 24C | 52.77 |
| 23O | 25C21 | 162CE1 | 88.84 | 23O | 25C21 | 19CD | 94.62 |
| 23O | 25C21 | 24CA | 35.38 | 23O | 25C21 | 19CD | 94.62 |
| 23O | 25C21 | 26CD1 | 42.49 | 23C | 25C21 | 23CA | 21.54 |
| 23C | 25C21 | 19NE2 | 63.77 | 23C | 25C21 | 26N | 80.57 |
| 23C | 25C21 | 24N | 17.67 | 23C | 25C21 | 25C | 85.73 |
| 23C | 25C21 | 24C | 48.08 | 23C | 25C21 | 19OE1 | 91.44 |
| 23C | 25C21 | 24CA | 30.02 | 23C | 25C21 | 19CD | 77.14 |
| 23C | 25C21 | 26CD1 | 56.82 | 162ND1 | 25C21 | 19NE2 | 82.13 |
| 162ND1 | 25C21 | 16lO | 66.39 | 162ND1 | 25C21 | 25C | 86.84 |
| 162ND1 | 25C21 | 162CE1 | 16.39 | 162ND1 | 25C21 | 19OE1 | 54.45 |
| 162ND1 | 25C21 | 163N | 49.87 | 162ND1 | 25C21 | 162CA | 38.64 |
| 162ND1 | 25C21 | 19CD | 68.76 | 23CA | 25C21 | 19NE2 | 59.28 |
| 23CA | 25C21 | 24N | 33.06 | 23CA | 25C21 | 24C | 65.84 |
| 23CA | 25C21 | 19OE1 | 85.51 | 23CA | 25C21 | 24CA | 49.18 |
| 23CA | 25C21 | 19CD | 72.54 | 23CA | 25C21 | 26CD1 | 76.75 |
| 19NE2 | 25C21 | 26N | 91.47 | 19NE2 | 25C21 | 24N | 51.72 |
| 19NE2 | 25C21 | 25C | 78.62 | 19NE2 | 25C21 | 24C | 57.38 |
| 19NE2 | 25C21 | 162CE1 | 66.80 | 19NE2 | 25C21 | 19OE1 | 27.71 |
| 19NE2 | 25C21 | 24CA | 59.21 | 19NE2 | 25C21 | 19CD | 13.58 |
| 26N | 25C21 | 24N | 70.38 | 26N | 25C21 | 25C | 17.60 |
| 26N | 25C21 | 24C | 40.64 | 26N | 25C21 | 162CE1 | 94.63 |
| 26N | 25C21 | 19OE1 | 94.99 | 26N | 25C21 | 24CA | 53.42 |
| 26N | 25C21 | 163N | 67.59 | 26N | 25C21 | 162CA | 96.43 |
| 26N | 25C21 | 19CD | 91.55 | 26N | 25C21 | 26CD1 | 40.50 |
| 24N | 25C21 | 25C | 71.62 | 24N | 25C21 | 24C | 32.79 |
| 24N | 25C21 | 19OE1 | 78.31 | 24N | 25C21 | 24CA | 16.97 |
| 24N | 25C21 | 19CD | 64.11 | 24N | 25C21 | 26CD1 | 58.21 |
| 16lO | 25C21 | 162CE1 | 82.76 | 16lO | 25C21 | 163N | 55.62 |
| 16lO | 25C21 | 162CA | 33.90 | 25C | 25C21 | 24C | 38.87 |
| 25C | 25C21 | 162CE1 | 78.56 | 25C | 25C21 | 19OE1 | 78.01 |
| 25C | 25C21 | 24CA | 55.90 | 25C | 25C21 | 163N | 64.97 |
| 25C | 25C21 | 162CA | 92.64 | 25C | 25C21 | 19CD | 76.23 |
| 25C | 25C21 | 26CD1 | 56.82 | 24C | 25C21 | 162CE1 | 98.56 |
| 24C | 25C21 | 19OE1 | 74.12 | 24C | 25C21 | 24CA | 18.29 |
| 24C | 25C21 | 19CD | 63.65 | 24C | 25C21 | 26CD1 | 49.92 |
| 162CE1 | 25C21 | 19OE1 | 39.16 | 162CE1 | 25C21 | 163N | 58.96 |
| 162CE1 | 25C21 | 162CA | 54.05 | 162CE1 | 25C21 | 19CD | 53.25 |
| 19OE1 | 25C21 | 24CA | 82.23 | 19OE1 | 25C21 | 163N | 94.60 |
| 19OE1 | 25C21 | 162CA | 93.01 | 19OE1 | 25C21 | 19CD | 14.34 |
| 24CA | 25C21 | 19CD | 69.26 | 24CA | 25C21 | 26CD1 | 46.30 |
| 163N | 25C21 | 162CA | 28.85 | 163N | 25C21 | 26CD1 | 94.44 |
| 25SG | 25O22 | 25N | 77.15 | 25SG | 25O22 | 25CB | 38.56 |
| 25SG | 25O22 | 25CA | 56.15 | 25SG | 25O22 | 24C | 89.30 |
| 25SG | 25O22 | 19OE1 | 86.57 | 25SG | 25O22 | 162ND1 | 43.24 |
| 25SG | 25O22 | 25C | 48.29 | 25SG | 25O22 | 26N | 51.24 |
| 25SG | 25O22 | 162CE1 | 50.40 | 25SG | 25O22 | 24O | 83.26 |
| 25N | 25O22 | 25CB | 51.87 | 25N | 25O22 | 19NE2 | 73.58 |
| 25N | 25O22 | 23C | 71.81 | 25N | 25O22 | 23CA | 95.33 |
| 25N | 25O22 | 25CA | 24.89 | 25N | 25O22 | 24N | 52.99 |
| 25N | 25O22 | 23O | 73.36 | 25N | 25O22 | 24C | 13.57 |
| 25N | 25O22 | 19CD | 75.82 | 25N | 25O22 | 19OE1 | 83.34 |
| 25N | 25O22 | 24CA | 35.40 | 25N | 25O22 | 22O | 81.27 |
| 25N | 25O22 | 25C | 29.02 | 25N | 25O22 | 26N | 34.61 |

TABLE XII-continued

Table of angles between atoms of the inhibitor and protein for all protein atoms within 5 Ångstroms of the inhibitor bis-(Cbz-leucinyl)-1,3-diamino-propan-2-one

| Atom 1 | Atom 2 | Atom 3 | Angle | Atom 1 | Atom 2 | Atom 3 | Angle |
|---|---|---|---|---|---|---|---|
| 25N | 25O22 | 23N | 91.35 | 25N | 25O22 | 162CE1 | 94.53 |
| 25N | 25O22 | 22C | 85.32 | 25N | 25O22 | 24O | 6.50 |
| 25CB | 25O22 | 19NE2 | 77.77 | 25CB | 25O22 | 25CA | 27.03 |
| 25CB | 25O22 | 24C | 65.38 | 25CB | 25O22 | 19CD | 66.62 |
| 25CB | 25O22 | 19OE1 | 58.82 | 25CB | 25O22 | 24CA | 87.22 |
| 25CB | 25O22 | 162ND1 | 52.46 | 25CB | 25O22 | 25C | 32.94 |
| 25CB | 25O22 | 26N | 48.44 | 25CB | 25O22 | 162CE1 | 44.82 |
| 25CB | 25O22 | 24O | 58.22 | 19NE2 | 25O22 | 23C | 87.29 |
| 19NE2 | 25O22 | 23CA | 80.68 | 19NE2 | 25O22 | 25CA | 75.11 |
| 19NE2 | 25O22 | 24N | 70.11 | 19NE2 | 25O22 | 24C | 73.32 |
| 19NE2 | 25O22 | 19CD | 15.53 | 19NE2 | 25O22 | 19OE1 | 32.76 |
| 19NE2 | 25O22 | 24CA | 76.24 | 19NE2 | 25O22 | 22O | 41.66 |
| 19NE2 | 25O22 | 162ND1 | 90.29 | 19NE2 | 25O22 | 25C | 91.32 |
| 19NE2 | 25O22 | 23N | 70.60 | 19NE2 | 25O22 | 162CE1 | 74.46 |
| 19NE2 | 25O22 | 22C | 55.07 | 19NE2 | 25O22 | 24O | 72.58 |
| 23C | 25O22 | 23CA | 27.25 | 23C | 25O22 | 25CA | 96.67 |
| 23C | 25O22 | 24N | 23.18 | 23C | 25O22 | 23O | 20.52 |
| 23C | 25O22 | 24C | 58.32 | 23C | 25O22 | 24CA | 36.50 |
| 23C | 25O22 | 22O | 49.90 | 23C | 25O22 | 25C | 95.16 |
| 23C | 25O22 | 26N | 86.14 | 23C | 25O22 | 23N | 30.10 |
| 23C | 25O22 | 22C | 39.20 | 23C | 25O22 | 24O | 65.47 |
| 23CA | 25O22 | 24N | 42.37 | 23CA | 25O22 | 23O | 41.32 |
| 23CA | 25O22 | 24C | 81.90 | 23CA | 25O22 | 19CD | 95.72 |
| 23CA | 25O22 | 24CA | 60.58 | 23CA | 25O22 | 22O | 39.10 |
| 23CA | 25O22 | 23N | 10.12 | 23CA | 25O22 | 22C | 25.72 |
| 23CA | 25O22 | 24O | 88.84 | 25CA | 25O22 | 24N | 77.38 |
| 25CA | 25O22 | 23O | 96.24 | 25CA | 25O22 | 24C | 38.44 |
| 25CA | 25O22 | 19CD | 70.44 | 25CA | 25O22 | 19OE1 | 70.91 |
| 25CA | 25O22 | 24CA | 60.28 | 25CA | 25O22 | 22O | 98.08 |
| 25CA | 25O22 | 162ND1 | 79.49 | 25CA | 25O22 | 25C | 16.40 |
| 25CA | 25O22 | 26N | 32.82 | 25CA | 25O22 | 162CE1 | 70.84 |
| 25CA | 25O22 | 24O | 31.31 | 24N | 25O22 | 23O | 38.32 |
| 24N | 25O22 | 24C | 39.66 | 24N | 25O22 | 19CD | 83.95 |
| 24N | 25O22 | 24CA | 19.43 | 24N | 25O22 | 22O | 42.54 |
| 24N | 25O22 | 25C | 80.28 | 24N | 25O22 | 26N | 76.76 |
| 24N | 25O22 | 23N | 39.05 | 24N | 25O22 | 22C | 38.22 |
| 24N | 25O22 | 24O | 46.50 | 23O | 25O22 | 24C | 61.42 |
| 23O | 25O22 | 24CA | 42.50 | 23O | 25O22 | 22O | 70.35 |
| 23O | 25O22 | 25C | 89.16 | 23O | 25O22 | 26N | 75.88 |
| 23O | 25O22 | 23N | 47.63 | 23O | 25O22 | 22C | 59.10 |
| 23O | 25O22 | 24O | 68.00 | 24C | 25O22 | 19CD | 79.18 |
| 24C | 25O22 | 19OE1 | 89.99 | 24C | 25O22 | 24CA | 21.85 |
| 24C | 25O22 | 22O | 71.83 | 24C | 25O22 | 25C | 41.07 |
| 24C | 25O22 | 26N | 42.17 | 24C | 25O22 | 23N | 78.42 |
| 24C | 25O22 | 22C | 73.88 | 24C | 25O22 | 24O | 7.15 |
| 19CD | 25O22 | 19OE1 | 17.46 | 19CD | 25O22 | 24CA | 86.98 |
| 19CD | 25O22 | 22O | 56.95 | 19CD | 25O22 | 162ND1 | 74.94 |
| 19CD | 25O22 | 25C | 86.74 | 19CD | 25O22 | 23N | 85.73 |
| 19CD | 25O22 | 162CE1 | 58.96 | 19CD | 25O22 | 22C | 70.31 |
| 19CD | 25O22 | 24O | 76.60 | 19OE1 | 25O22 | 22O | 73.26 |
| 19OE1 | 25O22 | 162ND1 | 57.54 | 19OE1 | 25O22 | 25C | 85.88 |
| 19OE1 | 25O22 | 162CE1 | 41.81 | 19OE1 | 25O22 | 22C | 86.38 |
| 19OE1 | 25O22 | 24O | 85.82 | 24CA | 25O22 | 22O | 59.15 |
| 24CA | 25O22 | 25C | 61.20 | 24CA | 25O22 | 26N | 57.49 |
| 24CA | 25O22 | 23N | 58.31 | 24CA | 25O22 | 22C | 57.09 |
| 24CA | 25O22 | 24O | 29.00 | 22O | 25O22 | 23N | 28.99 |
| 22O | 25O22 | 22C | 13.41 | 22O | 25O22 | 24O | 76.18 |
| 162ND1 | 25O22 | 25C | 81.58 | 162ND1 | 25O22 | 26N | 91.32 |
| 162ND1 | 25O22 | 162CE1 | 16.64 | 25C | 25O22 | 26N | 17.25 |
| 25C | 25O22 | 162CE1 | 77.24 | 25C | 25O22 | 24O | 34.98 |
| 26N | 25O22 | 162CE1 | 90.62 | 26N | 25O22 | 24O | 38.49 |
| 23N | 25O22 | 22C | 15.60 | 23N | 25O22 | 24O | 84.97 |
| 22C | 25C22 | 24O | 79.45 | 160O | 25C23 | 160CB | 36.76 |
| 67OH | 25C23 | 67CE1 | 30.78 | 160O | 25C24 | 160CB | 45.57 |
| 160O | 25C24 | 160C | 10.69 | 160O | 25C24 | 160CA | 28.84 |
| 160O | 25C24 | 160N | 35.35 | 160CB | 25C24 | 160C | 34.90 |
| 160CB | 25C24 | 209CD2 | 74.30 | 160CB | 25C24 | 160CA | 18.76 |
| 160CB | 25C24 | 160N | 30.63 | 160C | 25C24 | 209CD2 | 96.30 |
| 160C | 25C24 | 160CA | 18.91 | 160C | 25C24 | 160N | 29.27 |
| 67CE1 | 25C24 | 209CD2 | 57.14 | 67CE1 | 25C24 | 67OH | 30.07 |
| 209CD2 | 25C24 | 160CA | 90.67 | 209CD2 | 25C24 | 67OH | 85.98 |
| 160CA | 25C24 | 160N | 17.56 | 160O | 25C25 | 160C | 5.82 |
| 160O | 25C25 | 160CB | 36.39 | 160C | 25C25 | 160CB | 31.49 |

TABLE XII-continued

Table of angles between atoms of the inhibitor and protein
for all protein atoms within 5 Ångstroms of the inhibitor
bis-(Cbz-leucinyl)-1,3-diamino-propan-2-one

| Atom 1 | Atom 2 | Atom 3 | Angle | Atom 1 | Atom 2 | Atom 3 | Angle |
|---|---|---|---|---|---|---|---|
| 67CE1 | 25C25 | 67OH | 30.77 | 67CE1 | 25C25 | 67CZ | 16.04 |
| 67OH | 25C25 | 67CZ | 16.48 | 67OH | 25C26 | 67CE1 | 31.37 |
| 67OH | 25C26 | 67CZ | 16.61 | 67CE1 | 25C26 | 67CZ | 17.15 |
| 67OH | 25C27 | 67CZ | 14.42 | 67OH | 25C27 | 67CE1 | 29.64 |
| 67CZ | 25C27 | 67CE1 | 16.82 | 67CE1 | 25C27 | 160O | 94.55 |
| 67OH | 25C28 | 67CE1 | 29.88 | 67OH | 25C28 | 67CZ | 13.63 |
| 67CE1 | 25C28 | 67CZ | 16.55 | 275OH2 | 25O30 | 161CA | 92.49 |
| 160O | 25O30 | 161CA | 34.81 | 160O | 25C31 | 161CA | 41.59 |
| 160O | 25C31 | 161O | 73.41 | 160O | 25C31 | 161C | 57.25 |
| 160O | 25C31 | 160C | 11.02 | 160O | 25C31 | 161N | 26.54 |
| 160O | 25C31 | 161CB | 50.31 | 161CA | 25C31 | 161O | 34.32 |
| 161CA | 25C31 | 161C | 20.25 | 161CA | 25C31 | 160C | 31.39 |
| 161CA | 25C31 | 161N | 15.77 | 161CA | 25C31 | 161CB | 16.64 |
| 161O | 25C31 | 275OH2 | 83.79 | 161O | 25C31 | 161C | 16.21 |
| 161O | 25C31 | 160C | 62.41 | 161O | 25C31 | 161N | 47.12 |
| 161O | 25C31 | 161CB | 38.54 | 275OH2 | 25C31 | 161C | 97.89 |
| 275OH2 | 25C31 | 161CB | 91.47 | 161C | 25C31 | 160C | 46.24 |
| 161C | 25C31 | 161N | 31.16 | 161C | 25C31 | 161CB | 30.39 |
| 160C | 25C31 | 161N | 15.86 | 160C | 25C31 | 161CB | 42.23 |
| 161N | 25C31 | 161CB | 29.11 | 160O | 25O32 | 161CA | 58.97 |
| 160O | 25O32 | 161C | 79.84 | 160O | 25O32 | 160C | 17.38 |
| 160O | 25O32 | 161N | 38.10 | 160O | 25O32 | 161CB | 67.22 |
| 160O | 25O32 | 162N | 74.42 | 160O | 25O32 | 160CA | 13.85 |
| 161CA | 25O32 | 161O | 45.01 | 161CA | 25O32 | 161C | 27.02 |
| 161CA | 25O32 | 160C | 43.17 | 161CA | 25O32 | 161N | 22.39 |
| 161CA | 25O32 | 161CB | 19.73 | 161CA | 25O32 | 162N | 31.22 |
| 161CA | 25O32 | 160CA | 49.48 | 161O | 25O32 | 161C | 21.40 |
| 161O | 25O32 | 160C | 83.84 | 161O | 25O32 | 161N | 63.21 |
| 161O | 25O32 | 161CB | 49.30 | 161O | 25O32 | 162N | 29.81 |
| 161O | 25O32 | 160CA | 88.75 | 161O | 25O32 | 275OH2 | 81.22 |
| 161C | 25O32 | 160C | 62.49 | 161C | 25O32 | 161N | 42.18 |
| 161C | 25O32 | 161CB | 39.00 | 161C | 25O32 | 162N | 12.22 |
| 161C | 25O32 | 160CA | 67.34 | 160C | 25O32 | 161N | 21.25 |
| 160C | 25O32 | 161CB | 55.00 | 160C | 25O32 | 162N | 57.22 |
| 160C | 25O32 | 160CA | 6.68 | 161N | 25O32 | 161CB | 37.70 |
| 161N | 25O32 | 162N | 39.25 | 161N | 25O32 | 160CA | 27.25 |
| 161CB | 25O32 | 162N | 47.45 | 161CB | 25O32 | 160CA | 61.67 |
| 161CB | 25O32 | 275OH2 | 93.88 | 162N | 25O32 | 160CA | 61.00 |
| 161O | 25C33 | 161C | 15.17 | 161O | 25C33 | 275OH2 | 81.48 |
| 161O | 25C33 | 161CA | 29.19 | 66O | 25C33 | 66N | 37.60 |
| 66O | 25C33 | 65CA | 66.72 | 161C | 25C33 | 275OH2 | 91.71 |
| 161C | 25C33 | 161CA | 18.22 | 66N | 25C33 | 275OH2 | 84.36 |
| 66N | 25C33 | 65CA | 29.78 | 275OH2 | 25C33 | 161CA | 86.95 |
| 275OH2 | 25C33 | 65CA | 56.91 | 66O | 25C34 | 66C | 9.95 |
| 66O | 25C34 | 66N | 42.43 | 66O | 25C34 | 26CB | 47.74 |
| 66O | 25C34 | 66CA | 25.52 | 66O | 25C34 | 67N | 13.89 |
| 66O | 25C34 | 26CG | 42.21 | 66O | 25C34 | 163CB | 91.47 |
| 66C | 25C34 | 66N | 36.15 | 66C | 25C34 | 26CB | 56.11 |
| 66C | 25C34 | 66CA | 18.24 | 66C | 25C34 | 67N | 11.90 |
| 66C | 25C34 | 26CG | 48.09 | 66N | 25C34 | 26CB | 65.07 |
| 66N | 25C34 | 66CA | 17.98 | 66N | 25C34 | 67N | 47.31 |
| 66N | 25C34 | 26CG | 48.82 | 26CB | 25C34 | 66CA | 60.10 |
| 26CB | 25C34 | 67N | 60.76 | 26CB | 25C34 | 26CG | 17.03 |
| 26CB | 25C34 | 163CB | 52.12 | 66CA | 25C34 | 67N | 29.36 |
| 66CA | 25C34 | 26CG | 46.86 | 161O | 25C34 | 163CB | 78.29 |
| 67N | 25C34 | 26CG | 56.10 | 67N | 25C34 | 163CB | 99.58 |
| 26CG | 25C34 | 163CB | 68.12 | 66O | 25C35 | 163CB | 89.09 |
| 66O | 25C35 | 66C | 7.53 | 66O | 25C35 | 67CD1 | 63.13 |
| 66O | 25C35 | 68SD | 68.36 | 66O | 25C35 | 26CB | 39.72 |
| 209CD2 | 25C35 | 134CB | 51.38 | 209CD2 | 25C35 | 67CD1 | 51.16 |
| 209CD2 | 25C35 | 68SD | 69.83 | 209CD2 | 25C35 | 160O | 84.17 |
| 134CB | 25C35 | 163CB | 64.65 | 134CB | 25C35 | 163N | 61.10 |
| 134CB | 25C35 | 68SD | 66.71 | 134CB | 25C35 | 160O | 74.73 |
| 134CB | 25C35 | 161O | 92.07 | 163CB | 25C35 | 66C | 96.13 |
| 163CB | 25C35 | 163N | 30.24 | 163CB | 25C35 | 68SD | 45.97 |
| 163CB | 25C35 | 26CB | 50.88 | 163CB | 25C35 | 161O | 80.11 |
| 66C | 25C35 | 67CD1 | 56.50 | 66C | 25C35 | 68SD | 71.94 |
| 66C | 25C35 | 26CB | 47.21 | 67CD1 | 25C35 | 68SD | 80.40 |
| 67CD1 | 25C35 | 26CB | 97.36 | 163N | 25C35 | 68SD | 74.50 |
| 163N | 25C35 | 160O | 89.86 | 163N | 25C35 | 26CB | 73.24 |
| 163N | 25C35 | 161O | 52.41 | 68SD | 25C35 | 26CB | 52.35 |
| 160O | 25C35 | 161O | 56.45 | 26CB | 25C35 | 161O | 98.49 |
| 161C | 25C36 | 161O | 18.57 | 161C | 25C36 | 162N | 20.01 |

TABLE XII-continued

Table of angles between atoms of the inhibitor and protein
for all protein atoms within 5 Ångstroms of the inhibitor
bis-(Cbz-leucinyl)-1,3-diamino-propan-2-one

| Atom 1 | Atom 2 | Atom 3 | Angle | Atom 1 | Atom 2 | Atom 3 | Angle |
|---|---|---|---|---|---|---|---|
| 161C | 25C36 | 160O | 62.57 | 161C | 25C36 | 163N | 67.45 |
| 161C | 25C36 | 161CA | 21.83 | 161C | 25C36 | 162C | 54.00 |
| 161C | 25C36 | 160C | 53.82 | 161C | 25C36 | 161N | 36.26 |
| 161C | 25C36 | 162CA | 34.07 | 161C | 25C36 | 163CA | 85.21 |
| 161C | 25C36 | 163CB | 99.05 | 161C | 25C36 | 162O | 59.74 |
| 161C | 25C36 | 160CB | 80.93 | 161C | 25C36 | 134CA | 96.31 |
| 161O | 25C36 | 162N | 33.64 | 161O | 25C36 | 160O | 74.48 |
| 161O | 25C36 | 163N | 66.90 | 161O | 25C36 | 161CA | 34.96 |
| 161O | 25C36 | 162C | 59.06 | 161O | 25C36 | 160C | 69.44 |
| 161O | 25C36 | 161N | 53.14 | 161O | 25C36 | 162CA | 38.64 |
| 161O | 25C36 | 163CA | 85.32 | 161O | 25C36 | 163CB | 94.16 |
| 161O | 25C36 | 162O | 69.06 | 161O | 25C36 | 160CB | 98.55 |
| 162N | 25C36 | 134CB | 89.78 | 162N | 25C36 | 160O | 71.09 |
| 162N | 25C36 | 163N | 52.42 | 162N | 25C36 | 161CA | 35.49 |
| 162N | 25C36 | 162C | 36.12 | 162N | 25C36 | 160C | 57.50 |
| 162N | 25C36 | 161N | 39.78 | 162N | 25C36 | 162CA | 19.47 |
| 162N | 25C36 | 163CA | 68.57 | 162N | 25C36 | 163CB | 85.10 |
| 162N | 25C36 | 162O | 39.89 | 162N | 25C36 | 160CB | 76.82 |
| 162N | 25C36 | 134CA | 77.09 | 134CB | 25C36 | 160O | 94.70 |
| 134CB | 25C36 | 163N | 73.72 | 134CB | 25C36 | 162C | 70.42 |
| 134CB | 25C36 | 160C | 84.32 | 134CB | 25C36 | 161N | 89.08 |
| 134CB | 25C36 | 162CA | 87.63 | 134CB | 25C36 | 163CA | 61.39 |
| 134CB | 25C36 | 163CB | 69.69 | 134CB | 25C36 | 162O | 57.00 |
| 134CB | 25C36 | 209CD2 | 50.87 | 134CB | 25C36 | 160CB | 57.37 |
| 134CB | 25C36 | 134CA | 14.58 | 160O | 25C36 | 161CA | 40.90 |
| 160O | 25C36 | 160C | 17.14 | 160O | 25C36 | 161N | 31.70 |
| 160O | 25C36 | 162CA | 90.56 | 160O | 25C36 | 162O | 96.89 |
| 160O | 25C36 | 209CD2 | 91.01 | 160O | 25C36 | 160CB | 37.47 |
| 160O | 25C36 | 134CA | 97.11 | 163N | 25C36 | 161CA | 87.43 |
| 163N | 25C36 | 162C | 18.84 | 163N | 25C36 | 161N | 90.13 |
| 163N | 25C36 | 162CA | 33.77 | 163N | 25C36 | 163CA | 18.45 |
| 163N | 25C36 | 163CB | 32.69 | 163N | 25C36 | 162O | 29.16 |
| 163N | 25C36 | 134CA | 60.25 | 161CA | 25C36 | 162C | 71.59 |
| 161CA | 25C36 | 160C | 34.60 | 161CA | 25C36 | 161N | 20.18 |
| 161CA | 25C36 | 162CA | 53.69 | 161CA | 25C36 | 162O | 73.10 |
| 161CA | 25C36 | 160CB | 64.88 | 161CA | 25C36 | 134CA | 99.89 |
| 162C | 25C36 | 160C | 86.67 | 162C | 25C36 | 161N | 71.72 |
| 162C | 25C36 | 162CA | 20.71 | 162C | 25C36 | 163CA | 32.55 |
| 162C | 25C36 | 163CB | 50.28 | 162C | 25C36 | 162O | 14.79 |
| 162C | 25C36 | 160CB | 91.85 | 162C | 25C36 | 134CA | 55.85 |
| 160C | 25C36 | 161N | 18.17 | 160C | 25C36 | 162CA | 76.54 |
| 160C | 25C36 | 162O | 79.80 | 160C | 25C36 | 209CD2 | 94.97 |
| 160C | 25C36 | 160CB | 31.31 | 160C | 25C36 | 134CA | 83.64 |
| 161N | 25C36 | 162CA | 59.12 | 161N | 25C36 | 162O | 67.84 |
| 161N | 25C36 | 160CB | 45.47 | 161N | 25C36 | 134CA | 83.93 |
| 162CA | 25C36 | 163CA | 51.16 | 162CA | 25C36 | 163CB | 66.24 |
| 162CA | 25C36 | 162O | 30.96 | 162CA | 25C36 | 160CB | 91.92 |
| 162CA | 25C36 | 134CA | 73.28 | 163CA | 25C36 | 163CB | 19.41 |
| 163CA | 25C36 | 162O | 35.58 | 163CA | 25C36 | 134CA | 50.10 |
| 163CA | 25C36 | 66O | 93.58 | 163CB | 25C36 | 162O | 54.97 |
| 163CB | 25C36 | 209CD2 | 96.16 | 163CB | 25C36 | 134CA | 62.02 |
| 163CB | 25C36 | 66O | 74.19 | 162O | 25C36 | 160CB | 79.17 |
| 162O | 25C36 | 134CA | 42.49 | 209CD2 | 25C36 | 160CB | 65.91 |
| 209CD2 | 25C36 | 134CA | 65.34 | 209CD2 | 25C36 | 66O | 80.01 |
| 160CB | 25C36 | 134CA | 61.85 | 209CD2 | 25C37 | 67CD1 | 67.58 |
| 209CD2 | 25C37 | 67CE1 | 72.61 | 209CD2 | 25C37 | 67CG | 78.13 |
| 209CD2 | 25C37 | 160O | 97.02 | 209CD2 | 25C37 | 67CZ | 85.11 |
| 209CD2 | 25C37 | 134CB | 51.48 | 209CD2 | 25C37 | 67CA | 84.67 |
| 209CD2 | 25C37 | 209CG | 2.50 | 67CD1 | 25C37 | 67CE1 | 21.97 |
| 67CD1 | 25C37 | 66O | 73.49 | 67CD1 | 25C37 | 67CG | 14.24 |
| 67CD1 | 25C37 | 67CZ | 29.56 | 67CD1 | 25C37 | 66C | 63.11 |
| 67CD1 | 25C37 | 67CA | 43.36 | 67CD1 | 25C37 | 209CG | 66.09 |
| 67CE1 | 25C37 | 66O | 88.74 | 67CE1 | 25C37 | 67CG | 32.18 |
| 67CE1 | 25C37 | 67CZ | 12.63 | 67CE1 | 25C37 | 66C | 77.14 |
| 67CE1 | 25C37 | 67CA | 63.67 | 67CE1 | 25C37 | 209CG | 72.01 |
| 66O | 25C37 | 67CG | 59.39 | 66O | 25C37 | 67CZ | 84.53 |
| 66O | 25C37 | 66C | 11.85 | 66O | 25C37 | 67CA | 35.08 |
| 67CG | 25C37 | 67CZ | 34.96 | 67CG | 25C37 | 66C | 48.87 |
| 67CG | 25C37 | 67CA | 31.56 | 67CG | 25C37 | 209CG | 76.30 |
| 160O | 25C37 | 134CB | 73.49 | 160O | 25C37 | 209CG | 99.48 |
| 67CZ | 25C37 | 66C | 72.68 | 67CZ | 25C37 | 67CA | 65.61 |
| 67CZ | 25C37 | 209CG | 84.57 | 66C | 25C37 | 67CA | 29.50 |
| 134CB | 25C37 | 209CG | 52.27 | 67CA | 25C37 | 209CG | 82.22 |

TABLE XII-continued

Table of angles between atoms of the inhibitor and protein
for all protein atoms within 5 Ångstroms of the inhibitor
bis-(Cbz-leucinyl)-1,3-diamino-propan-2-one

| Atom 1 | Atom 2 | Atom 3 | Angle | Atom 1 | Atom 2 | Atom 3 | Angle |
|---|---|---|---|---|---|---|---|
| 65CA | 25C38 | 66N | 35.46 | 65CA | 25C38 | 66O | 74.46 |
| 65CA | 25C38 | 26CD1 | 58.84 | 65CA | 25C38 | 275OH2 | 67.35 |
| 65CA | 25C38 | 65C | 19.07 | 65CA | 25C38 | 23O | 55.20 |
| 65CA | 25C38 | 26CB | 86.32 | 65CA | 25C38 | 26CG | 69.11 |
| 65CA | 25C38 | 64O | 33.75 | 65CA | 25C38 | 65N | 11.94 |
| 161O | 25C38 | 25SG | 65.22 | 161O | 25C38 | 275OH2 | 84.21 |
| 161O | 25C38 | 161C | 10.24 | 66N | 25C38 | 66O | 39.10 |
| 66N | 25C38 | 26CD1 | 49.39 | 66N | 25C38 | 275OH2 | 95.80 |
| 66N | 25C38 | 65C | 16.72 | 66N | 25C38 | 23O | 75.10 |
| 66N | 25C38 | 26CB | 62.01 | 66N | 25C38 | 26CG | 49.74 |
| 66N | 25C38 | 64O | 67.28 | 66N | 25C38 | 65N | 46.94 |
| 66O | 25C38 | 26CD1 | 55.62 | 66O | 25C38 | 65C | 55.45 |
| 66O | 25C38 | 23O | 98.46 | 66O | 25C38 | 26CB | 41.40 |
| 66O | 25C38 | 26CG | 43.32 | 66O | 25C38 | 65N | 85.60 |
| 26CD1 | 25C38 | 25SG | 77.15 | 26CD1 | 25C38 | 65C | 49.46 |
| 26CD1 | 25C38 | 23O | 44.41 | 26CD1 | 25C38 | 26CB | 32.56 |
| 26CD1 | 25C38 | 26CG | 15.85 | 26CD1 | 25C38 | 64O | 87.10 |
| 26CD1 | 25C38 | 65N | 61.51 | 25SG | 25C38 | 23O | 70.52 |
| 25SG | 25C38 | 26CB | 68.80 | 25SG | 25C38 | 26CG | 76.92 |
| 25SG | 25C38 | 161C | 68.97 | 275OH2 | 25C38 | 65C | 83.85 |
| 275OH2 | 25C38 | 23O | 87.47 | 275OH2 | 25C38 | 64O | 35.10 |
| 275OH2 | 25C38 | 161C | 89.52 | 275OH2 | 25C38 | 65N | 61.32 |
| 65C | 25C38 | 23O | 62.91 | 65C | 25C38 | 26CB | 71.13 |
| 65C | 25C38 | 26CG | 55.52 | 65C | 25C38 | 64O | 52.20 |
| 65C | 25C38 | 65N | 30.26 | 23O | 25C38 | 26CB | 73.10 |
| 23O | 25C38 | 26CG | 59.68 | 23O | 25C38 | 64O | 61.47 |
| 23O | 25C38 | 65N | 47.46 | 26CB | 25C38 | 26CG | 17.91 |
| 26CB | 25C38 | 65N | 91.96 | 26CG | 25C38 | 65N | 74.13 |
| 64O | 25C38 | 65N | 26.26 | 65CA | 25O39 | 66N | 45.40 |
| 65CA | 25O39 | 65C | 23.65 | 65CA | 25O39 | 275OH2 | 89.27 |
| 65CA | 25O39 | 64O | 46.55 | 65CA | 25O39 | 65N | 17.11 |
| 65CA | 25O39 | 26CD1 | 69.73 | 65CA | 25O39 | 23O | 68.59 |
| 65CA | 25O39 | 64C | 33.21 | 65CA | 25O39 | 66O | 84.46 |
| 65CA | 25O39 | 66CA | 54.04 | 65CA | 25O39 | 65O | 20.83 |
| 65CA | 25O39 | 26CG | 77.43 | 65CA | 25O39 | 26NE1 | 55.20 |
| 65CA | 25O39 | 66C | 71.68 | 66N | 25O39 | 65C | 22.01 |
| 66N | 25O39 | 64O | 89.22 | 66N | 25O39 | 65N | 62.07 |
| 66N | 25O39 | 26CD1 | 54.96 | 66N | 25O39 | 23O | 90.19 |
| 66N | 25O39 | 64C | 78.37 | 66N | 25O39 | 66O | 39.27 |
| 66N | 25O39 | 66CA | 8.76 | 66N | 25O39 | 65O | 25.54 |
| 66N | 25O39 | 26CG | 51.40 | 66N | 25O39 | 26NE1 | 49.00 |
| 66N | 25O39 | 66C | 26.33 | 65C | 25O39 | 64O | 69.28 |
| 65C | 25O39 | 65N | 40.08 | 65C | 25O39 | 26CD1 | 57.43 |
| 65C | 25O39 | 23O | 76.91 | 65C | 25O39 | 64C | 56.85 |
| 65C | 25O39 | 66O | 60.83 | 65C | 25O39 | 66CA | 30.50 |
| 65C | 25O39 | 65O | 3.97 | 65C | 25O39 | 26CG | 60.36 |
| 65C | 25O39 | 26NE1 | 45.73 | 65C | 25O39 | 66C | 48.13 |
| 275OH2 | 25O39 | 64O | 44.70 | 275OH2 | 25O39 | 65N | 79.36 |
| 275OH2 | 25O39 | 64C | 61.39 | 275OH2 | 25O39 | 161O | 78.76 |
| 64O | 25O39 | 65N | 34.67 | 64O | 25O39 | 23O | 76.69 |
| 64O | 25O39 | 64C | 16.94 | 64O | 25O39 | 66CA | 97.89 |
| 64O | 25O39 | 65O | 67.08 | 64O | 25O39 | 26NE1 | 93.96 |
| 65N | 25O39 | 26CD1 | 75.00 | 65N | 25O39 | 23O | 58.94 |
| 65N | 25O39 | 64C | 18.53 | 65N | 25O39 | 66CA | 70.56 |
| 65N | 25O39 | 65O | 36.76 | 65N | 25O39 | 26CG | 85.84 |
| 65N | 25O39 | 26NE1 | 60.15 | 65N | 25O39 | 66C | 88.15 |
| 26CD1 | 25O39 | 23O | 49.08 | 26CD1 | 25O39 | 64C | 91.52 |
| 26CD1 | 25O39 | 66O | 56.07 | 26CD1 | 25O39 | 66CA | 53.07 |
| 26CD1 | 25O39 | 65O | 56.44 | 26CD1 | 25O39 | 26CG | 14.63 |
| 26CD1 | 25O39 | 26NE1 | 14.91 | 26CD1 | 25O39 | 66C | 54.99 |
| 23O | 25O39 | 64C | 64.20 | 23O | 25O39 | 66CA | 93.33 |
| 23O | 25O39 | 65O | 73.30 | 23O | 25O39 | 26CG | 63.07 |
| 23O | 25O39 | 26NE1 | 44.74 | 23O | 25O39 | 66CA | 87.09 |
| 64C | 25O39 | 65O | 53.98 | 64C | 25O39 | 26NE1 | 77.02 |
| 66O | 25O39 | 66CA | 30.52 | 66O | 25O39 | 65O | 63.93 |
| 66O | 25O39 | 26CG | 42.81 | 66O | 25O39 | 26NE1 | 62.05 |
| 66O | 25O39 | 66C | 13.06 | 66CA | 25O39 | 65O | 33.85 |
| 66CA | 25O39 | 26CG | 47.00 | 66CA | 25O39 | 26NE1 | 49.86 |
| 66CA | 25O39 | 66C | 17.64 | 65O | 25O39 | 26CG | 60.51 |
| 65O | 25O39 | 26NE1 | 44.00 | 65O | 25O39 | 66C | 51.39 |
| 26CG | 25O39 | 26NE1 | 26.93 | 26CG | 25O39 | 66C | 44.17 |
| 26NE1 | 25O39 | 66C | 57.23 | 25SG | 25N40 | 161O | 83.77 |
| 25SG | 25N40 | 26CD1 | 96.23 | 25SG | 25N40 | 26N | 54.32 |

TABLE XII-continued

Table of angles between atoms of the inhibitor and protein for all protein atoms within 5 Ångstroms of the inhibitor bis-(Cbz-leucinyl)-1,3-diamino-propan-2-one

| Atom 1 | Atom 2 | Atom 3 | Angle | Atom 1 | Atom 2 | Atom 3 | Angle |
|---|---|---|---|---|---|---|---|
| 25SG | 25N40 | 23O | 88.72 | 25SG | 25N40 | 26CB | 85.40 |
| 25SG | 25N40 | 163N | 48.48 | 25SG | 25N40 | 25CB | 12.78 |
| 25SG | 25N40 | 2GCG | 93.55 | 25SG | 25N40 | 161C | 83.44 |
| 25SG | 25N40 | 25N | 43.46 | 25SG | 25N40 | 162CA | 55.83 |
| 25SG | 25N40 | 26CA | 67.26 | 25SG | 25N40 | 23C | 77.46 |
| 25SG | 25N40 | 163CB | 56.68 | 25SG | 25N40 | 25CA | 30.38 |
| 25SG | 25N40 | 25C | 40.47 | 161O | 25N40 | 163N | 62.30 |
| 161O | 25N40 | 25CB | 96.42 | 161O | 25N40 | 161C | 9.97 |
| 161O | 25N40 | 162CA | 34.15 | 161O | 25N40 | 163CB | 90.03 |
| 26CD1 | 25N40 | 26N | 45.97 | 26CD1 | 25N40 | 23O | 47.29 |
| 26CD1 | 25N40 | 26CB | 34.59 | 26CD1 | 25N40 | 25CB | 83.86 |
| 26CD1 | 25N40 | 26CG | 16.42 | 26CD1 | 25N40 | 25N | 56.97 |
| 26CD1 | 25N40 | 65CA | 53.52 | 26CD1 | 25N40 | 66O | 51.90 |
| 26CD1 | 25N40 | 26CA | 42.89 | 26CD1 | 25N40 | 66N | 44.25 |
| 26CD1 | 25N40 | 23C | 56.28 | 26CD1 | 25N40 | 163CB | 84.60 |
| 26CD1 | 25N40 | 25CA | 66.03 | 26CD1 | 25N40 | 25C | 58.27 |
| 26N | 25N40 | 23O | 70.59 | 26N | 25N40 | 26CB | 33.25 |
| 26N | 25N40 | 163N | 70.68 | 26N | 25N40 | 25CB | 44.21 |
| 26N | 25N40 | 26CG | 39.40 | 26N | 25N40 | 25N | 34.54 |
| 26N | 25N40 | 65CA | 99.36 | 26N | 25N40 | 66O | 73.26 |
| 26N | 25N40 | 162CA | 97.09 | 26N | 25N40 | 26CA | 16.76 |
| 26N | 25N40 | 66N | 85.93 | 26N | 25N40 | 23C | 69.38 |
| 26N | 25N40 | 163CB | 48.13 | 26N | 25N40 | 25CA | 29.29 |
| 26N | 25N40 | 25C | 13.85 | 23O | 25N40 | 26CB | 79.60 |
| 23O | 25N40 | 25CB | 77.95 | 23O | 25N40 | 26CG | 63.18 |
| 23O | 25N40 | 25N | 49.38 | 23O | 25N40 | 65CA | 52.49 |
| 23O | 25N40 | 66O | 94.81 | 23O | 25N40 | 26CA | 79.46 |
| 23O | 25N40 | 66N | 70.07 | 23O | 25N40 | 23C | 13.03 |
| 23O | 25N40 | 25CA | 66.29 | 23O | 25N40 | 25C | 73.80 |
| 26CB | 25N40 | 163N | 81.30 | 26CB | 25N40 | 25CB | 76.86 |
| 26CB | 25N40 | 26CG | 18.52 | 26CB | 25N40 | 25N | 64.46 |
| 26CB | 25N40 | 65CA | 80.54 | 26CB | 25N40 | 66O | 40.01 |
| 26CB | 25N40 | 26CA | 18.15 | 26CB | 25N40 | 66N | 57.97 |
| 26CB | 25N40 | 23C | 85.39 | 26CB | 25N40 | 163CB | 51.83 |
| 26CB | 25N40 | 25CA | 62.52 | 26CB | 25N40 | 25C | 46.36 |
| 163N | 25N40 | 25CB | 57.29 | 163N | 25N40 | 26CG | 99.16 |
| 163N | 25N40 | 161C | 55.09 | 163N | 25N40 | 25N | 84.86 |
| 163N | 25N40 | 66O | 96.57 | 163N | 25N40 | 162CA | 29.80 |
| 163N | 25N40 | 26CA | 70.11 | 163N | 25N40 | 163CB | 29.52 |
| 163N | 25N40 | 25CA | 67.98 | 163N | 25N40 | 25C | 62.99 |
| 25CB | 25N40 | 26CG | 82.58 | 25CB | 25N40 | 161C | 96.21 |
| 25CB | 25N40 | 25N | 30.92 | 25CB | 25N40 | 162CA | 68.31 |
| 25CB | 25N40 | 26CA | 58.91 | 25CB | 25N40 | 23C | 67.68 |
| 25CB | 25N40 | 163CB | 58.44 | 25CB | 25N40 | 25CA | 17.83 |
| 25CB | 25N40 | 25C | 30.57 | 26CG | 25N40 | 25N | 61.46 |
| 26CG | 25N40 | 65CA | 64.22 | 26CG | 25N40 | 66O | 41.69 |
| 26CG | 25N40 | 26CA | 30.63 | 26CG | 25N40 | 66N | 46.53 |
| 26CG | 25N40 | 23C | 71.01 | 26CG | 25N40 | 163CB | 69.91 |
| 26CG | 25N40 | 25CA | 65.57 | 26CG | 25N40 | 25C | 53.15 |
| 161C | 25N40 | 162CA | 29.49 | 161C | 25N40 | 163CB | 81.51 |
| 25N | 25N40 | 65CA | 97.53 | 25N | 25N40 | 162CA | 99.23 |
| 25N | 25N40 | 26CA | 50.89 | 25N | 25N40 | 23C | 41.97 |
| 25N | 25N40 | 163CB | 74.65 | 25N | 25N40 | 25CA | 16.92 |
| 25N | 25N40 | 25C | 28.88 | 65CA | 25N40 | 66O | 62.01 |
| 65CA | 25N40 | 26CA | 94.78 | 65CA | 25N40 | 66N | 28.94 |
| 65CA | 25N40 | 23C | 64.73 | 66O | 25N40 | 26CA | 57.46 |
| 66O | 25N40 | 66N | 33.09 | 66O | 25N40 | 163CB | 72.28 |
| 66O | 25N40 | 25C | 86.11 | 162CA | 25N40 | 26CA | 99.40 |
| 162CA | 25N40 | 163CB | 59.22 | 162CA | 25N40 | 25CA | 84.50 |
| 162CA | 25N40 | 25C | 86.43 | 26CA | 25N40 | 66N | 75.24 |
| 26CA | 25N40 | 23C | 81.32 | 26CA | 25N40 | 163CB | 42.44 |
| 26CA | 25N40 | 25CA | 45.63 | 26CA | 25N40 | 25C | 28.66 |
| 66N | 25N40 | 23C | 83.06 | 66N | 25N40 | 25C | 99.63 |
| 23C | 25N40 | 25CA | 58.57 | 23C | 25N40 | 25C | 69.36 |
| 163CB | 25N40 | 25CA | 59.45 | 163CB | 25N40 | 25C | 46.39 |
| 25CA | 25N40 | 25C | 17.68 | 25SG | 25C41 | 25N | 62.70 |
| 25SG | 25C41 | 26N | 62.65 | 25SG | 25C41 | 25CB | 23.96 |
| 25SG | 25C41 | 25CA | 43.98 | 25SG | 25C41 | 24N | 98.96 |
| 25SG | 25C41 | 24C | 76.68 | 25SG | 25C41 | 25C | 48.95 |
| 25SG | 25C41 | 26CB | 86.53 | 25SG | 25C41 | 24CA | 95.08 |
| 25SG | 25C41 | 161O | 70.41 | 25SG | 25C41 | 26CA | 70.68 |
| 23O | 25C41 | 25N | 69.35 | 23O | 25C41 | 23C | 19.72 |
| 23O | 25C41 | 26CD1 | 58.41 | 23O | 25C41 | 26N | 90.56 |

TABLE XII-continued

Table of angles between atoms of the inhibitor and protein for all protein atoms within 5 Ångstroms of the inhibitor bis-(Cbz-leucinyl)-1,3-diamino-propan-2-one

| Atom 1 | Atom 2 | Atom 3 | Angle | Atom 1 | Atom 2 | Atom 3 | Angle |
|---|---|---|---|---|---|---|---|
| 23O | 25C41 | 25CA | 89.48 | 23O | 25C41 | 23CA | 34.94 |
| 23O | 25C41 | 24N | 31.63 | 23O | 25C41 | 24C | 57.25 |
| 23O | 25C41 | 25C | 94.72 | 23O | 25C41 | 26CB | 91.35 |
| 23O | 25C41 | 26CG | 73.21 | 23O | 25C41 | 24CA | 37.60 |
| 23O | 25C41 | 65CA | 57.07 | 23O | 25C41 | 26NE1 | 46.32 |
| 23O | 25C41 | 26CA | 94.04 | 25N | 25C41 | 23C | 58.58 |
| 25N | 25C41 | 26CD1 | 71.53 | 25N | 25C41 | 26N | 42.84 |
| 25N | 25C41 | 25CB | 39.04 | 25N | 25C41 | 25CA | 20.25 |
| 25N | 25C41 | 23CA | 71.04 | 25N | 25C41 | 24N | 41.24 |
| 25N | 25C41 | 24C | 14.76 | 25N | 25C41 | 25C | 33.26 |
| 25N | 25C41 | 26CB | 72.91 | 25N | 25C41 | 26CG | 71.59 |
| 25N | 25C41 | 24CA | 32.43 | 25N | 25C41 | 26NE1 | 71.77 |
| 25N | 25C41 | 26CA | 57.10 | 23C | 25C41 | 26CD1 | 72.85 |
| 23C | 25C41 | 26N | 90.94 | 23C | 25C41 | 25CB | 91.53 |
| 23C | 25C41 | 25CA | 78.46 | 23C | 25C41 | 23CA | 20.98 |
| 23C | 25C41 | 24N | 17.34 | 23C | 25C41 | 24C | 50.23 |
| 23C | 25C41 | 25C | 89.47 | 23C | 25C41 | 26CG | 86.15 |
| 23C | 25C41 | 24CA | 32.48 | 23C | 25C41 | 65CA | 75.78 |
| 23C | 25C41 | 26NE1 | 61.91 | 23C | 25C41 | 26CA | 99.05 |
| 26CD1 | 25C41 | 26N | 51.41 | 26CD1 | 25C41 | 25CA | 79.66 |
| 26CD1 | 25C41 | 23CA | 92.59 | 26CD1 | 25C41 | 24N | 70.00 |
| 26CD1 | 25C41 | 24C | 58.88 | 26CD1 | 25C41 | 25C | 66.43 |
| 26CD1 | 25C41 | 26CB | 34.11 | 26CD1 | 25C41 | 26CG | 15.31 |
| 26CD1 | 25C41 | 24CA | 54.83 | 26CD1 | 25C41 | 65CA | 55.19 |
| 26CD1 | 25C41 | 26NE1 | 12.42 | 26CD1 | 25C41 | 26CA | 44.47 |
| 26N | 25C41 | 25CB | 51.65 | 26N | 25C41 | 25CA | 35.77 |
| 26N | 25C41 | 24N | 75.80 | 26N | 25C41 | 24C | 42.85 |
| 26N | 25C41 | 25C | 16.65 | 26N | 25C41 | 26CB | 33.09 |
| 26N | 25C41 | 26CG | 41.38 | 26N | 25C41 | 24CA | 58.47 |
| 26N | 25C41 | 26NE1 | 60.33 | 26N | 25C41 | 26CA | 14.86 |
| 25CB | 25C41 | 25CA | 22.08 | 25CB | 25C41 | 23CA | 94.98 |
| 25CB | 25C41 | 24N | 75.58 | 25CB | 25C41 | 24C | 53.42 |
| 25CB | 25C41 | 25C | 35.13 | 25CB | 25C41 | 26CB | 82.86 |
| 25CB | 25C41 | 26CG | 92.88 | 25CB | 25C41 | 24CA | 71.25 |
| 25CB | 25C41 | 161O | 93.68 | 25CB | 25C41 | 26CA | 64.25 |
| 25CA | 25C41 | 23CA | 88.69 | 25CA | 25C41 | 24N | 61.20 |
| 25CA | 25C41 | 24C | 32.93 | 25CA | 25C41 | 25C | 20.29 |
| 25CA | 25C41 | 26CB | 68.87 | 25CA | 25C41 | 26CG | 74.42 |
| 25CA | 25C41 | 24CA | 52.13 | 25CA | 25C41 | 26NE1 | 83.73 |
| 25CA | 25C41 | 26CA | 50.39 | 23CA | 25C41 | 24N | 33.53 |
| 23CA | 25C41 | 24C | 66.67 | 23CA | 25C41 | 24CA | 51.61 |
| 23CA | 25C41 | 65CA | 80.98 | 23CA | 25C41 | 26NE1 | 80.92 |
| 24N | 25C41 | 24C | 33.63 | 24N | 25C41 | 25C | 72.54 |
| 24N | 25C41 | 26CB | 93.33 | 24N | 25C41 | 26CG | 80.45 |
| 24N | 25C41 | 24CA | 18.67 | 24N | 25C41 | 65CA | 88.30 |
| 24N | 25C41 | 26NE1 | 61.55 | 24N | 25C41 | 26CA | 85.94 |
| 24C | 25C41 | 25C | 39.29 | 24C | 25C41 | 26CB | 67.28 |
| 24C | 25C41 | 26CG | 61.65 | 24C | 2SC41 | 24CA | 19.66 |
| 24C | 25C41 | 26NE1 | 57.67 | 24C | 25C41 | 26CA | 54.90 |
| 25C | 25C41 | 26CB | 49.26 | 25C | 25C41 | 26CG | 57.75 |
| 25C | 25C41 | 24CA | 58.24 | 25C | 25C41 | 26NE1 | 73.78 |
| 25C | 25C41 | 26CA | 30.51 | 26CB | 25C41 | 26CG | 18.80 |
| 26CB | 25C41 | 24CA | 74.83 | 26CB | 25C41 | 65CA | 78.82 |
| 26CB | 25C41 | 26NE1 | 46.51 | 26CB | 25C41 | 26CA | 18.80 |
| 26CG | 25C41 | 24CA | 63.20 | 26CG | 25C41 | 65CA | 65.01 |
| 26CG | 25C41 | 26NE1 | 27.72 | 26CG | 25C41 | 26CA | 31.31 |
| 24CA | 25C41 | 65CA | 87.25 | 24CA | 25C41 | 26NE1 | 48.94 |
| 24CA | 25C41 | 26CA | 67.55 | 65CA | 25C41 | 26NE1 | 49.22 |
| 65CA | 25C41 | 26CA | 95.86 | 26NE1 | 25C41 | 26CA | 55.54 |
| 275OH2 | 25N42 | 161O | 84.19 | 275OH2 | 25N42 | 66N | 91.61 |
| 275OH2 | 25N42 | 65CA | 62.05 | 275OH2 | 25N42 | 161C | 94.32 |
| 275OH2 | 25N42 | 161CA | 94.57 | 161O | 25N42 | 161C | 13.86 |
| 161O | 25N42 | 160O | 61.38 | 161O | 25N42 | 161CA | 29.35 |
| 66N | 25N42 | 66O | 34.84 | 66N | 25N42 | 65CA | 29.86 |
| 66O | 25N42 | 65CA | 63.11 | 161C | 25N42 | 160O | 47.97 |
| 161C | 25N42 | 161CA | 17.98 | 160O | 25N42 | 161CA | 33.22 |

TABLE XIII

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 184CB | 25C1 | 184O | 38.19 | 184CB | 25C1 | 184CG | 19.52 |
| 184CB | 25C1 | 184CD2 | 33.79 | 184CB | 25C1 | 184CE3 | 43.09 |
| 184CB | 25C1 | 188CD1 | 58.81 | 184O | 25C1 | 184CG | 56.83 |
| 184O | 25C1 | 184CD2 | 71.93 | 184O | 25C1 | 184CE3 | 78.59 |
| 184O | 25C1 | 188CD1 | 69.71 | 184CG | 25C1 | 184CD2 | 17.68 |
| 184CG | 25C1 | 184CE3 | 32.58 | 184CG | 25C1 | 188CD1 | 65.18 |
| 184CD2 | 25C1 | 184CE3 | 17.04 | 184CD2 | 25C1 | 188CD1 | 58.90 |
| 184CE3 | 25C1 | 188CD1 | 45.42 | 184O | 25C2 | 184CB | 44.21 |
| 184O | 25C2 | 18OD1 | 53.44 | 184O | 25C2 | 184C | 13.95 |
| 184O | 25C2 | 184CA | 33.42 | 184O | 25C2 | 184CG | 63.00 |
| 184CB | 25C2 | 18OD1 | 67.91 | 184CB | 25C2 | 184C | 34.94 |
| 184CB | 25C2 | 184CA | 20.32 | 184CB | 25C2 | 184CG | 19.43 |
| 18OD1 | 25C2 | 184C | 45.96 | 18OD1 | 25C2 | 184CA | 48.12 |
| 18OD1 | 25C2 | 184CG | 73.56 | 184C | 25C2 | 184CA | 20.19 |
| 184C | 25C2 | 184CG | 52.12 | 184CA | 25C2 | 184CG | 33.37 |
| 18OD1 | 25C3 | 184CB | 80.07 | 18OD1 | 25C3 | 184O | 59.68 |
| 18OD1 | 25C3 | 184CA | 57.15 | 18OD1 | 25C3 | 184CG | 89.66 |
| 18OD1 | 25C3 | 184C | 51.33 | 18OD1 | 25C3 | 184CD1 | 82.13 |
| 18OD1 | 25C3 | 18CG | 11.24 | 18OD1 | 25C3 | 18ND2 | 27.16 |
| 18OD1 | 25C3 | 20O | 73.60 | 184CB | 25C3 | 184O | 44.39 |
| 184CB | 25C3 | 184CA | 22.92 | 184CB | 25C3 | 184CG | 22.24 |
| 184CB | 25C3 | 184C | 36.34 | 184CB | 25C3 | 184CD1 | 37.05 |
| 184CB | 25C3 | 18CG | 84.56 | 184CB | 25C3 | 18ND2 | 96.50 |
| 184CB | 25C3 | 184CD2 | 33.32 | 184O | 25C3 | 184CA | 36.38 |
| 184O | 25C3 | 184CG | 66.41 | 184O | 25C3 | 184C | 16.67 |
| 184O | 25C3 | 184CD1 | 77.34 | 184O | 25C3 | 18CG | 56.51 |
| 184O | 25C3 | 18ND2 | 60.61 | 184O | 25C3 | 184CD2 | 76.89 |
| 184CA | 25C3 | 184CG | 37.43 | 184CA | 25C3 | 184C | 21.29 |
| 184CA | 25C3 | 184CD1 | 42.36 | 184CA | 25C3 | 18CG | 62.14 |
| 184CA | 25C3 | 18ND2 | 75.37 | 184CA | 25C3 | 184CD2 | 52.39 |
| 184CG | 25C3 | 184C | 56.26 | 184CG | 25C3 | 184CD1 | 18.80 |
| 184CG | 25C3 | 18CG | 97.29 | 184CG | 25C3 | 184CD2 | 15.81 |
| 184CG | 25C3 | 20O | 99.33 | 184C | 25C3 | 184CD1 | 63.60 |
| 184C | 25C3 | 18CG | 51.80 | 184C | 25C3 | 18ND2 | 61.00 |
| 184C | 25C3 | 184CD2 | 69.50 | 184CD1 | 25C3 | 18CG | 91.92 |
| 184CD1 | 25C3 | 184CD2 | 27.91 | 184CD1 | 25C3 | 20O | 80.68 |
| 18CG | 25C3 | 18ND2 | 16.43 | 18CG | 25C3 | 20O | 80.57 |
| 18ND2 | 25C3 | 20O | 85.65 | 184CG | 25C4 | 184CD1 | 22.16 |
| 184CG | 25C4 | 184CB | 23.25 | 184CG | 25C4 | 184NE1 | 33.38 |
| 184CG | 25C4 | 184CD2 | 20.04 | 184CG | 25C4 | 184CA | 36.56 |
| 184CG | 25C4 | 18OD1 | 84.23 | 184CG | 25C4 | 184CE2 | 31.43 |
| 184CG | 25C4 | 184O | 59.49 | 184CG | 25C4 | 184CE3 | 31.14 |
| 184CG | 25C4 | 184C | 50.73 | 184CD1 | 25C4 | 184CB | 40.60 |
| 184CD1 | 25C4 | 184NE1 | 19.22 | 184CD1 | 25C4 | 184CD2 | 33.07 |
| 184CD1 | 25C4 | 184CA | 43.38 | 184CD1 | 25C4 | 18OD1 | 80.63 |
| 184CD1 | 25C4 | 184CE2 | 30.49 | 184CD1 | 25C4 | 20O | 96.73 |
| 184CD1 | 25C4 | 184O | 72.55 | 184CD1 | 25C4 | 184CE3 | 47.65 |
| 184CD1 | 25C4 | 184C | 60.18 | 184CB | 25C4 | 184NE1 | 55.95 |
| 184CB | 25C4 | 184CD2 | 38.71 | 184CB | 25.C4 | 184CA | 20.96 |
| 184CB | 25C4 | 18OD1 | 69.40 | 184CB | 25C4 | 184CE2 | 54.07 |
| 184CB | 25C4 | 184O | 36.44 | 184CB | 25C4 | 184CE3 | 42.67 |
| 184CB | 25C4 | 184C | 29.74 | 184NE1 | 25C4 | 184CD2 | 31.83 |
| 184NE1 | 25C4 | 184CA | 62.30 | 184NE1 | 25C4 | 18OD1 | 97.90 |
| 184NE1 | 25C4 | 184CE2 | 18.20 | 184NE1 | 25C4 | 20O | 93.72 |
| 184NE1 | 25C4 | 184O | 90.55 | 184NE1 | 25C4 | 184CE3 | 45.60 |
| 184NE1 | 25C4 | 184C | 78.96 | 184CD2 | 25C4 | 184CA | 55.86 |
| 184CD2 | 25C4 | 184CE2 | 18.77 | 184CD2 | 25C4 | 184O | 74.24 |
| 184CD2 | 25C4 | 184CE3 | 14.78 | 184CD2 | 25C4 | 184C | 68.30 |
| 184CA | 25C4 | 18OD1 | 49.23 | 184CA | 25C4 | 184CE2 | 67.15 |
| 184CA | 25C4 | 184O | 30.22 | 184CA | 25C4 | 184CE3 | 62.73 |
| 184CA | 25C4 | 184C | 16.85 | 18OD1 | 25C4 | 20O | 73.28 |
| 18OD1 | 25C4 | 184O | 46.75 | 18OD1 | 25C4 | 184C | 42.18 |
| 184CE2 | 25C4 | 184O | 90.51 | 184CE2 | 25C4 | 184CE3 | 29.58 |
| 184CE2 | 25C4 | 184C | 82.12 | 184O | 25C4 | 184CE3 | 73.98 |
| 184O | 25C4 | 184C | 14.33 | 184CE3 | 25C4 | 184C | 71.72 |
| 184CG | 25C5 | 184CD2 | 22.73 | 184CG | 25C5 | 184CD1 | 20.69 |
| 184CG | 25C5 | 184CE2 | 35.01 | 184CG | 25C5 | 184NE1 | 33.46 |
| 184CG | 25C5 | 184CB | 21.39 | 184CG | 25C5 | 184CE3 | 38.46 |
| 184CG | 25C5 | 184CZ2 | 50.35 | 184CG | 25C5 | 184CZ3 | 51.39 |
| 184CG | 25C5 | 184CA | 29.48 | 184CD2 | 25C5 | 184CD1 | 34.47 |
| 184CD2 | 25C5 | 184CE2 | 21.03 | 184CD2 | 25C5 | 184NE1 | 33.32 |
| 184CD2 | 25C5 | 184CB | 39.17 | 184CD2 | 25C5 | 184CE3 | 19.36 |
| 184CD2 | 25C5 | 184CZ2 | 31.82 | 184CD2 | 25C5 | 184CZ3 | 29.20 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 184CD2 | 25C5 | 184CA | 51.36 | 184CD1 | 25C5 | 184CE2 | 33.24 |
| 184CD1 | 25C5 | 184NE1 | 19.76 | 184CD1 | 25C5 | 184CB | 37.53 |
| 184CD1 | 25C5 | 184CE3 | 53.61 | 184CD1 | 25C5 | 184CZ2 | 49.12 |
| 184CD1 | 25C5 | 184CZ3 | 62.53 | 184CD1 | 25C5 | 184CA | 36.61 |
| 184CE2 | 25C5 | 184NE1 | 19.71 | 184CE2 | 25C5 | 184CB | 55.77 |
| 184CE2 | 25C5 | 184CE3 | 34.70 | 184CE2 | 25C5 | 184CZ2 | 16.25 |
| 184CE2 | 25C5 | 184CZ3 | 34.98 | 184CE2 | 25C5 | 184CA | 63.76 |
| 184NE1 | 25C5 | 184CB | 54.14 | 184NE1 | 25C5 | 184CE3 | 51.39 |
| 184NE1 | 25C5 | 184CZ2 | 32.74 | 184NE1 | 25C5 | 184CZ3 | 54.44 |
| 184NE1 | 25C5 | 184CA | 56.07 | 184CB | 25C5 | 184CE3 | 47.44 |
| 184CB | 25C5 | 184CZ2 | 70.15 | 184CB | 25C5 | 184CZ3 | 62.99 |
| 184CB | 25C5 | 184CA | 16.19 | 184CE3 | 25C5 | 184CZ2 | 37.12 |
| 184CE3 | 25C5 | 184CZ3 | 15.81 | 184CE3 | 25C5 | 184CA | 62.73 |
| 184CZ2 | 25C5 | 184CZ3 | 29.69 | 184CZ2 | 25C5 | 184CA | 79.60 |
| 184CZ3 | 25C5 | 184CA | 77.85 | 184CD2 | 25C6 | 184CE3 | 19.98 |
| 184CD2 | 25C6 | 184CG | 20.21 | 184CD2 | 25C6 | 184CB | 36.83 |
| 184CD2 | 25C6 | 184CE2 | 17.00 | 184CD2 | 25C6 | 184CZ3 | 30.72 |
| 184CD2 | 25C6 | 184CD1 | 27.90 | 184CE3 | 25C6 | 184CG | 37.11 |
| 184CE3 | 25C6 | 184CB | 46.74 | 184CE3 | 25C6 | 184CE2 | 31.55 |
| 184CE3 | 25C6 | 184CZ3 | 16.21 | 184CE3 | 25C6 | 184CD1 | 47.70 |
| 184CG | 25C6 | 184CB | 20.58 | 184CG | 25C6 | 184CE2 | 29.67 |
| 184CG | 25C6 | 184CZ3 | 50.48 | 184CG | 25C6 | 184CD1 | 15.71 |
| 184CB | 25C6 | 184CE2 | 49.78 | 184CB | 25C6 | 184CZ3 | 62.65 |
| 184CB | 25C6 | 184CD1 | 32.55 | 184CE2 | 25C6 | 184CZ3 | 34.33 |
| 184CE2 | 25C6 | 184CD1 | 27.45 | 184CZ3 | 25C6 | 184CD1 | 57.71 |
| 20O | 25C7 | 19CG | 65.72 | 20O | 25C7 | 20C | 13.67 |
| 20O | 25C7 | 20N | 42.52 | 20O | 25C7 | 18OD1 | 88.27 |
| 20O | 25C7 | 19CD | 74.17 | 20O | 25C7 | 20CA | 32.34 |
| 20O | 25C7 | 19NE2 | 65.37 | 20O | 25C7 | 19OE1 | 87.32 |
| 20O | 25C7 | 19C | 42.11 | 184CD1 | 25C7 | 19CG | 67.76 |
| 184CD1 | 25C7 | 184NE1 | 21.55 | 184CD1 | 25C7 | 184CG | 19.86 |
| 184CD1 | 25C7 | 18OD1 | 84.02 | 184CD1 | 25C7 | 19CD | 60.66 |
| 184CD1 | 25C7 | 184CE2 | 29.40 | 184CD1 | 25C7 | 184CB | 34.91 |
| 184CD1 | 25C7 | 19NE2 | 73.46 | 184CD1 | 25C7 | 184CD2 | 28.08 |
| 184CD1 | 25C7 | 184CA | 40.17 | 184CD1 | 25C7 | 183O | 43.72 |
| 184CD1 | 25C7 | 19OE1 | 47.61 | 184CD1 | 25C7 | 19C | 99.25 |
| 19CG | 25C7 | 184NE1 | 69.79 | 19CG | 25C7 | 184CG | 86.16 |
| 19CG | 25C7 | 20C | 70.46 | 19CG | 25C7 | 20N | 50.72 |
| 19CG | 25C7 | 18OD1 | 75.31 | 19CG | 25C7 | 19CD | 20.77 |
| 19CG | 25C7 | 20CA | 67.17 | 19CG | 25C7 | 184CE2 | 86.39 |
| 19CG | 25C7 | 184CB | 91.37 | 19CG | 25C7 | 19NE2 | 32.57 |
| 19CG | 25C7 | 184CD2 | 94.84 | 19CG | 25C7 | 184CA | 78.19 |
| 19CG | 25C7 | 183O | 44.08 | 19CG | 25C7 | 19OE1 | 28.49 |
| 19CG | 25C7 | 19C | 38.77 | 184NE1 | 25C7 | 184CG | 34.11 |
| 184NE1 | 25C7 | 19CD | 55.36 | 184NE1 | 25C7 | 184CE2 | 16.60 |
| 184NE1 | 25C7 | 184CB | 52.97 | 184NE1 | 25C7 | 19NE2 | 62.84 |
| 184NE1 | 25C7 | 184CD2 | 29.31 | 184NE1 | 25C7 | 184CA | 61.52 |
| 184NE1 | 25C7 | 183O | 60.91 | 184NE1 | 25C7 | 19OE1 | 42.84 |
| 184CG | 25C7 | 18OD1 | 81.09 | 184CG | 25C7 | 19CD | 80.51 |
| 184CG | 25C7 | 184CE2 | 31.09 | 184CG | 25C7 | 184CB | 19.37 |
| 184CG | 25C7 | 19NE2 | 92.98 | 184CG | 25C7 | 184CD2 | 17.53 |
| 184CG | 25C7 | 184CA | 33.64 | 184CG | 25C7 | 183O | 53.42 |
| 184CG | 25C7 | 19OE1 | 67.47 | 20C | 25C7 | 20N | 35.03 |
| 20C | 25C7 | 18OD1 | 76.84 | 20C | 25C7 | 19CD | 82.78 |
| 20C | 25C7 | 20CA | 20.30 | 20C | 25C7 | 19NE2 | 76.56 |
| 20C | 25C7 | 183O | 97.75 | 20C | 25C7 | 19OE1 | 95.52 |
| 20C | 25C7 | 19C | 38.85 | 20N | 25C7 | 18OD1 | 48.08 |
| 20N | 25C7 | 19CD | 70.24 | 20N | 25C7 | 20CA | 19.43 |
| 20N | 25C7 | 19NE2 | 74.34 | 20N | 25C7 | 184CA | 87.18 |
| 20N | 25C7 | 183O | 63.69 | 20N | 25C7 | 19OE1 | 79.16 |
| 20N | 25C7 | 19C | 12.46 | 1SOD1 | 25C7 | 19CD | 94.22 |
| 18OD1 | 25C7 | 20CA | 56.55 | 18OD1 | 25C7 | 184CB | 64.46 |
| 18OD1 | 25C7 | 184CD2 | 98.02 | 1BOD1 | 25C7 | 184CA | 47.47 |
| 18OD1 | 25C7 | 183O | 48.16 | 18OD1 | 25C7 | 19OE1 | 93.80 |
| 18OD1 | 25C7 | 19C | 55.42 | 19CD | 25C7 | 20CA | 84.64 |
| 19CD | 25C7 | 184CE2 | 71.23 | 19CD | 25C7 | 184CB | 91.94 |
| 19CD | 25C7 | 19NE2 | 17.10 | 19CD | 25C7 | 184CD2 | 83.77 |
| 19CD | 25C7 | 184CA | 84.58 | 19CD | 25C7 | 183O | 54.34 |
| 19CD | 25C7 | 19OE1 | 13.19 | 19CD | 25C7 | 19C | 57.87 |
| 20CA | 25C7 | 19NE2 | 84.21 | 20CA | 25C7 | 183O | 82.52 |
| 20CA | 25C7 | 19OE1 | 95.40 | 20CA | 25C7 | 19C | 28.93 |
| 184CE2 | 25C7 | 184CB | 50.04 | 184CE2 | 25C7 | 19NE2 | 76.55 |
| 184CE2 | 25C7 | 184CD2 | 18.00 | 184CE2 | 25C7 | 184CA | 64.00 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 184CE2 | 25C7 | 183O | 72.92 | 184CE2 | 25C7 | 19OE1 | 59.12 |
| 184CB | 25C7 | 184CD2 | 34.04 | 184CB | 25C7 | 184CA | 19.42 |
| 184CB | 25C7 | 183O | 50.23 | 184CB | 25C7 | 19OE1 | 79.91 |
| 19NE2 | 25C7 | 184CD2 | 92.14 | 19NE2 | 25C7 | 183O | 71.31 |
| 19NE2 | 25C7 | 19OE1 | 27.20 | 19NE2 | 25C7 | 19C | 62.12 |
| 184CD2 | 25C7 | 184CA | 50.81 | 184CD2 | 25C7 | 183O | 69.19 |
| 184CD2 | 25C7 | 19OE1 | 70.74 | 184CA | 25C7 | 183O | 34.36 |
| 184CA | 25C7 | 19OE1 | 74.90 | 184CA | 25C7 | 19C | 87.64 |
| 183O | 25C7 | 19OE1 | 48.64 | 183O | 25C7 | 19C | 59.18 |
| 19OE1 | 25C7 | 19C | 67.25 | 20O | 25O8 | 20C | 10.26 |
| 20O | 25S8 | 19CG | 58.52 | 20O | 25O8 | 19NE2 | 68.66 |
| 20O | 25O8 | 19CD | 71.25 | 20O | 25O8 | 20CA | 23.15 |
| 20O | 25O8 | 20N | 31.47 | 20O | 25O8 | 21N | 16.79 |
| 20O | 25O8 | 21CA | 28.59 | 20C | 25O8 | 19CG | 64.70 |
| 20C | 25O8 | 19NE2 | 78.30 | 20C | 25O8 | 19CD | 79.37 |
| 20C | 25O8 | 20CA | 16.86 | 20C | 25O8 | 20N | 30.40 |
| 20C | 25O8 | 21N | 12.70 | 20C | 25O8 | 21CA | 28.94 |
| 184NE1 | 25O8 | 184CD1 | 18.63 | 184NE1 | 25O8 | 19CG | 59.96 |
| 184NE1 | 25O8 | 19NE2 | 61.10 | 184NE1 | 25O8 | 19CD | 50.56 |
| 184NE1 | 25O8 | 184CE2 | 16.07 | 184NE1 | 25O8 | 20N | 95.41 |
| 184NE1 | 25O8 | 184CG | 27.36 | 184CD1 | 25O8 | 19CG | 54.74 |
| 184CD1 | 25O8 | 19NE2 | 67.50 | 184CD1 | 25O8 | 19CD | 52.79 |
| 184CD1 | 25O8 | 184CE2 | 28.00 | 184CD1 | 25O8 | 20CA | 98.14 |
| 184CD1 | 25O8 | 20N | 81.88 | 184CD1 | 25O8 | 184CG | 15.43 |
| 19CG | 25O8 | 19NE2 | 32.50 | 19CG | 25S8 | 19CD | 19.73 |
| 19CG | 25O8 | 184CE2 | 76.01 | 19CG | 25O8 | 20CA | 58.57 |
| 19CG | 25O8 | 20N | 42.57 | 19CG | 25O8 | 184CG | 68.67 |
| 19CG | 25O8 | 21N | 75.23 | 19CG | 25O8 | 21CA | 84.51 |
| 19NE2 | 25O8 | 19CD | 17.06 | 19NE2 | 25O8 | 184CE2 | 74.74 |
| 19NE2 | 25O8 | 20CA | 80.50 | 19NE2 | 25O8 | 20N | 68.75 |
| 19NE2 | 25O8 | 184CG | 82.83 | 19NE2 | 25O8 | 21N | 83.53 |
| 19NE2 | 25O8 | 21CA | 83.71 | 19CD | 25O8 | 184CE2 | 66.00 |
| 19CD | 25O8 | 20CA | 76.51 | 19CD | 25O8 | 20N | 61.57 |
| 19CD | 25O8 | 184CG | 68.20 | 19CD | 25O8 | 21N | 87.76 |
| 19CD | 25O8 | 21CA | 92.52 | 184CE2 | 25O8 | 184CG | 27.48 |
| 20CA | 25O8 | 20N | 17.27 | 20CA | 25O8 | 21N | 28.61 |
| 20CA | 25O8 | 21CA | 45.46 | 20N | 25O8 | 184CG | 88.95 |
| 20N | 25O8 | 21N | 43.10 | 20N | 25O8 | 21CA | 58.85 |
| 21N | 25O8 | 21CA | 16.97 | 20O | 25C9 | 19NE2 | 82.43 |
| 20O | 25C9 | 19CD | 79.79 | 20O | 25C9 | 19CG | 60.88 |
| 20O | 25C9 | 20C | 3.58 | 20O | 25C9 | 22O | 59.91 |
| 20O | 25C9 | 184CD1 | 98.95 | 20O | 25C9 | 19OE1 | 91.12 |
| 20O | 25C9 | 22N | 39.58 | 20O | 25C9 | 21CA | 31.39 |
| 20O | 25C9 | 21OE1 | 65.02 | 19NE2 | 25C9 | 19CD | 19.36 |
| 19NE2 | 25C9 | 19CG | 36.33 | 19NE2 | 25C9 | 184NE1 | 69.05 |
| 19NE2 | 25C9 | 20C | 86.00 | 19NE2 | 25C9 | 22O | 36.71 |
| 19NE2 | 25C9 | 184CD1 | 71.62 | 19NE2 | 25C9 | 19OE1 | 26.23 |
| 19NE2 | 25C9 | 22N | 69.60 | 19NE2 | 25C9 | 184CE2 | 82.17 |
| 19NE2 | 25C9 | 21CA | 96.36 | 19CD | 25C9 | 19CG | 21.85 |
| 19CD | 25C9 | 184NE1 | 54.74 | 19CD | 25C9 | 20C | 83.26 |
| 19CD | 25C9 | 22O | 50.79 | 19CD | 25C9 | 184CD1 | 53.82 |
| 19CD | 25C9 | 19OE1 | 12.53 | 19CD | 25C9 | 22N | 79.86 |
| 19CD | 25C9 | 184CE2 | 69.35 | 19CG | 25C9 | 184NE1 | 61.67 |
| 19CG | 25C9 | 20C | 64.10 | 19CG | 25C9 | 22O | 53.24 |
| 19CG | 25C9 | 184CD1 | 53.39 | 19CG | 25C9 | 19OE1 | 30.83 |
| 19CG | 25C9 | 22N | 72.73 | 19CG | 25C9 | 184CE2 | 76.64 |
| 19CG | 25C9 | 21CA | 87.99 | 184NE1 | 25C9 | 184CD1 | 16.96 |
| 184NE1 | 25C9 | 19OE1 | 43.53 | 184NE1 | 25C9 | 184CE2 | 15.12 |
| 20C | 25C9 | 22O | 62.84 | 20C | 25C9 | 19OE1 | 94.48 |
| 20C | 25C9 | 22N | 40.82 | 20C | 25C9 | 21CA | 29.72 |
| 20C | 25C9 | 21OE1 | 62.22 | 22O | 25C9 | 19OE1 | 61.50 |
| 22O | 25C9 | 22N | 33.67 | 22O | 25C9 | 21CA | 61.98 |
| 22O | 25C9 | 21OE1 | 90.36 | 184CD1 | 25C9 | 19OE1 | 45.59 |
| 184CD1 | 25C9 | 184CE2 | 27.01 | 19OE1 | 25C9 | 22N | 92.00 |
| 19OE1 | 25C9 | 184CE2 | 57.64 | 22N | 25C9 | 21CA | 28.69 |
| 22N | 25C9 | 21OE1 | 58.53 | 21CA | 25C9 | 21OE1 | 36.88 |
| 20O | 25O10 | 22O | 85.43 | 20O | 25O10 | 19CD | 97.70 |
| 20O | 25O10 | 19CG | 73.17 | 20O | 25O10 | 22N | 56.64 |
| 20O | 25O10 | 20C | 5.18 | 20O | 25O10 | 22C | 86.37 |
| 20O | 25O10 | 21CA | 39.27 | 20O | 25O10 | 21C | 51.49 |
| 20O | 25O10 | 21N | 20.36 | 20O | 25O10 | 22CA | 70.79 |
| 20O | 25O10 | 19CB | 67.40 | 20O | 25O10 | 20N | 28.18 |
| 20O | 25O10 | 20CA | 10.76 | 20O | 25O10 | 21OE1 | 68.78 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 19NE2 | 25O10 | 22O | 52.26 | 19NE2 | 25O10 | 19CD | 20.65 |
| 19NE2 | 25O10 | 19CG | 42.35 | 19NE2 | 25O10 | 22N | 96.61 |
| 19NE2 | 25O10 | 22C | 66.07 | 19NE2 | 25O10 | 19OE1 | 22.91 |
| 19NE2 | 25O10 | 22CA | 82.67 | 19NE2 | 25O10 | 19CB | 43.12 |
| 19NE2 | 25O10 | 20N | 84.11 | 19NE2 | 25O10 | 23N | 64.93 |
| 19NE2 | 25O10 | 184NE1 | 62.68 | 19NE2 | 25O10 | 23CA | 53.12 |
| 22O | 25O10 | 19CD | 65.17 | 22O | 25O10 | 19CG | 68.00 |
| 22O | 25O10 | 22N | 45.38 | 22O | 25O10 | 20C | 81.85 |
| 22O | 25O10 | 22C | 15.92 | 22O | 25O10 | 21CA | 79.66 |
| 22O | 25O10 | 21C | 61.19 | 22O | 25O10 | 21N | 79.35 |
| 22O | 25O10 | 19OE1 | 72.72 | 22O | 25O10 | 22CA | 30.41 |
| 22O | 25O10 | 19CB | 55.31 | 22O | 25O10 | 20N | 77.38 |
| 22O | 25O10 | 23N | 24.55 | 22O | 25O10 | 20CA | 82.51 |
| 22O | 25O10 | 23CA | 30.74 | 19CD | 25O10 | 19CG | 24.88 |
| 19CD | 25O10 | 20C | 99.46 | 19CD | 25O10 | 22C | 80.69 |
| 19CD | 25O10 | 19OE1 | 10.13 | 19CD | 25O10 | 22CA | 93.93 |
| 19CD | 25O10 | 19CB | 31.83 | 19CD | 25O10 | 20N | 69.77 |
| 19CD | 25O10 | 23N | 82.79 | 19CD | 25O10 | 20CA | 87.09 |
| 19CD | 25O10 | 184NE1 | 49.90 | 19CD | 25O10 | 23CA | 72.96 |
| 19CG | 25O10 | 22N | 93.59 | 19CG | 25O10 | 20C | 75.37 |
| 19CG | 25O10 | 22C | 83.51 | 19CG | 25O10 | 21N | 89.04 |
| 19CG | 25O10 | 19OE1 | 32.51 | 19CG | 25O10 | 22CA | 89.71 |
| 19CG | 25O10 | 19CB | 14.55 | 19CG | 25O10 | 20N | 45.05 |
| 19CG | 25O10 | 23N | 91.20 | 19CG | 25O10 | 20CA | 62.46 |
| 19CG | 25O10 | 184NE1 | 58.10 | 19CG | 25O10 | 23CA | 87.28 |
| 22N | 25O10 | 20C | 51.51 | 22N | 25O10 | 22C | 36.02 |
| 22N | 25O10 | 21CA | 34.76 | 22N | 25O10 | 21C | 15.90 |
| 22N | 25O10 | 21N | 40.79 | 22N | 25O10 | 22CA | 16.92 |
| 22N | 25O10 | 19CB | 79.30 | 22N | 25O10 | 20N | 69.27 |
| 22N | 25O10 | 23N | 46.59 | 22N | 25O10 | 20CA | 61.11 |
| 22N | 25O10 | 21OE1 | 66.06 | 22N | 25O10 | 23CA | 63.27 |
| 20C | 25O10 | 22C | 81.89 | 20C | 25O10 | 21CA | 35.03 |
| 20C | 25O10 | 21C | 46.40 | 20C | 25O10 | 21N | 15.83 |
| 20C | 25O10 | 22CA | 65.90 | 20C | 25O10 | 19CB | 68.42 |
| 20C | 25O10 | 20N | 30.90 | 20C | 25O10 | 23N | 95.35 |
| 20C | 25O10 | 20CA | 14.07 | 20C | 25O10 | 21OE1 | 66.77 |
| 22C | 25O10 | 21CA | 70.57 | 22C | 25O10 | 21C | 50.65 |
| 22C | 25O10 | 21N | 75.18 | 22C | 25O10 | 19OE1 | 87.67 |
| 22C | 25O10 | 22CA | 19.15 | 22C | 25O10 | 19CB | 70.26 |
| 22C | 25O10 | 12ON | 85.66 | 22C | 25O10 | 23N | 14.18 |
| 22C | 25O10 | 20CA | 86.38 | 22C | 25O10 | 21OE1 | 94.63 |
| 22C | 25O10 | 23CA | 28.51 | 21CA | 25O10 | 21C | 20.23 |
| 21CA | 25O10 | 21N | 19.26 | 21CA | 25O10 | 22CA | 51.43 |
| 21CA | 25O10 | 19CB | 95.98 | 21CA | 25O10 | 20N | 65.09 |
| 21CA | 25O10 | 23N | 79.47 | 21CA | 25O10 | 20CA | 49.07 |
| 21CA | 25O10 | 21OE1 | 39.22 | 21CA | 25O10 | 23CA | 96.32 |
| 21C | 25O10 | 21N | 32.16 | 21C | 25O10 | 22CA | 31.67 |
| 21C | 25O10 | 19CB | 90.80 | 21C | 25O10 | 20N | 71.25 |
| 21C | 25O10 | 23N | 59.25 | 21C | 25O10 | 20CA | 58.84 |
| 21C | 25O10 | 21OE1 | 50.69 | 21C | 25O10 | 23CA | 76.11 |
| 21N | 25O10 | 22CA | 57.03 | 21N | 25O10 | 19CB | 80.04 |
| 21N | 25O10 | 20N | 45.98 | 21N | 25O10 | 23N | 87.15 |
| 21N | 25O10 | 20CA | 29.82 | 21N | 25O10 | 21OE1 | 54.21 |
| 19OE1 | 25O10 | 19CB | 41.46 | 19OE1 | 25O10 | 20N | 77.43 |
| 19OE1 | 25O10 | 23N | 87.76 | 19OE1 | 25O10 | 20CA | 94.86 |
| 19OE1 | 25O10 | 184NE1 | 41.58 | 19OE1 | 25O10 | 23CA | 75.81 |
| 22CA | 25O10 | 19CB | 75.23 | 22CA | 25O10 | 2ON | 77.28 |
| 22CA | 25O10 | 23N | 30.13 | 22CA | 25O10 | 20CA | 73.19 |
| 22CA | 25O10 | 21OE1 | 78.69 | 22CA | 25O10 | 23CA | 46.56 |
| 19CB | 25O10 | 20N | 41.01 | 19CB | 25O10 | 23N | 79.42 |
| 19CB | 25O10 | 20CA | 57.32 | 19CB | 25O10 | 184NE1 | 72.38 |
| 19CB | 25O10 | 23CA | 78.47 | 20N | 25O10 | 23N | 99.51 |
| 20N | 25O10 | 20CA | 17.43 | 20N | 25O10 | 184NE1 | 88.50 |
| 20N | 25O10 | 21OE1 | 96.89 | 23N | 25O10 | 21OE1 | 95.90 |
| 23N | 25O10 | 23CA | 16.87 | 20CA | 25O10 | 21OE1 | 79.48 |
| 19NE2 | 25C11 | 19CD | 13.29 | 19NE2 | 25C11 | 184NE1 | 59.74 |
| 19NE2 | 25C11 | 22O | 32.16 | 19CD | 25C11 | 184NE1 | 46.55 |
| 19CD | 25C11 | 22O | 44.12 | 184NE1 | 25C11 | 22O | 89.70 |
| 19NE2 | 25C12 | 22O | 39.61 | 19NE2 | 25C12 | 23CA | 60.70 |
| 19NE2 | 25C12 | 22C | 55.91 | 19NE2 | 25C12 | 23N | 65.25 |
| 19NE2 | 25C12 | 22OH2 | 93.02 | 19NE2 | 25C12 | 22N | 67.68 |
| 19NE2 | 25C12 | 19CD | 8.19 | 19NE2 | 25C12 | 20O | 56.75 |
| 22O | 25C12 | 23CA | 39.57 | 22O | 25C12 | 22C | 16.82 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 22O | 25C12 | 23N | 31.30 | 22O | 25C12 | 224OH2 | 75.08 |
| 22O | 25C12 | 22N | 34.48 | 22O | 25C12 | 19CD | 46.01 |
| 22O | 25C12 | 20O | 50.49 | 23CA | 25C12 | 22C | 33.54 |
| 23CA | 25C12 | 23N | 19.76 | 23CA | 25C12 | 224OH2 | 36.28 |
| 23CA | 25C12 | 22N | 62.96 | 23CA | 25C12 | 19CD | 68.87 |
| 23CA | 25C12 | 20O | 89.77 | 22C | 25C12 | 23N | 17.94 |
| 22C | 25C12 | 224OH2 | 64.69 | 22C | 25C12 | 22N | 29.81 |
| 22C | 25C12 | 19CD | 62.67 | 22C | 25C12 | 20O | 58.58 |
| 23N | 25C12 | 224OH2 | 46.80 | 23N | 25C12 | 22N | 44.68 |
| 23N | 25C12 | 19CD | 73.05 | 23N | 25C12 | 20O | 76.44 |
| 224OH2 | 25C12 | 22N | 89.06 | 22N | 25C12 | 19CD | 71.05 |
| 22N | 25C12 | 20O | 37.38 | 19CD | 25C12 | 20O | 54.60 |
| 21OE1 | 25C13 | 22N | 66.00 | 21OE1 | 25C13 | 22C | 95.57 |
| 21OE1 | 25C13 | 22O | 97.18 | 21OE1 | 25C13 | 21C | 51.73 |
| 22N | 25C13 | 22C | 29.65 | 22N | 25C13 | 23N | 43.65 |
| 22N | 25C13 | 22O | 33.57 | 22N | 25C13 | 21C | 15.61 |
| 22N | 25C13 | 23CA | 58.56 | 22C | 25C13 | 23N | 16.28 |
| 22C | 25C13 | 22O | 14.98 | 22C | 25C13 | 21C | 44.10 |
| 22C | 25C13 | 23CA | 29.00 | 23N | 25C13 | 22O | 27.57 |
| 23N | 25C13 | 21C | 56.18 | 23N | 25C13 | 23CA | 17.03 |
| 22O | 25C13 | 21C | 49.18 | 22O | 25C13 | 23CA | 33.12 |
| 21C | 25C13 | 23CA | 72.30 | 22N | 25C14 | 21C | 21.24 |
| 22N | 25C14 | 22C | 38.14 | 22N | 25C14 | 21OE1 | 82.54 |
| 22N | 25C14 | 23N | 56.21 | 22N | 25C14 | 22CA | 22.02 |
| 22N | 25C14 | 21CA | 36.01 | 22N | 25C14 | 21O | 33.22 |
| 22N | 25C14 | 22O | 40.42 | 22N | 25C14 | 23CA | 70.62 |
| 22N | 25C14 | 20O | 41.05 | 22N | 25C14 | 21CB | 49.85 |
| 22N | 25C14 | 21CD | 75.68 | 21C | 25C14 | 22C | 58.12 |
| 21C | 25C14 | 21OE1 | 65.17 | 21C | 25C14 | 23N | 74.13 |
| 21C | 25C14 | 22CA | 37.70 | 21C | 25C14 | 21CA | 21.82 |
| 21C | 25C14 | 21O | 17.02 | 21C | 25C14 | 22O | 61.64 |
| 21C | 25C14 | 23CA | 90.21 | 21C | 25C14 | 20O | 46.27 |
| 21C | 25C14 | 21CB | 30.54 | 21C | 25C14 | 21CD | 59.45 |
| 22C | 25C14 | 23N | 20.02 | 22C | 25C14 | 22CA | 22.87 |
| 22C | 25C14 | 21CA | 73.72 | 22C | 25C14 | 21O | 63.62 |
| 22C | 25C14 | 22O | 16.99 | 22C | 25C14 | 23CA | 32.48 |
| 22C | 25C14 | 20O | 63.32 | 22C | 25C14 | 21CB | 87.93 |
| 21OE1 | 25C14 | 21CA | 46.55 | 21OE1 | 25C14 | 21O | 68.11 |
| 21OE1 | 25C14 | 20O | 64.41 | 21OE1 | 25C14 | 21CB | 34.92 |
| 21OE1 | 25C14 | 21CD | 7.92 | 23N | 25C14 | 22CA | 36.43 |
| 23N | 25C14 | 21CA | 92.21 | 23N | 25C14 | 21O | 75.11 |
| 23N | 25C14 | 22O | 32.42 | 23N | 25C14 | 23CA | 17.87 |
| 23N | 25C14 | 20O | 82.87 | 22CA | 25C14 | 21CA | 56.88 |
| 22CA | 25C14 | 21O | 40.83 | 22CA | 25C14 | 22O | 34.41 |
| 22CA | 25C14 | 23CA | 53.03 | 22CA | 25C14 | 20O | 60.12 |
| 22CA | 25C14 | 21CB | 68.24 | 22CA | 25C14 | 21CD | 96.45 |
| 21CA | 25C14 | 21O | 34.25 | 21CA | 25C14 | 22O | 71.57 |
| 21CA | 25C14 | 20O | 35.31 | 21CA | 25C14 | 21CB | 17.17 |
| 21CA | 25C14 | 21CD | 39.72 | 21O | 25C14 | 22O | 71.78 |
| 21O | 25C14 | 23CA | 92.77 | 21O | 25C14 | 20O | 63.21 |
| 21O | 25C14 | 21CB | 34.50 | 21O | 25C14 | 21CD | 64.40 |
| 22O | 25C14 | 23CA | 37.01 | 22O | 25C14 | 20O | 51.83 |
| 22O | 25C14 | 21CB | 88.01 | 23CA | 25C14 | 20O | 88.32 |
| 20O | 25C14 | 21CB | 50.65 | 20O | 25C14 | 21CD | 56.60 |
| 21CB | 25C14 | 21CD | 30.13 | 21OE1 | 25C15 | 21CD | 12.20 |
| 21OE1 | 25C15 | 21NE2 | 26.50 | 21OE1 | 25C15 | 21CA | 39.20 |
| 21OE1 | 25C15 | 20O | 65.35 | 21CD | 25C15 | 21NE2 | 16.43 |
| 21CD | 25C15 | 21CA | 39.53 | 21CD | 25C15 | 20O | 59.46 |
| 21NE2 | 25C15 | 21CA | 53.49 | 21NE2 | 25C15 | 20O | 65.84 |
| 21CA | 25C15 | 20O | 32.72 | 19NE2 | 25C16 | 19CD | 16.53 |
| 19NE2 | 25C16 | 162ND1 | 88.72 | 19NE2 | 25C16 | 19OE1 | 31.45 |
| 19NE2 | 25C16 | 162CE1 | 76.13 | 19NE2 | 25C16 | 184NE1 | 68.38 |
| 19NE2 | 25C16 | 184CE2 | 84.59 | 19NE2 | 25C16 | 25SG | 70.09 |
| 19NE2 | 25C16 | 23CA | 54.01 | 19NE2 | 25C16 | 22O | 29.07 |
| 19CD | 25C16 | 162ND1 | 77.07 | 19CD | 25C16 | 19OE1 | 16.88 |
| 19CD | 25C16 | 162CE1 | 62.31 | 19CD | 25C16 | 184NE1 | 52.74 |
| 19CD | 25C16 | 184CZ2 | 85.13 | 19CD | 25C16 | 184CE2 | 69.00 |
| 19CD | 25C16 | 25SG | 69.54 | 19CD | 25C16 | 23CA | 69.33 |
| 19CD | 25C16 | 22O | 45.46 | 162ND1 | 25C16 | 19OE1 | 60.33 |
| 162ND1 | 25C16 | 162CE1 | 17.92 | 162ND1 | 25C16 | 184NE1 | 63.79 |
| 162ND1 | 25C16 | 184CZ2 | 60.49 | 162ND1 | 25C16 | 184CE2 | 63.53 |
| 162ND1 | 25C16 | 25SG | 43.67 | 19OE1 | 25C16 | 162CE1 | 45.48 |
| 19OE1 | 25C16 | 184NE1 | 45.86 | 19OE1 | 25C16 | 184CZ2 | 75.36 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 19OE1 | 25C16 | 184CE2 | 61.18 | 19OE1 | 25C16 | 25SG | 59.93 |
| 19OE1 | 25C16 | 23CA | 78.49 | 19OE1 | 25C16 | 22O | 60.19 |
| 162CE1 | 25C16 | 184NE1 | 47.41 | 162CE1 | 25C16 | 184CZ2 | 52.59 |
| 162CE1 | 25C16 | 184CE2 | 50.53 | 162CE1 | 25C16 | 25SG | 51.17 |
| 184NE1 | 25C16 | 184CZ2 | 32.85 | 184NE1 | 25C16 | 184CE2 | 16.26 |
| 184NE1 | 25C16 | 25SG | 93.75 | 184NE1 | 25C16 | 22O | 94.69 |
| 184CZ2 | 25C16 | 184CE2 | 17.00 | 25SG | 25C16 | 23CA | 63.45 |
| 25SG | 25C16 | 22O | 79.20 | 23CA | 25C16 | 22O | 32.47 |
| 19NE2 | 25O17 | 184NE1 | 87.64 | 19NE2 | 25O17 | 162CE1 | 97.12 |
| 19NE2 | 25O17 | 19OE1 | 40.11 | 19NE2 | 25O17 | 19CD | 22.12 |
| 19NE2 | 25617 | 184CD1 | 77.66 | 19NE2 | 25O17 | 25CB | 62.38 |
| 19NE2 | 25O17 | 25SG | 74.14 | 19NE2 | 25O17 | 19CG | 26.63 |
| 184NE1 | 25O17 | 162CE1 | 65.10 | 184NE1 | 25O17 | 162ND1 | 86.13 |
| 184NE1 | 25O17 | 19OE1 | 60.63 | 184NE1 | 25O17 | 19CD | 67.63 |
| 184NE1 | 25O17 | 184CZ2 | 42.58 | 184NE1 | 25O17 | 184CE2 | 20.97 |
| 184NE1 | 25O17 | 162NE2 | 55.54 | 184NE1 | 25O17 | 162CG | 83.50 |
| 184NE1 | 25O17 | 184CD1 | 10.23 | 184NE1 | 25O17 | 25CB | 94.14 |
| 184NE1 | 25O17 | 19CG | 61.07 | 184NE1 | 25O17 | 162CD2 | 67.31 |
| 184NE1 | 25O17 | 184CH2 | 48.57 | 162CE1 | 25O17 | 162ND1 | 23.08 |
| 162CE1 | 25O17 | 19OE1 | 59.61 | 162CE1 | 25O17 | 19CD | 80.14 |
| 162CE1 | 25O17 | 184CZ2 | 69.34 | 162CE1 | 25O17 | 184CE2 | 67.58 |
| 162CE1 | 25O17 | 162NE2 | 14.63 | 162CE1 | 25O17 | 162CG | 29.19 |
| 162CE1 | 25O17 | 184CD1 | 69.18 | 162CE1 | 25917 | 25CB | 46.12 |
| 162CE1 | 25O17 | 25SG | 57.25 | 162CE1 | 25O17 | 19CG | 86.83 |
| 162CE1 | 25O17 | 162CD2 | 22.83 | 162CE1 | 25O17 | 184CH2 | 73.20 |
| 162ND1 | 25O17 | 19OE1 | 77.34 | 162ND1 | 25O17 | 19CD | 96.95 |
| 162ND1 | 25O17 | 184CZ2 | 77.78 | 162ND1 | 25O17 | 184CE2 | 83.59 |
| 162ND1 | 25O17 | 162NE2 | 30.71 | 162ND1 | 25O17 | 162CG | 13.98 |
| 162ND1 | 25O17 | 184CD1 | 91.47 | 162ND1 | 25O17 | 25CB | 47.42 |
| 162ND1 | 25O17 | 25SG | 46.98 | 162ND1 | 25O17 | 162CD2 | 23.75 |
| 162ND1 | 25O17 | 184CH2 | 79.38 | 19OE1 | 25O17 | 19CD | 20.54 |
| 19OE1 | 25O17 | 184CZ2 | 99.66 | 19OE1 | 25O17 | 184CE2 | 80.49 |
| 19OE1 | 25O17 | 162NE2 | 66.69 | 19OE1 | 25O17 | 162CG | 88.06 |
| 19OE1 | 25O17 | 184CD1 | 53.52 | 19OE1 | 25O17 | 25CB | 44.71 |
| 19OE1 | 25O17 | 25SG | 67.03 | 19OE1 | 25O17 | 19CG | 28.75 |
| 19OE1 | 25O17 | 162CD2 | 81.23 | 19CD | 25O17 | 184CE2 | 88.60 |
| 19CD | 25O17 | 162NE2 | 86.77 | 19CD | 25O17 | 184CD1 | 58.23 |
| 19CD | 25O17 | 25CB | 57.61 | 19CD | 25O17 | 25SG | 76.46 |
| 19CD | 25O17 | 19CG | 12.28 | 184CZ2 | 25O17 | 184CE2 | 21.82 |
| 184CZ2 | 25O17 | 162NE2 | 54.71 | 184CZ2 | 25O17 | 162CG | 66.69 |
| 184CZ2 | 25O17 | 184CD1 | 52.41 | 184CZ2 | 25O17 | 162CD2 | 54.17 |
| 184CZ2 | 25O17 | 184CH2 | 6.39 | 184CE2 | 25O17 | 162NE2 | 54.32 |
| 184CE2 | 25O17 | 162CG | 76.31 | 184CE2 | 25O17 | 184CD1 | 30.61 |
| 184CE2 | 25O17 | 19CG | 81.59 | 184CE2 | 25O17 | 162CD2 | 60.79 |
| 184CE2 | 25O17 | 184CH2 | 27.64 | 162NE2 | 25O17 | 162CG | 29.72 |
| 162NE2 | 25O17 | 184CD1 | 61.67 | 162NE2 | 25O17 | 25CB | 60.57 |
| 162NE2 | 25O17 | 25SG | 71.37 | 162NE2 | 25O17 | 19CG | 90.84 |
| 162NE2 | 25O17 | 162CD2 | 15.82 | 162NE2 | 25O17 | 184CH2 | 58.64 |
| 162CG | 25O17 | 184CD1 | 90.78 | 162CC | 25O17 | 25CB | 61.39 |
| 162CG | 25O17 | 25SG | 59.43 | 162CG | 25O17 | 162CD2 | 16.23 |
| 162CG | 25O17 | 184CH2 | 67.39 | 184CD1 | 25O17 | 25CB | 91.37 |
| 184CD1 | 25O17 | 19CG | 51.04 | 184CD1 | 25O17 | 162CD2 | 74.86 |
| 184CD1 | 25O17 | 184CH2 | 58.22 | 25CB | 25O17 | 25SG | 23.19 |
| 25CB | 25O17 | 19CG | 69.56 | 25CB | 25O17 | 162CD2 | 65.94 |
| 25SG | 25O17 | 19CG | 88.74 | 25SG | 25O17 | 162CD2 | 70.29 |
| 162CD2 | 25O17 | 184CH2 | 56.25 | 19NE2 | 25N18 | 25SG | 74.49 |
| 19NE2 | 25N18 | 162ND1 | 81.92 | 19NE2 | 25N18 | 23CA | 57.55 |
| 19NE2 | 25N18 | 224OH2 | 93.53 | 19NE2 | 25N18 | 162CE1 | 67.31 |
| 19NE2 | 25N18 | 19CD | 12.59 | 19NE2 | 25N18 | 25CB | 55.64 |
| 19NE2 | 25N18 | 19OE1 | 26.71 | 25SG | 25N18 | 162ND1 | 48.92 |
| 25SG | 25N18 | 161O | 67.41 | 25SG | 25N18 | 23CA | 74.24 |
| 25SG | 25N18 | 224OH2 | 87.02 | 25SG | 25N18 | 162CE1 | 53.82 |
| 25SG | 25N18 | 19CD | 69.72 | 25SG | 25N18 | 25CB | 21.75 |
| 25SG | 25N18 | 19OE1 | 60.33 | 162ND1 | 25N18 | 161O | 62.58 |
| 162ND1 | 25N18 | 162CE1 | 16.19 | 162ND1 | 25N18 | 19CD | 69.87 |
| 162ND1 | 25N18 | 25CB | 43.26 | 162ND1 | 25N18 | 19OE1 | 55.30 |
| 161O | 25N18 | 224OH2 | 98.16 | 161O | 25N18 | 162CE1 | 78.73 |
| 161O | 25N18 | 25CB | 84.03 | 23CA | 25N18 | 224OH2 | 36.29 |
| 23CA | 25N18 | 19CD | 68.30 | 23CA | 25N18 | 25CB | 74.55 |
| 23CA | 25N18 | 19OE1 | 77.72 | 224OH2 | 25N18 | 25CB | 98.57 |
| 162CE1 | 25N18 | 19CD | 54.91 | 162CE1 | 25N18 | 25CB | 40.63 |
| 162CE1 | 25N18 | 19OE1 | 40.66 | 19CD | 25N18 | 25CB | 48.94 |
| 19CD | 25N18 | 19OE1 | 14.63 | 25CB | 25N18 | 19OE1 | 38.63 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 25SG | 25N19 | 162ND1 | 68.67 | 25SG | 25N19 | 161O | 97.88 |
| 25SG | 25N19 | 25CB | 26.20 | 25SG | 25N19 | 162CE1 | 69.25 |
| 25SG | 25N19 | 162CA | 69.30 | 25SG | 25N19 | 162CG | 76.89 |
| 25SG | 25N19 | 19NE2 | 81.47 | 25SG | 25N19 | 162CB | 81.47 |
| 25SG | 25N19 | 161C | 91.20 | 25SG | 25N19 | 23CA | 80.48 |
| 25SG | 25N19 | 162N | 79.54 | 25SG | 25N19 | 19OE1 | 67.38 |
| 25SG | 25N19 | 224OH2 | 96.97 | 162ND1 | 25N19 | 161O | 84.02 |
| 162ND1 | 25N19 | 25CB | 55.97 | 162ND1 | 25N19 | 162CE1 | 17.34 |
| 162ND1 | 25N19 | 162CA | 46.46 | 162ND1 | 25N19 | 162CG | 15.15 |
| 162ND1 | 25N19 | 19NE2 | 86.65 | 162ND1 | 25N19 | 162CB | 34.28 |
| 162ND1 | 25N19 | 161C | 76.02 | 162ND1 | 25N19 | 162N | 61.82 |
| 162ND1 | 25N19 | 19OE1 | 59.63 | 161O | 25N19 | 162CA | 41.35 |
| 161O | 25N19 | 162CG | 69.81 | 161O | 25N19 | 162CB | 49.97 |
| 161O | 25N19 | 161C | 8.90 | 161O | 25N19 | 162N | 24.76 |
| 25CB | 25N19 | 162CE1 | 49.59 | 25CB | 25N19 | 162CA | 78.03 |
| 25CB | 25N19 | 162CG | 68.95 | 25CB | 25N19 | 19NE2 | 60.40 |
| 25CB | 25N19 | 162CB | 81.67 | 25CB | 25N19 | 23CA | 80.10 |
| 25CB | 25N19 | 162N | 92.77 | 25CB | 25N19 | 19OE1 | 41.65 |
| 162CE1 | 25N19 | 162CA | 63.58 | 162CE1 | 25N19 | 162CG | 31.41 |
| 162CE1 | 25N19 | 19NE2 | 69.42 | 162CE1 | 25N19 | 162CB | 51.18 |
| 162CE1 | 25N19 | 161C | 93.28 | 162CE1 | 25N19 | 162N | 79.16 |
| 162CE1 | 25N19 | 19OE1 | 42.84 | 162CA | 25N19 | 162CG | 35.79 |
| 162CA | 25N19 | 162CB | 20.40 | 162CA | 25N19 | 161C | 32.47 |
| 162CA | 25N19 | 162N | 16.68 | 162CG | 25N19 | 162CB | 19.86 |
| 162CG | 25N19 | 161C | 62.27 | 162CG | 25N19 | 162N | 49.28 |
| 162CG | 25N19 | 19OE1 | 74.24 | 19NE2 | 25N19 | 23CA | 51.93 |
| 19NE2 | 25N19 | 19OE1 | 27.73 | 19NE2 | 25N19 | 224OH2 | 83.06 |
| 162CB | 25N19 | 161C | 42.44 | 162CB | 25N19 | 162N | 30.28 |
| 162CB | 25N19 | 19OE1 | 93.88 | 161C | 25N19 | 162N | 15.85 |
| 23CA | 25N19 | 19OE1 | 74.91 | 23CA | 25N19 | 224OH2 | 33.48 |
| 19NE2 | 25N20 | 184NE1 | 66.71 | 19NE2 | 25N20 | 19CD | 16.40 |
| 19NE2 | 25N20 | 20O | 61.92 | 19NE2 | 25N20 | 184CE2 | 83.41 |
| 19NE2 | 25N20 | 184CZ2 | 92.74 | 19NE2 | 25N20 | 184CD1 | 65.86 |
| 19NE2 | 25N20 | 19OE1 | 25.29 | 19NE2 | 25N20 | 19CG | 28.13 |
| 184NE1 | 25N20 | 19CD | 51.81 | 184NE1 | 25N20 | 20O | 92.93 |
| 184NE1 | 25N20 | 184CE2 | 17.64 | 184NE1 | 25N20 | 184CZ2 | 33.11 |
| 184NE1 | 25N20 | 184CD1 | 14.57 | 184NE1 | 25N20 | 19OE1 | 41.63 |
| 184NE1 | 25N20 | 19CG | 54.80 | 19CD | 25N20 | 20o | 61.53 |
| 19CD | 25N20 | 184CE2 | 69.14 | 19CD | 25N20 | 184CZ2 | 80.93 |
| 19CD | 25N20 | 184CD1 | 49.60 | 19CD | 25N20 | 19OE1 | 13.44 |
| 19CD | 25N20 | 19CG | 17.37 | 20O | 25N20 | 184CD1 | 79.82 |
| 20O | 25N20 | 19OE1 | 74.00 | 20O | 25N20 | 19CG | 46.41 |
| 184CE2 | 25N20 | 184CZ2 | 17.72 | 184CE2 | 25N20 | 184CD1 | 27.30 |
| 184CE2 | 25N20 | 19OE1 | 58.12 | 184CE2 | 25N20 | 19CG | 72.23 |
| 184CZ2 | 25N20 | 184CD1 | 44.82 | 184CZ2 | 25N20 | 19OE1 | 68.30 |
| 184CZ2 | 25N20 | 19CG | 87.39 | 184CD1 | 25N20 | 19OE1 | 43.08 |
| 184CD1 | 25N20 | 19CG | 47.27 | 19OE1 | 25N20 | 19CG | 27.95 |
| 25SG | 25C21 | 25CB | 34.16 | 25SG | 25C21 | 25N | 59.13 |
| 25SG | 25C21 | 162ND1 | 63.16 | 25SG | 25C21 | 23O | 95.53 |
| 25SG | 25C21 | 25CA | 41.14 | 25SG | 25C21 | 161O | 90.20 |
| 25SG | 25C21 | 162CE1 | 64.32 | 25SG | 25C21 | 24N | 94.43 |
| 25SG | 25C21 | 19OE1 | 78.34 | 25SG | 25C21 | 162CA | 58.84 |
| 25SG | 25C21 | 19CD | 91.01 | 25SG | 25C21 | 26N | 32.55 |
| 25SG | 25C21 | 25C | 28.93 | 25SG | 25C21 | 24C | 64.37 |
| 25SG | 25C21 | 162CG | 63.81 | 25SG | 25C21 | 163N | 30.18 |
| 25CB | 25C21 | 25N | 41.43 | 25CB | 25C21 | 162ND1 | 57.90 |
| 25CB | 25C21 | 23C | 92.08 | 25CB | 25C21 | 23O | 94.39 |
| 25CB | 25C21 | 25CA | 20.31 | 25CB | 25C21 | 19NE2 | 70.68 |
| 25CB | 25C21 | 162CE1 | 48.50 | 25CB | 25C21 | 24N | 77.34 |
| 25CB | 25C21 | 19OE1 | 44.80 | 25CB | 25C21 | 162CA | 77.90 |
| 25CB | 25C21 | 19CD | 56.86 | 25CB | 25C21 | 26N | 42.39 |
| 25CB | 25C21 | 25C | 26.69 | 25CB | 25C21 | 24C | 49.86 |
| 25CB | 25C21 | 162CG | 64.53 | 25CB | 25C21 | 163N | 55.35 |
| 25N | 25C21 | 162ND1 | 98.16 | 25N | 25C21 | 23CA | 69.54 |
| 25N | 25C21 | 23C | 50.81 | 25N | 25C21 | 23O | 54.24 |
| 25N | 25C21 | 25CA | 21.67 | 25N | 25C21 | 19NE2 | 62.10 |
| 25N | 25C21 | 162CE1 | 85.44 | 25N | 25C21 | 24N | 37.13 |
| 25N | 25C21 | 19OE1 | 55.93 | 25N | 25C21 | 19CD | 56.26 |
| 25N | 25C21 | 26N | 35.66 | 25N | 25C21 | 25C | 30.32 |
| 25N | 25C21 | 24C | 8.74 | 25N | 25C21 | 163N | 88.85 |
| 162ND1 | 25C21 | 25CA | 78.14 | 162ND1 | 25C21 | 19NE2 | 84.09 |
| 162ND1 | 25C21 | 161O | 65.36 | 162ND1 | 25C21 | 162CE1 | 16.67 |
| 162ND1 | 25C21 | 19OE1 | 59.98 | 162ND1 | 25C21 | 162CA | 39.67 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 162ND1 | 25C21 | 19CD | 72.99 | 162ND1 | 25C21 | 26N | 92.87 |
| 162ND1 | 25C21 | 25C | 80.82 | 162ND1 | 25C21 | 162CG | 9.83 |
| 162ND1 | 25C21 | 163N | 47.12 | 23CA | 25C21 | 23C | 22.59 |
| 23CA | 25C21 | 23O | 35.84 | 23CA | 25C21 | 25CA | 90.84 |
| 23CA | 25C21 | 19NE2 | 61.29 | 23CA | 25C21 | 224OH2 | 38.65 |
| 23CA | 25C21 | 24N | 32.44 | 23CA | 25C21 | 19OE1 | 87.52 |
| 23CA | 25C21 | 19CD | 73.32 | 23CA | 25C21 | 26N | 93.91 |
| 23CA | 25C21 | 25C | 97.86 | 23CA | 25C21 | 24C | 62.65 |
| 23CA | 25C21 | 23O | 18.06 | 23C | 25C21 | 25CA | 72.44 |
| 23C | 25C21 | 19NE2 | 67.14 | 23C | 25C21 | 224OH2 | 52.52 |
| 23C | 25C21 | 24N | 16.23 | 23C | 25C21 | 19OE1 | 85.86 |
| 23C | 25C21 | 19CD | 74.76 | 23C | 25C21 | 26N | 71.38 |
| 23C | 25C21 | 25C | 76.60 | 23C | 25C21 | 24C | 42.81 |
| 23O | 25C21 | 25CA | 74.11 | 23O | 25C21 | 19NE2 | 84.69 |
| 23O | 25C21 | 224OH2 | 51.69 | 23O | 25C21 | 24N | 29.95 |
| 23O | 25C21 | 19CD | 90.88 | 23O | 25C21 | 26N | 63.28 |
| 23O | 25C21 | 25C | 72.90 | 23O | 25C21 | 24C | 45.50 |
| 25CA | 25C21 | 19NE2 | 68.27 | 25CA | 25C21 | 162CE1 | 67.59 |
| 25CA | 25C21 | 24N | 58.61 | 25CA | 25C21 | 19OE1 | 50.41 |
| 25CA | 25C21 | 162CA | 95.22 | 25CA | 25C21 | 19CD | 57.40 |
| 25CA | 25C21 | 26N | 30.73 | 25CA | 25C21 | 25C | 16.57 |
| 25CA | 25C21 | 24C | 29.77 | 25CA | 25C21 | 162CG | 84.82 |
| 25CA | 25C21 | 163N | 69.11 | 19NE2 | 25C21 | 162CE1 | 68.48 |
| 19NE2 | 25C21 | 224OH2 | 93.44 | 19NE2 | 25C21 | 24N | 55.94 |
| 19NE2 | 25C21 | 19OE1 | 29.51 | 19NE2 | 25C21 | 19CD | 14.63 |
| 19NE2 | 25C21 | 26N | 96.37 | 19NE2 | 25C21 | 25C | 84.76 |
| 19NE2 | 25C21 | 24C | 64.60 | 19NE2 | 25C21 | 162CG | 93.25 |
| 161O | 25C21 | 162CE1 | 81.61 | 161O | 25C21 | 162CA | 35.10 |
| 161O | 25C21 | 162CG | 55.78 | 161O | 25C21 | 163N | 60.78 |
| 162CE1 | 25C21 | 19OE1 | 43.32 | 162CE1 | 25C21 | 162CA | 55.76 |
| 162CE1 | 25C21 | 19CD | 56.63 | 162CE1 | 25C21 | 26N | 88.80 |
| 162CE1 | 25C21 | 25C | 74.35 | 162CE1 | 25C21 | 24C | 94.10 |
| 162CE1 | 25C21 | 162CG | 26.49 | 162CE1 | 25C21 | 163N | 57.15 |
| 224OH2 | 25C21 | 24N | 67.70 | 224OH2 | 25C21 | 24C | 94.80 |
| 24N | 25C21 | 19OE1 | 70.64 | 24N | 25C21 | 19CD | 60.95 |
| 24N | 25C21 | 26N | 64.52 | 24N | 25C21 | 25C | 65.81 |
| 24N | 25C21 | 24C | 30.33 | 19OE1 | 25C21 | 162CA | 98.48 |
| 19OE1 | 25C21 | 19CD | 15.08 | 19OE1 | 25C21 | 26N | 81.12 |
| 19OE1 | 25C21 | 25C | 66.02 | 19OE1 | 25C21 | 24C | 62.63 |
| 19OE1 | 25C21 | 162CG | 69.79 | 19OE1 | 25C21 | 163N | 90.46 |
| 162CA | 25C21 | 26N | 89.91 | 162CA | 25C21 | 25C | 87.29 |
| 162CA | 25C21 | 162CG | 30.51 | 162CA | 25C21 | 163N | 28.80 |
| 19CD | 25C21 | 26N | 87.36 | 19CD | 25C21 | 25C | 73.91 |
| 19CD | 25C21 | 24C | 60.95 | 19CD | 25C21 | 162CG | 82.63 |
| 26N | 25C21 | 25C | 15.95 | 26N | 25C21 | 24C | 37.06 |
| 26N | 25C21 | 162CG | 95.38 | 26N | 25C21 | 163N | 61.27 |
| 25C | 25C21 | 24C | 35.55 | 25C | 25C21 | 162CG | 85.16 |
| 25C | 25C21 | 163N | 58.98 | 24C | 25C21 | 163N | 94.51 |
| 162CG | 25C21 | 163N | 42.83 | 25SG | 25O22 | 25CB | 38.49 |
| 25SG | 25O22 | 25N | 68.14 | 25SG | 25O22 | 25CA | 51.61 |
| 25SG | 25O22 | 23O | 92.70 | 25SG | 25O22 | 19OE1 | 92.24 |
| 25SG | 25O22 | 162ND1 | 54.00 | 25SG | 25O22 | 24C | 76.75 |
| 25SG | 25O22 | 162CE1 | 62.63 | 25SG | 25O22 | 24CA | 92.42 |
| 25SG | 25O22 | 25C | 41.17 | 25SG | 25O22 | 26N | 39.32 |
| 19NE2 | 25O22 | 25CB | 90.81 | 19NE2 | 25O22 | 23CA | 83.72 |
| 19NE2 | 25O22 | 25N | 82.91 | 19NE2 | 25O22 | 23C | 90.92 |
| 19NE2 | 25O22 | 25CA | 85.84 | 19NE2 | 25O22 | 24N | 75.03 |
| 19NE2 | 25O22 | 19CD | 18.29 | 19NE2 | 25O22 | 19OE1 | 36.86 |
| 19NE2 | 25O22 | 22O | 40.88 | 19NE2 | 25O22 | 162ND1 | 93.79 |
| 19NE2 | 25O22 | 24C | 82.04 | 19NE2 | 25O22 | 23N | 71.12 |
| 19NE2 | 25O22 | 162CE1 | 77.66 | 19NE2 | 25O22 | 24CA | 80.86 |
| 19NE2 | 25O22 | 22C | 54.65 | 19NE2 | 25O22 | 25C | 99.55 |
| 25CB | 25O22 | 25N | 47.57 | 25CB | 25O22 | 25CA | 24.14 |
| 25CB | 25O22 | 24N | 93.92 | 25CB | 25O22 | 19CD | 72.69 |
| 25CB | 25O22 | 19OE1 | 55.94 | 25CB | 25O22 | 162ND1 | 53.00 |
| 25CB | 25O22 | 24C | 58.84 | 25CB | 25O22 | 162CE1 | 47.93 |
| 25CB | 25O22 | 24CA | 78.52 | 25CB | 25O22 | 25C | 26.37 |
| 25CB | 25O22 | 26N | 39.92 | 23CA | 25O22 | 25N | 86.84 |
| 23CA | 25O22 | 23C | 27.45 | 23CA | 25O22 | 24N | 40.92 |
| 23CA | 25O22 | 23O | 40.51 | 23CA | 25O22 | 19CD | 98.21 |
| 23CA | 25O22 | 22O | 43.20 | 23CA | 25O22 | 24C | 75.56 |
| 23CA | 25O22 | 23N | 12.75 | 23CA | 25O22 | 224OH2 | 38.92 |
| 23CA | 25O22 | 24CA | 55.88 | 23CA | 25O22 | 22C | 29.08 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 25N | 25O22 | 23C | 61.42 | 25N | 25O22 | 25CA | 23.44 |
| 25N | 25O22 | 24N | 46.54 | 25N | 25O22 | 23O | 61.31 |
| 25N | 25O22 | 19CD | 72.72 | 25N | 25O22 | 19OE1 | 69.34 |
| 25N | 25O22 | 22O | 78.77 | 25N | 25O22 | 24C | 11.28 |
| 25N | 25O22 | 23N | 87.24 | 25N | 25O22 | 162CE1 | 91.85 |
| 25N | 25O22 | 24CA | 30.96 | 25N | 25O22 | 22C | 83.18 |
| 25N | 25O22 | 25C | 27.52 | 25N | 25O22 | 26N | 31.88 |
| 23C | 25O22 | 25CA | 84.51 | 23C | 25O22 | 24N | 21.22 |
| 23C | 25O22 | 23O | 19.47 | 23C | 25O22 | 19CD | 98.72 |
| 23C | 25O22 | 22O | 52.92 | 23C | 25O22 | 24C | 50.34 |
| 23C | 25O22 | 23N | 34.26 | 23C | 25O22 | 224OH2 | 55.48 |
| 23C | 25O22 | 24CA | 31.37 | 23C | 25O22 | 22C | 43.43 |
| 23C | 25O22 | 25C | 83.00 | 23C | 25O22 | 26N | 74.42 |
| 25CA | 25O22 | 24N | 69.81 | 25CA | 25O22 | 23O | 81.49 |
| 25CA | 25O22 | 19CD | 70.36 | 25CA | 25O22 | 19OE1 | 59.53 |
| 25CA | 25O22 | 22O | 96.17 | 25CA | 25O22 | 162ND1 | 76.96 |
| 25CA | 25O22 | 24C | 34.73 | 25CA | 25O22 | 162CE1 | 69.68 |
| 25CA | 25O22 | 24CA | 54.41 | 25CA | 25O22 | 25C | 13.77 |
| 25CA | 25922 | 26N | 28.59 | 24N | 25O22 | 23O | 35.89 |
| 24N | 25O22 | 19CD | 79.36 | 24N | 25O22 | 19OE1 | 90.36 |
| 24N | 25O22 | 22O | 44.09 | 24N | 25O22 | 24C | 35.42 |
| 24N | 25O22 | 23N | 40.92 | 25b22 | 224OH2 | 75.53 |
| 24N | 25O22 | 24CA | 16.33 | 24N | 25O22 | 22C | 41.01 |
| 24N | 25O22 | 25C | 72.48 | 24N | 25O22 | 26N | 69.02 |
| 23O | 25O22 | 22O | 72.38 | 23O | 25O22 | 24C | 51.99 |
| 23O | 25O22 | 23N | 50.70 | 23O | 25O22 | 224OH2 | 53.17 |
| 23O | 25O22 | 24CA | 37.85 | 23O | 25O22 | 22C | 62.29 |
| 23O | 25O22 | 25C | 75.63 | 23O | 25O22 | 26N | 63.41 |
| 19CD | 25O22 | 19OE1 | 19.08 | 19CD | 25O22 | 22O | 55.19 |
| 19CD | 25O22 | 162ND1 | 80.93 | 19CD | 25O22 | 24C | 75.07 |
| 19CD | 25O22 | 23N | 86.19 | 19CD | 25O22 | 162CE1 | 63.77 |
| 19CD | 25O22 | 24CA | 80.05 | 19CD | 25O22 | 22C | 69.54 |
| 19CD | 25O22 | 25C | 84.09 | 19CD | 25O22 | 26N | 98.42 |
| 19OE1 | 25O22 | 22O | 73.71 | 19OE1 | 25O22 | 162ND1 | 64.15 |
| 19OE1 | 25O22 | 24C | 75.30 | 19OE1 | 25O22 | 162CE1 | 46.77 |
| 19OE1 | 25O22 | 24CA | 86.24 | 19OE1 | 25O22 | 22C | 88.09 |
| 19OE1 | 25O22 | 25C | 72.43 | 19OE1 | 25O22 | 26N | 87.99 |
| 22O | 25O22 | 24C | 70.73 | 22O | 25O22 | 23N | 31.00 |
| 22O | 25O22 | 224OH2 | 78.01 | 22O | 25O22 | 24CA | 57.51 |
| 22O | 25O22 | 22C | 14.38 | 162ND1 | 25O22 | 162CE1 | 17.38 |
| 162ND1 | 25922 | 25C | 77.53 | 162ND1 | 25O22 | 26N | 86.27 |
| 24C | 25O22 | 23N | 76.28 | 24C | 25O22 | 24CA | 19.68 |
| 24C | 25O22 | 22C | 73.43 | 24C | 25O22 | 25C | 37.56 |
| 24C | 25O22 | 26N | 38.26 | 23N | 25O22 | 224OH2 | 48.26 |
| 23N | 25O22 | 24CA | 57.15 | 23N | 25O22 | 22C | 16.66 |
| 162CE1 | 25O22 | 25C . | 74.28 | 162CE1 | 25O22 | 26N | 86.57 |
| 224OH2 | 25O22 | 24CA | 86.57 | 224OH2 | 25O22 | 22C | 63.94 |
| 24CA | 25O22 | 22C | 56.72 | 24CA | 25O22 | 25C | 56.18 |
| 24CA | 25O22 | 26N | 53.14 | 25C | 25O22 | 26N | 15.75 |
| 61OD1 | 25C23 | 59O | 92.71 | 61OD1 | 25C23 | 264OH2 | 51.41 |
| 61OD1 | 25C23 | 61CG | 13.18 | 61OD1 | 25C23 | 61OD2 | 26.94 |
| 61OD1 | 25C23 | 59C | 87.40 | 59O | 25C23 | 67CD2 | 91.32 |
| 59O | 25C23 | 264OH2 | 79.96 | 59O | 25C23 | 61CG | 79.93 |
| 59O | 25C23 | 61OD2 | 71.08 | 59O | 25C23 | 59C | 5.39 |
| 67CE2 | 25C23 | 67CD2 | 18.11 | 67CD2 | 25C23 | 59C | 92.59 |
| 264OH2 | 25C23 | 61CG | 46.02 | 264OH2 | 25C23 | 61OD2 | 33.75 |
| 264OH2 | 25C23 | 59C | 77.27 | 61CG | 25C23 | 61OD2 | 15.44 |
| 61CG | 25C23 | 59C | 74.68 | 61OD2 | 25C23 | 59C | 66.25 |
| 59C | 25C24 | 60ND2 | 58.48 | 59O | 25C24 | 60CA | 44.55 |
| 59O | 25C24 | 59C | 9.80 | 59O | 25C24 | 61CG | 88.32 |
| 59O | 25C24 | 60C | 54.30 | 59O | 25C24 | 61N | 71.19 |
| 59O | 25C24 | 60N | 26.62 | 59O | 25C24 | 70OD1 | 52.26 |
| 59O | 25C24 | 61OD2 | 75.43 | 59O | 25C24 | 60CG | 60.011 |
| 59O | 25C24 | 60CB | 55.47 | 59O | 25C24 | 67N | 96.69 |
| 61OD1 | 25C24 | 60CA | 80.24 | 61OD1 | 25C24 | 59C | 97.84 |
| 61OD1 | 25C24 | 61CG | 15.04 | 61OD1 | 25C24 | 66CA | 87.60 |
| 61OD1 | 25C24 | 60C | 61.23 | 61OD1 | 25C24 | 61N | 50.12 |
| 61OD1 | 25C24 | 60N | 89.60 | 61OD1 | 25C24 | 61OD2 | 27.04 |
| 61OD1 | 25C24 | 60CB | 87.33 | 61OD1 | 25C24 | 65O | 55.48 |
| 67CD2 | 25C24 | 60ND2 | 70.35 | 67CD2 | 25C24 | 67CE2 | 21.12 |
| 67CD2 | 25C24 | 66CA | 60.05 | 67CD2 | 25C24 | 70OD1 | 65.25 |
| 67CD2 | 25C24 | 60CG | 77.71 | 67CD2 | 25C24 | 60CB | 94.80 |
| 67CD2 | 25C24 | 67N | 38.69 | 67CD2 | 25C24 | 66C | 42.86 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 67CD2 | 25C24 | 65O | 91.74 | 67CD2 | 25C24 | 67CG | 7.62 |
| 60ND2 | 25C24 | 67CE2 | 91.22 | 60ND2 | 25C24 | 60CA | 41.72 |
| 60ND2 | 25C24 | 59C | 52.47 | 60ND2 | 25C24 | 66CA | 51.12 |
| 60ND2 | 25C24 | 60C | 59.58 | 60ND2 | 25C24 | 61N | 66.53 |
| 60ND2 | 25C24 | 60N | 44.60 | 60ND2 | 25C24 | 70OD1 | 41.24 |
| 60ND2 | 25C24 | 60CG | 12.36 | 60ND2 | 25C24 | 60CB | 29.62 |
| 60ND2 | 25C24 | 67N | 38.69 | 60ND2 | 25C24 | 66C | 49.79 |
| 60ND2 | 25C24 | 65O | 68.79 | 60ND2 | 25C24 | 67CG | 64.10 |
| 67CE2 | 25C24 | 66CA | 70.56 | 67CE2 | 25C24 | 70OD1 | 82.90 |
| 67CE2 | 25C24 | 60CG | 97.67 | 67CE2 | 25C24 | 67N | 56.69 |
| 67CE2 | 25C24 | 66C | 55.71 | 67CE2 | 25C24 | 65O | 96.69 |
| 67CE2 | 25C24 | 67CG | 28.20 | 60CA | 25C24 | 59C | 34.75 |
| 60CA | 25C24 | 61CG | 65.91 | 60CA | 25C24 | 66CA | 65.63 |
| 60CA | 25C24 | 60C | 19.12 | 60CA | 25C24 | 61N | 32.35 |
| 60CA | 25C24 | 60N | 17.94 | 60CA | 25C24 | 70OD1 | 70.97 |
| 60CA | 25C24 | 61OD2 | 62.09 | 60CA | 25C24 | 60CG | 32.72 |
| 60CA | 25C24 | 60CB | 16.35 | 60CA | 25C24 | 67N | 73.13 |
| 60CA | 25C24 | 66C | 76.33 | 60CA | 25C24 | 65O | 56.57 |
| 59C | 25C24 | 61CG | 83.18 | 59C | 25C24 | 66CA | 96.04 |
| 59C | 25C24 | 60C | 45.42 | 59C | 25C24 | 61N | 62.28 |
| 59C | 25C24 | 60N | 16.82 | 59C | 25C24 | 70OD1 | 54.54 |
| 59C | 25C24 | 61oD2 | 71.72 | 59C | 25C24 | 60CG | 52.21 |
| 59C | 25C24 | 60CB | 46.02 | 59C | 25C24 | 67N | 91.16 |
| 59C | 25C24 | 65O | 91.18 | 61CG | 25C24 | 66CA | 85.83 |
| 61CG | 25C24 | 60C | 46.79 | 61CG | 25C24 | 61N | 37.73 |
| 61CG | 25C24 | 60N | 74.56 | 61CG | 25C24 | 61OD2 | 15.30 |
| 61CG | 25C24 | 60CG | 92.19 | 61CG | 25C24 | 60CB | 74.64 |
| 61CG | 25C24 | 65O | 52.44 | 66CA | 25C24 | 60C | 69.53 |
| 66CA | 25C24 | 61N | 60.35 | 66CA | 25C24 | 60N | 81.05 |
| 66CA | 25C24 | 70OD1 | 85.92 | 66CA | 25C24 | 61OD2 | 97.05 |
| 66CA | 25C24 | 60CG | 45.49 | 66CA | 25C24 | 60CB | 50.81 |
| 66CA | 25C24 | 67N | 29.45 | 66CA | 25C24 | 66C | 17.50 |
| 66CA | 25C24 | 65O | 33.39 | 66CA | 25C24 | 67CG | 60.31 |
| 60C | 25C24 | 61N | 16.90 | 60C | 25C24 | 60N | 31.03 |
| 60C | 25C24 | 70OD1 | 89.71 | 60C | 25C24 | 61OD2 | 43.83 |
| 60C | 25C24 | 60CG | 49.02 | 60C | 25C24 | 60CB | 30.73 |
| 60C | 25C24 | 67N | 85.40 | 60C | 25C24 | 66C | 84.14 |
| 60C | 25C24 | 65O | 49.16 | 61N | 25C24 | 60N | 47.32 |
| 61N | 25C24 | 61OD2 | 41.00 | 61N | 25C24 | 60CG | 54.47 |
| 61N | 25C24 | 60CB | 37.23 | 61N | 25C24 | 67N | 82.57 |
| 61N | 25C24 | 66C | 77.02 | 61N | 25C24 | 65O | 34.06 |
| 60N | 25C24 | 70OD1 | 61.08 | 60N | 25C24 | 61OD2 | 66.32 |
| 60N | 25C24 | 60CG | 40.42 | 60N | 25C24 | 60CB | 30.28 |
| 66N | 25C24 | 67N | 81.86 | 60N | 25C24 | 66C | 88.80 |
| 60N | 25C24 | 65O | 74.46 | 70OD1 | 25C24 | 60CG | 53.02 |
| 70OD1 | 25C24 | 60CB | 66.53 | 70OD1 | 25C24 | 67N | 60.32 |
| 70OD1 | 25C24 | 66C | 75.88 | 70OD1 | 25C24 | 67CG | 57.76 |
| 61OD2 | 25C24 | 60CG | 92.66 | 61OD2 | 25C24 | 60CB | 74.33 |
| 61OD2 | 25C24 | 65O | 64.27 | 60CG | 25C24 | 60CB | 18.33 |
| 60CG | 25C24 | 67N | 41.67 | 60CG | 25C24 | 66C | 48.95 |
| 60CG | 25C24 | 65O | 57.71 | 60CG | 25C24 | 67CG | 72.33 |
| 60CB | 25C24 | 67N | 56.95 | 60CB | 25C24 | 66C | 60.17 |
| 60CB | 25C24 | 65O | 49.72 | 60CB | 25C24 | 67CG | 90.00 |
| 67N | 25C24 | 66C | 15.58 | 67N | 25C24 | 65O | 62.20 |
| 67N | 25C24 | 67CG | 35.72 | 66C | 25C24 | 65O | 50.68 |
| 66C | 25C24 | 67CG | 42.81 | 65O | 25C24 | 67CG | 93.15 |
| 66CA | 25C25 | 67CD2 | 74.47 | 66CA | 25C25 | 67CE2 | 88.53 |
| 66CA | 25C25 | 60ND2 | 59.31 | 66CA | 25C25 | 66N | 21.62 |
| 66CA | 25C25 | 65O | 44.29 | 66CA | 25C25 | 66C | 21.53 |
| 66CA | 25C25 | 65C | 36.30 | 66CA | 25C25 | 60CA | 74.60 |
| 66CA | 25C25 | 61N | 73.02 | 66CA | 25C25 | 67N | 33.98 |
| 66CA | 25C25 | 60C | 79.39 | 66CA | 25C25 | 60CG | 50.06 |
| 66CA | 25C25 | 66O | 28.68 | 66CA | 25C25 | 60CB | 56.47 |
| 66CA | 25C25 | 61CB | 88.35 | 66CA | 25C25 | 67CG | 69.03 |
| 66CA | 25C25 | 67CZ | 89.74 | 61OD1 | 25C25 | 66N | 99.44 |
| 61OD1 | 25C25 | 65O | 70.37 | 61OD1 | 25C25 | 65C | 80.66 |
| 61OD1 | 25C25 | 60CA | 81.54 | 61OD1 | 25C25 | 61CG | 15.19 |
| 61OD1 | 25C25 | 61N | 55.29 | 61OD1 | 25C25 | 59O | 88.76 |
| 61OD1 | 25C25 | 60C | 62.96 | 61OD1 | 25C25 | 60CB | 93.30 |
| 61OD1 | 25C25 | 61CB | 28.06 | 61OD1 | 25C25 | 61OD2 | 23.60 |
| 67CD2 | 25C25 | 67CE2 | 22.80 | 67CD2 | 25C25 | 60ND2 | 71.72 |
| 67CD2 | 25C25 | 66N | 86.08 | 67CD2 | 25C25 | 66C | 52.97 |
| 67CD2 | 25C25 | 59O | 98.99 | 67CD2 | 25C25 | 67N | 45.03 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 67CD2 | 25C25 | 60CG | 81.76 | 67CD2 | 25C25 | 66O | 50.77 |
| 67CD2 | 25C25 | 67CG | 6.70 | 67CD2 | 25C25 | 67CZ | 27.35 |
| 67C 2 | 25C25 | 60ND2 | 94.29 | 67CE2 | 25C25 | 66N | 93.17 |
| 67CE2 | 25C25 | 66C | 67.80 | 67CE2 | 25C25 | 67N | 64.98 |
| 67CE2 | 25C25 | 66O | 60.61 | 67CE2 | 25C25 | 67CG | 29.23 |
| 67CE2 | 25C25 | 67CZ | 4.94 | 60ND2 | 25C25 | 66N | 80.00 |
| 60ND2 | 25C25 | 65O | 81.55 | 60ND2 | 25C25 | 66C | 58.26 |
| 60ND2 | 25C25 | 65C | 87.34 | 60ND2 | 25C25 | 60CA | 40.17 |
| 60ND2 | 25C25 | 61N | 69.84 | 60ND2 | 25C25 | 59O | 49.72 |
| 60ND2 | 25C25 | 67N | 43.92 | 60ND2 | 25C25 | 60C | 58.97 |
| 60ND2 | 25C25 | 60CG | 15.02 | 60ND2 | 25C25 | 66O | 71.48 |
| 60ND2 | 25C25 | 60CB | 31.11 | 60ND2 | 25C25 | 67CG | 65.78 |
| 60ND2 | 25C25 | 61OD2 | 99.69 | 60ND2 | 25C25 | 67CZ | 99.01 |
| 66N | 25C25 | 65O | 33.95 | 66N | 25C25 | 66C | 36.67 |
| 66N | 25C25 | 65C | 19.02 | 66N | 25C25 | 60CA | 86.34 |
| 66N | 25C25 | 61CG | 95.07 | 66N | 25C25 | 61N | 72.60 |
| 66N | 25C25 | 67N | 53.18 | 66N | 25C25 | 60C | 84.37 |
| 66N | 25C25 | 60CG | 68.93 | 66N | 25C25 | 66O | 35.32 |
| 66N | 25C25 | 60CB | 70.27 | 66N | 25C25 | 61CB | 77.27 |
| 66N | 25C25 | 67CG | 82.14 | 66N | 25C25 | 67CZ | 92.55 |
| 65O | 25C25 | 66C | 65.47 | 65O | 25C25 | 65C | 17.60 |
| 65O | 25C25 | 60CA | 65.59 | 65O | 25C25 | 61CG | 62.59 |
| 65O | 25C25 | 61N | 40.94 | 65O | 25C25 | 67N | 77.29 |
| 65O | 25C25 | 60C | 55.85 | 65O | 25C25 | 60CG | 66.65 |
| 65O | 25C25 | 66O | 68.27 | 65O | 25C25 | 60CB | 56.61 |
| 65O | 25C25 | 61CB | 44.60 | 65O | 25C25 | 61OD2 | 71.81 |
| 66C | 25C25 | 65C | 54.91 | 66C | 25C25 | 60CA | 86.39 |
| 66C | 25C25 | 61N | 92.94 | 66C | 25C25 | 67N | 17.99 |
| 66C | 25C25 | 60C | 96.20 | 66C | 25C25 | 60CG | 55.13 |
| 66C | 25C25 | 66O | 13.59 | 66C | 25C25 | 60CB | 68.10 |
| 66C | 25C25 | 67CG | 47.70 | 66C | 25C25 | 67CZ | 69.56 |
| 65C | 25C25 | 60CA | 80.60 | 65C | 25C25 | 61CG | 76.13 |
| 65C | 25C25 | 61N | 58.52 | 65C | 25C25 | 67N | 70.10 |
| 65C | 25C25 | 60C | 73.03 | 65C | 25C25 | 60CG | 73.62 |
| 65C | 25C25 | 66O | 54.32 | 65C | 25C25 | 60CB | 68.42 |
| 60CA | 25C25 | 61CB | 58.45 | 65C | 25C25 | 61OD2 | 86.99 |
| 60CA | 25C25 | 61CG | 66.63 | 60CA | 25C25 | 61N | 34.12 |
| 60CA | 25C25 | 59O | 39.03 | 60CA | 25C25 | 67N | 78.67 |
| 60CA | 25C25 | 60C | 19.48 | 60CA | 25C25 | 60CG | 33.49 |
| 60CA | 25C25 | 66O | 99.43 | 60CA | 25C25 | 60CB | 18.48 |
| 60CA | 25C25 | 61CB | 63.35 | 60CA | 25C25 | 61OD2 | 59.93 |
| 61CG | 25C25 | 61N | 40.61 | 61CG | 25C25 | 59O | 78.90 |
| 61CG | 25C25 | 60C | 47.83 | 61CG | 25C25 | 60CG | 96.99 |
| 61CG | 25C25 | 60CB | 78.15 | 61CG | 25C25 | 61CB | 17.99 |
| 61CG | 25C25 | 61OD2 | 13.48 | 61N | 25C25 | 59O | 66.77 |
| 61N | 25C25 | 67N | 95.02 | 61N | 25C25 | 60C | 16.92 |
| 61N | 25C25 | 60CG | 57.64 | 61N | 25C25 | 60CB | 39.04 |
| 61N | 25C25 | 61CB | 30.85 | 61N | 25C25 | 61OD2 | 41.41 |
| 59O | 25C25 | 67N | 92.29 | 59O | 25C25 | 60C | 49.98 |
| 59O | 25C25 | 60CG | 59.13 | 59O | 25C25 | 60CB | 52.99 |
| 59O | 25C25 | 61CB | 86.68 | 59O | 25C25 | 67CG | 96.56 |
| 59O | 25C25 | 61OD2 | 66.16 | 67N | 25C25 | 60C | 93.00 |
| 67N | 25C25 | 60CG | 45.25 | 67N | 25C25 | 66O | 28.92 |
| 67N | 25C25 | 60CB | 62.00 | 67N | 25C25 | 67CG | 38.59 |
| 67N | 25C25 | 67CZ | 68.17 | 60C | 25C25 | 60CG | 49.75 |
| 60C | 25C25 | 60CB | 31.34 | 60C | 25C25 | 61CB | 44.00 |
| 60C | 25C25 | 61OD2 | 43.11 | 60CG | 25C25 | 66O | 68.70 |
| 60CG | 25C25 | 60CB | 18.86 | 60CG | 25C25 | 61CB | 88.11 |
| 60CG | 25C25 | 67CG | 75.30 | 60CG | 25C25 | 61OD2 | 92.65 |
| 66O | 25C25 | 60CB | 81.00 | 66O | 25C25 | 67CG | 47.02 |
| 66O | 25C25 | 67CZ | 61.34 | 60CB | 25C25 | 61CB | 69.79 |
| 60CB | 25C25 | 67CG | 94.15 | 60CB | 25C25 | 61OD2 | 74.45 |
| 61CB | 25C25 | 61OD2 | 28.84 | 67CG | 25C25 | 67CZ | 33.62 |
| 61OD1 | 25C26 | 65O | 71.36 | 61OD1 | 25C26 | 65C | 85.76 |
| 61OD1 | 25C26 | 61CG | 11.35 | 61OD1 | 25C26 | 61CB | 26.51 |
| 61OD1 | 25C26 | 61N | 48.33 | 61OD1 | 25C26 | 65CA | 84.59 |
| 61OD1 | 25C26 | 61OD2 | 15.64 | 67CE2 | 25C26 | 66CA | 78.50 |
| 67CE2 | 25C26 | 66N | 89.75 | 67CE2 | 25C26 | 67CD2 | 19.87 |
| 67CE2 | 25C26 | 66C | 60.32 | 67CE2 | 25C26 | 67CZ | 10.65 |
| 67CE2 | 25C26 | 66O | 56.85 | 66CA | 25C26 | 66N | 21.30 |
| 66CA | 25C26 | 65O | 40.66 | 66CA | 25C26 | 65C | 35.52 |
| 66CA | 25C26 | 67CD2 | 62.19 | 66CA | 25C26 | 61CG | 97.24 |
| 66CA | 25C26 | 66C | 18.45 | 66CA | 25C26 | 61CB | 83.20 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 66CA | 25C26 | 61N | 61.53 | 66CA | 25C26 | 67CZ | 84.37 |
| 66CA | 25C26 | 65CA | 50.10 | 66CA | 25C26 | 66O | 28.03 |
| 66N | 25C26 | 65O | 32.82 | 66N | 25C26 | 65C | 19.16 |
| 66N | 25C26 | 67CD2 | 77.48 | 66N | 25C26 | 61CG | 94.77 |
| 66N | 25C26 | 66C | 32.67 | 66N | 25C26 | 61CB | 77.42 |
| 66N | 25C26 | 61N | 65.23 | 66N | 25C26 | 67CZ | 92.40 |
| 66N | 25C26 | 65CA | 29.97 | 66N | 25C26 | 66O | 32.92 |
| 65O | 25C26 | 65C | 17.65 | 65O | 25C26 | 61CG | 61.95 |
| 65O | 25C26 | 66C | 58.76 | 65O | 25C26 | 61CB | 44.89 |
| 65O | 25C26 | 61N | 36.15 | 65O | 25C26 | 65CA | 29.75 |
| 65O | 25C26 | 61OD2 | 69.17 | 65O | 25C26 | 66O | 64.19 |
| 65C | 25C26 | 67CD2 | 96.05 | 65C | 25C26 | 61CG | 77.55 |
| 65C | 25C26 | 66C | 50.78 | 65C | 25C26 | 61CB | 59.53 |
| 65C | 25C26 | 61N | 53.71 | 65C | 25C26 | 65CA | 16.87 |
| 65C | 25C26 | 61OD2 | 85.83 | 65C | 25C26 | 66O | 52.07 |
| 67CD2 | 25C26 | 66C | 45.30 | 67CD2 | 25C26 | 67CZ | 29.89 |
| 67CD2 | 25C26 | 66O | 46.56 | 61CG | 25C26 | 61CB | 18.38 |
| 61CG | 25C26 | 61N | 36.98 | 61CG | 25C26 | 65CA | 79.04 |
| 61CG | 25C26 | 61OD2 | 11.28 | 66C | 25C26 | 61N | 78.34 |
| 66C | 25C26 | 67CZ | 65.93 | 66C | 25C26 | 65CA | 62.43 |
| 66C | 25C26 | 66O | 14.16 | 61CB | 25C26 | 61N | 29.95 |
| 61CB | 25C26 | 65CA | 60.78 | 61CB | 25C26 | 61OD2 | 28.51 |
| 61N | 25C26 | 65CA | 64.34 | 61N | 25C26 | 61OD2 | 38.83 |
| 61N | 25C26 | 66O | 89.56 | 67CZ | 25C26 | 66O | 59.87 |
| 65CA | 25C26 | 61OD2 | 89.18 | 65CA | 25C26 | 66O | 59.63 |
| 61OD1 | 25C27 | 61CG | 5.16 | 61OD1 | 25C27 | 61OD2 | 15.09 |
| 67CE2 | 25C27 | 67CD2 | 15.74 | 67CE2 | 25C27 | 67OH | 28.29 |
| 61CG | 25C27 | 61OD2 | 12.69 | 67CD2 | 25C27 | 67OH | 44.01 |
| 61OD1 | 25C28 | 61CG | 9.27 | 61OD1 | 25C28 | 264OH2 | 52.17 |
| 61OD1 | 25C28 | 61OD2 | 23.20 | 67CE2 | 25C28 | 67CD2 | 15.49 |
| 61CG | 25C28 | 264OH2 | 46.24 | 61CG | 25C28 | 61OD2 | 14.74 |
| 264OH2 | 25C28 | 61OD2 | 33.06 | 66N | 25C29 | 65C | 24.86 |
| 66N | 25C29 | 65O | 39.60 | 66N | 25C29 | 66CA | 24.12 |
| 66N | 25C29 | 65CA | 41.74 | 66N | 25C29 | 67CE2 | 94.22 |
| 66N | 25C29 | 64O | 81.94 | 66N | 25C29 | 66C | 34.73 |
| 66N | 25C29 | 66O | 37.60 | 66N | 25C29 | 65N | 53.80 |
| 66N | 25C29 | 67CD2 | 79.01 | 66N | 25C29 | 61CG | 98.70 |
| 66N | 25C29 | 64C | 70.01 | 66N | 25C29 | 61CB | 84.65 |
| 65C | 25C29 | 65O | 20.60 | 65C | 25C29 | 66CA | 42.11 |
| 65C | 25C29 | 65CA | 24.93 | 65C | 25C29 | 61OD1 | 91.42 |
| 65C | 25C29 | 64O | 61.11 | 65C | 25C29 | 66C | 58.05 |
| 65C | 25C29 | 66O | 62.45 | 65C | 25C29 | 65N | 31.53 |
| 65C | 25C29 | 61CG | 79.83 | 65C | 25C29 | 64C | 47.67 |
| 65C | 25C29 | 61CB | 63.17 | 65O | 25C29 | 66CA | 46.14 |
| 65O | 25C29 | 65CA | 39.66 | 65O | 25C29 | 61OD1 | 71.78 |
| 65O | 25C29 | 64O | 64.40 | 65O | 25C29 | 66C | 65.45 |
| 65O | 25C29 | 66O | 74.94 | 65O | 25C29 | 65N | 37.56 |
| 65O | 25C29 | 61CG | 60.19 | 65O | 25C29 | 64C | 50.20 |
| 65O | 25C29 | 61CB | 45.06 | 66CA | 25C29 | 65CA | 64.24 |
| 66CA | 25C29 | 67CE2 | 75.91 | 66CA | 25C29 | 66C | 19.63 |
| 66CA | 25C29 | 66O | 32.86 | 66CA | 25C29 | 65N | 73.62 |
| 66CA | 25C29 | 67CD2 | 59.00 | 66CA | 25C29 | 61CG | 93.56 |
| 66CA | 25C29 | 64C | 89.77 | 66CA | 25C29 | 61CB | 85.67 |
| 65CA | 25C29 | 61OD1 | 97.52 | 65CA | 25C29 | 64O | 40.31 |
| 65CA | 25C29 | 66C | 76.17 | 65CA | 25C29 | 66O | 74.54 |
| 65CA | 25C29 | 65N | 15.70 | 65CA | 25C29 | 61CG | 87.20 |
| 65CA | 25C29 | 64C | 29.78 | 65CA | 25C29 | 61CB | 68.64 |
| 61OD1 | 25C29 | 64O | 78.88 | 61OD1 | 25C29 | 65N | 83.10 |
| 61OD1 | 25C29 | 61CG | 11.60 | 61OD1 | 25C29 | 64C | 76.76 |
| 61OD1 | 25C29 | 61CB | 29.29 | 67CE2 | 25C29 | 66C | 59.68 |
| 67CE2 | 25C29 | 66O | 59.54 | 67CE2 | 25C29 | 67CD2 | 17.43 |
| 64O | 25C29 | 65N | 29.62 | 64O | 25C29 | 61CG | 73.88 |
| 64O | 25C29 | 64C | 14.26 | 64O | 25C29 | 61CB | 59.65 |
| 66C | 25C29 | 66O | 16.37 | 66C | 25C29 | 65N | 88.46 |
| 66C | 25C29 | 67CD2 | 44.33 | 66O | 25C29 | 65N | 89.10 |
| 66O | 25C29 | 67CD2 | 48.06 | 65N | 25C29 | 61CG | 73.50 |
| 65N | 25C29 | 64C | 16.31 | 65N | 25C29 | 61CB | 55.08 |
| 61CG | 25C29 | 64C | 69.32 | 61CG | 25C29 | 61CB | 18.57 |
| 64C | 25C29 | 61CB | 52.55 | 66N | 25O30 | 67CE2 | 95.44 |
| 66N | 25O30 | 65C | 20.14 | 66N | 25O30 | 66O | 41.64 |
| 66N | 25O30 | 66CA | 20.76 | 66N | 25O30 | 65CA | 36.46 |
| 66N | 25O30 | 66C | 35.12 | 66N | 25O30 | 67CD2 | 78.01 |
| 66N | 25O30 | 65O | 28.77 | 66N | 25O30 | 64O | 70.26 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 67CE2 | 25O30 | 66O | 66.02 | 67CE2 | 25O30 | 66CA | 75.33 |
| 67CE2 | 25O30 | 66C | 62.32 | 67CE2 | 25O30 | 67CD2 | 17.44 |
| 67CE2 | 25O30 | 67CZ | 17.35 | 67CE2 | 25O30 | 67OH | 32.31 |
| 65C | 25O30 | 66O | 61.78 | 65C | 25O30 | 66CA | 35.78 |
| 65C | 25O30 | 65CA | 21.92 | 65C | 25O30 | 66C | 54.08 |
| 65C | 25O30 | 67CD2 | 93.11 | 65C | 25O30 | 65O | 13.87 |
| 65C | 25O30 | 64O | 51.57 | 66O | 25O30 | 66CA | 34.58 |
| 66O | 25O30 | 65CA | 74.20 | 66O | 25O30 | 66C | 16.71 |
| 66O | 25O30 | 67CD2 | 51.17 | 66O | 25O30 | 67CZ | 70.40 |
| 66O | 25O30 | 67OH | 86.34 | 66O | 25O30 | 65O | 68.48 |
| 66CA | 25O30 | 65CA | 55.92 | 66CA | 25O30 | 66C | 20.67 |
| 66CA | 25O30 | 67CD2 | 58.02 | 66CA | 25O30 | 67CZ | 88.15 |
| 66CA | 25O30 | 65O | 36.77 | 66CA | 25O30 | 64O | 87.19 |
| 65CA | 25O30 | 66C | 71.35 | 65CA | 25O30 | 65O | 31.68 |
| 65CA | 25O30 | 64O | 35.13 | 66C | 25O30 | 67CD2 | 45.28 |
| 66C | 25O30 | 67CZ | 71.68 | 66C | 25O30 | 67OH | 89.19 |
| 66C | 25O30 | 65O | 57.23 | 67CD2 | 25O30 | 67CZ | 31.46 |
| 67CD2 | 25O30 | 67OH | 48.52 | 67CD2 | 25O30 | 65O | 89.19 |
| 67CZ | 25O30 | 67OH | 17.73 | 65O | 25O30 | 64O | 52.71 |
| 66N | 25C31 | 65CA | 39.43 | 66N | 25C31 | 65C | 19.88 |
| 66N | 25C31 | 66O | 41.44 | 66N | 25C31 | 66CA | 16.42 |
| 66N | 25C31 | 64O | 73.76 | 66N | 25C31 | 66C | 31.86 |
| 66N | 25C31 | 65O | 24.99 | 66N | 25C31 | 67CE2 | 78.02 |
| 66N | 25C31 | 65N | 48.58 | 65CA | 25C31 | 65C | 22.92 |
| 65CA | 25C31 | 66O | 78.51 | 65CA | 25C31 | 66CA | 54.89 |
| 65CA | 25C31 | 64O | 37.80 | 65CA | 25C31 | 66C | 71.14 |
| 65CA | 25C31 | 65O | 28.31 | 65CA | 25C31 | 65N | 10.41 |
| 65C | 25C31 | 66O | 61.32 | 65C | 25C31 | 66CA | 33.07 |
| 65C | 25C31 | 64O | 54.01 | 65C | 25C31 | 66C | 51.04 |
| 65C | 25C31 | 65O | 9.78 | 65C | 25C31 | 67CE2 | 90.50 |
| 65C | 25C31 | 65N | 30.23 | 66O | 25C31 | 66CA | 32.38 |
| 66O | 25C31 | 66C | 14.52 | 66O | 25C31 | 65O | 65.09 |
| 66O | 25C31 | 67CE2 | 56.24 | 66O | 25C31 | 65N | 88.60 |
| 66CA | 25C31 | 64O | 86.14 | 66CA | 25C31 | 66C | 19.15 |
| 66CA | 25C31 | 65O | 33.97 | 66CA | 25C31 | 67CE2 | 61.64 |
| 66CA | 25C31 | 65N | 63.22 | 64O | 25C31 | 65O | 52.33 |
| 64O | 25C31 | 65N | 27.39 | 66C | 25C31 | 65O | 53.03 |
| 66C | 25C31 | 67CE2 | 52.59 | 66C | 25C31 | 65N | 80.44 |
| 65O | 25C31 | 67CE2 | 85.62 | 65O | 25C31 | 65N | 32.85 |
| 65CA | 25O32 | 64O | 42.64 | 65CA | 25O32 | 66N | 34.36 |
| 65CA | 25O32 | 65C | 19.66 | 65CA | 25O32 | 64C | 30.83 |
| 65CA | 25O32 | 65N | 14.60 | 64O | 25O32 | 66N | 73.09 |
| 64O | 25O32 | 65C | 55.36 | 64O | 25O32 | 64C | 12.34 |
| 64O | 25O32 | 65N | 28.48 | 66N | 25O32 | 65C | 17.74 |
| 66N | 25O32 | 64C | 63.03 | 66N | 25O32 | 65N | 48.15 |
| 65C | 25O32 | 64C | 45.59 | 65C | 25O32 | 65N | 31.63 |
| 64C | 25O32 | 65N | 16.37 | 66O | 25O33 | 66N | 39.03 |
| 66O | 25C33 | 65CA | 71.47 | 66O | 25C33 | 25SG | 98.45 |
| 66O | 25C33 | 65C | 53.71 | 66O | 25C33 | 66C | 9.09 |
| 66N | 25C33 | 65CA | 32.53 | 66N | 25C33 | 25SG | 95.78 |
| 66N | 25C33 | 65C | 14.69 | 66N | 25C33 | 66C | 30.21 |
| 161O | 25C33 | 161C | 15.33 | 161O | 25C33 | 25SG | 60.66 |
| 65CA | 25C33 | 25SG | 88.64 | 65CA | 25C33 | 65C | 18.08 |
| 65CA | 25C33 | 66C | 62.73 | 161C | 25C33 | 25SG | 68.01 |
| 25SG | 25C33 | 65C | 94.64 | 65C | 25C33 | 66C | 44.83 |
| 66O | 25C34 | 163CB | 85.75 | 66O | 25C34 | 66N | 32.40 |
| 161C | 25C34 | 161O | 16.73 | 161C | 25C34 | 162N | 17.83 |
| 161C | 25C34 | 163N | 62.24 | 161C | 25C34 | 162CA | 31.39 |
| 161C | 25C34 | 162C | 47.88 | 161C | 25C34 | 25SG | 73.05 |
| 161C | 25C34 | 161CA | 18.94 | 161C | 25C34 | 163CB | 92.63 |
| 161O | 25C34 | 162N | 30.34 | 161O | 25C34 | 163N | 65.51 |
| 161O | 25C34 | 162CA | 35.76 | 161O | 25C34 | 162C | 54.67 |
| 161O | 25C34 | 25SG | 62.53 | 161O | 25C34 | 161CA | 30.82 |
| 161O | 25C34 | 163CB | 95.27 | 162N | 25C34 | 163N | 46.66 |
| 162N | 25C34 | 162CA | 18.35 | 162N | 25C34 | 162C | 31.03 |
| 162N | 25C34 | 25SG | 69.25 | 162N | 25C34 | 161CA | 31.09 |
| 162N | 25C34 | 163CB | 76.34 | 163N | 25C34 | 162CA | 31.03 |
| 163N | 25C34 | 162C | 16.65 | 163N | 25C34 | 25SG | 45.82 |
| 163N | 25C34 | 161CA | 77.75 | 163N | 25C34 | 163CB | 30.49 |
| 162CA | 25C34 | 162C | 19.01 | 162CA | 25C34 | 25SG | 52.46 |
| 162CA | 25C34 | 161CA | 48.32 | 162CA | 25C3 | 163CB | 61.52 |
| 162C | 25C34 | 25SG | 55.74 | 162C | 25C34 | 161CA | 61.81 |
| 162C | 25C34 | 163CB | 45.32 | 25SG | 25C34 | 161CA | 91.65 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 25SG | 25C35 | 163CB | 53.96 | 25SG | 25C34 | 66N | 87.39 |
| 66O | 25C35 | 66C | 2.57 | 66O | 25C35 | 163CB | 96.66 |
| 66O | 25C35 | 26CB | 46.90 | 66O | 25C35 | 66N | 29.09 |
| 66O | 25C35 | 67CA | 31.24 | 66O | 25C35 | 68SD | 77.53 |
| 66O | 25C35 | 67CD1 | 62.23 | 66O | 25C35 | 67CE1 | 72.23 |
| 66C | 25C35 | 163CB | 98.61 | 66C | 25C35 | 26CB | 49.23 |
| 66C | 25C35 | 66N | 30.32 | 66C | 25C35 | 67CA | 29.98 |
| 66C | 25C35 | 68SD | 78.11 | 66C | 25C35 | 67CD1 | 59.82 |
| 66C | 25C35 | 67CE1 | 69.68 | 163CB | 25C35 | 26CB | 51.66 |
| 163CB | 25C35 | 67CA | 90.92 | 163CB | 25C35 | 209CD2 | 95.04 |
| 163CB | 25C35 | 68SD | 41.03 | 26CB | 25C35 | 66N | 52.74 |
| 26CB | 25C35 | 67CA | 56.99 | 26CB | 25C35 | 68SD | 53.93 |
| 26CB | 25C35 | 67CD1 | 97.81 | 66N | 25C35 | 67CA | 60.27 |
| 66N | 25C35 | 67CD1 | 84.58 | 66N | 25C35 | 67CE1 | 89.12 |
| 67CA | 25C35 | 209CD2 | 76.21 | 67CA | 25C35 | 68SD | 56.79 |
| 67CA | 25C35 | 67CD1 | 40.85 | 67CA | 25C35 | 67CE1 | 55.83 |
| 209CD2 | 25C35 | 68SD | 66.55 | 209CD2 | 25C35 | 67CD1 | 48.98 |
| 209CD2 | 25C35 | 67CE1 | 49.09 | 68SD | 25C35 | 67CD1 | 78.05 |
| 68SD | 25C35 | 67CE1 | 92.43 | 67CD1 | 25C35 | 67CE1 | 16.13 |
| 66O | 25C36 | 68SD | 96.83 | 66O | 25C36 | 26CB | 52.43 |
| 66O | 25C36 | 66C | 6.57 | 66O | 25C36 | 67CA | 36.71 |
| 66O | 25C36 | 26CX | 70.05 | 68SD | 25C36 | 163CB | 57.33 |
| 68SD | 25C36 | 163CA | 70.03 | 68SD | 25C36 | 134CB | 84.74 |
| 68SD | 25C36 | 163N | 89.11 | 68SD | 25C36 | 26CB | 67.27 |
| 68SD | 25C36 | 68CE | 22.41 | 68SD | 25C36 | 209CD2 | 84.13 |
| 68SD | 25C36 | 66C | 90.48 | 68SD | 25C36 | 67CA | 67.81 |
| 68SD | 25C36 | 162C | 99.30 | 68SD | 25C36 | 26CX | 59.77 |
| 163CB | 25C36 | 163CA | 20.06 | 163CB | 25C36 | 134CB | 81.47 |
| 163CB | 25C36 | 163N | 34.18 | 163CB | 25C36 | 26CB | 62.38 |
| 163CB | 25C36 | 68CE | 60.98 | 163CB | 25C36 | 162C | 48.31 |
| 163CB | 25C36 | 26CX | 44.78 | 163CA | 25C36 | 134CB | 65.51 |
| 163CA | 25C36 | 163N | 19.48 | 163CA | 25C36 | 26CB | 80.86 |
| 163CA | 25C36 | 68CE | 65.92 | 163CA | 25C36 | 162C | 30.24 |
| 163CA | 25C36 | 26CX | 63.59 | 134CB | 25C36 | 163N | 69.86 |
| 134CB | 25C36 | 68CE | 62.66 | 134CB | 25C36 | 209CD2 | 53.95 |
| 134CB | 25C36 | 162C | 59.74 | 163N | 25C36 | 26CB | 84.29 |
| 163N | 25C36 | 68CE | 85.05 | 163N | 25C36 | 162C | 15.50 |
| 163N | 25C36 | 26CX | 69.23 | 26CB | 25C36 | 68CE | 88.83 |
| 26CB | 25C36 | 66C | 50.37 | 26CB | 25C36 | 67CA | 61.54 |
| 26CB | 25C36 | 162C | 98.98 | 26CB | 25C36 | 26CX | 17.62 |
| 68CE | 25C36 | 209CD2 | 68.72 | 68CE | 25C36 | 67CA | 82.83 |
| 68CE | 25C36 | 162C | 90.28 | 68CE | 25C36 | 26CX | 78.81 |
| 209CD2 | 25C36 | 67CA | 82.71 | 66C | 25C36 | 67CA | 30.72 |
| 66C | 25C36 | 26CX | 67.86 | 67CA | 25C36 | 26CX | 75.01 |
| 162C | 25C36 | 26CX | 84.54 | 66O | 25C36 | 67CE1 | 76.69 |
| 66O | 25C37 | 67CZ | 72.75 | 66O | 25C37 | 67CD1 | 64.04 |
| 66O | 25C37 | 67OH | 86.40 | 66O | 25C37 | 67CE2 | 57.39 |
| 66O | 25C37 | 67CG | 48.64 | 67CE1 | 25C37 | 209CD2 | 60.17 |
| 67CE1 | 25C37 | 67CZ | 18.76 | 67CE1 | 25C37 | 67CD1 | 18.19 |
| 67CE1 | 25C37 | 67OH | 31.37 | 67CE1 | 25C37 | 67CE2 | 29.99 |
| 67CE1 | 25C37 | 67CG | 29.19 | 209CD2 | 25C37 | 67CZ | 78.42 |
| 209CD2 | 25C37 | 67CD1 | 57.12 | 209CD2 | 25C37 | 67OH | 84.22 |
| 209CD2 | 25C37 | 67CE2 | 89.26 | 209CD2 | 25C37 | 134CB | 51.72 |
| 209CD2 | 25C37 | 67CG | 70.82 | 67CZ | 25C37 | 67CD1 | 31.75 |
| 67CZ | 25C37 | 67OH | 17.50 | 67CZ | 25C37 | 67CE2 | 16.32 |
| 67CZ | 25C37 | 67CG | 34.21 | 67CD1 | 25C37 | 67OH | 47.81 |
| 67CD1 | 25C37 | 67CE2 | 34.53 | 67CD1 | 25C37 | 67CG | 15.87 |
| 67OH | 25C37 | 160O | 98.96 | 67OH | 25C37 | 67CE2 | 29.39 |
| 67OH | 25C37 | 67CG | 51.71 | 160O | 25C37 | 134CB | 78.01 |
| 67CE2 | 25C37 | 67CG | 28.65 | 65CA | 25C38 | 66N | 37.26 |
| 65CA | 25C38 | 66O | 76.23 | 65CA | 25C38 | 26CD1 | 57.25 |
| 65CA | 25C38 | 65C | 19.78 | 65CA | 25C38 | 23O | 54.21 |
| 65CA | 25C38 | 224OH2 | 55.95 | 65CA | 25C38 | 26CB | 85.45 |
| 65CA | 25C38 | 65N | 11.58 | 65CA | 25C38 | 26CG | 68.24 |
| 25SG | 25C38 | 26CD1 | 77.09 | 25SG | 25C38 | 23O | 67.47 |
| 25SG | 25C38 | 161O | 68.31 | 25SG | 25C38 | 224OH2 | 89.14 |
| 25SG | 25C38 | 26CB | 70.06 | 25SG | 25C38 | 26CG | 76.35 |
| 66N | 25C38 | 66O | 39.10 | 66N | 25C38 | 26CD1 | 47.09 |
| 66N | 25C38 | 65C | 17.53 | 66N | 25C38 | 23O | 72.97 |
| 66N | 25C38 | 224OH2 | 92.76 | 66N | 25C38 | 26CB | 59.41 |
| 66N | 25C38 | 65N | 48.17 | 66N | 25C38 | 26CG | 48.12 |
| 66O | 25C38 | 26CD1 | 61.41 | 66O | 25C38 | 65C | 56.61 |
| 66O | 25C38 | 26CB | 46.70 | 66O | 25C38 | 65N | 87.28 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 66O | 25C38 | 26CG | 50.49 | 26CD1 | 25C38 | 65C | 48.65 |
| 26CD1 | 25C38 | 23O | 40.99 | 26CD1 | 25C38 | 224OH2 | 85.80 |
| 26CD1 | 25C38 | 26CB | 32.92 | 26CD1 | 25C38 | 65N | 59.48 |
| 26CD1 | 25C38 | 26CG | 15.33 | 65C | 25C38 | 23O | 62.21 |
| 65C | 25C38 | 224OH2 | 75.31 | 65C | 25C38 | 26CB | 70.46 |
| 65C | 25C38 | 65N | 30.67 | 65C | 25C38 | 26CG | 55.38 |
| 23O | 25C38 | 224OH2 | 47.84 | 23O | 25C38 | 26CB | 69.70 |
| 23O | 25C38 | 65N | 46.94 | 23O | 25C38 | 26CG | 55.26 |
| 161O | 25C38 | 224OH2 | 93.60 | 224OH2 | 25C38 | 65N | 44.65 |
| 26CB | 25C38 | 65N | 90.52 | 26CB | 25C38 | 26CG | 18.20 |
| 65N | 25C38 | 26CG | 72.50 | 66N | 25C38 | 26CD1 | 65.73 |
| 66N | 25O39 | 65CA | 47.24 | 66N | 25O39 | 65C | 22.10 |
| 66N | 25O39 | 66O | 47.99 | 66N | 25O39 | 23O | 95.16 |
| 66N | 25O39 | 26CG | 65.86 | 66N | 25O39 | 26CB | 78.81 |
| 66N | 25O39 | 26NE1 | 58.35 | 66N | 25O39 | 66CA | 14.64 |
| 66N | 25O39 | 66C | 34.63 | 66N | 25O39 | 65N | 57.39 |
| 66N | 25O39 | 65O | 22.72 | 66N | 25O39 | 26CX | 95.35 |
| 66N | 25O39 | 26CD2 | 57.58 | 26CD1 | 25O39 | 65CA | 77.50 |
| 26CD1 | 25O39 | 65C | 65.28 | 26CD1 | 25O39 | 66O | 80.81 |
| 26CD1 | 25O39 | 23O | 52.52 | 26CD1 | 25O39 | 26CG | 20.44 |
| 26CD1 | 25O39 | 26CB | 42.80 | 26CD1 | 25O39 | 25SG | 91.26 |
| 26CD1 | 25O39 | 26NE1 | 14.54 | 26CD1 | 25O39 | 66CA | 62.36 |
| 26CD1 | 25O39 | 66C | 69.41 | 26CD1 | 25O39 | 65N | 74.38 |
| 26CD1 | 25O39 | 26N | 49.70 | 26CD1 | 25O39 | 65O | 61.20 |
| 26CD1 | 25O39 | 23C | 59.40 | 26CD1 | 25O39 | 26CX | 47.75 |
| 26CD1 | 25O39 | 224OH2 | 98.62 | 26CD1 | 25O39 | 26CD2 | 17.11 |
| 65CA | 25O39 | 65C | 25.89 | 65CA | 25O39 | 66O | 94.13 |
| 65CA | 25O39 | 23O | 66.29 | 65CA | 25O39 | 26CG | 92.00 |
| 65CA | 25O39 | 26NE1 | 63.11 | 65CA | 25O39 | 66CA | 61.64 |
| 65CA | 25O39 | 66C | 81.81 | 65CA | 25O39 | 65N | 12.36 |
| 65CA | 25O39 | 65O | 27.30 | 65CA | 25O39 | 23C | 72.79 |
| 65CA | 25O39 | 224OH2 | 56.03 | 65CA | 25O39 | 26CD2 | 82.72 |
| 65C | 25O39 | 66O | 70.06 | 65C | 25O39 | 23O | 78.02 |
| 65C | 25O39 | 26CG | 73.56 | 65C | 25O39 | 26CB | 92.36 |
| 65C | 25O39 | 26NE1 | 53.27 | 65C | 25O39 | 66CA | 36.02 |
| 65C | 25O39 | 66C | 56.60 | 65C | 25O39 | 65N | 35.32 |
| 65C | 25O39 | 65O | 4.12 | 65C | 25O39 | 23C | 86.65 |
| 65C | 25O39 | 224OH2 | 81.45 | 65C | 25O39 | 26CD2 | 64.11 |
| 66O | 25O39 | 26CG | 65.04 | 66O | 25O39 | 26CB | 58.06 |
| 66O | 25O39 | 26NE1 | 84.63 | 66O | 25O39 | 66CA | 35.35 |
| 66O | 25O39 | 66C | 15.25 | 66O | 25O39 | 26N | 91.09 |
| 66O | 25O39 | 65O | 70.58 | 66O | 25O39 | 26CX | 73.00 |
| 66O | 25O39 | 26CD2 | 63.97 | 23O | 25O39 | 26CG | 71.55 |
| 23O | 25O39 | 26CB | 88.75 | 23O | 25O39 | 25SG | 73.57 |
| 23O | 25O39 | 26NE1 | 46.88 | 23O | 25O39 | 65N | 54.73 |
| 23O | 25O39 | 26N | 69.90 | 23O | 25O39 | 65O | 75.20 |
| 23O | 25O39 | 23C | 9.35 | 23O | 25O39 | 26CX | 82.73 |
| 23O | 25O39 | 224OH2 | 48.87 | 23O | 25O39 | 26CD2 | 69.59 |
| 26CG | 25O39 | 26CB | 23.44 | 26CG | 25O39 | 25SG | 90.54 |
| 26CG | 25O39 | 26NE1 | 33.09 | 26CG | 25O39 | 66CA | 57.23 |
| 26CG | 25O39 | 66C | 56.85 | 26CG | 25O39 | 65N | 91.62 |
| 26CG | 25O39 | 26N | 42.86 | 26CG | 25O39 | 65O | 69.92 |
| 26CG | 25O39 | 23C | 77.26 | 26CG | 25O39 | 26CX | 33.37 |
| 26CG | 25O39 | 26CD2 | 9.50 | 26CG | 25O39 | 25SG | 80.06 |
| 26CB | 25O39 | 26NE1 | 56.36 | 26CB | 25O39 | 66CA | 66.31 |
| 26CB | 25O39 | 66C | 56.61 | 26CB | 25O39 | 26N | 34.26 |
| 26CB | 25O39 | 65O | 89.29 | 26CB | 25O39 | 23C | 92.00 |
| 26CB | 25O39 | 26CX | 17.14 | 26CB | 25O39 | 26CD2 | 31.88 |
| 25SG | 25O39 | 26N | 48.14 | 25SG | 25O39 | 23C | 65.56 |
| 25SG | 25O39 | 26CX | 62.98 | 25SG | 25O39 | 224OH2 | 85.27 |
| 25SG | 25O39 | 26CD2 | 98.66 | 25SG | 25O39 | 66CA | 58.87 |
| 26NE1 | 25O39 | 66C | 71.02 | 26NE1 | 25O39 | 65N | 59.89 |
| 26NE1 | 25O39 | 26N | 63.22 | 26NE1 | 25O39 | 65O | 49.16 |
| 26NE1 | 25O39 | 23C | 55.32 | 26NE1 | 25O39 | 26CX | 62.29 |
| 26NE1 | 25O39 | 224OH2 | 88.14 | 26NE1 | 25O39 | 26CD2 | 26.49 |
| 66CA | 25O39 | 66C | 20.82 | 66CA | 25O39 | 65N | 71.23 |
| 66CA | 25O39 | 26N | 98.43 | 66CA | 25O39 | 65O | 35.79 |
| 66CA | 25O39 | 26CX | 83.32 | 66CA | 25O39 | 26CD2 | 50.40 |
| 66C | 25O39 | 65N | 91.92 | 66C | 25O39 | 26N | 90.87 |
| 66C | 25O39 | 65O | 56.59 | 66C | 25O39 | 26CX | 73.34 |
| 66C | 25O39 | 26CD2 | 53.53 | 66C | 25O39 | 65O | 35.54 |
| 65N | 25O39 | 23C | 60.74 | 65N | 25O39 | 224OH2 | 46.37 |
| 65N | 25O39 | 26CD2 | 82.99 | 65N | 25O39 | 23C | 68.72 |

TABLE XIII-continued

Table of angles between atoms of the inhibitor and protein for all protein atoms within 5 Angstroms of the inhibitor 2,2'-N,N'-bis-benzyloxycarbonyl-L-leucinylcarbohydrazide.

| Atom 1 | Atom 2 | Atom 3 | Angle | Atom 1 | Atom 2 | Atom 3 | Angle |
|---|---|---|---|---|---|---|---|
| 26N | 25O39 | 26CX | 18.10 | 26N | 25O39 | 26CD2 | 51.68 |
| 65O | 25O39 | 23C | 84.01 | 65O | 25O39 | 224OH2 | 81.91 |
| 65O | 25O39 | 26CD2 | 60.44 | 65O | 25O39 | 26CX | 83.51 |
| 23C | 25O39 | 224OH2 | 45.98 | 23C | 25O39 | 26CD2 | 76.48 |
| 26CX | 25O39 | 26CD2 | 42.86 | 25SG | 25N40 | 161O | 86.06 |
| 25SG | 25N40 | 23O | 74.10 | 25SG | 25N40 | 161C | 85.73 |
| 25SG | 25N40 | 23C | 68.83 | 25SG | 25N40 | 23CA | 76.96 |
| 25SG | 25N40 | 162CA | 56.65 | 25SG | 25N40 | 25CB | 6.53 |
| 25SG | 25N40 | 26CD1 | 72.41 | 161O | 25N40 | 161C | 12.75 |
| 161O | 25N40 | 162CA | 33.97 | 161O | 25N40 | 25CB | 90.20 |
| 224OH2 | 25N40 | 23O | 52.97 | 224OH2 | 25N40 | 65CA | 57.51 |
| 224OH2 | 25N40 | 23C | 49.02 | 224OH2 | 25N40 | 23CA | 35.43 |
| 224OH2 | 25N40 | 26CD1 | 85.10 | 23O | 25N40 | 65CA | 51.31 |
| 23O | 25N40 | 23C | 13.96 | 23O | 25N40 | 23CA | 29.87 |
| 23O | 25N40 | 25CB | 68.50 | 23O | 25N40 | 26CD1 | 37.36 |
| 65CA | 25N40 | 23C | 62.89 | 65CA | 25N40 | 23CA | 68.80 |
| 65CA | 25N40 | 26CD1 | 48.33 | 161C | 25N40 | 162CA | 29.53 |
| 161C | 25N40 | 25CB | 90.88 | 23C | 25N40 | 23CA | 18.22 |
| 23C | 25N40 | 25CB | 62.59 | 23C | 25N40 | 26CD1 | 49.62 |
| 23CA | 25N40 | 25CB | 70.43 | 23CA | 25N40 | 26CD1 | 67.09 |
| 162CA | 25N40 | 25CB | 62.21 | 25CB | 25N40 | 26CD1 | 70.23 |
| 25SG | 25N41 | 23C | 99.66 | 25SG | 25N41 | 25CB | 18.83 |
| 25SG | 25N41 | 25N | 49.91 | 25SG | 25N41 | 24N | 86.40 |
| 25SG | 25N41 | 161O | 75.97 | 25SG | 25N41 | 26CD1 | 82.58 |
| 25SG | 25N41 | 25CA | 32.30 | 25SG | 25N41 | 26N | 41.60 |
| 23O | 25N41 | 224OH2 | 68.49 | 23O | 25N41 | 23C | 20.89 |
| 23O | 25N41 | 23CA | 42.41 | 23O | 25N41 | 25CB | 89.72 |
| 23O | 25N41 | 25N | 55.16 | 23O | 25N41 | 24N | 28.91 |
| 23O | 25N41 | 65CA | 55.11 | 23O | 25N41 | 26CD1 | 40.72 |
| 23O | 25N41 | 25CA | 71.69 | 23O | 25N41 | 26N | 66.61 |
| 23O | 25N41 | 23N | 44.84 | 224OH2 | 25N41 | 23 | 65.79 |
| 224OH2 | 25N41 | 23CA | 48.09 | 224OH2 | 25N41 | 24N | 78.14 |
| 224OH2 | 25N41 | 65CA | 60.11 | 224OH2 | 25N41 | 26CD1 | 98.71 |
| 224OH2 | 25N41 | 23N | 46.92 | 23C | 25N41 | 23CA | 25.44 |
| 23C | 25N41 | 25CB | 82.83 | 23C | 25N41 | 25N | 49.85 |
| 23C | 25N41 | 24N | 13.60 | 23C | 25N41 | 65CA | 73.03 |
| 23C | 25N41 | 26CD1 | 59.09 | 23C | 25N41 | 25CA | 67.43 |
| 23C | 25N41 | 26N | 73.57 | 23C | 25N41 | 23N | 27.92 |
| 23CA | 25N41 | 25CB | 95.07 | 23CA | 25N41 | 25N | 68.21 |
| 23CA | 25N41 | 24N | 33.15 | 23CA | 25N41 | 65CA | 80.89 |
| 23CA | 25N41 | 26CD1 | 83.00 | 23CA | 25N41 | 25CA | 84.37 |
| 23CA | 25N41 | 26N | 97.47 | 23CA | 25N41 | 23N | 2.51 |
| 25CB | 25N41 | 25N | 34.64 | 25CB | 25N41 | 24N | 69.27 |
| 25CB | 25N41 | 161O | 90.28 | 25CB | 25N41 | 26CD1 | 80.97 |
| 25CB | 25N41 | 25CA | 18.50 | 25CB | 25N41 | 26N | 41.33 |
| 25CB | 25N41 | 23N | 95.93 | 25CB | 25N41 | 24N | 36.95 |
| 25N | 25N41 | 26CD1 | 57.65 | 25N | 25N41 | 25CA | 17.61 |
| 25N | 25N41 | 26N | 34.79 | 25N | 25N41 | 23N | 69.91 |
| 24N | 25N41 | 65CA | 83.83 | 24N | 25N41 | 26CD1 | 59.64 |
| 24N | 25N41 | 25CA | 54.36 | 24N | 25N41 | 26N | 64.38 |
| 24N | 25N41 | 23N | 35.31 | 24N | 25N41 | 26CD1 | 50.18 |
| 65CA | 25N41 | 26N | 90.57 | 65CA | 25N41 | 23N | 82.10 |
| 26CD1 | 25N41 | 25CA | 64.68 | 26CD1 | 25N41 | 26N | 41.23 |
| 26CD1 | 25N41 | 23N | 85.46 | 26CD1 | 25N41 | 26N | 29.42 |
| 25CA | 25N41 | 23N | 85.82 | 25CA | 25N41 | 23N | 99.68 |
| 66O | 25N42 | 66N | 49.20 | 66O | 25N42 | 65CA | 85.32 |
| 66O | 25N42 | 66C | 14.31 | 66O | 25N42 | 65C | 66.36 |
| 66O | 25N42 | 66CA | 34.57 | 66O | 25N42 | 67CE2 | 59.50 |
| 66N | 25N42 | 65CA | 37.29 | 66N | 25N42 | 66C | 37.91 |
| 66N | 25N42 | 65C | 17.17 | 66N | 25N42 | 66CA | 18.36 |
| 66N | 25N42 | 67CE2 | 79.25 | 66N | 25N42 | 66C | 75.14 |
| 65CA | 25N42 | 65C | 21.61 | 65CA | 25N42 | 66CA | 55.24 |
| 66C | 25N42 | 65C | 54.69 | 66C | 25N42 | 66CA | 21.22 |
| 66C | 25N42 | 67CE2 | 55.45 | 66C | 25N42 | 66CA | 34.04 |
| 65C | 25N42 | 67CE2 | 88.07 | 65C | 25N42 | 67CE2 | 63.12 |

TABLE XIV

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 184CB | 25C1 | 184CG | 19.63 | 184CB | 25C1 | 184O | 37.95 |
| 184CB | 25C1 | 184CD2 | 33.99 | 184CB | 25C1 | 184CE3 | 43.05 |
| 184CB | 25C1 | 188CD1 | 60.59 | 184CG | 25C1 | 184O | 56.47 |
| 184CG | 25C1 | 184CD2 | 18.11 | 184CG | 25C1 | 184CE3 | 33.19 |
| 184CG | 25C1 | 188CD1 | 68.63 | 184O | 25C1 | 184CD2 | 71.92 |
| 184O | 25C1 | 184CE3 | 78.39 | 184O | 25C1 | 188CD1 | 69.15 |
| 184CD2 | 25C1 | 184CE3 | 17.41 | 184CD2 | 25C1 | 188CD1 | 62.78 |
| 184CE3 | 25C1 | 188CD1 | 48.96 | 184O | 25C2 | 184CB | 47.37 |
| 184O | 25C2 | 184C | 14.60 | 184O | 25C2 | 184CG | 67.03 |
| 184O | 25C2 | 184CA | 35.09 | 184O | 25C2 | 184CD2 | 79.86 |
| 184O | 25C2 | 184CD1 | 72.22 | 184O | 25C2 | 18ND2 | 51.81 |
| 184CB | 25C2 | 184C | 37.41 | 184CB | 25C2 | 184CG | 20.57 |
| 184CB | 25C2 | 184CA | 21.23 | 184CB | 25C2 | 184CD2 | 32.66 |
| 184CB | 25C2 | 184CD1 | 31.54 | 184CB | 25C2 | 18ND2 | 83.90 |
| 184C | 25C2 | 184CG | 55.27 | 184C | 25C2 | 184CA | 21.27 |
| 184C | 25C2 | 184CD2 | 69.82 | 184C | 25C2 | 184CD1 | 58.47 |
| 184C | 25C2 | 18ND2 | 51.06 | 184CG | 25C2 | 184CA | 35.04 |
| 184CG | 25C2 | 184CD2 | 16.66 | 184CG | 25C2 | 184CD1 | 15.49 |
| 184CG | 25C2 | 18ND2 | 93.96 | 184CA | 25C2 | 184CD2 | 50.81 |
| 184CA | 25C2 | 184CD1 | 37.24 | 184CA | 25C2 | 18ND2 | 62.72 |
| 184CD2 | 25C2 | 184CD1 | 26.96 | 184CD1 | 25C2 | 18ND2 | 86.49 |
| 184O | 25C3 | 184CB | 45.92 | 184O | 25C3 | 184CA | 37.85 |
| 184O | 25C3 | 184C | 17.54 | 184O | 25C3 | 18OD1 | 72.66 |
| 184O | 25C3 | 184CG | 67.51 | 184O | 25C3 | 184CD1 | 78.54 |
| 184O | 25C3 | 18ND2 | 59.83 | 184O | 25C3 | 18CG | 62.25 |
| 184O | 25C3 | 184CD2 | 77.25 | 184CB | 25C3 | 184CA | 23.15 |
| 184CB | 25C3 | 184C | 38.05 | 184CB | 25C3 | 18OD1 | 86.49 |
| 184CB | 25C3 | 184CG | 21.78 | 184CB | 25C3 | 184CD1 | 36.65 |
| 184CB | 25C3 | 18ND2 | 94.41 | 184CB | 25C3 | 18CG | 86.35 |
| 184CB | 25C3 | 184CD2 | 32.23 | 184CA | 25C3 | 184C | 22.46 |
| 184CA | 25C3 | 18OD1 | 63.82 | 184CA | 25C3 | 184CG | 37.27 |
| 184CA | 25C3 | 184CD1 | 42.13 | 184CA | 25C3 | 18ND2 | 72.53 |
| 184CA | 25C3 | 18CG | 63.26 | 184CA | 25C3 | 184CD2 | 51.60 |
| 184C | 25C3 | 18OD1 | 61.36 | 184C | 25C3 | 184CG | 57.47 |
| 184C | 25C3 | 184CD1 | 64.57 | 184C | 25C3 | 18ND2 | 57.87 |
| 184C | 25C3 | 18CG | 54.50 | 184C | 25C3 | 184CD2 | 70.12 |
| 18OD1 | 25C3 | 184CG | 91.25 | 18OD1 | 25C3 | 184CD1 | 79.96 |
| 18OD1 | 25C3 | 18ND2 | 31.05 | 18OD1 | 25C3 | 18CG | 15.09 |
| 184CG | 25C3 | 184CD1 | 18.78 | 184CG | 25C3 | 18CG | 96.39 |
| 184CG | 25C3 | 184CD2 | 15.20 | 184CD1 | 25C3 | 18CG | 88.85 |
| 184CD1 | 25C3 | 184CD2 | 27.59 | 18ND2 | 25C3 | 18CG | 16.95 |
| 184CD1 | 25C4 | 184CG | 19.46 | 184CD1 | 25C4 | 184CB | 35.62 |
| 184CD1 | 25C4 | 18OD1 | 77.64 | 184CD1 | 25C4 | 20O | 86.16 |
| 184CD1 | 25C4 | 184CA | 39.47 | 184CD1 | 25C4 | 184NE1 | 16.76 |
| 184CD1 | 25C4 | 184CD2 | 28.36 | 184CD1 | 25C4 | 184O | 68.14 |
| 184CD1 | 25C4 | 184CE2 | 25.97 | 184CG | 25C4 | 184CB | 20.21 |
| 184CG | 25C4 | 18OD1 | 84.29 | 184CG | 25C4 | 184CA | 33.31 |
| 184CG | 25C4 | 184NE1 | 29.37 | 184CG | 25C4 | 184CD2 | 16.86 |
| 184CG | 25C4 | 184O | 56.12 | 184CG | 25C4 | 184CE2 | 26.96 |
| 184CB | 25C4 | 18OD1 | 74.62 | 184CB | 25C4 | 184CA | 19.60 |
| 184CB | 25C4 | 184NE1 | 48.98 | 184CB | 25C4 | 184CD2 | 33.22 |
| 184CB | 25C4 | 184O | 36.02 | 184CB | 25C4 | 184CE2 | 46.70 |
| 18OD1 | 25C4 | 20O | 64.59 | 18OD1 | 25C4 | 184CA | 55.04 |
| 18OD1 | 25C4 | 184NE1 | 91.09 | 18OD1 | 25C4 | 184O | 58.00 |
| 20O | 25C4 | 184NE1 | 82.83 | 20O | 25C4 | 184CE2 | 96.86 |
| 184CA | 25C4 | 184NE1 | 55.98 | 184CA | 25C4 | 184CD2 | 49.56 |
| 184CA | 25C4 | 184O | 30.00 | 184CA | 25C4 | 184CE2 | 59.49 |
| 184NE1 | 25C4 | 184CD2 | 27.93 | 184NE1 | 25C4 | 184O | 83.70 |
| 184NE1 | 25C4 | 184CE2 | 15.77 | 184CD2 | 25C4 | 184O | 68.31 |
| 184CD2 | 25C4 | 184CE2 | 16.44 | 184O | 25C4 | 184CE2 | 82.69 |
| 184CG | 25C5 | 184CD1 | 18.11 | 184CG | 25C5 | 184CD2 | 18.49 |
| 184CG | 25C5 | 184NE1 | 28.96 | 184CG | 25C5 | 184CE2 | 29.05 |
| 184CG | 25C5 | 184CB | 17.96 | 184CD1 | 25C5 | 184CD2 | 29.17 |
| 184CD1 | 25C5 | 184NE1 | 17.37 | 184CD1 | 25C5 | 184CE2 | 28.25 |
| 184CD1 | 25C5 | 184CB | 32.12 | 184CD2 | 25C5 | 184NE1 | 28.48 |
| 184CD2 | 25C5 | 184CE2 | 17.52 | 184CD2 | 25C5 | 184CB | 32.46 |
| 184NE1 | 25C5 | 184CE2 | 16.92 | 184NE1 | 25C5 | 184CB | 46.34 |
| 184CE2 | 25C5 | 184CB | 46.48 | 184CD2 | 25C6 | 184CG | 18.41 |
| 184CD2 | 25C6 | 184CE3 | 17.57 | 184CD2 | 25C6 | 184CB | 32.70 |
| 184CD2 | 25C6 | 184CE2 | 16.35 | 184CD2 | 25C6 | 184CD1 | 26.98 |
| 184CG | 25C6 | 184CE3 | 33.10 | 184CG | 25C6 | 184CB | 18.26 |
| 184CG | 25C6 | 184CE2 | 27.66 | 184CG | 25C6 | 184CD1 | 15.78 |
| 184CE3 | 25C6 | 184CB | 40.99 | 184CE3 | 25C6 | 143OE1 | 88.61 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 184CE3 | 25C6 | 184CE2 | 29.17 | 184CE3 | 25C6 | 184CD1 | 44.38 |
| 184CB | 25C6 | 184CE2 | 45.38 | 184CB | 25C6 | 184CD1 | 30.55 |
| 184CE2 | 25C6 | 184CD1 | 26.20 | 20O | 25C7 | 20C | 19.21 |
| 20O | 25C7 | 20CA | 39.07 | 20O | 25C7 | 20N | 45.05 |
| 20O | 25C7 | 18OD1 | 87.05 | 20O | 25C7 | 19CG | 55.64 |
| 20O | 25C7 | 21NE2 | 74.51 | 20O | 25C7 | 21N | 24.68 |
| 20O | 25C7 | 18CG | 94.59 | 20O | 25C7 | 19C | 40.56 |
| 20C | 25C7 | 20CA | 23.55 | 20C | 25C7 | 20N | 38.22 |
| 20C | 25C7 | 18OD1 | 77.28 | 20C | 25C7 | 19CG | 67.04 |
| 20C | 25C7 | 21NE2 | 71.32 | 20C | 25C7 | 21N | 11.95 |
| 20C | 25C7 | 18CG | 83.17 | 20C | 25C7 | 19C | 38.66 |
| 20CA | 25C7 | 20N | 21.87 | 20CA | 25C7 | 18OD1 | 54.50 |
| 20CA | 25C7 | 19CG | 66.31 | 20CA | 25C7 | 21NE2 | 87.33 |
| 20CA | 25C7 | 21N | 31.76 | 20CA | 25C7 | 18CG | 59.80 |
| 20CA | 25C7 | 19C | 28.41 | 20N | 25C7 | 18OD1 | 42.02 |
| 20N | 25C7 | 184CD1 | 96.35 | 20N | 25C7 | 19CG | 47.93 |
| 20N | 25C7 | 21N | 49.41 | 20N | 25C7 | 18CG | 49.82 |
| 20N | 25C7 | 19C | 10.08 | 20N | 25C7 | 184CA | 86.28 |
| 18OD1 | 25C7 | 184CD1 | 83.02 | 18OD1 | 25C7 | 19CG | 66.42 |
| 18OD1 | 25C7 | 21N | 86.24 | 18OD1 | 25C7 | 184NE1 | 98.06 |
| 18OD1 | 25C7 | 184CG | 83.82 | 18OD1 | 25C7 | 18CG | 8.98 |
| 18OD1 | 25C7 | 19C | 48.05 | 18OD1 | 25C7 | 184CA | 54.56 |
| 184CD1 | 25C7 | 19CG | 55.25 | 184CD1 | 25C7 | 184NE1 | 16.81 |
| 184CD1 | 25C7 | 184CG | 16.56 | 184CD1 | 25C7 | 18CG | 85.33 |
| 184CD1 | 25C7 | 19C | 89.88 | 184CD1 | 25C7 | 184CA | 36.29 |
| 19CG | 25C7 | 21N | 77.73 | 19CG | 25C7 | 184NE1 | 56.16 |
| 19CG | 25C7 | 184CG | 70.76 | 19CG | 25C7 | 18CG | 74.86 |
| 19CG | 25C7 | 19C | 38.66 | 19CG | 25C7 | 184CA | 68.46 |
| 21NE2 | 25C7 | 21N | 59.46 | 21N | 25C7 | 18CG | 91.06 |
| 21N | 25C7 | 19C | 50.55 | 21N | 25C7 | 184CG | 28.00 |
| 184NE1 | 25C7 | 19C | 94.36 | 184NE1 | 25C7 | 184CA | 52.97 |
| 184CG | 25C7 | 18CG | 83.54 | 184CG | 25C7 | 184CA | 30.15 |
| 18CG | 25C7 | 19C | 56.53 | 18CG | 25C7 | 184CA | 53.47 |
| 19C | 25C7 | 184CA | 85.50 | 20O | 25O8 | 19CG | 74.18 |
| 20O | 25O8 | 20C | 14.24 | 20O | 25O8 | 20N | 45.16 |
| 20O | 25O8 | 19CD | 84.08 | 20O | 25O8 | 20CA | 33.67 |
| 20O | 25O8 | 18OD1 | 81.17 | 20O | 25O8 | 19C | 43.87 |
| 20O | 25O8 | 21N | 14.62 | 20O | 25O8 | 19CB | 65.10 |
| 20O | 25O8 | 19NE2 | 73.97 | 20O | 25O8 | 184CD1 | 71.14 |
| 19CG | 25O8 | 20C | 79.40 | 19CG | 25O8 | 184NE1 | 74.25 |
| 19CG | 25O8 | 20N | 55.59 | 19CG | 25O8 | 19CD | 22.00 |
| 19CG | 25O8 | 20CA | 73.82 | 19CG | 25O8 | 19OE1 | 34.44 |
| 19CG | 25O8 | 184CG | 85.17 | 19CG | 25O8 | 18OD1 | 70.42 |
| 19CG | 25O8 | 184CE2 | 88.06 | 19CG | 25O8 | 19C | 42.61 |
| 19CG | 25O8 | 21N | 87.25 | 19CG | 25O8 | 19CB | 11.43 |
| 19CG | 25O8 | 19NE2 | 28.77 | 19CG | 25O8 | 18O | 42.56 |
| 19CG | 25O8 | 184CD2 | 93.05 | 19CG | 25O8 | 184NE1 | 21.99 |
| 184CD1 | 25O8 | 19CD | 64.82 | 184CD1 | 25O8 | 19OE1 | 49.70 |
| 184CD1 | 25O8 | 184CG | 15.65 | 184CD1 | 25O8 | 18OD1 | 83.93 |
| 184CD1 | 25O8 | 184CE2 | 27.56 | 184CD1 | 25O8 | 19CB | 80.03 |
| 184CD1 | 25O8 | 19NE2 | 77.46 | 184CD1 | 25O8 | 18O | 43.29 |
| 184CD1 | 25O8 | 184CD2 | 22.85 | 20C | 25O8 | 20N | 37.96 |
| 20C | 25O8 | 19CD | 93.27 | 20C | 25O8 | 20CA | 21.59 |
| 20C | 25O8 | 18OD1 | 70.08 | 20C | 25O8 | 19C | 41.74 |
| 20C | 25O8 | 21N | 10.44 | 20C | 25O8 | 19CB | 68.90 |
| 20C | 25O8 | 19NE2 | 85.00 | 184NE1 | 25O8 | 19CD | 59.98 |
| 184NE1 | 25O8 | 19OE1 | 43.21 | 184NE1 | 25O8 | 184CG | 31.35 |
| 184NE1 | 25O8 | 184CE2 | 13.82 | 184NE1 | 25O8 | 19CB | 85.19 |
| 184NE1 | 25O8 | 19NE2 | 69.30 | 184NE1 | 25O8 | 18O | 60.22 |
| 184NE1 | 25O8 | 184CD2 | 24.73 | 20N | 25O8 | 19CD | 76.55 |
| 20N | 25O8 | 20CA | 20.72 | 20N | 25O8 | 19OE1 | 89.93 |
| 20N | 25O8 | 18OD1 | 38.33 | 20N | 25O8 | 19C | 14.64 |
| 20N | 25O8 | 21N | 48.38 | 20N | 25O8 | 19CB | 44.35 |
| 20N | 25O8 | 19NE2 | 76.55 | 20N | 25O8 | 18O | 65.49 |
| 19CD | 25O8 | 20CA | 92.98 | 19CD | 25O8 | 19OE1 | 16.77 |
| 19CD | 25O8 | 184CG | 80.43 | 19CD | 25O8 | 18OD1 | 91.12 |
| 19CD | 25O8 | 184CE2 | 73.34 | 19CD | 25O8 | 19C | 62.65 |
| 19CD | 25O8 | 21N | 98.59 | 19CD | 25O8 | 19CB | 32.44 |
| 19CD | 25O8 | 19NE2 | 14.03 | 19CD | 25O8 | 18O | 53.18 |
| 19CD | 25O8 | 184CD2 | 82.97 | 20CA | 25O8 | 18OD1 | 48.49 |
| 20CA | 25O8 | 19C | 31.25 | 20CA | 25O8 | 21N | 31.00 |
| 20CA | 25O8 | 19CB | 62.39 | 20CA | 25O8 | 19NE2 | 89.43 |
| 20CA | 25O8 | 18O | 85.40 | 19OE1 | 25O8 | 184CG | 65.32 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 19OE1 | 25O8 | 18OD1 | 95.73 | 19OE1 | 25O8 | 184CE2 | 56.63 |
| 19OE1 | 25O8 | 19C | 77.00 | 19OE1 | 25O8 | 19CB | 45.84 |
| 19OE1 | 25O8 | 19NE2 | 27.83 | 19OE1 | 25O8 | 183O | 50.05 |
| 19OE1 | 25O8 | 184CD2 | 66.42 | 184CG | 25O8 | 18OD1 | 81.85 |
| 184CG | 25O8 | 184CE2 | 29.41 | 184CG | 25O8 | 19CB | 92.98 |
| 184CG | 25O8 | 19NE2 | 93.11 | 184CG | 25O8 | 183O | 51.14 |
| 184CG | 25O8 | 184CD2 | 15.78 | 18OD1 | 25O8 | 19C | 48.36 |
| 18OD1 | 25O8 | 21N | 79.10 | 18OD1 | 25O8 | 19CB | 63.32 |
| 18OD1 | 25O8 | 19NE2 | 98.90 | 18OD1 | 25O8 | 183O | 49.03 |
| 18OD1 | 25O8 | 184CD2 | 97.37 | 184CE2 | 25O8 | 19CB | 98.94 |
| 184CE2 | 25O8 | 19NE2 | 81.67 | 184CE2 | 25O8 | 183O | 70.16 |
| 184CE2 | 25O8 | 184CD2 | 16.41 | 19C | 25O8 | 21N | 51.75 |
| 19C | 25O8 | 19CB | 31.18 | 19C | 25O8 | 19NE2 | 61.93 |
| 19C | 25O8 | 183O | 62.03 | 21N | 25O8 | 19CB | 77.34 |
| 21N | 25O8 | 19NE2 | 88.58 | 19CB | 25O8 | 19NE2 | 35.99 |
| 19CB | 25O8 | 183O | 45.66 | 19NE2 | 25O8 | 183O | 66.29 |
| 19NE2 | 25O8 | 184CD2 | 93.54 | 183O | 25O8 | 184CD2 | 64.88 |
| 20O | 25C9 | 19CG | 60.67 | 20O | 25C9 | 19CD | 76.38 |
| 20O | 25C9 | 19OE1 | 92.50 | 20O | 25C9 | 20C | 7.58 |
| 20O | 25C9 | 19NE2 | 72.45 | 20O | 25C9 | 21NE2 | 67.37 |
| 184NE1 | 25C9 | 184CD1 | 20.97 | 184NE1 | 25C9 | 19CG | 68.64 |
| 184NE1 | 25C9 | 19CD | 59.83 | 184NE1 | 25C9 | 19OE1 | 43.65 |
| 184NE1 | 25C9 | 184CE2 | 16.49 | 184NE1 | 25C9 | 19NE2 | 71.84 |
| 184NE1 | 25C9 | 184CG | 26.81 | 184NE1 | 25C9 | 184CZ2 | 28.68 |
| 184CD1 | 25C9 | 19CG | 60.92 | 184CD1 | 25C9 | 19CD | 60.57 |
| 184CD1 | 25C9 | 19OE1 | 48.05 | 184CD1 | 25C9 | 184CE2 | 31.05 |
| 184CD1 | 25C9 | 19NE2 | 75.62 | 184CD1 | 25C9 | 184CG | 13.88 |
| 184CD1 | 25C9 | 184CZ2 | 46.32 | 19CG | 25C9 | 19CD | 21.52 |
| 19CG | 25C9 | 19OE1 | 33.58 | 19CG | 25C9 | 20C | 65.19 |
| 19CG | 25C9 | 184CE2 | 85.10 | 19CG | 25C9 | 19NE2 | 31.33 |
| 19CG | 25C9 | 184CG | 73.53 | 19CG | 25C9 | 184CZ2 | 95.37 |
| 19CD | 25C9 | 19OE1 | 16.79 | 19CD | 25C9 | 20C | 82.31 |
| 19CD | 25C9 | 184CE2 | 75.59 | 19CD | 25C9 | 19NE2 | 15.81 |
| 19CD | 25C9 | 184CG | 74.44 | 19CD | 25C9 | 184CZ2 | 81.71 |
| 19OE1 | 25C9 | 20C | 97.96 | 19OE1 | 25C9 | 184CE2 | 59.01 |
| 19OE1 | 25C9 | 19NE2 | 28.56 | 19OE1 | 25C9 | 184CG | 61.65 |
| 19OE1 | 25C9 | 184CZ2 | 65.02 | 20C | 25C9 | 19NE2 | 79.44 |
| 20C | 25C9 | 21NE2 | 62.11 | 184CE2 | 25C9 | 19NE2 | 86.32 |
| 184CE2 | 25C9 | 184CG | 28.77 | 184CE2 | 25C9 | 184CZ2 | 15.52 |
| 19NE2 | 25C9 | 184CG | 89.47 | 19NE2 | 25C9 | 184CZ2 | 89.08 |
| 184CG | 25C9 | 184CZ2 | 43.90 | 184NE1 | 25O10 | 184CE2 | 19.56 |
| 184NE1 | 25O10 | 184CD1 | 19.15 | 184NE1 | 25O10 | 20O | 98.89 |
| 184NE1 | 25O10 | 184CZ2 | 34.13 | 184NE1 | 25O10 | 184CD2 | 27.67 |
| 184NE1 | 25O10 | 184CG | 27.32 | 184CE2 | 25O10 | 184CD1 | 31.59 |
| 184CE2 | 25O10 | 184CZ2 | 18.04 | 184CE2 | 25O10 | 184CD2 | 16.51 |
| 184CE2 | 25O10 | 184CG | 28.75 | 184CD1 | 25O10 | 20O | 88.35 |
| 184CD1 | 25O10 | 184CZ2 | 49.32 | 184CD1 | 25O10 | 184CD2 | 28.37 |
| 184CD1 | 25O10 | 184CG | 15.83 | 20O | 25O10 | 184CG | 99.14 |
| 20O | 25O10 | 21NE2 | 63.32 | 184CZ2 | 25O10 | 184CD2 | 30.98 |
| 184CZ2 | 25O10 | 184CG | 46.20 | 184CD2 | 25O10 | 184CG | 17.35 |
| 19NE2 | 25C11 | 22O | 38.20 | 19NE2 | 25C11 | 19CD | 17.94 |
| 19NE2 | 25C11 | 20O | 68.83 | 19NE2 | 25C11 | 19OE1 | 29.76 |
| 19NE2 | 25C11 | 184NE1 | 67.70 | 19NE2 | 25C11 | 22C | 51.21 |
| 19NE2 | 25C11 | 23CA | 50.68 | 19NE2 | 25C11 | 19CG | 29.78 |
| 19NE2 | 25C11 | 22N | 68.31 | 19NE2 | 25C11 | 23N | 56.54 |
| 22O | 25C11 | 19CD | 51.52 | 22O | 25C11 | 20O | 54.51 |
| 22O | 25C11 | 19OE1 | 66.66 | 22O | 25C11 | 22C | 14.40 |
| 22O | 25C11 | 23CA | 34.19 | 22O | 25C11 | 19CG | 50.00 |
| 22O | 25C11 | 22N | 32.97 | 22O | 25C11 | 23N | 26.65 |
| 19CD | 25C11 | 20O | 64.43 | 19CD | 25C11 | 19OE1 | 15.96 |
| 19CD | 25C11 | 184NE1 | 51.25 | 19CD | 25C11 | 22C | 65.67 |
| 19CD | 25C11 | 23CA | 68.61 | 19CD | 25C11 | 19CG | 17.66 |
| 19CD | 25C11 | 22N | 76.34 | 19CD | 25C11 | 23N | 73.36 |
| 20O | 25C11 | 19OE1 | 76.37 | 20O | 25C11 | 184NE1 | 85.38 |
| 20O | 25C11 | 22C | 60.00 | 20O | 25C11 | 23CA | 87.97 |
| 20O | 25C11 | 19CG | 47.41 | 20O | 25C11 | 22N | 38.68 |
| 20O | 25C11 | 23N | 75.19 | 20O | 25C11 | 184NE1 | 38.17 |
| 19OE1 | 25C11 | 22C | 80.44 | 19OE1 | 25C11 | 23CA | 78.31 |
| 19OE1 | 25C11 | 19CG | 29.35 | 19OE1 | 25C11 | 22N | 92.26 |
| 19OE1 | 25C11 | 23N | 86.19 | 184NE1 | 25C11 | 19CG | 53.83 |
| 22C | 25C11 | 23CA | 29.04 | 22C | 25C11 | 19CG | 64.17 |
| 22C | 25C11 | 22N | 28.19 | 22C | 25C11 | 23N | 15.42 |
| 23CA | 25C11 | 19CG | 76.14 | 23CA | 25C11 | 22N | 56.58 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 23CA | 25C11 | 23N | 16.87 | 19CG | 25C11 | 22N | 66.36 |
| 19CG | 25C11 | 23N | 75.77 | 22N | 2SC11 | 23N | 40.54 |
| 22O | 25C12 | 22C | 17.89 | 22O | 25C12 | 22N | 39.45 |
| 22O | 25C12 | 23N | 32.43 | 22O | 25C12 | 23CA | 38.69 |
| 22O | 25C12 | 20O | 56.27 | 22O | 25C12 | 21C | 55.84 |
| 22O | 25C12 | 22CA | 31.37 | 22O | 25C12 | 21CA | 67.07 |
| 22O | 25C12 | 19NE2 | 35.21 | 22C | 25C12 | 22N | 34.05 |
| 22C | 25C12 | 23N | 18.76 | 22C | 25C12 | 23CA | 33.51 |
| 22C | 25C12 | 20O | 65.66 | 22C | 25C12 | 21C | 49.03 |
| 22C | 25C12 | 22CA | 18.77 | 22C | 25C12 | 21CA | 64.80 |
| 22C | 25C12 | 19NE2 | 51.68 | 22N | 25C12 | 23N | 49.61 |
| 22N | 25C12 | 23CA | 67.28 | 22N | 25C12 | 20O | 43.43 |
| 22N | 25C12 | 21C | 16.39 | 22N | 25C12 | 22CA | 18.17 |
| 22N | 25C12 | 21OE1 | 71.11 | 22N | 25C12 | 21CA | 30.79 |
| 22N | 25C12 | 19NE2 | 70.87 | 23N | 25C12 | 23CA | 19.64 |
| 23N | 25C12 | 20C | 84.42 | 23N | 25C12 | 21C | 62.12 |
| 23N | 25C12 | 22CA | 31.69 | 23N | 25C12 | 21CA | 79.89 |
| 23N | 25C12 | 19NE2 | 58.72 | 23CA | 25C12 | 20O | 94.95 |
| 23CA | 25C12 | 21C | 81.09 | 23CA | 25C12 | 22CA | 50.18 |
| 23CA | 25C12 | 21CA | 98.06 | 23CA | 25C12 | 19NE2 | 50.86 |
| 20O | 25C12 | 21C | 45.48 | 20O | 25C12 | 22CA | 58.80 |
| 20O | 25C12 | 21OE1 | 66.04 | 20O | 25C12 | 21CA | 35.16 |
| 20O | 25C12 | 19NE2 | 63.11 | 21C | 25C12 | 22CA | 30.96 |
| 21C | 25C12 | 21OE1 | 55.27 | 21C | 25C12 | 21CA | 18.83 |
| 21C | 25C12 | 19NE2 | 86.29 | 22CA | 25C12 | 21OE1 | 85.66 |
| 22CA | 25C12 | 21CA | 48.22 | 22CA | 25C12 | 19NE2 | 66.48 |
| 21OE1 | 25C12 | 21CA | 42.41 | 21CA | 25C12 | 19NE2 | 90.68 |
| 21OE1 | 25C13 | 21CD | 12.45 | 21OE1 | 25C13 | 21CA | 47.08 |
| 21OE1 | 25C13 | 22N | 76.49 | 21OE1 | 25C13 | 21C | 61.27 |
| 21OE1 | 25C13 | 20O | 69.05 | 21OE1 | 25C13 | 21NE2 | 23.98 |
| 21CD | 25C13 | 21CA | 41.21 | 21CD | 25C13 | 22N | 71.61 |
| 21CD | 25C13 | 21C | 58.15 | 21CD | 25C13 | 20O | 57.98 |
| 21CD | 25C13 | 21NE2 | 14.96 | 21CA | 25C13 | 22N | 30.42 |
| 21CA | 25C13 | 21C | 18.99 | 21CA | 25C13 | 20O | 33.62 |
| 21CA | 25C13 | 21NE2 | 51.09 | 22N | 25C13 | 21C | 16.45 |
| 22N | 25C13 | 20O | 38.35 | 22N | 25C13 | 21NE2 | 80.82 |
| 21C | 25C13 | 20O | 42.37 | 21C | 25C13 | 21NE2 | 69.53 |
| 20O | 25C13 | 21NE2 | 58.27 | 21OE1 | 25C14 | 21C | 80.26 |
| 21OE1 | 25C14 | 21CA | 58.86 | 21OE1 | 25C14 | 22N | 95.27 |
| 21OE1 | 25C14 | 21CD | 11.97 | 21OE1 | 25C14 | 21O | 83.12 |
| 21OE1 | 25C14 | 21CB | 43.94 | 21OE1 | 25C14 | 21CG | 26.08 |
| 21OE1 | 25C14 | 21NE2 | 17.70 | 21OE1 | 25C14 | 20O | 71.89 |
| 21C | 25C14 | 21CA | 23.60 | 21C | 25C14 | 22N | 19.79 |
| 21C | 25C14 | 21CD | 70.89 | 21C | 25C14 | 21O | 18.03 |
| 21C | 25C14 | 21CB | 37.30 | 21C | 25C14 | 22CA | 32.39 |
| 21C | 25C14 | 21CG | 54.18 | 21C | 25C14 | 22C | 48.65 |
| 21C | 25C14 | 21NE2 | 78.83 | 21C | 25C14 | 23N | 61.74 |
| 21C | 25C14 | 20O | 44.43 | 21CA | 25C14 | 22N | 36.47 |
| 21CA | 25C14 | 21CD | 48.38 | 21CA | 25C14 | 21O | 36.17 |
| 21CA | 25C14 | 21CB | 21.86 | 21CA | 25C14 | 22CA | 53.26 |
| 21CA | 25C14 | 21CG | 33.45 | 21CA | 25C14 | 22C | 65.81 |
| 21CA | 25C14 | 21NE2 | 55.36 | 21CA | 25C14 | 23N | 80.87 |
| 21CA | 25C14 | 20O | 33.68 | 22N | 25C14 | 21CD | 84.38 |
| 22N | 25C14 | 21O | 33.19 | 22N | 25C14 | 21CB | 55.22 |
| 22N | 25C14 | 22CA | 17.77 | 22N | 25C14 | 21CG | 69.86 |
| 22N | 25C14 | 22C | 29.90 | 22N | 25C14 | 21NE2 | 89.31 |
| 22N | 25C14 | 23N | 44.46 | 22N | 25C14 | 20O | 39.38 |
| 21CD | 25C14 | 21O | 76.50 | 21CD | 25C14 | 21CB | 36.73 |
| 21CD | 25C14 | 21CG | 18.01 | 21CD | 25C14 | 21NE2 | 12.68 |
| 21CD | 25C14 | 20O | 60.03 | 21O | 25C14 | 21CB | 39.79 |
| 21O | 25C14 | 22CA | 37.66 | 21O | 25C14 | 21CG | 58.51 |
| 21O | 25C14 | 22C | 56.26 | 21O | 25C14 | 21NE2 | 86.99 |
| 21O | 25C14 | 23N | 65.51 | 21O | 25C14 | 20O | 62.32 |
| 21CB | 25C14 | 22CA | 69.70 | 21CB | 25C14 | 21CG | 18.72 |
| 21CB | 25C14 | 22C | 85.11 | 21CB | 25C14 | 21NE2 | 47.76 |
| 21CB | 25C14 | 23N | 98.97 | 21CB | 25C14 | 20O | 53.00 |
| 22CA | 25C14 | 21CG | 86.05 | 22CA | 25C14 | 22C | 18.65 |
| 22CA | 25C14 | 23N | 29.45 | 22CA | 25C14 | 20O | 54.92 |
| 21CG | 25C14 | 22C | 99.21 | 21CG | 25C14 | 21NE2 | 29.49 |
| 21CG | 25C14 | 20O | 54.91 | 22C | 25C14 | 23N | 15.74 |
| 22C | 25C14 | 20O | 55.72 | 21NE2 | 25C14 | 20O | 58.56 |
| 23N | 25C14 | 20O | 70.69 | 21OE1 | 25C15 | 21CD | 18.02 |
| 21OE1 | 25C15 | 21NE2 | 36.11 | 21OE1 | 25C15 | 21CA | 45.66 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 21OE1 | 25C15 | 20O | 74.47 | 21OE1 | 25C15 | 21CG | 20.94 |
| 21CD | 25C15 | 21NE2 | 20.43 | 21CD | 25C15 | 21CA | 42.29 |
| 21CD | 25C15 | 20O | 63.32 | 21CD | 25C15 | 21CG | 11.31 |
| 21NE2 | 25C15 | 21CA | 56.77 | 21NE2 | 25C15 | 20O | 66.57 |
| 21NE2 | 25C15 | 21CG | 29.05 | 21CA | 25C15 | 20O | 33.79 |
| 21CA | 25C15 | 21CG | 31.00 | 20O | 25C15 | 21CG | 54.47 |
| 19NE2 | 25C16 | 19OE1 | 34.42 | 19NE2 | 25C16 | 19CD | 19.70 |
| 19NE2 | 25C16 | 23CA | 57.42 | 19NE2 | 25C16 | 184NE1 | 74.14 |
| 19NE2 | 25C16 | 22O | 38.47 | 19NE2 | 25C16 | 162ND1 | 77.08 |
| 19NE2 | 25C16 | 19CG | 27.65 | 19NE2 | 25C16 | 23N | 58.92 |
| 19NE2 | 25C16 | 22C | 50.59 | 19OE1 | 25C16 | 19CD | 18.10 |
| 19OE1 | 25C16 | 23CA | 91.00 | 19OE1 | 25C16 | 184NE1 | 41.37 |
| 19OE1 | 25C16 | 22O | 70.27 | 19OE1 | 25C16 | 162ND1 | 54.22 |
| 19OE1 | 25C16 | 19CG | 28.11 | 19OE1 | 25C16 | 23N | 93.23 |
| 19OE1 | 25C16 | 22C | 83.37 | 19OE1 | 25C16 | 184CZ2 | 67.06 |
| 19CD | 25C16 | 23CA | 76.87 | 19CD | 25C16 | 184NE1 | 54.73 |
| 19CD | 25C16 | 22O | 52.37 | 19CD | 25C16 | 162ND1 | 70.37 |
| 19CD | 25C16 | 19CG | 14.40 | 19CD | 25C16 | 23N | 76.48 |
| 19CD | 25C16 | 22C | 65.58 | 19CD | 25C16 | 184CZ2 | 83.17 |
| 23CA | 25C16 | 22O | 36.36 | 23CA | 25C16 | 19CG | 79.64 |
| 23CA | 25C16 | 23N | 16.38 | 23CA | 25C16 | 22C | 28.95 |
| 184NE1 | 25C16 | 162ND1 | 56.55 | 184NE1 | 25C16 | 19CG | 54.16 |
| 184NE1 | 25C16 | 184CZ2 | 30.24 | 22O | 25C16 | 19CG | 48.64 |
| 22O | 25C16 | 23N | 26.88 | 22O | 25C16 | 22C | 13.31 |
| 162ND1 | 25C16 | 19CG | 82.32 | 162ND1 | 25C16 | 184CZ2 | 51.21 |
| 19CG | 25C16 | 23N | 75.10 | 19CG | 25C16 | 22C | 61.77 |
| 19CG | 25C16 | 184CZ2 | 84.32 | 23N | 25C16 | 22C | 15.32 |
| 162ND1 | 25S17 | 184CZ2 | 72.20 | 162ND1 | 25S17 | 184NE1 | 73.37 |
| 162ND1 | 25S17 | 162CE1 | 19.38 | 162ND1 | 25S17 | 19OE1 | 64.03 |
| 162ND1 | 25S17 | 184CE2 | 73.12 | 162ND1 | 25S17 | 162CG | 16.82 |
| 162ND1 | 25S17 | 19CD | 76.25 | 162ND1 | 25S17 | 19NE2 | 80.24 |
| 162ND1 | 25S17 | 162CB | 31.46 | 162ND1 | 25S17 | 184CH2 | 75.04 |
| 162ND1 | 25S17 | 162NE2 | 24.22 | 162ND1 | 25S17 | 184CD1 | 76.19 |
| 184CZ2 | 25S17 | 184NE1 | 40.35 | 184CZ2 | 25S17 | 162CE1 | 61.98 |
| 184CZ2 | 25S17 | 19OE1 | 82.50 | 184CZ2 | 25S17 | 184CE2 | 20.39 |
| 184CZ2 | 25S17 | 162CG | 64.57 | 184CZ2 | 25S17 | 19CD | 94.35 |
| 184CZ2 | 25S17 | 162CB | 73.92 | 184CZ2 | 25S17 | 184CH2 | 9.57 |
| 184CZ2 | 25S17 | 162NE2 | 50.06 | 184CZ2 | 25S17 | 184CD1 | 46.22 |
| 184NE1 | 25S17 | 162CE1 | 54.53 | 184NE1 | 25S17 | 19OE1 | 45.35 |
| 184NE1 | 25S17 | 184CE2 | 20.06 | 184NE1 | 25S17 | 162CG | 77.66 |
| 184NE1 | 25S17 | 19CD | 54.83 | 184NE1 | 25S17 | 19NE2 | 71.53 |
| 184NE1 | 25S17 | 162CB | 94.60 | 184NE1 | 25S17 | 184CH2 | 49.77 |
| 184NE1 | 25S17 | 162NE2 | 51.06 | 184NE1 | 25S17 | 184CD1 | 6.15 |
| 162CE1 | 25S17 | 19OE1 | 48.96 | 162CE1 | 25S17 | 184CE2 | 57.43 |
| 162CE1 | 25S17 | 162CG | 30.44 | 162CE1 | 25S17 | 19CD | 62.94 |
| 162CE1 | 25S17 | 19NE2 | 71.39 | 162CE1 | 25S17 | 162CB | 48.22 |
| 162CE1 | 25S17 | 184CH2 | 67.56 | 162CE1 | 25S17 | 162NE2 | 13.10 |
| 162CE1 | 25S17 | 184CD1 | 56.98 | 19OE1 | 25S17 | 184CE2 | 64.06 |
| 19OE1 | 25S17 | 162CG | 78.89 | 19OE1 | 25S17 | 19CD | 14.86 |
| 19OE1 | 25S17 | 19NE2 | 29.15 | 19OE1 | 25S17 | 162CB | 95.48 |
| 19OE1 | 25S17 | 184CH2 | 91.95 | 19OE1 | 25S17 | 162NE2 | 57.76 |
| 19OE1 | 25S17 | 184CD1 | 41.33 | 184CE2 | 25S17 | 162CG | 71.43 |
| 184CE2 | 25S17 | 19CD | 74.69 | 184CE2 | 25S17 | 19NE2 | 91.37 |
| 184CE2 | 25S17 | 162CB | 85.35 | 184CE2 | 25S17 | 184CH2 | 29.73 |
| 184CE2 | 25S17 | 162NE2 | 48.91 | 184CE2 | 25S17 | 184CD1 | 25.84 |
| 162CG | 25S17 | 19CD | 92.05 | 162CG | 25S17 | 19NE2 | 97.02 |
| 162CG | 25S17 | 162CB | 18.20 | 162CG | 25S17 | 184CH2 | 64.89 |
| 162CG | 25S17 | 162NE2 | 27.13 | 162CG | 25S17 | 184CD1 | 81.91 |
| 19CD | 25S17 | 19NE2 | 16.70 | 19CD | 25S17 | 162NE2 | 72.44 |
| 19CD | 25S17 | 184CD1 | 49.68 | 19NE2 | 25S17 | 162NE2 | 82.84 |
| 19NE2 | 25S17 | 184CD1 | 66.32 | 162CB | 25S17 | 184CH2 | 71.34 |
| 162CB | 25S17 | 162NE2 | 45.10 | 162CB | 25S17 | 184CD1 | 99.30 |
| 184CH2 | 25S17 | 162NE2 | 54.91 | 184CH2 | 25S17 | 184CD1 | 55.56 |
| 162NE2 | 25S17 | 184CD1 | 54.94 | 19NE2 | 25N18 | 23CA | 73.04 |
| 19NE2 | 25N18 | 19CD | 18.20 | 19NE2 | 25N18 | 22O | 43.17 |
| 19NE2 | 25N18 | 19OE1 | 33.64 | 19NE2 | 25N18 | 23C | 62.17 |
| 19NE2 | 25N18 | 25SG | 78.34 | 19NE2 | 25N18 | 23N | 70.88 |
| 19NE2 | 25N18 | 22C | 57.87 | 19NE2 | 25N18 | 25CB | 58.17 |
| 19NE2 | 25N18 | 24N | 45.44 | 19NE2 | 25N18 | 162ND1 | 81.06 |
| 19NE2 | 25N18 | 25N | 41.89 | 19NE2 | 25N18 | 23O | 71.35 |
| 23CA | 25N18 | 19CD | 90.63 | 23CA | 25N18 | 22O | 43.03 |
| 23CA | 25N18 | 23C | 19.70 | 23CA | 25N18 | 25SG | 84.26 |
| 23CA | 25N18 | 23N | 17.82 | 23CA | 25N18 | 22C | 32.08 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 23CA | 25N18 | 25CB | 90.92 | 23CA | 25N18 | 24N | 31.17 |
| 23CA | 25N18 | 25N | 62.49 | 23CA | 25N18 | 23O | 26.79 |
| 19CD | 25N18 | 22O | 55.64 | 19CD | 25N18 | 19OE1 | 17.64 |
| 19CD | 25N18 | 23C | 80.36 | 19CD | 25N18 | 25SG | 84.40 |
| 19CD | 25N18 | 23N | 86.18 | 19CD | 25N18 | 22C | 71.10 |
| 19CD | 25N18 | 25CB | 60.97 | 19CD | 25N18 | 24N | 63.63 |
| 19CD | 25N18 | 162ND1 | 70.54 | 19CD | 25N18 | 25N | 54.63 |
| 19CD | 25N18 | 23O | 89.15 | 22O | 25N18 | 19OE1 | 73.27 |
| 22O | 25N18 | 23C | 46.87 | 22O | 25N18 | 23N | 31.78 |
| 22O | 25N18 | 22C | 15.47 | 22O | 25N18 | 25CB | 93.37 |
| 22O | 25N18 | 24N | 37.57 | 22O | 25N18 | 25N | 64.91 |
| 22O | 25N18 | 23O | 60.03 | 19OE1 | 25N18 | 23C | 93.60 |
| 19OE1 | 25N18 | 25SG | 78.94 | 19OE1 | 25N18 | 22C | 88.73 |
| 19OE1 | 25N18 | 25CB | 54.74 | 19OE1 | 25N18 | 24N | 77.36 |
| 19OE1 | 25N18 | 162ND1 | 53.80 | 19OE1 | 25N18 | 25N | 59.44 |
| 19OE1 | 25N18 | 23O | 99.98 | 23C | 25N18 | 25SG | 66.71 |
| 23C | 25N18 | 23N | 34.39 | 23C | 25N18 | 22C | 42.39 |
| 23C | 25N18 | 25CB | 71.24 | 23C | 25N18 | 24N | 16.74 |
| 23C | 25N18 | 25N | 43.13 | 23C | 25N18 | 23O | 13.17 |
| 25SG | 25N18 | 25CB | 24.23 | 25SG | 25N18 | 24N | 67.84 |
| 25SG | 25N18 | 162ND1 | 54.04 | 25SG | 25N18 | 25N | 40.11 |
| 25SG | 25N18 | 23O | 57.50 | 23N | 25N18 | 22C | 17.29 |
| 23N | 25N18 | 24N | 39.13 | 23N | 25N18 | 25N | 73.32 |
| 23N | 25N18 | 23O | 44.07 | 22C | 25N18 | 24N | 39.37 |
| 22C | 25N18 | 25N | 71.95 | 22C | 25N18 | 23O | 54.65 |
| 25CB | 25N18 | 24N | 64.90 | 25CB | 25N18 | 162ND1 | 43.82 |
| 25CB | 25N18 | 25N | 30.73 | 25CB | 25N18 | 23O | 66.97 |
| 24N | 25N18 | 25N | 34.26 | 24N | 25N18 | 23O | 27.47 |
| 162ND1 | 25N18 | 25N | 73.32 | 25N | 25N18 | 23O | 43.35 |
| 25SG | 25C19 | 25CB | 30.95 | 25SG | 25C19 | 19NE2 | 87.88 |
| 25SG | 25C19 | 162ND1 | 72.09 | 25SG | 25C19 | 23CA | 92.18 |
| 25SG | 25C19 | 19OE1 | 90.53 | 25SG | 25C19 | 161O | 75.25 |
| 25SG | 25C19 | 19CD | 92.51 | 25SG | 25C19 | 25N | 44.77 |
| 25SG | 25C19 | 23C | 73.06 | 25SG | 25C19 | 162CE1 | 76.49 |
| 25SG | 25C19 | 25CA | 36.53 | 25SG | 25C19 | 23O | 62.97 |
| 25SG | 25C19 | 162CG | 75.04 | 25SG | 25C19 | 24N | 71.77 |
| 25SG | 25C19 | 162CA | 61.03 | 25CB | 25C19 | 19NE2 | 64.00 |
| 25CB | 25C19 | 162ND1 | 55.38 | 25CB | 25C19 | 23CA | 96.18 |
| 25CB | 25C19 | 19OE1 | 59.77 | 25CB | 25C19 | 161O | 94.40 |
| 25CB | 25C19 | 19CD | 63.98 | 25CB | 25C19 | 25N | 33.81 |
| 25CB | 25C19 | 23C | 76.97 | 25CB | 25C19 | 162CE1 | 52.78 |
| 25CB | 25C19 | 25CA | 15.71 | 25CB | 25C19 | 23O | 73.90 |
| 25CB | 25C19 | 162CG | 63.84 | 25CB | 25C19 | 24N | 67.67 |
| 25CB | 25C19 | 162CA | 66.83 | 19NE2 | 25C19 | 162ND1 | 88.64 |
| 19NE2 | 25C19 | 23CA | 60.82 | 19NE2 | 25C19 | 19OE1 | 31.76 |
| 19NE2 | 25C19 | 19CD | 16.34 | 19NE2 | 25C19 | 25N | 44.95 |
| 19NE2 | 25C19 | 23C | 56.12 | 19NE2 | 25C19 | 162CE1 | 73.67 |
| 19NE2 | 25C19 | 25CA | 52.15 | 19NE2 | 25C19 | 23O | 68.16 |
| 19NE2 | 25C19 | 24N | 41.52 | 162ND1 | 25C19 | 19OE1 | 59.55 |
| 162ND1 | 25C19 | 161O | 71.43 | 162ND1 | 25C19 | 19CD | 75.22 |
| 162ND1 | 25C19 | 25N | 86.60 | 162ND1 | 25C19 | 162CE1 | 15.59 |
| 162ND1 | 25C19 | 25CA | 68.74 | 162ND1 | 25C19 | 162CG | 12.11 |
| 162ND1 | 25C19 | 162CA | 39.22 | 23CA | 25C19 | 19OE1 | 92.31 |
| 23CA | 25C19 | 19CD | 76.28 | 23CA | 25C19 | 25N | 62.61 |
| 23CA | 25C19 | 23C | 19.89 | 23CA | 25C19 | 25CA | 81.01 |
| 23CA | 25C19 | 23O | 29.74 | 23CA | 25C19 | 24N | 29.49 |
| 19OE1 | 25C19 | 19CD | 16.09 | 19OE1 | 25C19 | 25N | 61.21 |
| 19OE1 | 25C19 | 23C | 87.07 | 19OE1 | 25C19 | 162CE1 | 43.98 |
| 19OE1 | 25C19 | 25CA | 56.66 | 19OE1 | 25C19 | 23O | 97.48 |
| 19OE1 | 25C19 | 162CG | 70.72 | 19OE1 | 25C19 | 24N | 71.88 |
| 19OE1 | 25C19 | 162CA | 98.02 | 161O | 25C19 | 162CE1 | 86.98 |
| 161O | 25C19 | 162CG | 60.30 | 161O | 25C19 | 162CA | 34.11 |
| 19CD | 25C19 | 25N | 54.73 | 19CD | 25C19 | 23C | 72.44 |
| 19CD | 25C19 | 162CE1 | 59.74 | 19CD | 25C19 | 25CA | 56.11 |
| 19CD | 25C19 | 23O | 84.17 | 19CD | 25C19 | 162CG | 86.63 |
| 19CD | 25C19 | 24N | 57.70 | 25N | 25C19 | 23C | 44.11 |
| 25N | 25C19 | 162CE1 | 79.19 | 25N | 25C19 | 25CA | 18.40 |
| 25N | 25C19 | 23O | 44.87 | 25N | 25C19 | 162CG | 96.59 |
| 25N | 25C19 | 24N | 33.86 | 25N | 25C19 | 162CA | 99.25 |
| 23C | 25C19 | 25CA | 62.33 | 23C | 25C19 | 23O | 14.57 |
| 23C | 25C19 | 24N | 15.37 | 162CE1 | 25C19 | 25CA | 63.05 |
| 162CE1 | 25C19 | 162CG | 26.96 | 162CE1 | 25C19 | 162CA | 54.63 |
| 25CA | 25C19 | 23O | 61.33 | 25CA | 25C19 | 162CG | 78.31 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 25CA | 25C19 | 24N | 52.11 | 25CA | 25C19 | 162CA | 82.37 |
| 23O | 25C19 | 24N | 26.74 | 162CG | 25C19 | 162CA | 30.21 |
| 20O | 25N20 | 19CD | 87.74 | 20O | 25N20 | 19NE2 | 89.20 |
| 20O | 25N20 | 19CG | 65.65 | 20O | 25N20 | 22O | 66.51 |
| 20O | 25N20 | 20C | 2.25 | 20O | 25N20 | 184CD1 | 99.19 |
| 20O | 25N20 | 22N | 43.43 | 20O | 25N20 | 22C | 67.94 |
| 20O | 25N20 | 21CA | 31.81 | 20O | 25N20 | 19CB | 59.50 |
| 19CD | 25N20 | 19NE2 | 20.94 | 19CD | 25N20 | 19CG | 24.17 |
| 19CD | 25N20 | 19OE1 | 18.66 | 19CD | 25N20 | 22O | 59.53 |
| 19CD | 25N20 | 184NE1 | 61.57 | 19CD | 25N20 | 20C | 89.98 |
| 19CD | 25N20 | 184CD1 | 58.87 | 19CD | 25N20 | 22N | 90.16 |
| 19CD | 25N20 | 22C | 72.14 | 19CD | 25N20 | 184CE2 | 73.87 |
| 19CD | 25N20 | 19CB | 28.25 | 19NE2 | 25N20 | 19CG | 38.17 |
| 19NE2 | 25N20 | 19OE1 | 34.54 | 19NE2 | 25N20 | 22O | 42.18 |
| 19NE2 | 25N20 | 184NE1 | 79.08 | 19NE2 | 25N20 | 20C | 91.23 |
| 19NE2 | 25N20 | 184CD1 | 79.14 | 19NE2 | 25N20 | 22N | 76.95 |
| 19NE2 | 25N20 | 22C | 53.71 | 19NE2 | 25N20 | 184CE2 | 90.08 |
| 19NE2 | 25N20 | 19CB | 35.63 | 19CG | 25N20 | 19OE1 | 37.15 |
| 19CG | 25N20 | 22O | 61.25 | 19CG | 25N20 | 184NE1 | 67.75 |
| 19CG | 25N20 | 20C | 67.89 | 19CG | 25N20 | 184CD1 | 57.44 |
| 19CG | 25N20 | 22N | 80.74 | 19CG | 25N20 | 22C | 74.00 |
| 19CG | 25N20 | 21CA | 93.39 | 19CG | 25N20 | 184CE2 | 80.81 |
| 19CG | 25N20 | 19CB | 11.02 | 19OE1 | 25N20 | 22O | 76.29 |
| 19OE1 | 25N20 | 184NE1 | 44.61 | 19OE1 | 25N20 | 184CD1 | 46.08 |
| 19OE1 | 25N20 | 22C | 88.22 | 19OE1 | 25N20 | 184CE2 | 56.16 |
| 19OE1 | 25N20 | 19CB | 44.63 | 22O | 25N20 | 20C | 67.58 |
| 22O | 25N20 | 22N | 36.33 | 22O | 25N20 | 22C | 13.03 |
| 22O | 25N20 | 21CA | 65.40 | 22O | 25N20 | 19CB | 51.11 |
| 184NE1 | 25N20 | 184CD1 | 17.40 | 184NE1 | 25N20 | 184CE2 | 13.10 |
| 184NE1 | 25N20 | 19CB | 78.62 | 20C | 25N20 | 22N | 43.20 |
| 20C | 25N20 | 22C | 68.49 | 20C | 25N20 | 21CA | 30.05 |
| 20C | 25N20 | 19CB | 61.74 | 184CD1 | 25N20 | 184CE2 | 27.05 |
| 184CD1 | 25N20 | 19CB | 68.40 | 22N | 25N20 | 22C | 29.81 |
| 22N | 25N20 | 21CA | 29.53 | 22N | 25N20 | 19CB | 69.93 |
| 22C | 25N20 | 21CA | 59.18 | 22C | 25N20 | 19CB | 63.62 |
| 21CA | 25N20 | 19CB | 84.67 | 184CE2 | 25N20 | 19CB | 91.71 |
| 162ND1 | 25C21 | 25SG | 76.59 | 162ND1 | 25C21 | 162CE1 | 18.63 |
| 162ND1 | 25C21 | 162CG | 18.63 | 162ND1 | 25C21 | 161O | 88.59 |
| 162ND1 | 25C21 | 25CB | 58.66 | 162ND1 | 25C21 | 162CB | 39.41 |
| 162ND1 | 25C21 | 19OE1 | 66.84 | 162ND1 | 25C21 | 162CA | 48.39 |
| 162ND1 | 25C21 | 19NE2 | 91.07 | 162ND1 | 25C21 | 19CD | 80.09 |
| 162ND1 | 25C21 | 162NE2 | 16.42 | 162ND1 | 25C21 | 161C | 78.48 |
| 162ND1 | 25C21 | 184CZ2 | 60.80 | 162ND1 | 25C21 | 162CD2 | 15.86 |
| 162ND1 | 25C21 | 184NE1 | 63.09 | 162ND1 | 25C21 | 162N | 62.96 |
| 25SG | 25C21 | 162CE1 | 82.30 | 25SG | 25C21 | 162CG | 85.48 |
| 25SG | 25C21 | 161O | 75.19 | 25SG | 25C21 | 25CB | 27.93 |
| 25SG | 25C21 | 162CB | 86.01 | 25SG | 25C21 | 19OE1 | 84.07 |
| 25SG | 25C21 | 162CA | 67.62 | 25SG | 25C21 | 19NE2 | 71.84 |
| 25SG | 25C21 | 19CD | 81.26 | 25SG | 25C21 | 162NE2 | 89.59 |
| 25SG | 25C21 | 161C | 76.87 | 25SG | 25C21 | 162CD2 | 91.13 |
| 25SG | 25C21 | 162N | 73.63 | 162CE1 | 25C21 | 162CG | 34.59 |
| 162CE1 | 25C21 | 25CB | 58.15 | 162CE1 | 25C21 | 162CB | 56.62 |
| 162CE1 | 25C21 | 19OE1 | 49.16 | 162CE1 | 25C21 | 162CA | 67.01 |
| 162CE1 | 25C21 | 19NE2 | 75.88 | 162CE1 | 25C21 | 19CD | 63.04 |
| 162CE1 | 25C21 | 162NE2 | 10.76 | 162CE1 | 25C21 | 161C | 97.04 |
| 162CE1 | 25C21 | 184CZ2 | 52.78 | 162CE1 | 25C21 | 162CD2 | 25.92 |
| 162CE1 | 25C21 | 184NE1 | 46.57 | 162CE1 | 25C21 | 162N | 81.54 |
| 162CG | 25C21 | 161O | 74.86 | 162CG | 25C21 | 25CB | 73.56 |
| 162CG | 25C21 | 162CB | 22.12 | 162CG | 25C21 | 19OE1 | 83.74 |
| 162CG | 25C21 | 162CA | 37.08 | 162CG | 25C21 | 19CD | 97.60 |
| 162CG | 25C21 | 162NE2 | 27.00 | 162CG | 25C21 | 161C | 64.13 |
| 162CG | 25C21 | 184CZ2 | 58.58 | 162CG | 25C21 | 162CD2 | 11.67 |
| 162CG | 25C21 | 184NE1 | 71.27 | 162CG | 25C21 | 162N | 49.24 |
| 161O | 25C21 | 25CB | 96.45 | 161O | 25C21 | 162CB | 53.58 |
| 161O | 25C21 | 162CA | 40.31 | 161O | 25C21 | 161C | 10.85 |
| 161O | 25C21 | 162CD2 | 86.16 | 161O | 25C21 | 162N | 25.81 |
| 25CB | 25C21 | 162CB | 84.13 | 25CB | 25C21 | 19OE1 | 58.32 |
| 25CB | 25C21 | 162CA | 73.26 | 25CB | 25C21 | 19NE2 | 55.61 |
| 25CB | 25C21 | 19CD | 59.29 | 25CB | 25C21 | 162NE2 | 67.37 |
| 25CB | 25C21 | 161C | 94.34 | 25CB | 25C21 | 162CD2 | 74.51 |
| 25CB | 25C21 | 184NE1 | 89.62 | 25CB | 25C21 | 162N | 85.19 |
| 162CB | 25C21 | 162CA | 21.46 | 162CB | 25C21 | 162NE2 | 48.98 |
| 162CB | 25C21 | 161C | 42.74 | 162CB | 25C21 | 184CZ2 | 70.53 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 162CB | 25C21 | 162CD2 | 32.77 | 162CB | 25C21 | 184NE1 | 90.36 |
| 162CB | 25C21 | 162N | 28.88 | 19OE1 | 25C21 | 19NE2 | 30.01 |
| 19OE1 | 25C21 | 19CD | 14.42 | 19OE1 | 25C21 | 162NE2 | 57.58 |
| 19OE1 | 25C21 | 184CZ2 | 67.32 | 19OE1 | 25C21 | 162CD2 | 74.15 |
| 19OE1 | 25C21 | 184NE1 | 37.69 | 162CA | 25C21 | 162NE2 | 62.57 |
| 162CA | 25C21 | 161C | 30.75 | 162CA | 25C21 | 184CZ2 | 91.75 |
| 162CA | 25C21 | 162CD2 | 48.73 | 162CA | 25C21 | 162N | 15.49 |
| 19NE2 | 25C21 | 19CD | 16.41 | 19NE2 | 25C21 | 162NE2 | 85.63 |
| 19NE2 | 25C21 | 184CZ2 | 94.21 | 19NE2 | 25C21 | 184NE1 | 63.87 |
| 19CD | 25C21 | 162NE2 | 71.85 | 19CD | 25C21 | 184CZ2 | 78.23 |
| 19CD | 25C21 | 162CD2 | 88.39 | 19CD | 25C21 | 184NE1 | 47.85 |
| 162NE2 | 25C21 | 161C | 91.07 | 162NE2 | 25C21 | 184CZ2 | 46.06 |
| 162NE2 | 25C21 | 162CD2 | 16.57 | 162NE2 | 25C21 | 184NE1 | 47.02 |
| 162NE2 | 25C21 | 162N | 75.95 | 161C | 25C21 | 162CD2 | 75.36 |
| 161C | 25C21 | 162N | 15.54 | 184CZ2 | 25C21 | 162CD2 | 49.06 |
| 184CZ2 | 25C21 | 184NE1 | 30.38 | 184CZ2 | 25C21 | 162N | 97.18 |
| 162CD2 | 25C21 | 184NE1 | 59.61 | 162CD2 | 25C21 | 162N | 60.72 |
| 25SG | 25C22 | 25CB | 34.32 | 25SG | 25C22 | 25N | 58.23 |
| 25SG | 25C22 | 23O | 96.62 | 25SG | 25C22 | 25CA | 41.06 |
| 25SG | 25C22 | 161O | 88.83 | 25SG | 25C22 | 19NE2 | 94.39 |
| 25SG | 25C22 | 24N | 94.80 | 25SG | 25C22 | 162ND1 | 67.14 |
| 25SG | 25C22 | 26N | 28.02 | 25SG | 25C22 | 24C | 63.81 |
| 25SG | 25C22 | 25C | 28.81 | 25SG | 25C22 | 162CA | 61.80 |
| 25SG | 25C22 | 26CD1 | 59.67 | 25CB | 25C22 | 25N | 41.88 |
| 25CB | 25C22 | 23C | 94.72 | 25CB | 25C22 | 23O | 97.61 |
| 25CB | 25C22 | 25CA | 20.48 | 25CB | 25C22 | 19NE2 | 62.01 |
| 25CB | 25C22 | 24N | 79.22 | 25CB | 25C22 | 162ND1 | 50.87 |
| 25CB | 25C22 | 26N | 40.24 | 25CB | 25C22 | 24C | 51.06 |
| 25CB | 25C22 | 25C | 25.68 | 25CB | 25C22 | 162CA | 70.19 |
| 25CB | 25C22 | 26CD1 | 77.04 | 25N | 25C22 | 23CA | 72.11 |
| 25N | 25C22 | 23C | 53.07 | 25N | 25C22 | 23O | 56.89 |
| 25N | 25C22 | 25CA | 21.75 | 25N | 25C22 | 19NE2 | 46.70 |
| 25N | 25C22 | 24N | 38.64 | 25N | 25C22 | 162ND1 | 88.45 |
| 25N | 25C22 | 26N | 36.83 | 25N | 25C22 | 24C | 9.50 |
| 25N | 25C22 | 25C | 29.43 | 25N | 25C22 | 26CD1 | 53.68 |
| 23CA | 25C22 | 23C | 23.35 | 23CA | 25C22 | 23O | 37.19 |
| 23CA | 25C22 | 25CA | 93.17 | 23CA | 25C22 | 19NE2 | 58.05 |
| 23CA | 25C22 | 24N | 33.59 | 23CA | 25C22 | 26N | 99.96 |
| 23CA | 25C22 | 24C | 64.82 | 23CA | 25C22 | 26CD1 | 78.54 |
| 23C | 25C22 | 23O | 18.81 | 23C | 25C22 | 25CA | 74.82 |
| 23C | 25C22 | 19NE2 | 57.79 | 23C | 25C22 | 24N | 16.66 |
| 23C | 25C22 | 26N | 76.83 | 23C | 25C22 | 24C | 44.46 |
| 23C | 25C22 | 25C | 78.94 | 23C | 25C22 | 26CD1 | 57.31 |
| 23O | 25C22 | 25CA | 77.22 | 23O | 25C22 | 19NE2 | 74.75 |
| 23O | 25C22 | 24N | 30.81 | 23O | 25C22 | 26N | 69.15 |
| 23O | 25C22 | 24C | 47.40 | 23O | 25C22 | 25C | 76.13 |
| 23O | 25C22 | 26CD1 | 41.43 | 25CA | 25C22 | 19NE2 | 54.59 |
| 25CA | 25C22 | 24N | 60.09 | 25CA | 25C22 | 162ND1 | 70.00 |
| 25CA | 25C22 | 26N | 30.49 | 25CA | 25C22 | 24C | 30.68 |
| 25CA | 25C22 | 25C | 15.62 | 25CA | 25C22 | 162CA | 89.97 |
| 25CA | 25C22 | 26CD1 | 62.21 | 161O | 25C22 | 162ND1 | 66.24 |
| 161O | 25C22 | 162CA | 34.26 | 19NE2 | 25C22 | 24N | 44.06 |
| 19NE2 | 25C22 | 162ND1 | 75.31 | 19NE2 | 25C22 | 26N | 82.03 |
| 19NE2 | 25C22 | 24C | 49.24 | 19NE2 | 25C22 | 25C | 69.71 |
| 19NE2 | 25C22 | 26CD1 | 96.23 | 24N | 25C22 | 26N | 68.47 |
| 24N | 25C22 | 24C | 31.27 | 24N | 25C22 | 25C | 66.84 |
| 24N | 25C22 | 26CD1 | 59.64 | 162ND1 | 25C22 | 26N | 88.16 |
| 162ND1 | 25C22 | 24C | 97.87 | 162ND1 | 25C22 | 25C | 75.88 |
| 162ND1 | 25C22 | 162CA | 38.60 | 26N | 25C22 | 24C | 39.22 |
| 26N | 25C22 | 25C | 15.72 | 26N | 25C22 | 162CA | 89.81 |
| 26N | 25C22 | 26CD1 | 37.42 | 24C | 25C22 | 25C | 35.57 |
| 24C | 25C22 | 26CD1 | 47.97 | 25C | 25C22 | 162CA | 86.23 |
| 25C | 25C22 | 26CD1 | 51.39 | 25SG | 25O23 | 25N | 74.67 |
| 25SG | 25O23 | 25CB | 38.15 | 25SG | 25O23 | 25CA | 54.63 |
| 25SG | 25O23 | 24C | 85.79 | 25SG | 25O23 | 26N | 43.64 |
| 25SG | 25O23 | 25C | 46.38 | 25SG | 25O23 | 19OE1 | 92.56 |
| 25SG | 25O23 | 26CD1 | 68.54 | 25SG | 25O23 | 162ND1 | 54.77 |
| 25SG | 25O23 | 24O | 79.70 | 23C | 25O23 | 25N | 73.70 |
| 23C | 25O23 | 23CA | 31.55 | 23C | 25O23 | 23O | 24.72 |
| 23C | 25O23 | 24N | 24.08 | 23C | 25O23 | 19NE2 | 78.98 |
| 23C | 25O23 | 25CA | 97.79 | 23C | 25O23 | 24C | 59.01 |
| 23C | 25O23 | 24CA | 36.52 | 23C | 25O23 | 23N | 33.47 |
| 23C | 25O23 | 22O | 48.06 | 23C | 25O23 | 19CD | 90.90 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 23C | 25O23 | 26N | 92.04 | 23C | 25O23 | 25C | 96.56 |
| 23C | 25O23 | 26CD1 | 66.16 | 23C | 25O23 | 22C | 38.64 |
| 23C | 25O23 | 24O | 64.99 | 25N | 25O23 | 23O | 75.80 |
| 25N | 25O23 | 25CB | 50.26 | 25N | 25O23 | 24N | 53.76 |
| 25N | 25O23 | 19NE2 | 61.26 | 25N | 25O23 | 25CA | 24.14 |
| 25N | 25O23 | 24C | 14.83 | 25N | 25O23 | 24CA | 37.18 |
| 25N | 25O23 | 23N | 97.04 | 25N | 25O23 | 22O | 79.60 |
| 25N | 25O23 | 19CD | 63.80 | 25N | 25O23 | 26N | 37.49 |
| 25N | 25O23 | 25C | 28.32 | 25N | 25O23 | 19OE1 | 68.00 |
| 25N | 25O23 | 26CD1 | 60.48 | 25N | 25O23 | 22C | 87.54 |
| 25N | 25O23 | 162ND1 | 89.51 | 25N | 25O23 | 24O | 9.64 |
| 23CA | 25O23 | 23O | 48.80 | 23CA | 25O23 | 24N | 46.69 |
| 23CA | 25O23 | 19NE2 | 77.35 | 23CA | 25O23 | 24C | 86.89 |
| 23CA | 25O23 | 24CA | 64.88 | 23CA | 25O23 | 23N | 7.95 |
| 23CA | 25O23 | 22O | 38.18 | 23CA | 25O23 | 19CD | 87.87 |
| 23CA | 25O23 | 26CD1 | 93.73 | 23CA | 25O23 | 22C | 23.48 |
| 23CA | 25O23 | 24O | 93.16 | 23O | 25O23 | 24N | 42.48 |
| 23O | 25O23 | 25CA | 97.01 | 23O | 25O23 | 24C | 61.75 |
| 23O | 25O23 | 24CA | 43.63 | 23O | 25O23 | 23N | 53.76 |
| 23O | 25O23 | 22O | 72.77 | 23O | 25O23 | 26N | 79.20 |
| 23O | 25O23 | 25C | 89.58 | 23O | 25O23 | 26CD1 | 44.93 |
| 23O | 25O23 | 22C | 62.49 | 23O | 25O23 | 24O | 66.16 |
| 25CB | 25O23 | 19NE2 | 75.63 | 25CB | 25O23 | 25CA | 26.15 |
| 25CB | 25O23 | 24C | 64.94 | 25CB | 25O23 | 24CA | 87.43 |
| 25CB | 25O23 | 19CD | 67.69 | 25CB | 25O23 | 26N | 43.69 |
| 25CB | 25O23 | 25C | 31.03 | 25CB | 25O23 | 19OE1 | 57.73 |
| 25CB | 25O23 | 26CD1 | 83.37 | 25CB | 25O23 | 162ND1 | 43.20 |
| 25CB | 25O23 | 24C | 59.04 | 24N | 25O23 | 19NE2 | 59.02 |
| 24N | 25O23 | 25CA | 77.52 | 24N | 25O23 | 24C | 40.38 |
| 24N | 25O23 | 24CA | 19.70 | 24N | 25O23 | 23N | 44.10 |
| 24N | 25O23 | 22C | 40.11 | 24N | 25O23 | 19CD | 70.43 |
| 24N | 25O23 | 26N | 81.70 | 24N | 25O23 | 25C | 80.42 |
| 24N | 25O23 | 19OE1 | 85.06 | 24N | 25O23 | 26CD1 | 70.58 |
| 24N | 25O23 | 22C | 39.18 | 24N | 25O23 | 24O | 46.65 |
| 19NE2 | 25O23 | 25CA | 66.95 | 19NE2 | 25O23 | 24C | 63.26 |
| 19NE2 | 25O23 | 24CA | 65.23 | 19NE2 | 25O23 | 23N | 69.48 |
| 19NE2 | 25O23 | 22O | 39.17 | 19NE2 | 25O23 | 19CD | 11.94 |
| 19NE2 | 25O23 | 26N | 96.41 | 19NE2 | 25O23 | 25C | 81.46 |
| 19NE2 | 25O23 | 19OE1 | 27.37 | 19NE2 | 25O23 | 22C | 53.87 |
| 19NE2 | 25O23 | 162ND1 | 76.87 | 19NE2 | 25O23 | 24O | 65.05 |
| 25CA | 25O23 | 24C | 38.79 | 25CA | 25O23 | 24CA | 61.29 |
| 25CA | 25O23 | 22O | 96.77 | 25CA | 25O23 | 19CD | 63.98 |
| 25CA | 25O23 | 26N | 31.96 | 25CA | 25O23 | 25C | 15.29 |
| 25CA | 25O23 | 19OE1 | 61.11 | 25CA | 25O23 | 26CD1 | 68.99 |
| 25CA | 25O23 | 162ND1 | 67.28 | 25CA | 25O23 | 24O | 32.93 |
| 24C | 25O23 | 24CA | 22.55 | 24C | 25O23 | 23N | 84.41 |
| 24C | 25O23 | 22O | 71.79 | 24C | 25O23 | 19CD | 68.91 |
| 24C | 25O23 | 26N | 44.17 | 24C | 25O23 | 25C | 40.07 |
| 24C | 25O23 | 19OE1 | 76.59 | 24C | 25O23 | 26CD1 | 54.93 |
| 24C | 25O23 | 22C | 77.02 | 24C | 25O23 | 24O | 6.27 |
| 24CA | 25O23 | 23N | 63.29 | 24CA | 25O23 | 22O | 57.79 |
| 24CA | 25O23 | 19CD | 74.68 | 24CA | 25O23 | 26N | 62.01 |
| 24CA | 25O23 | 25C | 61.72 | 24CA | 25O23 | 19OE1 | 86.76 |
| 24CA | 25O23 | 26CD1 | 55.98 | 24CA | 25O23 | 22C | 58.75 |
| 24CA | 25O23 | 24O | 28.67 | 23N | 25O23 | 22O | 30.31 |
| 23N | 25O23 | 19CD | 79.92 | 23N | 25O23 | 19OE1 | 93.90 |
| 23N | 25O23 | 26CD1 | 98.39 | 23N | 25O23 | 22C | 15.63 |
| 23N | 25O23 | 24O | 90.66 | 22O | 25O23 | 19CD | 49.86 |
| 22O | 25O23 | 19OE1 | 64.43 | 22O | 25O23 | 22C | 14.70 |
| 22O | 25O23 | 24O | 77.07 | 19CD | 25O23 | 26N | 95.38 |
| 19CD | 25O23 | 25C | 79.18 | 19CD | 25O23 | 19OE1 | 15.44 |
| 19CD | 25O23 | 22C | 64.49 | 19CD | 25O23 | 162ND1 | 64.94 |
| 19CD | 25O23 | 24O | 69.44 | 26N | 25O23 | 25C | 16.77 |
| 26N | 25O23 | 19OE1 | 92.94 | 26N | 25O23 | 26CD1 | 39.94 |
| 26N | 25O23 | 162ND1 | 84.95 | 26N | 25O23 | 24O | 38.78 |
| 25C | 25O23 | 19OE1 | 76.17 | 25C | 25O23 | 26CD1 | 55.41 |
| 25C | 25O23 | 162ND1 | 74.20 | 25C | 25O23 | 24O | 33.82 |
| 19OE1 | 25O23 | 22C | 78.82 | 19OE1 | 25O23 | 162ND1 | 49.50 |
| 19OE1 | 25O23 | 24O | 75.54 | 26CD1 | 25O23 | 24O | 54.16 |
| 22C | 25O23 | 24O | 82.96 | 162ND1 | 25O23 | 24O | 99.10 |
| 64O | 25C24 | 61OD1 | 49.69 | 64O | 25C25 | 61OD1 | 65.86 |
| 64O | 25C25 | 64C | 4.04 | 64O | 25C25 | 65CA | 36.03 |
| 64O | 25C25 | 61CG | 60.48 | 64O | 25C25 | 65N | 18.55 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 61OD1 | 25C25 | 64C | 66.57 | 61OD1 | 25C25 | 65CA | 65.57 |
| 61OD1 | 25C25 | 61CG | 12.80 | 61OD1 | 25C25 | 65N | 65.27 |
| 64C | 25C25 | 65CA | 32.21 | 64C | 25C25 | 61CG | 62.08 |
| 64C | 25C25 | 65N | 14.69 | 65CA | 25C25 | 61CG | 68.81 |
| 65CA | 25C25 | 65N | 17.52 | 65N | 25C25 | 61CG | 64.30 |
| 64O | 25C26 | 61OD1 | 75.97 | 64O | 25C26 | 65CA | 46.13 |
| 64O | 25C26 | 65C | 60.97 | 64O | 25C26 | 64C | 10.65 |
| 64O | 25C26 | 66N | 77.86 | 64O | 25C26 | 61CG | 67.54 |
| 64O | 25C26 | 65N | 27.99 | 64O | 25C26 | 65O | 58.42 |
| 64O | 25C26 | 61CB | 50.52 | 61OD1 | 25C26 | 65CA | 81.67 |
| 61OD1 | 25C26 | 65C | 66.87 | 61OD1 | 25C26 | 64C | 74.15 |
| 61OD1 | 25C26 | 66N | 75.37 | 61OD1 | 25C26 | 61CG | 10.88 |
| 61OD1 | 25C26 | 65N | 75.81 | 61OD1 | 25C26 | 65O | 51.81 |
| 61OD1 | 25C26 | 61CB | 25.47 | 65CA | 25C26 | 65C | 22.26 |
| 65CA | 25C26 | 64C | 35.83 | 65CA | 25C26 | 66N | 33.99 |
| 65CA | 25C26 | 61CG | 80.84 | 65CA | 25C26 | 65N | 18.46 |
| 65CA | 25C26 | 65O | 32.38 | 65CA | 25C26 | 61CB | 65.67 |
| 65C | 25C26 | 64C | 50.43 | 65C | 25C26 | 66N | 17.99 |
| 65C | 25C26 | 61CG | 69.56 | 65C | 25C26 | 65N | 34.42 |
| 65C | 25C26 | 65O | 15.34 | 65C | 25C26 | 61CB | 58.96 |
| 64C | 25C26 | 66N | 67.22 | 64C | 25C26 | 61CG | 67.20 |
| 64C | 25C26 | 65N | 17.48 | 64C | 25C26 | 65O | 48.92 |
| 64C | 25C26 | 61CB | 49.45 | 66N | 25C26 | 61CG | 80.82 |
| 66N | 25C26 | 65N | 50.23 | 66N | 25C26 | 65O | 29.57 |
| 66N | 25C26 | 61CB | 73.71 | 61CG | 25C26 | 65N | 71.80 |
| 61CG | 25C26 | 65O | 54.22 | 61CG | 25C26 | 61CB | 17.81 |
| 65N | 25C26 | 65O | 36.92 | 65N | 25C26 | 61CB | 54.59 |
| 65O | 25C26 | 61CB | 44.43 | 61OD1 | 25C27 | 64O | 56.92 |
| 61OD1 | 25C27 | 66N | 69.33 | 61OD1 | 25C27 | 65C | 57.67 |
| 61OD1 | 25C27 | 65CA | 66.06 | 61OD1 | 25C27 | 61CG | 5.76 |
| 64O | 25C27 | 66N | 63.73 | 64O | 25C27 | 65C | 48.11 |
| 64O | 25C27 | 65CA | 35.11 | 64O | 25C27 | 61CG | 54.18 |
| 66N | 25C27 | 67CE2 | 75.89 | 66N | 25C27 | 65C | 16.74 |
| 66N | 25C27 | 65CA | 30.26 | 66N | 25C27 | 61CG | 73.19 |
| 66N | 25C27 | 67OH | 95.43 | 67CE2 | 25C27 | 65C | 91.10 |
| 67CE2 | 25C27 | 67OH | 29.04 | 65C | 25C27 | 65CA | 18.79 |
| 65C | 25C27 | 61CG | 60.50 | 65CA | 25C27 | 61CG | 67.06 |
| 61OD1 | 25C28 | 67CE2 | 87.37 | 67OH | 25C28 | 67CE2 | 29.20 |
| 67CE2 | 25C30 | 66CA | 87.59 | 67CE2 | 25C30 | 67CD2 | 20.16 |
| 67CE2 | 25C30 | 67CZ | 18.73 | 67CE2 | 25C30 | 67OH | 34.56 |
| 67CE2 | 25C30 | 66C | 70.31 | 67CE2 | 25C30 | 66O | 70.72 |
| 67CE2 | 25C30 | 67CG | 25.18 | 66N | 25C30 | 61OD1 | 77.24 |
| 66N | 25C30 | 66CA | 21.80 | 66N | 25C30 | 67CD2 | 87.09 |
| 66N | 25C30 | 65C | 18.44 | 66N | 25C30 | 66C | 34.83 |
| 66N | 25C30 | 66O | 37.41 | 66N | 25C30 | 65O | 28.55 |
| 66N | 25C30 | 65CA | 30.87 | 66N | 25C30 | 67CG | 79.90 |
| 61OD1 | 25C30 | 66CA | 79.21 | 61OD1 | 25C30 | 65C | 61.19 |
| 61OD1 | 25C30 | 66C | 99.06 | 61OD1 | 25C30 | 65O | 48.69 |
| 61OD1 | 25C30 | 65CA | 65.35 | 66CA | 25C30 | 67CD2 | 68.10 |
| 66CA | 25C30 | 67CZ | 95.64 | 66CA | 25C30 | 65C | 34.85 |
| 66CA | 25C30 | 66C | 20.50 | 66CA | 25C30 | 66O | 32.31 |
| 66CA | 25C30 | 65O | 36.26 | 66CA | 25C30 | 65CA | 51.45 |
| 66CA | 25C30 | 67CG | 63.14 | 67CD2 | 25C30 | 67CZ | 35.10 |
| 67CD2 | 25C30 | 67OH | 53.38 | 67CD2 | 25C30 | 66C | 52.50 |
| 67CD2 | 25C30 | 66O | 56.67 | 67CD2 | 25C30 | 67CG | 11.66 |
| 67CZ | 25C30 | 67OH | 19.01 | 67CZ | 25C30 | 66C | 75.82 |
| 67CZ | 25C30 | 66O | 70.92 | 67CZ | 25C30 | 67CG | 34.09 |
| 65C | 25C30 | 66C | 52.09 | 65C | 25C30 | 66O | 55.84 |
| 65C | 25C30 | 65O | 14.76 | 65C | 25C30 | 65CA | 18.69 |
| 65C | 25C30 | 67CG | 97.10 | 67OH | 25C30 | 66C | 93.31 |
| 67OH | 25C30 | 66O | 85.90 | 67OH | 25C30 | 67CG | 53.10 |
| 66C | 25C30 | 66O | 15.93 | 66C | 25C30 | 65O | 56.33 |
| 66C | 25C30 | 65CA | 65.39 | 66C | 25C30 | 67CG | 45.14 |
| 66O | 25C30 | 65O | 64.17 | 66O | 25C30 | 65CA | 64.29 |
| 66O | 25C30 | 67CG | 46.61 | 65O | 25C30 | 65CA | 29.99 |
| 65O | 25C30 | 67CG | 98.82 | 67CE2 | 25O31 | 67CZ | 25.44 |
| 67CE2 | 25O31 | 67OH | 43.21 | 67CE2 | 25O31 | 67CD2 | 21.71 |
| 67CE2 | 25O31 | 66O | 86.23 | 67CE2 | 25O31 | 66C | 79.23 |
| 67CE2 | 25O31 | 66CA | 90.96 | 67CE2 | 25O31 | 67CE1 | 36.09 |
| 67CE2 | 25O31 | 67CG | 31.92 | 67CE2 | 25O31 | 67CD1 | 36.21 |
| 67CE2 | 25O31 | 67N | 65.41 | 67CZ | 25O31 | 67OH | 23.53 |
| 67CZ | 25O31 | 67CD2 | 40.63 | 67CZ | 25O31 | 66O | 90.28 |
| 67CZ | 25O31 | 66C | 90.73 | 67CZ | 25O31 | 67CE1 | 17.83 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 67CZ | 25O31 | 67CG | 39.73 | 67CZ | 25O31 | 67CD1 | 30.41 |
| 67CZ | 25O31 | 67N | 78.58 | 67OH | 25O31 | 67CD2 | 62.56 |
| 67OH | 25O31 | 67CE1 | 36.02 | 67OH | 25O31 | 67CG | 63.25 |
| 67OH | 25O31 | 67CD1 | 52.26 | 67CD2 | 25O31 | 66O | 66.16 |
| 67CD2 | 25O31 | 66N | 90.96 | 67CD2 | 25O31 | 66C | 57.61 |
| 67CD2 | 25O31 | 66CA | 69.91 | 67CD2 | 25O31 | 67CE1 | 41.91 |
| 67CD2 | 25O31 | 67CG | 16.99 | 67CD2 | 25O31 | 67CD1 | 31.58 |
| 67CD2 | 25O31 | 67N | 43.75 | 66O | 25O31 | 66N | 42.55 |
| 66O | 25O31 | 66C | 18.09 | 66O | 25O31 | 66CA | 35.81 |
| 66O | 25O31 | 67CE1 | 75.32 | 66O | 25O31 | 67CG | 54.80 |
| 66O | 25O31 | 65C | 57.68 | 66O | 25O31 | 67CD1 | 59.89 |
| 66O | 25O31 | 67N | 27.36 | 66O | 25O31 | 65CA | 66.84 |
| 66N | 25O31 | 66C | 37.22 | 66N | 25O31 | 66CA | 21.24 |
| 66N | 25O31 | 67CG | 88.11 | 66N | 25O31 | 65C | 15.16 |
| 66N | 25O31 | 67CD1 | 99.35 | 66N | 25O31 | 67N | 49.30 |
| 66N | 25O31 | 65CA | 28.53 | 66C | 25O31 | 66CA | 21.98 |
| 66C | 25O31 | 67CE1 | 79.50 | 66C | 25O31 | 67CG | 51.32 |
| 66C | 25O31 | 65C | 51.46 | 66C | 25O31 | 67CD1 | 62.32 |
| 66C | 25O31 | 67N | 13.91 | 66C | 25O31 | 65CA | 65.42 |
| 66CA | 25O31 | 67CE1 | 99.90 | 66CA | 25O31 | 67CG | 68.85 |
| 66CA | 25O31 | 65C | 32.23 | 66CA | 25O31 | 67CD1 | 82.55 |
| 66CA | 25O31 | 67N | 30.44 | 66CA | 25O31 | 65CA | 48.87 |
| 67CE1 | 25O31 | 67CG | 33.08 | 67CE1 | 25O31 | 67CD1 | 17.35 |
| 67CE1 | 25O31 | 67N | 69.51 | 67CG | 25O31 | 67CD1 | 17.79 |
| 67CG | 25O31 | 67N | 38.86 | 65C | 25O31 | 67N | 62.38 |
| 65C | 25O31 | 65CA | 17.93 | 67CD1 | 25O31 | 67N | 52.17 |
| 67N | 25O31 | 65CA | 77.82 | 66O | 25C32 | 66N | 41.03 |
| 66O | 25C32 | 67CZ | 76.35 | 66O | 25C32 | 67OH | 95.33 |
| 66O | 25C32 | 67CE2 | 69.48 | 66O | 25C32 | 66C | 15.10 |
| 66O | 25C32 | 66CA | 31.92 | 66O | 25C32 | 65CA | 69.81 |
| 66O | 25C32 | 65C | 56.36 | 66O | 25C32 | 67CE1 | 66.82 |
| 66O | 25C32 | 67CD2 | 53.70 | 66N | 25C32 | 67CE2 | 87.72 |
| 66N | 25C32 | 66C | 33.67 | 66N | 25C32 | 66CA | 17.88 |
| 66N | 25C32 | 65CA | 31.90 | 66N | 25C32 | 65C | 15.39 |
| 66N | 25C32 | 67CD2 | 73.68 | 67CZ | 25C32 | 67OH | 19.19 |
| 67CZ | 25C32 | 67CE2 | 19.23 | 67CZ | 25C32 | 66C | 73.63 |
| 67CZ | 25C32 | 66CA | 85.66 | 67CZ | 25C32 | 67CE1 | 16.63 |
| 67CZ | 25C32 | 67CD2 | 30.02 | 67CZ | 25C32 | 67CE2 | 33.49 |
| 67OH | 25C32 | 66C | 92.69 | 67OH | 25C32 | 67CE1 | 30.65 |
| 67OH | 25C32 | 67CD2 | 47.69 | 67CE2 | 25C32 | 66C | 62.32 |
| 67CE2 | 25C32 | 66CA | 70.20 | 67CE2 | 25C32 | 65C | 96.55 |
| 67CE2 | 25C32 | 67CE1 | 30.87 | 67CE2 | 25C32 | 67CD2 | 16.03 |
| 66C | 25C32 | 66CA | 19.46 | 66C | 25C32 | 65CA | 65.30 |
| 66C | 25C32 | 65C | 48.62 | 66C | 25C32 | 67CE1 | 68.20 |
| 66C | 25C32 | 67CD2 | 46.37 | 66CA | 25C32 | 65CA | 49.19 |
| 66CA | 25C32 | 65C | 30.83 | 66CA | 25C32 | 67CE1 | 84.10 |
| 66CA | 25C32 | 67CD2 | 55.84 | 65CA | 25C32 | 65C | 19.14 |
| 65C | 25C32 | 67CD2 | 84.41 | 67CE1 | 25C32 | 67CD2 | 33.97 |
| 67OH | 25O33 | 67CZ | 16.87 | 67OH | 25O33 | 66N | 97.69 |
| 67OH | 25O33 | 67CE2 | 28.97 | 67OH | 25O33 | 160O | 89.11 |
| 67CZ | 25O33 | 66N | 81.70 | 67CZ | 25O33 | 67CE2 | 16.30 |
| 67CZ | 25O33 | 160O | 93.56 | 66N | 25O33 | 67CE2 | 69.22 |
| 66O | 25C34 | 66N | 39.13 | 66O | 25C34 | 65CA | 71.17 |
| 66O | 25C34 | 25SG | 87.16 | 66O | 25C34 | 65C | 53.66 |
| 66O | 25C34 | 66C | 9.91 | 66N | 25C34 | 65CA | 32.59 |
| 66N | 25C34 | 25SG | 85.90 | 66N | 25C34 | 65C | 14.62 |
| 66N | 25C34 | 66C | 30.25 | 161O | 25C34 | 161C | 15.14 |
| 161O | 25C34 | 25SG | 60.22 | 161O | 25C34 | 160O | 61.47 |
| 65CA | 25C34 | 25SG | 79.10 | 65CA | 25C34 | 65C | 18.14 |
| 65CA | 25C34 | 66C | 62.76 | 161C | 25C34 | 25SG | 68.39 |
| 161C | 25C34 | 160O | 48.09 | 25SG | 25C34 | 65C | 84.17 |
| 25SG | 25C34 | 66C | 90.62 | 65C | 25C34 | 66C | 44.86 |
| 161O | 25C35 | 160O | 72.48 | 161O | 25C35 | 161C | 18.16 |
| 161O | 25C35 | 162N | 31.48 | 161O | 25C35 | 161CA | 33.51 |
| 161O | 25C35 | 163N | 64.70 | 161O | 25C35 | 160C | 64.27 |
| 161O | 25C35 | 25SG | 63.17 | 161O | 25C35 | 162CA | 35.94 |
| 161O | 25C35 | 161N | 48.76 | 161O | 25C35 | 162C | 54.37 |
| 160O | 25C35 | 161C | 58.42 | 160O | 25C35 | 162N | 63.10 |
| 160O | 25C35 | 161CA | 39.04 | 160O | 25C35 | 160C | 13.43 |
| 160O | 25C35 | 162CA | 80.67 | 160O | 25C35 | 161N | 27.44 |
| 160O | 25C35 | 162C | 86.34 | 161C | 25C35 | 162N | 17.93 |
| 161C | 25C35 | 161CA | 20.68 | 161C | 25C35 | 163N | 61.49 |
| 161C | 25C35 | 160C | 48.25 | 161C | 25C35 | 25SG | 75.24 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 161C | 25C35 | 162CA | 31.05 | 161C | 25C35 | 161N | 32.29 |
| 161C | 25C35 | 162C | 47.54 | 66O | 25C35 | 25SG | 85.01 |
| 162N | 25C35 | 161CA | 32.91 | 162N | 25C35 | 163N | 45.91 |
| 162N | 25C35 | 160C | 50.42 | 162N | 25C35 | 25SG | 71.74 |
| 162N | 25C35 | 162CA | 17.88 | 162N | 25C35 | 161N | 35.87 |
| 162N | 25C35 | 162C | 30.79 | 161CA | 25C35 | 163N | 78.80 |
| 161CA | 25C35 | 160C | 31.32 | 161CA | 25C35 | 25SG | 95.35 |
| 161CA | 25C35 | 162CA | 49.73 | 161CA | 25C35 | 161N | 17.33 |
| 161CA | 25C35 | 162C | 63.45 | 163N | 25C35 | 160C | 88.14 |
| 163N | 25C35 | 25SG | 47.65 | 163N | 25C35 | 162CA | 30.56 |
| 163N | 25C35 | 161N | 77.99 | 163N | 25C35 | 162C | 15.86 |
| 160C | 25C35 | 162CA | 67.69 | 160C | 25C35 | 161N | 15.98 |
| 160C | 25C35 | 162C | 72.94 | 25SG | 25C35 | 162CA | 55.42 |
| 25SG | 25C35 | 162C | 57.22 | 162CA | 25C35 | 161N | 53.66 |
| 162CA | 25C35 | 162C | 18.43 | 161N | 25C35 | 162C | 62.17 |
| 66O | 25C36 | 163CB | 99.95 | 66O | 25C36 | 66C | 0.80 |
| 66O | 25C36 | 25SG | 91.26 | 66O | 25C36 | 68SD | 70.79 |
| 66O | 25C36 | 26CB | 44.37 | 163CB | 25C36 | 163N | 35.50 |
| 163CB | 25C36 | 163CA | 19.65 | 163CB | 25C36 | 134CB | 72.59 |
| 163CB | 25C36 | 162C | 49.56 | 163CB | 25C36 | 25SG | 58.45 |
| 163CB | 25C36 | 68SD | 45.87 | 163CB | 25C36 | 162N | 79.29 |
| 163CB | 25C36 | 161C | 92.40 | 163CB | 25C36 | 26CB | 57.89 |
| 163N | 25C36 | 163CA | 19.24 | 163N | 25C36 | 134CB | 72.07 |
| 163N | 25C36 | 162C | 15.66 | 163N | 25C36 | 25SG | 48.74 |
| 163N | 25C36 | 160O | 94.75 | 163N | 25C36 | 68SD | 80.23 |
| 163N | 25C36 | 162N | 44.07 | 163N | 25C36 | 161C | 56.92 |
| 163N | 25C36 | 26CB | 84.19 | 163CA | 25C36 | 134CB | 63.35 |
| 163CA | 25C36 | 162C | 30.81 | 163CA | 25C36 | 25SG | 59.31 |
| 163CA | 25C36 | 68SD | 61.48 | 163CA | 25C36 | 162N | 60.75 |
| 163CA | 25C36 | 161C | 74.90 | 163CA | 25C36 | 26CB | 76.21 |
| 134CB | 25C36 | 162C | 66.02 | 134CB | 25C36 | 160O | 71.49 |
| 134CB | 25C36 | 68SD | 70.15 | 134CB | 25C36 | 162N | 74.57 |
| 134CB | 25C36 | 161C | 86.37 | 162C | 25C36 | 25SG | 57.47 |
| 162C | 25C36 | 160O | 79.13 | 162C | 25C36 | 68SD | 91.74 |
| 162C | 25C36 | 162N | 29.94 | 162C | 25C36 | 161C | 44.33 |
| 162C | 25C36 | 26CB | 99.68 | 66C | 25C36 | 25SG | 91.85 |
| 66C | 25C36 | 68SD | 71.28 | 66C | 25C36 | 26CB | 45.17 |
| 25SG | 25C36 | 68SD | 94.27 | 25SG | 25C36 | 162N | 65.87 |
| 25SG | 25C36 | 161C | 65.98 | 25SG | 25C36 | 26CB | 58.75 |
| 160O | 25C36 | 162N | 52.97 | 160O | 25C36 | 161C | 46.61 |
| 68SD | 25C36 | 26CB | 51.40 | 162N | 25C36 | 161C | 15.56 |
| 66O | 25C37 | 67CD1 | 72.85 | 66O | 25C37 | 67CE1 | 84.55 |
| 66O | 25C37 | 66C | 7.48 | 66O | 25C37 | 67CG | 55.90 |
| 66O | 25C37 | 67CZ | 77.27 | 66O | 25C37 | 67CA | 36.66 |
| 66O | 25C37 | 68SD | 75.55 | 66O | 25C37 | 163CB | 87.96 |
| 66O | 25C37 | 68CE | 96.44 | 66O | 25C37 | 67N | 20.80 |
| 67CD1 | 25C37 | 67CE1 | 21.00 | 67CD1 | 25C37 | 209CD2 | 54.83 |
| 67CD1 | 25C37 | 66C | 65.41 | 67CD1 | 25C37 | 67CG | 16.96 |
| 67CD1 | 25C37 | 67CZ | 32.06 | 67CD1 | 25C37 | 67CA | 45.91 |
| 67CD1 | 25C37 | 68SD | 86.51 | 67CD1 | 25C37 | 68CE | 88.92 |
| 67CD1 | 25C37 | 67N | 53.96 | 67CE1 | 25C37 | 209CD2 | 57.96 |
| 67CE1 | 25C37 | 66C | 77.24 | 67CE1 | 25C37 | 67CG | 32.77 |
| 67CE1 | 25C37 | 67CZ | 16.58 | 67CE1 | 25C37 | 67CA | 64.93 |
| 67CE1 | 25C37 | 67N | 69.10 | 209CD2 | 25C37 | 134CB | 54.20 |
| 209CD2 | 25C37 | 67CG | 69.67 | 209CD2 | 25C37 | 67CZ | 74.22 |
| 209CD2 | 25C37 | 67CA | 82.39 | 209CD2 | 25C37 | 68SD | 72.35 |
| 209CD2 | 25C37 | 68CE | 57.34 | 209CD2 | 25C37 | 67N | 98.27 |
| 209CD2 | 25C37 | 160O | 99.57 | 66C | 25C37 | 67CG | 48.46 |
| 66C | 25C37 | 67CZ | 70.63 | 66C | 25C37 | 67CA | 31.49 |
| 66C | 25C37 | 68SD | 76.55 | 66C | 25C37 | 163CB | 93.59 |
| 66C | 25C37 | 68CE | 96.76 | 66C | 25C37 | 67N | 14.69 |
| 134CB | 25C37 | 68SD | 73.29 | 134CB | 25C37 | 163CB | 66.42 |
| 134CB | 25C37 | 68CE | 52.90 | 134CB | 25C37 | 160O | 70.87 |
| 67CG | 25C37 | 67CZ | 36.23 | 67CG | 25C37 | 67CA | 32.41 |
| 67CG | 25C37 | 68SD | 83.13 | 67CG | 25C37 | 68CE | 91.57 |
| 67CG | 25C37 | 67N | 37.47 | 67CZ | 25C37 | 67CA | 67.51 |
| 67CZ | 25C37 | 67N | 66.38 | 67CZ | 25C37 | 160O | 95.75 |
| 67CA | 25C37 | 68SD | 57.53 | 67CA | 25C37 | 163CB | 92.22 |
| 67CA | 25C37 | 68CE | 73.28 | 67CA | 25C37 | 67N | 17.05 |
| 68SD | 25C37 | 163CB | 43.37 | 68SD | 25C37 | 68CE | 21.25 |
| 68SD | 25C37 | 67N | 68.73 | 163CB | 25C37 | 68CE | 46.72 |
| 163CB | 25C37 | 67N | 95.05 | 68CE | 25C37 | 67N | 87.13 |
| 66O | 25C38 | 26CB | 65.13 | 66O | 25C38 | 66C | 6.46 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 66O | 25C38 | 26CA | 86.69 | 66O | 25C38 | 26N | 98.55 |
| 66O | 25C38 | 68SD | 86.25 | 66O | 25C38 | 26CG | 59.16 |
| 66O | 25C38 | 26CD1 | 64.07 | 66O | 25C38 | 66N | 34.26 |
| 66O | 25C38 | 67CA | 29.20 | 66O | 25C38 | 67N | 14.41 |
| 66O | 25C38 | 66CA | 18.99 | 163CB | 25C38 | 26CB | 81.15 |
| 163CB | 25C38 | 25SG | 73.30 | 163CB | 25C38 | 163N | 37.84 |
| 163CB | 25C38 | 26CA | 60.80 | 163CB | 25C38 | 26N | 60.85 |
| 163CB | 25C38 | 163CA | 18.86 | 163CB | 25C38 | 68SD | 54.22 |
| 163CB | 25C38 | 26CG | 95.41 | 163CB | 25C38 | 162C | 48.20 |
| 26CB | 25C38 | 25SG | 80.09 | 26CB | 25C38 | 66C | 58.81 |
| 26CB | 25C38 | 26CA | 21.77 | 26CB | 25C38 | 26N | 35.93 |
| 26CB | 25C38 | 163CA | 98.31 | 26CB | 25C38 | 68SD | 66.22 |
| 26CB | 25C38 | 26CG | 18.06 | 26CB | 25C38 | 26CD1 | 34.61 |
| 26CB | 25C38 | 66N | 65.47 | 26CB | 25C38 | 67CA | 61.54 |
| 26CB | 25C38 | 67N | 56.77 | 26CB | 25C38 | 66CA | 58.47 |
| 25SG | 25C38 | 163N | 55.98 | 25SG | 25C38 | 26CA | 68.25 |
| 25SG | 25C38 | 26N | 47.87 | 25SG | 25C38 | 163CA | 68.75 |
| 25SG | 25C38 | 26CG | 73.64 | 25SG | 25C38 | 26CD1 | 61.85 |
| 25SG | 25C38 | 66N | 91.11 | 25SG | 25C38 | 162C | 60.63 |
| 163N | 25C38 | 26CA | 87.46 | 163N | 25C38 | 26N | 76.37 |
| 163N | 25C38 | 163CA | 20.53 | 163N | 25C38 | 68SD | 89.44 |
| 163N | 25C38 | 162C | 12.27 | 66C | 25C38 | 26CA | 80.45 |
| 66C | 25C38 | 26N | 92.09 | 66C | 25C38 | 68SD | 84.88 |
| 66C | 25C38 | 26CG | 52.75 | 66C | 25C38 | 26CD1 | 58.32 |
| 66C | 25C38 | 66N | 32.59 | 66C | 25C38 | 67CA | 29.60 |
| 66C | 25C38 | 67N | 12.87 | 66C | 25C38 | 66CA | 15.91 |
| 26CA | 25C38 | 26N | 20.39 | 26CA | 25C38 | 163CA | 77.00 |
| 26CA | 25C38 | 68SD | 62.23 | 26CA | 25C38 | 26CG | 34.72 |
| 26CA | 25C38 | 26CD1 | 45.79 | 26CA | 25C38 | 66N | 84.74 |
| 26CA | 25C38 | 67CA | 78.68 | 26CA | 25C38 | 67N | 77.24 |
| 26CA | 25C38 | 66CA | 79.85 | 26CA | 25C38 | 162C | 99.66 |
| 26N | 25C38 | 163CA | 72.27 | 26N | 25C38 | 68SD | 79.71 |
| 26N | 25C38 | 26CG | 39.78 | 26N | 25C38 | 26CD1 | 42.14 |
| 26N | 25C38 | 66N | 85.55 | 26N | 25C38 | 67CA | 97.07 |
| 26N | 25C38 | 67N | 92.29 | 26N | 25C38 | 66CA | 86.55 |
| 26N | 25C38 | 162C | 87.67 | 163CA | 25C38 | 68SD | 68.96 |
| 163CA | 25C38 | 162C | 29.60 | 68SD | 25C38 | 26CG | 83.61 |
| 68SD | 25C38 | 67CA | 57.57 | 68SD | 25C38 | 67N | 72.28 |
| 68SD | 25C38 | 66CA | 98.54 | 68SD | 25C38 | 162C | 96.25 |
| 26CG | 25C38 | 26CD1 | 17.49 | 26CG | 25C38 | 66N | 50.02 |
| 26CG | 25C38 | 67CA | 65.74 | 26CG | 25C38 | 67N | 55.48 |
| 26CG | 25C38 | 66CA | 47.14 | 26CG | 25C38 | 66N | 43.47 |
| 26CD1 | 25C38 | 67CA | 78.32 | 26CD1 | 25C38 | 67N | 64.92 |
| 26CD1 | 25C38 | 66CA | 47.51 | 66N | 25C38 | 67CA | 62.18 |
| 66N | 25C38 | 67N | 45.30 | 66N | 25C38 | 66CA | 17.02 |
| 67CA | 25C38 | 67N | 17.03 | 67CA | 25C38 | 66CA | 45.35 |
| 67N | 25C38 | 66CA | 28.38 | 65CA | 25C39 | 66N | 38.23 |
| 65CA | 25C39 | 66O | 77.80 | 65CA | 25C39 | 65C | 20.22 |
| 65CA | 25C39 | 26CD1 | 57.59 | 65CA | 25C39 | 65N | 12.86 |
| 65CA | 25C39 | 23O | 51.79 | 65CA | 25C39 | 66CA | 49.23 |
| 25SG | 25C39 | 161O | 71.00 | 25SG | 25C39 | 26CD1 | 64.51 |
| 25SG | 25C39 | 161C | 75.18 | 25SG | 25C39 | 23O | 59.23 |
| 66N | 25C39 | 66O | 39.58 | 66N | 25C39 | 65C | 18.09 |
| 66N | 25C39 | 26CD1 | 47.02 | 66N | 25C39 | 65N | 50.53 |
| 66N | 25C39 | 23O | 71.29 | 66N | 25C39 | 66CA | 11.02 |
| 66O | 25C39 | 65C | 57.60 | 66O | 25C39 | 26CD1 | 57.39 |
| 66O | 25C39 | 65N | 89.89 | 66O | 25C39 | 23O | 96.66 |
| 66O | 25C39 | 66CA | 28.57 | 161O | 25C39 | 161C | 12.79 |
| 65C | 25C39 | 26CD1 | 48.36 | 65C | 25C39 | 65N | 32.45 |
| 65C | 25C39 | 23O | 59.69 | 65C | 25C39 | 66CA | 29.05 |
| 26CD1 | 25C39 | 65N | 60.85 | 26CD1 | 25C39 | 23O | 40.56 |
| 26CD1 | 25C39 | 66CA | 47.30 | 65N | 25C39 | 23O | 44.53 |
| 65N | 25C39 | 66CA | 61.43 | 23O | 25C39 | 66CA | 77.82 |
| 66N | 25O40 | 65CA | 49.46 | 66N | 25O40 | 26CD1 | 65.76 |
| 66N | 25O40 | 65C | 23.27 | 66N | 25O40 | 66O | 49.28 |
| 66N | 25O40 | 66CA | 14.40 | 66N | 25O40 | 26CG | 63.42 |
| 66N | 25O40 | 65N | 61.07 | 66N | 25O40 | 26NE1 | 58.78 |
| 66N | 25O40 | 66C | 34.93 | 66N | 25O40 | 23O | 92.25 |
| 66N | 25O40 | 26CB | 74.00 | 66N | 25O40 | 65O | 24.57 |
| 65CA | 25O40 | 26CD1 | 79.08 | 65CA | 25O40 | 65C | 27.14 |
| 65CA | 25O40 | 66O | 98.43 | 65CA | 25O40 | 66CA | 63.57 |
| 65CA | 25O40 | 26CG | 90.14 | 65CA | 25O40 | 65N | 13.53 |
| 65CA | 25O40 | 26NE1 | 63.17 | 65CA | 25O40 | 66C | 84.39 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Atom 3 | Angle | Atom 1 | Atom 2 | Atom 3 | Angle |
|---|---|---|---|---|---|---|---|
| 65CA | 25O40 | 23O | 63.91 | 65CA | 25O40 | 65O | 28.53 |
| 26CD1 | 25O40 | 65C | 65.35 | 26CD1 | 25O40 | 25SG | 80.06 |
| 26CD1 | 25O40 | 66O | 75.51 | 26CD1 | 25O40 | 66CA | 61.87 |
| 26CD1 | 25O40 | 26CG | 17.43 | 26CD1 | 25O40 | 65N | 76.84 |
| 26CD1 | 25O40 | 26NE1 | 16.20 | 26CD1 | 25O40 | 66C | 66.92 |
| 26CD1 | 25O40 | 23O | 50.44 | 26CD1 | 25O40 | 26CB | 36.73 |
| 26CD1 | 25O40 | 65O | 60.57 | 26CD1 | 25O40 | 26N | 42.40 |
| 65C | 25O40 | 66O | 72.49 | 65C | 25O40 | 66CA | 36.77 |
| 65C | 25O40 | 26CG | 70.55 | 65C | 25O40 | 65N | 37.88 |
| 65C | 25O40 | 26NE1 | 52.57 | 65C | 25O40 | 66C | 57.85 |
| 65C | 25O40 | 23O | 74.40 | 65C | 25O40 | 26CB | 86.99 |
| 65C | 25O40 | 65O | 4.93 | 25SG | 25O40 | 26CG | 82.32 |
| 25SG | 25O40 | 26NE1 | 89.52 | 25SG | 25O40 | 23O | 68.61 |
| 25SG | 25O40 | 26CB | 75.26 | 25SG | 25O40 | 26N | 44.90 |
| 66O | 25O40 | 66CA | 36.06 | 66O | 25O40 | 26CG | 60.15 |
| 66O | 25O40 | 26NE1 | 82.09 | 66O | 25O40 | 66C | 15.20 |
| 66O | 25O40 | 26CB | 51.97 | 66O | 25O40 | 65O | 73.07 |
| 66O | 25O40 | 26N | 81.84 | 66CA | 25O40 | 26CG | 55.19 |
| 66CA | 25O40 | 65N | 74.60 | 66CA | 25O40 | 26NE1 | 59.26 |
| 66CA | 25O40 | 66C | 21.11 | 66CA | 25O40 | 23O | 98.28 |
| 66CA | 25O40 | 26CB | 62.10 | 66CA | 25O40 | 65O | 37.02 |
| 66CA | 25O40 | 26N | 91.86 | 26CG | 25O40 | 65N | 90.75 |
| 26CG | 25O40 | 26NE1 | 31.46 | 26CG | 25O40 | 66C | 54.19 |
| 26CG | 25O40 | 23O | 67.47 | 26CG | 25O40 | 26CB | 20.67 |
| 26CG | 25O40 | 65O | 66.40 | 26CG | 25O40 | 26N | 38.44 |
| 65N | 25O40 | 26NE1 | 60.66 | 65N | 25O40 | 66C | 95.71 |
| 65N | 25O40 | 23O | 52.18 | 65N | 25O40 | 65O | 37.84 |
| 26NE1 | 25O40 | 66C | 70.37 | 26NE1 | 25O40 | 23O | 42.57 |
| 26NE1 | 25O40 | 26CB | 51.93 | 26NE1 | 25O40 | 65O | 47.64 |
| 26NE1 | 25O40 | 26N | 57.31 | 66C | 25O40 | 26CB | 52.36 |
| 66C | 25O40 | 65O | 58.10 | 66C | 25O40 | 26N | 83.81 |
| 23O | 25O40 | 26CB | 83.39 | 23O | 25O40 | 65O | 70.59 |
| 23O | 25O40 | 26N | 67.33 | 26CB | 25O40 | 65O | 83.51 |
| 26CB | 25O40 | 26N | 31.46 | 25SG | 25N41 | 16IO | 86.79 |
| 25SG | 25N41 | 16IC | 87.19 | 25SG | 25N41 | 23O | 62.77 |
| 25SG | 25N41 | 66N | 93.69 | 16IO | 25N41 | 16IC | 11.62 |
| 65CA | 25N41 | 23O | 51.79 | 65CA | 25N41 | 65N | 15.59 |
| 65CA | 25N41 | 66N | 29.14 | 23O | 25N41 | 65N | 44.44 |
| 23O | 25N41 | 66N | 64.51 | 65N | 25N41 | 66N | 44.25 |
| 25SG | 25N42 | 23O | 85.08 | 25SG | 25N42 | 23CA | 98.91 |
| 25SG | 25N42 | 23C | 83.87 | 25SG | 25N42 | 16IO | 78.66 |
| 25SG | 25N42 | 25CB | 15.26 | 25SG | 25N42 | 25N | 39.74 |
| 25SG | 25N42 | 26CD1 | 63.71 | 25SG | 25N42 | 24N | 72.85 |
| 23O | 25N42 | 23CA | 37.86 | 23O | 25N42 | 23C | 18.24 |
| 23O | 25N42 | 65CA | 60.94 | 23O | 25N42 | 25CB | 79.36 |
| 23O | 25N42 | 65N | 52.05 | 23O | 25N42 | 25N | 48.33 |
| 23O | 25N42 | 26CD1 | 43.36 | 23O | 25N42 | 24N | 25.15 |
| 23CA | 25N42 | 23C | 22.71 | 23CA | 25N42 | 65CA | 87.12 |
| 23CA | 25N42 | 25CB | 85.89 | 23CA | 25N42 | 65N | 70.74 |
| 23CA | 25N42 | 25N | 60.69 | 23CA | 25N42 | 26CD1 | 80.64 |
| 23CA | 25N42 | 24N | 29.02 | 23C | 25N42 | 65CA | 77.61 |
| 23C | 25N42 | 25CB | 74.03 | 23C | 25N42 | 65N | 65.78 |
| 23C | 25N42 | 25N | 44.16 | 23C | 25N42 | 26CD1 | 58.52 |
| 23C | 25N42 | 24N | 11.74 | 65CA | 25N42 | 65N | 18.58 |
| 65CA | 25N42 | 25N | 98.97 | 65CA | 25N42 | 26CD1 | 51.99 |
| 65CA | 25N42 | 24N | 86.08 | 16IO | 25N42 | 25CB | 84.39 |
| 25CB | 25N42 | 25N | 31.12 | 25CB | 25N42 | 26CD1 | 68.91 |
| 25CB | 25N42 | 24N | 62.41 | 65N | 25N42 | 25N | 97.62 |
| 65N | 25N42 | 26CD1 | 59.56 | 65N | 25N42 | 24N | 76.12 |
| 25N | 25N42 | 26CD1 | 50.78 | 25N | 25N42 | 24N | 33.18 |
| 26CD1 | 25N42 | 24N | 57.77 | 66O | 25N43 | 66N | 50.46 |
| 66O | 25N43 | 66C | 15.63 | 66O | 25N43 | 66CA | 35.78 |
| 66O | 25N43 | 65CA | 83.97 | 66O | 25N43 | 65C | 66.03 |
| 66O | 25N43 | 67CZ | 75.44 | 66O | 25N43 | 67CE2 | 67.55 |
| 66O | 25N43 | 67CE1 | 68.04 | 66O | 25N43 | 67N | 16.30 |
| 66N | 25N43 | 66C | 39.54 | 66N | 25N43 | 66CA | 19.49 |
| 66N | 25N43 | 65CA | 35.70 | 66N | 25N43 | 65C | 15.67 |
| 66N | 25N43 | 67CE2 | 84.94 | 66N | 25N43 | 67N | 47.36 |
| 66C | 25N43 | 66CA | 21.89 | 66C | 25N43 | 65CA | 75.04 |
| 66C | 25N43 | 65C | 55.08 | 66C | 25N43 | 67CZ | 72.67 |
| 66C | 25N43 | 67CE2 | 61.03 | 66C | 25N43 | 67CE1 | 69.65 |
| 66C | 25N43 | 67N | 8.63 | 66CA | 25N43 | 65CA | 54.94 |
| 66CA | 25N43 | 65C | 34.13 | 66CA | 25N43 | 67CZ | 83.41 |

TABLE XIV-continued

Table of angles between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazine.

| Atom 1 | Atom 2 | Atom 3 | Angle | Atom 1 | Atom 2 | Atom 3 | Angle |
|---|---|---|---|---|---|---|---|
| 66CA | 25N43 | 67CE2 | 68.23 | 66CA | 25N43 | 67CE1 | 85.39 |
| 66CA | 25N43 | 67N | 28.69 | 65CA | 25N43 | 65C | 21.08 |
| 65CA | 25N43 | 67N | 83.04 | 65C | 25N43 | 67CE2 | 93.39 |
| 65C | 25N43 | 67N | 62.65 | 67CZ | 25N43 | 67CE2 | 16.72 |
| 67CZ | 25N43 | 67CE1 | 16.22 | 67CZ | 25N43 | 67N | 64.53 |
| 67CE2 | 25N43 | 67CE1 | 28.45 | 67CE2 | 25N43 | 67N | 53.83 |
| 67CE1 | 25N43 | 67N | 61.03 | | | | |

TABLE XV

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 184CD1 | 25C1 | 184CB | 39.64 | 184CD1 | 25C1 | 184CG | 20.72 |
| 184CD1 | 25C1 | 184O | 79.67 | 184CD1 | 25C1 | 18OD1 | 92.08 |
| 184CD1 | 25C1 | 184CA | 45.35 | 184CD1 | 25C1 | 184C | 65.97 |
| 184CD1 | 25C1 | 18CG | 95.35 | 184CD1 | 25C1 | 20O | 95.11 |
| 184CD1 | 25C1 | 184NE1 | 15.46 | 184CD1 | 25C1 | 184CD2 | 28.37 |
| 184CB | 25C1 | 184CG | 22.78 | 184CB | 25C1 | 184O | 43.71 |
| 184CB | 25C1 | 18OD1 | 91.44 | 184CB | 25C1 | 184CA | 22.80 |
| 184CB | 25C1 | 18ND2 | 86.39 | 184CB | 25C1 | 184C | 35.31 |
| 184CB | 25C1 | 18CG | 84.04 | 184CB | 25C1 | 184NE1 | 51.55 |
| 184CB | 25C1 | 184CD2 | 34.26 | 184O | 25C1 | 184O | 66.36 |
| 184CG | 25C1 | 184CA | 38.32 | 184CG | 25C1 | 184C | 56.18 |
| 184CG | 25C1 | 18CG | 98.73 | 184CG | 25C1 | 184NE1 | 29.35 |
| 184CG | 25C1 | 184CD2 | 15.76 | 184O | 25C1 | 18OD1 | 69.22 |
| 184O | 25C1 | 184CA | 35.76 | 184O | 25C1 | 18ND2 | 48.03 |
| 184O | 25C1 | 184C | 16.21 | 184O | 25C1 | 18CG | 54.71 |
| 184O | 25C1 | 184NE1 | 93.86 | 184O | 25C1 | 184CD2 | 77.07 |
| 18OD1 | 25C1 | 184CA | 68.65 | 18OD1 | 25C1 | 18ND2 | 32.37 |
| 18OD1 | 25C1 | 184C | 63.21 | 18OD1 | 25C1 | 18CG | 16.11 |
| 18OD1 | 25C1 | 20O | 62.46 | 184CA | 25C1 | 18ND2 | 67.26 |
| 184CA | 25C1 | 184C | 20.72 | 184CA | 25C1 | 18CG | 62.00 |
| 184CA | 25C1 | 184NE1 | 60.54 | 184CA | 25C1 | 184CD2 | 53.33 |
| 18ND2 | 25C1 | 184C | 51.16 | 18ND2 | 25C1 | 18CG | 17.75 |
| 18ND2 | 25C1 | 20O | 89.83 | 184C | 25C1 | 18CG | 51.58 |
| 184C | 25C1 | 184NE1 | 80.98 | 184C | 25C1 | 184CD2 | 69.47 |
| 18CG | 25C1 | 20O | 77.96 | 20O | 25C1 | 184NE1 | 90.38 |
| 184NE1 | 25C1 | 184CD2 | 28.12 | 18OD1 | 25C2 | 184CA | 82.66 |
| 18OD1 | 25C2 | 20O | 82.02 | 18OD1 | 25C2 | 18CG | 17.46 |
| 18OD1 | 25C2 | 20N | 42.19 | 18OD1 | 25C2 | 18ND2 | 35.11 |
| 18OD1 | 25C2 | 184O | 74.48 | 18OD1 | 25C2 | 19CG | 79.73 |
| 18OD1 | 25C2 | 184C | 70.99 | 18OD1 | 25C2 | 183O | 67.05 |
| 18OD1 | 25C2 | 20CA | 48.76 | 18OD1 | 25C2 | 20C | 68.51 |
| 18OD1 | 25C2 | 19N | 41.49 | 18OD1 | 25C2 | 184N | 80.79 |
| 18OD1 | 25C2 | 19C | 47.49 | 18OD1 | 25C2 | 183C | 74.42 |
| 18OD1 | 25C2 | 18CB | 20.67 | 184CD1 | 25C2 | 184CA | 49.69 |
| 184CD1 | 25C2 | 184CG | 20.47 | 184CD1 | 25C2 | 184CB | 40.02 |
| 184CD1 | 25C2 | 184O | 80.18 | 184CD1 | 25C2 | 19CG | 63.56 |
| 184CD1 | 25C2 | 184C | 69.76 | 184CD1 | 25C2 | 184NE1 | 15.99 |
| 184CD1 | 25C2 | 183O | 53.74 | 184CD1 | 25C2 | 19N | 85.37 |
| 184CD1 | 25C2 | 184N | 44.38 | 184CD1 | 25C2 | 184CD2 | 23.21 |
| 184CD1 | 25C2 | 183C | 46.49 | 184CA | 25C2 | 18CG | 70.97 |
| 184CA | 25C2 | 184CG | 39.55 | 184CA | 25C2 | 18ND2 | 72.06 |
| 184CA | 25C2 | 184CB | 22.96 | 184CA | 25C2 | 184O | 35.00 |
| 184CA | 25C2 | 19CG | 83.11 | 184CA | 25C2 | 184C | 20.65 |
| 184CA | 25C2 | 184NE1 | 65.57 | 184CA | 25C2 | 183O | 40.23 |
| 184CA | 25C2 | 19N | 70.98 | 184CA | 25C2 | 184N | 13.04 |
| 184CA | 25C2 | 184CD2 | 51.91 | 184CA | 25C2 | 183C | 28.28 |
| 184CA | 25C2 | 18CB | 62.55 | 20O | 25C2 | 18CG | 98.28 |
| 20O | 25C2 | 20N | 45.78 | 20O | 25C2 | 19CG | 69.54 |
| 20O | 25C2 | 20CA | 33.26 | 20O | 25C2 | 20C | 13.52 |
| 20O | 25C2 | 19N | 80.94 | 20O | 25C2 | 24IOH2 | 94.87 |
| 20O | 25C2 | 19C | 50.12 | 18CG | 25C2 | 20N | 59.60 |
| 18CG | 25C2 | 18ND2 | 19.96 | 18CG | 25C2 | 184CB | 91.12 |
| 18CG | 25C2 | 184O | 57.44 | 18CG | 25C2 | 19CG | 91.35 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 18CG | 25C2 | 184C | 56.05 | 18CG | 25C2 | 183O | 66.77 |
| 18CG | 25C2 | 20CA | 65.32 | 18CG | 25C2 | 20C | 84.82 |
| 18CG | 25C2 | 19N | 51.19 | 18CG | 25C2 | 184N | 72.42 |
| 18CG | 25C2 | 19C | 64.04 | 18CG | 25C2 | 183C | 70.48 |
| 18CG | 25C2 | 18CB | 11.35 | 184CG | 25C2 | 184CB | 22.17 |
| 184CG | 25C2 | 184O | 63.20 | 184CG | 25C2 | 19CG | 82.47 |
| 184CG | 25C2 | 184C | 56.51 | 184CG | 25C2 | 184NE1 | 31.65 |
| 184CG | 25C2 | 183O | 60.77 | 184CG | 25C2 | 19N | 95.86 |
| 184CG | 25C2 | 184N | 40.46 | 184CG | 25C2 | 184CD2 | 12.76 |
| 184CG | 25C2 | 183C | 49.79 | 20N | 25C2 | 18ND2 | 76.27 |
| 20N | 25C2 | 19CG | 52.54 | 20N | 25C2 | 183O | 72.94 |
| 20N | 25C2 | 20CA | 19.39 | 20N | 25C2 | 20C | 34.03 |
| 20N | 25C2 | 19N | 38.18 | 20N | 25C2 | 184N | 99.39 |
| 20N | 25C2 | 19C | 11.58 | 20N | 25C2 | 183C | 85.38 |
| 20N | 25C2 | 18CB | 59.41 | 18ND2 | 25C2 | 184CB | 87.16 |
| 18ND2 | 25C2 | 184O | 47.43 | 18ND2 | 25C2 | 184C | 52.81 |
| 18ND2 | 25C2 | 183O | 80.93 | 18ND2 | 25C2 | 20CA | 77.11 |
| 18ND2 | 25C2 | 20C | 94.81 | 18ND2 | 25C2 | 19N | 70.92 |
| 18ND2 | 25C2 | 184N | 77.97 | 18ND2 | 25C2 | 241OH2 | 87.90 |
| 18ND2 | 25C2 | 19C | 82.49 | 18ND2 | 25C2 | 183C | 81.11 |
| 18ND2 | 25C2 | 18CB | 28.59 | 184CB | 25C2 | 184O | 41.08 |
| 184CB | 25C2 | 19CG | 93.42 | 184CB | 25C2 | 184C | 35.36 |
| 184CB | 25C2 | 184NE1 | 53.47 | 184CB | 25C2 | 183O | 58.06 |
| 184CB | 25C2 | 19N | 92.03 | 184CB | 25C2 | 184N | 30.81 |
| 184CB | 25C2 | 241OH2 | 98.67 | 184CB | 25C2 | 184CD2 | 32.23 |
| 184CB | 25C2 | 183C | 45.37 | 184CB | 25C2 | 18CB | 84.11 |
| 184O | 25C2 | 184C | 16.82 | 184O | 25C2 | 184NE1 | 94.48 |
| 184C | 25C2 | 183O | 69.02 | 184O | 25C2 | 19N | 87.53 |
| 184O | 25C2 | 184N | 47.05 | 184O | 25C2 | 241OH2 | 86.44 |
| 184C | 25C2 | 184CD2 | 71.78 | 184O | 25C2 | 183C | 59.90 |
| 184O | 25C2 | 18CB | 55.54 | 19CG | 25C2 | 184C | 97.61 |
| 19CG | 25C2 | 184NE1 | 62.79 | 19CG | 25C2 | 183O | 45.36 |
| 19CG | 25C2 | 20CA | 67.99 | 19CG | 25C2 | 20C | 68.52 |
| 19CG | 25C2 | 19N | 40.19 | 19CG | 25C2 | 184N | 70.06 |
| 19CG | 25C2 | 19C | 41.14 | 19CG | 25C2 | 184CD2 | 86.47 |
| 19CG | 25C2 | 183C | 55.31 | 19CG | 25C2 | 18CB | 82.88 |
| 184C | 25C2 | 184NE1 | 85.37 | 184C | 25C2 | 183O | 52.27 |
| 184C | 25C2 | 19N | 73.95 | 184C | 25C2 | 184N | 31.18 |
| 184C | 25C2 | 184CD2 | 67.55 | 184C | 25C2 | 183C | 43.16 |
| 184C | 25C2 | 18CB | 50.40 | 184NE1 | 25C2 | 183O | 65.82 |
| 184NE1 | 25C2 | 19N | 93.08 | 184NE1 | 25C2 | 184N | 60.22 |
| 184NE1 | 25C2 | 184CD2 | 27.19 | 184NE1 | 25C2 | 183C | 60.67 |
| 183O | 25C2 | 20CA | 92.25 | 183O | 25C2 | 19N | 35.35 |
| 183O | 25C2 | 184N | 28.06 | 183O | 25C2 | 19C | 63.84 |
| 183O | 25C2 | 184CD2 | 71.98 | 183O | 25C2 | 183C | 12.70 |
| 183O | 25C2 | 18CB | 55.43 | 2DCA | 25C2 | 20C | 19.77 |
| 20CA | 25C2 | 19N | 57.18 | 20CA | 25C2 | 19C | 29.86 |
| 20CA | 25C2 | 18CB | 69.00 | 20C | 25C2 | 19N | 71.24 |
| 20C | 25C2 | 241OH2 | 99.96 | 20C | 25C2 | 19C | 40.54 |
| 20C | 25C2 | 18CB | 88.76 | 19N | 25C2 | 184N | 61.22 |
| 19N | 25C2 | 19C | 30.91 | 19N | 25C2 | 183C | 47.43 |
| 19N | 25C2 | 18CB | 42.94 | 184N | 25C2 | 19C | 91.32 |
| 184N | 25C2 | 184CD2 | 53.18 | 184N | 25C2 | 183C | 15.60 |
| 184N | 25C2 | 18CB | 62.40 | 241OH2 | 25C2 | 184CD2 | 94.01 |
| 19C | 25C2 | 183C | 76.51 | 19C | 25C2 | 18CB | 61.35 |
| 184CD2 | 25C2 | 183C | 61.73 | 183C | 25C2 | 18CB | 59.34 |
| 20O | 25C3 | 19CG | 91.80 | 20O | 25C3 | 20N | 53.46 |
| 20O | 25C3 | 18OD1 | 84.67 | 20O | 25C3 | 20C | 13.71 |
| 20O | 25C3 | 20CA | 35.80 | 20O | 25C3 | 19CD | 97.07 |
| 20O | 25C3 | 19C | 58.10 | 20O | 25C3 | 19N | 89.89 |
| 20O | 25C3 | 19CB | 82.19 | 20O | 25C3 | 18CG | 93.78 |
| 20O | 25C3 | 19CA | 76.43 | 20O | 25C3 | 19NE2 | 84.73 |
| 20O | 25C3 | 21N | 7.78 | 184CD1 | 25C3 | 19CG | 71.43 |
| 184CD1 | 25C3 | 184NE1 | 19.86 | 184CD1 | 25C3 | 19CD | 64.18 |
| 184CD1 | 25C3 | 184CG | 15.82 | 184CD1 | 25C3 | 183O | 49.75 |
| 184CD1 | 25C3 | 19N | 83.17 | 184CD1 | 25C3 | 184CA | 39.91 |
| 184CD1 | 25C3 | 19CB | 82.78 | 184CD1 | 25C3 | 18CG | 94.02 |
| 184CD1 | 25C3 | 19CA | 92.64 | 184CD1 | 25C3 | 19NE2 | 76.30 |
| 184CD1 | 25C3 | 184CB | 30.78 | 184CD1 | 25C3 | 19OE1 | 50.83 |
| 184CD1 | 25C3 | 184CE2 | 22.67 | 19CG | 25C3 | 20N | 61.01 |
| 19CG | 25C3 | 18OD1 | 81.71 | 19CG | 25C3 | 20C | 85.09 |
| 19CG | 25C3 | 184NE1 | 72.26 | 19CG | 25C3 | 20CA | 79.11 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 19CG | 25C3 | 19CD | 19.52 | 19CG | 25C3 | 184CG | 85.19 |
| 19CG | 25C3 | 19C | 46.68 | 19CG | 25C3 | 183O | 45.20 |
| 19CG | 25C3 | 19N | 40.95 | 19CG | 25C3 | 184CA | 79.09 |
| 19CG | 25C3 | 19CB | 14.28 | 19CG | 25C3 | 18CG | 86.69 |
| 19CG | 25C3 | 19CA | 32.54 | 19CG | 25C3 | 19NE2 | 29.74 |
| 19CG | 25C3 | 184CB | 89.69 | 19CG | 25C3 | 19OE1 | 27.37 |
| 19CG | 25C3 | 21N | 86.08 | 19CG | 25C3 | 184CE2 | 83.99 |
| 20N | 25C3 | 18OD1 | 41.77 | 20N | 25C3 | 20C | 39.98 |
| 20N | 25C3 | 20CA | 21.31 | 20N | 25C3 | 19CD | 78.54 |
| 20N | 25C3 | 19C | 14.86 | 20N | 25C3 | 183O | 71.47 |
| 20N | 25C3 | 19N | 37.66 | 20N | 25C3 | 184CA | 95.61 |
| 20N | 25C3 | 19CB | 46.74 | 20N | 25C3 | 18CG | 52.23 |
| 20N | 25C3 | 19CA | 30.40 | 20N | 25C3 | 19NE2 | 78.92 |
| 20N | 25C3 | 19OE1 | 88.38 | 20N | 25C3 | 21N | 45.77 |
| 18OD1 | 25C3 | 20C | 71.90 | 18OD1 | 25C3 | 20CA | 50.00 |
| 18OD1 | 25C3 | 184CG | 95.90 | 18OD1 | 25C3 | 19C | 51.61 |
| 18OD1 | 25C3 | 183O | 58.74 | 18OD1 | 25C3 | 19N | 40.87 |
| 18OD1 | 25C3 | 184CA | 63.14 | 18OD1 | 25C3 | 19CB | 70.42 |
| 18OD1 | 25C3 | 18CG | 10.53 | 18OD1 | 25C3 | 19CA | 52.41 |
| 18OD1 | 25C3 | 184CB | 79.52 | 18OD1 | 25C3 | 21N | 78.64 |
| 20C | 25C3 | 20CA | 22.29 | 20C | 25C3 | 19CD | 94.40 |
| 20C | 25C3 | 19C | 46.10 | 20C | 25C3 | 19N | 77.00 |
| 20C | 25C3 | 19CB | 73.57 | 20C | 25C3 | 18CG | 81.47 |
| 20C | 25C3 | 19CA | 64.92 | 20C | 25C3 | 19NE2 | 84.78 |
| 20C | 25C3 | 21N | 6.74 | 184NE1 | 25C3 | 19CD | 58.87 |
| 184NE1 | 25C3 | 184CG | 31.08 | 184NE1 | 25C3 | 183O | 64.98 |
| 184NE1 | 25C3 | 19N | 95.87 | 184NE1 | 25C3 | 184CA | 59.73 |
| 184NE1 | 25C3 | 19CB | 85.90 | 184NE1 | 25C3 | 19NE2 | 66.72 |
| 184NE1 | 25C3 | 184CB | 48.57 | 184NE1 | 25C3 | 19OE1 | 46.24 |
| 184NE1 | 25C3 | 184CE2 | 11.83 | 20CA | 25C3 | 19CD | 94.19 |
| 20CA | 25C3 | 19C | 33.03 | 20CA | 25C3 | 183O | 92.18 |
| 20CA | 25C3 | 19N | 58.66 | 20CA | 25C3 | 19CB | 65.28 |
| 20CA | 25C3 | 18CG | 59.95 | 20CA | 25C3 | 19CA | 51.05 |
| 20CA | 25C3 | 19NE2 | 90.04 | 20CA | 25C3 | 21N | 28.97 |
| 19CD | 25C3 | 184CG | 79.74 | 19CD | 25C3 | 19C | 63.74 |
| 19CD | 25C3 | 183O | 55.90 | 19CD | 25C3 | 19N | 60.04 |
| 19CD | 25C3 | 184CA | 84.73 | 19CD | 25C3 | 19CB | 32.93 |
| 19CD | 25C3 | 19CA | 51.74 | 19CD | 25C3 | 19NE2 | 15.91 |
| 19CD | 25C3 | 184CB | 89.68 | 19CD | 25C3 | 19OE1 | 13.39 |
| 19CD | 25C3 | 21N | 93.33 | 19CD | 25C3 | 184CE2 | 70.59 |
| 184CG | 25C3 | 183O | 54.91 | 184CG | 25C3 | 19N | 88.52 |
| 184CG | 25C3 | 184CA | 32.83 | 184CG | 25C3 | 19CB | 95.04 |
| 184CG | 25C3 | 18CG | 87.10 | 184CG | 25C3 | 19NE2 | 92.12 |
| 184CG | 25C3 | 184CB | 17.79 | 184CG | 25C3 | 19OE1 | 66.46 |
| 184CG | 25C3 | 184CE2 | 27.27 | 19C | 25C3 | 183O | 65.15 |
| 19C | 25C3 | 19N | 32.44 | 19C | 25C3 | 184CA | 94.94 |
| 19C | 25C3 | 19CB | 32.53 | 19C | 25C3 | 18CG | 61.42 |
| 19C | 25C3 | 19CA | 18.94 | 19C | 25C3 | 19NE2 | 64.39 |
| 19C | 25C3 | 19OE1 | 73.97 | 19C | 25C3 | 21N | 50.41 |
| 183O | 25C3 | 19N | 33.87 | 183O | 25C3 | 184CA | 35.08 |
| 183O | 25C3 | 19CB | 47.01 | 183O | 25C3 | 18CG | 56.73 |
| 183O | 25C3 | 19CA | 47.13 | 183O | 25C3 | 19NE2 | 71.34 |
| 183O | 25C3 | 184CB | 50.06 | 183O | 25C3 | 19OE1 | 50.42 |
| 183O | 25C3 | 184CE2 | 72.00 | 19N | 25C3 | 184CA | 62.75 |
| 19N | 25C3 | 19CB | 31.18 | 19N | 25C3 | 18CG | 46.02 |
| 19N | 25C3 | 19CA | 17.94 | 19N | 25C3 | 19NE2 | 69.90 |
| 19N | 25C3 | 184CB | 80.68 | 19N | 25C3 | 19OE1 | 63.48 |
| 19N | 25C3 | 21N | 82.11 | 184CA | 25C3 | 19CB | 82.09 |
| 184CA | 25C3 | 18CG | 54.80 | 184CA | 25C3 | 19CA | 79.48 |
| 184CA | 25C3 | 184CB | 18.58 | 184CA | 25C3 | 19OE1 | 74.55 |
| 184CA | 25C3 | 184CE2 | 59.43 | 19CB | 25C3 | 18CG | 76.90 |
| 19CB | 25C3 | 19CA | 18.91 | 19CB | 25C3 | 19NE2 | 39.32 |
| 19CB | 25C3 | 184CB | 95.96 | 19CB | 25C3 | 19OE1 | 41.65 |
| 19CB | 25C3 | 21N | 75.62 | 19CB | 25C3 | 184CE2 | 97.49 |
| 18CG | 25C3 | 19CA | 59.97 | 18CG | 25C3 | 184CB | 70.15 |
| 18CG | 25C3 | 21N | 88.18 | 19CA | 25C3 | 19NE2 | 57.54 |
| 19CA | 25C3 | 184CB | 96.61 | 19CA | 25C3 | 19OE1 | 59.34 |
| 19CA | 25C3 | 21N | 68.88 | 19NE2 | 25C3 | 19OE1 | 26.89 |
| 19NE2 | 25C3 | 21N | 82.33 | 19NE2 | 25C3 | 184CE2 | 77.62 |
| 184CB | 25C3 | 19OE1 | 77.28 | 184CB | 25C3 | 184CE2 | 44.87 |
| 19OE1 | 25C3 | 184CE2 | 58.06 | 20O | 25C4 | 20C | 5.29 |
| 20O | 25C4 | 19CG | 73.30 | 20O | 25C4 | 20N | 37.40 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 20O | 25C4 | 20CA | 22.70 | 20O | 25C4 | 19CD | 84.35 |
| 20O | 25C4 | 18OD1 | 61.35 | 20O | 25C4 | 19NE2 | 78.63 |
| 184CD1 | 25C4 | 184NE1 | 19.87 | 184CD1 | 25C4 | 19CG | 58.10 |
| 184CD1 | 25C4 | 20N | 90.23 | 184CD1 | 25C4 | 184CG | 14.72 |
| 184CD1 | 25C4 | 19CD | 55.97 | 184CD1 | 25C4 | 184CE2 | 27.01 |
| 184CD1 | 25C4 | 18OD1 | 75.63 | 184CD1 | 25C4 | 19NE2 | 69.64 |
| 184NE1 | 25C4 | 19CG | 63.14 | 184NE1 | 25C4 | 184CG | 28.26 |
| 184NE1 | 25C4 | 19CD | 53.91 | 184NE1 | 25C4 | 184CE2 | 14.23 |
| 184NE1 | 25C4 | 18OD1 | 94.59 | 184NE1 | 25C4 | 19NE2 | 63.81 |
| 20C | 25C4 | 19CG | 69.98 | 20C | 25C4 | 20N | 32.25 |
| 20C | 25C4 | 20CA | 17.47 | 20C | 25C4 | 19CD | 82.18 |
| 20C | 25C4 | 18OD1 | 56.22 | 20C | 25C4 | 19NE2 | 77.77 |
| 19CG | 25C4 | 20N | 46.51 | 19CG | 25C4 | 184CG | 71.25 |
| 19CG | 25C4 | 20CA | 62.49 | 19CG | 25C4 | 19CD | 18.45 |
| 19CG | 25C4 | 184CE2 | 77.31 | 19CG | 25C4 | 18OD1 | 59.85 |
| 19CG | 25C4 | 19NE2 | 29.19 | 20N | 25C4 | 184CG | 96.60 |
| 20N | 25C4 | 20CA | 17.63 | 20N | 25C4 | 19CD | 63.68 |
| 20N | 25C4 | 18OD1 | 30.95 | 20N | 25C4 | 19NE2 | 67.31 |
| 184CG | 25C4 | 19CD | 70.61 | 184CG | 25C4 | 184CE2 | 27.62 |
| 184CG | 25C4 | 18OD1 | 75.70 | 184CG | 25C4 | 241OH2 | 87.84 |
| 184CG | 25C4 | 19NE2 | 84.36 | 20CA | 25C4 | 19CD | 78.25 |
| 20CA | 25C4 | 18OD1 | 38.85 | 20CA | 25C4 | 241OH2 | 97.61 |
| 20CA | 25C4 | 19NE2 | 78.54 | 19CD | 25C4 | 184CE2 | 67.82 |
| 19CD | 25C4 | 18OD1 | 78.00 | 19CD | 25C4 | 19NE2 | 15.45 |
| 184CE2 | 25C4 | 241OH2 | 99.63 | 184CE2 | 25C4 | 19NE2 | 76.63 |
| 18OD1 | 25C4 | 241OH2 | 82.91 | 18OD1 | 25C4 | 19NE2 | 87.95 |
| 20O | 25C5 | 184CD1 | 97.18 | 184CD1 | 25C5 | 184NE1 | 18.35 |
| 184CD1 | 25C5 | 184CG | 16.64 | 184CD1 | 25C5 | 184CE2 | 27.73 |
| 184CD1 | 25C5 | 184CD2 | 26.39 | 184NE1 | 25C5 | 184CG | 28.44 |
| 184NE1 | 25C5 | 184CE2 | 16.30 | 184NE1 | 25C5 | 184CD2 | 26.54 |
| 184CG | 25C5 | 184CE2 | 27.87 | 184CG | 25C5 | 184CD2 | 16.56 |
| 184CE2 | 25C5 | 184CD2 | 16.34 | 184CD1 | 25C6 | 184CG | 18.54 |
| 184CD1 | 25C6 | 184CB | 33.62 | 184CD1 | 25C6 | 184NE1 | 17.14 |
| 184CD1 | 25C6 | 20O | 88.08 | 184CD1 | 25C6 | 184CD2 | 28.33 |
| 184CD1 | 25C6 | 184CE2 | 26.95 | 184CG | 25C6 | 184CB | 19.13 |
| 184CG | 25C6 | 184NE1 | 29.00 | 184CG | 25C6 | 184CD2 | 17.43 |
| 184CG | 25C6 | 184CE2 | 27.74 | 184CB | 25C6 | 184NE1 | 47.54 |
| 184CB | 25C6 | 184CD2 | 32.76 | 184CB | 25C6 | 184CE2 | 46.38 |
| 184NE1 | 25C6 | 20O | 88.62 | 184NE1 | 25C6 | 184CD2 | 27.82 |
| 184NE1 | 25C6 | 184CE2 | 16.20 | 184CD2 | 25C6 | 184CE2 | 16.68 |
| 20O | 25C7 | 20C | 5.94 | 20O | 25C7 | 19NE2 | 91.02 |
| 20O | 25C7 | 19CG | 72.12 | 20O | 25C7 | 19CD | 89.31 |
| 20O | 25C7 | 21CA | 34.14 | 20O | 25C7 | 22O | 65.12 |
| 20O | 25C7 | 21N | 17.69 | 20O | 25C7 | 21C | 46.47 |
| 20C | 25C7 | 19NE2 | 86.13 | 20C | 25C7 | 19CG | 69.33 |
| 20C | 25C7 | 19CD | 85.63 | 20C | 25C7 | 21CA | 31.54 |
| 20C | 25C7 | 22O | 59.23 | 20C | 25C7 | 21N | 14.16 |
| 20C | 25C7 | 21C | 42.01 | 19NE2 | 25C7 | 19CG | 32.17 |
| 19NE2 | 25C7 | 184NE1 | 66.44 | 19NE2 | 25C7 | 19CD | 17.05 |
| 19NE2 | 25C7 | 21CA | 93.37 | 19NE2 | 25C7 | 22O | 37.10 |
| 19NE2 | 25C7 | 184CD1 | 69.09 | 19NE2 | 25C7 | 21N | 87.99 |
| 19NE2 | 25C7 | 21C | 79.11 | 19CG | 25C7 | 184NE1 | 58.99 |
| 19CG | 25C7 | 19CD | 19.56 | 19CG | 25C7 | 21CA | 91.19 |
| 19CG | 25C7 | 22O | 50.36 | 19CG | 25C7 | 184CD1 | 52.04 |
| 19CG | 25C7 | 21N | 77.89 | 19CG | 25C7 | 21C | 84.98 |
| 184NE1 | 25C7 | 19CD | 53.40 | 184NE1 | 25C7 | 184CD1 | 16.66 |
| 19CD | 25C7 | 22O | 49.22 | 19CD | 25C7 | 184CD1 | 53.17 |
| 19CD | 25C7 | 21N | 91.50 | 19CD | 25C7 | 21C | 90.15 |
| 21CA | 25C7 | 22O | 56.87 | 21CA | 25C7 | 21N | 17.50 |
| 21CA | 25C7 | 21C | 18.03 | 22O | 25C7 | 21N | 55.41 |
| 22O | 25C7 | 21C | 42.02 | 21N | 25C7 | 21C | 28.94 |
| 19NE2 | 25O8 | 19CD | 20.48 | 19NE2 | 25O8 | 184NE1 | 81.39 |
| 19NE2 | 25O8 | 20O | 89.30 | 19NE2 | 25O8 | 19CG | 35.60 |
| 19NE2 | 25O8 | 19OE1 | 30.68 | 19NE2 | 25O8 | 22O | 40.85 |
| 19NE2 | 25O8 | 184CD1 | 79.20 | 19NE2 | 25O8 | 184CE2 | 92.69 |
| 19CD | 25O8 | 184NE1 | 63.10 | 19CD | 25O8 | 20O | 86.55 |
| 19CD | 25O8 | 19CG | 21.39 | 19CD | 25O8 | 19OE1 | 15.46 |
| 19CD | 25O8 | 22O | 55.33 | 19CD | 25O8 | 184CD1 | 58.99 |
| 19CD | 25O8 | 184CE2 | 75.44 | 184NE1 | 25O8 | 19CG | 65.39 |
| 184NE1 | 25O8 | 19OE1 | 50.75 | 184NE1 | 25O8 | 184CD1 | 16.57 |
| 184NE1 | 25O8 | 184CE2 | 13.19 | 20O | 25O8 | 19CG | 66.59 |
| 20O | 25O8 | 19OE1 | 99.26 | 20O | 25O8 | 22O | 62.20 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 20O | 25O8 | 184CD1 | 90.68 | 19CG | 25O8 | 19OE1 | 32.68 |
| 19CG | 25O8 | 22O | 53.93 | 19CG | 25O8 | 184CD1 | 54.99 |
| 19CG | 25O8 | 184CE2 | 78.58 | 19OE1 | 25O8 | 22O | 69.68 |
| 19OE1 | 25O8 | 184CD1 | 50.54 | 19OE1 | 25O8 | 184CE2 | 62.13 |
| 184CD1 | 25O8 | 184CE2 | 26.99 | 19NE2 | 25C9 | 184NE1 | 68.02 |
| 19NE2 | 25C9 | 19CD | 15.81 | 184NE1 | 25C9 | 19CD | 52.53 |
| 162ND1 | 25C11 | 184CZ2 | 58.70 | 162ND1 | 25C11 | 162CE1 | 15.57 |
| 184CZ2 | 25C11 | 162CE1 | 49.86 | 162ND1 | 25C14 | 162CG | 20.80 |
| 162ND1 | 25C14 | 162CB | 38.90 | 162ND1 | 25C14 | 162CE1 | 17.70 |
| 162ND1 | 25C14 | 162CA | 43.05 | 162ND1 | 25C14 | 161O | 71.97 |
| 162ND1 | 25C14 | 184CZ2 | 66.72 | 162ND1 | 25C14 | 162CD2 | 25.28 |
| 162ND1 | 25C14 | 161OD1 | 87.80 | 162ND1 | 25C14 | 162N | 60.63 |
| 162ND1 | 25C14 | 162NE2 | 23.20 | 162ND1 | 25C14 | 161C | 71.88 |
| 162ND1 | 25C14 | 25SG | 43.89 | 162CG | 25C14 | 162CB | 21.88 |
| 162CG | 25C14 | 162CE1 | 32.41 | 162CG | 25C14 | 162CA | 35.32 |
| 162CG | 25C14 | 161O | 70.65 | 162CG | 25C14 | 184CZ2 | 61.27 |
| 162CG | 25C14 | 162CD2 | 14.29 | 162CG | 25C14 | 161OD1 | 69.93 |
| 162CG | 25C14 | 162N | 50.52 | 162CG | 25C14 | 162NE2 | 26.85 |
| 162CG | 25C14 | 161C | 65.13 | 162CG | 25C14 | 25SG | 60.65 |
| 162CB | 25C14 | 162CE1 | 53.68 | 162CB | 25C14 | 162CA | 20.45 |
| 162CB | 25C14 | 161O | 55.44 | 162CB | 25C14 | 184CZ2 | 75.70 |
| 162CB | 25C14 | 162CD2 | 33.63 | 162CB | 25C14 | 161OD1 | 49.02 |
| 162CB | 25C14 | 162N | 30.67 | 162CB | 25C14 | 162NE2 | 48.52 |
| 162CB | 25C14 | 161C | 46.38 | 162CB | 25C14 | 25SG | 66.67 |
| 162CE1 | 25C14 | 162CA | 60.62 | 162CE1 | 25C14 | 161O | 88.83 |
| 162CE1 | 25C14 | 184CZ2 | 55.07 | 162CE1 | 25C14 | 162CD2 | 27.92 |
| 162CE1 | 25C14 | 162N | 78.11 | 162CE1 | 25C14 | 162NE2 | 14.38 |
| 162CE1 | 25C14 | 161C | 89.56 | 162CE1 | 25C14 | 25SG | 51.14 |
| 162CA | 25C14 | 161O | 35.99 | 162CA | 25C14 | 184CZ2 | 94.99 |
| 162CA | 25C14 | 162CD2 | 49.43 | 162CA | 25C14 | 161OD1 | 50.42 |
| 162CA | 25C14 | 162N | 17.63 | 162CA | 25C14 | 162NE2 | 60.81 |
| 162CA | 25C14 | 161C | 30.12 | 162CA | 25C14 | 25SG | 53.36 |
| 161O | 25C14 | 162CD2 | 84.93 | 161O | 25C14 | 161OD1 | 54.15 |
| 161O | 25C14 | 162N | 27.79 | 161O | 25C14 | 162NE2 | 93.77 |
| 161O | 25C14 | 161C | 14.72 | 161O | 25C14 | 25SG | 53.31 |
| 184CZ2 | 25C14 | 162CD2 | 47.18 | 184CZ2 | 25C14 | 161OD1 | 98.34 |
| 184CZ2 | 25C14 | 162NE2 | 43.71 | 184CZ2 | 25C14 | 161OD1 | 77.69 |
| 162CD2 | 25C14 | 162N | 63.80 | 162CD2 | 25C14 | 162NE2 | 16.69 |
| 162CD2 | 25C14 | 161C | 78.91 | 162CD2 | 25C14 | 25SG | 69.06 |
| 161OD1 | 25C14 | 162N | 36.11 | 161OD1 | 25C14 | 162NE2 | 94.34 |
| 161OD1 | 25C14 | 161C | 39.94 | 162N | 25C14 | 162NE2 | 77.07 |
| 162N | 25C14 | 161C | 15.92 | 162N | 25C14 | 25SG | 64.86 |
| 162NE2 | 25C14 | 161C | 90.92 | 162NE2 | 25C14 | 25SG | 64.04 |
| 161C | 25C14 | 25SG | 63.90 | 162CB | 25O15 | 162ND1 | 47.26 |
| 162CB | 25O15 | 162CG | 27.43 | 162CB | 25O15 | 161OD1 | 63.34 |
| 162CB | 25O15 | 162CA | 23.06 | 162CB | 25O15 | 162CE1 | 60.10 |
| 162CB | 25O15 | 162CD2 | 40.37 | 162CB | 25O15 | 162N | 35.92 |
| 162CB | 25O15 | 184CZ2 | 91.76 | 162CB | 25O15 | 162NE2 | 55.17 |
| 162CB | 25O15 | 161C | 52.53 | 162CB | 25O15 | 161O | 60.45 |
| 162CB | 25O15 | 137CB | 54.06 | 162CB | 25O15 | 161CG | 69.17 |
| 162CB | 25O15 | 137O | 87.23 | 162CB | 25O15 | 161CB | 73.81 |
| 162CB | 25O15 | 184CH2 | 88.25 | 162ND1 | 25O15 | 162CG | 25.12 |
| 162ND1 | 25O15 | 162CA | 49.83 | 162ND1 | 25O15 | 162CE1 | 16.98 |
| 162ND1 | 25O15 | 162CD2 | 32.89 | 162ND1 | 25O15 | 162N | 70.32 |
| 162ND1 | 25O15 | 184CZ2 | 74.09 | 162ND1 | 25O15 | 162NE2 | 26.96 |
| 162ND1 | 25O15 | 161C | 78.97 | 162ND1 | 25O15 | 161O | 74.28 |
| 162ND1 | 25O15 | 137CB | 88.45 | 162ND1 | 25O15 | 184CH2 | 81.61 |
| 162CG | 25O15 | 161OD1 | 90.25 | 162CG | 25O15 | 162CA | 41.57 |
| 162CG | 25O15 | 162CE1 | 33.66 | 162CG | 25O15 | 162CD2 | 17.25 |
| 162CG | 25O15 | 162N | 60.35 | 162CG | 25O15 | 184CZ2 | 70.97 |
| 162CG | 25O15 | 162NE2 | 28.08 | 162CG | 25O15 | 161C | 74.63 |
| 162CG | 25O15 | 161O | 77.02 | 162CG | 25O15 | 137CB | 63.77 |
| 162CG | 25O15 | 161CG | 96.60 | 162CG | 25O15 | 137O | 97.22 |
| 162CG | 25O15 | 184CH2 | 72.59 | 161OD1 | 25O15 | 162CA | 61.62 |
| 161OD1 | 25O15 | 162CD2 | 98.29 | 161OD1 | 25O15 | 162N | 43.32 |
| 161OD1 | 25O15 | 161C | 45.80 | 161OD1 | 25O15 | 161O | 60.74 |
| 161OD1 | 25O15 | 137CB | 55.90 | 161OD1 | 25O15 | 161CG | 11.21 |
| 161OD1 | 25O15 | 137O | 59.03 | 161OD1 | 25O15 | 161CB | 28.61 |
| 162CA | 25O15 | 162CE1 | 66.36 | 162CA | 25O15 | 162CD2 | 58.17 |
| 162CA | 25O15 | 162N | 20.56 | 162CA | 25O15 | 162NE2 | 68.37 |
| 162CA | 25O15 | 161C | 33.06 | 162CA | 25O15 | 161O | 37.86 |
| 162CA | 25O15 | 137CB | 73.81 | 162CA | 25O15 | 161CG | 62.82 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 162CA | 25O15 | 161CB | 60.45 | 162CE1 | 25O15 | 162CD2 | 31.95 |
| 162CE1 | 25O15 | 162N | 86.92 | 162CE1 | 25O15 | 184CZ2 | 59.12 |
| 162CE1 | 25O15 | 162NE2 | 17.11 | 162CE1 | 25O15 | 161C | 95.94 |
| 162CE1 | 25O15 | 161O | 90.42 | 162CE1 | 25O15 | 137CB | 90.07 |
| 162CE1 | 25O15 | 184CH2 | 68.68 | 162CD2 | 25O15 | 162N | 75.70 |
| 162CD2 | 25O15 | 184CZ2 | 53.94 | 162CD2 | 25O15 | 162NE2 | 17.99 |
| 162CD2 | 25O15 | 161C | 91.05 | 162CD2 | 25O15 | 161O | 94.26 |
| 162CD2 | 25O15 | 137CB | 58.26 | 162CD2 | 25O15 | 137O | 88.29 |
| 162CD2 | 25O15 | 184CH2 | 55.47 | 162N | 25O15 | 162NE2 | 88.07 |
| 162N | 25O15 | 161C | 17.35 | 162N | 25O15 | 161O | 30.00 |
| 162N | 25O15 | 137CB | 72.58 | 162N | 25O15 | 161CG | 42.77 |
| 162N | 25O15 | 137O | 95.02 | 162N | 25O15 | 161CB | 40.21 |
| 184CZ2 | 25O15 | 162NE2 | 47.88 | 184CZ2 | 25O15 | 137CB | 69.04 |
| 184CZ2 | 25O15 | 137O | 71.73 | 184CZ2 | 25O15 | 184CH2 | 14.31 |
| 162NE2 | 25O15 | 161O | 99.69 | 162NE2 | 25O15 | 137CB | 74.12 |
| 162NE2 | 25O15 | 184CH2 | 54.65 | 161C | 25O15 | 161O | 15.92 |
| 161C | 25O15 | 137CB | 87.40 | 161C | 25O15 | 161CG | 40.49 |
| 161C | 25O15 | 161CB | 30.37 | 161O | 25O15 | 161CG | 53.91 |
| 161O | 25O15 | 161CB | 39.98 | 137CB | 25O15 | 161CG | 67.10 |
| 137CB | 25O15 | 137O | 34.26 | 137CB | 25O15 | 161CB | 84.07 |
| 137CB | 25O15 | 184CH2 | 56.32 | 161CG | 25O15 | 137O | 67.49 |
| 161CG | 25O15 | 161CB | 17.89 | 137O | 25O15 | 161CB | 84.60 |
| 137O | 25O15 | 184CH2 | 57.69 | 162ND1 | 25N16 | 25SG | 57.00 |
| 162ND1 | 25N16 | 161O | 81.16 | 162ND1 | 25N16 | 162CE1 | 17.28 |
| 162ND1 | 25N16 | 162CG | 17.24 | 162ND1 | 25N16 | 162CA | 44.41 |
| 162ND1 | 25N16 | 162CB | 35.55 | 162ND1 | 25N16 | 161C | 76.08 |
| 162ND1 | 25N16 | 25CB | 47.59 | 162ND1 | 25N16 | 162N | 61.35 |
| 162ND1 | 25N16 | 19NE2 | 78.00 | 25SG | 25N16 | 161O | 66.73 |
| 25SG | 25N16 | 162CE1 | 60.44 | 25SG | 25N16 | 162CG | 69.41 |
| 25SG | 25N16 | 162CA | 62.55 | 25SG | 25N16 | 162CB | 74.95 |
| 25SG | 25N16 | 161C | 75.51 | 25SG | 25N16 | 25CB | 22.32 |
| 25SG | 25N16 | 162N | 74.12 | 25SG | 25N16 | 19NE2 | 65.05 |
| 161O | 25N16 | 162CE1 | 97.79 | 161O | 25N16 | 162CG | 74.22 |
| 161O | 25N16 | 162CA | 38.96 | 161O | 25N16 | 162CB | 57.51 |
| 161O | 25N16 | 161C | 14.31 | 161O | 25N16 | 25CB | 86.73 |
| 161O | 25N16 | 162N | 28.02 | 162CE1 | 25N16 | 162CG | 31.36 |
| 162CE1 | 25N16 | 162CA | 61.69 | 162CE1 | 25N16 | 162CB | 51.34 |
| 162CE1 | 25N16 | 161C | 93.35 | 162CE1 | 25N16 | 25CB | 44.14 |
| 162CE1 | 25N16 | 162N | 78.58 | 162CE1 | 25N16 | 19NE2 | 62.97 |
| 162CG | 25N16 | 162CA | 35.27 | 162CG | 25N16 | 162CB | 20.22 |
| 162CG | 25N16 | 161C | 65.76 | 162CG | 25N16 | 25CB | 63.85 |
| 162CG | 25N16 | 162N | 49.75 | 162CG | 25N16 | 19NE2 | 94.18 |
| 162CA | 25N16 | 162CB | 20.52 | 162CA | 25N16 | 161C | 31.69 |
| 162CA | 25N16 | 25CB | 71.57 | 162CA | 25N16 | 162N | 17.61 |
| 162CB | 25N16 | 161C | 47.01 | 162CB | 25N16 | 25CB | 76.68 |
| 162CB | 25N16 | 162N | 30.74 | 161C | 25N16 | 25CB | 92.93 |
| 161C | 25N16 | 162N | 16.27 | 25CB | 25N16 | 162N | 87.03 |
| 25CB | 25N16 | 19NE2 | 47.50 | 25SG | 25N17 | 162ND1 | 74.24 |
| 25SG | 25N17 | 162CA | 87.90 | 25SG | 25N17 | 162CG | 86.46 |
| 25SG | 25N17 | 162CB | 97.30 | 25SG | 25N17 | 25CB | 24.15 |
| 25SG | 25N17 | 162CE1 | 70.19 | 25SG | 25N17 | 163N | 54.13 |
| 25SG | 25N17 | 162C | 71.67 | 25SG | 25N17 | 162CD2 | 84.79 |
| 161O | 25N17 | 162CA | 52.13 | 161O | 25N17 | 161O | 16.50 |
| 161O | 25N17 | 162CG | 92.62 | 161O | 25N17 | 162CB | 71.30 |
| 161O | 25N17 | 162N | 34.71 | 161O | 25N17 | 163N | 65.25 |
| 161O | 25N17 | 162C | 55.77 | 161O | 25N17 | 161CA | 17.53 |
| 162ND1 | 25N17 | 162CA | 56.42 | 162ND1 | 25N17 | 161C | 95.91 |
| 162ND1 | 25N17 | 162CG | 18.78 | 162ND1 | 25N17 | 162CB | 41.07 |
| 162ND1 | 25N17 | 162N | 76.00 | 162ND1 | 25N17 | 25CB | 57.57 |
| 162ND1 | 25N17 | 162CE1 | 14.79 | 162ND1 | 25N17 | 163N | 54.56 |
| 162ND1 | 25N17 | 162C | 55.20 | 162ND1 | 25N17 | 162CD2 | 12.12 |
| 162CA | 25N17 | 161C | 40.29 | 162CA | 25N17 | 162CG | 41.09 |
| 162CA | 25N17 | 162CB | 23.23 | 162CA | 25N17 | 162N | 21.53 |
| 162CA | 25N17 | 25CB | 91.56 | 162CA | 25N17 | 162CE1 | 71.02 |
| 162CA | 25N17 | 163N | 33.82 | 162CA | 25N17 | 162C | 16.39 |
| 162CA | 25N17 | 161CA | 50.27 | 162CA | 25N17 | 162CD2 | 49.51 |
| 161C | 25N17 | 162CG | 78.57 | 161C | 25N17 | 162CB | 56.40 |
| 161C | 25N17 | 162N | 19.96 | 161C | 25N17 | 163N | 62.31 |
| 161C | 25N17 | 162C | 48.62 | 161C | 25N17 | 161CA | 10.96 |
| 161C | 25N17 | 162CD2 | 87.05 | 162CG | 25N17 | 162CB | 22.57 |
| 162CG | 25N17 | 162N | 58.64 | 162CG | 25N17 | 25CB | 73.95 |
| 162CG | 25N17 | 162CE1 | 33.00 | 162CG | 25N17 | 163N | 51.02 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 162CG | 25N17 | 162C | 44.96 | 162CG | 25N17 | 161CA | 86.42 |
| 162CG | 25N17 | 162CD2 | 8.55 | 162CB | 25N17 | 162N | 36.69 |
| 162CB | 25N17 | 25CB | 91.50 | 162CB | 25N17 | 162CE1 | 55.54 |
| 162CB | 25N17 | 163N | 48.31 | 162CB | 25N17 | 162C | 34.62 |
| 162CB | 25N17 | 161CA | 63.87 | 162CB | 25N17 | 162CD2 | 30.83 |
| 162N | 25N17 | 162CE1 | 90.79 | 162N | 25N17 | 163N | 50.48 |
| 162N | 25N17 | 162C | 33.85 | 162N | 25N17 | 161CA | 29.03 |
| 162N | 25N17 | 162CD2 | 67.15 | 25CB | 25N17 | 162CE1 | 49.52 |
| 25CB | 25N17 | 163N | 61.60 | 25CB | 25N17 | 162C | 77.64 |
| 25CB | 25N17 | 162CD2 | 69.50 | 162CE1 | 25N17 | 163N | 64.51 |
| 162CE1 | 25N17 | 162C | 68.30 | 162CE1 | 25N17 | 162CD2 | 25.14 |
| 163N | 25N17 | 162C | 17.55 | 163N | 25N17 | 161CA | 73.19 |
| 163N | 25N17 | 162CD2 | 56.08 | 162C | 25N17 | 161CA | 59.51 |
| 162C | 25N17 | 162CD2 | 52.20 | 161CA | 25N17 | 162CD2 | 94.68 |
| 184NE1 | 25C18 | 19NE2 | 72.19 | 184NE1 | 25C18 | 184CZ2 | 34.15 |
| 184NE1 | 25C18 | 162ND1 | 64.76 | 184NE1 | 25C18 | 162CE1 | 49.26 |
| 184NE1 | 25C18 | 19CD | 55.65 | 184NE1 | 25C18 | 19OE1 | 48.22 |
| 184NE1 | 25C18 | 184CE2 | 16.77 | 19NE2 | 25C18 | 162ND1 | 74.92 |
| 19NE2 | 25C18 | 162CE1 | 65.60 | 19NE2 | 25C18 | 19CD | 16.66 |
| 19NE2 | 25C18 | 19OE1 | 29.19 | 19NE2 | 25C18 | 184CE2 | 88.46 |
| 184CZ2 | 25C18 | 162ND1 | 61.13 | 184CZ2 | 25C18 | 162CE1 | 54.08 |
| 184CZ2 | 25C18 | 19CD | 87.16 | 184CZ2 | 25C18 | 19OE1 | 75.81 |
| 184CZ2 | 25C18 | 184CE2 | 17.74 | 162ND1 | 25C18 | 162CE1 | 17.06 |
| 162ND1 | 25C18 | 19CD | 67.56 | 162ND1 | 25C18 | 19OE1 | 52.95 |
| 162ND1 | 25C18 | 184CE2 | 64.20 | 162CE1 | 25C18 | 19CD | 54.80 |
| 162CE1 | 25C18 | 19OE1 | 39.41 | 162CE1 | 25C18 | 184CE2 | 52.06 |
| 19CD | 25C18 | 19OE1 | 15.45 | 19CD | 25C18 | 184CE2 | 71.81 |
| 19OE1 | 25C18 | 184CE2 | 62.64 | 25SG | 25C19 | 25CB | 30.92 |
| 25SG | 25C19 | 16lO | 96.60 | 25SG | 25C19 | 162ND1 | 68.37 |
| 25SG | 25C19 | 25N | 49.94 | 25SG | 25C19 | 25CA | 32.83 |
| 25SG | 25C19 | 23O | 90.89 | 25SG | 25C19 | 162CE1 | 65.52 |
| 25SG | 25C19 | 162CA | 73.52 | 25SG | 25C19 | 19NE2 | 86.96 |
| 25SG | 25C19 | 23C | 92.63 | 25SG | 25C19 | 163N | 42.91 |
| 25SG | 25C19 | 161C | 94.64 | 25SG | 25C19 | 162CG | 71.57 |
| 25SG | 25C19 | 19OE1 | 68.21 | 25SG | 25C19 | 25C | 20.12 |
| 25SG | 25C19 | 26N | 28.60 | 25CB | 25C19 | 162ND1 | 59.73 |
| 25CB | 25C19 | 25N | 36.66 | 25CB | 25C19 | 25CA | 17.74 |
| 25CB | 25C19 | 23O | 86.02 | 25CB | 25C19 | 162CE1 | 48.75 |
| 25CB | 25C19 | 162CA | 86.55 | 25CB | 25C19 | 19NE2 | 56.95 |
| 25CB | 25C19 | 23C | 79.82 | 25CB | 25C19 | 163N | 62.99 |
| 25CB | 25C19 | 23CA | 90.53 | 25CB | 25C19 | 162CG | 68.32 |
| 25CB | 25C19 | 19OE1 | 37.70 | 25CB | 25C19 | 25C | 26.97 |
| 25CB | 25C19 | 26N | 42.42 | 16lO | 25C19 | 162ND1 | 80.02 |
| 16lO | 25C19 | 162CE1 | 96.21 | 16lO | 25C19 | 162CA | 38.78 |
| 16lO | 25C19 | 163N | 57.58 | 16lO | 25C19 | 161C | 9.12 |
| 16lO | 25C19 | 162CG | 68.74 | 162ND1 | 25C19 | 25N | 95.15 |
| 162ND1 | 25C19 | 25CA | 77.47 | 162ND1 | 25C19 | 162CE1 | 16.21 |
| 162ND1 | 25C19 | 162CA | 42.69 | 162ND1 | 25C19 | 19NE2 | 79.46 |
| 162ND1 | 25C19 | 163N | 49.40 | 162ND1 | 25C19 | 161C | 71.09 |
| 162ND1 | 25C19 | 162CG | 11.30 | 162ND1 | 25C19 | 19OE1 | 54.54 |
| 162ND1 | 25C19 | 25C | 81.37 | 162ND1 | 25C19 | 26N | 95.47 |
| 25N | 25C19 | 25CA | 20.26 | 25N | 25C19 | 23O | 49.36 |
| 25N | 25C19 | 162CE1 | 81.63 | 25N | 25C19 | 19NE2 | 50.17 |
| 25N | 25C19 | 23C | 44.73 | 25N | 25C19 | 163N | 92.43 |
| 25N | 25C19 | 23CA | 59.48 | 25N | 25C19 | 19OE1 | 52.21 |
| 25N | 25C19 | 25C | 30.33 | 25N | 25C19 | 26N | 33.58 |
| 25CA | 25C19 | 23O | 69.09 | 25CA | 25C19 | 162CE1 | 66.04 |
| 25CA | 25C19 | 19NE2 | 56.58 | 25CA | 25C19 | 23C | 64.91 |
| 25CA | 25C19 | 163N | 73.45 | 25CA | 25C19 | 23CA | 78.58 |
| 25CA | 25C19 | 162CG | 85.89 | 25CA | 25C19 | 19OE1 | 46.47 |
| 25CA | 25C19 | 25C | 17.28 | 25CA | 25C19 | 26N | 29.70 |
| 23O | 25C19 | 19NE2 | 67.81 | 23O | 25C19 | 23C | 15.74 |
| 23O | 25C19 | 23CA | 30.61 | 23O | 25C19 | 19OE1 | 88.93 |
| 23O | 25C19 | 25C | 71.99 | 23O | 25C19 | 26N | 63.05 |
| 162CE1 | 25C19 | 162CA | 58.48 | 162CE1 | 25C19 | 19NE2 | 63.81 |
| 162CE1 | 25C19 | 163N | 59.21 | 162CE1 | 25C19 | 161C | 87.29 |
| 162CE1 | 25C19 | 162CG | 27.50 | 162CE1 | 25C19 | 19OE1 | 38.34 |
| 162CE1 | 25C19 | 25C | 73.76 | 162CE1 | 25C19 | 26N | 89.08 |
| 162CA | 25C19 | 163N | 31.32 | 162CA | 25C19 | 161C | 30.71 |
| 162CA | 25C19 | 162CG | 31.93 | 162CA | 25C19 | 19OE1 | 96.39 |
| 162CA | 25C19 | 25C | 93.49 | 162CA | 25C19 | 26N | 99.54 |
| 19NE2 | 25C19 | 23C | 52.36 | 19NE2 | 25C19 | 23CA | 47.51 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 19NE2 | 25C19 | 162CG | 90.36 | 19NE2 | 25C19 | 19OE1 | 27.54 |
| 19NE2 | 25C19 | 25C | 73.76 | 19NE2 | 25C19 | 26N | 82.78 |
| 23C | 25C19 | 23CA | 18.96 | 23C | 25C19 | 19OE1 | 75.13 |
| 23C | 25C19 | 25C | 72.57 | 23C | 25C19 | 26N | 67.65 |
| 163N | 25C19 | 161C | 53.30 | 163N | 25C19 | 162CG | 44.32 |
| 163N | 25C19 | 19OE1 | 88.05 | 163N | 25C19 | 25C | 63.02 |
| 163N | 25C19 | 26N | 68.23 | 23CA | 25C19 | 19OE1 | 74.37 |
| 23CA | 25C19 | 25C | 89.19 | 23CA | 25C19 | 26N | 86.09 |
| 161C | 25C19 | 162CG | 59.79 | 162CG | 25C19 | 19OE1 | 65.83 |
| 162CG | 25C19 | 25C | 87.18 | 162CG | 25C19 | 26N | 99.91 |
| 19OE1 | 25C19 | 25C | 62.33 | 19OE1 | 25C19 | 26N | 76.16 |
| 25C | 25C19 | 26N | 15.58 | 25SG | 25O20 | 25CB | 34.29 |
| 25SG | 25O20 | 25N | 58.41 | 25SG | 25O20 | 23O | 94.11 |
| 25SG | 25O20 | 162ND1 | 57.05 | 25SG | 25O20 | 25CA | 42.72 |
| 25SG | 25O20 | 19OE1 | 79.03 | 25SG | 25O20 | 19CD | 92.36 |
| 25SG | 25O20 | 24N | 95.32 | 25SG | 25O20 | 162OE1 | 62.12 |
| 25SG | 25O20 | 161O | 62.41 | 25SG | 25O20 | 24C | 65.93 |
| 25CB | 25O20 | 19NE2 | 70.39 | 25CB | 25O20 | 23C | 93.15 |
| 25CB | 25O20 | 25N | 40.44 | 25CB | 25O20 | 23O | 94.44 |
| 25CB | 25O20 | 162ND1 | 54.11 | 25CB | 25O20 | 25CA | 19.78 |
| 25CB | 25O20 | 19OE1 | 46.09 | 25CB | 25O20 | 19CD | 58.16 |
| 25CB | 25O20 | 24N | 78.39 | 25CB | 25O20 | 162CE1 | 47.36 |
| 25CB | 25O20 | 161O | 92.37 | 25CB | 25O20 | 24C | 49.33 |
| 19NE2 | 25O20 | 23CA | 63.45 | 19NE2 | 25O20 | 23C | 67.92 |
| 19NE2 | 25O20 | 25N | 61.15 | 19NE2 | 25O20 | 23O | 85.94 |
| 19NE2 | 25O20 | 162ND1 | 88.31 | 19NE2 | 25O20 | 25CA | 65.49 |
| 19NE2 | 25O20 | 19OE1 | 31.85 | 19NE2 | 25O20 | 19CD | 15.16 |
| 19NE2 | 25O20 | 24N | 55.12 | 19NE2 | 25O20 | 162CE1 | 71.33 |
| 19NE2 | 25O20 | 24C | 60.20 | 19NE2 | 25O20 | 23N | 58.44 |
| 23CA | 25O20 | 23C | 24.00 | 23CA | 25O20 | 25N | 73.06 |
| 23CA | 25O20 | 23O | 37.74 | 23CA | 25O20 | 25CA | 93.15 |
| 23CA | 25O20 | 19OE1 | 94.06 | 23CA | 25O20 | 19CD | 77.95 |
| 23CA | 25O20 | 24N | 33.98 | 23CA | 25O20 | 24C | 64.37 |
| 23CA | 25O20 | 23N | 6.16 | 23C | 25O20 | 25N | 52.77 |
| 23C | 25O20 | 23O | 18.86 | 23C | 25O20 | 25CA | 73.50 |
| 23C | 25O20 | 19OE1 | 92.10 | 23C | 25O20 | 19CD | 79.18 |
| 23C | 25O20 | 24N | 16.93 | 23C | 25O20 | 24C | 43.85 |
| 23C | 25O20 | 23N | 28.31 | 25N | 25O20 | 23O | 55.74 |
| 25N | 25O20 | 162ND1 | 94.17 | 25N | 25O20 | 25CA | 20.73 |
| 25N | 25O20 | 19OE1 | 59.69 | 25N | 25O20 | 19CD | 59.03 |
| 25N | 25O20 | 24N | 39.08 | 25N | 25O20 | 162CE1 | 84.24 |
| 25N | 25O20 | 24C | 8.93 | 25N | 25O20 | 23N | 74.25 |
| 23O | 25O20 | 25CA | 75.11 | 23O | 25O20 | 19CD | 95.79 |
| 23O | 25O20 | 24N | 31.46 | 23O | 25O20 | 24C | 47.72 |
| 23O | 25O20 | 23N | 43.41 | 162ND1 | 25O20 | 25CA | 73.82 |
| 162ND1 | 25O20 | 19OE1 | 58.12 | 162ND1 | 25O20 | 19CD | 73.91 |
| 162ND1 | 25O20 | 162CE1 | 17.08 | 162ND1 | 25O20 | 161O | 63.55 |
| 25CA | 25O20 | 19OE1 | 51.34 | 25CA | 25O20 | 19CD | 57.52 |
| 25CA | 25O20 | 24N | 59.36 | 25CA | 25O20 | 162CE1 | 65.59 |
| 25CA | 25O20 | 24C | 29.65 | 25CA | 25O20 | 23N | 93.68 |
| 19OE1 | 25O20 | 19CD | 16.69 | 19OE1 | 25O20 | 24N | 75.92 |
| 19OE1 | 25O20 | 162CE1 | 41.10 | 19OE1 | 25O20 | 24C | 64.20 |
| 19OE1 | 25O20 | 23N | 89.60 | 19CD | 25O20 | 24N | 64.32 |
| 19CD | 25O20 | 162CE1 | 56.83 | 19CD | 25O20 | 24C | 60.79 |
| 19CD | 25O20 | 23N | 73.22 | 24N | 25O20 | 24C | 30.42 |
| 24N | 25O20 | 23N | 35.59 | 162CE1 | 25O20 | 161O | 80.58 |
| 162CE1 | 25O20 | 24C | 92.22 | 24C | 25O20 | 23N | 65.85 |
| 160CD1 | 25C21 | 158O | 97.34 | 160CD1 | 25C21 | 160CG | 23.97 |
| 160CD1 | 25C21 | 16OCB | 37.71 | 160CD1 | 25C21 | 160N | 66.46 |
| 160CD1 | 25C21 | 158C | 87.61 | 160CD1 | 25C21 | 160CA | 53.04 |
| 158O | 25C21 | 16OCG | 75.13 | 158O | 25C21 | 160CB | 77.51 |
| 158O | 25C21 | 160N | 47.16 | 158O | 25C21 | 158C | 10.74 |
| 158O | 25C21 | 160CA | 63.99 | 160CG | 25C21 | 160CB | 22.63 |
| 160CG | 25C21 | 160N | 43.47 | 160CG | 25C21 | 158C | 66.36 |
| 160CG | 25C21 | 160CA | 33.10 | 160CB | 25C21 | 160N | 33.28 |
| 160CB | 25C21 | 158C | 71.92 | 160CB | 25C21 | 160CA | 16.60 |
| 16ON | 25C21 | 158C | 44.97 | 160N | 25C21 | 160CA | 17.43 |
| 158C | 25C21 | 160CA | 60.36 | 160CD1 | 25C22 | 160CG | 21.04 |
| 160CD1 | 25C22 | 160CB | 35.29 | 160CD1 | 25C22 | 209CD2 | 57.75 |
| 160CD1 | 25C22 | 209CD1 | 70.22 | 160CD1 | 25C22 | 158O | 76.29 |
| 160CG | 25C22 | 160CB | 20.86 | 160CG | 25C22 | 209CD2 | 73.30 |
| 160CG | 25C22 | 209CD1 | 90.52 | 160CG | 25C22 | 158O | 57.61 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 160CB | 25C22 | 209CD2 | 69.60 | 160CB | 25C22 | 209CD1 | 94.36 |
| 160CB | 25C22 | 158O | 61.33 | 209CD2 | 25C22 | 209CD1 | 29.68 |
| 160CD1 | 25C23 | 209CD2 | 57.43 | 160CD1 | 25C23 | 160CB | 34.09 |
| 160CD1 | 25C23 | 160O | 71.45 | 160CD1 | 25C23 | 160CG | 18.98 |
| 209CD2 | 25C23 | 67CE1 | 66.23 | 209CD2 | 25C23 | 160CB | 73.03 |
| 209CD2 | 25C23 | 160O | 88.66 | 209CD2 | 25C23 | 67OH | 97.28 |
| 209CD2 | 25C23 | 160CG | 72.08 | 209CD2 | 25C23 | 67CZ | 81.22 |
| 67CE1 | 25C23 | 67OH | 31.06 | 67CE1 | 25C23 | 67CZ | 15.09 |
| 160CB | 25C23 | 160O | 37.90 | 160CB | 25C23 | 160CG | 19.32 |
| 160O | 25C23 | 160CG | 56.76 | 67OH | 25C23 | 67CZ | 16.25 |
| 160O | 25C24 | 160CB | 44.46 | 160O | 25C24 | 160C | 11.63 |
| 160O | 25C24 | 160CA | 31.06 | 160O | 25C24 | 160N | 41.50 |
| 160O | 25C24 | 160CD1 | 75.56 | 160O | 25C24 | 160CG | 62.09 |
| 160CB | 25C24 | 160C | 34.19 | 160CB | 25C24 | 160CA | 18.85 |
| 160CB | 25C24 | 160N | 32.07 | 160CB | 25C24 | 160CD1 | 32.04 |
| 160CB | 25C24 | 160CG | 18.03 | 160C | 25C24 | 160CA | 19.45 |
| 160C | 25C24 | 160N | 31.04 | 160C | 25C24 | 160CD1 | 66.04 |
| 160C | 25C24 | 160CG | 51.26 | 160CA | 25C24 | 160N | 18.21 |
| 160CA | 25C24 | 160CD1 | 50.13 | 160CA | 25C24 | 160CG | 33.24 |
| 160N | 25C24 | 160CD1 | 57.42 | 160N | 25C24 | 160CG | 38.76 |
| 160CD1 | 25C24 | 160CG | 18.66 | 67CE1 | 25C24 | 67OH | 28.53 |
| 160O | 25C25 | 160N | 52.68 | 160O | 25C25 | 160CB | 48.40 |
| 160O | 25C25 | 160CA | 37.54 | 160O | 25C25 | 160C | 16.03 |
| 160O | 25C25 | 160CG | 68.51 | 160O | 25C25 | 160CD1 | 77.48 |
| 160O | 25C25 | 159C | 58.15 | 160O | 25C25 | 159CA | 73.59 |
| 160O | 25C25 | 158C | 96.27 | 160N | 25C25 | 160CB | 39.49 |
| 160N | 25C25 | 158O | 51.80 | 160N | 25C25 | 160CA | 21.57 |
| 160N | 25C25 | 160C | 36.87 | 160N | 25C25 | 160CG | 45.04 |
| 160N | 25C25 | 160CD1 | 63.96 | 160N | 25C25 | 159C | 10.14 |
| 160N | 25C25 | 159CA | 27.45 | 160N | 25C25 | 158C | 43.72 |
| 160CB | 25C25 | 158O | 77.37 | 160CB | 25C25 | 160CA | 22.69 |
| 160CB | 25C25 | 160C | 37.96 | 160CB | 25C25 | 160CG | 20.22 |
| 160CB | 25C25 | 160CD1 | 31.90 | 160CB | 25C25 | 159C | 49.57 |
| 160CB | 25C25 | 159CA | 65.68 | 160CB | 25C25 | 158C | 69.44 |
| 158O | 25C25 | 160CA | 71.03 | 158O | 25C25 | 160C | 88.59 |
| 158O | 25C25 | 160CG | 65.33 | 158O | 25C25 | 160CD1 | 77.45 |
| 158O | 25C25 | 159C | 46.06 | 158O | 25C25 | 159CA | 33.23 |
| 158O | 25C25 | 158C | 8.40 | 160CA | 25C25 | 160C | 22.25 |
| 160CA | 25C25 | 160CG | 37.31 | 160CA | 25C25 | 160CD1 | 53.48 |
| 160CA | 25C25 | 159C | 31.20 | 160CA | 25C25 | 159CA | 48.92 |
| 160CA | 25C25 | 158C | 62.65 | 160C | 25C25 | 160CG | 56.85 |
| 160C | 25C25 | 160CD1 | 69.51 | 160C | 25C25 | 159C | 43.18 |
| 160C | 25C25 | 159CA | 59.72 | 160C | 25C25 | 158C | 80.59 |
| 160CG | 25C25 | 160CD1 | 19.02 | 160CG | 25C25 | 159C | 53.50 |
| 160CG | 25C25 | 159CA | 65.18 | 160CG | 25C25 | 158C | 58.66 |
| 160CD1 | 25C25 | 159C | 72.53 | 160CD1 | 25C25 | 159CA | 83.50 |
| 160CD1 | 25C25 | 158C | 72.33 | 159C | 25C25 | 159CA | 17.81 |
| 159C | 25C25 | 158C | 38.66 | 159CA | 25C25 | 158C | 27.96 |
| 158O | 25C26 | 160N | 61.78 | 158O | 25C26 | 160CB | 92.43 |
| 158O | 25C26 | 160CG | 82.57 | 158O | 25C26 | 158C | 10.10 |
| 158O | 25C26 | 160CA | 80.14 | 158O | 25C26 | 160CD1 | 98.52 |
| 158O | 25C26 | 159C | 50.29 | 158O | 25C26 | 159CA | 34.65 |
| 158O | 25C26 | 160C | 92.37 | 158O | 25C26 | 159N | 20.44 |
| 158O | 25C26 | 158CA | 18.72 | 160N | 25C26 | 160CB | 40.08 |
| 160N | 25C26 | 160CG | 50.16 | 160N | 25C26 | 158C | 54.73 |
| 160N | 25C26 | 160CA | 20.14 | 160N | 25C26 | 160CD1 | 70.80 |
| 160N | 25C26 | 160O | 45.75 | 160N | 25C26 | 159C | 12.46 |
| 160N | 25C26 | 159CA | 31.73 | 160N | 25C26 | 160C | 31.11 |
| 160N | 25C26 | 159N | 41.35 | 160N | 25C26 | 158CA | 65.61 |
| 160CB | 25C26 | 160CG | 23.66 | 160CB | 25C26 | 158C | 82.75 |
| 160CB | 25C26 | 160CA | 21.78 | 160CB | 25C26 | 16GCD1 | 36.20 |
| 160CB | 25C26 | 160O | 42.04 | 160CB | 25C26 | 159C | 51.11 |
| 160CB | 25C26 | 159CA | 70.60 | 160CB | 25C26 | 160C | 32.83 |
| 160CB | 25C26 | 159N | 74.02 | 160CB | 25C26 | 158CA | 86.07 |
| 160CG | 25C26 | 158C | 72.51 | 160CG | 25C26 | 160CA | 39.22 |
| 160CG | 25C26 | 160CD1 | 21.40 | 160CG | 25C26 | 160O | 65.66 |
| 160CG | 25C26 | 159C | 58.12 | 160CG | 25C26 | 159CA | 73.32 |
| 160CG | 25C26 | 160C | 55.17 | 160CG | 25C26 | 159N | 69.08 |
| 160CG | 25C26 | 158CA | 70.57 | 158C | 25C26 | 160CA | 71.90 |
| 158C | 25C26 | 160CD1 | 88.97 | 158C | 25C26 | 160O | 99.96 |
| 158C | 25C26 | 159C | 44.20 | 158C | 25C26 | 159CA | 31.81 |
| 158C | 25C26 | 160C | 85.81 | 158C | 25C26 | 159N | 14.55 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 158C | 25C26 | 158CA | 15.01 | 160CA | 25C26 | 160CD1 | 56.75 |
| 160CA | 25C26 | 160O | 33.81 | 160CA | 25C26 | 159C | 32.58 |
| 160CA | 25C26 | 159CA | 51.87 | 160CA | 25C26 | 160C | 19.16 |
| 160CA | 25C26 | 159N | 59.89 | 160CA | 25C26 | 158CA | 80.10 |
| 160CD1 | 25C26 | 160O | 74.72 | 160CD1 | 25C26 | 159C | 79.44 |
| 160CD1 | 25C26 | 159CA | 94.53 | 160CD1 | 25C26 | 160C | 68.62 |
| 160CD1 | 25C26 | 159N | 88.47 | 160CD1 | 25C26 | 158CA | 83.00 |
| 160C | 25C26 | 159C | 55.78 | 160O | 25C26 | 159CA | 71.36 |
| 160C | 25C26 | 160C | 15.23 | 160O | 25C26 | 159N | 85.80 |
| 159C | 25C26 | 159CA | 19.31 | 159C | 25C26 | 160C | 42.08 |
| 159C | 25C26 | 159N | 30.09 | 159C | 25C26 | 158CA | 56.63 |
| 159CA | 25C26 | 160C | 59.37 | 159CA | 25C26 | 159N | 17.84 |
| 159CA | 25C26 | 158CA | 46.52 | 160C | 25C26 | 159N | 72.10 |
| 160C | 25C26 | 158CA | 96.40 | 159N | 25C26 | 158CA | 28.80 |
| 160O | 25C27 | 160C | 5.58 | 160O | 25C27 | 160CB | 36.45 |
| 67OH | 25C27 | 67CE1 | 31.65 | 67OH | 25C27 | 67CZ | 17.00 |
| 67CE1 | 25C27 | 67CZ | 17.03 | 160C | 25C27 | 160CB | 31.24 |
| 160O | 25O28 | 160C | 3.01 | 160O | 25O28 | 161CA | 33.47 |
| 160C | 25O28 | 160CB | 35.39 | 160O | 25O28 | 161N | 15.24 |
| 160O | 25O28 | 160CA | 17.00 | 160C | 25O28 | 161O | 59.68 |
| 160C | 25O28 | 161C | 45.54 | 160C | 25O28 | 161CA | 33.37 |
| 160C | 25O28 | 160CB | 34.06 | 160C | 25O28 | 161N | 14.62 |
| 160C | 25O28 | 160CA | 16.50 | 160C | 25O28 | 161C | 58.60 |
| 160C | 25O28 | 161C | 44.40 | 161CA | 25O28 | 160CB | 65.80 |
| 161CA | 25O28 | 161N | 18.92 | 161CA | 25O28 | 160CA | 49.84 |
| 161CA | 25O28 | 161O | 28.96 | 161CA | 25O28 | 161C | 17.13 |
| 160CB | 25O28 | 161N | 47.18 | 160CB | 25O28 | 160CA | 19.23 |
| 160CB | 25O28 | 161C | 84.88 | 160CB | 25O28 | 161C | 71.68 |
| 161N | 25O28 | 160CA | 30.98 | 161N | 25O28 | 161O | 44.50 |
| 161N | 25O28 | 161C | 30.43 | 160CA | 25O28 | 161O | 73.79 |
| 160CA | 25O28 | 161C | 59.64 | 161O | 25O28 | 161C | 14.21 |
| 160O | 25C29 | 160C | 8.30 | 160O | 25C29 | 161O | 64.77 |
| 160O | 25C29 | 161CA | 35.29 | 160O | 25C29 | 161C | 50.76 |
| 160O | 25C29 | 161N | 20.86 | 160C | 25C29 | 161O | 58.92 |
| 160C | 25C29 | 161CA | 30.98 | 160C | 25C29 | 161C | 44.50 |
| 160C | 25C29 | 161N | 14.62 | 161O | 25C29 | 161CA | 30.36 |
| 161O | 25C29 | 161C | 14.65 | 161O | 25C29 | 66O | 98.33 |
| 161O | 25C29 | 161N | 44.35 | 161CA | 25C29 | 161C | 18.41 |
| 161CA | 25C29 | 161N | 17.07 | 161C | 25C29 | 161N | 30.04 |
| 66O | 25C29 | 67CE1 | 67.43 | 67CE1 | 25O30 | 66O | 85.21 |
| 67CE1 | 25O30 | 67CD1 | 18.89 | 67CE1 | 25O30 | 67CZ | 18.55 |
| 67CE1 | 25O30 | 66C | 76.83 | 67CE1 | 25O30 | 67OH | 30.56 |
| 67CE1 | 25O30 | 67CG | 30.00 | 67CE1 | 25O30 | 67CE2 | 29.39 |
| 66O | 25O30 | 67CD1 | 68.13 | 66O | 25O30 | 67CZ | 86.99 |
| 66O | 25O30 | 66C | 13.74 | 66O | 25O30 | 67CG | 55.33 |
| 66O | 25O30 | 67CE2 | 73.81 | 66O | 25O30 | 67CZ | 32.19 |
| 67CD1 | 25O30 | 66C | 61.85 | 67CD1 | 25O30 | 67OH | 47.68 |
| 67CD1 | 25O30 | 67CG | 16.18 | 67CD1 | 25O30 | 67CE2 | 34.38 |
| 67CZ | 25O30 | 66C | 75.55 | 67CZ | 25O30 | 67OH | 16.91 |
| 67CZ | 25O30 | 67CG | 34.81 | 67CZ | 25O30 | 67CE2 | 15.93 |
| 66C | 25O30 | 67OH | 90.11 | 66C | 25O30 | 67CG | 47.06 |
| 66C | 25O30 | 67CE2 | 61.38 | 67OH | 25O30 | 67CG | 51.72 |
| 67OH | 25O30 | 67CE2 | 28.75 | 67CG | 25O30 | 67CE2 | 28.79 |
| 161O | 25C31 | 161C | 15.89 | 161O | 25C31 | 163CB | 92.78 |
| 161O | 25C31 | 163N | 61.31 | 161O | 25C31 | 25SG | 64.02 |
| 161O | 25C31 | 160O | 63.87 | 161O | 25C31 | 161CA | 29.15 |
| 161O | 25C31 | 162N | 24.80 | 161O | 25C31 | 162C | 50.12 |
| 161O | 25C31 | 162CA | 32.14 | 161C | 25C31 | 163CB | 90.31 |
| 161C | 25C31 | 163N | 58.98 | 161C | 25C31 | 25SG | 74.60 |
| 161C | 25C31 | 160O | 51.49 | 161C | 25C31 | 161CA | 18.45 |
| 161C | 25C31 | 162N | 14.50 | 161C | 25C31 | 162C | 44.52 |
| 161C | 25C31 | 162CA | 29.60 | 66O | 25C31 | 163CB | 84.58 |
| 66O | 25C31 | 25SG | 96.91 | 163CB | 25C31 | 163N | 31.73 |
| 163CB | 25C31 | 25SG | 54.53 | 163CB | 25C31 | 162N | 76.07 |
| 163CB | 25C31 | 162C | 45.95 | 163CB | 25C31 | 162CA | 61.61 |
| 163N | 25C31 | 25SG | 46.05 | 163N | 25C31 | 160O | 95.54 |
| 163N | 25C31 | 161CA | 75.21 | 163N | 25C31 | 162N | 45.16 |
| 163N | 25C31 | 162C | 16.28 | 163N | 25C31 | 162CA | 29.89 |
| 25SG | 25C31 | 161CA | 92.28 | 25SG | 25C31 | 162N | 68.65 |
| 25SG | 25C31 | 162C | 56.25 | 25SG | 25C31 | 162CA | 53.18 |
| 160O | 25C31 | 161CA | 34.72 | 160O | 25C31 | 162N | 58.12 |
| 160O | 25C31 | 162C | 79.70 | 160O | 25C31 | 162CA | 74.94 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 161CA | 25C31 | 162N | 30.24 | 161CA | 25C31 | 162C | 59.56 |
| 161CA | 25C31 | 162CA | 47.15 | 162N | 25C31 | 162C | 30.15 |
| 162N | 25C31 | 162CA | 17.36 | 162C | 25C31 | 162CA | 18.28 |
| 66O | 25C32 | 66C | 6.90 | 66O | 25C32 | 26CB | 47.54 |
| 66O | 25C32 | 66N | 33.71 | 66O | 25C32 | 67CA | 32.46 |
| 66O | 25C32 | 67N | 16.73 | 66O | 25C32 | 68SD | 78.15 |
| 66O | 25C32 | 66CA | 18.01 | 66C | 25C32 | 26CB | 54.44 |
| 66C | 25C32 | 66N | 33.07 | 66C | 25C32 | 67CA | 31.49 |
| 66C | 25C32 | 67N | 13.91 | 66C | 25C32 | 68SD | 82.32 |
| 66C | 25C32 | 66CA | 15.84 | 163CB | 25C32 | 26CB | 63.43 |
| 163CB | 25C32 | 161O | 78.07 | 163CB | 25C32 | 68SD | 47.45 |
| 26CB | 25C32 | 66N | 59.39 | 26CB | 25C32 | 67CA | 62.90 |
| 26CB | 25C32 | 67N | 59.03 | 26CB | 25C32 | 68SD | 57.55 |
| 26CB | 25C32 | 66CA | 57.10 | 66N | 25C32 | 67CA | 64.54 |
| 66N | 25C32 | 67N | 46.76 | 66N | 25C32 | 66CA | 17.45 |
| 67CA | 25C32 | 67N | 17.89 | 67CA | 25C32 | 68SD | 59.36 |
| 67CA | 25C32 | 66CA | 47.17 | 67N | 25C32 | 68SD | 73.47 |
| 67N | 25C32 | 66CA | 29.33 | 68SD | 25C32 | 66CA | 96.00 |
| 66O | 25C33 | 68SD | 88.15 | 66O | 25C33 | 67CA | 38.20 |
| 66O | 25C33 | 66C | 8.09 | 66O | 25C33 | 67CD1 | 67.84 |
| 66O | 25C33 | 26CB | 42.16 | 66O | 25C33 | 163CB | 58.04 |
| 68SD | 25C33 | 209CD2 | 90.24 | 68SD | 25C33 | 68CE | 24.67 |
| 68SD | 25C33 | 134CB | 82.77 | 68SD | 25C33 | 67CA | 68.81 |
| 68SD | 25C33 | 66C | 87.57 | 68SD | 25C33 | 67CD1 | 97.64 |
| 68SD | 25C33 | 163CA | 69.15 | 68SD | 25C33 | 26CB | 61.04 |
| 68SD | 25C33 | 163N | 85.62 | 163C13 | 25C33 | 68CE | 66.68 |
| 163CB | 25C33 | 134CB | 76.70 | 163CB | 25C33 | 163CA | 16.69 |
| 163CB | 25C33 | 26CB | 62.05 | 163CB | 25C33 | 163N | 28.80 |
| 209CD2 | 25C33 | 68CE | 67.71 | 209CD2 | 25C33 | 134CB | 48.90 |
| 209CD2 | 25C33 | 67CA | 91.59 | 209CD2 | 25C33 | 67CD1 | 58.37 |
| 68CE | 25C33 | 134CB | 60.70 | 68CE | 25C33 | 67CA | 80.55 |
| 68CE | 25C33 | 67CD1 | 93.40 | 68CE | 25C33 | 163CA | 71.10 |
| 68CE | 25C33 | 26CB | 85.68 | 68CE | 25C33 | 163N | 88.13 |
| 134CB | 25C33 | 163CA | 63.97 | 134CB | 25C33 | 163N | 69.60 |
| 67CA | 25C33 | 66C | 31.31 | 67CA | 25C33 | 67CD1 | 43.75 |
| 67CA | 25C33 | 26CB | 61.06 | 66C | 25C33 | 67CD1 | 59.98 |
| 66C | 25C33 | 26CB | 47.92 | 163CA | 25C33 | 26CB | 77.85 |
| 163CA | 25C33 | 163N | 17.21 | 26CB | 25C33 | 163N | 81.08 |
| 134CB | 25C34 | 163CB | 98.21 | 134CB | 25C34 | 209CD2 | 58.87 |
| 134CB | 25C34 | 134CA | 20.10 | 134CB | 25C34 | 163CA | 84.05 |
| 134CB | 25C34 | 163N | 93.22 | 134CB | 25C34 | 68SD | 90.66 |
| 134CB | 25C34 | 162O | 68.42 | 134CB | 25C34 | 162C | 84.53 |
| 134CB | 25C34 | 68CE | 68.29 | 134CB | 25C34 | 160O | 90.59 |
| 134CB | 25C34 | 133O | 48.20 | 134CB | 25C34 | 134C | 23.47 |
| 134CB | 25C34 | 134N | 22.08 | 163CB | 25C34 | 134CA | 80.28 |
| 163CB | 25C34 | 163CA | 22.29 | 163CB | 25C34 | 163N | 35.89 |
| 163CB | 25C34 | 68SD | 54.05 | 163CB | 25C34 | 162O | 61.05 |
| 163CB | 25C34 | 162C | 53.04 | 163CB | 25C34 | 68CE | 66.68 |
| 163CB | 25C34 | 161O | 82.47 | 163CB | 25C34 | 66O | 82.69 |
| 163CB | 25C34 | 161C | 87.58 | 163CB | 25C34 | 133O | 51.04 |
| 163CB | 25C34 | 134C | 88.38 | 163CB | 25C34 | 134N | 76.48 |
| 209CD2 | 25C34 | 134CA | 78.36 | 209CD2 | 25C34 | 68SD | 85.07 |
| 209CD2 | 25C34 | 68CE | 68.09 | 209CD2 | 25C34 | 160O | 89.46 |
| 209CD2 | 25C34 | 66O | 98.98 | 209CD2 | 25C34 | 133O | 91.98 |
| 209CD2 | 25C34 | 134C | 80.67 | 209CD2 | 25C34 | 134N | 73.48 |
| 134CA | 25C34 | 163CA | 64.27 | 134CA | 25C34 | 163N | 73.36 |
| 134CA | 25C34 | 68SD | 87.47 | 134CA | 25C34 | 162O | 50.99 |
| 134CA | 25C34 | 162C | 66.34 | 134CA | 25C34 | 68CE | 68.94 |
| 134CA | 25C34 | 160O | 96.11 | 134CA | 25C34 | 161C | 93.44 |
| 134CA | 25C34 | 133O | 34.17 | 134CA | 25C34 | 134C | 14.63 |
| 134CA | 25C34 | 134N | 13.38 | 163CA | 25C34 | 163N | 20.60 |
| 163CA | 25C34 | 68SD | 71.18 | 163CA | 25C34 | 162O | 39.10 |
| 163CA | 25C34 | 162C | 33.94 | 163CA | 25C34 | 68CE | 76.73 |
| 163CA | 25C34 | 161O | 73.90 | 163CA | 25C34 | 161C | 74.17 |
| 163CA | 25C34 | 133O | 43.83 | 163CA | 25C34 | 134C | 69.19 |
| 163CA | 25C34 | 134N | 64.70 | 163N | 25C34 | 68SD | 89.44 |
| 163N | 25C34 | 162O | 30.77 | 163N | 25C34 | 162C | 17.88 |
| 163N | 25C34 | 68CE | 97.26 | 163N | 25C34 | 160O | 97.64 |
| 163N | 25C34 | 161O | 53.38 | 163N | 25C34 | 161C | 53.96 |
| 163N | 25C34 | 133O | 61.87 | 163N | 25C34 | 134C | 73.07 |
| 163N | 25C34 | 134N | 77.98 | 68SD | 25C34 | 68CE | 23.41 |
| 68SD | 25C34 | 66O | 65.12 | 68SD | 25C34 | 133O | 57.26 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 68SD | 25C34 | 134N | 74.79 | 162O | 25C34 | 162C | 16.36 |
| 162O | 25C34 | 160O | 80.07 | 162O | 25C34 | 161O | 57.49 |
| 162O | 25C34 | 161C | 48.98 | 162O | 25C34 | 133O | 57.78 |
| 162O | 25C34 | 134C | 45.59 | 162O | 25C34 | 134N | 60.64 |
| 162C | 25C34 | 160O | 82.14 | 162C | 25C34 | 161O | 46.60 |
| 162C | 25C34 | 161C | 42.17 | 162C | 25C34 | 133O | 66.02 |
| 162C | 25C34 | 134C | 61.91 | 162C | 25C34 | 134N | 74.59 |
| 68CE | 25C34 | 66O | 84.63 | 68CE | 25C34 | 133O | 46.00 |
| 68CE | 25C34 | 134C | 83.30 | 68CE | 25C34 | 134N | 55.59 |
| 160O | 25C34 | 161O | 52.91 | 160O | 25C34 | 161C | 45.36 |
| 160O | 25C34 | 134C | 81.68 | 161O | 25C34 | 66O | 93.09 |
| 161O | 25C34 | 161C | 14.42 | 161O | 25C34 | 134C | 94.94 |
| 161C | 25C34 | 134C | 81.60 | 133O | 25C34 | 134C | 47.42 |
| 133O | 25C34 | 134N | 26.12 | 134C | 25C34 | 134N | 27.76 |
| 209CD2 | 25C35 | 67CD1 | 84.45 | 209CD2 | 25C35 | 67CE1 | 80.21 |
| 209CD2 | 25C35 | 68SD | 97.07 | 209CD2 | 25C35 | 209CG | 14.43 |
| 209CD2 | 25C35 | 68CE | 73.57 | 209CD2 | 25C35 | 234OH2 | 69.51 |
| 209CD2 | 25C35 | 134CB | 48.83 | 209CD2 | 25C35 | 67CZ | 91.21 |
| 67CD1 | 25C35 | 66O | 85.63 | 67CD1 | 25C35 | 67CA | 57.17 |
| 67CD1 | 25C35 | 67CE1 | 19.94 | 67CD1 | 25C35 | 67CG | 19.64 |
| 67CD1 | 25C35 | 67CB | 37.21 | 67CD1 | 25C35 | 209CG | 80.87 |
| 67CD1 | 25C35 | 66C | 72.49 | 67CD1 | 25C35 | 234OH2 | 56.52 |
| 67CD1 | 25C35 | 67N | 60.31 | 67CD1 | 25C35 | 68N | 77.14 |
| 67CD1 | 25C35 | 67C | 68.08 | 67CD1 | 25C35 | 67CZ | 24.12 |
| 67CD1 | 25C35 | 67CD2 | 23.57 | 66O | 25C35 | 67CA | 43.70 |
| 66O | 25C35 | 67CE1 | 93.34 | 66O | 25C35 | 67CG | 67.30 |
| 66O | 25C35 | 67CB | 61.47 | 66O | 25C35 | 68SD | 79.58 |
| 66O | 25C35 | 66C | 13.35 | 66O | 25C35 | 234OH2 | 97.49 |
| 66O | 25C35 | 67N | 29.17 | 66O | 25C35 | 68N | 61.59 |
| 66O | 25C35 | 67C | 49.59 | 66O | 25C35 | 67CZ | 83.31 |
| 66O | 25C35 | 67CD2 | 62.47 | 67CA | 25C35 | 67CE1 | 74.54 |
| 67CA | 25C35 | 67CG | 38.46 | 67CA | 25C35 | 67CB | 21.40 |
| 67CA | 25C35 | 68SD | 71.28 | 67CA | 25C35 | 68CE | 86.07 |
| 67CA | 25C35 | 66C | 33.51 | 67CA | 25C35 | 234OH2 | 54.58 |
| 67CA | 25C35 | 67N | 17.55 | 67CA | 25C35 | 68N | 31.22 |
| 67CA | 25C35 | 67C | 15.46 | 67CA | 25C35 | 67CZ | 70.81 |
| 67CA | 25C35 | 67CD2 | 42.99 | 67CE1 | 25C35 | 67CG | 36.15 |
| 67CE1 | 25C35 | 67CB | 56.18 | 67CE1 | 25C35 | 209CG | 81.63 |
| 67CE1 | 25C35 | 66C | 81.58 | 67CE1 | 25C35 | 234OH2 | 73.50 |
| 67CE1 | 25C35 | 67N | 73.49 | 67CE1 | 25C35 | 68N | 96.98 |
| 67CE1 | 25C35 | 67C | 86.96 | 67CE1 | 25C35 | 67CZ | 11.55 |
| 67CE1 | 25C35 | 67CD2 | 33.63 | 67CG | 25C35 | 67CB | 21.11 |
| 67CG | 25C35 | 209CG | 95.25 | 67CG | 25C35 | 66C | 53.96 |
| 67CG | 25C35 | 234OH2 | 55.92 | 67CG | 25C35 | 67N | 40.77 |
| 67CG | 25C35 | 68N | 62.93 | 67CG | 25C35 | 67C | 51.10 |
| 67CG | 25C35 | 67CZ | 34.20 | 67CG | 25C35 | 67CD2 | 11.75 |
| 67CB | 25C35 | 68SD | 84.13 | 67CB | 25C35 | 209CG | 94.85 |
| 67CB | 25C35 | 68CE | 92.04 | 67CB | 25C35 | 66C | 49.06 |
| 67CB | 25C35 | 234OH2 | 43.66 | 67CB | 25C35 | 67N | 32.31 |
| 67CB | 25C35 | 68N | 41.83 | 67CB | 25C35 | 67C | 30.89 |
| 67CB | 25C35 | 67CZ | 55.30 | 67CB | 25C35 | 67CD2 | 30.26 |
| 68SD | 25C35 | 209CG | 86.31 | 68SD | 25C35 | 68CE | 23.56 |
| 68SD | 25C35 | 66C | 84.14 | 68SD | 25C35 | 234OH2 | 65.58 |
| 68SD | 25C35 | 67N | 81.24 | 68SD | 25C35 | 134CB | 74.35 |
| 68SD | 25C35 | 68N | 42.38 | 68SD | 25C35 | 67C | 56.14 |
| 209CG | 25C35 | 68CE | 63.48 | 209CG | 25C35 | 234OH2 | 55.92 |
| 209CG | 25C35 | 134CB | 53.71 | 209CG | 25C35 | 68N | 92.87 |
| 209CG | 25C35 | 67CZ | 93.16 | 68CE | 25C35 | 234OH2 | 58.89 |
| 68CE | 25C35 | 67N | 99.75 | 68CE | 25C35 | 134CB | 57.04 |
| 68CE | 25C35 | 68N | 54.84 | 68CE | 25C35 | 67C | 70.76 |
| 66C | 25C35 | 234OH2 | 88.09 | 66C | 25C35 | 67N | 16.98 |
| 66C | 25C35 | 68N | 57.38 | 66C | 25C35 | 67C | 42.97 |
| 66C | 25C35 | 67CZ | 72.32 | 66C | 25C35 | 67CD2 | 49.60 |
| 234OH2 | 25C35 | 67N | 71.60 | 234OH2 | 25C35 | 134CB | 98.59 |
| 234OH2 | 25C35 | 68N | 41.88 | 234OH2 | 25C35 | 67C | 48.67 |
| 234OH2 | 25C35 | 67CZ | 80.56 | 234OH2 | 25C35 | 67CD2 | 67.67 |
| 67N | 25C35 | 68N | 46.13 | 67N | 25C35 | 67C | 30.25 |
| 67N | 25C35 | 67CZ | 66.52 | 67N | 25C35 | 67CD2 | 39.87 |
| 68N | 25C35 | 67C | 16.06 | 68N | 25C35 | 67CZ | 97.13 |
| 68N | 25C35 | 67CD2 | 71.07 | 67C | 25C35 | 67CZ | 84.80 |
| 67C | 25C35 | 67CD2 | 57.44 | 67CZ | 25C35 | 67CD2 | 27.90 |
| 161O | 25C36 | 25SG | 73.45 | 161O | 25C36 | 161C | 9.23 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 161O | 25C36 | 163N | 54.83 | 25SG | 25C36 | 161C | 78.40 |
| 25SG | 25C36 | 65CA | 99.90 | 25SG | 25C36 | 26CD1 | 71.50 |
| 25SG | 25C36 | 163N | 45.03 | 25SG | 25C36 | 26CB | 68.53 |
| 66O | 25C36 | 66N | 37.32 | 66O | 25C36 | 65CA | 68.43 |
| 66O | 25C36 | 26CD1 | 49.39 | 66O | 25C36 | 26CB | 39.54 |
| 161C | 25C36 | 163N | 52.99 | 66N | 25C36 | 65CA | 31.50 |
| 66N | 25C36 | 26CD1 | 39.27 | 66N | 25C36 | 26CB | 55.35 |
| 65CA | 25C36 | 26CD1 | 45.88 | 65CA | 25C36 | 26CB | 73.66 |
| 26CD1 | 25C36 | 26CB | 29.63 | 163N | 25C36 | 26CB | 78.56 |
| 66N | 25O37 | 65CA | 42.38 | 66N | 25O37 | 66O | 46.15 |
| 66N | 25O37 | 65C | 19.40 | 66N | 25O37 | 66CA | 14.20 |
| 66N | 25O37 | 66C | 33.73 | 66N | 25O37 | 26CD1 | 46.03 |
| 66N | 25O37 | 65N | 50.68 | 66N | 25O37 | 64O | 71.48 |
| 66N | 25O37 | 26CB | 60.88 | 66N | 25O37 | 26CG | 47.75 |
| 65CA | 25O37 | 66O | 87.59 | 65CA | 25O37 | 65C | 23.08 |
| 65CA | 25O37 | 66CA | 56.55 | 65CA | 25O37 | 66C | 75.97 |
| 65CA | 25O37 | 26CD1 | 55.04 | 65CA | 25O37 | 65N | 8.31 |
| 65CA | 25O37 | 64O | 33.61 | 65CA | 25O37 | 26CB | 84.88 |
| 65CA | 25O37 | 26CG | 67.58 | 66O | 25O37 | 65C | 65.32 |
| 66O | 25O37 | 66CA | 32.98 | 66O | 25O37 | 66C | 13.52 |
| 66O | 25O37 | 26CD1 | 56.53 | 66O | 25O37 | 65N | 95.80 |
| 66O | 25O37 | 26CB | 40.45 | 66O | 25O37 | 26CG | 44.04 |
| 65C | 25O37 | 66CA | 33.51 | 65C | 25O37 | 66C | 53.13 |
| 65C | 25O37 | 26CD1 | 48.33 | 65C | 25O37 | 65N | 31.35 |
| 65C | 25O37 | 64O | 52.95 | 65C | 25O37 | 26CB | 72.24 |
| 65C | 25O37 | 26CG | 56.09 | 161O | 25O37 | 25SG | 57.00 |
| 66CA | 25O37 | 66C | 19.92 | 66CA | 25O37 | 26CD1 | 50.28 |
| 66CA | 25O37 | 65N | 64.84 | 66CA | 25O37 | 64O | 84.47 |
| 66CA | 25O37 | 26CB | 56.17 | 66CA | 25O37 | 26CG | 47.05 |
| 66C | 25O37 | 26CD1 | 55.02 | 66C | 25O37 | 65N | 84.27 |
| 66C | 25O37 | 26CB | 47.54 | 66C | 25O37 | 26CG | 45.65 |
| 26CD1 | 25O37 | 25SG | 70.87 | 26CD1 | 25O37 | 65N | 59.66 |
| 26CD1 | 25O37 | 64O | 86.49 | 26CD1 | 25O37 | 26CB | 31.10 |
| 26CD1 | 25O37 | 26CG | 15.01 | 25SG | 25O37 | 26CB | 64.40 |
| 25SG | 25O37 | 26CG | 71.37 | 65N | 25O37 | 64O | 27.18 |
| 65N | 25O37 | 26CB | 90.35 | 65N | 25O37 | 26CG | 73.15 |
| 26CB | 25O37 | 26CG | 17.30 | 161O | 25N38 | 161C | 6.07 |
| 161O | 25N38 | 162CA | 37.32 | 161O | 25N38 | 163N | 66.42 |
| 161O | 25N38 | 162N | 19.53 | 161O | 25N38 | 162C | 50.16 |
| 161O | 25N38 | 161CA | 13.58 | 161O | 25N38 | 163CB | 91.46 |
| 25SG | 25N38 | 162CA | 69.08 | 25SG | 25N38 | 163N | 53.99 |
| 25SG | 25N38 | 162N | 87.78 | 25SG | 25N38 | 25CB | 2.51 |
| 25SG | 25N38 | 162C | 65.56 | 25SG | 25N38 | 163CB | 56.74 |
| 161C | 25N38 | 162CA | 34.04 | 161C | 25N38 | 163N | 61.45 |
| 161C | 25N38 | 162N | 15.39 | 161C | 25N38 | 162C | 45.21 |
| 161C | 25N38 | 161CA | 14.75 | 161C | 25N38 | 163CB | 85.67 |
| 162CA | 25N38 | 163N | 32.71 | 162CA | 25N38 | 162N | 18.81 |
| 162CA | 25N38 | 25CB | 71.19 | 162CA | 25N38 | 162C | 18.79 |
| 162CA | 25N38 | 161CA | 48.73 | 162CA | 25N38 | 163CB | 62.05 |
| 163N | 25N38 | 162N | 47.03 | 163N | 25N38 | 25CB | 56.49 |
| 163N | 25N38 | 162C | 16.27 | 163N | 25N38 | 161CA | 74.28 |
| 163N | 25N38 | 163CB | 29.78 | 162N | 25N38 | 25CB | 89.84 |
| 162N | 25N38 | 162C | 30.82 | 162N | 25N38 | 161CA | 29.96 |
| 162N | 25N38 | 163CB | 73.48 | 25CB | 25N38 | 162C | 68.00 |
| 25CB | 25N38 | 163CB | 58.75 | 162C | 25N38 | 161CA | 58.33 |
| 162C | 25N38 | 163CB | 43.86 | 161CA | 25N38 | 163CB | 95.28 |
| 25SG | 25N39 | 161C | 88.31 | 25SG | 25N39 | 23O | 88.64 |
| 25SG | 25N39 | 25CB | 14.83 | 25SG | 25N39 | 23C | 82.58 |
| 25SG | 25N39 | 161C | 85.92 | 25SG | 25N39 | 25N | 41.66 |
| 25SG | 25N39 | 23CA | 91.29 | 25SG | 25N39 | 25CA | 24.80 |
| 25SG | 25N39 | 162CA | 58.01 | 161O | 25N39 | 25CB | 99.78 |
| 161O | 25N39 | 161C | 3.40 | 161O | 25N39 | 162CA | 31.86 |
| 23O | 25N39 | 25CB | 77.70 | 23O | 25N39 | 23C | 14.66 |
| 23O | 25N39 | 65CA | 50.70 | 23O | 25N39 | 25N | 47.04 |
| 23O | 25N39 | 23CA | 29.83 | 23O | 25N39 | 25CA | 63.85 |
| 25CB | 25N39 | 23C | 69.66 | 25CB | 25N39 | 161C | 97.02 |
| 25CB | 25N39 | 25N | 31.35 | 25CB | 25N39 | 23CA | 76.81 |
| 25CB | 25N39 | 25CA | 16.71 | 25CB | 25N39 | 162CA | 68.20 |
| 23C | 25N39 | 65CA | 64.77 | 23C | 25N39 | 25N | 41.89 |
| 23C | 25N39 | 23CA | 18.46 | 23C | 25N39 | 25CA | 58.51 |
| 161C | 25N39 | 162CA | 28.91 | 65CA | 25N39 | 25N | 88.24 |
| 65CA | 25N39 | 23CA | 73.18 | 25N | 25N39 | 23CA | 54.84 |

TABLE XV-continued

Table of angles between atoms of the inhibitor and protein for all protein atoms within 5 Angstroms of the inhibitor 2-[N-(3-benzyloxybenzoyl))]-2'-[N'-(N-benzyloxycarbonyl-L-leucinyl)]carbohydrazide.

| Atom 1 | Atom 2 | Atom 3 | Angle | Atom 1 | Atom 2 | Atom 3 | Angle |
|---|---|---|---|---|---|---|---|
| 25N | 25N39 | 25CA | 16.92 | 25N | 25N39 | 162CA | 99.14 |
| 23CA | 25N39 | 25CA | 69.81 | 25CA | 25N39 | 162CA | 82.61 |
| 160O | 25N40 | 161O | 83.18 | 160O | 25N40 | 161C | 65.67 |
| 160O | 25N40 | 161CA | 44.84 | 160O | 25N40 | 160C | 14.22 |
| 160O | 25N40 | 161N | 30.23 | 160O | 25N40 | 162N | 67.90 |
| 161O | 25N40 | 161C | 19.36 | 161O | 25N40 | 161CA | 38.54 |
| 161O | 25N40 | 160C | 72.40 | 161O | 25N40 | 161N | 54.55 |
| 161O | 25N40 | 162N | 26.72 | 161C | 25N40 | 161CA | 23.35 |
| 161C | 25N40 | 160C | 53.79 | 161C | 25N40 | 161N | 35.96 |
| 161C | 25N40 | 162N | 13.14 | 161CA | 25N40 | 160C | 35.76 |
| 161CA | 25N40 | 161N | 19.52 | 161CA | 25N40 | 162N | 31.98 |
| 160C | 25N40 | 161N | 17.87 | 160C | 25N40 | 162N | 54.39 |
| 161N | 25N40 | 162N | 37.86 | | | | |

TABLE XVI

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 184O | 25C1 | 184CD1 | 70.91 |
| 184O | 25C1 | 184CG | 59.71 |
| 184O | 25C1 | 184CB | 40.07 |
| 184O | 25C1 | 184CA | 32.41 |
| 184O | 25C1 | 18OD1 | 51.11 |
| 184O | 25C1 | 184C | 14.14 |
| 184O | 25C1 | 184NE1 | 85.23 |
| 184O | 25C1 | 184CD2 | 70.75 |
| 184CD1 | 25C1 | 184CG | 18.26 |
| 184CD1 | 25C1 | 184CB | 34.36 |
| 184CD1 | 25C1 | 184CA | 39.63 |
| 184CD1 | 25C1 | 18OD1 | 88.02 |
| 184CD1 | 25C1 | 184C | 58.65 |
| 184CD1 | 25C1 | 184NE1 | 15.36 |
| 184CD1 | 25C1 | 184CD2 | 26.43 |
| 184CG | 25C1 | 184CB | 19.78 |
| 184CG | 25C1 | 184CA | 33.68 |
| 184CG | 25C1 | 18OD1 | 90.72 |
| 184CG | 25C1 | 184C | 50.19 |
| 184CG | 25C1 | 184NE1 | 27.27 |
| 184CG | 25C1 | 184CD2 | 15.55 |
| 184CB | 25C1 | 184CA | 19.99 |
| 184CB | 25C1 | 18OD1 | 77.76 |
| 184CB | 25C1 | 184C | 31.92 |
| 184CB | 25C1 | 184NE1 | 46.53 |
| 184CB | 25C1 | 184CD2 | 31.52 |
| 184CA | 25C1 | 18OD1 | 58.36 |
| 184CA | 25C1 | 184C | 19.14 |
| 184CA | 25C1 | 184NE1 | 54.76 |
| 184CA | 25C1 | 184CD2 | 48.54 |
| 18OD1 | 25C1 | 184C | 48.87 |
| 184C | 25C1 | 184NE1 | 73.60 |
| 184C | 25C1 | 184CD2 | 63.42 |
| 184NE1 | 25C1 | 184CD2 | 26.12 |
| 20O | 25C2 | 20C | 16.36 |
| 20O | 25C2 | 21NE2 | 67.96 |
| 20O | 25C2 | 20N | 38.80 |
| 20O | 25C2 | 20CA | 32.93 |
| 20O | 25C2 | 19CG | 52.37 |
| 20O | 25C2 | 18OD1 | 81.91 |
| 20C | 25C2 | 21NE2 | 65.02 |
| 20C | 25C2 | 20N | 33.58 |
| 20C | 25C2 | 20CA | 20.23 |
| 20C | 25C2 | 19CG | 62.24 |
| 20C | 25C2 | 18OD1 | 73.06 |
| 21NE2 | 25C2 | 20N | 97.72 |
| 21NE2 | 25C2 | 20CA | 79.83 |
| 21NE2 | 25C2 | 20N | 95.12 |
| 184CD1 | 25C2 | 19CG | 55.67 |
| 184CD1 | 25C2 | 18OD1 | 86.02 |
| 184CD1 | 25C2 | 184NE1 | 16.52 |
| 184CD1 | 25C2 | 184CG | 16.21 |
| 184CD1 | 25C2 | 184CA | 36.11 |
| 20N | 25C2 | 20CA | 19.09 |
| 20N | 25C2 | 19CG | 44.54 |
| 20N | 25C2 | 18OD1 | 43.33 |
| 20N | 25C2 | 18CA | 81.17 |
| 20CA | 25C2 | 19CG | 60.59 |
| 20CA | 25C2 | 18OD1 | 53.05 |
| 20CA | 25C2 | 184CA | 98.88 |
| 19CG | 25C2 | 18OD1 | 66.67 |
| 19CG | 25C2 | 184NE1 | 60.03 |
| 19CG | 25C2 | 184CG | 69.53 |
| 19CG | 25C2 | 184CA | 62.53 |
| 18OD1 | 25C2 | 184CG | 83.94 |
| 18OD1 | 25C2 | 184CA | 53.91 |
| 184NE1 | 25C2 | 184CG | 27.27 |
| 184NE1 | 25C2 | 184CA | 52.47 |
| 184CG | 25C2 | 184CA | 30.07 |
| 20O | 25C3 | 21NE2 | 68.98 |
| 20O | 25C3 | 20C | 12.74 |
| 20O | 25C3 | 19CG | 52.30 |
| 20O | 25C3 | 19CD | 62.76 |
| 184CD1 | 25C3 | 184NE1 | 19.43 |
| 184CD1 | 25C3 | 19CG | 57.07 |
| 184CD1 | 25C3 | 184CG | 15.46 |
| 184CD1 | 25C3 | 184CE2 | 27.70 |
| 184CD1 | 25C3 | 19CD | 51.26 |
| 184NE1 | 25C3 | 19CG | 64.69 |
| 184NE1 | 25C3 | 184CG | 28.26 |
| 184NE1 | 25C3 | 184CE2 | 15.28 |
| 184NE1 | 25C3 | 19CD | 52.93 |
| 21NE2 | 25C3 | 20C | 62.81 |
| 20C | 25C3 | 19CG | 59.85 |
| 20C | 25C3 | 19CD | 72.69 |
| 19CG | 25C3 | 184CG | 69.91 |
| 19CG | 25C3 | 184CE2 | 79.68 |
| 19CG | 25C3 | 19CD | 17.58 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 184CG | 25C3 | 184CE2 | 27.82 |
| 184CG | 25C3 | 19CD | 66.23 |
| 184CE2 | 25C3 | 19CD | 68.19 |
| 184NE1 | 25C4 | 184CD1 | 21.40 |
| 184NE1 | 25C4 | 184CE2 | 20.66 |
| 184NE1 | 25C4 | 184CG | 31.78 |
| 184NE1 | 25C4 | 184CD2 | 31.15 |
| 184NE1 | 25C4 | 184CZ2 | 34.27 |
| 184CD1 | 25C4 | 184CE2 | 34.03 |
| 184CD1 | 25C4 | 184CG | 18.28 |
| 184CD1 | 25C4 | 184CD2 | 31.27 |
| 184CD1 | 25C4 | 184CZ2 | 51.25 |
| 184CE2 | 25C4 | 184CG | 32.35 |
| 184CE2 | 25C4 | 184CD2 | 18.86 |
| 184CE2 | 25C4 | 184CZ2 | 17.60 |
| 184CG | 25C4 | 184CD2 | 19.32 |
| 184CG | 25C4 | 184CZ2 | 49.25 |
| 184CD2 | 25C4 | 184CZ2 | 32.53 |
| 184CE2 | 25C5 | 184NE1 | 21.44 |
| 184CE2 | 25C5 | 184CD2 | 21.99 |
| 184CE2 | 25C5 | 184CD1 | 35.25 |
| 184CE2 | 25C5 | 184CG | 36.03 |
| 184CE2 | 25C5 | 184CZ2 | 17.88 |
| 184CE2 | 25C5 | 184CE3 | 33.85 |
| 184CE2 | 25C5 | 184CB | 53.93 |
| 184CE2 | 25C5 | 184CH2 | 28.11 |
| 184CE2 | 25C5 | 184CZ3 | 34.04 |
| 184NE1 | 25C5 | 184CD2 | 35.23 |
| 184NE1 | 25C5 | 184CD1 | 21.39 |
| 184NE1 | 25C5 | 184CG | 35.13 |
| 184NE1 | 25C5 | 184CZ2 | 35.43 |
| 184NE1 | 25C5 | 184CE3 | 51.78 |
| 184NE1 | 25C5 | 184CB | 52.94 |
| 184NE1 | 25C5 | 184CH2 | 48.87 |
| 184NE1 | 25C5 | 184CZ3 | 55.18 |
| 184CD2 | 25C5 | 184CD1 | 35.19 |
| 184CD2 | 25C5 | 184CG | 22.35 |
| 184CD2 | 25C5 | 184CZ2 | 34.58 |
| 184CD2 | 25C5 | 184CE3 | 17.91 |
| 184CD2 | 25C5 | 184CB | 36.19 |
| 184CD2 | 25C5 | 184CH2 | 34.79 |
| 184CD2 | 25C5 | 184CZ3 | 28.60 |
| 184CD1 | 25C5 | 184CG | 21.04 |
| 184CD1 | 25C5 | 184CZ2 | 52.70 |
| 184CD1 | 25C5 | 184CE3 | 52.87 |
| 184CD1 | 25C5 | 184CB | 34.98 |
| 184CD1 | 25C5 | 184CH2 | 62.57 |
| 184CD1 | 25C5 | 184CZ3 | 62.67 |
| 184CG | 25C5 | 184CZ2 | 53.00 |
| 184CG | 25C5 | 184CE3 | 36.87 |
| 184CG | 25C5 | 184CB | 18.54 |
| 184CG | 25C5 | 184CH2 | 56.68 |
| 184CG | 25C5 | 184CZ3 | 50.46 |
| 184CZ2 | 25C5 | 184CE3 | 38.17 |
| 184CZ2 | 25C5 | 184CB | 69.96 |
| 184CZ2 | 25C5 | 184CH2 | 15.84 |
| 184CZ2 | 25C5 | 184CZ3 | 29.77 |
| 184CE3 | 25C5 | 184CB | 44.40 |
| 184CE3 | 25C5 | 184CH2 | 29.96 |
| 184CE3 | 25C5 | 184CZ3 | 16.03 |
| 184CB | 25C5 | 184CH2 | 70.55 |
| 184CB | 25C5 | 184CZ3 | 60.21 |
| 184CH2 | 25C5 | 184CZ3 | 16.60 |
| 184CG | 25C6 | 184CD1 | 20.02 |
| 184CG | 25C6 | 184CB | 21.95 |
| 184CG | 25C6 | 184CD2 | 20.42 |
| 184CG | 25C6 | 184O | 61.94 |
| 184CG | 25C6 | 184NE1 | 30.53 |
| 184CG | 25C6 | 184CE2 | 30.58 |
| 184CG | 25C6 | 184CA | 33.96 |
| 184CG | 25C6 | 184CE3 | 33.66 |
| 184CG | 25C6 | 184C | 50.16 |
| 184CD1 | 25C6 | 184CB | 37.32 |
| 184CD1 | 25C6 | 184CD2 | 32.14 |
| 184CD1 | 25C6 | 184O | 71.19 |
| 184CD1 | 25C6 | 184NE1 | 17.93 |
| 184CD1 | 25C6 | 184CE2 | 29.87 |
| 184CD1 | 25C6 | 184CA | 39.85 |
| 184CD1 | 25C6 | 184CE3 | 48.53 |
| 184CD1 | 25C6 | 184C | 57.95 |
| 184CB | 25C6 | 184CD2 | 37.74 |
| 184CB | 25C6 | 184O | 40.76 |
| 184CB | 25C6 | 184NE1 | 51.79 |
| 184CB | 25C6 | 184CE2 | 51.93 |
| 184CB | 25C6 | 184CA | 19.22 |
| 184CB | 25C6 | 184CE3 | 43.86 |
| 184CB | 25C6 | 184C | 30.42 |
| 184CD2 | 25C6 | 184O | 78.21 |
| 184CD2 | 25C6 | 184NE1 | 30.21 |
| 184CD2 | 25C6 | 184CE2 | 18.12 |
| 184CD2 | 25C6 | 184CA | 53.55 |
| 184CD2 | 25C6 | 184CE3 | 16.59 |
| 184CD2 | 25C6 | 184C | 68.06 |
| 184O | 25C6 | 184NE1 | 88.69 |
| 184O | 25C6 | 184CE2 | 92.47 |
| 184O | 25C6 | 184CA | 31.36 |
| 184O | 25C6 | 184CE3 | 80.46 |
| 184O | 25C6 | 184C | 13.35 |
| 184NE1 | 25C6 | 184CE2 | 17.71 |
| 184NE1 | 25C6 | 184CA | 57.51 |
| 184NE1 | 25C6 | 184CE3 | 45.78 |
| 184NE1 | 25C6 | 184C | 75.58 |
| 184CE2 | 25C6 | 184CA | 63.83 |
| 184CE2 | 25C6 | 184CE3 | 30.35 |
| 184CE2 | 25C6 | 184C | 80.70 |
| 184CA | 25C6 | 184CE3 | 62.43 |
| 184CA | 25C6 | 184C | 18.09 |
| 184CE3 | 25C6 | 184C | 73.23 |
| 184NE1 | 25C7 | 184CE2 | 21.08 |
| 184NE1 | 25C7 | 184CZ2 | 38.55 |
| 184NE1 | 25C7 | 184CD1 | 16.84 |
| 184NE1 | 25C7 | 184CD2 | 27.78 |
| 184NE1 | 25C7 | 184CH2 | 48.97 |
| 184NE1 | 25C7 | 184CG | 24.53 |
| 184CE2 | 25C7 | 184CZ2 | 20.61 |
| 184CE2 | 25C7 | 184CD1 | 31.07 |
| 184CE2 | 25C7 | 184CD2 | 15.35 |
| 184CE2 | 25C7 | 184CH2 | 28.47 |
| 184CE2 | 25C7 | 184CG | 26.62 |
| 184CZ2 | 25C7 | 184CD1 | 51.38 |
| 184CZ2 | 25C7 | 184CD2 | 31.85 |
| 184CZ2 | 25C7 | 184CH2 | 13.39 |
| 184CZ2 | 25C7 | 184CG | 46.61 |
| 184CD1 | 25C7 | 184CD2 | 28.53 |
| 184CD1 | 25C7 | 184CH2 | 59.02 |
| 184CD1 | 25C7 | 184CG | 15.12 |
| 184CD2 | 25C7 | 184CH2 | 33.93 |
| 184CD2 | 25C7 | 184CG | 16.91 |
| 184CH2 | 25C7 | 184CG | 50.64 |
| 184NE1 | 25O8 | 184CE2 | 19.75 |
| 184NE1 | 25O8 | 184CZ2 | 37.94 |
| 184NE1 | 25O8 | 184CD1 | 15.31 |
| 184NE1 | 25O8 | 19NE2 | 71.47 |
| 184NE1 | 25O8 | 19CD | 57.15 |
| 184CE2 | 25O8 | 184CZ2 | 19.95 |
| 184CE2 | 25O8 | 184CD1 | 31.02 |
| 184CE2 | 25O8 | 19NE2 | 90.51 |
| 184CE2 | 25O8 | 19CD | 76.72 |
| 184CZ2 | 25O8 | 184CD1 | 50.82 |
| 184CZ2 | 25O8 | 19CD | 92.06 |
| 184CD1 | 25O8 | 19NE2 | 67.22 |
| 184CD1 | 25O8 | 19CD | 51.55 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 19NE2 | 25O8 | 19CD | 15.86 |
| 184NE1 | 25C9 | 184CZ2 | 42.18 |
| 184NE1 | 25C9 | 184CE2 | 21.04 |
| 184NE1 | 25C9 | 162ND1 | 65.62 |
| 184NE1 | 25C9 | 162CE1 | 48.16 |
| 184NE1 | 25C9 | 184CD1 | 10.29 |
| 184NE1 | 25C9 | 19NE2 | 73.80 |
| 184NE1 | 25C9 | 19OE1 | 48.69 |
| 184NE1 | 25C9 | 19CD | 57.90 |
| 184NE1 | 25C9 | 184CH2 | 49.13 |
| 184CZ2 | 25C9 | 184CE2 | 21.63 |
| 184CZ2 | 25C9 | 162ND1 | 65.18 |
| 184CZ2 | 25C9 | 162CE1 | 57.30 |
| 184CZ2 | 25C9 | 184CD1 | 51.49 |
| 184CZ2 | 25C9 | 19OE1 | 86.41 |
| 184CZ2 | 25C9 | 19CD | 98.49 |
| 184CZ2 | 25C9 | 184CH2 | 7.78 |
| 184CE2 | 25C9 | 162ND1 | 66.81 |
| 184CE2 | 25C9 | 162CE1 | 52.84 |
| 184CE2 | 25C9 | 184CD1 | 29.90 |
| 184CE2 | 25C9 | 19NE2 | 94.57 |
| 184CE2 | 25C9 | 19OE1 | 68.42 |
| 184CE2 | 25C9 | 19CD | 78.74 |
| 184CE2 | 25C9 | 184CH2 | 28.19 |
| 162ND1 | 25C9 | 162CE1 | 18.04 |
| 162ND1 | 25C9 | 184CD1 | 72.19 |
| 162ND1 | 25C9 | 19NE2 | 76.32 |
| 162ND1 | 25C9 | 19CE1 | 58.44 |
| 162ND1 | 25C9 | 19CD | 71.67 |
| 1G2ND1 | 25C9 | 184CH2 | 70.09 |
| 162CE1 | 25C9 | 184CD1 | 54.22 |
| 162CE1 | 25C9 | 19NE2 | 69.37 |
| 162CE1 | 25C9 | 19OE1 | 46.03 |
| 1E2CE1 | 25C9 | 19CD | 60.55 |
| 162CE1 | 25C9 | 184CH2 | 63.87 |
| 184CD1 | 25C9 | 19NE2 | 66.83 |
| 184CD1 | 25C9 | 19OE1 | 44.17 |
| 184CD1 | 25C9 | 19CD | 50.99 |
| 184CD1 | 25C9 | 184CH2 | 58.03 |
| 19NE2 | 25C9 | 19OE1 | 27.69 |
| 19NE2 | 25C9 | 19CD | 15.92 |
| 19OE1 | 25C9 | 19CD | 14.75 |
| 19OE1 | 25C9 | 184CH2 | 94.16 |
| 184NE1 | 25O10 | 162ND1 | 90.68 |
| 184NE1 | 25O10 | 1E2CE1 | 67.15 |
| 184NE1 | 25O10 | 184CE2 | 23.02 |
| 184NE1 | 25O10 | 184CZ2 | 46.79 |
| 184NE1 | 25O10 | 19OE1 | 64.53 |
| 184NE1 | 25O10 | 184CD1 | 12.02 |
| 184NE1 | 25O10 | 19NE2 | 90.63 |
| 184NE1 | 25O10 | 19CD | 72.30 |
| 184NE1 | 25O10 | 162CG | 91.69 |
| 184NE1 | 25O10 | 162NE2 | 63.41 |
| 184NE1 | 25O10 | 184CD2 | 16.34 |
| 184NE1 | 25O10 | 184CH2 | 50.63 |
| 184NE1 | 25O10 | 162CD2 | 76.58 |
| 184NE1 | 25O10 | 184CG | 0.86 |
| 162ND1 | 25O10 | 162CE1 | 25.39 |
| 162ND1 | 25O10 | 184CE2 | 85.65 |
| 162ND1 | 25O10 | 184CZ2 | 80.71 |
| 162ND1 | 25O10 | 19OE1 | 79.25 |
| 162ND1 | 25O10 | 184CD1 | 93.79 |
| 162ND1 | 25O10 | 19NE2 | 99.71 |
| 162ND1 | 25O10 | 19CD | 94.77 |
| 162ND1 | 25O10 | 162CG | 11.75 |
| 162ND1 | 25O10 | 162NE2 | 27.28 |
| 162ND1 | 25O10 | 184CD2 | 87.44 |
| 162ND1 | 25O10 | 184CH2 | 80.29 |
| 162ND1 | 25O10 | 162CD2 | 17.27 |
| 162ND1 | 25O10 | 162CB | 25.40 |
| 162ND1 | 25O10 | 25CB | 48.85 |
| 162ND1 | 25O10 | 184CG | 91.42 |
| 162ND1 | 25O10 | 25SG | 48.57 |
| 162CE1 | 25O10 | 184CE2 | 67.89 |
| 162CE1 | 25O10 | 184CZ2 | 72.02 |
| 162CE1 | 25O10 | 19OE1 | 61.36 |
| 162CE1 | 25O10 | 184CD1 | 68.78 |
| 162CE1 | 25O10 | 19NE2 | 90.18 |
| 162CE1 | 25O10 | 19CD | 78.77 |
| 162CE1 | 25O10 | 162CG | 32.27 |
| 162CE1 | 25O10 | 162NE2 | 9.58 |
| 162CE1 | 25O10 | 184CD2 | 67.64 |
| 162CE1 | 25O10 | 184CH2 | 73.24 |
| 162CE1 | 25O10 | 162CD2 | 21.07 |
| 162CE1 | 25O10 | 162CB | 48.98 |
| 162CE1 | 25O10 | 25CB | 50.48 |
| 162CE1 | 25O10 | 184CG | 67.80 |
| 162CE1 | 25O10 | 25SG | 61.27 |
| 184CE2 | 25O10 | 184CZ2 | 23.77 |
| 184CE2 | 25O10 | 19OE1 | 85.64 |
| 184CE2 | 25O10 | 184CD1 | 35.04 |
| 184CE2 | 25O10 | 19CD | 95.11 |
| 184CE2 | 25O10 | 162CG | 82.23 |
| 184CE2 | 25O10 | 162NE2 | 60.72 |
| 184CE2 | 25O10 | 184CD2 | 6.70 |
| 184CE2 | 25O10 | 184CH2 | 27.61 |
| 184CE2 | 25O10 | 162CD2 | 68.81 |
| 184CE2 | 25O10 | 162CB | 92.97 |
| 184CE2 | 25O10 | 184CG | 23.63 |
| 184CZ2 | 25O10 | 184CD1 | 58.81 |
| 184CZ2 | 25O10 | 162CG | 73.16 |
| 184CZ2 | 25O10 | 162NE2 | 62.79 |
| 184CZ2 | 25C10 | 184CD2 | 30.47 |
| 184CZ2 | 25O10 | 184CH2 | 3.84 |
| 184CZ2 | 25O10 | 162CD2 | 63.78 |
| 184CZ2 | 25O10 | 162CB | 78.57 |
| 184CZ2 | 25O10 | 184CG | 47.41 |
| 19OE1 | 25O10 | 184CD1 | 54.02 |
| 19OE1 | 25C10 | 19NE2 | 33.65 |
| 19OE1 | 25O10 | 19CD | 17.62 |
| 19OE1 | 25O10 | 162CG | 90.23 |
| 19OE1 | 25O10 | 162NE2 | 68.58 |
| 19CE1 | 25O10 | 184CD2 | 79.62 |
| 19OE1 | 25O10 | 162CD2 | 82.33 |
| 19CE1 | 25O10 | 25CB | 46.49 |
| 19OE1 | 25O10 | 184CG | 64.24 |
| 19OE1 | 25O10 | 25SG | 67.15 |
| 184CD1 | 25O10 | 19NE2 | 78.67 |
| 184CD1 | 25O10 | 19CD | 60.49 |
| 184CD1 | 25O10 | 162CG | 97.06 |
| 184CD1 | 25O10 | 162NE2 | 67.08 |
| 184CD1 | 25O10 | 184CD2 | 28.35 |
| 184CD1 | 25O10 | 184CH2 | 62.64 |
| 184CD1 | 25O10 | 162CD2 | 81.91 |
| 184CD1 | 25O10 | 25CB | 94.29 |
| 184CD1 | 25O10 | 184CG | 11.41 |
| 19NE2 | 25O10 | 19CD | 18.97 |
| 19NE2 | 25O10 | 162NE2 | 98.89 |
| 19NE2 | 25O10 | 25CB | 52.31 |
| 19NE2 | 25O10 | 184CG | 90.06 |
| 19NE2 | 25O10 | 25SG | 64.08 |
| 19CD | 25O10 | 162NE2 | 86.19 |
| 19CD | 25O10 | 184CD2 | 88.53 |
| 19CD | 25O10 | 162CD2 | 99.61 |
| 19CD | 25O10 | 25CB | 54.29 |
| 19CD | 25O10 | 184CG | 71.79 |
| 19CD | 25O10 | 25SG | 71.77 |
| 162CG | 25O10 | 162NE2 | 30.49 |
| 162CG | 25O10 | 184CD2 | 85.26 |
| 162CG | 25O10 | 184CH2 | 72.15 |
| 162CG | 25O10 | 162CD2 | 15.20 |
| 162CG | 25O10 | 162CB | 16.86 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 162CG | 25O10 | 25CB | 60.05 |
| 162CG | 25O10 | 184CG | 92.50 |
| 162CG | 25O10 | 25SG | 56.96 |
| 162NE2 | 25O10 | 184CD2 | 61.36 |
| 162NE2 | 25O10 | 184CH2 | 63.86 |
| 162NE2 | 25O10 | 162CD2 | 16.25 |
| 162NE2 | 25O10 | 162CB | 47.22 |
| 162NE2 | 25O10 | 25CB | 59.84 |
| 162NE2 | 25O10 | 184CG | 64.14 |
| 162NE2 | 25O10 | 25SG | 69.18 |
| 184CD2 | 25O10 | 184CH2 | 34.30 |
| 184CD2 | 25O10 | 162CD2 | 71.14 |
| 184CD2 | 25O10 | 162CB | 97.22 |
| 184CD2 | 25O10 | 184CG | 16.94 |
| 184CH2 | 25O10 | 162CD2 | 63.64 |
| 184CH2 | 25910 | 162CB | 76.54 |
| 184CH2 | 25O10 | 184CG | 51.24 |
| 162CD2 | 25O10 | 162CB | 31.36 |
| 162CD2 | 25O10 | 25CB | 62.62 |
| 162CD2 | 25O10 | 184CG | 77.38 |
| 162CD2 | 25O10 | 25SG | 65.53 |
| 162CB | 25O10 | 25CB | 66.47 |
| 162CB | 25O10 | 25SG | 56.57 |
| 25CB | 25O10 | 25SG | 21.55 |
| 161O | 25C11 | 162ND1 | 77.52 |
| 161O | 25C11 | 162CB | 48.77 |
| 161O | 25C11 | 162CG | 66.44 |
| 161O | 25C11 | 161C | 9.16 |
| 161O | 25C11 | 161OD1 | 44.79 |
| 161O | 25C11 | 162CE1 | 89.91 |
| 161O | 25C11 | 162CA | 34.68 |
| 162ND1 | 25C11 | 162CB | 36.88 |
| 162ND1 | 25C11 | 162CG | 18.06 |
| 162ND1 | 25C11 | 184CZ2 | 57.93 |
| 162ND1 | 25C11 | 161C | 73.11 |
| 162ND1 | 25C11 | 161OD1 | 88.11 |
| 162ND1 | 25C11 | 162CE1 | 12.39 |
| 162ND1 | 25C11 | 162CA | 43.39 |
| 162CB | 25C11 | 162CG | 20.08 |
| 162CB | 25C11 | 184CZ2 | 75.16 |
| 162CB | 25C11 | 161C | 41.40 |
| 162CB | 25C11 | 161OD1 | 51.91 |
| 162CB | 25C11 | 162CE1 | 47.69 |
| 162CB | 25C11 | 162CA | 18.23 |
| 162CG | 25C11 | 184CZ2 | 60.65 |
| 162CG | 25C11 | 161C | 60.17 |
| 162CG | 25C11 | 161OD1 | 70.16 |
| 162CG | 25C11 | 162CE1 | 27.75 |
| 162CG | 25C11 | 162CA | 32.09 |
| 184CZ2 | 25C11 | 161OD1 | 96.89 |
| 184CZ2 | 25C11 | 162CE1 | 48.52 |
| 184CZ2 | 25C11 | 162CA | 91.88 |
| 161C | 25C11 | 161OD1 | 38.12 |
| 161C | 25C11 | 162CE1 | 85.41 |
| 161C | 25C11 | 162CA | 29.74 |
| 161OD1 | 25C11 | 162CE1 | 97.18 |
| 161OD1 | 25C11 | 162CA | 54.92 |
| 162CE1 | 25C11 | 162CA | 55.72 |
| 161O | 25C12 | 161OD1 | 53.96 |
| 161O | 25C12 | 161CG | 50.90 |
| 161O | 25C12 | 161C | 12.09 |
| 161O | 25C12 | 162CB | 45.66 |
| 161O | 25C12 | 161CB | 38.06 |
| 161O | 25C12 | 162ND1 | 64.70 |
| 161OD1 | 25C12 | 161CG | 14.06 |
| 161OD1 | 25C12 | 161C | 42.27 |
| 161OD1 | 25C12 | 162CB | 55.80 |
| 161OD1 | 25C12 | 161CB | 30.86 |
| 161OD1 | 25C12 | 162ND1 | 86.96 |
| 161CG | 25C12 | 161C | 40.85 |
| 161CG | 25C12 | 162CB | 65.21 |
| 161CG | 25C12 | 161CB | 19.00 |
| 161CG | 25C12 | 162ND1 | 96.52 |
| 161C | 25C12 | 162CB | 40.99 |
| 161C | 25C12 | 161CB | 31.65 |
| 161C | 25C12 | 162ND1 | 65.80 |
| 162CB | 25C12 | 161CB | 67.55 |
| 162CB | 25C12 | 162ND1 | 31.38 |
| 161CB | 25C12 | 162ND1 | 96.34 |
| 161OD1 | 25C13 | 137O | 81.25 |
| 161OD1 | 25C13 | 137C | 63.73 |
| 161OD1 | 25C13 | 138N | 56.48 |
| 161OD1 | 25C13 | 138CA | 69.03 |
| 161OD1 | 25C13 | 137CB | 63.42 |
| 161OD1 | 25C13 | 161CG | 11.19 |
| 161OD1 | 25C13 | 161O | 44.97 |
| 161OD1 | 25C13 | 162CB | 53.52 |
| 161OD1 | 25C13 | 137CA | 54.88 |
| 137O | 25C13 | 137C | 17.61 |
| 137O | 25C13 | 138N | 31.56 |
| 137O | 25C13 | 184CZ2 | 73.45 |
| 137O | 25C13 | 138CA | 38.68 |
| 137O | 25C13 | 137CB | 38.26 |
| 137O | 25C13 | 143NE2 | 53.14 |
| 137O | 25C13 | 161CG | 88.09 |
| 137O | 25C13 | 184CH2 | 57.10 |
| 137O | 25C13 | 162CB | 89.51 |
| 137O | 25C13 | 137CA | 30.26 |
| 137C | 25C13 | 138N | 18.18 |
| 137C | 25C13 | 184CZ2 | 85.16 |
| 137C | 25C13 | 138CA | 33.43 |
| 137C | 25C13 | 137CB | 33.67 |
| 137C | 25C13 | 143NE2 | 68.48 |
| 137C | 25C13 | 161CG | 70.50 |
| 137C | 25C13 | 184CH2 | 70.29 |
| 137C | 25C13 | 162CB | 80.53 |
| 137C | 25C13 | 137CA | 17.92 |
| 138N | 25C13 | 138CA | 19.51 |
| 138N | 25C13 | 137CB | 49.22 |
| 138N | 25C13 | 143NE2 | 71.83 |
| 138N | 25C13 | 161CG | 60.17 |
| 138N | 25C13 | 184CH2 | 87.76 |
| 138N | 25C13 | 162CB | 88.70 |
| 138N | 25C13 | 137CA | 30.79 |
| 184CZ2 | 25C13 | 137CB | 62.75 |
| 184CZ2 | 25C13 | 143NE2 | 73.88 |
| 184CZ2 | 25C13 | 184CH2 | 16.99 |
| 184CZ2 | 25C13 | 162CB | 71.91 |
| 184CZ2 | 25C13 | 137CA | 79.40 |
| 138CA | 25C13 | 137CB | 66.92 |
| 138CA | 25C13 | 143NE2 | 60.03 |
| 138CA | 25C13 | 161CG | 69.26 |
| 138CA | 25C13 | 184CH2 | 94.51 |
| 138CA | 25C13 | 137CA | 49.37 |
| 137CB | 25C13 | 143NE2 | 87.28 |
| 137CB | 25C13 | 161CG | 74.16 |
| 137CB | 25C13 | 161O | 86.27 |
| 137CB | 25C13 | 184CH2 | 53.95 |
| 137CB | 25C13 | 162CB | 51.39 |
| 137CB | 25C13 | 137CA | 18.78 |
| 143NE2 | 25C13 | 184CH2 | 61.44 |
| 143NE2 | 25C13 | 137CA | 83.39 |
| 161CG | 25C13 | 161O | 44.82 |
| 161CG | 25C13 | 162CB | 62.01 |
| 161CG | 25C13 | 137CA | 64.10 |
| 161O | 25C13 | 162CB | 40.52 |
| 161O | 25C13 | 137CA | 89.27 |
| 184CH2 | 25C13 | 162CB | 78.30 |
| 184CH2 | 25C13 | 137CA | 67.80 |
| 162CB | 25C13 | 137CA | 62.63 |
| 143NE2 | 25C14 | 184CZ2 | 89.78 |
| 143NE2 | 25C14 | 137O | 59.02 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 143NE2 | 25C14 | 184CH2 | 73.23 |
| 143NE2 | 25C14 | 143CD | 7.66 |
| 143NE2 | 25C14 | 137C | 70.92 |
| 143NE2 | 25C14 | 138CA | 63.43 |
| 143NE2 | 25C14 | 138N | 72.92 |
| 184CZ2 | 25C14 | 137O | 73.56 |
| 184CZ2 | 25C14 | 184CH2 | 18.41 |
| 184CZ2 | 25C14 | 143CD | 82.48 |
| 184CZ2 | 25C14 | 137C | 80.26 |
| 184CZ2 | 25C14 | 138N | 95.58 |
| 137O | 25C14 | 184CH2 | 58.32 |
| 137O | 25C14 | 143CD | 59.13 |
| 137O | 25C14 | 137C | 14.37 |
| 137O | 25C14 | 138CA | 35.52 |
| 137O | 25C14 | 138N | 26.67 |
| 184CH2 | 25C14 | 143CD | 66.37 |
| 184CH2 | 25C14 | 137C | 67.66 |
| 184CH2 | 25C14 | 138CA | 93.75 |
| 184CH2 | 25C14 | 138N | 83.05 |
| 143CD | 25C14 | 137C | 72.08 |
| 143CD | 25C14 | 138CA | 68.38 |
| 143CD | 25C14 | 138N | 76.11 |
| 137C | 25C14 | 138CA | 29.93 |
| 137C | 25C14 | 138N | 15.47 |
| 438CA | 25C14 | 138N | 17.13 |
| 161OD1 | 25C15 | 138CA | 95.49 |
| 161OD1 | 25C15 | 138N | 74.59 |
| 161OD1 | 25C15 | 137C | 77.97 |
| 161OD1 | 25C15 | 138CB | 88.03 |
| 161OD1 | 25C15 | 137O | 95.93 |
| 161OD1 | 25C15 | 161CG | 16.54 |
| 161OD1 | 25C15 | 137CA | 62.55 |
| 161OD1 | 25C15 | 161ND2 | 28.48 |
| 161OD1 | 25C15 | 137N | 44.50 |
| 161OD1 | 25C15 | 137CB | 65.90 |
| 161OD1 | 25C15 | 138OG | 75.32 |
| 161OD1 | 25C15 | 161CB | 26.73 |
| 161OD1 | 25C15 | 161O | 41.09 |
| 138CA | 25C15 | 138N | 26.47 |
| 138CA | 25C15 | 137C | 42.87 |
| 138CA | 25C15 | 138CB | 25.16 |
| 138CA | 25C15 | 137O | 47.79 |
| 138CA | 25C15 | 161CG | 93.95 |
| 138CA | 25C15 | 137CA | 58.55 |
| 138CA | 25C15 | 161ND2 | 78.54 |
| 138CA | 25C15 | 137N | 64.03 |
| 138CA | 25C15 | 138C | 11.03 |
| 138CA | 25C15 | 137CB | 75.54 |
| 138CA | 25C15 | 143NE2 | 66.87 |
| 138CA | 25C15 | 138OG | 29.01 |
| 138CA | 25C15 | 138O | 24.54 |
| 138N | 25C15 | 137C | 22.54 |
| 138N | 25C15 | 138CB | 42.08 |
| 138N | 25C15 | 137O | 37.92 |
| 138N | 25C15 | 161CG | 78.54 |
| 138N | 25C15 | 137CA | 33.52 |
| 138N | 25C15 | 161ND2 | 66.91 |
| 138N | 25C15 | 137N | 37.71 |
| 138N | 25C15 | 138C | 32.59 |
| 138N | 25C15 | 137CB | 52.24 |
| 138N | 25C15 | 143NE2 | 80.31 |
| 138N | 25C15 | 138OG | 36.11 |
| 138N | 25C15 | 161CB | 95.16 |
| 138N | 25C15 | 138O | 46.34 |
| 137C | 25C15 | 138CB | 63.59 |
| 137C | 25C15 | 137O | 19.93 |
| 137C | 25C15 | 161CG | 87.64 |
| 137C | 25C15 | 137CA | 18.45 |
| 137C | 25C15 | 161ND2 | 80.75 |
| 137C | 25C15 | 137N | 33.66 |
| 137C | 25C15 | 138C | 43.43 |
| 137C | 25C15 | 137CB | 32.73 |
| 137C | 25C15 | 143NE2 | 72.28 |
| 137C | 25C15 | 138OG | 58.64 |
| 137C | 25C15 | 138O | 53.23 |
| 138CB | 25C15 | 137O | 72.42 |
| 138CB | 25C15 | 161CG | 80.25 |
| 138CB | 25C15 | 137CA | 75.11 |
| 138CB | 25C15 | 161ND2 | 63.55 |
| 138CB | 25C15 | 137N | 73.01 |
| 138CB | 25C15 | 138C | 33.69 |
| 138CB | 25C15 | 137CB | 94.23 |
| 138CB | 25C15 | 143NE2 | 84.72 |
| 138CB | 25C15 | 138OG | 13.06 |
| 138CB | 25C15 | 161CB | 92.07 |
| 138CB | 25C15 | 138O | 41.98 |
| 137O | 25C15 | 137CA | 33.44 |
| 137O | 25C15 | 137N | 51.60 |
| 137O | 25C15 | 138C | 43.03 |
| 137O | 25C15 | 137CB | 37.73 |
| 137O | 25C15 | 143NE2 | 53.68 |
| 137O | 25C15 | 138OG | 71.49 |
| 137O | 25C15 | 138O | 46.98 |
| 161CG | 25C15 | 137CA | 74.83 |
| 161CG | 25C15 | 161ND2 | 16.70 |
| 161CG | 25C15 | 137N | 56.04 |
| 161CG | 25C15 | 137CB | 81.22 |
| 161CG | 25C15 | 138OG | 68.77 |
| 161CG | 25C15 | 161CB | 16.63 |
| 161CG | 25C15 | 161O | 45.51 |
| 137CA | 25C15 | 161ND2 | 72.19 |
| 137CA | 25C15 | 137N | 18.82 |
| 137CA | 25C15 | 138C | 61.01 |
| 137CA | 25C15 | 137CB | 19.45 |
| 137CA | 25C15 | 143NE2 | 86.99 |
| 137CA | 25C15 | 138OG | 66.83 |
| 137CA | 25C15 | 161CB | 89.10 |
| 137CA | 25C15 | 138O | 71.60 |
| 137CA | 25C15 | 161O | 90.57 |
| 161ND2 | 25C15 | 137N | 54.06 |
| 161ND2 | 25C15 | 138C | 89.54 |
| 161ND2 | 25C15 | 137CB | 83.68 |
| 161ND2 | 25C15 | 138OG | 52.25 |
| 161ND2 | 25C15 | 161CB | 30.53 |
| 161ND2 | 25C15 | 161O | 62.17 |
| 137N | 25C15 | 138C | 69.92 |
| 137N | 25C15 | 137CB | 31.11 |
| 137N | 25C15 | 138OG | 61.80 |
| 137N | 25C15 | 161CB | 70.66 |
| 137N | 25C15 | 138O | 82.86 |
| 137N | 25C15 | 161O | 77.59 |
| 138C | 25C15 | 137CB | 75.69 |
| 138C | 25C15 | 143NE2 | 55.85 |
| 138C | 25C15 | 138OG | 39.61 |
| 138C | 25C15 | 138O | 14.34 |
| 137CB | 25C15 | 143NE2 | 85.14 |
| 137CB | 25C15 | 138OG | 86.28 |
| 137CB | 25C15 | 161CB | 91.92 |
| 137CB | 25C15 | 138O | 83.44 |
| 137CB | 25C15 | 161O | 82.09 |
| 143NE2 | 25C15 | 138OG | 94.34 |
| 143NE2 | 25C15 | 138O | 43.49 |
| 138OG | 25C15 | 161CB | 82.00 |
| 138OG | 25C15 | 138O | 50.85 |
| 161CB | 25C15 | 161O | 34.58 |
| 161O | 25C16 | 162ND1 | 76.53 |
| 161O | 25C16 | 161C | 3.98 |
| 161O | 25C16 | 162CB | 45.40 |
| 161O | 25C16 | 25SG | 72.69 |
| 161O | 25C16 | 162CA | 34.24 |
| 161O | 25C16 | 162CG | 62.41 |
| 161O | 25C16 | 162N | 17.52 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
| --- | --- | --- | --- |
| 162ND1 | 25C16 | 161C | 72.86 |
| 162ND1 | 25C16 | 162CB | 33.34 |
| 162ND1 | 25C16 | 25SG | 49.81 |
| 162ND1 | 25C16 | 162CA | 43.06 |
| 162ND1 | 25C16 | 162CG | 15.65 |
| 162ND1 | 25C16 | 162N | 59.06 |
| 161C | 25C16 | 162CB | 41.47 |
| 161C | 25C16 | 25SG | 71.63 |
| 161C | 25C16 | 162CA | 30.96 |
| 161C | 25C16 | 162CG | 58.58 |
| 161C | 25C16 | 162N | 14.06 |
| 162CB | 25C16 | 25SG | 60.72 |
| 162CB | 25C16 | 162CA | 19.06 |
| 162CB | 25C16 | 162CG | 17.85 |
| 162CB | 25C16 | 162N | 29.15 |
| 25SG | 25C16 | 162CA | 49.45 |
| 25SG | 25C16 | 162CG | 54.90 |
| 25SG | 25C16 | 162N | 61.48 |
| 162CA | 25C16 | 162CG | 30.90 |
| 162CA | 25C16 | 162N | 16.94 |
| 162CG | 25C16 | 162N | 45.31 |
| 161O | 25O17 | 161C | 2.40 |
| 161O | 25N18 | 25SG | 94.42 |
| 161O | 25N18 | 162ND1 | 86.25 |
| 161O | 25N18 | 162CA | 41.79 |
| 161O | 25N18 | 162CB | 49.55 |
| 161O | 25N18 | 161C | 8.51 |
| 161O | 25N18 | 162CG | 69.44 |
| 161O | 25N18 | 162CE1 | 97.59 |
| 161O | 25N18 | 162N | 24.49 |
| 25SG | 25N18 | 162ND1 | 65.37 |
| 25SG | 25N18 | 162CA | 62.23 |
| 25SG | 25N18 | 162CB | 74.73 |
| 25SG | 25N18 | 161C | 86.60 |
| 25SG | 25N18 | 162CG | 67.87 |
| 25SG | 25N18 | 25CB | 21.50 |
| 25SG | 25N18 | 162CE1 | 64.64 |
| 25SG | 25N18 | 162N | 73.85 |
| 25SG | 25N18 | 19NE2 | 67.61 |
| 25SG | 25N18 | 23CA | 79.71 |
| 162ND1 | 25N18 | 162CA | 50.07 |
| 162ND1 | 25N18 | 162CB | 36.70 |
| 162ND1 | 25N18 | 161C | 79.92 |
| 162ND1 | 25N18 | 162CG | 16.82 |
| 162ND1 | 25N18 | 25CB | 53.33 |
| 162ND1 | 25N18 | 162CE1 | 11.34 |
| 162ND1 | 25N18 | 162N | 65.85 |
| 162ND1 | 25N18 | 19NE2 | 73.54 |
| 162CA | 25N18 | 162CB | 21.06 |
| 162CA | 25N18 | 161C | 33.62 |
| 162CA | 25N18 | 162CG | 34.82 |
| 162CA | 25N18 | 25CB | 70.27 |
| 162CA | 25N18 | 162CE1 | 60.64 |
| 162CA | 25N18 | 162N | 17.53 |
| 162CB | 25N18 | 161C | 43.55 |
| 162CB | 25N18 | 162CG | 19.91 |
| 162CB | 25N18 | 25CB | 75.42 |
| 162CB | 25N18 | 162CE1 | 48.04 |
| 162CB | 25N18 | 162N | 31.25 |
| 161C | 25N18 | 162CG | 63.15 |
| 161C | 25N18 | 162CE1 | 91.21 |
| 161C | 25N18 | 162N | 16.15 |
| 162CG | 25N18 | 25CB | 61.89 |
| 162CG | 25N18 | 162CE1 | 28.15 |
| 162CG | 25N18 | 162N | 49.49 |
| 162CG | 25N18 | 19NE2 | 89.96 |
| 25CB | 25N18 | 162CE1 | 48.89 |
| 25CB | 25N18 | 162N | 85.68 |
| 25CB | 25N18 | 19NE2 | 49.72 |
| 25CB | 25N18 | 23CA | 76.32 |
| 162CE1 | 25N18 | 162N | 76.89 |
| 162CE1 | 25N18 | 19NE2 | 62.43 |
| 19NE2 | 25N18 | 23CA | 47.71 |
| 25SG | 25C19 | 161O | 93.76 |
| 25SG | 25C19 | 23CA | 98.71 |
| 25SG | 25C19 | 25CB | 19.06 |
| 25SG | 25C19 | 162ND1 | 55.42 |
| 25SG | 25C19 | 23C | 83.02 |
| 25SG | 25C19 | 162CA | 57.95 |
| 25SG | 25C19 | 161C | 85.45 |
| 25SG | 25C19 | 23O | 84.21 |
| 25SG | 25C19 | 25N | 39.84 |
| 161O | 25C19 | 162ND1 | 68.34 |
| 161O | 25C19 | 162CA | 36.84 |
| 161O | 25C19 | 161C | 9.82 |
| 23CA | 25C19 | 25CB | 86.55 |
| 23CA | 25C19 | 23C | 19.53 |
| 23CA | 25C19 | 23O | 30.41 |
| 23CA | 25C19 | 25N | 58.86 |
| 25CB | 25C19 | 162ND1 | 49.56 |
| 25CB | 25C19 | 23C | 74.71 |
| 25CB | 25C19 | 162CA | 67.81 |
| 25CB | 25C19 | 161C | 97.94 |
| 25CB | 25C19 | 23O | 80.56 |
| 25CB | 25C19 | 25N | 30.79 |
| 162ND1 | 25C19 | 162CA | 42.46 |
| 162ND1 | 25C19 | 161C | 67.39 |
| 162ND1 | 25C19 | 25N | 78.08 |
| 23C | 25C19 | 23O | 15.10 |
| 23C | 25C19 | 25N | 44.37 |
| 162CA | 25C19 | 161C | 30.60 |
| 162CA | 25C19 | 25N | 96.99 |
| 23O | 25C19 | 25N | 49.95 |
| 184CZ2 | 25N20 | 162ND1 | 57.46 |
| 184CZ2 | 25N20 | 184NE1 | 33.66 |
| 184CZ2 | 25N20 | 184CE2 | 16.92 |
| 184CZ2 | 25N20 | 162CE1 | 48.47 |
| 162ND1 | 25N20 | 184NE1 | 53.53 |
| 162ND1 | 25N20 | 184CE2 | 56.14 |
| 162ND1 | 25N20 | 162CE1 | 14.39 |
| 184NE1 | 25N20 | 184CE2 | 17.07 |
| 184NE1 | 25N20 | 162CE1 | 39.26 |
| 184CE2 | 25N20 | 162CE1 | 43.67 |
| 161O | 25C21 | 25SG | 97.39 |
| 161O | 25C21 | 161C | 15.35 |
| 161O | 25C21 | 162CA | 39.27 |
| 161O | 25C21 | 162N | 27.81 |
| 161O | 25C21 | 161CA | 24.14 |
| 161O | 25C21 | 25CB | 98.96 |
| 25SG | 25C21 | 161C | 94.07 |
| 25SG | 25C21 | 162CA | 60.19 |
| 25SG | 25C21 | 162N | 78.17 |
| 25SG | 25C21 | 65CA | 98.56 |
| 25SG | 25C21 | 25CB | 7.84 |
| 161C | 25C21 | 162CA | 33.93 |
| 161C | 25C21 | 162N | 16.70 |
| 161C | 25C21 | 161CA | 15.71 |
| 161C | 25C21 | 25CB | 97.60 |
| 162CA | 25C21 | 162N | 19.15 |
| 162CA | 25C21 | 161CA | 48.75 |
| 162CA | 25C21 | 25CB | 63.75 |
| 162N | 25C21 | 161CA | 30.04 |
| 162N | 25C21 | 25CB | 82.42 |
| 65CA | 25C21 | 25CB | 98.99 |
| 25SG | 25C22 | 25CB | 34.66 |
| 25SG | 25C22 | 25N | 70.64 |
| 25SG | 25C22 | 25CA | 48.75 |
| 25SG | 25C22 | 19NE2 | 98.64 |
| 25SG | 25C22 | 24C | 78.81 |
| 25SG | 25C22 | 162ND1 | 56.90 |
| 25SG | 25C22 | 26N | 47.65 |
| 25SG | 25C22 | 25C | 40.82 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 25SG | 25C22 | 161O | 81.68 |
| 25SG | 25C22 | 24CA | 97.30 |
| 25SG | 25C22 | 162CA | 49.19 |
| 25SG | 25C22 | 163N | 21.43 |
| 25SG | 25C22 | 26CD1 | 82.19 |
| 25CB | 25C22 | 25N | 45.70 |
| 25CB | 25C22 | 25CA | 23.52 |
| 25CB | 25C22 | 24N | 85.13 |
| 25CB | 25C22 | 19NE2 | 64.70 |
| 25CB | 25C22 | 24C | 56.87 |
| 25CB | 25C22 | 162ND1 | 56.29 |
| 25CB | 25C22 | 26N | 47.43 |
| 25CB | 25C22 | 25C | 31.07 |
| 25CB | 25C22 | 24CA | 75.01 |
| 25CB | 25C22 | 162CA | 74.58 |
| 25CB | 25C22 | 163N | 53.55 |
| 25CB | 25C22 | 26CD1 | 84.62 |
| 25N | 25C22 | 25CA | 23.10 |
| 25N | 25C22 | 23C | 59.53 |
| 25N | 25C22 | 23CA | 76.19 |
| 25N | 25C22 | 23O | 65.52 |
| 25N | 25C22 | 24N | 41.74 |
| 25N | 25C22 | 19NE2 | 55.79 |
| 25N | 25C22 | 24C | 11.64 |
| 25N | 25C22 | 162ND1 | 98.55 |
| 25N | 25C22 | 26N | 37.79 |
| 25N | 25C22 | 25C | 31.73 |
| 25N | 25C22 | 24CA | 29.34 |
| 25N | 25C22 | 163N | 92.04 |
| 25N | 25C22 | 26CD1 | 53.86 |
| 25CA | 25C22 | 23C | 82.62 |
| 25CA | 25C22 | 23CA | 98.07 |
| 25CA | 25C22 | 23O | 87.79 |
| 25CA | 25C22 | 24N | 64.51 |
| 25CA | 25C22 | 19NE2 | 62.14 |
| 25CA | 25C22 | 24C | 33.67 |
| 25CA | 25C22 | 162ND1 | 79.26 |
| 25CA | 25C22 | 26N | 32.62 |
| 25CA | 25C22 | 25C | 17.41 |
| 25CA | 25C22 | 24CA | 52.26 |
| 25CA | 25C22 | 162CA | 95.54 |
| 25CA | 25C22 | 163N | 70.10 |
| 25CA | 25C22 | 26CD1 | 64.67 |
| 23C | 25C22 | 23CA | 22.66 |
| 23C | 25C22 | 23O | 17.69 |
| 23C | 25C22 | 24N | 19.11 |
| 23C | 25C22 | 19NE2 | 64.93 |
| 23C | 25C22 | 24C | 49.94 |
| 23C | 25C22 | 26N | 82.64 |
| 23C | 25C22 | 25C | 87.50 |
| 23C | 25C22 | 24CA | 31.15 |
| 23C | 25C22 | 26CD1 | 58.43 |
| 23CA | 25C22 | 23O | 35.06 |
| 23CA | 25C22 | 24N | 35.02 |
| 23CA | 25C22 | 19NE2 | 59.32 |
| 23CA | 25C22 | 24C | 68.76 |
| 23CA | 25C22 | 24CA | 51.14 |
| 23CA | 25C22 | 26CD1 | 80.22 |
| 23O | 25C22 | 24N | 32.37 |
| 23O | 25C22 | 19NE2 | 82.31 |
| 23O | 25C22 | 24C | 54.24 |
| 23O | 25C22 | 26N | 77.95 |
| 23O | 25C22 | 25C | 87.44 |
| 23O | 25C22 | 24CA | 36.53 |
| 23O | 25C22 | 26CD1 | 46.14 |
| 24N | 25C22 | 19NE2 | 52.35 |
| 24N | 25C22 | 24C | 33.74 |
| 24N | 25C22 | 26N | 70.95 |
| 24N | 25C22 | 25C | 71.93 |
| 24N | 25C22 | 24CA | 17.11 |
| 24N | 25C22 | 26CD1 | 57.95 |
| 19NE2 | 25C22 | 24C | 60.62 |
| 19NE2 | 25C22 | 162ND1 | 74.96 |
| 19NE2 | 25C22 | 26N | 91.86 |
| 19NE2 | 25C22 | 25C | 79.36 |
| 19NE2 | 25C22 | 24CA | 60.80 |
| 24C | 25C22 | 26N | 39.04 |
| 24C | 25C22 | 25C | 38.21 |
| 24C | 25C22 | 24CA | 18.87 |
| 24C | 25C22 | 163N | 99.80 |
| 24C | 25C22 | 26CD1 | 45.21 |
| 162ND1 | 25C22 | 26N | 99.77 |
| 162ND1 | 25C22 | 25C | 85.70 |
| 162ND1 | 25C22 | 161O | 61.42 |
| 162ND1 | 25C22 | 162CA | 41.62 |
| 162ND1 | 25C22 | 163N | 51.67 |
| 26N | 25C22 | 25C | 16.78 |
| 26N | 25C22 | 24CA | 53.95 |
| 26N | 25C22 | 162CA | 94.45 |
| 26N | 25C22 | 163N | 65.37 |
| 26N | 25C22 | 26CD1 | 38.29 |
| 25C | 25C22 | 24CA | 56.48 |
| 25C | 25C22 | 162CA | 90.01 |
| 25C | 25C22 | 163N | 61.59 |
| 25C | 25C22 | 26CD1 | 53.65 |
| 161O | 25C22 | 162CA | 33.51 |
| 161O | 25C22 | 163N | 60.45 |
| 24CA | 25C22 | 26CD1 | 44.43 |
| 162CA | 25C22 | 163N | 29.15 |
| 163N | 25C22 | 26CD1 | 93.88 |
| 25SG | 25O23 | 25N | 73.79 |
| 25SG | 25O23 | 25CB | 39.28 |
| 25SG | 25O23 | 25CA | 55.31 |
| 25SG | 25O23 | 24C | 83.85 |
| 25SG | 25O23 | 19OE1 | 93.34 |
| 25SG | 25O23 | 162ND1 | 57.67 |
| 25SG | 25O23 | 25C | 46.54 |
| 25SG | 25O23 | 26N | 46.32 |
| 25SG | 25O23 | 162CE1 | 63.52 |
| 25N | 25O23 | 25CB | 50.74 |
| 25N | 25O23 | 19NE2 | 75.64 |
| 25N | 25O23 | 23CA | 93.95 |
| 25N | 25O23 | 23C | 70.21 |
| 25N | 25O23 | 24N | 51.30 |
| 25N | 25O23 | 25CA | 24.54 |
| 25N | 25O23 | 23O | 71.33 |
| 25N | 25O23 | 24C | 13.19 |
| 25N | 25O23 | 19CD | 72.43 |
| 25N | 25O23 | 19OE1 | 71.68 |
| 25N | 25O23 | 24CA | 34.54 |
| 25N | 25O23 | 22O | 81.27 |
| 25N | 25O23 | 23N | 91.47 |
| 25N | 25O23 | 25C | 27.51 |
| 25N | 25O23 | 26N | 31.41 |
| 25N | 25O23 | 22C | 85.55 |
| 25N | 25O23 | 162CE1 | 95.76 |
| 25CB | 25O23 | 19NE2 | 84.85 |
| 25CB | 25O23 | 25CA | 26.21 |
| 25CB | 25O23 | 24C | 63.90 |
| 25CB | 25O23 | 19CD | 71.92 |
| 25CB | 25O23 | 19OE1 | 57.57 |
| 25CB | 25O23 | 24CA | 85.27 |
| 25CB | 25O23 | 162ND1 | 56.16 |
| 25CB | 25O23 | 25C | 29.27 |
| 25CB | 25O23 | 26N | 43.07 |
| 25CB | 25O23 | 162CE1 | 50.07 |
| 19NE2 | 25O23 | 23CA | 79.80 |
| 19NE2 | 25O23 | 23C | 86.33 |
| 19NE2 | 25O23 | 24N | 70.00 |
| 19NE2 | 25O23 | 25CA | 78.56 |
| 19NE2 | 25O23 | 24C | 75.95 |
| 19NE2 | 25O23 | 19CD | 14.24 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 19NE2 | 25O23 | 19OE1 | 31.36 |
| 19NE2 | 25O23 | 24CA | 76.27 |
| 19NE2 | 25O23 | 22O | 39.90 |
| 19NE2 | 25O23 | 162ND1 | 87.36 |
| 19NE2 | 25O23 | 23N | 69.25 |
| 19NE2 | 25O23 | 25C | 92.00 |
| 19NE2 | 25O23 | 22C | 53.68 |
| 19NE2 | 25O23 | 162CE1 | 73.60 |
| 23CA | 25O23 | 23C | 26.89 |
| 23CA | 25O23 | 24N | 42.72 |
| 23CA | 25O23 | 23O | 37.90 |
| 23CA | 25O23 | 24C | 81.01 |
| 23CA | 25O23 | 19CD | 93.90 |
| 23CA | 25O23 | 24CA | 59.79 |
| 23CA | 25O23 | 22O | 39.98 |
| 23CA | 25O23 | 23N | 10.55 |
| 23CA | 25O23 | 22C | 26.16 |
| 23C | 25O23 | 24N | 23.21 |
| 23C | 25O23 | 25CA | 94.66 |
| 23C | 25O23 | 23O | 17.05 |
| 23C | 25O23 | 24C | 57.02 |
| 23C | 25O23 | 19CD | 98.07 |
| 23C | 25O23 | 24CA | 35.84 |
| 23C | 25O23 | 22O | 50.35 |
| 23C | 25O23 | 23N | 31.08 |
| 23C | 25O23 | 25C | 92.95 |
| 23C | 25O23 | 26N | 83.85 |
| 23C | 25O23 | 22C | 39.73 |
| 24N | 25O23 | 25CA | 75.53 |
| 24N | 25O23 | 23O | 35.32 |
| 24N | 25O23 | 24C | 38.60 |
| 24N | 25O23 | 19CD | 79.21 |
| 24N | 25O23 | 19OE1 | 91.96 |
| 24N | 25O23 | 24CA | 18.27 |
| 24N | 25O23 | 22O | 43.58 |
| 24N | 25O23 | 23N | 40.76 |
| 24N | 25O23 | 25C | 77.49 |
| 24N | 25O23 | 26N | 73.33 |
| 24N | 25O23 | 22C | 39.68 |
| 25CA | 25O23 | 23O | 94.04 |
| 25CA | 25O23 | 24C | 37.72 |
| 25CA | 25O23 | 19CD | 69.69 |
| 25CA | 25O23 | 19OE1 | 61.67 |
| 25CA | 25O23 | 24CA | 59.08 |
| 25CA | 25O23 | 22O | 98.54 |
| 25CA | 25O23 | 162ND1 | 81.63 |
| 25CA | 25O23 | 25C | 13.70 |
| 25CA | 25O23 | 26N | 29.03 |
| 25CA | 25O23 | 162CE1 | 73.11 |
| 23O | 25O23 | 24C | 58.97 |
| 23O | 25O23 | 24CA | 40.61 |
| 23O | 25O23 | 22O | 67.32 |
| 23O | 25O23 | 23N | 45.18 |
| 23O | 25O23 | 25C | 88.46 |
| 23O | 25O23 | 26N | 76.05 |
| 23O | 25O23 | 22C | 56.12 |
| 24C | 25O23 | 19CD | 76.06 |
| 24C | 25O23 | 19OE1 | 79.00 |
| 24C | 25O23 | 24CA | 21.38 |
| 24C | 25O23 | 22O | 72.85 |
| 24C | 25O23 | 23N | 79.21 |
| 24C | 25O23 | 25C | 39.06 |
| 24C | 25O23 | 26N | 38.39 |
| 24C | 25O23 | 22C | 74.96 |
| 19CD | 25O23 | 19OE1 | 17.16 |
| 19CD | 25O23 | 24CA | 81.63 |
| 19CD | 25O23 | 22O | 53.92 |
| 19CD | 25O23 | 162ND1 | 75.34 |
| 19CD | 25O23 | 23N | 83.37 |
| 19CD | 25O23 | 25C | 83.39 |
| 19CD | 25O23 | 26N | 97.86 |
| 19CD | 25O23 | 22C | 67.74 |
| 19CD | 25O23 | 162CE1 | 60.88 |
| 19OE1 | 25O23 | 24CA | 90.13 |
| 19OE1 | 25O23 | 22O | 71.06 |
| 19OE1 | 25O23 | 162ND1 | 60.32 |
| 19OE1 | 25O23 | 25C | 74.84 |
| 19OE1 | 25O23 | 26N | 90.69 |
| 19OE1 | 25O23 | 22C | 84.88 |
| 19OE1 | 25O23 | 162CE1 | 45.33 |
| 24CA | 25O23 | 22O | 59.13 |
| 24CA | 25O23 | 23N | 58.89 |
| 24CA | 25O23 | 25C | 59.55 |
| 24CA | 25O23 | 26N | 55.16 |
| 24CA | 25O23 | 22C | 57.43 |
| 22O | 25O23 | 23N | 29.49 |
| 22O | 25O23 | 22C | 13.82 |
| 162ND1 | 25O23 | 25C | 84.77 |
| 162ND1 | 25O23 | 26N | 95.34 |
| 162ND1 | 25O23 | 162CE1 | 15.15 |
| 23N | 25O23 | 22C | 15.68 |
| 25C | 25O23 | 26N | 16.15 |
| 25C | 25O23 | 162CE1 | 79.30 |
| 26N | 25O23 | 162CE1 | 92.61 |
| 59O | 25C24 | 61OD2 | 91.98 |
| 59O | 25C24 | 60CA | 42.04 |
| 59O | 25C24 | 61N | 69.68 |
| 59O | 25C24 | 60ND2 | 53.63 |
| 59O | 25C24 | 60C | 52.10 |
| 59O | 25C24 | 59C | 9.13 |
| 59O | 25C24 | 67CD2 | 94.90 |
| 59O | 25C24 | 61CB | 94.67 |
| 59O | 25C24 | 60N | 25.18 |
| 59O | 25C24 | 65O | 98.75 |
| 59O | 25C24 | 66CA | 92.74 |
| 59O | 25C24 | 61CG | 94.59 |
| 61OD2 | 25C24 | 60CA | 80.40 |
| 61OD2 | 25C24 | 61N | 53.38 |
| 61OD2 | 25C24 | 60C | 60.45 |
| 61OD2 | 25C24 | 59C | 89.44 |
| 61OD2 | 25C24 | 61CB | 30.44 |
| 61OD2 | 25C24 | 60N | 85.15 |
| 61OD2 | 25C24 | 65O | 70.09 |
| 61OD2 | 25C24 | 61CG | 12.52 |
| 60CA | 25C24 | 61N | 33.63 |
| 60CA | 25C24 | 60ND2 | 37.06 |
| 60CA | 25C24 | 60C | 20.13 |
| 60CA | 25C24 | 59C | 32.92 |
| 60CA | 25C24 | 67CD2 | 94.92 |
| 60CA | 25C24 | 61CB | 64.63 |
| 60CA | 25C24 | 60N | 16.87 |
| 60CA | 25C24 | 65O | 56.77 |
| 60CA | 25C24 | 66CA | 57.08 |
| 60CA | 25C24 | 61CG | 74.69 |
| 61N | 25C24 | 60ND2 | 64.13 |
| 61N | 25C24 | 60C | 17.58 |
| 61N | 25C24 | 59C | 61.42 |
| 61N | 25C24 | 61CB | 31.27 |
| 61N | 25C24 | 60N | 47.40 |
| 61N | 25C24 | 65O | 35.46 |
| 61N | 25C24 | 66CA | 57.56 |
| 61N | 25C24 | 61CG | 44.25 |
| 60ND2 | 25C24 | 60C | 56.24 |
| 60ND2 | 25C24 | 67CE2 | 75.32 |
| 60ND2 | 25C24 | 59C | 47.84 |
| 60ND2 | 25C24 | 67CD2 | 57.88 |
| 60ND2 | 25C24 | 61CB | 93.87 |
| 60ND2 | 25C24 | 60N | 39.84 |
| 60ND2 | 25C24 | 65O | 66.16 |
| 60ND2 | 25C24 | 66CA | 42.71 |
| 60C | 25C24 | 59C | 43.92 |
| 60C | 25C24 | 61CB | 46.05 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 60C | 25C24 | 60N | 30.63 |
| 60C | 25C24 | 65O | 50.56 |
| 60C | 25C24 | 66CA | 64.32 |
| 60C | 25C24 | 61CG | 54.63 |
| 67CE2 | 25C24 | 67CD2 | 17.47 |
| 67CE2 | 25C24 | 66CA | 72.97 |
| 59C | 25C24 | 67CD2 | 95.05 |
| 59C | 25C24 | 61CB | 88.03 |
| 59C | 25C24 | 60N | 16.05 |
| 59C | 25C24 | 65O | 89.64 |
| 59C | 25C24 | 66CA | 84.79 |
| 59C | 25C24 | 61CG | 90.22 |
| 67CD2 | 25C24 | 60N | 94.87 |
| 67CD2 | 25C24 | 65O | 94.21 |
| 67CD2 | 25C24 | 66CA | 61.75 |
| 61CB | 25C24 | 60N | 76.56 |
| 61CB | 25C24 | 65O | 39.70 |
| 61CB | 25C24 | 66CA | 72.80 |
| 61CB | 25C24 | 61CG | 18.05 |
| 60N | 25C24 | 65O | 73.63 |
| 60N | 25C24 | 66CA | 70.86 |
| 60N | 25C24 | 61CG | 82.69 |
| 65O | 25C24 | 66CA | 33.53 |
| 65O | 25C24 | 61CG | 57.60 |
| 66CA | 25C24 | 61CG | 90.84 |
| 61OD2 | 25C25 | 61CB | 42.75 |
| 61OD2 | 25C25 | 61N | 69.21 |
| 61OD2 | 25C25 | 61CG | 18.75 |
| 61OD2 | 25C25 | 65O | 92.92 |
| 61OD2 | 25C25 | 60C | 73.08 |
| 61OD2 | 25C25 | 61CA | 51.10 |
| 61OD2 | 25C25 | 59O | 97.68 |
| 61OD2 | 25C25 | 60CA | 92.69 |
| 61OD2 | 25C25 | 61OD1 | 17.96 |
| 61OD2 | 25C25 | 60O | 63.26 |
| 61CB | 25C25 | 61N | 40.79 |
| 61CB | 25C25 | 61CG | 24.59 |
| 61CB | 25C25 | 65O | 50.21 |
| 61CB | 25C25 | 60C | 55.95 |
| 61CB | 25C25 | 61CA | 21.34 |
| 61CB | 25C25 | 60CA | 75.07 |
| 61CB | 25C25 | 61OD1 | 27.44 |
| 61CB | 25C25 | 65C | 60.47 |
| 61CB | 25C25 | 60O | 54.86 |
| 61CB | 25C25 | 66CA | 83.99 |
| 61N | 25C25 | 61CG | 58.00 |
| 61N | 25C25 | 65O | 42.60 |
| 61N | 25C25 | 60C | 18.61 |
| 61N | 25C25 | 61CA | 20.61 |
| 61N | 25C25 | 59O | 69.42 |
| 61N | 25C25 | 60CA | 34.61 |
| 61N | 25C25 | 61OD1 | 62.35 |
| 61N | 25C25 | 65C | 54.60 |
| 61N | 25C25 | 60O | 25.90 |
| 61N | 25C25 | 66CA | 60.64 |
| 61CG | 25C25 | 65O | 74.72 |
| 61CG | 25C25 | 60C | 67.35 |
| 61CG | 25C25 | 61CA | 37.75 |
| 61CG | 25C25 | 60CA | 88.04 |
| 61CG | 25C25 | 61OD1 | 4.51 |
| 61CG | 25C25 | 65C | 84.40 |
| 61CG | 25C25 | 60O | 60.77 |
| 65O | 25C25 | 60C | 58.12 |
| 65O | 25C25 | 61CA | 47.61 |
| 65O | 25C25 | 60CA | 61.97 |
| 65O | 25C25 | 61OD1 | 77.08 |
| 65O | 25C25 | 65C | 12.55 |
| 65O | 25C25 | 60O | 68.17 |
| 65O | 25C25 | 66CA | 34.76 |
| 60C | 25C25 | 61CA | 34.62 |
| 60C | 25C25 | 59O | 51.04 |
| 60C | 25C25 | 60CA | 20.69 |
| 60C | 25C25 | 61OD1 | 71.85 |
| 60C | 25C25 | 65C | 68.94 |
| 60C | 25C25 | 60O | 12.51 |
| 60C | 25C25 | 66CA | 66.29 |
| 61CA | 25C25 | 59O | 84.06 |
| 61CA | 25C25 | 60CA | 53.97 |
| 61CA | 25C25 | 61OD1 | 41.99 |
| 61CA | 25C25 | 65C | 60.01 |
| 61CA | 25C25 | 60O | 34.68 |
| 61CA | 25C25 | 66CA | 75.36 |
| 59O | 25C25 | 60CA | 38.70 |
| 59O | 25C25 | 60O | 49.63 |
| 59O | 25C25 | 66CA | 83.86 |
| 60CA | 25C25 | 61CD1 | 92.54 |
| 60CA | 25C25 | 65C | 69.48 |
| 60CA | 25C25 | 60O | 29.48 |
| 60CA | 25C25 | 66CA | 56.22 |
| 61OD1 | 25C25 | 65C | 86.17 |
| 61OD1 | 25C25 | 60O | 65.14 |
| 65C | 25C25 | 60O | 79.72 |
| 65C | 25C25 | 66CA | 29.00 |
| 60O | 25C25 | 66CA | 78.80 |
| 61CB | 25C26 | 65O | 57.98 |
| 61CB | 25C26 | 61OD2 | 40.43 |
| 61CB | 25C26 | 61CG | 23.23 |
| 61CB | 25C26 | 61N | 39.07 |
| 61CB | 25C26 | 65C | 73.35 |
| 61CB | 25C26 | 61CA | 18.97 |
| 61CB | 25C26 | 64O | 64.81 |
| 61CB | 25C26 | 66N | 88.64 |
| 61CB | 25C26 | 66CA | 94.09 |
| 61CB | 25C26 | 60C | 49.39 |
| 61CB | 25C26 | 65CA | 72.50 |
| 61CB | 25C26 | 64C | 54.69 |
| 61CB | 25C26 | 61OD1 | 25.08 |
| 61CB | 25C26 | 60CA | 66.90 |
| 65O | 25C26 | 61OD2 | 96.74 |
| 65O | 25C26 | 61CG | 81.20 |
| 65O | 25C26 | 61N | 45.23 |
| 65O | 25C26 | 65C | 17.69 |
| 65O | 25C26 | 61CA | 49.81 |
| 65O | 25C26 | 64O | 56.41 |
| 65O | 25C26 | 66N | 30.68 |
| 65O | 25C26 | 66CA | 39.57 |
| 65O | 25C26 | 60C | 55.87 |
| 65O | 25C26 | 65CA | 28.89 |
| 65O | 25C26 | 64C | 44.41 |
| 65O | 25C26 | 61OD1 | 82.28 |
| 65O | 25C26 | 60CA | 58.71 |
| 61OD2 | 25C26 | 61CG | 19.08 |
| 61OD2 | 25C26 | 61N | 60.79 |
| 61OD2 | 25C26 | 61CA | 47.71 |
| 61OD2 | 25C26 | 64O | 94.75 |
| 61OD2 | 25C26 | 60C | 60.86 |
| 61OD2 | 25C26 | 64C | 89.54 |
| 61OD2 | 25C26 | 61OD1 | 23.61 |
| 61OD2 | 25C26 | 60CA | 75.67 |
| 61CG | 25C26 | 61N | 54.13 |
| 61CG | 25C26 | 65C | 96.40 |
| 61CG | 25C26 | 61CA | 36.24 |
| 61CG | 25C26 | 64O | 76.97 |
| 61CG | 25C26 | 60C | 59.38 |
| 61CG | 25C26 | 65CA | 93.65 |
| 61CG | 25C26 | 64C | 70.68 |
| 61CG | 25C26 | 61OD1 | 7.62 |
| 61CG | 25C26 | 60CA | 76.74 |
| 61N | 25C26 | 65C | 62.37 |
| 61N | 25C26 | 61CA | 20.12 |
| 61N | 25C26 | 64O | 88.15 |
| 61N | 25C26 | 66N | 69.41 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 61N | 25C26 | 66CA | 64.66 |
| 61N | 25C26 | 60C | 13.98 |
| 61N | 25C26 | 65CA | 73.06 |
| 61N | 25C26 | 64C | 74.50 |
| 61N | 25C26 | 61OD1 | 59.89 |
| 61N | 25C26 | 60CA | 28.83 |
| 65C | 25C26 | 61CA | 67.25 |
| 65C | 25C26 | 64O | 51.79 |
| 65C | 25C26 | 66N | 17.38 |
| 65C | 25C26 | 66CA | 33.55 |
| 65C | 25C26 | 60C | 71.82 |
| 65C | 25C26 | 65CA | 17.23 |
| 65C | 25C26 | 64C | 43.45 |
| 65C | 25C26 | 61OD1 | 96.15 |
| 65C | 25C26 | 60CA | 71.11 |
| 61CA | 25C26 | 64O | 76.04 |
| 61CA | 25C26 | 66N | 79.28 |
| 61CA | 25C26 | 66CA | 79.89 |
| 61CA | 25C26 | 60C | 31.02 |
| 61CA | 25C26 | 65CA | 72.24 |
| 61CA | 25C26 | 64C | 63.54 |
| 61CA | 25C26 | 61OD1 | 40.94 |
| 61CA | 25C26 | 60CA | 48.15 |
| 64O | 25C26 | 66N | 65.51 |
| 64O | 25C26 | 66CA | 84.31 |
| 64O | 25C26 | 65CA | 35.23 |
| 64O | 25C26 | 64C | 13.78 |
| 64O | 25C26 | 61OD1 | 71.21 |
| 66N | 25C26 | 66CA | 19.09 |
| 66N | 25C26 | 60C | 75.28 |
| 66N | 25C26 | 65CA | 30.56 |
| 66N | 25C26 | 64C | 59.39 |
| 66N | 25C26 | 60CA | 69.05 |
| 66CA | 25C26 | 60C | 66.08 |
| 66CA | 25C26 | 65CA | 49.11 |
| 66CA | 25C26 | 64C | 76.99 |
| 66CA | 25C26 | 60CA | 55.34 |
| 60C | 25C26 | 65CA | 84.60 |
| 60C | 25C26 | 64C | 88.43 |
| 60C | 25C26 | 61OD1 | 66.22 |
| 60C | 25C26 | 60CA | 17.82 |
| 65CA | 25C26 | 64C | 29.29 |
| 65CA | 25C26 | 61OD1 | 91.21 |
| 65CA | 25C26 | 60CA | 86.87 |
| 64C | 25C26 | 61OD1 | 66.22 |
| 64C | 25C26 | 60CA | 98.77 |
| 61OD1 | 25C26 | 60CA | 83.78 |
| 65O | 25C27 | 65C | 19.69 |
| 65O | 25C27 | 66N | 35.95 |
| 65O | 25C27 | 66CA | 44.75 |
| 65O | 25C27 | 65CA | 32.29 |
| 65O | 25C27 | 64O | 53.20 |
| 65O | 25C27 | 61CB | 45.32 |
| 65O | 25C27 | 66C | 62.38 |
| 65O | 25C27 | 61N | 36.43 |
| 65O | 25C27 | 61OD2 | 72.86 |
| 65O | 25C27 | 66O | 66.33 |
| 65C | 25C27 | 66N | 20.59 |
| 65C | 25C27 | 66CA | 38.16 |
| 65C | 25C27 | 65CA | 18.27 |
| 65C | 25C27 | 64O | 50.92 |
| 65C | 25C27 | 61CB | 62.98 |
| 65C | 25C27 | 66C | 52.26 |
| 65C | 25C27 | 61N | 55.57 |
| 65C | 25C27 | 61OD2 | 91.46 |
| 65C | 25C27 | 66O | 51.89 |
| 66N | 25C27 | 66CA | 22.16 |
| 66N | 25C27 | 65CA | 32.66 |
| 66N | 25C27 | 64O | 68.31 |
| 66N | 25C27 | 61CB | 81.26 |
| 66N | 25C27 | 66C | 32.35 |
| 66N | 25C27 | 61N | 66.24 |
| 66N | 25C27 | 67CD2 | 86.04 |
| 66N | 25C27 | 66O | 31.43 |
| 66CA | 25C27 | 67CE2 | 84.05 |
| 66CA | 25C27 | 65CA | 53.89 |
| 66CA | 25C27 | 64O | 88.87 |
| 66CA | 25C27 | 61CB | 86.12 |
| 66CA | 25C27 | 66C | 18.33 |
| 66CA | 25C27 | 61N | 61.78 |
| 66CA | 25C27 | 67CD2 | 68.00 |
| 66CA | 25C27 | 67CZ | 89.01 |
| 66CA | 25C27 | 66O | 27.54 |
| 67CE2 | 25C27 | 66C | 68.52 |
| 67CE2 | 25C27 | 67CD2 | 16.65 |
| 67CE2 | 25C27 | 67CZ | 16.31 |
| 67CE2 | 25C27 | 66O | 70.63 |
| 65CA | 25C27 | 64O | 35.68 |
| 65CA | 25C27 | 61CB | 65.69 |
| 65CA | 25C27 | 66C | 64.52 |
| 65CA | 25C27 | 61N | 68.03 |
| 65CA | 25C27 | 61OD2 | 94.09 |
| 65CA | 25C27 | 66O | 59.86 |
| 64O | 25C27 | 61CB | 54.95 |
| 64O | 25C27 | 61N | 76.01 |
| 64O | 25C27 | 61OD2 | 75.54 |
| 64O | 25C27 | 66O | 93.93 |
| 61CB | 25C27 | 61N | 30.76 |
| 61CB | 25C27 | 61OD2 | 28.82 |
| 66C | 25C27 | 61N | 78.83 |
| 66C | 25C27 | 67CD2 | 53.68 |
| 66C | 25C27 | 67CZ | 71.38 |
| 66C | 25C27 | 66O | 13.90 |
| 61N | 25C27 | 61OD2 | 45.79 |
| 61N | 25C27 | 66O | 89.25 |
| 67CD2 | 25C27 | 67CZ | 28.76 |
| 67CD2 | 25C27 | 66O | 58.30 |
| 67CZ | 25C27 | 66O | 69.31 |
| 67CE2 | 25C28 | 67CD2 | 23.52 |
| 67CE2 | 25C28 | 67CZ | 20.96 |
| 67CE2 | 25C28 | 67OH | 35.20 |
| 67CE2 | 25C28 | 66C | 86.92 |
| 67CE2 | 25C28 | 67CG | 33.10 |
| 67CE2 | 25C28 | 67N | 73.57 |
| 67CE2 | 25C28 | 67CE1 | 29.88 |
| 67CE2 | 25C28 | 60ND2 | 85.55 |
| 67CE2 | 25C28 | 66O | 85.99 |
| 67CE2 | 25C28 | 67CD1 | 33.21 |
| 67CD2 | 25C28 | 67CZ | 38.76 |
| 67CD2 | 25C28 | 66CA | 84.93 |
| 67CD2 | 25C28 | 67OH | 56.87 |
| 67CD2 | 25C28 | 66C | 66.69 |
| 67CD2 | 25C28 | 67CG | 16.19 |
| 67CD2 | 25C28 | 67N | 51.42 |
| 67CD2 | 25C28 | 67CE1 | 37.73 |
| 67CD2 | 25C28 | 60ND2 | 63.64 |
| 67CD2 | 25C28 | 66O | 69.45 |
| 67CD2 | 25C28 | 67CD1 | 28.35 |
| 67CZ | 25C28 | 67OH | 19.51 |
| 67CZ | 25C28 | 66C | 88.11 |
| 67CZ | 25C28 | 67CG | 39.85 |
| 67CZ | 25C28 | 67N | 79.74 |
| 67CZ | 25C28 | 67CE1 | 15.82 |
| 67CZ | 25C28 | 66O | 82.16 |
| 67CZ | 25C28 | 67CD1 | 29.69 |
| 66CA | 25C28 | 66C | 21.36 |
| 66CA | 25C28 | 66N | 20.18 |
| 66CA | 25C28 | 67CG | 73.95 |
| 66CA | 25C28 | 65O | 39.39 |
| 66CA | 25C28 | 67N | 33.53 |
| 66CA | 25C28 | 65C | 33.20 |
| 66CA | 25C28 | 67CE1 | 94.77 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 66CA | 25C28 | 60ND2 | 46.84 |
| 66CA | 25C28 | 66O | 30.13 |
| 66CA | 25C28 | 67CD1 | 79.87 |
| 67OH | 25C28 | 67CG | 59.35 |
| 67OH | 25C28 | 67N | 98.79 |
| 67OH | 25C28 | 67CE1 | 31.87 |
| 67OH | 25C28 | 66O | 96.91 |
| 67OH | 25C28 | 67CD1 | 48.13 |
| 66C | 25C28 | 66N | 33.87 |
| 66C | 25C28 | 67CG | 53.83 |
| 66C | 25C28 | 65O | 60.02 |
| 66C | 25C28 | 67N | 17.65 |
| 66C | 25C28 | 65C | 50.69 |
| 66C | 25C28 | 67CE1 | 73.54 |
| 66C | 25C28 | 60ND2 | 49.87 |
| 66C | 25C28 | 66O | 14.26 |
| 66C | 25C28 | 67CD1 | 58.53 |
| 66N | 25C28 | 67CG | 86.97 |
| 66N | 25C28 | 65O | 30.60 |
| 66N | 25C28 | 67N | 50.32 |
| 66N | 25C28 | 65C | 17.37 |
| 66N | 25C28 | 67CE1 | 99.34 |
| 66N | 25C28 | 60ND2 | 66.19 |
| 66N | 25C28 | 66O | 33.91 |
| 66N | 25C28 | 67CD1 | 87.99 |
| 67CG | 25C28 | 67N | 41.20 |
| 67CG | 25C28 | 67CE1 | 31.84 |
| 67CG | 25C28 | 60ND2 | 64.79 |
| 67CG | 25C28 | 66O | 54.35 |
| 67CG | 25C28 | 67CD1 | 16.69 |
| 65O | 25C28 | 67N | 72.54 |
| 65O | 25C28 | 65C | 16.08 |
| 65O | 25C28 | 60ND2 | 67.97 |
| 65O | 25C28 | 66O | 63.89 |
| 67N | 25C28 | 65C | 66.13 |
| 67N | 25C28 | 67CE1 | 67.52 |
| 67N | 25C28 | 60ND2 | 39.36 |
| 67N | 25C28 | 66O | 28.39 |
| 67N | 25C28 | 67CD1 | 50.73 |
| 65C | 25C28 | 60ND2 | 73.05 |
| 65C | 25C28 | 66O | 51.14 |
| 67CE1 | 25C28 | 60ND2 | 96.62 |
| 67CE1 | 25C28 | 66O | 66.57 |
| 67CE1 | 25C28 | 67CD1 | 17.05 |
| 60ND2 | 25C28 | 66O | 64.03 |
| 60ND2 | 25C28 | 67CD1 | 80.40 |
| 66O | 25C28 | 67CD1 | 54.11 |
| 67CE2 | 25C29 | 67CD2 | 24.48 |
| 67CE2 | 25C29 | 60ND2 | 95.45 |
| 67CE2 | 25C29 | 67CZ | 15.31 |
| 67CE2 | 25C29 | 66CA | 94.75 |
| 67CE2 | 25C29 | 67CG | 30.54 |
| 67CE2 | 25C29 | 67OH | 29.52 |
| 67CE2 | 25C29 | 67N | 69.16 |
| 67CE2 | 25C29 | 66C | 76.62 |
| 67CE2 | 25C29 | 70OD1 | 69.19 |
| 67CD2 | 25C29 | 60ND2 | 70.99 |
| 67CD2 | 25C29 | 67CZ | 35.94 |
| 67CD2 | 25C29 | 66CA | 77.68 |
| 67CD2 | 25C29 | 67CG | 11.52 |
| 67CD2 | 25C29 | 67OH | 52.86 |
| 67CD2 | 25C29 | 67N | 48.30 |
| 67CD2 | 25C29 | 66C | 59.66 |
| 67CD2 | 25C29 | 70OD1 | 48.35 |
| 60ND2 | 25C29 | 59O | 51.92 |
| 60ND2 | 25C29 | 66CA | 47.48 |
| 60ND2 | 25C29 | 67CG | 67.53 |
| 60ND2 | 25C29 | 67N | 39.60 |
| 60ND2 | 25C29 | 60CA | 34.92 |
| 60ND2 | 25C29 | 66C | 48.58 |
| 60ND2 | 25C29 | 70OD1 | 36.76 |
| 60ND2 | 25C29 | 65O | 66.66 |
| 59O | 25C29 | 66CA | 91.68 |
| 59O | 25C29 | 67N | 91.44 |
| 59O | 25C29 | 60CA | 36.13 |
| 59O | 25C29 | 66C | 99.32 |
| 59O | 25C29 | 70OD1 | 57.47 |
| 59O | 25C29 | 65O | 87.31 |
| 67CZ | 25C29 | 66CA | 92.71 |
| 67CZ | 25C29 | 67CG | 37.70 |
| 67CZ | 25C29 | 67OH | 17.56 |
| 67CZ | 25C29 | 67N | 72.63 |
| 67CZ | 25C29 | 66C | 75.91 |
| 67CZ | 25C29 | 70OD1 | 83.35 |
| 66CA | 25C29 | 67CG | 67.01 |
| 66CA | 25C29 | 67N | 30.81 |
| 66CA | 25C29 | 60CA | 57.52 |
| 66CA | 25C29 | 66C | 18.31 |
| 66CA | 25C29 | 70OD1 | 76.75 |
| 66CA | 25C29 | 65O | 34.30 |
| 67CG | 25C29 | 67OH | 55.25 |
| 67CG | 25C29 | 67N | 38.92 |
| 67CG | 25C29 | 66C | 48.79 |
| 67CG | 25C29 | 70OD1 | 52.17 |
| 67OH | 25C29 | 67N | 88.91 |
| 67OH | 25C29 | 66C | 89.71 |
| 67OH | 25C29 | 70OD1 | 98.59 |
| 67N | 25C29 | 60CA | 68.41 |
| 67N | 25C29 | 66C | 16.09 |
| 67N | 25C29 | 70OD1 | 52.40 |
| 67N | 25C29 | 65O | 64.97 |
| 60CA | 25C29 | 66C | 69.66 |
| 60CA | 25C29 | 70OD1 | 64.85 |
| 60CA | 25C29 | 65O | 52.85 |
| 66C | 25C29 | 70OD1 | 68.06 |
| 66C | 25C29 | 65O | 51.98 |
| 65C | 25C30 | 66N | 22.36 |
| 65C | 25C30 | 65O | 19.60 |
| 65C | 25C30 | 65CA | 24.11 |
| 65C | 25C30 | 64O | 60.69 |
| 65C | 25C30 | 66CA | 37.47 |
| 65C | 25C30 | 64C | 47.70 |
| 65C | 25C30 | 65N | 31.97 |
| 65C | 25C30 | 66C | 52.44 |
| 65C | 25C30 | 66O | 56.13 |
| 66N | 25C30 | 65O | 36.76 |
| 66N | 25C30 | 65CA | 39.03 |
| 66N | 25C30 | 64O | 81.12 |
| 66N | 25C30 | 66CA | 20.96 |
| 66N | 25C30 | 64C | 68.55 |
| 66N | 25C30 | 65N | 51.94 |
| 66N | 25C30 | 66C | 31.15 |
| 66N | 25C30 | 66O | 33.85 |
| 65O | 25C30 | 65CA | 37.88 |
| 65O | 25C30 | 64O | 60.O9 |
| 65O | 25C30 | 66CA | 42.53 |
| 65O | 25C30 | 64C | 47.65 |
| 65O | 25C30 | 65N | 37.00 |
| 65O | 25C30 | 66C | 60.78 |
| 65O | 25C30 | 66O | 69.10 |
| 65CA | 25C30 | 64O | 43.45 |
| 65CA | 25C30 | 66CA | 58.77 |
| 65CA | 25C30 | 64C | 32.33 |
| 65CA | 25C30 | 65N | 16.26 |
| 65CA | 25C30 | 66C | 69.64 |
| 65CA | 25C30 | 66O | 67.50 |
| 64O | 25C30 | 66CA | 98.08 |
| 64O | 25C30 | 64C | 13.08 |
| 64O | 25C30 | 65N | 29.19 |
| 66CA | 25C30 | 64C | 85.02 |
| 66CA | 25C30 | 65N | 69.41 |
| 66CA | 25C30 | 66C | 18.61 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 66CA | 25C30 | 66O | 30.64 |
| 64C | 25C30 | 65N | 16.80 |
| 64C | 25C30 | 66C | 99.65 |
| 64C | 25C30 | 66O | 99.64 |
| 65N | 25C30 | 66C | 83.08 |
| 65N | 25C30 | 66O | 82.93 |
| 66C | 25C30 | 66O | 15.25 |
| 66N | 25O31 | 65C | 17.32 |
| 66N | 25O31 | 67CZ | 97.91 |
| 66N | 25O31 | 65CA | 31.08 |
| 66N | 25O31 | 64O | 62.95 |
| 66N | 25O31 | 66CA | 17.26 |
| 66N | 25O31 | 66O | 33.20 |
| 66N | 25O31 | 67CE1 | 92.81 |
| 66N | 25O31 | 67CE2 | 86.83 |
| 66N | 25O31 | 65O | 26.88 |
| 66N | 25O31 | 66C | 29.04 |
| 65C | 25O31 | 65CA | 19.09 |
| 65C | 25O31 | 64O | 46.34 |
| 65C | 25O31 | 66CA | 30.23 |
| 65C | 25O31 | 66O | 50.48 |
| 65C | 25O31 | 67CE2 | 97.89 |
| 65C | 25O31 | 65O | 13.61 |
| 65C | 25O31 | 66C | 45.49 |
| 67OH | 25O31 | 67CZ | 17.55 |
| 67OH | 25O31 | 66CA | 98.18 |
| 67OH | 25O31 | 66O | 90.84 |
| 67OH | 25O31 | 67CE1 | 29.52 |
| 67OH | 25O31 | 67CE2 | 29.04 |
| 67OH | 25O31 | 66C | 87.47 |
| 67CZ | 25O31 | 66CA | 81.60 |
| 67CZ | 25O31 | 66O | 73.49 |
| 67CZ | 25O31 | 67CE1 | 16.52 |
| 67CZ | 25O31 | 67CE2 | 16.35 |
| 67CZ | 25O31 | 66C | 69.99 |
| 65CA | 25O31 | 64O | 34.51 |
| 65CA | 25O31 | 66CA | 47.38 |
| 65CA | 25O31 | 66O | 60.33 |
| 65CA | 25O31 | 65O | 28.52 |
| 65CA | 25O31 | 66C | 59.78 |
| 64O | 25O31 | 66CA | 76.15 |
| 64O | 25O31 | 66O | 94.57 |
| 64O | 25O31 | 65O | 44.97 |
| 64C | 25O31 | 66C | 91.77 |
| 66CA | 25O31 | 66O | 28.82 |
| 66CA | 25O31 | 67CE1 | 78.69 |
| 66CA | 25O31 | 67CE2 | 69.71 |
| 66CA | 25O31 | 65O | 33.12 |
| 66CA | 25O31 | 66C | 17.65 |
| 66O | 25O31 | 67CE1 | 63.44 |
| 66O | 25O31 | 67CE2 | 68.73 |
| 66O | 25O31 | 65O | 58.85 |
| 66O | 25O31 | 66C | 14.31 |
| 67CE1 | 25O31 | 67CE2 | 28.45 |
| 67CE1 | 25O31 | 66C | 63.77 |
| 67CE2 | 25O31 | 65O | 93.08 |
| 67CE2 | 25O31 | 66C | 61.53 |
| 65O | 25O31 | 66C | 50.53 |
| 66O | 25C32 | 66N | 36.46 |
| 66O | 25C32 | 65CA | 64.42 |
| 66O | 25C32 | 65C | 52.71 |
| 66O | 25C32 | 67CE1 | 69.47 |
| 66O | 25C32 | 66C | 14.32 |
| 66O | 25C32 | 67CZ | 76.69 |
| 66O | 25C32 | 66CA | 29.45 |
| 66O | 25C32 | 67OH | 92.97 |
| 66N | 25C32 | 65CA | 31.01 |
| 66N | 25C32 | 65C | 16.26 |
| 66N | 25C32 | 67CE1 | 96.14 |
| 66N | 25C32 | 66C | 30.68 |
| 66N | 25C32 | 67CZ | 95.21 |
| 66N | 25C32 | 66CA | 16.64 |
| 65CA | 25C32 | 65C | 18.68 |
| 65CA | 25C32 | 66C | 61.49 |
| 65CA | 25C32 | 66CA | 46.86 |
| 65C | 25C32 | 66C | 46.16 |
| 65C | 25C32 | 66CA | 29.55 |
| 67CE1 | 25C32 | 66C | 67.09 |
| 67CE1 | 25C32 | 67CZ | 16.76 |
| 67CE1 | 25C32 | 66CA | 79.83 |
| 67CE1 | 25C32 | 67OH | 29.00 |
| 66C | 25C32 | 67CZ | 70.31 |
| 66C | 25C32 | 66CA | 18.10 |
| 66C | 25C32 | 67OH | 85.85 |
| 67CZ | 25C32 | 66CA | 78.64 |
| 67CZ | 25C32 | 67OH | 16.35 |
| 66CA | 25C32 | 67OH | 92.05 |
| 67CE1 | 25O33 | 67CZ | 18.11 |
| 67CE1 | 25O33 | 67OH | 32.18 |
| 67CE1 | 25O33 | 66O | 70.79 |
| 67CE1 | 25O33 | 67CD1 | 16.55 |
| 67CE1 | 25O33 | 2530H2 | 91.77 |
| 67CZ | 25O33 | 67OH | 17.82 |
| 67CZ | 25O33 | 66O | 76.31 |
| 67CZ | 25O33 | 67CD1 | 30.29 |
| 67CZ | 25O33 | 2530H2 | 94.53 |
| 67OH | 25O33 | 66O | 93.31 |
| 67OH | 25O33 | 67CD1 | 47.11 |
| 67OH | 25O33 | 2530H2 | 82.17 |
| 66O | 25O33 | 67CD1 | 55.11 |
| 2530H2 | 25O33 | 160O | 32.53 |
| 66O | 25C34 | 66N | 39.24 |
| 66O | 25C34 | 65CA | 72.10 |
| 66O | 25C34 | 65C | 54.84 |
| 66O | 25C34 | 25SG | 98.30 |
| 66O | 25C34 | 66C | 10.30 |
| 66N | 25C34 | 65CA | 33.35 |
| 66N | 25C34 | 65C | 15.62 |
| 66N | 25C34 | 25SG | 96.34 |
| 66N | 25C34 | 66C | 31.01 |
| 65CA | 25C34 | 65C | 18.75 |
| 65CA | 25C34 | 25SG | 85.74 |
| 65CA | 25C34 | 66C | 64.35 |
| 65C | 25C34 | 25SG | 95.57 |
| 65C | 25C34 | 66C | 46.29 |
| 25SG | 25C34 | 161O | 60.31 |
| 25SG | 25C34 | 161C | 66.90 |
| 161O | 25C34 | 161C | 14.93 |
| 66O | 25C35 | 66C | 7.49 |
| 66O | 25C35 | 68CE | 57.46 |
| 66O | 25C35 | 66N | 35.66 |
| 66O | 25C35 | 163CB | 89.86 |
| 66O | 25C35 | 66CA | 21.29 |
| 66C | 25C35 | 68CE | 64.25 |
| 66C | 25C35 | 66N | 32.33 |
| 66C | 25C35 | 163CB | 97.34 |
| 66C | 25C35 | 66CA | 16.42 |
| 68CE | 25C35 | 66N | 88.65 |
| 68CE | 25C35 | 163CB | 42.93 |
| 68CE | 25C35 | 163N | 71.03 |
| 68CE | 25C35 | 66CA | 78.09 |
| 66N | 25C35 | 66CA | 16.42 |
| 163CB | 25C35 | 163N | 28.84 |
| 66O | 25C36 | 68CE | 48.64 |
| 66O | 25C36 | 67CD1 | 56.25 |
| 66O | 25C36 | 67CE1 | 67.39 |
| 134CB | 25C36 | 209CD2 | 53.33 |
| 134CB | 25C36 | 68CE | 70.27 |
| 134CB | 25C36 | 160O | 87.04 |
| 134CB | 25C36 | 162N | 72.66 |
| 134CB | 25C36 | 160C | 74.39 |
| 134CB | 25C36 | 161C | 86.84 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 134CB | 25C36 | 161CA | 88.42 |
| 134CB | 25C36 | 161N | 74.11 |
| 134CB | 25C36 | 160CB | 54.87 |
| 209CD2 | 25C36 | 68CE | 80.58 |
| 209CD2 | 25C36 | 160O | 88.38 |
| 209CD2 | 25C36 | 160C | 87.02 |
| 209CD2 | 25C36 | 67CD1 | 54.52 |
| 209CD2 | 25C36 | 67CE1 | 55.35 |
| 209CD2 | 25C36 | 161N | 98.98 |
| 209CD2 | 25C36 | 160CB | 57.71 |
| 68CE | 25C36 | 67CD1 | 70.75 |
| 68CE | 25C36 | 67CE1 | 87.36 |
| 160O | 25C36 | 162N | 60.06 |
| 160O | 25C36 | 160C | 14.84 |
| 160O | 25C36 | 161C | 52.10 |
| 160O | 25C36 | 161CA | 34.02 |
| 160O | 25C36 | 161N | 27.16 |
| 160O | 25C36 | 160CB | 35.85 |
| 162N | 25C36 | 16OC | 49.38 |
| 162N | 25C36 | 161C | 15.90 |
| 162N | 25C36 | 161CA | 29.60 |
| 162N | 25C36 | 161N | 33.75 |
| 162N | 25C36 | 160CB | 69.36 |
| 160C | 25C36 | 161C | 45.30 |
| 160C | 25C36 | 161CA | 29.33 |
| 160C | 25C36 | 161N | 15.76 |
| 160C | 25C36 | 160CB | 29.68 |
| 161C | 25C36 | 161CA | 18.21 |
| 161C | 25C36 | 161N | 30.25 |
| 161C | 25C36 | 160CB | 71.28 |
| 161CA | 25C36 | 161N | 17.23 |
| 161CA | 25C36 | 160CB | 58.05 |
| 67CD1 | 25C36 | 67CE1 | 16.61 |
| 67CE1 | 25C36 | 160CB | 96.33 |
| 161N | 25C36 | 160CB | 41.59 |
| 162N | 25C37 | 162C | 38.77 |
| 162N | 25C37 | 163N | 55.65 |
| 162N | 25C37 | 162O | 43.88 |
| 162N | 25C37 | 161C | 19.66 |
| 162N | 25C37 | 161N | 43.11 |
| 162N | 25C37 | 162CA | 20.61 |
| 162N | 25C37 | 161CA | 36.42 |
| 162N | 25C37 | 16OC | 61.64 |
| 162N | 25C37 | 163CA | 72.52 |
| 162N | 25C37 | 163CB | 88.83 |
| 162N | 25C37 | 160O | 71.57 |
| 162N | 25C37 | 160CB | 86.86 |
| 162N | 25C37 | 134CA | 86.74 |
| 162N | 25C37 | 161O | 27.40 |
| 162N | 25C37 | 160CA | 69.38 |
| 134CB | 25C37 | 162C | 80.90 |
| 134CB | 25C37 | 163N | 83.96 |
| 134CB | 25C37 | 162O | 64.46 |
| 134CB | 25C37 | 161N | 96.15 |
| 134CB | 25C37 | 162CA | 99.27 |
| 134CB | 25C37 | 160C | 92.07 |
| 134CB | 25C37 | 163CA | 69.42 |
| 134CB | 25C37 | 163CB | 75.64 |
| 134CB | 25C37 | 160CB | 64.54 |
| 134CB | 25C37 | 134CA | 17.37 |
| 134CB | 25C37 | 16QCA | 74.76 |
| 134CB | 25C37 | 68CE | 75.20 |
| 134CB | 25C37 | 209CD2 | 53.65 |
| 162C | 25C37 | 163N | 20.04 |
| 162C | 25C37 | 162O | 18.39 |
| 162C | 25C37 | 161C | 56.63 |
| 162C | 25C37 | 161N | 77.75 |
| 162C | 25C37 | 162CA | 22.08 |
| 162C | 25C37 | 161CA | 75.17 |
| 162C | 25C37 | 160C | 94.90 |
| 162C | 25C37 | 163CA | 33.93 |
| 162C | 25C37 | 163CB | 51.74 |
| 162C | 25C37 | 134CA | 63.54 |
| 162C | 25C37 | 161O | 57.80 |
| 162C | 25C37 | 160CA | 95.14 |
| 162C | 25C37 | 68CE | 93.53 |
| 163N | 25C37 | 162O | 33.61 |
| 163N | 25C37 | 161C | 70.64 |
| 163N | 25C37 | 161N | 97.07 |
| 163N | 25C37 | 162CA | 35.65 |
| 163N | 25C37 | 161CA | 91.41 |
| 163N | 25C37 | 163CA | 19.33 |
| 163N | 25C37 | 163CB | 33.19 |
| 163N | 25C37 | 134CA | 67.66 |
| 163N | 25C37 | 161O | 67.69 |
| 163N | 25C37 | 68CE | 75.10 |
| 162O | 25C37 | 161C | 63.53 |
| 162O | 25C37 | 161N | 73.01 |
| 162O | 25C37 | 162CA | 34.99 |
| 162O | 25C37 | 161CA | 77.20 |
| 162O | 25C37 | 160C | 87.26 |
| 162O | 25C37 | 163CA | 38.61 |
| 162O | 25C37 | 163CB | 58.25 |
| 162O | 25C37 | 160CB | 91.83 |
| 162O | 25C37 | 134CA | 47.36 |
| 162O | 25C37 | 161O | 68.76 |
| 162O | 25C37 | 160CA | 82.84 |
| 162O | 25C37 | 68CE | 96.46 |
| 161C | 25C37 | 161N | 37.46 |
| 161C | 25C37 | 162CA | 35.43 |
| 161C | 25C37 | 161CA | 21.87 |
| 161C | 25C37 | 160C | 54.49 |
| 161C | 25C37 | 163CA | 89.14 |
| 161C | 25C37 | 160O | 59.67 |
| 161C | 25C37 | 160CB | 85.75 |
| 161C | 25C37 | 161O | 13.22 |
| 161C | 25C37 | 160CA | 67.48 |
| 161N | 25C37 | 162CA | 63.61 |
| 161N | 25C37 | 161CA | 20.70 |
| 161N | 25C37 | 160C | 18.54 |
| 161N | 25C37 | 160O | 30.38 |
| 161N | 25C37 | 160CB | 48.33 |
| 161N | 25C37 | 134CA | 92.03 |
| 161N | 25C37 | 161O | 49.54 |
| 161N | 25C37 | 160CA | 30.13 |
| 162CA | 25C37 | 161CA | 55.77 |
| 162CA | 25C37 | 160C | 82.09 |
| 162CA | 25C37 | 163CA | 53.72 |
| 162CA | 25C37 | 163CB | 68.64 |
| 162CA | 25C37 | 160O | 92.06 |
| 162CA | 25C37 | 134CA | 82.32 |
| 162CA | 25C37 | 161O | 35.74 |
| 162CA | 25C37 | 160CA | 88.24 |
| 161CA | 25C37 | 160C | 34.21 |
| 161CA | 25C37 | 160O | 37.80 |
| 161CA | 25C37 | 160CB | 67.22 |
| 161CA | 25C37 | 161O | 31.20 |
| 161CA | 25C37 | 160CA | 49.65 |
| 160C | 25C37 | 160O | 15.98 |
| 160C | 25C37 | 160CB | 33.38 |
| 160C | 25C37 | 134CA | 93.50 |
| 160C | 25C37 | 161O | 65.32 |
| 160C | 25C37 | 160CA | 17.61 |
| 160C | 25C37 | 209CD2 | 89.23 |
| 163CA | 25C37 | 163CB | 19.64 |
| 163CA | 25C37 | 134CA | 55.20 |
| 163CA | 25C37 | 161O | 86.98 |
| 163CA | 25C37 | 68CE | 59.96 |
| 163CB | 25C37 | 134CA | 65.55 |
| 163CB | 25C37 | 161O | 97.16 |
| 163CB | 25C37 | 68CE | 41.99 |
| 160O | 25C37 | 160CB | 38.98 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 160O | 25C37 | 161O | 67.69 |
| 160O | 25C37 | 160CA | 29.34 |
| 160O | 25C37 | 209CD2 | 86.31 |
| 160CB | 25C37 | 134CA | 72.65 |
| 160CB | 25C37 | 161O | 97.76 |
| 160OB | 25C37 | 160CA | 18.30 |
| 160CB | 25C37 | 209CD2 | 58.20 |
| 134CA | 25C37 | 160CA | 77.94 |
| 134CA | 25C37 | 68CE | 77.56 |
| 134CA | 25C37 | 209CD2 | 71.01 |
| 161O | 25C37 | 160CA | 79.66 |
| 160CA | 25C37 | 209CD2 | 76.48 |
| 68CE | 25C37 | 209CD2 | 74.72 |
| 209CD2 | 25C38 | 67CD1 | 74.87 |
| 209CD2 | 25C38 | 67CE1 | 73.16 |
| 209CD2 | 25C38 | 134CB | 65.56 |
| 209CD2 | 25C38 | 209CG | 16.73 |
| 209CD2 | 25C38 | 67CG | 84.81 |
| 67CD1 | 25C38 | 67CE1 | 20.70 |
| 67CD1 | 25C38 | 68OE | 89.96 |
| 67CD1 | 25C38 | 66O | 66.53 |
| 67CD1 | 25C38 | 209CG | 75.95 |
| 67CD1 | 25C38 | 67CG | 12.21 |
| 67CD1 | 25C38 | 67CA | 42.12 |
| 67CE1 | 25C38 | 66O | 77.82 |
| 67CE1 | 25C38 | 209CG | 80.22 |
| 67CE1 | 25C38 | 67CG | 30.41 |
| 67CE1 | 25C38 | 67CA | 60.82 |
| 68CE | 25C38 | 134CB | 80.62 |
| 68CE | 25C38 | 66O | 53.63 |
| 68CE | 25C38 | 209CG | 90.75 |
| 68CE | 25C38 | 67CG | 80.08 |
| 68CE | 25C38 | 67CA | 50.64 |
| 134CB | 25C38 | 209CG | 59.36 |
| 66O | 25C38 | 67CG | 54.73 |
| 66O | 25C38 | 67CA | 34.43 |
| 209CG | 25C38 | 67CG | 83.39 |
| 209CG | 25C38 | 67CA | 92.38 |
| 67CG | 25C38 | 67CA | 30.58 |
| 65CA | 25C39 | 66N | 39.58 |
| 65CA | 25C39 | 66O | 81.69 |
| 65CA | 25C39 | 26CD1 | 58.77 |
| 65CA | 25C39 | 65C | 21.13 |
| 65CA | 25C39 | 26CB | 87.77 |
| 65CA | 25C39 | 26CG | 70.14 |
| 65CA | 25C39 | 66C | 70.43 |
| 65CA | 25C39 | 65N | 10.50 |
| 65CA | 25C39 | 26N | 97.84 |
| 65CA | 25C39 | 66CA | 51.95 |
| 65CA | 25C39 | 23O | 44.24 |
| 25SG | 25C39 | 26CD1 | 80.82 |
| 25SG | 25C39 | 26CB | 77.99 |
| 25SG | 25C39 | 26CG | 82.69 |
| 25SG | 25C39 | 26N | 48.23 |
| 25SG | 25C39 | 23O | 74.80 |
| 25SG | 25C39 | 161O | 65.02 |
| 66N | 25C39 | 66O | 42.13 |
| 66N | 25C39 | 26CD1 | 49.89 |
| 66N | 25C39 | 65C | 18.53 |
| 66N | 25C39 | 26CB | 61.31 |
| 66N | 25C39 | 26CG | 50.14 |
| 66N | 25C39 | 66C | 30.88 |
| 66N | 25C39 | 65N | 49.74 |
| 66N | 25C39 | 26N | 85.92 |
| 66N | 25C39 | 66CA | 12.40 |
| 66N | 25C39 | 23O | 70.96 |
| 66O | 25C39 | 26CD1 | 64.20 |
| 66O | 25C39 | 65C | 60.58 |
| 66O | 25C39 | 26CB | 46.66 |
| 66O | 25C39 | 26CG | 51.76 |
| 66O | 25C39 | 66C | 11.26 |
| 66O | 25C39 | 65N | 91.86 |
| 66O | 25C39 | 26N | 76.72 |
| 66O | 25C39 | 66CA | 29.74 |
| 26CD1 | 25C39 | 65C | 52.77 |
| 26CD1 | 25C39 | 26CB | 33.76 |
| 26CD1 | 25C39 | 26CG | 16.02 |
| 26CD1 | 25C39 | 66C | 59.08 |
| 26CD1 | 25C39 | 65N | 61.27 |
| 26CD1 | 25C39 | 26N | 40.34 |
| 26CD1 | 25C39 | 66CA | 52.43 |
| 26CD1 | 25C39 | 23O | 46.03 |
| 65C | 25C39 | 26CB | 74.04 |
| 65C | 25C39 | 26CG | 59.01 |
| 65C | 25C39 | 66C | 49.32 |
| 65C | 25C39 | 65N | 31.45 |
| 65C | 25C39 | 26N | 92.79 |
| 65C | 25C39 | 66CA | 30.85 |
| 65C | 25C39 | 23O | 58.16 |
| 26CB | 25C39 | 26CG | 18.51 |
| 26CB | 25C39 | 66C | 48.81 |
| 26CB | 25C39 | 65N | 92.88 |
| 26CB | 25C39 | 26N | 30.42 |
| 26CB | 25C39 | 66CA | 55.33 |
| 26CB | 25C39 | 23O | 78.36 |
| 26CG | 25C39 | 66C | 49.18 |
| 26CG | 25C39 | 65N | 74.55 |
| 26CG | 25C39 | 26N | 35.79 |
| 26CG | 25C39 | 66CA | 48.23 |
| 26CG | 25C39 | 23O | 61.96 |
| 66C | 25C39 | 65N | 80.62 |
| 66C | 25C39 | 26N | 79.15 |
| 66C | 25C39 | 66CA | 18.48 |
| 66C | 25C39 | 23O | 96.37 |
| 65N | 25C39 | 26N | 97.76 |
| 65N | 25C39 | 66CA | 62.14 |
| 65N | 25C39 | 23O | 37.19 |
| 26N | 25C39 | 66CA | 83.19 |
| 26N | 25C39 | 23O | 67.94 |
| 66CA | 25C39 | 23O | 81.21 |
| 66N | 25O40 | 66O | 55.03 |
| 66N | 25O40 | 26CD1 | 68.97 |
| 66N | 25O40 | 65CA | 46.68 |
| 66N | 25O40 | 26CB | 85.08 |
| 66N | 25O40 | 26CG | 70.07 |
| 66N | 25O40 | 65C | 21.06 |
| 66N | 25O40 | 66C | 40.07 |
| 66N | 25O40 | 66CA | 17.56 |
| 66N | 25O40 | 26NE1 | 58.94 |
| 66N | 25O40 | 65N | 53.77 |
| 66N | 25O40 | 23O | 82.65 |
| 66N | 25O40 | 26CD2 | 60.09 |
| 66N | 25O40 | 65O | 19.20 |
| 66N | 25O40 | 26CE2 | 54.44 |
| 66O | 25O40 | 26CD1 | 89.64 |
| 66O | 25O40 | 26CB | 63.20 |
| 66O | 25O40 | 26CG | 71.47 |
| 66O | 25O40 | 65C | 75.92 |
| 66O | 25O40 | 66C | 15.74 |
| 66O | 25O40 | 66CA | 38.45 |
| 66O | 25O40 | 26N | 99.32 |
| 66O | 25O40 | 26NE1 | 91.06 |
| 66O | 25O40 | 26CA | 79.34 |
| 66O | 25O40 | 26CD2 | 68.55 |
| 66O | 25O40 | 65O | 74.21 |
| 66O | 25O40 | 68CE | 47.85 |
| 66O | 25O40 | 26CE2 | 78.85 |
| 26CD1 | 25O40 | 65CA | 74.34 |
| 26CD1 | 25O40 | 26CB | 46.12 |
| 26CD1 | 25O40 | 26CG | 22.72 |
| 26CD1 | 25O40 | 65C | 67.94 |
| 26CD1 | 25O40 | 66C | 79.23 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 26CD1 | 25O40 | 66CA | 69.49 |
| 26CD1 | 25O40 | 25SG | 92.07 |
| 26CD1 | 25O40 | 26N | 50.30 |
| 26CD1 | 25O40 | 26NE1 | 14.37 |
| 26CD1 | 25O40 | 26CA | 50.84 |
| 26CD1 | 25O40 | 65N | 70.61 |
| 26CD1 | 25O40 | 23O | 51.41 |
| 26CD1 | 25O40 | 26CD2 | 21.35 |
| 26CD1 | 25O40 | 65O | 66.27 |
| 26CD1 | 25O40 | 68CE | 92.41 |
| 26CD1 | 25O40 | 26CE2 | 14.76 |
| 26CD1 | 25O40 | 25N | 52.65 |
| 65CA | 25O40 | 26CG | 91.43 |
| 65CA | 25O40 | 65C | 25.75 |
| 65CA | 25O40 | 66C | 86.58 |
| 65CA | 25O40 | 66CA | 64.21 |
| 65CA | 25O40 | 26NE1 | 60.05 |
| 65CA | 25O40 | 65N | 8.97 |
| 65CA | 25O40 | 23O | 48.18 |
| 65CA | 25O40 | 26CD2 | 82.47 |
| 65CA | 25O40 | 65O | 27.92 |
| 65CA | 25O40 | 26CE2 | 67.12 |
| 65CA | 25O40 | 25N | 97.61 |
| 26CB | 25O40 | 26CG | 24.84 |
| 26CB | 25O40 | 65C | 97.95 |
| 26CB | 25O40 | 66C | 63.62 |
| 26CB | 25O40 | 66CA | 72.60 |
| 26CB | 25O40 | 25SG | 89.79 |
| 26CB | 25O40 | 26N | 37.46 |
| 26CB | 25O40 | 26NE1 | 58.62 |
| 26CB | 25O40 | 26CA | 19.07 |
| 26CB | 25O40 | 23O | 95.25 |
| 26CB | 25O40 | 26CD2 | 33.11 |
| 26CB | 25O40 | 65O | 95.49 |
| 26CB | 25O40 | 68CE | 46.43 |
| 26CB | 25O40 | 26CE2 | 49.00 |
| 26CB | 25O40 | 25N | 67.75 |
| 26CG | 25O40 | 65C | 77.41 |
| 26CG | 25O40 | 66C | 64.77 |
| 26CG | 25O40 | 66CA | 63.32 |
| 26CG | 25O40 | 25SG | 97.02 |
| 26CG | 25O40 | 26N | 44.89 |
| 26CG | 25O40 | 26NE1 | 33.94 |
| 26CG | 25O40 | 26CA | 35.84 |
| 26CG | 25O40 | 65N | 89.76 |
| 26CG | 25O40 | 23O | 74.03 |
| 26CG | 25O40 | 26CD2 | 10.27 |
| 26CG | 25O40 | 65O | 75.16 |
| 26CG | 25O40 | 68CE | 70.18 |
| 26CG | 25O40 | 26CE2 | 24.36 |
| 26CG | 25O40 | 25N | 62.89 |
| 65C | 25O40 | 66C | 61.12 |
| 65C | 25O40 | 66CA | 38.51 |
| 65C | 25O40 | 26NE1 | 54.62 |
| 65C | 25O40 | 65N | 32.73 |
| 65C | 25O40 | 23O | 65.00 |
| 65C | 25O40 | 26CD2 | 67.24 |
| 65O | 25O40 | 65O | 2.52 |
| 66C | 25O40 | 26CE2 | 55.73 |
| 66C | 25O40 | 66CA | 22.95 |
| 66C | 25O40 | 26NE1 | 78.03 |
| 66C | 25O40 | 26CA | 81.98 |
| 66C | 25O40 | 65N | 93.83 |
| 66C | 25O40 | 26CD2 | 59.43 |
| 66C | 25O40 | 65O | 59.25 |
| 66C | 25O40 | 68CE | 60.81 |
| 66C | 25O40 | 26CE2 | 66.69 |
| 66CA | 25O40 | 26NE1 | 63.40 |
| 66CA | 25O40 | 26CA | 91.57 |
| 66CA | 25O40 | 65N | 71.07 |
| 66CA | 25O40 | 23O | 96.11 |
| 66CA | 25O40 | 26CD2 | 54.65 |
| 66CA | 25O40 | 65O | 36.50 |
| 66CA | 25O40 | 68CE | 82.71 |
| 66CA | 25O40 | 26CE2 | 54.95 |
| 25SG | 25O40 | 26N | 53.76 |
| 25SG | 25O40 | 26CA | 70.74 |
| 25SG | 25O40 | 23O | 76.38 |
| 25SG | 25O40 | 68CE | 91.56 |
| 25SG | 25O40 | 25N | 39.87 |
| 26N | 25O40 | 26NE1 | 64.06 |
| 26N | 25O40 | 26CA | 19.99 |
| 26N | 25O40 | 23O | 77.54 |
| 26N | 25O40 | 26CD2 | 54.76 |
| 26N | 25O40 | 68CE | 65.32 |
| 26N | 25O40 | 26CE2 | 62.82 |
| 26N | 25O40 | 25N | 33.74 |
| 26NE1 | 25O40 | 26CA | 65.10 |
| 26NE1 | 25O40 | 65N | 56.73 |
| 26NE1 | 25O40 | 23O | 44.12 |
| 26NE1 | 25O40 | 26CD2 | 28.39 |
| 26NE1 | 25O40 | 65O | 53.18 |
| 26NE1 | 25O40 | 26CE2 | 12.89 |
| 26NE1 | 25O40 | 25N | 60.41 |
| 26CA | 25O40 | 23O | 91.40 |
| 26CA | 25O40 | 26CD2 | 45.97 |
| 26CA | 25O40 | 68CE | 49.24 |
| 26CA | 25O40 | 26CE2 | 59.06 |
| 26CA | 25O40 | 25N | 53.14 |
| 65N | 25O40 | 23O | 39.46 |
| 65N | 25O40 | 26CD2 | 81.69 |
| 65N | 25O40 | 65O | 34.59 |
| 65N | 25O40 | 26CE2 | 65.52 |
| 65N | 25O40 | 25N | 89.01 |
| 23O | 25O40 | 26CD2 | 71.57 |
| 23O | 25O40 | 65O | 65.65 |
| 23O | 25O40 | 26CE2 | 57.01 |
| 23O | 25O40 | 25N | 49.58 |
| 26CD2 | 25O40 | 65O | 64.96 |
| 26CD2 | 25O40 | 68CE | 75.92 |
| 26CD2 | 25O40 | 26CE2 | 16.58 |
| 26CD2 | 25O40 | 25N | 69.33 |
| 65O | 25O40 | 26CE2 | 53.78 |
| 68CE | 25O40 | 26CE2 | 92.46 |
| 68CE | 25O40 | 25N | 97.92 |
| 26CE2 | 25O40 | 25N | 67.27 |
| 25SG | 25N41 | 161O | 80.59 |
| 25SG | 25N41 | 23O | 90.56 |
| 25SG | 25N41 | 26CD1 | 82.77 |
| 25SG | 25N41 | 25CB | 9.91 |
| 25SG | 25N41 | 23C | 79.09 |
| 25SG | 25N41 | 25N | 40.23 |
| 25SG | 25N41 | 161C | 80.64 |
| 25SG | 25N41 | 26N | 46.58 |
| 25SG | 25N41 | 162CA | 52.67 |
| 25SG | 25N41 | 163N | 39.29 |
| 65CA | 25N41 | 23O | 48.79 |
| 65CA | 25N41 | 26CD1 | 53.27 |
| 65CA | 25N41 | 66N | 31.72 |
| 65CA | 25N41 | 23C | 63.36 |
| 65CA | 25N41 | 65N | 14.93 |
| 65CA | 25N41 | 65C | 15.53 |
| 65CA | 25N41 | 25N | 93.22 |
| 65CA | 25N41 | 26N | 91.88 |
| 161O | 25N41 | 25CB | 89.53 |
| 161O | 25N41 | 161C | 13.63 |
| 161O | 25N41 | 162CA | 33.89 |
| 161O | 25N41 | 163N | 62.20 |
| 23O | 25N41 | 26CD1 | 48.03 |
| 23O | 25N41 | 66N | 68.57 |
| 23O | 25N41 | 25CB | 80.86 |
| 23O | 25N41 | 23C | 14.88 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
|---|---|---|---|
| 23O | 25N41 | 65N | 39.21 |
| 23O | 25N41 | 65C | 57.67 |
| 23O | 25N41 | 25N | 51.81 |
| 23O | 25N41 | 26N | 71.06 |
| 26CD1 | 25N41 | 66N | 42.24 |
| 26CD1 | 25N41 | 25CB | 74.76 |
| 26CD1 | 25N41 | 23C | 56.38 |
| 26CD1 | 25N41 | 65N | 58.93 |
| 26CD1 | 25N41 | 65C | 46.09 |
| 26CD1 | 25N41 | 25N | 50.77 |
| 26CD1 | 25N41 | 26N | 38.61 |
| 26CD1 | 25N41 | 163N | 98.70 |
| 66N | 25N41 | 23C | 82.86 |
| 66N | 25N41 | 65N | 46.23 |
| 66N | 25N41 | 65C | 16.19 |
| 66N | 25N41 | 25N | 92.91 |
| 66N | 25N41 | 26N | 75.02 |
| 25CB | 25N41 | 23C | 69.90 |
| 25CB | 25N41 | 25N | 30.33 |
| 25CB | 25N41 | 161C | 90.33 |
| 25CB | 25N41 | 26N | 40.90 |
| 25CB | 25N41 | 162CA | 62.56 |
| 25CB | 25N41 | 163N | 48.01 |
| 23C | 25N41 | 65N | 52.61 |
| 23C | 25N41 | 65C | 72.52 |
| 23C | 25N41 | 25N | 43.58 |
| 23C | 25N41 | 26N | 69.77 |
| 65N | 25N41 | 65C | 30.16 |
| 65N | 25N41 | 25N | 89.00 |
| 65N | 25N41 | 26N | 96.17 |
| 65C | 25N41 | 25N | 93.25 |
| 65C | 25N41 | 26N | 83.49 |
| 25N | 25N41 | 26N | 33.34 |
| 25N | 25N41 | 162CA | 92.88 |
| 25N | 25N41 | 163N | 75.53 |
| 161C | 25N41 | 162CA | 28.77 |
| 161C | 25N41 | 163N | 54.46 |
| 26N | 25N41 | 162CA | 89.00 |
| 26N | 25N41 | 163N | 62.08 |
| 162CA | 25N41 | 163N | 28.61 |
| 25SG | 25C42 | 25N | 61.47 |
| 25SG | 25C42 | 25CB | 23.02 |
| 25SG | 25C42 | 24N | 99.07 |
| 25SG | 25C42 | 26N | 58.96 |
| 25SG | 25C42 | 25CA | 42.76 |
| 25SG | 25C42 | 24C | 76.26 |
| 25SG | 25C42 | 24CA | 95.01 |
| 25SG | 25C42 | 25C | 46.56 |
| 25SG | 25C42 | 26CG | 94.70 |
| 25SG | 25C42 | 26CB | 80.63 |
| 23O | 25C42 | 23C | 20.90 |
| 23O | 25C42 | 25N | 72.70 |
| 23O | 25C42 | 26CD1 | 61.41 |
| 23O | 25C42 | 65CA | 57.62 |
| 23O | 25C42 | 23CA | 37.29 |
| 23O | 25C42 | 24N | 34.67 |
| 23O | 25C42 | 26N | 92.67 |
| 23O | 25C42 | 25CA | 92.41 |
| 23O | 25C42 | 24C | 59.75 |
| 23O | 25C42 | 24CA | 39.73 |
| 23O | 25C42 | 65N | 43.51 |
| 23O | 25C42 | 26NE1 | 46.24 |
| 23O | 25C42 | 25C | 96.61 |
| 23C | 25C42 | 26CG | 73.49 |
| 23O | 25C42 | 66N | 75.31 |
| 23O | 25C42 | 65C | 62.99 |
| 23O | 25C42 | 26CB | 90.54 |
| 23C | 25C42 | 25N | 60.95 |
| 23C | 25C42 | 26CD1 | 74.34 |
| 23C | 25C42 | 65CA | 77.95 |
| 23C | 25C42 | 25CB | 94.36 |
| 23C | 25C42 | 23CA | 22.31 |
| 23C | 25C42 | 24N | 19.02 |
| 23C | 25C42 | 26N | 92.21 |
| 23C | 25C42 | 25CA | 80.52 |
| 23C | 25C42 | 24C | 52.38 |
| 23C | 25C42 | 24CA | 33.67 |
| 23C | 25C42 | 65N | 62.45 |
| 23C | 25C42 | 26NE1 | 61.04 |
| 23C | 25C42 | 25C | 90.42 |
| 23C | 25C42 | 26CC | 85.04 |
| 23C | 25C42 | 66N | 95.80 |
| 23C | 25C42 | 65C | 83.89 |
| 25N | 25C42 | 26CD1 | 66.35 |
| 25N | 25C42 | 25CB | 38.84 |
| 25N | 25C42 | 23CA | 73.38 |
| 25N | 25C42 | 24N | 41.94 |
| 25N | 25C42 | 26N | 41.41 |
| 25N | 25C42 | 25CA | 19.88 |
| 25N | 25C42 | 24C | 16.17 |
| 25N | 25C42 | 24CA | 33.54 |
| 25N | 25C42 | 26NE1 | 68.49 |
| 25N | 25C42 | 25C | 31.76 |
| 25N | 25C42 | 26CG | 65.77 |
| 25N | 25C42 | 26CB | 67.36 |
| 26CD1 | 25C42 | 65CA | 59.61 |
| 26CD1 | 25C42 | 25CB | 93.02 |
| 26CD1 | 25C42 | 23CA | 96.28 |
| 26CD1 | 25C42 | 24N | 69.60 |
| 26CD1 | 25C42 | 26N | 46.05 |
| 26CD1 | 25C42 | 25CA | 73.18 |
| 26CD1 | 25C42 | 24C | 52.84 |
| 26CD1 | 25C42 | 24CA | 52.35 |
| 26CD1 | 25C42 | 65N | 66.14 |
| 26CD1 | 25C42 | 26NE1 | 15.58 |
| 26CD1 | 25C42 | 25C | 60.30 |
| 26CD1 | 25C42 | 26CG | 12.37 |
| 26CD1 | 25C42 | 66N | 42.73 |
| 26CD1 | 25C42 | 65C | 47.92 |
| 26CD1 | 25C42 | 26CB | 29.69 |
| 65CA | 25C42 | 23CA | 85.42 |
| 65CA | 25C42 | 24N | 91.42 |
| 65CA | 25C42 | 24CA | 88.16 |
| 65CA | 25C42 | 65N | 17.82 |
| 65CA | 25C42 | 26NE1 | 51.70 |
| 65CA | 25C42 | 26CG | 67.28 |
| 65CA | 25C42 | 66N | 29.94 |
| 65CA | 25C42 | 65C | 14.64 |
| 65CA | 25C42 | 26CB | 78.77 |
| 25CB | 25C42 | 23CA | 97.37 |
| 25CB | 25C42 | 24N | 76.40 |
| 25CB | 25C42 | 26N | 48.95 |
| 25CE | 25C42 | 25CA | 21.77 |
| 25CB | 25C42 | 24C | 54.30 |
| 25CB | 25C42 | 24CA | 72.26 |
| 25CB | 25C42 | 25C | 33.23 |
| 25CB | 25C42 | 26CG | 86.02 |
| 25CB | 25C42 | 26CB | 76.81 |
| 23CA | 25C42 | 24N | 35.27 |
| 23CA | 25C42 | 25CA | 90.57 |
| 23CA | 25C42 | 24C | 69.58 |
| 23CA | 25C42 | 24CA | 53.60 |
| 23CA | 25C42 | 65N | 67.73 |
| 23CA | 25C42 | 26NE1 | 82.24 |
| 23CA | 25C42 | 65C | 95.61 |
| 24N | 25C42 | 26N | 75.74 |
| 24N | 25C42 | 25CA | 61.52 |
| 24N | 25C42 | 24C | 34.63 |
| 24N | 25C42 | 24CA | 19.12 |
| 24N | 25C42 | 65N | 78.18 |
| 24N | 25C42 | 26NE1 | 60.00 |
| 24N | 25C42 | 25C | 71.96 |

TABLE XVI-continued

Table of angles between atoms of the inhibitor and protein for all protein atoms within 5 Ångstroms of the inhibitor 4-[N-[(phenylmethoxy)carbonyl]-L-leucyl]-1-[N-[(Phenylmethoxy)carbonyl]-L-leucyl]-3-pyrrolidinone

| Atom 1 | Atom 2 | Atom 3 | Angle in degrees |
| --- | --- | --- | --- |
| 24N | 25C42 | 26CG | 77.77 |
| 24N | 25C42 | 65C | 93.70 |
| 24N | 25C42 | 26CB | 89.98 |
| 26N | 25C42 | 25CA | 34.07 |
| 26N | 25C42 | 24C | 41.33 |
| 26N | 25C42 | 24CA | 58.54 |
| 26N | 25C42 | 25NE1 | 58.48 |
| 26N | 25C42 | 25C | 16.06 |
| 26N | 25C42 | 25CG | 37.28 |
| 26N | 25C42 | 66N | 80.08 |
| 26N | 25C42 | 65C | 91.09 |
| 26N | 25C42 | 25CB | 29.32 |
| 25CA | 25C42 | 24C | 33.53 |
| 25CA | 25C42 | 24CA | 52.86 |
| 25CA | 25C42 | 26NE1 | 80.09 |
| 25CA | 25C42 | 25C | 18.89 |
| 25CA | 25C42 | 26CG | 68.25 |
| 25CA | 25C42 | 26CB | 63.36 |
| 24C | 25C42 | 24CA | 20.14 |
| 24C | 25C42 | 65N | 97.32 |
| 24C | 25C42 | 26NE1 | 52.89 |
| 24C | 25C42 | 25C | 38.23 |
| 24C | 25C42 | 26CG | 54.87 |
| 24C | 25C42 | 66N | 95.24 |
| 24C | 25C42 | 65C | 96.26 |
| 24C | 25C42 | 26CB | 60.96 |
| 24CA | 25C42 | 65N | 79.58 |
| 24CA | 25C42 | 26NE1 | 45.69 |
| 24CA | 25C42 | 25C | 58.08 |
| 24CA | 25C42 | 26CG | 59.27 |
| 24CA | 25C42 | 66N | 89.86 |
| 24CA | 25C42 | 65C | 85.80 |
| 24CA | 25C42 | 26CB | 70.86 |
| 65N | 25C42 | 26NE1 | 54.04 |
| 65N | 25C42 | 26CG | 76.36 |
| 65N | 25C42 | 66N | 46.51 |
| 65N | 25C42 | 65C | 30.57 |
| 65N | 25C42 | 26CB | 90.76 |
| 26NE1 | 25C42 | 25C | 70.82 |
| 26NE1 | 25C42 | 26CG | 27.95 |
| 26NE1 | 25C42 | 66N | 44.28 |
| 26NE1 | 25C42 | 65C | 43.42 |
| 26NE1 | 25C42 | 26CB | 45.27 |
| 25C | 25C42 | 26CG | 52.79 |
| 25C | 25C42 | 66N | 96.14 |
| 25C | 25C42 | 26CB | 45.17 |
| 26CG | 25C42 | 66N | 44.88 |
| 26CG | 25C42 | 65C | 53.98 |
| 26CG | 25C42 | 26CB | 17.32 |
| 66N | 25C42 | 65C | 15.94 |
| 66N | 25C42 | 26CB | 51.51 |
| 65C | 25C42 | 26CB | 64.35 |
| 66N | 25N43 | 65CA | 39.20 |
| 66N | 25N43 | 66O | 42.83 |
| 66N | 25N43 | 65C | 19.66 |
| 66N | 25N43 | 66C | 33.44 |
| 66N | 25N43 | 66CA | 16.52 |
| 66N | 25N43 | 64O | 67.91 |
| 66N | 25N43 | 65O | 24.48 |
| 66N | 25N43 | 65N | 47.82 |
| 65CA | 25N43 | 66O | 79.74 |
| 65CA | 25N43 | 65C | 22.72 |
| 65CA | 25N43 | 66C | 72.52 |
| 65CA | 25N43 | 66CA | 54.97 |
| 65CA | 25N43 | 64O | 35.80 |
| 65CA | 25N43 | 65O | 27.77 |
| 65CA | 25N43 | 65N | 9.59 |
| 66O | 25N43 | 65C | 62.50 |
| 66O | 25N43 | 66C | 14.75 |
| 66O | 25N43 | 66CA | 32.80 |
| 66O | 25N43 | 65O | 66.04 |
| 66O | 25N43 | 65N | 89.14 |
| 65C | 25N43 | 66C | 52.38 |
| 65C | 25N43 | 66CA | 33.37 |
| 65C | 25N43 | 64O | 48.27 |
| 65C | 25N43 | 65O | 9.39 |
| 65C | 25N43 | 65N | 29.76 |
| 65C | 25N43 | 66CA | 19.82 |
| 65C | 25N43 | 64O | 99.32 |
| 65C | 25N43 | 65O | 54.13 |
| 65C | 25N43 | 65N | 81.27 |
| 66CA | 25N43 | 64O | 79.51 |
| 66CA | 25N43 | 65O | 34.33 |
| 66CA | 25N43 | 65N | 62.98 |
| 64O | 25N43 | 65O | 45.20 |
| 64O | 25N43 | 65N | 26.86 |
| 65O | 25N43 | 65N | 32.42 |

TABLE XVII

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
| --- | --- | --- | --- | --- | --- | --- | --- |
| 67CE2 | 25C1 | 67CD2 | 21.66 | 67CE2 | 25C1 | 60ND2 | 88.40 |
| 67CE2 | 25C1 | 67CZ | 15.07 | 67CE2 | 25C1 | 23IOH2 | 72.49 |
| 67CE2 | 25C1 | 67OH | 28.98 | 67CE2 | 25C1 | 66CA | 80.69 |
| 67CE2 | 25C1 | 67CG | 26.79 | 67CE2 | 25C1 | 70ND2 | 78.17 |
| 67CD2 | 25C1 | 60ND2 | 67.38 | 67CD2 | 25C1 | 67CZ | 33.45 |
| 67CD2 | 25C1 | 23IOH2 | 62.87 | 67CD2 | 25C1 | 67OH | 49.60 |

TABLE XVII-continued

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
|---|---|---|---|---|---|---|---|
| 67CD2 | 25C1 | 66CA | 68.97 | 67CD2 | 25C1 | 67CG | 10.46 |
| 67CD2 | 25C1 | 70ND2 | 58.29 | 60ND2 | 25C1 | 67CZ | 95.36 |
| 60ND2 | 25C1 | 59O | 49.64 | 60ND2 | 25C1 | 231OH2 | 73.76 |
| 60ND2 | 25C1 | 66CA | 42.03 | 60ND2 | 25C1 | 65O | 60.94 |
| 60ND2 | 25C1 | 67CG | 61.96 | 60ND2 | 25C1 | 70ND2 | 36.62 |
| 67CZ | 25C1 | 231OH2 | 87.30 | 67CZ | 25C1 | 67OH | 16.70 |
| 67CZ | 25C1 | 66CA | 77.40 | 67CZ | 25C1 | 67CG | 34.47 |
| 67CZ | 25C1 | 70ND2 | 91.66 | 59O | 25C1 | 231OH2 | 59.15 |
| 59O | 25C1 | 66CA | 86.93 | 59O | 25C1 | 65O | 85.11 |
| 59O | 25C1 | 70ND2 | 43.49 | 231OH2 | 25C1 | 67OH | 96.03 |
| 231OH2 | 25C1 | 67CG | 71.00 | 231OH2 | 25C1 | 70ND2 | 37.14 |
| 67OH | 25C1 | 66CA | 87.65 | 67OH | 25C1 | 67CG | 51.17 |
| 66CA | 25C1 | 65O | 33.94 | 66CA | 25C1 | 67CG | 58.73 |
| 66CA | 25C1 | 70ND2 | 75.50 | 65O | 25C1 | 67CG | 92.09 |
| 65O | 25C1 | 70ND2 | 97.34 | 67CG | 25C1 | 70ND2 | 60.11 |
| 67CE2 | 25C2 | 67CZ | 20.70 | 67CE2 | 25C2 | 67CD2 | 20.73 |
| 67CE2 | 25C2 | 67OH | 36.29 | 67CE2 | 25C2 | 66CA | 91.85 |
| 67CE2 | 25C2 | 67CE1 | 28.15 | 67CE2 | 25C2 | 60ND2 | 82.91 |
| 67CE2 | 25C2 | 66C | 74.08 | 67CE2 | 25C2 | 67CG | 28.19 |
| 67CE2 | 25C2 | 67N | 63.54 | 67CZ | 25C2 | 67CD2 | 36.53 |
| 67CZ | 25C2 | 67OH | 19.80 | 67CZ | 25C2 | 66CA | 91.39 |
| 67CZ | 25C2 | 66N | 97.52 | 67CZ | 25C2 | 67CE1 | 14.08 |
| 67CZ | 25C2 | 60ND2 | 96.48 | 67CZ | 25C2 | 66C | 73.78 |
| 67CZ | 25C2 | 67CG | 36.08 | 67CA | 25C2 | 67N | 68.45 |
| 67CD2 | 25C2 | 67OH | 55.27 | 67CD2 | 25C2 | 66CA | 75.10 |
| 67CD2 | 25C2 | 66N | 89.93 | 67CD2 | 25C2 | 67CE1 | 35.97 |
| 67CD2 | 25C2 | 60ND2 | 62.30 | 67CD2 | 25C2 | 66C | 58.50 |
| 67CD2 | 25C2 | 67CG | 13.99 | 67CD2 | 25C2 | 67N | 45.40 |
| 67OH | 25C2 | 67CE1 | 30.01 | 67OH | 25C2 | 66C | 90.02 |
| 67OH | 25C2 | 67CG | 55.88 | 67OH | 25C2 | 67N | 87.15 |
| 66CA | 25C2 | 65O | 39.05 | 66CA | 25C2 | 66N | 18.31 |
| 66CA | 25C2 | 65C | 31.60 | 66CA | 25C2 | 67CE1 | 77.85 |
| 66CA | 25C2 | 60ND2 | 42.40 | 66CA | 25C2 | 66C | 17.99 |
| 66CA | 25C2 | 67CG | 63.85 | 66CA | 25C2 | 67N | 29.89 |
| 65O | 25C2 | 66N | 29.44 | 65O | 25C2 | 65C | 15.02 |
| 65O | 25C2 | 60ND2 | 62.06 | 65O | 25C2 | 66C | 56.82 |
| 65O | 25C2 | 67N | 68.16 | 66N | 25C2 | 65C | 16.65 |
| 66N | 25C2 | 67CE1 | 83.45 | 66N | 25C2 | 60ND2 | 59.05 |
| 66N | 25C2 | 66C | 31.58 | 66N | 25C2 | 67CG | 77.19 |
| 66N | 25C2 | 67N | 46.44 | 65C | 25C2 | 67CE1 | 99.01 |
| 65C | 25C2 | 60ND2 | 65.42 | 65C | 25C2 | 66C | 47.55 |
| 65C | 25C2 | 67CG | 29.84 | 67CE1 | 25C2 | 67N | 61.39 |
| 67CE1 | 25C2 | 60ND2 | 88.93 | 67CE1 | 25C2 | 66C | 60.58 |
| 67CE1 | 25C2 | 67CG | 29.84 | 67CE1 | 25C2 | 67N | 57.26 |
| 60ND2 | 25C2 | 66C | 44.34 | 60ND2 | 25C2 | 67CG | 60.48 |
| 60ND2 | 25C2 | 67N | 35.75 | 66C | 25C2 | 67CG | 46.38 |
| 66C | 25C2 | 67N | 15.93 | 67CG | 25C2 | 67N | 35.42 |
| 65O | 25C3 | 65C | 17.88 | 65O | 25C3 | 66CA | 41.69 |
| 65O | 25C3 | 66N | 32.43 | 65O | 25C3 | 61CB | 43.31 |
| 65O | 25C3 | 65CA | 28.80 | 65O | 25C3 | 61CG | 61.48 |
| 65O | 25C3 | 61OD1 | 68.40 | 65C | 25C3 | 66CA | 35.13 |
| 65C | 25C3 | 66B | 18.49 | 65C | 25C3 | 61CB | 59.01 |
| 65C | 25C3 | 65CA | 16.90 | 65C | 25C3 | 61CG | 77.19 |
| 65C | 25C3 | 61OD1 | 85.63 | 65CA | 25C3 | 66N | 20.18 |
| 66CA | 25C3 | 67CE2 | 75.24 | 66CA | 25C3 | 61CB | 82.37 |
| 66CA | 25C3 | 65CA | 50.05 | 66CA | 25C3 | 61CG | 99.19 |
| 66CA | 25C3 | 67CZ | 76.99 | 66CA | 25C3 | 67OH | 90.94 |
| 66N | 25C3 | 67CE2 | 90.18 | 66N | 25C3 | 61CB | 75.69 |
| 66N | 25C3 | 65CA | 30.59 | 66N | 25C3 | 61CG | 93.89 |
| 66N | 25C3 | 67CZ | 87.56 | 66N | 25C3 | 67OH | 98.55 |
| 67CE2 | 25C3 | 67CZ | 16.06 | 67CE2 | 25C3 | 67OH | 28.37 |
| 61CB | 25C3 | 65CA | 59.68 | 61CB | 25C3 | 61CG | 18.24 |
| 61CB | 25C3 | 61OD1 | 28.38 | 65CA | 25C3 | 61CG | 76.44 |
| 65CA | 25C3 | 61OD1 | 88.03 | 61CG | 25C3 | 61OD1 | 14.65 |
| 67CZ | 25C3 | 67OH | 15.78 | 65O | 25C4 | 61CG | 81.72 |
| 65O | 25C4 | 61CB | 56.74 | 65O | 25C4 | 61OD1 | 92.04 |
| 65O | 25C4 | 61OD2 | 90.06 | 65O | 25C4 | 65C | 13.06 |
| 65O | 25C4 | 61N | 47.80 | 65O | 25C4 | 61CA | 52.82 |
| 65O | 25C4 | 66CA | 34.06 | 65O | 25C4 | 66N | 23.80 |
| 65O | 25C4 | 60C | 59.87 | 65O | 25C4 | 65CA | 23.94 |
| 61CG | 25C4 | 61CB | 24.99 | 61CG | 25C4 | 61OD1 | 20.63 |
| 61CG | 25C4 | 61OD2 | 17.88 | 61CG | 25C4 | 65C | 91.97 |

TABLE XVII-continued

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
|---|---|---|---|---|---|---|---|
| 61CG | 25C4 | 61N | 50.91 | 61CG | 25C4 | 61CA | 33.78 |
| 61CG | 25C4 | 60C | 56.14 | 61CG | 25C4 | 65CA | 87.08 |
| 61CB | 25C4 | 61OD1 | 39.37 | 61CB | 25C4 | 61OD2 | 36.30 |
| 61CB | 25C4 | 65C | 67.18 | 61CB | 25C4 | 61N | 35.38 |
| 61CB | 25C4 | 61CA | 16.65 | 61CB | 25C4 | 66CA | 87.99 |
| 61CB | 25C4 | 66N | 80.49 | 61CB | 25C4 | 60C | 47.22 |
| 61CB | 25C4 | 65CA | 64.13 | 61OD1 | 25C4 | 61OD2 | 33.84 |
| 61OD1 | 25C4 | 61N | 49.82 | 61OD1 | 25C4 | 61CA | 39.25 |
| 61OD1 | 25C4 | 60C | 48.15 | 61OD2 | 25C4 | 65C | 97.59 |
| 61OD2 | 25C4 | 61N | 67.70 | 61OD2 | 25C4 | 61CA | 49.40 |
| 61OD2 | 25C4 | 60C | 73.98 | 61OD2 | 25C4 | 65CA | 88.32 |
| 65C | 25C4 | 61N | 60.83 | 65C | 25C4 | 61CA | 65.24 |
| 65C | 25C4 | 66CA | 30.77 | 65C | 25C4 | 66N | 15.04 |
| 65C | 25C4 | 60C | 72.43 | 65C | 25C4 | 65CA | 16.09 |
| 61N | 25C4 | 61CA | 19.04 | 61N | 25C4 | 66CA | 65.40 |
| 61N | 25C4 | 66N | 67.36 | 61N | 25C4 | 60C | 15.56 |
| 61N | 25C4 | 65CA | 68.40 | 61CA | 25C4 | 66CA | 78.91 |
| 61CA | 25C4 | 66N | 75.90 | 61CA | 25C4 | 60C | 30.75 |
| 61CA | 25C4 | 65CA | 67.27 | 66CA | 25C4 | 66N | 17.65 |
| 66CA | 25C4 | 60C | 69.36 | 66CA | 25C4 | 65CA | 45.82 |
| 66N | 25C4 | 60C | 75.84 | 66N | 25C4 | 65CA | 28.52 |
| 60C | 25C4 | 65CA | 82.21 | 61OD1 | 25C5 | 61CG | 21.34 |
| 61OD1 | 25C5 | 61CB | 38.98 | 61OD1 | 25C5 | 61N | 54.59 |
| 61OD1 | 25C5 | 65O | 86.61 | 61OD1 | 25C5 | 60C | 57.24 |
| 61OD1 | 25C5 | 61OD2 | 31.11 | 61OD1 | 25C5 | 59O | 91.41 |
| 61OD1 | 25C5 | 60CA | 77.36 | 61OD1 | 25C5 | 61CA | 39.29 |
| 61OD1 | 25C5 | 60O | 47.14 | 61CG | 25C5 | 61CB | 23.42 |
| 61CG | 25C5 | 61N | 53.21 | 61CG | 25C5 | 65O | 71.11 |
| 61CG | 25C5 | 60C | 63.55 | 61CG | 25C5 | 61OD2 | 15.46 |
| 61CG | 25C5 | 60CA | 84.04 | 61CG | 25C5 | 61CA | 34.30 |
| 61CG | 25C5 | 60O | 58.88 | 61CB | 25C5 | 61N | 36.38 |
| 61CB | 25C5 | 65O | 48.37 | 61CB | 25C5 | 60C | 52.26 |
| 61CB | 25C5 | 61OD2 | 34.12 | 61CB | 25C5 | 60CA | 70.23 |
| 61CB | 25C5 | 61CA | 19.16 | 61CB | 25C5 | 60O | 54.58 |
| 61CB | 25C5 | 60ND2 | 92.51 | 61N | 25C5 | 65O | 46.30 |
| 61N | 25C5 | 60C | 18.83 | 61N | 25C5 | 61OD2 | 67.79 |
| 61N | 25C5 | 59O | 68.18 | 61N | 25C5 | 60CA | 33.92 |
| 61N | 25C5 | 61CA | 19.02 | 61N | 25C5 | 60O | 29.73 |
| 61N | 25C5 | 60ND2 | 59.73 | 65O | 25C5 | 60C | 62.13 |
| 65O | 25C5 | 61OD2 | 76.92 | 65O | 25C5 | 59O | 97.98 |
| 65O | 25C5 | 60CA | 63.97 | 65O | 25C5 | 61CA | 50.38 |
| 65O | 25C5 | 60O | 75.74 | 65O | 25C5 | 60ND2 | 60.02 |
| 60C | 25C5 | 61OD2 | 79.00 | 60C | 25C5 | 59O | 50.32 |
| 60C | 25C5 | 60CA | 20.70 | 60C | 25C5 | 61CA | 33.16 |
| 60C | 25C5 | 60O | 15.46 | 60C | 25C5 | 60ND2 | 54.15 |
| 61OD2 | 25C5 | 60CA | 99.43 | 61OD2 | 25C5 | 61CA | 48.77 |
| 61OD2 | 25C5 | 60O | 73.92 | 59O | 25C5 | 60CA | 36.41 |
| 59O | 25C5 | 61CA | 83.15 | 59O | 25C5 | 60O | 49.36 |
| 59O | 25C5 | 60ND2 | 45.49 | 60CA | 25C5 | 61CA | 51.88 |
| 60CA | 25C5 | 60O | 31.33 | 60CA | 25C5 | 60ND2 | 34.90 |
| 61CA | 25C5 | 60O | 36.38 | 61CA | 25C5 | 60ND2 | 78.49 |
| 60O | 25C5 | 60ND2 | 66.22 | 59O | 25C6 | 61OD1 | 84.33 |
| 59O | 25C6 | 60CA | 37.74 | 59O | 25C6 | 60ND2 | 52.70 |
| 59O | 25C6 | 60C | 49.43 | 59O | 25C6 | 59C | 7.16 |
| 59O | 25C6 | 231OH2 | 61.67 | 59O | 25C6 | 65O | 96.01 |
| 59O | 25C6 | 61N | 65.44 | 59O | 25C6 | 61CG | 94.50 |
| 61OD1 | 25C6 | 60CA | 67.00 | 61OD1 | 25C6 | 60C | 47.52 |
| 61OD1 | 25C6 | 59C | 79.80 | 61OD1 | 25C6 | 65O | 65.95 |
| 61OD1 | 25C6 | 61N | 43.14 | 61OD1 | 25C6 | 61CG | 14.44 |
| 60CA | 25C6 | 60ND2 | 38.07 | 60CA | 25C6 | 60C | 19.60 |
| 60CA | 25C6 | 59C | 30.68 | 60CA | 25C6 | 231OH2 | 90.52 |
| 60CA | 25C6 | 65O | 58.49 | 60CA | 25C6 | 61N | 31.11 |
| 60CA | 25C6 | 61CG | 70.16 | 60ND2 | 25C6 | 60C | 55.78 |
| 60ND2 | 25C6 | 59C | 49.33 | 60ND2 | 25C6 | 231OH2 | 69.41 |
| 60ND2 | 25C6 | 65O | 60.19 | 60ND2 | 25C6 | 61N | 59.59 |
| 60ND2 | 25C6 | 67CE2 | 71.07 | 60C | 25C6 | 59C | 42.53 |
| 60C | 25C6 | 65O | 53.64 | 60C | 25C6 | 61N | 16.42 |
| 60C | 25C6 | 61CG | 50.89 | 59C | 25C6 | 231OH2 | 67.54 |
| 59C | 25C6 | 65O | 89.09 | 59C | 25C6 | 61N | 58.40 |
| 59C | 25C6 | 61CG | 89.02 | 231OH2 | 25C6 | 67CE2 | 58.91 |
| 65O | 25C6 | 61N | 38.82 | 65O | 25C6 | 61CG | 54.53 |
| 65O | 25C6 | 67CE2 | 90.16 | 61N | 25C6 | 61CG | 41.32 |

TABLE XVII-continued

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
| --- | --- | --- | --- | --- | --- | --- | --- |
| 65C | 25C7 | 65C | 20.61 | 65O | 25C7 | 66N | 35.57 |
| 65C | 25C7 | 65CA | 37.59 | 65O | 25C7 | 64O | 63.61 |
| 65O | 25C7 | 66CA | 40.23 | 65O | 25C7 | 65N | 36.78 |
| 65O | 25C7 | 64C | 50.16 | 65C | 25C7 | 66N | 20.13 |
| 65C | 25C7 | 65CA | 22.56 | 65C | 25C7 | 64O | 58.37 |
| 65C | 25C7 | 66CA | 34.64 | 65C | 25C7 | 65N | 30.89 |
| 65C | 25C7 | 64C | 46.81 | 66N | 25C7 | 65CA | 35.80 |
| 66N | 25C7 | 64O | 74.14 | 66N | 25C7 | 66CA | 19.87 |
| 66N | 25C7 | 65N | 48.83 | 66N | 25C7 | 64C | 64.44 |
| 65CA | 25C7 | 64O | 38.35 | 65CA | 25C7 | 66CA | 54.61 |
| 65CA | 25C7 | 65N | 16.17 | 65CA | 25C7 | 64C | 29.70 |
| 64C | 25C7 | 66CA | 92.52 | 64O | 25C7 | 65N | 28.03 |
| 64O | 25C7 | 64C | 13.53 | 66CA | 25C7 | 65N | 65.51 |
| 66CA | 25C7 | 64C | 81.44 | 66CA | 25C7 | 67OH | 89.07 |
| 65N | 25C7 | 64C | 15.93 | 66N | 25O8 | 65C | 20.16 |
| 66N | 25O8 | 66CA | 21.24 | 66N | 25O8 | 65O | 33.23 |
| 66N | 25O8 | 65CA | 33.75 | 66N | 25O8 | 67CE1 | 98.44 |
| 66N | 25O8 | 67CE2 | 98.98 | 66N | 25O8 | 66C | 34.36 |
| 66N | 25O8 | 66O | 36.02 | 66N | 25O8 | 64O | 65.86 |
| 65C | 25O8 | 66CA | 35.77 | 65C | 25O8 | 65O | 17.66 |
| 65C | 25O8 | 65CA | 20.48 | 65C | 25O8 | 66C | 52.97 |
| 65C | 25O8 | 66O | 56.18 | 65C | 25O8 | 64O | 48.74 |
| 66CA | 25O8 | 65O | 39.76 | 66CA | 25O8 | 67CZ | 88.60 |
| 66CA | 25O8 | 65CA | 53.75 | 66CA | 25O8 | 67CE1 | 82.16 |
| 66CA | 25O8 | 67CE2 | 78.01 | 66CA | 25O8 | 66C | 19.45 |
| 66CA | 25O8 | 66O | 29.94 | 66CA | 25O8 | 64O | 84.46 |
| 67OH | 25O8 | 67CZ | 19.19 | 67OH | 25O8 | 67CE1 | 31.81 |
| 67OH | 25O8 | 67CE2 | 31.82 | 67OH | 25O8 | 66C | 93.01 |
| 67OH | 25O8 | 66O | 95.44 | 65O | 25O8 | 65CA | 33.40 |
| 65O | 25O8 | 66C | 59.16 | 65O | 25O8 | 66O | 66.79 |
| 65O | 25O8 | 64O | 51.69 | 67CZ | 25O8 | 67CE1 | 17.96 |
| 67CZ | 25O8 | 67CE2 | 17.62 | 67CZ | 25O8 | 66C | 73.92 |
| 67CZ | 25O8 | 66O | 77.47 | 65CA | 25O8 | 66C | 67.93 |
| 65CA | 25O8 | 66O | 66.32 | 65CA | 25O8 | 64O | 32.46 |
| 67CE1 | 25O8 | 67CE2 | 30.82 | 67CE1 | 25O8 | 66C | 64.46 |
| 67CE1 | 25O8 | 66O | 64.18 | 67CE2 | 25O8 | 66C | 67.34 |
| 67CE2 | 25O8 | 66O | 75.18 | 66C | 25O8 | 66O | 15.05 |
| 66O | 25O8 | 64O | 98.36 | 66N | 25C9 | 65C | 19.56 |
| 66N | 25C9 | 65CA | 35.74 | 66N | 25C9 | 66CA | 18.50 |
| 66N | 25C9 | 65O | 29.44 | 66N | 25C9 | 66O | 37.27 |
| 66N | 25C9 | 64O | 68.91 | 66N | 25C9 | 66C | 32.34 |
| 66N | 25C9 | 67CE1 | 91.45 | 66N | 25C9 | 67CZ | 94.14 |
| 65C | 25C9 | 65CA | 21.89 | 65C | 25C9 | 66CA | 33.21 |
| 65C | 25C9 | 65O | 14.71 | 65C | 25C9 | 66O | 56.83 |
| 65C | 25C9 | 64O | 50.85 | 65C | 25C9 | 66C | 50.46 |
| 65CA | 25C9 | 66CA | 53.09 | 65CA | 25C9 | 65O | 31.99 |
| 65CA | 25C9 | 66O | 69.79 | 65CA | 25C9 | 64O | 34.59 |
| 65CA | 25C9 | 66C | 67.96 | 66CA | 25C9 | 65O | 35.79 |
| 66CA | 25C9 | 66O | 30.43 | 66CA | 25C9 | 64O | 83.99 |
| 66CA | 25C9 | 66C | 18.68 | 66CA | 25C9 | 67OH | 90.57 |
| 66CA | 25C9 | 67CE1 | 74.02 | 66CA | 25C9 | 67CZ | 75.67 |
| 65O | 25C9 | 66O | 64.42 | 65O | 25C9 | 64O | 51.51 |
| 65O | 25C9 | 66C | 54.47 | 65O | 25C9 | 67CZ | 97.86 |
| 66O | 25C9 | 66C | 15.18 | 66O | 25C9 | 67OH | 88.11 |
| 66O | 25C9 | 67CE1 | 62.23 | 66O | 25C9 | 67CZ | 72.01 |
| 66C | 25C9 | 67OH | 81.72 | 66C | 25C9 | 67CE1 | 59.79 |
| 66C | 25C9 | 67CZ | 65.61 | 67OH | 25C9 | 67CE1 | 28.34 |
| 67OH | 25C9 | 67CZ | 16.24 | 67CE1 | 25C9 | 67CZ | 16.27 |
| 65CA | 25O10 | 64O | 37.93 | 65CA | 25O10 | 65C | 19.98 |
| 65CA | 25O10 | 66N | 32.25 | 64O | 25O10 | 65C | 52.12 |
| 64O | 25O10 | 66N | 68.39 | 65C | 25O10 | 66N | 17.19 |
| 66N | 25N11 | 66O | 46.02 | 66N | 25N11 | 66C | 38.85 |
| 66N | 25N11 | 66CA | 20.73 | 66N | 25N11 | 65C | 17.46 |
| 66N | 25N11 | 65CA | 33.59 | 66N | 25N11 | 67CD1 | 91.49 |
| 66N | 25N11 | 65O | 24.15 | 66N | 25N11 | 67N | 48.38 |
| 66O | 25N11 | 66C | 17.87 | 66O | 25N11 | 66CA | 35.52 |
| 66O | 25N11 | 65C | 63.48 | 66O | 25N11 | 67CE1 | 75.71 |
| 66O | 25N11 | 65CA | 76.62 | 66O | 25N11 | 67CZ | 83.40 |
| 66O | 25N11 | 67CD1 | 58.50 | 66O | 25N11 | 67OH | 99.66 |
| 66O | 25N11 | 65O | 67.57 | 66O | 25N11 | 67N | 24.87 |
| 66C | 25N11 | 66CA | 21.72 | 66C | 25N11 | 65C | 54.97 |
| 66C | 25N11 | 67CE1 | 70.15 | 66C | 25N11 | 65CA | 72.37 |

TABLE XVII-continued

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
|---|---|---|---|---|---|---|---|
| 66C | 25N11 | 67CZ | 73.23 | 66C | 25N11 | 67CD1 | 54.55 |
| 66C | 25N11 | 67OH | 88.69 | 66C | 25N11 | 65O | 55.57 |
| 66C | 25N11 | 67N | 11.56 | 66CA | 25N11 | 65C | 34.29 |
| 66CA | 25N11 | 67CE1 | 83.75 | 66CA | 25N11 | 65CA | 53.45 |
| 66CA | 25N11 | 67CZ | 81.15 | 66CA | 25N11 | 67CD1 | 71.00 |
| 66CA | 25N11 | 67OH | 93.79 | 66CA | 25N11 | 65O | 33.86 |
| 66CA | 25N11 | 67N | 28.86 | 65C | 25N11 | 65CA | 20.50 |
| 65C | 25N11 | 65O | 12.17 | 65C | 25N11 | 67N | 63.15 |
| 67CE1 | 25N11 | 67CZ | 16.97 | 67CE1 | 25N11 | 67CD1 | 17.33 |
| 67CE1 | 25N11 | 67OH | 28.98 | 67CE1 | 25N11 | 67N | 58.73 |
| 65CA | 25N11 | 65O | 29.33 | 65CA | 25N11 | 67N | 81.90 |
| 67CZ | 25N11 | 67CD1 | 29.85 | 67CZ | 25N11 | 67OH | 16.29 |
| 67CZ | 25N11 | 65O | 95.29 | 67CZ | 25N11 | 67N | 61.81 |
| 67CD1 | 25N11 | 67OH | 44.88 | 67CD1 | 25N11 | 65O | 98.49 |
| 67CD1 | 25N11 | 67N | 43.62 | 67OH | 25N11 | 67N | 77.48 |
| 65O | 25N11 | 67N | 61.50 | 66N | 25C12 | 66N | 39.81 |
| 66C | 25C12 | 66C | 13.28 | 66O | 25C12 | 65CA | 68.49 |
| 66O | 25C12 | 66CA | 28.41 | 66O | 25C12 | 65C | 53.90 |
| 66N | 25C12 | 66C | 32.53 | 66N | 25C12 | 65CA | 30.03 |
| 66N | 25C12 | 66CA | 16.05 | 66N | 25C12 | 65C | 14.10 |
| 16lO | 25C12 | 16lC | 14.53 | 66C | 25C12 | 65CA | 62.55 |
| 66C | 25C12 | 66CA | 17.90 | 66C | 25C12 | 65C | 45.95 |
| 65CA | 25C12 | 66CA | 45.67 | 65CA | 25C12 | 65C | 17.89 |
| 66CA | 25C12 | 65C | 28.39 | 66O | 25C13 | 66N | 46.61 |
| 66O | 25C13 | 65CA | 81.12 | 66O | 25C13 | 26CB | 42.40 |
| 66O | 25C13 | 66C | 12.53 | 66O | 25C13 | 26CD1 | 59.74 |
| 66O | 25C13 | 65C | 61.86 | 66O | 25C13 | 66CA | 31.09 |
| 66O | 25C13 | 26CG | 46.38 | 66O | 25C13 | 26N | 73.59 |
| 66N | 25C13 | 65CA | 34.83 | 66N | 25C13 | 26CB | 65.68 |
| 66N | 25C13 | 66C | 35.92 | 66N | 25C13 | 26CD1 | 50.75 |
| 66N | 25C13 | 65C | 15.26 | 66N | 25C13 | 66CA | 16.54 |
| 66N | 25C13 | 26CG | 52.33 | 66N | 25C13 | 26N | 87.54 |
| 25SG | 25C13 | 26CB | 74.78 | 25SG | 25C13 | 26CD1 | 73.77 |
| 25SG | 25C13 | 26CG | 78.01 | 25SG | 25C13 | 26N | 43.94 |
| 25SG | 25C13 | 16lO | 62.15 | 65CA | 25C13 | 26CB | 87.36 |
| 65CA | 25C13 | 66C | 70.75 | 65CA | 25C13 | 26CD1 | 57.53 |
| 65CA | 25C13 | 65C | 20.04 | 65CA | 25C13 | 66CA | 51.26 |
| 65CA | 25C13 | 26CG | 69.09 | 65CA | 25C13 | 26N | 94.25 |
| 26CB | 25C13 | 66C | 51.08 | 26CB | 25C13 | 26CD1 | 34.05 |
| 26CB | 25C13 | 65C | 76.87 | 26CB | 25C13 | 66CA | 59.32 |
| 26CB | 25C13 | 26CG | 18.75 | 26CB | 25C13 | 26N | 31.21 |
| 66C | 25C13 | 26CD1 | 60.72 | 66C | 25C13 | 65C | 50.94 |
| 66C | 25C13 | 66CA | 19.59 | 66C | 25C13 | 26CG | 50.32 |
| 66C | 25C13 | 26N | 81.92 | 26CD1 | 25C13 | 65C | 54.60 |
| 26CD1 | 25C13 | 66CA | 55.37 | 26CD1 | 25C13 | 26CG | 16.44 |
| 26CD1 | 25C13 | 26N | 38.73 | 65C | 25C13 | 66CA | 31.37 |
| 65C | 25C13 | 26CG | 60.91 | 65C | 25C13 | 26N | 93.30 |
| 66CA | 25C13 | 26CG | 51.05 | 66CA | 25C13 | 26N | 86.68 |
| 26CG | 25C13 | 26N | 35.89 | 25SG | 25N14 | 23O | 84.00 |
| 25SG | 25N14 | 26CD1 | 79.14 | 25SG | 25N14 | 16lO | 68.92 |
| 25SG | 25N14 | 26N | 43.55 | 25SG | 25N14 | 23C | 74.81 |
| 25SG | 25N14 | 26CB | 70.46 | 25SG | 25N14 | 26CG | 77.79 |
| 65CA | 25N14 | 66N | 36.05 | 65CA | 25N14 | 23O | 53.08 |
| 65CA | 25N14 | 26CD1 | 61.64 | 65CA | 25N14 | 65C | 18.94 |
| 65CA | 25N14 | 66O | 73.48 | 65CA | 25N14 | 65N | 12.48 |
| 65CA | 25N14 | 26N | 99.87 | 65CA | 25N14 | 23C | 64.69 |
| 65CA | 25N14 | 26CB | 84.32 | 65CA | 25N14 | 26CG | 69.23 |
| 66N | 25N14 | 23O | 73.08 | 66N | 25N14 | 26CD1 | 49.53 |
| 66N | 25N14 | 65C | 17.28 | 66N | 25N14 | 66O | 37.50 |
| 66N | 25N14 | 65N | 47.78 | 66N | 25N14 | 26N | 82.41 |
| 66N | 25N14 | 23C | 86.05 | 66N | 25N14 | 26CB | 56.95 |
| 66N | 25N14 | 26CG | 48.25 | 23O | 25N14 | 26CD1 | 46.64 |
| 23O | 25N14 | 65C | 63.98 | 23O | 25N14 | 66O | 96.33 |
| 23O | 25N14 | 65N | 44.52 | 23O | 25N14 | 26N | 67.73 |
| 23O | 25N14 | 23C | 13.02 | 23O | 25N14 | 26CB | 76.26 |
| 23O | 25N14 | 26CG | 60.45 | 26CD1 | 25N14 | 65C | 55.15 |
| 26CD1 | 25N14 | 66O | 52.89 | 26CD1 | 25N14 | 65N | 64.11 |
| 26CD1 | 25N14 | 26N | 38.34 | 26CD1 | 25N14 | 23C | 54.90 |
| 26CD1 | 25N14 | 26CB | 30.70 | 26CD1 | 25N14 | 26CG | 13.86 |
| 65C | 25N14 | 66O | 54.77 | 65C | 25N14 | 65N | 31.08 |
| 65C | 25N14 | 26N | 92.32 | 65C | 25N14 | 23C | 76.79 |
| 65C | 25N14 | 26CB | 70.71 | 65C | 25N14 | 26CG | 58.49 |

TABLE XVII-continued

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
|---|---|---|---|---|---|---|---|
| 66O | 25N14 | 65N | 84.80 | 66O | 25N14 | 26N | 64.25 |
| 66O | 25N14 | 26CB | 35.42 | 66O | 25N14 | 26CG | 41.33 |
| 65N | 25N14 | 23C | 54.87 | 65N | 25N14 | 26CB | 90.63 |
| 65N | 25N14 | 26CG | 74.10 | 26N | 25N14 | 23C | 67.48 |
| 26N | 25N14 | 26CB | 29.19 | 26N | 25N14 | 26CG | 34.32 |
| 23C | 25N14 | 26CB | 82.14 | 23C | 25N14 | 26CG | 68.17 |
| 26CB | 25N14 | 26CG | 17.47 | 161O | 25C15 | 25SG | 89.42 |
| 161O | 25C15 | 161C | 13.49 | 161O | 25C15 | 162CA | 34.91 |
| 161O | 25C15 | 162N | 23.43 | 161O | 25C15 | 161CA | 23.63 |
| 25SG | 25C15 | 161C | 88.53 | 25SG | 25C15 | 162CA | 57.17 |
| 25SG | 25C15 | 162N | 74.53 | 161C | 25C15 | 162CA | 31.37 |
| 161C | 25C15 | 162N | 14.79 | 161C | 25C15 | 161CA | 16.28 |
| 162CA | 25C15 | 162N | 17.76 | 162CA | 25C15 | 161CA | 46.94 |
| 162N | 25C15 | 161CA | 29.37 | 65CA | 25C15 | 230OH2 | 72.79 |
| 25SG | 25C16 | 26N | 61.11 | 25SG | 25C16 | 25N | 59.97 |
| 25SG | 25C16 | 25CB | 23.02 | 25SG | 25C16 | 25CA | 42.42 |
| 25SG | 25C16 | 26CB | 88.58 | 25SG | 25C16 | 24N | 92.96 |
| 25SG | 25C16 | 25C | 48.34 | 25SG | 25C16 | 24C | 74.43 |
| 25SG | 25C16 | 26CA | 71.25 | 25SG | 25C16 | 24CA | 91.58 |
| 23O | 25C16 | 26CD1 | 61.77 | 23O | 25C16 | 26N | 94.53 |
| 23O | 25C16 | 25N | 67.24 | 23O | 25C16 | 23C | 18.20 |
| 23O | 25C16 | 65CA | 58.52 | 23O | 25C16 | 25CA | 87.06 |
| 23O | 25C16 | 26CG | 77.13 | 23O | 25C16 | 26NE4 | 47.29 |
| 23O | 25C16 | 26CB | 97.08 | 23O | 25C16 | 66N | 79.63 |
| 23O | 25C16 | 24N | 30.53 | 23O | 25C16 | 23CA | 32.27 |
| 23O | 25C16 | 25C | 94.82 | 23O | 25C16 | 24C | 56.19 |
| 23O | 25C16 | 26CA | 99.54 | 23O | 25C16 | 24CA | 36.83 |
| 23O | 25C16 | 65C | 67.39 | 23O | 25C16 | 65N | 45.21 |
| 26CD1 | 25C16 | 26N | 51.13 | 26CD1 | 25C16 | 25N | 68.54 |
| 26CD1 | 25C16 | 23C | 73.51 | 26CD1 | 25C16 | 65CA | 68.04 |
| 26CD1 | 25C16 | 25CB | 97.25 | 26CD1 | 25C16 | 25CA | 76.12 |
| 26CD1 | 25C16 | 26CG | 15.44 | 26CD1 | 25C16 | 26NE1 | 15.45 |
| 26CD1 | 25C16 | 26CB | 35.76 | 26CD1 | 25C16 | 66N | 52.08 |
| 26CD1 | 25C16 | 24N | 69.01 | 26CD1 | 25C16 | 23CA | 92.69 |
| 26CD1 | 25C16 | 25C | 63.96 | 26CD1 | 25C16 | 24C | 55.05 |
| 26CD1 | 25C16 | 26CA | 44.91 | 26CD1 | 25C16 | 24CA | 52.83 |
| 26CD1 | 25C16 | 65C | 56.87 | 26CD1 | 25C16 | 66O | 54.10 |
| 26CD1 | 25C16 | 65N | 69.48 | 26N | 25C16 | 25N | 44.67 |
| 26N | 25C16 | 23C | 93.12 | 26N | 25C16 | 25CB | 51.34 |
| 26N | 25C16 | 25CA | 35.79 | 26N | 25C16 | 26CG | 42.62 |
| 26N | 25C16 | 26NE1 | 63.79 | 26N | 25C16 | 26CB | 34.80 |
| 26N | 25C16 | 66N | 93.89 | 26N | 25C16 | 24N | 77.38 |
| 26N | 25C16 | 25C | 16.11 | 26N | 25C16 | 24C | 44.64 |
| 26N | 25C16 | 26CA | 16.33 | 26N | 25C16 | 24CA | 61.13 |
| 26N | 25C16 | 66O | 70.60 | 25N | 25C16 | 23C | 56.44 |
| 25N | 25C16 | 25CB | 37.16 | 25N | 25C16 | 25CA | 19.86 |
| 25N | 25C16 | 26CG | 71.75 | 25N | 25C16 | 26NE1 | 70.29 |
| 25N | 25C16 | 26CB | 75.60 | 25N | 25C16 | 24N | 39.16 |
| 25N | 25C16 | 23CA | 68.19 | 25N | 25C16 | 25C | 33.83 |
| 25N | 25C16 | 24C | 15.28 | 25N | 25C16 | 26CA | 60.18 |
| 25N | 25C16 | 24CA | 31.81 | 23C | 25C16 | 65CA | 74.98 |
| 23C | 25C16 | 25CB | 86.20 | 23C | 25C16 | 25CA | 75.86 |
| 23C | 25C16 | 26CG | 87.97 | 23C | 25C16 | 26NE1 | 60.92 |
| 23C | 25C16 | 66N | 97.84 | 23C | 25C16 | 24N | 17.30 |
| 23C | 25C16 | 23CA | 19.93 | 23C | 25C16 | 25C | 88.48 |
| 23C | 25C16 | 24C | 49.42 | 23C | 25C16 | 24CA | 32.05 |
| 23C | 25C16 | 65C | 85.33 | 23C | 25C16 | 65N | 60.76 |
| 65CA | 25C16 | 26CG | 76.49 | 65CA | 25C16 | 26NE1 | 57.92 |
| 65CA | 25C16 | 26CB | 90.45 | 65CA | 25C16 | 66N | 33.37 |
| 65CA | 25C16 | 24N | 89.01 | 65CA | 25C16 | 23CA | 76.80 |
| 65CA | 25C16 | 24CA | 90.04 | 65CA | 25C16 | 65C | 17.45 |
| 65CA | 25C16 | 66O | 68.34 | 65CA | 25C16 | 65N | 14.75 |
| 25CB | 25C16 | 25CA | 21.65 | 25CB | 25C16 | 26CG | 93.09 |
| 25CB | 25C16 | 26CB | 85.06 | 25CB | 25C16 | 24N | 70.81 |
| 25CB | 25C16 | 23CA | 89.00 | 25CB | 25C16 | 25C | 35.50 |
| 25CB | 25C16 | 24C | 52.00 | 25CB | 25C16 | 26CA | 65.90 |
| 25CB | 25C16 | 24CA | 68.59 | 25CA | 25C16 | 26CG | 73.95 |
| 25CA | 25C16 | 26NE1 | 82.49 | 25CA | 25C16 | 26CB | 70.49 |
| 25CA | 25C16 | 24N | 58.71 | 25CA | 25C16 | 23CA | 85.38 |
| 25CA | 25C16 | 25C | 20.38 | 25CA | 25C16 | 24C | 32.49 |
| 25CA | 25C16 | 26CA | 52.03 | 25CA | 25C16 | 24CA | 51.06 |
| 26CG | 25C16 | 26NE1 | 30.69 | 26CG | 25C16 | 26CB | 20.39 |

TABLE XVII-continued

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
|---|---|---|---|---|---|---|---|
| 26CG | 25C16 | 66N | 52.82 | 26CG | 25C16 | 24N | 81.30 |
| 26CG | 25C16 | 25C | 57.74 | 26CG | 25C16 | 24C | 60.85 |
| 26CG | 25C16 | 26CA | 32.36 | 26CG | 25C16 | 24CA | 63.73 |
| 26CG | 25C16 | 65C | 62.21 | 26CG | 25C16 | 66O | 43.58 |
| 26CG | 25C16 | 65N | 80.99 | 26NE1 | 25C16 | 26CB | 51.09 |
| 26NE1 | 25C16 | 66N | 51.16 | 26NE1 | 25C16 | 24N | 59.98 |
| 26NE1 | 25C16 | 23CA | 79.09 | 26NE1 | 25C16 | 25C | 74.44 |
| 26NE1 | 25C16 | 24C | 55.27 | 26NE1 | 25C16 | 26CA | 59.77 |
| 26NE1 | 25C16 | 24CA | 46.88 | 26NE1 | 25C16 | 65C | 50.71 |
| 26NE1 | 25C16 | 66O | 63.77 | 26NE1 | 25C16 | 65N | 56.44 |
| 26CB | 25C16 | 66N | 60.55 | 26CB | 25C16 | 24N | 96.31 |
| 26CB | 25C16 | 25C | 50.81 | 26CB | 25C16 | 24C | 69.20 |
| 26CB | 25C16 | 26CA | 19.18 | 26CB | 25C16 | 24CA | 77.92 |
| 26CB | 25C16 | 65C | 73.91 | 26CB | 25C16 | 66O | 36.73 |
| 26CB | 25C16 | 65N | 98.03 | 66N | 25C16 | 26CA | 79.58 |
| 66N | 25C16 | 24CA | 97.14 | 66N | 25C16 | 65C | 16.15 |
| 66N | 25C16 | 66O | 35.16 | 66N | 25C16 | 65N | 46.29 |
| 24N | 25C16 | 23CA | 32.77 | 24N | 25C16 | 25C | 71.39 |
| 24N | 25C16 | 24C | 32.88 | 24N | 25C16 | 26CA | 88.94 |
| 24N | 25C16 | 24CA | 18.41 | 24N | 25C16 | 65C | 96.24 |
| 24N | 25C16 | 65N | 75.67 | 23CA | 25C16 | 24C | 65.31 |
| 23CA | 25C16 | 24CA | 50.41 | 23CA | 25C16 | 65C | 91.28 |
| 23CA | 25C16 | 65N | 62.12 | 25C | 25C16 | 24C | 39.37 |
| 25C | 25C16 | 26CA | 31.92 | 25C | 25C16 | 24CA | 58.36 |
| 25C | 25C16 | 66O | 85.95 | 25C | 25C16 | 26CA | 57.54 |
| 24C | 25C16 | 24CA | 19.36 | 24C | 25C16 | 65N | 97.77 |
| 26CA | 25C16 | 24CA | 71.17 | 26CA | 25C16 | 65C | 92.26 |
| 26CA | 25C16 | 66O | 54.28 | 24CA | 25C16 | 65C | 91.93 |
| 24CA | 25C16 | 65N | 79.37 | 65C | 25C16 | 66O | 51.31 |
| 65C | 25C16 | 65N | 30.19 | 66O | 25C16 | 65N | 81.41 |
| 25SG | 25C17 | 25CB | 33.36 | 25SG | 25C17 | 25N | 69.53 |
| 25SG | 25C17 | 25CA | 47.13 | 25SG | 25C17 | 26N | 51.70 |
| 25SG | 25C17 | 25C | 42.10 | 25SG | 25C17 | 16IO | 81.99 |
| 25SG | 25C17 | 162ND1 | 45.09 | 25SG | 25C17 | 24C | 78.33 |
| 25SG | 25C17 | 26CD1 | 91.04 | 25SG | 25C17 | 19NE2 | 91.40 |
| 25SG | 25C17 | 24CA | 96.69 | 25SG | 25C17 | 163N | 23.29 |
| 25SG | 25C17 | 162CA | 48.75 | 25CB | 25C17 | 25N | 43.65 |
| 25CB | 25C17 | 25CA | 23.36 | 25CB | 25C17 | 23C | 97.56 |
| 25CB | 25C17 | 26N | 52.35 | 25CB | 25C17 | 24N | 79.60 |
| 25CB | 25C17 | 25C | 34.92 | 25CB | 25C17 | 162ND1 | 47.80 |
| 25CB | 25C17 | 24C | 54.50 | 25CB | 25C17 | 26CD1 | 89.27 |
| 25CB | 25C17 | 19NE2 | 59.46 | 25CB | 25C17 | 24CA | 71.68 |
| 25CB | 25C17 | 163N | 55.20 | 25CB | 25C17 | 162CA | 73.99 |
| 25N | 25C17 | 25CA | 22.58 | 25N | 25C17 | 23O | 63.36 |
| 25N | 25C17 | 23C | 56.78 | 25N | 25C17 | 26N | 42.10 |
| 25N | 25C17 | 23CA | 72.74 | 25N | 25C17 | 24N | 39.75 |
| 25N | 25C17 | 25C | 33.56 | 25N | 25C17 | 162ND1 | 89.46 |
| 25N | 25C17 | 24C | 11.07 | 25N | 25C17 | 26CD1 | 57.00 |
| 25N | 25C17 | 19NE2 | 52.78 | 25N | 25C17 | 24CA | 28.26 |
| 25N | 25C17 | 163N | 92.62 | 25CA | 25C17 | 23O | 85.24 |
| 25CA | 25C17 | 23C | 79.30 | 25CA | 25C17 | 26N | 36.07 |
| 25CA | 25C17 | 23CA | 93.96 | 25CA | 25C17 | 24N | 61.96 |
| 25CA | 25C17 | 25C | 19.74 | 25CA | 25C17 | 162ND1 | 71.14 |
| 25CA | 25C17 | 24C | 32.47 | 25CA | 25C17 | 26CD1 | 67.46 |
| 25CA | 25C17 | 19NE2 | 60.34 | 25CA | 25C17 | 24CA | 50.61 |
| 25CA | 25C17 | 163N | 70.36 | 25CA | 25C17 | 162CA | 94.23 |
| 23O | 25C17 | 23C | 18.25 | 23O | 25C17 | 26N | 78.82 |
| 23O | 25C17 | 23CA | 34.40 | 23O | 25C17 | 24N | 31.56 |
| 23O | 25C17 | 25C | 86.35 | 23O | 25C17 | 24C | 52.82 |
| 23O | 25C17 | 26CD1 | 45.95 | 23O | 25C17 | 19NE2 | 76.58 |
| 23O | 25C17 | 23OOH2 | 65.85 | 23O | 25C17 | 24CA | 35.23 |
| 23C | 25C17 | 26N | 84.24 | 23C | 25C17 | 23CA | 21.57 |
| 23C | 25C17 | 24N | 17.96 | 23C | 25C17 | 25C | 86.44 |
| 23C | 25C17 | 24C | 48.18 | 23C | 25C17 | 26CD1 | 59.52 |
| 23C | 25C17 | 19NE2 | 58.61 | 23C | 25C17 | 23OOH2 | 60.40 |
| 23C | 25C17 | 24CA | 30.09 | 26N | 25C17 | 24N | 73.12 |
| 26N | 25C17 | 25C | 17.65 | 26N | 25C17 | 162ND1 | 93.89 |
| 26N | 25C17 | 24C | 42.62 | 26N | 25C17 | 26CD1 | 40.31 |
| 26N | 25C17 | 19NE2 | 93.61 | 26N | 25C17 | 24CA | 56.29 |
| 26N | 25C17 | 163N | 67.72 | 26N | 25C17 | 162CA | 96.10 |
| 23CA | 25C17 | 24N | 33.68 | 23CA | 25C17 | 24C | 66.27 |
| 23CA | 25C17 | 26CD1 | 79.75 | 23CA | 25C17 | 19NE2 | 53.84 |

TABLE XVII-continued

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
|---|---|---|---|---|---|---|---|
| 23CA | 25C17 | 230OH2 | 40.17 | 23CA | 25C17 | 24CA | 49.58 |
| 24N | 25C17 | 25C | 71.51 | 24N | 25C17 | 24C | 32.59 |
| 24N | 25C17 | 26CD1 | 59.47 | 24N | 25C17 | 19NE2 | 47.60 |
| 24N | 25C17 | 230OH2 | 73.74 | 24N | 25C17 | 24CA | 16.96 |
| 25C | 25C17 | 162ND1 | 79.14 | 25C | 25C17 | 24C | 38.92 |
| 25C | 25C17 | 26CD1 | 55.45 | 25C | 25C17 | 19NE2 | 79.80 |
| 25C | 25C17 | 24CA | 56.38 | 25C | 25C17 | 163N | 62.85 |
| 25C | 25C17 | 162CA | 90.50 | 161O | 25C17 | 162ND1 | 62.06 |
| 161O | 25C17 | 230OH2 | 90.45 | 161O | 25C17 | 163N | 60.08 |
| 161O | 25C17 | 162CA | 33.46 | 162ND1 | 25C17 | 19NE2 | 71.55 |
| 162ND1 | 25C17 | 163N | 44.58 | 162ND1 | 25C17 | 162CA | 38.78 |
| 24C | 25C17 | 26CD1 | 48.36 | 24C | 25C17 | 19NE2 | 57.22 |
| 24C | 25C17 | 24CA | 18.38 | 26CD1 | 25C17 | 24CA | 46.21 |
| 19NE2 | 25C17 | 230OH2 | 73.47 | 19NE2 | 25C17 | 24CA | 57.12 |
| 230OH2 | 25C17 | 24CA | 89.69 | 163N | 25C17 | 162CA | 28.44 |
| 25SG | 25C18 | 161O | 91.87 | 25SG | 25C18 | 25CB | 20.14 |
| 25SG | 25C18 | 23CA | 98.61 | 25SG | 25C18 | 161C | 85.38 |
| 25SG | 25C18 | 23O | 83.74 | 25SG | 25C18 | 23C | 83.16 |
| 25SG | 25C18 | 162ND1 | 47.66 | 25SG | 25C18 | 162CA | 57.49 |
| 25SG | 25C18 | 25N | 40.60 | 161O | 25C18 | 161C | 8.04 |
| 161O | 25C18 | 162ND1 | 67.18 | 161O | 25C18 | 162CA | 35.14 |
| 230OH2 | 25C18 | 23CA | 43.13 | 230OH2 | 25C18 | 23O | 66.88 |
| 230OH2 | 25C18 | 23C | 61.23 | 25CB | 25C18 | 23CA | 84.02 |
| 25CB | 25C18 | 161C | 98.23 | 25CB | 25C18 | 23O | 77.59 |
| 25CB | 25C18 | 23C | 72.21 | 25CB | 25C18 | 162ND1 | 43.49 |
| 25CB | 25C18 | 162CA | 68.17 | 25CB | 25C18 | 25N | 30.01 |
| 23CA | 25C18 | 23O | 30.55 | 23CA | 25C18 | 23C | 19.20 |
| 23CA | 25C18 | 25N | 58.06 | 161C | 25C18 | 162ND1 | 65.74 |
| 161C | 25C18 | 162CA | 30.20 | 23O | 25C18 | 23C | 15.25 |
| 23O | 25C18 | 25N | 47.60 | 23C | 25C18 | 25N | 43.17 |
| 162ND1 | 25C18 | 162CA | 39.32 | 162ND1 | 25C18 | 25N | 72.26 |
| 162CA | 25C18 | 25N | 96.88 | 66O | 25C19 | 67CE1 | 68.17 |
| 66O | 25C19 | 67CD1 | 54.92 | 160O | 25C19 | 161C | 52.84 |
| 160O | 25C19 | 161CA | 35.03 | 160O | 25C19 | 161O | 63.95 |
| 160O | 25C19 | 162N | 57.36 | 67CE1 | 25C19 | 67CD1 | 17.17 |
| 161C | 25C19 | 161CA | 18.68 | 161C | 25C19 | 161O | 14.83 |
| 161C | 25C19 | 162N | 15.27 | 161CA | 25C19 | 161O | 29.02 |
| 161CA | 25C19 | 162N | 28.85 | 161O | 25C19 | 162N | 26.37 |
| 66O | 25C20 | 67CD1 | 61.25 | 66O | 25C20 | 163CB | 94.46 |
| 66O | 25C20 | 66C | 9.87 | 66O | 25C20 | 68SD | 69.49 |
| 66O | 25C20 | 67CE1 | 71.63 | 66O | 25C20 | 26CB | 36.33 |
| 67CD1 | 25C20 | 66C | 52.72 | 67CD1 | 25C20 | 68SD | 78.08 |
| 67CD1 | 25C20 | 67CE1 | 17.64 | 67CD1 | 25C20 | 26CB | 92.78 |
| 163CB | 25C20 | 68SD | 53.55 | 163CB | 25C20 | 163N | 29.80 |
| 163CB | 25C20 | 134CB | 65.83 | 163CB | 25C20 | 26CB | 58.92 |
| 66C | 25C20 | 68SD | 74.07 | 66C | 25C20 | 67CE1 | 62.03 |
| 66C | 25C20 | 26CB | 46.18 | 68SD | 25C20 | 67CE1 | 95.08 |
| 68SD | 25C20 | 163N | 82.16 | 68SD | 25C20 | 134CB | 71.67 |
| 68SD | 25C20 | 26CB | 55.82 | 163N | 25C20 | 134CB | 62.79 |
| 163N | 25C20 | 26CB | 80.06 | 67CD1 | 25C21 | 209CD2 | 74.52 |
| 67CD1 | 25C21 | 67CE1 | 21.15 | 67CD1 | 25C21 | 66O | 65.47 |
| 67CD1 | 25C21 | 68SD | 94.26 | 67CD1 | 25C21 | 67CA | 41.35 |
| 67CD1 | 25C21 | 67CG | 10.50 | 67CD1 | 25C21 | 209CG | 78.82 |
| 67CD1 | 25C21 | 66C | 53.86 | 209CD2 | 25C21 | 67CE1 | 74.15 |
| 209CD2 | 25C21 | 68SD | 93.95 | 209CD2 | 25C21 | 134CB | 66.63 |
| 209CD2 | 25C21 | 67CA | 99.15 | 209CD2 | 25C21 | 67CG | 80.75 |
| 209CD2 | 25C21 | 209CG | 13.43 | 209CD2 | 25C21 | 68CE | 78.53 |
| 67CE1 | 25C21 | 66O | 75.62 | 67CE1 | 25C21 | 67CA | 60.36 |
| 67CE1 | 25C21 | 67CG | 30.58 | 67CE1 | 25C21 | 209CG | 82.83 |
| 67CE1 | 25C21 | 66C | 64.25 | 66O | 25C21 | 68SD | 70.26 |
| 66O | 25C21 | 67CA | 36.25 | 66O | 25C21 | 67CG | 56.88 |
| 66O | 25C21 | 68CE | 92.80 | 66O | 25C21 | 66C | 11.70 |
| 68SD | 25C21 | 134CB | 81.96 | 68SD | 25C21 | 67CA | 59.58 |
| 68SD | 25C21 | 67CG | 85.39 | 68SD | 25C21 | 209CG | 80.91 |
| 68SD | 25C21 | 68CE | 22.58 | 68SD | 25C21 | 66C | 74.79 |
| 134CB | 25C21 | 209CG | 61.74 | 134CB | 25C21 | 68CE | 60.74 |
| 67CA | 25C21 | 67CG | 30.85 | 67CA | 25C21 | 209CG | 95.15 |
| 67CA | 25C21 | 68CE | 78.69 | 67CA | 25C21 | 66C | 29.16 |
| 67CG | 25C21 | 209CG | 82.94 | 67CG | 25C21 | 68CE | 99.01 |
| 67CG | 25C21 | 66C | 45.56 | 209CG | 25C21 | 68CE | 65.12 |
| 68CE | 25C21 | 66C | 97.17 | 163N | 25C22 | 163CB | 41.38 |
| 163N | 25C22 | 162C | 21.72 | 163N | 25C22 | 163CA | 22.86 |

TABLE XVII-continued

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
|---|---|---|---|---|---|---|---|
| 163N | 25C22 | 162O | 35.18 | 163N | 25C22 | 162CA | 35.98 |
| 163N | 25C22 | 162N | 54.90 | 163N | 25C22 | 134CB | 83.08 |
| 163N | 25C22 | 25SG | 48.42 | 163N | 25C22 | 161C | 68.41 |
| 163N | 25C22 | 68SD | 98.47 | 163N | 25C22 | 161O | 68.27 |
| 163N | 25C22 | 134CA | 66.14 | 163CB | 25C22 | 162C | 60.85 |
| 163CB | 25C22 | 163CA | 23.53 | 163CB | 25C22 | 162O | 65.54 |
| 163CB | 25C22 | 162CA | 77.32 | 163CB | 25C22 | 162N | 96.04 |
| 163CB | 25C22 | 134CB | 83.53 | 163CB | 25C22 | 25SG | 60.46 |
| 163CB | 25C22 | 66O | 95.09 | 163CB | 25C22 | 68SD | 58.15 |
| 163CB | 25C22 | 134CA | 68.94 | 162C | 25C22 | 163CA | 38.46 |
| 162C | 25C22 | 162O | 18.52 | 162C | 25C22 | 162CA | 21.19 |
| 162C | 25C22 | 162N | 35.80 | 162C | 25C22 | 134CB | 73.18 |
| 162C | 25C22 | 25SG | 61.51 | 162C | 25C22 | 161C | 51.73 |
| 162C | 25C22 | 161O | 56.33 | 162C | 25C22 | 134CA | 58.55 |
| 163CA | 25C22 | 162O | 42.12 | 163CA | 25C22 | 162CA | 57.32 |
| 163CA | 25C22 | 162N | 74.25 | 163CA | 25C22 | 134CB | 72.12 |
| 163CA | 25C22 | 25SG | 61.97 | 163CA | 25C22 | 161C | 89.59 |
| 163CA | 25C22 | 68SD | 76.50 | 163CA | 25C22 | 161O | 90.96 |
| 163CA | 25C22 | 134CA | 55.19 | 162O | 25C22 | 162CA | 34.60 |
| 162O | 25C22 | 162N | 40.22 | 162O | 25C22 | 134CB | 54.86 |
| 162O | 25C22 | 25SG | 79.79 | 162O | 25C22 | 161C | 57.52 |
| 162O | 25C22 | 161O | 66.63 | 162O | 25C22 | 134CA | 41.20 |
| 162CA | 25C22 | 162N | 20.16 | 162CA | 25C22 | 134CB | 87.29 |
| 162CA | 25C22 | 25SG | 55.65 | 162CA | 25C22 | 161C | 32.48 |
| 162CA | 25C22 | 161O | 35.17 | 162CA | 25C22 | 134CA | 75.53 |
| 162N | 25C22 | 134CB | 81.91 | 162N | 25C22 | 25SG | 71.75 |
| 162N | 25C22 | 161C | 17.31 | 162N | 25C22 | 161O | 28.19 |
| 162N | 25C22 | 134CA | 75.24 | 134CB | 25C22 | 161C | 94.20 |
| 134CB | 25C22 | 68SD | 76.86 | 134CB | 25C22 | 134CA | 17.24 |
| 25SG | 25C22 | 161C | 71.58 | 25SG | 25C22 | 66O | 87.43 |
| 25SG | 25C22 | 161O | 59.61 | 161C | 25C22 | 161O | 14.91 |
| 161C | 25C22 | 134CA | 90.49 | 66O | 25C22 | 68SD | 61.09 |
| 68SD | 25C22 | 134CA | 77.47 | 161O | 25N23 | 25SG | 96.69 |
| 161O | 25N23 | 162ND1 | 87.98 | 161O | 25N23 | 161C | 7.60 |
| 161O | 25N23 | 162CA | 42.67 | 161O | 25N23 | 162CB | 53.10 |
| 161O | 25N23 | 162N | 24.12 | 161O | 25N23 | 162CG | 72.20 |
| 161O | 25N23 | 162CE1 | 99.02 | 25SG | 25N23 | 162ND1 | 58.85 |
| 25SG | 25N23 | 161C | 90.78 | 25SG | 25N23 | 162CA | 65.10 |
| 25SG | 25N23 | 162CB | 74.63 | 25SG | 25N23 | 25CB | 22.39 |
| 25SG | 25N23 | 162N | 78.71 | 25SG | 25N23 | 162CG | 65.53 |
| 25SG | 25N23 | 162CE1 | 56.82 | 162ND1 | 25N23 | 161C | 80.81 |
| 162ND1 | 25N23 | 162CA | 47.69 | 162ND1 | 25N23 | 162CB | 35.43 |
| 162ND1 | 25N23 | 25CB | 47.77 | 162ND1 | 25N23 | 162N | 64.92 |
| 162ND1 | 25N23 | 162CG | 16.11 | 162ND1 | 25N23 | 162CE1 | 11.08 |
| 161C | 25N23 | 162CA | 35.07 | 161C | 25N23 | 162CB | 46.35 |
| 161C | 25N23 | 162N | 16.53 | 161C | 25N23 | 162CG | 65.21 |
| 161C | 25N23 | 162CE1 | 91.80 | 162CA | 25N23 | 162CB | 20.44 |
| 162CA | 25N23 | 25CB | 73.45 | 162CA | 25N23 | 162N | 18.55 |
| 162CA | 25N23 | 162CG | 33.95 | 162CA | 25N23 | 162CE1 | 58.16 |
| 162CB | 25N23 | 25CB | 75.17 | 162CB | 25N23 | 162N | 31.96 |
| 162CB | 25N23 | 162CG | 19.34 | 162CB | 25N23 | 162CE1 | 46.49 |
| 25CB | 25N23 | 162N | 90.62 | 25CB | 25N23 | 162CG | 59.94 |
| 25CB | 25N23 | 162CE1 | 41.59 | 162N | 25N23 | 162CG | 49.81 |
| 162N | 25N23 | 162CE1 | 75.77 | 162CG | 25N23 | 162CE1 | 27.14 |
| 161O | 25C24 | 162ND1 | 71.20 | 161O | 25C24 | 25SG | 68.87 |
| 161O | 25C24 | 25CB | 86.70 | 161O | 25C24 | 162CE1 | 84.02 |
| 161O | 25C24 | 161C | 5.61 | 161O | 25C24 | 162CG | 60.27 |
| 230OH2 | 25C24 | 19NE2 | 82.86 | 230OH2 | 25C24 | 23CA | 39.21 |
| 162ND1 | 25C24 | 25SG | 49.38 | 162ND1 | 25C24 | 19NE2 | 75.30 |
| 162ND1 | 25C24 | 25CB | 42.32 | 162ND1 | 25C24 | 162CE1 | 12.89 |
| 162ND1 | 25C24 | 161C | 66.20 | 162ND1 | 25C24 | 162CG | 13.50 |
| 25SG | 25C24 | 19NE2 | 69.24 | 25SG | 25C24 | 25CB | 21.54 |
| 25SG | 25C24 | 162CE1 | 51.86 | 25SG | 25C24 | 161C | 67.93 |
| 25SG | 25C24 | 23CA | 75.54 | 25SG | 25C24 | 162CG | 55.53 |
| 19NE2 | 25C24 | 25CB | 50.50 | 19NE2 | 25C24 | 162CE1 | 63.30 |
| 19NE2 | 25C24 | 23CA | 49.37 | 19NE2 | 25C24 | 162CG | 88.70 |
| 25CB | 25C24 | 162CE1 | 38.82 | 25CB | 25C24 | 161C | 84.51 |
| 25CB | 25C24 | 23CA | 72.33 | 25CB | 25C24 | 162CG | 53.33 |
| 162CE1 | 25C24 | 161C | 79.07 | 162CE1 | 25C24 | 162CG | 25.60 |
| 161C | 25C24 | 162CG | 54.95 | 230OH2 | 25O25 | 23CA | 52.31 |
| 233OH2 | 25O25 | 22O | 74.89 | 230OH2 | 25O25 | 23N | 49.81 |
| 233OH2 | 25O25 | 23C | 64.37 | 23CA | 25O25 | 19NE2 | 59.20 |

TABLE XVII-continued

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
|---|---|---|---|---|---|---|---|
| 23CA | 25O25 | 25SG | 80.98 | 23CA | 25O25 | 22O | 33.94 |
| 23CA | 25O25 | 23N | 14.51 | 23CA | 25O25 | 23C | 15.82 |
| 19NE2 | 25O25 | 25SG | 68.80 | 19NE2 | 25O25 | 22O | 32.41 |
| 19NE2 | 25O25 | 23N | 57.42 | 19NE2 | 25O25 | 23C | 55.28 |
| 25SG | 25O25 | 22O | 87.84 | 25SG | 25O25 | 161O | 56.79 |
| 25SG | 25O25 | 23N | 93.48 | 25SG | 25O25 | 23C | 65.16 |
| 22O | 25O25 | 23N | 26.63 | 22O | 25O25 | 23C | 39.45 |
| 23N | 25O25 | 23C | 29.23 | 162ND1 | 25C26 | 161O | 70.33 |
| 162ND1 | 25C26 | 162CG | 16.51 | 162ND1 | 25C26 | 184CZ2 | 61.61 |
| 162ND1 | 25C26 | 162CB | 33.57 | 162ND1 | 25C26 | 162CE1 | 14.30 |
| 162ND1 | 25C26 | 184NE1 | 54.26 | 161O | 25C26 | 162CG | 62.73 |
| 161O | 25C26 | 162CB | 46.80 | 161O | 25C26 | 162CE1 | 84.49 |
| 162CG | 25C26 | 184CZ2 | 58.73 | 162CG | 25C26 | 162CB | 18.91 |
| 162CG | 25C26 | 162CE1 | 27.71 | 162CG | 25C26 | 184NE1 | 61.32 |
| 184CZ2 | 25C26 | 162CB | 69.73 | 184CZ2 | 25C26 | 162CE1 | 53.77 |
| 184CZ2 | 25C26 | 184NE1 | 30.35 | 162CB | 25C26 | 162CE1 | 46.35 |
| 162CB | 25C26 | 184NE1 | 78.86 | 162CE1 | 25C26 | 184NE1 | 40.84 |
| 161O | 25C27 | 161OD1 | 53.78 | 161O | 25C27 | 161C | 11.71 |
| 161O | 25C27 | 162CB | 46.13 | 161O | 25C27 | 162ND1 | 62.87 |
| 161OD1 | 25C27 | 161C | 42.77 | 161OD1 | 25C27 | 162CB | 55.70 |
| 161OD1 | 25C27 | 162ND1 | 86.16 | 161C | 25C27 | 162CB | 40.57 |
| 161C | 25C27 | 162ND1 | 63.10 | 162CB | 25C27 | 162ND1 | 30.49 |
| 161OD1 | 25C28 | 137O | 69.81 | 161OD1 | 25C28 | 161O | 54.98 |
| 161OD1 | 25C28 | 137C | 53.96 | 161OD1 | 25C28 | 137CB | 55.92 |
| 161OD1 | 25C28 | 162CB | 61.51 | 161OD1 | 25C28 | 161CG | 11.62 |
| 161OD1 | 25C28 | 138N | 47.36 | 161OD1 | 25C28 | 161C | 42.86 |
| 137O | 25C28 | 137C | 15.86 | 137O | 25C28 | 184CZ2 | 70.21 |
| 137O | 25C28 | 137CB | 37.24 | 137O | 25C28 | 162CB | 85.15 |
| 137O | 25C28 | 161CG | 80.00 | 137O | 25C28 | 138N | 27.64 |
| 137O | 25C28 | 184CH2 | 55.56 | 161O | 25C28 | 137CB | 84.76 |
| 161O | 25C28 | 162CB | 45.37 | 161O | 25C28 | 161CG | 49.97 |
| 161O | 25C28 | 161C | 13.42 | 137C | 25C28 | 184CZ2 | 81.49 |
| 137C | 25C28 | 137CB | 32.38 | 137C | 25C28 | 162CB | 78.21 |
| 137C | 25C28 | 161CG | 64.18 | 137C | 25C28 | 138N | 15.77 |
| 137C | 25C28 | 184CH2 | 68.22 | 137C | 25C28 | 161C | 90.09 |
| 184CZ2 | 25C28 | 137CB | 63.63 | 184CZ2 | 25C28 | 162CB | 70.10 |
| 184CZ2 | 25C28 | 138N | 96.79 | 184CZ2 | 25C28 | 184CH2 | 15.72 |
| 137CB | 25C28 | 162CB | 47.93 | 137CB | 25C28 | 161CG | 67.40 |
| 137CB | 25C28 | 138N | 45.63 | 137CB | 25C28 | 184CH2 | 56.70 |
| 137CB | 25C28 | 161C | 73.01 | 162CB | 25C28 | 161CG | 66.72 |
| 162CB | 25C28 | 138N | 87.00 | 162CB | 25C28 | 184CH2 | 76.56 |
| 162CB | 25C28 | 161C | 39.92 | 161CG | 25C28 | 138N | 55.54 |
| 161CG | 25C28 | 161C | 39.76 | 138N | 25C28 | 184CH2 | 82.84 |
| 138N | 25C28 | 161C | 88.57 | 161OD1 | 25C29 | 161CG | 17.77 |
| 161OD1 | 25C29 | 161CB | 38.20 | 161OD1 | 25C29 | 137C | 69.75 |
| 161OD1 | 25C29 | 138N | 63.36 | 161OD1 | 25C29 | 161O | 67.46 |
| 161OD1 | 25C29 | 137O | 86.87 | 161OD1 | 25C29 | 138CA | 77.48 |
| 161OD1 | 25C29 | 137CB | 66.56 | 161OD1 | 25C29 | 161C | 51.63 |
| 161OD1 | 25C29 | 137CA | 57.43 | 161OD1 | 25C29 | 137N | 38.54 |
| 161OD1 | 25C29 | 161ND2 | 20.78 | 161OD1 | 25C29 | 162CB | 69.24 |
| 161OD1 | 25C29 | 138CB | 70.48 | 161OD1 | 25C29 | 161CA | 39.44 |
| 161OD1 | 25C29 | 162N | 49.70 | 161CG | 25C29 | 161CB | 23.57 |
| 161CG | 25C29 | 137C | 84.96 | 161CG | 25C29 | 138N | 74.84 |
| 161CG | 25C29 | 161O | 62.41 | 161CG | 25C29 | 138CA | 84.52 |
| 161CG | 25C29 | 137CB | 84.24 | 161CG | 25C29 | 161C | 49.09 |
| 161CG | 25C29 | 137CA | 74.70 | 161CG | 25C29 | 137N | 55.87 |
| 161CG | 25C29 | 161ND2 | 11.82 | 161CG | 25C29 | 162CB | 78.89 |
| 161CG | 25C29 | 138CB | 72.41 | 161CG | 25C29 | 161CA | 31.89 |
| 161CG | 25C29 | 162N | 53.19 | 161CB | 25C29 | 138N | 98.38 |
| 161CB | 25C29 | 161C | 43.85 | 161CB | 25C29 | 137CB | 99.44 |
| 161CB | 25C29 | 161C | 35.43 | 161CB | 25C29 | 137CA | 94.94 |
| 161CB | 25C29 | 137N | 76.23 | 161CB | 25C29 | 161ND2 | 33.15 |
| 161CB | 25C29 | 162CB | 75.97 | 161CB | 25C29 | 138CB | 91.71 |
| 161CB | 25C29 | 161CA | 16.99 | 161CB | 25C29 | 162N | 46.28 |
| 137C | 25C29 | 138N | 19.59 | 137C | 25C29 | 137O | 17.39 |
| 137C | 25C29 | 138CA | 35.03 | 137C | 25C29 | 137CB | 35.61 |
| 137C | 25C29 | 137CA | 20.11 | 137C | 25C29 | 137N | 34.13 |
| 137C | 25C29 | 161ND2 | 78.64 | 137C | 25C29 | 162CB | 84.64 |
| 137C | 25C29 | 138CB | 50.91 | 137C | 25C29 | 162N | 96.62 |
| 138N | 25C29 | 137O | 32.46 | 138N | 25C29 | 138CA | 20.27 |
| 138N | 25C29 | 137CB | 52.67 | 138N | 25C29 | 137CA | 33.41 |
| 138N | 25C29 | 137N | 37.77 | 138N | 25C29 | 161ND2 | 65.96 |

TABLE XVII-continued

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
|---|---|---|---|---|---|---|---|
| 138N | 25C29 | 162CB | 98.96 | 138N | 25C29 | 138CB | 32.14 |
| 161O | 25C29 | 137CB | 93.41 | 161O | 25C29 | 161C | 16.38 |
| 161O | 25C29 | 137N | 91.81 | 161O | 25C29 | 161ND2 | 74.07 |
| 161C | 25C29 | 162CB | 47.11 | 161O | 25C29 | 161CA | 30.52 |
| 161O | 25C29 | 162N | 27.28 | 137O | 25C29 | 138CA | 39.55 |
| 137O | 25C29 | 137CB | 39.61 | 137O | 25C29 | 137CA | 32.50 |
| 137O | 25C29 | 137N | 49.84 | 137O | 25C29 | 161ND2 | 95.83 |
| 137O | 25C29 | 162CB | 87.74 | 137O | 25C29 | 138CB | 58.44 |
| 138CA | 25C29 | 137CB | 70.56 | 138CA | 25C29 | 137CA | 52.71 |
| 138CA | 25C29 | 137N | 57.82 | 138CA | 25C29 | 161ND2 | 73.59 |
| 138CA | 25C29 | 138CB | 19.26 | 137CB | 25C29 | 161C | 82.69 |
| 137CB | 25C29 | 137CA | 20.23 | 137CB | 25C29 | 137N | 32.22 |
| 137CB | 25C29 | 161ND2 | 84.94 | 137CB | 25C29 | 162CB | 49.44 |
| 137CB | 25C29 | 138CB | 84.72 | 137CB | 25C29 | 161CA | 89.09 |
| 137CB | 25C29 | 162N | 67.71 | 161C | 25C29 | 137CA | 89.83 |
| 161C | 25C29 | 137N | 76.15 | 161C | 25C29 | 161ND2 | 60.90 |
| 161C | 25C29 | 162CB | 43.16 | 161C | 25C29 | 161CA | 18.88 |
| 161C | 25C29 | 162N | 15.26 | 137CA | 25C29 | 137N | 18.89 |
| 137CA | 25C29 | 161ND2 | 71.91 | 137CA | 25C29 | 162CB | 66.00 |
| 137CA | 25C29 | 138CB | 65.00 | 137CA | 25C29 | 161CA | 89.85 |
| 137CA | 25C29 | 162N | 76.62 | 137N | 25C29 | 161ND2 | 53.90 |
| 137N | 25C29 | 162CB | 64.20 | 137N | 25C29 | 138CB | 63.74 |
| 137N | 25C29 | 161CA | 72.67 | 137N | 25C29 | 162N | 65.28 |
| 161ND2 | 25C29 | 162CB | 88.34 | 161ND2 | 25O29 | 138CB | 60.67 |
| 161ND2 | 25C29 | 161CA | 43.56 | 161ND2 | 25C29 | 162N | 64.33 |
| 162CB | 25C29 | 161CA | 59.23 | 162CB | 25C29 | 162N | 29.75 |
| 161CA | 25C29 | 162N | 29.47 | 137O | 25C30 | 143NE2 | 59.46 |
| 137O | 25C30 | 184CZ2 | 69.76 | 137O | 25C30 | 137C | 14.57 |
| 137O | 25C30 | 138CA | 35.79 | 137O | 25C30 | 184CH2 | 56.99 |
| 137O | 25C30 | 138N | 26.64 | 143NE2 | 25C30 | 184CZ2 | 83.66 |
| 143NE2 | 25C30 | 137C | 71.37 | 143NE2 | 25C30 | 138CA | 63.07 |
| 143NE2 | 25C30 | 184CH2 | 68.61 | 143NE2 | 25C30 | 138N | 72.68 |
| 184CZ2 | 25C30 | 137C | 78.03 | 184CZ2 | 25C30 | 184CH2 | 16.45 |
| 184CZ2 | 25C30 | 138N | 93.46 | 137C | 25C30 | 138CA | 30.17 |
| 137C | 25C30 | 184CH2 | 67.67 | 137C | 25C30 | 138N | 15.43 |
| 138CA | 25C30 | 184CH2 | 92.20 | 138CA | 25C30 | 138N | 17.17 |
| 184CH2 | 25C30 | 138N | 82.69 | 184CZ2 | 25N31 | 184NE1 | 33.41 |
| 184CZ2 | 25N31 | 184CE2 | 17.32 | 184CZ2 | 25N31 | 162ND1 | 57.89 |
| 184CZ2 | 25N31 | 19NE2 | 96.35 | 184NE1 | 25N31 | 184CE2 | 16.98 |
| 184NE1 | 25N31 | 162ND1 | 53.50 | 184NE1 | 25N31 | 19NE2 | 63.65 |
| 184CE2 | 25N31 | 162ND1 | 57.86 | 184CE2 | 25N31 | 19NE2 | 80.63 |
| 162ND1 | 25N31 | 19NE2 | 68.39 | 184NE1 | 25C32 | 184CE2 | 19.92 |
| 184NE1 | 25C32 | 184CZ2 | 38.87 | 184NE1 | 25C32 | 19NE2 | 81.55 |
| 184NE1 | 25C32 | 19OE1 | 51.17 | 184NE1 | 25C32 | 19CD | 64.02 |
| 184NE1 | 25C32 | 184CD1 | 13.69 | 184NE1 | 25C32 | 162ND1 | 58.56 |
| 184NE1 | 25C32 | 162CE1 | 44.43 | 184CE2 | 25C32 | 184CZ2 | 20.46 |
| 184CE2 | 25C32 | 19OE1 | 70.66 | 184CE2 | 25C32 | 19CD | 83.94 |
| 184CE2 | 25C32 | 184CD1 | 29.80 | 184CE2 | 25C32 | 162ND1 | 62.83 |
| 184CE2 | 25C32 | 162CE1 | 52.80 | 184CZ2 | 25C32 | 190E1 | 86.31 |
| 184CZ2 | 25C32 | 184CD1 | 50.14 | 184CZ2 | 25C32 | 162ND1 | 60.09 |
| 184CZ2 | 25C32 | 162CE1 | 56.05 | 19NE2 | 25C32 | 190E1 | 31.34 |
| 19NE2 | 25C32 | 19CD | 17.91 | 19NE2 | 25C32 | 184CD1 | 75.00 |
| 19NE2 | 25C32 | 162ND1 | 75.92 | 19NE2 | 25C32 | 162CE1 | 69.31 |
| 19OE1 | 25C32 | 19CD | 16.54 | 19OE1 | 25C32 | 184CD1 | 47.47 |
| 19OE1 | 25C32 | 162ND1 | 56.39 | 19OE1 | 25C32 | 162CE1 | 44.21 |
| 19CD | 25C32 | 184CD1 | 57.09 | 19CD | 25C32 | 162ND1 | 70.79 |
| 19CD | 25C32 | 162CE1 | 60.09 | 184CD1 | 25C32 | 162ND1 | 69.23 |
| 184CD1 | 25C32 | 162CE1 | 53.91 | 162ND1 | 25C32 | 162CE1 | 16.00 |
| 184NE1 | 25O33 | 19CE1 | 71.37 | 184NE1 | 25O33 | 19CD | 86.43 |
| 184NE1 | 25O33 | 184CE2 | 20.79 | 184NE1 | 25O33 | 184CD1 | 17.17 |
| 184NE1 | 25O33 | 162CE1 | 60.07 | 184NE1 | 25O33 | 184CZ2 | 41.79 |
| 184NE1 | 25O33 | 162ND1 | 76.01 | 184NE1 | 25O33 | 19CG | 80.45 |
| 184NE1 | 25O33 | 184CD2 | 16.63 | 184NE1 | 25O33 | 162NE2 | 50.59 |
| 184NE1 | 25O33 | 184CG | 13.72 | 184NE1 | 25O33 | 162CG | 72.21 |
| 184NE1 | 25O33 | 25CB | 93.48 | 19OE1 | 25O33 | 19NE2 | 40.72 |
| 19OE1 | 25O33 | 19CD | 21.44 | 19OE1 | 25O33 | 184CE2 | 91.61 |
| 19OE1 | 25O33 | 184CD1 | 61.45 | 19OE1 | 25O33 | 162CE1 | 59.41 |
| 19OE1 | 25O33 | 162ND1 | 74.45 | 19OE1 | 25O33 | 19CG | 30.46 |
| 19OE1 | 25O33 | 184CD2 | 87.26 | 19OE1 | 25O33 | 162NE2 | 64.69 |
| 19OE1 | 25O33 | 184CG | 72.71 | 19OE1 | 25O33 | 162CG | 83.38 |
| 19OE1 | 25O33 | 25CB | 44.37 | 19NE2 | 25O33 | 19CD | 22.85 |
| 19NE2 | 25O33 | 184CD1 | 95.28 | 19NE2 | 25O33 | 162CE1 | 91.27 |

TABLE XVII-continued

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
|---|---|---|---|---|---|---|---|
| 19NE2 | 25O33 | 162ND1 | 97.51 | 19NE2 | 25O33 | 19CG | 32.33 |
| 19NE2 | 25O33 | 25CB | 55.21 | 19CD | 25O33 | 184CD1 | 73.73 |
| 19CD | 25O33 | 162CE1 | 79.91 | 19CD | 25O33 | 162ND1 | 92.65 |
| 19CD | 25O33 | 19CG | 15.53 | 19CD | 25O33 | 162NE2 | 85.98 |
| 19CD | 25O33 | 184CG | 83.64 | 19CD | 25O33 | 25CB | 55.10 |
| 184CE2 | 25O33 | 184CD1 | 35.82 | 184CE2 | 25O33 | 162CE1 | 66.09 |
| 184CE2 | 25O33 | 184CZ2 | 21.88 | 184CE2 | 25O33 | 162ND1 | 76.32 |
| 184CE2 | 25O33 | 184CD2 | 10.76 | 184CE2 | 25O33 | 162NE2 | 54.99 |
| 184CE2 | 25O33 | 184CG | 26.75 | 184CE2 | 25O33 | 162CG | 68.94 |
| 184CD1 | 25O33 | 162CE1 | 68.79 | 184CD1 | 25O33 | 184CZ2 | 57.65 |
| 184CD1 | 25O33 | 162ND1 | 87.29 | 184CD1 | 25O33 | 19CG | 64.62 |
| 184CD1 | 25O33 | 184CD2 | 27.61 | 184CD1 | 25O33 | 162NE2 | 61.38 |
| 184CD1 | 25O33 | 184CG | 11.29 | 184CD1 | 25O33 | 162CG | 85.74 |
| 184CD1 | 25O33 | 25CB | 93.60 | 162CE1 | 25O33 | 184CZ2 | 67.50 |
| 162CE1 | 25O33 | 162ND1 | 20.07 | 162CE1 | 25O33 | 19CG | 89.40 |
| 162CE1 | 25O33 | 184CD2 | 72.00 | 162CE1 | 25O33 | 162NE2 | 11.22 |
| 162CE1 | 25O33 | 184CG | 72.92 | 162CE1 | 25O33 | 162CG | 25.06 |
| 162CE1 | 25O33 | 25CB | 41.49 | 184CZ2 | 25O33 | 162ND1 | 70.13 |
| 184CZ2 | 25O33 | 184CD2 | 31.61 | 184CZ2 | 25O33 | 162NE2 | 56.74 |
| 184CZ2 | 25O33 | 184CG | 48.49 | 184CZ2 | 25O33 | 162CG | 60.18 |
| 162ND1 | 25O33 | 184CD2 | 84.61 | 162ND1 | 25O33 | 162NE2 | 25.95 |
| 162ND1 | 25O33 | 184CG | 89.59 | 162ND1 | 25O33 | 162CG | 11.10 |
| 162ND1 | 25O33 | 25CB | 42.38 | 19CG | 25O33 | 184CD2 | 91.76 |
| 19CG | 25C33 | 162NE2 | 93.17 | 19CG | 25O33 | 184CG | 74.56 |
| 19CG | 25O33 | 25CB | 70.08 | 184CD2 | 25O33 | 162NE2 | 61.34 |
| 184CD2 | 25O33 | 184CG | 17.21 | 184CD2 | 25O33 | 162CG | 78.20 |
| 162NE2 | 25O33 | 184CG | 63.94 | 162NE2 | 25O33 | 162CG | 26.05 |
| 162NE2 | 25O33 | 25CB | 52.56 | 184CG | 25O33 | 162CG | 85.93 |
| 162CG | 25O33 | 25CB | 53.49 | 184NE1 | 25O34 | 184CE2 | 18.11 |
| 184NE1 | 25O34 | 184CZ2 | 33.70 | 184NE1 | 25O34 | 19NE2 | 70.03 |
| 184NE1 | 25O34 | 184CD1 | 15.57 | 184NE1 | 25O34 | 19CD | 56.05 |
| 184NE1 | 25O34 | 19OE1 | 43.11 | 184CE2 | 25O34 | 184CZ2 | 18.11 |
| 184CE2 | 25634 | 19NE2 | 87.63 | 184CE2 | 25O34 | 184CD1 | 28.12 |
| 184CE2 | 25O34 | 19CD | 74.10 | 184CE2 | 25O34 | 19OE1 | 60.83 |
| 184CZ2 | 25O34 | 19NE2 | 97.82 | 184CZ2 | 25O34 | 184CD1 | 46.02 |
| 184CZ2 | 25O34 | 19CD | 86.79 | 184CZ2 | 25O34 | 19OE1 | 72.54 |
| 19NE2 | 25O34 | 184CD1 | 68.22 | 19NE2 | 25O34 | 19CD | 16.05 |
| 19NE2 | 25O34 | 19OE1 | 26.92 | 184CD1 | 25O34 | 19CD | 52.52 |
| 184CD1 | 25C34 | 19OE1 | 42.67 | 19CD | 25O34 | 19OE1 | 14.42 |
| 20O | 25C35 | 19NE2 | 68.42 | 20O | 25C35 | 19CD | 70.46 |
| 20O | 25C35 | 19CG | 55.17 | 20O | 25C35 | 19OE1 | 84.98 |
| 20O | 25C35 | 21NE2 | 59.84 | 20O | 25C35 | 21OE1 | 59.50 |
| 19NE2 | 25C35 | 184NE1 | 74.82 | 19NE2 | 25C35 | 19CD | 18.63 |
| 19NE2 | 25C35 | 19CG | 33.10 | 19NE2 | 25C35 | 184CD1 | 76.03 |
| 19NE2 | 25C35 | 19OE1 | 29.73 | 19NE2 | 25C35 | 184CE2 | 89.27 |
| 184NE1 | 25C35 | 19CD | 61.33 | 184NE1 | 25C35 | 19CG | 69.26 |
| 184NE1 | 25C35 | 184CD1 | 18.20 | 184NE1 | 25C35 | 19OE1 | 46.19 |
| 184NE1 | 25C35 | 184CE2 | 15.64 | 19CD | 25C35 | 19CG | 20.18 |
| 19CD | 25C35 | 184CD1 | 59.00 | 19CD | 25C35 | 19OE1 | 15.55 |
| 19CD | 25C35 | 184CE2 | 76.79 | 19CG | 25C35 | 184CD1 | 60.31 |
| 19CG | 25C35 | 19OE1 | 31.00 | 19CG | 25C35 | 184CE2 | 84.62 |
| 184CD1 | 25C35 | 19OE1 | 46.45 | 184CD1 | 25C35 | 184CE2 | 27.90 |
| 19OE1 | 25C35 | 184CE2 | 61.48 | 21NE2 | 25C35 | 21OE1 | 26.73 |
| 21NE2 | 25C36 | 20O | 62.73 | 21NE2 | 25C36 | 21CD | 14.08 |
| 20O | 25C36 | 19CG | 49.13 | 20O | 25C36 | 21CD | 53.84 |
| 184CD1 | 25C36 | 184NE1 | 18.40 | 184CD1 | 25C36 | 184CG | 16.42 |
| 184CD1 | 25C36 | 184CE2 | 27.92 | 184CD1 | 25C36 | 19CG | 56.22 |
| 184NE1 | 25C36 | 184CG | 28.30 | 184NE1 | 25C36 | 184CE2 | 16.44 |
| 184NE1 | 25C36 | 19CG | 61.95 | 184CG | 25C36 | 184CE2 | 27.91 |
| 184CG | 25C36 | 19CG | 70.47 | 184CE2 | 25C36 | 19CG | 78.31 |
| 21NE2 | 25C37 | 20O | 79.74 | 21NE2 | 25C37 | 21CD | 16.72 |
| 21NE2 | 25C37 | 21OE1 | 29.73 | 21NE2 | 25C37 | 20C | 72.88 |
| 20O | 25C37 | 21CD | 66.28 | 20O | 25C37 | 21OE1 | 66.79 |
| 20O | 25C37 | 20C | 14.00 | 21CD | 25C37 | 21OE1 | 16.17 |
| 21CD | 25C37 | 20C | 62.16 | 21OE1 | 25C37 | 20C | 66.88 |
| 21NE2 | 25C38 | 21CD | 9.90 | 21NE2 | 25C38 | 20O | 63.92 |
| 21CD | 25C38 | 20O | 54.43 | 184CG | 25C40 | 184CB | 20.90 |
| 184CG | 25C40 | 184CD2 | 19.97 | 184CG | 25C40 | 184CD1 | 18.76 |
| 184CG | 25C40 | 184CE2 | 29.83 | 184CG | 25C40 | 184NE1 | 29.07 |
| 184CG | 25C40 | 184CE3 | 34.09 | 184CG | 25C40 | 184O | 55.54 |
| 184CG | 25C40 | 184CA | 32.20 | 184CB | 25C40 | 184CD2 | 36.24 |
| 184CB | 25C40 | 184CD1 | 35.47 | 184CB | 25C40 | 184CE2 | 50.10 |

TABLE XVII-continued

Table of angles between atoms of the inhibitor and protein for all protein atoms within 5 Ångstroms of the inhibitor 4-[N-[(4-pyridylmethoxy)carbonyl]-L-leucyl]-1-[N-(phenylmethoxy)carbonyl]-L-leucyl]-3-pyrrolidinone

| Atom 1 | Atom 2 | Atom 3 | Angle | Atom 1 | Atom 2 | Atom 3 | Angle |
|---|---|---|---|---|---|---|---|
| 184CB | 25C40 | 184NE1 | 49.38 | 184CB | 25C40 | 184CE3 | 43.19 |
| 184CB | 25C40 | 184O | 34.81 | 184CB | 25C40 | 184CA | 17.73 |
| 184CD2 | 25C40 | 184CD1 | 30.80 | 184CD2 | 25C40 | 184CE2 | 17.77 |
| 184CD2 | 25C40 | 184NE1 | 29.02 | 184CD2 | 25C40 | 184CE3 | 17.34 |
| 184CD2 | 25C40 | 184O | 69.94 | 184CD2 | 25C40 | 184CA | 51.16 |
| 184CD1 | 25C40 | 184CE2 | 28.86 | 184CD1 | 25C40 | 184NE1 | 17.14 |
| 184CD1 | 25C40 | 184CE3 | 47.95 | 184CD1 | 25C40 | 184O | 66.59 |
| 184CE2 | 25C40 | 184CE3 | 30.61 | 184CE2 | 25C40 | 184O | 84.89 |
| 184CE2 | 25C40 | 184CA | 61.54 | 184NE1 | 25C40 | 184CE3 | 45.35 |
| 184NE1 | 25C40 | 184O | 82.69 | 184NE1 | 25C40 | 184CA | 55.30 |
| 184CE3 | 25C40 | 184O | 71.49 | 184CE3 | 25C40 | 184CA | 60.55 |
| 184O | 25C40 | 184CA | 28.85 | 184CD1 | 25C41 | 184CG | 21.77 |
| 184CD1 | 25C41 | 184NE1 | 21.97 | 184CD1 | 25C41 | 184CD2 | 35.07 |
| 184CD1 | 25C41 | 184CE2 | 34.98 | 184CD1 | 25C41 | 184CB | 36.36 |
| 184CD1 | 25C41 | 184CE3 | 51.22 | 184CD1 | 25C41 | 184CZ2 | 50.86 |
| 184CD1 | 25C41 | 184CA | 37.30 | 184CG | 25C41 | 184NE1 | 35.87 |
| 184CG | 25C41 | 184CD2 | 21.86 | 184CG | 25C41 | 184CE2 | 35.60 |
| 184CG | 25C41 | 184CB | 19.28 | 184CG | 25C41 | 184CE3 | 34.71 |
| 184CG | 25C41 | 184CZ2 | 50.97 | 184CG | 25C41 | 184CA | 30.15 |
| 184NE1 | 25C41 | 184CD2 | 34.95 | 184NE1 | 25C41 | 184CE2 | 20.95 |
| 184NE1 | 25C41 | 184CB | 54.49 | 184NE1 | 25C41 | 184CE3 | 50.02 |
| 184NE1 | 25C41 | 184CZ2 | 33.28 | 184NE1 | 25C41 | 184CA | 58.90 |
| 184CD2 | 25C41 | 184CE2 | 21.45 | 184CD2 | 25C41 | 184CB | 36.52 |
| 184CD2 | 25C41 | 184CE3 | 16.39 | 184CD2 | 25C41 | 184CZ2 | 32.78 |
| 184CD2 | 25C41 | 184CA | 51.13 | 184CE2 | 25C41 | 184CB | 54.20 |
| 184CE2 | 25C41 | 184CE3 | 32.31 | 184CE2 | 25C41 | 184CZ2 | 16.30 |
| 184CE2 | 25C41 | 184CA | 65.12 | 184CB | 25C41 | 184CE3 | 43.07 |
| 184CB | 25C41 | 184CZ2 | 68.63 | 184CB | 25C41 | 184CA | 17.27 |
| 184CE3 | 25C41 | 184CZ2 | 36.53 | 184CE3 | 25C41 | 184CA | 59.94 |
| 184CZ2 | 25C41 | 184CA | 80.95 | 25SG | 25O42 | 25CB | 38.64 |
| 25SG | 25O42 | 25N | 73.56 | 25SG | 25O42 | 25CA | 53.59 |
| 25SG | 25O42 | 24C | 84.78 | 25SG | 25O42 | 19OE1 | 88.63 |
| 25SG | 25O42 | 25C | 44.83 | 25SG | 25O42 | 26N | 45.60 |
| 25SG | 25O42 | 162ND1 | 49.49 | 25SG | 25O42 | 162CE1 | 54.51 |
| 25SG | 25O42 | 26CD1 | 74.03 | 25CB | 25O42 | 25N | 49.39 |
| 25CB | 25O42 | 19NE2 | 81.36 | 25CB | 25O42 | 24N | 99.21 |
| 25CB | 25O42 | 25CA | 25.75 | 25CB | 25O42 | 24C | 62.76 |
| 25CB | 25O42 | 24CA | 84.14 | 25CB | 25O42 | 19CD | 66.86 |
| 25CB | 25O42 | 19OE1 | 53.70 | 25CB | 25O42 | 25C | 31.71 |
| 25CB | 25O42 | 26N | 46.47 | 25CB | 25O42 | 162ND1 | 47.29 |
| 25CB | 25O42 | 162CE1 | 39.19 | 25CB | 25O42 | 26CD1 | 82.79 |
| 25N | 25O42 | 23C | 70.38 | 25N | 25O42 | 23CA | 94.53 |
| 25N | 25O42 | 19NE2 | 73.90 | 25N | 25O42 | 24N | 51.16 |
| 25N | 25O42 | 25CA | 23.79 | 25N | 25O42 | 23O | 72.18 |

TABLE XVIII

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 242OH2 | 25C1 | 18OD1 | 67.89 | 242OH2 | 25C1 | 18CG | 56.00 |
| 242OH2 | 25C1 | 18ND2 | 40.01 | 242OH2 | 25C1 | 184O | 81.97 |
| 242OH2 | 25C1 | 184C | 88.17 | 242OH2 | 25C1 | 21NE2 | 62.78 |
| 242OH2 | 25C1 | 20N | 79.06 | 18OD1 | 25C1 | 184CD1 | 79.40 |
| 18OD1 | 25C1 | 184CB | 74.81 | 18OD1 | 25C1 | 184CG | 85.32 |
| 18OD1 | 25C1 | 184CA | 53.47 | 18OD1 | 25C1 | 18CG | 11.94 |
| 18OD1 | 25C1 | 18ND2 | 28.26 | 18OD1 | 25C1 | 184NE1 | 92.34 |
| 18OD1 | 25C1 | 184O | 58.92 | 18OD1 | 25C1 | 184C | 49.03 |
| 18OD1 | 25C1 | 21NE2 | 93.14 | 18OD1 | 25C1 | 20N | 41.90 |
| 184CD1 | 25C1 | 184CB | 38.10 | 184CD1 | 25C1 | 184CG | 19.94 |
| 184CD1 | 25C1 | 184CA | 42.92 | 184CD1 | 25C1 | 18CG | 90.87 |
| 184CD1 | 25C1 | 184NE1 | 15.56 | 184CD1 | 25C1 | 184O | 71.50 |
| 184CD1 | 25C1 | 184CD2 | 27.97 | 184CD1 | 25C1 | 184C | 61.10 |
| 184CD1 | 25C1 | 20N | 84.09 | 184CB | 25C1 | 184CG | 21.98 |
| 184CB | 25C1 | 184CA | 21.35 | 184CB | 25C1 | 18CG | 81.80 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 184CB | 25C1 | 18ND2 | 96.15 | 184CB | 25C1 | 184NE1 | 50.19 |
| 184CB | 25C1 | 184O | 36.35 | 184CB | 25C1 | 184CD2 | 33.73 |
| 184CB | 25C1 | 184C | 32.01 | 184CG | 25C1 | 184CA | 36.19 |
| 184CG | 25C1 | 18CG | 95.04 | 184CG | 25C1 | 184NE1 | 28.76 |
| 184CG | 25C1 | 184O | 58.26 | 184CG | 25C1 | 184CD2 | 15.95 |
| 184CG | 25C1 | 184C | 51.91 | 184CA | 25C1 | 18CG | 60.97 |
| 184CA | 25C1 | 18ND2 | 76.21 | 184CA | 25C1 | 184NE1 | 58.19 |
| 184CA | 25C1 | 184O | 30.82 | 184CA | 25C1 | 184CD2 | 51.40 |
| 184CA | 25C1 | 184C | 18.27 | 184CA | 25C1 | 20N | 84.75 |
| 18CG | 25C1 | 18ND2 | 16.83 | 18CG | 25C1 | 184O | 59.45 |
| 18CG | 25C1 | 184C | 52.65 | 18CG | 25C1 | 21NE2 | 87.86 |
| 18CG | 25C1 | 20N | 45.88 | 18ND2 | 25C1 | 184O | 68.25 |
| 18ND2 | 25C1 | 184C | 65.08 | 18ND2 | 25C1 | 21NE2 | 75.52 |
| 18ND2 | 25C1 | 20N | 49.20 | 184NE1 | 25C1 | 184O | 85.54 |
| 184NE1 | 25C1 | 184CD2 | 27.58 | 184NE1 | 25C1 | 184C | 76.21 |
| 184NE1 | 25C1 | 20N | 87.93 | 184O | 25C1 | 184CD2 | 69.09 |
| 184O | 25C1 | 184C | 14.96 | 184CD2 | 25C1 | 184C | 65.57 |
| 184C | 25C1 | 20N | 87.94 | 21NE2 | 25C1 | 20N | 61.73 |
| 184CD1 | 25C2 | 184CG | 20.80 | 184CD1 | 25C2 | 184NE1 | 19.39 |
| 184CD1 | 25C2 | 184CD2 | 32.31 | 184CD1 | 25C2 | 184CB | 37.15 |
| 184CD1 | 25C2 | 184CE2 | 30.89 | 184CD1 | 25C2 | 18OD1 | 66.60 |
| 184CD1 | 25C2 | 184CA | 37.97 | 184CD1 | 25C2 | 184CE3 | 47.14 |
| 184CG | 25C2 | 184NE1 | 32.65 | 184CG | 25C2 | 184CD2 | 20.10 |
| 184CG | 25C2 | 184CB | 20.97 | 184CG | 25C2 | 184CE2 | 31.76 |
| 184CG | 25C2 | 18OD1 | 71.61 | 184CG | 25C2 | 184CA | 31.32 |
| 184CG | 25C2 | 184CE3 | 31.69 | 184NE1 | 25C2 | 184CD2 | 31.41 |
| 184NE1 | 25C2 | 184CB | 52.95 | 184NE1 | 25C2 | 184CE2 | 18.36 |
| 184NE1 | 25C2 | 18OD1 | 83.70 | 184NE1 | 25C2 | 184CA | 57.03 |
| 184NE1 | 25C2 | 184CE3 | 45.36 | 184CD2 | 25C2 | 184CB | 36.72 |
| 184CD2 | 25C2 | 184CE2 | 18.93 | 184CD2 | 25C2 | 18OD1 | 91.69 |
| 184CD2 | 25C2 | 184CA | 50.71 | 184CD2 | 25C2 | 184CE3 | 15.04 |
| 184CB | 25C2 | 184CE2 | 52.15 | 184CB | 25C2 | 242OH2 | 91.69 |
| 184CB | 25C2 | 18OD1 | 60.47 | 184CB | 25C2 | 184CA | 17.64 |
| 184CB | 25C2 | 184CE3 | 41.82 | 184CE2 | 25C2 | 18OD1 | 97.37 |
| 184CE2 | 25C2 | 184CA | 62.35 | 184CE2 | 25C2 | 184CE3 | 29.53 |
| 242OH2 | 25C2 | 18OD1 | 48.28 | 242OH2 | 25C2 | 184CA | 79.74 |
| 18OD1 | 25C2 | 184CA | 43.08 | 184CA | 25C2 | 184CE3 | 58.53 |
| 184NE1 | 25C3 | 184CD1 | 20.69 | 184NE1 | 25C3 | 184CE2 | 18.79 |
| 184NE1 | 25C3 | 184CG | 31.66 | 184NE1 | 25C3 | 184CD2 | 29.94 |
| 184NE1 | 25C3 | 184CZ2 | 30.27 | 184CD1 | 25C3 | 184CE2 | 31.79 |
| 184CD1 | 25C3 | 184CG | 18.43 | 184CD1 | 25C3 | 184CD2 | 29.94 |
| 184CD1 | 25C3 | 20O | 97.66 | 184CD1 | 25C3 | 184CZ2 | 46.78 |
| 184CE2 | 25C3 | 184CG | 31.39 | 184CE2 | 25C3 | 184CD2 | 18.34 |
| 184CE2 | 25C3 | 184CZ2 | 15.37 | 184CG | 25C3 | 184CD2 | 18.68 |
| 184CG | 25C3 | 184CZ2 | 46.08 | 184CD2 | 25C3 | 184CZ2 | 30.03 |
| 20O | 25C3 | 21NE2 | 47.07 | 20O | 25C4 | 19CG | 63.08 |
| 20O | 25C4 | 20C | 13.93 | 20O | 25C4 | 21NE2 | 58.24 |
| 20O | 25C4 | 20N | 38.94 | 20O | 25C4 | 19CD | 73.49 |
| 20O | 25C4 | 20CA | 29.58 | 20O | 25C4 | 21OE1 | 64.57 |
| 20O | 25C4 | 18OD1 | 80.18 | 20O | 25C4 | 21CD | 55.60 |
| 20O | 25C4 | 19NE2 | 66.42 | 20O | 25C4 | 21N | 18.83 |
| 19CG | 25C4 | 20C | 69.89 | 19CG | 25C4 | 184CD1 | 59.97 |
| 19CG | 25C4 | 184NE1 | 63.38 | 19CG | 25C4 | 20N | 48.04 |
| 19CG | 25C4 | 19CD | 19.27 | 19CG | 25C4 | 20CA | 64.22 |
| 19CG | 25C4 | 184CG | 73.51 | 19CG | 25C4 | 18OD1 | 63.24 |
| 19CG | 25C4 | 184CE2 | 77.80 | 19CG | 25C4 | 19NE2 | 28.95 |
| 19CG | 25C4 | 21N | 80.44 | 20C | 25C4 | 21NE2 | 47.51 |
| 20C | 25C4 | 20N | 34.03 | 20C | 25C4 | 19CD | 83.36 |
| 20C | 25C4 | 20CA | 19.08 | 20C | 25C4 | 21OE1 | 60.05 |
| 20C | 25C4 | 18OD1 | 71.76 | 20C | 25C4 | 21CD | 48.39 |
| 20C | 25C4 | 19NE2 | 78.43 | 20C | 25C4 | 21N | 11.83 |
| 184CD1 | 25C4 | 184NE1 | 19.36 | 184CD1 | 25C4 | 20N | 90.20 |
| 184CD1 | 25C4 | 19CD | 56.87 | 184CD1 | 25C4 | 184CG | 14.62 |
| 184CD1 | 25C4 | 18OD1 | 63.59 | 184CD1 | 25C4 | 184CE2 | 26.99 |
| 184CD1 | 25C4 | 19NE2 | 70.60 | 184NE1 | 25C4 | 19CD | 53.18 |
| 184NE1 | 25C4 | 184CG | 27.61 | 184NE1 | 25C4 | 18OD1 | 82.57 |
| 184NE1 | 25C4 | 184CE2 | 14.41 | 184NE1 | 25C4 | 19NE2 | 63.56 |
| 21NE2 | 25C4 | 20N | 70.04 | 21NE2 | 25C4 | 20CA | 52.20 |
| 21NE2 | 25C4 | 21OE1 | 28.00 | 21NE2 | 25C4 | 18OD1 | 83.21 |
| 21NE2 | 25C4 | 21CD | 15.16 | 21NE2 | 25C4 | 21N | 39.44 |
| 20N | 25C4 | 19CD | 66.67 | 20N | 25C4 | 20CA | 18.60 |
| 20N | 25C4 | 21OE1 | 91.11 | 20N | 25C4 | 184CG | 96.83 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 20N | 25C4 | 18OD1 | 41.94 | 20N | 25C4 | 21CD | 77.35 |
| 20N | 25C4 | 19NE2 | 70.35 | 20N | 25C4 | 21N | 45.53 |
| 19CD | 25C4 | 20CA | 81.50 | 19CD | 25C4 | 184CG | 71.48 |
| 19CD | 25C4 | 18OD1 | 79.99 | 19CD | 25C4 | 184CE2 | 66.85 |
| 19CD | 25C4 | 19NE2 | 15.24 | 19CD | 25C4 | 21N | 92.20 |
| 20CA | 25C4 | 21OE1 | 72.56 | 20CA | 25C4 | 18OD1 | 52.69 |
| 20CA | 25C4 | 21CD | 58.76 | 20CA | 25C4 | 19NE2 | 81.60 |
| 20CA | 25C4 | 21N | 28.99 | 21OE1 | 25C4 | 21CD | 14.61 |
| 21OE1 | 25C4 | 21N | 48.49 | 184CG | 25C4 | 18OD1 | 62.90 |
| 184CG | 25C4 | 184CE2 | 27.32 | 184CG | 25C4 | 19NE2 | 85.13 |
| 18OD1 | 25C4 | 184CE2 | 89.23 | 18OD1 | 25C4 | 21CD | 97.26 |
| 18OD1 | 25C4 | 19NE2 | 92.18 | 18OD1 | 25C4 | 21N | 80.98 |
| 184CE2 | 25C4 | 19NE2 | 75.84 | 21CD | 25C4 | 21N | 37.64 |
| 19NE2 | 25C4 | 21N | 85.10 | 20O | 25C5 | 20N | 55.48 |
| 20O | 25C5 | 20C | 21.07 | 20O | 25C5 | 20CA | 44.11 |
| 20O | 25C5 | 19CG | 71.84 | 20O | 25C5 | 21NE2 | 66.85 |
| 20O | 25C5 | 19C | 51.82 | 20O | 25C5 | 21N | 24.93 |
| 20O | 25C5 | 19CD | 75.35 | 20O | 25C5 | 19N | 84.18 |
| 20O | 25C5 | 19CA | 67.21 | 20O | 25C5 | 19CB | 67.59 |
| 20O | 25C5 | 21CD | 58.45 | 20O | 25C5 | 19C | 39.96 |
| 20O | 25C5 | 21OE1 | 62.69 | 20N | 25C5 | 20C | 45.30 |
| 20N | 25C5 | 20CA | 25.13 | 20N | 25C5 | 18OD1 | 58.18 |
| 20N | 25C5 | 19CG | 59.77 | 20N | 25C5 | 21NE2 | 88.80 |
| 20N | 25C5 | 19C | 15.04 | 20N | 25C5 | 21N | 55.27 |
| 20N | 25C5 | 242OH2 | 88.85 | 20N | 25C5 | 18CG | 53.24 |
| 20N | 25C5 | 19CD | 75.42 | 20N | 25C5 | 19N | 36.29 |
| 20N | 25C5 | 19CA | 29.03 | 20N | 25C5 | 19CB | 45.65 |
| 20N | 25C5 | 21CD | 91.99 | 20N | 25C5 | 18ND2 | 55.37 |
| 20N | 25C5 | 19O | 20.80 | 20N | 25C5 | 183O | 72.28 |
| 20C | 25C5 | 20CA | 26.08 | 20C | 25C5 | 18OD1 | 98.89 |
| 20C | 25C5 | 19CG | 82.87 | 20C | 25C5 | 21NE2 | 55.09 |
| 20C | 25C5 | 19C | 48.39 | 20C | 25C5 | 21N | 11.08 |
| 20C | 25C5 | 242OH2 | 97.88 | 20C | 25C5 | 18CG | 90.40 |
| 20C | 25C5 | 19CD | 90.83 | 20C | 25C5 | 19N | 80.24 |
| 20C | 25C5 | 19CA | 66.78 | 20C | 25C5 | 19CB | 74.20 |
| 20C | 25C5 | 21CD | 51.59 | 20C | 25C5 | 18ND2 | 83.45 |
| 20C | 25C5 | 19O | 38.43 | 20C | 25C5 | 21OE1 | 61.08 |
| 20CA | 25C5 | 18OD1 | 72.87 | 20CA | 25C5 | 19CG | 80.41 |
| 20CA | 25C5 | 21NE2 | 63.95 | 20CA | 25C5 | 19C | 35.76 |
| 20CA | 25C5 | 21N | 33.35 | 20CA | 25C5 | 242OH2 | 81.51 |
| 20CA | 25C5 | 18CG | 64.36 | 20CA | 25C5 | 19CD | 93.94 |
| 20CA | 25C5 | 19N | 61.13 | 20CA | 25C5 | 19CA | 53.26 |
| 20CA | 25C5 | 19CB | 67.53 | 20CA | 25C5 | 21CD | 66.97 |
| 20CA | 25C5 | 18ND2 | 58.72 | 20CA | 25C5 | 19O | 32.23 |
| 20CA | 25C5 | 183O | 97.26 | 20CA | 25C5 | 21OE1 | 79.78 |
| 18OD1 | 25C5 | 19CG | 80.27 | 18OD1 | 25C5 | 19C | 65.37 |
| 18OD1 | 25C5 | 184CD1 | 74.17 | 18OD1 | 25C5 | 242OH2 | 54.74 |
| 18OD1 | 25C5 | 18CG | 10.85 | 18OD1 | 25C5 | 19CD | 93.30 |
| 18OD1 | 25C5 | 184NE1 | 90.85 | 18OD1 | 25C5 | 19N | 40.79 |
| 18OD1 | 25C5 | 19CA | 57.69 | 18OD1 | 25C5 | 19CB | 70.95 |
| 18OD1 | 25C5 | 18ND2 | 26.15 | 18OD1 | 25C5 | 19O | 76.52 |
| 18OD1 | 25C5 | 184CG | 70.18 | 18OD1 | 25C5 | 183O | 49.64 |
| 19CG | 25C5 | 19C | 45.54 | 19CG | 25C5 | 184CD1 | 61.26 |
| 19CG | 25C5 | 21N | 92.85 | 19CG | 25C5 | 18CG | 85.81 |
| 19CG | 25C5 | 19CD | 16.55 | 19CG | 25C5 | 184NE1 | 60.42 |
| 19CG | 25C5 | 19N | 42.09 | 19CG | 25C5 | 19CA | 32.92 |
| 19CG | 25C5 | 19CB | 14.39 | 19CG | 25C5 | 18ND2 | 99.14 |
| 19CG | 25C5 | 19O | 48.69 | 19CG | 25C5 | 184CG | 74.77 |
| 19CG | 25C5 | 183O | 42.29 | 21NE2 | 25C5 | 19C | 99.03 |
| 21NE2 | 25C5 | 21N | 44.87 | 21NE2 | 25C5 | 242OH2 | 63.97 |
| 21NE2 | 25C5 | 18CG | 97.62 | 21NE2 | 25C5 | 21CD | 14.03 |
| 21NE2 | 25C5 | 18ND2 | 81.87 | 21NE2 | 25C5 | 19O | 91.86 |
| 21NE2 | 25C5 | 21OE1 | 25.97 | 19C | 25C5 | 184CD1 | 99.04 |
| 19C | 25C5 | 21N | 59.38 | 19C | 25C5 | 18CG | 62.98 |
| 19C | 25C5 | 19CD | 60.71 | 19C | 25C5 | 19N | 32.80 |
| 19C | 25C5 | 19CA | 18.65 | 19C | 25C5 | 19CB | 31.95 |
| 19C | 25C5 | 21CD | 99.25 | 19C | 25C5 | 18ND2 | 68.17 |
| 19C | 25C5 | 19O | 11.87 | 19C | 25C5 | 183O | 65.75 |
| 184CD1 | 25C5 | 18CG | 85.01 | 184CD1 | 25C5 | 19CD | 55.30 |
| 184CD1 | 25C5 | 184NE1 | 16.94 | 184CD1 | 25C5 | 19N | 71.72 |
| 184CD1 | 25C5 | 19CA | 80.51 | 184CD1 | 25C5 | 19CB | 70.19 |
| 184CD1 | 25C5 | 18ND2 | 99.06 | 184CD1 | 25C5 | 184CG | 14.35 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 184CD1 | 25C5 | 183O | 35.61 | 21N | 25C5 | 242OH2 | 94.26 |
| 21N | 25C5 | 18CG | 95.93 | 21N | 25C5 | 19CD | 99.24 |
| 21N | 25C5 | 19N | 90.87 | 21N | 25C5 | 19CA | 77.83 |
| 21N | 25C5 | 19CB | 84.96 | 21N | 25C5 | 21CD | 40.54 |
| 21N | 25C5 | 18ND2 | 86.56 | 21N | 25C5 | 19O | 49.51 |
| 21N | 25C5 | 21OE1 | 50.14 | 242OH2 | 25C5 | 18CG | 48.98 |
| 242OH2 | 25C5 | 19N | 93.10 | 242OH2 | 25C5 | 21CD | 77.70 |
| 242OH2 | 25C5 | 18ND2 | 37.02 | 242OH2 | 25C5 | 184CG | 92.59 |
| 242OH2 | 25C5 | 21OE1 | 85.45 | 18CG | 25C5 | 19N | 44.21 |
| 18CG | 25C5 | 19CA | 59.10 | 18CG | 25C5 | 19CB | 74.72 |
| 18CG | 25C5 | 18ND2 | 15.95 | 18CG | 25C5 | 19O | 73.12 |
| 18CG | 25C5 | 184CG | 80.57 | 18CG | 25C5 | 183O | 59.45 |
| 19CD | 25C5 | 184NE1 | 49.55 | 19CD | 25C5 | 19N | 57.74 |
| 19CD | 25C5 | 19CA | 49.44 | 19CD | 25C5 | 19CB | 30.83 |
| 19CD | 25C5 | 19O | 61.72 | 19CD | 25C5 | 184CG | 69.64 |
| 19CD | 25C5 | 183O | 48.36 | 184NE1 | 25C5 | 19N | 82.36 |
| 184NE1 | 25C5 | 19CA | 86.84 | 184NE1 | 25C5 | 19CB | 72.47 |
| 184NE1 | 25C5 | 184CG | 26.82 | 184NE1 | 25C5 | 183O | 47.92 |
| 19N | 25C5 | 19CA | 18.06 | 19N | 25C5 | 19CB | 30.56 |
| 19N | 25C5 | 18ND2 | 57.06 | 19N | 25C5 | 19O | 44.42 |
| 19N | 25C5 | 184CG | 78.07 | 19N | 25C5 | 183O | 36.14 |
| 19CA | 25C5 | 19CB | 18.64 | 19CA | 25C5 | 18ND2 | 69.26 |
| 19CA | 25C5 | 19O | 28.69 | 19CA | 25C5 | 184CG | 89.98 |
| 19CA | 25C5 | 183O | 47.24 | 19CB | 25C5 | 18ND2 | 86.66 |
| 19CB | 25C5 | 19O | 37.11 | 19CB | 25C5 | 184CG | 82.34 |
| 19CB | 25C5 | 183O | 43.36 | 21CD | 25C5 | 18ND2 | 94.92 |
| 21CD | 25C5 | 19O | 90.00 | 21CD | 25C5 | 21CE1 | 14.31 |
| 18ND2 | 25C5 | 19O | 76.17 | 18ND2 | 25C5 | 184CG | 92.52 |
| 18ND2 | 25C5 | 183O | 75.40 | 19O | 25C5 | 183O | 75.72 |
| 19O | 25C5 | 21OE1 | 98.98 | 184CG | 25C5 | 183O | 42.87 |
| 18OD1 | 25C6 | 242OH2 | 77.61 | 18OD1 | 25C6 | 20N | 62.12 |
| 18OD1 | 25C6 | 18CG | 14.65 | 18OD1 | 25C6 | 18ND2 | 34.76 |
| 18OD1 | 25C6 | 20CA | 76.78 | 18OD1 | 25C6 | 184CD1 | 84.66 |
| 18OD1 | 25C6 | 20C | 97.24 | 18OD1 | 25C6 | 19CG | 77.43 |
| 18OD1 | 25C6 | 184CA | 51.93 | 18OD1 | 25C6 | 184CG | 83.75 |
| 18OD1 | 25C6 | 184CB | 70.76 | 18OD1 | 25C6 | 19N | 38.61 |
| 18OD1 | 25C6 | 19C | 62.85 | 18OD1 | 25C6 | 183O | 51.93 |
| 18OD1 | 25C6 | 244OH2 | 87.25 | 18OD1 | 25C6 | 184NE1 | 97.99 |
| 242OH2 | 25C6 | 18CG | 65.17 | 242OH2 | 25C6 | 18ND2 | 48.30 |
| 242OH2 | 25C6 | 20CA | 92.93 | 242OH2 | 25C6 | 21NE2 | 71.65 |
| 242OH2 | 25C6 | 184CA | 99.99 | 242OH2 | 25C6 | 244OH2 | 54.20 |
| 20N | 25C6 | 18CG | 61.40 | 20N | 25C6 | 18ND2 | 64.85 |
| 20N | 25C6 | 20CA | 22.20 | 20N | 25C6 | 20O | 43.67 |
| 20N | 25C6 | 20C | 36.81 | 20N | 25C6 | 21NE2 | 80.01 |
| 20N | 25C6 | 19CG | 49.35 | 20N | 25C6 | 19N | 37.08 |
| 20N | 25C6 | 19C | 10.50 | 20N | 25C6 | 183O | 71.86 |
| 20N | 25C6 | 244OH2 | 62.38 | 18CG | 25C6 | 18ND2 | 20.14 |
| 18CG | 25C6 | 20CA | 71.10 | 18CG | 25C6 | 184CD1 | 99.10 |
| 18CG | 25C6 | 20C | 92.50 | 18CG | 25C6 | 19CG | 87.70 |
| 18CG | 25C6 | 184CA | 64.20 | 18CG | 25C6 | 184CG | 96.81 |
| 18CG | 25C6 | 184CB | 82.01 | 18CG | 25C6 | 19N | 47.68 |
| 18CG | 25C6 | 19C | 65.05 | 18CG | 25C6 | 183O | 66.43 |
| 18CG | 25C6 | 244OH2 | 73.82 | 18ND2 | 25C6 | 20CA | 66.38 |
| 18ND2 | 25C6 | 20C | 86.96 | 18ND2 | 25C6 | 21NE2 | 91.35 |
| 18ND2 | 25C6 | 184CA | 81.21 | 18ND2 | 25C6 | 184CB | 96.97 |
| 18ND2 | 25C6 | 19N | 63.62 | 18ND2 | 25C6 | 19C | 71.84 |
| 18ND2 | 25C6 | 183O | 86.52 | 18ND2 | 25C6 | 244OH2 | 56.34 |
| 20CA | 25C6 | 20O | 36.02 | 20CA | 25C6 | 20C | 21.45 |
| 20CA | 25C6 | 21NE2 | 58.02 | 20CA | 25C6 | 19CG | 66.36 |
| 20CA | 25C6 | 19N | 58.93 | 20CA | 25C6 | 19C | 31.05 |
| 20CA | 25C6 | 183O | 94.02 | 20CA | 25C6 | 244OH2 | 42.94 |
| 20O | 25C6 | 20C | 17.19 | 20O | 25C6 | 21NE2 | 55.96 |
| 20O | 25C6 | 19CG | 53.96 | 20O | 25C6 | 19N | 73.45 |
| 20O | 25C6 | 19C | 43.47 | 20O | 25C6 | 183O | 95.13 |
| 20O | 25C6 | 244OH2 | 65.82 | 20O | 25C6 | 184NE1 | 94.22 |
| 184CD1 | 25C6 | 19CG | 55.80 | 184CD1 | 25C6 | 184CA | 40.42 |
| 184CD1 | 25C6 | 184CG | 17.20 | 184CD1 | 25C6 | 184CB | 33.57 |
| 184CD1 | 25C6 | 19N | 72.31 | 184CD1 | 25C6 | 19C | 91.74 |
| 184CD1 | 25C6 | 183O | 36.78 | 184CD1 | 25C6 | 184NE1 | 14.58 |
| 20C | 25C6 | 21NE2 | 47.89 | 20C | 25C6 | 19CG | 64.56 |
| 20C | 25C6 | 19N | 72.48 | 20C | 25C6 | 19C | 41.10 |
| 20C | 25C6 | 244OH2 | 49.53 | 21NE2 | 25C6 | 19C | 87.32 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 21NE2 | 25C6 | 244OH2 | 35.45 | 19CG | 25C6 | 184CA | 76.21 |
| 19CG | 25C6 | 184CG | 72.47 | 19CG | 25C6 | 184CB | 83.57 |
| 19CG | 25C6 | 19N | 40.03 | 19CG | 25C6 | 19C | 38.92 |
| 19CG | 25C6 | 183O | 42.08 | 19CG | 25C6 | 184NE1 | 53.94 |
| 184CA | 25C6 | 184CG | 32.82 | 184CA | 25C6 | 184CB | 19.38 |
| 184CA | 25C6 | 19N | 63.55 | 184CA | 25C6 | 19C | 94.44 |
| 184CA | 25C6 | 183O | 34.70 | 184CA | 25C6 | 184NE1 | 54.88 |
| 184CG | 25C6 | 184CB | 18.90 | 184CG | 25C6 | 19N | 82.27 |
| 184CG | 25C6 | 183O | 45.36 | 184CG | 25C6 | 184NE1 | 27.16 |
| 184CB | 25C6 | 19N | 80.80 | 184CB | 25C6 | 183O | 46.93 |
| 184CB | 25C6 | 184NE1 | 45.74 | 19N | 25C6 | 19C | 31.43 |
| 19N | 25C6 | 183O | 36.92 | 19N | 25C6 | 244OH2 | 93.07 |
| 19N | 25C6 | 184NE1 | 79.67 | 19C | 25C6 | 183O | 63.42 |
| 19C | 25C6 | 244OH2 | 72.61 | 19C | 25C6 | 184NE1 | 92.57 |
| 183O | 25C6 | 184NE1 | 47.52 | 20O | 25C7 | 19CG | 66.72 |
| 20O | 25C7 | 20C | 8.16 | 20O | 25C7 | 19CD | 83.83 |
| 20O | 25C7 | 19NE2 | 82.44 | 20O | 25C7 | 22O | 56.54 |
| 20O | 25C7 | 22N | 36.30 | 20O | 25C7 | 21CA | 31.83 |
| 20O | 25C7 | 19OE1 | 95.92 | 20O | 25C7 | 21OE1 | 66.65 |
| 20O | 25C7 | 21N | 17.17 | 20O | 25C7 | 20N | 30.97 |
| 20O | 25C7 | 21NE2 | 51.64 | 20O | 25C7 | 20CA | 19.21 |
| 19CG | 25C7 | 20C | 71.45 | 19CG | 25C7 | 19CD | 21.67 |
| 19CG | 25C7 | 19NE2 | 34.92 | 19CG | 25C7 | 22O | 55.96 |
| 19CG | 25C7 | 184NE1 | 60.44 | 19CG | 25C7 | 22N | 79.46 |
| 19CG | 25C7 | 21CA | 96.64 | 19CG | 25C7 | 19OE1 | 30.14 |
| 19CG | 25C7 | 21N | 83.86 | 19CG | 25C7 | 184CD1 | 53.93 |
| 19CG | 25C7 | 20N | 45.16 | 19CG | 25C7 | 20CA | 61.57 |
| 20C | 25C7 | 19CD | 89.91 | 20C | 25C7 | 19NE2 | 89.95 |
| 20C | 25C7 | 22O | 64.63 | 20C | 25C7 | 22N | 42.08 |
| 20C | 25C7 | 21CA | 30.95 | 20C | 25C7 | 21OE1 | 60.76 |
| 20C | 25C7 | 21N | 13.74 | 20C | 25C7 | 20N | 31.22 |
| 20C | 25C7 | 21NE2 | 43.84 | 20C | 25C7 | 20CA | 15.80 |
| 19CD | 25C7 | 19NE2 | 18.60 | 19CD | 25C7 | 22O | 53.43 |
| 19CD | 25C7 | 184NE1 | 53.45 | 19CD | 25C7 | 22N | 85.40 |
| 19CD | 25C7 | 19OE1 | 13.55 | 19CD | 25C7 | 184CD1 | 54.25 |
| 19CD | 25C7 | 20N | 66.44 | 19CD | 25C7 | 20CA | 82.18 |
| 19NE2 | 25C7 | 22O | 38.61 | 19NE2 | 25C7 | 184NE1 | 67.89 |
| 19NE2 | 25C7 | 22N | 73.27 | 19NE2 | 25C7 | 19OE1 | 28.20 |
| 19NE2 | 25C7 | 21N | 97.49 | 19NE2 | 25C7 | 184CD1 | 71.68 |
| 19NE2 | 25C7 | 20N | 74.18 | 19NE2 | 25C7 | 20CA | 86.96 |
| 22O | 25C7 | 22N | 35.17 | 22O | 25C7 | 21CA | 64.61 |
| 22O | 25C7 | 19OE1 | 65.85 | 22O | 25C7 | 21N | 66.20 |
| 22O | 25C7 | 20N | 67.78 | 22O | 25C7 | 20CA | 70.65 |
| 184NE1 | 25C7 | 19OE1 | 40.45 | 184NE1 | 25C7 | 184CD1 | 16.51 |
| 184NE1 | 25C7 | 20N | 91.81 | 22N | 25C7 | 21CA | 29.87 |
| 22N | 25C7 | 19OE1 | 98.77 | 22N | 25C7 | 21OE1 | 70.75 |
| 22N | 25C7 | 21N | 36.58 | 22N | 25C7 | 20N | 63.54 |
| 22N | 25C7 | 21NE2 | 72.49 | 22N | 25C7 | 20CA | 5$.44 |
| 21CA | 25C7 | 21OE1 | 42.69 | 21CA | 25C7 | 21N | 17.64 |
| 21CA | 25C7 | 20N | 61.95 | 21CA | 25C7 | 21NE2 | 43.40 |
| 21CA | 25C7 | 20CA | 46.53 | 19OE1 | 25C7 | 184CD1 | 43.68 |
| 19CE1 | 25C7 | 20N | 74.85 | 19OE1 | 25C7 | 20CA | 91.61 |
| 21OE1 | 25C7 | 21N | 49.78 | 21OE1 | 25C7 | 20N | 86.97 |
| 21OE1 | 25C7 | 21NE2 | 27.10 | 21OE1 | 25C7 | 20CA | 70.13 |
| 21N | 25C7 | 20N | 44.95 | 21N | 25C7 | 21NE2 | 38.79 |
| 21N | 25C7 | 20CA | 28.96 | 184CD1 | 25C7 | 20N | 77.27 |
| 184CD1 | 25C7 | 20CA | 92.17 | 20N | 25C7 | 21NE2 | 62.89 |
| 20N | 25C7 | 20CA | 17.26 | 21NE2 | 25C7 | 20CA | 47.61 |
| 20C | 25O8 | 184NE1 | 98.56 | 20O | 25O8 | 19NE2 | 64.94 |
| 20C | 25O8 | 19CD | 64.80 | 20O | 25O8 | 19CG | 49.58 |
| 20O | 25O8 | 184CD1 | 86.05 | 20O | 25O8 | 19OE1 | 77.25 |
| 184NE1 | 25O8 | 19NE2 | 65.95 | 184NE1 | 25O8 | 19CD | 51.39 |
| 184NE1 | 25O8 | 19CG | 55.21 | 184NE1 | 25O8 | 184CE2 | 15.43 |
| 184NE1 | 25O8 | 184CD1 | 14.81 | 184NE1 | 25O8 | 19OE1 | 39.31 |
| 19NE2 | 25O8 | 19CD | 16.73 | 19NE2 | 25O8 | 19CG | 29.82 |
| 19NE2 | 25O8 | 184CE2 | 79.52 | 19NE2 | 25O8 | 184CD1 | 66.86 |
| 19NE2 | 25O8 | 19OE1 | 26.64 | 19CD | 25O8 | 19CG | 18.32 |
| 19CD | 25O8 | 184CE2 | 66.04 | 19CD | 25O8 | 184CD1 | 50.50 |
| 19CD | 25O8 | 19OE1 | 13.90 | 19CG | 25O8 | 184CE2 | 70.62 |
| 19CG | 25O8 | 184CD1 | 48.50 | 19CG | 25O8 | 19OE1 | 28.11 |
| 184CE2 | 25O8 | 184CD1 | 26.04 | 184CE2 | 25O8 | 19OE1 | 53.16 |
| 184CD1 | 25O8 | 19OE1 | 41.64 | 184NE1 | 25C9 | 19NE2 | 75.95 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 184NE1 | 25C9 | 19CD | 58.34 | 184NE1 | 25C9 | 184CE2 | 18.51 |
| 184NE1 | 25C9 | 184CZ2 | 36.32 | 184NE1 | 25C9 | 19OE1 | 46.11 |
| 184NE1 | 25C9 | 162CE1 | 47.88 | 184NE1 | 25C9 | 184CD1 | 13.15 |
| 184NE1 | 25C9 | 19CG | 58.03 | 19NE2 | 25C9 | 19CD | 18.37 |
| 19NE2 | 25C9 | 184CE2 | 93.09 | 19NE2 | 25C9 | 19OE1 | 30.69 |
| 19NE2 | 25C9 | 162CE1 | 65.23 | 19NE2 | 25C9 | 184CD1 | 73.02 |
| 19NE2 | 25C9 | 19CG | 30.00 | 19CD | 25C9 | 184CE2 | 76.16 |
| 19CD | 25C9 | 184CZ2 | 89.88 | 19CD | 25C9 | 19OE1 | 16.50 |
| 19CD | 25C9 | 162CE1 | 58.87 | 19CD | 25C9 | 184CD1 | 54.66 |
| 19CD | 25C9 | 19CG | 17.52 | 184CE2 | 25C9 | 184CZ2 | 19.20 |
| 184CE2 | 25C9 | 19OE1 | 62.52 | 184CE2 | 25C9 | 162CE1 | 49.95 |
| 184CE2 | 25C9 | 184CD1 | 28.40 | 184CE2 | 25C9 | 19CG | 76.51 |
| 184CZ2 | 25C9 | 19OE1 | 74.32 | 184CZ2 | 25C9 | 162CE1 | 47.31 |
| 184CZ2 | 25C9 | 184CD1 | 47.47 | 184CZ2 | 25C9 | 19CG | 93.64 |
| 19OE1 | 25C9 | 162CE1 | 43.44 | 19OE1 | 25C9 | 184CD1 | 46.14 |
| 19OE1 | 25C9 | 19CG | 29.61 | 162CE1 | 25C9 | 184CD1 | 58.96 |
| 162CE1 | 25C9 | 19CG | 72.86 | 184CD1 | 25C9 | 19CG | 50.05 |
| 184NE1 | 25O10 | 184CE2 | 25.08 | 184NE1 | 25O10 | 184CZ2 | 48.91 |
| 184NE1 | 25O10 | 19OE1 | 62.37 | 184NE1 | 25O10 | 19CD | 75.84 |
| 184NE1 | 25O10 | 184CD1 | 15.34 | 184NE1 | 25O10 | 162CE1 | 66.14 |
| 184NE1 | 25O10 | 19NE2 | 95.76 | 184NE1 | 25O10 | 162ND1 | 81.12 |
| 184NE1 | 25O10 | 19CG | 70.87 | 184NE1 | 25O10 | 184CD2 | 22.23 |
| 184NE1 | 25O10 | 162NE2 | 52.65 | 184NE1 | 25O10 | 184CH2 | 53.72 |
| 184NE1 | 25O10 | 184CG | 14.63 | 184CE2 | 25O10 | 184CZ2 | 25.03 |
| 184CE2 | 25O10 | 19OE1 | 84.37 | 184CE2 | 25O10 | 184CD1 | 37.35 |
| 184CE2 | 25O10 | 162OE1 | 66.88 | 184CE2 | 25O10 | 162ND1 | 77.00 |
| 184CE2 | 25O10 | 19CG | 95.89 | 184CE2 | 25O10 | 184CD2 | 1O.58 |
| 184CE2 | 25O10 | 162NE2 | 51.22 | 184CE2 | 25O10 | 184CH2 | 28.91 |
| 184CE2 | 25O10 | 184CG | 26.65 | 184CZ2 | 25O10 | 19OE1 | 99.91 |
| 184CZ2 | 25O10 | 184CD1 | 62.29 | 184CZ2 | 25O10 | 162CE1 | 61.92 |
| 184CZ2 | 25O10 | 162ND1 | 65.32 | 184CZ2 | 25O10 | 184CD2 | 33.91 |
| 184CZ2 | 25O10 | 162NE2 | 48.17 | 184CZ2 | 25O10 | 184CH2 | 7.17 |
| 184CZ2 | 25O10 | 184CG | 51.50 | 19OE1 | 25O10 | 19CD | 19.97 |
| 19OE1 | 25O10 | 184CD1 | 59.90 | 19OE1 | 25O10 | 162CE1 | 56.15 |
| 19OE1 | 25O10 | 19NE2 | 35.40 | 19OE1 | 25O10 | 162ND1 | 68.84 |
| 19OE1 | 25O10 | 19CG | 33.29 | 19OE1 | 25O10 | 184CD2 | 84.51 |
| 19OE1 | 25O10 | 162NE2 | 60.20 | 19OE1 | 25O10 | 184CG | 72.32 |
| 19CD | 25O10 | 184CD1 | 68.82 | 19CD | 25O10 | 162CE1 | 74.19 |
| 19CD | 25O10 | 19NE2 | 20.25 | 19CD | 25O10 | 162ND1 | 84.51 |
| 19CD | 25O10 | 19CG | 19.19 | 19CD | 25O10 | 184CD2 | 97.71 |
| 19CD | 25O10 | 162NE2 | 79.91 | 19CD | 25O10 | 184CG | 82.24 |
| 184CD1 | 25O10 | 162CE1 | 78.10 | 184CD1 | 25O10 | 19NE2 | 89.03 |
| 184CD1 | 25O10 | 162ND1 | 94.07 | 184CD1 | 25O10 | 19CG | 59.77 |
| 184CD1 | 25O10 | 184CD2 | 30.63 | 184CD1 | 25O10 | 162NE2 | 66.09 |
| 184CD1 | 25O10 | 184CH2 | 66.12 | 184CD1 | 25O10 | 184CG | 13.45 |
| 162CE1 | 25O10 | 19NE2 | 78.81 | 162CE1 | 25O10 | 162ND1 | 16.74 |
| 162CE1 | 25O10 | 19CG | 89.36 | 162CE1 | 25O10 | 184CD2 | 75.74 |
| 162CE1 | 25O10 | 162NE2 | 15.66 | 162CE1 | 25O10 | 184CH2 | 68.07 |
| 162CE1 | 25O10 | 184CG | 80.42 | 19NE2 | 25O10 | 162ND1 | 83.89 |
| 19NE2 | 25O10 | 19CG | 33.67 | 19NE2 | 25O10 | 162NE2 | 89.03 |
| 162ND1 | 25O10 | 184CD2 | 86.96 | 162ND1 | 25O10 | 162NE2 | 28.50 |
| 162ND1 | 25O10 | 184CH2 | 70.03 | 162ND1 | 25O10 | 184CG | 94.80 |
| 19CG | 25O10 | 184CD2 | 90.39 | 19CG | 25O10 | 162NE2 | 91.46 |
| 19CG | 25O10 | 184CG | 72.81 | 184CD2 | 25O10 | 162NE2 | 60.21 |
| 184CD2 | 25O10 | 184CH2 | 36.32 | 184CD2 | 25O10 | 184CG | 18.11 |
| 162NE2 | 25O10 | 184CH2 | 54.84 | 162NE2 | 25O10 | 184CG | 66.33 |
| 184CH2 | 25O10 | 184CG | 54.39 | 162ND1 | 25C11 | 162CE1 | 18.33 |
| 162ND1 | 25C11 | 184CZ2 | 57.54 | 162ND1 | 25C11 | 19NE2 | 74.67 |
| 162ND1 | 25C11 | 162CG | 12.31 | 162CE1 | 25C11 | 184CZ2 | 47.54 |
| 162CE1 | 25C11 | 19NE2 | 62.12 | 162CE1 | 25C11 | 162CG | 26.24 |
| 184CZ2 | 25C11 | 19NE2 | 86.59 | 184CZ2 | 25C11 | 162CG | 53.23 |
| 19NE2 | 25C11 | 162CG | 86.37 | 162ND1 | 25C12 | 16O | 52.69 |
| 161OD1 | 25C13 | 162ND1 | 77.53 | 161OD1 | 25C13 | 161CG | 13.50 |
| 161OD1 | 25C13 | 161O | 49.60 | 161OD1 | 25C13 | 162CB | 47.00 |
| 161OD1 | 25C13 | 162CG | 64.44 | 161OD1 | 25C13 | 137O | 63.21 |
| 162ND1 | 25C13 | 161CG | 86.85 | 162ND1 | 25C13 | 161O | 55.29 |
| 162ND1 | 25C13 | 184CZ2 | 52.94 | 162ND1 | 25C13 | 162CB | 31.13 |
| 162ND1 | 25C13 | 162CG | 16.56 | 162ND1 | 25C13 | 137O | 91.79 |
| 161CG | 25C13 | 161O | 48.18 | 161CG | 25C13 | 162CB | 57.82 |
| 161CG | 25C13 | 162CG | 75.53 | 161CG | 25C13 | 137O | 72.06 |
| 161C | 25C13 | 162CB | 45.12 | 161O | 25C13 | 162CG | 55.63 |
| 184CZ2 | 25C13 | 162CB | 67.90 | 184CZ2 | 25C13 | 162CG | 52.88 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 184CZ2 | 25C13 | 137O | 65.96 | 162CB | 25C13 | 162CG | 17.71 |
| 162CB | 25C13 | 137O | 73.09 | 162CG | 25C13 | 137O | 76.90 |
| 161OD1 | 25C14 | 162CB | 67.52 | 161OD1 | 25C14 | 162CG | 91.93 |
| 161OD1 | 25C14 | 161O | 65.79 | 161OD1 | 25C14 | 161C | 49.33 |
| 161OD1 | 25C14 | 162CA | 65.70 | 161OD1 | 25C14 | 161CG | 13.81 |
| 161OD1 | 25C14 | 162N | 48.26 | 161OD1 | 25C14 | 137CB | 61.84 |
| 161OD1 | 25C14 | 161CB | 32.59 | 161OD1 | 25C14 | 162CD2 | 97.90 |
| 161OD1 | 25C14 | 137C | 54.56 | 161OD1 | 25C14 | 161CA | 38.35 |
| 161OD1 | 25C14 | 137O | 68.99 | 161OD1 | 25C14 | 137CA | 49.42 |
| 162ND1 | 25C14 | 162CB | 44.41 | 162ND1 | 25C14 | 162CG | 23.28 |
| 162ND1 | 25C14 | 161O | 75.37 | 162ND1 | 25C14 | 161C | 79.50 |
| 162ND1 | 25C14 | 162CA | 48.35 | 162ND1 | 25C14 | 162N | 68.54 |
| 162ND1 | 25C14 | 162CE1 | 14.58 | 162ND1 | 25C14 | 137CB | 81.24 |
| 162ND1 | 25C14 | 162CD2 | 28.11 | 162ND1 | 25C14 | 184CZ2 | 60.58 |
| 162ND1 | 25C14 | 162NE2 | 21.94 | 162ND1 | 25C14 | 161CA | 95.48 |
| 162ND1 | 25C14 | 137CA | 97.09 | 162CB | 25C14 | 162CG | 25.05 |
| 162CB | 25C14 | 161O | 62.89 | 162CB | 25C14 | 161C | 53.94 |
| 162CB | 25C14 | 162CA | 21.95 | 162CB | 25C14 | 161CG | 76.82 |
| 162CB | 25C14 | 162N | 35.96 | 162CB | 25C14 | 162CE1 | 55.50 |
| 162CB | 25C14 | 137CB | 53.40 | 162CB | 25C14 | 161CB | 80.35 |
| 162CB | 25C14 | 162CD2 | 35.20 | 162CB | 25C14 | 184CZ2 | 83.43 |
| 162CB | 25C14 | 137C | 81.05 | 162CB | 25C14 | 162NE2 | 49.18 |
| 162CB | 25C14 | 161CA | 65.39 | 162CB | 25C14 | 137O | 88.14 |
| 162CB | 25C14 | 137CA | 63.27 | 162CG | 25C14 | 161O | 77.15 |
| 162CG | 25C14 | 161C | 73.93 | 162CG | 25C14 | 162CA | 38.93 |
| 162CG | 25C14 | 162N | 57.98 | 162CG | 25C14 | 162CE1 | 31.20 |
| 162CG | 25C14 | 137CB | 59.50 | 162CG | 25C14 | 162CD2 | 13.71 |
| 162CG | 25C14 | 184CZ2 | 62.16 | 162CG | 25C14 | 137C | 90.53 |
| 162CG | 25C14 | 162NE2 | 24.37 | 162CG | 25C14 | 161CA | 87.82 |
| 162CG | 25C14 | 137O | 91.83 | 162CG | 25C14 | 137CA | 74.49 |
| 161O | 25C14 | 161C | 17.83 | 161O | 25C14 | 162CA | 41.16 |
| 161O | 25C14 | 161CG | 59.81 | 161O | 25C14 | 162N | 32.33 |
| 161O | 25C14 | 162CE1 | 89.00 | 161O | 25C14 | 161CB | 43.28 |
| 161O | 25C14 | 162CD2 | 90.86 | 161O | 25C14 | 162NE2 | 95.79 |
| 161O | 25C14 | 161CA | 28.30 | 161C | 25C14 | 162CA | 35.01 |
| 161C | 25C14 | 161CG | 45.86 | 161C | 25C14 | 162N | 18.49 |
| 161C | 25C14 | 162CE1 | 94.05 | 161C | 25C14 | 137CB | 91.74 |
| 161C | 25C14 | 161CB | 34.16 | 161C | 25C14 | 162CD2 | 87.05 |
| 161C | 25C14 | 162NE2 | 96.49 | 161C | 25C14 | 161CA | 16.14 |
| 161C | 25C14 | 137CA | 88.79 | 162CA | 25C14 | 161CG | 70.29 |
| 162CA | 25C14 | 162N | 20.32 | 162CA | 25C14 | 162CE1 | 62.52 |
| 162CA | 25C14 | 137CB | 73.16 | 162CA | 25C14 | 161CB | 66.66 |
| 162CA | 25C14 | 162CD2 | 52.11 | 162CA | 25C14 | 137C | 96.91 |
| 162CA | 25C14 | 162NE2 | 62.05 | 162CA | 25C14 | 161CA | 49.32 |
| 162CA | 25C14 | 137CA | 79.58 | 161CG | 25C14 | 162N | 50.67 |
| 161CG | 25C14 | 137CB | 75.47 | 161CG | 25C14 | 161CB | 20.44 |
| 161CG | 25C14 | 137C | 64.73 | 161CG | 25C14 | 161CA | 31.54 |
| 161CG | 25C14 | 137O | 78.60 | 161CG | 25C14 | 137CA | 62.23 |
| 162N | 25C14 | 162CE1 | 82.81 | 162N | 25C14 | 137CB | 75.61 |
| 162N | 25C14 | 161CB | 46.58 | 162N | 25C14 | 162CD2 | 70.31 |
| 162N | 25C14 | 137C | 90.94 | 162N | 25C14 | 162NE2 | 81.86 |
| 162N | 25C14 | 161CA | 29.89 | 162N | 25C14 | 137CA | 76.03 |
| 162CE1 | 25C14 | 137CB | 81.53 | 162CE1 | 25C14 | 162CD2 | 28.99 |
| 162CE1 | 25C14 | 184CZ2 | 47.31 | 162CE1 | 25C14 | 162NE2 | 14.94 |
| 162CE1 | 25C14 | 137CA | 98.37 | 137CB | 25C14 | 161CB | 93.78 |
| 137CB | 25C14 | 162CD2 | 53.66 | 137CB | 25C14 | 184CZ2 | 66.27 |
| 137CB | 25C14 | 137C | 31.04 | 137CB | 25C14 | 162NE2 | 66.78 |
| 137CB | 25C14 | 161CA | 91.93 | 137CB | 25C14 | 137O | 34.84 |
| 137CB | 25C14 | 137CA | 16.94 | 161CB | 25C14 | 137C | 85.13 |
| 161CB | 25C14 | 161CA | 18.06 | 161CB | 25C14 | 137O | 98.82 |
| 161CB | 25C14 | 137CA | 82.61 | 162CD2 | 25C14 | 184CZ2 | 49.12 |
| 162CD2 | 25C14 | 137C | 84.06 | 162CD2 | 25C14 | 162NE2 | 16.33 |
| 162CD2 | 25C14 | 137O | 82.53 | 162CD2 | 25C14 | 137CA | 70.12 |
| 184CZ2 | 25C14 | 137C | 79.92 | 184CZ2 | 25C14 | 162NE2 | 40.56 |
| 184CZ2 | 25C14 | 137O | 67.98 | 184CZ2 | 25C14 | 137CA | 79.44 |
| 137C | 25C14 | 162NE2 | 95.36 | 137C | 25C14 | 161CA | 92.71 |
| 137C | 25C14 | 137O | 14.52 | 137C | 25C14 | 137CA | 17.79 |
| 162NE2 | 25C14 | 137O | 90.59 | 162NE2 | 25C14 | 137CA | 83.69 |
| 161CA | 25C14 | 137CA | 84.51 | 137O | 25C14 | 137CA | 28.01 |
| 137O | 25C15 | 184CZ2 | 82.18 | 137O | 25C15 | 184CH2 | 65.00 |
| 137O | 25C15 | 137C | 15.27 | 137O | 25C15 | 161OD1 | 65.35 |
| 137O | 25C15 | 138CA | 35.59 | 137O | 25C15 | 138N | 27.26 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 137O | 25C15 | 137CB | 35.12 | 184CZ2 | 25C15 | 184CH2 | 18.93 |
| 184CZ2 | 25C15 | 137C | 89.79 | 184CZ2 | 25C15 | 137CB | 65.87 |
| 184CH2 | 25C15 | 137C | 74.80 | 184CH2 | 25C15 | 138N | 90.34 |
| 184CH2 | 25C15 | 137CB | 56.59 | 137C | 25C15 | 161OD1 | 50.24 |
| 137C | 25C15 | 138CA | 30.23 | 137C | 25C15 | 138N | 15.68 |
| 137C | 25C15 | 137CB | 30.32 | 161OD1 | 25C15 | 138CA | 56.67 |
| 161OD1 | 25C15 | 138N | 45.35 | 161OD1 | 25C15 | 137CB | 48.96 |
| 161C | 25C14 | 161CB | 34.16 | 161C | 25C14 | 162CD2 | 87.05 |
| 161C | 25C14 | 162NE2 | 96.49 | 161C | 25C14 | 161CA | 16.14 |
| 161C | 25C14 | 137CA | 88.79 | 162CA | 25C14 | 161CG | 70.29 |
| 162CA | 25C14 | 162N | 20.32 | 162CA | 25C14 | 162CE1 | 62.52 |
| 162CA | 25C14 | 137CB | 73.16 | 162CA | 25C14 | 161CB | 66.66 |
| 162CA | 25C14 | 162CD2 | 52.11 | 162CA | 25C14 | 137C | 96.91 |
| 162CA | 25C14 | 162NE2 | 62.05 | 162CA | 25C14 | 161CA | 49.32 |
| 162CA | 25C14 | 137CA | 79.58 | 161CG | 25C14 | 162N | 50.67 |
| 161CG | 25C14 | 137CB | 75.47 | 161CG | 25C14 | 161CB | 20.44 |
| 161CG | 25C14 | 137C | 64.73 | 161CG | 25C14 | 161CA | 31.54 |
| 161CG | 25C14 | 137O | 78.60 | 161CG | 25C14 | 137CA | 62.23 |
| 162N | 25C14 | 162CE1 | 82.81 | 162N | 25C14 | 137CB | 75.61 |
| 162N | 25C14 | 161CB | 46.58 | 162N | 25C14 | 162CD2 | 70.31 |
| 162N | 25C14 | 137C | 90.94 | 162N | 25C14 | 162NE2 | 81.86 |
| 162N | 25C14 | 161CA | 29.89 | 162N | 25C14 | 137CA | 76.03 |
| 162CE1 | 25C14 | 137CB | 81.53 | 162CE1 | 25C14 | 162CD2 | 28.99 |
| 162CE1 | 25C14 | 184CZ2 | 47.31 | 162CE1 | 25C14 | 162NE2 | 14.94 |
| 162CE1 | 25C14 | 137CA | 98.37 | 137CB | 25C14 | 161CB | 93.78 |
| 137CB | 25C14 | 162CD2 | 53.66 | 137CB | 25C14 | 184CZ2 | 66.27 |
| 137CB | 25C14 | 137C | 31.04 | 137CB | 25C14 | 162NE2 | 66.78 |
| 137CB | 25C14 | 161CA | 91.93 | 137CB | 25C14 | 137O | 34.84 |
| 137CB | 25C14 | 137CA | 16.94 | 161CB | 25C14 | 137C | 85.13 |
| 161CB | 25C14 | 161CA | 18.06 | 161CB | 25C14 | 137O | 98.82 |
| 161CB | 25C14 | 137CA | 82.81 | 162CD2 | 25C14 | 184CZ2 | 49.12 |
| 162CD2 | 25C14 | 137C | 84.06 | 162CD2 | 25C14 | 162NE2 | 16.33 |
| 162CD2 | 25C14 | 137O | 82.53 | 162CD2 | 25C14 | 137CA | 70.12 |
| 184CZ2 | 25C14 | 137C | 79.92 | 184CZ2 | 25C14 | 162NE2 | 40.56 |
| 184CZ2 | 25C14 | 137O | 67.98 | 184CZ2 | 25C14 | 137CA | 79.44 |
| 137C | 25C14 | 162NE2 | 95.36 | 137C | 25C14 | 161CA | 92.71 |
| 137C | 25C14 | 137O | 14.52 | 137C | 25C14 | 137CA | 17.79 |
| 162NE2 | 25C14 | 137O | 90.59 | 162NE2 | 25C14 | 137CA | 83.69 |
| 161CA | 25C14 | 137CA | 84.51 | 137O | 25C14 | 137CA | 28.01 |
| 137O | 25C15 | 184CZ2 | 82.18 | 137O | 25C15 | 184CH2 | 65.00 |
| 137O | 25C15 | 137C | 15.27 | 137O | 25C15 | 161OD1 | 65.35 |
| 137O | 25C15 | 138CA | 35.59 | 137O | 25C15 | 138N | 27.26 |
| 137O | 25C15 | 137CB | 35.12 | 184CZ2 | 25C15 | 184CH2 | 18.93 |
| 184CZ2 | 25C15 | 137C | 89.79 | 184CZ2 | 25C15 | 137CB | 65.87 |
| 184CH2 | 25C15 | 137C | 74.80 | 184CH2 | 25C15 | 138N | 90.34 |
| 184CH2 | 25C15 | 137CB | 56.59 | 137C | 25C15 | 161OD1 | 50.24 |
| 137C | 25C15 | 138CA | 30.23 | 137C | 25C15 | 138N | 15.68 |
| 137C | 25C15 | 137CB | 30.32 | 161OD1 | 25C15 | 138CA | 56.67 |
| 161OD1 | 25C15 | 138N | 45.35 | 161OD1 | 25C15 | 137CB | 48.96 |
| 138CA | 25C15 | 138N | 17.26 | 138CA | 25C15 | 137CB | 59.96 |
| 138N | 25C15 | 137CB | 43.35 | 162ND1 | 25C16 | 25SG | 47.96 |
| 162ND1 | 25C16 | 19NE2 | 81.02 | 162ND1 | 25C16 | 162CE1 | 17.42 |
| 162ND1 | 25C16 | 161O | 59.00 | 25SG | 25C16 | 19NE2 | 64.48 |
| 25SG | 25C16 | 162CE1 | 51.01 | 25SG | 25C16 | 23CA | 79.30 |
| 25SG | 25C16 | 161O | 61.60 | 19NE2 | 25C16 | 162CE1 | 65.94 |
| 19NE2 | 25C16 | 23CA | 51.63 | 162CE1 | 25C16 | 161O | 76.23 |
| 23CA | 25O17 | 19NE2 | 63.28 | 23CA | 25O17 | 23C | 18.00 |
| 23CA | 25O17 | 23N | 16.04 | 23CA | 25O17 | 22O | 36.68 |
| 23CA | 25O17 | 25SG | 86.81 | 23CA | 25O17 | 22C | 27.89 |
| 23CA | 25O17 | 19CD | 75.23 | 23CA | 25O17 | 23O | 26.79 |
| 23CA | 25O17 | 24N | 26.12 | 19NE2 | 25O17 | 23C | 56.89 |
| 19NE2 | 25O17 | 23N | 63.52 | 19NE2 | 25O17 | 22O | 37.86 |
| 19NE2 | 25O17 | 25SG | 64.03 | 19NE2 | 25O17 | 22C | 51.98 |
| 19NE2 | 25O17 | 19CD | 12.01 | 19NE2 | 25O17 | 23O | 67.69 |
| 19NE2 | 25O17 | 24N | 42.39 | 23C | 25O17 | 23N | 32.96 |
| 23C | 25O17 | 22O | 43.34 | 23C | 25O17 | 25SG | 68.82 |
| 23C | 25O17 | 22C | 40.37 | 23C | 25O17 | 19CD | 68.57 |
| 23C | 25O17 | 23O | 13.76 | 23C | 25O17 | 24N | 14.50 |
| 23N | 25O17 | 22O | 28.82 | 23N | 25O17 | 22C | 15.59 |
| 23N | 25O17 | 19CD | 74.62 | 23N | 25O17 | 23O | 42.84 |
| 23N | 25O17 | 24N | 36.39 | 22O | 25.O17 | 25SG | 92.75 |
| 22O | 25O17 | 22C | 14.54 | 22O | 25O17 | 19CD | 47.50 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 22O | 25O17 | 23O | 57.03 | 22O | 25O17 | 24N | 35.11 |
| 25SG | 25O17 | 19CD | 63.67 | 25SG | 25O17 | 23O | 64.10 |
| 25SG | 25O17 | 24N | 64.69 | 22C | 25O17 | 19CD | 61.99 |
| 22C | 25O17 | 23O | 52.87 | 22C | 25O17 | 24N | 37.51 |
| 19CD | 25O17 | 23O | 78.75 | 19CD | 25O17 | 24N | 54.07 |
| 23O | 25O17 | 24N | 64.69 | 25SG | 25N18 | 162ND1 | 59.84 |
| 25SG | 25N18 | 161O | 84.84 | 25SG | 25N18 | 162CE1 | 58.94 |
| 25SG | 25N18 | 25CB | 19.83 | 25SG | 25N18 | 162CG | 65.68 |
| 25SG | 25N18 | 161C | 84.84 | 25SG | 25N18 | 162CA | 63.77 |
| 25SG | 25N18 | 162CB | 72.00 | 25SG | 25N18 | 19NE2 | 64.56 |
| 162ND1 | 25N18 | 161O | 77.72 | 162ND1 | 25N18 | 162CE1 | 17.48 |
| 162ND1 | 25N18 | 26CB | 52.80 | 162ND1 | 25N18 | 1562CG | 12.09 |
| 162ND1 | 25N18 | 161C | 70.93 | 162ND1 | 25N18 | 162CA | 42.08 |
| 162ND1 | 25N18 | 162CB | 29.83 | 162ND1 | 25N18 | 19NE2 | 80.21 |
| 161O | 25N18 | 162CE1 | 95.07 | 161O | 25N18 | 162CG | 66.81 |
| 161O | 25N18 | 161C | 7.83 | 161O | 25N18 | 162CA | 36.26 |
| 161O | 25N18 | 162CB | 49.33 | 162CE1 | 25N18 | 25CB | 45.72 |
| 162CE1 | 25N18 | 162CG | 29.21 | 162CE1 | 25N18 | 161C | 88.39 |
| 162CE1 | 25N18 | 162CA | 59.10 | 162CE1 | 25N18 | 162CB | 47.16 |
| 162CE1 | 25N18 | 19NE2 | 63.44 | 25CB | 25N18 | 162CG | 62.19 |
| 25CB | 25N18 | 161C | 98.68 | 25CB | 25N18 | 162CA | 72.18 |
| 25CB | 25N18 | 162CB | 74.19 | 25CB | 25N18 | 19NE2 | 48.00 |
| 162CG | 25N18 | 161C | 59.70 | 162CG | 25N18 | 162CA | 32.47 |
| 162CG | 25N18 | 162CB | 17.97 | 162CG | 25N18 | 19NE2 | 92.29 |
| 161C | 25N18 | 162CA | 30.47 | 161C | 25N18 | 162CB | 41.99 |
| 162CA | 25N18 | 162CB | 18.49 | 25SG | 25C19 | 161O | 87.86 |
| 25SG | 25C19 | 25CB | 17.43 | 25SG | 25C19 | 162ND1 | 51.44 |
| 25SG | 25C19 | 23O | 85.01 | 25SG | 25C19 | 23C | 84.49 |
| 25SG | 25C19 | 25N | 40.23 | 25SG | 25C19 | 161C | 84.17 |
| 25SG | 25C19 | 162CE1 | 48.33 | 25SG | 25C19 | 19NE2 | 65.89 |
| 161O | 25C19 | 162ND1 | 65.41 | 161O | 25C19 | 161C | 3.96 |
| 161O | 25C19 | 162CE1 | 79.95 | 25CB | 25C19 | 162ND1 | 50.53 |
| 25CB | 25C19 | 23CA | 87.26 | 25CB | 25C19 | 23O | 79.49 |
| 25CB | 25C19 | 23C | 74.66 | 25CB | 25C19 | 25N | 31.30 |
| 25CB | 25C19 | 161C | 97.21 | 25CB | 25C19 | 162CE1 | 42.12 |
| 25CB | 25C19 | 19NE2 | 48.60 | 162ND1 | 25C19 | 25N | 81.01 |
| 162ND1 | 25C19 | 161C | 61.89 | 162ND1 | 25C19 | 162CE1 | 14.54 |
| 162ND1 | 25C19 | 19NE2 | 72.57 | 23CA | 25C19 | 23O | 31.62 |
| 23CA | 25C19 | 23C | 19.66 | 23CA | 25C19 | 25N | 60.25 |
| 23CA | 25C19 | 19NE2 | 49.27 | 23O | 25C19 | 23C | 15.91 |
| 23O | 25C19 | 25N | 48.22 | 23O | 25C19 | 19NE2 | 64.33 |
| 23C | 25C19 | 25N | 44.48 | 23C | 25C19 | 19NE2 | 49.75 |
| 25N | 25C19 | 162CE1 | 70.28 | 25N | 25C19 | 19NE2 | 41.94 |
| 161C | 25C19 | 162CE1 | 76.42 | 162CE1 | 25C19 | 19NE2 | 58.03 |
| 19NE2 | 25N20 | 184NE1 | 61.55 | 19NE2 | 25N20 | 184CZ2 | 88.39 |
| 19NE2 | 25N20 | 162CE1 | 59.51 | 19NE2 | 25N20 | 19CD | 15.18 |
| 184NE1 | 25N20 | 184CZ2 | 30.44 | 184NE1 | 25N20 | 162CE1 | 42.35 |
| 184NE1 | 25N20 | 19CD | 46.54 | 184CZ2 | 25N20 | 162CE1 | 43.21 |
| 184CZ2 | 25N20 | 19CD | 74.46 | 162CE1 | 25N20 | 19CD | 52.22 |
| 161O | 25C21 | 25SG | 96.09 | 161O | 25C21 | 161C | 6.24 |
| 161O | 25C21 | 162CA | 33.10 | 161O | 25C21 | 162N | 17.36 |
| 161O | 25C21 | 162ND1 | 61.84 | 161O | 25C21 | 25CB | 99.78 |
| 161O | 25C21 | 163N | 59.11 | 25SG | 25C21 | 161C | 94.55 |
| 25SG | 25C21 | 162CA | 63.31 | 25SG | 25C21 | 162N | 80.59 |
| 25SG | 25C21 | 162ND1 | 43.09 | 25SG | 25C21 | 25CB | 6.39 |
| 25SG | 25C21 | 163N | 44.50 | 161C | 25C21 | 162CA | 31.26 |
| 161C | 25C21 | 162N | 14.07 | 161C | 25C21 | 162ND1 | 63.41 |
| 161C | 25C21 | 25CB | 98.77 | 161C | 25C21 | 163N | 55.24 |
| 162CA | 25C21 | 162N | 17.54 | 162CA | 25C21 | 162ND1 | 37.75 |
| 162CA | 25C21 | 25CB | 67.54 | 162CA | 25C21 | 163N | 28.93 |
| 162N | 25C21 | 162ND1 | 52.75 | 162N | 25C21 | 25CB | 85.01 |
| 162N | 25C21 | 163N | 41.75 | 162ND1 | 25C21 | 25CB | 43.42 |
| 162ND1 | 25C21 | 163N | 45.75 | 25CB | 25C21 | 163N | 50.47 |
| 25SG | 25C22 | 25CB | 32.60 | 25SG | 25C22 | 25N | 72.57 |
| 25SG | 25C22 | 25CA | 49.33 | 25SG | 25C22 | 19NE2 | 93.81 |
| 25SG | 25C22 | 26N | 55.18 | 25SG | 25C22 | 162ND1 | 47.43 |
| 25SG | 25C22 | 24C | 82.40 | 25SG | 25C22 | 25C | 44.53 |
| 25SG | 25C22 | 162CE1 | 48.15 | 25SG | 25C22 | 161O | 75.53 |
| 25SG | 25C22 | 26CD1 | 94.13 | 25SG | 25C22 | 19OE1 | 68.36 |
| 25SG | 25C22 | 19CD | 81.56 | 25CB | 25C22 | 25N | 46.75 |
| 25CB | 25C22 | 25CA | 24.63 | 25CB | 25C22 | 19NE2 | 63.05 |
| 25CB | 25C22 | 24N | 85.73 | 25CB | 25C22 | 26N | 52.12 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 25CB | 25C22 | 162ND1 | 56.93 | 25CB | 25C22 | 24C | 57.01 |
| 25CB | 25C22 | 25C | 34.57 | 25CB | 25C22 | 162CE1 | 46.25 |
| 25CB | 25C22 | 24CA | 75.71 | 25CB | 25C22 | 26CD1 | 92.36 |
| 25CB | 25C22 | 19OE1 | 41.24 | 25CB | 25C22 | 19CD | 51.95 |
| 25N | 25C22 | 25CA | 23.55 | 25N | 25C22 | 23O | 65.42 |
| 25N | 25C22 | 23C | 60.13 | 25N | 25C22 | 23CA | 77.28 |
| 25N | 25C22 | 19NE2 | 54.87 | 25N | 25C22 | 24N | 43.20 |
| 25N | 25C22 | 26N | 39.45 | 25N | 25C22 | 24C | 10.31 |
| 25N | 25C22 | 25C | 33.15 | 25N | 25C22 | 162CE1 | 88.28 |
| 25N | 25C22 | 24CA | 29.39 | 25N | 25C22 | 26CD1 | 58.64 |
| 25N | 25C22 | 19OE1 | 57.16 | 25N | 25C22 | 19CD | 54.20 |
| 25CA | 25C22 | 23O | 88.34 | 25CA | 25C22 | 23C | 83.54 |
| 25CA | 25C22 | 23CA | 99.22 | 25CA | 25C22 | 19NE2 | 61.73 |
| 25CA | 25C22 | 24N | 66.05 | 25CA | 25C22 | 26N | 35.11 |
| 25CA | 25C22 | 162ND1 | 81.55 | 25CA | 25C22 | 24C | 33.75 |
| 25CA | 25C22 | 25C | 19.23 | 25CA | 25C22 | 162CE1 | 69.99 |
| 25CA | 25C22 | 24CA | 52.91 | 25CA | 25C22 | 26CD1 | 70.42 |
| 25CA | 25C22 | 19OE1 | 50.96 | 25CA | 25C22 | 19CD | 55.14 |
| 23O | 25C22 | 23C | 19.26 | 23O | 25C22 | 23CA | 35.89 |
| 23O | 25C22 | 19NE2 | 79.72 | 23O | 25C22 | 24N | 32.92 |
| 23O | 25C22 | 26N | 78.15 | 23O | 25C22 | 24C | 55.15 |
| 23O | 25C22 | 25C | 88.29 | 23O | 25C22 | 24CA | 36.77 |
| 23O | 25C22 | 26CD1 | 45.35 | 23O | 25C22 | 19CD | 90.80 |
| 23C | 25C22 | 23CA | 22.09 | 23C | 25C22 | 19NE2 | 61.06 |
| 23C | 25C22 | 24N | 18.52 | 23C | 25C22 | 26N | 84.89 |
| 23C | 25C22 | 24C | 50.29 | 23C | 25C22 | 25C | 89.80 |
| 23C | 25C22 | 24CA | 31.49 | 23C | 25C22 | 26CD1 | 60.86 |
| 23C | 25C22 | 19OE1 | 86.44 | 23C | 25C22 | 19CD | 72.74 |
| 23CA | 25C22 | 19NE2 | 57.32 | 23CA | 25C22 | 24N | 34.39 |
| 23CA | 25C22 | 24C | 68.55 | 23CA | 25C22 | 24CA | 51.33 |
| 23CA | 25C22 | 26CD1 | 81.00 | 23CA | 25C22 | 19OE1 | 84.42 |
| 23CA | 25C22 | 19CD | 70.13 | 19NE2 | 25C22 | 24N | 48.45 |
| 19NE2 | 25C22 | 26N | 93.13 | 19NE2 | 25C22 | 162ND1 | 81.54 |
| 19NE2 | 25C22 | 24C | 55.55 | 19NE2 | 25C22 | 25C | 80.63 |
| 19NE2 | 25C22 | 162CE1 | 65.93 | 19NE2 | 25C22 | 24CA | 57.12 |
| 19NE2 | 25C22 | 19OE1 | 27.13 | 19NE2 | 25C22 | 19CD | 12.81 |
| 24N | 25C22 | 26N | 74.25 | 24N | 25C22 | 24C | 34.17 |
| 24N | 25C22 | 25C | 75.06 | 24N | 25C22 | 24CA | 17.99 |
| 24N | 25C22 | 26CD1 | 62.40 | 24N | 25C22 | 19OE1 | 70.97 |
| 24N | 25C22 | 19CD | 58.41 | 26N | 25C22 | 24C | 43.27 |
| 26N | 25C22 | 25C | 17.72 | 26N | 25C22 | 162CE1 | 96.42 |
| 26N | 25C22 | 24CA | 56.30 | 26N | 25C22 | 26CD1 | 41.56 |
| 26N | 25C22 | 19OE1 | 86.07 | 26N | 25C22 | 19CD | 89.17 |
| 162ND1 | 25C22 | 25C | 87.29 | 162ND1 | 25C22 | 162CE1 | 16.50 |
| 162ND1 | 25C22 | 161C | 57.76 | 162ND1 | 25C22 | 19OE1 | 57.61 |
| 162ND1 | 25C22 | 19CD | 70.43 | 24C | 25C22 | 25C | 40.95 |
| 24C | 25C22 | 162CE1 | 97.34 | 24C | 25C22 | 24CA | 19.17 |
| 24C | 25C22 | 26CD1 | 53.28 | 24C | 25C22 | 19OE1 | 63.13 |
| 24C | 25C22 | 19CD | 57.60 | 25C | 25C22 | 162CE1 | 79.88 |
| 25C | 25C22 | 24CA | 58.50 | 25C | 25C22 | 26CD1 | 58.12 |
| 25C | 25C22 | 19OE1 | 69.35 | 25C | 25C22 | 19CD | 74.36 |
| 162CE1 | 25C22 | 161O | 74.20 | 162CE1 | 25C22 | 19OE1 | 41.17 |
| 162CE1 | 25C22 | 19CD | 54.32 | 24CA | 25C22 | 26CD1 | 49.39 |
| 24CA | 25C22 | 19OE1 | 73.34 | 24CA | 25C22 | 19CD | 63.76 |
| 19OE1 | 25C22 | 19CD | 14.35 | 25SG | 25O23 | 25N | 75.69 |
| 25SG | 25O23 | 25CB | 37.11 | 25SG | 25O23 | 25CA | 54.99 |
| 25SG | 25O23 | 24C | 90.69 | 25SG | 25O23 | 19OE1 | 83.77 |
| 25SG | 25O23 | 25C | 48.15 | 25SG | 25O23 | 26N | 51.79 |
| 25SG | 25O23 | 162ND1 | 44.43 | 25SG | 25O23 | 162CE1 | 52.19 |
| 25SG | 25O23 | 24O | 85.50 | 25N | 25O23 | 25CB | 51.43 |
| 25N | 25O23 | 19NE2 | 75.55 | 25N | 25O23 | 23C | 76.45 |
| 25N | 25O23 | 24N | 57.15 | 25N | 25O23 | 23O | 76.49 |
| 25N | 25O23 | 25CA | 24.40 | 25N | 25O23 | 24C | 15.43 |
| 25N | 25O23 | 24CA | 38.06 | 25N | 25O23 | 19CD | 72.15 |
| 25N | 25O23 | 19OE1 | 71.82 | 25N | 25O23 | 22O | 86.12 |
| 25N | 25O23 | 25C | 27.77 | 25N | 25O23 | 26N | 33.20 |
| 25N | 25O23 | 23N | 97.97 | 25N | 25O23 | 162CE1 | 94.44 |
| 25N | 25O23 | 24O | 9.85 | 25N | 25O23 | 22C | 91.69 |
| 25CB | 25O23 | 19NE2 | 80.56 | 25CB | 25O23 | 25CA | 27.06 |
| 25CB | 25O23 | 24C | 66.23 | 25CB | 25O23 | 24CA | 89.22 |
| 25CB | 25O23 | 19CD | 67.04 | 25CB | 25O23 | 19OE1 | 52.55 |
| 25CB | 25O23 | 25C | 33.18 | 25CB | 25O23 | 26N | 48.61 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 25CB | 25O23 | 162ND1 | 52.03 | 25CB | 25O23 | 162CE1 | 45.88 |
| 25CB | 25O23 | 24O | 59.52 | 19NE2 | 25O23 | 23C | 84.54 |
| 19NE2 | 25O23 | 24N | 66.47 | 19NE2 | 25O23 | 23CA | 78.32 |
| 19NE2 | 25O23 | 25CA | 77.61 | 19NE2 | 25O23 | 24C | 71.54 |
| 19NE2 | 25O23 | 24CA | 74.20 | 19NE2 | 25O23 | 19CD | 14.67 |
| 19NE2 | 25O23 | 19OE1 | 32.03 | 19NE2 | 25O23 | 22O | 39.73 |
| 19NE2 | 25O23 | 25C | 93.21 | 19NE2 | 25O23 | 23N | 68.79 |
| 19NE2 | 25O23 | 162ND1 | 89.64 | 19NE2 | 25O23 | 162CE1 | 73.89 |
| 19NE2 | 25O23 | 24O | 69.92 | 19NE2 | 25O23 | 22C | 53.32 |
| 23C | 25O23 | 24N | 24.58 | 23C | 25O23 | 23CA | 28.13 |
| 23C | 25O23 | 23O | 21.76 | 23C | 25O23 | 24C | 61.59 |
| 23C | 25O23 | 24CA | 38.61 | 23C | 25O23 | 19CD | 97.49 |
| 23C | 25O23 | 22O | 49.19 | 23C | 25O23 | 25C | 99.27 |
| 23C | 25O23 | 26N | 90.14 | 23C | 25O23 | 23N | 30.80 |
| 23C | 25O23 | 24O | 68.35 | 23C | 25O23 | 22C | 39.19 |
| 24N | 25O23 | 23CA | 44.35 | 24N | 25O23 | 23O | 40.46 |
| 24N | 25O23 | 25CA | 80.66 | 24N | 25O23 | 24C | 41.72 |
| 24N | 25O23 | 24CA | 20.87 | 24N | 25O23 | 19CD | 77.11 |
| 24N | 25O23 | 19OE1 | 91.57 | 24N | 25O23 | 22O | 41.76 |
| 24N | 25O23 | 25C | 83.71 | 24N | 25O23 | 26N | 80.39 |
| 24N | 25O23 | 23N | 41.16 | 24N | 25O23 | 24O | 47.80 |
| 24N | 25O23 | 22C | 39.24 | 23CA | 25O23 | 23O | 43.14 |
| 23CA | 25O23 | 24C | 85.95 | 23CA | 25O23 | 24CA | 63.70 |
| 23CA | 25O23 | 19CD | 92.98 | 23CA | 25O23 | 22O | 38.70 |
| 23CA | 25O23 | 23N | 9.54 | 23CA | 25O23 | 24O | 92.15 |
| 23CA | 25O23 | 22C | 25.05 | 23O | 25O23 | 25CA | 99.19 |
| 23O | 25O23 | 24C | 64.48 | 23O | 25O23 | 24CA | 44.29 |
| 23O | 25O23 | 22O | 70.90 | 23O | 25O23 | 25C | 91.92 |
| 23O | 25O23 | 26N | 78.46 | 23O | 25O23 | 23N | 49.19 |
| 23O | 25O23 | 24O | 71.18 | 23O | 25O23 | 22C | 60.24 |
| 25CA | 25O23 | 24C | 39.48 | 25CA | 25O23 | 24CA | 62.38 |
| 25CA | 25O23 | 19CD | 68.41 | 25CA | 25O23 | 19OE1 | 60.76 |
| 25CA | 25O23 | 25C | 15.95 | 25CA | 25O23 | 26N | 32.35 |
| 25CA | 25O23 | 162ND1 | 79.08 | 25CA | 25O23 | 162CE1 | 71.50 |
| 25CA | 25O23 | 24O | 32.98 | 24C | 25O23 | 24CA | 22.98 |
| 24C | 25O23 | 19CD | 72.19 | 24C | 25O23 | 19OE1 | 76.64 |
| 24C | 25O23 | 22O | 73.41 | 24C | 25O23 | 25C | 42.54 |
| 24C | 25O23 | 26N | 44.02 | 24C | 25O23 | 23N | 82.66 |
| 24C | 25O23 | 24O | 6.88 | 24C | 25O23 | 22C | 77.34 |
| 24CA | 25O23 | 19CD | 80.54 | 24CA | 25O23 | 19OE1 | 90.57 |
| 24CA | 25O23 | 22O | 60.20 | 24CA | 25O23 | 25C | 63.31 |
| 24CA | 25O23 | 26N | 59.62 | 24CA | 25O23 | 23N | 61.69 |
| 24CA | 25O23 | 24O | 29.75 | 24CA | 25O23 | 22C | 59.80 |
| 19CD | 25O23 | 19OE1 | 17.43 | 19CD | 25O23 | 22O | 54.37 |
| 19CD | 25O23 | 25C | 84.36 | 19CD | 25O23 | 26N | 99.96 |
| 19CD | 25O23 | 23N | 83.45 | 19CD | 25O23 | 162ND1 | 76.89 |
| 19CD | 25O23 | 162CE1 | 60.68 | 19CD | 25O23 | 24O | 68.84 |
| 19CD | 25O23 | 22C | 67.98 | 19OE1 | 25O23 | 22O | 71.76 |
| 19OE1 | 25O23 | 25C | 76.10 | 19OE1 | 25O23 | 26N | 93.05 |
| 19OE1 | 25O23 | 162ND1 | 60.98 | 19OE1 | 25O23 | 162CE1 | 44.53 |
| 19OE1 | 25O23 | 24O | 71.61 | 19OE1 | 25O23 | 22C | 85.33 |
| 22O | 25O23 | 23N | 29.15 | 22O | 25O23 | 24O | 76.62 |
| 22O | 25O23 | 22C | 13.64 | 25C | 25O23 | 26N | 17.16 |
| 25C | 25O23 | 162ND1 | 82.30 | 25C | 25O23 | 162CE1 | 78.86 |
| 25C | 25O23 | 24O | 37.62 | 26N | 25O23 | 162ND1 | 92.78 |
| 26N | 25O23 | 162CE1 | 92.75 | 26N | 25O23 | 24O | 41.67 |
| 23N | 25O23 | 24O | 88.33 | 23N | 25O23 | 22C | 15.51 |
| 162ND1 | 25O23 | 162CE1 | 16.46 | 24O | 25O23 | 22C | 81.85 |
| 65CA | 25C24 | 66N | 33.46 | 65CA | 25C24 | 65C | 20.36 |
| 65CA | 25C24 | 64O | 36.58 | 65CA | 25C24 | 66O | 68.87 |
| 66N | 25C24 | 65C | 17.64 | 66N | 25C24 | 64O | 67.62 |
| 66N | 25C24 | 66O | 36.45 | 65C | 25C24 | 64O | 50.58 |
| 65C | 25C24 | 66O | 53.76 | 66O | 25C25 | 66N | 40.06 |
| 66O | 25C25 | 66C | 8.90 | 66O | 25C25 | 65CA | 70.27 |
| 66O | 25C25 | 65C | 53.58 | 161O | 25C25 | 161C | 14.86 |
| 161O | 25C25 | 161CA | 28.19 | 161O | 25C25 | 25SG | 60.39 |
| 66N | 25C25 | 66C | 31.52 | 66N | 25C25 | 65CA | 30.22 |
| 66N | 25C25 | 25SG | 91.38 | 66N | 25C25 | 65C | 14.24 |
| 161C | 25C25 | 161CA | 17.63 | 161C | 25C25 | 25SG | 69.22 |
| 66C | 25C25 | 65CA | 61.71 | 66C | 25C25 | 65C | 44.80 |
| 65CA | 25C25 | 25SG | 82.36 | 65CA | 25C25 | 65C | 17.73 |
| 161CA | 25C25 | 25SG | 86.68 | 25SG | 25C25 | 65C | 92.33 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 66O | 25C26 | 66C | 3.30 | 66O | 25C26 | 163CB | 87.58 |
| 161O | 25C26 | 161C | 15.84 | 161O | 25C26 | 163N | 56.85 |
| 161O | 25C26 | 160O | 61.70 | 161O | 25C26 | 163CB | 84.35 |
| 161O | 25C26 | 162N | 27.01 | 161O | 25C26 | 161CA | 28.97 |
| 161C | 25C26 | 163N | 55.26 | 161C | 25C26 | 160O | 50.24 |
| 161C | 25C26 | 163CB | 84.79 | 161C | 25C26 | 162N | 15.32 |
| 161C | 25C26 | 161CA | 17.79 | 163N | 25C26 | 160O | 95.75 |
| 163N | 25C26 | 163CB | 29.64 | 163N | 25C26 | 162N | 42.53 |
| 163N | 25C26 | 161CA | 71.03 | 66C | 25C26 | 163CB | 89.72 |
| 160O | 25C26 | 162N | 56.11 | 160O | 25C26 | 161CA | 33.06 |
| 163CB | 25C26 | 162N | 72.06 | 162N | 25C26 | 161CA | 28.56 |
| 160O | 25C27 | 160C | 16.28 | 160O | 25C27 | 161CA | 39.86 |
| 160O | 25C27 | 161C | 59.69 | 160O | 25C27 | 161N | 29.94 |
| 160O | 25C27 | 161O | 70.88 | 160O | 25C27 | 160CB | 39.29 |
| 160O | 25C27 | 134CB | 91.77 | 160O | 25C27 | 162N | 65.04 |
| 160C | 25C27 | 161CA | 33.56 | 160C | 25C27 | 161C | 50.71 |
| 160C | 25C27 | 161N | 17.29 | 160C | 25C27 | 161O | 64.68 |
| 160C | 25C27 | 160CB | 32.70 | 160C | 25C27 | 134CB | 77.93 |
| 160C | 25C27 | 162N | 52.23 | 161CA | 25C27 | 161C | 20.25 |
| 161CA | 25C27 | 161N | 19.14 | 161CA | 25C27 | 161O | 31.54 |
| 161CA | 25C27 | 160CB | 64.50 | 161CA | 25C27 | 134CB | 90.77 |
| 161CA | 25C27 | 162N | 30.47 | 161C | 25C27 | 161N | 33.69 |
| 161C | 25C27 | 161O | 15.99 | 161C | 25C27 | 160CB | 77.36 |
| 161C | 25C27 | 134CB | 85.39 | 161C | 25C27 | 162N | 15.75 |
| 161N | 25C27 | 161O | 48.38 | 161N | 25C27 | 160CB | 45.58 |
| 161N | 25C27 | 134CB | 77.13 | 161N | 25C27 | 162N | 35.42 |
| 161O | 25C27 | 160CB | 93.10 | 161O | 25C27 | 134CB | 96.47 |
| 161O | 25C27 | 162N | 27.78 | 66O | 25C27 | 209CD2 | 83.62 |
| 160CB | 25C27 | 134CB | 56.56 | 160CB | 25C27 | 162N | 71.89 |
| 160CB | 25C27 | 209CD2 | 69.27 | 134CB | 25C27 | 162N | 69.95 |
| 134CB | 25C27 | 209CD2 | 49.25 | 160O | 25C28 | 160C | 11.12 |
| 160O | 25C28 | 161CA | 34.92 | 160O | 25C28 | 161N | 22.64 |
| 160C | 25C28 | 161CA | 30.68 | 160C | 25C28 | 161N | 14.74 |
| 67CE1 | 25C28 | 66O | 57.93 | 67CE1 | 25C28 | 67CD1 | 16.20 |
| 161CA | 25C28 | 161N | 17.22 | 66O | 25C28 | 67CD1 | 44.47 |
| 209CD2 | 25C29 | 134CB | 68.69 | 209CD2 | 25C29 | 160CB | 90.30 |
| 209CD2 | 25C29 | 67CD1 | 65.58 | 209CD2 | 25C29 | 66O | 98.85 |
| 209CD2 | 25C29 | 209CG | 7.93 | 209CD2 | 25C29 | 67CE1 | 70.23 |
| 134CB | 25C29 | 160CB | 68.29 | 134CB | 25C29 | 160C | 85.31 |
| 134CB | 25C29 | 209CG | 62.21 | 160O | 25C29 | 160CB | 42.09 |
| 160O | 25C29 | 160C | 15.52 | 160CB | 25C29 | 160C | 33.72 |
| 160CB | 25C29 | 209CG | 83.59 | 67CD1 | 25C29 | 66O | 45.57 |
| 67CD1 | 25C29 | 209CG | 73.48 | 67CD1 | 25C29 | 67CE1 | 16.51 |
| 66O | 25C29 | 67CE1 | 56.12 | 209CG | 25C29 | 67CE1 | 77.57 |
| 66O | 25C30 | 66N | 46.15 | 66O | 25C30 | 65CA | 82.36 |
| 66O | 25C30 | 26CD1 | 69.05 | 66O | 25C30 | 26CB | 54.83 |
| 66C | 25C30 | 65C | 61.73 | 66O | 25C30 | 66C | 12.32 |
| 66O | 25C30 | 66CA | 31.12 | 66O | 25C30 | 26CG | 57.20 |
| 66O | 25C30 | 26N | 86.09 | 66O | 25C30 | 163CB | 86.18 |
| 66N | 25C30 | 65CA | 36.68 | 66N | 25C30 | 26CD1 | 45.40 |
| 66N | 25C30 | 26CB | 62.49 | 66N | 25C30 | 65C | 16.57 |
| 66N | 25C30 | 66C | 34.22 | 66N | 25C30 | 66CA | 15.04 |
| 66N | 25C30 | 26CG | 48.20 | 66N | 25C30 | 26N | 85.31 |
| 25SG | 25C30 | 26CD1 | 80.34 | 25SG | 25C30 | 26CB | 78.23 |
| 25SG | 25C30 | 161O | 67.14 | 25SG | 25C30 | 26CG | 83.17 |
| 25SG | 25C30 | 26N | 47.19 | 25SG | 25C30 | 163CB | 52.42 |
| 25SG | 25C30 | 163N | 44.84 | 65CA | 25C30 | 26CD1 | 53.97 |
| 65CA | 25C30 | 26CB | 86.07 | 65CA | 25C30 | 65C | 20.64 |
| 65CA | 25C30 | 66C | 70.78 | 65CA | 25C30 | 66CA | 51.58 |
| 65CA | 25C30 | 26CG | 67.39 | 65CA | 25C30 | 26N | 93.38 |
| 26CD1 | 25C30 | 26CB | 34.81 | 26CD1 | 25C30 | 65C | 49.80 |
| 26CD1 | 25C30 | 66C | 59.13 | 26CD1 | 25C30 | 66CA | 50.39 |
| 26CD1 | 25C30 | 26CG | 17.00 | 26CD1 | 25C30 | 26N | 42.15 |
| 26CD1 | 25C30 | 163CB | 83.57 | 26CB | 25C30 | 65C | 74.87 |
| 26CB | 25C30 | 66C | 51.73 | 26CB | 25C30 | 66CA | 56.97 |
| 26CB | 25C30 | 26CG | 18.84 | 26CB | 25C30 | 26N | 31.41 |
| 26CB | 25C30 | 163CB | 54.44 | 26CB | 25C30 | 163N | 82.52 |
| 65C | 25C30 | 66C | 50.25 | 65C | 25C30 | 66CA | 31.10 |
| 65C | 25C30 | 26CG | 58.02 | 65C | 25C30 | 26N | 91.94 |
| 161O | 25C30 | 163CB | 83.35 | 161O | 25C30 | 163N | 54.69 |
| 66C | 25C30 | 66CA | 19.22 | 66C | 25C30 | 26CG | 49.60 |
| 66C | 25C30 | 26N | 82.89 | 66C | 25C30 | 163CB | 92.24 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 66CA | 25C30 | 26CG | 47.25 | 66CA | 25C30 | 26N | 84.74 |
| 26CG | 25C30 | 26N | 37.73 | 26CG | 25C30 | 163CB | 71.86 |
| 26CG | 25C30 | 163N | 98.68 | 26N | 25C30 | 163CB | 44.77 |
| 26N | 25C30 | 163N | 65.10 | 163CB | 25C30 | 163N | 28.72 |
| 66O | 25O31 | 66N | 61.37 | 66O | 25O31 | 26CB | 77.21 |
| 66O | 25O31 | 26CD1 | 95.50 | 66O | 25O31 | 66C | 18.26 |
| 66O | 25O31 | 26CG | 80.22 | 66O | 25O31 | 66CA | 41.13 |
| 66O | 25O31 | 65C | 76.22 | 66O | 25O31 | 65CA | 98.52 |
| 66O | 25O31 | 26CA | 93.42 | 66O | 25O31 | 26NE1 | 92.30 |
| 66O | 25O31 | 67N | 17.71 | 66O | 25O31 | 26CD2 | 73.43 |
| 66O | 25O31 | 65O | 71.00 | 66N | 25O31 | 26CB | 86.34 |
| 66N | 25O31 | 26CD1 | 59.28 | 66N | 25O31 | 66C | 45.73 |
| 66N | 25O31 | 26CG | 65.50 | 66N | 25O31 | 66CA | 21.43 |
| 66N | 25O31 | 65C | 16.23 | 66N | 25O31 | 65CA | 39.07 |
| 66N | 25O31 | 26NE1 | 49.90 | 66N | 25O31 | 67N | 52.44 |
| 66N | 25O31 | 26CD2 | 57.23 | 66N | 25O31 | 65O | 11.55 |
| 26CB | 25O31 | 26CD1 | 45.93 | 26CB | 25O31 | 66C | 70.12 |
| 26CB | 25O31 | 26CG | 25.17 | 26CB | 25O31 | 66CA | 76.25 |
| 26CB | 25O31 | 65C | 96.29 | 26CB | 25O31 | 26N | 36.99 |
| 26CB | 25O31 | 26CA | 18.87 | 26CB | 25O31 | 25SG | 86.19 |
| 26CB | 25O31 | 26NE1 | 53.75 | 26CB | 25O31 | 67N | 63.56 |
| 26CB | 25O31 | 163CB | 61.81 | 26CB | 25O31 | 26CD2 | 30.74 |
| 26CB | 25O31 | 65O | 94.86 | 26CD1 | 25O31 | 66C | 78.62 |
| 26CD1 | 25O31 | 26CG | 22.75 | 26CD1 | 25O31 | 66CA | 65.15 |
| 26CD1 | 25O31 | 65C | 60.18 | 26CD1 | 25O31 | 65CA | 62.48 |
| 26CD1 | 25O31 | 26N | 50.53 | 26CD1 | 25O31 | 26CA | 52.01 |
| 26CD1 | 25O31 | 25SG | 86.23 | 26CD1 | 25O31 | 26NE1 | 10.06 |
| 26CD1 | 25O31 | 67N | 77.85 | 26CD1 | 25O31 | 163CB | 97.88 |
| 26CD1 | 25O31 | 26CD2 | 24.53 | 26CD1 | 25O31 | 65O | 61.57 |
| 66C | 25O31 | 26CG | 66.43 | 66C | 25O31 | 66CA | 24.43 |
| 66C | 25O31 | 65C | 61.60 | 66C | 25O31 | 65CA | 84.54 |
| 66C | 25O31 | 26CA | 88.49 | 66C | 25O31 | 26NE1 | 74.51 |
| 66C | 25O31 | 67N | 8.31 | 66C | 25O31 | 26CD2 | 58.54 |
| 66C | 25O31 | 65O | 56.49 | 26CG | 25O31 | 66CA | 61.97 |
| 26CG | 25O31 | 65C | 72.65 | 26CG | 25O31 | 65CA | 81.58 |
| 26CG | 25O31 | 26N | 45.87 | 26CG | 25O31 | 26CA | 37.48 |
| 26CG | 25O31 | 25SG | 92.89 | 26CG | 25O31 | 26NE1 | 29.02 |
| 26CG | 25O31 | 67N | 62.96 | 26CG | 25O31 | 163CB | 84.79 |
| 26CG | 25O31 | 26CD2 | 9.01 | 26CG | 25O31 | 65O | 72.10 |
| 66CA | 25O31 | 65C | 37.55 | 66CA | 25O31 | 65CA | 60.47 |
| 66CA | 25O31 | 26CA | 94.80 | 66CA | 25O31 | 26NE1 | 58.06 |
| 66CA | 25O31 | 67N | 31.03 | 66CA | 25O31 | 26CD2 | 52.97 |
| 66CA | 25O31 | 65O | 32.59 | 65C | 25O31 | 65CA | 22.96 |
| 65C | 25O31 | 26NE1 | 50.12 | 65C | 25O31 | 67N | 68.57 |
| 65C | 25O31 | 26CD2 | 65.66 | 65C | 25O31 | 65O | 5.21 |
| 65CA | 25O31 | 26NE1 | 53.45 | 65CA | 25O31 | 67N | 91.50 |
| 65CA | 25O31 | 26CD2 | 77.14 | 65CA | 25O31 | 65O | 28.05 |
| 26N | 25O31 | 26CA | 20.41 | 26N | 25O31 | 25SG | 49.78 |
| 26N | 25O31 | 26NE1 | 60.51 | 26N | 25O31 | 163CB | 48.83 |
| 26N | 25O31 | 26CD2 | 54.87 | 26CA | 25O31 | 25SG | 67.76 |
| 26CA | 25O31 | 26NE1 | 61.63 | 26CA | 25O31 | 67N | 81.48 |
| 26CA | 25O31 | 163CB | 47.51 | 26CA | 25O31 | 26CD2 | 45.43 |
| 25SG | 25O31 | 26NE1 | 93.17 | 25SG | 25O31 | 163CB | 52.44 |
| 26NE1 | 25O31 | 67N | 75.15 | 26NE1 | 25O31 | 26CD2 | 27.61 |
| 26NE1 | 25O31 | 65O | 51.59 | 67N | 25O31 | 26CD2 | 55.84 |
| 67N | 25O31 | 65O | 63.57 | 163CB | 25O31 | 26CD2 | 92.09 |
| 26CD2 | 25O31 | 65O | 64.59 | 25SG | 25N32 | 161O | 82.28 |
| 25SG | 25N32 | 23O | 84.49 | 25SG | 25N32 | 26CD1 | 88.80 |
| 25SG | 25N32 | 26N | 50.25 | 25SG | 25N32 | 25CB | 9.66 |
| 25SG | 25N32 | 25N | 39.55 | 25SG | 25N32 | 163N | 46.38 |
| 25SG | 25N32 | 26CB | 79.05 | 25SG | 25N32 | 161C | 82.48 |
| 25SG | 25N32 | 23C | 74.25 | 161O | 25N32 | 25CB | 91.92 |
| 61O | 25N32 | 163N | 57.92 | 161O | 25N32 | 161C | 9.03 |
| 65CA | 25N32 | 66N | 32.94 | 65CA | 25N32 | 23O | 48.76 |
| 65CA | 25N32 | 26CD1 | 52.31 | 65CA | 25N32 | 26N | 94.41 |
| 65CA | 25N32 | 25N | 92.40 | 65CA | 25N32 | 65C | 17.26 |
| 65CA | 25N32 | 66O | 67.39 | 65CA | 25N32 | 26CB | 78.37 |
| 65CA | 25N32 | 23C | 60.93 | 65CA | 25N32 | 23O | 68.51 |
| 66N | 25N32 | 26CD1 | 41.20 | 66N | 25N32 | 26N | 79.04 |
| 66N | 25N32 | 25N | 94.92 | 66N | 25N32 | 65C | 15.81 |
| 66N | 25N32 | 66O | 35.14 | 66N | 25N32 | 26CB | 53.15 |
| 66N | 25N32 | 23C | 81.78 | 23O | 25N32 | 26CD1 | 46.25 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 23O | 25N32 | 26N | 67.84 | 23O | 25N32 | 25CB | 76.13 |
| 23O | 25N32 | 25N | 47.96 | 23O | 25N32 | 65C | 59.32 |
| 23O | 25N32 | 66O | 99.28 | 23O | 25N32 | 26CB | 75.73 |
| 23O | 25N32 | 23C | 13.32 | 26CD1 | 25N32 | 23C | 55.94 |
| 26CD1 | 25N32 | 25CB | 79.55 | 26CD1 | 25N32 | 25N | 54.01 |
| 26CD1 | 25N32 | 65C | 45.85 | 26CD1 | 25N32 | 66O | 57.60 |
| 26CD1 | 25N32 | 26CB | 31.68 | 26CD1 | 25N32 | 23C | 55.94 |
| 26N | 25N32 | 25CB | 42.72 | 26N | 25N32 | 25N | 33.34 |
| 26N | 25N32 | 65C | 87.61 | 26N | 25N32 | 66O | 74.76 |
| 26N | 25N32 | 163N | 67.13 | 26N | 25N32 | 26CB | 30.37 |
| 26N | 25N32 | 23C | 68.06 | 25CB | 25N32 | 25N | 30.07 |
| 25CB | 25N32 | 163N | 53.14 | 25CB | 25N32 | 26CB | 72.55 |
| 25CB | 25N32 | 161C | 92.10 | 25CB | 25N32 | 23C | 66.78 |
| 25N | 25N32 | 65C | 95.38 | 25N | 25N32 | 163N | 80.01 |
| 25N | 25N32 | 26CB | 60.55 | 25N | 25N32 | 23C | 41.68 |
| 65C | 25N32 | 66O | 50.19 | 65C | 25N32 | 26CB | 65.71 |
| 65C | 25N32 | 23C | 72.49 | 66O | 25N32 | 163N | 92.86 |
| 66O | 25N32 | 26CB | 44.71 | 163N | 25N32 | 26CB | 78.55 |
| 163N | 25N32 | 161C | 52.17 | 26CB | 25N32 | 23C | 82.47 |
| 25SG | 25C33 | 25N | 62.03 | 25SG | 25C33 | 26N | 67.44 |
| 25SG | 25C33 | 25CB | 22.53 | 25SG | 25C33 | 25CA | 44.14 |
| 25SG | 25C33 | 25C | 51.85 | 25SG | 25C33 | 24N | 94.55 |
| 25SG | 25C33 | 24C | 75.69 | 25SG | 25C33 | 26CB | 94.29 |
| 25SG | 25C33 | 24CA | 93.12 | 25SG | 25C33 | 26CA | 77.03 |
| 25SG | 25C33 | 161O | 66.31 | 23O | 25C33 | 25N | 68.18 |
| 23O | 25C33 | 26CD1 | 60.30 | 23O | 25C33 | 26N | 92.61 |
| 23O | 25C33 | 23C | 18.66 | 23O | 25C33 | 25CA | 89.03 |
| 23O | 25C33 | 65CA | 56.48 | 23O | 25C33 | 25C | 96.38 |
| 23O | 25C33 | 24N | 30.61 | 23O | 25C33 | 24C | 56.80 |
| 23O | 25C33 | 26CG | 75.69 | 23O | 25C33 | 26CB | 94.54 |
| 23O | 25C33 | 23CA | 32.16 | 23O | 25C33 | 66N | 77.02 |
| 23O | 25C33 | 24CA | 37.25 | 23O | 25C33 | 26CA | 97.15 |
| 23O | 25C33 | 26NE1 | 47.95 | 23O | 25C33 | 65C | 65.17 |
| 23O | 25C33 | 65N | 43.20 | 25N | 25C33 | 26CD1 | 73.26 |
| 25N | 25C33 | 26N | 44.51 | 25N | 25C33 | 25CB | 39.50 |
| 25N | 25C33 | 23C | 59.79 | 25N | 25C33 | 25CA | 20.88 |
| 25N | 25C33 | 25C | 34.96 | 25N | 25C33 | 24N | 40.75 |
| 25N | 25C33 | 24C | 13.79 | 25N | 25C33 | 26CG | 73.79 |
| 25N | 25C33 | 26CB | 75.59 | 25N | 25C33 | 23CA | 69.58 |
| 25N | 25C33 | 24CA | 31.77 | 25N | 25C33 | 26CA | 59.60 |
| 25N | 25C33 | 26NE1 | 73.01 | 25N | 25C33 | 26N | 53.40 |
| 26CD1 | 25C33 | 23C | 74.18 | 26CD1 | 25C33 | 25CA | 82.03 |
| 26CD1 | 25C33 | 65CA | 58.73 | 26CD1 | 25C33 | 25C | 69.11 |
| 26CD1 | 25C33 | 24N | 71.72 | 26CD1 | 25C33 | 24C | 61.69 |
| 26CD1 | 25C33 | 26CG | 15.97 | 26CD1 | 25C33 | 26CB | 35.58 |
| 26CD1 | 25C33 | 23CA | 91.94 | 26CD1 | 25C33 | 66N | 43.00 |
| 26CD1 | 25C33 | 24CA | 56.83 | 26CD1 | 25C33 | 26CA | 46.45 |
| 26CD1 | 25C33 | 26NE1 | 12.72 | 26CD1 | 25C33 | 65C | 47.83 |
| 26CD1 | 25C33 | 65N | 61.48 | 26N | 25C33 | 25CB | 53.84 |
| 26N | 25C33 | 23C | 92.65 | 26N | 25C33 | 25CA | 37.01 |
| 26N | 25C33 | 25C | 17.36 | 26N | 25C33 | 25N | 77.69 |
| 26N | 25C33 | 24C | 45.23 | 26N | 25C33 | 26CG | 43.00 |
| 26N | 25C33 | 26CB | 34.40 | 26N | 25C33 | 66N | 88.08 |
| 26N | 25C33 | 24CA | 60.35 | 26N | 25C33 | 26CA | 15.70 |
| 26N | 25C33 | 26NE1 | 62.43 | 26N | 25C33 | 65C | 98.83 |
| 25CB | 25C33 | 23C | 89.77 | 25CB | 25C33 | 25CA | 22.60 |
| 25CB | 25C33 | 25C | 36.53 | 25CB | 25C33 | 24N | 74.40 |
| 25CB | 25C33 | 24C | 53.16 | 25CB | 25C33 | 26CG | 96.54 |
| 25CB | 25C33 | 26CB | 86.56 | 25CB | 23CA | | 92.73 |
| 25CB | 25C33 | 24CA | 70.80 | 25CB | 26CA | | 67.26 |
| 25CB | 25C33 | 161O | 88.61 | 23C | 25CA | | 78.15 |
| 23C | 25C33 | 65CA | 73.62 | 23C | 25C | | 90.88 |
| 23C | 25C33 | 24N | 17.05 | 23C | 24C | | 49.66 |
| 23C | 25C33 | 26CG | 88.11 | 23C | 23CA | | 19.27 |
| 23C | 25C33 | 66N | 95.67 | 23C | 24CA | | 63.32 |
| 23C | 25C33 | 26NE1 | 62.90 | 23C | 65C | | 83.62 |
| 23C | 25C33 | 65N | 59.43 | 25CA | 25C | | 21.13 |
| 25CA | 25C33 | 24N | 61.20 | 25CA | 24C | | 33.01 |
| 25CA | 25C33 | 26CG | 76.92 | 25CA | 26CB | | 71.41 |
| 25CA | 25C33 | 23CA | 87.72 | 25CA | 24CA | | 52.23 |
| 25CA | 25C33 | 26CA | 52.44 | 25CA | 26NE1 | | 85.76 |
| 65CA | 25C33 | 24N | 87.00 | 65CA | 26CG | | 69.63 |

TABLE XVIII-continued

Table of angles between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Atom 3 | Angle | Atom 1 | Atom 2 | Atom 3 | Angle |
|---|---|---|---|---|---|---|---|
| 65CA | 25C33 | 26CB | 84.46 | 65CA | 23CA | | 76.25 |
| 65CA | 25C33 | 66N | 32.22 | 65CA | 24CA | | 88.00 |
| 65CA | 25C33 | 26NE1 | 51.85 | 65CA | 65C | | 16.56 |
| 65CA | 25C33 | 65N | 14.77 | 25C | 24N | | 74.16 |
| 25C | 25C33 | 24C | 41.26 | 25C | 26CG | | 60.10 |
| 25C | 25C33 | 26CB | 51.20 | 25C | 24CA | | 59.94 |
| 25C | 25C33 | 26CA | 31.86 | 25C | 26NE1 | | 76.48 |
| 24N | 25C33 | 24C | 33.23 | 24N | 25C33 | 26CG | 82.78 |
| 24N | 25C33 | 26CB | 96.28 | 24N | 25C33 | 23CA | 32.00 |
| 24N | 25C33 | 24CA | 18.67 | 24N | 25C33 | 26CA | 88.81 |
| 24N | 25C33 | 26NE1 | 62.87 | 24N | 25C33 | 65C | 93.98 |
| 24N | 25C33 | 65N | 73.77 | 24C | 25C33 | 26CG | 64.93 |
| 24N | 25C33 | 26CB | 70.95 | 24C | 25C33 | 23CA | 64.79 |
| 24N | 25C33 | 24CA | 19.55 | 24C | 25C33 | 26CA | 58.29 |
| 24N | 25C33 | 26ND1 | 59.98 | 24C | 25C33 | 65N | 96.26 |
| 26CG | 25C33 | 26CB | 19.61 | 26CG | 25C33 | 66N | 46.12 |
| 26CG | 25C33 | 24CA | 65.68 | 26CG | 25C33 | 26CA | 32.66 |
| 26CG | 25C33 | 26NE1 | 28.68 | 26CG | 25C33 | 65C | 55.83 |
| 26CG | 25C33 | 65N | 75.10 | 26CB | 25C33 | 66N | 55.47 |
| 26CB | 25C33 | 24CA | 77.83 | 26CB | 25C33 | 26CA | 19.41 |
| 26CB | 25C33 | 26NE1 | 48.27 | 26CB | 25C33 | 65C | 68.78 |
| 26CB | 25C33 | 65N | 92.50 | 23CA | 25C33 | 24CA | 50.00 |
| 23CA | 25C33 | 26NE1 | 79.91 | 23CA | 25C33 | 65C | 89.99 |
| 23CA | 25C33 | 65N | 61.53 | 66N | 25C33 | 24CA | 94.59 |
| 66N | 25C33 | 26CA | 74.61 | 66N | 25C33 | 26NE1 | 44.61 |
| 66N | 25C33 | 65C | 15.82 | 66N | 25C33 | 65N | 45.20 |
| 24CA | 25C33 | 26CA | 70.41 | 24CA | 25C33 | 26NE1 | 50.59 |
| 24CA | 25C33 | 65C | 89.84 | 24CA | 25C33 | 65N | 77.59 |
| 26CA | 25C33 | 26NE1 | 57.80 | 26CA | 25C33 | 65C | 87.10 |
| 26NE1 | 25C33 | 65C | 44.55 | 26NE1 | 25C33 | 65N | 51.65 |
| 65C | 25C33 | 65N | 29.48 | 66O | 25N34 | 66N | 45.23 |
| 66O | 25N34 | 65CA | 78.78 | 66O | 25N34 | 65C | 62.40 |
| 66O | 25N34 | 66C | 13.36 | 66O | 25N34 | 66CA | 32.35 |
| 66N | 25N34 | 65CA | 34.26 | 66N | 25N34 | 65C | 17.63 |
| 66N | 25N34 | 66C | 35.00 | 66N | 25N34 | 66CA | 17.78 |
| 65CA | 25N34 | 65C | 20.48 | 65CA | 25N34 | 66C | 69.25 |
| 65CA | 25N34 | 66CA | 51.09 | 65C | 25N34 | 66C | 51.11 |
| 65C | 25N34 | 66CA | 31.81 | 65C | 25N34 | 66CA | 19.75 |

TABLE XIX

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 20O | 25C1 | 20C | 8.55 | 20O | 25C1 | 21CA | 35.54 |
| 20O | 25C1 | 20N | 33.52 | 20O | 25C1 | 21N | 19.74 |
| 20O | 25C1 | 21NE2 | 53.30 | 20O | 25C1 | 19CB | 70.43 |
| 20O | 25C1 | 19CD | 89.13 | 20O | 25C1 | 20CA | 16.45 |
| 20O | 25C1 | 19CG | 72.65 | 20C | 25C1 | 21CA | 32.39 |
| 20C | 25C1 | 20N | 30.42 | 20C | 25C1 | 21N | 14.60 |
| 20C | 25C1 | 21NE2 | 58.84 | 20C | 25C1 | 19CB | 64.58 |
| 20C | 25C1 | 19CD | 81.24 | 20C | 25C1 | 20CA | 14.64 |
| 20C | 25C1 | 19CG | 65.09 | 184NE1 | 25C1 | 184CD1 | 18.88 |
| 184NE1 | 25C1 | 20N | 99.03 | 184NE1 | 25C1 | 19CB | 64.29 |
| 184NE1 | 25C1 | 19CD | 56.93 | 184NE1 | 25C1 | 184CE2 | 13.44 |
| 184NE1 | 25C1 | 19CG | 68.65 | 184CD1 | 25C1 | 20N | 85.82 |
| 184CD1 | 25C1 | 19CB | 57.54 | 184CD1 | 25C1 | 19CD | 61.12 |
| 184CD1 | 25C1 | 184CE2 | 26.51 | 184CD1 | 25C1 | 19CG | 67.61 |
| 21CA | 25C1 | 20N | 60.42 | 21CA | 25C1 | 21N | 18.12 |
| 21CA | 25C1 | 21NE2 | 47.16 | 21CA | 25C1 | 19CB | 84.18 |
| 21CA | 25C1 | 19CD | 86.47 | 21CA | 25C1 | 20CA | 46.79 |
| 21CA | 25C1 | 19CG | 75.79 | 20N | 25C1 | 21N | 42.62 |
| 20N | 25C1 | 21NE2 | 86.39 | 20N | 25C1 | 19CB | 39.01 |
| 20N | 25C1 | 19CD | 64.17 | 20N | 25C1 | 20CA | 17.07 |
| 20N | 25C1 | 19CG | 47.30 | 21N | 25C1 | 21NE2 | 54.26 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 21N | 25C1 | 19CB | 71.03 | 21N | 25C1 | 19CD | 81.02 |
| 21N | 25C1 | 20CA | 28.72 | 21N | 25C1 | 19CG | 66.90 |
| 21NE2 | 25C1 | 20CA | 69.50 | 19CB | 25C1 | 19CD | 29.32 |
| 19CB | 25C1 | 20CA | 54.83 | 19CB | 25C1 | 184CE2 | 77.66 |
| 19CB | 25C1 | 19CG | 17.68 | 19CD | 25C1 | 20CA | 76.69 |
| 19CD | 25C1 | 184CE2 | 69.09 | 19CD | 25C1 | 19CG | 17.08 |
| 20CA | 25C1 | 19CG | 59.66 | 184CE2 | 25C1 | 19CG | 81.78 |
| 20O | 25C2 | 21NE2 | 59.99 | 20O | 25C2 | 20C | 2.48 |
| 20O | 25C2 | 184NE1 | 99.98 | 20O | 25C2 | 184CD1 | 92.85 |
| 21NE2 | 25C2 | 241OH2 | 86.01 | 21NE2 | 25C2 | 20C | 59.23 |
| 20C | 25C2 | 184CD1 | 93.86 | 184NE1 | 25C2 | 184CD1 | 16.12 |
| 241OH2 | 25C3 | 21NE2 | 97.71 | 20O | 25C3 | 21NE2 | 54.27 |
| 20O | 25C3 | 184CD1 | 87.74 | 20O | 25C3 | 20C | 3.17 |
| 21NE2 | 25C3 | 20C | 54.18 | 184CD1 | 25C3 | 20C | 88.87 |
| 241OH2 | 25C4 | 184O | 97.32 | 20O | 25C4 | 18OD1 | 66.74 |
| 20O | 25C4 | 184CD1 | 99.13 | 20O | 25C4 | 18CG | 78.46 |
| 20O | 25C4 | 18ND2 | 91.26 | 20O | 25C4 | 20C | 7.41 |
| 20O | 25C4 | 184NE1 | 94.68 | 20O | 25C4 | 20N | 34.24 |
| 18OD1 | 25C4 | 184CD1 | 86.06 | 18OD1 | 25C4 | 184CG | 91.60 |
| 18OD1 | 25C4 | 184O | 62.83 | 18OD1 | 25C4 | 184CB | 82.77 |
| 18OD1 | 25C4 | 184CA | 64.10 | 18OD1 | 25C4 | 18CG | 12.46 |
| 18OD1 | 25C4 | 18ND2 | 28.21 | 18OD1 | 25C4 | 20C | 59.47 |
| 18OD1 | 25C4 | 184NE1 | 97.79 | 18OD1 | 25C4 | 20N | 35.84 |
| 18OD1 | 25C4 | 184C | 57.15 | 184CD1 | 25C4 | 184CG | 17.48 |
| 184CD1 | 25C4 | 184O | 65.93 | 184CD1 | 25C4 | 184CB | 33.13 |
| 184CD1 | 25C4 | 184CA | 37.60 | 184CD1 | 25C4 | 18CG | 88.07 |
| 184CD1 | 25C4 | 18ND2 | 95.74 | 184CD1 | 25C4 | 20C | 99.37 |
| 184CD1 | 25C4 | 184NE1 | 15.35 | 184CD1 | 25C4 | 20N | 82.14 |
| 184CD1 | 25C4 | 184C | 55.11 | 184CG | 25C4 | 184O | 54.64 |
| 184CG | 25C4 | 184CB | 18.72 | 184CG | 25C4 | 184CA | 31.21 |
| 184CG | 25C4 | 18CG | 89.91 | 184CG | 25C4 | 18ND2 | 92.98 |
| 184CG | 25C4 | 184NE1 | 27.12 | 184CG | 25C4 | 20N | 96.33 |
| 184CG | 25C4 | 184C | 46.92 | 184O | 25C4 | 184CB | 36.11 |
| 184O | 25C4 | 184CA | 29.52 | 184O | 25C4 | 18CG | 52.77 |
| 184O | 25C4 | 18ND2 | 45.59 | 184O | 25C4 | 184NE1 | 80.28 |
| 184O | 25C4 | 20N | 93.80 | 184O | 25C4 | 184C | 13.81 |
| 184CB | 25C4 | 184CA | 18.71 | 184CB | 25C4 | 18CG | 77.83 |
| 184CB | 25C4 | 18ND2 | 77.39 | 184CB | 25C4 | 184NE1 | 45.48 |
| 184CB | 25C4 | 20N | 98.33 | 184CB | 25C4 | 184C | 30.19 |
| 184CA | 25C4 | 18CG | 59.86 | 184CA | 25C4 | 18ND2 | 61.77 |
| 184CA | 25C4 | 184NE1 | 52.74 | 184CA | 25C4 | 20N | 81.89 |
| 184CA | 25C4 | 184C | 17.52 | 18CG | 25C4 | 18ND2 | 16.14 |
| 18CG | 25C4 | 20C | 71.10 | 18CG | 25C4 | 20N | 48.30 |
| 18CG | 25C4 | 184C | 49.48 | 18ND2 | 25C4 | 20C | 83.86 |
| 18ND2 | 25C4 | 20N | 63.67 | 18ND2 | 25C4 | 184C | 47.21 |
| 20C | 25C4 | 184NE1 | 96.84 | 20C | 25C4 | 20N | 28.14 |
| 184NE1 | 25C4 | 20N | 86.08 | 184NE1 | 25C4 | 184C | 70.17 |
| 20N | 25C4 | 184C | 83.78 | 20O | 25C5 | 18OD1 | 80.82 |
| 20O | 25C5 | 20N | 45.03 | 20O | 25C5 | 20C | 11.42 |
| 20O | 25C5 | 18CG | 91.75 | 20O | 25C5 | 19CB | 74.81 |
| 20O | 25C5 | 20CA | 30.47 | 20O | 25C5 | 19N | 82.23 |
| 20O | 25C5 | 19C | 51.72 | 20O | 25C5 | 19CA | 69.30 |
| 18OD1 | 25C5 | 20N | 46.49 | 18OD1 | 25C5 | 184CA | 77.31 |
| 18OD1 | 25C5 | 20C | 70.82 | 18OD1 | 25C5 | 18CG | 11.80 |
| 18OD1 | 25C5 | 184CB | 96.95 | 18OD1 | 25C5 | 19CB | 72.36 |
| 18OD1 | 25C5 | 183O | 66.28 | 18OD1 | 25C5 | 184O | 67.87 |
| 18OD1 | 25C5 | 20CA | 51.82 | 18OD1 | 25C5 | 19N | 42.94 |
| 18OD1 | 25C5 | 184C | 64.99 | 18OD1 | 25C5 | 18ND2 | 27.18 |
| 18OD1 | 25C5 | 19C | 53.47 | 18OD1 | 25C5 | 19CA | 55.00 |
| 184CD1 | 25C5 | 184CG | 18.87 | 184CD1 | 25C5 | 184NE1 | 17.79 |
| 184CD1 | 25C5 | 184CA | 44.65 | 184CD1 | 25C5 | 184CB | 36.67 |
| 184CD1 | 25C5 | 19CB | 67.07 | 184CD1 | 25C5 | 183O | 47.98 |
| 184CD1 | 25C5 | 184O | 72.91 | 184CD1 | 25C5 | 19N | 80.31 |
| 184CD1 | 25C5 | 184C | 63.25 | 184CD1 | 25C5 | 19C | 98.13 |
| 184CD1 | 25C5 | 19CA | 81.55 | 184CD1 | 25C5 | 184CD2 | 22.19 |
| 20N | 25C5 | 20C | 33.70 | 20N | 25C5 | 18CG | 58.10 |
| 20N | 25C5 | 19CB | 44.66 | 20N | 25C5 | 183O | 72.78 |
| 20N | 25C5 | 20CA | 18.20 | 20N | 25C5 | 19N | 38.00 |
| 20N | 25C5 | 18ND2 | 73.36 | 20N | 25C5 | 19C | 13.46 |
| 20N | 25C5 | 19CA | 30.03 | 184CG | 25C5 | 184NE1 | 31.64 |
| 184CG | 25C5 | 184CA | 35.78 | 184CG | 25C5 | 184CB | 20.39 |
| 184CG | 25C5 | 19CB | 83.44 | 184CG | 25C5 | 183O | 54.59 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 184CG | 25C5 | 184O | 58.05 | 184CG | 25C5 | 19N | 89.86 |
| 184CG | 25C5 | 184C | 51.94 | 184CG | 25C5 | 19CA | 95.52 |
| 184CG | 25C5 | 184CD2 | 13.48 | 184NE1 | 25C5 | 184CA | 62.33 |
| 184NE1 | 25C5 | 184CB | 51.80 | 184NE1 | 25C5 | 19CB | 68.57 |
| 184NE1 | 25C5 | 183O | 61.84 | 184NE1 | 25C5 | 184O | 89.24 |
| 184NE1 | 25C5 | 19N | 89.54 | 184NE1 | 25C5 | 184C | 80.74 |
| 184NE1 | 25C5 | 19C | 99.19 | 184NE1 | 25C5 | 19CA | 85.71 |
| 184NE1 | 25C5 | 184CD2 | 26.19 | 184CA | 25C5 | 18CG | 69.03 |
| 184CA | 25C5 | 184CB | 20.92 | 184CA | 25C5 | 19CB | 77.96 |
| 184CA | 25C5 | 183O | 36.00 | 184CA | 25C5 | 184O | 31.59 |
| 184CA | 25C5 | 19N | 66.93 | 184CA | 25C5 | 184C | 18.86 |
| 184CA | 25C5 | 18ND2 | 67.71 | 184CA | 25C5 | 19C | 97.51 |
| 184CA | 25C5 | 19CA | 80.33 | 184CA | 25C5 | 184CD2 | 49.00 |
| 20C | 25C5 | 18CG | 82.15 | 20C | 25C5 | 19CB | 67.05 |
| 20C | 25C5 | 20CA | 19.43 | 20C | 25C5 | 19N | 71.23 |
| 20C | 25C5 | 18ND2 | 92.73 | 20C | 25C5 | 19C | 41.28 |
| 20C | 25C5 | 19CA | 59.31 | 18CG | 25C5 | 184CB | 87.50 |
| 18CG | 25C5 | 19CB | 79.43 | 18CG | 25C5 | 183O | 64.87 |
| 18CG | 25C5 | 184O | 56.38 | 18CG | 25C5 | 20CA | 63.40 |
| 18CG | 25C5 | 19N | 48.70 | 18CG | 25C5 | 184C | 54.85 |
| 18CG | 25C5 | 18ND2 | 16.71 | 18CG | 25C5 | 19C | 64.20 |
| 18CG | 25C5 | 19CA | 63.20 | 184CB | 25C5 | 19CB | 90.65 |
| 184CB | 25C5 | 183O | 52.34 | 184CB | 25C5 | 184O | 37.66 |
| 184CB | 25C5 | 19N | 86.29 | 184CB | 25C5 | 184C | 32.87 |
| 184CB | 25C5 | 18ND2 | 82.52 | 184CB | 25C5 | 19CA | 97.44 |
| 184CB | 25C5 | 241OH2 | 93.49 | 184CB | 25C5 | 184CD2 | 31.41 |
| 19CB | 25C5 | 183O | 42.37 | 19CB | 25C5 | 20CA | 60.88 |
| 19CB | 25C5 | 19N | 30.92 | 19CB | 25C5 | 184C | 88.12 |
| 19CB | 25C5 | 18ND2 | 95.45 | 19CB | 25C5 | 19C | 31.26 |
| 19CB | 25C5 | 19CA | 18.10 | 19CB | 25C5 | 184CD2 | 89.12 |
| 183O | 25C5 | 184O | 61.91 | 183O | 25C5 | 20CA | 90.84 |
| 183O | 25C5 | 19N | 35.42 | 183O | 25C5 | 184C | 46.49 |
| 183O | 25C5 | 18ND2 | 74.22 | 183O | 25C5 | 19C | 63.18 |
| 183O | 25C5 | 19CA | 45.18 | 183O | 25C5 | 184CD2 | 66.30 |
| 184O | 25C5 | 19N | 81.26 | 184O | 25C5 | 184C | 15.43 |
| 184O | 25C5 | 18ND2 | 46.67 | 184O | 25C5 | 19CA | 98.50 |
| 184O | 25C5 | 241OH2 | 80.65 | 184O | 25C5 | 184CD2 | 68.07 |
| 20CA | 25C5 | 19N | 55.69 | 20CA | 25C5 | 18ND2 | 75.55 |
| 20CA | 25C5 | 19C | 30.17 | 20CA | 25C5 | 19CA | 47.94 |
| 19N | 25C5 | 184C | 68.55 | 19N | 25C5 | 18ND2 | 64.53 |
| 19N | 25C5 | 19C | 31.12 | 19N | 25C5 | 19CA | 17.72 |
| 184C | 25C5 | 18ND2 | 50.25 | 184C | 25C5 | 19C | 99.32 |
| 184C | 25C5 | 19CA | 85.02 | 184C | 25C5 | 241OH2 | 95.85 |
| 184C | 25C5 | 184CD2 | 64.13 | 18ND2 | 25C5 | 19C | 80.57 |
| 18ND2 | 25C5 | 19CA | 79.75 | 18ND2 | 25C5 | 241OH2 | 86.00 |
| 19C | 25C5 | 19CA | 18.28 | 241OH2 | 25C5 | 184CD2 | 93.94 |
| 20O | 25C6 | 20C | 12.91 | 20O | 25C6 | 20N | 48.34 |
| 20O | 25C6 | 19CB | 91.47 | 20O | 25C6 | 18OD1 | 72.52 |
| 20O | 25C6 | 19CG | 86.64 | 20O | 25C6 | 20CA | 29.66 |
| 20O | 25C6 | 19C | 58.59 | 20O | 25C6 | 19CA | 78.30 |
| 20O | 25C6 | 19N | 85.64 | 20O | 25C6 | 21N | 15.81 |
| 20O | 25C6 | 19NE2 | 96.10 | 184CD1 | 25C6 | 184NE1 | 21.76 |
| 184CD1 | 25C6 | 19CB | 75.50 | 184CD1 | 25C6 | 18OD1 | 95.54 |
| 184CD1 | 25C6 | 19CG | 83.68 | 184CD1 | 25C6 | 184CG | 14.32 |
| 184CD1 | 25C6 | 19CD | 72.31 | 184CD1 | 25C6 | 19CA | 87.17 |
| 184CD1 | 25C6 | 19OE1 | 56.50 | 184CD1 | 25C6 | 19N | 79.17 |
| 184CD1 | 25C6 | 184CE2 | 25.40 | 184CD1 | 25C6 | 183O | 45.26 |
| 184CD1 | 25C6 | 184CA | 35.59 | 184CD1 | 25C6 | 184CB | 27.68 |
| 184CD1 | 25C6 | 19NE2 | 80.74 | 184NE1 | 25C6 | 19CB | 80.25 |
| 184NE1 | 25C6 | 19CG | 80.79 | 184NE1 | 25C6 | 184CG | 30.82 |
| 184NE1 | 25C6 | 19CD | 64.39 | 184NE1 | 25C6 | 19CA | 96.31 |
| 184NE1 | 25C6 | 19OE1 | 49.89 | 184NE1 | 25C6 | 19N | 93.83 |
| 184NE1 | 25C6 | 184CE2 | 11.71 | 184NE1 | 25C6 | 183O | 62.24 |
| 184NE1 | 25C6 | 184CA | 57.31 | 184NE1 | 25C6 | 184CB | 47.06 |
| 184NE1 | 25C6 | 19NE2 | 68.19 | 20C | 25C6 | 20N | 37.04 |
| 20C | 25C6 | 19CB | 78.57 | 20C | 25C6 | 18OD1 | 67.96 |
| 20C | 25C6 | 19CG | 74.74 | 20C | 25C6 | 20CA | 19.73 |
| 20C | 25C6 | 19C | 45.89 | 20C | 25C6 | 19CD | 90.64 |
| 20C | 25C6 | 19CA | 65.64 | 20C | 25C6 | 19N | 74.27 |
| 20C | 25C6 | 21N | 11.50 | 20C | 25C6 | 19NE2 | 87.59 |
| 20N | 25C6 | 19CB | 50.10 | 20N | 25C6 | 18OD1 | 42.87 |
| 20N | 25C6 | 19CG | 57.53 | 20N | 25C6 | 20CA | 19.02 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 20N | 25C6 | 19C | 16.56 | 20N | 25C6 | 19CD | 76.93 |
| 20N | 25C6 | 19CA | 32.67 | 20N | 25C6 | 19OE1 | 86.01 |
| 20N | 25C6 | 19N | 37.35 | 20N | 25C6 | 183O | 71.42 |
| 20N | 25C6 | 21N | 45.38 | 20N | 25C6 | 184CA | 93.41 |
| 20N | 25C6 | 19NE2 | 82.82 | 19CB | 25C6 | 18OD1 | 71.17 |
| 19CB | 25C6 | 19CG | 20.52 | 19CB | 25C6 | 184CG | 87.09 |
| 19CB | 25C6 | 20CA | 67.16 | 19CB | 25C6 | 19C | 34.76 |
| 19CB | 25C6 | 19CD | 33.99 | 19CB | 25C6 | 19CA | 18.63 |
| 19CB | 25C6 | 19OE1 | 37.17 | 19CB | 25C6 | 19N | 30.79 |
| 19CB | 25C6 | 184CE2 | 91.78 | 19CB | 25C6 | 183O | 42.56 |
| 19CB | 25C6 | 21N | 80.11 | 19CB | 25C6 | 184CA | 74.81 |
| 19CB | 25C6 | 184CB | 88.09 | 19CB | 25C6 | 19NE2 | 46.70 |
| 18OD1 | 25C6 | 19CG | 88.69 | 18OD1 | 25C6 | 184CG | 91.56 |
| 18OD1 | 25C6 | 20CA | 49.91 | 18OD1 | 25C6 | 19C | 53.85 |
| 18OD1 | 25C6 | 19CA | 54.76 | 18OD1 | 25C6 | 19N | 40.79 |
| 18OD1 | 25C6 | 183O | 58.55 | 18OD1 | 25C6 | 21N | 79.33 |
| 18OD1 | 25C6 | 184CA | 61.28 | 18OD1 | 25C6 | 184CB | 76.32 |
| 19CG | 25C6 | 184CG | 97.34 | 19CG | 25C6 | 20CA | 70.01 |
| 19CG | 25C6 | 19C | 41.04 | 19CG | 25C6 | 19CD | 19.41 |
| 19CG | 25C6 | 19CA | 33.94 | 19CG | 25C6 | 19OE1 | 31.04 |
| 19CG | 25C6 | 19N | 50.11 | 19CG | 25C6 | 184CE2 | 92.31 |
| 19CG | 25C6 | 183O | 60.89 | 19CG | 25C6 | 21N | 72.24 |
| 19CG | 25C6 | 184CA | 92.44 | 19CG | 25C6 | 19NE2 | 28.22 |
| 184CG | 25C6 | 19CD | 86.63 | 184CG | 25C6 | 19CA | 96.09 |
| 184CG | 25C6 | 19OE1 | 70.82 | 184CG | 25C6 | 19N | 84.76 |
| 184CG | 25C6 | 184CE2 | 28.58 | 184CG | 25C6 | 183O | 51.08 |
| 184CG | 25C6 | 184CA | 30.50 | 184CG | 25C6 | 184CB | 16.46 |
| 184CG | 25C6 | 19NE2 | 94.82 | 20CA | 25C6 | 19C | 32.41 |
| 20CA | 25C6 | 19CD | 88.73 | 20CA | 25C6 | 19CA | 50.99 |
| 20CA | 25C6 | 19N | 56.06 | 20CA | 25C6 | 183O | 89.93 |
| 20CA | 25C6 | 21N | 30.16 | 20CA | 25C6 | 19NE2 | 90.65 |
| 19C | 25C6 | 19CD | 60.43 | 19C | 25C6 | 19CA | 19.75 |
| 19C | 25C6 | 19OE1 | 69.63 | 19C | 25C6 | 19N | 32.09 |
| 19C | 25C6 | 183O | 64.40 | 19C | 25C6 | 21N | 50.78 |
| 19C | 25C6 | 184CA | 92.13 | 19C | 25C6 | 19NE2 | 67.14 |
| 19CD | 25C6 | 19CA | 51.19 | 19CD | 25C6 | 19OE1 | 15.82 |
| 19CD | 25C6 | 19N | 64.65 | 19CD | 25C6 | 184CE2 | 75.35 |
| 19CD | 25C6 | 183O | 64.06 | 19CD | 25C6 | 21N | 85.72 |
| 19CD | 25C6 | 184CA | 91.40 | 19CD | 25C6 | 184CB | 96.57 |
| 19CD | 25C6 | 19NE2 | 14.56 | 19CA | 25C6 | 19OE1 | 55.80 |
| 19CA | 25C6 | 19N | 18.35 | 19CA | 25C6 | 183O | 45.71 |
| 19CA | 25C6 | 21N | 70.13 | 19CA | 25C6 | 184CA | 75.80 |
| 19CA | 25C6 | 184CB | 92.14 | 19CA | 25C6 | 19NE2 | 62.13 |
| 19OE1 | 25C6 | 19N | 64.68 | 19OE1 | 25C6 | 184CE2 | 61.31 |
| 19OE1 | 25C6 | 183O | 54.29 | 19OE1 | 25C6 | 184CA | 77.83 |
| 19OE1 | 25C6 | 184CB | 81.20 | 19OE1 | 25C6 | 19NE2 | 26.71 |
| 19N | 25C6 | 183O | 34.10 | 19N | 25C6 | 21N | 81.52 |
| 19N | 25C6 | 184CA | 60.05 | 19N | 25C6 | 184CB | 77.37 |
| 19N | 25C6 | 19NE2 | 77.44 | 184CE2 | 25C6 | 183O | 69.91 |
| 184CE2 | 25C6 | 184CA | 58.41 | 184CE2 | 25C6 | 184CB | 44.79 |
| 184CE2 | 25C6 | 19NE2 | 77.70 | 183O | 25C6 | 184CA | 32.25 |
| 183O | 25C6 | 184CB | 46.82 | 183O | 25C6 | 19NE2 | 78.49 |
| 21N | 25C6 | 19NE2 | 80.31 | 184CA | 25C6 | 184CB | 17.72 |
| 20O | 25O7 | 21CA | 42.87 | 20O | 25O7 | 20C | 13.38 |
| 20O | 25O7 | 21C | 58.81 | 20O | 25O7 | 19CD | 93.04 |
| 20O | 25O7 | 21O | 73.65 | 20O | 25O7 | 22O | 77.10 |
| 20O | 25O7 | 21N | 27.93 | 20O | 25O7 | 19CG | 74.84 |
| 20O | 25O7 | 19OE1 | 98.59 | 20O | 25O7 | 184CD1 | 93.22 |
| 20O | 25O7 | 19CB | 66.24 | 21CA | 25O7 | 20C | 34.50 |
| 21CA | 25O7 | 19NE2 | 96.98 | 21CA | 25O7 | 21C | 20.45 |
| 21CA | 25O7 | 19CD | 99.50 | 21CA | 25O7 | 21O | 32.06 |
| 21CA | 25O7 | 22O | 59.78 | 21CA | 25O7 | 21N | 18.66 |
| 21CA | 25O7 | 19CG | 84.02 | 21CA | 25O7 | 19CB | 87.69 |
| 20C | 25O7 | 19NE2 | 92.76 | 20C | 25O7 | 21C | 47.32 |
| 20C | 25O7 | 19CD | 85.47 | 20C | 25O7 | 21O | 62.79 |
| 20C | 25O7 | 22O | 64.15 | 20C | 25O7 | 21N | 16.77 |
| 20C | 25O7 | 19CG | 67.03 | 20C | 25O7 | 19OE1 | 93.62 |
| 20C | 25O7 | 184CD1 | 98.91 | 20C | 25O7 | 19CB | 62.11 |
| 19NE2 | 25O7 | 21C | 79.95 | 19NE2 | 25O7 | 19CD | 17.34 |
| 19NE2 | 25O7 | 184NE1 | 69.42 | 19NE2 | 25O7 | 21O | 80.15 |
| 19NE2 | 25O7 | 22O | 37.30 | 19NE2 | 25O7 | 21N | 90.94 |
| 19NE2 | 25O7 | 19CG | 30.25 | 19NE2 | 25O7 | 19OE1 | 27.55 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 19NE2 | 25O7 | 184CD1 | 74.17 | 19NE2 | 25O7 | 19CB | 45.70 |
| 21C | 25O7 | 19CD | 86.46 | 21C | 25O7 | 21O | 15.78 |
| 21C | 25O7 | 22O | 43.07 | 21C | 25O7 | 21N | 30.95 |
| 21C | 25O7 | 19CG | 74.61 | 21C | 25O7 | 19CB | 83.86 |
| 19CD | 25O7 | 184NE1 | 58.81 | 19CD | 25O7 | 21O | 90.75 |
| 19CD | 25O7 | 22O | 44.18 | 19CD | 25O7 | 21N | 88.47 |
| 19CD | 25O7 | 19CG | 18.45 | 19CD | 25O7 | 19OE1 | 14.37 |
| 19CD | 25O7 | 184CD1 | 60.00 | 19CD | 25O7 | 19CB | 29.83 |
| 184NE1 | 25O7 | 19CG | 69.06 | 184NE1 | 25O7 | 19OE1 | 44.47 |
| 184NE1 | 25O7 | 184CD1 | 15.81 | 184NE1 | 25O7 | 19CB | 60.87 |
| 21O | 25O7 | 22O | 46.84 | 21O | 25O7 | 21N | 46.16 |
| 21O | 25O7 | 19CG | 82.83 | 21O | 25O7 | 19CB | 95.13 |
| 22O | 25O7 | 21N | 56.64 | 22O | 25O7 | 19CG | 37.32 |
| 22O | 25O7 | 19OE1 | 58.55 | 22O | 25O7 | 19CB | 52.98 |
| 21N | 25O7 | 19CG | 70.99 | 21N | 25O7 | 19OE1 | 99.59 |
| 21N | 25O7 | 19CB | 71.16 | 19CG | 25O7 | 19OE1 | 28.77 |
| 19CG | 25O7 | 184CD1 | 65.14 | 19CG | 25O7 | 19CB | 17.77 |
| 19OE1 | 25O7 | 184CD1 | 46.81 | 19OE1 | 25O7 | 19CB | 32.36 |
| 184CD1 | 25O7 | 19CB | 52.79 | 19NE2 | 25C8 | 184NE1 | 74.20 |
| 19NE2 | 25C8 | 19CD | 17.18 | 19NE2 | 25C8 | 20O | 86.21 |
| 19NE2 | 25C8 | 19OE1 | 28.35 | 19NE2 | 25C8 | 22O | 35.57 |
| 19NE2 | 25C8 | 21O | 77.21 | 19NE2 | 25C8 | 184CE2 | 85.22 |
| 184NE1 | 25C8 | 19CD | 60.55 | 184NE1 | 25C8 | 20O | 90.70 |
| 184NE1 | 25C8 | 19OE1 | 46.23 | 184NE1 | 25C8 | 184CE2 | 14.61 |
| 19CD | 25C8 | 20O | 76.90 | 19CD | 25C8 | 19OE1 | 15.08 |
| 19CD | 25C8 | 22O | 42.30 | 19CD | 25C8 | 21O | 84.98 |
| 19CD | 25C8 | 184CE2 | 73.32 | 20O | 25C8 | 19OE1 | 83.60 |
| 20O | 25C8 | 22O | 62.93 | 20O | 25C8 | 21O | 59.11 |
| 19OE1 | 25C8 | 22O | 57.39 | 19OE1 | 25C8 | 184CE2 | 58.44 |
| 22O | 25C8 | 21O | 42.86 | 184NE1 | 25C9 | 19CD | 81.47 |
| 184NE1 | 25C9 | 19OE1 | 63.24 | 184NE1 | 25C9 | 184CE2 | 17.78 |
| 184NE1 | 25C9 | 184CD1 | 15.24 | 184NE1 | 25C9 | 184CZ2 | 36.54 |
| 184NE1 | 25C9 | 19CG | 84.02 | 184NE1 | 25C9 | 162NE2 | 48.91 |
| 184NE1 | 25C9 | 162CD2 | 64.08 | 184NE1 | 25C9 | 19CB | 68.93 |
| 19NE2 | 25C9 | 19CD | 22.29 | 19NE2 | 25C9 | 19OE1 | 38.48 |
| 19NE2 | 25C9 | 184CD1 | 96.98 | 19NE2 | 25C9 | 19CG | 31.33 |
| 19NE2 | 25C9 | 162NE2 | 73.61 | 19NE2 | 25C9 | 22O | 33.83 |
| 19NE2 | 25C9 | 162CD2 | 72.04 | 19NE2 | 25C9 | 19CB | 48.00 |
| 19CD | 25C9 | 19OE1 | 20.30 | 19CD | 25C9 | 184CE2 | 96.87 |
| 19CD | 25C9 | 184CD1 | 75.05 | 19CD | 25C9 | 19CG | 16.69 |
| 19CD | 25C9 | 162NE2 | 65.70 | 19CD | 25C9 | 22O | 43.91 |
| 19CD | 25C9 | 162CD2 | 70.64 | 19CD | 25C9 | 19CB | 28.29 |
| 19OE1 | 25C9 | 184CE2 | 77.36 | 19OE1 | 25C9 | 184CD1 | 59.86 |
| 19OE1 | 25C9 | 184CZ2 | 88.34 | 19OE1 | 25C9 | 19CG | 32.36 |
| 19OE1 | 25C9 | 162NE2 | 47.50 | 19OE1 | 25C9 | 22O | 64.20 |
| 19OE1 | 25C9 | 162CD2 | 55.96 | 19OE1 | 25C9 | 19CB | 33.06 |
| 184CE2 | 25C9 | 184CD1 | 31.58 | 184CE2 | 25C9 | 184CZ2 | 19.41 |
| 184CE2 | 25C9 | 162NE2 | 49.67 | 184CE2 | 25C9 | 162CD2 | 61.51 |
| 184CE2 | 25C9 | 19CB | 86.67 | 184CD1 | 25C9 | 184CZ2 | 50.94 |
| 184CD1 | 25C9 | 19CG | 73.85 | 184CD1 | 25C9 | 162NE2 | 59.35 |
| 184CD1 | 25C9 | 162CD2 | 75.48 | 184CD1 | 25C9 | 19CB | 57.22 |
| 184CZ2 | 25C9 | 162NE2 | 48.81 | 184CZ2 | 25C9 | 162CD2 | 55.09 |
| 19CG | 25C9 | 162NE2 | 79.83 | 19CG | 25C9 | 22O | 36.66 |
| 19CG | 25C9 | 162CD2 | 86.65 | 19CG | 25C9 | 19CB | 17.77 |
| 162NE2 | 25C9 | 162CD2 | 16.38 | 162NE2 | 25C9 | 19CB | 77.35 |
| 22O | 25C9 | 19CB | 51.74 | 162CD2 | 25C9 | 19CB | 88.41 |
| 184NE1 | 25C10 | 184CZ2 | 41.93 | 184NE1 | 25C10 | 19NE2 | 89.55 |
| 184NE1 | 25C10 | 184CE2 | 20.67 | 184NE1 | 25C10 | 162CD2 | 76.32 |
| 184NE1 | 25C10 | 19OE1 | 57.76 | 184NE1 | 25C10 | 162NE2 | 56.54 |
| 184NE1 | 25C10 | 19CD | 70.87 | 184NE1 | 25C10 | 184CD1 | 8.43 |
| 184NE1 | 25C10 | 162CG | 77.88 | 184NE1 | 25C10 | 184CH2 | 49.27 |
| 184NE1 | 25C10 | 162CE1 | 51.80 | 184CZ2 | 25C10 | 184CE2 | 21.41 |
| 184CZ2 | 2SC10 | 162CD2 | 68.85 | 184CZ2 | 25C10 | 19OE1 | 92.45 |
| 184CZ2 | 25C10 | 162NE2 | 58.15 | 184CZ2 | 25C10 | 184CD1 | 50.03 |
| 184CZ2 | 25C10 | 162CG | 61.13 | 184CZ2 | 25C10 | 184CH2 | 7.67 |
| 184CZ2 | 25C10 | 162CE1 | 46.19 | 184CZ2 | 25C10 | 162CD2 | 81.68 |
| 19NE2 | 25C10 | 19OE1 | 34.40 | 19NE2 | 25C10 | 162NE2 | 79.07 |
| 19NE2 | 25C10 | 19CD | 18.69 | 19NE2 | 25C10 | 184CD1 | 83.31 |
| 19NE2 | 25C10 | 162CG | 94.78 | 19NE2 | 25C10 | 162CE1 | 90.70 |
| 184CE2 | 25C10 | 162CD2 | 73.19 | 184CE2 | 25C10 | 19OE1 | 75.46 |
| 184CE2 | 25C10 | 162NE2 | 56.50 | 184CE2 | 25C10 | 19CD | 90.32 |
| 184CE2 | 25C10 | 184CD1 | 28.64 | 184CE2 | 25C10 | 162CG | 70.03 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 184CE2 | 25C10 | 184CH2 | 28.62 | 184CE2 | 25C10 | 162CE1 | 47.27 |
| 162CD2 | 25C10 | 19OE1 | 63.96 | 162CD2 | 25C10 | 162NE2 | 20.18 |
| 162CD2 | 25C10 | 19CD | 77.09 | 162CD2 | 25C10 | 184CD1 | 81.08 |
| 162CD2 | 25C10 | 162CG | 13.20 | 162CD2 | 25C10 | 184CH2 | 71.00 |
| 162CD2 | 25C10 | 162CE1 | 25.99 | 19OE1 | 25C10 | 162NE2 | 52.28 |
| 19OE1 | 25C10 | 19CD | 17.69 | 19OE1 | 25C10 | 184CD1 | 53.34 |
| 19OE1 | 25C10 | 162CG | 76.09 | 19OE1 | 25C10 | 184CH2 | 99.88 |
| 19OE1 | 25C10 | 162CE1 | 61.59 | 162NE2 | 25C10 | 19CD | 68.59 |
| 162NE2 | 25C10 | 184CD1 | 60.95 | 162NE2 | 2SC10 | 162CG | 26.84 |
| 162NE2 | 25C10 | 184CH2 | 62.65 | 162NE2 | 25C10 | 162CE1 | 12.34 |
| 19CD | 25C10 | 184CD1 | 64.80 | 19CD | 25C10 | 162CG | 90.03 |
| 19CD | 25C10 | 184CH2 | 71.00 | 19CD | 25C10 | 162CG | 84.10 |
| 19CD | 25C10 | 162CE1 | 78.73 | 184CD1 | 25C10 | 162CG | 84.10 |
| 184CD1 | 25C10 | 184CH2 | 57.23 | 184CD1 | 25C10 | 162CE1 | 57.81 |
| 162CG | 25C10 | 184CH2 | 61.82 | 162CG | 25C10 | 162CE1 | 26.29 |
| 184CH2 | 25C10 | 162CE1 | 50.38 | 184CZ2 | 25C11 | 184NE1 | 33.44 |
| 184CZ2 | 25C11 | 162CD2 | 58.33 | 184CZ2 | 25C11 | 184CE2 | 16.76 |
| 184CZ2 | 25C11 | 19NE2 | 94.98 | 184CZ2 | 25C11 | 162NE2 | 47.17 |
| 184NE1 | 25C11 | 162CD2 | 59.46 | 184NE1 | 25C11 | 184CE2 | 17.00 |
| 184NE1 | 2SC11 | 19NE2 | 65.09 | 184NE1 | 25C11 | 162NE2 | 43.40 |
| 162CD2 | 25C11 | 184CE2 | 59.69 | 162CD2 | 25C11 | 19NE2 | 64.20 |
| 162CD2 | 25C11 | 162NE2 | 16.09 | 184CE2 | 25C11 | 19NE2 | 81.10 |
| 184CE2 | 2SC11 | 162NE2 | 45.09 | 19NE2 | 25C11 | 162NE2 | 60.40 |
| 162CD2 | 25S14 | 184CZ2 | 63.39 | 162CD2 | 25S14 | 162CG | 18.68 |
| 162CD2 | 25S14 | 162CB | 36.19 | 162CD2 | 25S14 | 161O | 65.32 |
| 162CD2 | 25S14 | 162NE2 | 15.75 | 162CD2 | 25S14 | 161OD1 | 86.18 |
| 162CD2 | 25S14 | 184CH2 | 70.43 | 184CZ2 | 25S14 | 162CG | 63.65 |
| 184CZ2 | 25S14 | 162CB | 78.78 | 184CZ2 | 25S14 | 162NE2 | 49.18 |
| 184CZ2 | 25S14 | 184CH2 | 14.76 | 162CG | 25S14 | 162CB | 20.04 |
| 162CG | 25S14 | 161O | 60.62 | 162CG | 25S14 | 162NE2 | 28.04 |
| 162CG | 25S14 | 161OD1 | 69.44 | 162CG | 25S14 | 184CH2 | 65.75 |
| 162CB | 25S14 | 161O | 46.23 | 162CB | 25S14 | 162NE2 | 47.97 |
| 162CB | 25S14 | 161OD1 | 50.06 | 162CB | 25S14 | 184CH2 | 76.80 |
| 161O | 25S14 | 162NE2 | 81.07 | 161O | 25S14 | 161OD1 | 48.28 |
| 162NE2 | 25S14 | 161OD1 | 97.37 | 162NE2 | 25S14 | 184CH2 | 58.34 |
| 161OD1 | 25S14 | 184CH2 | 95.88 | 184CZ2 | 25O15 | 184CH2 | 22.20 |
| 184CZ2 | 25O15 | 162CG | 77.78 | 184CZ2 | 25O15 | 162CD2 | 73.98 |
| 184CZ2 | 25O15 | 137O | 88.43 | 184CZ2 | 25O15 | 162CB | 96.58 |
| 184CZ2 | 25O15 | 184CE2 | 11.44 | 184CZ2 | 25O15 | 137CB | 79.42 |
| 184CZ2 | 25O15 | 162ND1 | 62.04 | 184CZ2 | 25O15 | 162NE2 | 56.17 |
| 184CZ2 | 25O15 | 162CE1 | 49.68 | 184CZ2 | 25O15 | 137C | 97.15 |
| 184CZ2 | 25O15 | 184NE1 | 27.38 | 184CZ2 | 25O15 | 184CZ3 | 22.14 |
| 184CH2 | 25O15 | 162CG | 83.63 | 184CH2 | 25O15 | 162CD2 | 86.91 |
| 184CH2 | 25O15 | 137O | 66.28 | 184CH2 | 25O15 | 162CB | 97.10 |
| 184CH2 | 25O15 | 184CE2 | 33.64 | 184CH2 | 25O15 | 137CB | 63.34 |
| 184CH2 | 25O15 | 162ND1 | 65.67 | 184CH2 | 25O15 | 162NE2 | 70.78 |
| 184CH2 | 25O15 | 162CE1 | 59.07 | 184CH2 | 25O15 | 137C | 75.65 |
| 184CH2 | 25O15 | 184NE1 | 49.58 | 184CH2 | 25O15 | 184CZ3 | 0.44 |
| 162CG | 25O15 | 162CD2 | 20.14 | 162CG | 25O15 | 137O | 98.89 |
| 162CG | 25O15 | 162CB | 21.58 | 162CG | 25O15 | 184CE2 | 75.94 |
| 162CG | 25O15 | 137CB | 60.62 | 162CG | 25O15 | 162ND1 | 18.08 |
| 162CG | 25O15 | 162NE2 | 30.14 | 162CG | 25O15 | 161OD1 | 74.08 |
| 162CG | 25O15 | 162CE1 | 28.30 | 162CG | 25O15 | 137C | 90.40 |
| 162CG | 25O15 | 184NE1 | 73.88 | 162CG | 25O15 | 184CZ3 | 84.03 |
| 162CD2 | 25O15 | 162CB | 38.15 | 162CD2 | 25O15 | 184CE2 | 68.37 |
| 162CD2 | 25O15 | 137CB | 79.85 | 162CD2 | 25O15 | 162ND1 | 30.08 |
| 162CD2 | 25O15 | 162NE2 | 17.97 | 162CD2 | 25O15 | 161OD1 | 89.07 |
| 162CD2 | 25O15 | 162CE1 | 28.23 | 162CD2 | 25O15 | 184NE1 | 61.40 |
| 162CD2 | 25O15 | 184CZ3 | 87.22 | 137O | 25O15 | 162CB | 88.99 |
| 137O | 25O15 | 184CE2 | 99.87 | 137O | 25O15 | 137CB | 38.31 |
| 137O | 25O15 | 162ND1 | 89.22 | 137O | 25O15 | 161OD1 | 64.44 |
| 137O | 25O15 | 162CE1 | 99.08 | 137O | 25O15 | 137C | 13.71 |
| 137O | 25O15 | 184CZ3 | 66.38 | 162CB | 25O15 | 184CE2 | 96.47 |
| 162CB | 25O15 | 137CB | 53.88 | 162CB | 25O15 | 162ND1 | 34.56 |
| 162CB | 25O15 | 162NE2 | 51.49 | 162CB | 25O15 | 161OD1 | 52.55 |
| 162CB | 25O15 | 162CE1 | 48.77 | 162CB | 25O15 | 137C | 77.54 |
| 162CB | 25O15 | 184NE1 | 95.45 | 162CB | 25O15 | 184CZ3 | 97.53 |
| 184CE2 | 25O15 | 137CB | 88.43 | 184CE2 | 25O15 | 162ND1 | 62.44 |
| 184CE2 | 25O15 | 162NE2 | 50.44 | 184CE2 | 25O15 | 162CE1 | 47.79 |
| 184CE2 | 25O15 | 184NE1 | 15.94 | 184CE2 | 25O15 | 184CZ3 | 33.57 |
| 137CB | 25O15 | 162ND1 | 52.03 | 137CB | 25O15 | 162NE2 | 80.03 |
| 137CB | 25O15 | 161OD1 | 58.03 | 137CB | 25O15 | 162CE1 | 64.80 |
| 137CB | 25O15 | 137C | 32.11 | 137CB | 25O15 | 184CZ3 | 63.70 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 162ND1 | 25O15 | 162NE2 | 28.43 | 162ND1 | 25O15 | 161OD1 | 83.20 |
| 162ND1 | 25O15 | 162CE1 | 16.55 | 162ND1 | 25O15 | 137C | 84.06 |
| 162ND1 | 25O15 | 184NE1 | 64.50 | 162ND1 | 25O15 | 184CZ3 | 66.08 |
| 162NE2 | 25O15 | 162CE1 | 16.59 | 162NE2 | 25O15 | 184NE1 | 44.67 |
| 162NE2 | 25O15 | 184CZ3 | 71.04 | 161OD1 | 25O15 | 162CE1 | 99.43 |
| 161OD1 | 25O15 | 137C | 51.29 | 162CE1 | 25O15 | 137C | 96.68 |
| 162CE1 | 25O15 | 184NE1 | 48.13 | 162CE1 | 25O15 | 184CZ3 | 59.41 |
| 137C | 25O15 | 184CZ3 | 75.83 | 184NE1 | 25O15 | 184CZ3 | 49.51 |
| 161OD1 | 25O16 | 161O | 49.89 | 161OD1 | 25O16 | 161CG | 14.03 |
| 161O | 25O16 | 161CG | 47.85 | 162CD2 | 25N17 | 162CG | 24.82 |
| 162CD2 | 25N17 | 161O | 98.82 | 162CD2 | 25N17 | 162CB | 49.71 |
| 162CD2 | 25N17 | 162CA | 57.32 | 162CD2 | 25N17 | 162NE2 | 15.00 |
| 162CD2 | 25N17 | 161C | 92.83 | 162CD2 | 25N17 | 25SG | 58.11 |
| 162CD2 | 25N17 | 162N | 75.97 | 162CD2 | 25N17 | 162ND1 | 25.66 |
| 162CD2 | 25N17 | 162CE1 | 19.01 | 162CD2 | 25N17 | 184CZ2 | 61.54 |
| 162CD2 | 25N17 | 25CB | 41.82 | 162CG | 25N17 | 161O | 86.86 |
| 162CG | 25N17 | 162CB | 26.56 | 162CG | 25N17 | 162CA | 42.37 |
| 162CG | 25N17 | 162NE2 | 34.27 | 162CG | 25N17 | 161C | 76.28 |
| 162CG | 25N17 | 25SG | 73.91 | 162CG | 25N17 | 162N | 58.18 |
| 162CG | 25N17 | 162ND1 | 11.86 | 162CG | 25N17 | 161OD1 | 80.11 |
| 162CG | 25N17 | 162CE1 | 24.71 | 162CG | 25N17 | 184CZ2 | 63.21 |
| 162CG | 25N17 | 25CB | 63.12 | 161O | 25N17 | 162CB | 64.87 |
| 161O | 25N17 | 162CA | 44.51 | 161O | 25N17 | 161C | 15.53 |
| 161O | 25N17 | 25SG | 72.13 | 161O | 25N17 | 162N | 31.00 |
| 161O | 25N17 | 162ND1 | 97.99 | 161O | 25N17 | 161OD1 | 55.13 |
| 161O | 25N17 | 25CB | 90.74 | 162CB | 25N17 | 162CA | 24.47 |
| 162CB | 25N17 | 162NE2 | 60.78 | 162CB | 25N17 | 161C | 51.89 |
| 162CB | 25N17 | 25SG | 82.14 | 162CB | 25N17 | 162N | 34.09 |
| 162CB | 25N17 | 162ND1 | 34.92 | 162CB | 25N17 | 161OD1 | 55.89 |
| 162CB | 25N17 | 162CE1 | 50.58 | 162CB | 25N17 | 184CZ2 | 81.16 |
| 162CB | 25N17 | 25CB | 79.93 | 162CA | 25N17 | 162NE2 | 71.74 |
| 162CA | 25N17 | 161C | 35.58 | 162CA | 25N17 | 25SG | 65.34 |
| 162CA | 25N17 | 162N | 19.04 | 162CA | 25N17 | 162ND1 | 53.71 |
| 162CA | 25N17 | 161OD1 | 60.49 | 162CA | 25N17 | 162CE1 | 66.39 |
| 162CA | 25N17 | 25CB | 71.10 | 162NE2 | 25N17 | 25SG | 65.94 |
| 162NE2 | 25N17 | 162N | 89.98 | 162NE2 | 25N17 | 162ND1 | 29.38 |
| 162NE2 | 25N17 | 162CE1 | 14.46 | 162NE2 | 25N17 | 184CZ2 | 48.97 |
| 162NE2 | 25N17 | 25CB | 46.17 | 161C | 25N17 | 25SG | 80.41 |
| 161C | 25N17 | 162N | 18.12 | 161C | 25N17 | 162ND1 | 86.43 |
| 161C | 25N17 | 161OD1 | 42.82 | 161C | 25N17 | 25CB | 95.81 |
| 25SG | 25N17 | 162N | 77.28 | 25SG | 25N17 | 162ND1 | 81.39 |
| 25SG | 25N17 | 162CE1 | 76.71 | 25SG | 25N17 | 25CB | 21.56 |
| 162N | 25N17 | 162ND1 | 68.34 | 162N | 25N17 | 161OD1 | 45.06 |
| 162N | 25N17 | 162CE1 | 82.88 | 162N | 25N17 | 25CB | 87.52 |
| 162ND1 | 25N17 | 161OD1 | 83.28 | 162ND1 | 25N17 | 162CE1 | 16.35 |
| 162ND1 | 25N17 | 184CZ2 | 51.35 | 162ND1 | 25N17 | 25CB | 67.28 |
| 161OD1 | 25N17 | 162CE1 | 99.02 | 161OD1 | 25N17 | 184CZ2 | 99.72 |
| 162CE1 | 25N17 | 184CZ2 | 43.80 | 162CE1 | 25N17 | 25CB | 58.69 |
| 184CZ2 | 25N17 | 25CB | 91.04 | 161O | 25C18 | 25SG | 88.17 |
| 161O | 25C18 | 162CD2 | 89.98 | 161O | 25C18 | 162CA | 40.67 |
| 161O | 25C18 | 161C | 9.73 | 161O | 25C18 | 162CG | 74.76 |
| 161O | 25C18 | 162CB | 55.30 | 161O | 25C18 | 162N | 24.42 |
| 25SG | 25C18 | 162CD2 | 63.21 | 25SG | 25C18 | 162CA | 69.19 |
| 25SG | 25C18 | 161C | 89.73 | 25SG | 25C18 | 162CG | 72.88 |
| 25SG | 25C18 | 162CB | 81.01 | 25SG | 25C18 | 25CB | 22.17 |
| 25SG | 25C18 | 19NE2 | 60.90 | 25SG | 25C18 | 162NE2 | 64.84 |
| 25SG | 25C18 | 162N | 81.28 | 162CD2 | 25C18 | 162CA | 49.41 |
| 162CD2 | 25C18 | 161C | 82.11 | 162CD2 | 25C18 | 162CG | 17.90 |
| 162CD2 | 25C18 | 162CB | 38.19 | 162CD2 | 25C18 | 25CB | 48.19 |
| 162CD2 | 25C18 | 19NE2 | 74.06 | 162CD2 | 25C18 | 162NE2 | 11.85 |
| 162CD2 | 25C18 | 162N | 65.91 | 162CA | 25C18 | 161C | 33.66 |
| 162CA | 25C18 | 162CG | 35.77 | 162CA | 25C18 | 162CB | 21.19 |
| 162CA | 25C18 | 25CB | 73.11 | 162CA | 25C18 | 162NE2 | 61.26 |
| 162CA | 25C18 | 162N | 17.67 | 161C | 25C18 | 162CG | 66.10 |
| 161C | 25C18 | 162CB | 46.17 | 161C | 25C18 | 162NE2 | 93.83 |
| 161C | 25C18 | 162N | 16.25 | 162CG | 25C18 | 162CB | 20.62 |
| 162CG | 25C18 | 25CB | 62.56 | 162CG | 25C18 | 19NE2 | 91.91 |
| 162CG | 25C18 | 162NE2 | 28.46 | 162CG | 25C18 | 162N | 50.34 |
| 162CB | 25C18 | 25CB | 77.17 | 162CB | 25C18 | 162NE2 | 49.07 |
| 162CB | 25C18 | 162N | 31.21 | 25CB | 25C18 | 19NE2 | 46.45 |
| 25CB | 25C18 | 162NE2 | 46.22 | 25CB | 25C18 | 162N | 89.13 |
| 19NE2 | 25C18 | 162NE2 | 63.90 | 162NE2 | 25C18 | 162N | 77.68 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 25SG | 25C19 | 25CB | 31.14 | 25SG | 25C19 | 162CD2 | 72.89 |
| 25SG | 25C19 | 161O | 97.36 | 25SG | 25C19 | 19NE2 | 87.55 |
| 25SG | 25C19 | 25N | 42.09 | 25SG | 25C19 | 25CA | 29.35 |
| 25SG | 25C19 | 23CA | 99.22 | 25SG | 25C19 | 162CA | 71.95 |
| 25SG | 25C19 | 23O | 76.04 | 25SG | 25C19 | 23C | 80.42 |
| 25SG | 25C19 | 162CG | 75.66 | 25SG | 25C19 | 162NE2 | 71.54 |
| 25SG | 25C19 | 19CD | 78.54 | 25SG | 25C19 | 19OE1 | 73.25 |
| 25SG | 25C19 | 161C | 92.06 | 25SG | 25C19 | 162CB | 81.06 |
| 25CB | 25C19 | 162CD2 | 57.89 | 25CB | 25C19 | 19NE2 | 60.82 |
| 25CB | 25C19 | 25N | 33.86 | 25CB | 25C19 | 25CA | 15.34 |
| 25CB | 25C19 | 23CA | 90.78 | 25CB | 25C19 | 162CA | 81.46 |
| 25CB | 25C19 | 23O | 81.85 | 25CB | 25C19 | 23C | 77.61 |
| 25CB | 25C19 | 162CG | 67.35 | 25CB | 25C19 | 162NE2 | 50.15 |
| 25CB | 25C19 | 19CD | 49.61 | 25CB | 25C19 | 19OE1 | 42.26 |
| 25CB | 25C19 | 162CB | 81.00 | 162CD2 | 25C19 | 161O | 78.28 |
| 162CD2 | 25C19 | 19NE2 | 84.27 | 162CD2 | 25C19 | 25N | 90.80 |
| 162CD2 | 25C19 | 25CA | 73.23 | 162CD2 | 25C19 | 162CA | 45.80 |
| 162CD2 | 25C19 | 162CG | 13.99 | 162CD2 | 25C19 | 162NE2 | 13.84 |
| 162CD2 | 25C19 | 19CD | 72.50 | 162CD2 | 25C19 | 19OE1 | 57.48 |
| 162CD2 | 25C19 | 161C | 71.45 | 162CD2 | 25C19 | 162CB | 32.02 |
| 161O | 25C19 | 162CA | 36.90 | 161O | 25C19 | 162CG | 64.31 |
| 161O | 25C19 | 162NE2 | 92.09 | 161O | 25C19 | 161C | 7.56 |
| 161O | 25C19 | 162CB | 46.27 | 19NE2 | 25C19 | 25N | 50.87 |
| 19NE2 | 25C19 | 25CA | 58.20 | 19NE2 | 25C19 | 23CA | 48.05 |
| 19NE2 | 25C19 | 23O | 68.25 | 19NE2 | 25C19 | 23C | 52.78 |
| 19NE2 | 25C19 | 162CG | 98.10 | 19NE2 | 25C19 | 162NE2 | 70.55 |
| 19NE2 | 25C19 | 19CD | 13.21 | 19NE2 | 25C19 | 19OE1 | 27.94 |
| 25N | 25C19 | 25CA | 19.24 | 25N | 25C19 | 23CA | 59.89 |
| 25N | 25C19 | 23O | 48.33 | 25N | 25C19 | 23C | 44.21 |
| 25N | 25C19 | 162NE2 | 80.81 | 25N | 25C19 | 19CD | 47.37 |
| 25N | 25C19 | 19OE1 | 51.79 | 25CA | 25C19 | 23CA | 78.48 |
| 25CA | 25C19 | 162CA | 93.16 | 25CA | 25C19 | 23O | 66.60 |
| 25CA | 25C19 | 23C | 63.45 | 25CA | 25C19 | 162CG | 82.49 |
| 25CA | 25C19 | 162NE2 | 65.00 | 25CA | 25C19 | 19CD | 49.86 |
| 25CA | 25C19 | 19OE1 | 47.62 | 25CA | 25C19 | 162CB | 95.23 |
| 23CA | 25C19 | 23O | 31.44 | 23CA | 25C19 | 23C | 19.68 |
| 23CA | 25C19 | 19CD | 59.89 | 23CA | 25C19 | 19OE1 | 75.03 |
| 162CA | 25C19 | 162CG | 32.75 | 162CA | 25C19 | 162NE2 | 59.16 |
| 162CA | 25C19 | 161C | 29.34 | 162CA | 25C19 | 162CB | 18.30 |
| 23O | 25C19 | 23C | 15.83 | 23O | 25C19 | 19CD | 75.71 |
| 23O | 25C19 | 19OE1 | 88.43 | 23C | 25C19 | 19CD | 61.25 |
| 23C | 25C19 | 19OE1 | 74.96 | 162CG | 25C19 | 162NE2 | 27.82 |
| 162CG | 25C19 | 19CD | 86.48 | 162CG | 25C19 | 19OE1 | 71.46 |
| 162CG | 25C19 | 161C | 57.47 | 162CG | 25C19 | 162CB | 18.04 |
| 162NE2 | 25C19 | 19CD | 58.67 | 162NE2 | 25C19 | 19OE1 | 43.65 |
| 162NE2 | 25C19 | 161C | 85.29 | 162NE2 | 25C19 | 162CB | 45.84 |
| 19CD | 25C19 | 19OE1 | 15.17 | 19OE1 | 25C19 | 162CB | 89.49 |
| 161C | 25C19 | 162CB | 39.48 | 19NE2 | 25O20 | 25SG | 93.68 |
| 19NE2 | 25O20 | 23CA | 67.16 | 19NE2 | 25O20 | 25CB | 65.25 |
| 19NE2 | 25O20 | 23C | 68.09 | 19NE2 | 25O20 | 19CD | 11.46 |
| 19NE2 | 25O20 | 23O | 84.29 | 19NE2 | 25O20 | 25N | 55.54 |
| 19NE2 | 25O20 | 19OE1 | 27.77 | 19NE2 | 25O20 | 24N | 52.93 |
| 19NE2 | 25O20 | 162CD2 | 84.48 | 19NE2 | 25O20 | 23N | 61.60 |
| 19NE2 | 25O20 | 25CA | 59.16 | 19NE2 | 25O20 | 22O | 33.73 |
| 25SG | 25O20 | 25CB | 29.49 | 25SG | 25O20 | 23C | 86.92 |
| 25SG | 25O20 | 19CD | 84.98 | 25SG | 25O20 | 23O | 77.98 |
| 25SG | 25O20 | 25N | 47.84 | 25SG | 25O20 | 19OE1 | 75.69 |
| 25SG | 25O20 | 24N | 81.49 | 25SG | 25O20 | 162CD2 | 54.46 |
| 25SG | 25O20 | 25CA | 35.73 | 25SG | 25O20 | 161O | 62.50 |
| 23CA | 25O20 | 23C | 23.99 | 23CA | 25O20 | 19CD | 77.34 |
| 23CA | 25O20 | 23O | 36.67 | 23CA | 25O20 | 25N | 69.78 |
| 23CA | 25O20 | 19OE1 | 93.50 | 23CA | 25O20 | 24N | 33.03 |
| 23CA | 25O20 | 23N | 10.73 | 23CA | 25O20 | 25CA | 87.65 |
| 23CA | 25O20 | 22O | 36.27 | 25CB | 25O20 | 23C | 83.77 |
| 25CB | 25O20 | 19CD | 55.78 | 25CB | 25O20 | 23O | 83.59 |
| 25CB | 25O20 | 25N | 34.83 | 25CB | 25O20 | 19OE1 | 46.44 |
| 25CB | 25O20 | 24N | 71.21 | 25CB | 25O20 | 162CD2 | 47.80 |
| 25CB | 25O20 | 25CA | 16.76 | 25CB | 25O20 | 22O | 91.65 |
| 25CB | 25O20 | 161O | 85.05 | 23C | 25O20 | 19CD | 75.06 |
| 23C | 25O20 | 23O | 17.82 | 23C | 25O20 | 25N | 49.05 |
| 23C | 25O20 | 19OE1 | 88.41 | 23C | 25O20 | 24N | 16.95 |
| 23C | 25O20 | 23N | 33.23 | 23C | 25O20 | 25CA | 67.04 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 23C | 25O20 | 22O | 47.64 | 19CD | 25O20 | 23O | 89.75 |
| 19CD | 25O20 | 25N | 52.63 | 19CD | 25O20 | 19OE1 | 16.53 |
| 19CD | 25O20 | 24N | 58.75 | 19CD | 25O20 | 162CD2 | 73.33 |
| 19CD | 25O20 | 23N | 72.54 | 19CD | 25O20 | 25CA | 52.30 |
| 19CD | 25O20 | 22O | 45.08 | 23O | 25O20 | 25N | 51.85 |
| 23O | 25O20 | 24N | 31.38 | 23O | 25O20 | 23N | 47.25 |
| 23O | 25O20 | 25CA | 68.11 | 23O | 25O20 | 22O | 65.37 |
| 25N | 25O20 | 19OE1 | 55.38 | 25N | 25O20 | 24N | 36.84 |
| 25N | 25O20 | 162CD2 | 82.30 | 25N | 25O20 | 23N | 74.87 |
| 25N | 25O20 | 25CA | 18.06 | 25N | 25O20 | 22O | 66.79 |
| 19OE1 | 25O20 | 24N | 71.53 | 19OE1 | 25O20 | 162CD2 | 56.81 |
| 19OE1 | 25O20 | 23N | 89.05 | 19OE1 | 25O20 | 25CA | 48.64 |
| 19OE1 | 25O20 | 22O | 61.51 | 24N | 25O20 | 23N | 38.39 |
| 24N | 25O20 | 25CA | 54.62 | 24N | 25O20 | 22O | 40.31 |
| 162CD2 | 25O20 | 25CA | 64.39 | 162CD2 | 25O20 | 161O | 59.56 |
| 23N | 25O20 | 25CA | 92.03 | 23N | 25O20 | 22O | 28.59 |
| 25CA | 25O20 | 22O | 79.45 | 25CA | 25O20 | 161O | 97.28 |
| 25SG | 25C21 | 161O | 94.20 | 25SG | 25C21 | 23O | 80.20 |
| 25SG | 25C21 | 25CB | 11.32 | 25SG | 25C21 | 23C | 74.97 |
| 25SG | 25C21 | 161C | 90.47 | 25SG | 25C21 | 23CA | 85.24 |
| 25SG | 25C21 | 162CA | 61.66 | 25SG | 25C21 | 25N | 34.26 |
| 25SG | 25C21 | 162CD2 | 42.75 | 161O | 25C21 | 25CB | 99.42 |
| 161O | 25C21 | 161C | 6.02 | 161O | 25C21 | 162CA | 32.54 |
| 161O | 25C21 | 162CD2 | 63.74 | 23O | 25C21 | 25CB | 75.76 |
| 23O | 25C21 | 23C | 15.44 | 23O | 25C21 | 65CA | 51.45 |
| 23O | 25C21 | 23CA | 31.46 | 23O | 25C21 | 25N | 46.40 |
| 25CB | 25C21 | 23C | 68.05 | 25CB | 25C21 | 161C | 96.56 |
| 25CB | 25C21 | 23CA | 75.96 | 2SCB | 25C21 | 162CA | 67.42 |
| 2SCB | 25C21 | 25N | 29.59 | 25CB | 25C21 | 162CD2 | 41.05 |
| 23C | 25C21 | 65CA | 65.91 | 23C | 25C21 | 23CA | 19.15 |
| 23C | 25C21 | 25N | 41.03 | 65CA | 25C21 | 23CA | 74.18 |
| 65CA | 25C21 | 25N | 90.25 | 161C | 25C21 | 162CA | 29.15 |
| 161C | 25C21 | 162CD2 | 63.15 | 23CA | 25C21 | 25N | 54.22 |
| 23CA | 25C21 | 162CD2 | 99.59 | 162CA | 25C21 | 25N | 95.84 |
| 162CA | 25C21 | 162CD2 | 38.23 | 25N | 25C21 | 162CD2 | 69.67 |
| 161O | 25N22 | 161C | 14.11 | 161O | 25N22 | 162CA | 41.10 |
| 161O | 25N22 | 162N | 27.68 | 161O | 25N22 | 163N | 72.60 |
| 161O | 25N22 | 162C | 56.36 | 161O | 25N22 | 161CA | 21.99 |
| 25SG | 25N22 | 162CA | 74.63 | 25SG | 25N22 | 162N | 94.42 |
| 25SG | 25N22 | 163N | 59.02 | 25SG | 25N22 | 25CB | 3.31 |
| 25SG | 25N22 | 162C | 70.77 | 161C | 25N22 | 162CA | 35.66 |
| 161C | 25N22 | 162N | 17.48 | 161C | 25N22 | 163N | 63.91 |
| 161C | 25N22 | 162C | 47.46 | 161C | 25N22 | 161CA | 15.87 |
| 162CA | 25N22 | 162N | 19.79 | 162CA | 25N22 | 163N | 32.40 |
| 162CA | 25N22 | 25CB | 71.33 | 162CA | 25N22 | 162C | 17.88 |
| 162CA | 25N22 | 161CA | 50.91 | 162N | 25N22 | 163N | 46.46 |
| 162N | 25N22 | 25CB | 91.12 | 162N | 25N22 | 162C | 29.99 |
| 162N | 25N22 | 161CA | 31.55 | 163N | 25N22 | 25CB | 56.10 |
| 163N | 25N22 | 162C | 16.47 | 163N | 25N22 | 161CA | 76.35 |
| 25CB | 25N22 | 162C | 67.57 | 162C | 25N22 | 161CA | 60.36 |
| 161O | 25C23 | 25SG | 74.84 | 161O | 25C23 | 161C | 14.77 |
| 161O | 25C23 | 162N | 24.77 | 161O | 25C23 | 162CA | 32.09 |
| 161O | 25C23 | 161CA | 26.81 | 25SG | 25C23 | 161C | 82.13 |
| 25SG | 25C23 | 65CA | 98.69 | 25SG | 25C23 | 162N | 73.79 |
| 25SG | 25C23 | 162CA | 57.15 | 25SG | 25C23 | 26CD1 | 66.11 |
| 25SG | 25C23 | 161CA | 99.24 | 25SG | 25C23 | 26CB | 66.49 |
| 161C | 25C23 | 162N | 14.87 | 161C | 25C23 | 162CA | 29.26 |
| 161C | 25C23 | 161CA | 17.21 | 66O | 25C23 | 65CA | 69.84 |
| 66O | 25C23 | 66N | 37.37 | 66O | 25C23 | 65C | 52.20 |
| 66O | 25C23 | 26CD1 | 54.29 | 66O | 25C23 | 26CB | 42.11 |
| 65CA | 25C23 | 66N | 32.68 | 65CA | 25C23 | 65C | 17.67 |
| 65CA | 25C23 | 26CD1 | 48.54 | 65CA | 25C23 | 26CB | 74.99 |
| 66N | 25C23 | 65C | 15.04 | 66N | 25C23 | 26CD1 | 43.34 |
| 66N | 25C23 | 26CB | 56.16 | 162N | 25C23 | 162CA | 17.00 |
| 162N | 25C23 | 161CA | 29.22 | 162CA | 25C23 | 161CA | 45.57 |
| 65C | 25C23 | 26CD1 | 42.77 | 65C | 25C23 | 26CB | 63.55 |
| 26CD1 | 25C23 | 26CB | 29.73 | 65CA | 25O24 | 66N | 44.96 |
| 65CA | 25O24 | 65C | 24.04 | 65CA | 25O24 | 66O | 88.80 |
| 65CA | 25O24 | 65N | 11.32 | 65CA | 25O24 | 26CD1 | 59.03 |
| 65CA | 25O24 | 66CA | 56.76 | 65CA | 25O24 | 66C | 76.00 |
| 6SCA | 25O24 | 64O | 31.19 | 65CA | 25O24 | 23O | 51.20 |
| 65CA | 25O24 | 26CG | 69.83 | 65CA | 25O24 | 26CB | 87.37 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 65CA | 25O24 | 65O | 23.39 | 65CA | 25O24 | 64C | 20.95 |
| 66N | 25O24 | 65C | 20.92 | 66N | 25O24 | 66O | 44.37 |
| 66N | 25O24 | 65N | 56.05 | 66N | 25O24 | 26CD1 | 51.61 |
| 66N | 25O24 | 66CA | 11.81 | 66N | 25O24 | 66C | 31.20 |
| 66N | 25O24 | 64O | 68.01 | 66N | 25O24 | 23O | 77.65 |
| 66N | 25O24 | 26CG | 49.90 | 66N | 25O24 | 26CB | 61.70 |
| 66N | 25O24 | 65O | 21.59 | 66N | 25O24 | 64C | 64.08 |
| 65C | 25O24 | 66O | 65.02 | 65C | 25O24 | 65N | 35.18 |
| 65C | 25O24 | 26CD1 | 51.98 | 65C | 25O24 | 66CA | 32.73 |
| 65C | 25O24 | 66C | 52.03 | 65C | 25O24 | 64O | 49.51 |
| 65C | 25O24 | 23O | 64.02 | 65C | 25O24 | 26CG | 57.07 |
| 65C | 25O24 | 26CB | 72.88 | 65C | 25O24 | 65O | 0.87 |
| 65C | 25O24 | 64C | 43.58 | 66O | 25O24 | 65N | 99.41 |
| 66O | 25O24 | 26CD1 | 61.59 | 66O | 25O24 | 66CA | 32.76 |
| 66O | 25O24 | 66C | 13.43 | 66O | 25O24 | 26CG | 47.99 |
| 66O | 25O24 | 26CB | 43.51 | 66O | 25O24 | 65O | 65.76 |
| 65N | 25O24 | 26CD1 | 62.12 | 65N | 25O24 | 66CA | 67.82 |
| 65N | 25O24 | 66C | 86.89 | 65N | 25O24 | 64O | 27.80 |
| 65N | 25O24 | 23O | 45.06 | 65N | 25O24 | 26CG | 74.86 |
| 65N | 25O24 | 26CB | 92.41 | 65N | 25O24 | 65O | 34.57 |
| 65N | 25O24 | 64C | 14.20 | 26CD1 | 25O24 | 25SG | 67.04 |
| 26CD1 | 25O24 | 66CA | 53.75 | 26CD1 | 25O24 | 66C | 58.39 |
| 26CD1 | 25O24 | 64O | 89.45 | 26CD1 | 25O24 | 23O | 41.01 |
| 26CD1 | 25O24 | 26CG | 15.28 | 26CD1 | 25O24 | 26CB | 31.14 |
| 26CD1 | 25O24 | 65O | 52.64 | 26CD1 | 25O24 | 64C | 76.32 |
| 25SG | 25O24 | 161O | 59.11 | 25SG | 25O24 | 23O | 57.25 |
| 25SG | 25O24 | 26CG | 69.72 | 25SG | 25O24 | 26CB | 63.45 |
| 66CA | 25O24 | 66C | 19.46 | 66CA | 25O24 | 64O | 78.88 |
| 66CA | 25O24 | 23O | 85.60 | 66CA | 25O24 | 26CG | 48.11 |
| 66CA | 25O24 | 26CB | 56.41 | 66CA | 25624 | 65O | 33.40 |
| 66CA | 25O24 | 64C | 75.76 | 66C | 25O24 | 64O | 97.72 |
| 66C | 25O24 | 23O | 96.86 | 66C | 25O24 | 26CG | 47.34 |
| 66C | 25O24 | 26CB | 48.38 | 66C | 25O24 | 65O | 52.74 |
| 66C | 25O24 | 64C | 95.21 | 64O | 25O24 | 23O | 69.05 |
| 64O | 25O24 | 65O | 48.66 | 64O | 25O24 | 64C | 14.27 |
| 23O | 25O24 | 26CG | 55.76 | 23O | 25O24 | 26CB | 67.79 |
| 23O | 25O24 | 65O | 64.06 | 23O | 25O24 | 64C | 55.23 |
| 26CG | 25O24 | 26CB | 17.62 | 26CG | 25O24 | 65O | 57.87 |
| 26CG | 25O24 | 64C | 88.94 | 26CB | 25C24 | 65O | 73.72 |
| 65O | 25O24 | 64C | 42.81 | 161O | 25C25 | 161C | 18.10 |
| 161O | 25C25 | 162N | 30.50 | 161O | 25C25 | 161CA | 32.52 |
| 161O | 25C25 | 163N | 64.43 | 161O | 25C25 | 25SG | 63.34 |
| 161O | 25C25 | 162CA | 35.10 | 161O | 25C25 | 162C | 53.40 |
| 161O | 25C25 | 163CB | 93.18 | 66O | 25C25 | 25SG | 99.66 |
| 66O | 25C25 | 66N | 34.44 | 66O | 25C25 | 163CB | 83.50 |
| 161C | 25C25 | 162N | 17.33 | 161C | 25C25 | 161CA | 19.80 |
| 161C | 25C25 | 163N | 60.64 | 161C | 25C25 | 25SG | 75.44 |
| 161C | 25C25 | 162CA | 30.92 | 161C | 25C25 | 162C | 46.09 |
| 161C | 25C25 | 163CB | 89.51 | 162N | 25C25 | 161CA | 32.24 |
| 162N | 25C25 | 163N | 44.92 | 162N | 25C25 | 25SG | 71.34 |
| 162N | 25C25 | 162CA | 18.08 | 162N | 25C25 | 162C | 29.44 |
| 162N | 25C25 | 163CB | 73.04 | 161CA | 25C25 | 163N | 77.08 |
| 161CA | 25C25 | 25SG | 94.58 | 161CA | 25C25 | 162CA | 49.19 |
| 161CA | 25C25 | 162C | 61.23 | 163N | 25C25 | 25SG | 49.61 |
| 163N | 25C25 | 162CA | 30.25 | 163N | 25C25 | 162C | 16.24 |
| 163N | 25C25 | 163CB | 29.19 | 25SG | 25C25 | 162CA | 54.70 |
| 25SG | 25C25 | 162C | 58.88 | 25SG | 25C25 | 66N | 88.50 |
| 25SG | 25C25 | 163CB | 57.12 | 162CA | 25C25 | 162C | 18.49 |
| 162CA | 25C25 | 163CB | 59.44 | 162C | 25C25 | 163CB | 43.61 |
| 66O | 25C26 | 26CB | 56.41 | 66O | 25C26 | 66C | 2.37 |
| 66O | 25C26 | 26CA | 74.83 | 66O | 25C26 | 68SD | 74.84 |
| 66O | 25C26 | 66N | 33.64 | 66O | 25C26 | 26N | 86.28 |
| 66O | 25C26 | 26CG | 50.23 | 66O | 25C26 | 26CD1 | 56.63 |
| 163CB | 25C26 | 26CB | 71.13 | 163CB | 25C26 | 163N | 35.96 |
| 163CB | 25C26 | 25SG | 68.31 | 163CB | 25C26 | 163CA | 18.75 |
| 163CB | 25C26 | 26CA | 53.74 | 163CB | 25C26 | 162C | 49.97 |
| 163CB | 25C26 | 68SD | 50.69 | 163CB | 25C26 | 161O | 96.76 |
| 163CB | 25C26 | 26N | 55.09 | 163CB | 25C26 | 26CG | 85.31 |
| 163CB | 25C26 | 162CA | 65.37 | 163CB | 25C26 | 161C | 92.67 |
| 163CB | 25C26 | 162N | 78.07 | 163CB | 25C26 | 26CD1 | 92.73 |
| 26CB | 25C26 | 163N | 98.44 | 26CB | 25C26 | 25SG | 73.00 |
| 26CB | 25C26 | 163CA | 88.50 | 26CB | 25C26 | 66C | 55.68 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 26CB | 25C26 | 26CA | 18.86 | 26CB | 25C26 | 68SD | 60.85 |
| 26CB | 25C26 | 66N | 60.69 | 26CB | 25C26 | 26N | 31.12 |
| 26CB | 25C26 | 26CG | 15.82 | 26CB | 25C26 | 26CD1 | 29.79 |
| 163N | 25C26 | 25SG | 54.34 | 163N | 25C26 | 163CA | 19.23 |
| 163N | 25C26 | 26CA | 79.60 | 163N | 25C26 | 162C | 16.17 |
| 163N | 25C26 | 68SD | 84.27 | 163N | 25C26 | 161O | 61.07 |
| 163N | 25C26 | 26N | 71.27 | 163N | 25C26 | 162CA | 29.41 |
| 163N | 25C26 | 161C | 57.02 | 163N | 25C26 | 162N | 43.18 |
| 25SG | 25C26 | 163CA | 65.77 | 25SG | 25C26 | 26CA | 61.96 |
| 25SG | 25C26 | 162C | 61.73 | 25SG | 25C26 | 161O | 58.28 |
| 25SG | 25C26 | 66N | 92.45 | 25SG | 25C26 | 26N | 44.25 |
| 25SG | 25C26 | 26CG | 71.07 | 25SG | 25C26 | 162CA | 54.19 |
| 25SG | 25C26 | 161C | 68.75 | 25SG | 25C26 | 162N | 67.87 |
| 25SG | 25C26 | 26CD1 | 61.51 | 163CA | 25C26 | 26CA | 70.22 |
| 163CA | 25C26 | 162C | 31.46 | 163CA | 25C26 | 68SD | 65.05 |
| 163CA | 25C26 | 161O | 79.96 | 163CA | 25C26 | 26N | 67.43 |
| 163CA | 25C26 | 162CA | 47.86 | 163CA | 25C26 | 161C | 74.37 |
| 163CA | 25C26 | 162N | 59.50 | 66C | 25C26 | 26CA | 74.25 |
| 66C | 25C26 | 68SD | 76.55 | 66C | 25C26 | 66N | 31.36 |
| 66C | 25C26 | 26N | 85.17 | 66C | 25C26 | 26CG | 48.83 |
| 66C | 25C26 | 26CD1 | 54.70 | 26CA | 25C26 | 162C | 95.72 |
| 26CA | 25C26 | 68SD | 58.01 | 26CA | 25C26 | 66N | 77.90 |
| 26CA | 25C26 | 26N | 17.81 | 26CA | 25C26 | 26CG | 31.59 |
| 26CA | 25C26 | 26CD1 | 40.72 | 162C | 25C26 | 68SD | 93.90 |
| 162C | 25C26 | 161O | 49.88 | 162C | 25C26 | 26N | 86.44 |
| 162C | 25C26 | 162CA | 18.09 | 162C | 25C26 | 161C | 42.92 |
| 162C | 25C26 | 162N | 28.10 | 68SD | 25C26 | 26N | 73.74 |
| 68SD | 25C26 | 26CG | 75.07 | 68SD | 25C26 | 26CD1 | 90.33 |
| 161O | 25C26 | 162CA | 32.21 | 161O | 25C26 | 161C | 14.49 |
| 161O | 25C26 | 162N | 26.44 | 66N | 25C26 | 26N | 79.75 |
| 66N | 25C26 | 26CG | 46.31 | 66N | 25C26 | 26CD1 | 41.21 |
| 26N | 25C26 | 26CG | 36.93 | 26N | 25C26 | 162CA | 89.41 |
| 26N | 25C26 | 26CD1 | 38.63 | 26CG | 25C26 | 26CD1 | 15.55 |
| 162CA | 25C26 | 161C | 28.03 | 162CA | 25C26 | 162N | 16.67 |
| 161C | 25C26 | 162N | 15.37 | 163CB | 25C27 | 68SD | 63.80 |
| 163CB | 25C27 | 163CA | 20.61 | 163CB | 25C27 | 163N | 36.17 |
| 163CB | 25C27 | 68CE | 66.45 | 163CB | 25C27 | 134CB | 82.27 |
| 163CB | 25C27 | 26CB | 68.13 | 163CB | 25C27 | 162C | 50.98 |
| 163CB | 25C27 | 162O | 55.96 | 163CB | 25C27 | 26CA | 50.39 |
| 68SD | 25C27 | 66O | 85.83 | 68SD | 25C27 | 163CA | 78.97 |
| 68SD | 25C27 | 163N | 98.79 | 68SD | 25C27 | 68CE | 27.50 |
| 68SD | 25C27 | 134CB | 86.61 | 68SD | 25C27 | 209CD2 | 77.07 |
| 68SD | 25C27 | 26CB | 65.47 | 68SD | 25C27 | 66C | 82.65 |
| 68SD | 25C27 | 26CA | 60.55 | 68SD | 25C27 | 67CA | 62.19 |
| 66O | 25C27 | 26CB | 49.09 | 66O | 25C27 | 66C | 4.22 |
| 66O | 25C27 | 26CA | 66.81 | 66O | 25C27 | 67CA | 32.70 |
| 163CA | 25C27 | 163N | 20.52 | 163CA | 25C27 | 68CE | 72.92 |
| 163CA | 25C27 | 134CB | 68.04 | 163CA | 25C27 | 26CB | 86.68 |
| 163CA | 25C27 | 162C | 32.08 | 163CA | 25C27 | 162O | 35.38 |
| 163CA | 25C27 | 26CA | 69.20 | 163N | 25C27 | 68CE | 93.00 |
| 163N | 25C27 | 134CB | 74.40 | 163N | 25C27 | 26CB | 90.05 |
| 163N | 25C27 | 162C | 16.34 | 163N | 25C27 | 162O | 27.46 |
| 163N | 25C27 | 26CA | 74.74 | 68CE | 25C27 | 134CB | 59.27 |
| 68CE | 25C27 | 209CD2 | 56.93 | 68CE | 25C27 | 26CB | 92.20 |
| 68CE | 25C27 | 162C | 98.29 | 68CE | 25C27 | 162O | 89.77 |
| 68CE | 25C27 | 26CA | 84.17 | 68CE | 25C27 | 67CA | 79.42 |
| 134CB | 25C27 | 209CD2 | 45.82 | 134CB | 25C27 | 162C | 65.01 |
| 134CB | 25C27 | 162O | 50.58 | 209CD2 | 25C27 | 162O | 95.82 |
| 209CD2 | 25C27 | 67CA | 79.47 | 26CB | 25C27 | 66C | 50.07 |
| 26CB | 25C27 | 26CA | 17.74 | 26CB | 25C27 | 67CA | 62.22 |
| 162C | 25C27 | 162O | 14.47 | 162C | 25C27 | 26CA | 90.70 |
| 66C | 25C27 | 26CA | 67.64 | 66C | 25C27 | 67CA | 28.48 |
| 26CA | 25C27 | 67CA | 76.24 | 134CB | 25C28 | 163CB | 94.94 |
| 134CB | 25C28 | 163N | 95.08 | 134CB | 25C28 | 162C | 86.92 |
| 134CB | 25C28 | 162O | 68.97 | 134CB | 25C28 | 163CA | 83.27 |
| 134CB | 25C28 | 209CD2 | 54.77 | 134CB | 25C28 | 134CA | 19.96 |
| 134CB | 25C28 | 162N | 96.63 | 134CB | 25C28 | 68CE | 62.89 |
| 134CB | 25C28 | 68SD | 87.41 | 134CB | 25C28 | 134C | 23.58 |
| 134CB | 25C28 | 161N | 87.00 | 163CB | 25C28 | 163N | 38.06 |
| 163CB | 25C28 | 162C | 57.44 | 163CB | 25C28 | 162O | 66.17 |
| 163CB | 25C28 | 163CA | 22.67 | 163CB | 25C28 | 134CA | 78.61 |
| 163CB | 25C28 | 162N | 88.44 | 163CB | 25C28 | 162CA | 69.97 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 163CB | 25C28 | 68CE | 60.09 | 163CB | 25C28 | 68SD | 51.61 |
| 163CB | 25C28 | 161C | 98.14 | 163CB | 25C28 | 66O | 84.86 |
| 163CB | 25C28 | 134C | 88.60 | 163CB | 25C28 | 161O | 91.88 |
| 163N | 25C28 | 162C | 20.41 | 163N | 25C28 | 162O | 35.09 |
| 163N | 25C28 | 163CA | 22.12 | 163N | 25C28 | 134CA | 75.15 |
| 163N | 25C28 | 162N | 50.53 | 163N | 25C28 | 162CA | 32.37 |
| 163N | 25C28 | 68CE | 93.09 | 163N | 25C28 | 68SD | 89.55 |
| 163N | 25C28 | 161C | 62.08 | 163N | 25C28 | 134C | 76.23 |
| 163N | 25C28 | 161O | 59.80 | 163N | 25C28 | 161N | 83.44 |
| 162C | 25C28 | 162O | 18.65 | 162C | 25C28 | 163CA | 37.49 |
| 162C | 25C28 | 134CA | 68.48 | 162C | 25C28 | 162N | 33.45 |
| 162C | 25C28 | 162CA | 18.81 | 162C | 25C28 | 161C | 48.13 |
| 162C | 25C28 | 134C | 64.60 | 162C | 25C28 | 161O | 50.86 |
| 162C | 25C28 | 161N | 64.31 | 162O | 25C28 | 163CA | 43.61 |
| 162O | 25C28 | 134CA | 51.60 | 162O | 25C28 | 162N | 38.24 |
| 162O | 25C28 | 162CA | 32.12 | 162O | 25C28 | 161C | 54.89 |
| 162O | 25C28 | 134C | 46.14 | 162O | 25C28 | 161O | 62.22 |
| 162O | 25C28 | 161N | 60.29 | 163CA | 25C28 | 134CA | 64.10 |
| 163CA | 25C28 | 162N | 70.64 | 163CA | 25C28 | 162CA | 53.50 |
| 163CA | 25C28 | 68CE | 71.06 | 163CA | 25C28 | 68SD | 70.42 |
| 163CA | 25C28 | 161C | 83.69 | 163CA | 25C28 | 134C | 70.58 |
| 163CA | 25C28 | 161O | 81.89 | 209CD2 | 25C28 | 134CA | 73.08 |
| 209CD2 | 25C28 | 68CE | 56.44 | 209CD2 | 25C28 | 68SD | 70.67 |
| 209CD2 | 25C28 | 66O | 90.11 | 209CD2 | 25C28 | 134C | 77.77 |
| 134CA | 25C28 | 162N | 84.78 | 134CA | 25C28 | 162CA | 83.66 |
| 134CA | 25C28 | 68CE | 63.87 | 134CA | 25C28 | 68SD | 86.25 |
| 134CA | 25C28 | 161C | 99.94 | 134CA | 25C28 | 134C | 14.94 |
| 134CA | 25C28 | 161N | 85.92 | 162N | 25C28 | 162CA | 18.62 |
| 162N | 25C28 | 161C | 16.67 | 162N | 25C28 | 134C | 73.76 |
| 162N | 25C28 | 161O | 26.48 | 162N | 25C28 | 161N | 33.69 |
| 162CA | 25C28 | 161C | 30.27 | 162CA | 25C28 | 134C | 76.50 |
| 162CA | 25C28 | 161O | 32.09 | 162CA | 25C28 | 161N | 52.27 |
| 68CE | 25C28 | 68SD | 24.56 | 68CE | 25C28 | 66O | 83.70 |
| 68CE | 25C28 | 134C | 78.45 | 68SD | 25C28 | 66O | 61.76 |
| 161C | 25C28 | 134C | 87.61 | 161C | 25C28 | 161O | 14.08 |
| 161C | 25C28 | 161N | 30.20 | 66O | 25C28 | 161O | 96.95 |
| 134C | 25C28 | 161N | 71.12 | 161O | 25C28 | 161N | 43.13 |
| 66O | 25C29 | 68SD | 95.60 | 66O | 25C29 | 67CA | 46.15 |
| 66O | 25C29 | 67CD1 | 76.62 | 66O | 25C29 | 66C | 11.19 |
| 66O | 25C29 | 67N | 28.20 | 66O | 25C29 | 68N | 68.80 |
| 66O | 25C29 | 67C | 53.21 | 66O | 25C29 | 67CB | 59.40 |
| 66O | 25C29 | 67CG | 63.57 | 66O | 25C29 | 234OH2 | 97.74 |
| 66O | 25C29 | 26CB | 45.24 | 66O | 25C29 | 67CE1 | 81.98 |
| 209CD2 | 25C29 | 68SD | 86.14 | 209CD2 | 25C29 | 67CD1 | 76.20 |
| 209CD2 | 25C29 | 68CE | 61.12 | 209CD2 | 25C29 | 68N | 93.85 |
| 209CD2 | 25C29 | 67CB | 92.20 | 209CD2 | 25C29 | 67CG | 87.96 |
| 209CD2 | 25C29 | 134CB | 44.39 | 209CD2 | 25C29 | 234OH2 | 59.00 |
| 209CD2 | 25C29 | 67CE1 | 74.42 | 68SD | 25C29 | 67CA | 76.30 |
| 68SD | 25C29 | 66C | 94.73 | 68SD | 25C29 | 68CE | 26.92 |
| 68SD | 25C29 | 67N | 86.90 | 68SD | 25C29 | 68N | 44.21 |
| 68SD | 25C29 | 67C | 58.54 | 68SD | 25C29 | 67CB | 85.01 |
| 68SD | 25C29 | 163CB | 50.89 | 68SD | 25C29 | 134CB | 79.09 |
| 68SD | 25C29 | 234OH2 | 57.89 | 68SD | 25C29 | 26CB | 61.09 |
| 67CA | 25C29 | 67CD1 | 50.51 | 67CA | 25C29 | 66C | 35.89 |
| 67CA | 25C29 | 68CE | 93.88 | 67CA | 25C29 | 67N | 18.53 |
| 67CA | 25C29 | 68N | 33.04 | 67CA | 25C29 | 67C | 17.87 |
| 67CA | 25C29 | 67CB | 18.28 | 67CA | 25C29 | 67CG | 34.89 |
| 67CA | 25C29 | 234OH2 | 51.94 | 67CA | 25C29 | 26CB | 68.39 |
| 67CA | 25C29 | 67CE1 | 64.72 | 67CD1 | 25C29 | 66C | 66.65 |
| 67CD1 | 25C29 | 67N | 56.05 | 67CD1 | 25C29 | 68N | 72.69 |
| 67CD1 | 25C29 | 67C | 65.26 | 67CD1 | 25C29 | 67CB | 33.63 |
| 67CD1 | 25C29 | 67CG | 15.94 | 67CD1 | 25C29 | 234OH2 | 57.55 |
| 67CD1 | 25C29 | 67CE1 | 15.80 | 66C | 25C29 | 67N | 17.49 |
| 66C | 25C29 | 68N | 61.93 | 66C | 25C29 | 67C | 45.45 |
| 66C | 25C29 | 67CB | 48.27 | 66C | 25C29 | 67CG | 52.89 |
| 66C | 25C29 | 234OH2 | 87.82 | 66C | 25C29 | 26CB | 52.23 |
| 66C | 25C29 | 67CE1 | 73.67 | 68CE | 25C29 | 68N | 61.24 |
| 68CE | 25C29 | 67C | 77.92 | 68CE | 25C29 | 67CB | 95.69 |
| 68CE | 25C29 | 163CB | 55.77 | 68CE | 25C29 | 134CB | 54.85 |
| 68CE | 25C29 | 234OH2 | 55.46 | 68CE | 25C29 | 26CB | 86.35 |
| 67N | 25C29 | 68N | 47.83 | 67N | 25C29 | 67C | 30.97 |
| 67N | 25C29 | 67CB | 31.65 | 67N | 25C29 | 67CG | 40.58 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 67N | 25C29 | 234OH2 | 70.44 | 67N | 25C29 | 26CB | 60.08 |
| 67N | 25C29 | 67CE1 | 66.83 | 68N | 25C29 | 67C | 16.87 |
| 68N | 25C29 | 67CB | 41.26 | 68N | 25C29 | 67CG | 60.50 |
| 68N | 25C29 | 163CB | 90.93 | 68N | 25C29 | 234OH2 | 36.37 |
| 68N | 25C29 | 26CB | 64.40 | 68N | 25C29 | 67CE1 | 88.49 |
| 67C | 25C29 | 67CB | 31.65 | 67C | 25C29 | 67CG | 50.66 |
| 67C | 25C29 | 163CB | 99.57 | 67C | 25C29 | 234OH2 | 46.71 |
| 67C | 25C29 | 26CB | 59.86 | 67C | 25C29 | 67CE1 | 80.48 |
| 67CB | 25C29 | 67CG | 19.43 | 67CB | 25C29 | 234OH2 | 44.01 |
| 67CB | 25C29 | 26CB | 86.67 | 67CB | 25C29 | 67CE1 | 48.89 |
| 67CG | 25C29 | 234OH2 | 54.79 | 67CG | 25C29 | 67CE1 | 29.95 |
| 163CB | 25C29 | 134CB | 64.77 | 163CB | 25C29 | 26CB | 55.99 |
| 134CB | 25C29 | 234OH2 | 92.26 | 234OH2 | 25C29 | 67CE1 | 70.61 |
| 66O | 25N30 | 66N | 36.00 | 66O | 25N30 | 66C | 10.42 |
| 66N | 25N30 | 66C | 31.15 | 161O | 25N30 | 161C | 14.88 |
| 161O | 25N30 | 161CA | 29.27 | 161O | 25N30 | 160O | 61.86 |
| 161C | 25N30 | 161CA | 18.36 | 161C | 25N30 | 160O | 49.77 |
| 161CA | 25N30 | 160O | 32.60 | 160O | 25C31 | 161CA | 38.22 |
| 160O | 25C31 | 160C | 13.90 | 160O | 25C31 | 161C | 56.07 |
| 160O | 25C31 | 161N | 27.07 | 160O | 25C31 | 161O | 68.03 |
| 161CA | 25C31 | 160C | 31.81 | 161CA | 25C31 | 161C | 19.14 |
| 161CA | 25C31 | 161N | 17.82 | 161CA | 25C31 | 161O | 29.81 |
| 160C | 25C31 | 161C | 46.85 | 160C | 25C31 | 161N | 16.04 |
| 160C | 25C31 | 161O | 60.44 | 161C | 25C31 | 161N | 30.84 |
| 161C | 25C31 | 161O | 14.70 | 66O | 25C31 | 67CE1 | 65.45 |
| 161N | 25C31 | 161O | 44.68 | 160O | 25O32 | 160C | 20.78 |
| 160O | 25O32 | 161CA | 51.99 | 160O | 25O32 | 161N | 38.37 |
| 160O | 25O32 | 161C | 74.30 | 160O | 25O32 | 160CB | 45.78 |
| 160O | 25O32 | 161O | 86.34 | 160O | 25O32 | 160CA | 28.59 |
| 160O | 25O32 | 162N | 77.29 | 160O | 25O32 | 161CB | 49.03 |
| 160C | 25O32 | 161CA | 42.82 | 160C | 25O32 | 161N | 21.72 |
| 160C | 25O32 | 161C | 61.05 | 160C | 25O32 | 160CB | 36.54 |
| 160C | 25O32 | 161O | 75.94 | 160C | 25O32 | 160CA | 16.12 |
| 160C | 25O32 | 162N | 59.68 | 160C | 25O32 | 161CB | 45.43 |
| 161CA | 25O32 | 161N | 24.13 | 161CA | 25O32 | 161C | 23.46 |
| 161CA | 25O32 | 160CB | 75.84 | 161CA | 25O32 | 161O | 34.47 |
| 161CA | 25O32 | 160CA | 57.38 | 161CA | 25O32 | 162N | 33.92 |
| 161CA | 25O32 | 161CB | 11.93 | 161N | 25O32 | 161C | 39.41 |
| 161N | 25O32 | 160CB | 51.73 | 161N | 25O32 | 161O | 54.76 |
| 161N | 25O32 | 160CA | 34.01 | 161N | 25O32 | 162N | 39.00 |
| 161N | 25O32 | 161CB | 31.34 | 161C | 25O32 | 160CB | 86.66 |
| 161C | 25O32 | 161O | 16.47 | 161C | 25O32 | 160CA | 72.47 |
| 161C | 25O32 | 162N | 16.93 | 161C | 25O32 | 161CB | 32.27 |
| 160CB | 25O32 | 160CA | 20.46 | 160CB | 25O32 | 162N | 76.70 |
| 160CB | 25O32 | 161CB | 81.15 | 161O | 25O32 | 160CA | 88.45 |
| 161O | 25O32 | 162N | 29.70 | 161O | 25O32 | 161CB | 38.78 |
| 160CA | 25O32 | 162N | 66.95 | 160CA | 25O32 | 161CB | 61.27 |
| 162N | 25O32 | 161CB | 45.15 | 67CE1 | 25C33 | 67CZ | 16.24 |
| 67CE1 | 25C33 | 67CD1 | 18.33 | 67CE1 | 25C33 | 67OH | 30.78 |
| 67CZ | 25C33 | 67CD1 | 31.64 | 67CZ | 25C33 | 67OH | 17.77 |
| 67CD1 | 25C33 | 67OH | 48.37 | 160O | 25C34 | 160C | 9.85 |
| 160O | 25C34 | 160CB | 38.05 | 67CE1 | 25C34 | 67OH | 31.14 |
| 67CE1 | 25C34 | 67CZ | 15.25 | 67CE1 | 25C34 | 67CD1 | 15.11 |
| 67OH | 25C34 | 67CZ | 17.26 | 67OH | 25C34 | 67CD1 | 45.96 |
| 67CZ | 25C34 | 67CD1 | 29.18 | 160C | 25C34 | 160CB | 29.90 |
| 67CE1 | 25C35 | 67OH | 32.70 | 67CE1 | 25C35 | 209CD2 | 77.34 |
| 67CE1 | 25C35 | 67CZ | 14.99 | 67CE1 | 25C35 | 67CD1 | 16.08 |
| 67CE1 | 25C35 | 209CD1 | 77.10 | 67OH | 25C35 | 67CZ | 17.98 |
| 67OH | 25C35 | 67CD1 | 48.74 | 67OH | 25C35 | 209CD1 | 99.59 |
| 209CD2 | 25C35 | 67CZ | 92.22 | 209CD2 | 25C35 | 67CD1 | 62.32 |
| 209CD2 | 25C35 | 160O | 97.37 | 209CD2 | 25C35 | 160CB | 70.82 |
| 209CD2 | 25C35 | 209CD1 | 31.32 | 67CZ | 25C35 | 67CD1 | 30.87 |
| 67CZ | 25C35 | 209CD1 | 88.81 | 67CD1 | 25C35 | 209CD1 | 67.63 |
| 160O | 25C35 | 160CB | 37.56 | 160CB | 25C35 | 209CD1 | 83.17 |
| 160O | 25N36 | 160CB | 39.26 | 160O | 25N36 | 160CD1 | 70.13 |
| 160O | 25N36 | 160CG | 56.11 | 160CB | 25N36 | 160CD1 | 30.89 |
| 160CB | 25N36 | 160CG | 18.76 | 160CD1 | 25N36 | 160CG | 18.07 |
| 67CE1 | 25N36 | 67OH | 27.00 | 160O | 25C37 | 160CB | 42.20 |
| 160O | 25C37 | 160N | 37.40 | 160O | 25C37 | 160C | 10.47 |
| 160O | 25C37 | 160CA | 28.50 | 160O | 25C37 | 160CG | 58.56 |
| 160O | 25C37 | 158O | 81.42 | 160CB | 25C37 | 160N | 31.80 |
| 160CB | 25C37 | 160C | 31.91 | 160CB | 25C37 | 160CA | 18.43 |

TABLE XIX-continued

Table of angles between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Atom 3 | Angle | Atom 1 | Atom 2 | Atom 3 | Angle |
|---|---|---|---|---|---|---|---|
| 160CB | 25C37 | 160CG | 17.89 | 160CB | 25C37 | 158O | 70.66 |
| 160N | 25C37 | 160C | 30.12 | 160N | 25C37 | 160CA | 17.61 |
| 160N | 25C37 | 160CG | 36.16 | 160N | 25C37 | 158O | 47.06 |
| 160C | 25C37 | 160CA | 18.39 | 160C | 25C37 | 160CG | 48.09 |
| 160C | 25C37 | 158O | 76.49 | 160CA | 25C37 | 160CG | 31.12 |
| 160CA | 25C37 | 158O | 63.78 | 160CG | 25C37 | 158O | 60.96 |
| 160O | 25N38 | 160C | 7.90 | 160O | 25N38 | 160CB | 39.77 |
| 160O | 25N38 | 160N | 32.65 | 160O | 25N38 | 160CA | 24.13 |
| 160C | 25N38 | 160CB | 32.02 | 160C | 25N38 | 160N | 29.52 |
| 160C | 25N38 | 160CA | 17.57 | 160CB | 25N38 | 160N | 29.89 |
| 160CB | 25N38 | 160CA | 18.19 | 160N | 25N38 | 160CA | 17.29 |

TABLE XX

Table of distances in Ångstroms between atoms of the inhibitor and protein for all protein atoms within 5 Ångstroms of the inhibitor 3(S)-3-[(N-benzyloxycarbonyl)-L-leucinyl]amino-5-methyl-1-(1-propoxy)-2-hexanone.

| Atom 1 | Atom 2 | Dist. | Atom 1 | Atom 2 | Dist. | Atom 1 | Atom 2 | Dist. |
|---|---|---|---|---|---|---|---|---|
| 25C1 | 242OH2 | 3.097 | 25C1 | 18OD1 | 3.745 | 25C1 | 184CB | 3.754 |
| 25C1 | 184CA | 3.830 | 25C1 | 18ND2 | 3.916 | 25C1 | 184O | 3.932 |
| 25C1 | 184CG | 3.975 | 25C1 | 184CD1 | 4.022 | 25C1 | 18CG | 4.158 |
| 25C1 | 184C | 4.165 | 25C1 | 184CD2 | 4.830 | 25C1 | 184NE1 | 4.840 |
| 25C1 | 20O | 4.895 | 25C2 | 18OD1 | 2.946 | 25C2 | 184CD1 | 3.510 |
| 25C2 | 184CA | 3.592 | 25C2 | 18CG | 3.620 | 25C2 | 20N | 3.785 |
| 25C2 | 18ND2 | 3.842 | 25C2 | 184CB | 3.886 | 25C2 | 242OH2 | 3.894 |
| 25C2 | 184CG | 3.897 | 25C2 | 20O | 3.948 | 25C2 | 183O | 4.106 |
| 25C2 | 184C | 4.198 | 25C2 | 19CG | 4.207 | 25C2 | 20CA | 4.229 |
| 25C2 | 19N | 4.334 | 25C2 | 184O | 4.367 | 25C2 | 184NE1 | 4.377 |
| 25C2 | 20C | 4.510 | 25C2 | 184N | 4.678 | 25C2 | 19C | 4.809 |
| 25C2 | 18CB | 4.827 | 25C2 | 183C | 4.828 | 25C2 | 18CA | 4.864 |
| 25C2 | 18C | 4.870 | 25C2 | 184CD2 | 4.940 | 25C2 | 19CA | 4.979 |
| 25C3 | 20O | 2.991 | 25C3 | 184CD1 | 3.420 | 25C3 | 19CG | 3.464 |
| 25C3 | 20N | 3.592 | 25C3 | 18OD1 | 3.738 | 25C3 | 20C | 3.852 |
| 25C3 | 184NE1 | 3.896 | 25C3 | 20CA | 4.002 | 25C3 | 184CG | 4.180 |
| 25C3 | 19CD | 4.295 | 25C3 | 19C | 4.443 | 25C3 | 19N | 4.455 |
| 25C3 | 184CA | 4.500 | 25C3 | 183O | 4.509 | 25C3 | 19CB | 4.596 |
| 25C3 | 184CB | 4.635 | 25C3 | 18CG | 4.662 | 25C3 | 19OE1 | 4.690 |
| 25C3 | 19CA | 4.707 | 25C3 | 184CE2 | 4.837 | 25C3 | 242OH2 | 4.986 |
| 25C4 | 20O | 3.250 | 25C4 | 184CD1 | 3.862 | 25C4 | 184NE1 | 3.932 |
| 25C4 | 20C | 4.284 | 25C4 | 19CG | 4.378 | 25C4 | 184CG | 4.519 |
| 25C4 | 184CE2 | 4.630 | 25C4 | 20N | 4.702 | 25C4 | 20CA | 4.823 |
| 25C4 | 19CD | 4.851 | 25C4 | 21NE2 | 4.914 | 25C4 | 18OD1 | 4.958 |
| 25C4 | 184CD2 | 4.971 | 25C5 | 184CD1 | 4.323 | 25C5 | 20O | 4.342 |
| 25C5 | 184NE1 | 4.439 | 25C5 | 184CG | 4.577 | 25C5 | 184CE2 | 4.766 |
| 25C5 | 242OH2 | 4.835 | 25C5 | 184CD2 | 4.858 | 25C5 | 21NE2 | 4.951 |
| 25C6 | 242OH2 | 3.703 | 25C6 | 184CG | 4.325 | 25C6 | 184CD1 | 4.403 |
| 25C6 | 184CB | 4.414 | 25C6 | 184CD2 | 4.792 | 25C6 | 184NE1 | 4.871 |
| 25C6 | 184CA | 4.873 | 25C6 | 18OD1 | 4.955 | 25C6 | 184O | 4.967 |
| 25C7 | 20O | 3.169 | 25C7 | 184NE1 | 4.191 | 25C7 | 20C | 4.372 |
| 25C7 | 19CG | 4.412 | 25C7 | 19CD | 4.508 | 25C7 | 184CD1 | 4.544 |
| 25C7 | 19NE2 | 4.715 | 25C7 | 19OE1 | 4.899 | 25C7 | 184CE2 | 4.927 |
| 25O8 | 184NE1 | 3.443 | 25O8 | 19CD | 3.459 | 25O8 | 19NE2 | 3.624 |
| 25O8 | 19OE1 | 3.712 | 25O8 | 19CG | 3.802 | 25O8 | 20O | 3.894 |
| 25O8 | 184CD1 | 4.085 | 25O8 | 184CE2 | 4.312 | 25O8 | 22O | 4.666 |
| 25O8 | 184CZ2 | 4.747 | 25C9 | 19NE2 | 3.833 | 25C9 | 184NE1 | 3.925 |
| 25C9 | 19CD | 3.963 | 25C9 | 19OE1 | 4.023 | 25C9 | 184CE2 | 4.572 |
| 25C9 | 184CZ2 | 4.604 | 25C9 | 19CG | 4.740 | 25C9 | 184CD1 | 4.906 |
| 25C9 | 22O | 4.956 | 25O10 | 19NE2 | 3.975 | 25O10 | 23CA | 4.264 |
| 25O10 | 19CD | 4.483 | 25O10 | 22O | 4.554 | 25O10 | 23N | 4.718 |
| 25O10 | 19OE1 | 4.724 | 25O10 | 22C | 4.857 | 25C11 | 162ND1 | 3.919 |
| 25C11 | 184CZ2 | 3.933 | 25C11 | 162CE1 | 4.435 | 25C11 | 184NE1 | 4.520 |
| 25C11 | 184CE2 | 4.600 | 25C11 | 162CG | 4.656 | 25C11 | 184CH2 | 4.932 |
| 25C11 | 162CB | 4.962 | 25C13 | 138OG | 4.932 | 25C15 | 138OG | 3.572 |
| 25C15 | 138CB | 4.696 | 25C15 | 138CA | 4.824 | 25C15 | 161OD1 | 4.950 |
| 25C16 | 162ND1 | 3.171 | 25C16 | 161O | 3.822 | 25C16 | 162CG | 3.975 |
| 25C16 | 162CE1 | 4.007 | 25C16 | 162CB | 4.112 | 25C16 | 25SG | 4.187 |

TABLE XX-continued

Table of distances in Ångstroms between atoms of the inhibitor and protein for all protein atoms within 5 Ångstroms of the inhibitor 3(S)-3-[(N-benzyloxycarbonyl)-L-leucinyl]amino-5-methyl-1-(1-propoxy)-2-hexanone.

| Atom 1 | Atom 2 | Dist. | Atom 1 | Atom 2 | Dist. | Atom 1 | Atom 2 | Dist. |
|---|---|---|---|---|---|---|---|---|
| 25C16 | 162CA | 4.258 | 25C16 | 161C | 4.677 | 25C16 | 184CZ2 | 4.751 |
| 25C16 | 25CB | 4.882 | 25C16 | 162N | 4.893 | 25C16 | 19OE1 | 4.906 |
| 25O17 | 162ND1 | 2.637 | 25O17 | 162CB | 2.951 | 25O17 | 161O | 3.023 |
| 25O17 | 162CG | 3.092 | 25O17 | 162CA | 3.124 | 25O17 | 161C | 3.669 |
| 25O17 | 162N | 3.731 | 25O17 | 162CE1 | 3.755 | 25O17 | 25SG | 4.071 |
| 25O17 | 161OD1 | 4.274 | 25O17 | 162CD2 | 4.298 | 25O17 | 162C | 4.467 |
| 25O17 | 162NE2 | 4.594 | 25O17 | 184CZ2 | 4.770 | 25O17 | 163N | 4.786 |
| 25O17 | 25CB | 4.931 | 25O17 | 161CA | 4.957 | 25O17 | 161CB | 4.964 |
| 25N18 | 25SG | 3.671 | 25N18 | 162ND1 | 3.834 | 25N18 | 161O | 3.966 |
| 25N18 | 25CB | 4.503 | 25N18 | 19NE2 | 4.507 | 25N18 | 23CA | 4.510 |
| 25N18 | 162CE1 | 4.582 | 25N18 | 162CA | 4.791 | 25N18 | 19OE1 | 4.810 |
| 25N18 | 162CG | 4.836 | 25N18 | 162CB | 4.998 | 25C19 | 25SG | 2.829 |
| 25C19 | 161O | 3.274 | 25C19 | 162ND1 | 4.108 | 25C19 | 25CB | 4.147 |
| 25C19 | 162CA | 4.350 | 25C19 | 161C | 4.428 | 25C19 | 23CA | 4.502 |
| 25C19 | 23O | 4.704 | 25C19 | 23C | 4.758 | 25C19 | 162N | 4.907 |
| 25C19 | 25N | 4.915 | 25C19 | 19NE2 | 4.957 | 25C19 | 163N | 4.992 |
| 25C19 | 162CE1 | 4.994 | 25C19 | 162CB | 4.997 | 25C20 | 161O | 3.580 |
| 25C20 | 25SG | 4.069 | 25C20 | 23CA | 4.393 | 25C20 | 23O | 4.523 |
| 25C20 | 23C | 4.786 | 25C20 | 161C | 4.808 | 25C21 | 161O | 3.316 |
| 25C21 | 161C | 4.462 | 25C22 | 161O | 2.892 | 25C22 | 161C | 3.848 |
| 25C22 | 161CA | 4.121 | 25C22 | 161CB | 4.359 | 25C23 | 64O | 4.590 |
| 25C23 | 161O | 4.811 | 25N24 | 184NE1 | 3.412 | 25N24 | 184CZ2 | 3.492 |
| 25N24 | 184CE2 | 3.750 | 25N24 | 19OE1 | 4.106 | 25N24 | 162ND1 | 4.147 |
| 25N24 | 162CE1 | 4.221 | 25N24 | 19CD | 4.432 | 25N24 | 19NE2 | 4.515 |
| 25N24 | 184CD1 | 4.633 | 25N24 | 184CH2 | 4.684 | 25C25 | 25SG | 1.822 |
| 25C25 | 25CB | 3.054 | 25C25 | 25N | 3.471 | 25C25 | 23O | 3.687 |
| 25C25 | 25CA | 3.792 | 25C25 | 23C | 3.793 | 25C25 | 23CA | 3.994 |
| 25C25 | 19NE2 | 4.214 | 25C25 | 162ND1 | 4.271 | 25C25 | 161O | 4.312 |
| 25C25 | 24N | 4.350 | 25C25 | 26N | 4.445 | 25C25 | 25C | 4.500 |
| 25C25 | 24C | 4.578 | 25C25 | 163N | 4.693 | 25C25 | 19OE1 | 4.797 |
| 25C25 | 162CA | 4.833 | 25C25 | 162CE1 | 4.899 | 25C25 | 24CA | 4.928 |
| 25C25 | 19CD | 4.983 | 25O26 | 25SG | 2.496 | 25O26 | 25N | 2.842 |
| 25O26 | 23C | 2.922 | 25O26 | 25CB | 2.985 | 25O26 | 23CA | 3.053 |
| 25O26 | 19NE2 | 3.071 | 25O26 | 23O | 3.183 | 25O26 | 24N | 3.337 |
| 25O26 | 25CA | 3.477 | 25O26 | 24C | 3.898 | 25O26 | 19CD | 3.997 |
| 25O26 | 19OE1 | 4.054 | 25O26 | 24CA | 4.110 | 25O26 | 23N | 4.413 |
| 25O26 | 22O | 4.471 | 25O26 | 25C | 4.502 | 25O26 | 26N | 4.555 |
| 25O26 | 162ND1 | 4.591 | 25O26 | 22C | 4.912 | 25O26 | 162CE1 | 4.933 |
| 25C27 | 25SG | 2.646 | 25C27 | 23O | 3.049 | 25C27 | 23C | 3.646 |
| 25C27 | 25N | 3.830 | 25C27 | 65CA | 3.894 | 25C27 | 25CB | 4.015 |
| 25C27 | 26CD1 | 4.040 | 25C27 | 26N | 4.152 | 25C27 | 23CA | 4.158 |
| 25C27 | 25CA | 4.348 | 25C27 | 24N | 4.411 | 25C27 | 24C | 4.634 |
| 25C27 | 25C | 4.654 | 25C27 | 161O | 4.714 | 25C27 | 65N | 4.725 |
| 25C27 | 26CB | 4.746 | 25C27 | 66N | 4.758 | 25C27 | 24CA | 4.780 |
| 25C27 | 26CG | 4.815 | 25C27 | 65C | 4.906 | 25O28 | 25SG | 3.234 |
| 25O28 | 65CA | 3.931 | 25O28 | 161O | 3.970 | 25O28 | 23O | 4.277 |
| 25O28 | 66N | 4.333 | 25O28 | 66O | 4.402 | 25O28 | 26CD1 | 4.553 |
| 25O28 | 65C | 4.712 | 25O28 | 26N | 4.830 | 25O28 | 26CB | 4.858 |
| 25O28 | 161C | 4.903 | 25O28 | 25CB | 4.910 | 25O28 | 163N | 4.929 |
| 25C29 | 66O | 3.071 | 25C29 | 66N | 3.131 | 25C29 | 65CA | 3.415 |
| 25C29 | 65C | 3.768 | 25C29 | 66C | 4.000 | 25C29 | 26CD1 | 4.084 |
| 25C29 | 66CA | 4.184 | 25C29 | 26CB | 4.278 | 25C29 | 25SG | 4.306 |
| 25C29 | 26CG | 4.529 | 25C29 | 23O | 4.746 | 25C29 | 65N | 4.756 |
| 25C29 | 161O | 4.948 | 25C29 | 65O | 4.978 | 25C29 | 26N | 4.985 |
| 25C30 | 66O | 3.147 | 25C30 | 66N | 3.696 | 25C30 | 66C | 4.040 |
| 25C30 | 65CA | 4.366 | 25C30 | 66CA | 4.428 | 25C30 | 65C | 4.461 |
| 25C30 | 161O | 4.799 | 25C31 | 66O | 3.488 | 25C31 | 161O | 4.535 |
| 25C31 | 66C | 4.544 | 25C31 | 161C | 4.739 | 25C31 | 66N | 4.865 |
| 25C31 | 163CB | 4.886 | 25C31 | 160O | 4.980 | | | |

TABLE XXI

Table of distance in Ångstroms between atoms of the inhibitor and protein for all protein atoms within 5 Ångstroms of the inhibitor bis-(Cbz-leucinyl)-1,3-diamino-propan-2-one.

| Atom 1 | Atom 2 | Dist. | Atom 1 | Atom 2 | Dist. | Atom 1 | Atom 2 | Dist. |
|---|---|---|---|---|---|---|---|---|
| 25C1 | 184CB | 3.966 | 25C1 | 184CG | 4.092 | 25C1 | 18OD1 | 4.178 |
| 25C1 | 184CD1 | 4.335 | 25C1 | 184CA | 4.489 | 25C1 | 184CD2 | 4.689 |
| 25C1 | 184O | 4.748 | 25C1 | 184C | 4.857 | 25C2 | 18OD1 | 3.023 |
| 25C2 | 184CD1 | 4.012 | 25C2 | 184CB | 4.046 | 25C2 | 184CA | 4.130 |
| 25C2 | 184CG | 4.135 | 25C2 | 18CG | 4.154 | 25C2 | 20O | 4.291 |
| 25C2 | 20N | 4.526 | 25C2 | 184C | 4.608 | 25C2 | 18ND2 | 4.696 |
| 25C2 | 20CA | 4.804 | 25C2 | 184NE1 | 4.825 | 25C2 | 184O | 4.835 |
| 25C2 | 20C | 4.924 | 25C2 | 19CG | 4.976 | 25C3 | 20O | 3.073 |
| 25C3 | 18OD1 | 3.568 | 25C3 | 20C | 3.908 | 25C3 | 20N | 3.934 |
| 25C3 | 184CD1 | 3.954 | 25C3 | 20CA | 4.129 | 25C3 | 19CG | 4.226 |
| 25C3 | 184CG | 4.484 | 25C3 | 184NE1 | 4.490 | 25C3 | 18CG | 4.696 |
| 25C3 | 184CB | 4.795 | 25C3 | 184CA | 4.856 | 25C3 | 19C | 4.885 |
| 25C3 | 19CD | 4.898 | 25C4 | 20O | 3.345 | 25C4 | 184CD1 | 4.222 |
| 25C4 | 184NE1 | 4.344 | 25C4 | 20C | 4.381 | 25C4 | 184CG | 4.772 |
| 25C4 | 19CG | 4.838 | 25C4 | 184CE2 | 4.948 | 25C4 | 18OD1 | 4.956 |
| 25C4 | 20N | 4.984 | 25C5 | 184CD1 | 4.521 | 25C5 | 184NE1 | 4.550 |
| 25C5 | 20O | 4.685 | 25C5 | 184CG | 4.727 | 25C5 | 184CE2 | 4.764 |
| 25C5 | 184CD2 | 4.873 | 25C6 | 184CG | 4.403 | 25C6 | 184CD1 | 4.580 |
| 25C6 | 184CD2 | 4.609 | 25C6 | 184CB | 4.657 | 25C6 | 184NE1 | 4.884 |
| 25C6 | 184CE2 | 4.906 | 25C7 | 20O | 2.849 | 25C7 | 20C | 4.026 |
| 25C7 | 184NE1 | 4.648 | 25C7 | 21CA | 4.664 | 25C7 | 19CD | 4.697 |
| 25C7 | 19CG | 4.714 | 25C7 | 21OE1 | 4.738 | 25C7 | 21N | 4.799 |
| 25C7 | 184CD1 | 4.844 | 25C7 | 19OE1 | 4.907 | 25C7 | 19NE2 | 4.961 |
| 25O8 | 20O | 3.212 | 25O8 | 19CD | 3.453 | 25O8 | 19OE1 | 3.622 |
| 25O8 | 19NE2 | 3.664 | 25O8 | 19CG | 3.806 | 25O8 | 184NE1 | 3.870 |
| 25O8 | 184CD1 | 4.265 | 25O8 | 20C | 4.432 | 25O8 | 22O | 4.540 |
| 25O8 | 184CE2 | 4.808 | 25O8 | 19CB | 4.983 | 25C9 | 19OE1 | 3.889 |
| 25C9 | 19NE2 | 3.915 | 25C9 | 19CD | 3.947 | 25C9 | 184NE1 | 4.155 |
| 25C9 | 20O | 4.391 | 25C9 | 19CG | 4.723 | 25C9 | 22O | 4.796 |
| 25C9 | 184CE2 | 4.909 | 25C9 | 184CD1 | 4.929 | 25O10 | 19NE2 | 4.578 |
| 25O10 | 20O | 4.660 | 25O10 | 22O | 4.792 | 25O10 | 19CD | 4.890 |
| 25O10 | 19OE1 | 4.963 | 25C11 | 162ND1 | 4.101 | 25C11 | 184CZ2 | 4.175 |
| 25C11 | 184NE1 | 4.284 | 25C11 | 162CE1 | 4.319 | 25C11 | 19OE1 | 4.351 |
| 25C11 | 184CE2 | 4.593 | 25C11 | 162CG | 4.929 | 25C11 | 19NE2 | 4.945 |
| 25C11 | 19CD | 4.953 | 25C15 | 184CZ2 | 4.332 | 25C15 | 184CH2 | 4.756 |
| 25C15 | 143OE1 | 4.901 | 25C15 | 137O | 4.938 | 25C16 | 162ND1 | 3.174 |
| 25C16 | 162CE1 | 3.757 | 25C16 | 162CG | 4.082 | 25C16 | 25SG | 4.189 |
| 25C16 | 161O | 4.344 | 25C16 | 19OE1 | 4.427 | 25C16 | 162CB | 4.457 |
| 25C16 | 162CA | 4.770 | 25C16 | 162NE2 | 4.792 | 25C16 | 19NE2 | 4.868 |
| 25C16 | 184CZ2 | 4.883 | 25C16 | 25CB | 4.955 | 25C16 | 184NE1 | 4.957 |
| 25C16 | 162CD2 | 4.977 | 25O17 | 162ND1 | 2.574 | 25O17 | 162CG | 3.155 |
| 25O17 | 1E2CB | 3.298 | 25O17 | 162CE1 | 3.479 | 25O17 | 161O | 3.597 |
| 25O17 | 162CA | 3.711 | 25O17 | 25SG | 4.141 | 25O17 | 161C | 4.187 |
| 25O17 | 162CD2 | 4.194 | 25O17 | 162N | 4.282 | 25O17 | 162NE2 | 4.329 |
| 25O17 | 161OD1 | 4.530 | 25O17 | 184CZ2 | 4.752 | 25O17 | 137CB | 4.842 |
| 25N18 | 25SG | 3.590 | 25N18 | 162ND1 | 3.689 | 25N18 | 162CE1 | 4.248 |
| 25N18 | 161O | 4.291 | 25N18 | 19NE2 | 4.292 | 25N18 | 19OE1 | 4.452 |
| 25N18 | 25CB | 4.467 | 25N18 | 23CA | 4.557 | 25N18 | 162CG | 4.791 |
| 25N18 | 19CD | 4.816 | 25C19 | 25SG | 2.732 | 25C19 | 161O | 3.385 |
| 25C19 | 162ND1 | 3.772 | 25C19 | 25CB | 4.081 | 25C19 | 162CA | 4.451 |
| 25C19 | 161C | 4.513 | 25C19 | 162CE1 | 4.560 | 25C19 | 23CA | 4.589 |
| 25C19 | 25N | 4.775 | 25C19 | 23C | 4.776 | 25C19 | 23O | 4.793 |
| 25C19 | 162CG | 4.797 | 25C19 | 19NE2 | 4.876 | 25C19 | 162CB | 4.935 |
| 25C19 | 162N | 4.994 | 25N20 | 184NE1 | 3.387 | 25N20 | 19OE1 | 3.405 |
| 25N20 | 19CD | 3.866 | 25N20 | 184CE2 | 4.004 | 25N20 | 19NE2 | 4.021 |
| 25N20 | 184CZ2 | 4.036 | 25N20 | 162CE1 | 4.357 | 25N20 | 184CD1 | 4.441 |
| 25N20 | 162ND1 | 4.565 | 25N20 | 19CG | 4.876 | 25C21 | 25SG | 1.768 |
| 25C21 | 25CB | 2.961 | 25C21 | 25N | 3.320 | 25C21 | 25CA | 3.665 |
| 25C21 | 23O | 3.874 | 25C21 | 23C | 3.876 | 25C21 | 162ND1 | 3.978 |
| 25C21 | 23CA | 4.127 | 25C21 | 19NE2 | 4.215 | 25C21 | 26N | 4.241 |
| 25C21 | 24N | 4.308 | 25C21 | 161O | 4.319 | 25C21 | 25C | 4.400 |
| 25C21 | 24C | 4.472 | 25C21 | 162CE1 | 4.510 | 25C21 | 19OE1 | 4.818 |
| 25C21 | 24CA | 4.852 | 25C21 | 163N | 4.871 | 25C21 | 162CA | 4.898 |
| 25C21 | 19CD | 4.974 | 25C21 | 26CD1 | 4.991 | 25O22 | 25SG | 2.461 |
| 25O22 | 25N | 2.747 | 25O22 | 25CB | 2.888 | 25O22 | 19NE2 | 3.089 |
| 25O22 | 23C | 3.118 | 25O22 | 23CA | 3.281 | 25O22 | 25CA | 3.369 |
| 25O22 | 24N | 3.372 | 25O22 | 23O | 3.479 | 25O22 | 24C | 3.834 |
| 25O22 | 19CD | 4.008 | 25O22 | 19OE1 | 4.090 | 25O22 | 24CA | 4.106 |
| 25O22 | 22O | 4.311 | 25O22 | 162ND1 | 4.396 | 25O22 | 25C | 4.432 |
| 25O22 | 26N | 4.446 | 25O22 | 23N | 4.563 | 25O22 | 162CE1 | 4.605 |
| 25O22 | 22C | 4.909 | 25O22 | 24O | 4.940 | 25C23 | 160O | 4.313 |
| 25C23 | 67OH | 4.425 | 25C23 | 67CE1 | 4.574 | 25C23 | 160CB | 4.873 |
| 25C24 | 160O | 3.278 | 25C24 | 160CB | 4.082 | 25C24 | 160C | 4.283 |

TABLE XXI-continued

Table of distance in Ångstroms between atoms of the inhibitor and protein for all protein atoms within 5 Ångstroms of the inhibitor bis-(Cbz-leucinyl)-1,3-diamino-propan-2-one.

| Atom 1 | Atom 2 | Dist. | Atom 1 | Atom 2 | Dist. | Atom 1 | Atom 2 | Dist. |
|---|---|---|---|---|---|---|---|---|
| 25C24 | 67CE1 | 4.352 | 25C24 | 209CD2 | 4.555 | 25C24 | 16OCA | 4.652 |
| 25C24 | 67OH | 4.750 | 25C24 | 160N | 4.847 | 25C25 | 160O | 3.120 |
| 25C25 | 160C | 4.287 | 25C25 | 67CE1 | 4.346 | 25C25 | 67OH | 4.617 |
| 25C25 | 16OCB | 4.802 | 25C25 | 67CZ | 4.867 | 25C26 | 160O | 4.072 |
| 25C26 | 67OH | 4.149 | 25C26 | 67CE1 | 4.572 | 25C26 | 67CZ | 4.684 |
| 25C27 | 67OH | 3.768 | 25C27 | 67CZ | 4.663 | 25C27 | 67CE1 | 4.776 |
| 25C27 | 160O | 4.939 | 25C28 | 67OH | 3.920 | 25C28 | 67CE1 | 4.781 |
| 25C28 | 67CZ | 4.836 | 25C29 | 160O | 4.671 | 25C29 | 67OH | 4.760 |
| 25O30 | 275OH2 | 4.167 | 25O30 | 160O | 4.205 | 25O30 | 161CA | 4.860 |
| 25C31 | 160O | 3.769 | 25C31 | 161CA | 4.036 | 25C31 | 161O | 4.057 |
| 25C31 | 275OH2 | 4.224 | 25C31 | 161C | 4.371 | 25C31 | 160C | 4.689 |
| 25C31 | 161N | 4.855 | 25C31 | 161CB | 4.868 | 25O32 | 160O | 2.767 |
| 25O32 | 161CA | 2.883 | 25O32 | 161O | 3.281 | 25O32 | 161C | 3.329 |
| 25O32 | 160C | 3.543 | 25O32 | 161N | 3.634 | 25O32 | 161CB | 3.892 |
| 25O32 | 162N | 4.376 | 25O32 | 16OCA | 4.974 | 25O32 | 275OH2 | 4.982 |
| 25C33 | 161O | 3.671 | 25C33 | 66O | 4.037 | 25C33 | 161C | 4.309 |
| 25C33 | 66N | 4.440 | 25C33 | 275OH2 | 4.717 | 25C33 | 161CA | 4.785 |
| 25C33 | 65CA | 4.801 | 25C34 | 66O | 2.806 | 25C34 | 66C | 3.890 |
| 25C34 | 66N | 4.077 | 25C34 | 26CB | 4.273 | 25C34 | 66CA | 4.590 |
| 25C34 | 161O | 4.797 | 25C34 | 67N | 4.862 | 25C34 | 26CG | 4.869 |
| 25C34 | 163CB | 4.955 | 25C35 | 66O | 3.565 | 25C35 | 209CD2 | 4.310 |
| 25C35 | 134CB | 4.451 | 25C35 | 163CB | 4.577 | 25C35 | 66C | 4.668 |
| 25C35 | 67CD1 | 4.755 | 25C35 | 163N | 4.786 | 25C35 | 68SD | 4.819 |
| 25C35 | 160O | 4.923 | 25C35 | 26CB | 4.937 | 25C35 | 161O | 4.979 |
| 25C36 | 161C | 3.690 | 25C36 | 161O | 3.856 | 25C36 | 162N | 3.868 |
| 25C36 | 134CB | 3.869 | 25C36 | 160O | 3.882 | 25C36 | 163N | 3.971 |
| 25C36 | 161CA | 4.066 | 25C36 | 162C | 4.114 | 25C36 | 160C | 4.145 |
| 25C36 | 161N | 4.238 | 25C36 | 162CA | 4.327 | 25C36 | 163CA | 4.508 |
| 25C36 | 163CB | 4.528 | 25C36 | 162O | 4.616 | 25C36 | 209CD | 4.772 |
| 25C36 | 16OCB | 4.841 | 25C36 | 134CA | 4.905 | 25C36 | 66O | 4.996 |
| 25C37 | 209CD2 | 3.499 | 25C37 | 67CD1 | 3.574 | 25C37 | 67CE | 3.696 |
| 25C37 | 66O | 3.889 | 25C37 | 67CG | 4.551 | 25C37 | 160O | 4.714 |
| 25C37 | 67CZ | 4.732 | 25C37 | 66C | 4.737 | 25C37 | 134CB | 4.814 |
| 25C37 | 67CA | 4.821 | 25C37 | 209CG | 4.994 | 25C38 | 65CA | 3.869 |
| 25C38 | 161O | 3.955 | 25C38 | 66N | 4.001 | 25C38 | 66O | 4.219 |
| 25C38 | 26CD1 | 4.264 | 25C38 | 25SG | 4.271 | 25C38 | 275OH | 4.287 |
| 25C38 | 65C | 4.487 | 25C38 | 23O | 4.627 | 25C38 | 26CB | 4.655 |
| 25C38 | 26CG | 4.792 | 25C38 | 64O | 4.873 | 25C38 | 161C | 4.899 |
| 25C38 | 65N | 4.993 | 25O39 | 65CA | 2.703 | 25O39 | 66N | 3.332 |
| 25O39 | 65C | 3.531 | 25O39 | 275OH2 | 3.677 | 25O39 | 64O | 3.733 |
| 25O39 | 65N | 3.795 | 25O39 | 26CD1 | 4.043 | 25O39 | 23O | 4.088 |
| 25O39 | 64C | 4.155 | 25O39 | 66O | 4.358 | 25O39 | 66CA | 4.647 |
| 25O39 | 65O | 4.732 | 25O39 | 26CG | 4.801 | 25O39 | 26NE | 4.806 |
| 25O39 | 161O | 4.910 | 25O39 | 66C | 4.976 | 25N40 | 25SG | 2.943 |
| 25N40 | 161O | 3.660 | 25N40 | 26CD1 | 4.126 | 25N40 | 26N | 4.248 |
| 25N40 | 23O | 4.287 | 25N40 | 26CB | 4.350 | 25N40 | 163N | 4.551 |
| 25N40 | 25CB | 4.560 | 25N40 | 26CG | 4.646 | 25N40 | 161C | 4.657 |
| 25N40 | 25N | 4.685 | 25N40 | 65CA | 4.705 | 25N40 | 66O | 4.809 |
| 25N40 | 162CA | 4.847 | 25N40 | 26CA | 4.856 | 25N40 | 66N | 4.876 |
| 25N40 | 23C | 4.933 | 25N40 | 163CB | 4.949 | 25N40 | 25CA | 4.979 |
| 25N40 | 25C | 4.984 | 25C41 | 25SG | 2.569 | 25C41 | 23O | 3.094 |
| 25C41 | 25N | 3.498 | 25C41 | 23C | 3.558 | 25C41 | 26CD | 3.732 |
| 25C41 | 26N | 3.810 | 25C41 | 25CB | 3.828 | 25C41 | 25CA | 4.081 |
| 25C41 | 23CA | 4.144 | 25C41 | 24N | 4.195 | 25C41 | 24C | 4.371 |
| 25C41 | 25C | 4.413 | 25C41 | 26CB | 4.509 | 25C41 | 26CG | 4.528 |
| 25C41 | 24CA | 4.533 | 25C41 | 161O | 4.584 | 25C41 | 65CA | 4.716 |
| 25C41 | 26NE1 | 4.762 | 25C41 | 26CA | 4.764 | 25N42 | 275OH | 3.989 |
| 25N42 | 161O | 4.257 | 25N42 | 66N | 4.573 | 25N42 | 66O | 4.641 |
| 25N42 | 65CA | 4.726 | 25N42 | 161C | 4.818 | 25N42 | 160O | 4.862 |
| 25N42 | 161CA | 4.871 | | | | | | |

TABLE XXII

Table of distances in Ångstroms between atoms of the inhibitor and protein for all protein atoms within 5 Ångstroms of the inhibitor 2,2'-N,N'-bis-benzyloxycarbonyl-L-leucinylcarbohydrazide.

| Atom 1 | Atom 2 | Dist. | Atom 1 | Atom 2 | Dist. | Atom 1 | Atom 2 | Dist. |
|---|---|---|---|---|---|---|---|---|
| 25C1 | 184CB | 4.217 | 25C1 | 184O | 4.458 | 25C1 | 184CG | 4.534 |
| 25C1 | 184CD2 | 4.719 | 25C1 | 184CE3 | 4.742 | 25C1 | 188CD1 | 4.982 |
| 25C2 | 184O | 3.589 | 25C2 | 184CB | 3.931 | 25C2 | 18OD1 | 4.344 |
| 25C2 | 184C | 4.365 | 25C2 | 184CA | 4.384 | 25C2 | 184CG | 4.474 |
| 25C3 | 18OD1 | 3.467 | 25C3 | 184CB | 3.731 | 25C3 | 184O | 3.805 |
| 25C3 | 184CA | 3.925 | 25C3 | 184CG | 4.004 | 25C3 | 184C | 4.224 |
| 25C3 | 184CD1 | 4.243 | 25C3 | 18CG | 4.424 | 25C3 | 18ND2 | 4.653 |
| 25C3 | 184CD2 | 4.783 | 25C3 | 20O | 4.954 | 25C4 | 184CG | 3.557 |
| 25C4 | 184CD1 | 3.557 | 25C4 | 184CB | 3.839 | 25C4 | 184NE1 | 4.069 |
| 25C4 | 184CD2 | 4.096 | 25C4 | 184CA | 4.267 | 25C4 | 18OD1 | 4.278 |
| 25C4 | 184CE2 | 4.376 | 25C4 | 20O | 4.406 | 25C4 | 184O | 4.793 |
| 25C4 | 184CE3 | 4.895 | 25C4 | 184C | 4.990 | 25C5 | 184CG | 3.622 |
| 25C5 | 184CD2 | 3.653 | 25C5 | 184CD1 | 3.870 | 25C5 | 184CE2 | 3.925 |
| 25C5 | 184NE1 | 4.046 | 25C5 | 184CB | 4.116 | 25C5 | 184CE3 | 4.153 |
| 25C5 | 184CZ2 | 4.632 | 25C5 | 184CZ3 | 4.798 | 25C5 | 184CA | 4.969 |
| 25C6 | 184CD2 | 4.011 | 25C6 | 184CE3 | 4.065 | 25C6 | 184CG | 4.134 |
| 25C6 | 184CB | 4.303 | 25C6 | 184CE2 | 4.616 | 25C6 | 184CZ3 | 4.700 |
| 25C6 | 184CD1 | 4.765 | 25C7 | 20O | 3.159 | 25C7 | 184CD1 | 3.353 |
| 25C7 | 19CG | 3.702 | 25C7 | 184NE1 | 3.716 | 25C7 | 184CG | 3.910 |
| 25C7 | 20C | 4.053 | 25C7 | 20N | 4.098 | 25C7 | 18OD1 | 4.206 |
| 25C7 | 19CD | 4.236 | 25C7 | 20CA | 4.370 | 25C7 | 184CE2 | 4.426 |
| 25C7 | 184CB | 4.474 | 25C7 | 19NE2 | 4.497 | 25C7 | 184CD2 | 4.546 |
| 25C7 | 184CA | 4.592 | 25C7 | 183O | 4.805 | 25C7 | 19OE1 | 4.886 |
| 25C7 | 19C | 4.994 | 25O8 | 20O | 2.990 | 25O8 | 20C | 4.056 |
| 25O8 | 184NE1 | 4.178 | 25O8 | 184CD1 | 4.264 | 25O8 | 19CG | 4.312 |
| 25O8 | 19NE2 | 4.344 | 25O8 | 19CD | 4.511 | 25O8 | 184CE2 | 4.748 |
| 25O8 | 20CA | 4.839 | 25O8 | 20N | 4.842 | 25O8 | 184CG | 4.873 |
| 25O8 | 21N | 4.938 | 25O8 | 21CA | 4.989 | 25C9 | 20O | 3.137 |
| 25C9 | 19NE2 | 3.361 | 25C9 | 19CD | 3.886 | 25C9 | 19CG | 4.087 |
| 25C9 | 184NE1 | 4.190 | 25C9 | 20C | 4.350 | 25C9 | 22O | 4.421 |
| 25C9 | 184CD1 | 4.624 | 25C9 | 19OE1 | 4.690 | 25C9 | 22N | 4.828 |
| 25C9 | 184CE2 | 4.870 | 25C9 | 21CA | 4.905 | 25C9 | 21OE1 | 4.986 |
| 25O10 | 20O | 2.532 | 25O10 | 19NE2 | 2.700 | 25O10 | 22O | 3.220 |
| 25O10 | 19CD | 3.446 | 25O10 | 19CG | 3.596 | 25O10 | 22N | 3.702 |
| 25O10 | 20C | 3.735 | 25O10 | 22C | 3.951 | 25O10 | 21CA | 4.210 |
| 25O10 | 21C | 4.416 | 25O10 | 21N | 4.441 | 25O10 | 19OE1 | 4.463 |
| 25O10 | 22CA | 4.519 | 25O10 | 19CB | 4.714 | 25O10 | 20N | 4.734 |
| 25O10 | 23N | 4.741 | 25O10 | 20CA | 4.838 | 25O10 | 184NE1 | 4.848 |
| 25O10 | 21OE1 | 4.906 | 25O10 | 23CA | 4.996 | 25C11 | 19NE2 | 3.727 |
| 25C11 | 19CD | 4.636 | 25C11 | 184NE1 | 4.779 | 25C11 | 22O | 4.911 |
| 25C12 | 19NE2 | 3.752 | 25C12 | 22O | 4.028 | 25C12 | 23CA | 4.150 |
| 25C12 | 22C | 4.246 | 25C12 | 23N | 4.275 | 25C12 | 224OH2 | 4.684 |
| 25C12 | 22N | 4.779 | 25C12 | 19CD | 4.925 | 25C12 | 20O | 4.975 |
| 25C13 | 21OE1 | 4.156 | 25C13 | 22N | 4.627 | 25C13 | 22C | 4.667 |
| 25C13 | 23N | 4.712 | 25C13 | 22O | 4.742 | 25C13 | 21C | 4.914 |
| 25C13 | 23CA | 4.953 | 25C14 | 22N | 3.473 | 25C14 | 21C | 3.659 |
| 25C14 | 22C | 3.759 | 25C14 | 21OE1 | 3.793 | 25C14 | 23N | 3.863 |
| 25C14 | 22CA | 3.868 | 25C14 | 21CA | 4.095 | 25C14 | 21O | 4.118 |
| 25C14 | 22O | 4.147 | 25C14 | 23CA | 4.513 | 25C14 | 20O | 4.765 |
| 25C14 | 21CB | 4.851 | 25C14 | 21CD | 4.885 | 25C15 | 21OE1 | 3.260 |
| 25C15 | 21CD | 4.221 | 25C15 | 21NE2 | 4.65O | 25C15 | 21CA | 4.882 |
| 25C15 | 20O | 4.924 | 25C16 | 19NE2 | 3.267 | 25C16 | 19CD | 4.074 |
| 25C16 | 162ND1 | 4.145 | 25C16 | 19OE1 | 4.238 | 25C16 | 162CE1 | 4.291 |
| 25C16 | 184NE1 | 4.295 | 25C16 | 184CZ2 | 4.540 | 25C16 | 184CE2 | 4.778 |
| 25C16 | 25SG | 4.792 | 25C16 | 23CA | 4.932 | 25C16 | 22O | 4.976 |
| 25O17 | 19NE2 | 3.075 | 25O17 | 184NE1 | 3.183 | 25O17 | 162CE1 | 3.232 |
| 25O17 | 162ND1 | 3.349 | 25O17 | 19OE1 | 3.394 | 25O17 | 19CD | 3.490 |
| 25O17 | 184CZ2 | 3.632 | 25O17 | 184CE2 | 3.732 | 25O17 | 162NE2 | 4.167 |
| 25O17 | 162CG | 4.366 | 25O17 | 184CD1 | 4.379 | 25O17 | 25CB | 4.553 |
| 25O17 | 25SG | 4.612 | 25O17 | 19CG | 4.742 | 25O17 | 162CD2 | 4.779 |
| 25O17 | 184CH2 | 4.923 | 25N18 | 19NE2 | 3.859 | 25N18 | 25SG | 4.056 |
| 25N18 | 162ND1 | 4.100 | 25N18 | 161O | 4.319 | 25N18 | 23CA | 4.407 |
| 25N18 | 224OH2 | 4.562 | 25N18 | 162CE1 | 4.601 | 25N18 | 19CD | 4.788 |
| 25N18 | 25CB | 4.834 | 25N18 | 19OE1 | 4.862 | 25N19 | 25SG | 2.787 |
| 25N19 | 162ND1 | 3.174 | 25N19 | 161O | 3.363 | 25N19 | 25CB | 3.873 |
| 25N19 | 162CE1 | 3.953 | 25N19 | 162CA | 4.146 | 25N19 | 162CG | 4.165 |
| 25N19 | 19NE2 | 4.334 | 25N19 | 162CB | 4.414 | 25N19 | 161C | 4.448 |
| 25N19 | 23CA | 4.774 | 25N19 | 162N | 4.806 | 25N19 | 19OE1 | 4.807 |
| 25N19 | 224OH2 | 4.923 | 25N20 | 19NE2 | 3.800 | 25N20 | 184NE1 | 4.071 |
| 25N20 | 19CD | 4.420 | 25N20 | 20O | 4.457 | 25N20 | 184CE2 | 4.475 |
| 25N20 | 184CZ2 | 4.573 | 25N20 | 184CD1 | 4.849 | 25N20 | 19OE1 | 4.977 |
| 25N20 | 19CG | 4.982 | 25C21 | 25SG | 1.799 | 25C21 | 25CB | 3.030 |
| 25C21 | 25N | 3.707 | 25C21 | 162ND1 | 3.784 | 25C21 | 23CA | 3.850 |

TABLE XXII-continued

Table of distances in Ångstroms between atoms of the inhibitor and protein for all protein atoms within 5 Ångstroms of the inhibitor 2,2'-N,N'-bis-benzyloxycarbonyl-L-leucinylcarbohydrazide.

| Atom 1 | Atom 2 | Dist. | Atom 1 | Atom 2 | Dist. | Atom 1 | Atom 2 | Dist. |
|---|---|---|---|---|---|---|---|---|
| 25C21 | 23C | 3.907 | 25C21 | 23O | 3.946 | 25C21 | 25CA | 3.958 |
| 25C21 | 19NE2 | 4.007 | 25C21 | 161O | 4.284 | 25C21 | 162CE1 | 4.379 |
| 25C21 | 22OH2 | 4.436 | 25C21 | 24N | 4.507 | 25C21 | 19OE1 | 4.543 |
| 25C21 | 162CA | 4.728 | 25C21 | 19CD | 4.730 | 25C21 | 26N | 4.758 |
| 25C21 | 25C | 4.830 | 25C21 | 24C | 4.870 | 25C21 | 162CG | 4.947 |
| 25C21 | 163N | 4.989 | 25O22 | 25SG | 2.443 | 25O22 | 19NE2 | 2.871 |
| 25O22 | 25CB | 2.954 | 25O22 | 23CA | 3.128 | 25O22 | 25N | 3.144 |
| 25O22 | 23C | 3.258 | 25O22 | 25CA | 3.641 | 25O22 | 24N | 3.649 |
| 25O22 | 23O | 3.656 | 25O22 | 19CD | 3.696 | 25O22 | 19OE1 | 3.727 |
| 25O22 | 22O | 4.038 | 25O22 | 162ND1 | 4.175 | 25O22 | 24C | 4.265 |
| 25O22 | 23N | 4.327 | 25O22 | 162CE1 | 4.422 | 25O22 | 22OH2 | 4.423 |
| 25O22 | 24CA | 4.529 | 25O22 | 22C | 4.622 | 25O22 | 25C | 4.800 |
| 25O22 | 26N | 4.898 | 25C23 | 61OD1 | 3.673 | 25C23 | 59O | 3.735 |
| 25C23 | 67CE2 | 4.205 | 25C23 | 67CD2 | 4.463 | 25C23 | 26OH2 | 4.473 |
| 25C23 | 61CG | 4.499 | 25C23 | 61OD2 | 4.706 | 25C23 | 59C | 4.887 |
| 25C24 | 59O | 3.179 | 25C24 | 61OD1 | 3.691 | 25C24 | 67CD2 | 3.717 |
| 25C24 | 60ND2 | 3.736 | 25C24 | 67CE2 | 3.832 | 25C24 | 60CA | 3.942 |
| 25C24 | 59C | 4.226 | 25C24 | 61CG | 4.362 | 25C24 | 66CA | 4.399 |
| 25C24 | 60C | 4.521 | 25C24 | 61N | 4.525 | 25C24 | 60N | 4.567 |
| 25C24 | 70OD1 | 4.595 | 25C24 | 61OD2 | 4.702 | 25C24 | 60CG | 4.710 |
| 25C24 | 60CB | 4.837 | 25C24 | 67N | 4.915 | 25C24 | 66C | 4.929 |
| 25C24 | 65O | 4.975 | 25C24 | 67CG | 4.986 | 25C25 | 66CA | 3.301 |
| 25C25 | 61OD1 | 3.379 | 25C25 | 67CD2 | 3.477 | 25C25 | 67CE2 | 3.538 |
| 25C25 | 60ND2 | 3.834 | 25C25 | 66N | 3.859 | 25C25 | 65O | 3.860 |
| 25C25 | 66C | 3.977 | 25C25 | 65C | 4.082 | 25C25 | 60CA | 4.110 |
| 25C25 | 61CG | 4.139 | 25C25 | 61N | 4.153 | 25C25 | 59O | 4.235 |
| 25C25 | 67N | 4.302 | 25C25 | 60C | 4.526 | 25C25 | 60CG | 4.585 |
| 25C25 | 66O | 4.675 | 25C25 | 60CB | 4.701 | 25C25 | 61CB | 4.755 |
| 25C25 | 67CG | 4.785 | 25C25 | 61OD2 | 4.825 | 25C25 | 67CZ | 4.879 |
| 25C26 | 61OD1 | 3.031 | 25C26 | 67CE2 | 3.662 | 25C26 | 66CA | 3.882 |
| 25C26 | 66N | 3.954 | 25C26 | 65O | 4.020 | 25C26 | 65C | 4.027 |
| 25C26 | 67CD2 | 4.058 | 25C26 | 61CG | 4.066 | 25C26 | 66C | 4.566 |
| 25C26 | 61CB | 4.672 | 25C26 | 61N | 4.764 | 25C26 | 67CZ | 4.811 |
| 25C26 | 65CA | 4.818 | 25C26 | 61OD2 | 4.956 | 25C26 | 66O | 4.959 |
| 25C27 | 61OD1 | 3.004 | 25C27 | 67CE2 | 4.045 | 25C27 | 61CG | 4.208 |
| 25C27 | 67CD2 | 4.744 | 25C27 | 61OD2 | 4.951 | 25C27 | 67OH | 4.988 |
| 25C28 | 61OD1 | 3.343 | 25C28 | 67CE2 | 4.306 | 25C28 | 61CG | 4.423 |
| 25C28 | 26OH2 | 4.506 | 25C28 | 61OD2 | 4.829 | 25C28 | 67CD2 | 4.927 |
| 25C29 | 66N | 3.077 | 25C29 | 65C | 3.103 | 25C29 | 65O | 3.481 |
| 25C29 | 66CA | 3.531 | 25C29 | 65CA | 3.578 | 25C29 | 61OD1 | 3.662 |
| 25C29 | 67CE2 | 4.189 | 25C29 | 64O | 4.192 | 25C29 | 66C | 4.265 |
| 25C29 | 66O | 4.382 | 25C29 | 65N | 4.522 | 25C29 | 67CD2 | 4.589 |
| 25C29 | 61CG | 4.593 | 25C29 | 64C | 4.738 | 25C29 | 61CB | 4.762 |
| 25O30 | 66N | 3.458 | 25O30 | 67CE2 | 3.803 | 25O30 | 65C | 3.840 |
| 25O30 | 66O | 4.008 | 25O30 | 66CA | 4.009 | 25O30 | 65CA | 4.053 |
| 25O30 | 66C | 4.287 | 25O30 | 67CD2 | 4.421 | 25O30 | 67CZ | 4.431 |
| 25O30 | 67OH | 4.470 | 25O30 | 65O | 4.551 | 25O30 | 64O | 4.750 |
| 25C31 | 66N | 3.498 | 25C31 | 65CA | 3.654 | 25C31 | 65C | 3.885 |
| 25C31 | 66O | 4.018 | 25C31 | 66CA | 4.416 | 25C31 | 64O | 4.463 |
| 25C31 | 66C | 4.608 | 25C31 | 65O | 4.872 | 25C31 | 67CE2 | 4.874 |
| 25C31 | 65N | 4.883 | 25O32 | 65CA | 3.690 | 25O32 | 64O | 3.833 |
| 25O32 | 66N | 4.273 | 25O32 | 65C | 4.343 | 25O32 | 64C | 4.667 |
| 25O32 | 65N | 4.681 | 25C33 | 66O | 3.876 | 25C33 | 66N | 4.173 |
| 25C33 | 161O | 4.383 | 25C33 | 65CA | 4.417 | 25C33 | 161C | 4.670 |
| 25C33 | 25SG | 4.802 | 25C33 | 65C | 4.843 | 25C33 | 66C | 4.902 |
| 25C34 | 66O | 3.833 | 25C34 | 161C | 4.228 | 25C34 | 161O | 4.287 |
| 25C34 | 162N | 4.305 | 25C34 | 163N | 4.452 | 25C34 | 162CA | 4.613 |
| 25C34 | 162C | 4.644 | 25C34 | 25SG | 4.656 | 25C34 | 161CA | 4.669 |
| 25C34 | 163CB | 4.789 | 25C34 | 66N | 4.994 | 25C35 | 66O | 2.981 |
| 25C35 | 66C | 4.208 | 25C35 | 163CB | 4.767 | 25C35 | 26CB | 4.871 |
| 25C35 | 66N | 4.887 | 25C35 | 67CA | 4.934 | 25C35 | 209CD2 | 4.958 |
| 25C35 | 68SD | 4.962 | 25C35 | 67CD1 | 4.992 | 25C35 | 67CE1 | 5.000 |
| 25C36 | 66O | 3.430 | 25C36 | 68SD | 3.532 | 25C36 | 163CB | 3.585 |
| 25C36 | 163CA | 4.250 | 25C36 | 134CB | 4.328 | 25C36 | 163N | 4.364 |
| 25C36 | 26CB | 4.411 | 25C36 | 68CE | 4.444 | 25C36 | 209CD2 | 4.518 |
| 25C36 | 66C | 4.580 | 25C36 | 67CA | 4.718 | 25C36 | 162C | 4.845 |
| 25C36 | 26CX | 4.975 | 25C37 | 66O | 3.900 | 25C37 | 67CE1 | 4.120 |
| 25C37 | 209CD2 | 4.133 | 25C37 | 67CZ | 4.304 | 25C37 | 67CD1 | 4.472 |
| 25C37 | 67OH | 4.559 | 25C37 | 160O | 4.722 | 25C37 | 67CE2 | 4.812 |
| 25C37 | 134CB | 4.928 | 25C37 | 67CG | 4.960 | 25C38 | 65CA | 3.685 |
| 25C38 | 25SG | 3.703 | 25C38 | 66N | 3.862 | 25C38 | 66O | 4.169 |
| 25C38 | 26CD1 | 4.241 | 25C38 | 65C | 4.328 | 25C38 | 23O | 4.331 |
| 25C38 | 161O | 4.500 | 25C38 | 22OH2 | 4.706 | 25C38 | 26CB | 4.746 |

TABLE XXII-continued

Table of distances in Ångstroms between atoms of the inhibitor and protein for all protein atoms within 5 Ångstroms of the inhibitor 2,2'-N,N'-bis-benzyloxycarbonyl-L-leucinylcarbohydrazide.

| Atom 1 | Atom 2 | Dist. | Atom 1 | Atom 2 | Dist. | Atom 1 | Atom 2 | Dist. |
|---|---|---|---|---|---|---|---|---|
| 25C38 | 65N | 4.855 | 25C38 | 26CG | 4.876 | 25O39 | 66N | 2.954 |
| 25O39 | 26CD1 | 3.044 | 25O39 | 65CA | 3.072 | 25O39 | 65C | 3.468 |
| 25O39 | 66O | 3.555 | 25O39 | 23O | 3.635 | 25O39 | 26CG | 3.715 |
| 25O39 | 26CB | 3.796 | 25O39 | 25SG | 3.860 | 25O39 | 26NE1 | 4.093 |
| 25O39 | 66CA | 4.102 | 25O39 | 66C | 4.239 | 25O39 | 65N | 4.292 |
| 25O39 | 26N | 4.359 | 25O39 | 65O | 4.668 | 25O39 | 23C | 4.669 |
| 25O39 | 26CX | 4.689 | 25O39 | 224OH2 | 4.850 | 25O39 | 26CD2 | 4.970 |
| 25N40 | 25SG | 3.113 | 25N40 | 161O | 3.678 | 25N40 | 224OH2 | 4.045 |
| 25N40 | 23O | 4.202 | 25N40 | 65CA | 4.334 | 25N40 | 161C | 4.525 |
| 25N40 | 23C | 4.779 | 25N40 | 23CA | 4.821 | 25N40 | 162CA | 4.878 |
| 25N40 | 25CB | 4.902 | 25N40 | 26CD1 | 4.925 | 25N41 | 25SG | 2.621 |
| 25N41 | 23O | 3.122 | 25N41 | 224OH2 | 3.404 | 25N41 | 23C | 3.447 |
| 25N41 | 23CA | 3.458 | 25N41 | 25CB | 4.118 | 25N41 | 25N | 4.161 |
| 25N41 | 24N | 4.403 | 25N41 | 65CA | 4.453 | 25N41 | 161O | 4.531 |
| 25N41 | 26CD1 | 4.572 | 25N41 | 25CA | 4.709 | 25N41 | 26N | 4.861 |
| 25N41 | 23N | 4.898 | 25N42 | 66O | 3.140 | 25N42 | 66N | 3.340 |
| 25N42 | 65CA | 3.978 | 25N42 | 66C | 4.005 | 25N42 | 65C | 4.084 |
| 25N42 | 66CA | 4.168 | 25N42 | 67CE2 | 4.883 | | | |

TABLE XXIII

Table of distances in Ångstroms between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Dist. | Atom 1 | Atom 2 | Dist. | Atom 1 | Atom 2 | Dist. |
|---|---|---|---|---|---|---|---|---|
| 25C1 | 184CB | 4.236 | 25C1 | 184CG | 4.418 | 25C1 | 184O | 4.425 |
| 25C1 | 184CD2 | 4.593 | 25C1 | 184CE3 | 4.660 | 25C1 | 188CD1 | 4.721 |
| 25C2 | 184O | 3.268 | 25C2 | 184CB | 3.689 | 25C2 | 184C | 4.080 |
| 25C2 | 184CG | 4.182 | 25C2 | 184CA | 4.182 | 25C2 | 184CD2 | 4.784 |
| 25C2 | 184CD1 | 4.821 | 25C2 | 18ND2 | 4.999 | 25C3 | 184O | 3.481 |
| 25C3 | 184CB | 3.729 | 25C3 | 184CA | 3.863 | 25C3 | 184C | 3.967 |
| 25C3 | 18OD1 | 4.001 | 25C3 | 184CG | 4.006 | 25C3 | 184CD1 | 4.249 |
| 25C3 | 18ND2 | 4.280 | 25C3 | 18CG | 4.516 | 25C3 | 184CD2 | 4.834 |
| 25C4 | 184CD1 | 4.005 | 25C4 | 184CG | 4.080 | 25C4 | 184CB | 4.302 |
| 25C4 | 18OD1 | 4.440 | 25C4 | 20O | 4.528 | 25C4 | 184CA | 4.558 |
| 25C4 | 184NE1 | 4.584 | 25C4 | 184CD2 | 4.705 | 25C4 | 184O | 4.729 |
| 25C4 | 184CE2 | 4.985 | 25C5 | 184CG | 4.312 | 25C5 | 184CD1 | 4.376 |
| 25C5 | 184CD2 | 4.504 | 25C5 | 184NE1 | 4.612 | 25C5 | 184CE2 | 4.694 |
| 25C5 | 184CB | 4.766 | 25C5 | 21NE2 | 4.820 | 25C6 | 184CD2 | 4.450 |
| 25C6 | 184CG | 4.480 | 25C6 | 184CE3 | 4.643 | 25C6 | 184CB | 4.744 |
| 25C6 | 143OE1 | 4.804 | 25C6 | 184CE2 | 4.925 | 25C6 | 184CD1 | 4.935 |
| 25C7 | 20O | 3.040 | 25C7 | 20C | 3.594 | 25C7 | 20CA | 3.795 |
| 25C7 | 20N | 3.853 | 25C7 | 18OD1 | 3.864 | 25C7 | 184CD1 | 4.135 |
| 25C7 | 19CG | 4.463 | 25C7 | 21NE2 | 4.595 | 25C7 | 21N | 4.617 |
| 25C7 | 184NE1 | 4.641 | 25C7 | 184CG | 4.659 | 25C7 | 18CG | 4.887 |
| 25C7 | 19C | 4.937 | 25C7 | 184CA | 4.958 | 25O8 | 20O | 2.667 |
| 25O8 | 19CG | 3.422 | 25O8 | 184CD1 | 3.450 | 25O8 | 20C | 3.631 |
| 25O8 | 184NE1 | 3.675 | 25O8 | 20N | 3.871 | 25O8 | 19CD | 3.993 |
| 25O8 | 20CA | 4.102 | 25O8 | 19OE1 | 4.232 | 25O8 | 184CG | 4.325 |
| 25O8 | 18OD1 | 4.411 | 25O8 | 184CE2 | 4.622 | 25O8 | 19C | 4.642 |
| 25O8 | 21N | 4.725 | 25O8 | 19CB | 4.727 | 25O8 | 19NE2 | 4.771 |
| 25O8 | 18O | 4.826 | 25O8 | 184CD2 | 4.974 | 25C9 | 20O | 3.188 |
| 25C9 | 184NE1 | 3.536 | 25C9 | 184CD1 | 3.844 | 25C9 | 19CG | 4.035 |
| 25C9 | 19CD | 4.106 | 25C9 | 19OE1 | 4.229 | 25C9 | 20C | 4.321 |
| 25C9 | 184CE2 | 4.325 | 25C9 | 19NE2 | 4.650 | 25C9 | 184CG | 4.743 |
| 25C9 | 184CZ2 | 4.957 | 25C9 | 21NE2 | 4.999 | 25O10 | 184NE1 | 3.675 |
| 25O10 | 184CE2 | 4.068 | 25O10 | 184CD1 | 4.137 | 25O10 | 20O | 4.244 |
| 25O10 | 184CZ2 | 4.481 | 25O10 | 184CD2 | 4.713 | 25O10 | 184CG | 4.754 |
| 25O10 | 21NE2 | 4.824 | 25C11 | 19NE2 | 4.159 | 25C11 | 22O | 4.229 |
| 25C11 | 19CD | 4.273 | 25C11 | 20O | 4.296 | 25C11 | 19OE1 | 4.447 |
| 25C11 | 184NE1 | 4.589 | 25C11 | 22C | 4.735 | 25C11 | 23CA | 4.867 |
| 25C11 | 19CG | 4.868 | 25C11 | 22N | 4.974 | 25C11 | 23N | 4.979 |
| 25C12 | 22O | 3.890 | 25C12 | 22C | 3.995 | 25C12 | 22N | 4.110 |
| 25C12 | 23N | 4.111 | 25C12 | 23CA | 4.306 | 25C12 | 20O | 4.346 |
| 25C12 | 21C | 4.588 | 25C12 | 22CA | 4.594 | 25C12 | 21OE1 | 4.629 |
| 25C12 | 21CA | 4.715 | 25C12 | 19NE2 | 4.762 | 25C13 | 21OE1 | 3.498 |

TABLE XXIII-continued

Table of distances in Ångstroms between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Dist. | Atom 1 | Atom 2 | Dist. | Atom 1 | Atom 2 | Dist. |
|---|---|---|---|---|---|---|---|---|
| 25C13 | 21CD | 4.390 | 25C13 | 21CA | 4.587 | 25C13 | 22N | 4.615 |
| 25C13 | 21C | 4.659 | 25C13 | 20O | 4.898 | 25C13 | 21NE2 | 4.928 |
| 25C14 | 21OE1 | 2.922 | 25C14 | 21C | 3.654 | 25C14 | 21CA | 3.785 |
| 25C14 | 22N | 3.919 | 25C14 | 21CD | 3.931 | 25C14 | 21O | 3.962 |
| 25C14 | 21CB | 4.117 | 25C14 | 22CA | 4.561 | 25C14 | 21CG | 4.659 |
| 25C14 | 22C | 4.749 | 25C14 | 21NE2 | 4.841 | 25C14 | 23N | 4.886 |
| 25C14 | 20O | 4.941 | 25C15 | 21OE1 | 2.917 | 25C15 | 21CD | 3.612 |
| 25C15 | 21NE2 | 3.794 | 25C15 | 21CA | 4.698 | 25C15 | 20O | 4.791 |
| 25C15 | 21CG | 4.892 | 25C16 | 19NE2 | 3.649 | 25C16 | 19OE1 | 3.851 |
| 25C16 | 19CD | 3.913 | 25C16 | 23CA | 4.390 | 25C16 | 184NE1 | 4.396 |
| 25C16 | 22O | 4.401 | 25C16 | 162ND1 | 4.744 | 25C16 | 19CG | 4.960 |
| 25C16 | 23N | 4.963 | 25C16 | 22C | 4.981 | 25C16 | 184CZ2 | 4.990 |
| 25S17 | 162ND1 | 3.565 | 25S17 | 184CZ2 | 3.585 | 25S17 | 184NE1 | 3.699 |
| 25S17 | 162CE1 | 3.945 | 25S17 | 19OE1 | 3.950 | 25S17 | 184CE2 | 3.994 |
| 25S17 | 162CG | 4.327 | 25S17 | 19CD | 4.502 | 25S17 | 19NE2 | 4.573 |
| 25S17 | 162CB | 4.756 | 25S17 | 184CH2 | 4.771 | 25S17 | 162NE2 | 4.811 |
| 25S17 | 184CD1 | 4.996 | 25N18 | 19NE2 | 3.269 | 25N18 | 23CA | 3.310 |
| 25N18 | 19CD | 3.941 | 25N18 | 22O | 3.976 | 25N18 | 19OE1 | 4.019 |
| 25N18 | 23C | 4.156 | 25N18 | 25SG | 4.177 | 25N18 | 23N | 4.187 |
| 25N18 | 22C | 4.455 | 25N18 | 25CB | 4.460 | 25N18 | 24N | 4.557 |
| 25N18 | 162ND1 | 4.710 | 25N18 | 25N | 4.758 | 25N18 | 23O | 4.840 |
| 25C19 | 25SG | 3.024 | 25C19 | 25CB | 3.565 | 25C19 | 19NE2 | 3.784 |
| 25C19 | 162ND1 | 3.801 | 25C19 | 23CA | 3.948 | 25C19 | 19OE1 | 4.215 |
| 25C19 | 16IO | 4.243 | 25C19 | 19CD | 4.411 | 25C19 | 25N | 4.416 |
| 25C19 | 23C | 4.434 | 25C19 | 162CE1 | 4.494 | 25C19 | 25CA | 4.626 |
| 25C19 | 23O | 4.822 | 25C19 | 162CG | 4.842 | 25C19 | 24N | 4.896 |
| 25C19 | 162CA | 4.932 | 25N20 | 20O | 3.090 | 25N20 | 19CD | 3.488 |
| 25N20 | 19NE2 | 3.690 | 25N20 | 19CG | 3.707 | 25N20 | 19OE1 | 3.805 |
| 25N20 | 22O | 3.918 | 25N20 | 184NE1 | 3.976 | 25N20 | 20C | 4.316 |
| 25N20 | 184CD1 | 4.488 | 25N20 | 22N | 4.551 | 25N20 | 22C | 4.673 |
| 25N20 | 21CA | 4.853 | 25N20 | 184CE2 | 4.906 | 25N20 | 19CB | 4.997 |
| 25C21 | 162ND1 | 2.861 | 25C21 | 25SG | 3.627 | 25C21 | 162CE1 | 3.661 |
| 25C21 | 162CG | 3.744 | 25C21 | 16IO | 3.811 | 25C21 | 25CB | 3.895 |
| 25C21 | 162CB | 3.972 | 25C21 | 19OE1 | 4.135 | 25C21 | 162CA | 4.169 |
| 25C21 | 19NE2 | 4.408 | 25C21 | 19CD | 4.664 | 25C21 | 162NE2 | 4.724 |
| 25C21 | 161C | 4.759 | 25C21 | 184CZ2 | 4.788 | 25C21 | 162CD2 | 4.789 |
| 25C21 | 184NE1 | 4.807 | 25C21 | 162N | 4.963 | 25C22 | 25SG | 1.806 |
| 25C22 | 25CB | 3.017 | 25C22 | 25N | 3.658 | 25C22 | 23CA | 3.756 |
| 25C22 | 23C | 3.777 | 25C22 | 23O | 3.783 | 25C22 | 25CA | 3.942 |
| 25C22 | 16IO | 4.202 | 25C22 | 19NE2 | 4.263 | 25C22 | 24N | 4.389 |
| 25C22 | 162ND1 | 4.411 | 25C22 | 26N | 4.767 | 25C22 | 24C | 4.797 |
| 25C22 | 25C | 4.896 | 25C22 | 162CA | 4.914 | 25C22 | 26CD1 | 4.985 |
| 25O23 | 25SG | 2.263 | 25O23 | 23C | 2.724 | 25O23 | 25N | 2.817 |
| 25O23 | 23CA | 2.863 | 25O23 | 23O | 2.953 | 25O23 | 25CB | 2.966 |
| 25O23 | 24N | 3.216 | 25O23 | 19NE2 | 3.371 | 25O23 | 25CA | 3.468 |
| 25O23 | 24C | 3.844 | 25O23 | 24CA | 4.001 | 25O23 | 23N | 4.229 |
| 25O23 | 22O | 4.346 | 25O23 | 19CD | 4.418 | 25O23 | 26N | 4.527 |
| 25O23 | 25C | 4.570 | 25O23 | 19OE1 | 4.594 | 25O23 | 26CD1 | 4.647 |
| 25O23 | 22C | 4.750 | 25O23 | 162ND1 | 4.926 | 25O23 | 24O | 4.984 |
| 25C24 | 64O | 4.232 | 25C24 | 61OD1 | 4.886 | 25C25 | 64O | 2.914 |
| 25C25 | 61OD1 | 4.012 | 25C25 | 64C | 4.121 | 25C25 | 65CA | 4.508 |
| 25C25 | 61CG | 4.803 | 25C25 | 65N | 4.812 | 25C26 | 64O | 3.004 |
| 25C26 | 61OD1 | 3.284 | 25C26 | 65CA | 3.778 | 25C26 | 65C | 4.006 |
| 25C26 | 64C | 4.052 | 25C26 | 66N | 4.292 | 25C26 | 61CG | 4.320 |
| 25C26 | 65N | 4.406 | 25C26 | 65O | 4.498 | 25C26 | 61CB | 4.929 |
| 25C27 | 61OD1 | 3.654 | 25C27 | 64O | 4.372 | 25C27 | 66N | 4.515 |
| 25C27 | 67CE2 | 4.579 | 25C27 | 65C | 4.592 | 25C27 | 65CA | 4.693 |
| 25C27 | 61CG | 4.839 | 25C27 | 67OH | 4.900 | 25C28 | 61OD1 | 4.602 |
| 25C28 | 67OH | 4.614 | 25C28 | 67CE2 | 4.849 | 25C30 | 67CE2 | 3.326 |
| 25C30 | 66N | 3.711 | 25C30 | 61OD1 | 3.817 | 25C30 | 66CA | 3.888 |
| 25C30 | 67CD2 | 3.908 | 25C30 | 67CZ | 4.039 | 25C30 | 65C | 4.143 |
| 25C30 | 67OH | 4.216 | 25C30 | 66C | 4.303 | 25C30 | 66O | 4.459 |
| 25C30 | 65O | 4.648 | 25C30 | 65CA | 4.662 | 25C30 | 67CG | 4.980 |
| 25O31 | 67CE2 | 2.958 | 25O31 | 67CZ | 3.233 | 25O31 | 67OH | 3.437 |
| 25O31 | 67CD2 | 3.606 | 25O31 | 66O | 3.722 | 25O31 | 66N | 3.758 |
| 25O31 | 66C | 3.942 | 25O31 | 66CA | 3.994 | 25O31 | 67CE1 | 4.053 |
| 25O31 | 67CG | 4.365 | 25O31 | 65C | 4.521 | 25O31 | 67CD1 | 4.543 |
| 25O31 | 67N | 4.754 | 25O31 | 65CA | 4.909 | 25C32 | 66O | 3.869 |
| 25C32 | 66N | 3.875 | 25C32 | 67CZ | 4.120 | 25C32 | 67OH | 4.127 |
| 25C32 | 67CE2 | 4.188 | 25C32 | 66C | 4.431 | 25C32 | 66CA | 4.512 |
| 25C32 | 65CA | 4.559 | 25C32 | 65C | 4.577 | 25C32 | 67CE1 | 4.683 |

TABLE XXIII-continued

Table of distances in Ångstroms between atoms of the inhibitor and protein for all protein atoms within 5 Ångstroms of the inhibitor (1S)-N-[2-[(1-benzyloxycarbonylamino)-3-methylbutyl]thiazol-4-ylcarbonyl]-N'-(N-benzyloxycarbonyl-L-leucinyl)hydrazide.

| Atom 1 | Atom 2 | Dist. | Atom 1 | Atom 2 | Dist. | Atom 1 | Atom 2 | Dist. |
|---|---|---|---|---|---|---|---|---|
| 25C32 | 67CD2 | 4.797 | 25O33 | 67OH | 4.349 | 25O33 | 67CZ | 4.706 |
| 25O33 | 66N | 4.896 | 25O33 | 67CE2 | 4.948 | 25O33 | 160O | 4.987 |
| 25C34 | 66O | 3.926 | 25C34 | 66N | 4.154 | 25C34 | 161O | 4.291 |
| 25C34 | 65CA | 4.393 | 25C34 | 161C | 4.680 | 25C34 | 25SG | 4.728 |
| 25C34 | 160O | 4.762 | 25C34 | 65C | 4.835 | 25C34 | 66C | 4.889 |
| 25C35 | 161O | 3.923 | 25C35 | 160C | 3.934 | 25C35 | 161C | 3.950 |
| 25C35 | 66O | 4.195 | 25C35 | 162N | 4.296 | 25C35 | 161CA | 4.330 |
| 25C35 | 163N | 4.545 | 25C35 | 160C | 4.652 | 25C35 | 25SG | 4.661 |
| 25C35 | 162CA | 4.717 | 25C35 | 161N | 4.821 | 25C35 | 162C | 4.844 |
| 25C36 | 66O | 3.516 | 25C36 | 163CB | 3.928 | 25C36 | 163N | 4.123 |
| 25C36 | 163CA | 4.451 | 25C36 | 134CB | 4.614 | 25C36 | 162C | 4.695 |
| 25C36 | 66C | 4.739 | 25C36 | 25SG | 4.777 | 25C36 | 160O | 4.790 |
| 25C36 | 68SD | 4.793 | 25C36 | 162N | 4.890 | 25C36 | 161C | 4.930 |
| 25C36 | 26CB | 4.984 | 25C37 | 66O | 3.229 | 25C37 | 67CD1 | 3.782 |
| 25C37 | 67CE1 | 3.814 | 25C37 | 209CD2 | 4.109 | 25C37 | 66C | 4.351 |
| 25C37 | 134CB | 4.449 | 25C37 | 67CG | 4.461 | 25C37 | 67CZ | 4.520 |
| 25C37 | 67CA | 4.594 | 25C37 | 68SD | 4.609 | 25C37 | 163CB | 4.822 |
| 25C37 | 68CE | 4.913 | 25C37 | 67N | 4.944 | 25C37 | 160O | 4.999 |
| 25C38 | 66O | 2.883 | 25C38 | 163CB | 3.258 | 25C38 | 26CB | 3.517 |
| 25C38 | 25SG | 3.915 | 25C38 | 163N | 4.010 | 25C38 | 66C | 4.045 |
| 25C38 | 26CA | 4.069 | 25C38 | 26N | 4.161 | 25C38 | 163CA | 4.178 |
| 25C38 | 68SD | 4.184 | 25C38 | 26CG | 4.396 | 25C38 | 26CD1 | 4.512 |
| 25C38 | 66N | 4.558 | 25C38 | 61CA | 4.916 | 25C38 | 67N | 4.916 |
| 25C38 | 66CA | 4.920 | 25C38 | 162C | 4.937 | 25C39 | 65CA | 3.532 |
| 25C39 | 25SG | 3.557 | 25C39 | 66N | 3.788 | 25C39 | 66O | 4.161 |
| 25C39 | 161O | 4.207 | 25C39 | 65C | 4.218 | 25C39 | 26CD1 | 4.481 |
| 25C39 | 65N | 4.664 | 25C39 | 161C | 4.925 | 25C39 | 23O | 4.951 |
| 25C39 | 66CA | 4.972 | 25O40 | 66N | 2.864 | 25O40 | 65CA | 2.895 |
| 25O40 | 26CD1 | 3.289 | 25O40 | 65C | 3.326 | 25O40 | 25SG | 3.487 |
| 25O40 | 66O | 3.497 | 25O40 | 66CA | 4.034 | 25O40 | 26CG | 4.074 |
| 25O40 | 65N | 4.098 | 25O40 | 26NE1 | 4.177 | 25O40 | 66C | 4.186 |
| 25O40 | 23O | 4.205 | 25O40 | 26CB | 4.291 | 25O40 | 65O | 4.516 |
| 25O40 | 26N | 4.644 | 25N41 | 25SG | 3.236 | 25N41 | 161O | 3.370 |
| 25N41 | 65CA | 4.079 | 25N41 | 161C | 4.343 | 25N41 | 23O | 4.777 |
| 25N41 | 65N | 4.879 | 25N41 | 66N | 4.926 | 25N42 | 25SG | 2.820 |
| 25N42 | 23O | 3.597 | 25N42 | 23CA | 3.792 | 25N42 | 23C | 3.925 |
| 25N42 | 65CA | 4.086 | 25N42 | 161O | 4.156 | 25N42 | 25CB | 4.397 |
| 25N42 | 65N | 4.514 | 25N42 | 25N | 4.705 | 25N42 | 26CD1 | 4.802 |
| 25N42 | 24N | 4.905 | 25N43 | 66O | 3.027 | 25N43 | 66N | 3.312 |
| 25N43 | 66C | 3.828 | 25N43 | 66CA | 4.057 | 25N43 | 65CA | 4.128 |
| 25N43 | 65C | 4.171 | 25N43 | 67CZ | 4.741 | 25N43 | 67CE2 | 4.807 |
| 25N43 | 67CE1 | 4.973 | 25N43 | 67N | 4.980 | | | |

TABLE XXIV

Table of distances in Ångstroms between atoms of the inhibitor and protein for all protein atoms within 5 Ångstroms of the inhibitor 2-[N-(3-benzyloxybenzoyl)]-2'-[N'-(N-benzyloxycarbonyl-L-leucinyl)]carbohydrazide.

| Atom 1 | Atom 2 | Dist. | Atom 1 | Atom 2 | Dist. | Atom 1 | Atom 2 | Dist. |
|---|---|---|---|---|---|---|---|---|
| 25C1 | 241OH2 | 3.570 | 25C1 | 184CD1 | 3.752 | 25C1 | 184CB | 3.771 |
| 25C1 | 184CG | 3.795 | 25C1 | 184O | 3.855 | 25C1 | 18OD1 | 3.918 |
| 25C1 | 184CA | 3.940 | 25C1 | 18ND2 | 4.077 | 25C1 | 184C | 4.295 |
| 25C1 | 18CG | 4.335 | 25C1 | 20O | 4.526 | 25C1 | 184NE1 | 4.545 |
| 25C1 | 184CD2 | 4.638 | 25C2 | 18OD1 | 2.991 | 25C2 | 184CD1 | 3.364 |
| 25C2 | 184CA | 3.673 | 25C2 | 20O | 3.682 | 25C2 | 18CG | 3.691 |
| 25C2 | 184CG | 3.828 | 25C2 | 20N | 3.856 | 25C2 | 18ND2 | 3.872 |
| 25C2 | 184CB | 3.927 | 25C2 | 184O | 4.146 | 25C2 | 19CG | 4.202 |
| 25C2 | 184C | 4.236 | 25C2 | 184NE1 | 4.236 | 25C2 | 183O | 4.241 |
| 25C2 | 20CA | 4.325 | 25C2 | 20C | 4.444 | 25C2 | 19N | 4.506 |
| 25C2 | 184N | 4.779 | 25C2 | 241OH2 | 4.781 | 25C2 | 19C | 4.859 |
| 25C2 | 184CD2 | 4.882 | 25C2 | 183C | 4.942 | 25C2 | 18CB | 4.966 |
| 25C3 | 20O | 2.766 | 25C3 | 184CD1 | 3.449 | 25C3 | 19CG | 3.485 |
| 25C3 | 20N | 3.566 | 25C3 | 18OD1 | 3.700 | 25C3 | 20C | 3.715 |
| 25C3 | 184NE1 | 3.945 | 25C3 | 20CA | 3.980 | 25C3 | 19CD | 4.274 |
| 25C3 | 184CG | 4.298 | 25C3 | 19C | 4.413 | 25C3 | 183O | 4.573 |

TABLE XXIV-continued

Table of distances in Ångstroms between atoms of the inhibitor and protein for all protein atoms within 5 Ångstroms of the inhibitor 2-[N-(3-benzyloxybenzoyl)]-2'-[N'-(N-benzyloxycarbonyl-L-leucinyl)]carbohydrazide.

| Atom 1 | Atom 2 | Dist. | Atom 1 | Atom 2 | Dist. | Atom 1 | Atom 2 | Dist. |
|---|---|---|---|---|---|---|---|---|
| 25C3 | 19N | 4.586 | 25C3 | 184CA | 4.627 | 25C3 | 19CB | 4.636 |
| 25C3 | 18CG | 4.663 | 25C3 | 19CA | 4.734 | 25C3 | 19NE2 | 4.739 |
| 25C3 | 184CB | 4.805 | 25C3 | 19OE1 | 4.890 | 25C3 | 21N | 4.941 |
| 25C3 | 184CE2 | 4.965 | 25C4 | 20O | 2.926 | 25C4 | 184CD1 | 3.912 |
| 25C4 | 184NE1 | 3.991 | 25C4 | 20C | 4.103 | 25C4 | 19CG | 4.382 |
| 25C4 | 20N | 4.662 | 25C4 | 184CG | 4.708 | 25C4 | 20CA | 4.787 |
| 25C4 | 19CD | 4.799 | 25C4 | 184CE2 | 4.822 | 25C4 | 18OD1 | 4.987 |
| 25C4 | 241OH2 | 4.989 | 25C4 | 19NE2 | 4.989 | 25C5 | 241OH2 | 3.832 |
| 25C5 | 20O | 3.929 | 25C5 | 184CD1 | 4.241 | 25C5 | 184NE1 | 4.312 |
| 25C5 | 184CG | 4.671 | 25C5 | 184CE2 | 4.778 | 25C5 | 184CD2 | 4.987 |
| 25C6 | 241OH2 | 2.940 | 25C6 | 184CD1 | 4.176 | 25C6 | 184CG | 4.243 |
| 25C6 | 184CB | 4.555 | 25C6 | 184NE1 | 4.583 | 25C6 | 20O | 4.631 |
| 25C6 | 184CD2 | 4.694 | 25C6 | 184CE2 | 4.889 | 25C7 | 20O | 2.932 |
| 25C7 | 20C | 4.097 | 25C7 | 19NE2 | 4.319 | 25C7 | 19CG | 4.452 |
| 25C7 | 184NE1 | 4.478 | 25C7 | 19CD | 4.533 | 25C7 | 21CA | 4.627 |
| 25C7 | 22O | 4.737 | 25C7 | 184CD1 | 4.756 | 25C7 | 21N | 4.840 |
| 25C7 | 21C | 4.925 | 25O8 | 19NE2 | 3.416 | 25O8 | 19CD | 3.782 |
| 25O8 | 184NE1 | 3.951 | 25O8 | 20O | 4.046 | 25O8 | 19CG | 4.180 |
| 25O8 | 19OE1 | 4.351 | 25O8 | 22O | 4.445 | 25O8 | 184CD1 | 4.559 |
| 25O8 | 184CE2 | 4.877 | 25C9 | 19NE2 | 4.211 | 25C9 | 184NE1 | 4.403 |
| 25C9 | 19CD | 4.724 | 25C11 | 162ND1 | 4.502 | 25C11 | 184CZ2 | 4.687 |
| 25C11 | 162CE1 | 4.868 | 25C14 | 162ND1 | 3.357 | 25C14 | 162CG | 3.831 |
| 25C14 | 162CB | 4.001 | 25C14 | 162CE1 | 4.036 | 25C14 | 162CA | 4.368 |
| 25C14 | 161O | 4.489 | 25C14 | 184CZ2 | 4.614 | 25C14 | 162CD2 | 4.682 |
| 25C14 | 161OD1 | 4.720 | 25C14 | 162N | 4.758 | 25C14 | 162NE2 | 4.766 |
| 25C14 | 161C | 4.794 | 25C14 | 25SG | 4.940 | 25O15 | 162CB | 3.130 |
| 25O15 | 162ND1 | 3.165 | 25O15 | 162CG | 3.174 | 25O15 | 161OD1 | 3.790 |
| 25O15 | 162CA | 3.794 | 25O15 | 162CE1 | 3.969 | 25O15 | 162CD2 | 4.004 |
| 25O15 | 162N | 4.125 | 25O15 | 184CZ2 | 4.191 | 25O15 | 162NE2 | 4.407 |
| 25O15 | 161C | 4.425 | 25O15 | 161O | 4.436 | 25O15 | 137CB | 4.597 |
| 25O15 | 161CG | 4.704 | 25O15 | 137O | 4.758 | 25O15 | 161CB | 4.862 |
| 25O15 | 184CH2 | 4.953 | 25N16 | 162ND1 | 3.293 | 25N16 | 25SG | 3.828 |
| 25N16 | 161O | 3.898 | 25N16 | 162CE1 | 4.030 | 25N16 | 162CG | 4.119 |
| 25N16 | 162CA | 4.252 | 25N16 | 162CB | 4.323 | 25N16 | 161C | 4.537 |
| 25N16 | 25CB | 4.583 | 25N16 | 162N | 4.723 | 25N16 | 19NE2 | 4.776 |
| 25N17 | 25SG | 2.713 | 25N17 | 161O | 2.829 | 25N17 | 162ND1 | 2.962 |
| 25N17 | 162CA | 3.321 | 25N17 | 161C | 3.640 | 25N17 | 162CG | 3.800 |
| 25N17 | 162CB | 3.840 | 25N17 | 162N | 3.876 | 25N17 | 25CB | 3.878 |
| 25N17 | 162CE1 | 3.946 | 25N17 | 163N | 4.346 | 25N17 | 162C | 4.395 |
| 25N17 | 161CA | 4.922 | 25N17 | 162CD2 | 4.988 | 25C18 | 184NE1 | 4.080 |
| 25C18 | 19NE2 | 4.103 | 25C18 | 184CZ2 | 4.414 | 25C18 | 162ND1 | 4.448 |
| 25C18 | 162CE1 | 4.452 | 25C18 | 19CD | 4.549 | 25C18 | 19OE1 | 4.597 |
| 25C18 | 184CE2 | 4.604 | 25C19 | 25SG | 1.793 | 25C19 | 25CB | 3.071 |
| 25C19 | 161O | 3.652 | 25C19 | 162ND1 | 3.659 | 25C19 | 25N | 4.072 |
| 25C19 | 25CA | 4.137 | 25C19 | 23O | 4.303 | 25C19 | 162CE1 | 4.350 |
| 25C19 | 162CA | 4.352 | 25C19 | 19NE2 | 4.435 | 25C19 | 23C | 4.511 |
| 25C19 | 163N | 4.621 | 25C19 | 23CA | 4.646 | 25C19 | 161C | 4.687 |
| 25C19 | 162CG | 4.766 | 25C19 | 19OE1 | 4.843 | 25C19 | 25C | 4.879 |
| 25C19 | 26N | 4.949 | 25O20 | 25SG | 2.529 | 25O20 | 25CB | 3.171 |
| 25O20 | 19NE2 | 3.371 | 25O20 | 23CA | 3.588 | 25O20 | 23C | 3.681 |
| 25O20 | 25N | 3.725 | 25O20 | 23O | 3.770 | 25O20 | 162ND1 | 4.071 |
| 25O20 | 25CA | 4.076 | 25O20 | 19OE1 | 4.231 | 25O20 | 19CD | 4.248 |
| 25O20 | 24N | 4.306 | 25O20 | 162CE1 | 4.450 | 25O20 | 161O | 4.781 |
| 25O20 | 24C | 4.875 | 25O20 | 23N | 4.969 | 25C21 | 160CD1 | 3.590 |
| 25C21 | 158O | 3.615 | 25C21 | 160CG | 3.707 | 25C21 | 160CB | 3.983 |
| 25C21 | 160N | 4.442 | 25C21 | 158C | 4.580 | 25C21 | 160CA | 4.835 |
| 25C22 | 160CD1 | 3.593 | 25C22 | 160CG | 4.157 | 25C22 | 160CB | 4.282 |
| 25C22 | 209CD2 | 4.511 | 25C22 | 209CD1 | 4.980 | 25C22 | 158O | 4.986 |
| 25C23 | 160CD1 | 4.157 | 25C23 | 209CD2 | 4.159 | 25C23 | 67CE1 | 4.205 |
| 25C23 | 160CB | 4.279 | 25C23 | 160O | 4.519 | 25C23 | 67OH | 4.588 |
| 25C23 | 160CG | 4.625 | 25C23 | 67CZ | 4.894 | 25C24 | 160O | 3.474 |
| 25C24 | 160CB | 3.993 | 25C24 | 160C | 4.419 | 25C24 | 160CA | 4.596 |
| 25C24 | 160N | 4.617 | 25C24 | 160CD1 | 4.665 | 25C24 | 160CG | 4.704 |
| 25C24 | 67CE1 | 4.808 | 25C24 | 67OH | 4.862 | 25C25 | 160O | 3.271 |
| 25C25 | 160N | 3.593 | 25C25 | 160CB | 3.664 | 25C25 | 158O | 3.952 |
| 25C25 | 160CA | 3.958 | 25C25 | 160C | 3.985 | 25C25 | 160CG | 4.302 |
| 25C25 | 160CD1 | 4.653 | 25C25 | 159C | 4.710 | 25C25 | 159CA | 4.972 |
| 25C25 | 158C | 4.995 | 25C26 | 158O | 2.899 | 25C26 | 160N | 3.477 |
| 25C26 | 160CB | 3.661 | 25C26 | 160CG | 3.791 | 25C26 | 158C | 3.973 |
| 25C26 | 160CA | 4.096 | 25C26 | 160CD1 | 4.159 | 25C26 | 160O | 4.202 |
| 25C26 | 159C | 4.497 | 25C26 | 159CA | 4.565 | 25C26 | 160C | 4.606 |
| 25C26 | 159N | 4.714 | 25C26 | 158CA | 4.955 | 25C27 | 160O | 3.338 |

TABLE XXIV-continued

Table of distances in Ångstroms between atoms of the inhibitor and protein for all protein atoms within 5 Ångstroms of the inhibitor 2-[N-(3-benzyloxybenzoyl)]-2'-[N'-(N-benzyloxycarbonyl-L-leucinyl)]carbohydrazide.

| Atom 1 | Atom 2 | Dist. | Atom 1 | Atom 2 | Dist. | Atom 1 | Atom 2 | Dist. |
|---|---|---|---|---|---|---|---|---|
| 25C27 | 67OH | 4.363 | 25C27 | 67CE1 | 4.376 | 25C27 | 160C | 4.512 |
| 25C27 | 67CZ | 4.684 | 25C27 | 160CB | 4.754 | 25O28 | 160O | 2.420 |
| 25O28 | 160C | 3.644 | 25O28 | 161CA | 4.394 | 25O28 | 160CB | 4.473 |
| 25O28 | 161N | 4.476 | 25O28 | 160CA | 4.624 | 25O28 | 161O | 4.916 |
| 25O28 | 161C | 4.988 | 25C29 | 160O | 3.266 | 25C29 | 160C | 4.372 |
| 25C29 | 161O | 4.438 | 25C29 | 161CA | 4.632 | 25C29 | 161C | 4.791 |
| 25C29 | 66O | 4.888 | 25C29 | 67CE1 | 4.893 | 25C29 | 161N | 4.959 |
| 25O30 | 67CE1 | 3.985 | 25O30 | 66O | 4.035 | 25O30 | 67CD1 | 4.256 |
| 25O30 | 67CZ | 4.313 | 25O30 | 160O | 4.446 | 25O30 | 66C | 4.682 |
| 25O30 | 67OH | 4.687 | 25O30 | 67CG | 4.823 | 25O30 | 67CE2 | 4.858 |
| 25C31 | 161O | 3.206 | 25C31 | 161C | 3.941 | 25C31 | 66O | 3.994 |
| 25C31 | 163CB | 4.458 | 25C31 | 163N | 4.486 | 25C31 | 25SG | 4.527 |
| 25C31 | 160O | 4.531 | 25C31 | 161CA | 4.598 | 25C31 | 162N | 4.697 |
| 25C31 | 162C | 4.753 | 25C31 | 162CA | 4.857 | 25C32 | 66O | 2.742 |
| 25C32 | 66C | 3.901 | 25C32 | 163CB | 4.205 | 25C32 | 26CB | 4.317 |
| 25C32 | 66N | 4.512 | 25C32 | 67CA | 4.651 | 25C32 | 161O | 4.691 |
| 25C32 | 67N | 4.724 | 25C32 | 68SD | 4.771 | 25C32 | 66CA | 4.830 |
| 25C33 | 66O | 3.447 | 25C33 | 68SD | 3.722 | 25C33 | 163CB | 3.798 |
| 25C33 | 209CD2 | 4.102 | 25C33 | 68CE | 4.212 | 25C33 | 134CB | 4.330 |
| 25C33 | 67CA | 4.465 | 25C33 | 66C | 4.538 | 25C33 | 67CD1 | 4.678 |
| 25C33 | 163CA | 4.689 | 25C33 | 26CB | 4.751 | 25C33 | 163N | 4.950 |
| 25C34 | 134CB | 3.099 | 25C34 | 163CB | 3.583 | 25C34 | 209CD2 | 3.879 |
| 25C34 | 134CA | 3.973 | 25C34 | 163CA | 3.984 | 25C34 | 163N | 4.154 |
| 25C34 | 68SD | 4.317 | 25C34 | 162O | 4.344 | 25C34 | 162C | 4.346 |
| 25C34 | 68CE | 4.364 | 25C34 | 160O | 4.704 | 25C34 | 161O | 4.819 |
| 25C34 | 66O | 4.910 | 25C34 | 161C | 4.924 | 25C34 | 133O | 4.972 |
| 25C34 | 134C | 4.977 | 25C34 | 134N | 4.991 | 25C35 | 209CD2 | 3.174 |
| 25C35 | 67CD1 | 3.240 | 25C35 | 66O | 3.588 | 25C35 | 67CA | 3.813 |
| 25C35 | 67CE1 | 3.871 | 25C35 | 67CG | 3.924 | 25C35 | 67CB | 4.168 |
| 25C35 | 68SD | 4.179 | 25C35 | 209CG | 4.360 | 25C35 | 68CE | 4.389 |
| 25C35 | 66C | 4.393 | 25C35 | 234OH2 | 4.424 | 25C35 | 67N | 4.535 |
| 25C35 | 134CB | 4.642 | 25C35 | 68N | 4.661 | 25C35 | 67C | 4.803 |
| 25C35 | 67CZ | 4.930 | 25C35 | 67CD2 | 4.976 | 25C36 | 161O | 3.232 |
| 25C36 | 25SG | 3.829 | 25C36 | 66O | 4.065 | 25C36 | 161C | 4.303 |
| 25C36 | 66N | 4.338 | 25C36 | 65CA | 4.529 | 25C36 | 26CD1 | 4.948 |
| 25C36 | 163N | 4.963 | 25C36 | 26CB | 5.000 | 25O37 | 66N | 3.256 |
| 25O37 | 65CA | 3.411 | 25O37 | 66O | 3.590 | 25O37 | 65C | 3.845 |
| 25O37 | 161O | 4.314 | 25O37 | 66CA | 4.368 | 25O37 | 66C | 4.383 |
| 25O37 | 26CD1 | 4.400 | 25O37 | 25SG | 4.578 | 25O37 | 65N | 4.736 |
| 25O37 | 64O | 4.804 | 25O37 | 26CB | 4.911 | 25O37 | 26CG | 4.987 |
| 25N38 | 161O | 2.583 | 25N38 | 25SG | 2.797 | 25N38 | 161C | 3.765 |
| 25N38 | 162CA | 4.301 | 25N38 | 163N | 4.348 | 25N38 | 162N | 4.497 |
| 25N38 | 25CB | 4.579 | 25N38 | 162C | 4.720 | 25N38 | 161CA | 4.814 |
| 25N38 | 163CB | 4.921 | 25N39 | 25SG | 2.623 | 25N39 | 161O | 3.421 |
| 25N39 | 23O | 3.947 | 25N39 | 25CB | 4.194 | 25N39 | 23C | 4.527 |
| 25N39 | 161C | 4.625 | 25N39 | 65CA | 4.670 | 25N39 | 25N | 4.673 |
| 25N39 | 23CA | 4.780 | 25N39 | 25CA | 4.961 | 25N39 | 162CA | 4.964 |
| 25N40 | 160O | 3.177 | 25N40 | 161O | 3.216 | 25N40 | 161C | 3.641 |
| 25N40 | 161CA | 3.804 | 25N40 | 16OC | 4.036 | 25N40 | 161N | 4.304 |
| 25N40 | 162N | 4.578 | 25N40 | 66O | 4.918 | | | |

TABLE XXV

Table of distances in Ångstroms between atoms of the inhibitor and protein for all protein atoms within 5 Ångstroms of the inhibitor 4-[N-[(phenylmethoxy)carbonyl)-L-leucyl]-1-[N-[(phenylmethoxy)carbonyl]-L-leucyl]-3-pyrrolidinone.

| Atom 1 | Atom 2 | Dist. | Atom 1 | Atom 2 | Dist. | Atom 1 | Atom 2 | Dist. |
|---|---|---|---|---|---|---|---|---|
| 25C1 | 184O | 4.017 | 25C1 | 184CD1 | 4.233 | 25C1 | 184CG | 4.294 |
| 25C1 | 184CB | 4.338 | 25C1 | 184CA | 4.431 | 25C1 | 18OD1 | 4.581 |
| 25C1 | 184C | 4.634 | 25C1 | 184NE1 | 4.872 | 25C1 | 184CD2 | 4.992 |
| 25C2 | 20O | 3.689 | 25C2 | 20C | 4.194 | 25C2 | 21NE2 | 4.254 |
| 25C2 | 184CD1 | 4.266 | 25C2 | 20N | 4.386 | 25C2 | 20CA | 4.394 |
| 25C2 | 19CG | 4.696 | 25C2 | 18OD1 | 4.707 | 25C2 | 184NE1 | 4.731 |
| 25C2 | 184CG | 4.742 | 25C2 | 184CA | 4.975 | 25C3 | 20O | 3.755 |
| 25C3 | 184CD1 | 4.039 | 25C3 | 184NE1 | 4.087 | 25C3 | 21NE2 | 4.111 |
| 25C3 | 20C | 4.569 | 25C3 | 19CG | 4.678 | 25C3 | 184CG | 4.714 |

TABLE XXV-continued

Table of distances in Ångstroms between atoms of the inhibitor and protein for all protein atoms within 5 Ångstroms of the inhibitor 4-[N-[(phenylmethoxy)carbonyl)-L-leucyl]-1-[N-[(phenylmethoxy)carbonyl]-L-leucyl)-3-pyrrolidinone.

| Atom 1 | Atom 2 | Dist. | Atom 1 | Atom 2 | Dist. | Atom 1 | Atom 2 | Dist. |
|---|---|---|---|---|---|---|---|---|
| 25C3 | 184CE2 | 4.790 | 25C3 | 19CD | 4.992 | 25C4 | 184NE1 | 3.514 |
| 25C4 | 184CD1 | 3.761 | 25C4 | 184CE2 | 3.871 | 25C4 | 184CG | 4.236 |
| 25C4 | 184CD2 | 4.302 | 25C4 | 184CZ2 | 4.446 | 25C4 | 21NE2 | 4.858 |
| 25C5 | 184CE2 | 3.679 | 25C5 | 184NE1 | 3.687 | 25C5 | 184CD2 | 3.688 |
| 25C5 | 184CD1 | 3.704 | 25C5 | 184CG | 3.711 | 25C5 | 184CZ2 | 4.317 |
| 25C5 | 184CE3 | 4.332 | 25C5 | 184CB | 4.417 | 25C5 | 184CH2 | 4.847 |
| 25C5 | 184CZ3 | 4.856 | 25C6 | 184CG | 3.747 | 25C6 | 184CD1 | 3.955 |
| 25C6 | 184CB | 3.964 | 25C6 | 184CD2 | 4.101 | 25C6 | 184O | 4.262 |
| 25C6 | 184NE1 | 4.395 | 25C6 | 184CE2 | 4.487 | 25C6 | 184CA | 4.531 |
| 25C6 | 184CE3 | 4.701 | 25C6 | 184C | 4.882 | 25C7 | 184NE1 | 3.584 |
| 25C7 | 184CE2 | 3.808 | 25C7 | 184CZ2 | 3.945 | 25C7 | 184CD1 | 4.327 |
| 25C7 | 184CD2 | 4.651 | 25C7 | 184CH2 | 4.855 | 25C7 | 184CG | 4.925 |
| 25O8 | 184NE1 | 3.393 | 25O8 | 184CE2 | 3.944 | 25O8 | 184CZ2 | 4.069 |
| 25O8 | 184CD1 | 4.312 | 25O8 | 19NE2 | 4.602 | 25O8 | 19CD | 4.825 |
| 25C9 | 184NE1 | 3.291 | 25C9 | 184CZ2 | 3.627 | 25C9 | 184CE2 | 3.765 |
| 25C9 | 162ND1 | 3.949 | 25C9 | 162CE1 | 4.256 | 25C9 | 184CD1 | 4.478 |
| 25C9 | 19NE2 | 4.492 | 25C9 | 19OE1 | 4.778 | 25C9 | 19CD | 4.791 |
| 25C9 | 184CH2 | 4.870 | 25O10 | 184NE1 | 2.688 | 25O10 | 162ND1 | 2.878 |
| 25O10 | 162CE1 | 3.073 | 25O10 | 184CE2 | 3.353 | 25O10 | 184CZ2 | 3.407 |
| 25O10 | 19OE1 | 3.804 | 25O10 | 184CD1 | 3.882 | 25O10 | 19NE2 | 3.911 |
| 25O10 | 19CD | 4.053 | 25O10 | 162CG | 4.083 | 25O10 | 162NE2 | 4.247 |
| 25O10 | 184CD2 | 4.680 | 25O10 | 184CH2 | 4.748 | 25O10 | 162CD2 | 4.767 |
| 25O10 | 162CB | 4.822 | 25O10 | 25CB | 4.894 | 25C10 | 184CG | 4.921 |
| 25O10 | 25SG | 4.959 | 25C11 | 161O | 3.603 | 25C11 | 162ND1 | 3.785 |
| 25C11 | 162CB | 4.170 | 25C11 | 162CG | 4.352 | 25C11 | 184CZ2 | 4.547 |
| 25C11 | 161C | 4.651 | 25C11 | 161OD1 | 4.678 | 25C11 | 162CE1 | 4.739 |
| 25C11 | 162CA | 4.759 | 25C12 | 161O | 3.598 | 25C12 | 161OD1 | 3.692 |
| 25C12 | 161CG | 4.426 | 25C12 | 161C | 4.497 | 25C12 | 162CB | 4.500 |
| 25C12 | 161CB | 4.644 | 25C12 | 162ND1 | 4.828 | 25C13 | 161OD1 | 3.668 |
| 25C13 | 137O | 3.927 | 25C13 | 137C | 4.080 | 25C13 | 138N | 4.272 |
| 25C13 | 184CZ2 | 4.318 | 25C13 | 138CA | 4.377 | 25C13 | 137CB | 4.500 |
| 25C13 | 143NE2 | 4.527 | 25C13 | 161CG | 4.603 | 25C13 | 161O | 4.651 |
| 25C13 | 184CH2 | 4.656 | 25C13 | 162CB | 4.732 | 25C13 | 137CA | 4.757 |
| 25C14 | 143NE2 | 3.452 | 25C14 | 184CZ2 | 4.059 | 25C14 | 137O | 4.191 |
| 25C14 | 184CH2 | 4.327 | 25C14 | 143CD | 4.676 | 25C14 | 137C | 4.726 |
| 25C14 | 138CA | 4.757 | 25C14 | 138N | 4.988 | 25C15 | 161OD1 | 3.025 |
| 25C15 | 138CA | 3.182 | 25C15 | 138N | 3.231 | 25C15 | 137C | 3.477 |
| 25C15 | 138CB | 3.598 | 25C15 | 137O | 3.616 | 25C15 | 161CG | 3.781 |
| 25C15 | 137CA | 4.362 | 25C15 | 161ND2 | 4.367 | 25C15 | 137N | 4.495 |
| 25C15 | 138C | 4.523 | 25C15 | 137CB | 4.599 | 25C15 | 143NE2 | 4.610 |
| 25C15 | 138OG | 4.662 | 25C15 | 161CB | 4.679 | 25C15 | 138O | 4.905 |
| 25C15 | 161O | 4.924 | 25C16 | 161O | 3.101 | 25C16 | 162ND1 | 4.231 |
| 25C16 | 161C | 4.310 | 25C16 | 162CB | 4.562 | 25C16 | 25SG | 4.612 |
| 25C16 | 162CA | 4.657 | 25C16 | 162CG | 4.876 | 25C16 | 162N | 4.992 |
| 25O17 | 161O | 3.437 | 25O17 | 161C | 4.661 | 25N18 | 161O | 3.143 |
| 25N18 | 25SG | 3.301 | 25N18 | 162ND1 | 3.608 | 25N18 | 162CA | 4.088 |
| 25N18 | 162CB | 4.239 | 25N18 | 161C | 4.252 | 25N18 | 162CG | 4.379 |
| 25N18 | 25CB | 4.462 | 25N18 | 162CE1 | 4.653 | 25N18 | 162N | 4.681 |
| 25N18 | 19NE2 | 4.948 | 25N18 | 23CA | 4.995 | 25C19 | 25SG | 2.850 |
| 25C19 | 161O | 3.592 | 25C19 | 23CA | 4.261 | 25C19 | 25CB | 4.284 |
| 25C19 | 162ND1 | 4.530 | 25C19 | 23C | 4.535 | 25C19 | 162CA | 4.545 |
| 25C19 | 161C | 4.613 | 25C19 | 23O | 4.725 | 25C19 | 25N | 4.814 |
| 25N20 | 184CZ2 | 4.159 | 25N20 | 162ND1 | 4.342 | 25N20 | 184NE1 | 4.452 |
| 25N20 | 184CE2 | 4.669 | 25N20 | 162CE1 | 4.970 | 25C21 | 161O | 3.074 |
| 25C21 | 25SG | 3.220 | 25C21 | 161C | 3.894 | 25C21 | 162CA | 4.288 |
| 25C21 | 162N | 4.439 | 25C21 | 65CA | 4.747 | 25C21 | 161CA | 4.860 |
| 25C21 | 25CB | 4.980 | 25C22 | 25SG | 1.762 | 25C22 | 25CB | 2.996 |
| 25C22 | 25N | 3.317 | 25C22 | 25CA | 3.720 | 25C22 | 23C | 3.769 |
| 25C22 | 23CA | 3.914 | 25C22 | 23O | 4.043 | 25C22 | 24N | 4.052 |
| 25C22 | 19NE2 | 4.196 | 25C22 | 24C | 4.394 | 25C22 | 162ND1 | 4.399 |
| 25C22 | 26N | 4.510 | 25C22 | 25C | 4.601 | 25C22 | 161O | 4.652 |
| 25C22 | 24CA | 4.697 | 25C22 | 162CA | 4.792 | 25C22 | 163N | 4.837 |
| 25C22 | 26CD1 | 4.881 | 25O23 | 25SG | 2.430 | 25O23 | 25N | 2.866 |
| 25O23 | 25CB | 2.896 | 25O23 | 19NE2 | 3.003 | 25O23 | 23CA | 3.259 |
| 25O23 | 23C | 3.263 | 25O23 | 24N | 3.328 | 25O23 | 25CA | 3.459 |
| 25O23 | 23O | 3.894 | 25O23 | 24C | 3.945 | 25O23 | 19CD | 4.004 |
| 25O23 | 19OE1 | 4.163 | 25O23 | 24CA | 4.166 | 25O23 | 22O | 4.360 |
| 25O23 | 162ND1 | 4.426 | 25O23 | 23N | 4.535 | 25O23 | 25C | 4.653 |
| 25O23 | 26N | 4.784 | 25O23 | 22C | 4.908 | 25O23 | 162CE1 | 4.912 |
| 25C24 | 59O | 3.356 | 25C24 | 61OD2 | 4.112 | 25C24 | 60CA | 4.139 |
| 25C24 | 61N | 4.252 | 25C24 | 60ND2 | 4.327 | 25C24 | 60C | 4.397 |
| 25C24 | 67CE2 | 4.413 | 25C24 | 59C | 4.424 | 25C24 | 67CD2 | 4.649 |

TABLE XXV-continued

Table of distances in Ångstroms between atoms of the inhibitor and protein for all protein atoms within 5 Ångstroms of the inhibitor 4-[N-[(phenylmethoxy)carbonyl)-L-leucyl]-1-[N-[(phenylmethoxy)carbonyl]-L-leucyl)-3-pyrrolidinone.

| Atom 1 | Atom 2 | Dist. | Atom 1 | Atom 2 | Dist. | Atom 1 | Atom 2 | Dist. |
|---|---|---|---|---|---|---|---|---|
| 25C24 | 61CB | 4.711 | 25C24 | 60N | 4.781 | 25C24 | 65O | 4.810 |
| 25C24 | 66CA | 4.888 | 25C24 | 61CG | 4.890 | 25C25 | 61OD2 | 2.979 |
| 25C25 | 61CB | 3.456 | 25C25 | 61N | 3.582 | 25C25 | 61CG | 3.623 |
| 25C25 | 65O | 4.058 | 25C25 | 60C | 4.074 | 25C25 | 61CA | 4.084 |
| 25C25 | 59O | 4.120 | 25C25 | 60CA | 4.277 | 25C25 | 61OD1 | 4.827 |
| 25C25 | 65C | 4.828 | 25C25 | 60O | 4.832 | 25C25 | 66CA | 4.907 |
| 25C26 | 61CB | 3.331 | 25C26 | 65O | 3.342 | 25C26 | 61OD2 | 3.552 |
| 25C26 | 61CG | 3.818 | 25C26 | 61N | 3.860 | 25C26 | 65C | 3.890 |
| 25C26 | 61CA | 4.226 | 25C26 | 64O | 4.287 | 25C26 | 66N | 4.362 |
| 25C26 | 66CA | 4.392 | 25C26 | 60C | 4.694 | 25C26 | 65CA | 4.697 |
| 25C26 | 64C | 4.855 | 25C26 | 61OD1 | 4.925 | 25C26 | 60CA | 4.944 |
| 25C27 | 65O | 3.537 | 25C27 | 65C | 3.661 | 25C27 | 66N | 3.764 |
| 25C27 | 66CA | 3.789 | 25C27 | 67CE2 | 4.460 | 25C27 | 65CA | 4.463 |
| 25C27 | 64O | 4.501 | 25C27 | 61CB | 4.521 | 25C27 | 66C | 4.533 |
| 25C27 | 61N | 4.713 | 25C27 | 67CD2 | 4.833 | 25C27 | 67CZ | 4.873 |
| 25C27 | 61OD2 | 4.935 | 25C27 | 66O | 4.986 | 25C28 | 67CE2 | 3.131 |
| 25C28 | 67CD2 | 3.493 | 25C28 | 67CZ | 3.739 | 25C28 | 66CA | 3.757 |
| 25C28 | 67OH | 4.121 | 25C28 | 66C | 4.151 | 25C28 | 66N | 4.180 |
| 25C28 | 67CG | 4.339 | 25C28 | 65O | 4.368 | 25C28 | 67N | 4.383 |
| 25C28 | 65C | 4.453 | 25C28 | 67CE1 | 4.537 | 25C28 | 60ND2 | 4.576 |
| 25C28 | 66O | 4.719 | 25C28 | 67CD1 | 4.789 | 25C29 | 67CE2 | 3.099 |
| 25C29 | 67CD2 | 3.367 | 25C29 | 60ND2 | 4.065 | 25C29 | 59O | 4.096 |
| 25C29 | 67CZ | 4.107 | 25C29 | 66CA | 4.348 | 25C29 | 67CG | 4.510 |
| 25C29 | 67OH | 4.532 | 25C29 | 67N | 4.689 | 25C29 | 60CA | 4.697 |
| 25C29 | 66C | 4.785 | 25C29 | 70OD1 | 4.794 | 25C29 | 65O | 4.942 |
| 25C30 | 65C | 3.364 | 25C30 | 66N | 3.477 | 25C30 | 65O | 3.676 |
| 25C30 | 65CA | 3.705 | 25C30 | 64O | 3.715 | 25C30 | 66CA | 3.996 |
| 25C30 | 64C | 4.521 | 25C30 | 65N | 4.571 | 25C30 | 66C | 4.606 |
| 25C30 | 66O | 4.690 | 25O31 | 66N | 4.304 | 25O31 | 65C | 4.471 |
| 25O31 | 67OH | 4.497 | 25O31 | 67CZ | 4.562 | 25O31 | 65CA | 4.615 |
| 25O31 | 64O | 4.643 | 25O31 | 66CA | 4.801 | 25O31 | 66O | 4.804 |
| 25O31 | 67CE1 | 4.862 | 25O31 | 67CE2 | 4.899 | 25O31 | 65O | 4.995 |
| 25O31 | 66C | 4.998 | 25C32 | 66O | 4.210 | 25C32 | 66N | 4.247 |
| 25C32 | 65CA | 4.648 | 25C32 | 65C | 4.675 | 25C32 | 67CE1 | 4.683 |
| 25C32 | 66C | 4.745 | 25C32 | 67CZ | 4.797 | 25C32 | 66CA | 4.862 |
| 25C32 | 67OH | 4.906 | 25O33 | 67CE1 | 4.116 | 25O33 | 67CZ | 4.445 |
| 25O33 | 67OH | 4.485 | 25O33 | 66O | 4.628 | 25O33 | 67CD1 | 4.718 |
| 25O33 | 25OH2 | 4.812 | 25O33 | 160O | 4.869 | 25C34 | 66O | 3.728 |
| 25C34 | 66N | 4.086 | 25C34 | 65CA | 4.283 | 25C34 | 65C | 4.685 |
| 25C34 | 25SG | 4.701 | 25C34 | 66C | 4.710 | 25C34 | 161O | 4.715 |
| 25C34 | 161C | 4.780 | 25C35 | 66O | 3.094 | 25C35 | 66C | 4.237 |
| 25C35 | 68CE | 4.248 | 25C35 | 66N | 4.449 | 25C35 | 163CB | 4.779 |
| 25C35 | 163N | 4.929 | 25C35 | 66CA | 4.993 | 25C36 | 66O | 4.248 |
| 25C36 | 134CB | 4.455 | 25C36 | 209CD2 | 4.608 | 25C36 | 68CE | 4.627 |
| 25C36 | 160O | 4.689 | 25C36 | 162N | 4.700 | 25C36 | 160C | 4.804 |
| 25C36 | 161C | 4.832 | 25C36 | 161CA | 4.852 | 25C36 | 67CD1 | 4.855 |
| 25C36 | 67CE1 | 4.866 | 25C36 | 161N | 4.905 | 25C36 | 160CB | 4.964 |
| 25C37 | 162N | 3.453 | 25C37 | 134CB | 3.566 | 25C37 | 162C | 3.722 |
| 25C37 | 163N | 3.858 | 25C37 | 162O | 3.881 | 25C37 | 161C | 3.888 |
| 25C37 | 161N | 4.019 | 25C37 | 162CA | 4.040 | 25C37 | 161CA | 4.109 |
| 25C37 | 160C | 4.197 | 25C37 | 163CA | 4.335 | 25C37 | 163CB | 4.414 |
| 25C37 | 160O | 4.461 | 25C37 | 160CB | 4.479 | 25C37 | 134CA | 4.485 |
| 25C37 | 161O | 4.643 | 25C37 | 160CA | 4.832 | 25C37 | 68CE | 4.842 |
| 25C37 | 209CD2 | 4.996 | 25C38 | 209CD2 | 3.377 | 25C38 | 67CD1 | 3.746 |
| 25C38 | 67CE1 | 3.972 | 25C38 | 68CE | 4.019 | 25C38 | 134CB | 4.063 |
| 25C38 | 66O | 4.117 | 25C38 | 209CG | 4.387 | 25C38 | 67CG | 4.813 |
| 25C38 | 67CA | 4.927 | 25C39 | 65CA | 3.495 | 25C39 | 25SG | 3.606 |
| 25C39 | 66N | 3.612 | 25C39 | 66O | 3.741 | 25C39 | 26CD1 | 4.029 |
| 25C39 | 65C | 4.099 | 25C39 | 26CB | 4.554 | 25C39 | 26CG | 4.652 |
| 25C39 | 66C | 4.666 | 25C39 | 65N | 4.740 | 25C39 | 26N | 4.747 |
| 25C39 | 66CA | 4.755 | 25C39 | 23O | 4.898 | 25C39 | 161O | 4.941 |
| 25O40 | 66N | 2.789 | 25O40 | 66O | 2.930 | 25O40 | 26CD1 | 2.937 |
| 25O40 | 65CA | 3.211 | 25O40 | 26CB | 3.444 | 25O40 | 26CG | 3.455 |
| 25O40 | 65C | 3.479 | 25O40 | 66C | 3.767 | 25O40 | 66CA | 3.842 |
| 25O40 | 25SG | 3.892 | 25O40 | 26N | 3.999 | 25O40 | 26NE1 | 4.011 |
| 25O40 | 26CA | 4.273 | 25O40 | 65N | 4.534 | 25O40 | 23O | 4.581 |
| 25O40 | 26CD2 | 4.697 | 25O40 | 65O | 4.703 | 25O40 | 68CE | 4.926 |
| 25O40 | 26CE2 | 4.943 | 25O40 | 25N | 4.988 | 25N41 | 25SG | 2.879 |
| 25N41 | 65CA | 3.789 | 25N41 | 161O | 4.253 | 25N41 | 23O | 4.382 |
| 25N41 | 26CD1 | 4.417 | 25N41 | 66N | 4.577 | 25N41 | 25CB | 4.611 |
| 25N41 | 23C | 4.734 | 25N41 | 65N | 4.734 | 25N41 | 65C | 4.774 |
| 25N41 | 25N | 4.800 | 25N41 | 161C | 4.855 | 25N41 | 26N | 4.870 |

TABLE XXV-continued

Table of distances in Ångstroms between atoms of the inhibitor and protein for all protein atoms within 5 Ångstroms of the inhibitor 4-[N-[(phenylmethoxy)carbonyl)-L-leucyl]-1-[N-[(phenylmethoxy)carbonyl]-L-leucyl)-3-pyrrolidinone.

| Atom 1 | Atom 2 | Dist. | Atom 1 | Atom 2 | Dist. | Atom 1 | Atom 2 | Dist. |
|---|---|---|---|---|---|---|---|---|
| 25N41 | 162CA | 4.874 | 25N41 | 163N | 4.932 | 25C42 | 25SG | 2.470 |
| 25C42 | 23O | 3.257 | 25C42 | 23C | 3.448 | 25C42 | 25N | 3.529 |
| 25C42 | 26CD1 | 3.714 | 25C42 | 65CA | 3.771 | 25C42 | 25CB | 3.843 |
| 25C42 | 23CA | 3.956 | 25C42 | 24N | 3.966 | 25C42 | 26N | 4.147 |
| 25C42 | 25CA | 4.156 | 25C42 | 24C | 4.282 | 25C42 | 24CA | 4.390 |
| 25C42 | 65N | 4.469 | 25C42 | 26NE1 | 4.524 | 25C42 | 25C | 4.662 |
| 25C42 | 26CG | 4.728 | 25C42 | 66N | 4.771 | 25C42 | 65C | 4.825 |
| 25C42 | 26CB | 4.981 | 25N43 | 66N | 3.501 | 25N43 | 65CA | 3.665 |
| 25N43 | 66O | 3.722 | 25N43 | 65C | 3.917 | 25N43 | 66C | 4.394 |
| 25N43 | 66CA | 4.413 | 25N43 | 64O | 4.690 | 25N43 | 65O | 4.923 |
| 25N43 | 65N | 4.930 | | | | | | |

TABLE XXVI

Table of distances in Ångstroms between atoms of the inhibitor and protein for all protein atoms within 5 Ångstroms of the inhibitor 4-[N-[(4-pyridylmethoxy)carbonyl]-L-leucyl]-1-[N-[(phenylmethoxy)carbonyl]-L-leucyl]-3-pyrrolidinone.

| Atom 1 | Atom 2 | Dist. | Atom 1 | Atom 2 | Dist. | Atom 1 | Atom 2 | Dist. |
|---|---|---|---|---|---|---|---|---|
| 25C1 | 242OH2 | 3.241 | 25C1 | 18OD1 | 3.446 | 25C1 | 184CD1 | 3.907 |
| 25C1 | 184CB | 3.929 | 25C1 | 184CG | 3.941 | 25C1 | 184CA | 4.202 |
| 25C1 | 18CG | 4.369 | 25C1 | 18ND2 | 4.563 | 25C1 | 184NE1 | 4.640 |
| 25C1 | 18O | 4.676 | 25C1 | 184CD2 | 4.729 | 25C1 | 184C | 4.752 |
| 25C1 | 21NE2 | 4.852 | 25C1 | 20N | 4.956 | 25C2 | 184CD1 | 3.751 |
| 25C2 | 184CG | 3.778 | 25C2 | 184NE1 | 4.100 | 25C2 | 184CD2 | 4.156 |
| 25C2 | 184CB | 4.179 | 25C2 | 184CE2 | 4.339 | 25C2 | 242OH2 | 4.411 |
| 25C2 | 18OD1 | 4.705 | 25C2 | 184CA | 4.841 | 25C2 | 184CE3 | 4.910 |
| 25C3 | 184NE1 | 3.789 | 25C3 | 184CD1 | 3.817 | 25C3 | 184CE2 | 4.203 |
| 25C3 | 184CG | 4.246 | 25C3 | 184CD2 | 4.475 | 25C3 | 20O | 4.505 |
| 25C3 | 184CZ2 | 4.908 | 25C3 | 21NE2 | 4.969 | 25C4 | 20O | 3.140 |
| 25C4 | 19CG | 4.004 | 25C4 | 20C | 4.011 | 25C4 | 184CD1 | 4.042 |
| 25C4 | 184NE1 | 4.079 | 25C4 | 21NE2 | 4.367 | 25C4 | 20N | 4.403 |
| 25C4 | 19CD | 4.509 | 25C4 | 20CA | 4.543 | 25C4 | 21OE1 | 4.778 |
| 25C4 | 184CG | 4.809 | 25C4 | 18OD1 | 4.811 | 25C4 | 184CE2 | 4.867 |
| 25C4 | 21CD | 4.895 | 25C4 | 19NE2 | 4.938 | 25C4 | 21N | 4.965 |
| 25C5 | 20O | 2.695 | 25C5 | 20N | 3.202 | 25C5 | 20C | 3.263 |
| 25C5 | 20CA | 3.407 | 25C5 | 18OD1 | 3.589 | 25C5 | 19CG | 3.659 |
| 25C5 | 21NE2 | 3.950 | 25C5 | 19C | 4.127 | 25C5 | 184CD1 | 4.183 |
| 25C5 | 21N | 4.369 | 25C5 | 242OH2 | 4.392 | 25C5 | 18CG | 4.548 |
| 25C5 | 19CD | 4.599 | 25C5 | 184NE1 | 4.619 | 25C5 | 19N | 4.620 |
| 25C5 | 19CA | 4.668 | 25C5 | 19CB | 4.730 | 25C5 | 21CD | 4.753 |
| 25C5 | 18ND2 | 4.801 | 25C5 | 19O | 4.927 | 25C5 | 184CG | 4.931 |
| 25C5 | 183O | 4.975 | 25C5 | 21OE1 | 4.987 | 25C6 | 18OD1 | 2.695 |
| 25C6 | 242OH2 | 3.232 | 25C6 | 20N | 3.572 | 25C6 | 18CG | 3.627 |
| 25C6 | 18ND2 | 3.837 | 25C6 | 20CA | 3.842 | 25C6 | 20O | 3.869 |
| 25C6 | 184CD1 | 4.122 | 25C6 | 20C | 4.133 | 25C6 | 21NE2 | 4.219 |
| 25C6 | 19CG | 4.448 | 25C6 | 184CA | 4.454 | 25C6 | 184CG | 4.538 |
| 25C6 | 184CB | 4.595 | 25C6 | 19N | 4.613 | 25C6 | 19C | 4.668 |
| 25C6 | 183O | 4.825 | 25C6 | 244OH2 | 4.841 | 25C6 | 184NE1 | 4.878 |
| 25C7 | 20O | 2.832 | 25C7 | 19CG | 3.901 | 25C7 | 20C | 3.960 |
| 25C7 | 19CD | 4.075 | 25C7 | 19NE2 | 4.108 | 25C7 | 22O | 4.387 |
| 25C7 | 184NE1 | 4.479 | 25C7 | 22N | 4.658 | 25C7 | 21CA | 4.703 |
| 25C7 | 19OE1 | 4.733 | 25C7 | 21OE1 | 4.734 | 25C7 | 21N | 4.779 |
| 25C7 | 184CD1 | 4.791 | 25C7 | 20N | 4.797 | 25C7 | 21NE2 | 4.850 |
| 25C7 | 20CA | 4.870 | 25O8 | 20O | 4.185 | 25O8 | 184NE1 | 4.318 |
| 25O8 | 19NE2 | 4.505 | 25O8 | 19CD | 4.575 | 25O8 | 19CG | 4.801 |
| 25O8 | 184CE2 | 4.904 | 25O8 | 184CD1 | 4.980 | 25O8 | 19OE1 | 4.989 |
| 25C9 | 184NE1 | 3.701 | 25C9 | 19NE2 | 4.091 | 25C9 | 19CD | 4.179 |
| 25C9 | 184CE2 | 4.209 | 25C9 | 184CZ2 | 4.214 | 25C9 | 19OE1 | 4.322 |
| 25C9 | 162CE1 | 4.669 | 25C9 | 184CD1 | 4.680 | 25C9 | 19CG | 4.819 |
| 25O10 | 184NE1 | 2.553 | 25O10 | 184CE2 | 3.148 | 25O10 | 184CZ2 | 3.297 |
| 25O10 | 19OE1 | 3.438 | 25O10 | 19CD | 3.591 | 25O10 | 184CD1 | 3.650 |
| 25O10 | 162CE1 | 3.653 | 25O10 | 19NE2 | 3.822 | 25O10 | 162ND1 | 4.295 |
| 25O10 | 19CG | 4.332 | 25O10 | 184CD2 | 4.379 | 25C10 | 162NE2 | 4.393 |
| 25O10 | 184CH2 | 4.579 | 25O10 | 184CG | 4.611 | 25C11 | 162ND1 | 3.950 |
| 25C11 | 162CE1 | 4.196 | 25C11 | 184CZ2 | 4.648 | 25C11 | 19NE2 | 4.924 |
| 25C11 | 162CG | 4.968 | 25C12 | 162ND1 | 4.717 | 25C12 | 161O | 4.982 |

TABLE XXVI-continued

Table of distances in Ångstroms between atoms of the inhibitor and protein for all protein atoms within 5 Ångstroms of the inhibitor 4-[N-[(4-pyridylmethoxy)carbonyl]-L-leucyl]-1-[N-[(phenylmethoxy)carbonyl]-L-leucyl]-3-pyrrolidinone.

| Atom 1 | Atom 2 | Dist. | Atom 1 | Atom 2 | Dist. | Atom 1 | Atom 2 | Dist. |
|---|---|---|---|---|---|---|---|---|
| 25C13 | 161OD1 | 4.017 | 25C13 | 162ND1 | 4.533 | 25C13 | 161CG | 4.712 |
| 25C13 | 161O | 4.749 | 25C13 | 184CZ2 | 4.831 | 25C13 | 162CB | 4.860 |
| 25C13 | 162CG | 4.864 | 25C13 | 137O | 4.980 | 25C14 | 161OD1 | 3.145 |
| 25C14 | 162ND | 3.354 | 25C14 | 162CB | 3.366 | 25C14 | 162CG | 3.508 |
| 25C14 | 161O | 3.685 | 25C14 | 161C | 3.990 | 25C14 | 162CA | 4.004 |
| 25C14 | 161CG | 4.037 | 25C14 | 162N | 4.168 | 25C14 | 162CE1 | 4.261 |
| 25C14 | 137CB | 4.367 | 25C14 | 161CB | 4.378 | 25C14 | 162CD2 | 4.476 |
| 25C14 | 184CZ2 | 4.641 | 25C14 | 137C | 4.815 | 25C14 | 162NE2 | 4.847 |
| 25C14 | 161CA | 4.867 | 25C14 | 137O | 4.907 | 25C14 | 137CA | 5.000 |
| 25C15 | 137O | 4.063 | 25C15 | 184CZ2 | 4.064 | 25C15 | 184CH2 | 4.220 |
| 25C15 | 137C | 4.530 | 25C15 | 161OD1 | 4.738 | 25C15 | 138CA | 4.806 |
| 25C15 | 138N | 4.887 | 25C15 | 137CB | 4.908 | 25C16 | 162ND1 | 4.014 |
| 25C16 | 25SG | 4.159 | 25C16 | 19NE2 | 4.348 | 25C16 | 162CE1 | 4.375 |
| 25C16 | 23CA | 4.579 | 25C16 | 161O | 4.665 | 25O17 | 23CA | 3.462 |
| 25O17 | 19NE2 | 3.921 | 25O17 | 23C | 4.371 | 25O17 | 23N | 4.429 |
| 25O17 | 22O | 4.568 | 25O17 | 25SG | 4.579 | 25O17 | 22C | 4.858 |
| 25O17 | 19CD | 4.877 | 25O17 | 23O | 4.921 | 25O17 | 24N | 4.983 |
| 25N18 | 25SG | 3.257 | 25N18 | 162ND1 | 3.402 | 25N18 | 161O | 3.468 |
| 25N18 | 162CE1 | 4.081 | 25N18 | 25CB | 4.457 | 25N18 | 162CG | 4.523 |
| 25N18 | 161C | 4.569 | 25N18 | 162CA | 4.582 | 25N18 | 162CB | 4.845 |
| 25N18 | 19NE2 | 4.859 | 25C19 | 25SG | 2.794 | 25C19 | 161O | 3.684 |
| 25C19 | 25CB | 4.234 | 25C19 | 162ND1 | 4.247 | 25C19 | 23CA | 4.366 |
| 25C19 | 23O | 4.457 | 25C19 | 23C | 4.497 | 25C19 | 25N | 4.673 |
| 25C19 | 161C | 4.876 | 25C19 | 162CE1 | 4.889 | 25C19 | 19NE2 | 4.898 |
| 25N20 | 19NE2 | 4.613 | 25N20 | 184NE1 | 4.773 | 25N20 | 184CZ2 | 4.805 |
| 25N20 | 162CE1 | 4.936 | 25N20 | 19CD | 4.991 | 25C21 | 161O | 2.879 |
| 25C21 | 25SG | 3.218 | 25C21 | 161C | 4.048 | 25C21 | 162CA | 4.631 |
| 25C21 | 162N | 4.811 | 25C21 | 65CA | 4.831 | 25C21 | 162ND1 | 4.843 |
| 25C21 | 25CB | 4.939 | 25C21 | 163N | 4.976 | 25C22 | 25SG | 1.746 |
| 25C22 | 25CB | 2.980 | 25C22 | 25N | 3.156 | 25C22 | 25CA | 3.592 |
| 25C22 | 23O | 3.702 | 25C22 | 23C | 3.712 | 25C22 | 23CA | 4.038 |
| 25C22 | 19NE2 | 4.077 | 25C22 | 24N | 4.130 | 25C22 | 26N | 4.232 |
| 25C22 | 162ND1 | 4.246 | 25C22 | 24C | 4.298 | 25C22 | 25C | 4.374 |
| 25C22 | 162CE1 | 4.608 | 25C22 | 24CA | 4.620 | 25C22 | 161O | 4.649 |
| 25C22 | 26CD1 | 4.828 | 25C22 | 19OE1 | 4.874 | 25C22 | 19CD | 4.942 |
| 25O23 | 25SG | 2.426 | 25O23 | 25N | 2.644 | 25O23 | 25CB | 2.944 |
| 25O23 | 19NE2 | 2.944 | 25O23 | 23C | 2.957 | 25O23 | 24N | 3.189 |
| 25O23 | 23CA | 3.211 | 25O23 | 23O | 3.326 | 25O23 | 25CA | 3.349 |
| 25O23 | 24C | 3.666 | 25O23 | 24CA | 3.882 | 25O23 | 19CD | 3.941 |
| 25O23 | 19OE1 | 4.099 | 25O23 | 22O | 4.365 | 25O23 | 25C | 4.451 |
| 25O23 | 26N | 4.481 | 25O23 | 23N | 4.525 | 25O23 | 162ND1 | 4.590 |
| 25O23 | 162CE1 | 4.629 | 25O23 | 24O | 4.773 | 25O23 | 22C | 4.910 |
| 25C24 | 65CA | 4.095 | 25C24 | 66N | 4.264 | 25C24 | 65C | 4.356 |
| 25C24 | 64O | 4.547 | 25C24 | 66O | 4.628 | 25C25 | 66O | 3.688 |
| 25C25 | 161O | 3.862 | 25C25 | 66N | 4.313 | 25C25 | 161C | 4.458 |
| 25C25 | 66C | 4.741 | 25C25 | 65CA | 4.778 | 25C25 | 161CA | 4.939 |
| 25C25 | 25SG | 4.963 | 25C25 | 65C | 4.974 | 25C26 | 66O | 3.481 |
| 25C26 | 161O | 4.269 | 25C26 | 161C | 4.491 | 25C26 | 163N | 4.695 |
| 25C26 | 66C | 4.696 | 25C26 | 160O | 4.785 | 25C26 | 163CB | 4.799 |
| 25C26 | 162N | 4.915 | 25C26 | 161CA | 4.923 | 25C27 | 160O | 3.472 |
| 25C27 | 160C | 4.089 | 25C27 | 161CA | 4.307 | 25C27 | 161C | 4.320 |
| 25C27 | 161N | 4.440 | 25C27 | 161O | 4.452 | 25C27 | 66O | 4.548 |
| 25C27 | 160CB | 4.699 | 25C27 | 134CB | 4.734 | 25C27 | 162N | 4.770 |
| 25C27 | 209CD2 | 4.918 | 25C28 | 160O | 3.351 | 25C28 | 160C | 4.338 |
| 25C28 | 67CE1 | 4.588 | 25C28 | 161CA | 4.739 | 25C28 | 66O | 4.818 |
| 25C28 | 161N | 4.934 | 25C28 | 67CD1 | 4.955 | 25C29 | 209CD2 | 3.439 |
| 25C29 | 134CB | 3.686 | 25C29 | 160O | 4.049 | 25C29 | 160CB | 4.234 |
| 25C29 | 160C | 4.490 | 25C29 | 67CD1 | 4.759 | 25C29 | 66O | 4.795 |
| 25C29 | 209CG | 4.839 | 25C29 | 67CE1 | 4.896 | 25C30 | 66O | 3.533 |
| 25C30 | 66N | 3.616 | 25C30 | 25SG | 3.883 | 25C30 | 65CA | 3.972 |
| 25C30 | 26CD1 | 4.246 | 25C30 | 26CB | 4.295 | 25C30 | 65C | 4.296 |
| 25C30 | 161O | 4.302 | 25C30 | 66C | 4.432 | 25C30 | 66CA | 4.591 |
| 25C30 | 26CG | 4.623 | 25C30 | 26N | 4.737 | 25C30 | 163CB | 4.852 |
| 25C30 | 163N | 4.940 | 25O31 | 66O | 2.635 | 25O31 | 66N | 2.846 |
| 25O31 | 26CB | 3.199 | 25O31 | 26CD1 | 3.340 | 25O31 | 66C | 3.423 |
| 25O31 | 26CG | 3.516 | 25O31 | 66CA | 3.653 | 25O31 | 65C | 3.792 |
| 25O31 | 65CA | 3.821 | 25O31 | 26N | 4.122 | 25O31 | 26CA | 4.160 |
| 25O31 | 25SG | 4.278 | 25O31 | 26NE1 | 4.531 | 25O31 | 67N | 4.618 |
| 25O31 | 163CB | 4.642 | 25O31 | 26CD2 | 4.797 | 25O31 | 65O | 4.959 |
| 25N32 | 25SG | 2.963 | 25N32 | 161O | 3.860 | 25N32 | 65CA | 4.049 |
| 25N32 | 66N | 4.382 | 25N32 | 23O | 4.384 | 25N32 | 26CD1 | 4.398 |
| 25N32 | 26N | 4.601 | 25N32 | 25CB | 4.628 | 25N32 | 25N | 4.764 |

TABLE XXVI-continued

Table of distances in Ångstroms between atoms of the inhibitor and protein for all protein atoms within 5 Ångstroms of the inhibitor 4-[N-[(4-pyridylmethoxy)carbonyl]-L-leucyl]-1-[N-[(phenylmethoxy)carbonyl]-L-leucyl]-3-pyrrolidinone.

| Atom 1 | Atom 2 | Dist. | Atom 1 | Atom 2 | Dist. | Atom 1 | Atom 2 | Dist. |
|---|---|---|---|---|---|---|---|---|
| 25N32 | 65C | 4.790 | 25N32 | 66C | 4.806 | 25N32 | 163N | 4.815 |
| 25N32 | 26CB | 4.836 | 25N32 | 161C | 4.880 | 25N32 | 23C | 4.985 |
| 25C33 | 25SG | 2.418 | 25C33 | 23O | 3.256 | 25C33 | 25N | 3.403 |
| 25C33 | 26CD1 | 3.587 | 25C33 | 26N | 3.672 | 25C33 | 25CB | 3.751 |
| 25C33 | 23C | 3.758 | 25C33 | 25CA | 3.959 | 25C33 | 65CA | 3.999 |
| 25C33 | 25C | 4.264 | 25C33 | 24N | 4.334 | 25C33 | 24C | 4.346 |
| 25C33 | 26CG | 4.388 | 25C33 | 26CB | 4.392 | 25C33 | 23CA | 4.425 |
| 25C33 | 66N | 4.510 | 25C33 | 24CA | 4.531 | 25C33 | 26CA | 4.616 |
| 25C33 | 26NE1 | 4.621 | 25C33 | 65C | 4.831 | 25C33 | 65N | 4.901 |
| 25C33 | 161O | 4.934 | 25N34 | 66O | 3.486 | 25N34 | 66N | 3.771 |
| 25N34 | 65CA | 4.261 | 25N34 | 65C | 4.264 | 25N34 | 66C | 4.330 |
| 25N34 | 65CA | 4.464 | 25N34 | 161O | 4.991 | | | |

TABLE XXVII

Table of distances in Ångstroms between atoms of the inhibitor and protein for all protein atoms within 5 Ångstroms of the inhibitor 4-[N-[(phenylmethoxy)carbonyl]-L-leucyl]-1-N[N-(methyl)-L-leucyl)]-3-pyrrolidinone.

| Atom 1 | Atom 2 | Dist. | Atom 1 | Atom 2 | Dist. | Atom 1 | Atom 2 | Dist. |
|---|---|---|---|---|---|---|---|---|
| 25C1 | 242OH2 | 3.241 | 25C1 | 18OD1 | 3.446 | 25C1 | 184CD1 | 3.907 |
| 25C1 | 184CB | 3.929 | 25C1 | 184CG | 3.941 | 25C1 | 184CA | 4.202 |
| 25C1 | 18CG | 4.369 | 25C1 | 18ND2 | 4.563 | 25C1 | 184NE1 | 4.640 |
| 25C1 | 184O | 4.676 | 25C1 | 184CD2 | 4.729 | 25C1 | 184C | 4.752 |
| 25C1 | 21NE2 | 4.852 | 25C1 | 20N | 4.956 | 25C2 | 184CD1 | 3.751 |
| 25C2 | 184CG | 3.778 | 25C2 | 184NE1 | 4.100 | 25C2 | 184CD2 | 4.156 |
| 25C2 | 184CB | 4.179 | 25C2 | 184CE2 | 4.339 | 25C2 | 242OH2 | 4.411 |
| 25C2 | 18OD1 | 4.705 | 25C2 | 184CA | 4.841 | 25C2 | 184CE3 | 4.910 |
| 25C3 | 184NE1 | 3.789 | 25C3 | 184CD1 | 3.817 | 25C3 | 184CE2 | 4.203 |
| 25C3 | 184CG | 4.246 | 25C3 | 184CD2 | 4.475 | 25C3 | 20O | 4.505 |
| 25C3 | 184CZ2 | 4.908 | 25C3 | 21NE2 | 4.969 | 25C4 | 20O | 3.140 |
| 25C4 | 19CG | 4.004 | 25C4 | 20C | 4.011 | 25C4 | 184CD1 | 4.042 |
| 25C4 | 184NE1 | 4.079 | 25C4 | 21NE2 | 4.367 | 25C4 | 20N | 4.403 |
| 25C4 | 19CD | 4.509 | 25C4 | 20CA | 4.543 | 25C4 | 21OE1 | 4.778 |
| 25C4 | 184CG | 4.809 | 25C4 | 18OD1 | 4.811 | 25C4 | 184CE2 | 4.867 |
| 25C4 | 21CD | 4.895 | 25C4 | 19NE2 | 4.938 | 25C4 | 21N | 4.965 |
| 25C5 | 20O | 2.695 | 25C5 | 20N | 3.202 | 25C5 | 20C | 3.263 |
| 25C5 | 20CA | 3.407 | 25C5 | 18OD1 | 3.589 | 25C5 | 19CG | 3.659 |
| 25C5 | 21NE2 | 3.950 | 25C5 | 19C | 4.127 | 25C5 | 184CD1 | 4.183 |
| 25C5 | 21N | 4.369 | 25C5 | 242OH2 | 4.392 | 25C5 | 18CG | 4.548 |
| 25C5 | 19CD | 4.599 | 25C5 | 184NE1 | 4.619 | 25C5 | 19N | 4.620 |
| 25C5 | 19CA | 4.668 | 25C5 | 19CB | 4.730 | 25C5 | 21CD | 4.753 |
| 25C5 | 18ND2 | 4.801 | 25C5 | 19O | 4.927 | 25C5 | 184CG | 4.931 |
| 25C5 | 183O | 4.975 | 25C5 | 21OE1 | 4.987 | 25C6 | 18OD1 | 2.695 |
| 25C6 | 242OH2 | 3.232 | 25C6 | 20N | 3.572 | 25C6 | 18CG | 3.627 |
| 25C6 | 18ND2 | 3.837 | 25C6 | 20CA | 3.842 | 25C6 | 20O | 3.869 |
| 25C6 | 184CD1 | 4.122 | 25C6 | 20C | 4.133 | 25C6 | 21NE2 | 4.219 |
| 25C6 | 19CG | 4.448 | 25C6 | 184CA | 4.454 | 25C6 | 184CG | 4.538 |
| 25C6 | 184CB | 4.595 | 25C6 | 19N | 4.613 | 25C6 | 19C | 4.668 |
| 25C6 | 183O | 4.825 | 25C6 | 244OH2 | 4.841 | 25C6 | 184NE1 | 4.878 |
| 25C7 | 20O | 2.832 | 25C7 | 19CG | 3.901 | 25C7 | 20C | 3.960 |
| 25C7 | 19CD | 4.075 | 25C7 | 19NE2 | 4.108 | 25C7 | 22O | 4.387 |
| 25C7 | 184NE1 | 4.479 | 25C7 | 22N | 4.658 | 25C7 | 21CA | 4.703 |
| 25C7 | 19OE1 | 4.733 | 25C7 | 21OE1 | 4.734 | 25C7 | 21N | 4.779 |
| 25C7 | 184CD1 | 4.791 | 25C7 | 20N | 4.797 | 25C7 | 21NE2 | 4.850 |
| 25C7 | 20CA | 4.870 | 25O8 | 20O | 4.185 | 25O8 | 184NE1 | 4.318 |
| 25O8 | 19NE2 | 4.505 | 25O8 | 19CD | 4.575 | 25O8 | 19CG | 4.801 |
| 25O8 | 184CE2 | 4.904 | 25O8 | 184CD1 | 4.980 | 25O8 | 19OE1 | 4.989 |
| 25C9 | 184NE1 | 3.701 | 25C9 | 19NE2 | 4.091 | 25C9 | 19CD | 4.179 |
| 25C9 | 184CE2 | 4.209 | 25C9 | 184CZ2 | 4.214 | 25C9 | 19OE1 | 4.322 |
| 25C9 | 162CE1 | 4.669 | 25C9 | 184CD1 | 4.680 | 25C9 | 19CG | 4.819 |
| 25O10 | 184NE1 | 2.553 | 25O10 | 184CE2 | 3.148 | 25O10 | 184CZ2 | 3.297 |
| 25O10 | 19OE1 | 3.438 | 25O10 | 19CD | 3.591 | 25O10 | 184CD1 | 3.650 |
| 25O10 | 162CE1 | 3.653 | 25O10 | 19NE2 | 3.822 | 25O10 | 162ND1 | 4.295 |
| 25O10 | 19CG | 4.332 | 25O10 | 184CD2 | 4.379 | 25O10 | 162NE2 | 4.393 |
| 25O10 | 184CH2 | 4.579 | 25O10 | 184CG | 4.611 | 25C11 | 162ND1 | 3.950 |
| 25C11 | 162CE1 | 4.196 | 25C11 | 184CZ2 | 4.648 | 25C11 | 19NE2 | 4.924 |
| 25C11 | 162CG | 4.968 | 25C12 | 162ND1 | 4.717 | 25C12 | 161O | 4.982 |

TABLE XXVII-continued

Table of distances in Ångstroms between atoms of the inhibitor and protein
for all protein atoms within 5 Ångstroms of the inhibitor
4-[N-[(phenylmethoxy)carbonyl]-L-leucyl]-1-N[N-(methyl)-L-leucyl]-3-pyrrolidinone.

| Atom 1 | Atom 2 | Dist. | Atom 1 | Atom 2 | Dist. | Atom 1 | Atom 2 | Dist. |
|---|---|---|---|---|---|---|---|---|
| 25C13 | 161OD1 | 4.017 | 25C13 | 162ND1 | 4.533 | 25C13 | 161CG | 4.712 |
| 25C13 | 161O | 4.749 | 25C13 | 184CZ2 | 4.831 | 25C13 | 162CB | 4.860 |
| 25C13 | 162CCG | 4.864 | 25C13 | 137O | 4.980 | 25C14 | 161OD1 | 3.145 |
| 25C14 | 162ND1 | 3.354 | 25C14 | 162CB | 3.366 | 25C14 | 162CG | 3.508 |
| 25C14 | 161O | 3.685 | 25C14 | 161C | 3.990 | 25C14 | 162CA | 4.004 |
| 25C14 | 161CG | 4.037 | 25C14 | 162N | 4.168 | 25C14 | 162CE1 | 4.261 |
| 25C14 | 137CB | 4.367 | 25C14 | 161CB | 4.378 | 25C14 | 162CD2 | 4.476 |
| 25C14 | 184CZ2 | 4.641 | 25C14 | 137C | 4.815 | 25C14 | 162NE2 | 4.847 |
| 25C14 | 161CA | 4.867 | 25C14 | 137O | 4.907 | 25C14 | 137CA | 5.000 |
| 25C15 | 137O | 4.063 | 25C15 | 184CZ2 | 4.064 | 25C15 | 184CH2 | 4.220 |
| 25C15 | 137C | 4.530 | 25C15 | 161OD1 | 4.738 | 25C15 | 138CA | 4.806 |
| 25C15 | 138N | 4.887 | 25C15 | 137CB | 4.908 | 25C16 | 162ND1 | 4.014 |
| 25C16 | 25SG | 4.159 | 25C16 | 19NE2 | 4.348 | 25C16 | 162CE1 | 4.375 |
| 25C16 | 23CA | 4.579 | 25C16 | 161O | 4.665 | 25O17 | 23CA | 3.462 |
| 25O17 | 19NE2 | 3.921 | 25O17 | 23C | 4.371 | 25O17 | 23N | 4.429 |
| 25O17 | 22O | 4.568 | 25O17 | 25SG | 4.579 | 25O17 | 22C | 4.85 |
| 25O17 | 19CD | 4.877 | 25O17 | 23O | 4.921 | 25O17 | 24N | 4.983 |
| 25N18 | 25SG | 3.257 | 25N18 | 162ND1 | 3.402 | 25N18 | 161O | 3.468 |
| 25N18 | 162CE1 | 4.081 | 25N18 | 25CB | 4.457 | 25N18 | 162CG | 4.523 |
| 25N18 | 161C | 4.569 | 25N18 | 162CA | 4.582 | 25N18 | 162CB | 4.845 |
| 25N18 | 19NE2 | 4.859 | 25C19 | 25SG | 2.794 | 25C19 | 161O | 3.684 |
| 25C19 | 25CB | 4.234 | 25C19 | 162ND1 | 4.247 | 25C19 | 23CA | 4.366 |
| 25C19 | 23O | 4.457 | 25C19 | 23C | 4.497 | 25C19 | 25N | 4.673 |
| 25C19 | 161C | 4.876 | 25C19 | 162CE1 | 4.889 | 25C19 | 19NE2 | 4.898 |
| 25N20 | 19NE2 | 4.613 | 25N20 | 184NE1 | 4.773 | 25N20 | 184CZ2 | 4.805 |
| 25N20 | 162CE1 | 4.936 | 25N20 | 19CD | 4.991 | 25C21 | 161O | 2.879 |
| 25C21 | 25SG | 3.218 | 25C21 | 161C | 4.048 | 25C21 | 162CA | 4.631 |
| 25C21 | 162N | 4.811 | 25C21 | 65CA | 4.831 | 25C21 | 162ND1 | 4.843 |
| 25C21 | 25CB | 4.939 | 25C21 | 163N | 4.976 | 25C22 | 25SG | 1.746 |
| 25C22 | 25CB | 2.980 | 25C22 | 25N | 3.156 | 25C22 | 25CA | 3.592 |
| 25C22 | 23O | 3.702 | 25C22 | 23C | 3.712 | 25C22 | 23CA | 4.038 |
| 25C22 | 19NE2 | 4.077 | 25C22 | 24N | 4.130 | 25C22 | 26N | 4.232 |
| 25C22 | 162ND1 | 4.246 | 25C22 | 24C | 4.298 | 25C22 | 25C | 4.374 |
| 25C22 | 162CE1 | 4.608 | 25C22 | 24CA | 4.620 | 25C22 | 161O | 4.649 |
| 25C22 | 26CD1 | 4.828 | 25C22 | 19OE1 | 4.874 | 25C22 | 19CD | 4.942 |
| 25O23 | 25SG | 2.426 | 25O23 | 25N | 2.644 | 25O23 | 25CB | 2.944 |
| 25O23 | 19NE2 | 2.944 | 25O23 | 23C | 2.957 | 25O23 | 24N | 3.189 |
| 25O23 | 23CA | 3.211 | 25O23 | 23O | 3.326 | 25O23 | 25CA | 3.349 |
| 25O23 | 24C | 3.666 | 25O23 | 24CA | 3.882 | 25O23 | 19CD | 3.941 |
| 25O23 | 19OE1 | 4.099 | 25O23 | 22O | 4.365 | 25O23 | 25C | 4.451 |
| 25O23 | 26N | 4.481 | 25O23 | 23N | 4.525 | 25O23 | 162ND1 | 4.590 |
| 25O23 | 162CE1 | 4.629 | 25O23 | 24O | 4.773 | 25O23 | 22C | 4.910 |
| 25C24 | 65CA | 4.095 | 25C24 | 66N | 4.264 | 25C24 | 65C | 4.356 |
| 25C24 | 64O | 4.547 | 25C24 | 66O | 4.628 | 25C25 | 66O | 3.688 |
| 25C25 | 161O | 3.862 | 25C25 | 66N | 4.313 | 25C25 | 161C | 4.458 |
| 25C25 | 66C | 4.741 | 25C25 | 65CA | 4.778 | 25C25 | 161CA | 4.939 |
| 25C25 | 25SG | 4.963 | 25C25 | 65C | 4.974 | 25C26 | 66O | 3.481 |
| 25C26 | 161O | 4.269 | 25C26 | 161C | 4.491 | 25C26 | 163N | 4.695 |
| 25C26 | 66C | 4.696 | 25C26 | 160O | 4.785 | 25C26 | 163CB | 4.799 |
| 25C26 | 162N | 4.915 | 25C26 | 161CA | 4.923 | 25C27 | 160O | 3.472 |
| 25C27 | 160C | 4.089 | 25C27 | 161CA | 4.307 | 25C27 | 161C | 4.320 |
| 25C27 | 161N | 4.440 | 25C27 | 161O | 4.452 | 25C27 | 66O | 4.548 |
| 25C27 | 160CB | 4.699 | 25C27 | 134CB | 4.734 | 25C27 | 162N | 4.770 |
| 25C27 | 209CD2 | 4.918 | 25C28 | 160O | 3.351 | 25C28 | 160C | 4.338 |
| 25C28 | 67CE1 | 4.588 | 25C28 | 161CA | 4.739 | 25C28 | 66O | 4.818 |
| 25C28 | 161N | 4.934 | 25C28 | 67CD1 | 4.955 | 25C29 | 209CD2 | 3.439 |
| 25C29 | 134CB | 3.686 | 25C29 | 160O | 4.049 | 25C29 | 160CB | 4.234 |
| 25C29 | 160C | 4.490 | 25C29 | 67CD1 | 4.759 | 25C29 | 66O | 4.795 |
| 25C29 | 209CG | 4.839 | 25C29 | 67CE1 | 4.896 | 25C30 | 66O | 3.533 |
| 25C30 | 66N | 3.616 | 25C30 | 25SG | 3.883 | 25C30 | 65CA | 3.972 |
| 25C30 | 26CD1 | 4.246 | 25C30 | 26CB | 4.295 | 25C30 | 65C | 4.296 |
| 25C30 | 161O | 4.302 | 25C30 | 66C | 4.432 | 25C30 | 66CA | 4.591 |
| 25C30 | 26CG | 4.623 | 25C30 | 26N | 4.737 | 25C30 | 163CB | 4.852 |
| 25C30 | 163N | 4.940 | 25O31 | 66O | 2.635 | 25O31 | 66N | 2.846 |
| 25O31 | 26CB | 3.199 | 25O31 | 26CD1 | 3.340 | 25O31 | 66C | 3.423 |
| 25O31 | 26CG | 3.516 | 25O31 | 66CA | 3.653 | 25O31 | 65C | 3.792 |
| 25O31 | 65CA | 3.821 | 25O31 | 26N | 4.122 | 25O31 | 26CA | 4.160 |
| 25O31 | 25SG | 4.278 | 25O31 | 26NE1 | 4.531 | 25O31 | 67N | 4.618 |
| 25O31 | 163CB | 4.642 | 25O31 | 26CD2 | 4.797 | 25O31 | 65O | 4.959 |
| 25N32 | 25SG | 2.963 | 25N32 | 161O | 3.860 | 25N32 | 65CA | 4.049 |
| 25N32 | 66N | 4.382 | 25N32 | 23O | 4.384 | 25N32 | 26CD1 | 4.398 |
| 25N32 | 26N | 4.601 | 25N32 | 25CB | 4.628 | 25N32 | 25N | 4.764 |
| 25N32 | 65C | 4.790 | 25N32 | 66O | 4.806 | 25N32 | 163N | 4.815 |

TABLE XXVII-continued

Table of distances in Ångstroms between atoms of the inhibitor and protein for all protein atoms within 5 Ångstroms of the inhibitor 4-[N-[(phenylmethoxy)carbonyl]-L-leucyl]-1-N[N-(methyl)-L-leucyl]-3-pyrrolidinone.

| Atom 1 | Atom 2 | Dist. | Atom 1 | Atom 2 | Dist. | Atom 1 | Atom 2 | Dist. |
|---|---|---|---|---|---|---|---|---|
| 25N32 | 26CB | 4.836 | 25N32 | 161C | 4.880 | 25N32 | 23C | 4.985 |
| 25C33 | 25SG | 2.418 | 25C33 | 23O | 3.256 | 25C33 | 25N | 3.403 |
| 25C33 | 26CD1 | 3.587 | 25C33 | 26N | 3.672 | 25C33 | 25CB | 3.751 |
| 25C33 | 23C | 3.758 | 25C33 | 25CA | 3.959 | 25C33 | 65CA | 3.999 |
| 25C33 | 25C | 4.264 | 25C33 | 24N | 4.334 | 25C33 | 24C | 4.346 |
| 25C33 | 26CG | 4.388 | 25C33 | 26CB | 4.392 | 25C33 | 23CA | 4.425 |
| 25C33 | 66N | 4.510 | 25C33 | 24CA | 4.531 | 25C33 | 26CA | 4.616 |
| 25C33 | 26NE1 | 4.621 | 25C33 | 65C | 4.831 | 25C33 | 65N | 4.901 |
| 25C33 | 161O | 4.934 | 25N34 | 66O | 3.486 | 25N34 | 66N | 3.771 |
| 25N34 | 65CA | 4.261 | 25N34 | 65C | 4.264 | 25N34 | 66C | 4.330 |
| 25N34 | 66CA | 4.464 | 25N34 | 161O | 4.991 | | | |

TABLE XXVIII

Table of distance in Ångstroms between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Dist. | Atom 1 | Atom 2 | Dist. | Atom 1 | Atom 2 | Dist. |
|---|---|---|---|---|---|---|---|---|
| 25C1 | 20O | 2.824 | 25C1 | 20C | 3.956 | 25C1 | 184NE1 | 4.078 |
| 25C1 | 184CD1 | 4.178 | 25C1 | 21CA | 4.600 | 25C1 | 20N | 4.704 |
| 25C1 | 21N | 4.706 | 25C1 | 21NE2 | 4.738 | 25C1 | 19CB | 4.859 |
| 25C1 | 19CD | 4.929 | 25C1 | 20CA | 4.947 | 25C1 | 184CE2 | 4.949 |
| 25C1 | 19CG | 4.998 | 25C2 | 20O | 3.367 | 25C2 | 21NE2 | 4.119 |
| 25C2 | 241OH2 | 4.309 | 25C2 | 20C | 4.592 | 25C2 | 184NE1 | 4.819 |
| 25C2 | 184CD1 | 4.860 | 25C3 | 241OH2 | 3.093 | 25C3 | 20O | 3.775 |
| 25C3 | 21NE2 | 4.450 | 25C3 | 184CD1 | 4.878 | 25C3 | 20C | 4.988 |
| 25C4 | 241OH2 | 3.480 | 25C4 | 20O | 3.717 | 25C4 | 18OD1 | 3.947 |
| 25C4 | 184CD1 | 4.219 | 25C4 | 184CG | 4.493 | 25C4 | 18O | 4.549 |
| 25C4 | 184CB | 4.602 | 25C4 | 184CA | 4.747 | 25C4 | 18CG | 4.754 |
| 25C4 | 18ND2 | 4.754 | 25C4 | 20C | 4.826 | 25C4 | 184NE1 | 4.840 |
| 25C4 | 20N | 4.964 | 25C4 | 184C | 4.980 | 25C5 | 20O | 3.239 |
| 25C5 | 18OD1 | 3.271 | 25C5 | 184CD1 | 3.400 | 25C5 | 20N | 3.933 |
| 25C5 | 184CG | 4.002 | 25C5 | 184NE1 | 4.111 | 25C5 | 184CA | 4.118 |
| 25C5 | 20C | 4.232 | 25C5 | 18CG | 4.245 | 25C5 | 184CB | 4.256 |
| 25C5 | 19CB | 4.402 | 25C5 | 183O | 4.499 | 25C5 | 18O | 4.503 |
| 25C5 | 20CA | 4.510 | 25C5 | 19N | 4.552 | 25C5 | 184C | 4.587 |
| 25C5 | 18ND2 | 4.606 | 25C5 | 19C | 4.765 | 25C5 | 19CA | 4.817 |
| 25C5 | 241OH2 | 4.867 | 25C5 | 184CD2 | 4.968 | 25C6 | 20O | 2.740 |
| 25C6 | 184CD1 | 3.361 | 25C6 | 184NE1 | 3.660 | 25C6 | 20C | 3.746 |
| 25C6 | 20N | 3.761 | 25C6 | 19CB | 3.788 | 25C6 | 18OD1 | 4.136 |
| 25C6 | 19CG | 4.290 | 25C6 | 184CC | 4.321 | 25C6 | 20CA | 4.335 |
| 25C6 | 19C | 4.361 | 25C6 | 19CD | 4.428 | 25C6 | 19CA | 4.488 |
| 25C6 | 19OE1 | 4.526 | 25C6 | 19N | 4.653 | 25C6 | 184CE2 | 4.729 |
| 25C6 | 183O | 4.737 | 25C6 | 21N | 4.769 | 25C6 | 184CA | 4.918 |
| 25C6 | 184CB | 4.981 | 25C6 | 19NE2 | 4.990 | 25O7 | 20O | 3.287 |
| 25O7 | 21CA | 4.138 | 25O7 | 20C | 4.173 | 25O7 | 19NE2 | 4.269 |
| 25O7 | 21C | 4.370 | 25O7 | 19CD | 4.416 | 25O7 | 184NE1 | 4.459 |
| 25O7 | 21O | 4.466 | 25O7 | 22O | 4.540 | 25O7 | 21N | 4.558 |
| 25O7 | 19CG | 4.663 | 25O7 | 19OE1 | 4.850 | 25O7 | 184CD1 | 4.897 |
| 25O7 | 19CB | 4.977 | 25C8 | 19NE2 | 4.003 | 25C8 | 184NE1 | 4.235 |
| 25C8 | 19CD | 4.404 | 25C8 | 20O | 4.665 | 25C8 | 19OE1 | 4.715 |
| 25C8 | 22O | 4.861 | 25C8 | 21O | 4.937 | 25C8 | 184CE2 | 4.948 |
| 25C9 | 184NE1 | 3.199 | 25C9 | 19NE2 | 3.212 | 25C9 | 19CD | 3.472 |
| 25C9 | 19OE1 | 3.533 | 25C9 | 184CE2 | 4.000 | 25C9 | 184CD1 | 4.152 |
| 25C9 | 184CZ2 | 4.206 | 25C9 | 19CG | 4.414 | 25C9 | 162NE2 | 4.653 |
| 25C9 | 22O | 4.860 | 25C9 | 162CD2 | 4.867 | 25C9 | 19CB | 4.910 |
| 25C10 | 184NE1 | 3.388 | 25C10 | 184CZ2 | 3.605 | 25C10 | 19NE2 | 3.666 |
| 25C10 | 184CE2 | 3.828 | 25C10 | 162CD2 | 3.878 | 25C10 | 19OE1 | 3.887 |
| 25C10 | 162NE2 | 3.948 | 25C10 | 19CD | 4.067 | 25C10 | 184CD1 | 4.615 |
| 25C10 | 162CG | 4.799 | 25C10 | 184CH2 | 4.859 | 25C10 | 162CE1 | 4.873 |
| 25C11 | 184CZ2 | 4.084 | 25C11 | 184NE1 | 4.519 | 25C11 | 162CD2 | 4.567 |
| 25C11 | 184CE2 | 4.664 | 25C11 | 19NE2 | 4.718 | 25C11 | 162NE2 | 4.920 |
| 25C13 | 19NE2 | 4.978 | 25S14 | 162CD2 | 3.947 | 25S14 | 184CZ2 | 4.113 |
| 25S14 | 162CG | 4.222 | 25S14 | 162CB | 4.332 | 25S14 | 161O | 4.574 |
| 25S14 | 162NE2 | 4.657 | 25S14 | 161OD1 | 4.760 | 25S14 | 184CH2 | 4.865 |
| 25O15 | 184CZ2 | 3.079 | 25O15 | 184CH2 | 3.580 | 25O15 | 162CG | 3.856 |
| 25O15 | 162CD2 | 3.881 | 25O15 | 137O | 3.985 | 25O15 | 162CB | 4.051 |

TABLE XXVIII-continued

Table of distance in Ångstroms between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Dist. | Atom 1 | Atom 2 | Dist. | Atom 1 | Atom 2 | Dist. |
|---|---|---|---|---|---|---|---|---|
| 25O15 | 184CE2 | 4.275 | 25O15 | 137CB | 4.300 | 25O15 | 162ND1 | 4.343 |
| 25O15 | 162NE2 | 4.364 | 25O15 | 161OD1 | 4.610 | 25O15 | 162CE1 | 4.620 |
| 25O15 | 137C | 4.663 | 25O15 | 184NE1 | 4.807 | 25O15 | 184CZ3 | 4.973 |
| 25O16 | 161OD1 | 4.484 | 25O16 | 161O | 4.575 | 25O16 | 161CG | 4.963 |
| 25N17 | 162CD2 | 2.828 | 25N17 | 162CG | 3.217 | 25N17 | 161O | 3.256 |
| 25N17 | 162CB | 3.276 | 25N17 | 162CA | 3.672 | 25N17 | 162NE2 | 3.893 |
| 25N17 | 161C | 4.006 | 25N17 | 25SG | 4.125 | 25N17 | 162N | 4.251 |
| 25N17 | 162ND1 | 4.353 | 25N17 | 161OD1 | 4.593 | 25N17 | 162CE1 | 4.665 |
| 25N17 | 184CZ2 | 4.778 | 25N17 | 25CB | 4.819 | 25C18 | 161O | 3.031 |
| 25C18 | 25SG | 3.290 | 25C18 | 162CD2 | 3.499 | 25C18 | 162CA | 4.069 |
| 25C18 | 161C | 4.107 | 25C18 | 162CG | 4.151 | 25C18 | 162CB | 4.188 |
| 25C18 | 25CB | 4.359 | 25C18 | 19NE2 | 4.573 | 25C18 | 162NE2 | 4.594 |
| 25C18 | 162N | 4.597 | 25C19 | 25SG | 1.931 | 25C19 | 25CB | 3.158 |
| 25C19 | 162CD2 | 3.616 | 25C19 | 161O | 3.716 | 25C19 | 19NE2 | 3.740 |
| 25C19 | 25N | 4.227 | 25C19 | 25CA | 4.306 | 25C19 | 23CA | 4.380 |
| 25C19 | 162CA | 4.405 | 25C19 | 23O | 4.494 | 25C19 | 23C | 4.496 |
| 25C19 | 162CG | 4.541 | 25C19 | 162NE2 | 4.577 | 25C19 | 19CD | 4.643 |
| 25C19 | 19OE1 | 4.705 | 25C19 | 161C | 4.813 | 25C19 | 162CB | 4.819 |
| 25O20 | 19NE2 | 2.778 | 25O20 | 25SG | 2.890 | 25O20 | 23CA | 3.251 |
| 25O20 | 25CB | 3.629 | 25O20 | 23C | 3.723 | 25O20 | 19CD | 3.918 |
| 25O20 | 23O | 4.030 | 25O20 | 25N | 4.152 | 25O20 | 19OE1 | 4.290 |
| 25O20 | 24N | 4.342 | 25O20 | 162CD2 | 4.356 | 25O20 | 23N | 4.524 |
| 25O20 | 25CA | 4.566 | 25O20 | 22O | 4.681 | 25O20 | 161O | 4.912 |
| 25C21 | 25SG | 2.532 | 25C21 | 161O | 3.420 | 25C21 | 23O | 4.107 |
| 25C21 | 25CB | 4.220 | 25C21 | 23C | 4.540 | 25C21 | 65CA | 4.542 |
| 25C21 | 161C | 4.578 | 25C21 | 23CA | 4.599 | 25C21 | 162CA | 4.793 |
| 25C21 | 25N | 4.822 | 25C21 | 162CD2 | 4.980 | 25N22 | 161O | 2.689 |
| 25N22 | 25SG | 2.783 | 25N22 | 161C | 3.649 | 25N22 | 162CA | 4.003 |
| 25N22 | 162N | 4.221 | 25N22 | 163N | 4.453 | 25N22 | 25CB | 4.578 |
| 25N22 | 162C | 4.691 | 25N22 | 161CA | 4.693 | 25N22 | 65CA | 4.839 |
| 25C23 | 161O | 3.461 | 25C23 | 25SG | 3.771 | 25C23 | 161C | 4.205 |
| 25C23 | 66O | 4.217 | 25C23 | 65CA | 4.220 | 25C23 | 66N | 4.268 |
| 25C23 | 162N | 4.828 | 25C23 | 162CA | 4.844 | 25C23 | 65C | 4.845 |
| 25C23 | 26CD1 | 4.890 | 25C23 | 161CA | 4.937 | 25C23 | 26CB | 4.974 |
| 25O24 | 65CA | 3.024 | 25O24 | 66N | 3.208 | 25O24 | 65C | 3.657 |
| 25O24 | 66O | 3.830 | 25O24 | 65N | 4.287 | 25O24 | 26CD1 | 4.326 |
| 25924 | 25SG | 4.394 | 25O24 | 66CA | 4.437 | 25O24 | 161O | 4.526 |
| 25O24 | 66C | 4.595 | 25O24 | 64O | 4.818 | 25O24 | 23O | 4.843 |
| 25O24 | 26CG | 4.879 | 25O24 | 26CB | 4.888 | 25O24 | 65O | 4.923 |
| 25O24 | 64C | 4.972 | 25C25 | 161O | 3.652 | 25C25 | 66O | 3.880 |
| 25C25 | 161C | 3.949 | 25C25 | 162N | 4.375 | 25C25 | 161CA | 4.493 |
| 25C25 | 163N | 4.584 | 25C25 | 25SG | 4.592 | 25C25 | 162CA | 4.608 |
| 25C25 | 162C | 4.759 | 25C25 | 66N | 4.805 | 25C25 | 163CB | 4.922 |
| 25C26 | 66O | 3.186 | 25C26 | 163CB | 3.703 | 25C26 | 26CB | 3.850 |
| 25C26 | 163N | 4.052 | 25C26 | 25SG | 4.357 | 25C26 | 163CA | 4.390 |
| 25C26 | 66C | 4.421 | 25C26 | 26CA | 4.561 | 25C26 | 162C | 4.598 |
| 25C26 | 68SD | 4.628 | 25C26 | 161O | 4.666 | 25C26 | 66N | 4.721 |
| 25C26 | 26N | 4.729 | 25C26 | 26CG | 4.770 | 25C26 | 162CA | 4.869 |
| 25C26 | 161C | 4.907 | 25C26 | 162N | 4.970 | 25C26 | 26CD1 | 4.999 |
| 25C27 | 163CB | 3.337 | 25C27 | 68SD | 3.583 | 25C27 | 66O | 3.590 |

TABLE XXVIII-continued

Table of distance in Ångstroms between atoms of the inhibitor and protein for all protein atoms within 5 Ångstroms of the inhibitor 1-N-(N-imidazole acetyl-leucinyl)-amino-3-N-(4-phenoxy-phenyl-sulfonyl)-amino-propan-2-one.

| Atom 1 | Atom 2 | Dist. | Atom 1 | Atom 2 | Dist. | Atom 1 | Atom 2 | Dist. |
|---|---|---|---|---|---|---|---|---|
| 25C27 | 163CA | 4.029 | 25C27 | 163N | 4.096 | 25C27 | 68CE | 4.156 |
| 25C27 | 134CB | 4.190 | 25C27 | 209CD2 | 4.248 | 25C27 | 26CB | 4.361 |
| 25C27 | 162C | 4.597 | 25C27 | 66C | 4.797 | 25C27 | 162O | 4.893 |
| 25C27 | 26CA | 4.943 | 25C27 | 67CA | 4.946 | 25C28 | 134CB | 3.049 |
| 25C28 | 163CB | 3.699 | 25C28 | 163N | 3.714 | 25C28 | 162C | 3.789 |
| 25C28 | 162O | 3.807 | 25C28 | 163CA | 3.820 | 25C28 | 209CD2 | 3.901 |
| 25C28 | 134CA | 3.967 | 25C28 | 162N | 4.239 | 25C28 | 162CA | 4.478 |
| 25C28 | 68CE | 4.498 | 25C28 | 68SD | 4.535 | 25C28 | 161C | 4.582 |
| 25C28 | 66O | 4.956 | 25C28 | 134C | 4.964 | 25C28 | 161O | 4.966 |
| 25C28 | 161N | 4.992 | 25C29 | 66O | 2.949 | 25C29 | 209CD2 | 3.567 |
| 25C29 | 68SD | 3.617 | 25C29 | 67CA | 3.759 | 25C29 | 67CD1 | 3.963 |
| 25C29 | 66C | 3.998 | 25C29 | 68CE | 4.231 | 25C29 | 67N | 4.370 |
| 25C29 | 68N | 4.410 | 25C29 | 67C | 4.555 | 25C29 | 67CB | 4.556 |
| 25C29 | 67CG | 4.589 | 25C29 | 163CB | 4.636 | 25C29 | 134CB | 4.685 |
| 25C29 | 234OH2 | 4.722 | 25C29 | 26CB | 4.726 | 25C29 | 67CE1 | 4.755 |
| 25N30 | 66O | 3.644 | 25N30 | 66N | 4.623 | 25N30 | 161O | 4.640 |
| 25N30 | 66C | 4.640 | 25N30 | 161C | 4.793 | 25N30 | 161CA | 4.888 |
| 25N30 | 160O | 4.908 | 25C31 | 160O | 3.792 | 25C31 | 161CA | 4.412 |
| 25C31 | 160C | 4.476 | 25C31 | 161C | 4.719 | 25C31 | 66O | 4.743 |
| 25C31 | 161N | 4.777 | 25C31 | 161O | 4.849 | 25C31 | 67CE1 | 4.934 |
| 25O32 | 160O | 2.720 | 25O32 | 160C | 3.270 | 25O32 | 161CA | 3.397 |
| 25O32 | 161N | 3.577 | 25O32 | 161C | 3.869 | 25O32 | 160CB | 4.202 |
| 25O32 | 161C | 4.268 | 25O32 | 160CA | 4.363 | 25O32 | 162N | 4.395 |
| 25O32 | 161CB | 4.698 | 25C33 | 67CE1 | 3.801 | 25C33 | 160O | 4.307 |
| 25C33 | 67CZ | 4.397 | 25C33 | 67CD1 | 4.397 | 25C33 | 67OH | 4.480 |
| 25C34 | 160O | 3.849 | 25C34 | 67CE1 | 4.011 | 25C34 | 67OH | 4.411 |
| 25C34 | 67CZ | 4.629 | 25C34 | 160C | 4.805 | 25C34 | 67CD1 | 4.850 |
| 25C34 | 160CB | 4.898 | 25C35 | 67CE1 | 3.694 | 25C35 | 67OH | 4.238 |
| 25C35 | 209CD2 | 4.447 | 25C35 | 67CZ | 4.449 | 25C35 | 67CD1 | 4.551 |
| 25C35 | 160O | 4.567 | 25C35 | 160CB | 4.790 | 25C35 | 209CD1 | 4.791 |
| 25N36 | 160C | 4.470 | 25N36 | 160CB | 4.515 | 25N36 | 160CD1 | 4.774 |
| 25N36 | 160CG | 4.825 | 25N36 | 67CE1 | 4.846 | 25N36 | 67OH | 4.964 |
| 25C37 | 160O | 3.691 | 25C37 | 160CB | 4.458 | 25C37 | 160N | 4.495 |
| 25C37 | 160C | 4.634 | 25C37 | 160CA | 4.822 | 25C37 | 160CG | 4.973 |
| 25C37 | 158O | 4.994 | 25N38 | 160O | 3.211 | 25N38 | 160C | 4.305 |
| 25N38 | 160CB | 4.681 | 25N38 | 160N | 4.817 | 25N38 | 160CA | 4.898 |

TABLE XXIX

Active site amino acid residues for Cathepsin K

| ASN | 18 | GLN | 19 | GLY | 20 | GLN | 21 |
|---|---|---|---|---|---|---|---|
| CYS | 22 | GLY | 23 | SER | 24 | CYS | 25 |
| TRP | 26 | ALA | 27 | PHE | 28 | SER | 29 |
| GLU | 59 | ASN | 60 | ASP | 61 | GLY | 64 |
| GLY | 65 | GLY | 66 | TYR | 67 | MET | 68 |
| ASN | 70 | ALA | 134 | ALA | 137 | SER | 138 |
| GLN | 143 | ASP | 158 | ASN | 159 | LEU | 160 |
| ASN | 161 | HIS | 162 | ALA | 163 | SER | 183 |
| TRP | 184 | TRP | 188 | LEU | 209 | | |

What is claimed is:

1. A method of identifying an inhibitor compound capable of binding to, and inhibiting the proteolytic activity of, cathepsin K, said method comprising:

introducing the protein coordinates of Table I into a suitable computer program so as to define an active site conformation of a cathepsin K molecule comprising an active site formed by the residues listed in Table XXIX, said active site defined by the protein coordinates of Table I, wherein said program displays the three-dimensional structure of the active site;

creating a three dimensional representation of the active site in said computer program;

displaying and superimposing a three dimensional representation of a test compound on the three dimensional representation of the active site;

assessing whether said test compound fits spatially into the active site;

preparing said test compound that fits spatially into the active site;

using said test compound in a biological assay for a protease characterized by said active site; and determining whether said test compound inhibits cathepsin K activity in said assay.

* * * * *

SEQUENCE LISTING

<160> NUMBER OF SEQ ID NOS: 7

<210> SEQ ID NO: 1
<211> LENGTH: 329
<212> TYPE: PRT
<213> ORGANISM: homo sapiens

<400> SEQUENCE: 1

```
Met Trp Gly Leu Lys Val Leu Leu Pro Val Val Ser Phe Ala Leu
 1               5                  10                  15

Tyr Pro Glu Glu Ile Leu Asp Thr His Trp Glu Leu Trp Lys Lys Thr
             20                  25                  30

His Arg Lys Gln Tyr Asn Asn Lys Val Asp Glu Ile Ser Arg Arg Leu
         35                  40                  45

Ile Trp Glu Lys Asn Leu Lys Tyr Ile Ser Ile His Asn Leu Glu Ala
 50                  55                  60

Ser Leu Gly Val His Thr Tyr Glu Leu Ala Met Asn His Leu Gly Asp
 65                  70                  75                  80

Met Thr Ser Glu Glu Val Val Gln Lys Met Thr Gly Leu Lys Val Pro
             85                  90                  95

Leu Ser His Ser Arg Ser Asn Asp Thr Leu Tyr Ile Pro Glu Trp Glu
             100                 105                 110

Gly Arg Ala Pro Asp Ser Val Asp Tyr Arg Lys Gly Tyr Val Thr
         115                 120                 125

Pro Val Lys Asn Gln Gly Gln Cys Gly Ser Cys Trp Ala Phe Ser Ser
 130                 135                 140

Val Gly Ala Leu Glu Gly Gln Leu Lys Lys Lys Thr Gly Lys Leu Leu
 145                 150                 155                 160

Asn Leu Ser Pro Gln Asn Leu Val Asp Cys Val Ser Glu Asn Asp Gly
             165                 170                 175

Cys Gly Gly Gly Tyr Met Thr Asn Ala Phe Gln Tyr Val Gln Lys Asn
             180                 185                 190

Arg Gly Ile Asp Ser Glu Asp Ala Tyr Pro Tyr Val Gly Gln Glu Glu
         195                 200                 205

Ser Cys Met Tyr Asn Pro Thr Gly Lys Ala Ala Lys Cys Arg Gly Tyr
 210                 215                 220

Arg Glu Ile Pro Glu Gly Asn Glu Lys Ala Leu Lys Arg Ala Val Ala
225                 230                 235                 240

Arg Val Gly Pro Val Ser Val Ala Ile Asp Ala Ser Leu Thr Ser Phe
             245                 250                 255

Gln Phe Tyr Ser Lys Gly Val Tyr Tyr Asp Glu Ser Cys Asn Ser Asp
             260                 265                 270

Asn Leu Asn His Ala Val Leu Ala Val Gly Tyr Gly Ile Gln Lys Gly
         275                 280                 285

Asn Lys His Trp Ile Ile Lys Asn Ser Trp Gly Glu Asn Trp Gly Asn
         290                 295                 300

Lys Gly Tyr Ile Leu Met Ala Arg Asn Lys Asn Asn Ala Cys Gly Ile
305                 310                 315                 320

Ala Asn Leu Ala Ser Phe Pro Lys Met
                 325
```

<210> SEQ ID NO: 2
<211> LENGTH: 331
<212> TYPE: PRT
<213> ORGANISM: homo sapiens

<400> SEQUENCE: 2

```
Met Lys Arg Leu Val Cys Val Leu Leu Val Cys Ser Ser Ala Val Ala
 1               5                  10                  15

Gln Leu His Lys Asp Pro Thr Leu Asp His Trp His Leu Trp Lys
             20                  25                  30

Lys Thr Tyr Gly Lys Gln Tyr Lys Glu Lys Asn Glu Glu Ala Val Arg
         35                  40                  45
```

Arg Leu Ile Trp Glu Lys Asn Leu Lys Phe Val Met Leu His Asn Leu
 50                  55                  60

Glu His Ser Met Gly Met His Ser Tyr Asp Leu Gly Met Asn His Leu
 65                  70                  75                  80

Gly Asp Met Thr Ser Glu Val Met Ser Leu Thr Ser Ser Leu Arg
                 85                  90                  95

Val Pro Ser Gln Trp Gln Arg Asn Ile Thr Tyr Lys Ser Asn Pro Asn
                100                 105                 110

Arg Ile Leu Pro Asp Ser Val Asp Trp Arg Glu Lys Gly Cys Val Thr
                115                 120                 125

Glu Val Lys Tyr Gln Gly Ser Cys Gly Ala Cys Trp Ala Phe Ser Ala
            130                 135                 140

Val Gly Ala Leu Glu Ala Gln Leu Lys Leu Lys Thr Gly Lys Leu Val
145                 150                 155                 160

Thr Leu Ser Ala Gln Asn Leu Val Asp Cys Ser Thr Glu Lys Tyr Gly
                165                 170                 175

Asn Lys Gly Cys Asn Gly Gly Phe Met Thr Thr Ala Phe Gln Tyr Ile
                180                 185                 190

Ile Asp Asn Lys Gly Ile Asp Ser Asp Ala Ser Tyr Pro Tyr Lys Ala
                195                 200                 205

Met Asp Gln Lys Cys Gln Tyr Asp Ser Lys Tyr Arg Ala Ala Thr Cys
            210                 215                 220

Ser Lys Tyr Thr Glu Leu Pro Tyr Gly Arg Glu Asp Val Leu Lys Glu
225                 230                 235                 240

Ala Val Ala Asn Lys Gly Pro Val Ser Val Gly Val Asp Ala Arg His
                245                 250                 255

Pro Ser Phe Phe Leu Tyr Arg Ser Gly Val Tyr Tyr Glu Pro Ser Cys
                260                 265                 270

Thr Gln Asn Val Asn His Gly Val Leu Val Val Gly Tyr Gly Asp Leu
            275                 280                 285

Asn Gly Lys Glu Tyr Trp Leu Val Lys Asn Ser Trp Gly His Asn Phe
            290                 295                 300

Gly Glu Glu Gly Tyr Ile Arg Met Ala Arg Asn Lys Gly Asn His Cys
305                 310                 315                 320

Gly Ile Ala Ser Phe Pro Ser Tyr Pro Glu Ile
                325                 330

<210> SEQ ID NO: 3
<211> LENGTH: 333
<212> TYPE: PRT
<213> ORGANISM: homo sapiens

<400> SEQUENCE: 3

Met Asn Pro Thr Leu Ile Leu Ala Ala Phe Cys Leu Gly Ile Ala Ser
 1               5                  10                  15

Ala Thr Leu Thr Phe Asp His Ser Leu Glu Ala Gln Trp Thr Lys Trp
                20                  25                  30

Lys Ala Met His Asn Arg Leu Tyr Gly Met Asn Glu Glu Gly Trp Arg
             35                  40                  45

Arg Ala Val Trp Glu Lys Asn Met Lys Met Ile Glu Leu His Asn Gln
 50                  55                  60

Glu Tyr Arg Glu Gly Lys His Ser Phe Thr Met Ala Met Asn Ala Phe
 65                  70                  75                  80

Gly Asp Met Thr Ser Glu Glu Phe Arg Gln Val Met Asn Gly Phe Gln

```
              85                  90                  95
Asn Arg Lys Pro Arg Lys Gly Lys Val Phe Gln Glu Pro Leu Phe Tyr
            100                 105                 110

Glu Ala Pro Arg Ser Val Asp Trp Arg Glu Lys Gly Tyr Val Thr Pro
            115                 120                 125

Val Lys Asn Gln Gly Gln Cys Gly Ser Cys Trp Ala Phe Ser Ala Thr
130                 135                 140

Gly Ala Leu Glu Gly Gln Met Phe Arg Lys Thr Gly Arg Leu Ile Ser
145                 150                 155                 160

Leu Ser Glu Gln Asn Leu Val Asp Cys Ser Gly Pro Gln Gly Asn Glu
                165                 170                 175

Gly Cys Asn Gly Gly Leu Met Asp Tyr Ala Phe Gln Tyr Val Gln Asp
            180                 185                 190

Asn Gly Gly Leu Asp Ser Glu Glu Ser Tyr Pro Tyr Glu Ala Thr Glu
            195                 200                 205

Glu Ser Cys Lys Tyr Asn Pro Lys Tyr Ser Val Ala Asn Asp Thr Gly
        210                 215                 220

Phe Val Asp Ile Pro Lys Gln Glu Lys Ala Leu Met Lys Ala Val Ala
225                 230                 235                 240

Thr Val Gly Pro Ile Ser Val Ala Ile Asp Ala Gly His Glu Ser Phe
                245                 250                 255

Leu Phe Tyr Lys Glu Gly Ile Tyr Phe Glu Pro Asp Cys Ser Ser Glu
            260                 265                 270

Asp Met Asp His Gly Val Leu Val Val Gly Tyr Gly Phe Glu Ser Thr
            275                 280                 285

Glu Ser Asp Asn Asn Lys Tyr Trp Leu Val Lys Asn Ser Trp Gly Glu
        290                 295                 300

Glu Trp Gly Met Gly Gly Tyr Val Lys Met Ala Lys Asp Arg Arg Asn
305                 310                 315                 320

His Cys Gly Ile Ala Ser Ala Ala Ser Tyr Pro Thr Val
                325                 330

<210> SEQ ID NO: 4
<211> LENGTH: 212
<212> TYPE: PRT
<213> ORGANISM: homo sapiens

<400> SEQUENCE: 4

Ile Pro Glu Tyr Val Asp Trp Arg Gln Lys Gly Ala Val Thr Pro Val
1               5                   10                  15

Lys Asn Gln Gly Ser Cys Gly Ser Cys Trp Ala Phe Ser Ala Val Val
            20                  25                  30

Thr Ile Glu Gly Ile Ile Lys Ile Arg Thr Gly Asn Leu Asn Gln Tyr
        35                  40                  45

Ser Glu Gln Glu Leu Leu Asp Cys Asp Arg Arg Ser Tyr Gly Cys Asn
    50                  55                  60

Gly Gly Tyr Pro Trp Ser Ala Leu Gln Leu Val Ala Gln Tyr Gly Ile
65                  70                  75                  80

His Tyr Arg Asn Thr Tyr Pro Tyr Glu Gly Val Gln Arg Tyr Cys Arg
                85                  90                  95

Ser Arg Glu Lys Gly Pro Tyr Ala Ala Lys Thr Asp Gly Val Arg Gln
            100                 105                 110

Val Gln Pro Tyr Asn Gln Gly Ala Leu Leu Tyr Ser Ile Ala Asn Gln
        115                 120                 125
```

```
Pro Val Ser Val Val Leu Gln Ala Ala Gly Lys Asp Phe Gln Leu Tyr
    130                 135                 140

Arg Gly Gly Ile Phe Val Gly Pro Cys Gly Asn Lys Val Asp His Ala
145                 150                 155                 160

Val Ala Ala Val Gly Tyr Gly Pro Asn Tyr Ile Leu Ile Lys Asn Ser
                165                 170                 175

Trp Gly Thr Gly Trp Gly Glu Asn Gly Tyr Ile Arg Ile Lys Arg Gly
                180                 185                 190

Thr Gly Asn Ser Tyr Gly Val Cys Gly Leu Tyr Thr Ser Ser Phe Tyr
                195                 200                 205

Pro Val Lys Asn
    210

<210> SEQ ID NO: 5
<211> LENGTH: 380
<212> TYPE: PRT
<213> ORGANISM: homo sapiens

<400> SEQUENCE: 5

Met Gly Leu Pro Lys Ser Phe Val Ser Met Ser Leu Leu Phe Phe Ser
1               5                   10                  15

Thr Leu Leu Ile Leu Ser Leu Ala Phe Asn Ala Lys Asn Leu Thr Gln
                20                  25                  30

Arg Thr Asn Asp Glu Val Lys Ala Met Tyr Glu Ser Trp Leu Ile Lys
            35                  40                  45

Tyr Gly Lys Ser Tyr Asn Ser Leu Gly Glu Trp Glu Arg Arg Phe Glu
    50                  55                  60

Ile Phe Lys Glu Thr Leu Arg Phe Ile Asp Glu His Asn Ala Asp Thr
65                  70                  75                  80

Asn Arg Ser Tyr Lys Val Gly Leu Asn Gln Phe Ala Asp Leu Thr Asp
                85                  90                  95

Glu Glu Phe Arg Ser Thr Tyr Leu Gly Phe Thr Ser Gly Ser Asn Lys
            100                 105                 110

Thr Lys Val Ser Asn Arg Tyr Glu Pro Arg Phe Gly Gln Val Leu Pro
        115                 120                 125

Ser Tyr Val Asp Trp Arg Ser Ala Gly Ala Val Val Asp Ile Lys Ser
    130                 135                 140

Gln Gly Glu Cys Gly Gly Cys Trp Ala Phe Ser Ala Ile Ala Thr Val
145                 150                 155                 160

Glu Gly Ile Asn Lys Ile Val Thr Gly Val Leu Ile Ser Leu Ser Glu
                165                 170                 175

Gln Glu Leu Ile Asp Cys Gly Arg Thr Gln Asn Thr Arg Gly Cys Asn
                180                 185                 190

Gly Gly Tyr Ile Thr Asp Gly Phe Gln Phe Ile Ile Asn Asn Gly Gly
                195                 200                 205

Ile Asn Thr Glu Glu Asn Tyr Pro Tyr Thr Ala Gln Asp Gly Glu Cys
    210                 215                 220

Asn Leu Asp Leu Gln Asn Glu Lys Tyr Val Thr Ile Asp Thr Tyr Glu
225                 230                 235                 240

Asn Val Pro Tyr Asn Asn Glu Trp Ala Leu Gln Thr Ala Val Thr Tyr
                245                 250                 255

Gln Pro Val Ser Val Ala Leu Asp Ala Ala Gly Asp Ala Phe Lys His
                260                 265                 270

Tyr Ser Ser Gly Ile Phe Thr Gly Pro Cys Gly Thr Ala Ile Asp His
            275                 280                 285
```

```
Ala Val Thr Ile Val Gly Tyr Gly Thr Glu Gly Ile Asp Tyr Trp
    290                 295                 300

Ile Val Lys Asn Ser Trp Asp Thr Thr Trp Gly Glu Gly Tyr Met
305                 310                 315                 320

Arg Ile Leu Arg Asn Val Gly Ala Gly Thr Cys Gly Ile Ala Thr
                325                 330                 335

Met Pro Ser Tyr Pro Val Lys Tyr Asn Asn Gln Asn His Pro Lys Pro
                340                 345                 350

Tyr Ser Ser Leu Ile Asn Pro Pro Ala Phe Ser Met Ser Lys Asp Gly
                355                 360                 365

Pro Val Gly Val Asp Asp Gly Gln Arg Tyr Ser Ala
    370                 375                 380

<210> SEQ ID NO: 6
<211> LENGTH: 335
<212> TYPE: PRT
<213> ORGANISM: homo sapiens

<400> SEQUENCE: 6

Met Trp Ala Thr Leu Pro Leu Cys Ala Gly Ala Trp Leu Leu Gly
  1               5                  10                  15

Val Pro Val Cys Gly Ala Ala Glu Leu Ser Val Asn Ser Leu Glu Lys
                 20                  25                  30

Phe His Phe Lys Ser Trp Met Ser Lys His Arg Lys Thr Tyr Ser Thr
             35                  40                  45

Glu Glu Tyr His His Arg Leu Gln Thr Phe Ala Ser Asn Trp Arg Lys
         50                  55                  60

Ile Asn Ala His Asn Asn Gly Asn His Thr Phe Lys Met Ala Leu Asn
65                   70                  75                  80

Gln Phe Ser Asp Met Ser Phe Ala Glu Ile Lys His Lys Tyr Leu Trp
                 85                  90                  95

Ser Glu Pro Gln Asn Cys Ser Ala Thr Lys Ser Asn Tyr Leu Arg Gly
                100                 105                 110

Thr Gly Pro Tyr Pro Pro Ser Val Asp Trp Arg Lys Lys Gly Asn Phe
            115                 120                 125

Val Ser Pro Val Lys Asn Gln Gly Ala Cys Gly Ser Cys Trp Thr Phe
    130                 135                 140

Ser Thr Thr Gly Ala Leu Glu Ser Ala Ile Ala Ile Ala Thr Gly Lys
145                 150                 155                 160

Met Leu Ser Leu Ala Glu Gln Gln Leu Val Asp Cys Ala Gln Asp Phe
                165                 170                 175

Asn Asn Tyr Gly Cys Gln Gly Gly Leu Pro Ser Gln Ala Phe Glu Tyr
            180                 185                 190

Ile Leu Tyr Asn Lys Gly Ile Met Gly Glu Asp Thr Tyr Pro Tyr Gln
        195                 200                 205

Gly Lys Asp Gly Tyr Cys Lys Phe Gln Pro Gly Lys Ala Ile Gly Phe
    210                 215                 220

Val Lys Asp Val Ala Asn Ile Thr Ile Tyr Asp Glu Glu Ala Met Val
225                 230                 235                 240

Glu Ala Val Ala Leu Tyr Asn Pro Val Ser Phe Ala Phe Glu Val Thr
                245                 250                 255

Gln Asp Phe Met Met Tyr Arg Thr Gly Ile Tyr Ser Ser Thr Ser Cys
            260                 265                 270

His Lys Thr Pro Asp Lys Val Asn His Ala Val Leu Ala Val Gly Tyr
```

```
                275                 280                 285
Gly Glu Lys Asn Gly Ile Pro Tyr Trp Ile Val Lys Asn Ser Trp Gly
            290                 295                 300
Pro Gln Trp Gly Met Asn Gly Tyr Phe Leu Ile Glu Arg Gly Lys Asn
305                 310                 315                 320
Met Cys Gly Leu Ala Ala Cys Ala Ser Tyr Pro Ile Pro Leu Val
                325                 330                 335

<210> SEQ ID NO: 7
<211> LENGTH: 339
<212> TYPE: PRT
<213> ORGANISM: homo sapiens

<400> SEQUENCE: 7

Met Trp Gln Leu Trp Ala Ser Leu Cys Cys Leu Leu Val Leu Ala Asn
1               5                   10                  15
Ala Arg Ser Arg Pro Ser Phe His Pro Val Ser Asp Glu Leu Val Asn
                20                  25                  30
Tyr Val Asn Lys Arg Asn Thr Thr Trp Gln Ala Gly His Asn Phe Tyr
            35                  40                  45
Asn Val Asp Met Ser Tyr Leu Lys Arg Leu Cys Gly Thr Phe Leu Gly
        50                  55                  60
Gly Pro Lys Pro Pro Gln Arg Val Met Phe Thr Glu Asp Leu Lys Leu
65                  70                  75                  80
Pro Ala Ser Phe Asp Ala Arg Glu Gln Trp Pro Gln Cys Pro Thr Ile
                85                  90                  95
Lys Glu Ile Arg Asp Gln Gly Ser Cys Gly Ser Cys Trp Ala Phe Gly
                100                 105                 110
Ala Val Glu Ala Ile Ser Asp Arg Ile Cys Ile His Thr Asn Ala His
            115                 120                 125
Val Ser Val Glu Val Ser Ala Glu Asp Leu Leu Thr Cys Cys Gly Ser
        130                 135                 140
Met Cys Gly Asp Gly Cys Asn Gly Gly Tyr Pro Ala Glu Ala Trp Asn
145                 150                 155                 160
Phe Trp Thr Arg Lys Gly Leu Val Ser Gly Gly Leu Tyr Glu Ser His
                165                 170                 175
Val Gly Cys Arg Pro Tyr Ser Ile Pro Pro Cys Glu His His Val Asn
            180                 185                 190
Gly Ser Arg Pro Pro Cys Thr Gly Glu Gly Asp Thr Pro Lys Cys Ser
        195                 200                 205
Lys Ile Cys Glu Pro Gly Tyr Ser Pro Thr Tyr Lys Gln Asp Lys His
210                 215                 220
Tyr Gly Tyr Asn Ser Tyr Ser Val Ser Asn Ser Glu Lys Asp Ile Met
225                 230                 235                 240
Ala Glu Ile Tyr Lys Asn Gly Pro Val Glu Gly Ala Phe Ser Val Tyr
                245                 250                 255
Ser Asp Phe Leu Leu Tyr Lys Ser Gly Val Tyr Gln His Val Thr Gly
            260                 265                 270
Glu Met Met Gly Gly His Ala Ile Arg Ile Leu Gly Trp Gly Val Glu
        275                 280                 285
Asn Gly Thr Pro Tyr Trp Leu Val Ala Asn Ser Trp Asn Thr Asp Trp
    290                 295                 300
Gly Asp Asn Gly Phe Phe Lys Ile Leu Arg Gly Gln Asp His Cys Gly
305                 310                 315                 320
```

```
Ile Glu Ser Glu Val Val Ala Gly Ile Pro Arg Thr Asp Gln Tyr Trp
            325                 330                 335
Glu Lys Ile
```